United States Patent
Luo et al.

(10) Patent No.: US 12,195,459 B2
(45) Date of Patent: Jan. 14, 2025

(54) GLUTARIMIDE-CONTAINING PAN-KRAS-MUTANT DEGRADER COMPOUNDS AND USES THEREOF

(71) Applicant: Tiger Biotherapeutics Inc., Cranbury, NJ (US)

(72) Inventors: Robert Luo, New City, NY (US); Ji Liu, Bellevue, WA (US); Pin Huang, Shanghai (CN); Jie Su, New York, NY (US); Yan Feng, Plainsboro, NJ (US); Ke Liu, Bellevue, WA (US); Jie Fan, New York, NY (US); Wei He, Zionsville, IN (US); Yimin Qian, Plainsboro, NJ (US)

(73) Assignee: Tiger Biotherapeutics Inc., Cranbury, NJ (US)

( * ) Notice: Subject to any disclaimer, the term of this patent is extended or adjusted under 35 U.S.C. 154(b) by 0 days.

(21) Appl. No.: 18/645,315

(22) Filed: Apr. 24, 2024

(65) Prior Publication Data

US 2024/0294527 A1   Sep. 5, 2024

Related U.S. Application Data

(62) Division of application No. 18/524,705, filed on Nov. 30, 2023.

(60) Provisional application No. 63/593,528, filed on Oct. 26, 2023, provisional application No. 63/385,453, filed on Nov. 30, 2022.

(51) Int. Cl.
C07D 471/04 (2006.01)
C07D 519/00 (2006.01)

(52) U.S. Cl.
CPC ......... C07D 471/04 (2013.01); C07D 519/00 (2013.01)

(58) Field of Classification Search
CPC .................................. C07D 471/04
USPC ..................................... 514/210.21
See application file for complete search history.

(56) References Cited

U.S. PATENT DOCUMENTS

2023/0321253 A1   10/2023   Lv et al.

FOREIGN PATENT DOCUMENTS

| CN | 115785199 A | 3/2023 |
|---|---|---|
| CN | 116332959 A | 6/2023 |
| CN | 116375742 A | 7/2023 |
| WO | WO 2019/195609 A2 | 10/2019 |
| WO | WO 2021/051034 A1 | 3/2021 |
| WO | WO 2022/132200 A1 | 6/2022 |
| WO | WO 2022/266206 A1 | 12/2022 |
| WO | WO 2023/077441 A1 | 5/2023 |
| WO | WO 2023/081476 A1 | 5/2023 |
| WO | WO 2023/116934 A1 | 6/2023 |
| WO | WO 2023/138524 A1 | 7/2023 |
| WO | WO 2023/141570 A2 | 7/2023 |
| WO | WO 2023/193085 A1 | 10/2023 |
| WO | WO 2023/215906 A1 | 11/2023 |

OTHER PUBLICATIONS

PCT International Search Report and Written Opinion, PCT Application No. PCT/US2023/081898, Mar. 22, 2024, 16 pages.
PCT International Search Report and Written Opinion, PCT Application No. PCT/US2023/081910, Mar. 22, 2024, 16 pages.
Troup, R. I. et al. "Current Strategies for the Design of PROTAC Linkers: A Critical Review." Exploration of Targeted Anti-Tumor Therapy, vol. 1, No. 5, Oct. 30, 2020, pp. 273-312.

*Primary Examiner* — Niloofar Rahmani
(74) *Attorney, Agent, or Firm* — Fenwick & West LLP; Stefan Ochiana; Brennan A. Murphy

(57) ABSTRACT

The present disclosure relates to novel pan-KRAS glutarimide-containing compounds with KRAS degradation activities, pharmaceutical compositions containing such compounds, and their use in prevention and treatment diseases and conditions.

46 Claims, 7 Drawing Sheets

GLUTARIMIDE-CONTAINING PAN-KRAS-MUTANT DEGRADER COMPOUNDS AND USES THEREOF

BACKGROUND

Targeted protein degradation (TPD) is a therapeutic modality to modulate proteins that have proved challenging to target with conventional small molecules. Some of these proteins have been intractable because, for example, their active sites are broad, have shallow pockets that are difficult to bridge with small molecules while others have "smooth" surfaces that offer few sites for a small molecule to bind or may not possess an active site to which small molecules could bind. Many of these difficult to target proteins play key roles in diseases, such as cancer. Proteolysis-targeting chimeras (PROTACs) are an example of such small molecules that enable TPD of specific proteins, such as KRAS mutant oncogenes (see Sakamoto and Deshaies, et al, PNAS 2001, 98, 8554-8559; and Burslem and Crews, Cell, 2020, 181: 102-114).

The KRAS gene is a member of the rat sarcoma viral oncogene family (RAS). KRAS is the most commonly mutated member of the RAS family and is considered to be the most common oncogenic gene driver in human cancers. KRAS mutations are most common in highly fatal cancers, including pancreatic ductal adenocarcinoma (PDAC), non-small-cell lung cancer (NSCLC), and colorectal cancer (CRC). The profile of KRAS mutations differs significantly among different cancer types. Moreover, KRAS mutations are dominated by single-base missense mutations, 98% of which are found at codon 12 (G12), codon 13 (G13), or codon 61 (Q61).

KRAS mutations occur in many cancers with different mutation frequencies, and there is also a large variation in mutation subtypes. For example, among the subtypes of KRAS mutations, KRAS (G12C) and KRAS (G12V) mutations are epidemiologically associated with smoking history, whereas KRAS (G12D) mutations are more common among individuals who do not smoke. The KRAS (G12C) mutant subtype has a cysteine residue (glycine position 12 is mutated to cysteine) and is the most common KRAS mutation in NSCLC. The KRAS (G12V) mutant has a valine residue (glycine at position 12 is mutated to valine) and individuals who smoke are more predisposed to NSCLC with KRAS (G12V) mutation. The KRAS (G12V) mutations occur in approximately 21% of patients with NSCLC with KRAS mutations (see Xie, at al, 2021, 11, 672612). The KRAS (G12D) mutation refers to the presence of an aspartic acid residue (glycine at position 12 is mutated to aspartic acid). KRAS (G12D) mutations occur in approximately 15% of patients with NSCLC with KRAS mutations. Also, KRAS (G12D) mutation is the most common KRAS mutation detected in carcinomas and adenocarcinomas. The KRAS (G12S) mutation refers to the presence of a serine acid residue (glycine at position 12 is mutated to serine). The KRAS (G12S) mutation has been observed in many patient tumors, occurring in 2.8% of colorectal adenocarcinoma and 2.5% of NSCLC (see Gao L, Shen W, (2022) Front Genet.; Zhang, Z. et al., (2022) Nat Chem Biol 18, 1177-1183). Moreover, KRAS wild-type amplifications are found in around 7% of all KRAS-altered cancers, ranking among the top alterations, and commonly occurring in ovarian, esophagogastric, and uterine cancers (see Herdeis L, et al., (2021) Curr Opin Struct Biol. 71:136-147).

The role of activated KRAS in malignancy was observed over thirty years ago (e.g., see Santos et al., (1984) Science 223:661-664). Aberrant expression of KRAS accounts for up to 20% of all cancers and oncogenic KRAS mutations that stabilize GTP binding and lead to constitutive activation of KRAS and downstream signaling have been reported in 25-30% of lung adenocarcinomas. (e.g., see Samatar and Poulikakos (2014) Nat Rev Drug Disc 13(12): 928-942).

The well-known role of KRAS in malignancy and the discovery of these frequent mutations in KRAS in various tumor types made KRAS a highly attractive target of the pharmaceutical industry for cancer therapy. Notwithstanding thirty years of large-scale discovery efforts to develop inhibitors of KRAS for treating cancer, no reversible KRAS inhibitor has yet demonstrated sufficient safety and/or efficacy to obtain regulatory approval (e.g., see McCormick (2015) Clin Cancer Res. 21 (8):1797-1801). Most recently, sotorasib and adagrasib, both covalent inhibitors of KRAS-G12C were approved by US FDA for patients with advanced NSCLC harboring KRAS-G12C mutation.

Compounds that inhibit KRAS activity are still highly desirable and under investigation, including those that disrupt effectors such as guanine nucleotide exchange factors (e.g., see Sun et al., (2012) Angew. Chem. Int. Ed. Engl. 51(25):6140-6143) as well recent advances in the covalent targeting of an allosteric pocket of KRAS G12C (e.g., see Ostrem et al., (2013) Nature 503:548-551 and Fell et al., (2018) ACS Med. Chem. Lett. 9:1230-1234).

Ubiquitin-Proteasome Pathway (UPP) is a critical pathway that regulates key regulatory proteins and degrades misfolded or abnormal proteins. UPP is central to multiple cellular processes, and if defective or imbalanced, leads to pathogenesis of a variety of diseases. The covalent attachment of ubiquitin to specific protein substrates is achieved through the action of E3 ubiquitin ligases.

There are hundreds of E3 ligases which facilitate the ubiquitination of different proteins in vivo, which can be divided into four families: HECT-domain E3s, U-box E3s, monomeric RING E3s and multi-subunit E3s. See generally Li et al. (PLOS One, 2008, 3, 1487), Berndsen et al. (Nat. Struct. Mol. Biol., 2014, 21, 301-307), Deshaies et al. (Ann. Rev. Biochem., 2009, 78, 399-437), and Wang et al. (Nat. Rev. Cancer., 2014, 14, 233-347).

The UPP is used to induce selective protein degradation by artificially ubiquitinating target proteins. Bifunctional compounds comprising a target protein-binding ligand and an E3 ubiquitin ligase ligand induce proteasome-mediated degradation of selected proteins via their recruitment to E3 ubiquitin ligase and subsequent ubiquitination. These drug-like molecules are capable of inducing the inactivation of a protein of interest upon addition to cells or administration to an animal or human.

PROTAC protein degraders are a class of molecules that have the potential to enable the modulation of these difficult to target proteins via TPD. PROTAC degraders are heterobifunctional small molecules consisting of two ligands (e.g., chemical moieties) joined by a linker. The roles of the two ligands are different. One ligand recruits and binds a protein of interest (i.e., target protein) while the other recruits and binds an E3 ubiquitin ligase. This simultaneous binding of the protein of interest and ligase by the PROTAC induces ubiquitylation of the protein of interest and its subsequent degradation by the ubiquitin-proteasome system (UPS), after which the PROTAC is recycled to target another copy of the protein of interest. This catalytic-type mechanism of action and event-driven pharmacology differentiate PROTACs from classical inhibitors, which have a one-to-one relationship with the protein of interest and whose pharmacology is driven by stoichiometry and, usually, by interactions with a catalytic site (see Bekes, et al, Nature Reviews Drug Discovery 2022, Vol 21, 181-200).

Compounds that can degrade proteins offer a different way to target previously undruggable targets, such as KRAS, by harnessing the power of the cell's natural waste disposal system to selectively eliminate cancer-associated proteins. Pan-degrader compounds can hit all the major KRAS forms (e.g., mutants, wildtype) that drive cancer rather than picking them off one by one, by targeting, for example, selectively only KRAS (G12C) or KRAS (G12D).

There remains an unmet medical need for novel pan-KRAS degrader compounds that can target various KRAS forms, such as compounds directed at targeting and degrading various KRAS forms, such as KRAS (G12C), KRAS (G12D), KRAS (G12S), KRAS (G12V), and/or KRAS (WT), in cancers.

SUMMARY

The present disclosure is directed to Protein-Protein Interaction Targeted Chimeras (PPI-TACs), which possess many advantages over conventional biochemical enzyme inhibitors and PROTACs. Unlike PROTACs that rely only on proximity by projecting one small molecule simultaneously to a targeted protein and E3 ligase, the PPI-TACs disclosed herein not only possess the ability to facilitate target protein and E3 ligase ternary complex formation but are also believed to direct protein-protein interactions between the targeted protein and E3 ligase, thus leading to enhanced degradation potency and selectivity. In some embodiments, the PPI-TACs work sub-stoichiometrically by inducing multiple rounds of degradation of target proteins. This is attributed to the PPI-TAC molecule being released from the proteosome-degraded protein to bind another target protein and E3 ubiquitin ligase, which in turn results in a greater potency compared to each isolated moiety binding to its respective target. In some embodiments, PPI-TACs disclosed herein can deplete target proteins that are not responsive to biochemical inhibition by binding accessible pockets that do not affect the biochemical activity of the target but still permit their degradation. It is believed that the PPI-TACs disclosed herein may achieve improved degradation selectivity and degradation potency due to the induced protein-protein interactions. In some embodiments, select PPI-TACs disclosed herein (e.g., compounds of Formula I) demonstrate a superior pharmacokinetics profile in in vivo studies (e.g., enhanced efficacy and decreased and/or no toxicity in subjects; improved drug absorption, distribution, metabolism, and/or excretion).

In some embodiments, the present disclosure provides KRAS degrader compounds, compositions comprising the disclosed compounds, and uses thereof. In some embodiments, the compounds disclosed herein comprise two ligands (e.g., two chemical scaffolds) joined by novel linker moieties, wherein the linker facilitates the orientation and/or position of the two ligands to bind to their respective targets. In some embodiments, one ligand recruits and binds the protein(s) of interest (e.g., KRAS forms, such as KRAS (G12C), KRAS (G12D), KRAS (G12S), KRAS (G12V), and/or KRAS (WT)) while the other ligand recruits and binds an E3 ubiquitin ligase. In some embodiments, one ligand binds to one or more KRAS forms. In some embodiments, the binding of said ligand to one or more KRAS forms is facilitated by the presence of a 4-7 membered N-containing heterocyclic group comprising at least one or more substitutions, wherein at least one substitution is a hydrogen bond donor (e.g., OH). In some embodiments, the binding of said ligand to one or more KRAS mutants is facilitated by the presence of a 6 membered N-containing heterocyclic group comprising at least two substitutions, wherein at least one substitution is a hydrogen bond donor (e.g., OH) and the other substitution is a small lipophilic group (e.g., methyl). In some embodiments, the presence of the 4-6 membered N-containing heterocyclic group (e.g., piperidine group substituted at position 3 with an OH group and a methyl group) allows for the molecules disclosed herein to bind to one or more KRAS forms. In some embodiments, the disclosed compounds may act as adapter molecules between the E3 ligase and the KRAS protein(s) thus redirecting the activity of the cell's natural protein degradation machinery, i.e., the ubiquitin-proteasome system (UPS).

In some embodiments, the present disclosure provides a compound, wherein the compound is represented by Formula I or is a pharmaceutically acceptable salt thereof:

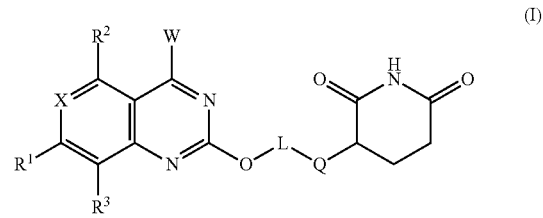

(I)

wherein:
  W is $NR^pR^q$ or a 5-12 membered monocyclic, bicyclic, bridged, or spiro heterocyclic group, wherein each of the $NR^pR^q$, monocyclic, bicyclic, bridged, or spiro heterocyclic group is independently substituted with 0, 1, 2, or 3 $R^a$;
  each $R^a$ is independently selected from H, halogen, cyano, hydroxy, $C_1$-$C_6$ alkyl, $C_3$-$C_6$ cycloalkyl, an oxo group, $C(=O)N(C_1$-$C_3$ alkyl$)_2$, and $C_1$-$C_6$ alkoxy, wherein the $C_1$-$C_6$ alkyl and $C_3$-$C_6$ cycloalkyl are optionally substituted with one or more groups selected from halogen, hydroxy, $C_1$-$C_3$ alkyl, $C_3$-$C_4$ cycloalkyl, and $N(C_1$-$C_3$ alkyl$)_2$; or two of the $R^a$ groups together with the atoms to which they are both attached form an optionally substituted 3- to 6-membered saturated, partially unsaturated, or heterocyclic ring, wherein the ring has 0 to 4 heteroatoms independently selected from N, S, and O;
  $R^1$ is a monocyclic or bicyclic aryl or heteroaryl, wherein the monocyclic or bicyclic aryl and heteroaryl are independently substituted with 0, 1, 2, 3, or 4 $R^b$;
  each $R^b$ is independently selected from halogen, cyano, hydroxy, amino, an oxo group, $C_1$-$C_4$ alkyl, $C_2$-$C_4$ alkenyl, $C_2$-$C_4$ alkynyl, $C_2$-$C_4$ hydroxyalkynyl, $C_1$-$C_3$ cyanoalkyl, $C_1$-$C_4$ haloalkyl, O—$C_1$-$C_3$ haloalkyl, S—$C_1$-$C_3$ haloalkyl, $C_1$-$C_3$ alkoxy, hydroxy $C_1$-$C_3$ alkyl, OC(=O)$R^p$, OC(=O))$NR^pR^q$, $CH_2C(=O)NR^pR^q$, $C_3$-$C_4$alkynyl-$NR^pR^q$, $NR^pR^q$, and $C_3$-$C_6$ cycloalkyl;
  each of $R^p$ and $R^q$ is independently selected from H, $C_1$-$C_6$ alkyl, $CO(C_1$-$C_6$ alkyl), $SO_2CH_3$, and $C_3$-$C_6$ cycloalkyl, wherein the $C_3$-$C_6$ cycloalkyl is optionally substituted with halogen;
  X is $CR^c$ or N;
  $R^c$ is selected from H, cyano, hydroxy, halogen, $C_1$-$C_5$ alkoxy, $C_1$-$C_8$ alkyl, $C_2$-$C_5$ alkenyl, and $C_3$-$C_5$ cycloalkyl, wherein each of the $C_1$-$C_5$ alkoxy, $C_1$-$C_5$ alkyl, C₂-C₅ alkenyl, and C₃-C₅ cycloalkyl is optionally substituted with halogen, hydroxy, amino, or cyano;

R² is H, halogen, C₁-C₃ alkyl, or a 4-6 membered N-containing heterocyclic group, wherein the heterocyclic group is independently substituted with 0, 1, or 2 R$^d$;

R$^d$ is selected from halogen, hydroxy, C₁-C₃ alkyl, and C₁-C₃ alkoxy;

R³ is selected from H, halogen, hydroxy, C₁-C₃ alkyl, C₁-C₃ haloalkyl, and C₃-C₆ cycloalkyl;

L is a linker with a backbone of 1 to 20 carbon atoms in length, wherein one or more carbon atoms are optionally substituted with halogen, alkylamino, hydroxy, cyano, C₁-C₅ alkyl, an oxo group, C₁-C₃ haloalkyl, C₁-C₄ alkoxy, or amide, wherein one or more carbon atoms of the backbone are optionally replaced by a divalent group independently selected from oxygen, cycloalkyl, heterocyclyl, spiroheterocyclyl, bridged heterocyclyl, aryl, and heteroaryl, and wherein each of the cycloalkyl, heterocyclyl, spiroheterocyclyl, bridged heterocyclyl, aryl, or heteroaryl is independently substituted with 0, 1, or 2 R$^e$;

each R$^e$ is independently selected from halogen, cyano, hydroxy, C₁-C₄ alkyl, C₁-C₄ alkenyl, C₃-C₅ cycloalkyl, C₁-C₄ haloalkyl, and C₁-C₄ alkoxy;

Q is 1 to 5 carbon atoms in length, wherein one or more carbon atoms are replaced by a divalent group selected from heterocyclyl, aryl, heteroaryl, amino, C(=O)—, C(=O)—NH—, and C(=O)N(R$^p$)—, and wherein each of the heterocyclyl, aryl, and heteroaryl is independently substituted with 0, 1, 2, or 3 R$^f$; and each R$^f$ is independently selected from halogen, hydroxy, C₁-C₃ alkyl, C₁-C₃ haloalkyl, C₁-C₅ alkoxy, and an oxo group.

In some embodiments, the compound of Formula I is represented by Formula IB:

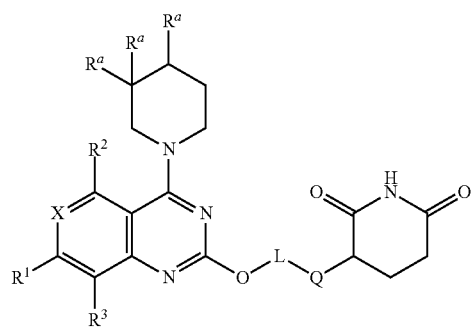

(IB)

wherein each R$^a$ is independently selected from H, hydroxy, C₁-C₃ alkyl, halogen, and C₁-C₃ alkoxy. In some embodiments, each R$^a$ is independently selected from methyl, ethyl, and hydroxy.

In some embodiments, the compound of Formula I is represented by Formula IB':

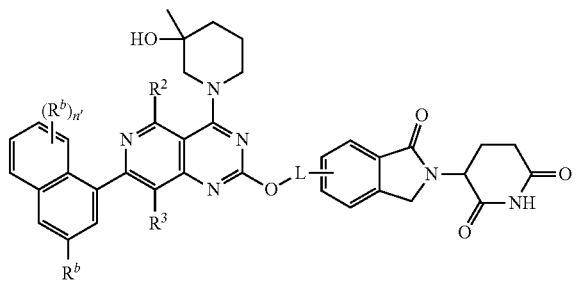

(IB')

wherein:

each R$^b$ is independently selected from halogen (such as F), hydroxy, amino, C₁-C₄ alkyl (such as ethyl), C₂-C₄ alkenyl, C₂-C₄ alkynyl, C₁-C₄ haloalkyl, and C₃-C₆ cycloalkyl;

R² is H or halogen;

R³ is H or halogen (such as F);

n' is 0, 1, or 2; and

L is selected from

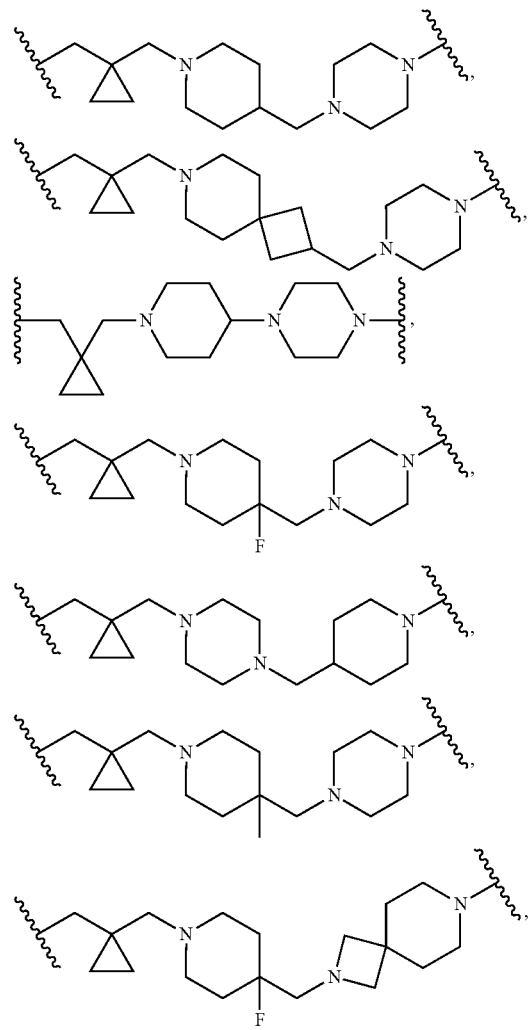

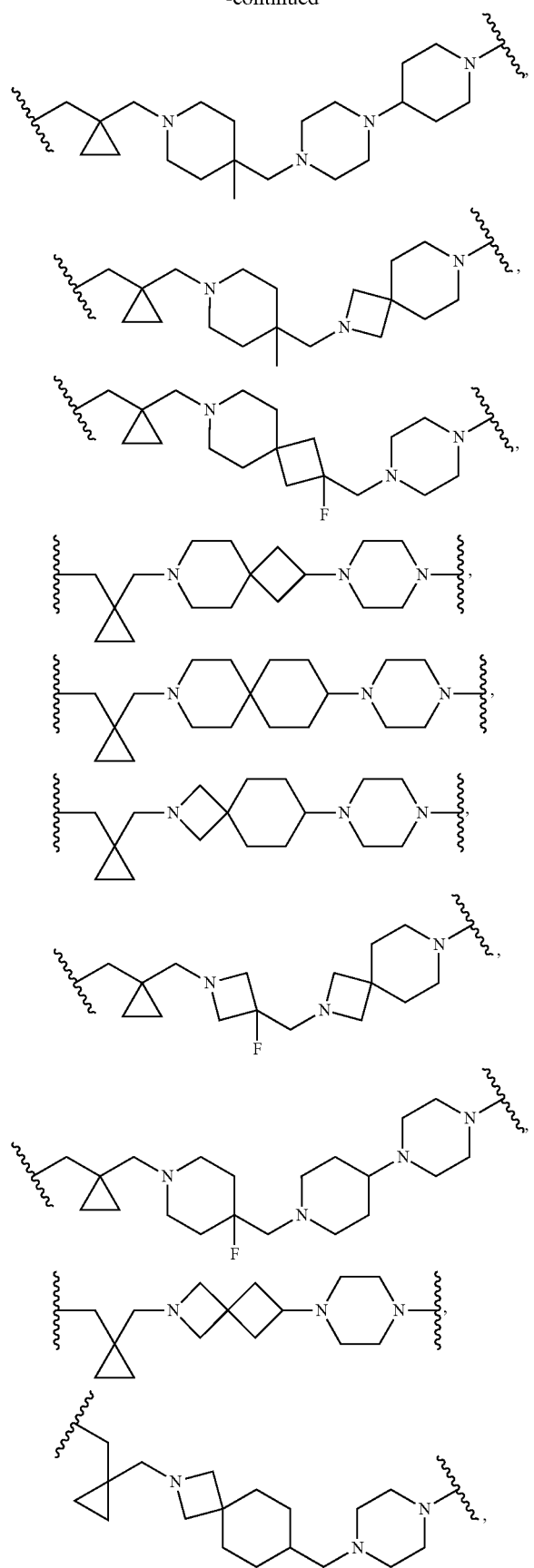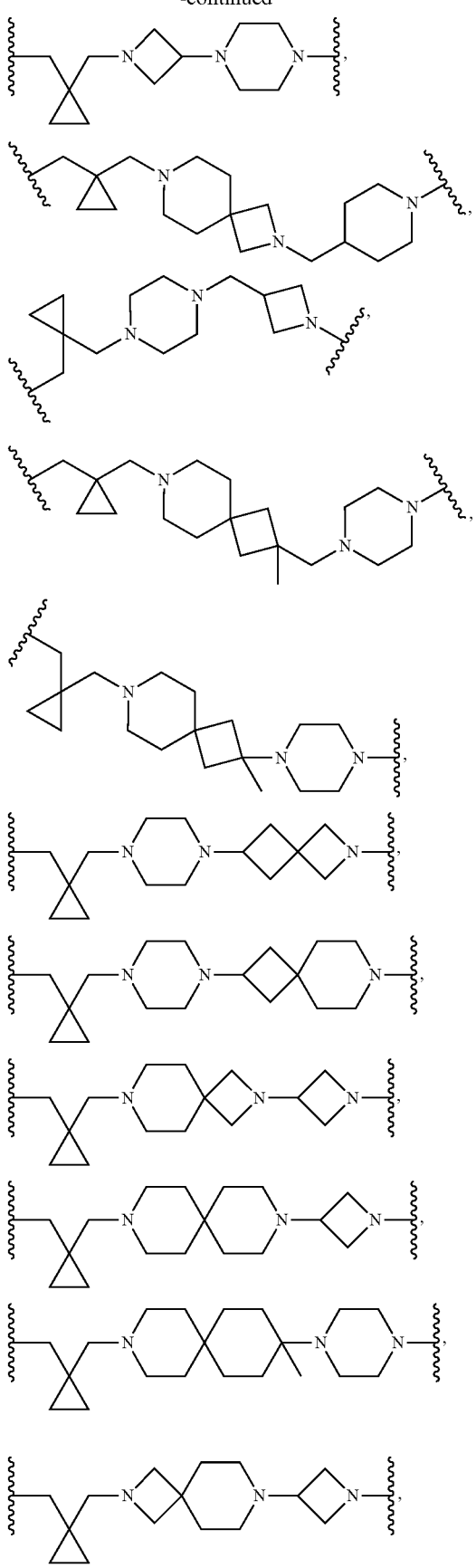

-continued

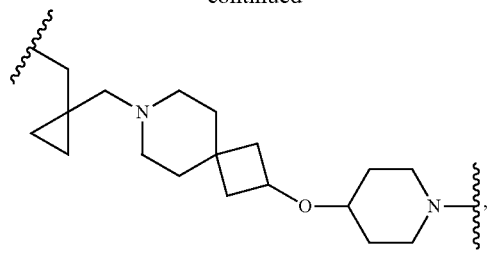

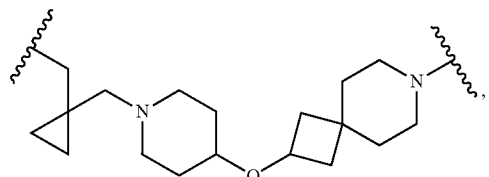

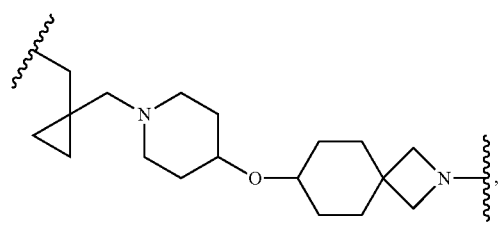

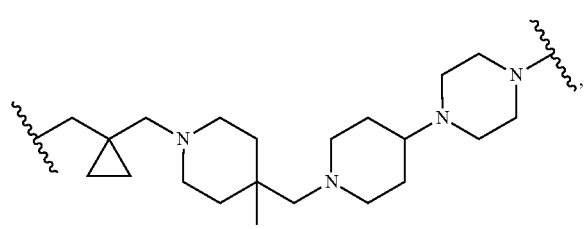

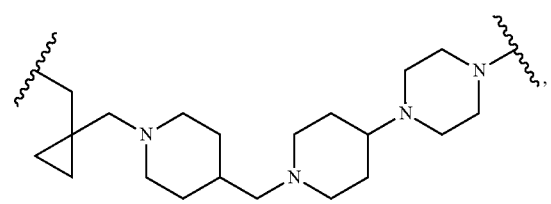

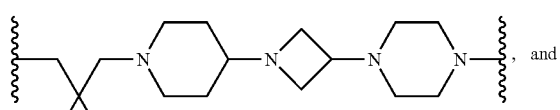

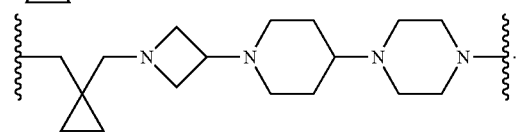

In some embodiments, the compound is represented by Formula IC or is a pharmaceutically acceptable salt thereof:

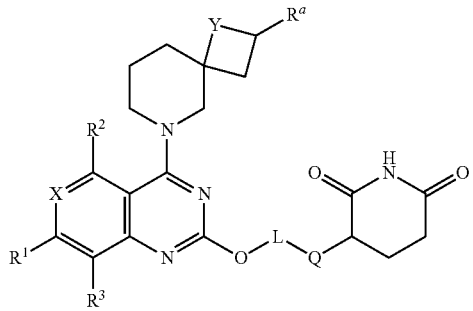

(IC)

wherein:
each $R^a$ is independently selected from hydrogen, halogen, cyano, hydroxy, and $C_1$-$C_6$ alkyl;

$R^1$ is a monocyclic or bicyclic aryl or heteroaryl, wherein the monocyclic or bicyclic aryl and heteroaryl are independently substituted with 0, 1, 2, 3, or 4 $R^b$;

each $R^b$ is independently selected from halogen, cyano, hydroxy, amino, and $C_1$-$C_4$ alkyl;

X is N;

Y is O or $CH_2$;

$R^2$ is H or halogen;

$R^3$ is halogen;

L is a linker with a backbone of 1 to 20 carbon atoms in length, wherein one or more carbon atoms are optionally substituted with halogen, alkylamino, hydroxy, cyano, $CFH_2$, $CF_2H$, $CF_3$, $C_1$-$C_5$ alkyl, an oxo group, $C_1$-$C_3$ haloalkyl, $C_1$-$C_4$ alkoxy, or amide, wherein one to eight carbon atoms of the backbone are optionally replaced by a divalent group independently selected from oxygen, cycloalkyl, monocyclic heterocyclic group, bridged heterocyclic group, spiro heterocyclic group, heterocyclyl, aryl, heteroaryl fused heterocyclyl, and heteroaryl, and wherein each of the cycloalkyl, monocyclic heterocyclic group, bridged heterocyclic group, spiro heterocyclic group, heteroaryl, heteroaryl fused heterocyclyl, heterocyclyl, aryl, or heteroaryl is independently substituted with 0, 1, or 2 $R^e$;

each $R^e$ is independently selected from halogen, cyano, hydroxy, $C_1$-$C_4$ alkyl, $C_1$-$C_4$ alkenyl, $C_3$-$C_5$ cycloalkyl, $C_1$-$C_4$ haloalkyl, and $C_1$-$C_4$ alkoxy;

Q is 1 to 5 carbon atoms in length, wherein one or more carbon atoms are replaced by a divalent group selected from heterocyclyl, aryl, heteroaryl, —NH—, —C(=O)—, and —C(=O)—NH—, and wherein each of the heterocyclyl, aryl, and heteroaryl is independently substituted with 0, 1, 2, 3, 4, or 5 $R^f$; and each $R^f$ is independently selected from halogen, hydroxy, $C_1$-$C_3$ alkyl, $C_1$-$C_3$ haloalkyl, $C_1$-$C_5$ alkoxy, and an oxo group.

In some embodiments, Q is selected from

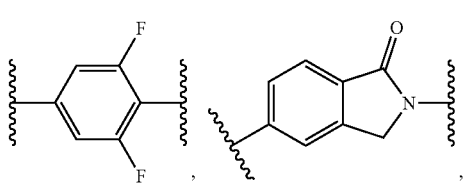

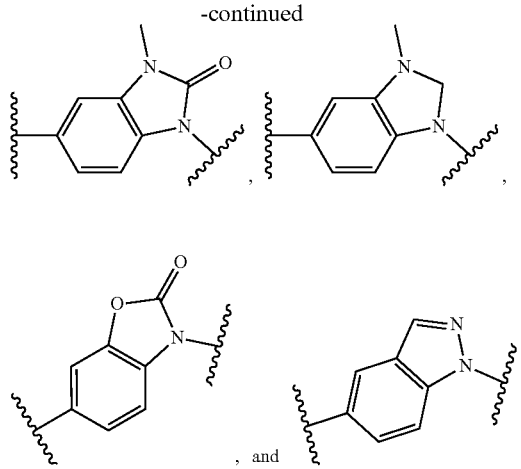
In some embodiments, L is selected from
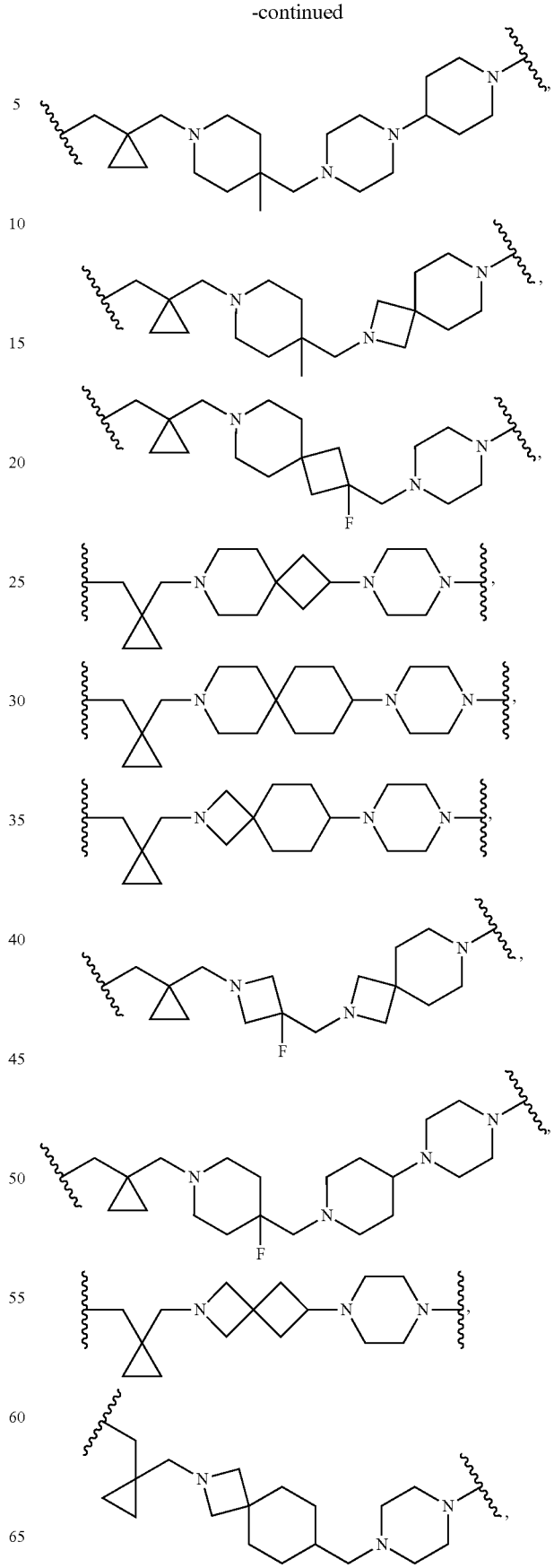

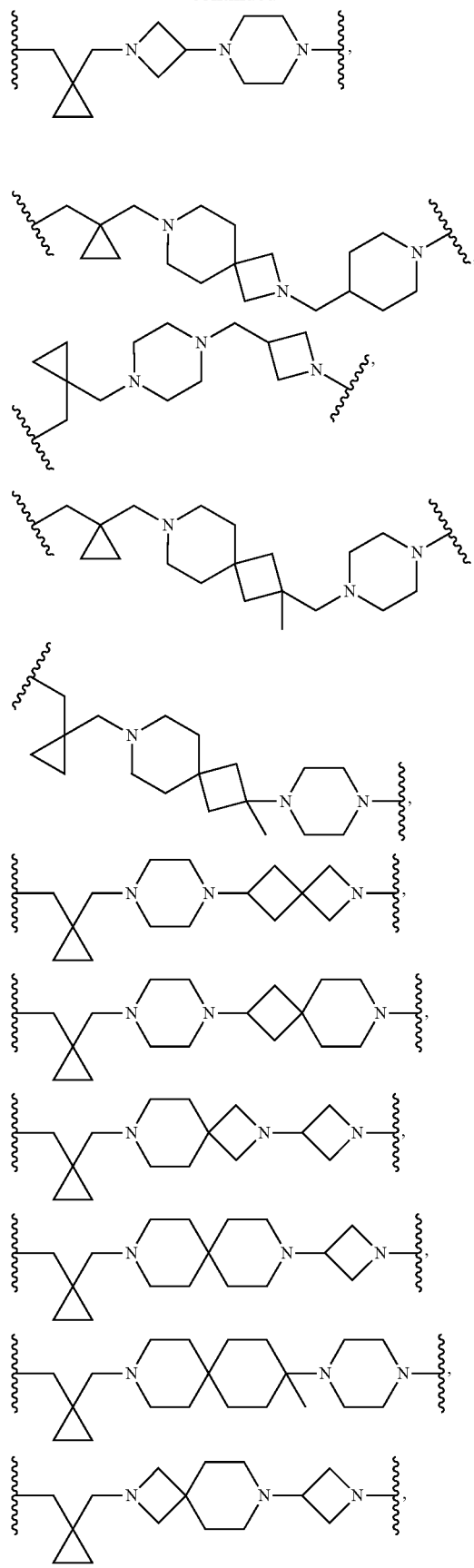
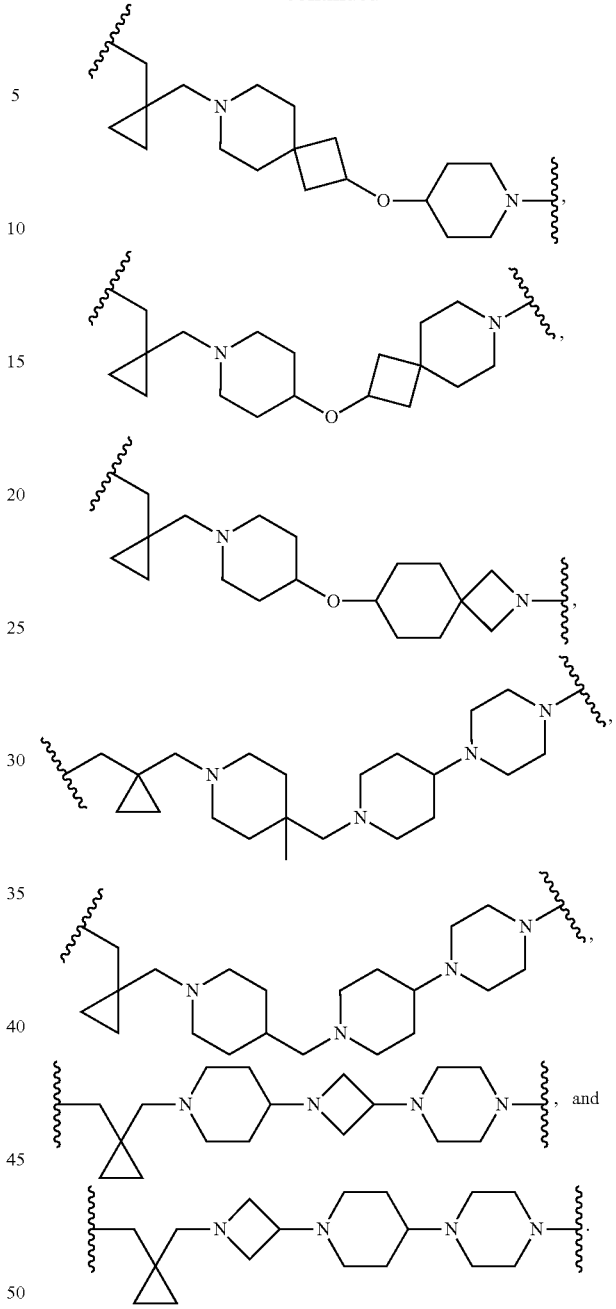

Also disclosed herein are methods of treatment. The disclosed methods may comprise treating a subject (e.g., a human subject) in need thereof, wherein the subject has a disease, such as cancer. The methods may comprise administering to the subject an effective amount of a compound disclosed herein. In some embodiments, the cancer is a KRAS-driven cancer (or mutant-associated cancer). In some embodiments, the KRAS-driven cancer is selected from breast cancer, lung cancer, pancreatic cancer, small bowel cancer, colorectal cancer, gall bladder cancer, thyroid cancer, liver cancer, bile duct cancer, ovarian cancer, endometrial cancer, cervical cancer, bladder cancer, prostate cancer, esophageal cancer, and blood cancer.

In some embodiments, the present disclosure provides compositions (e.g., pharmaceutical compositions) comprising one or more compounds of disclosed herein (e.g., Formula I) and one or more pharmaceutically acceptable carriers, pharmaceutically acceptable vehicles, pharmaceutically acceptable excipients, or combinations thereof.

DETAILED DESCRIPTION

Definitions

Figure 1:
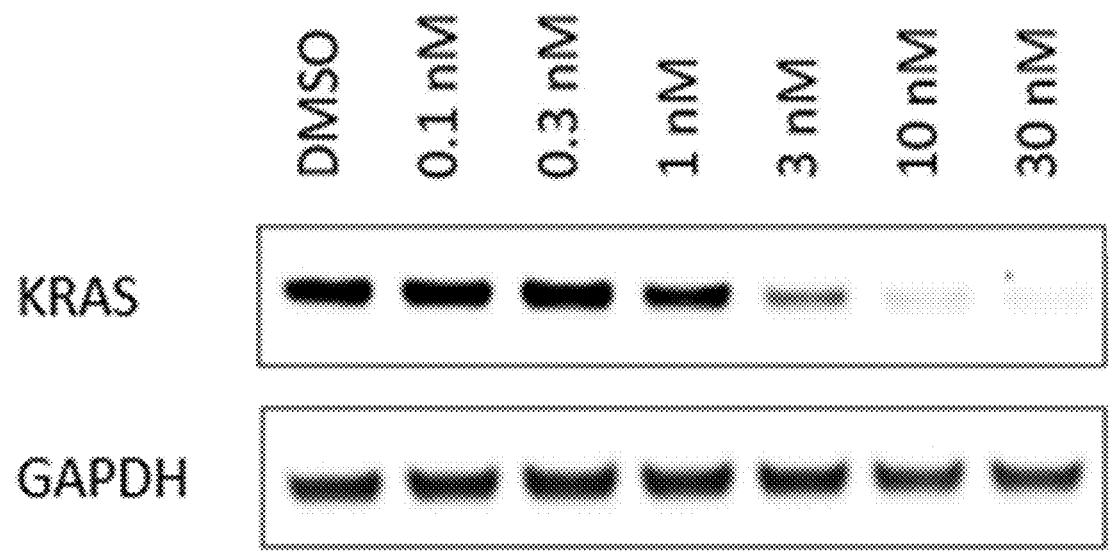
FIG. 1 illustrates the KRAS G12V degradative activity of exemplary compound 1 in a SW620 cell line 24 hours after administration.
Figure 2:
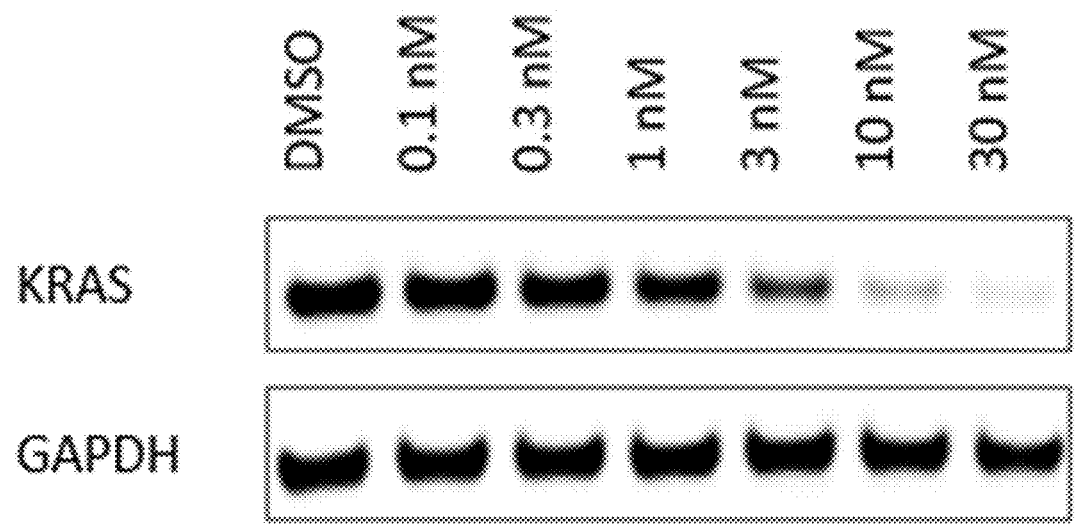
FIG. 2 illustrates the KRAS G12D degradative activity of exemplary compound 1 in a AsPC1 cell line 24 hours after administration.
Figure 3:
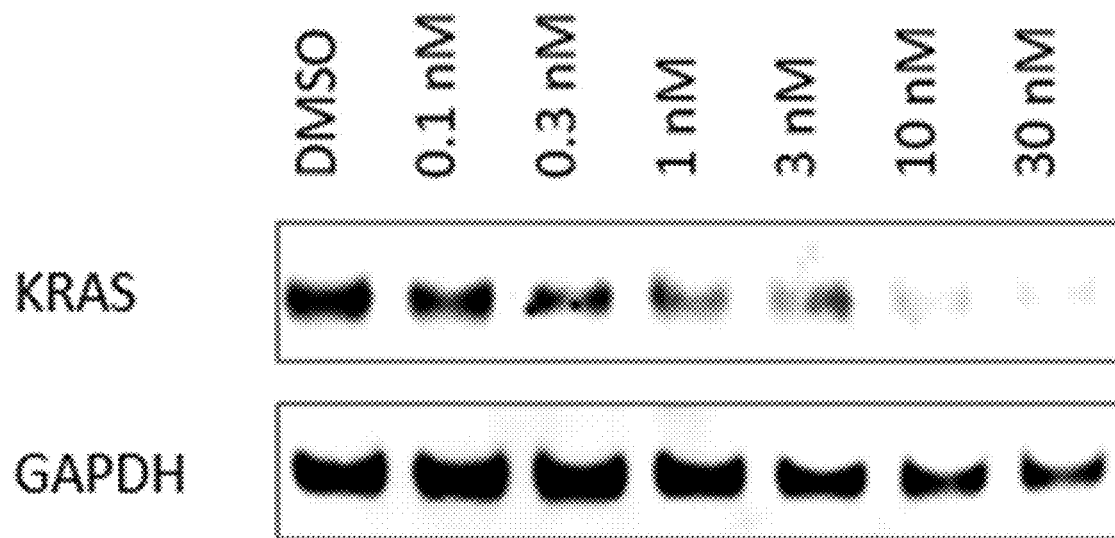
FIG. 3 illustrates the KRAS G12C degradative activity of exemplary compound 1 in a MIA PaCa2 cell line 24 hours after administration.
Figure 4:
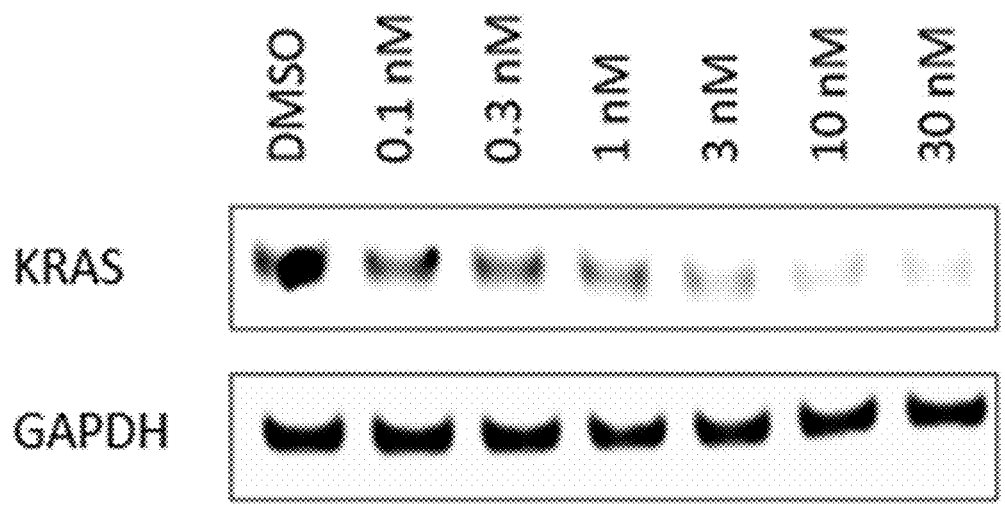
FIG. 4 illustrates the KRAS G12S degradative activity of exemplary compound 1 in a A549 cell line 24 hours after administration.
Figure 5:
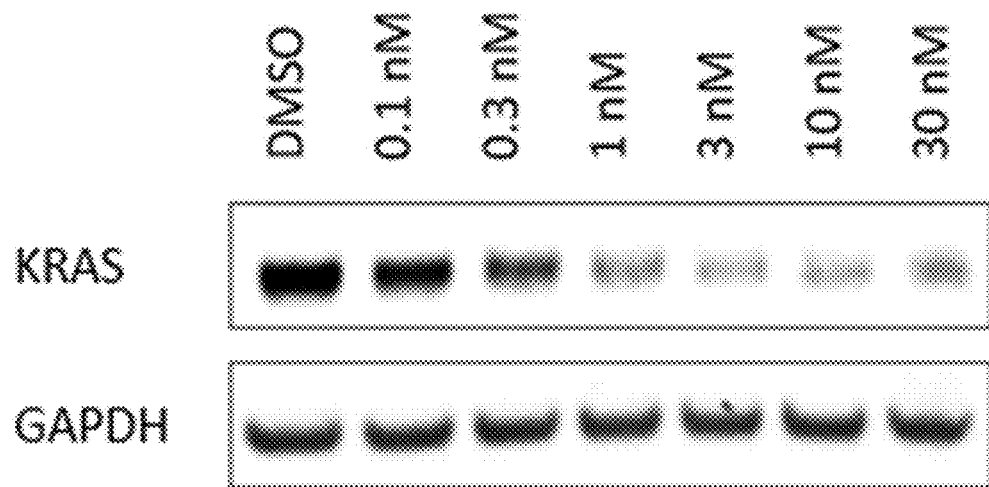
FIG. 5 illustrates the KRAS wildtype (WT) degradative activity of exemplary compound 1 in a MCF7 cell line 24 hours after administration.

When describing the embodiments of the present disclosure, which may include compounds and pharmaceutically acceptable salts thereof, pharmaceutical compositions containing such compounds and methods of using such compounds and compositions, the following terms, if present, have the following meanings unless otherwise indicated.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

Compounds of this disclosure include those described generally above, and are further illustrated by the classes, subclasses, and species disclosed herein. As used herein, the following definitions shall apply unless otherwise indicated. For purposes of this disclosure, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The abbreviations used herein have their conventional meaning without the chemical and biological arts. The chemical structures and formulae set forth herein are constructed according to the standard rules of chemical valency known in the chemical arts.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocyclyl", "cycloaliphatic", or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In some embodiments, aliphatic groups contain 1-4 aliphatic carbon atoms. In some embodiments, aliphatic groups contain 1-3 aliphatic carbon atoms. In some embodiments, aliphatic groups contain 1-2 aliphatic carbon atoms. In some embodiments, "cycloaliphatic" (or "carbocyclyl" or "cycloalkyl") refers to a monocyclic $C_3$-$C_7$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substituted nitrogen of a heterocyclic ring, for example N (as in 3,4-dihydro-2H-pyrrolyl), NH (as in pyrrolidinyl) or NR (as in N-substituted pyrrolidinyl)).

The term "unsaturated", as used herein, means that a moiety has one or more units of unsaturation.

The term "alkylene" refers to a divalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

As used herein, the term "cyclopropylenyl" refers to a divalent cyclopropyl group of the following structure:

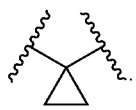

As used herein, the term "bridged bicyclic" refers to any bicyclic ring system, i.e., carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bridged bicyclics include:

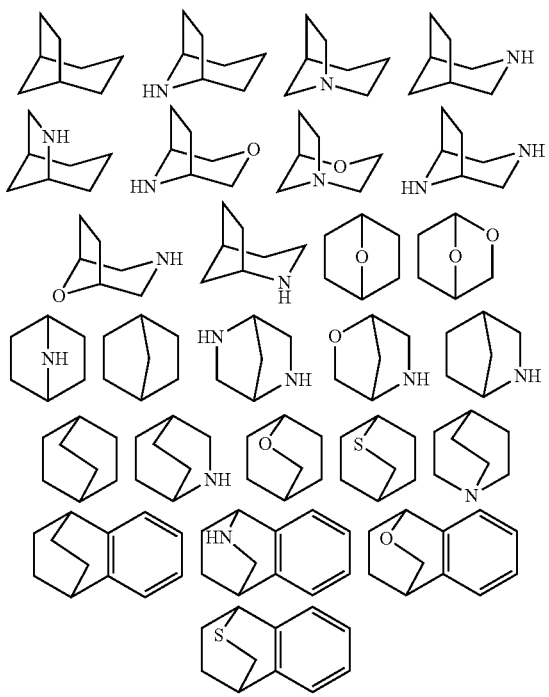

A dash ("-") that is not between two letters or symbols is used to indicate a point of attachment for a substituent. For example, —CN is attached through the carbon atom.

When a range of values is listed, it is intended to encompass each value and sub-range within the range. For example, "$C_1$-$C_6$ alkyl" is intended to encompass $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "acyl" as used herein refers to R—C(O)— groups such as, but not limited to, (alkyl)-C(O)—, (alkenyl)-C(O)—, (alkynyl)-C(O)—, (aryl)-C(O)—, (cycloalkyl)-C(O)—, (heteroaryl)-C(O)—, and (heterocyclyl)-C(O)—, wherein the group is attached to the parent molecular structure through the carbonyl functionality. In some embodiments, it is a C1-10 acyl radical which refers to the total number of chain or ring atoms of the, for example, alkyl, alkenyl, alkynyl, aryl, cycloalkyl, or heteroaryl, portion plus the carbonyl carbon of acyl. For example, a C4-acyl has three other ring or chain atoms plus carbonyl.

The term "alkenyl" as used herein refers to an unsaturated straight or branched hydrocarbon having at least one carbon-carbon double bond, such as a straight or branched group of 2 8 carbon atoms, referred to herein as ($C_2$-$C_8$)alkenyl. Exemplary alkenyl groups include, but are not limited to, vinyl, allyl, butenyl, pentenyl, hexenyl, butadienyl, pentadienyl, hexadienyl, 2-ethylhexenyl, 2 propyl 2-butenyl, and 4-(2-methyl-3-butene)-pentenyl.

The term "alkyl" as used herein refers to a saturated straight or branched hydrocarbon, such as a straight or branched group of 1 to 8 carbon atoms, referred to herein as $C_{1-8}$ alkyl. Exemplary alkyl groups include, but are not limited to, methyl, ethyl, propyl, isopropyl, 2-methyl-1-propyl, 2-methyl-2-propyl, 2-methyl-1-butyl, 3 methyl-1-butyl, 2-methyl-3-butyl, 2,2-dimethyl-1-propyl, 2-methyl-1-pentyl, 3 methyl-1-pentyl, 4-methyl-1-pentyl, 2-methyl-2-pentyl, 3-methyl-2-pentyl, 4 methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, and octyl. In some embodiments, "alkyl" is a straight-chain hydrocarbon. In some embodiments, "alkyl" is a branched hydrocarbon.

The term "alkoxy" means a straight or branched chain saturated hydrocarbon containing 1-12 carbon atoms containing a terminal "O" in the chain, e.g., —O(alkyl). Examples of alkoxy groups include, without limitation, methoxy, ethoxy, propoxy, butoxy, t-butoxy, or pentoxy groups.

The term "alkylene" as used herein refers to a divalent alkyl radical. Representative examples of C1-10 alkylene include, but are not limited to, methylene, ethylene, n-propylene, iso-propylene, n-butylene, sec-butylene, iso-butylene, tert-butylene, n-pentylene, isopentylene, neopentylene, n-hexylene, 3-methylhexylene, 2,2-dimethylpentylene, 2,3-dimethylpentylene, n-heptylene, n-octylene, n-nonylene and n-decylene.

The term "alkynyl" as used herein refers to an unsaturated straight or branched hydrocarbon having at least one carbon-carbon triple bond, such as a straight or branched group of 2 to 8 carbon atoms, referred to herein as $(C_2-C_8)$alkynyl. Exemplary alkynyl groups include, but are not limited to, ethynyl, propynyl, butynyl, pentynyl, hexynyl, methylpropynyl, 4-methyl-1-butynyl, 4-propyl-2-pentynyl, and 4 butyl 2 hexynyl.

The term "aryl" herein refers to an all carbon monocyclic or fused-ring polycyclic (i.e., rings which share adjacent pairs of carbon atoms) groups having a completely conjugated pi-electron system. An aryl group may be selected from: monocyclic carbocyclic aromatic rings, for example, phenyl; bicyclic ring systems such as 7-12 membered, e.g., 9-10 membered, bicyclic ring systems wherein at least one ring is carbocyclic and aromatic, selected, for example, from naphthalene, indane, and 1,2,3,4-tetrahydroquinoline; and tricyclic ring systems such as 10-15 membered tricyclic ring systems wherein at least one ring is carbocyclic and aromatic, for example, fluorene.

For example, the aryl group may be a 6-membered carbocyclic aromatic ring fused to a 5- to 7-membered cycloalkyl or heterocyclic ring optionally comprising at least one heteroatom selected from N, O, and S, provided that the point of attachment is at the carbocyclic aromatic ring when the carbocyclic aromatic ring is fused with a heterocyclic ring, and the point of attachment can be at the carbocyclic aromatic ring or at the cycloalkyl group when the carbocyclic aromatic ring is fused with a cycloalkyl group. Divalent radicals formed from substituted benzene derivatives and having the free valences at ring atoms are named as substituted phenylene radicals. Divalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene.

The term "heteroaryl" refers to groups having 5 to 10 ring atoms, preferably 5, 6, or 9 ring atoms; having 6, 10, or 14π electrons shared in a cyclic array; and having, in addition to carbon atoms, from one to five heteroatoms. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring (or in the case of a divalent fused heteroarylene ring system, at least one radical or point of attachment is on a heteroaromatic ring). Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbozolyl, acridinyl, phenazinyl, phenothiazinyl, phenoxazinyl, tetrahydrquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring", "heteroaryl group", or "heteroaromatic", any of which terms include rings that are optionally substituted.

The term "cyano" as used herein refers to CN.

The term "cycloalkyl" as used herein refers to a saturated or unsaturated cyclic, bicyclic, or bridged bicyclic hydrocarbon group of 3-16 carbons, or 3-8 carbons, referred to herein as "$(C_3-C_8)$cycloalkyl," derived from a cycloalkane. Exemplary cycloalkyl groups include, but are not limited to, cyclohexanes, cyclohexenes, cyclopentanes, and cyclopentenes. Cycloalkyl groups may be substituted with alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Cycloalkyl groups can be fused to other cycloalkyl (saturated or partially unsaturated), aryl, or heterocyclyl groups, to form a bicycle, tetracycle, etc. The term "cycloalkyl" also includes bridged and spiro-fused cyclic structures which may or may not contain heteroatoms.

The terms "halo" or "halogen" as used herein refer to —F, —Cl, —Br, and/or —I.

"Haloalkyl" means an alkyl group substituted with one or more halogens. Examples of haloalkyl groups include, but are not limited to, trifluoromethyl, difluoromethyl, pentafluoroethyl, trichloromethyl, etc.

A "heterocyclyl" or "heterocyclic" group is a ring structure having from 3 to 12 atoms, for example 4 to 8 atoms, wherein one or more atoms are selected from the group consisting of N, O, and S wherein the ring N atom may be oxidized to N—O, and the ring S atom may be oxidized to SO or $SO_2$, the remainder of the ring atoms being carbon. The heterocyclyl may be a monocyclic, a bicyclic, a spirocyclic, or a bridged ring system. The heterocyclic group is independently optionally substituted on a ring nitrogen atom with alkyl, aralkyl, alkylcarbonyl, or on sulfur with lower alkyl. Examples of heterocyclic groups include, without limitation, epoxy, azetidinyl, aziridinyl, tetrahydrofuranyl, tetrahydropyranyl, pyrrolidinyl, pyrrolidinonyl, piperidinyl, piperazinyl, imidazolidinyl, imidazopyridinyl, thiazolidinyl, dithianyl, trithianyl, dioxolanyl, oxazolidinyl, oxazolidinonyl, decahydroquinolinyl, piperidonyl, 4-piperidinonyl, quinuclidinyl, thiomorpholinyl, morpholinyl, azepanyl, oxazepanyl, azabicyclohexanyls, azabicycloheptanyl, azabicyclooctanyls, azabicyclononanyls (e.g., octahydroindolizinyl), azaspiroheptanyls, dihydro-1H,3H,5H-oxazolo[3,4-c]oxazolyl, tetrahydro-1'H,3'H-spiro[cyclopropane-1,2'-pyrrolizine], hexahydro-1H-pyrrolizinyl, hexahydro-1H-pyrrolo[2,1-c][1,4]oxazinyl, octahydroindolizinyl, oxaazaspirononanyls, oxaazaspirooctanyls, diazaspirononanyls, oxaazabiocycloheptanyls, hexahydropyrrolizinyl 4(1H)-oxide, tetrahydro-2H-thiopyranyl 1-oxide and tetrahydro-2H-thiopyranyl 1,1-dioxide. Specifically excluded from the scope of this term are compounds having adjacent annular O and/or S atoms.

A "spirocycle", "spirocyclyl", or "spirocyclylene" refers to a chemical entity having two heterocyclyl or two cycloalkyl moieties as defined herein, or to a combination of one or more heterocyclyl and one or more cycloalkyl moiety, having one ring atom in common, i.e., the two rings are connected via one common ring atom. Some exemplary spirocyclic ring systems, yet non-limiting examples of spirocyclic ring systems, include

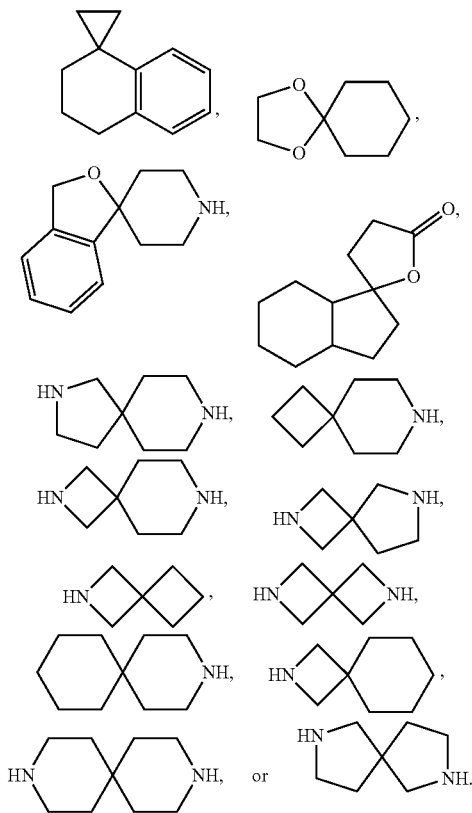

As used herein, the term "partially unsaturated" refers to a ring moiety that includes at least one double or triple bond. The term "partially unsaturated" is intended to encompass rings having multiple sites of unsaturation but is not intended to include aryl or heteroaryl moieties, as herein defined.

As used herein and unless otherwise specified, the suffix "-ene" is used to describe a divalent group. Thus, any of the terms above can be modified with the suffix "-ene" to describe a divalent version of that moiety. For example, a divalent carbocycle is "carbocyclylene", a divalent aryl ring is "arylene", a divalent benzene ring is "phenylene", a divalent heterocycle is "heterocyclylene", a divalent heteroaryl ring is "heteroarylene", a divalent alkyl chain is "alkylene", a divalent alkenyl chain is "alkylene", a divalent alkynyl chain is "alkynylene", and so forth.

As described herein, compounds of the disclosure may, when specified, contain "optionally substituted" moieties. In general, the term "substituted", whether preceded by the term "optionally" or not, means that one or more hydrogens of the designated moiety are replaced with a suitable substituent. "Substituted" applies to one or more hydrogens that are either explicit or implicit from the structure (e.g.,

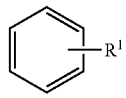

refers to at least

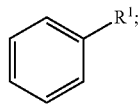

and

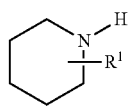

refers to at least

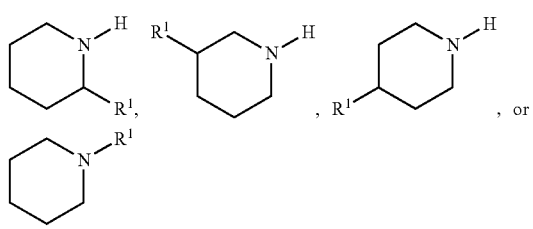

In addition, in a polycyclic ring system, substituents may, unless otherwise indicated, replace a hydrogen on any individual ring (e.g.,

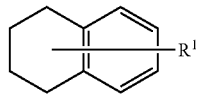

refers to at least

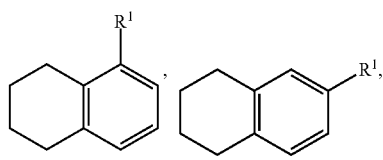

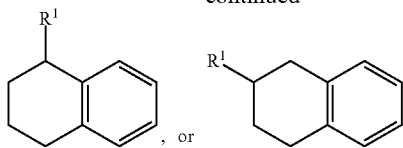
, or

Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are those that result in the formation of stable or chemically feasible compounds. The term "stable", as used herein, refers to compounds that are not substantially altered when subjected to conditions to allow for their purification, detection, and, in certain embodiments, their recovery, purification, and use for one or more of the purposes disclosed herein.

The term "oxo", as used herein, means an oxygen that is double bonded to a carbon atom thereby forming a carbonyl.

The terms "hydroxy" and "hydroxyl" as used herein refer to —OH.

Some of the compounds may exist with different points of attachment of hydrogen, referred to as "tautomers." For example, compounds including carbonyl $CH_2C(O)$— groups (keto forms) may undergo tautomerism to form hydroxyl —CH—C(OH)— groups (enol forms). Both keto and enol forms, individually as well as mixtures thereof, are also intended to be included where applicable.

The compounds, tautomers, solvates, or pharmaceutically acceptable salts of the disclosure may contain an asymmetric center and may thus exist as enantiomers. For example, where the compounds possess two or more asymmetric centers, they may additionally exist as diastereoisomers. Enantiomers and diastereoisomers fall within the broader class of stereoisomers. All such possible stereoisomers as substantially pure resolved enantiomers, racemic mixtures thereof, as well as mixtures of diastereoisomers are intended to be included in this disclosure. All stereoisomers of the compounds, tautomers, solvates, and pharmaceutically acceptable salts thereof are intended to be included. Unless specifically mentioned otherwise, reference to one isomer applies to any of the possible isomers. Whenever the isomeric composition is unspecified, all possible isomers are included.

The compounds, tautomers, solvates, or pharmaceutically acceptable salts of the disclosure may contain, in some embodiments, a meso moiety, be a meso compound, or have meso isomerism.

Diastereomeric mixtures can be separated into their individual diastereoisomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. Enantiomers can also be separated by use of a chiral HPLC column.

"Stereoisomer" or "optical isomer" mean a stable isomer that has at least one chiral atom or restricted rotation giving rise to perpendicular dissymmetric planes (e.g., certain biphenyls, allenes, and spiro compounds) and can rotate plane-polarized light. Because asymmetric centers and other chemical structure exist in the compounds of the disclosure which may give rise to stereoisomerism, the disclosure contemplates stereoisomers and mixtures thereof. The compounds of the disclosure and their salts include asymmetric carbon atoms and may therefore exist as single stereoisomers, racemates, and as mixtures of enantiomers and diastereomers. Typically, such compounds will be prepared as a racemic mixture. If desired, however, such compounds can be prepared or isolated as pure stereoisomers, i.e., as individual enantiomers or diastereomers, or as stereoisomer-enriched mixtures. As discussed in more detail below, individual stereoisomers of compounds are prepared by synthesis from optically active starting materials containing the desired chiral centers or by preparation of mixtures of enantiomeric products followed by separation or resolution, such as conversion to a mixture of diastereomers followed by separation or recrystallization, chromatographic techniques, use of chiral resolving agents, or direct separation of the enantiomers on chiral chromatographic columns. Starting compounds of particular stereochemistry are either commercially available or are made by the methods described below and resolved by techniques well-known in the art.

It is well-known in the art that the biological and pharmacological activity of a compound is sensitive to the stereochemistry of the compound. Thus, for example, enantiomers often exhibit strikingly different biological activity including differences in pharmacokinetic properties, including metabolism, protein binding, and the like, and pharmacological properties, including the type of activity displayed, the degree of activity, toxicity, and the like. Thus, one skilled in the art will appreciate that one enantiomer may be more active or may exhibit beneficial effects when enriched relative to the other enantiomer or when separated from the other enantiomer. Additionally, one skilled in the art would know how to separate, enrich, or selectively prepare the enantiomers of the compounds of this disclosure and the knowledge of the prior art.

Thus, although the racemic form of drug may be used, it is often less effective than administering an equal amount of enantiomerically pure drug; indeed, in some cases, one enantiomer may be pharmacologically inactive and would merely serve as a simple diluent. For example, although ibuprofen had been previously administered as a racemate, it has been shown that only the S-isomer of ibuprofen is effective as an anti-inflammatory agent (in the case of ibuprofen, however, although the R-isomer is inactive, it is converted in vivo to the S-isomer, thus, the rapidity of action of the racemic form of the drug is less than that of the pure S-isomer). Furthermore, the pharmacological activities of enantiomers may have distinct biological activity. For example, S-penicillamine is a therapeutic agent for chronic arthritis, while R-penicillamine is toxic. Indeed, some purified enantiomers have advantages over the racemates, as it has been reported that purified individual isomers have faster transdermal penetration rates compared to the racemic mixture. See U.S. Pat. Nos. 5,114,946 and 4,818,541.

In some embodiments, the compound is a racemic mixture of (S)- and (R)-isomers. In other embodiments, provided herein is a mixture of compounds wherein individual compounds of the mixture exist predominately in an (S)- or (R)-isomeric configuration. For example, the compound mixture has an (S)-enantiomeric excess of greater than 55%, 60%, 65%, 70%, 75%, 80%, 85%, 90%, 95%, 96%, 97%, 98%, 99%, 99.5%, or more. In other embodiments, the compound mixture has an (S)-enantiomeric excess of greater than 55% to 99.5%, greater than 60% to 99.5%, greater than 65% to 99.5%, greater than 70% to 99.5%, greater than 75% to 99.5%, greater than 80% to 99.5%, greater than 85% to 99.5%, greater than 90% to 99.5%, greater than 95% to 99.5%, greater than 96% to 99.5%, greater than 97% to 99.5%, greater than 98% to greater than 99.5%, greater than 99% to 99.5%, or more. In other embodiments, the compound mixture has an (R)-enantiomeric purity of greater than 55%, 60%, 65%, 70%, 75%, 80%, 85%, 90%, 95%, 96%, 97%, 98%, 99%, 99.5% or more. In some other embodiments, the compound mixture has an (R)-enantiomeric excess of greater than 55% to 99.5%, greater than 60% to 99.5%, greater than 65% to 99.5%, greater than 70% to 99.5%, greater than 75% to 99.5%, greater than 80% to 99.5%, greater than 85% to 99.5%, greater than 90% to 99.5%, greater than 95% to 99.5%, greater than 96% to 99.5%, greater than 97% to 99.5%, greater than 98% to greater than 99.5%, greater than 99% to 99.5% or more.

Individual stereoisomers of compounds of the present disclosure can be prepared synthetically from commercially available starting materials that contain asymmetric or stereogenic centers, or by preparation of racemic mixtures followed by resolution methods well known to those of ordinary skill in the art. These methods of resolution are exemplified by: (1) attachment of a mixture of enantiomers to a chiral auxiliary, separation of the resulting mixture of diastereomers by recrystallization or chromatography and liberation of the optically pure product from the auxiliary; (2) salt formation employing an optically active resolving agent; or (3) direct separation of the mixture of optical enantiomers on chiral chromatographic columns. Stereoisomeric mixtures can also be resolved into their component stereoisomers by well-known methods, such as chiral-phase gas chromatography, chiral-phase high performance liquid chromatography, crystallizing the compound as a chiral salt complex, or crystallizing the compound in a chiral solvent. Stereoisomers can also be obtained from stereoisomerically-pure intermediates, reagents, and catalysts by well-known asymmetric synthetic methods.

Thus, if one enantiomer is pharmacologically more active, less toxic, or has a preferred disposition in the body than the other enantiomer, it would be therapeutically more beneficial to administer that enantiomer preferentially.

The term "pharmaceutically acceptable carrier" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

Additionally, as used herein refers to pharmaceutical excipients, for example, pharmaceutically, physiologically, acceptable organic or inorganic carrier substances suitable for enteral or parenteral application that do not deleteriously react with the active agent. Suitable pharmaceutically acceptable carriers include water, salt solutions (such as Ringer's solution), alcohols, oils, gelatins, and carbohydrates such as lactose, amylose or starch, fatty acid esters, hydroxymethylcellulose, and polyvinylpyrrolidone. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the disclosure.

The term "pharmaceutically acceptable composition" as used herein refers to a composition comprising at least one compound as disclosed herein formulated together with one or more pharmaceutically acceptable carriers.

The term "pharmaceutically acceptable salt(s)" refers to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to sulfate, citrate, matate, acetate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1, 1'-methylene-bis-(2-hydroxy-3-naphthoate)) salts. Compounds included in the present compositions that include an amino moiety may form pharmaceutically acceptable salts with various amino acids, in addition to the acids mentioned above. Compounds included in the present compositions, that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts.

Chemical names were generated using PerkinElmer ChemDraw® Professional, version 17.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present disclosure encompasses various stereoisomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly. In some embodiments, an enantiomer or stereoisomer may be provided substantially free of the corresponding enantiomer.

As used herein, "cancer" refers to diseases, disorders, and conditions that involve abnormal cell growth with the potential to invade or spread to other parts of the body. Exemplary cancers include, but are not limited to, breast cancer, lung cancer, pancreatic cancer, small bowel cancer, colorectal cancer, gall bladder cancer, thyroid cancer, liver cancer, bile duct cancer, ovarian cancer, endometrial cancer, cervical cancer, bladder cancer, prostate cancer, esophageal cancer, and blood cancer.

As used herein, the term "subject" refers to an animal. Typically, the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit," "inhibition," or "inhibiting" refers to the reduction or suppression of a given condition, symptom, or disorder, or disease, or a significant decrease in the baseline activity of a biological activity or process.

A "dosing regimen" (or "therapeutic regimen"), as that term is used herein, is a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses.

As will be understood from context, a "reference" compound is one that is sufficiently similar to a particular compound of interest to permit a relevant comparison. In some embodiments, information about a reference compound is obtained simultaneously with information about a particular compound. In some embodiments, comparison of a particular compound of interest with a reference compound establishes identity with, similarity to, or difference of the particular compound of interest relative to the compound.

As used herein, the phrase "therapeutic agent" refers to any agent that has a therapeutic effect and/or elicits a desired biological and/or pharmacological effect, when administered to a subject.

As used herein, the term "therapeutically effective amount" refers to an amount of a therapeutic agent that confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). In particular, the "therapeutically effective amount" refers to an amount of a therapeutic agent effective to treat, ameliorate, or prevent a desired disease or condition, or to exhibit a detectable therapeutic or preventive effect, such as by ameliorating symptoms associated with the disease, preventing or delaying the onset of the disease or condition, and/or also lessening the severity or frequency of symptoms of the disease or condition. A therapeutically effective amount is commonly administered in a dosing regimen that may comprise multiple doses. For any particular therapeutic agent, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular subject may depend upon a variety of factors including the disorder being treated and the severity of the disorder; the activity of the specific therapeutic agent employed; the specific composition employed; the age, body weight, general health, sex and diet of the subject; the time of administration, route of administration, and/or rate of excretion or metabolism of the specific therapeutic agent employed; the duration of the treatment; and like factors as is well known in the medical arts.

As used herein, the term "treat," "treating," or "treatment" of any disease or disorder refers in one embodiment, to ameliorating the disease or disorder (i.e., slowing or arresting or reducing the development of the disease or at least one of the clinical symptoms thereof). In another embodiment "treat," "treating," or "treatment" refers to alleviating or ameliorating at least one physical parameter including those which may not be discernible by the patient. In yet another embodiment, "treat," "treating," or "treatment" refers to modulating the disease or disorder, either physically (e.g., through stabilization of a discernible symptom), physiologically, (e.g., through stabilization of a physical parameter), or both. In yet another embodiment, "treat," "treating," or "treatment" refers to preventing or delaying the onset or development or progression of the disease or disorder.

As used herein, a subject is "in need of" a treatment if such subject would benefit biologically, medically or in quality of life from such treatment.

Additionally, unless otherwise stated, structures described herein are also meant to include compounds that differ only in the presence of one or more isotopically enriched atoms. For example, compounds having the present structures except for the replacement of hydrogen by deuterium ($^2$H) or tritium ($^3$H), or the replacement of a carbon by a $^{13}$C- or $^{14}$C-carbon atom are within the scope of this disclosure. Such compounds may be useful as, for example, analytical tools, probes in biological assays, or therapeutic agents.

Compounds

In some embodiments, provided herein is a compound, wherein the compound is represented by Formula I or is a pharmaceutically acceptable salt thereof:

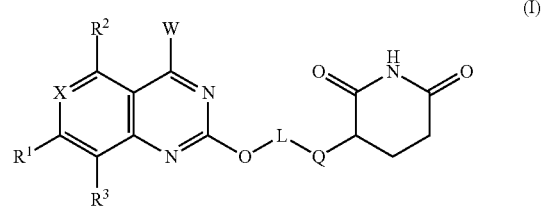

wherein:
W is $NR^pR^q$ or a 5-12 membered monocyclic, bicyclic, bridged, or spiro heterocyclic group, wherein each of the $NR^pR^a$, monocyclic, bicyclic, bridged, or spiro heterocyclic group is independently substituted with 0, 1, 2, or 3 $R^a$;

each $R^a$ is independently selected from H, halogen, cyano, hydroxy, $C_1$-$C_6$ alkyl, $C_3$-$C_6$ cycloalkyl, an oxo group, $C(=O)N(C_1$-$C_3$ alkyl)$_2$, $NHC(=O)C_1$-$C_3$alkyl, $NHC(=O)O(C_1$-$C_3$alkyl), and $C_1$-$C_6$ alkoxy, wherein the $C_1$-$C_6$ alkyl and $C_3$-$C_6$ cycloalkyl are optionally substituted with one or more groups selected from halogen, hydroxy, $C_1$-$C_3$ alkyl, $C_3$-$C_4$ cycloalkyl, and $N(C_1$-$C_3$ alkyl)$_2$; or two of the $R^a$ groups together with the atoms to which they are both attached form an optionally substituted 3- to 6-membered saturated, partially unsaturated, or heterocyclic ring, wherein the ring has 0 to 4 heteroatoms independently selected from N, S, and O;

$R^1$ is a monocyclic or bicyclic aryl or heteroaryl, wherein the monocyclic or bicyclic aryl and heteroaryl are independently substituted with 0, 1, 2, 3, or 4 $R^b$, each $R^b$ is independently selected from halogen, cyano, hydroxy, amino, an oxo group, $C_1$-$C_4$ alkyl, $C_2$-$C_4$ alkenyl, $C_2$-$C_4$ alkynyl, $C_2$-$C_4$ hydroxyalkynyl, $C_1$-$C_3$ cyanoalkyl, $C_1$-$C_4$ haloalkyl, O—$C_1$-$C_3$ haloalkyl, S—$C_1$-$C_3$ haloalkyl, $C_1$-$C_3$ alkoxy, hydroxy $C_1$-$C_3$ alkyl, $OC(=O)R^p$, $OC(=O)NR^pR^q$, $CH_2C(=O)NR^pR^q$, $C_3$-$C_4$alkynyl-$NR^pR^q$, —$NR^pR^q$, and $C_3$-$C_6$ cycloalkyl;

each of $R^p$ and $R^q$ is independently selected from H, $C_1$-$C_6$ alkyl, $CO(C_1$-$C_6$ alkyl), $SO_2CH_3$, and $C_3$-$C_6$ cycloalkyl, wherein the $C_3$-$C_6$ cycloalkyl is optionally substituted with halogen;

X is $CR^c$ or N;

$R^c$ is selected from H, cyano, hydroxy, halogen, $C_1$-$C_5$ alkoxy, $C_1$-$C_5$ alkyl, $C_2$-$C_5$ alkenyl, and $C_3$-$C_5$ cycloalkyl, wherein each of the $C_1$-$C_5$ alkoxy, $C_1$-$C_5$ alkyl, $C_2$-$C_5$ alkenyl, and $C_3$-$C_5$ cycloalkyl is optionally substituted with halogen, hydroxy, amino, or cyano;

$R^2$ is H, halogen, $C_1$-$C_3$ alkyl, or a 4-6 membered N-containing heterocyclic group, wherein the heterocyclic group is independently substituted with 0, 1, or 2 $R^d$;

$R^d$ is selected from halogen, hydroxy, $C_1$-$C_3$ alkyl, and $C_1$-$C_3$ alkoxy;

$R^3$ is selected from H, halogen, hydroxy, $C_1$-$C_3$ alkyl, $C_1$-$C_3$ haloalkyl, and $C_3$-$C_6$ cycloalkyl;

L is a linker with a backbone of 1 to 20 carbon atoms in length, wherein one or more carbon atoms are optionally substituted with halogen, alkylamino, hydroxy, cyano, $CFH_2$, $CF_2H$, $CF_3$, $C_1$-$C_8$ alkyl, an oxo group, $C_1$-$C_3$ haloalkyl, $C_1$-$C_4$ alkoxy, or amide, wherein one to eight carbon atoms of the backbone are optionally replaced by a divalent group independently selected from oxygen, cycloalkyl, heterocyclyl, spiroheterocyclyl, bridged heterocyclyl, aryl, and heteroaryl, and wherein each of the cycloalkyl, spiroheterocyclyl, bridged heterocyclyl, heterocyclyl, aryl, or heteroaryl is independently substituted with 0, 1, or 2 $R^e$;

each $R^e$ is independently selected from halogen, cyano, hydroxy, $C_1$-$C_4$ alkyl, $C_1$-$C_4$ alkenyl, $C_3$-$C_8$ cycloalkyl, $C_1$-$C_4$ haloalkyl, and $C_1$-$C_4$ alkoxy;

Q is 1 to 5 carbon atoms in length, wherein one or more carbon atoms are replaced by a divalent group selected from heterocyclyl, aryl, heteroaryl, —NH—, —C(=O)—, —C(=O)—NH—, and —C(=O)N($R^p$)—, and wherein each of the heterocyclyl, aryl, and heteroaryl is independently substituted with 0, 1, 2, 3, 4, or 5 $R^f$; and each $R^f$ is independently selected from halogen, hydroxy, $C_1$-$C_3$ alkyl, $C_1$-$C_3$ haloalkyl, $C_1$-$C_5$ alkoxy, and an oxo group.

In some embodiments, the compound of Formula I is represented by Formula IA:

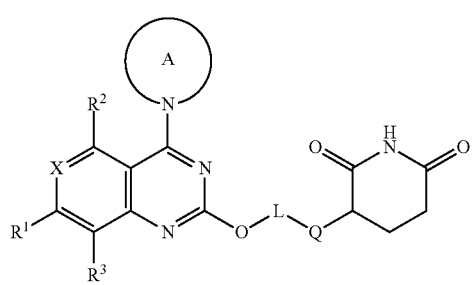

(IA)

wherein ring A is a 5-12 membered monocyclic, bridged, or spiro heterocyclic group, wherein each of the monocyclic, bridged, or spiro heterocyclic group is independently substituted with 0, 1, 2, or 3 $R^a$.

In some embodiments, the compound of Formula I is represented by Formula IB:

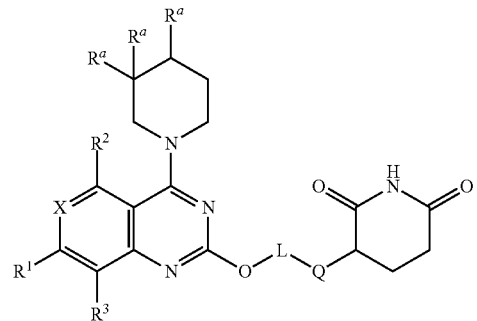

(IB)

wherein each $R^a$ is independently selected from H, hydroxy, $C_1$-$C_3$ alkyl, halogen, $NHC(=O)C_1$-$C_3$alkyl, $NHC(=O)O(C_1$-$C_3$alkyl), and $C_1$-$C_3$ alkoxy.

In some embodiments, the compound of Formula I is represented by Formula IB':

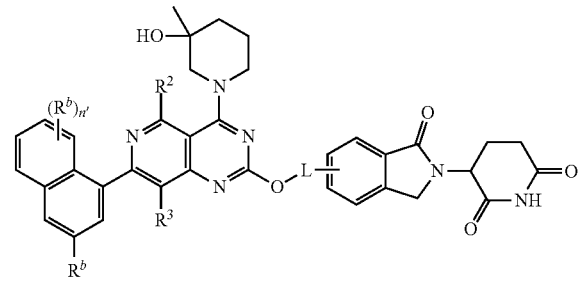

(IB')

wherein:

each $R^b$ is independently selected from halogen (such as F), hydroxy, amino, $C_1$-$C_4$ alkyl (such as ethyl), $C_2$-$C_4$ alkenyl, $C_2$-$C_4$ alkynyl, $C_1$-$C_4$ haloalkyl, and $C_3$-$C_6$ cycloalkyl;

$R^2$ is H or halogen;

$R^3$ is H or halogen (such as F);

n' is 0, 1, or 2; and

L is selected from

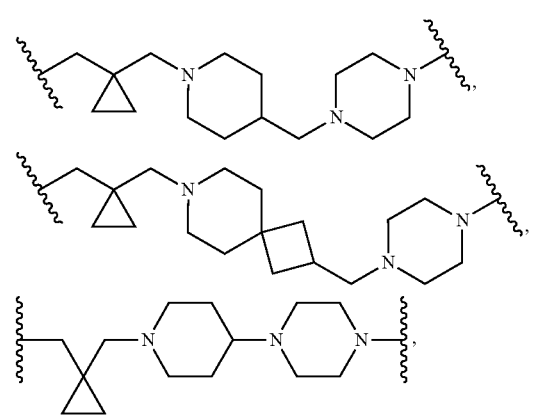

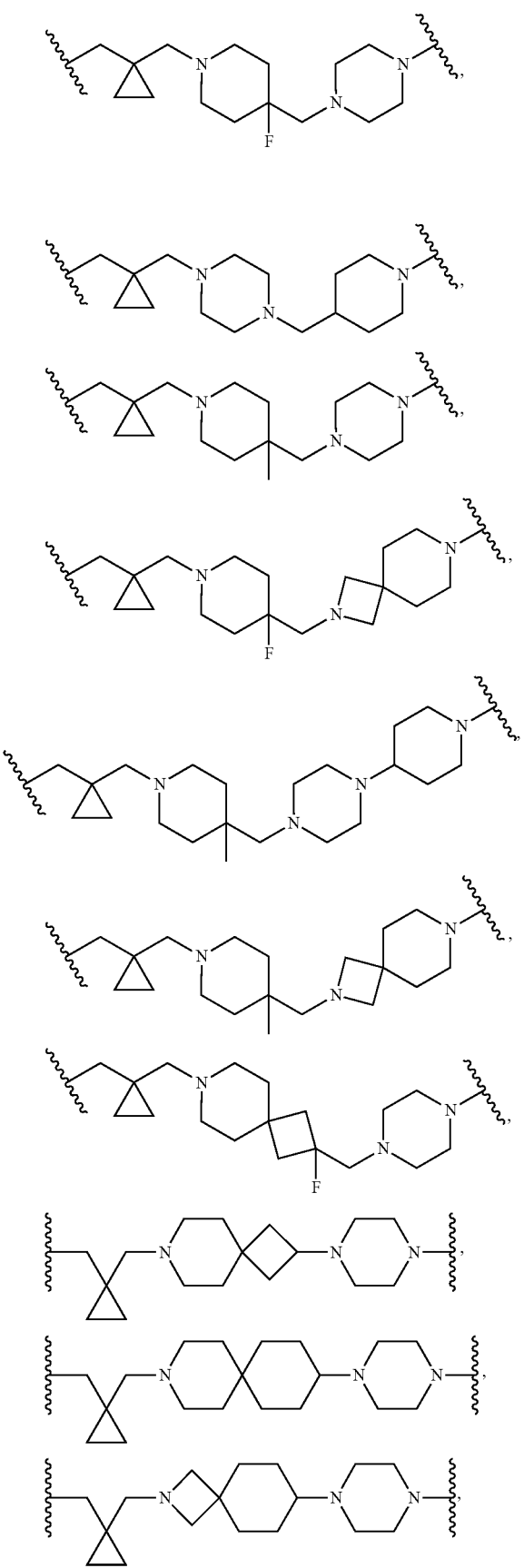
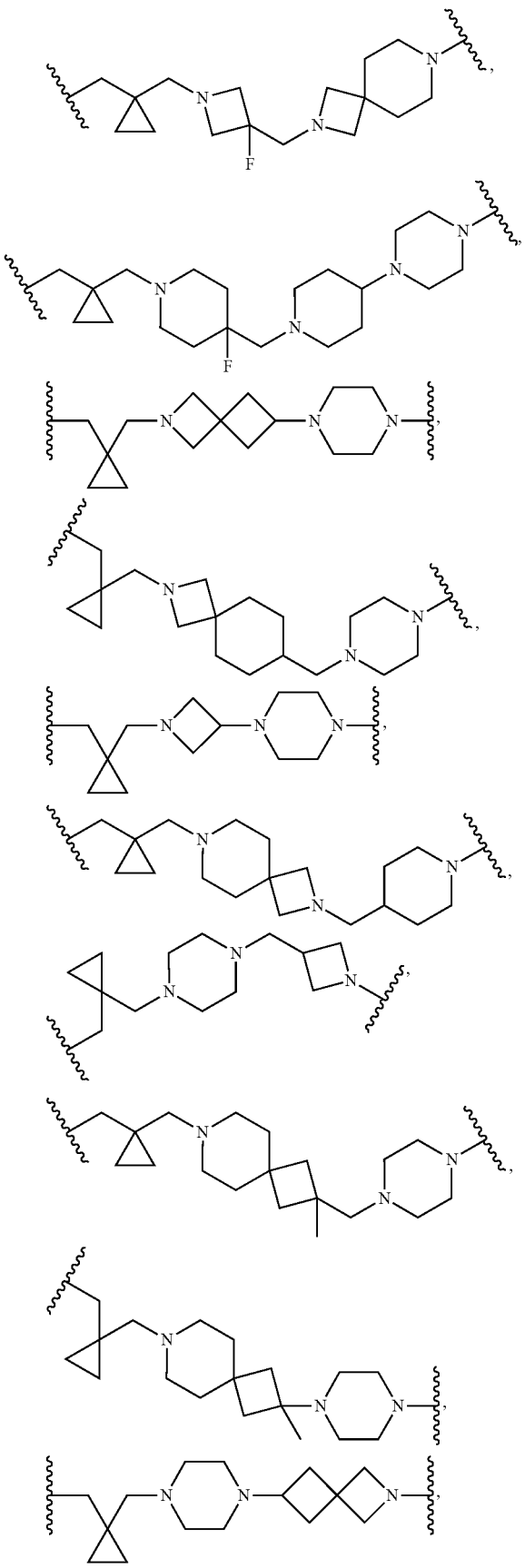

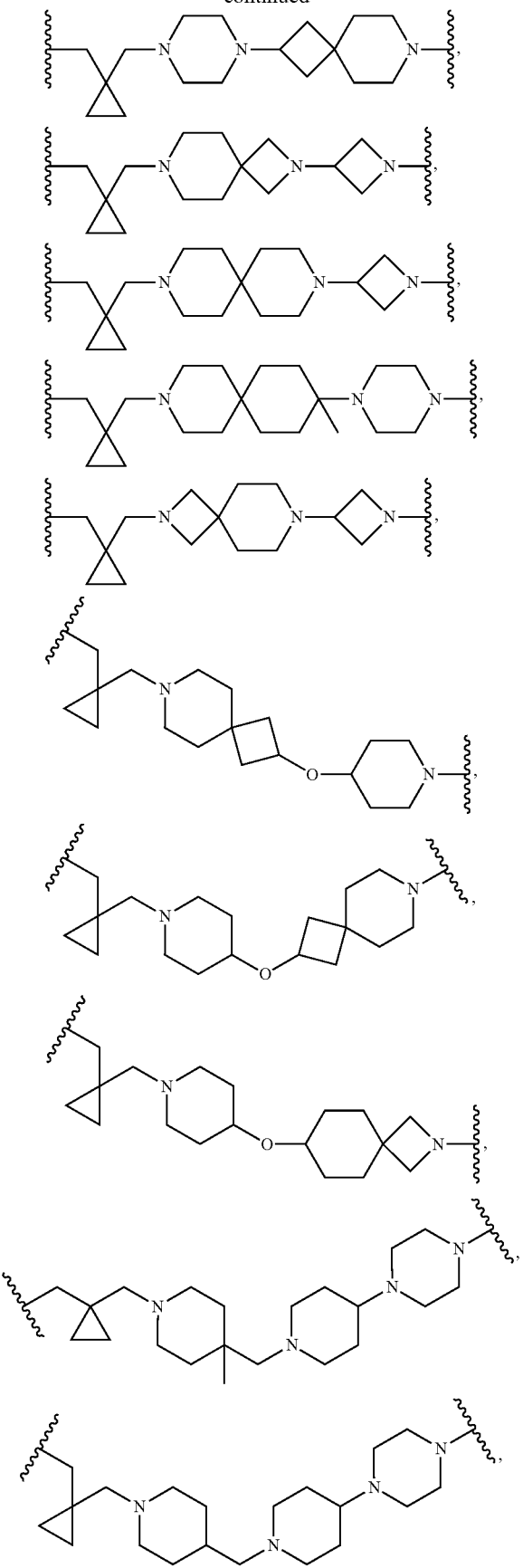

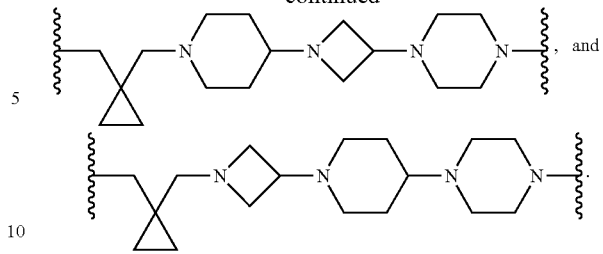

In some embodiments, the compound of Formula I is represented by Formula IC:

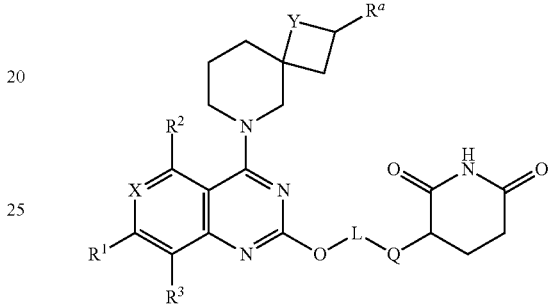

(IC)

wherein:
$R^a$ is selected from H, hydroxy, $C_1$-$C_3$ alkyl, and $C_1$-$C_3$ alkoxy; and
Y is O or CH2.

In some embodiments, the compound of Formula I is represented by Formula ID:

(ID)

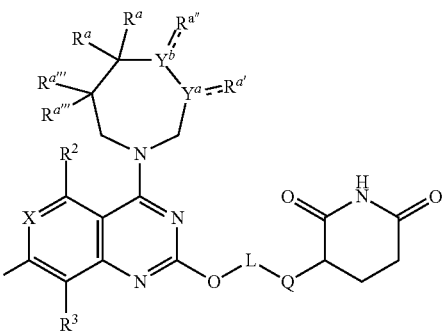

wherein:
$\text{-----}$ is a single bond or a double bond;
$R^a$ is independently selected from H, O, hydroxy, and $C_1$-$C_3$ alkyl;
$Y^a$ is O, N, NH, C, CH, or CH2;
$Y^b$ is O, N, NH, C, CH, or CH2;
$R^{a\prime}$ is H, $C_1$-$C_3$ alkyl, NH, N, S, or O;
$R^{a\prime\prime}$ is H, $C_1$-$C_3$ alkyl, NH, N, S, or O; or R$^{a'}$ and R$^{a''}$ together with the atoms to which they are both attached form an optionally substituted 3- to 6-membered saturated, partially unsaturated, or heterocyclic aromatic ring, wherein the ring has 0 to 3 heteroatoms independently selected from N, S, and O; and where the 3- to 6-membered saturated, partially unsaturated, or heterocyclic aromatic ring can be further independently substituted with halogen and amide; and each R$^{a'''}$ is independently selected from H, hydroxy, and C$_1$-C$_3$ alkyl.

In some embodiments, the compound of Formula I is represented by Formula IE:

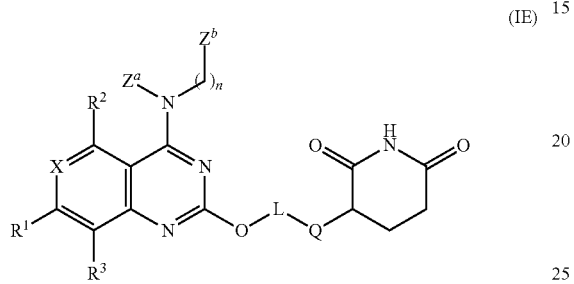

(IE)

wherein:

Z$^a$ is H or C$_1$-C$_3$ alkyl;

Z$^b$ is a C$_3$-C$_5$ cycloalkyl, wherein the C$_3$-C$_5$ cycloalkyl is optionally substituted with halogen, hydroxy, N(C$_1$-C$_3$ alkyl)$_2$, or C$_1$-C$_3$ alkyl; and n is 0, 1, or 2.

In some embodiments, X is N.

In some embodiments, X is CR$^c$.

In some embodiments, R$^c$ is selected from H, cyano, halogen, and C$_1$-C$_3$ alkyl.

In some embodiments, R$^c$ is selected from H, Cl, F, methyl, and ethyl.

In some embodiments, R$^c$ is H or F.

In some embodiments, ring A is a 5-9 membered monocyclic, bridged, or spiro heterocyclic group, wherein each of the monocyclic, bridged, or spiro heterocyclic group is independently substituted with 0, 1, 2, or 3 R$^a$.

In some embodiments, ring A is a 6-8 membered N-containing monocyclic or bridged heterocyclic group, wherein each of the monocyclic or bridged heterocyclic group is independently substituted with 0, 1, or 2 R$^a$. In some embodiments, ring A is a 6 membered N-containing monocyclic heterocyclic group, wherein the monocyclic heterocyclic group is independently substituted with 1 or 2 R$^a$. In some embodiments, the monocyclic heterocyclic group is independently substituted with 2 R$^a$. In some embodiments, one R$^a$ is a methyl and the other R$^a$ is a hydroxy group. In some embodiments, the monocyclic heterocyclic group is saturated. In some embodiments, the saturated monocyclic heterocyclic group is piperidine.

In some embodiments, each R$^a$ is independently selected from halogen, hydroxy, C$_1$-C$_4$ alkyl, and C$_1$-C$_4$ alkoxy.

In some embodiments, each R$^a$ is independently selected from hydroxy, F, C$_1$-C$_3$ alkyl, and C$_1$-C$_3$ alkoxy.

In some embodiments, each R$^a$ is independently selected from hydroxy, F, methyl, and methoxy. In some embodiments, each R$^a$ is independently hydroxy or methyl.

In some embodiments, W is selected from

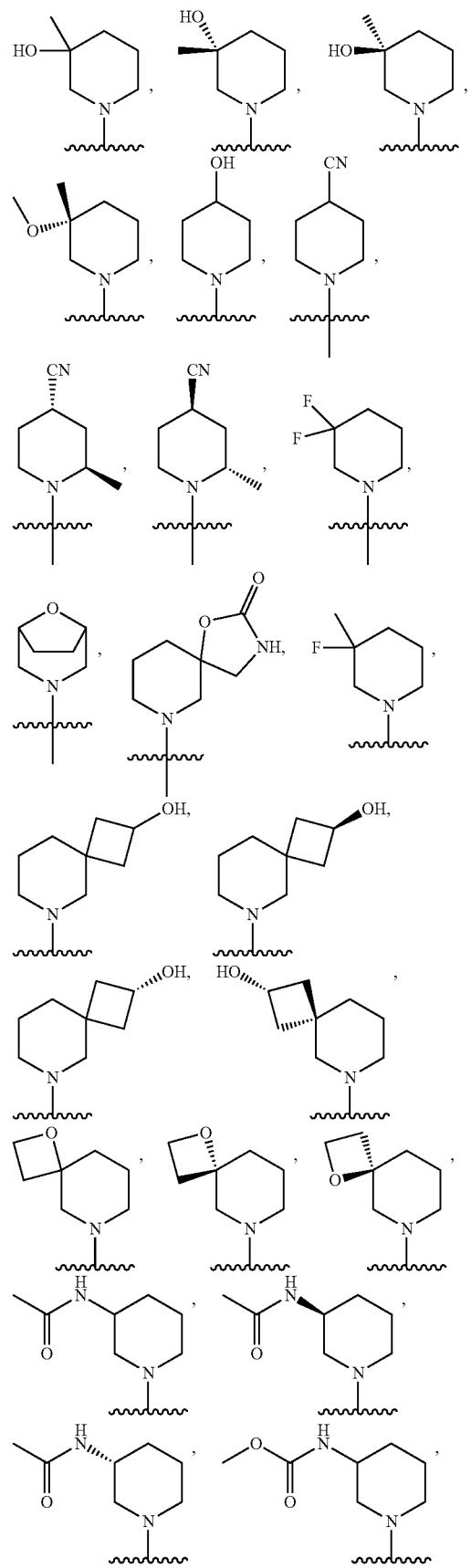

-continued
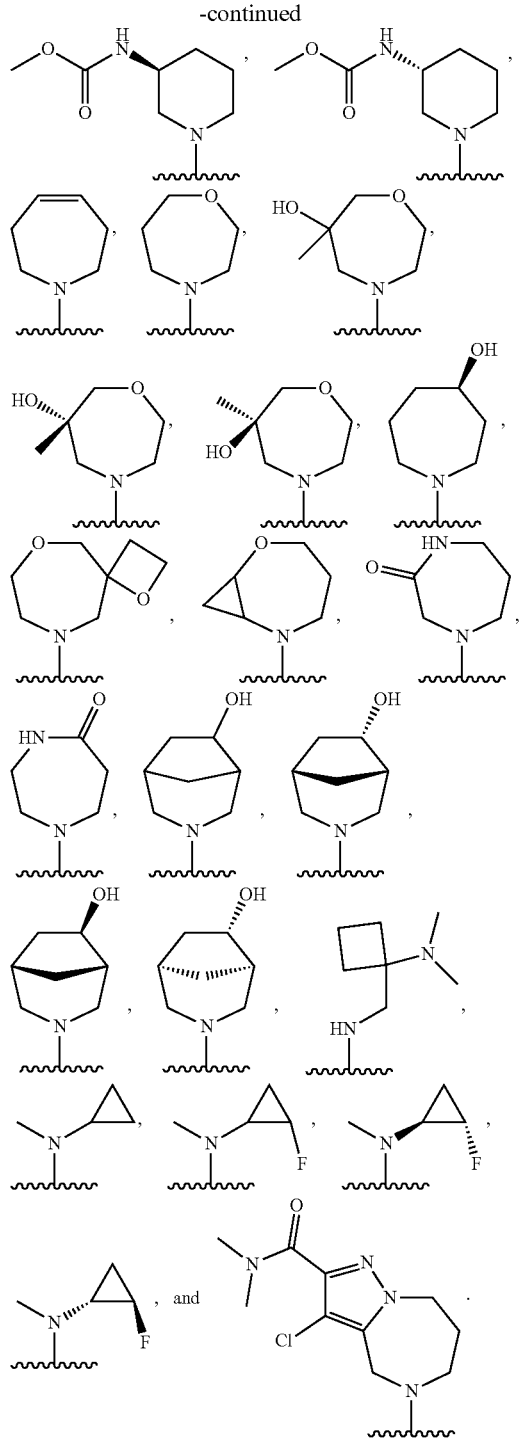
In some embodiments, W is
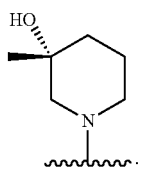
In some embodiments, W is
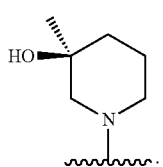 [SMILES: *N1CCC[C@](C)(O)C1]
In some embodiments, W is
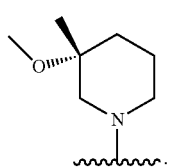 [SMILES: *N1CCC[C@@](C)(OC)C1]
In some embodiments, W is
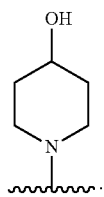
In some embodiments, W is
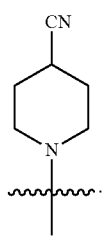
In some embodiments, W is
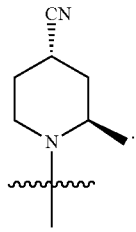 [SMILES: *N1CC[C@H](C#N)C[C@H]1C]
In some embodiments, W is
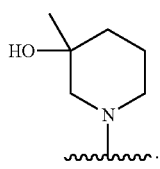

In some embodiments, W is
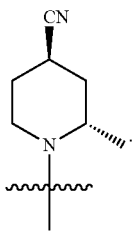 [SMILES: *N1CC[C@@H](C#N)C[C@@H]1C]
In some embodiments, W is
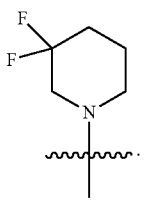
In some embodiments, W is
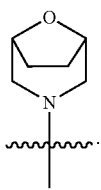
In some embodiments, W is
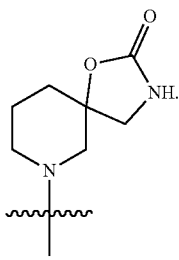 [SMILES: *N1CCCC2(CNC(=O)O2)C1]
In some embodiments, W is
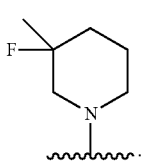
In some embodiments, W is
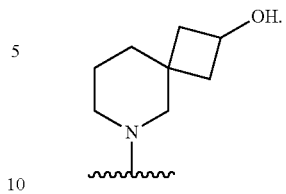
In some embodiments, W is
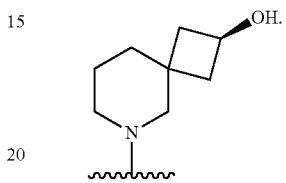
In some embodiments, W is
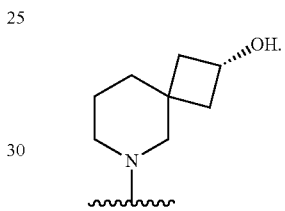
In some embodiments, W is
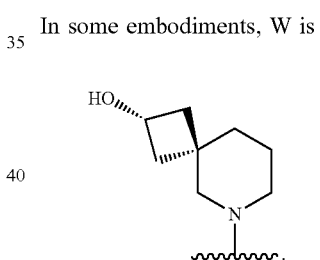
In some embodiments, W is
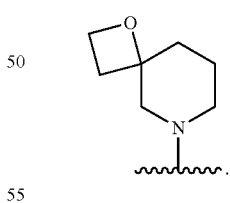
In some embodiments, W is
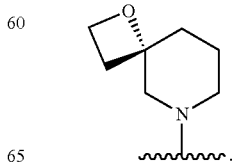

In some embodiments, W is
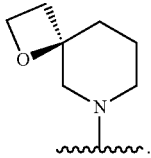
In some embodiments, W is
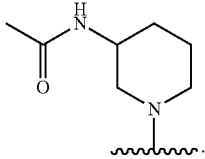 [SMILES: *N1CCCC(NC(C)=O)C1]
In some embodiments, W is
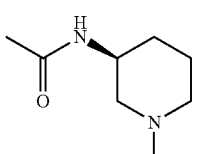
In some embodiments, W is
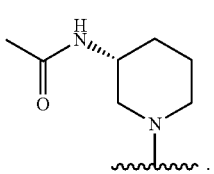 [SMILES: *N1CCC[C@@H](NC(C)=O)C1]
In some embodiments, W is
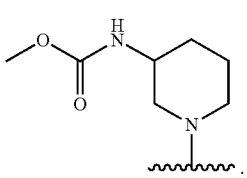 [SMILES: *N1CCCC(NC(=O)OC)C1]
In some embodiments, W is
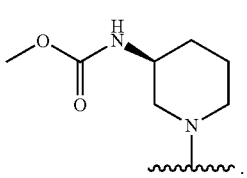 [SMILES: *N1CCC[C@H](NC(=O)OC)C1]
In some embodiments, W is
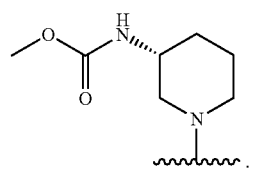
In some embodiments, W is
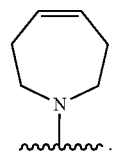
In some embodiments, W is
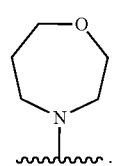
In some embodiments, W is
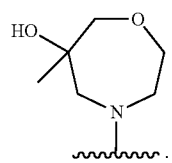
In some embodiments, W is
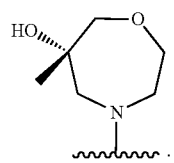
In some embodiments, W is
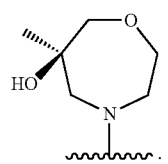

In some embodiments, W is
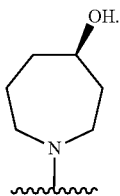
In some embodiments, W is is
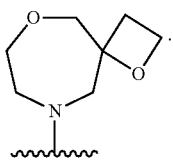
In some embodiments, W is
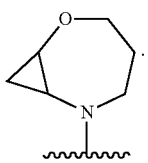
In some embodiments, W is
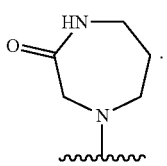
In some embodiments, W is
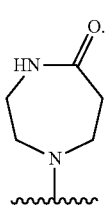
In some embodiments, W is
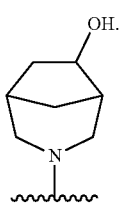
In some embodiments, W is
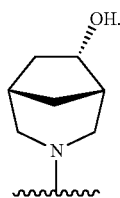
In some embodiments, W is
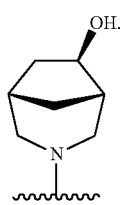 [SMILES: *N1C[C@H]2C[C@@H](C1)[C@H](O)C2]
In some embodiments, W is
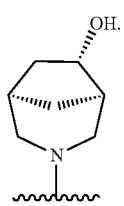
In some embodiments, W is
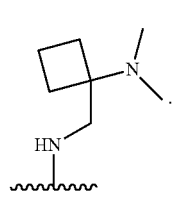 [SMILES: *NCC1(N(C)C)CCC1]
In some embodiments, W is
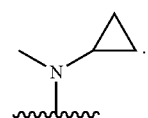 [SMILES: *N(C)C1CC1]
In some embodiments, W is
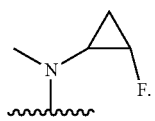

In some embodiments, W is

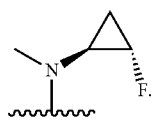 [SMILES: *N(C)[C@H]1C[C@@H]1F]

In some embodiments, W is

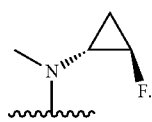

In some embodiments, W is

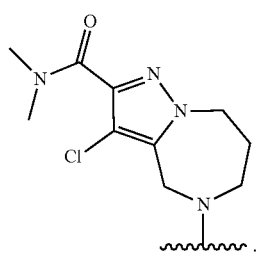

In some embodiments, L is a linker with a backbone of 1 to 15 carbon atoms in length, wherein one or more carbon atoms are optionally substituted with halogen, hydroxy, cyano, $C_1$-$C_3$ alkoxy, an oxo group, or amide, wherein one or more carbon atoms of the backbone are optionally replaced by a divalent group selected from oxygen, cycloalkyl, heterocyclyl, and aryl, and wherein the cycloalkyl, heterocyclyl, and aryl are each independently substituted with 0, 1, or 2 $R^e$. In some embodiments, L is a linker with a backbone of 1 to 15 carbon atoms in length, wherein one or more carbon atoms are optionally substituted with halogen, alkylamino, hydroxy, an oxo group, or amide, wherein one or more carbon atoms of the backbone are optionally replaced by a divalent group selected from oxygen, carbonyl, cycloalkyl, spiro heterocyclyl, heterobicyclyl, or a heteroaryl fused heterocyclyl, and wherein the cycloalkyl, spiro heterocyclyl, heterobicyclyl, or heteroaryl fused heterocyclyl are each independently substituted with 0, 1, or 2 $R^e$.

In some embodiments, L is a linker with a backbone of 1 to 12 carbon atoms in length, wherein one or more carbon atoms of the backbone are optionally replaced by a divalent group selected from oxygen, cycloalkyl, and heterocyclyl, and wherein the cycloalkyl and heterocyclyl are each independently substituted with 0, 1, or 2 $R^e$. In some embodiments, the heterocyclyl is a spiro heterocyclyl, heterobicyclyl, or a heteroaryl fused heterocyclyl. In some embodiments, L is a linker with a backbone of 1 to 10 carbon atoms in length, wherein one or more carbon atoms are optionally substituted with halogen, alkylamino, hydroxy, an oxo group, or amide, wherein one or more carbon atoms of the backbone are optionally replaced by a divalent group selected from oxygen, carbonyl, cycloalkyl, spiro heterocyclyl, heterobicyclyl, or a heteroaryl fused heterocyclyl, and wherein the cycloalkyl, spiro heterocyclyl, heterobicyclyl, or heteroaryl fused heterocyclyl are each independently substituted with 0, 1, or 2 $R^e$.

Without wishing to be bound by any particular theory, in certain embodiments, a linker moiety (e.g., L) of the present disclosure is a feature that may facilitate certain conformations that allow for the disclosed compounds to eliminate (by degradation) one or more mutated proteins (such as KRAS mutants) while sparing, in some embodiments, the wild type. Additionally, and without wishing to be bound by any particular theory, it is believed that the linker present in the disclosed degraders influences "drug likeness" and pharmacokinetics, where pH, tissue distribution, off-target toxicity, metabolic clearance, blood stream and cerebrospinal fluid distribution are affected by the identity of the linker moiety disclosed herein, among other things.

As described herein, linker moieties as drawn from left to right represent the same connectivity as depicted in Formula I, IA, IB, IB', IC, ID, and IE. For example,

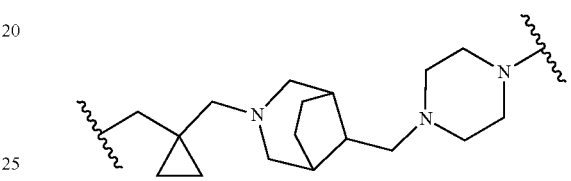

represents

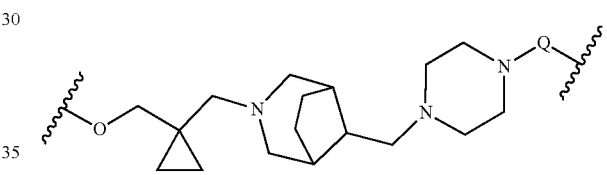

in Formula I.

In some embodiments, each $R^e$ is independently selected from halogen, hydroxy, cyano, $C_1$-$C_3$ alkyl, $C_3$-$C_4$ cycloalkyl, and $C_1$-$C_3$ haloalkyl.

In some embodiments, each $R^e$ is independently selected from hydroxy, Cl, F, methyl, ethyl, methoxy, and ethoxy.

In some embodiments, each $R^e$ is independently selected from hydroxy, F, methyl, ethyl, and methoxy.

In some embodiments, L is a linker with a backbone of 1 to 10 carbon atoms in length, wherein one or more carbon atoms of the backbone are optionally replaced by a divalent group selected from oxygen, cycloalkyl, heterocyclyl, and aryl, wherein the cycloalkyl, heterocyclyl, and aryl are each independently substituted with 0, 1, or 2 $R^e$, and wherein each $R^e$ is independently selected from cyano, hydroxy, methoxy, $CF_3$, F, methyl, ethyl, and isopropyl.

In some embodiments, the one or more carbon atoms of the backbone are optionally replaced by a divalent group selected from optionally substituted cyclopropyl, cyclobutyl, cyclohexyl, azetidinyl, pyrrolidinyl, piperidinyl, piperazinyl, or a 7-12 membered spiro heterocyclic group.

In some embodiments, the one or more carbon atoms of the backbone are optionally replaced by a divalent group selected from cyclopropyl, cyclobutyl, cyclohexyl, azetidinyl, pyrrolidinyl, piperidinyl, piperazinyl, or a 7-12 membered spiro heterocyclic group.

In some embodiments, the one or more carbon atoms of the backbone are optionally replaced by an optionally substituted cyclopropylene.

In some embodiments, the one or more carbon atoms of the backbone are optionally replaced by an optionally substituted cyclobutylene.

In some embodiments, the one or more carbon atoms of the backbone are optionally replaced by an optionally substituted cyclohexylene.

In some embodiments, the one or more carbon atoms of the backbone are optionally replaced by an optionally substituted azetidinylene.

In some embodiments, the one or more carbon atoms of the backbone are optionally replaced by an optionally substituted pyrrolidinylene.

In some embodiments, the one or more carbon atoms of the backbone are optionally replaced by an optionally substituted piperidinylene.

In some embodiments, the one or more carbon atoms of the backbone are optionally replaced by an optionally substituted piperizinylene.

In some embodiments, L is selected from

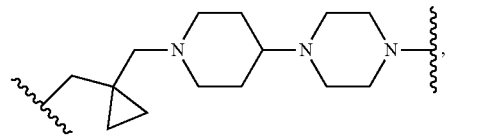

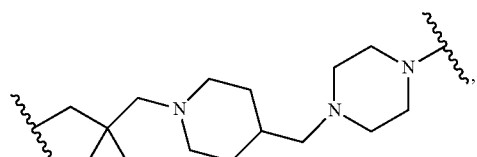

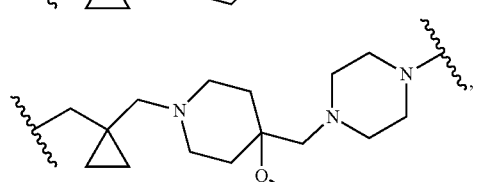

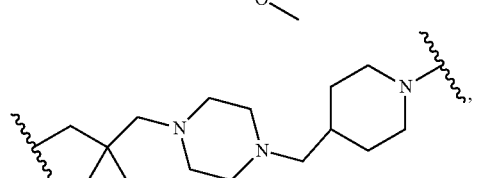

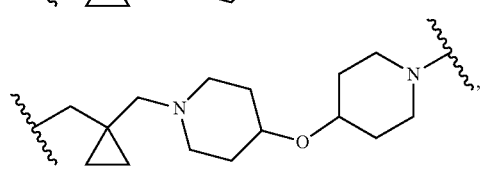

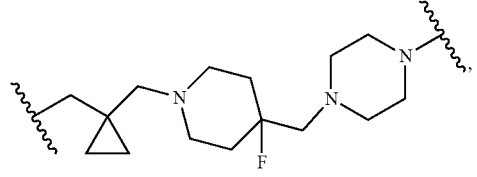

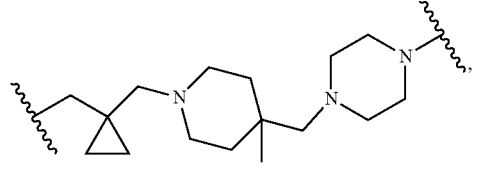

-continued

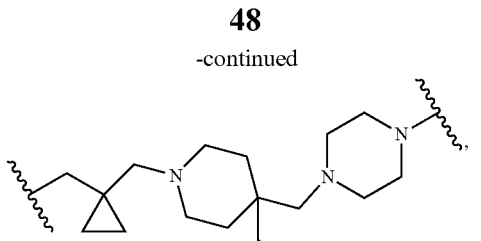

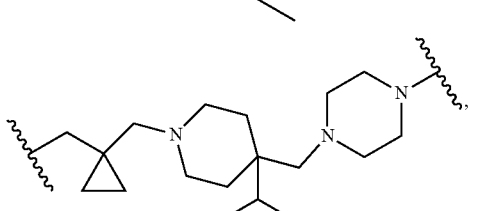

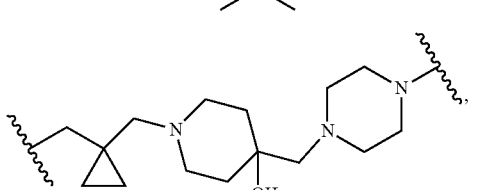

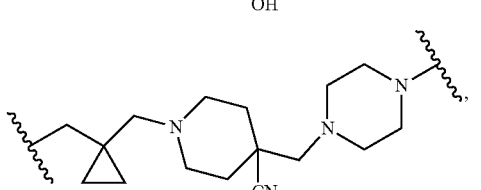

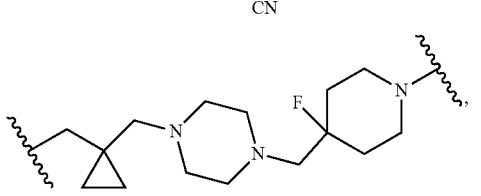

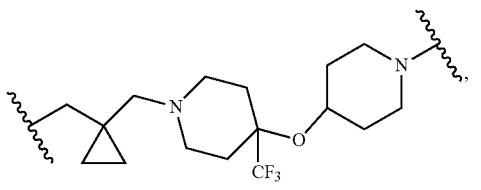

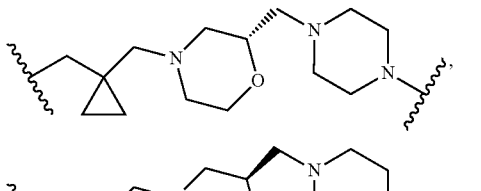

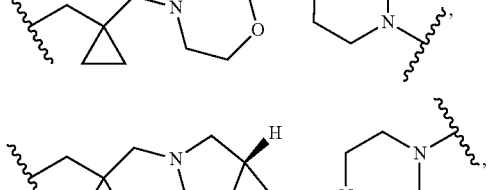

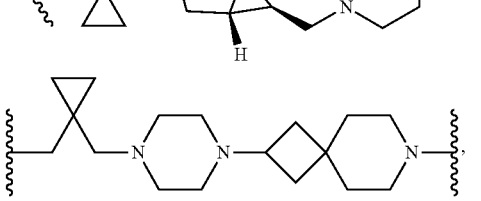

-continued
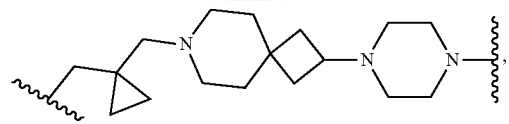
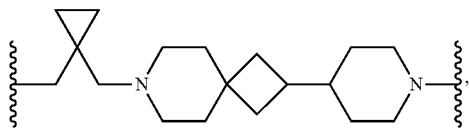
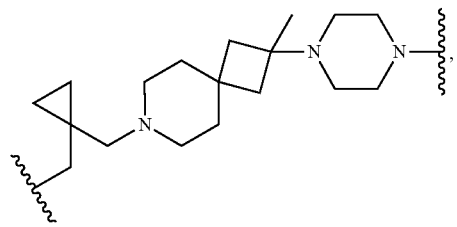
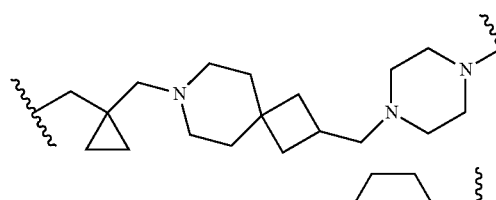
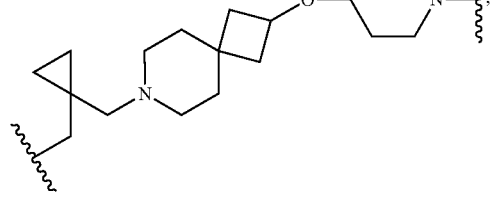
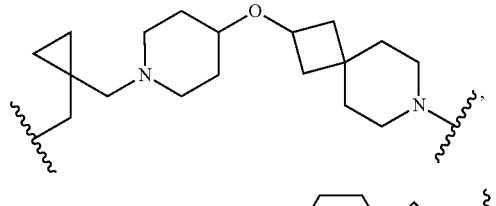
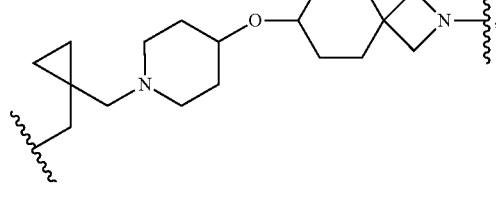
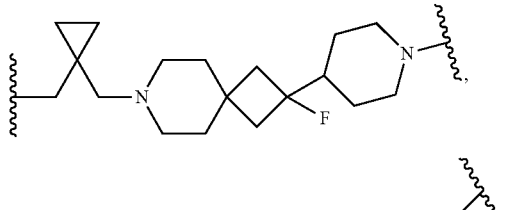
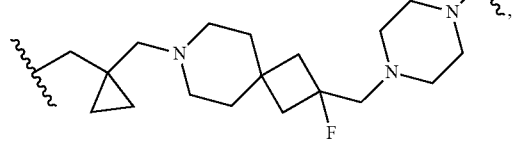
-continued
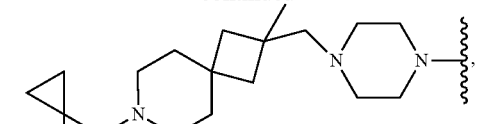
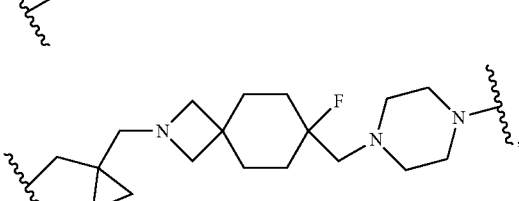
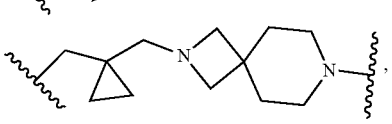
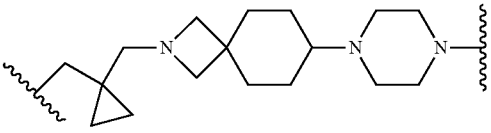
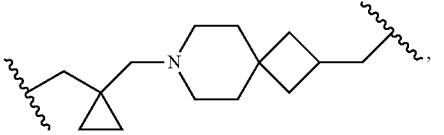
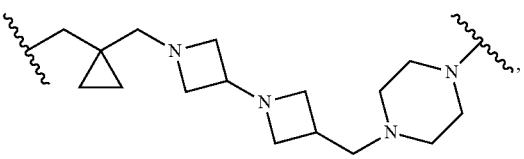
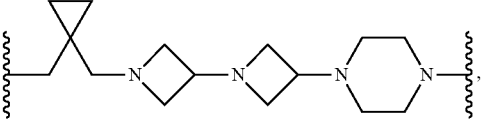
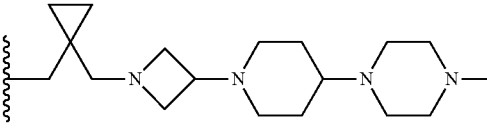
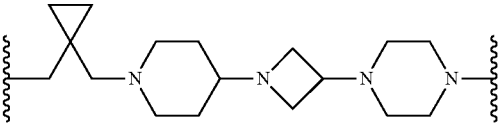
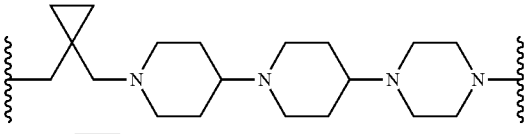
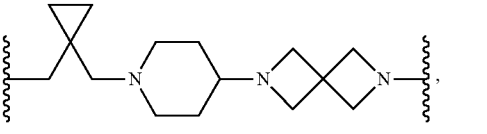
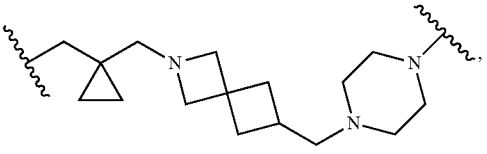

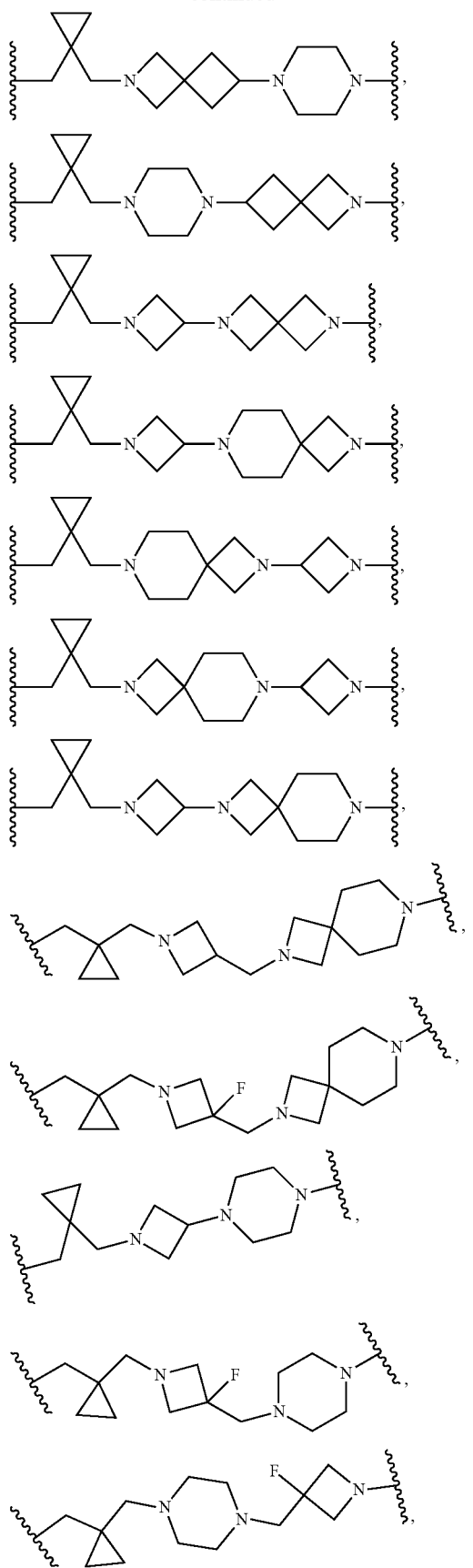
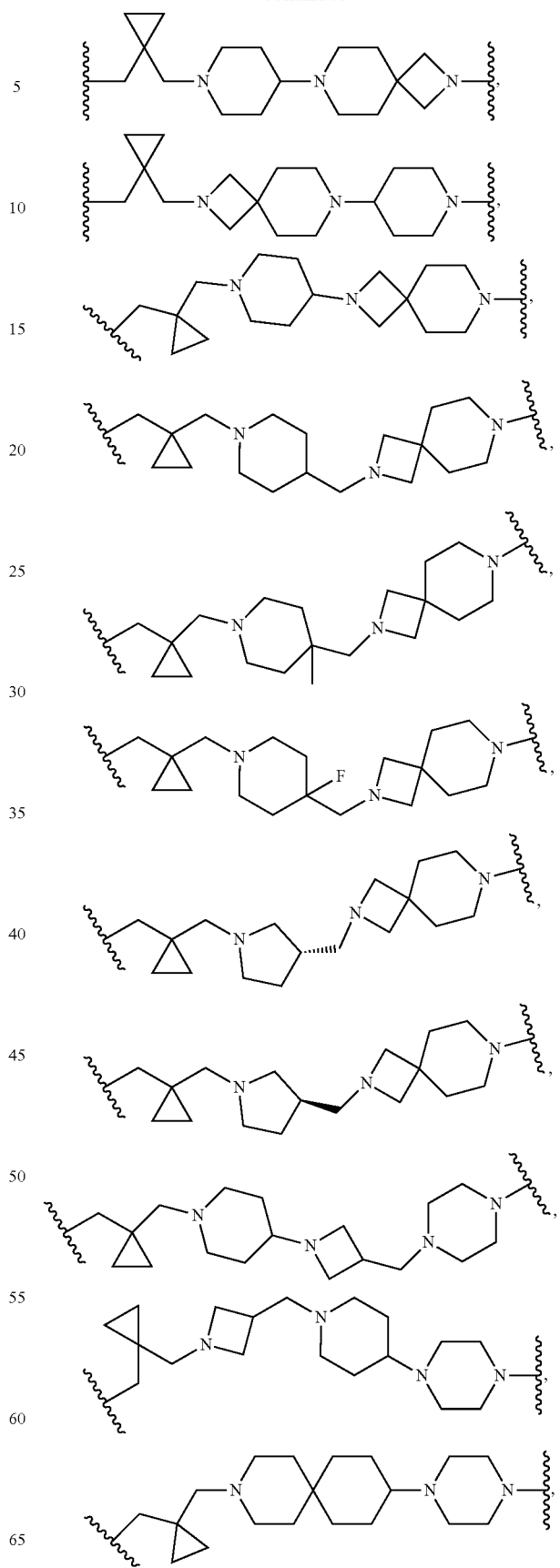

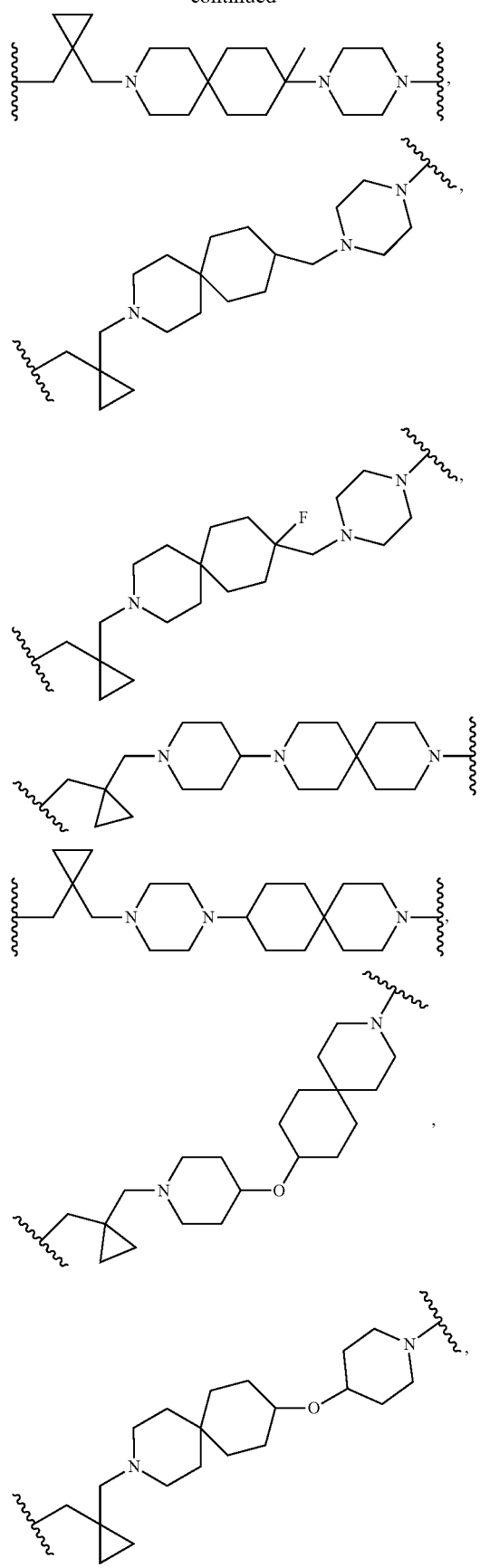
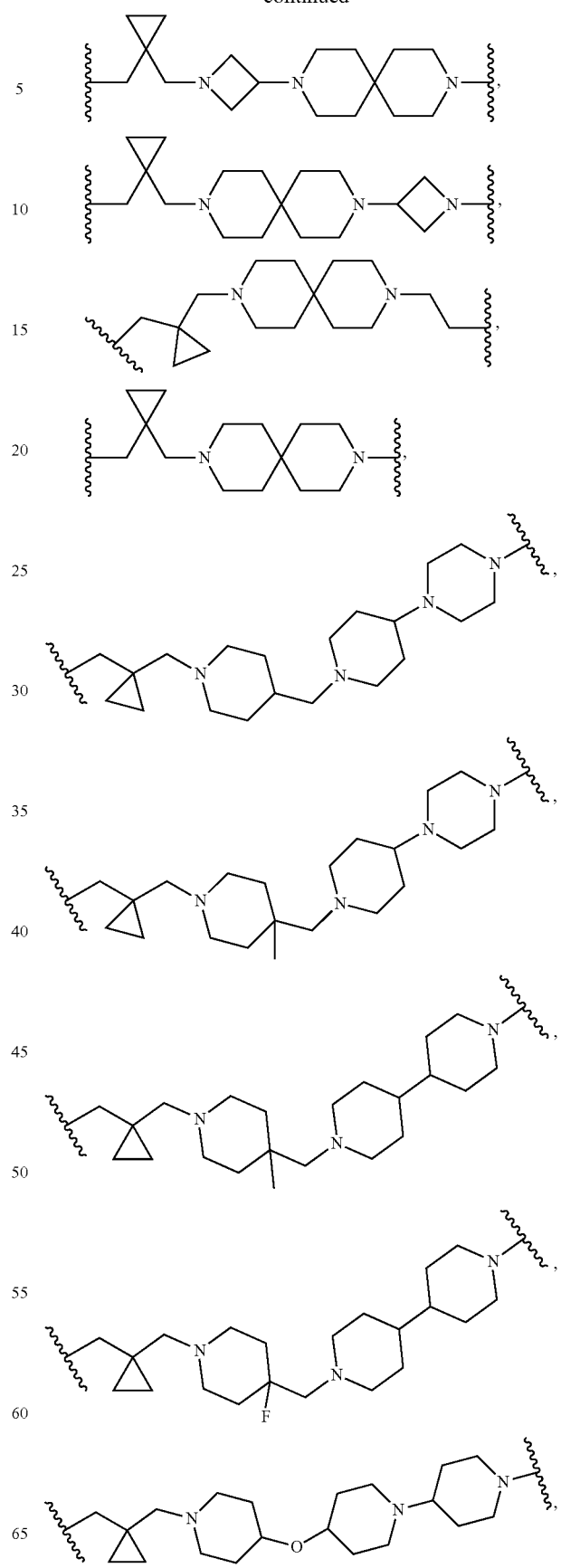

-continued
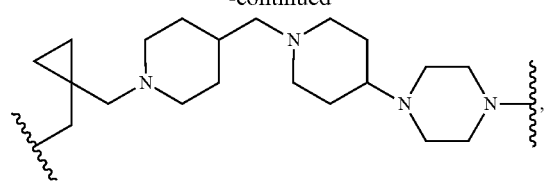
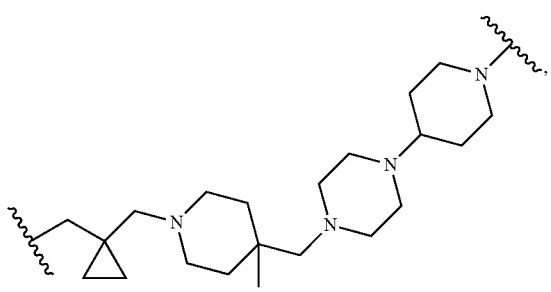
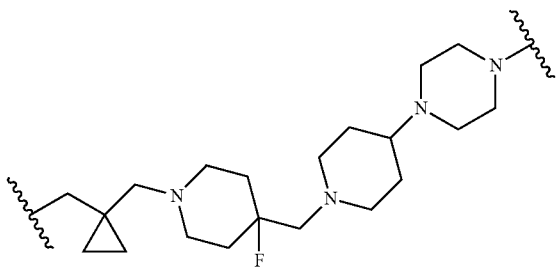
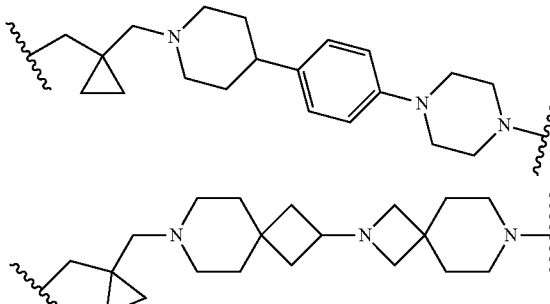
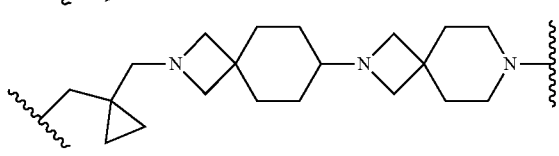
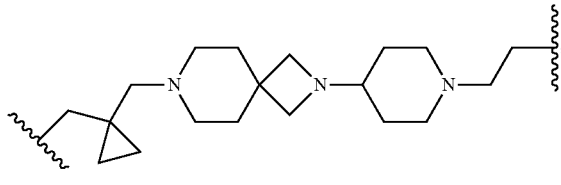
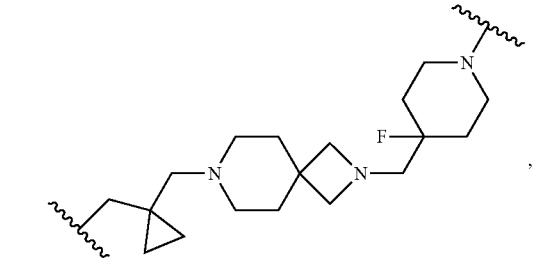
-continued
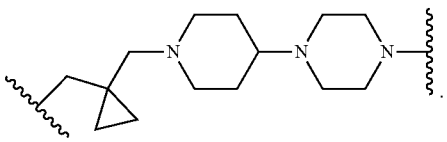 [SMILES: *CC1(CN2CCC(N3CCN(*)CC3)CC2)CC1], and
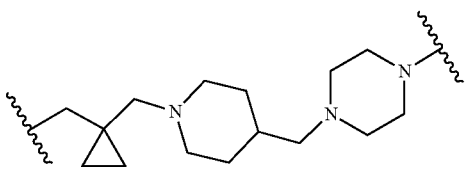
In some embodiments, L is
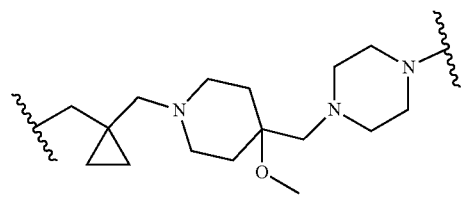
In some embodiments, L is
In some embodiments, L is In some embodiments, L is
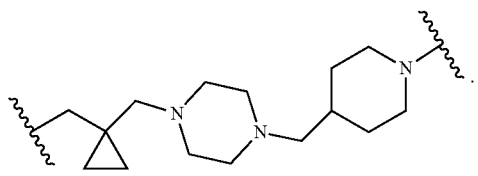 [SMILES: *CC1(CN2CCN(CC3CCN(*)CC3)CC2)CC1]
In some embodiments, L is
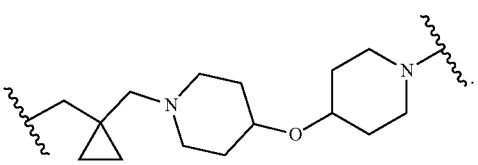 [SMILES: *CC1(CN2CCC(OC3CCN(*)CC3)CC2)CC1]
In some embodiments, L is
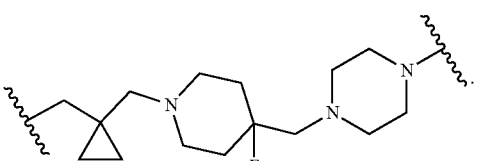
In some embodiments, L is
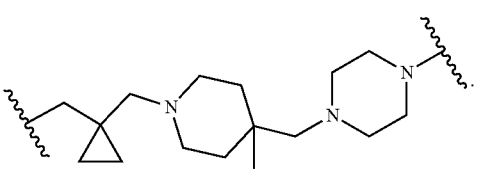 [SMILES: *CC1(CN2CCC(C)(CN3CCN(*)CC3)CC2)CC1]
In some embodiments, L is
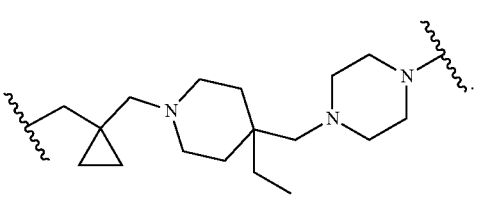 [SMILES: *CC1(CN2CCC(CC)(CN3CCN(*)CC3)CC2)CC1]
In some embodiments, L is
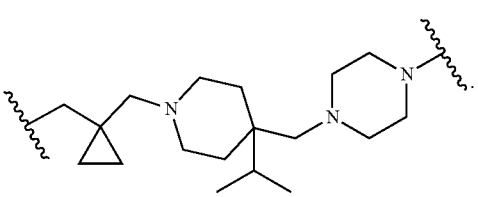 [SMILES: *CC1(CN2CCC(CN3CCN(*)CC3)(C(C)C)CC2)CC1]
In some embodiments, L is
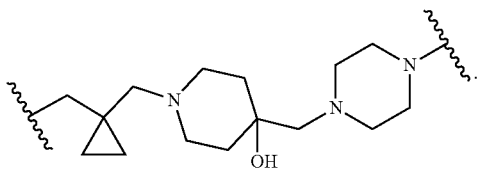 [SMILES: *CC1(CN2CCC(O)(CN3CCN(*)CC3)CC2)CC1]
In some embodiments, L is
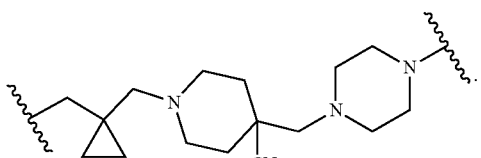
In some embodiments, L is
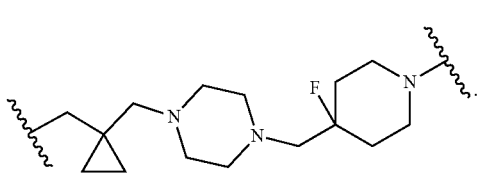 [SMILES: *CC1(CN2CCN(CC3(F)CCN(*)CC3)CC2)CC1]
In some embodiments, L is
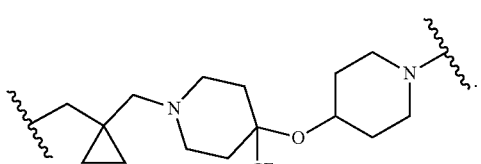
In some embodiments, L is
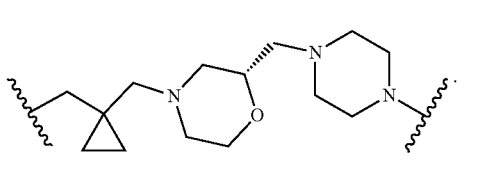 [SMILES: *CC1(CN2CCO[C@@H](CN3CCN(*)CC3)C2)CC1]
In some embodiments, L is
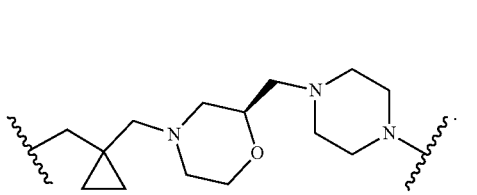 [SMILES: *CC1(CN2CCO[C@H](CN3CCN(*)CC3)C2)CC1]

In some embodiments, L is
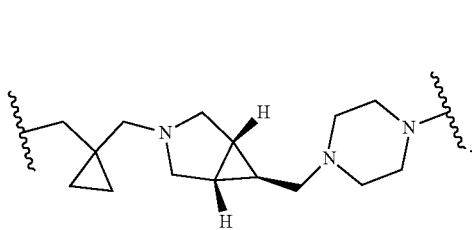 [SMILES: *CC1(CN2C[C@@H]3[C@@H](CN4CCN(*)CC4)[C@@H]3C2)CC1]
In some embodiments, L is
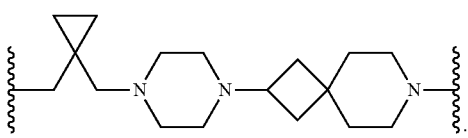 [SMILES: *CC1(CN2CCN(C3CC4(CCN(*)CC4)C3)CC2)CC1]
In some embodiments, L is
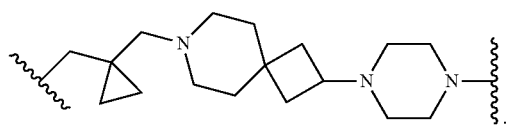 [SMILES: *CC1(CN2CCC3(CC2)CC(N2CCN(*)CC2)C3)CC1]
In some embodiments, L is
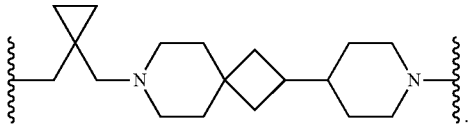
In some embodiments, L is
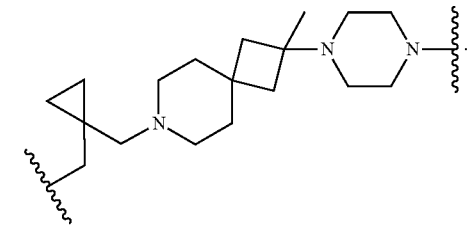 [SMILES: *CC1(CN2CCC3(CC2)CC(C)(N2CCN(*)CC2)C3)CC1 ; "."]
In some embodiments, L is
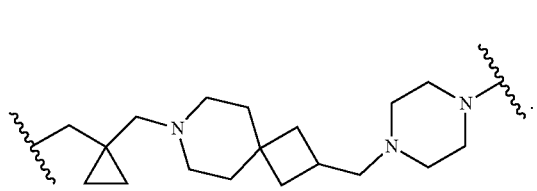 [SMILES: *CC1(CN2CCC3(CC2)CC(CN2CCN(*)CC2)C3)CC1]
In some embodiments, L is
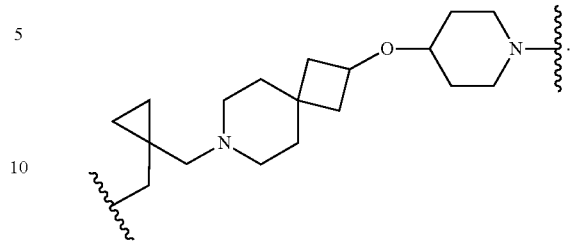
In some embodiments, L is
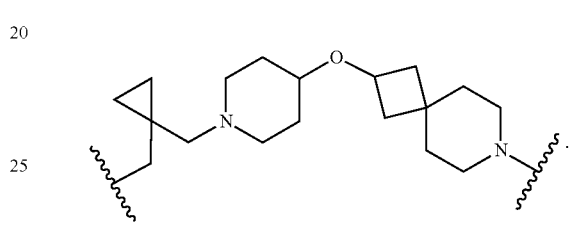
In some embodiments, L is
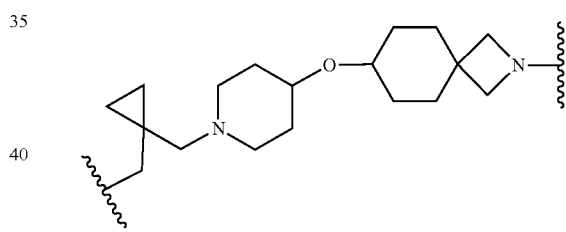
In some embodiments, L is
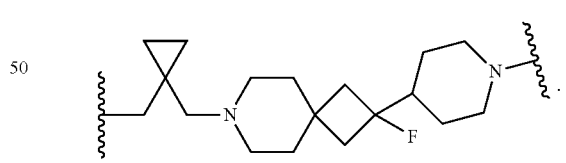
In some embodiments, L is
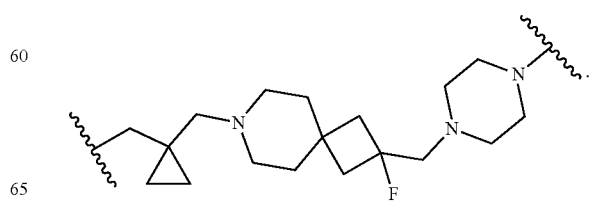

In some embodiments, L is
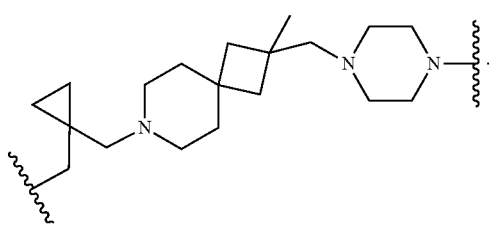 [SMILES: *CC1(CN2CCC3(CC2)CC(C)(CN2CCN(*)CC2)C3)CC1 ; "."]
In some embodiments, L is
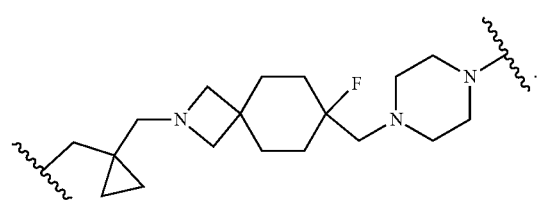 [SMILES: *CC1(CN2CC3(CCC(F)(CN4CCN(*)CC4)CC3)C2)CC1 ; "."]
In some embodiments, L is
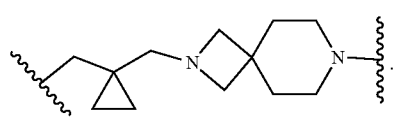 [SMILES: *CC1(CN2CC3(CCN(*)CC3)C2)CC1]
In some embodiments, L is
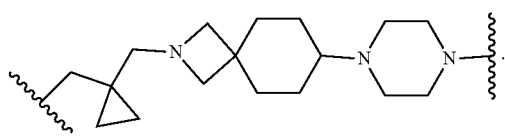 [SMILES: *CC1(CN2CC3(CCC(N4CCN(*)CC4)CC3)C2)CC1 ; "."]
In some embodiments, L is
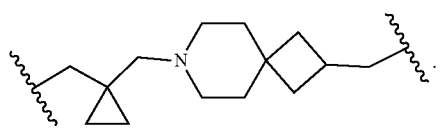 [SMILES: *CC1CC2(CCN(CC3(C*)CC3)CC2)C1]
In some embodiments, L is
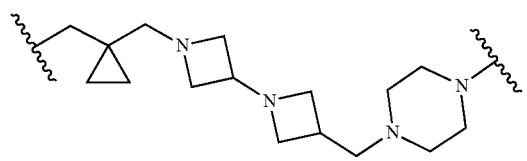
In some embodiments, L is
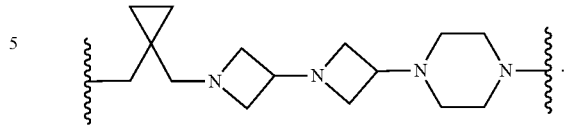
In some embodiments, L is
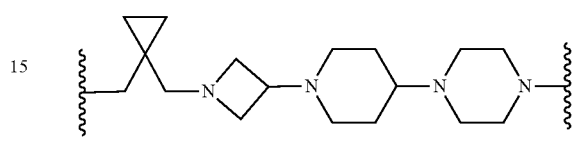
In some embodiments, L is
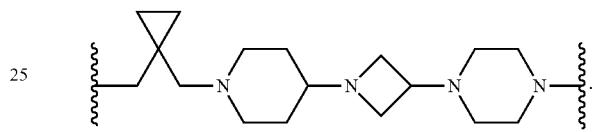
In some embodiments, L is
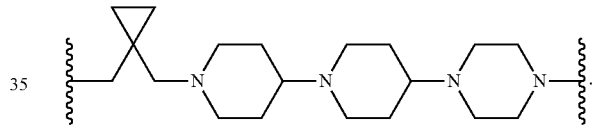
In some embodiments, L is
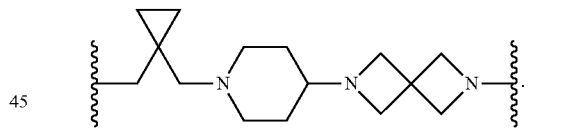
In some embodiments, L is
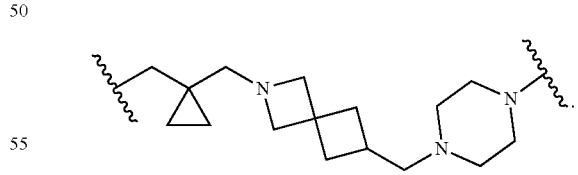
In some embodiments, L is
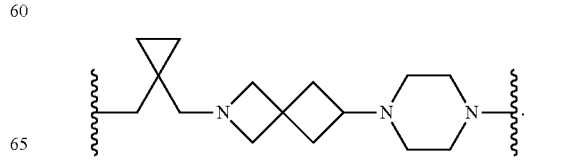

In some embodiments, L is
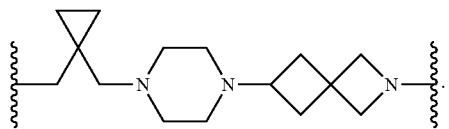 [SMILES: *CC1(CN2CCN(C3CC4(C3)CN(*)C4)CC2)CC1]
In some embodiments, L is
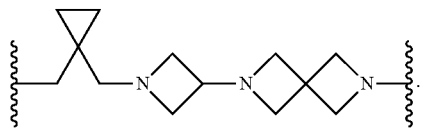 [SMILES: *CC1(CN2CC(N3CC4(CN(*)C4)C3)C2)CC1]
In some embodiments, L is
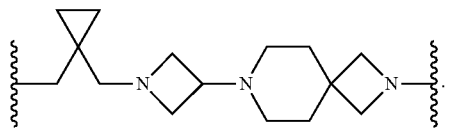 [SMILES: *CC1(CN2CC(N3CCC4(CC3)CN(*)C4)C2)CC1]
In some embodiments, L is
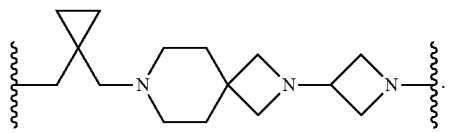 [SMILES: *CC1(CN2CCC3(CC2)CN(C2CN(*)C2)C3)CC1]
In some embodiments, L is
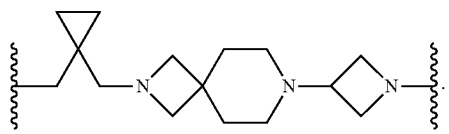 [SMILES: *CC1(CN2CC3(CCN(C4CN(*)C4)CC3)C2)CC1]
In some embodiments, L is
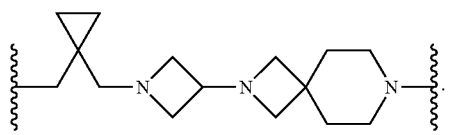 [SMILES: *CC1(CN2CC(N3CC4(CCN(*)CC4)C3)C2)CC1]
In some embodiments, L is
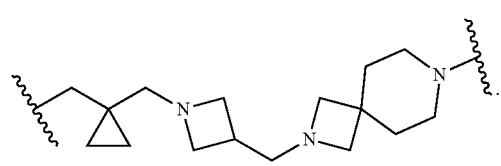 [SMILES: *CC1(CN2CC(CN3CC4(CCN(*)CC4)C3)C2)CC1]
In some embodiments, L is
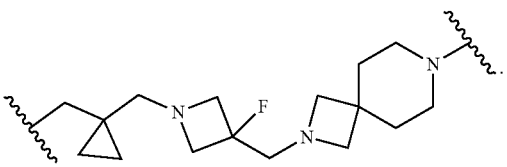 [SMILES: *CC1(CN2CC(F)(CN3CC4(CCN(*)CC4)C3)C2)CC1]
In some embodiments, L is
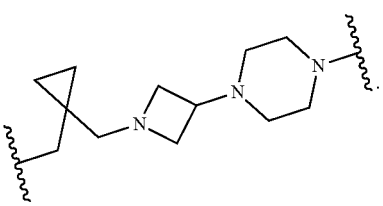 [SMILES: *CC1(CN2CC(N3CCN(*)CC3)C2)CC1]
In some embodiments, L is
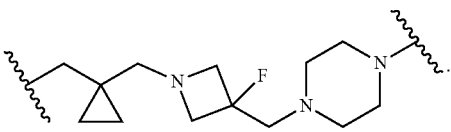 [SMILES: *CC1(CN2CC(F)(CN3CCN(*)CC3)C2)CC1]
In some embodiments, L is
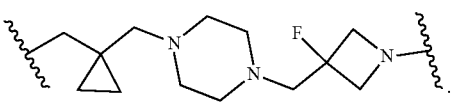 [SMILES: *CC1(CN2CCN(CC3(F)CN(*)C3)CC2)CC1]
In some embodiments, L is
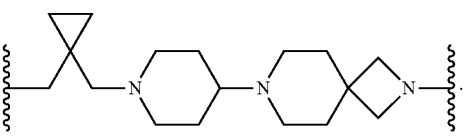 [SMILES: *CC1(CN2CCC(N3CCC4(CC3)CN(*)C4)CC2)CC1]
In some embodiments, L is
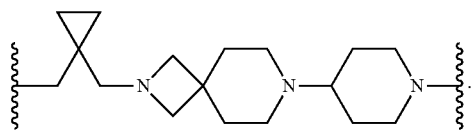 [SMILES: *CC1(CN2CC3(CCN(C4CCN(*)CC4)CC3)C2)CC1]
In some embodiments, L is
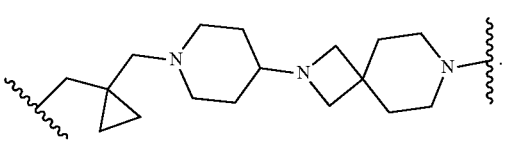 [SMILES: *CC1(CN2CCC(N3CC4(CCN(*)CC4)C3)CC2)CC1]

In some embodiments, L is
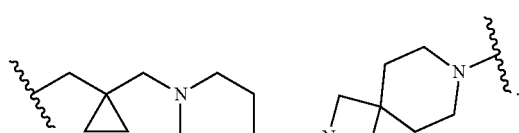
In some embodiments, L is
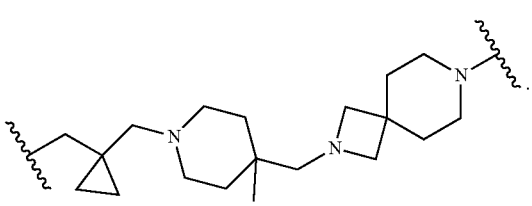 [SMILES: *CC1(CN2CCC(C)(CN3CC4(CCN(*)CC4)C3)CC2)CC1]
In some embodiments, L is
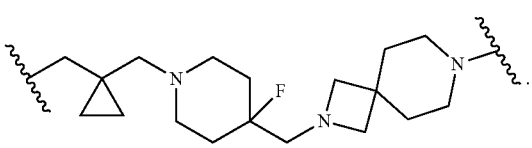 [SMILES: *CC1(CN2CCC(F)(CN3CC4(CCN(*)CC4)C3)CC2)CC1]
In some embodiments, L is
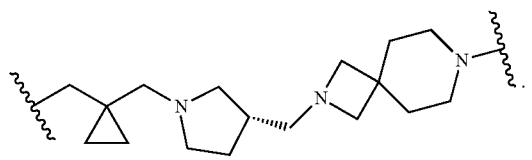 [SMILES: *CC1(CN2CC[C@@H](CN3CC4(CCN(*)CC4)C3)C2)CC1]
In some embodiments, L is
In some embodiments, L is
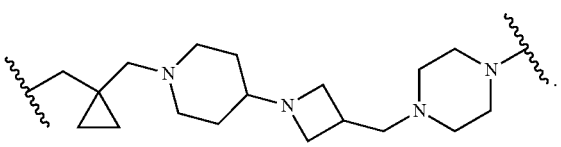 [SMILES: *CC1(CN2CCC(N3CC(CN4CCN(*)CC4)C3)CC2)CC1]
In some embodiments, L is
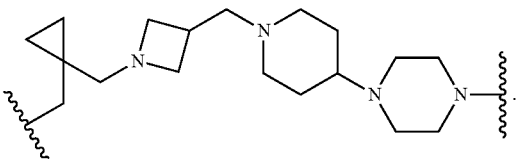 [SMILES: *CC1(CN2CC(CN3CCC(N4CCN(*)CC4)CC3)C2)CC1]
In some embodiments, L is
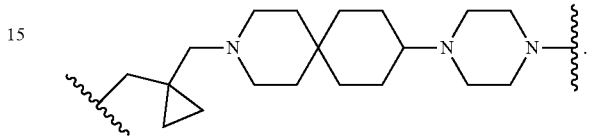
In some embodiments, L is
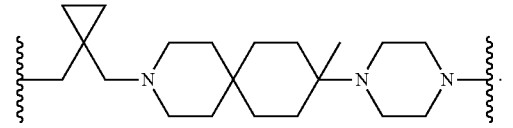
In some embodiments, L is
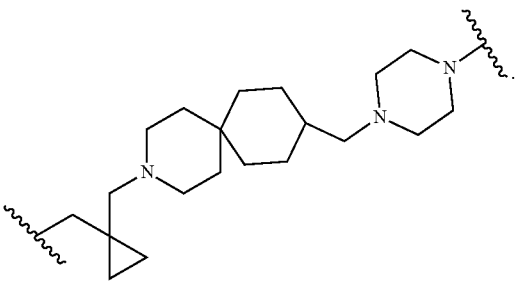 [SMILES: *CC1(CN2CCC3(CCC(CN4CCN(*)CC4)CC3)CC2)CC1]
In some embodiments, L is
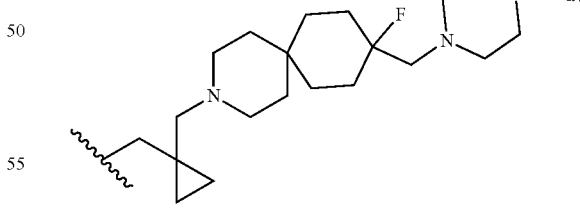
In some embodiments, L is
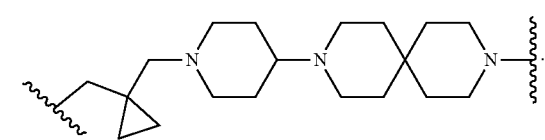 [SMILES: *CC1(CN2CCC(N3CCC4(CCN(*)CC4)CC3)CC2)CC1]

In some embodiments, L is
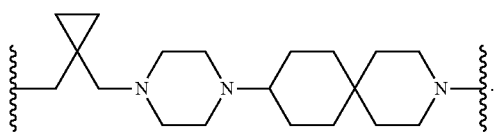
In some embodiments, L is
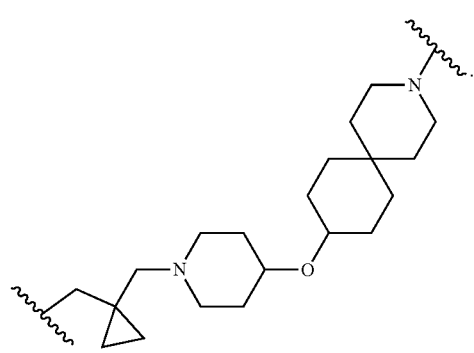 [SMILES: *CC1(CN2CCC(OC3CCC4(CC3)CCN(*)CC4)CC2)CC1]
In some embodiments, L is
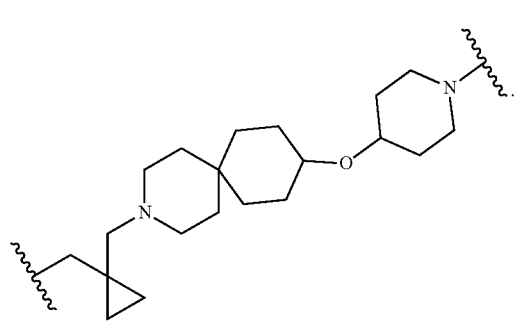 [SMILES: *CC1(CN2CCC3(CCC(OC4CCN(*)CC4)CC3)CC2)CC1]
In some embodiments, L is
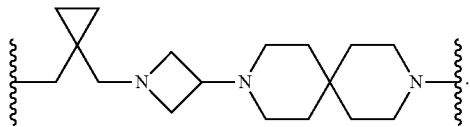
In some embodiments, L is
In some embodiments, L is
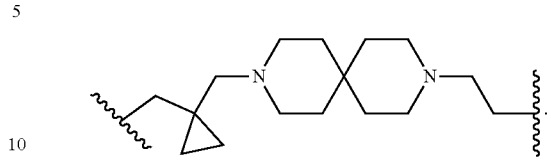
In some embodiments, L is
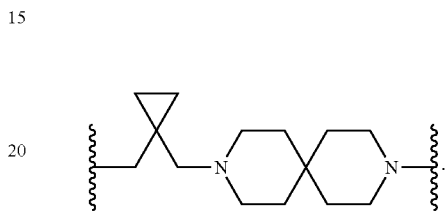
In some embodiments, L is
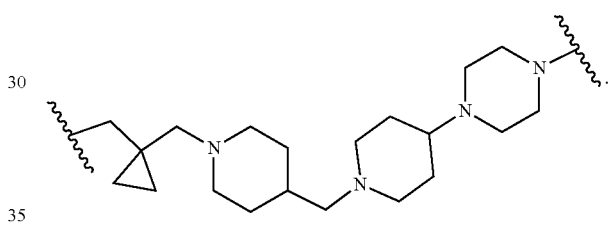
In some embodiments, L is
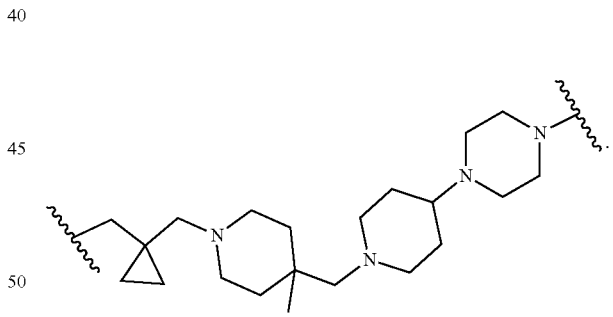
In some embodiments, L is
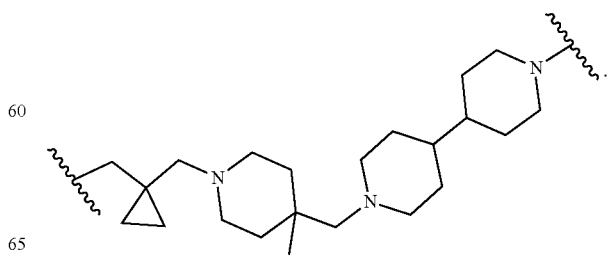

In some embodiments, L is
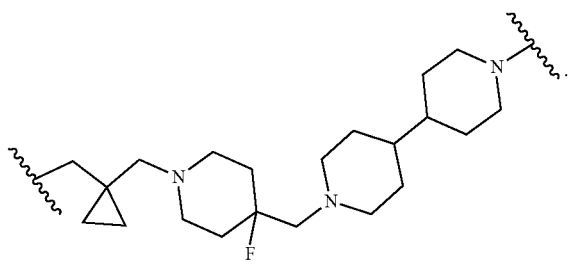 [SMILES: *CC1(CN2CCC(F)(CN3CCC(C4CCN(*)CC4)CC3)CC2)CC1]
In some embodiments, L is
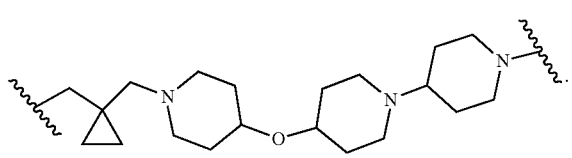 [SMILES: *CC1(CN2CCC(OC3CCN(C4CCN(*)CC4)CC3)CC2)CC1]
In some embodiments, L is
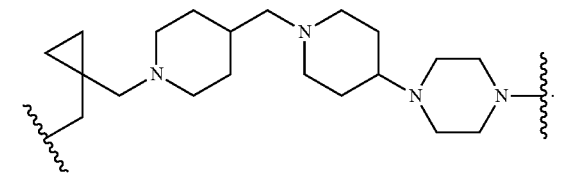 [SMILES: *CC1(CN2CCC(CN3CCC(N4CCN(*)CC4)CC3)CC2)CC1]
In some embodiments, L is
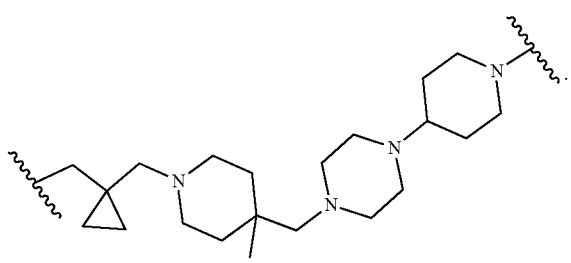 [SMILES: *CC1(CN2CCC(C)(CN3CCN(C4CCN(*)CC4)CC3)CC2)CC1]
In some embodiments, L is
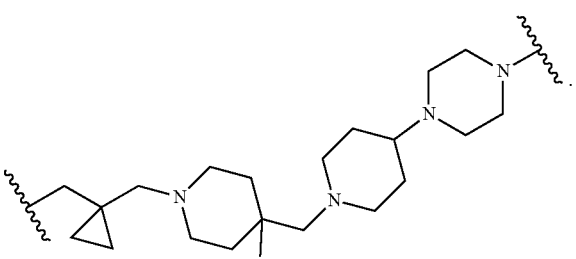
In some embodiments, L is
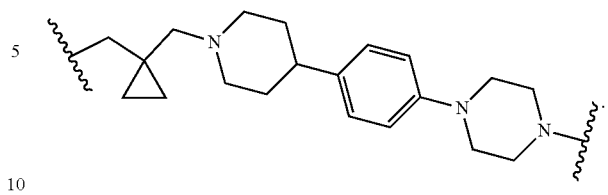
In some embodiments, L is
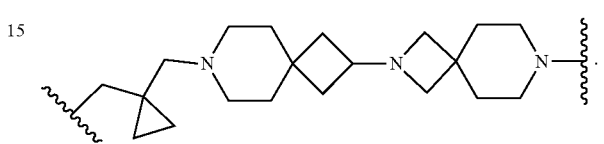
In some embodiments, L is
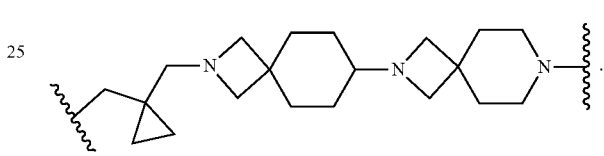
In some embodiments, L is
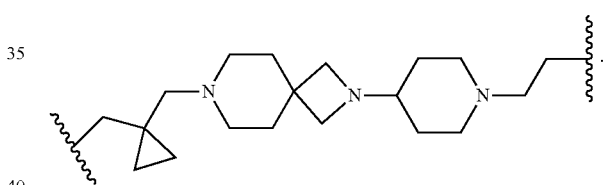
In some embodiments, L is
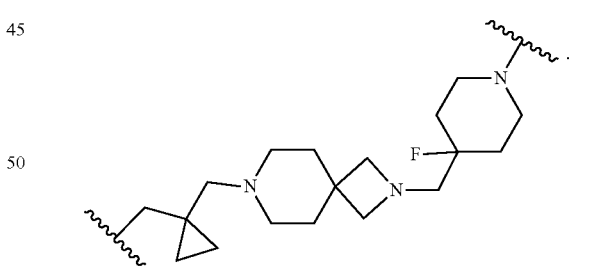
In some embodiments, L is
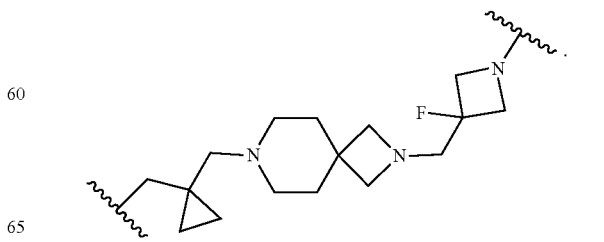

In some embodiments, L is

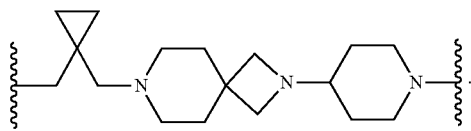 [SMILES: *CC1(CN2CCC3(CC2)CN(C2CCN(*)CC2)C3)CC1 ; "."]

In some embodiments, L is

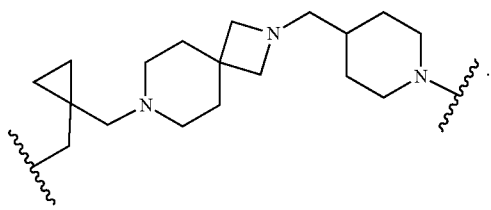 [SMILES: *CC1(CN2CCC3(CC2)CN(CC2CCN(*)CC2)C3)CC1]

In some embodiments, L is

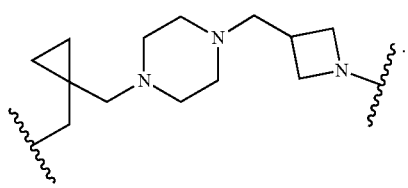 [SMILES: *CC1(CN2CCN(CC3CN(*)C3)CC2)CC1]

In some embodiments, Q is 1 to 5 carbon atoms in length, wherein one or more carbon atoms are replaced by a divalent group selected from heterocyclyl, aryl, heteroaryl, —NH—, —C(=O)—, and —C(=O)—NH—, and wherein the heterocyclyl, aryl, and heteroaryl are each independently substituted with 0, 1, or 2 $R^f$.

In some embodiments, Q is 1 to 5 carbon atoms in length, wherein one or more carbon atoms are replaced by a divalent group selected from isoindolinonyl, phthalimidyl, pyridinyl, phenyl, phthalazinonyl, and —C(=O)—NH—, wherein each of the isoindolinonyl, phthalimidyl, pyridinyl, phenyl, and phthalazinonyl is independently substituted with 0 or 1 $R^f$.

In some embodiments, each $R^f$ is independently selected from halogen, hydroxy, methyl, ethyl, and an oxo group.

In some embodiments, each $R^f$ is independently selected from Cl, F, and methyl.

In some embodiments, $R^f$ is Cl.

In some embodiments, $R^f$ is F.

In some embodiments, $R^f$ is methyl.

In some embodiments, Q is selected from

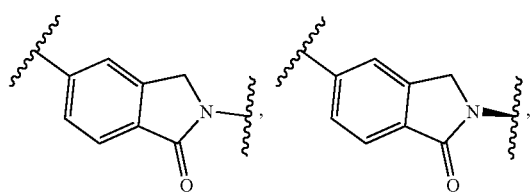

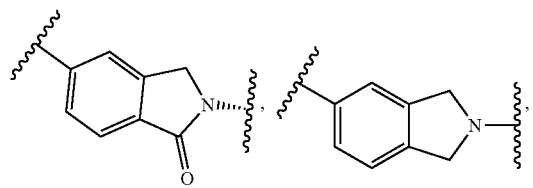

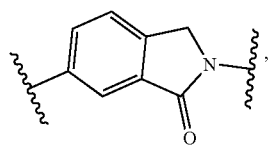

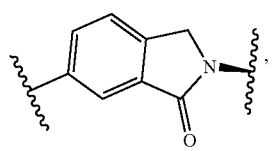

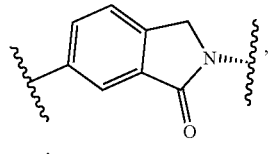

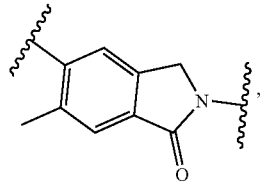

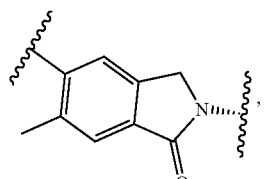

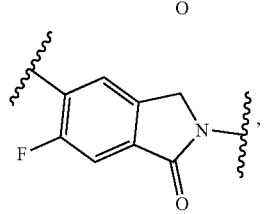

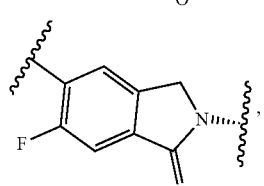

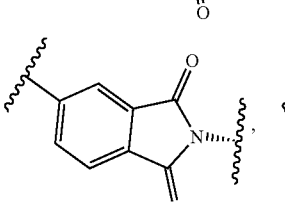

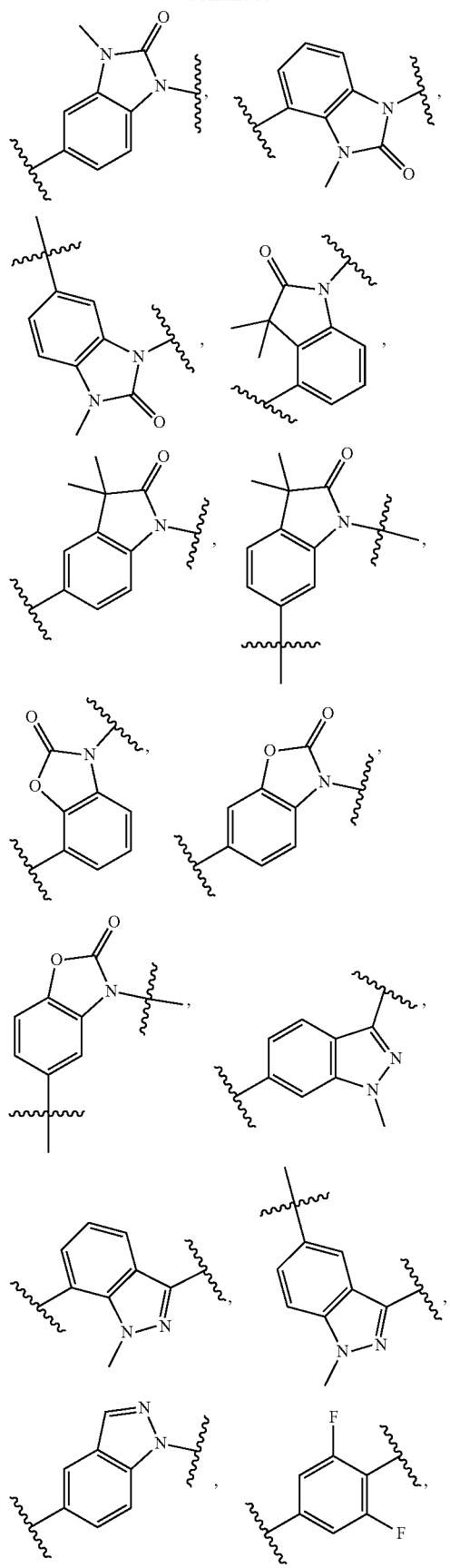
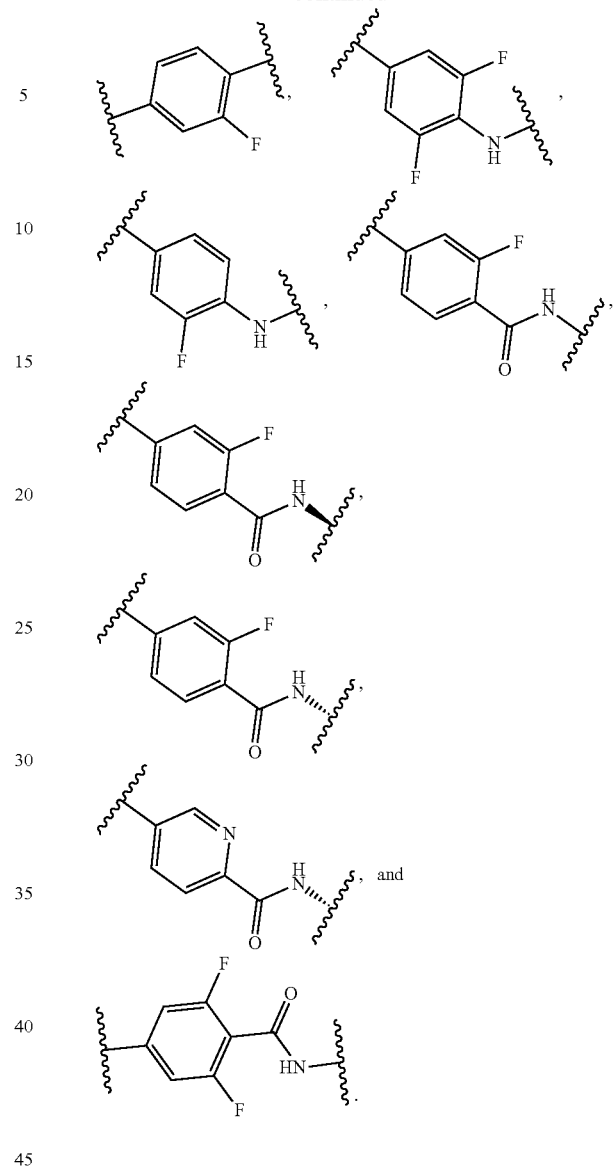
In some embodiments, Q is
In some embodiments, Q is
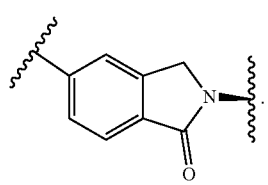

In some embodiments, Q is
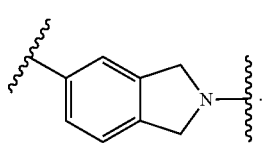 [SMILES: *c1ccc2c(c1)CN(*)C2 ; "."]
In some embodiments, Q is
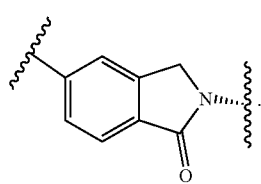
In some embodiments, Q is
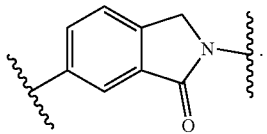
In some embodiments, Q is
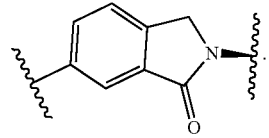
In some embodiments, Q is
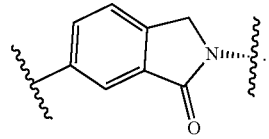
In some embodiments, Q is
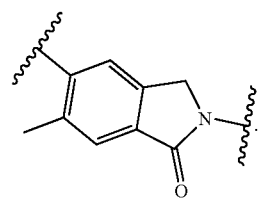 [SMILES: *c1cc2c(cc1C)C(=O)N(*)C2]
In some embodiments, Q is
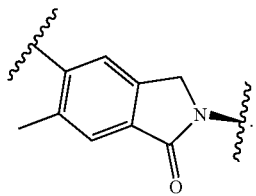
In some embodiments, Q is
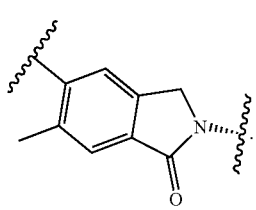
In some embodiments, Q is
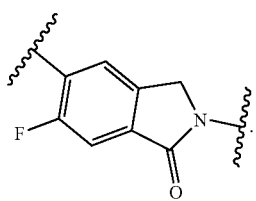 [SMILES: *c1cc2c(cc1F)C(=O)N(*)C2]
In some embodiments, Q is
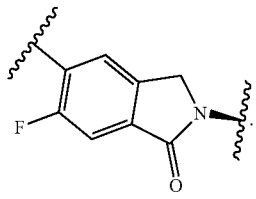
In some embodiments, Q is
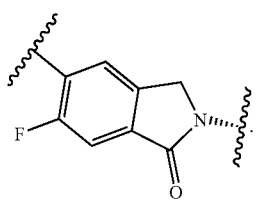

In some embodiments, Q is
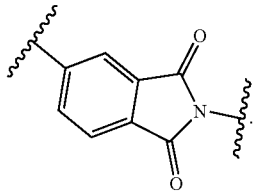 [SMILES: *c1ccc2c(c1)C(=O)N(*)C2=O]
In some embodiments, Q is
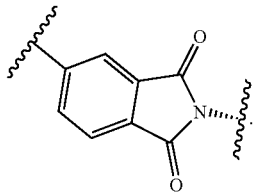
In some embodiments, Q is
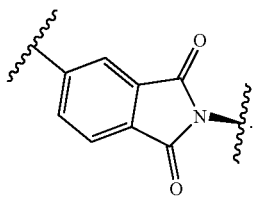
In some embodiments, Q is
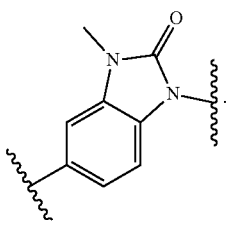 [SMILES: *c1ccc2c(c1)n(C)c(=O)n2*]
In some embodiments, Q is
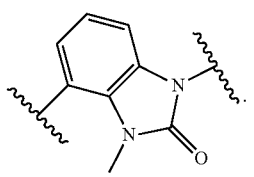 [SMILES: *c1cccc2c1n(C)c(=O)n2*]
In some embodiments, Q is
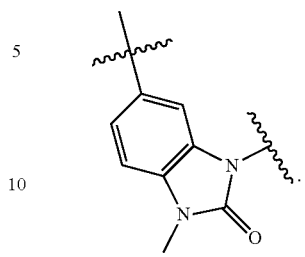
In some embodiments, Q is
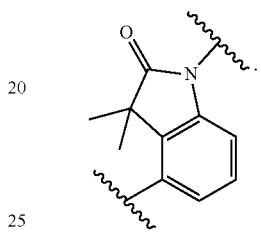
In some embodiments, Q is
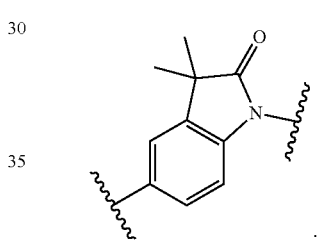
In some embodiments, Q is
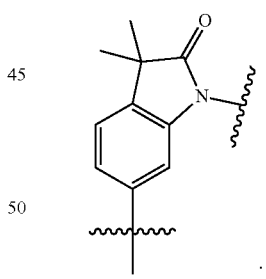
In some embodiments, Q is
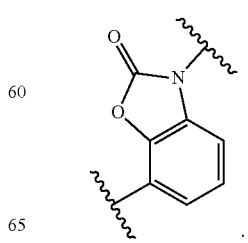

In some embodiments, Q is
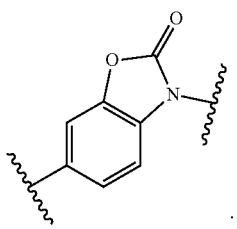 [SMILES: *c1ccc2c(c1)oc(=O)n2*]
In some embodiments, Q is
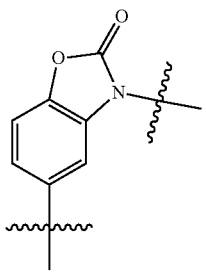
In some embodiments, Q is
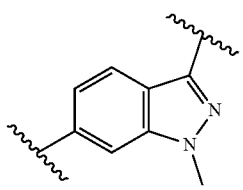
In some embodiments, Q is
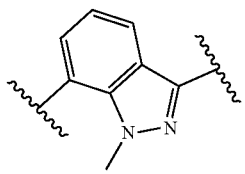
In some embodiments, Q is
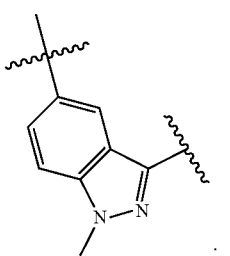 [SMILES: *c1ccc2c(c1)c(*)nn2C]
In some embodiments, Q is
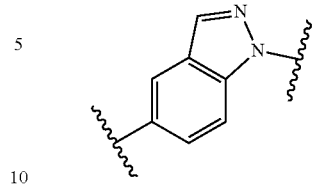
In some embodiments, Q is
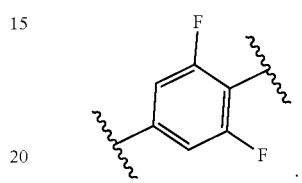
In some embodiments, Q is
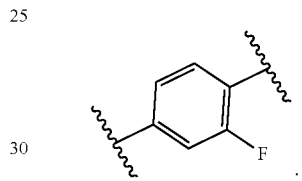
In some embodiments, Q is
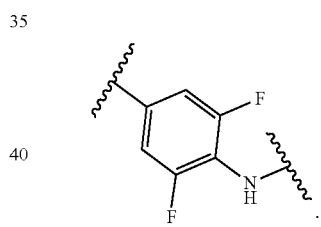
In some embodiments, Q is
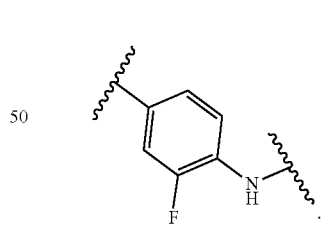
In some embodiments, Q is
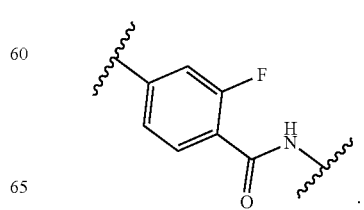

In some embodiments, Q is

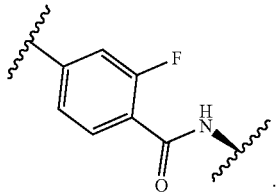

In some embodiments, Q is

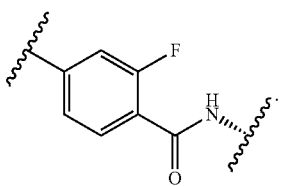

In some embodiments, Q is

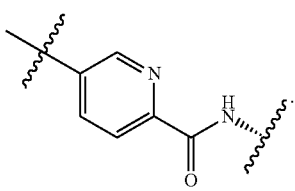

In some embodiments, Q is

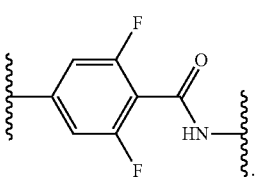 [SMILES: *NC(=O)c1c(F)cc(*)cc1F]

In some embodiments, $R^1$ is a monocyclic or bicyclic aryl or monocyclic heteroaryl, wherein each of the monocyclic or bicyclic aryl and monocyclic heteroaryl is independently substituted with 0, 1, 2, or 3 $R^b$.

In some embodiments, $R^1$ is selected from phenyl, naphthyl, and pyridinyl, wherein each of the phenyl, naphthyl, and pyridinyl is substituted with 0, 1, 2, or 3 $R^b$.

In some embodiments, each $R^b$ is selected from halogen, cyano, hydroxy, amino, $C_1$-$C_4$ alkyl, $C_2$-$C_4$ alkynyl, $C_1$-$C_3$ haloalkyl, and $C_1$-$C_3$ alkoxy.

In some embodiments, each $R^b$ is selected from halogen, hydroxy, amino, $C_1$-$C_3$ alkyl, $C_2$-$C_3$ alkynyl, and $C_1$-$C_2$ haloalkyl.

In some embodiments, each $R^b$ is selected from Cl, F, hydroxy, amino, methyl, ethyl, $CF_3$, and $C_2$ alkynyl.

In some embodiments, $R^1$ is selected from

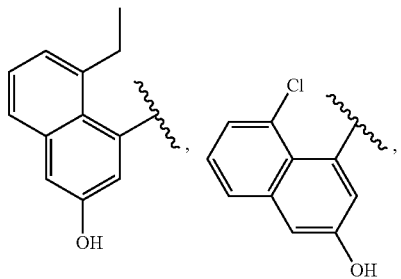

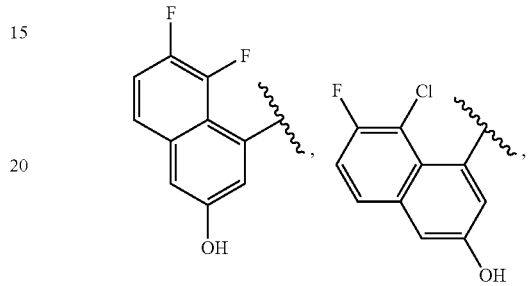

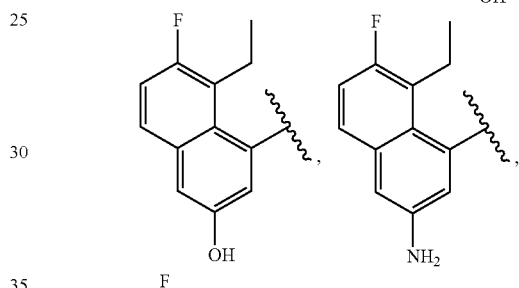

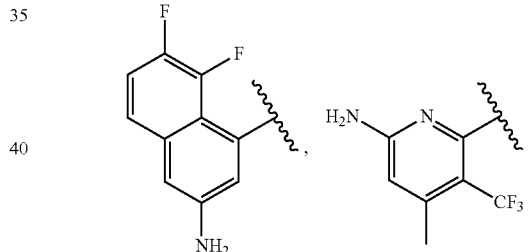

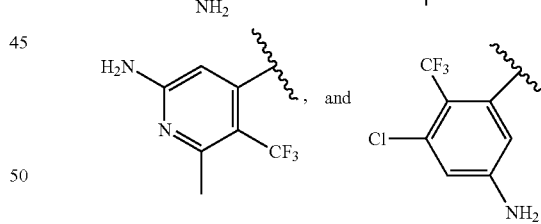

In some embodiments, $R^1$ is selected from

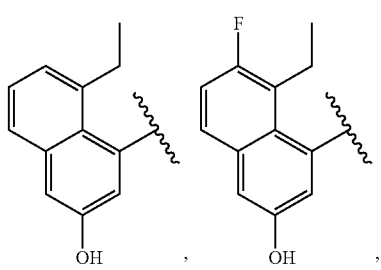

-continued
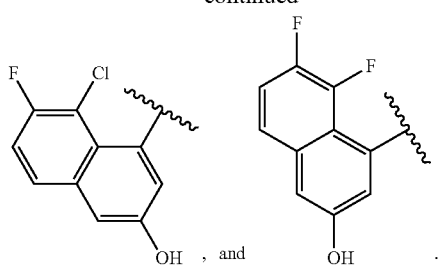, and
In some embodiments, R¹ is
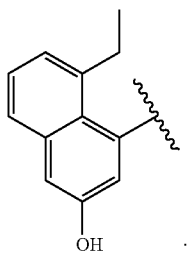 [SMILES: *c1cc(O)cc2cccc(CC)c12]
In some embodiments, R¹ is
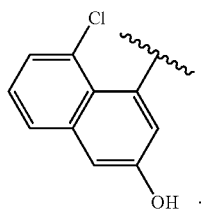 [SMILES: *c1cc(O)cc2cccc(Cl)c12]
In some embodiments, R¹ is
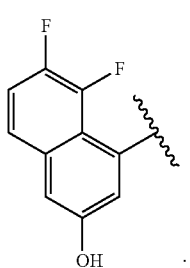 [SMILES: *c1cc(O)cc2ccc(F)c(F)c12]
In embodiments, R¹ is
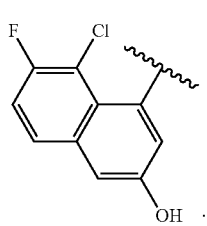 [SMILES: *c1cc(O)cc2ccc(F)c(Cl)c12]
In some embodiments, R¹ is
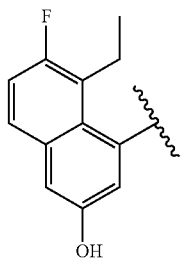
In embodiments, R¹ is
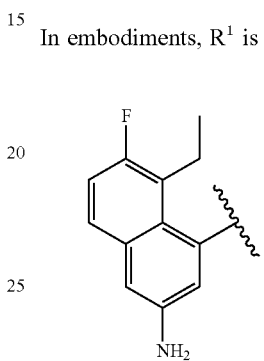
In some embodiments, R¹ is
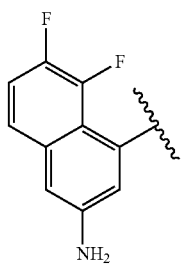
In embodiments, R¹ is
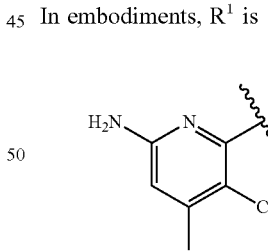
In some embodiments, R¹ is
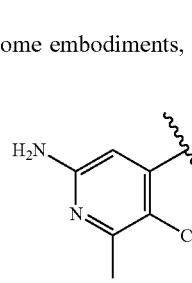

In embodiments, $R^1$ is

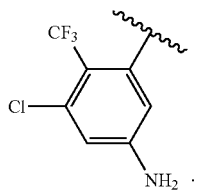

In some embodiments, $R^2$ is H or F.
In some embodiments, $R^2$ is H.
In some embodiments, $R^3$ is selected from H, halogen (such as F), and hydroxy.
In some embodiments, $R^3$ is F.
Additional aspects of this disclosure are set forth in the following embodiments:

Embodiment 1. A compound, wherein the compound is represented by Formula IB' or is a pharmaceutically acceptable salt thereof:

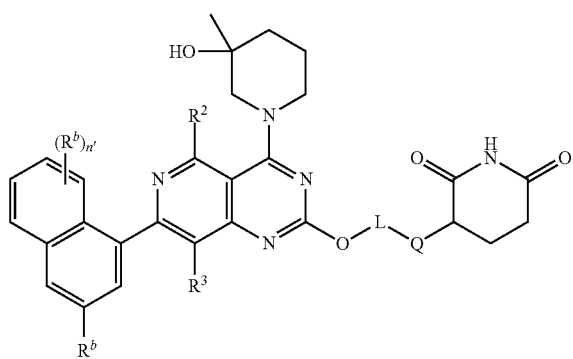

(IB')

wherein:
each $R^b$ is independently selected from halogen, hydroxy, amino, and $C_1$-$C_4$ alkyl;
n' is 1 or 2;
$R^2$ is H;
$R^3$ is halogen;
Q is selected from

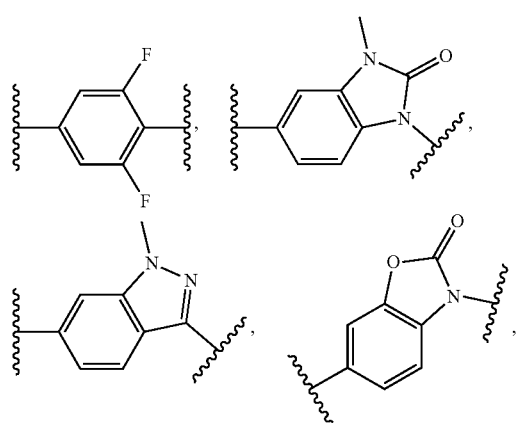

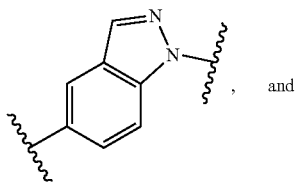, and

and
L is selected from

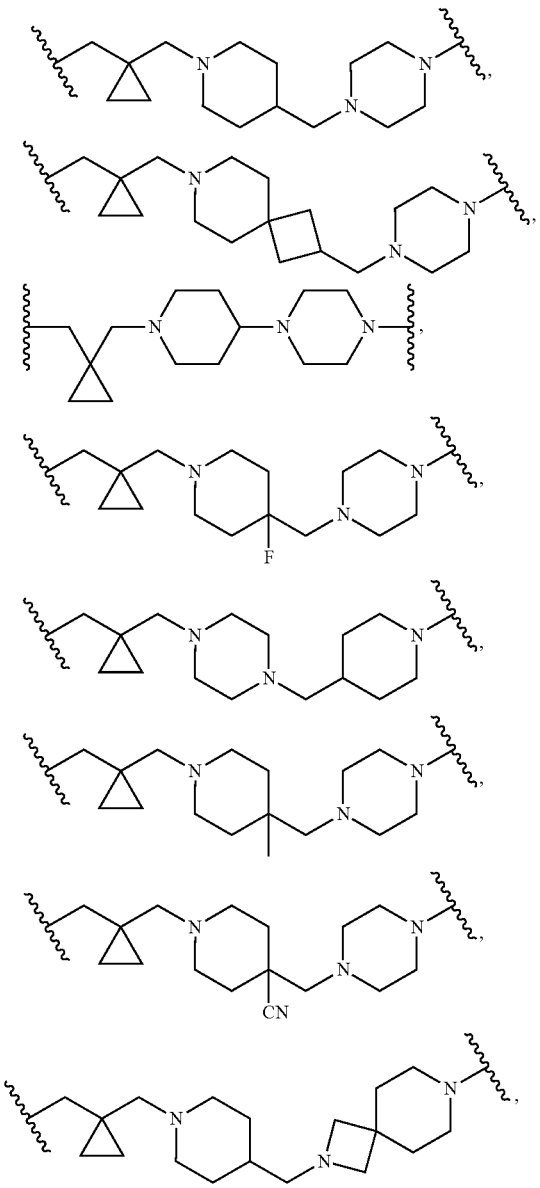

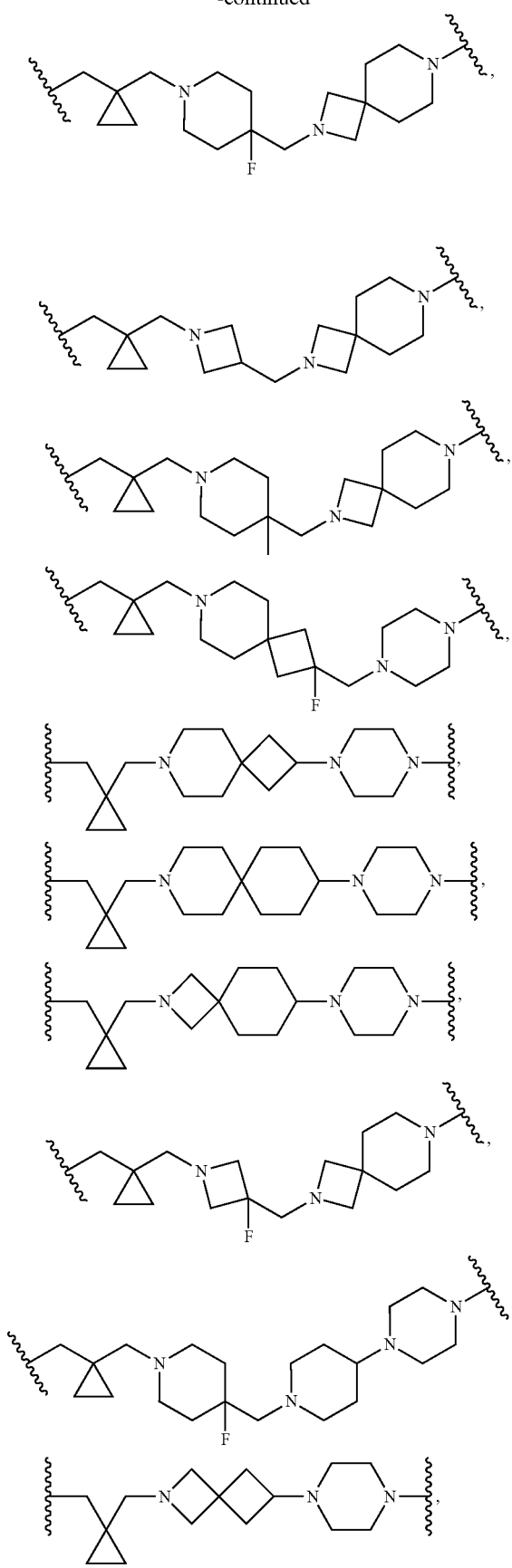
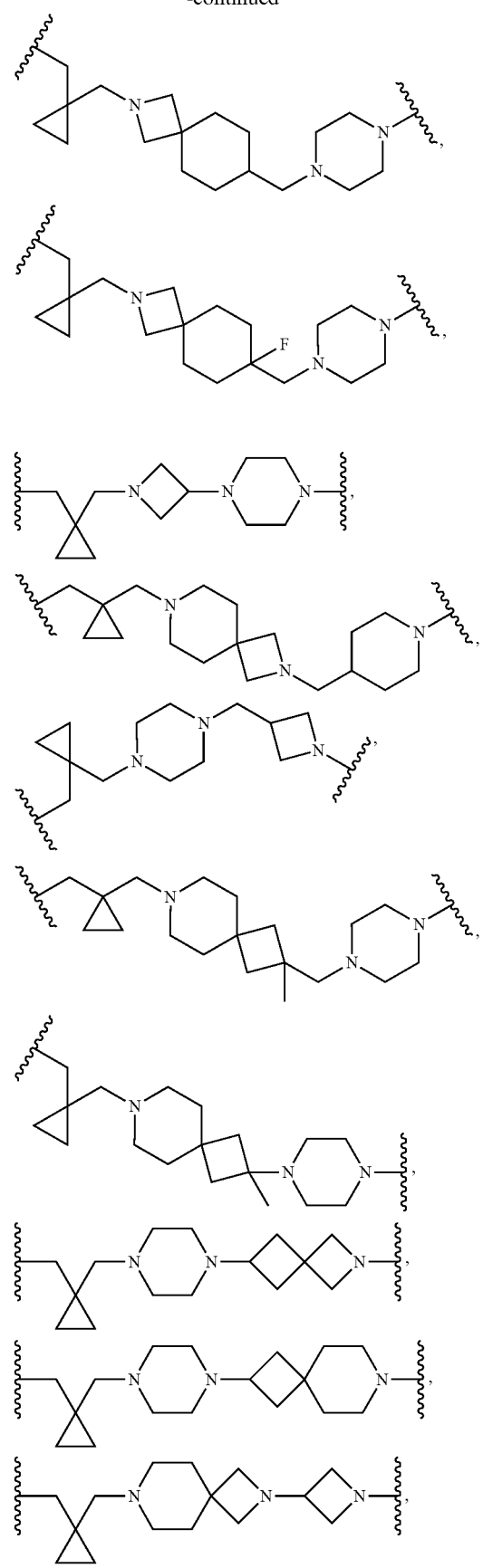

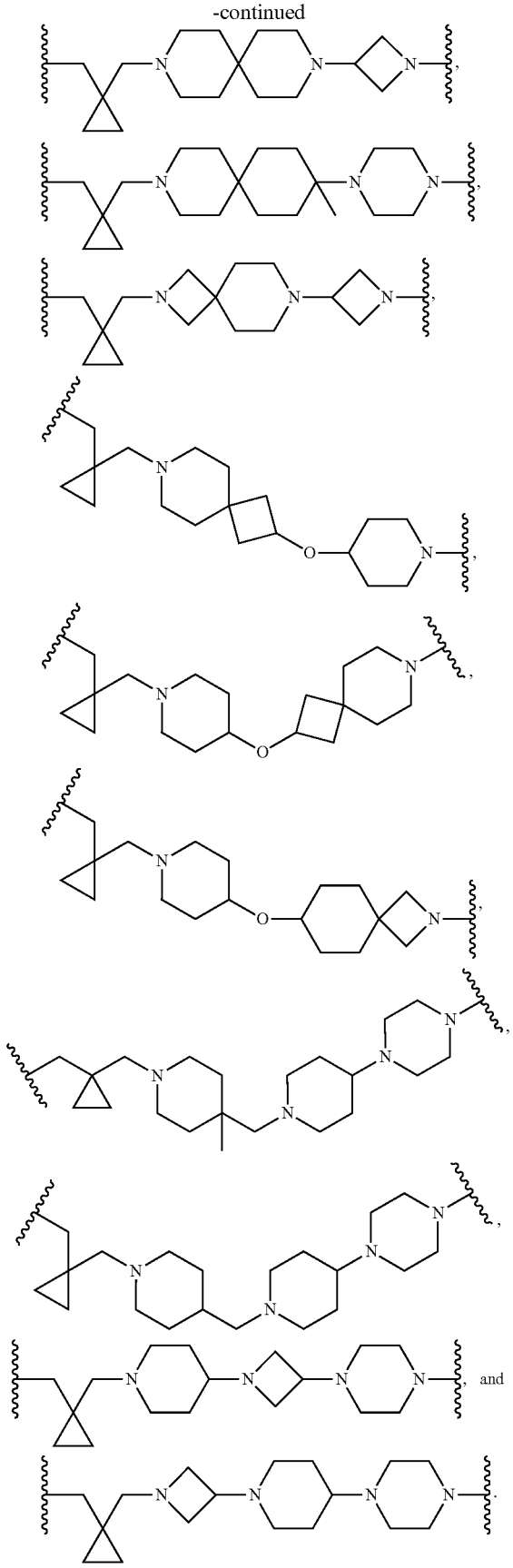
Embodiment 2. The compound of embodiment 1, wherein Q is
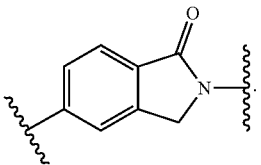 [SMILES: *c1ccc2c(c1)CN(*)C2=O]
Embodiment 3. The compound of embodiment 1 or 2, wherein L is selected from
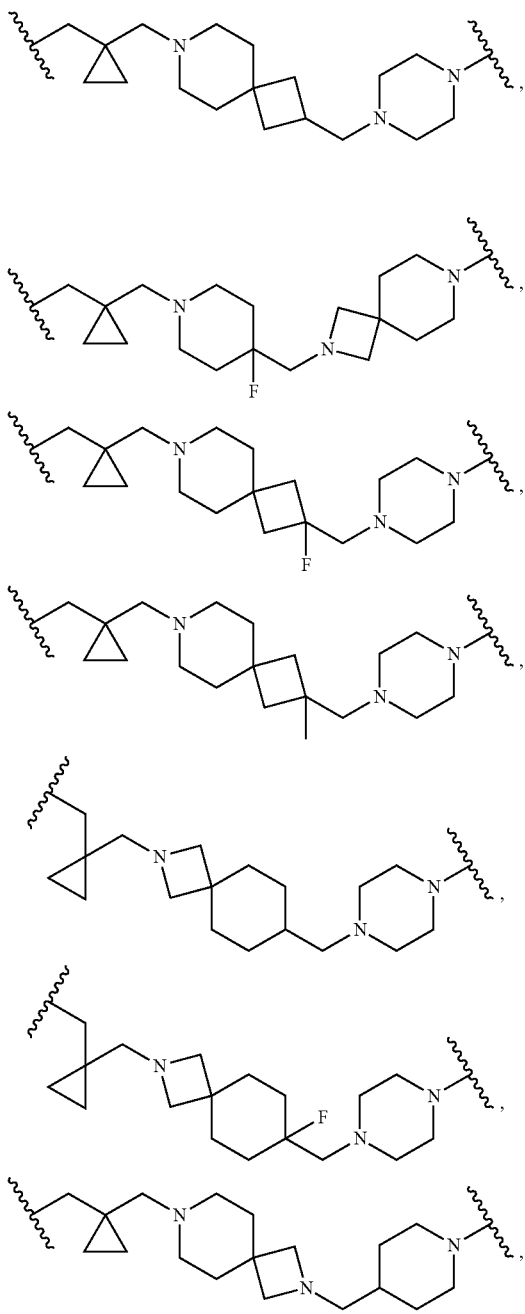

-continued
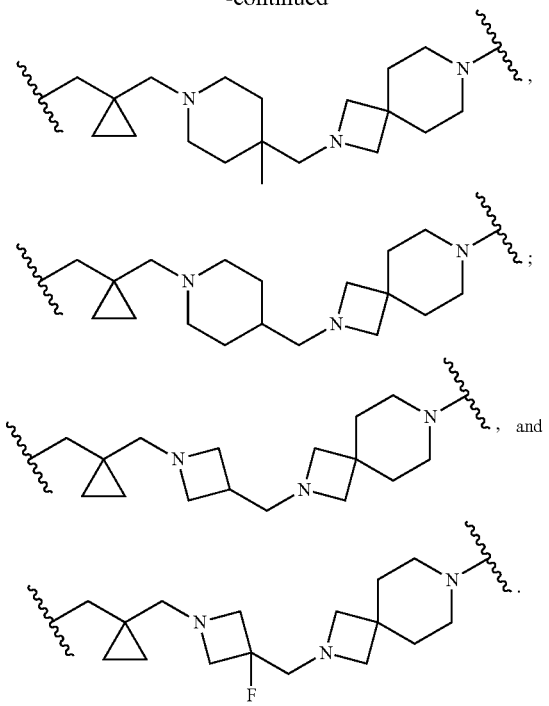
Embodiment 4. The compound of embodiment 1 or 2, wherein L is selected from
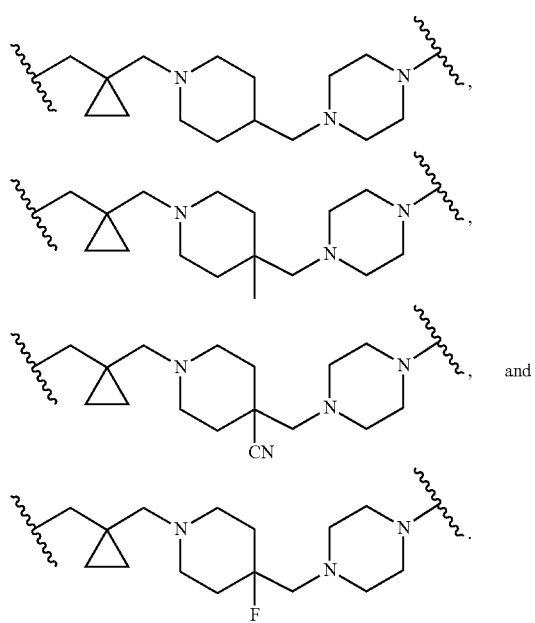
Embodiment 5. The compound of embodiment 1 or 2, wherein L is selected from
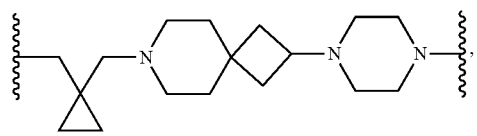
-continued
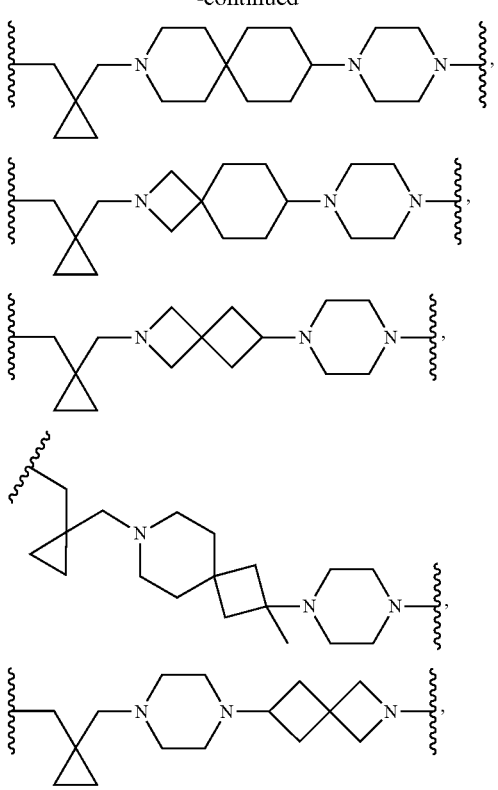
Embodiment 6. The compound of any one of embodiments 1-5, wherein $R^1$ is selected from
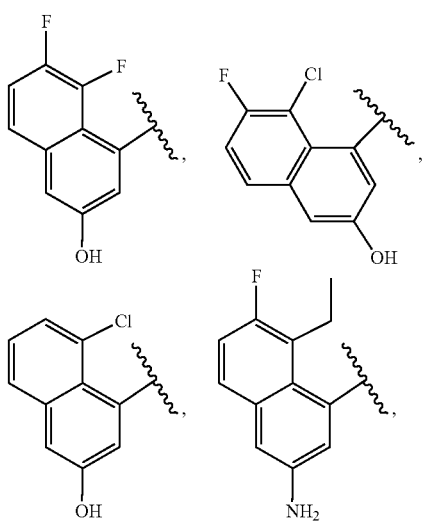

-continued
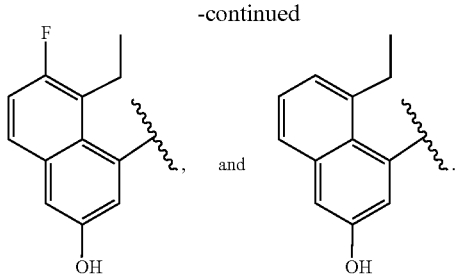
Embodiment 7. The compound of embodiment 6, wherein R$^1$ is selected from
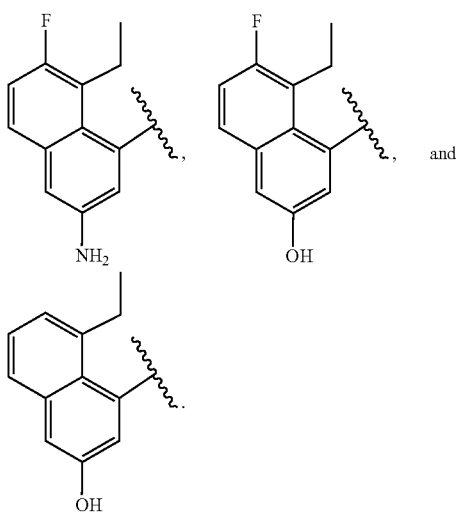
Embodiment 8. The compound of embodiment 7, wherein R$^1$ is
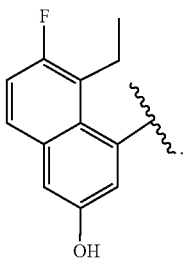 [SMILES: *c1cc(O)cc2ccc(F)c(CC)c12]
Embodiment 9. The compound of embodiment 7, wherein R$^1$ is
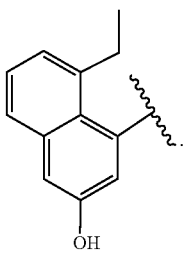 [SMILES: *c1cc(O)cc2cccc(CC)c12]
Embodiment 10. The compound of any one of embodiments 1-9, wherein the compound is selected from
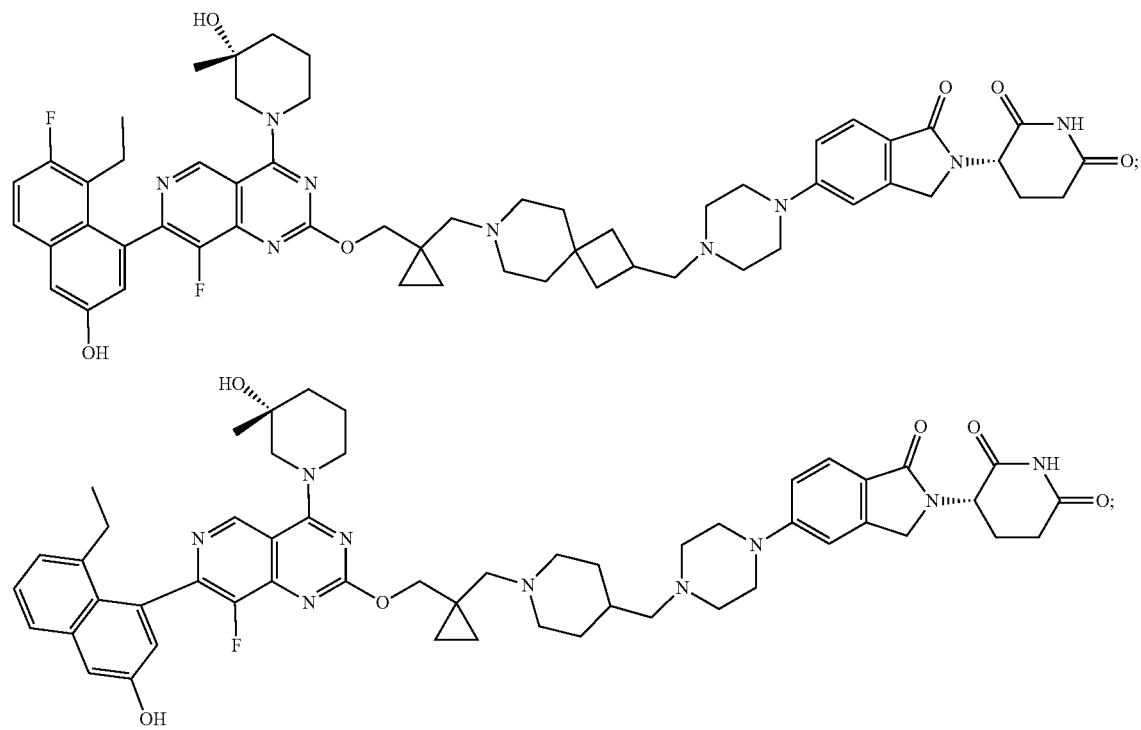

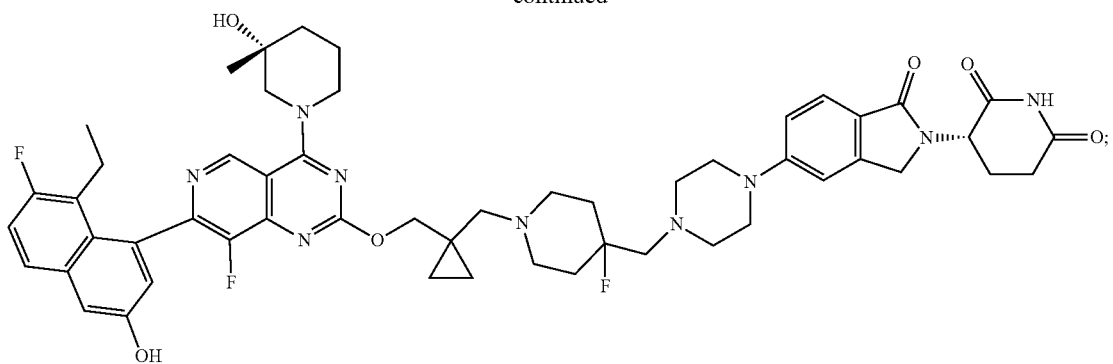
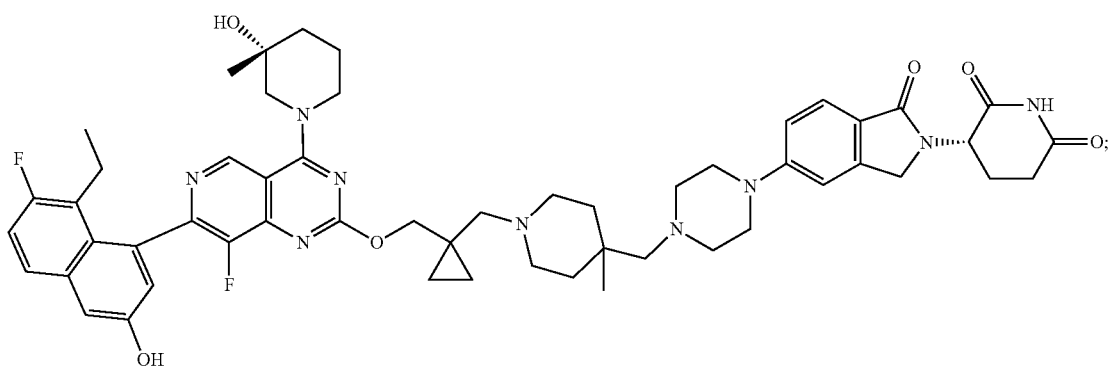
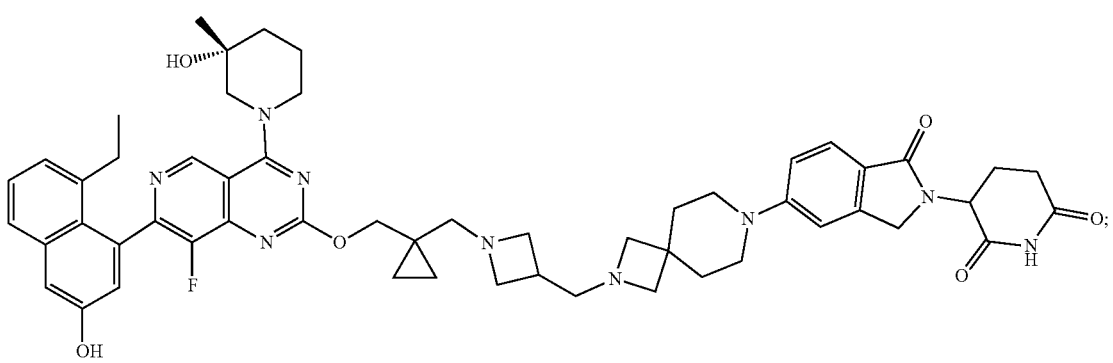
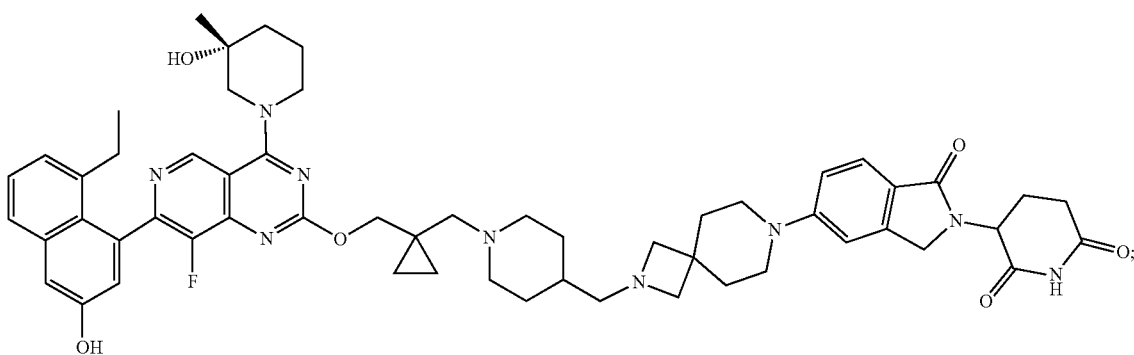

-continued
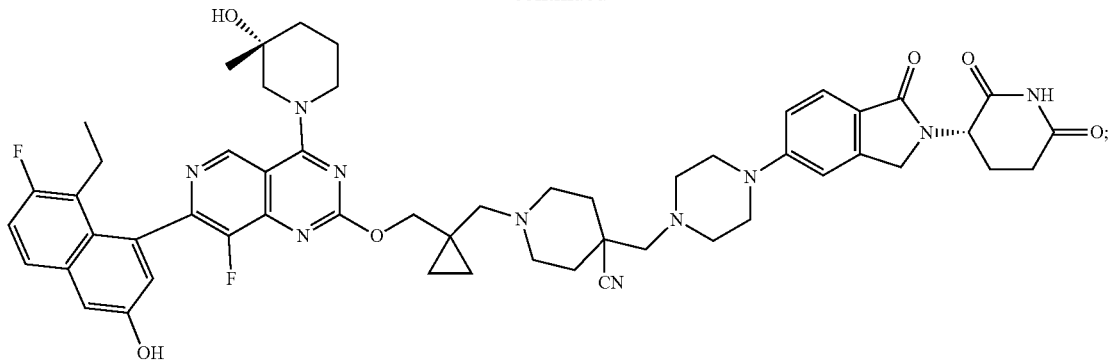 [SMILES: CCc1c(F)ccc2cc(O)cc(-c3ncc4c(N5CCC[C@@](C)(O)C5)nc(OCC5(CN6CCC(CN7CCN(c8ccc9c(c8)CN([C@H]8CCC(=O)NC8=O)C9=O)CC7)CC6)CC5)nc4c3F)c12]
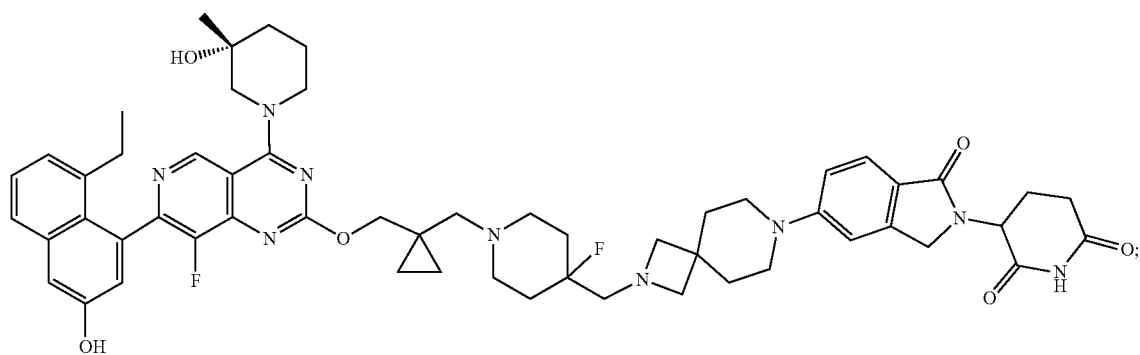
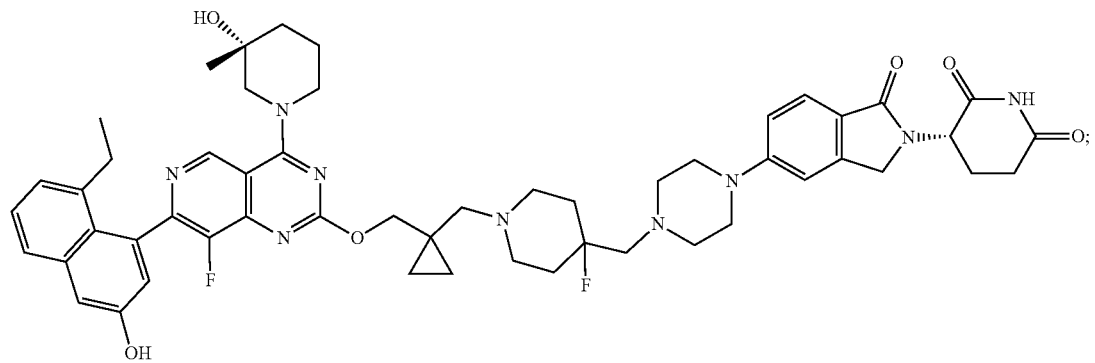
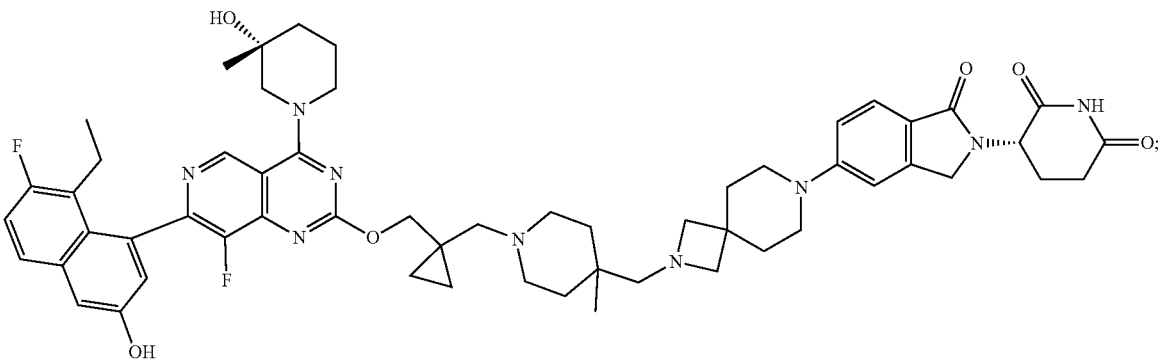

-continued
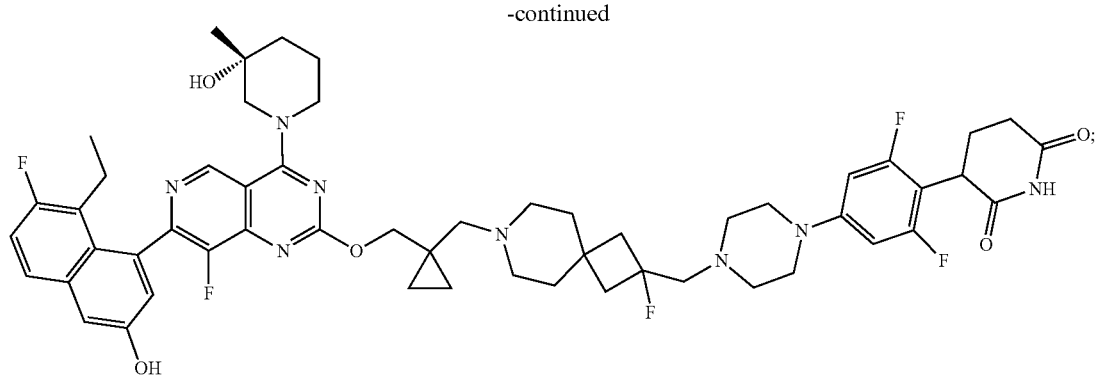
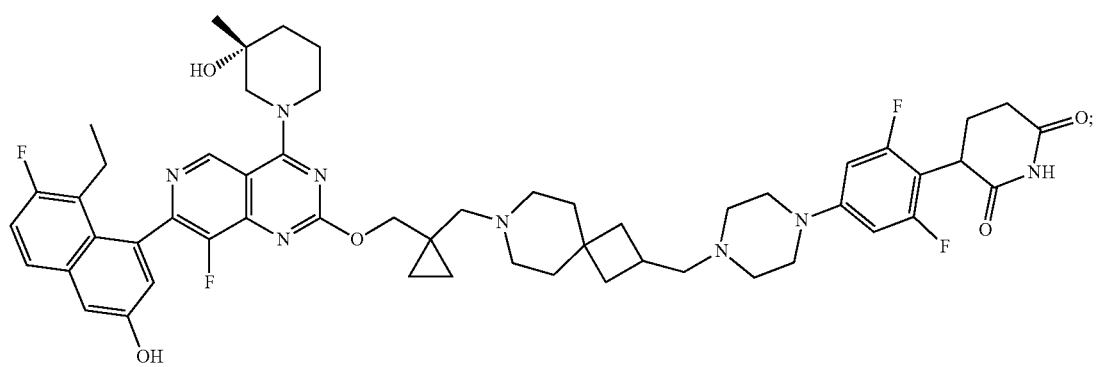
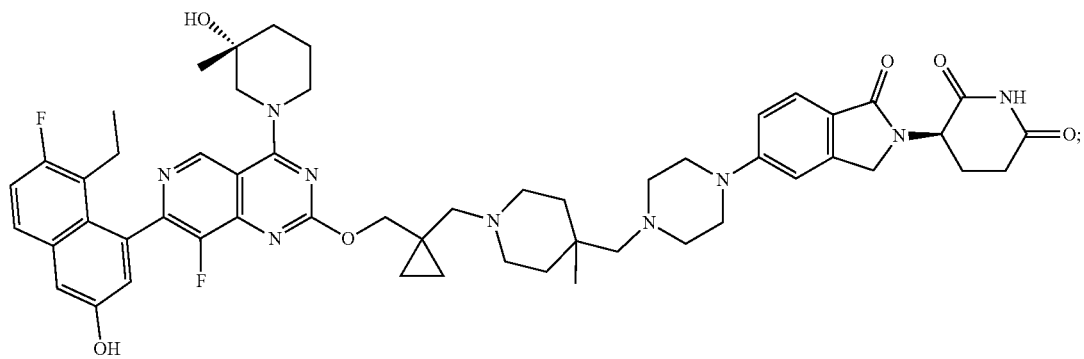
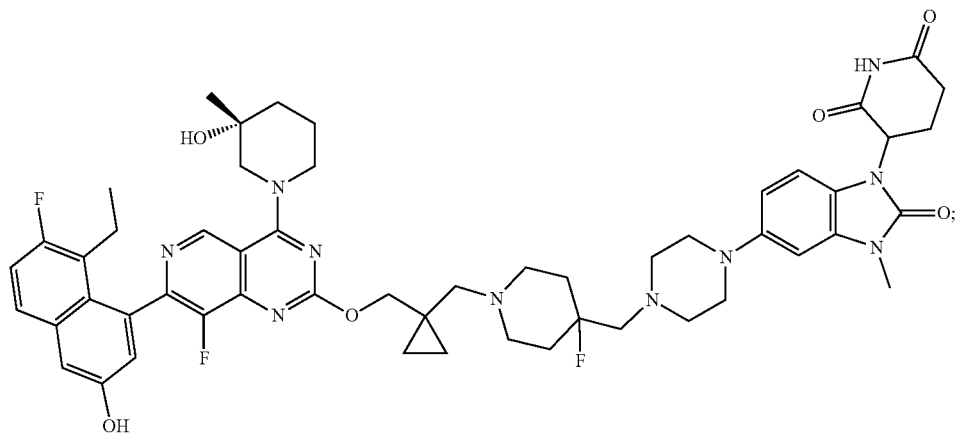

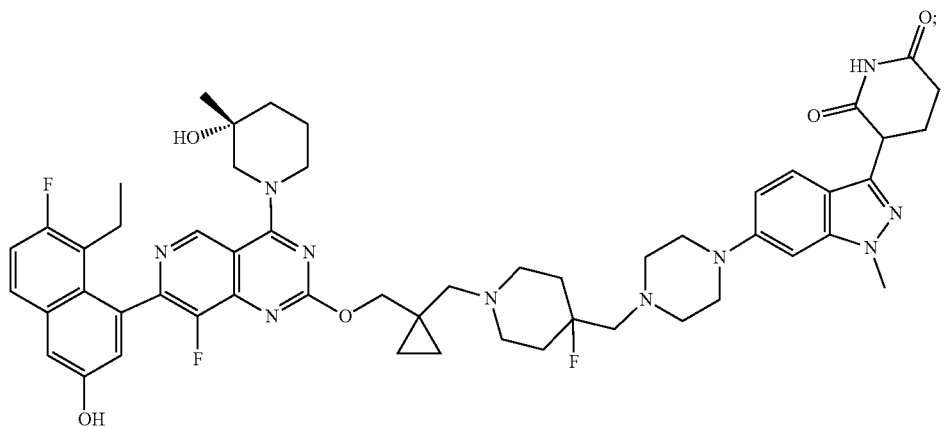
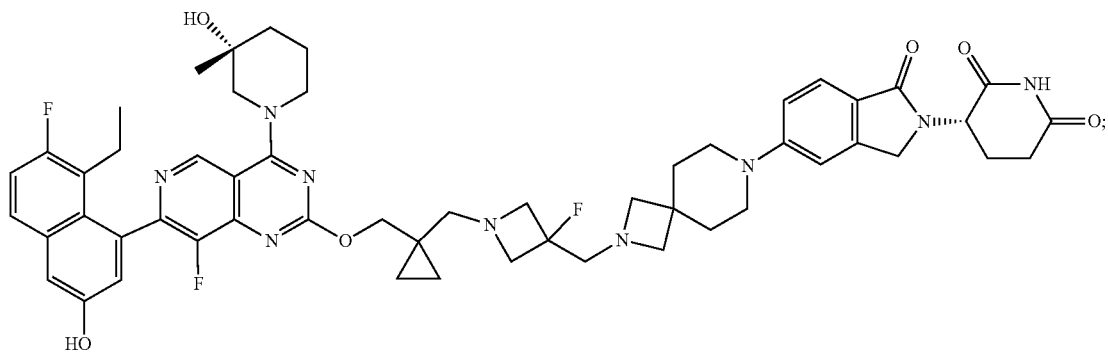
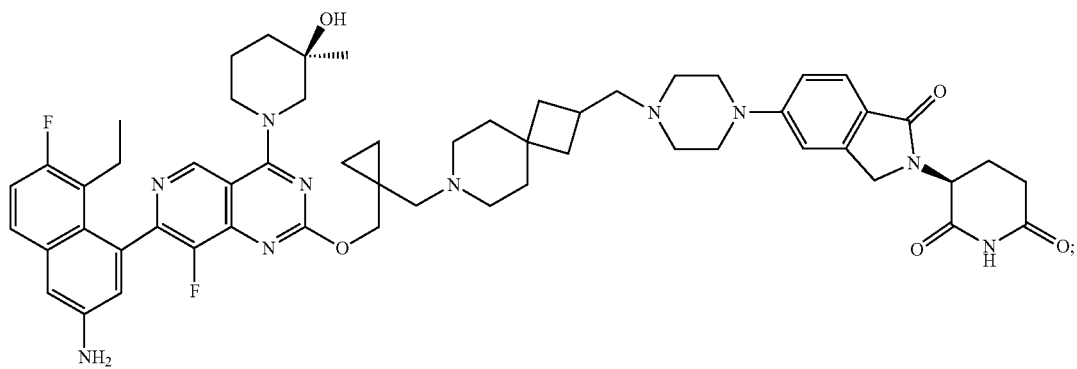
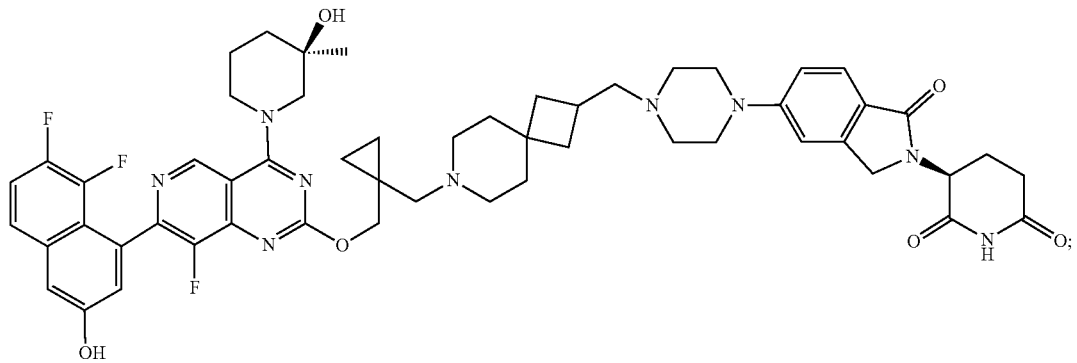

-continued
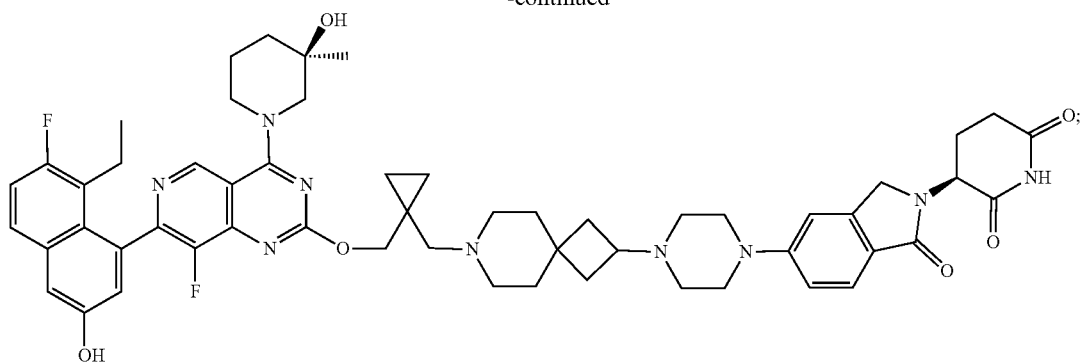
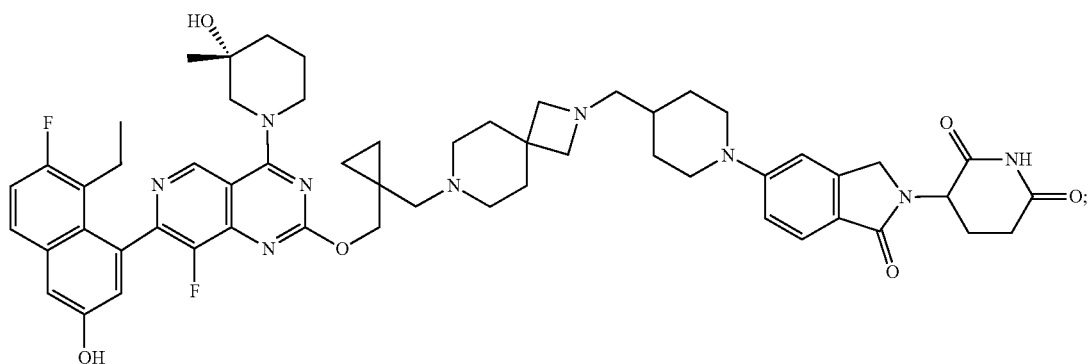
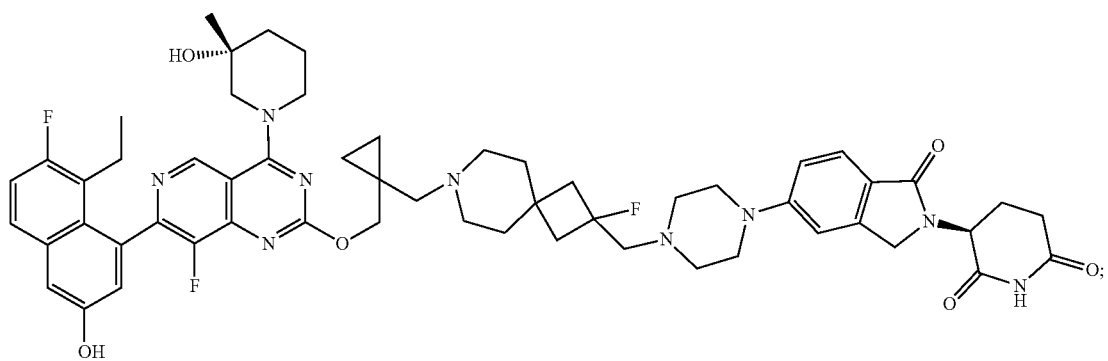
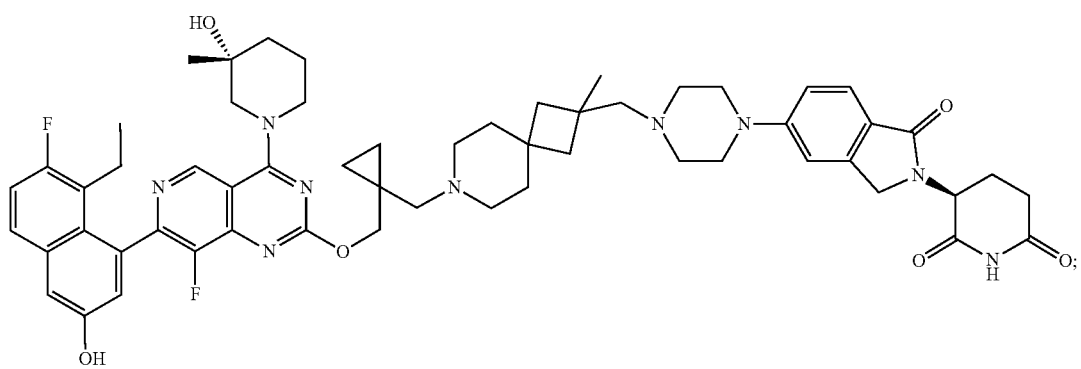

-continued
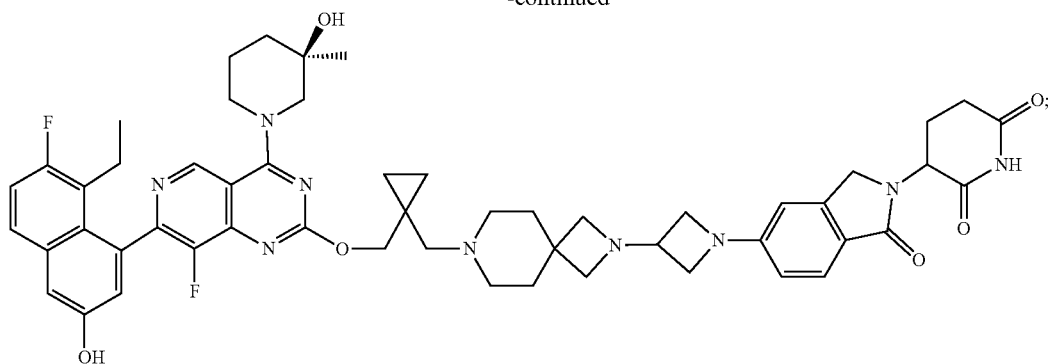
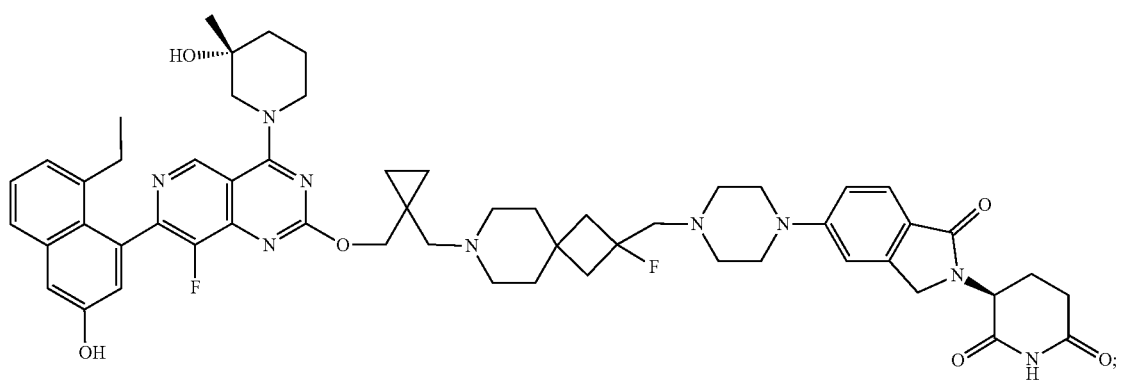
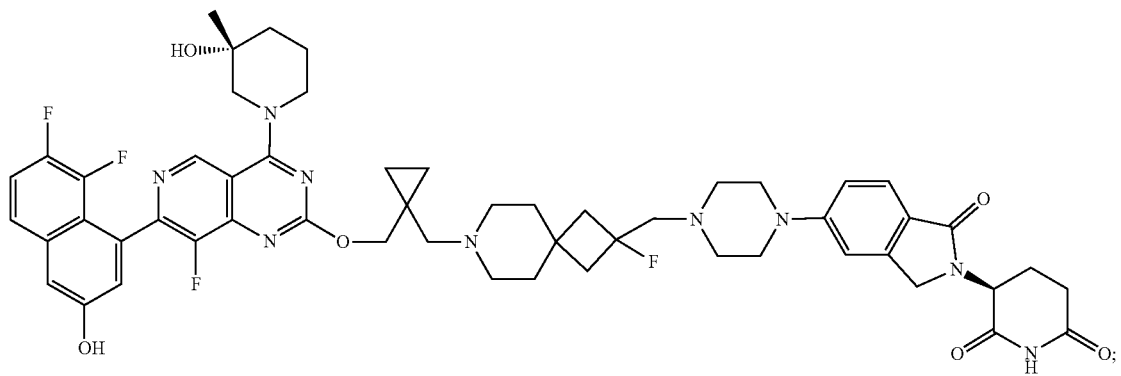
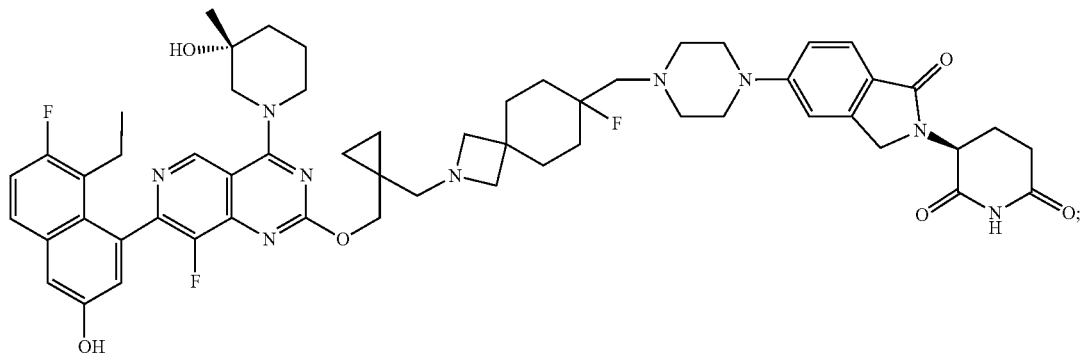

107 108
-continued
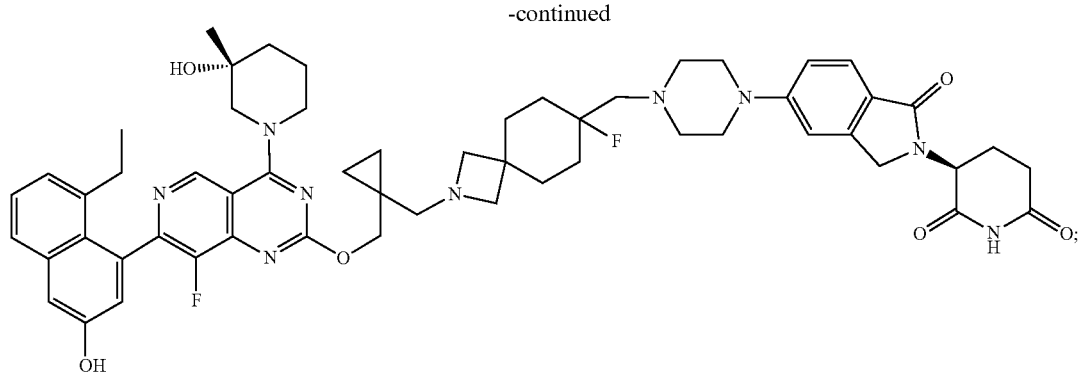
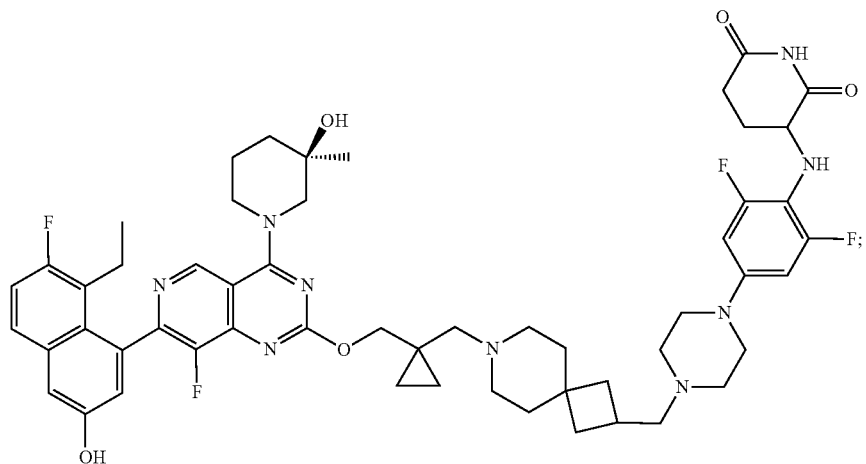
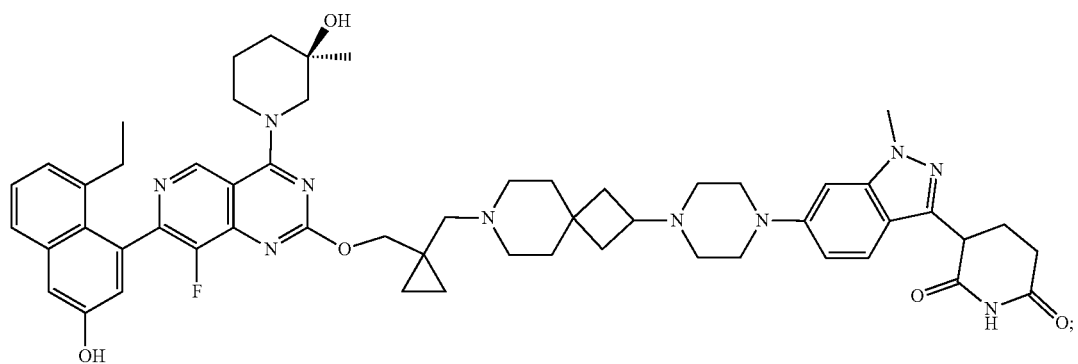
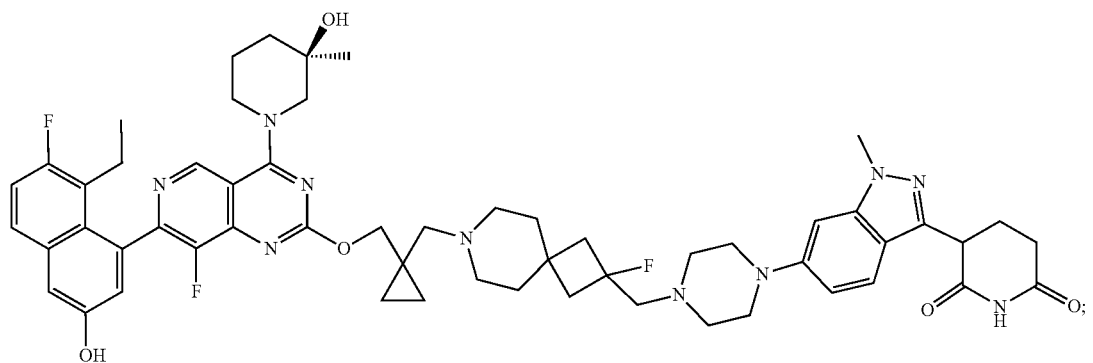

-continued
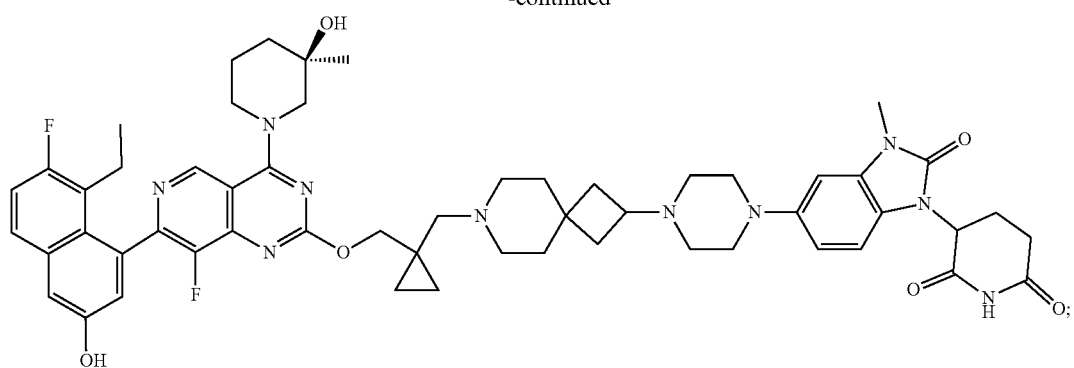
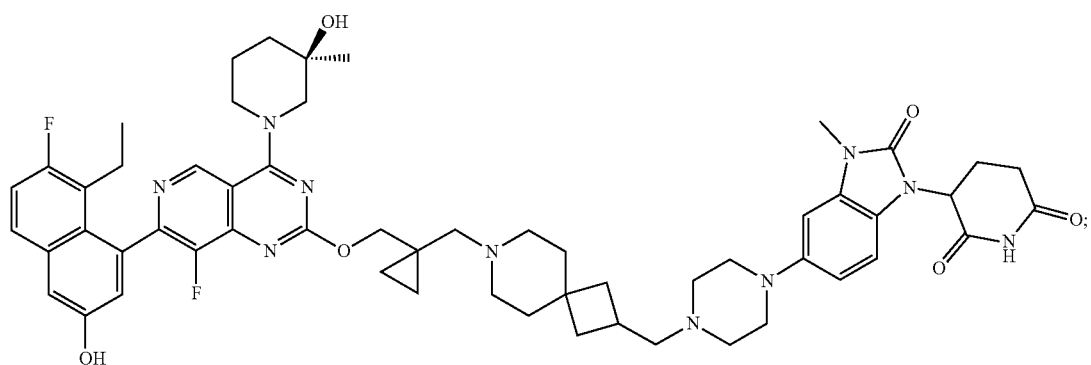
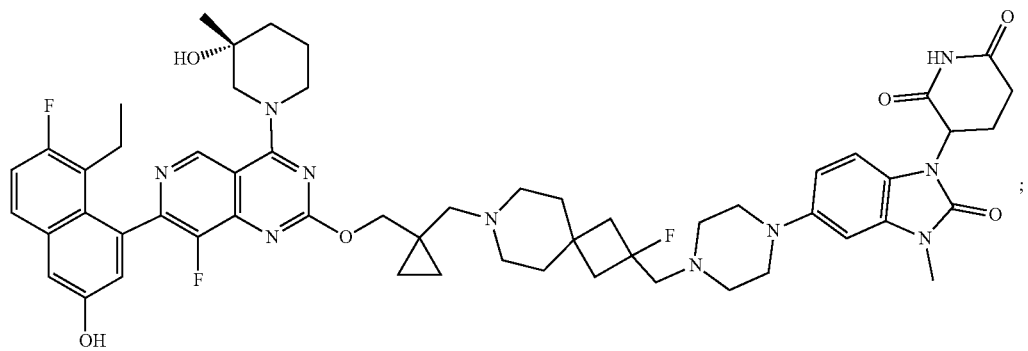
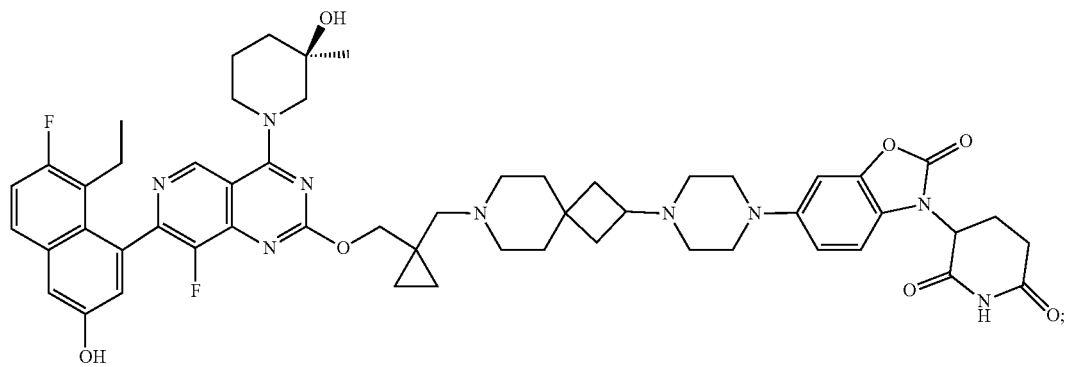

-continued
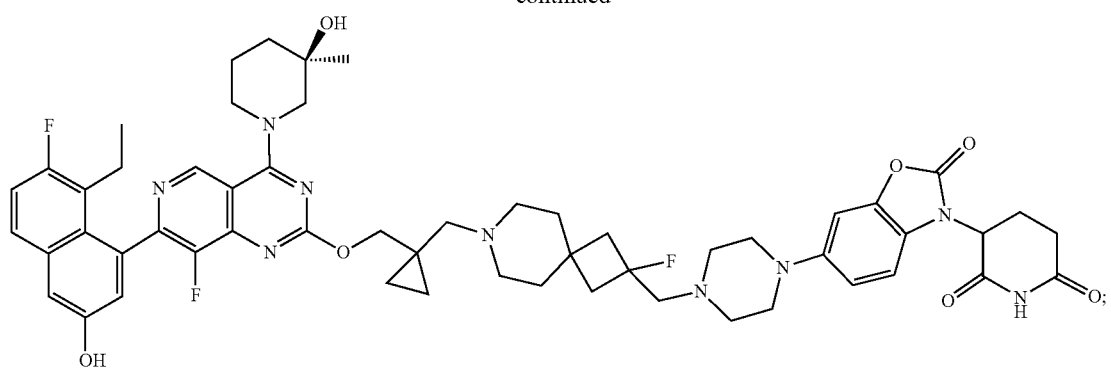
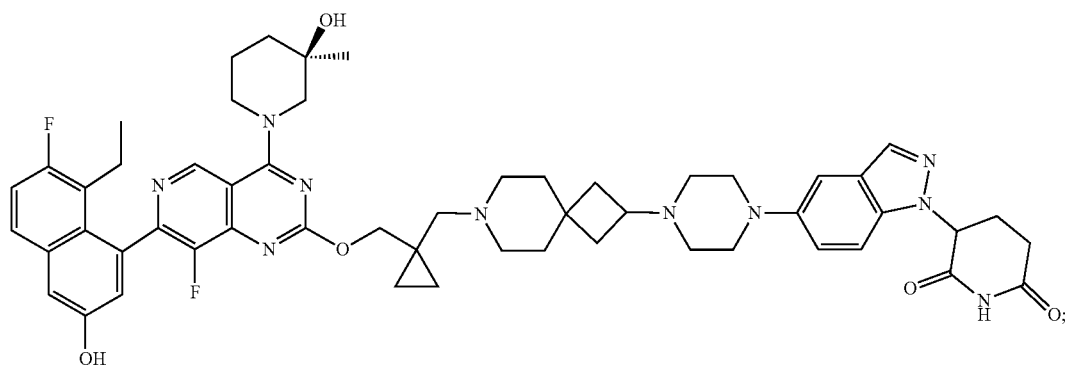
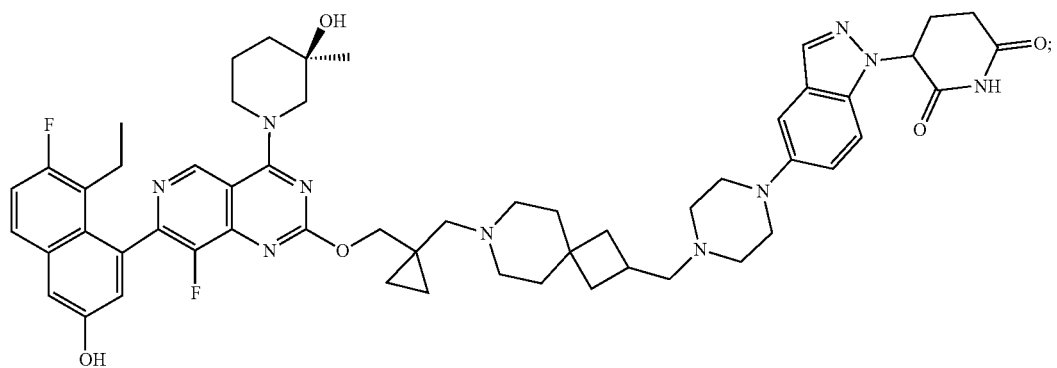
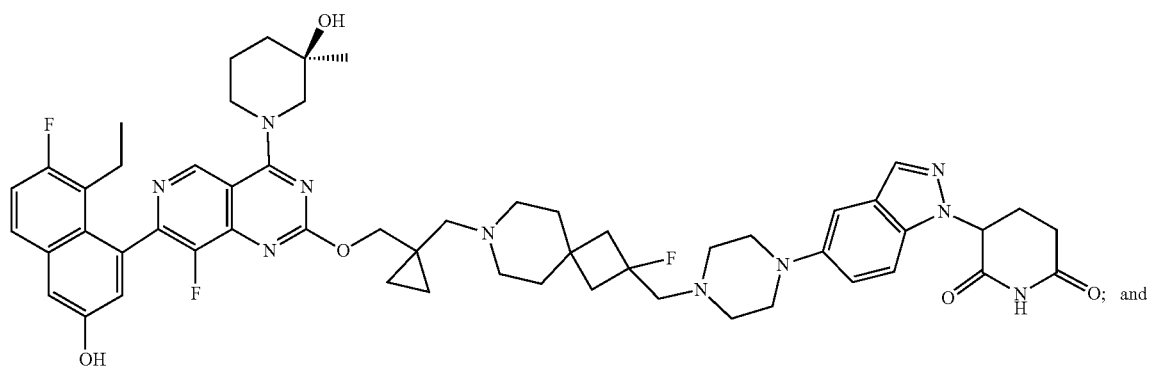
and

-continued

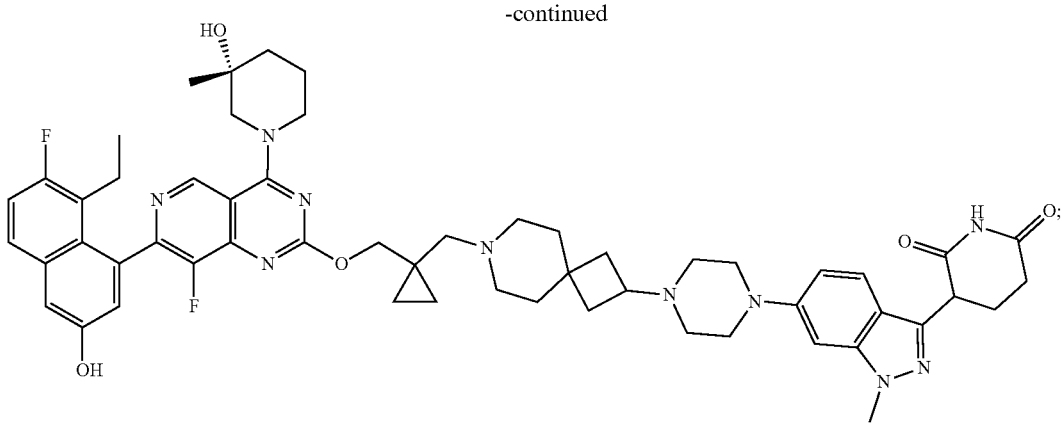

or a pharmaceutically acceptable salt thereof.

Embodiment 11. A compound, wherein the compound is represented by Formula IC or is a pharmaceutically acceptable salt thereof:

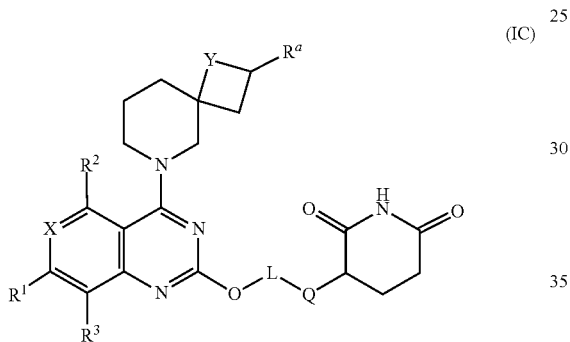

(IC)

wherein:
each $R^a$ is independently selected from H, halogen, cyano, hydroxy, and $C_1$-$C_6$ alkyl;
$R^1$ is a monocyclic or bicyclic aryl or heteroaryl, wherein the monocyclic or bicyclic aryl and heteroaryl are independently substituted with 0, 1, 2, 3, or 4 $R^b$; each $R^b$ is independently selected from halogen, cyano, hydroxy, amino, and $C_1$-$C_4$ alkyl;
X is N;
Y is O or $CH_2$;
$R^2$ is H or halogen;
$R^3$ is halogen;
L is a linker with a backbone of 1 to 20 carbon atoms in length, wherein one or more carbon atoms are optionally substituted with halogen, alkylamino, hydroxy, cyano, $CFH_2$, $CF_2H$, $CF_3$, $C_1$-$C_5$ alkyl, an oxo group, $C_1$-$C_3$ haloalkyl, $C_1$-$C_4$ alkoxy, or amide, wherein one to eight carbon atoms of the backbone are optionally replaced by a divalent group independently selected from oxygen, cycloalkyl, monocyclic heterocyclic group, bridged heterocyclic group, spiro heterocyclic group, heterocyclyl, aryl, heteroaryl fused heterocyclyl, and heteroaryl, and wherein each of the cycloalkyl, monocyclic heterocyclic group, bridged heterocyclic group, spiro heterocyclic group, heteroaryl, heteroaryl fused heterocyclyl, heterocyclyl, aryl, or heteroaryl is independently substituted with 0, 1, or 2 $R^e$;

each $R^e$ is independently selected from halogen, cyano, hydroxy, $C_1$-$C_4$ alkyl, $C_1$-$C_4$ alkenyl, $C_3$-$C_5$ cycloalkyl, $C_1$-$C_4$ haloalkyl, and $C_1$-$C_4$ alkoxy;

Q is 1 to 5 carbon atoms in length, wherein one or more carbon atoms are replaced by a divalent group selected from heterocyclyl, aryl, heteroaryl, —NH—, —C(=O)—, and —C(=O)—NH—, and wherein each of the heterocyclyl, aryl, and heteroaryl is independently substituted with 0, 1, 2, 3, 4, or 5 $R^f$, and each $R^f$ is independently selected from halogen, hydroxy, $C_1$-$C_3$ alkyl, $C_1$-$C_3$ haloalkyl, $C_1$-$C_5$ alkoxy, and an oxo group.

Embodiment 12. The compound of embodiment 11, wherein Q is selected from

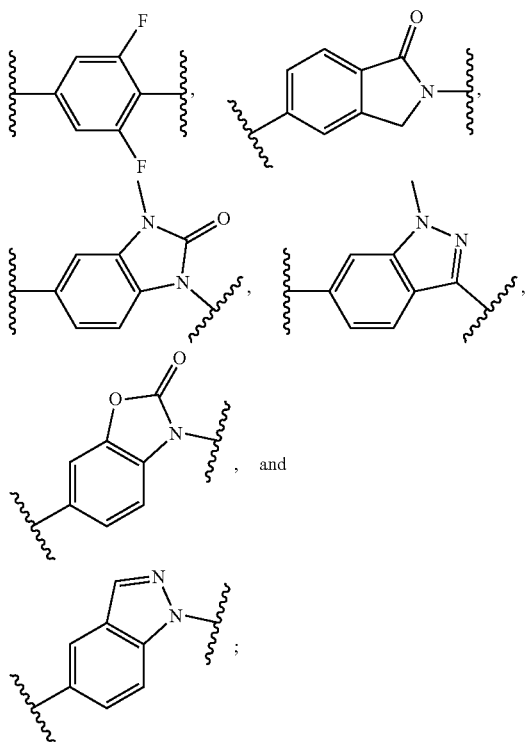

, and and
L is selected from
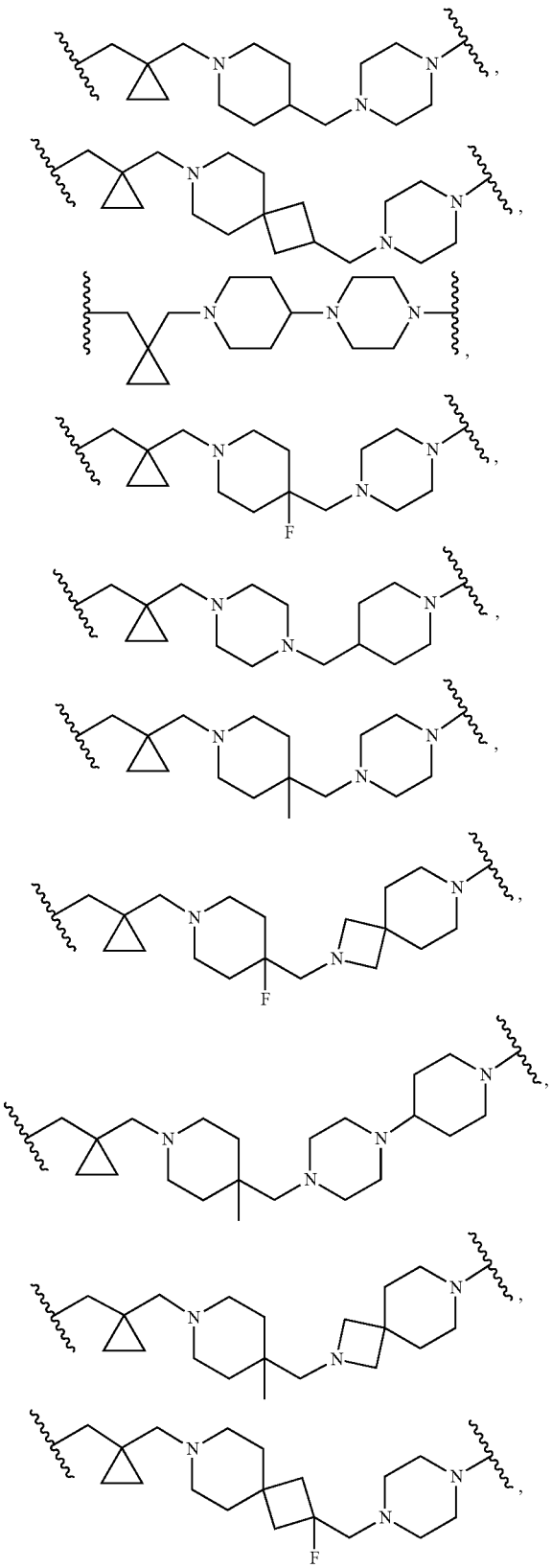
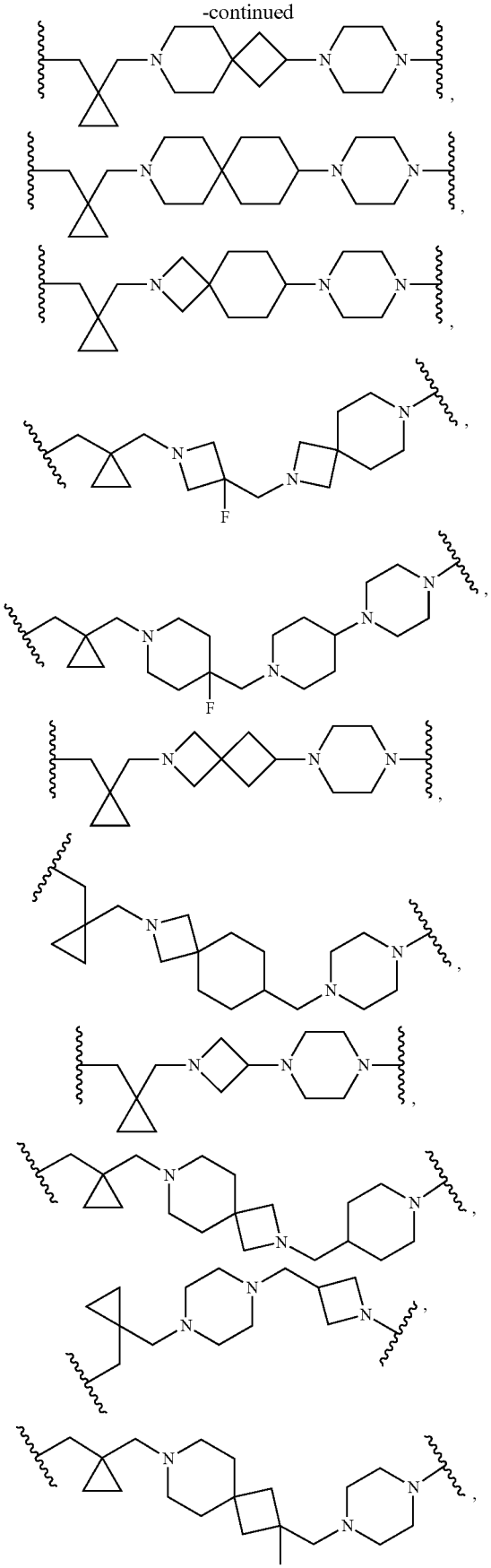

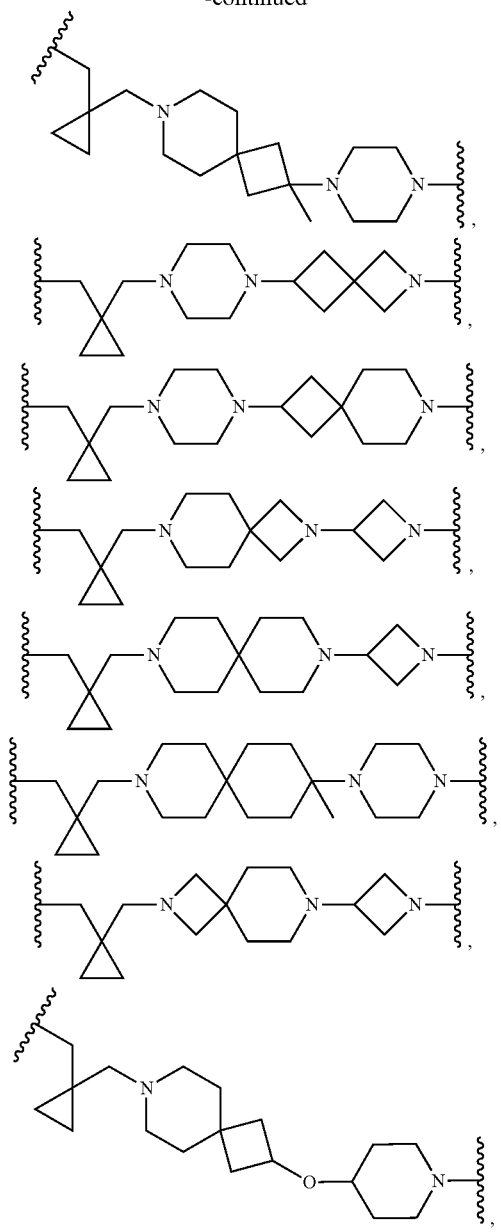
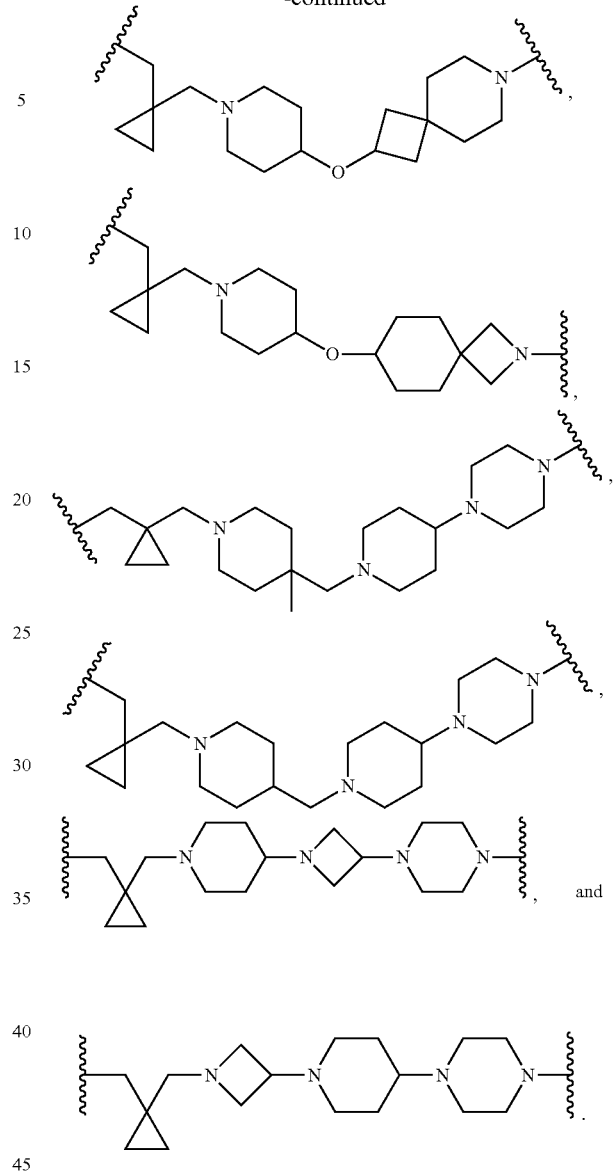
Embodiment 13. The compound of embodiment 11, wherein the compound is selected from
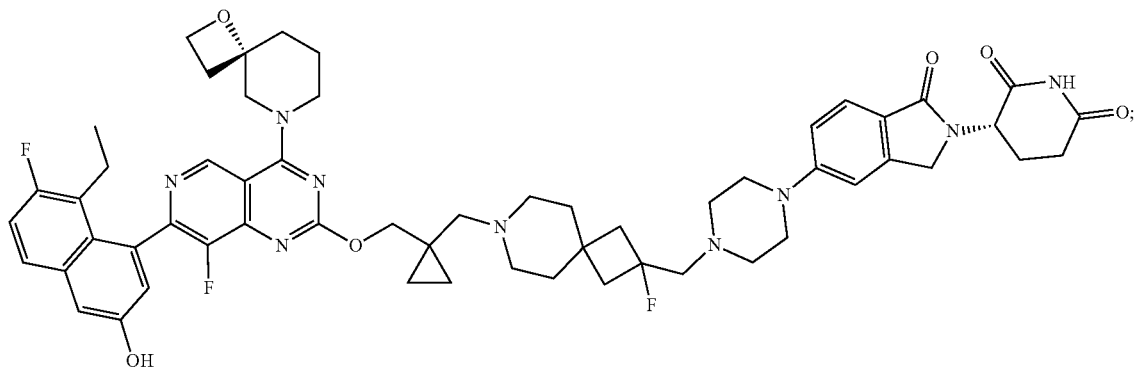

-continued
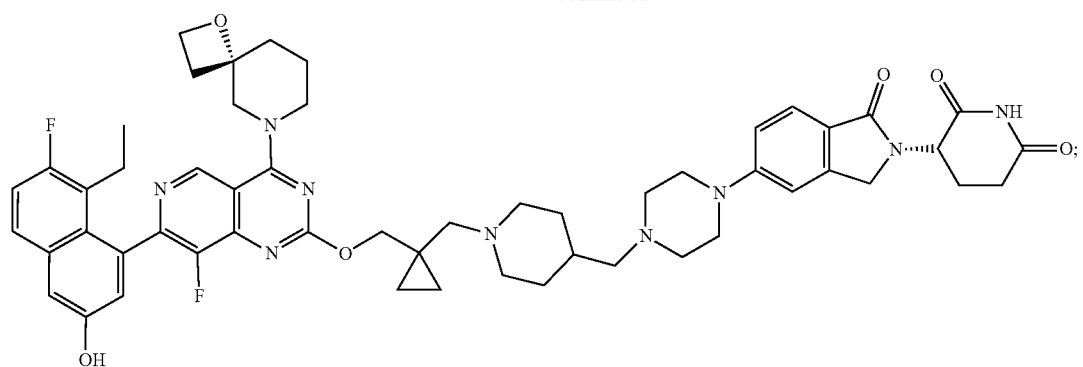
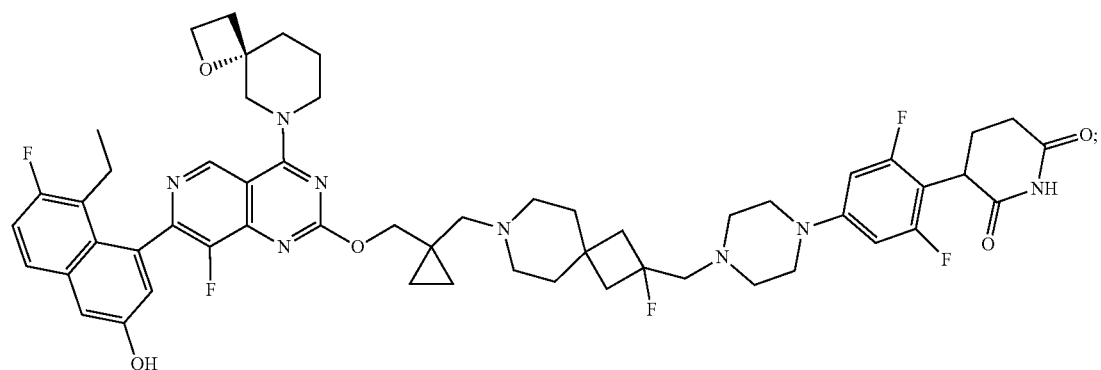
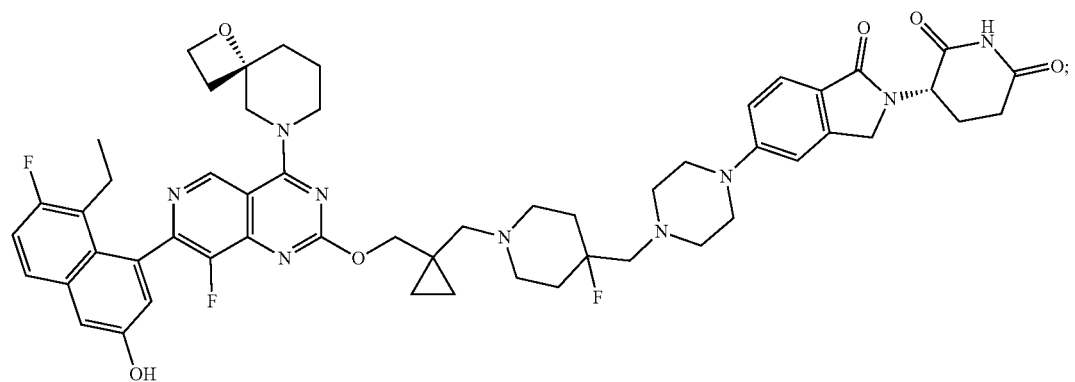
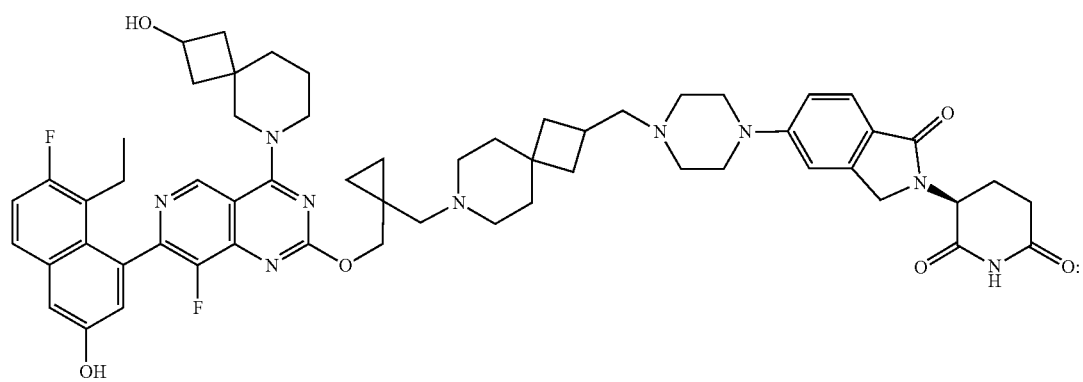

-continued
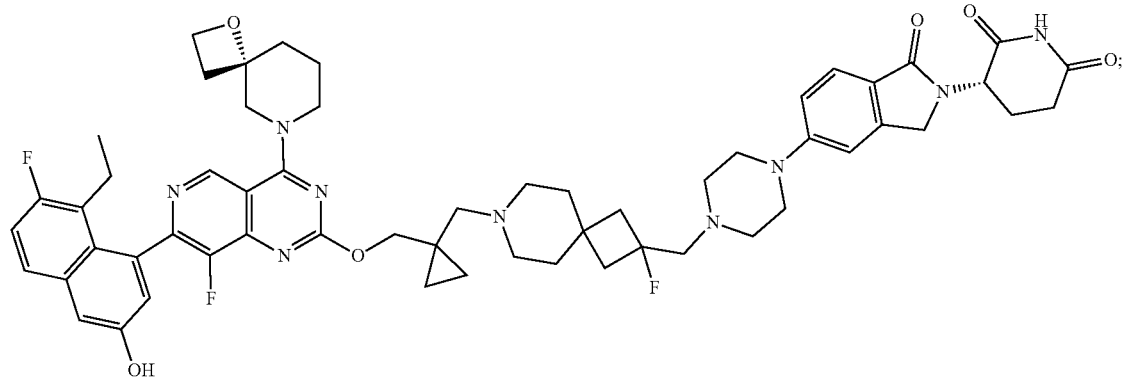
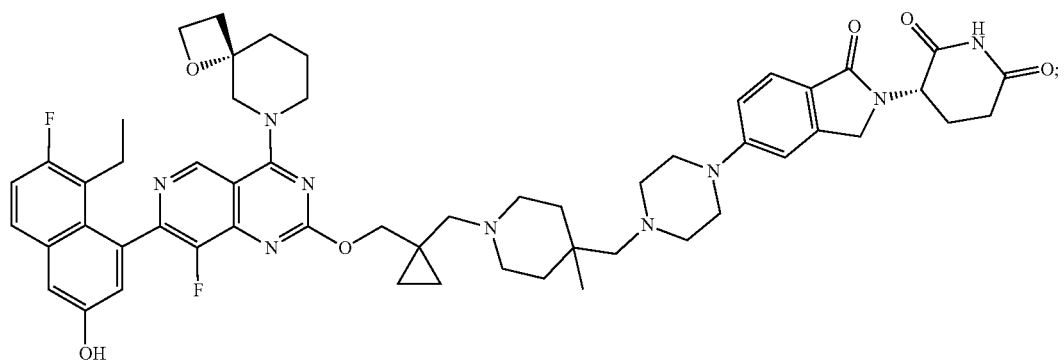
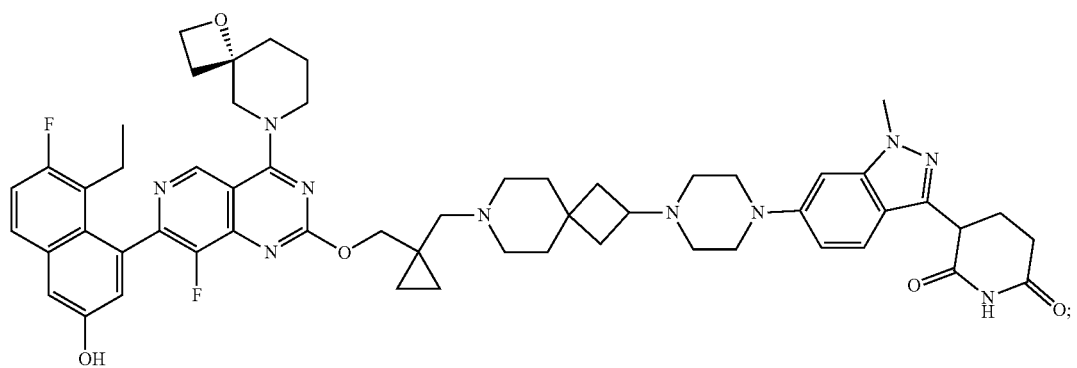
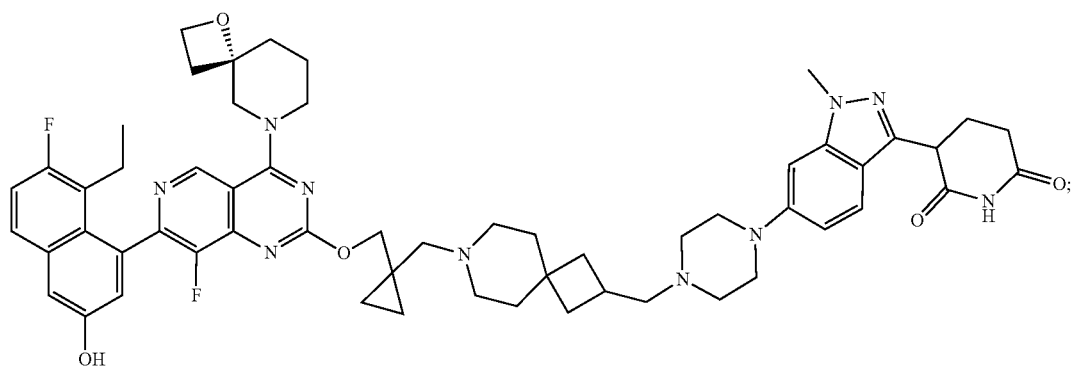

-continued
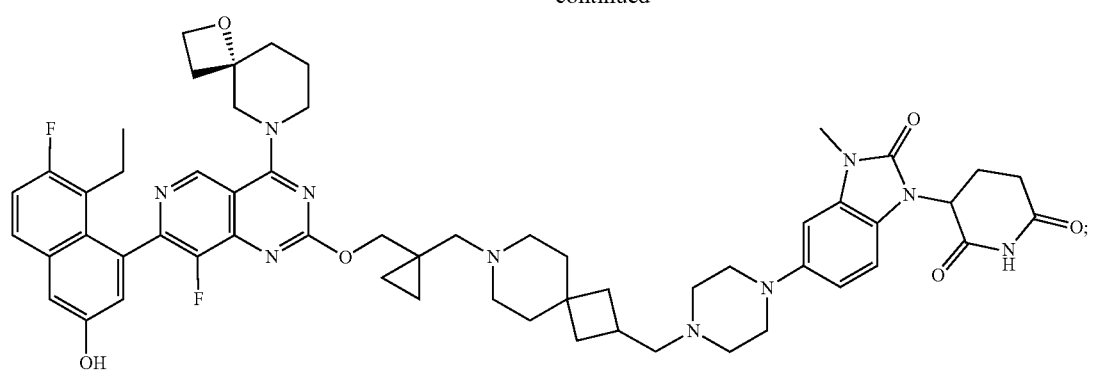
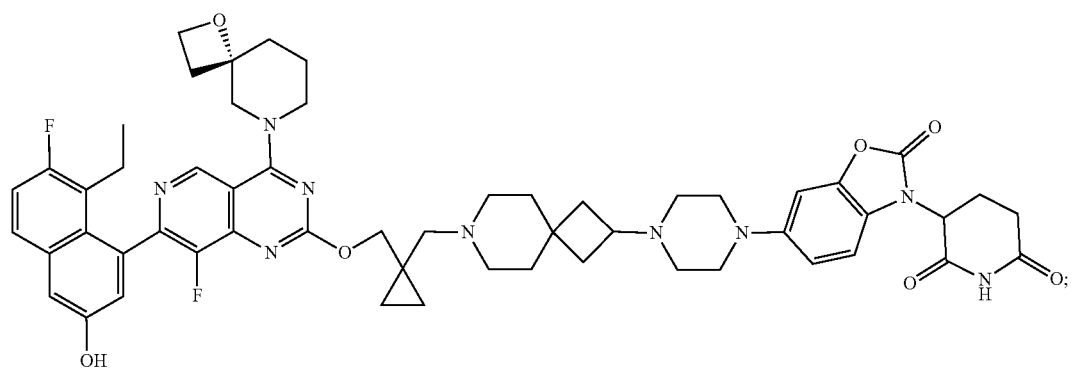
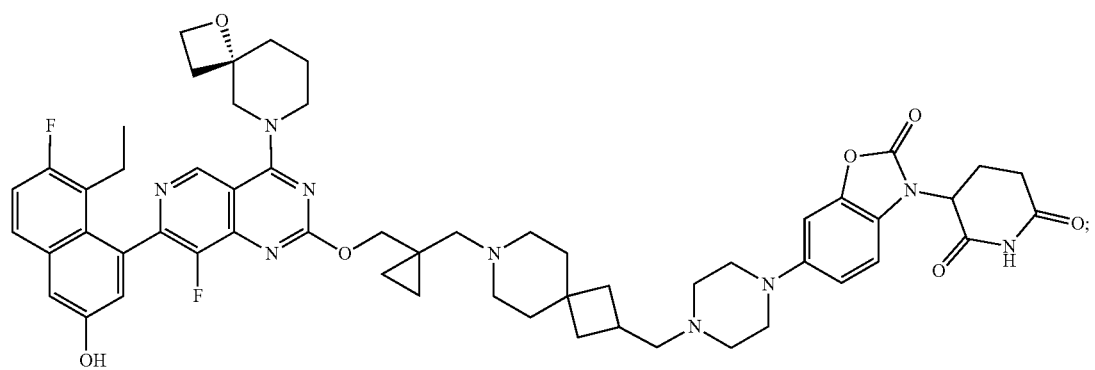
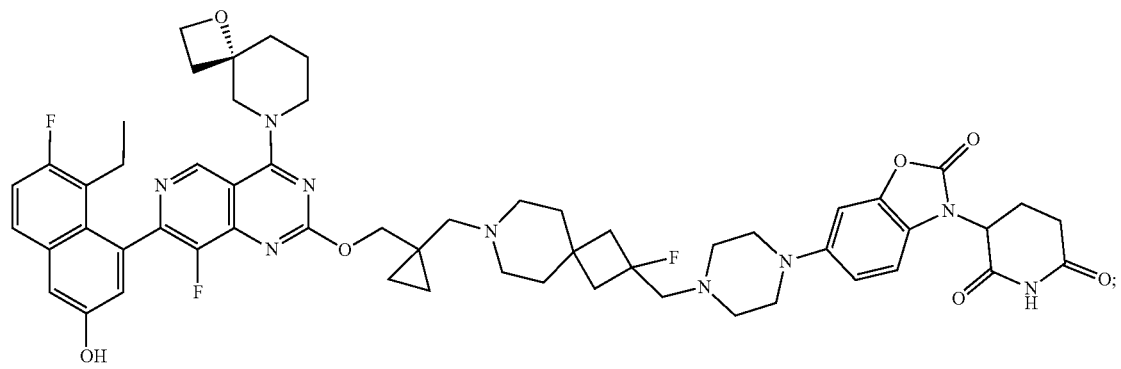

-continued
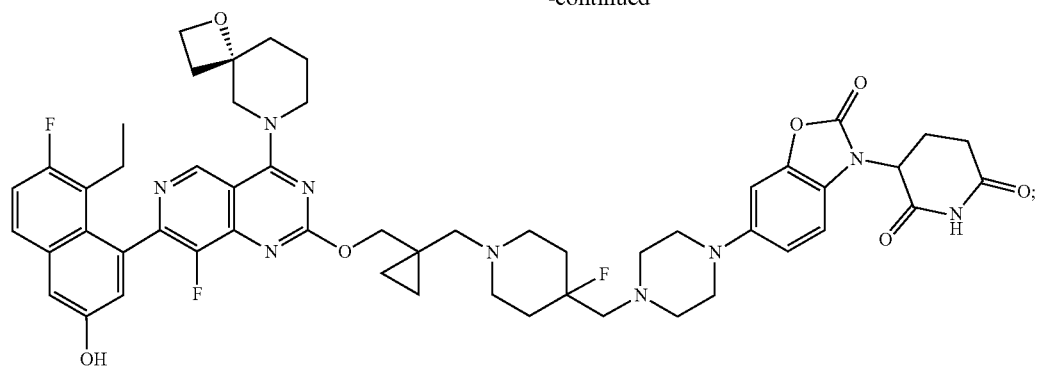
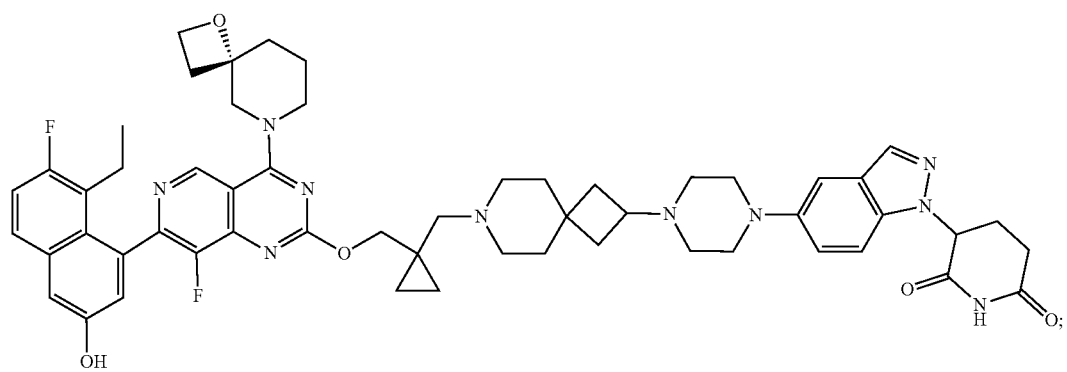
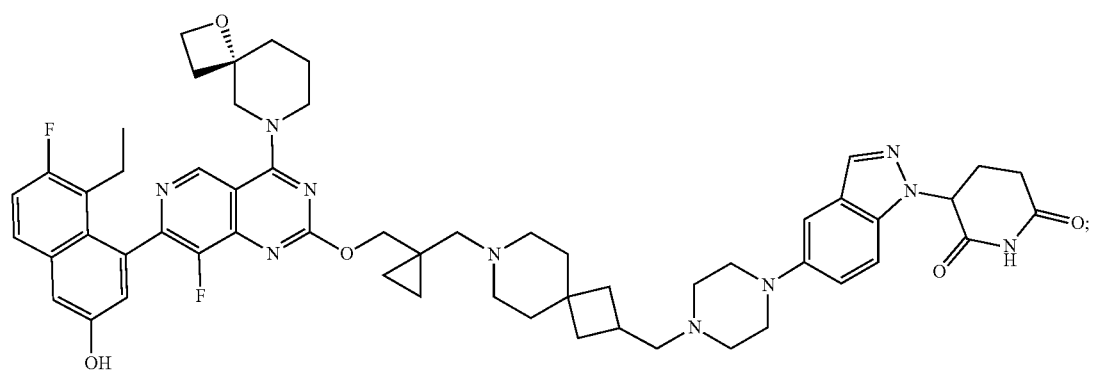
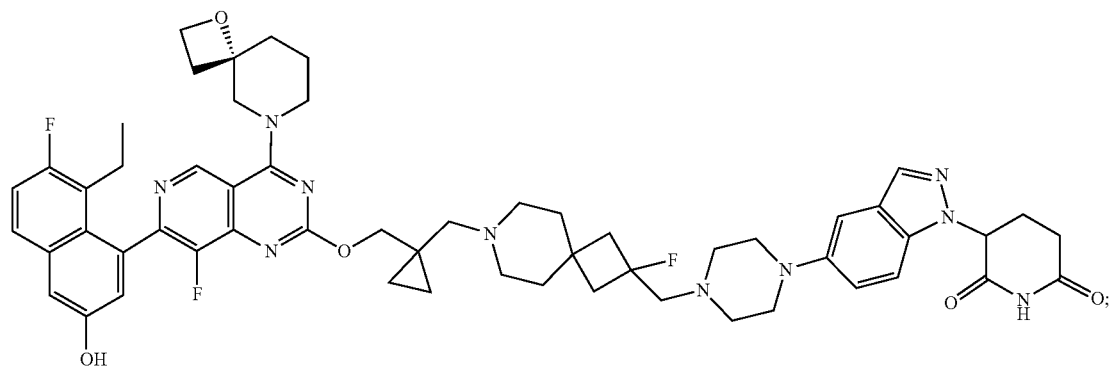

-continued

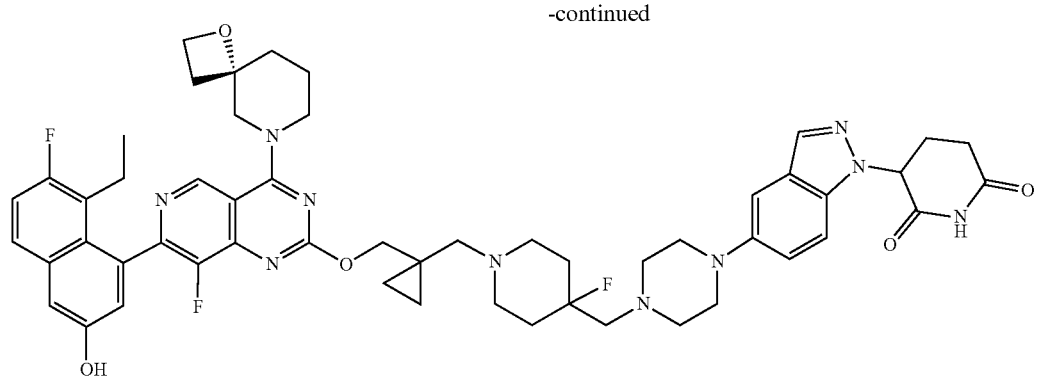

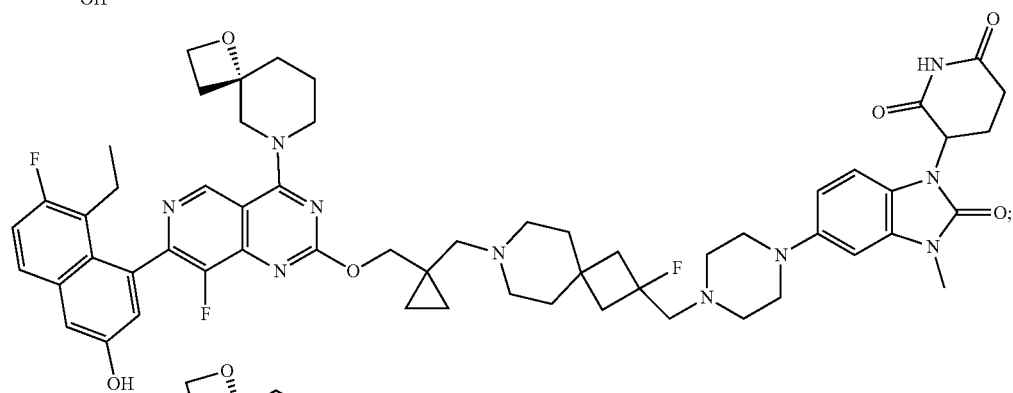

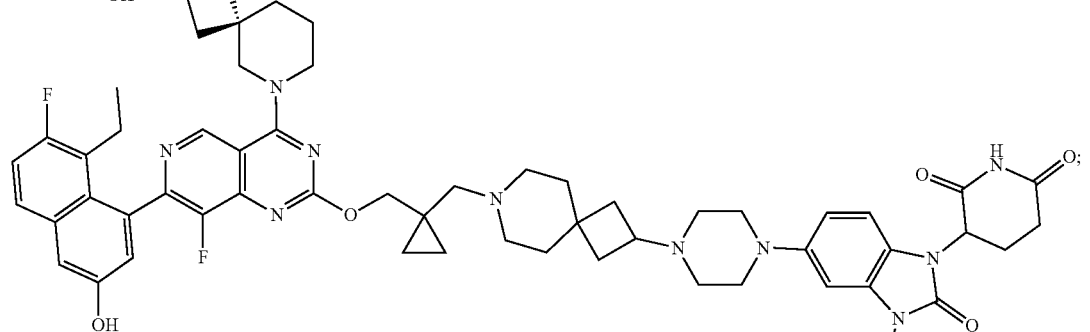

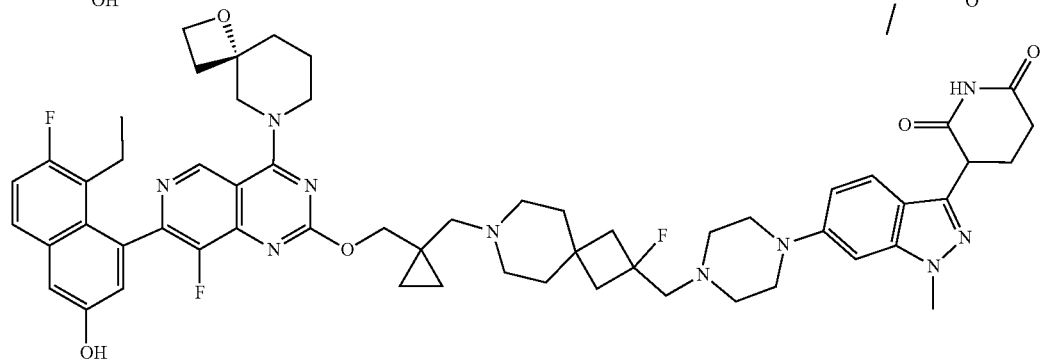

or a pharmaceutically acceptable salt thereof.

Embodiment 14. A pharmaceutical composition comprising a therapeutically effective amount of a compound according to any one of embodiments 1-10 and one or more pharmaceutically acceptable carriers, pharmaceutically acceptable vehicles, pharmaceutically acceptable excipients, or combinations thereof.

Embodiment 15. A method for degrading KRAS in a cell, comprising contacting the cell with at least one compound according to any one of embodiments 1-10.

Embodiment 16. The method of embodiment 15, wherein the KRAS is a mutant (preferably the KRAS mutant is KRAS G12V, KRAS G12D, KRAS G12C, and/or KRAS G12S).

Embodiment 17. A method of treating cancer in a subject in need thereof, comprising administering to the subject an effective amount of at least one compound according to any one of embodiments 1-10 or a pharmaceutical composition according to embodiment 14.

Embodiment 18. The method of embodiment 17, wherein the cancer is selected from lung cancer, pancreatic cancer, small bowel cancer, colorectal cancer, gall bladder cancer, thyroid cancer, liver cancer, bile duct cancer, cervical cancer, bladder cancer, prostate cancer, esophageal cancer, and blood cancer.

Embodiment 19. A method of treating cancer in a patient in need thereof, the method comprising (a) determining that the cancer is associated with one or more KRAS mutations; and (b) administering to the patient a therapeutically effective amount of the compound according to any one of embodiments 1-10 or a pharmaceutical composition according to embodiment 14.

Embodiment 20. A method of treating cancer associated with one or more KRAS mutations in a patient in need thereof, comprising administering to the patient a therapeutically effective amount of the compound according to any one of embodiments 1-10 or the pharmaceutical composition according to embodiment 14.

Embodiment 21. A pharmaceutical composition comprising a therapeutically effective amount of a compound according to embodiment 12 or 13 and one or more pharmaceutically acceptable carriers, pharmaceutically acceptable vehicles, pharmaceutically acceptable excipients, or combinations thereof.

Embodiment 22. A method for degrading KRAS in a cell, comprising contacting the cell with at least one compound according to embodiment 12 or 13.

Embodiment 23. The method of embodiment 22, wherein the KRAS is a mutant (preferably the KRAS mutant is KRAS G12V, KRAS G12D, KRAS G12C, and/or KRAS G12S).

Embodiment 24. A method of treating cancer in a subject in need thereof, comprising administering to the subject an effective amount of at least one compound according to embodiment 12 or 13.

Embodiment 25. A method of treating cancer in a patient in need thereof, the method comprising (a) determining that the cancer is associated with one or more KRAS mutations; and (b) administering to the patient a therapeutically effective amount of the compound according to embodiment 12 or 13.

Embodiment 26. A method of treating cancer associated with one or more KRAS mutations in a patient in need thereof, comprising administering to the patient a therapeutically effective amount of the compound according to embodiment 12 or 13.

Embodiment 27. The method of embodiment 26, wherein the cancer is selected from selected from lung cancer, pancreatic cancer, small bowel cancer, colorectal cancer, gall bladder cancer, thyroid cancer, liver cancer, bile duct cancer, cervical cancer, bladder cancer, prostate cancer, esophageal cancer, and blood cancer.

In some embodiments, provided herein is a compound chosen from the compounds listed in Table 1 or a tautomer, stereoisomer or a mixture of stereoisomers, or a pharmaceutically acceptable salt, or hydrate, or deuterated derivative of any of the foregoing.

TABLE 1

Exemplary Compounds of the Present Disclosure

| Cpd # | Structure and IUPAC Name |
|---|---|
| 1 | 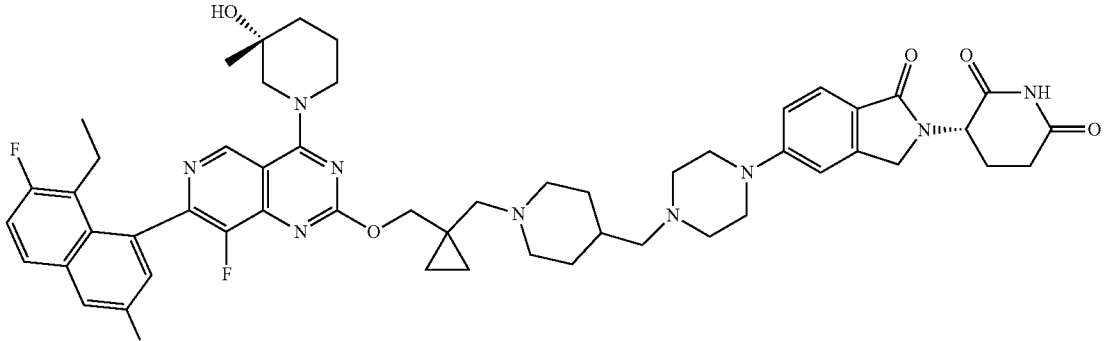<br>(S)-3-(5-(4-((1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione |
| 2 | 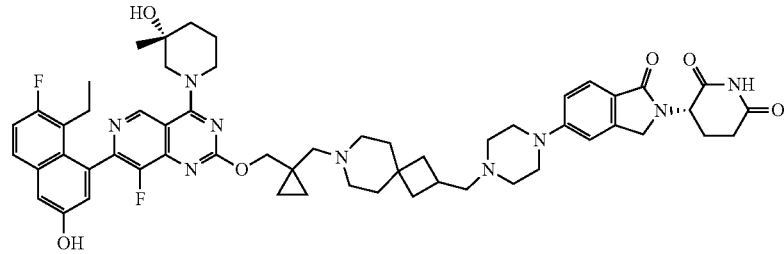 [SMILES: CCc1c(F)ccc2cc(O)cc(-c3ncc4c(N5CCC[C@@](C)(O)C5)nc(OCC5(CN6CCC7(CC6)CC(CN6CCN(c8ccc9c(c8)CN([C@H]8CCC(=O)NC8=O)C9=O)CC6)C7)CC5)nc4c3F)c12]<br>(S)-3-(5-(4-((7-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |

TABLE 1-continued

Exemplary Compounds of the Present Disclosure

| Cpd # | Structure and IUPAC Name |
|---|---|
| 3 | 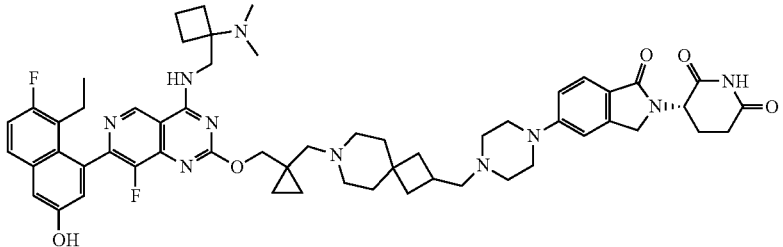 [SMILES: CCc1c(F)ccc2cc(O)cc(-c3ncc4c(NCC5(N(C)C)CCC5)nc(OCC5(CN6CCC7(CC6)CC(CN6CCN(c8ccc9c(c8)CN([C@H]8CCC(=O)NC8=O)C9=O)CC6)C7)CC5)nc4c3F)c12]<br>(S)-3-(5-(4-((7-((1-(((4-(((1-(dimethylamino)cyclobutyl)methyl)amino)-7-(8-ethyl-7-fluoro-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |
| 4 | 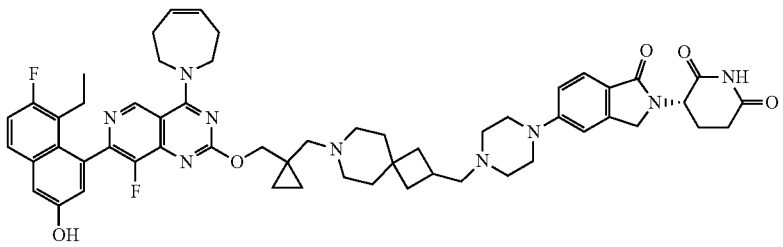 [SMILES: CCc1c(F)ccc2cc(O)cc(-c3ncc4c(N5CCC=CCC5)nc(OCC5(CN6CCC7(CC6)CC(CN6CCN(c8ccc9c(c8)CN([C@H]8CCC(=O)NC8=O)C9=O)CC6)C7)CC5)nc4c3F)c12]<br>(S)-3-(5-(4-((7-((1-(((7-(8-ethyl-7-fluoro-3-hydroxynaphthalen-1-yl)-8-fluoro-4-(2,3,6,7-tetrahydro-1H-azepin-1-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |
| 5 | 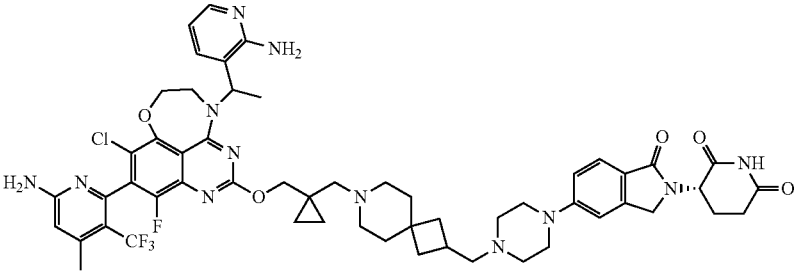 [SMILES: Cc1cc(N)nc(-c2c(Cl)c3c4c(nc(OCC5(CN6CCC7(CC6)CC(CN6CCN(c8ccc9c(c8)CN([C@H]8CCC(=O)NC8=O)C9=O)CC6)C7)CC5)nc4c2F)N(C(C)c2cccnc2N)CCO3)c1C(F)(F)F]<br>(3S)-3-(5-(4-((7-((1-(((9-(6-amino-4-methyl-3-(trifluoromethyl)pyridin-2-yl)-4-(1-(2-aminopyridin-3-yl)ethyl)-8-chloro-10-fluoro-5,6-dihydro-4H-[1,4]oxazepino[5,6,7-de]quinazolin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |
| 6 | 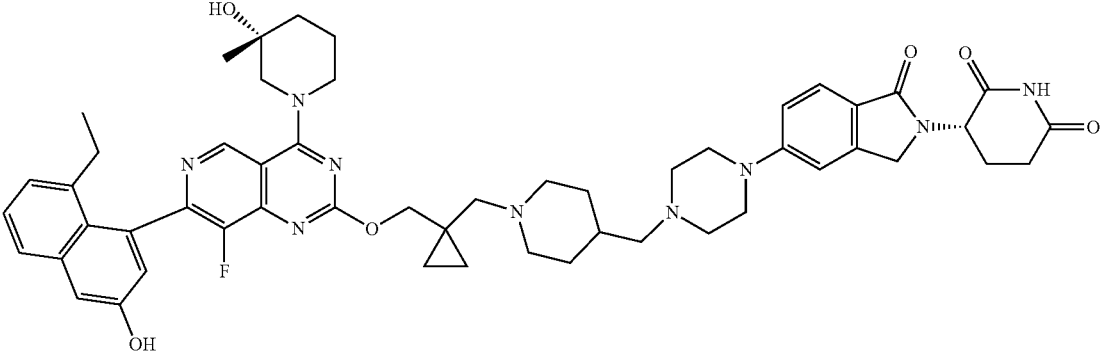 [SMILES: CCc1cccc2cc(O)cc(-c3ncc4c(N5CCC[C@@](C)(O)C5)nc(OCC5(CN6CCC(CN7CCN(c8ccc9c(c8)CN([C@H]8CCC(=O)NC8=O)C9=O)CC7)CC6)CC5)nc4c3F)c12]<br>(S)-3-(5-(4-((1-((1-(((7-(8-ethyl-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione |

TABLE 1-continued

Exemplary Compounds of the Present Disclosure

| Cpd # | Structure and IUPAC Name |
|---|---|
| 7 | 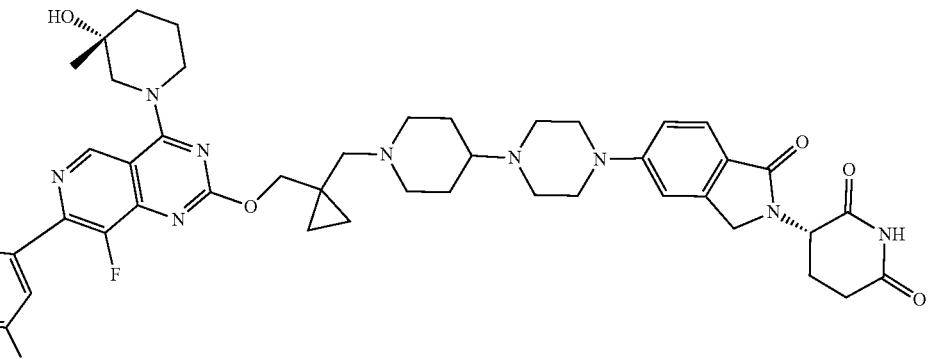<br>(S)-3-(5-(4-(1-(((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)piperazin-1-yl)-1-oxoisoindolin-2-yl)piperidine-2,6-dione |
| 8 | 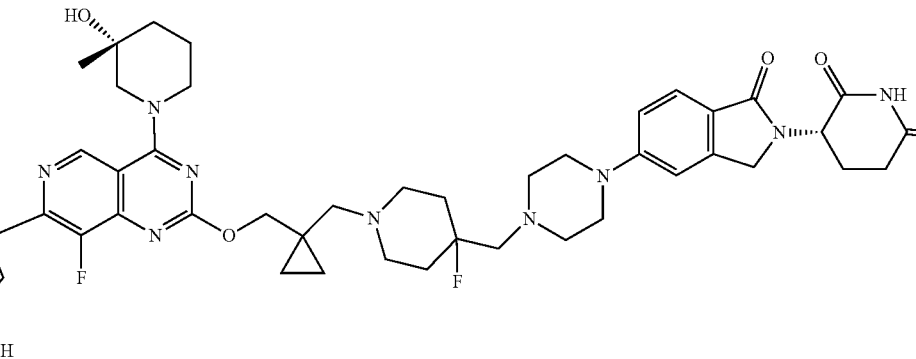<br>(S)-3-(5-(4-((1-(((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-4-fluoropiperidin-4-yl)methyl)piperazin-1-yl)-1-oxoisoindolin-2-yl)piperidine-2,6-dione |
| 9 | 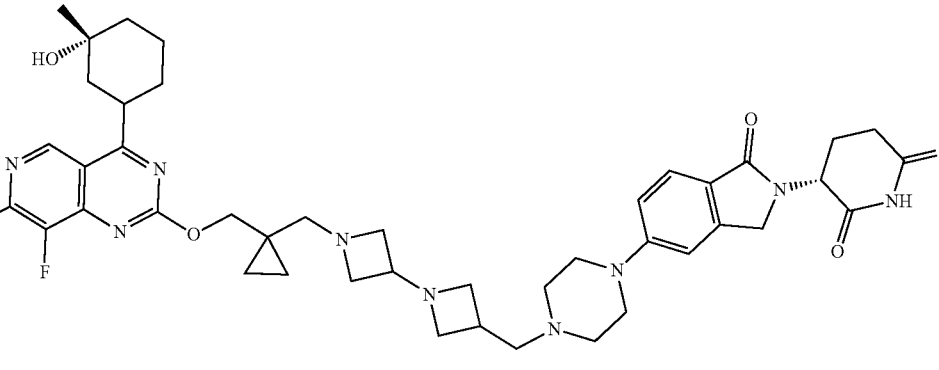<br>(R)-3-(5-(4-((1'-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-[1,3'-biazetidin]-3-yl)methyl)piperazin-1-yl)-1-oxoisoindolin-2-yl)piperidine-2,6-dione |

TABLE 1-continued

Exemplary Compounds of the Present Disclosure

| Cpd # | Structure and IUPAC Name |
|---|---|
| 10 | 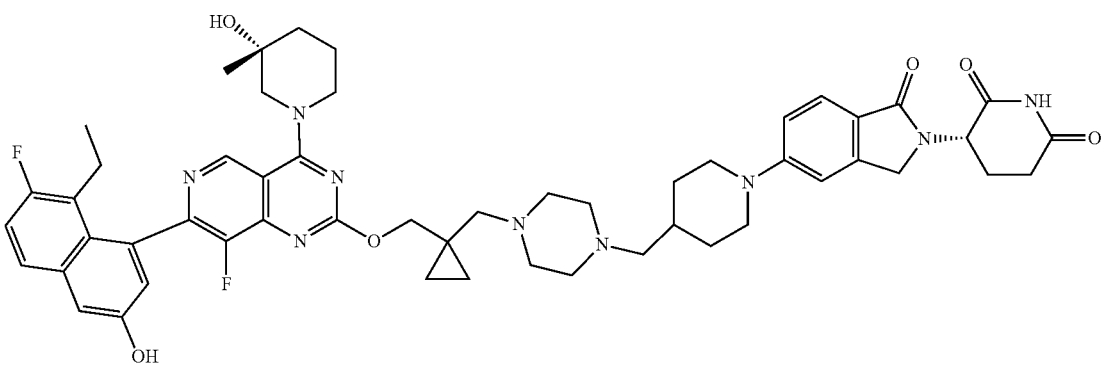 [SMILES: CCc1c(F)ccc2cc(O)cc(-c3ncc4c(N5CCC[C@@](C)(O)C5)nc(OCC5(CN6CCN(CC7CCN(c8ccc9c(c8)CN([C@H]8CCC(=O)NC8=O)C9=O)CC7)CC6)CC5)nc4c3F)c12]<br>(S)-3-(5-(4-((4-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperazin-1-yl)methyl)piperidin-1-yl)-1-oxoisoindolin-2-yl)piperidine-2,6-dione |
| 11 | 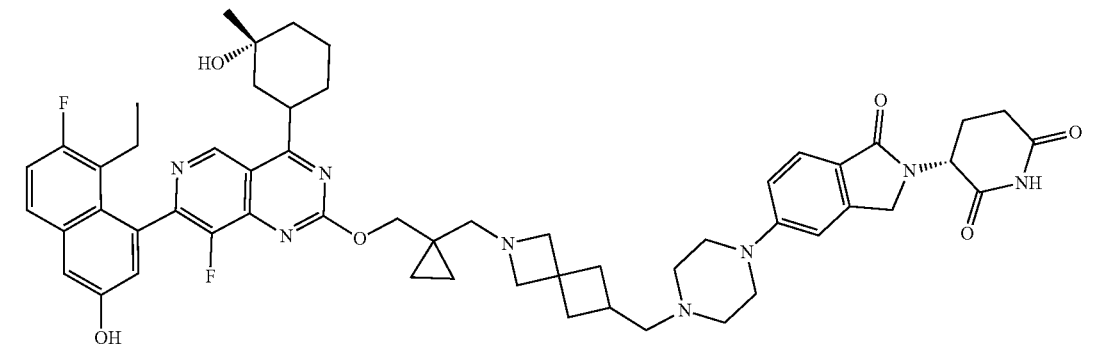 [SMILES: CCc1c(F)ccc2cc(O)cc(-c3ncc4c(C5CCC[C@@](C)(O)C5)nc(OCC5(CN6CC7(CC(CN8CCN(c9ccc%10c(c9)CN([C@@H]9CCC(=O)NC9=O)C%10=O)CC8)C7)C6)CC5)nc4c3F)c12]<br>(R)-3-(5-(4-((2-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-2-azaspiro[3.3]heptan-6-yl)methyl)piperazin-1-yl)-1-oxoisoindolin-2-yl)piperidine-2,6-dione |
| 12 | 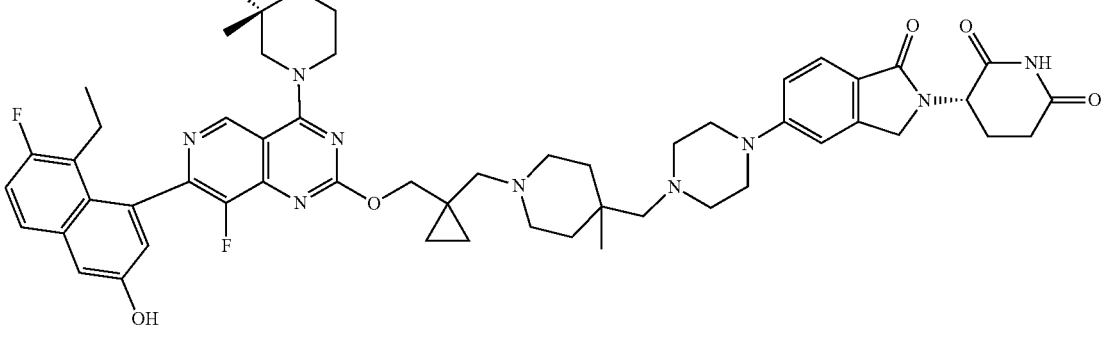<br>(S)-3-(5-(4-((1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-4-methylpiperidin-4-yl)methyl)piperazin-1-yl)-1-oxoisoindolin-2-yl)piperidine-2,6-dione |

TABLE 1-continued

Exemplary Compounds of the Present Disclosure

| Cpd # | Structure and IUPAC Name |
|---|---|
| 13 | 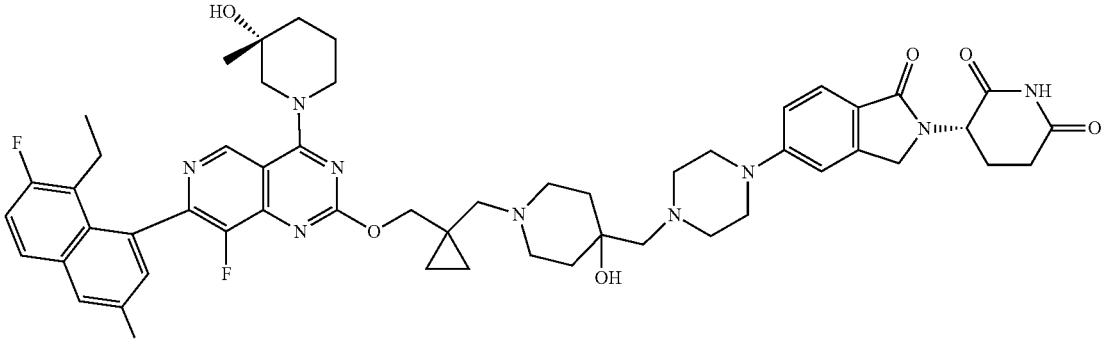

(S)-3-(5-(4-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-4-hydroxypiperidin-4-yl)methyl)piperazin-1-yl)-1-oxoisoindolin-2-yl)piperidine-2,6-dione |
| 14 | 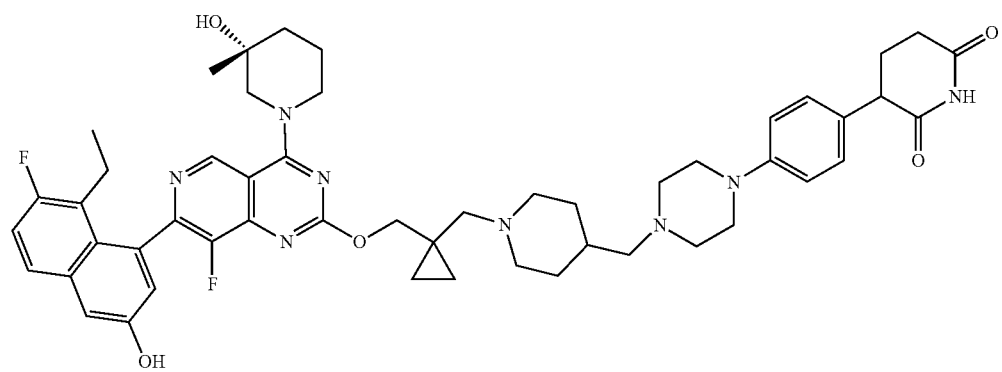 [SMILES: CCc1c(F)ccc2cc(O)cc(-c3ncc4c(N5CCC[C@@](C)(O)C5)nc(OCC5(CN6CCC(CN7CCN(c8ccc(C9CCC(=O)NC9=O)cc8)CC7)CC6)CC5)nc4c3F)c12]

3-(4-(4-((1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)methyl)piperazin-1-yl)phenyl)piperidine-2,6-dione |
| 15 | 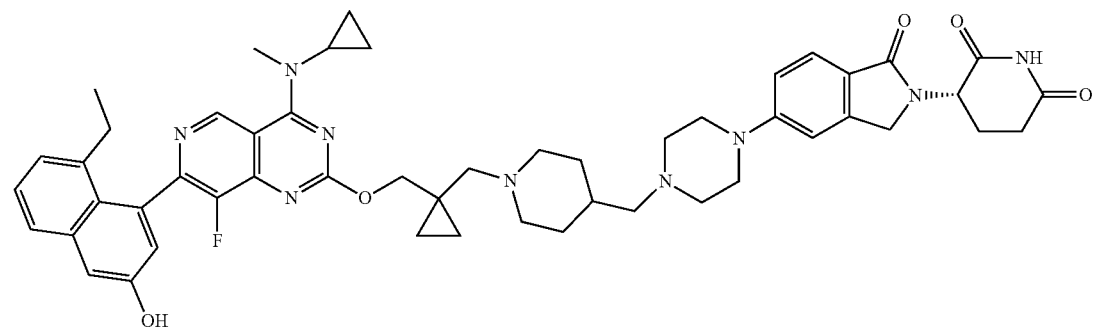 [SMILES: CCc1cccc2cc(O)cc(-c3ncc4c(N(C)C5CC5)nc(OCC5(CN6CCC(CN7CCN(c8ccc9c(c8)CN([C@H]8CCC(=O)NC8=O)C9=O)CC7)CC6)CC5)nc4c3F)c12]

(S)-3-(5-(4-((1-((1-(((4-(cyclopropyl(methyl)amino)-7-(8-ethyl-3-hydroxynaphthalen-1-yl)-8-fluoropyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione |

TABLE 1-continued

Exemplary Compounds of the Present Disclosure

| Cpd # | Structure and IUPAC Name |
|---|---|
| 16 | 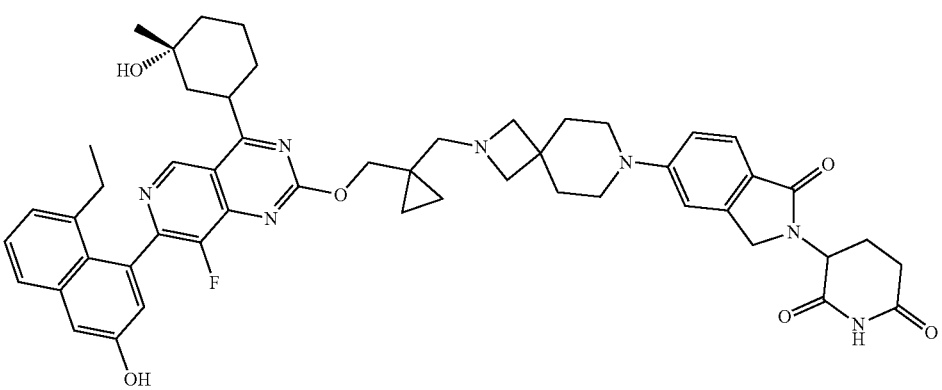 [SMILES: CCc1cccc2cc(O)cc(-c3ncc4c(C5CCC[C@@](C)(O)C5)nc(OCC5(CN6CC7(CCN(c8ccc9c(c8)CN(C8CCC(=O)NC8=O)C9=O)CC7)C6)CC5)nc4c3F)c12]<br>3-(5-(2-((1-(((7-(8-ethyl-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-2,7-diazaspiro[3.5]nonan-7-yl)-1-oxoisoindolin-2-yl)piperidine-2,6-dione |
| 17 | 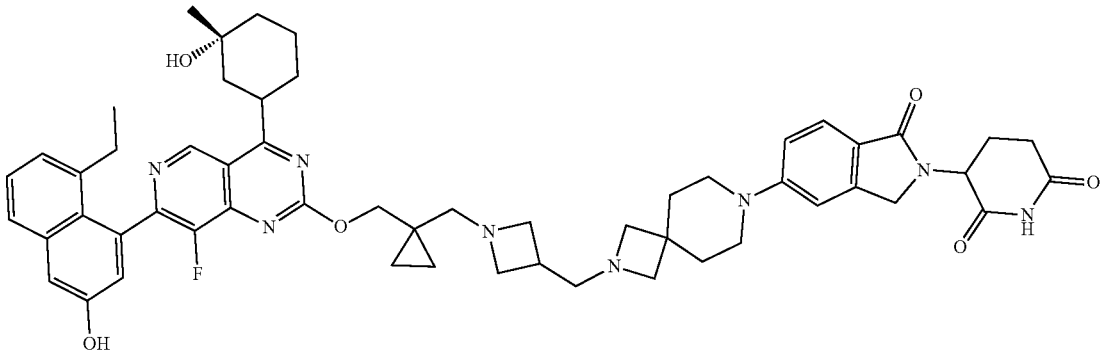 [SMILES: CCc1cccc2cc(O)cc(-c3ncc4c(C5CCC[C@@](C)(O)C5)nc(OCC5(CN6CC(CN7CC8(CCN(c9ccc%10c(c9)CN(C9CCC(=O)NC9=O)C%10=O)CC8)C7)C6)CC5)nc4c3F)c12]<br>3-(5-(2-((1-((1-(((7-(8-ethyl-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)azetidin-3-yl)methyl)-2,7-diazaspiro[3.5]nonan-7-yl)-1-oxoisoindolin-2-yl)piperidine-2,6-dione |
| 18 | 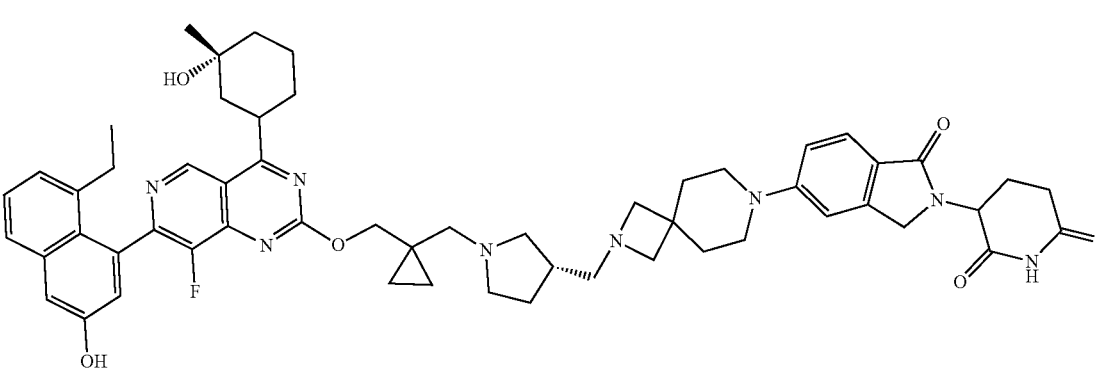<br>3-(5-(2-(((R)-1-((1-(((7-(8-ethyl-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)pyrrolidin-3-yl)methyl)-2,7-diazaspiro[3.5]nonan-7-yl)-1-oxoisoindolin-2-yl)piperidine-2,6-dione |

TABLE 1-continued

Exemplary Compounds of the Present Disclosure

| Cpd # | Structure and IUPAC Name |
|---|---|
| 19 | 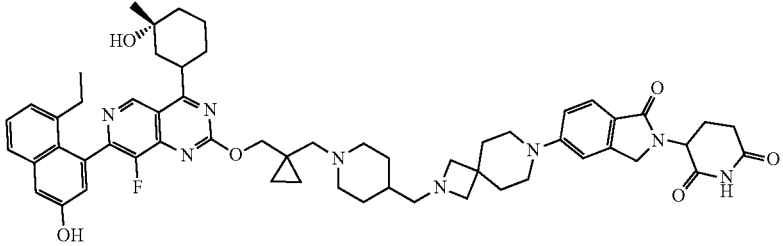 [SMILES: CCc1cccc2cc(O)cc(-c3ncc4c(C5CCC[C@@](C)(O)C5)nc(OCC5(CN6CCC(CN7CC8(CCN(c9ccc%10c(c9)CN(C9CCC(=O)NC9=O)C%10=O)CC8)C7)CC6)CC5)nc4c3F)c12]<br>3-(5-(2-((1-((1-(((7-(8-ethyl-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)methyl)-2,7-diazaspiro[3.5]nonan-7-yl)-1-oxoisoindolin-2-yl)piperidine-2,6-dione |
| 20 | 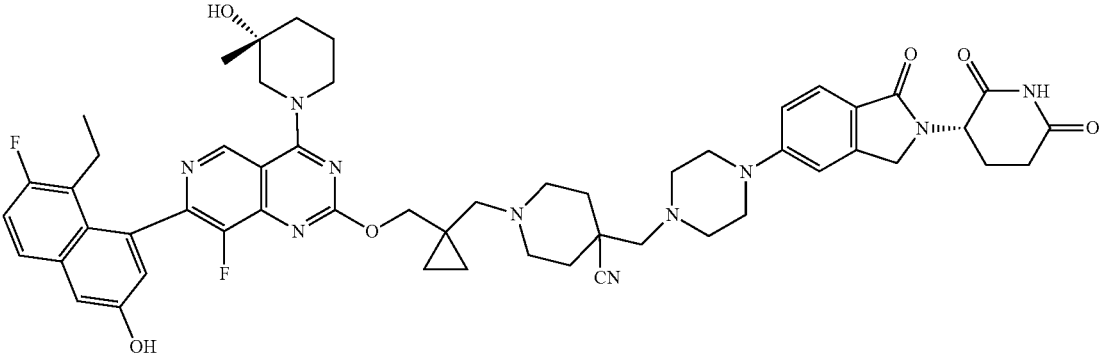<br>4-((4-(2-((S)-2,6-dioxopiperidin-3-yl)-1-oxoisoindolin-5-yl)piperazin-1-yl)methyl)-1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidine-4-carbonitrile |
| 21 | 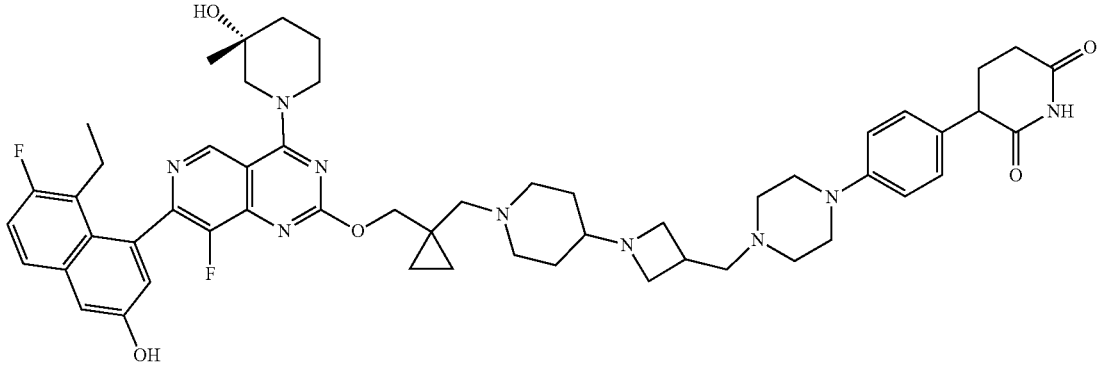 [SMILES: CCc1c(F)ccc2cc(O)cc(-c3ncc4c(N5CCC[C@@](C)(O)C5)nc(OCC5(CN6CCC(N7CC(CN8CCN(c9ccc(C%10CCC(=O)NC%10=O)cc9)CC8)C7)CC6)CC5)nc4c3F)c12]<br>3-(4-(4-((1-(1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)azetidin-3-yl)methyl)piperazin-1-yl)phenyl)piperidine-2,6-dione |

TABLE 1-continued

Exemplary Compounds of the Present Disclosure

| Cpd # | Structure and IUPAC Name |
|---|---|
| 22 | 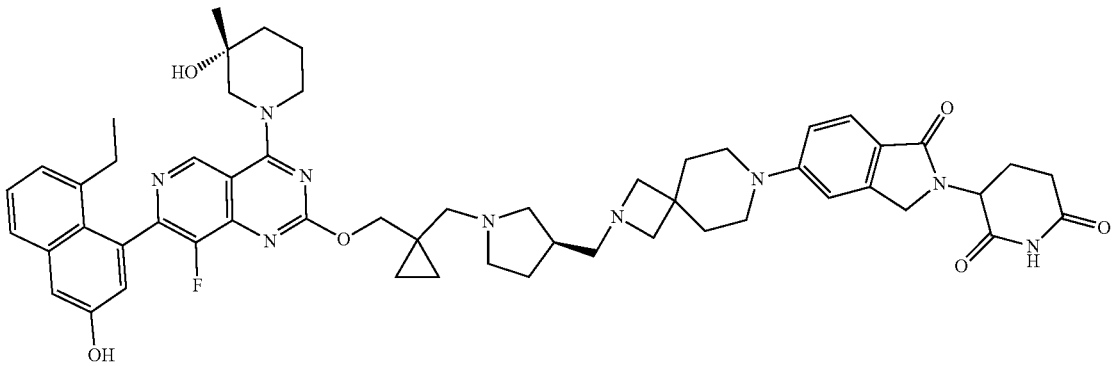 [SMILES: CCc1cccc2cc(O)cc(-c3ncc4c(N5CCC[C@@](C)(O)C5)nc(OCC5(CN6CC[C@H](CN7CC8(CCN(c9ccc%10c(c9)CN(C9CCC(=O)NC9=O)C%10=O)CC8)C7)C6)CC5)nc4c3F)c12] 3-(5-(2-(((S)-1-((1-(((7-(8-ethyl-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)pyrrolidin-3-yl)methyl)-2,7-diazaspiro[3.5]nonan-7-yl)-1-oxoisoindolin-2-yl)piperidine-2,6-dione |
| 23 | 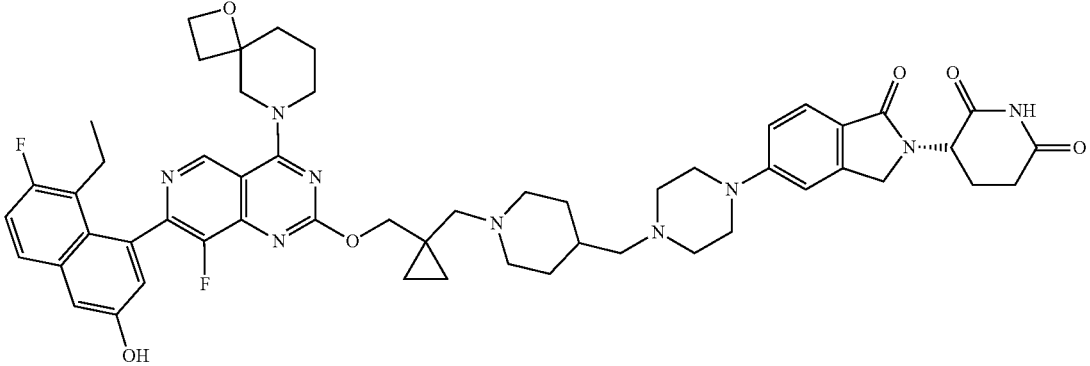 (3S)-3-(5-(4-((1-((1-(((7-(8-ethyl-7-fluoro-3-hydroxynaphthalen-1-yl)-8-fluoro-4-(1-oxa-6-azaspiro[3.5]nonan-6-yl)pyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione |
| 24 | 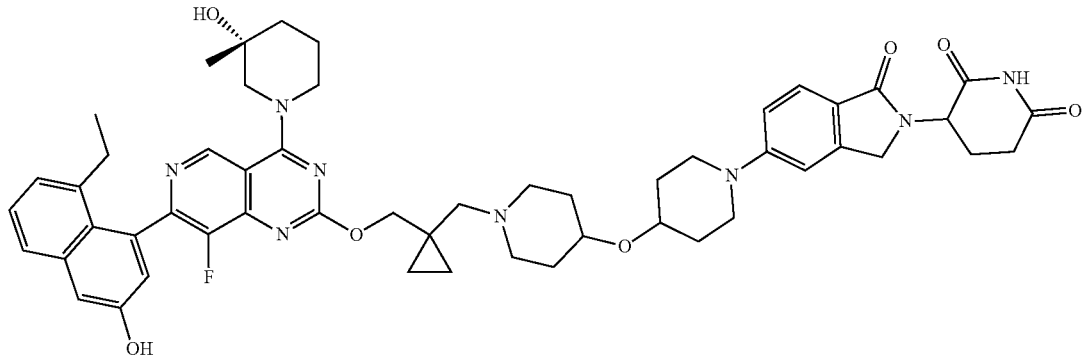 [SMILES: CCc1cccc2cc(O)cc(-c3ncc4c(N5CCC[C@@](C)(O)C5)nc(OCC5(CN6CCC(OC7CCN(c8ccc9c(c8)CN(C8CCC(=O)NC8=O)C9=O)CC7)CC6)CC5)nc4c3F)c12] 3-(5-(4-((1-((1-(((7-(8-ethyl-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)oxy)piperidin-1-yl)-1-oxoisoindolin-2-yl)piperidine-2,6-dione |

TABLE 1-continued

Exemplary Compounds of the Present Disclosure

| Cpd # | Structure and IUPAC Name |
|---|---|
| 25 | 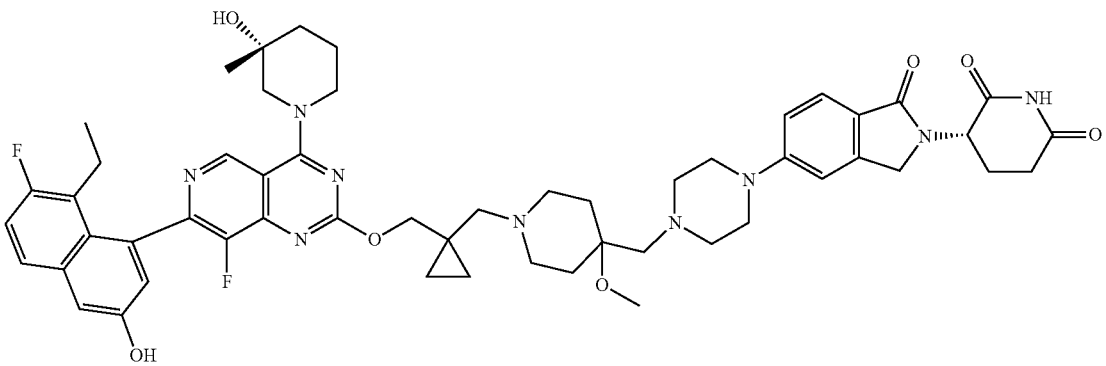 [SMILES: CCc1c(F)ccc2cc(O)cc(-c3ncc4c(N5CCC[C@@](C)(O)C5)nc(OCC5(CN6CCC(CN7CCN(c8ccc9c(c8)CN([C@H]8CCC(=O)NC8=O)C9=O)CC7)(OC)CC6)CC5)nc4c3F)c12]<br>(S)-3-(5-(4-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-4-methoxypiperidin-4-yl)methyl)piperazin-1-yl)-1-oxoisoindolin-2-yl)piperidine-2,6-dione |
| 26 | 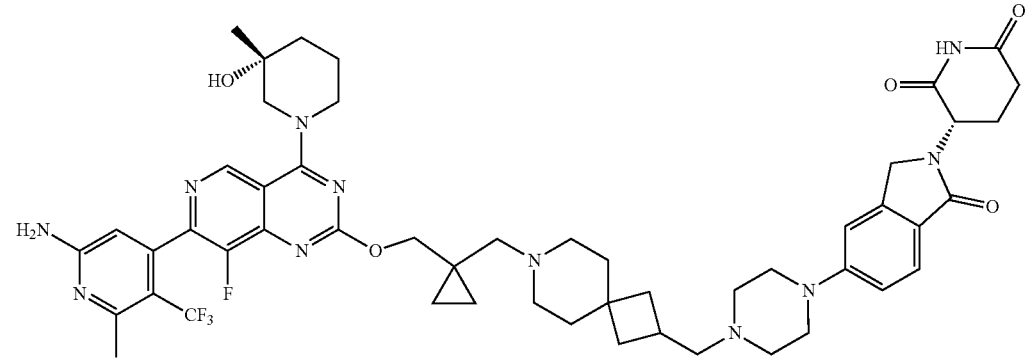 [SMILES: Cc1nc(N)cc(-c2ncc3c(N4CCC[C@@](C)(O)C4)nc(OCC4(CN5CCC6(CC5)CC(CN5CCN(c7ccc8c(c7)CN([C@H]7CCC(=O)NC7=O)C8=O)CC5)C6)CC4)nc3c2F)c1C(F)(F)F]<br>(S)-3-(5-(4-((7-((1-(((7-(6-amino-2-methyl-3-(trifluoromethyl)pyridin-4-yl)-8-fluoro-4-((R)-3-hydroxy-3-methylpiperidin-1-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |
| 27 | 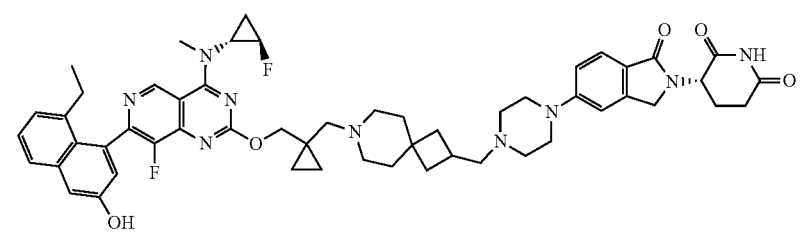 [SMILES: CCc1cccc2cc(O)cc(-c3ncc4c(N(C)[C@@H]5C[C@H]5F)nc(OCC5(CN6CCC7(CC6)CC(CN6CCN(c8ccc9c(c8)CN([C@H]8CCC(=O)NC8=O)C9=O)CC6)C7)CC5)nc4c3F)c12]<br>(S)-3-(5-(4-((7-((1-(((7-(8-ethyl-3-hydroxynaphthalen-1-yl)-8-fluoro-4-(((1R,2R)-2-fluorocyclopropyl)(methyl)amino)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |

TABLE 1-continued

Exemplary Compounds of the Present Disclosure

| Cpd # | Structure and IUPAC Name |
|---|---|
| 28 | 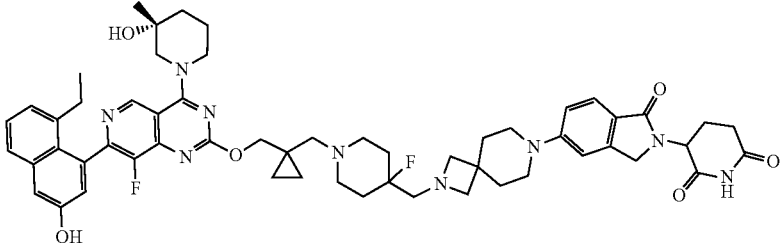 [SMILES: CCc1cccc2cc(O)cc(-c3ncc4c(N5CCC[C@@](C)(O)C5)nc(OCC5(CN6CCC(F)(CN7CC8(CCN(c9ccc%10c(c9)CN(C9CCC(=O)NC9=O)C%10=O)CC8)C7)CC6)CC5)nc4c3F)c12]<br>3-(5-(2-((1-(((7-(8-ethyl-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-4-fluoropiperidin-4-yl)methyl)-2,7-diazaspiro[3.5]nonan-7-yl)-1-oxoisoindolin-2-yl)piperidine-2,6-dione |
| 29 | 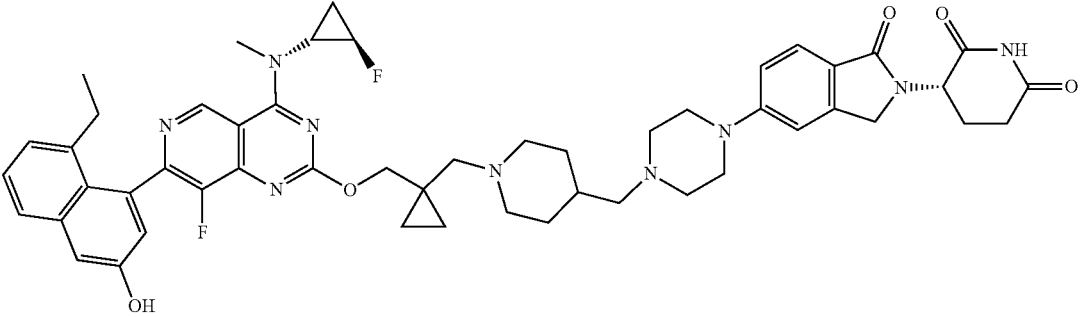<br>(S)-3-(5-(4-((1-((1-(((7-(8-ethyl-3-hydroxynaphthalen-1-yl)-8-fluoro-4-(((1R,2R)-2-fluorocyclopropyl)(methyl)amino)pyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione |
| 30 | 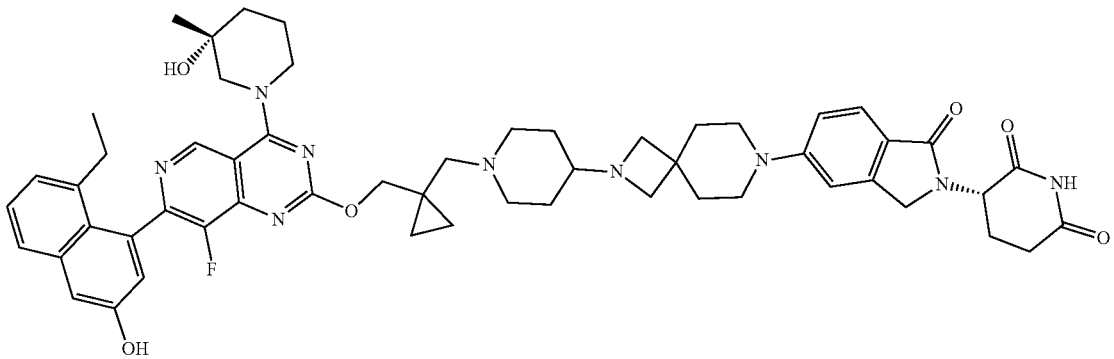 [SMILES: CCc1cccc2cc(O)cc(-c3ncc4c(N5CCC[C@@](C)(O)C5)nc(OCC5(CN6CCC(N7CC8(CCN(c9ccc%10c(c9)CN([C@H]9CCC(=O)NC9=O)C%10=O)CC8)C7)CC6)CC5)nc4c3F)c12]<br>(S)-3-(5-(2-(1-((1-(((7-(8-ethyl-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)-2,7-diazaspiro[3.5]nonan-7-yl)-1-oxoisoindolin-2-yl)piperidine-2,6-dione |

TABLE 1-continued

Exemplary Compounds of the Present Disclosure

| Cpd # | Structure and IUPAC Name |
|---|---|
| 31 | 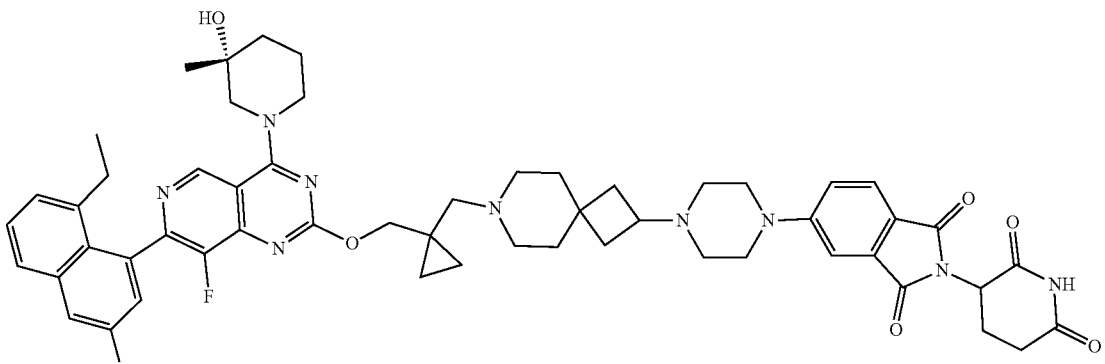<br>2-(2,6-dioxopiperidin-3-yl)-5-(4-(7-((1-(((7-(8-ethyl-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-azaspiro[3.5]nonan-2-yl)piperazin-1-yl)isoindoline-1,3-dione |
| 32 | 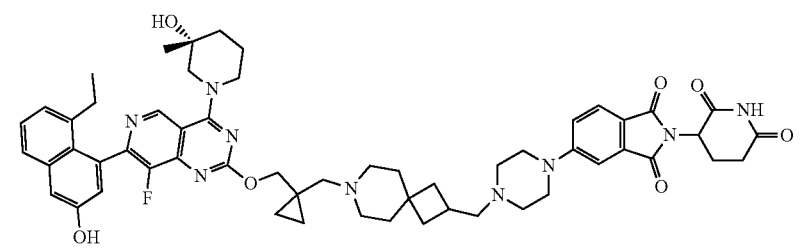 [SMILES: CCc1cccc2cc(O)cc(-c3ncc4c(N5CCC[C@@](C)(O)C5)nc(OCC5(CN6CCC7(CC6)CC(CN6CCN(c8ccc9c(c8)C(=O)N(C8CCC(=O)NC8=O)C9=O)CC6)C7)CC5)nc4c3F)c12]<br>2-(2,6-dioxopiperidin-3-yl)-5-(4-((7-((1-(((7-(8-ethyl-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-azaspiro[3.5]nonan-2-yl)methyl)piperazin-1-yl)isoindoline-1,3-dione |
| 33 | 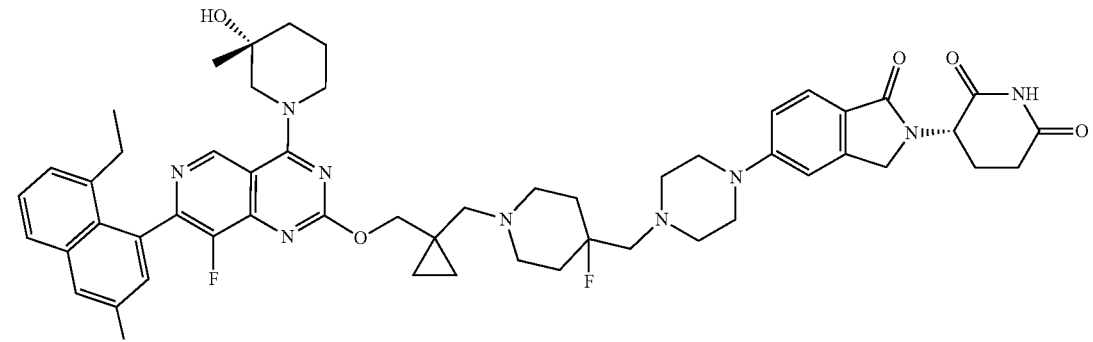<br>(S)-3-(5-(4-((1-((1-(((7-(8-ethyl-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-4-fluoropiperidin-4-yl)methyl)piperazin-1-yl)-1-oxoisoindolin-2-yl)piperidine-2,6-dione |

TABLE 1-continued

Exemplary Compounds of the Present Disclosure

| Cpd # | Structure and IUPAC Name |
|---|---|
| 34 | 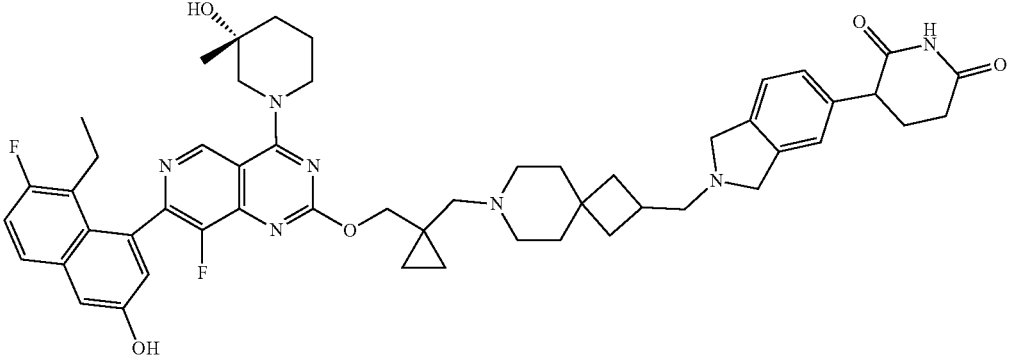 [SMILES: CCc1c(F)ccc2cc(O)cc(-c3ncc4c(N5CCC[C@@](C)(O)C5)nc(OCC5(CN6CCC7(CC6)CC(CN6Cc8ccc(C9CCC(=O)NC9=O)cc8C6)C7)CC5)nc4c3F)c12] 3-(2-((7-(((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-azaspiro[3.5]nonan-2-yl)methyl)isoindolin-5-yl)piperidine-2,6-dione |
| 35 | 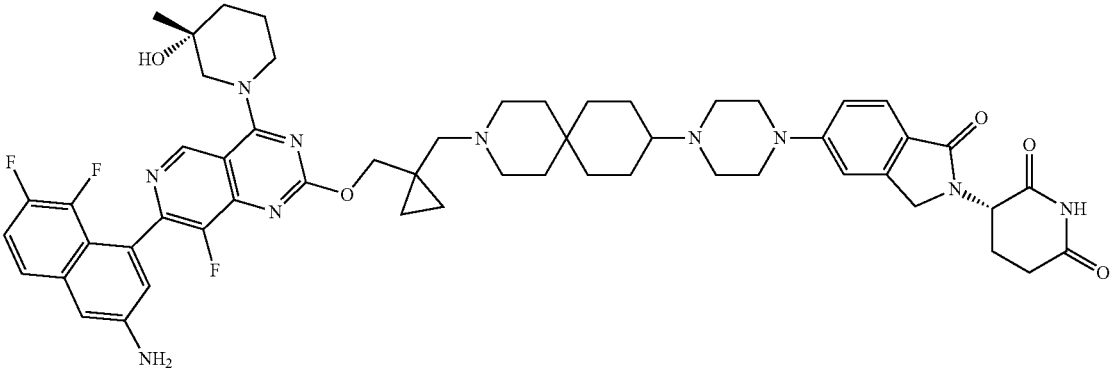 [SMILES: C[C@@]1(O)CCCN(c2nc(OCC3(CN4CCC5(CCC(N6CCN(c7ccc8c(c7)CN([C@H]7CCC(=O)NC7=O)C8=O)CC6)CC5)CC4)CC3)nc3c(F)c(-c4cc(N)cc5ccc(F)c(F)c45)ncc23)C1] (S)-3-(5-(4-(3-((1-(((7-(3-amino-7,8-difluoronaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-3-azaspiro[5.5]undecan-9-yl)piperazin-1-yl)-1-oxoisoindolin-2-yl)piperidine-2,6-dione |
| 36 | 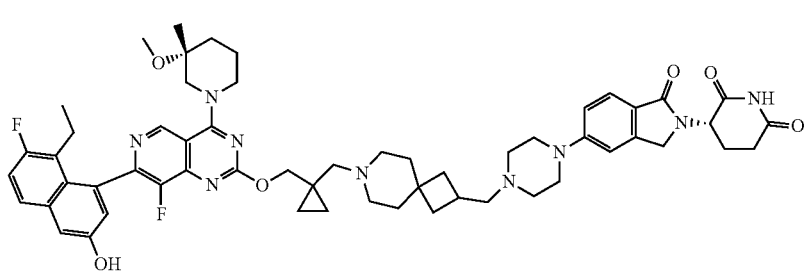 [SMILES: CCc1c(F)ccc2cc(O)cc(-c3ncc4c(N5CCC[C@@](C)(OC)C5)nc(OCC5(CN6CCC7(CC6)CC(CN6CCN(c8ccc9c(c8)CN([C@H]8CCC(=O)NC8=O)C9=O)CC6)C7)CC5)nc4c3F)c12] (S)-3-(5-(4-((7-((1-(((7-(8-ethyl-7-fluoro-3-hydroxynaphthalen-1-yl)-8-fluoro-4-((R)-3-methoxy-3-methylpiperidin-1-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |

TABLE 1-continued

Exemplary Compounds of the Present Disclosure

| Cpd # | Structure and IUPAC Name |
|---|---|
| 37 | 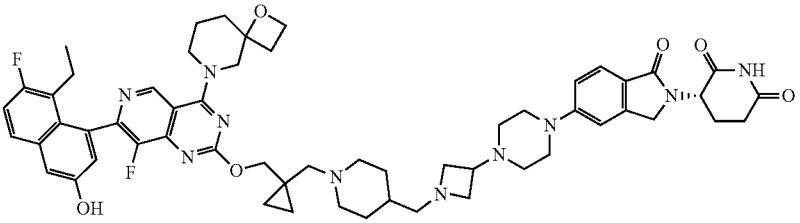 [SMILES: CCc1c(F)ccc2cc(O)cc(-c3ncc4c(N5CCCC6(CCO6)C5)nc(OCC5(CN6CCC(CN7CC(N8CCN(c9ccc%10c(c9)CN([C@H]9CCC(=O)NC9=O)C%10=O)CC8)C7)CC6)CC5)nc4c3F)c12]<br>(3S)-3-(5-(4-(1-((1-(((1-(((7-(8-ethyl-7-fluoro-3-hydroxynaphthalen-1-yl)-8-fluoro-4-(1-oxa-6-azaspiro[3.5]nonan-6-yl)pyrido[4,3-d]pyrimidin-2-yl)oxy)methyl)cyclopropyl)methyl)piperidin-4-yl)methyl)azetidin-3-yl)piperazin-1-yl)-1-oxoisoindolin-2-yl)piperidine-2,6-dione |
| 38 | 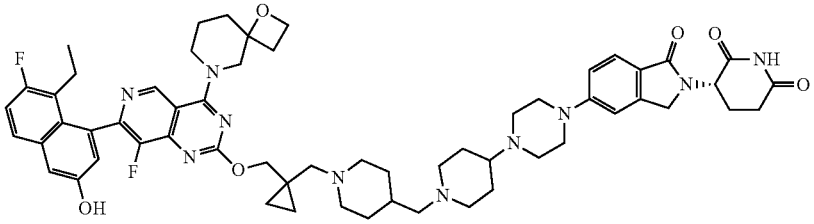 [SMILES: CCc1c(F)ccc2cc(O)cc(-c3ncc4c(N5CCCC6(CCO6)C5)nc(OCC5(CN6CCC(CN7CCC(N8CCN(c9ccc%10c(c9)CN([C@H]9CCC(=O)NC9=O)C%10=O)CC8)CC7)CC6)CC5)nc4c3F)c12]<br>(3S)-3-(5-(4-(1-((1-(((1-(((7-(8-ethyl-7-fluoro-3-hydroxynaphthalen-1-yl)-8-fluoro-4-(1-oxa-6-azaspiro[3.5]nonan-6-yl)pyrido[4,3-d]pyrimidin-2-yl)oxy)methyl)cyclopropyl)methyl)piperidin-4-yl)methyl)piperidin-4-yl)piperazin-1-yl)-1-oxoisoindolin-2-yl)piperidine-2,6-dione |
| 39 | 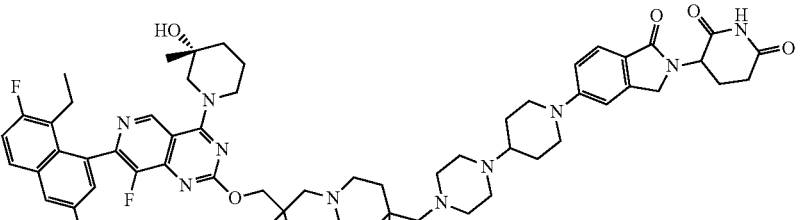<br>3-(5-(4-(4-((1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-4-methylpiperidin-4-yl)methyl)piperazin-1-yl)piperidin-1-yl)-1-oxoisoindolin-2-yl)piperidine-2,6-dione |
| 40 | 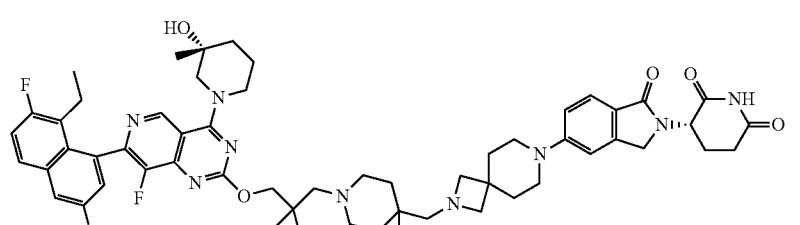<br>(S)-3-(5-(2-((1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-4-methylpiperidin-4-yl)methyl)-2,7-diazaspiro[3.5]nonan-7-yl)-1-oxoisoindolin-2-yl)piperidine-2,6-dione |

TABLE 1-continued

Exemplary Compounds of the Present Disclosure

| Cpd # | Structure and IUPAC Name |
|---|---|
| 41 | 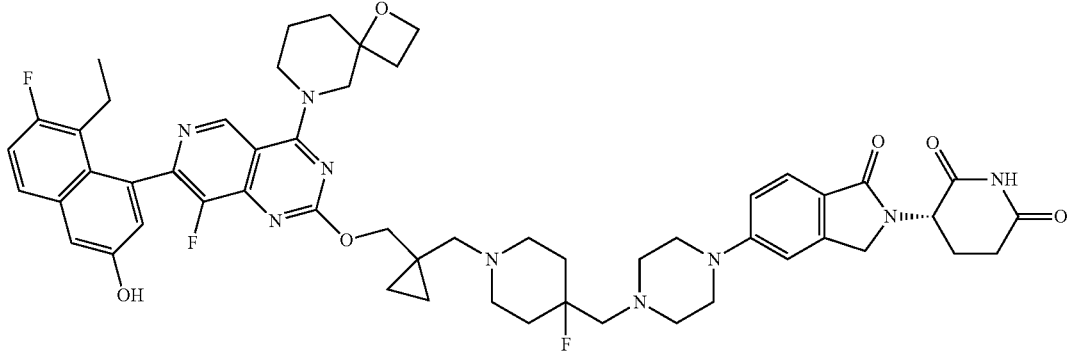 [SMILES: CCc1c(F)ccc2cc(O)cc(-c3ncc4c(N5CCCC6(CCO6)C5)nc(OCC5(CN6CCC(F)(CN7CCN(c8ccc9c(c8)CN([C@H]8CCC(=O)NC8=O)C9=O)CC7)CC6)CC5)nc4c3F)c12]<br>(3S)-3-(5-(4-((1-(((1-(((7-(8-ethyl-7-fluoro-3-hydroxynaphthalen-1-yl)-8-fluoro-4-(1-oxa-6-azaspiro[3.5]nonan-6-yl)pyrido[4,3-d]pyrimidin-2-yl)oxy)methyl)cyclopropyl)methyl)-4-fluoropiperidin-4-yl)methyl)piperazin-1-yl)-1-oxoisoindolin-2-yl)piperidine-2,6-dione |
| 42 | 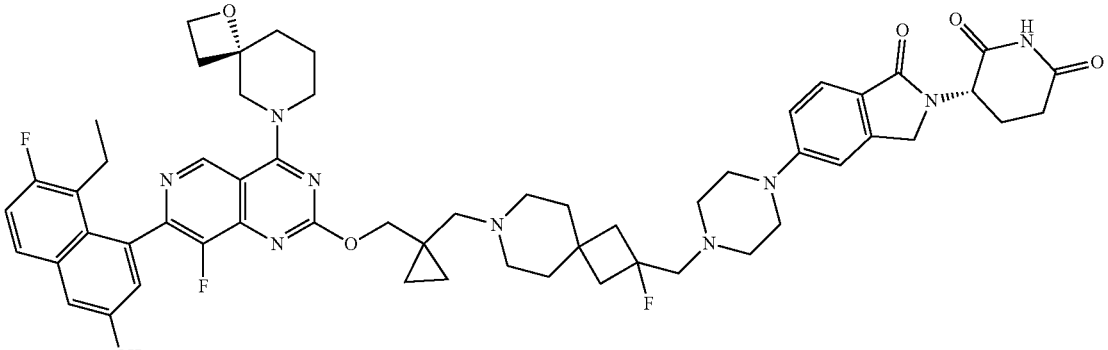<br>(3S)-3-(5-(4-((7-((1-(((7-(8-ethyl-7-fluoro-3-hydroxynaphthalen-1-yl)-8-fluoro-4-(1-oxa-6-azaspiro[3.5]nonan-6-yl)pyrido[4,3-d]pyrimidin-2-yl)oxy)methyl)cyclopropyl)methyl)-2-fluoro-7-azaspiro[3.5]nonan-2-yl)methyl)piperazin-1-yl)-1-oxoisoindolin-2-yl)piperidine-2,6-dione |
| 43 | 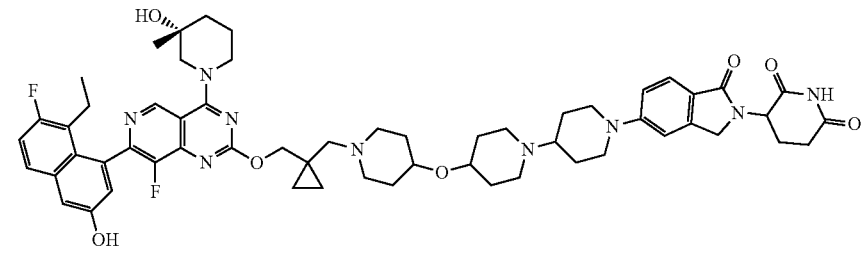 [SMILES: CCc1c(F)ccc2cc(O)cc(-c3ncc4c(N5CCC[C@@](C)(O)C5)nc(OCC5(CN6CCC(OC7CCN(C8CCN(c9ccc%10c(c9)CN(C9CCC(=O)NC9=O)C%10=O)CC8)CC7)CC6)CC5)nc4c3F)c12]<br>3-(5-(4-((1-(((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)oxy)-[1,4'-bipiperidin]-1'-yl)-1-oxoisoindolin-2-yl)piperidine-2,6-dione |

TABLE 1-continued

Exemplary Compounds of the Present Disclosure

| Cpd # | Structure and IUPAC Name |
|---|---|
| 44 | 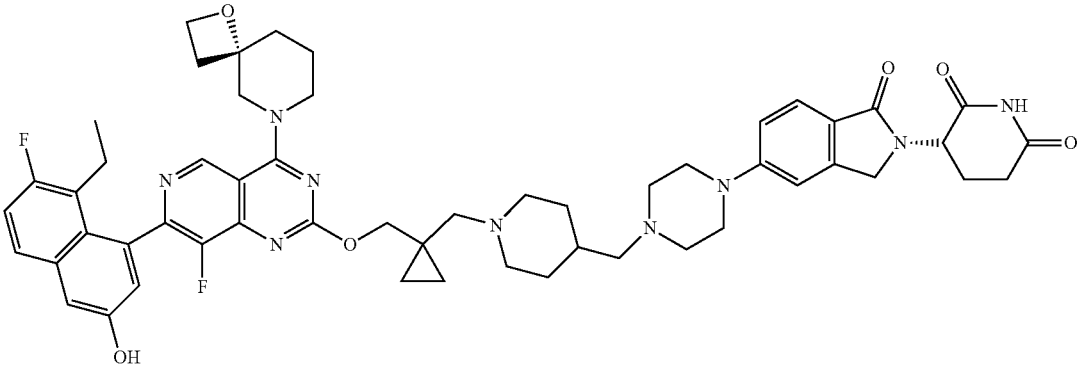<br>(S)-3-(5-(4-((1-(((7-(8-ethyl-7-fluoro-3-hydroxynaphthalen-1-yl)-8-fluoro-4-((S)-1-oxa-6-azaspiro[3.5]nonan-6-yl)pyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione |
| 45 | 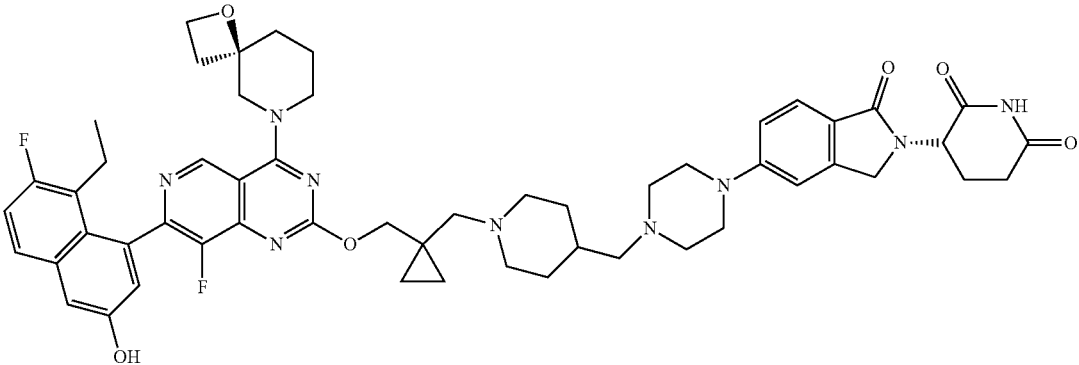<br>(S)-3-(5-(4-((1-(((7-(8-ethyl-7-fluoro-3-hydroxynaphthalen-1-yl)-8-fluoro-4-((R)-1-oxa-6-azaspiro[3.5]nonan-6-yl)pyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione |
| 46 | 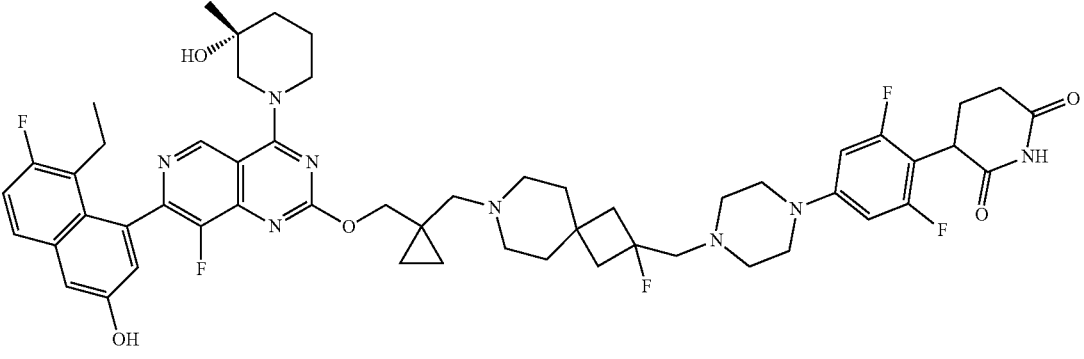 [SMILES: CCc1c(F)ccc2cc(O)cc(-c3ncc4c(N5CCC[C@@](C)(O)C5)nc(OCC5(CN6CCC7(CC6)CC(F)(CN6CCN(c8cc(F)c(C9CCC(=O)NC9=O)c(F)c8)CC6)C7)CC5)nc4c3F)c12]<br>3-(4-(4-((7-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-2-fluoro-7-azaspiro[3.5]nonan-2-yl)methyl)piperazin-1-yl)-2,6-difluorophenyl)piperidine-2,6-dione |

TABLE 1-continued

Exemplary Compounds of the Present Disclosure

| Cpd # | Structure and IUPAC Name |
|---|---|
| 47 | 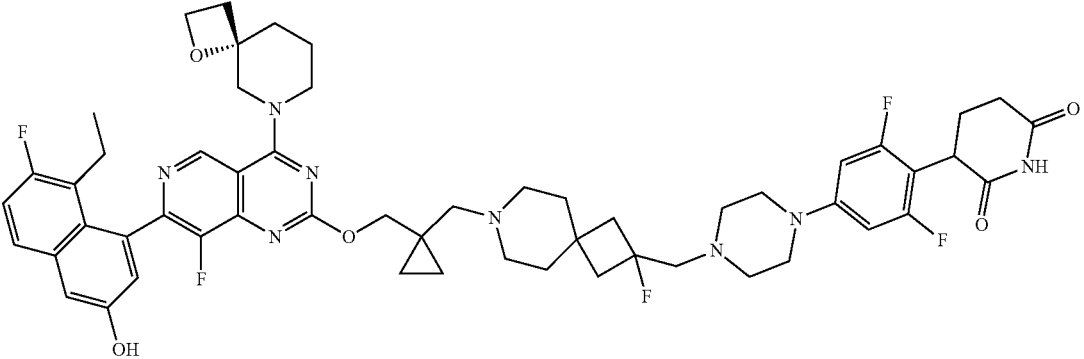 [SMILES: CCc1c(F)ccc2cc(O)cc(-c3ncc4c(N5CCC[C@]6(CCO6)C5)nc(OCC5(CN6CCC7(CC6)CC(F)(CN6CCN(c8cc(F)c(C9CCC(=O)NC9=O)c(F)c8)CC6)C7)CC5)nc4c3F)c12]<br>3-(4-(4-((7-((1-(((7-(8-ethyl-7-fluoro-3-hydroxynaphthalen-1-yl)-8-fluoro-4-((S)-1-oxa-6-azaspiro[3.5]nonan-6-yl)pyrido[4,3-d]pyrimidin-2-yl)oxy)methyl)cyclopropyl)methyl)-2-fluoro-7-azaspiro[3.5]nonan-2-yl)methyl)piperazin-1-yl)-2,6-difluorophenyl)piperidine-2,6-dione |
| 48 | 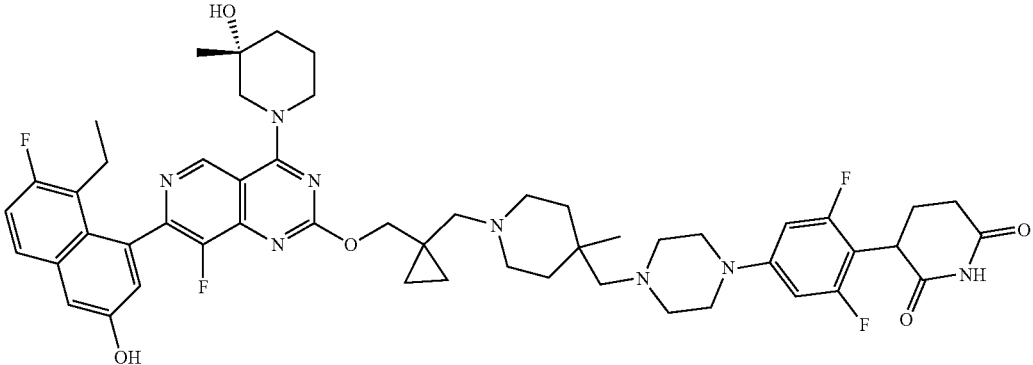 [SMILES: CCc1c(F)ccc2cc(O)cc(-c3ncc4c(N5CCC[C@@](C)(O)C5)nc(OCC5(CN6CCC(C)(CN7CCN(c8cc(F)c(C9CCC(=O)NC9=O)c(F)c8)CC7)CC6)CC5)nc4c3F)c12]<br>3-(4-(4-((1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-4-methylpiperidin-4-yl)methyl)piperazin-1-yl)-2,6-difluorophenyl)piperidine-2,6-dione |
| 49 | 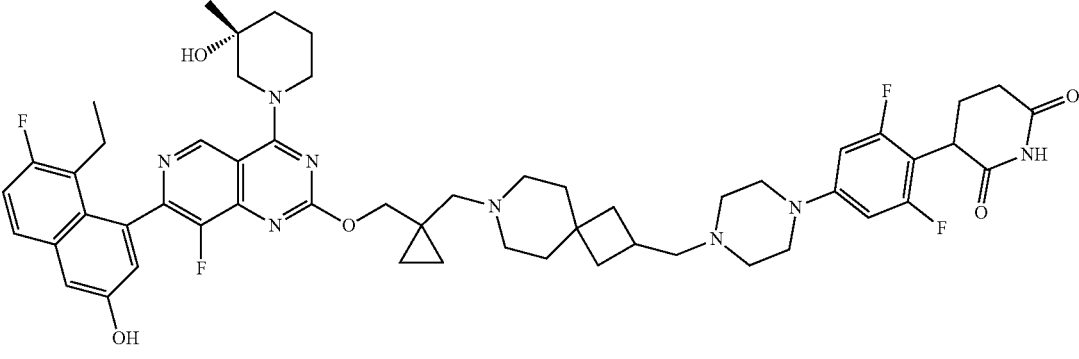 [SMILES: CCc1c(F)ccc2cc(O)cc(-c3ncc4c(N5CCC[C@@](C)(O)C5)nc(OCC5(CN6CCC7(CC6)CC(CN6CCN(c8cc(F)c(C9CCC(=O)NC9=O)c(F)c8)CC6)C7)CC5)nc4c3F)c12]<br>3-(4-(4-((7-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-azaspiro[3.5]nonan-2-yl)methyl)piperazin-1-yl)-2,6-difluorophenyl)piperidine-2,6-dione |

TABLE 1-continued

Exemplary Compounds of the Present Disclosure

| Cpd # | Structure and IUPAC Name |
|---|---|
| 50 | 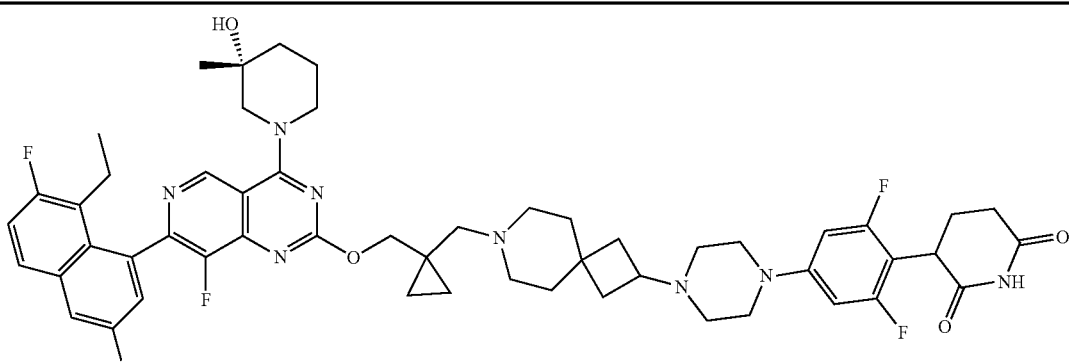<br>3-(4-(4-(7-(((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-azaspiro[3.5]nonan-2-yl)piperazin-1-yl)-2,6-difluorophenyl)piperidine-2,6-dione |
| 51 | 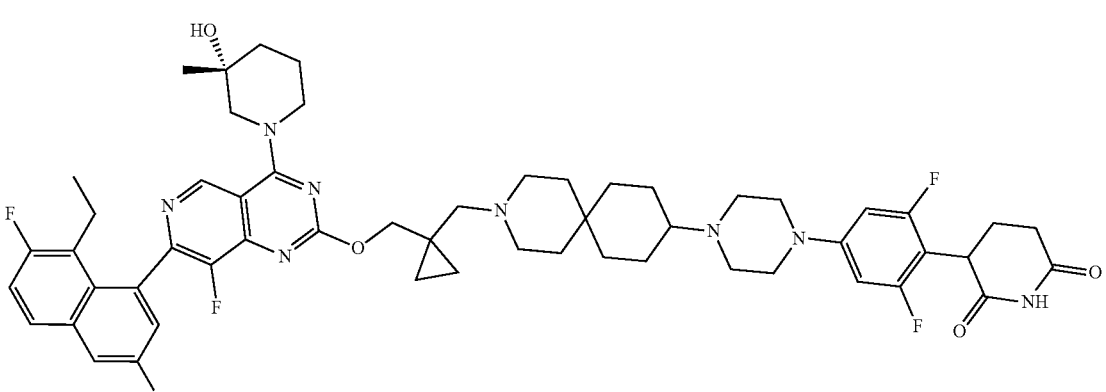<br>3-(4-(4-(3-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-3-azaspiro[5.5]undecan-9-yl)piperazin-1-yl)-2,6-difluorophenyl)piperidine-2,6-dione |
| 52 | 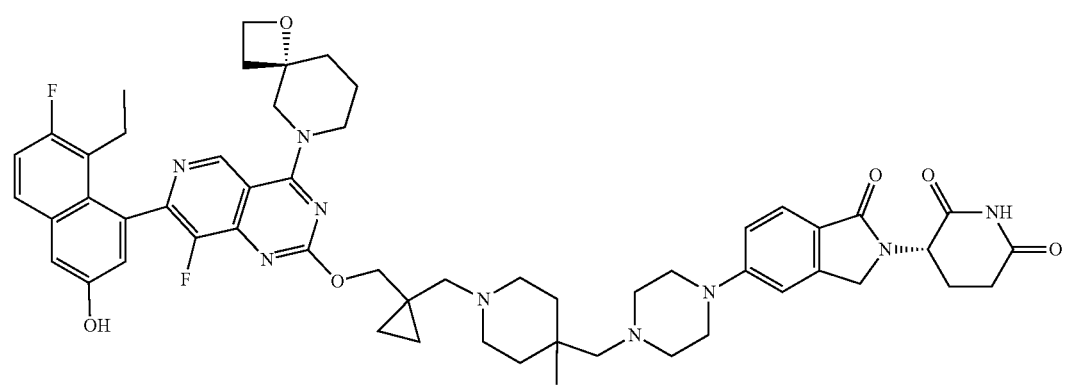 [SMILES: CCc1c(F)ccc2cc(O)cc(-c3ncc4c(N5CCC[C@]6(CCO6)C5)nc(OCC5(CN6CCC(C)(CN7CCN(c8ccc9c(c8)CN([C@H]8CCC(=O)NC8=O)C9=O)CC7)CC6)CC5)nc4c3F)c12]<br>(S)-3-(5-(4-((1-((1-(((7-(8-ethyl-7-fluoro-3-hydroxynaphthalen-1-yl)-8-fluoro-4-((S)-1-oxa-6-azaspiro[3.5]nonan-6-yl)pyrido[4,3-d]pyrimidin-2-yl)oxy)methyl)cyclopropyl)methyl)-4-methylpiperidin-4-yl)methyl)piperazin-1-yl)-1-oxoisoindolin-2-yl)piperidine-2,6-dione |

TABLE 1-continued

Exemplary Compounds of the Present Disclosure

| Cpd # | Structure and IUPAC Name |
|---|---|
| 53 | 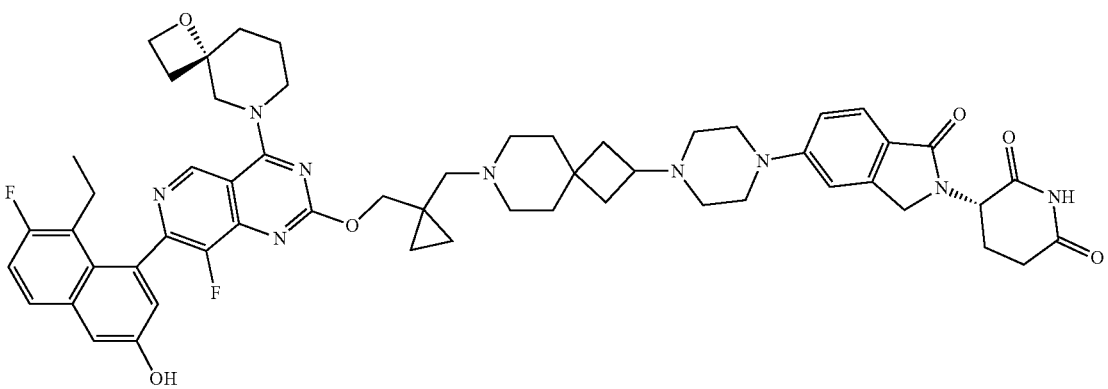 [SMILES: CCc1c(F)ccc2cc(O)cc(-c3ncc4c(N5CCC[C@]6(CCO6)C5)nc(OCC5(CN6CCC7(CC6)CC(N6CCN(c8ccc9c(c8)CN([C@H]8CCC(=O)NC8=O)C9=O)CC6)C7)CC5)nc4c3F)c12]<br>(S)-3-(5-(4-(7-((1-(((7-(8-ethyl-7-fluoro-3-hydroxynaphthalen-1-yl)-8-fluoro-4-((S)-1-oxa-6-azaspiro[3.5]nonan-6-yl)pyrido[4,3-d]pyrimidin-2-yl)oxy)methyl)cyclopropyl)methyl)-7-azaspiro[3.5]nonan-2-yl)piperazin-1-yl)-1-oxoisoindolin-2-yl)piperidine-2,6-dione |
| 54 | 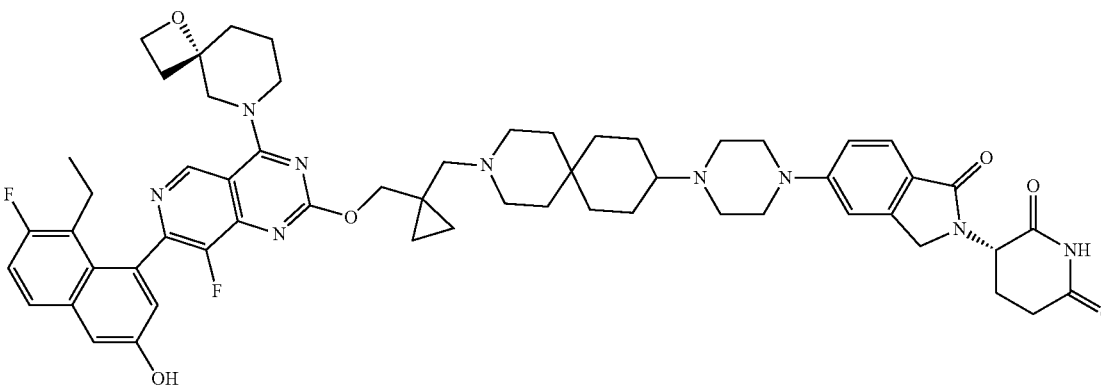 [SMILES: CCc1c(F)ccc2cc(O)cc(-c3ncc4c(N5CCC[C@]6(CCO6)C5)nc(OCC5(CN6CCC7(CCC(N8CCN(c9ccc%10c(c9)CN([C@H]9CCC(=O)NC9=O)C%10=O)CC8)CC7)CC6)CC5)nc4c3F)c12]<br>(S)-3-(5-(4-(3-((1-(((7-(8-ethyl-7-fluoro-3-hydroxynaphthalen-1-yl)-8-fluoro-4-((S)-1-oxa-6-azaspiro[3.5]nonan-6-yl)pyrido[4,3-d]pyrimidin-2-yl)oxy)methyl)cyclopropyl)methyl)-3-azaspiro[5.5]undecan-9-yl)piperazin-1-yl)-1-oxoisoindolin-2-yl)piperidine-2,6-dione |
| 55 | 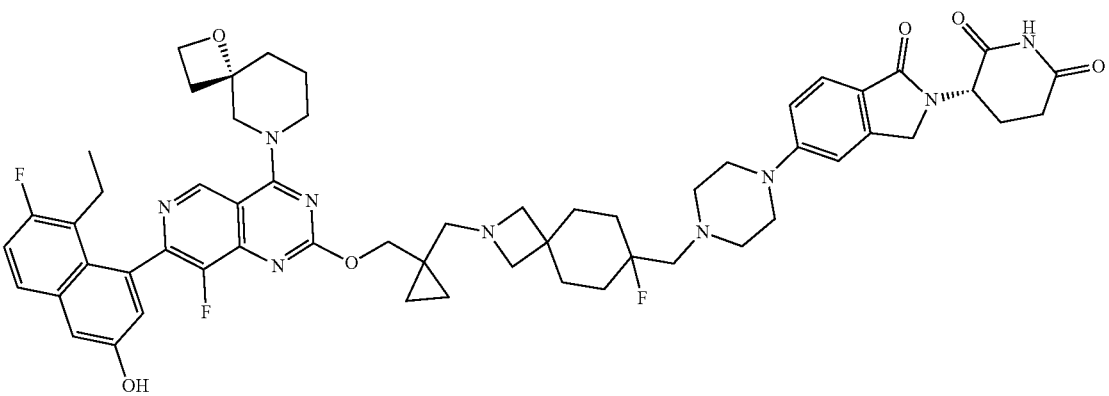 [SMILES: CCc1c(F)ccc2cc(O)cc(-c3ncc4c(N5CCC[C@]6(CCO6)C5)nc(OCC5(CN6CC7(CCC(F)(CN8CCN(c9ccc%10c(c9)CN([C@H]9CCC(=O)NC9=O)C%10=O)CC8)CC7)C6)CC5)nc4c3F)c12]<br>(S)-3-(5-(4-((2-((1-(((7-(8-ethyl-7-fluoro-3-hydroxynaphthalen-1-yl)-8-fluoro-4-((S)-1-oxa-6-azaspiro[3.5]nonan-6-yl)pyrido[4,3-d]pyrimidin-2-yl)oxy)methyl)cyclopropyl)methyl)-7-fluoro-2-azaspiro[3.5]nonan-7-yl)methyl)piperazin-1-yl)-1-oxoisoindolin-2-yl)piperidine-2,6-dione |

TABLE 1-continued

Exemplary Compounds of the Present Disclosure

| Cpd # | Structure and IUPAC Name |
|---|---|
| 56 | 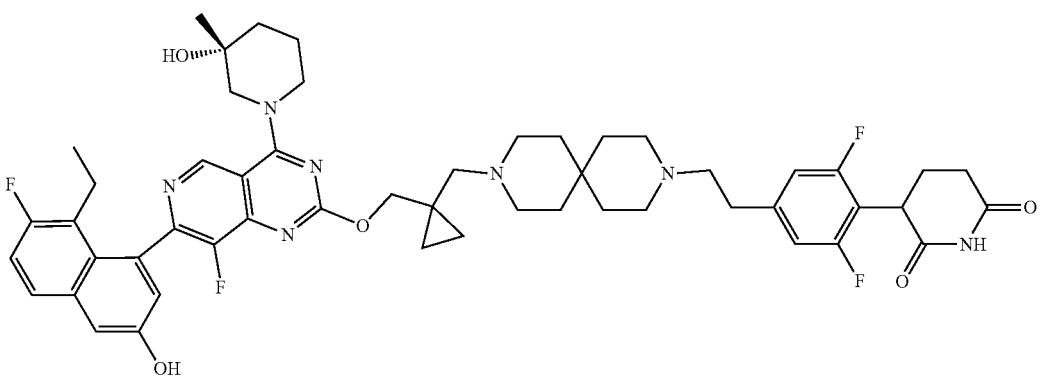 [SMILES: CCc1c(F)ccc2cc(O)cc(-c3ncc4c(N5CCC[C@@](C)(O)C5)nc(OCC5(CN6CCC7(CCN(CCc8cc(F)c(C9CCC(=O)NC9=O)c(F)c8)CC7)CC6)CC5)nc4c3F)c12]<br>3-(4-(2-(9-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-3,9-diazaspiro[5.5]undecan-3-yl)ethyl)-2,6-difluorophenyl)piperidine-2,6-dione |
| 57 | 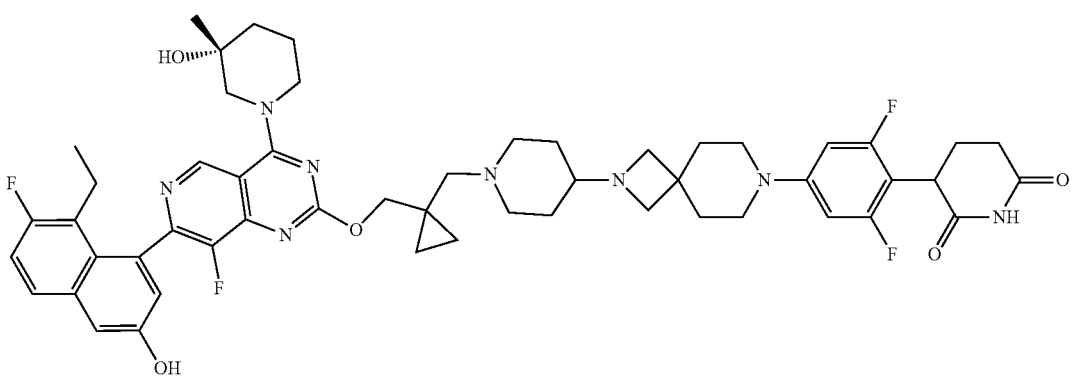 [SMILES: CCc1c(F)ccc2cc(O)cc(-c3ncc4c(N5CCC[C@@](C)(O)C5)nc(OCC5(CN6CCC(N7CC8(CCN(c9cc(F)c(C%10CCC(=O)NC%10=O)c(F)c9)CC8)C7)CC6)CC5)nc4c3F)c12]<br>3-(4-(2-(1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)-2,7-diazaspiro[3.5]nonan-7-yl)-2,6-difluorophenyl)piperidine-2,6-dione |
| 58 | 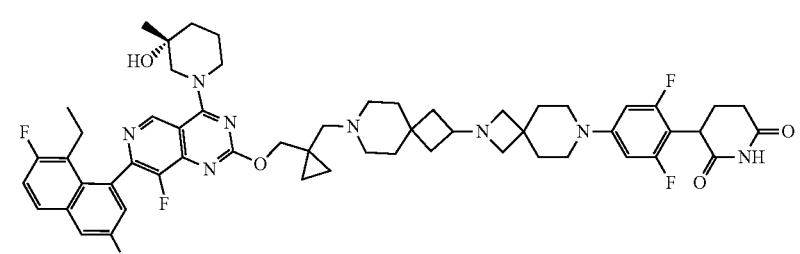<br>3-(4-(2-(7-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-azaspiro[3.5]nonan-2-yl)-2,7-diazaspiro[3.5]nonan-7-yl)-2,6-difluorophenyl)piperidine-2,6-dione |

TABLE 1-continued

Exemplary Compounds of the Present Disclosure

| Cpd # | Structure and IUPAC Name |
|---|---|
| 59 | 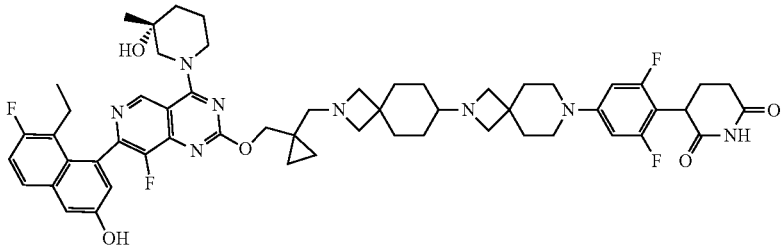 [SMILES: CCc1c(F)ccc2cc(O)cc(-c3ncc4c(N5CCC[C@@](C)(O)C5)nc(OCC5(CN6CC7(CCC(N8CC9(CCN(c%10cc(F)c(C%11CCC(=O)NC%11=O)c(F)c%10)CC9)C8)CC7)C6)CC5)nc4c3F)c12]<br>3-(4-(2-(2-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-2-azaspiro[3.5]nonan-7-yl)-2,7-diazaspiro[3.5]nonan-7-yl)-2,6-difluorophenyl)piperidine-2,6-dione |
| 60 | 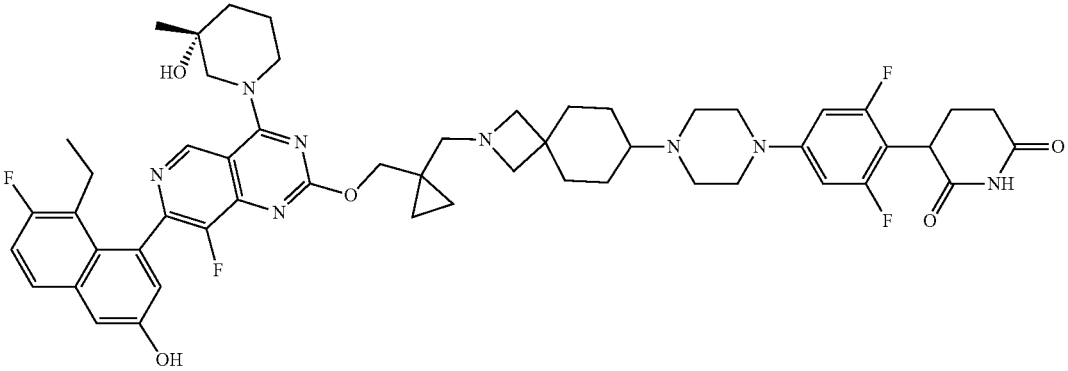 [SMILES: CCc1c(F)ccc2cc(O)cc(-c3ncc4c(N5CCC[C@@](C)(O)C5)nc(OCC5(CN6CC7(CCC(N8CCN(c9cc(F)c(C%10CCC(=O)NC%10=O)c(F)c9)CC8)CC7)C6)CC5)nc4c3F)c12]<br>3-(4-(4-(2-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-2-azaspiro[3.5]nonan-7-yl)piperazin-1-yl)-2,6-difluorophenyl)piperidine-2,6-dione |
| 61 | 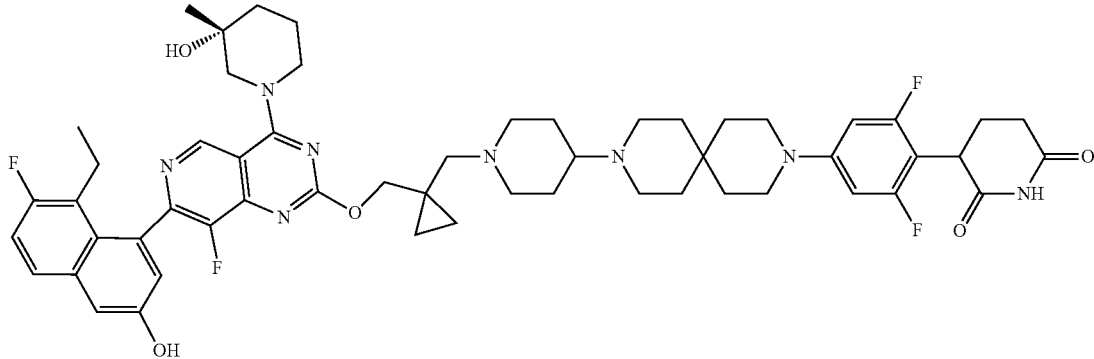 [SMILES: CCc1c(F)ccc2cc(O)cc(-c3ncc4c(N5CCC[C@@](C)(O)C5)nc(OCC5(CN6CCC(N7CCC8(CCN(c9cc(F)c(C%10CCC(=O)NC%10=O)c(F)c9)CC8)CC7)CC6)CC5)nc4c3F)c12]<br>3-(4-(9-(1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)-3,9-diazaspiro[5.5]undecan-3-yl)-2,6-difluorophenyl)piperidine-2,6-dione |

TABLE 1-continued

Exemplary Compounds of the Present Disclosure

| Cpd # | Structure and IUPAC Name |
|---|---|
| 62 | 3-(4-(2-(4-(7-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-2,7-diazaspiro[3.5]nonan-2-yl)piperidin-1-yl)ethyl)-2,6-difluorophenyl)piperidine-2,6-dione |
| 63 | (R)-3-(5-(4-((1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-4-methylpiperidin-4-yl)methyl)piperazin-1-yl)-1-oxoisoindolin-2-yl)piperidine-2,6-dione |
| 64 | 3-(5-(4-((1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-4-fluoropiperidin-4-yl)methyl)piperazin-1-yl)-3-methyl-2-oxo-2,3-dihydro-1H-benzo[d]imidazol-1-yl)piperidine-2,6-dione |

TABLE 1-continued

Exemplary Compounds of the Present Disclosure

| Cpd # | Structure and IUPAC Name |
|---|---|
| 65 | 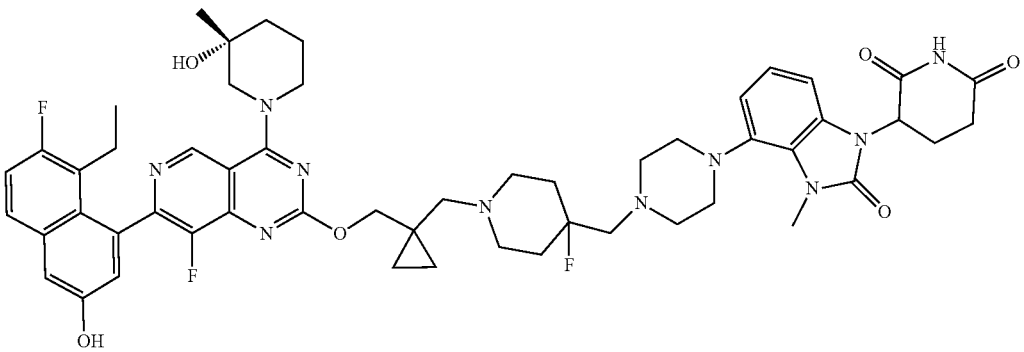 [SMILES: CCc1c(F)ccc2cc(O)cc(-c3ncc4c(N5CCC[C@@](C)(O)C5)nc(OCC5(CN6CCC(F)(CN7CCN(c8cccc9c8n(C)c(=O)n9C8CCC(=O)NC8=O)CC7)CC6)CC5)nc4c3F)c12]<br>3-(4-(4-((1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-4-fluoropiperidin-4-yl)methyl)piperazin-1-yl)-3-methyl-2-oxo-2,3-dihydro-1H-benzo[d]imidazol-1-yl)piperidine-2,6-dione |
| 66 | 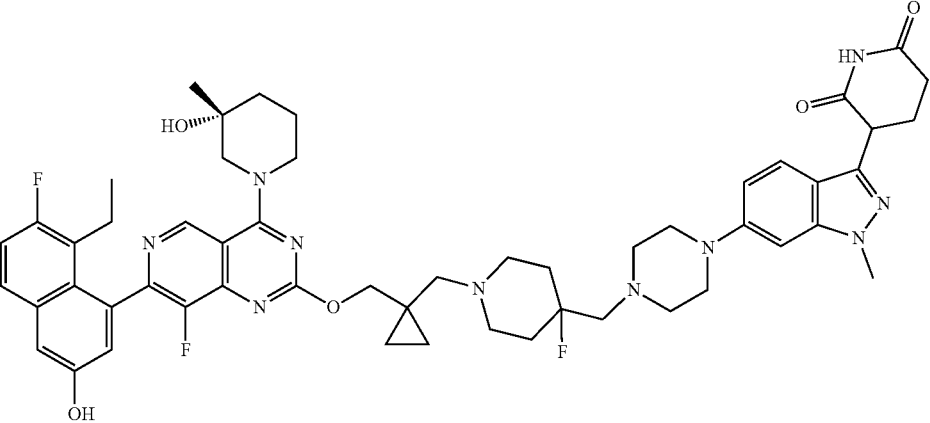 [SMILES: CCc1c(F)ccc2cc(O)cc(-c3ncc4c(N5CCC[C@@](C)(O)C5)nc(OCC5(CN6CCC(F)(CN7CCN(c8ccc9c(C%10CCC(=O)NC%10=O)nn(C)c9c8)CC7)CC6)CC5)nc4c3F)c12]<br>3-(6-(4-((1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-4-fluoropiperidin-4-yl)methyl)piperazin-1-yl)-1-methyl-1H-indazol-3-yl)piperidine-2,6-dione |
| 67 | 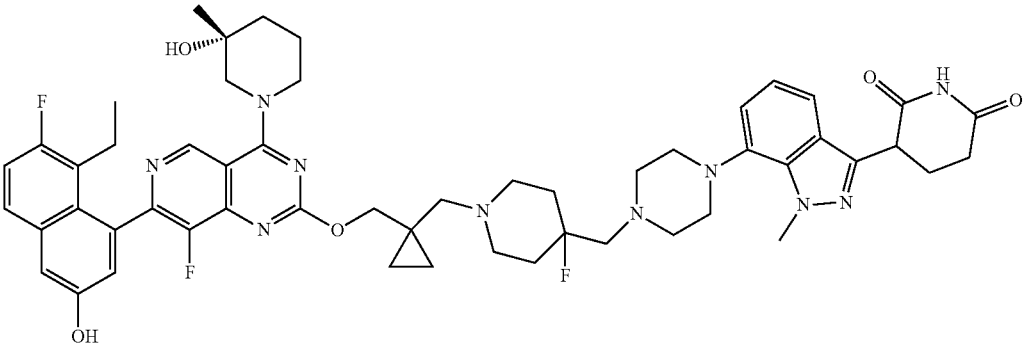 [SMILES: CCc1c(F)ccc2cc(O)cc(-c3ncc4c(N5CCC[C@@](C)(O)C5)nc(OCC5(CN6CCC(F)(CN7CCN(c8cccc9c(C%10CCC(=O)NC%10=O)nn(C)c89)CC7)CC6)CC5)nc4c3F)c12]<br>3-(7-(4-((1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-4-fluoropiperidin-4-yl)methyl)piperazin-1-yl)-1-methyl-1H-indazol-3-yl)piperidine-2,6-dione |

TABLE 1-continued

Exemplary Compounds of the Present Disclosure

| Cpd # | Structure and IUPAC Name |
|---|---|
| 68 | 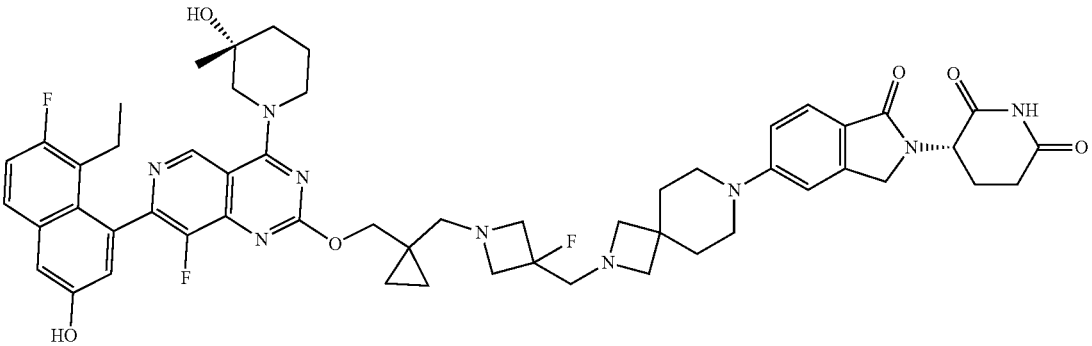 [SMILES: CCc1c(F)ccc2cc(O)cc(-c3ncc4c(N5CCC[C@@](C)(O)C5)nc(OCC5(CN6CC(F)(CN7CC8(CCN(c9ccc%10c(c9)CN([C@H]9CCC(=O)NC9=O)C%10=O)CC8)C7)C6)CC5)nc4c3F)c12]<br>(S)-3-(5-(2-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-3-fluoroazetidin-3-yl)methyl)-2,7-diazaspiro[3.5]nonan-7-yl)-1-oxoisoindolin-2-yl)piperidine-2,6-dione |
| 69 | 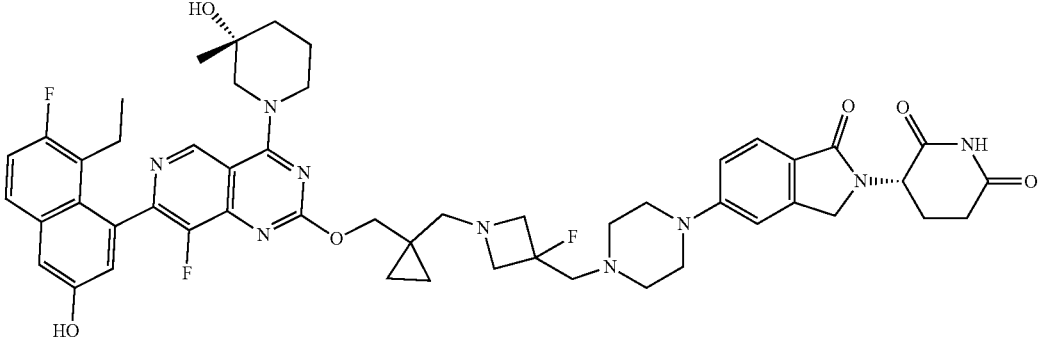 [SMILES: CCc1c(F)ccc2cc(O)cc(-c3ncc4c(N5CCC[C@@](C)(O)C5)nc(OCC5(CN6CC(F)(CN7CCN(c8ccc9c(c8)CN([C@H]8CCC(=O)NC8=O)C9=O)CC7)C6)CC5)nc4c3F)c12]<br>(S)-3-(5-(4-((1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-3-fluoroazetidin-3-yl)methyl)piperazin-1-yl)-1-oxoisoindolin-2-yl)piperidine-2,6-dione |
| 70 | 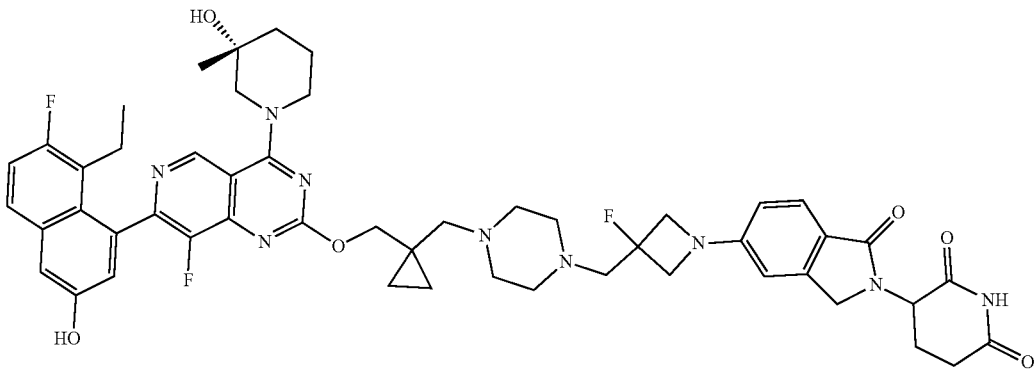 [SMILES: CCc1c(F)ccc2cc(O)cc(-c3ncc4c(N5CCC[C@@](C)(O)C5)nc(OCC5(CN6CCN(CC7(F)CN(c8ccc9c(c8)CN(C8CCC(=O)NC8=O)C9=O)C7)CC6)CC5)nc4c3F)c12]<br>3-(5-(3-((4-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperazin-1-yl)methyl)-3-fluoroazetidin-1-yl)-1-oxoisoindolin-2-yl)piperidine-2,6-dione |

TABLE 1-continued

Exemplary Compounds of the Present Disclosure

| Cpd # | Structure and IUPAC Name |
|---|---|
| 71 | 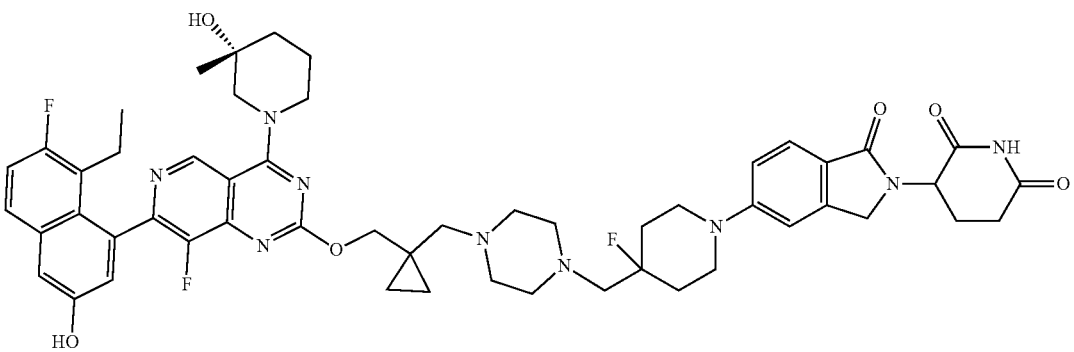 [SMILES: CCc1c(F)ccc2cc(O)cc(-c3ncc4c(N5CCC[C@@](C)(O)C5)nc(OCC5(CN6CCN(CC7(F)CCN(c8ccc9c(c8)CN(C8CCC(=O)NC8=O)C9=O)CC7)CC6)CC5)nc4c3F)c12]<br>3-(5-(4-((4-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperazin-1-yl)methyl)-4-fluoropiperidin-1-yl)-1-oxoisoindolin-2-yl)piperidine-2,6-dione |
| 72 | 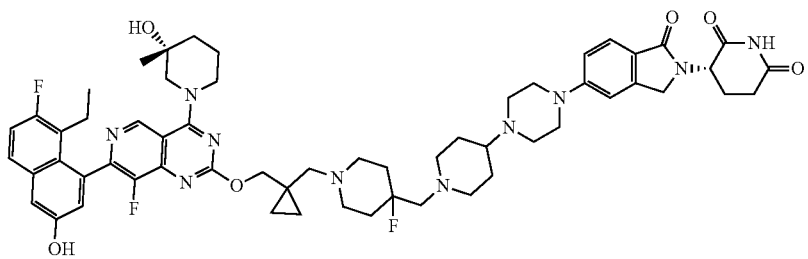 [SMILES: CCc1c(F)ccc2cc(O)cc(-c3ncc4c(N5CCC[C@@](C)(O)C5)nc(OCC5(CN6CCC(F)(CN7CCC(N8CCN(c9ccc%10c(c9)CN([C@H]9CCC(=O)NC9=O)C%10=O)CC8)CC7)CC6)CC5)nc4c3F)c12]<br>(S)-3-(5-(4-(1-((1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-4-fluoropiperidin-4-yl)methyl)piperidin-4-yl)piperazin-1-yl)-1-oxoisoindolin-2-yl)piperidine-2,6-dione |
| 73 | 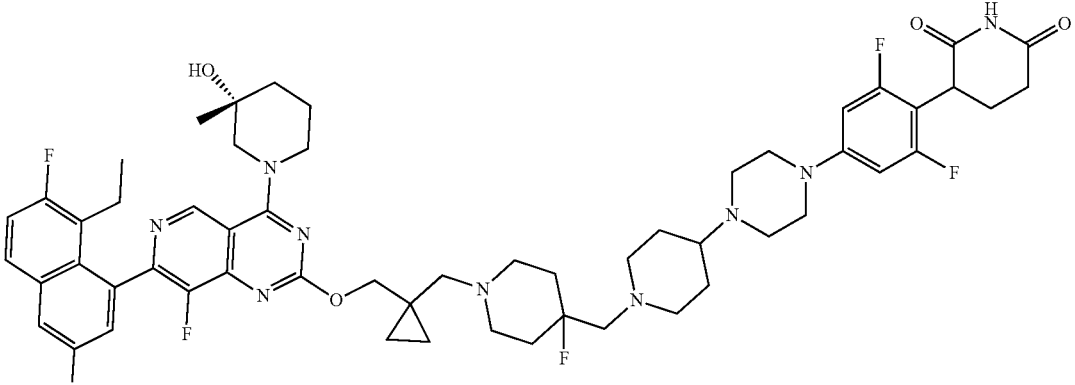<br>3-(4-(4-(1-((1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-4-fluoropiperidin-4-yl)methyl)piperidin-4-yl)piperazin-1-yl)-2,6-difluorophenyl)piperidine-2,6-dione |

TABLE 1-continued

Exemplary Compounds of the Present Disclosure

| Cpd # | Structure and IUPAC Name |
|---|---|
| 74 | 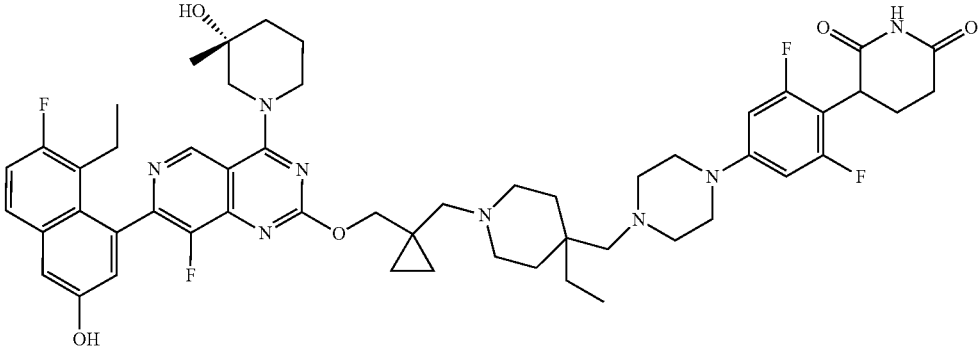 [SMILES: CCc1c(F)ccc2cc(O)cc(-c3ncc4c(N5CCC[C@@](C)(O)C5)nc(OCC5(CN6CCC(CC)(CN7CCN(c8cc(F)c(C9CCC(=O)NC9=O)c(F)c8)CC7)CC6)CC5)nc4c3F)c12]<br>3-(4-(4-((4-ethyl-1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)methyl)piperazin-1-yl)-2,6-difluorophenyl)piperidine-2,6-dione |
| 75 | 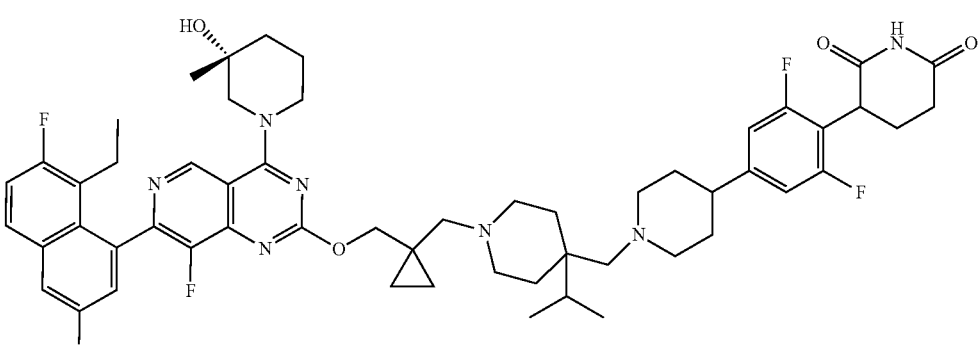<br>3-(4-(4-((1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-4-isopropylpiperidin-4-yl)methyl)piperazin-1-yl)-2,6-difluorophenyl)piperidine-2,6-dione |
| 76 | 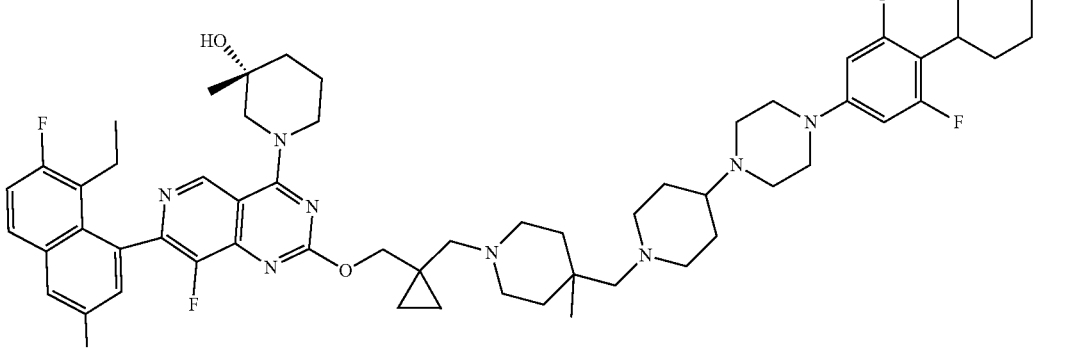<br>3-(4-(4-(1-((1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-4-methylpiperidin-4-yl)methyl)piperidin-4-yl)piperazin-1-yl)-2,6-difluorophenyl)piperidine-2,6-dione |

TABLE 1-continued

Exemplary Compounds of the Present Disclosure

| Cpd # | Structure and IUPAC Name |
|---|---|
| 77 | 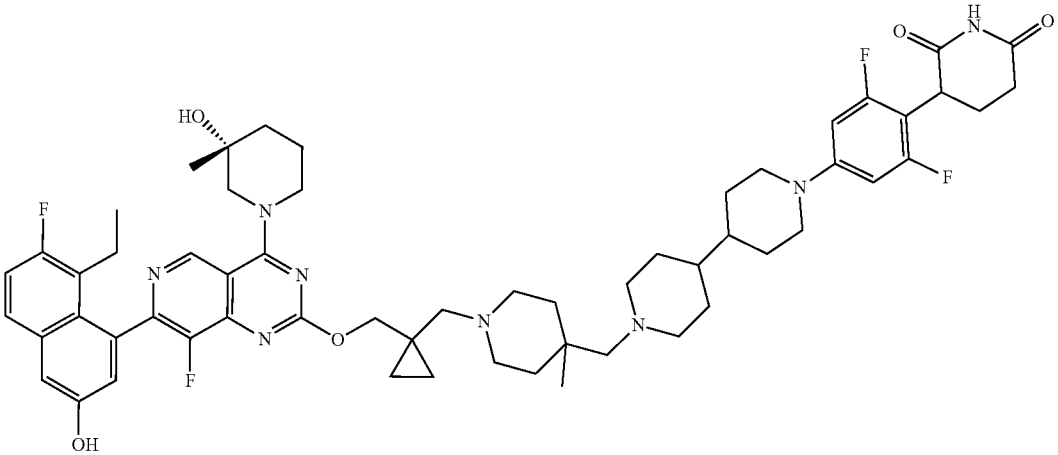 [SMILES: CCc1c(F)ccc2cc(O)cc(-c3ncc4c(N5CCC[C@@](C)(O)C5)nc(OCC5(CN6CCC(C)(CN7CCC(C8CCN(c9cc(F)c(C%10CCC(=O)NC%10=O)c(F)c9)CC8)CC7)CC6)CC5)nc4c3F)c12]<br>3-(4-(1'-((1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-4-methylpiperidin-4-yl)methyl)-[4,4'-bipiperidin]-1-yl)-2,6-difluorophenyl)piperidine-2,6-dione |
| 78 | 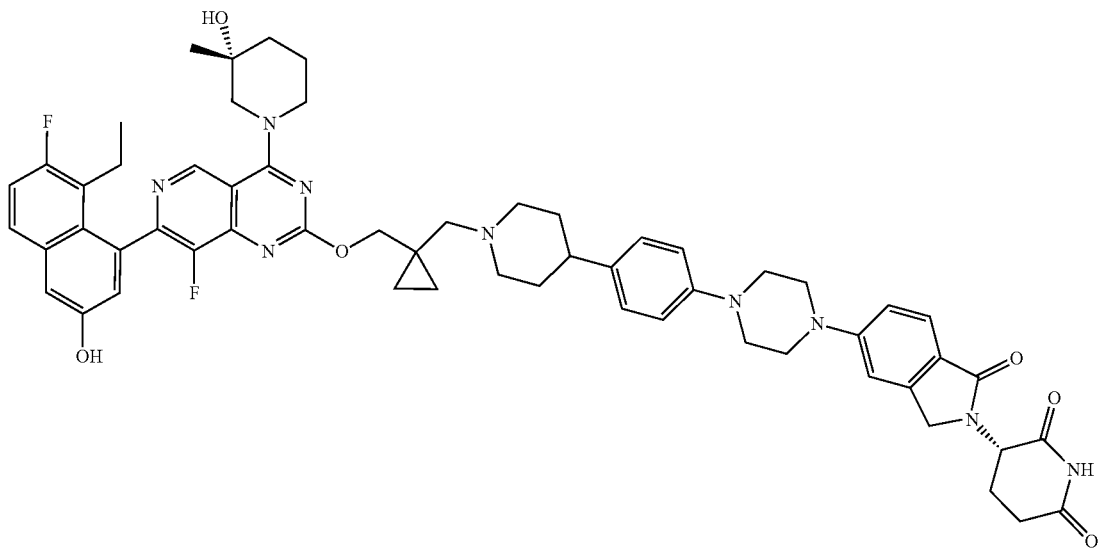 [SMILES: CCc1c(F)ccc2cc(O)cc(-c3ncc4c(N5CCC[C@@](C)(O)C5)nc(OCC5(CN6CCC(c7ccc(N8CCN(c9ccc%10c(c9)CN([C@H]9CCC(=O)NC9=O)C%10=O)CC8)cc7)CC6)CC5)nc4c3F)c12]<br>(S)-3-(5-(4-(4-(1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)phenyl)piperazin-1-yl)-1-oxoisoindolin-2-yl)piperidine-2,6-dione |

| Cpd # | Structure and IUPAC Name |
|---|---|
| 79 | 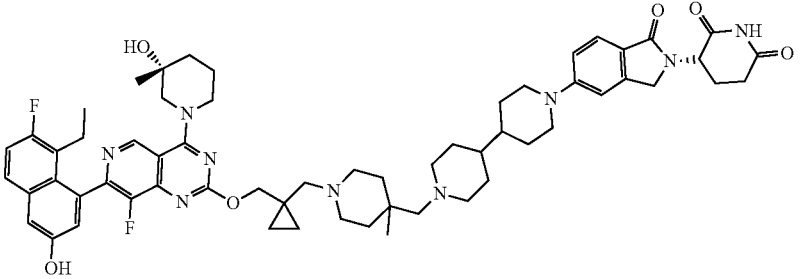<br>(S)-3-(5-(1'-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-4-methylpiperidin-4-yl)methyl)-[4,4'-bipiperidin]-1-yl)-1-oxoisoindolin-2-yl)piperidine-2,6-dione |
| 80 | 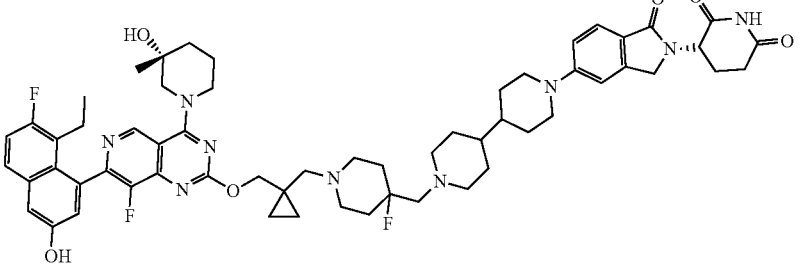<br>(S)-3-(5-(1'-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-4-fluoropiperidin-4-yl)methyl)-[4,4'-bipiperidin]-1-yl)-1-oxoisoindolin-2-yl)piperidine-2,6-dione |
| 81 | 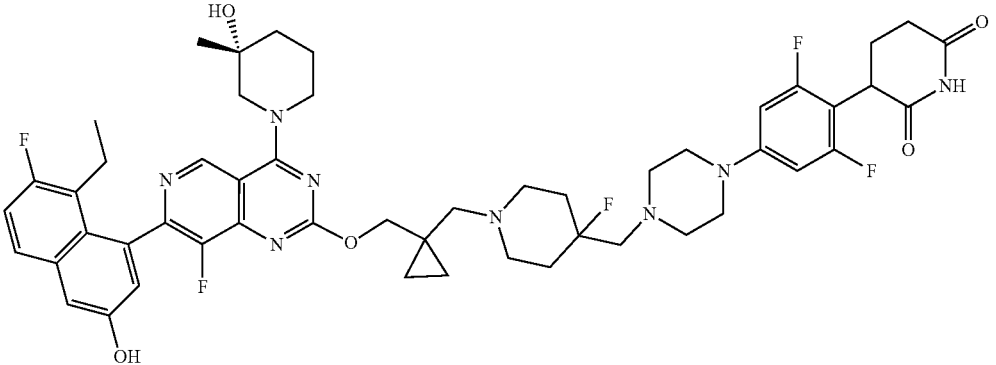 [SMILES: CCc1c(F)ccc2cc(O)cc(-c3ncc4c(N5CCC[C@@](C)(O)C5)nc(OCC5(CN6CCC(F)(CN7CCN(c8cc(F)c(C9CCC(=O)NC9=O)c(F)c8)CC7)CC6)CC5)nc4c3F)c12]<br>3-(4-(4-((1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-4-fluoropiperidin-4-yl)methyl)piperazin-1-yl)-2,6-difluorophenyl)piperidine-2,6-dione |

TABLE 1-continued

Exemplary Compounds of the Present Disclosure

| Cpd # | Structure and IUPAC Name |
|---|---|
| 82 | 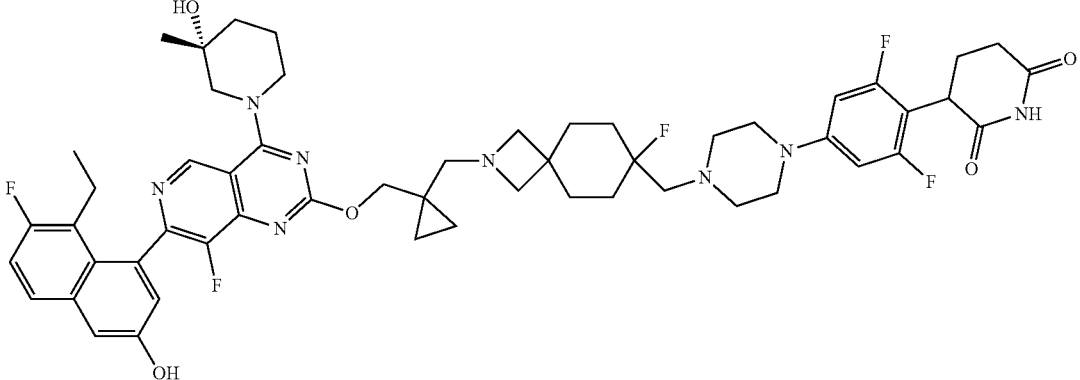 [SMILES: CCc1c(F)ccc2cc(O)cc(-c3ncc4c(N5CCC[C@@](C)(O)C5)nc(OCC5(CN6CC7(CCC(F)(CN8CCN(c9cc(F)c(C%10CCC(=O)NC%10=O)c(F)c9)CC8)CC7)C6)CC5)nc4c3F)c12]<br>3-(4-(4-((2-((1-((((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-fluoro-2-azaspiro[3.5]nonan-7-yl)methyl)piperazin-1-yl)-2,6-difluorophenyl)piperidine-2,6-dione |
| 83 | 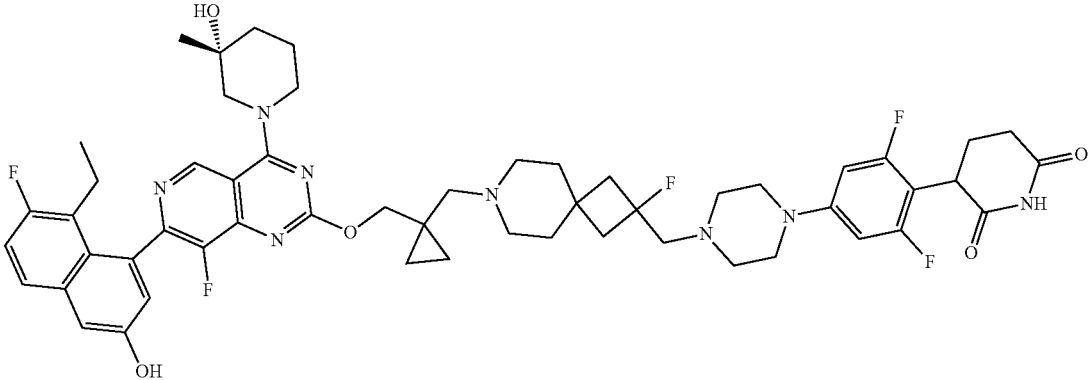 [SMILES: CCc1c(F)ccc2cc(O)cc(-c3ncc4c(N5CCC[C@@](C)(O)C5)nc(OCC5(CN6CCC7(CC6)CC(F)(CN6CCN(c8cc(F)c(C9CCC(=O)NC9=O)c(F)c8)CC6)C7)CC5)nc4c3F)c12]<br>3-(4-(4-((7-((1-((((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-2-fluoro-7-azaspiro[3.5]nonan-2-yl)methyl)piperazin-1-yl)-2,6-difluorophenyl)piperidine-2,6-dione |
| 84 | 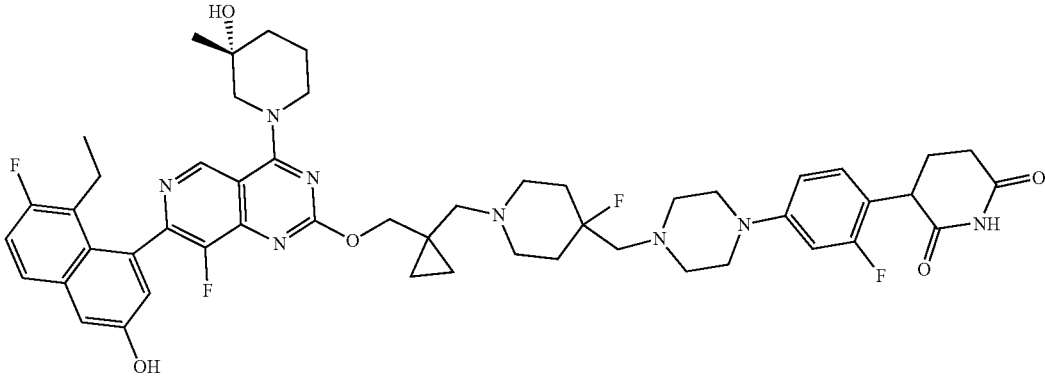 [SMILES: CCc1c(F)ccc2cc(O)cc(-c3ncc4c(N5CCC[C@@](C)(O)C5)nc(OCC5(CN6CCC(F)(CN7CCN(c8ccc(C9CCC(=O)NC9=O)c(F)c8)CC7)CC6)CC5)nc4c3F)c12]<br>3-(4-(4-((1-((1-((((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-4-fluoropiperidin-4-yl)methyl)piperazin-1-yl)-2-fluorophenyl)piperidine-2,6-dione |

TABLE 1-continued

Exemplary Compounds of the Present Disclosure

| Cpd # | Structure and IUPAC Name |
|---|---|
| 85 | 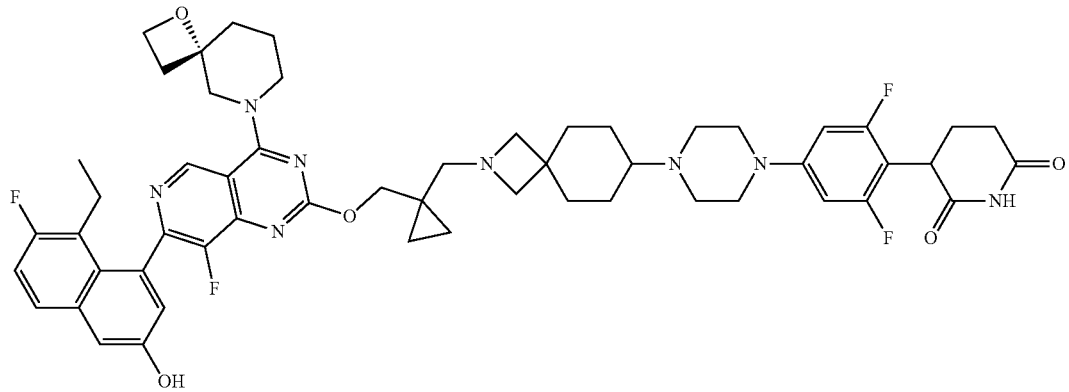 [SMILES: CCc1c(F)ccc2cc(O)cc(-c3ncc4c(N5CCC[C@]6(CCO6)C5)nc(OCC5(CN6CC7(CCC(N8CCN(c9cc(F)c(C%10CCC(=O)NC%10=O)c(F)c9)CC8)CC7)C6)CC5)nc4c3F)c12]<br>3-(4-(4-(2-((1-(((7-(8-ethyl-7-fluoro-3-hydroxynaphthalen-1-yl)-8-fluoro-4-((S)-1-oxa-6-azaspiro[3.5]nonan-6-yl)pyrido[4,3-d]pyrimidin-2-yl)oxy)methyl)cyclopropyl)methyl)-2-azaspiro[3.5]nonan-7-yl)piperazin-1-yl)-2,6-difluorophenyl)piperidine-2,6-dione |
| 86 | 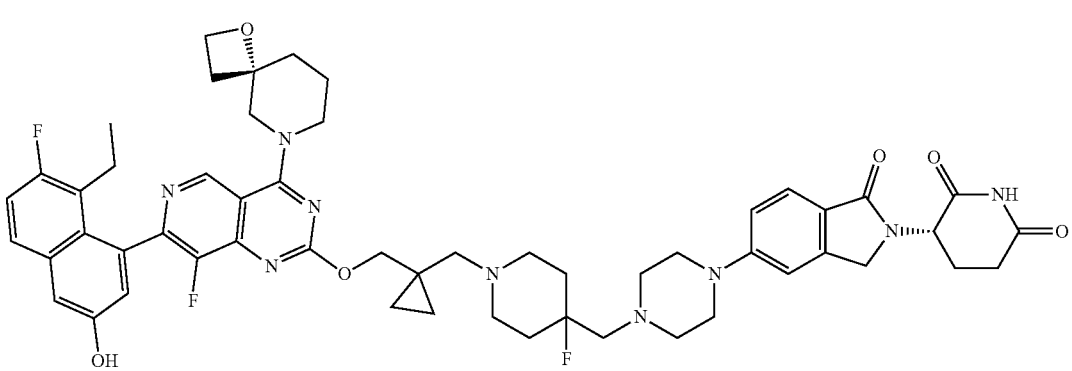 [SMILES: CCc1c(F)ccc2cc(O)cc(-c3ncc4c(N5CCC[C@]6(CCO6)C5)nc(OCC5(CN6CCC(F)(CN7CCN(c8ccc9c(c8)CN([C@H]8CCC(=O)NC8=O)C9=O)CC7)CC6)CC5)nc4c3F)c12]<br>(S)-3-(5-(4-((1-((1-(((7-(8-ethyl-7-fluoro-3-hydroxynaphthalen-1-yl)-8-fluoro-4-((S)-1-oxa-6-azaspiro[3.5]nonan-6-yl)pyrido[4,3-d]pyrimidin-2-yl)oxy)methyl)cyclopropyl)methyl)-4-fluoropiperidin-4-yl)methyl)piperazin-1-yl)-1-oxoisoindolin-2-yl)piperidine-2,6-dione |
| 87 | 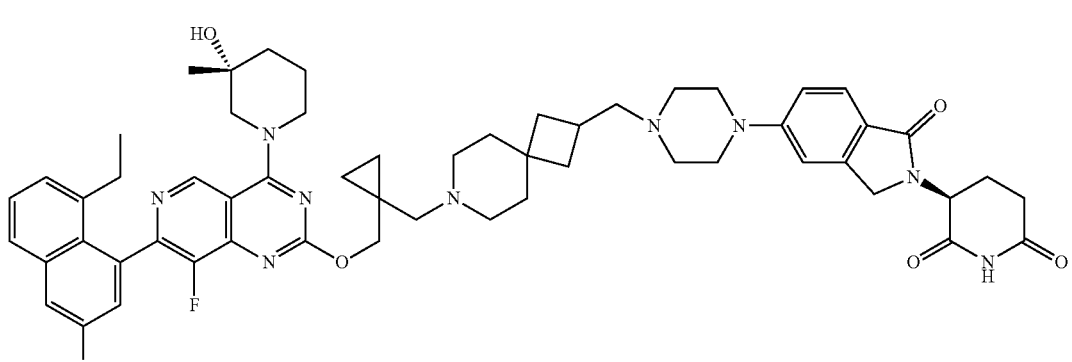<br>(S)-3-(5-(4-((7-((1-(((7-(8-ethyl-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |

TABLE 1-continued

Exemplary Compounds of the Present Disclosure

| Cpd # | Structure and IUPAC Name |
|---|---|
| 88 | 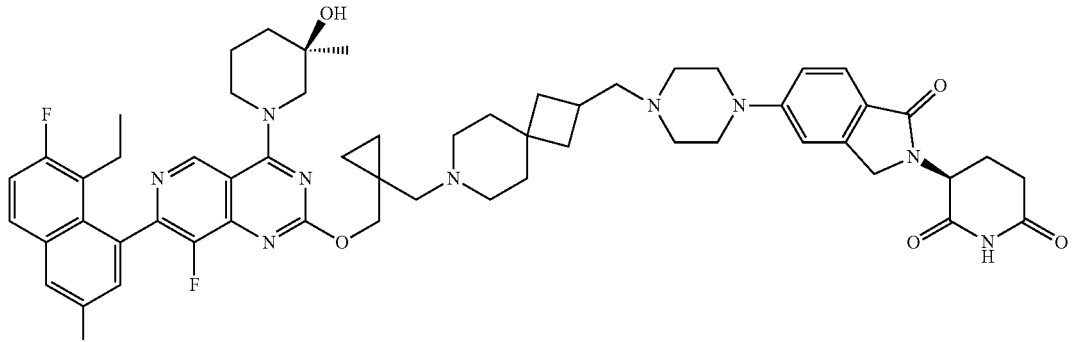<br>(S)-3-(5-(4-((7-((1-(((7-(3-amino-8-ethyl-7-fluoronaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |
| 89 | 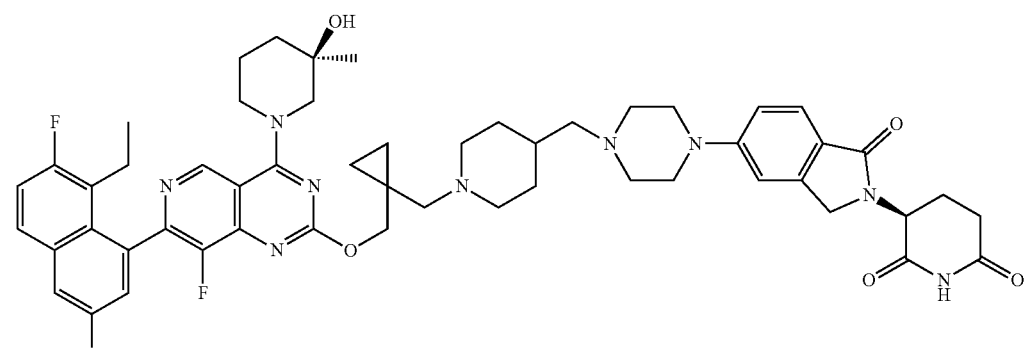<br>(S)-3-(5-(4-((1-((1-(((7-(3-amino-8-ethyl-7-fluoronaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione |
| 90 | 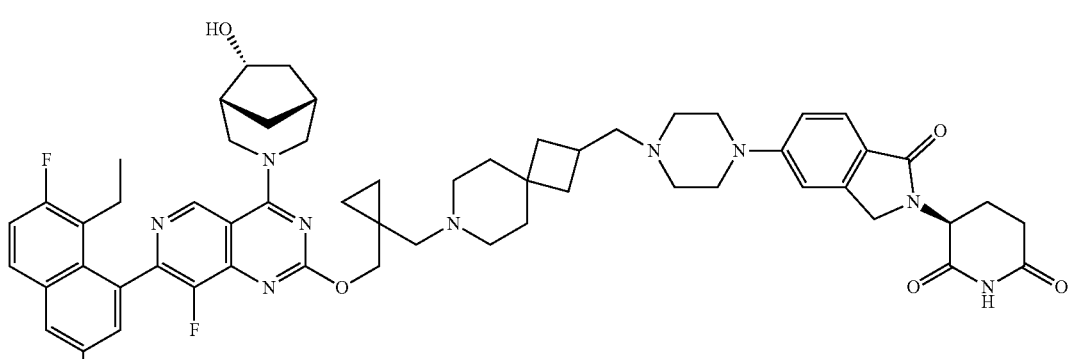<br>(S)-3-(5-(4-((7-((1-(((7-(8-ethyl-7-fluoro-3-hydroxynaphthalen-1-yl)-8-fluoro-4-((1R,5R,6R)-6-hydroxy-3-azabicyclo[3.2.1]octan-3-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |

TABLE 1-continued

Exemplary Compounds of the Present Disclosure

| Cpd # | Structure and IUPAC Name |
|---|---|
| 91 | 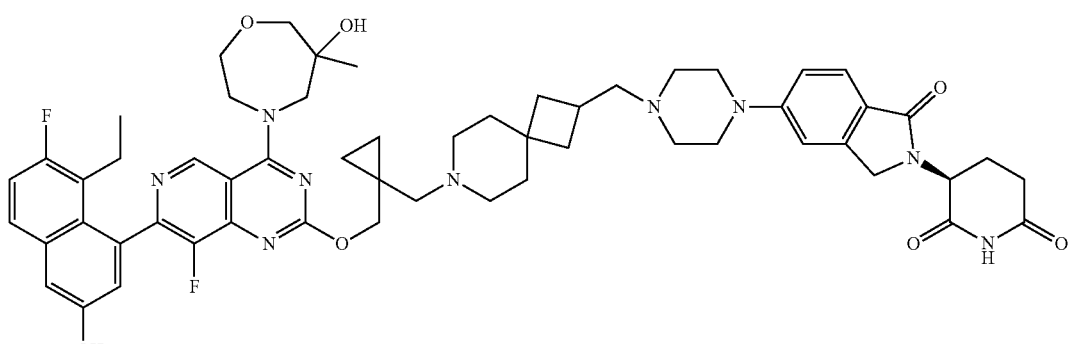<br>(3S)-3-(5-(4-((7-((1-(((7-(8-ethyl-7-fluoro-3-hydroxynaphthalen-1-yl)-8-fluoro-4-(6-hydroxy-6-methyl-1,4-oxazepan-4-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |
| 92 | 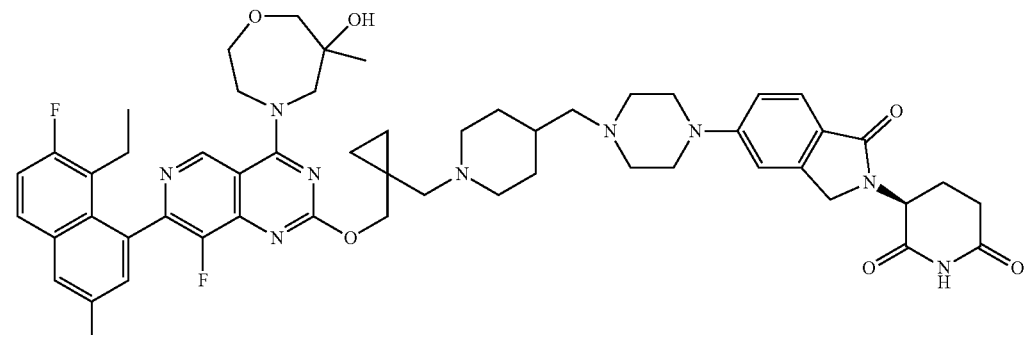<br>(3S)-3-(5-(4-((1-((1-(((7-(8-ethyl-7-fluoro-3-hydroxynaphthalen-1-yl)-8-fluoro-4-(6-hydroxy-6-methyl-1,4-oxazepan-4-yl)pyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione |
| 93 | 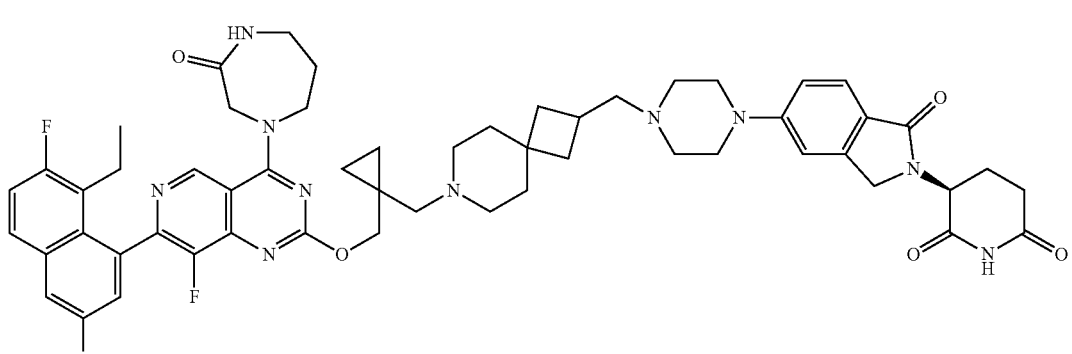<br>(S)-3-(5-(4-((7-((1-(((7-(8-ethyl-7-fluoro-3-hydroxynaphthalen-1-yl)-8-fluoro-4-(3-oxo-1,4-diazepan-1-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |

TABLE 1-continued

Exemplary Compounds of the Present Disclosure

| Cpd # | Structure and IUPAC Name |
|---|---|
| 94 | (S)-3-chloro-5-(2-((1-((2-(((4-(2-(2,6-dioxopiperidin-3-yl)-1-oxoisoindolin-5-yl)piperazin-1-yl)methyl)-7-azaspiro[3.5]nonan-7-yl)methyl)cyclopropyl)methoxy)-7-(8-ethyl-7-fluoro-3-hydroxynaphthalen-1-yl)-8-fluoropyrido[4,3-d]pyrimidin-4-yl)-N,N-dimethyl-5,6,7,8-tetrahydro-4H-pyrazolo[1,5-a][1,4]diazepine-2-carboxamide |
| 95 | (S)-3-(5-(4-((1-((1-(((7-(8-ethyl-7-fluoro-3-hydroxynaphthalen-1-yl)-8-fluoro-4-(3-oxo-1,4-diazepan-1-yl)pyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione |
| 96 | (S)-3-(5-(4-((1-((1-(((7-(8-ethyl-7-fluoro-3-hydroxynaphthalen-1-yl)-8-fluoro-4-((1R,5R,6R)-6-hydroxy-3-azabicyclo[3.2.1]octan-3-yl)pyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione |

TABLE 1-continued

Exemplary Compounds of the Present Disclosure

| Cpd # | Structure and IUPAC Name |
|---|---|
| 97 | 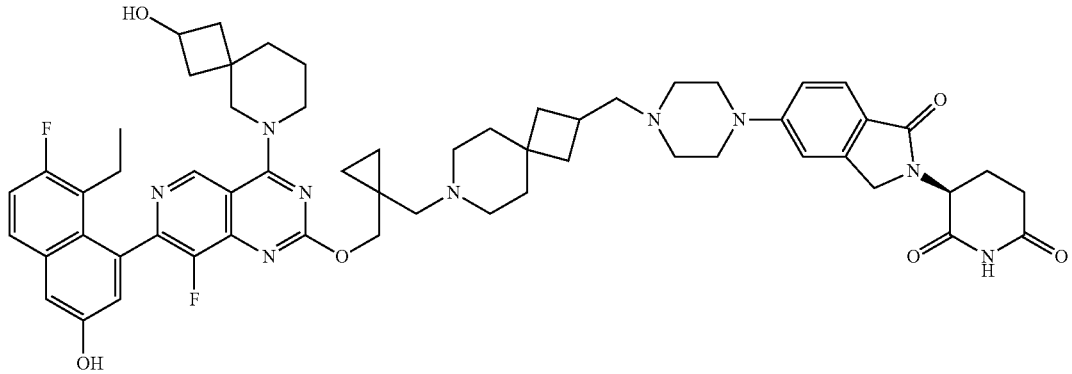 [SMILES: CCc1c(F)ccc2cc(O)cc(-c3ncc4c(N5CCCC6(CC(O)C6)C5)nc(OCC5(CN6CCC7(CC6)CC(CN6CCN(c8ccc9c(c8)CN([C@H]8CCC(=O)NC8=O)C9=O)CC6)C7)CC5)nc4c3F)c12]<br>(S)-3-(5-(4-((7-((1-(((7-(8-ethyl-7-fluoro-3-hydroxynaphthalen-1-yl)-8-fluoro-4-(2-hydroxy-6-azaspiro[3.5]nonan-6-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |
| 98 | 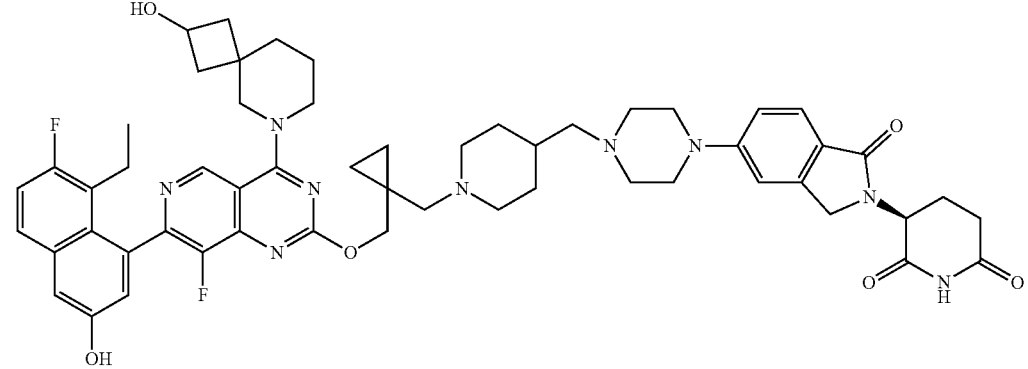 [SMILES: CCc1c(F)ccc2cc(O)cc(-c3ncc4c(N5CCCC6(CC(O)C6)C5)nc(OCC5(CN6CCC(CN7CCN(c8ccc9c(c8)CN([C@H]8CCC(=O)NC8=O)C9=O)CC7)CC6)CC5)nc4c3F)c12]<br>(S)-3-(5-(4-((1-((1-(((7-(8-ethyl-7-fluoro-3-hydroxynaphthalen-1-yl)-8-fluoro-4-(2-hydroxy-6-azaspiro[3.5]nonan-6-yl)pyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione |
| 99 | 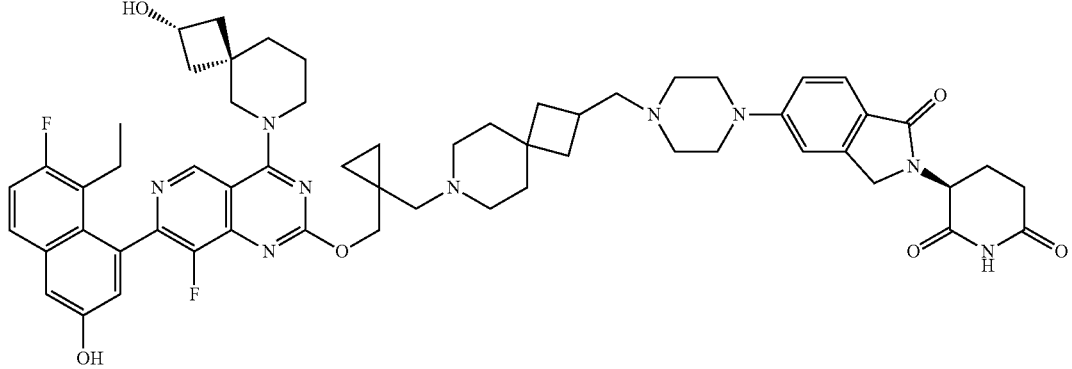 [SMILES: CCc1c(F)ccc2cc(O)cc(-c3ncc4c(N5CCC[C@]6(C5)C[C@H](O)C6)nc(OCC5(CN6CCC7(CC6)CC(CN6CCN(c8ccc9c(c8)CN([C@H]8CCC(=O)NC8=O)C9=O)CC6)C7)CC5)nc4c3F)c12]<br>(S)-3-(5-(4-((7-((1-(((7-(8-ethyl-7-fluoro-3-hydroxynaphthalen-1-yl)-8-fluoro-4-((2s,4r)-2-hydroxy-6-azaspiro[3.5]nonan-6-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |

TABLE 1-continued

Exemplary Compounds of the Present Disclosure

| Cpd # | Structure and IUPAC Name |
|---|---|
| 100 | 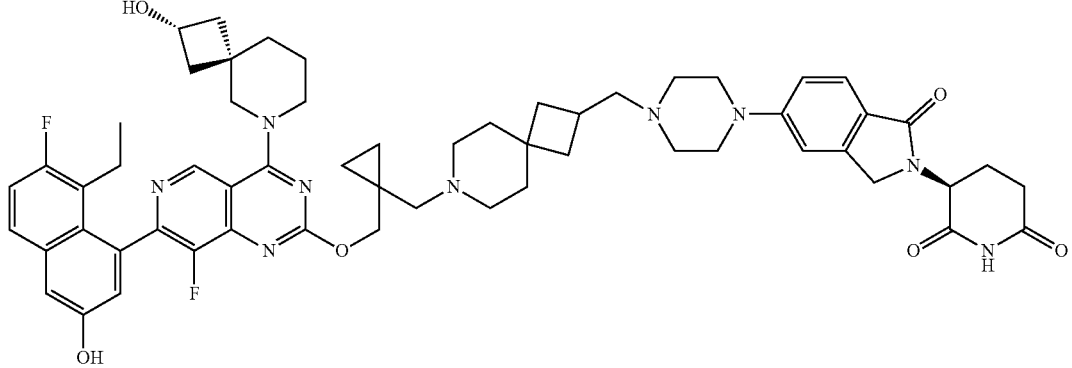 [SMILES: CCc1c(F)ccc2cc(O)cc(-c3ncc4c(N5CCC[C@]6(C5)C[C@@H](O)C6)nc(OCC5(CN6CCC7(CC6)CC(CN6CCN(c8ccc9c(c8)CN([C@H]8CCC(=O)NC8=O)C9=O)CC6)C7)CC5)nc4c3F)c12]<br>(S)-3-(5-(4-((7-((1-(((7-(8-ethyl-7-fluoro-3-hydroxynaphthalen-1-yl)-8-fluoro-4-((2r,4s)-2-hydroxy-6-azaspiro[3.5]nonan-6-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |
| 101 | 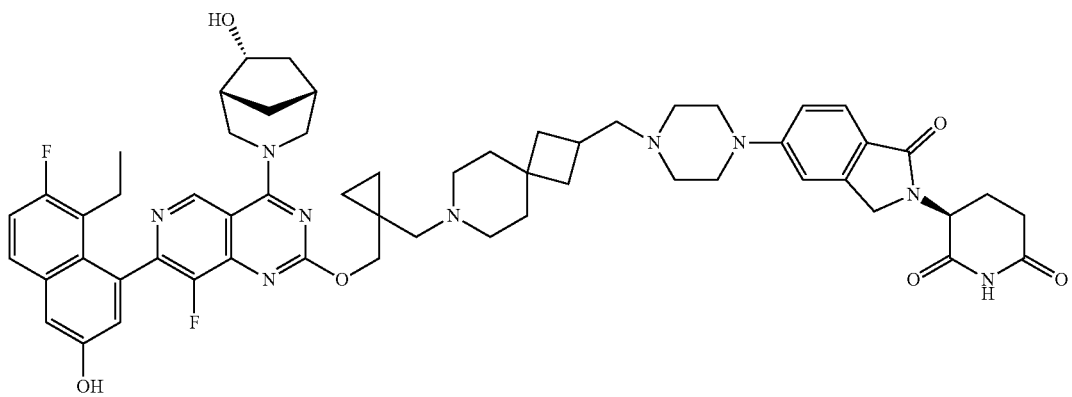 [SMILES: CCc1c(F)ccc2cc(O)cc(-c3ncc4c(N5C[C@@H]6C[C@H](C5)[C@H](O)C6)nc(OCC5(CN6CCC7(CC6)CC(CN6CCN(c8ccc9c(c8)CN([C@H]8CCC(=O)NC8=O)C9=O)CC6)C7)CC5)nc4c3F)c12]<br>(S)-3-(5-(4-((7-((1-(((7-(8-ethyl-3-hydroxynaphthalen-1-yl)-8-fluoro-4-((1R,5R,6R)-6-hydroxy-3-azabicyclo[3.2.1]octan-3-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |
| 102 | 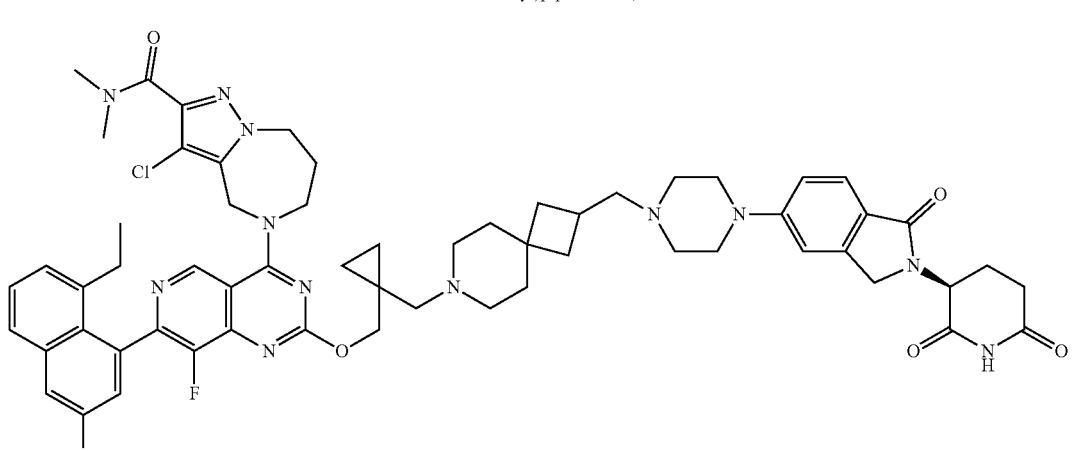<br>(S)-3-chloro-5-(2-((1-((2-((4-(2-(2,6-dioxopiperidin-3-yl)-1-oxoisoindolin-5-yl)piperazin-1-yl)methyl)-7-azaspiro[3.5]nonan-7-yl)methyl)cyclopropyl)methoxy)-7-(8-ethyl-3-hydroxynaphthalen-1-yl)-8-fluoropyrido[4,3-d]pyrimidin-4-yl)-N,N-dimethyl-5,6,7,8-tetrahydro-4H-pyrazolo[1,5-a][1,4]diazepine-2-carboxamide |

TABLE 1-continued

Exemplary Compounds of the Present Disclosure

| Cpd # | Structure and IUPAC Name |
|---|---|
| 103 | 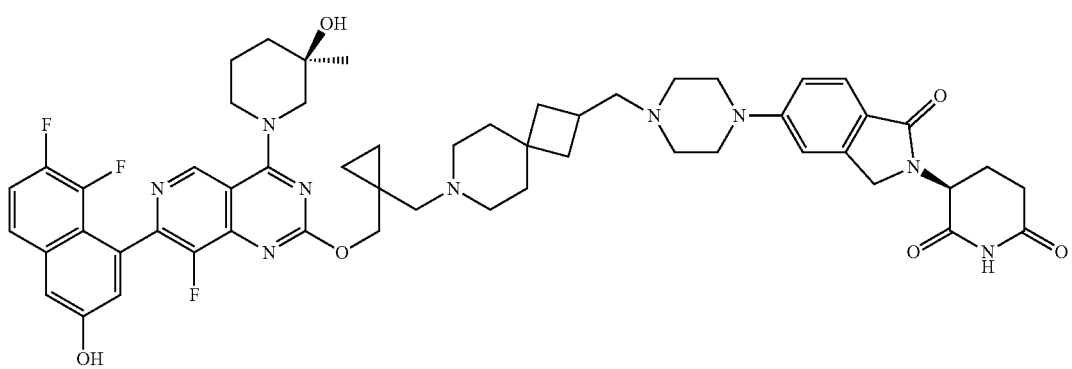 [SMILES: C[C@@]1(O)CCCN(c2nc(OCC3(CN4CCC5(CC4)CC(CN4CCN(c6ccc7c(c6)CN([C@H]6CCC(=O)NC6=O)C7=O)CC4)C5)CC3)nc3c(F)c(-c4cc(O)cc5ccc(F)c(F)c45)ncc23)C1]<br>(S)-3-(5-(4-((7-((1-(((7-(7,8-difluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |
| 104 | 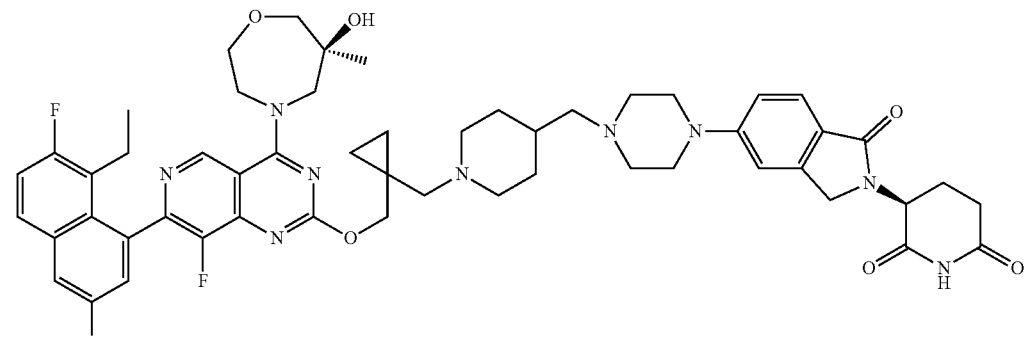<br>(S)-3-(5-(4-((1-((1-(((7-(8-ethyl-7-fluoro-3-hydroxynaphthalen-1-yl)-8-fluoro-4-((S)-6-hydroxy-6-methyl-1,4-oxazepan-4-yl)pyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione |
| 105 | 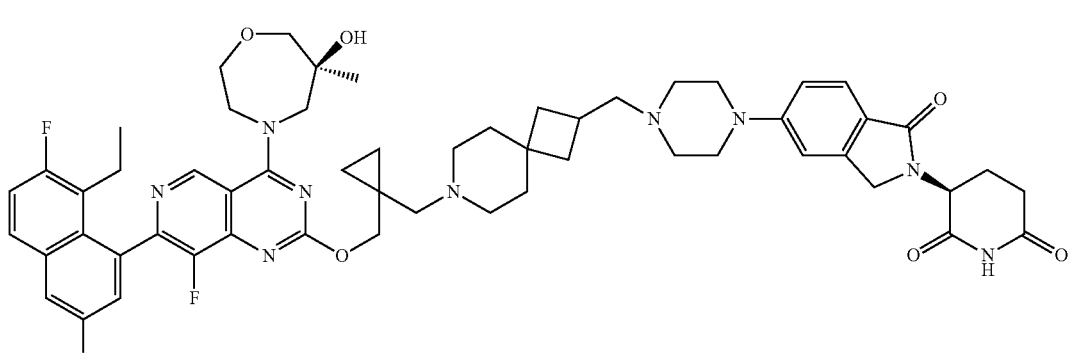<br>(S)-3-(5-(4-((7-((1-(((7-(8-ethyl-7-fluoro-3-hydroxynaphthalen-1-yl)-8-fluoro-4-((S)-6-hydroxy-6-methyl-1,4-oxazepan-4-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |

TABLE 1-continued

Exemplary Compounds of the Present Disclosure

| Cpd # | Structure and IUPAC Name |
|---|---|
| 106 | 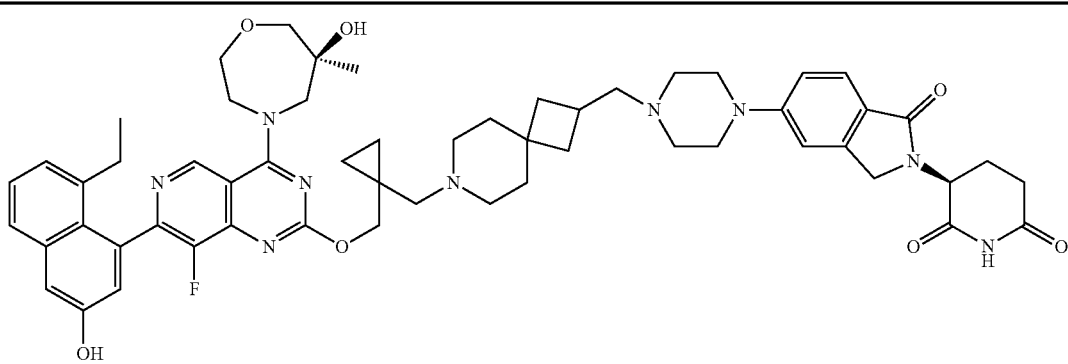<br>(S)-3-(5-(4-((7-((1-(((7-(8-ethyl-3-hydroxynaphthalen-1-yl)-8-fluoro-4-((S)-6-hydroxy-6-methyl-1,4-oxazepan-4-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |
| 107 | 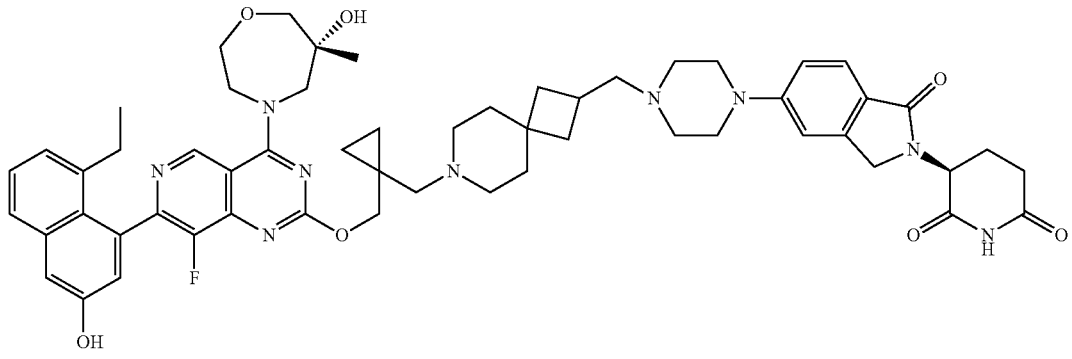 [SMILES: CCc1cccc2cc(O)cc(-c3ncc4c(N5CCOC[C@](C)(O)C5)nc(OCC5(CN6CCC7(CC6)CC(CN6CCN(c8ccc9c(c8)CN([C@H]8CCC(=O)NC8=O)C9=O)CC6)C7)CC5)nc4c3F)c12]<br>(S)-3-(5-(4-((7-((1-(((7-(8-ethyl-3-hydroxynaphthalen-1-yl)-8-fluoro-4-((R)-6-hydroxy-6-methyl-1,4-oxazepan-4-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |
| 108 | 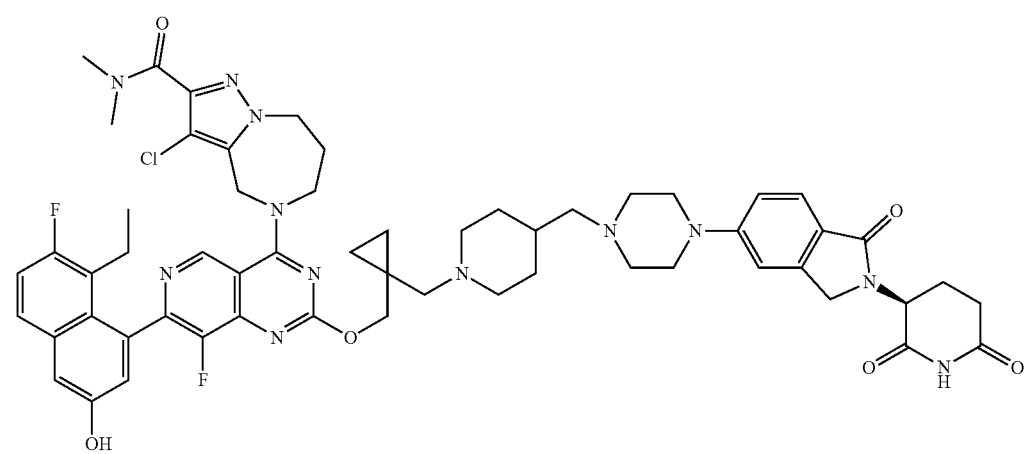 [SMILES: CCc1c(F)ccc2cc(O)cc(-c3ncc4c(N5CCCn6nc(C(=O)N(C)C)c(Cl)c6C5)nc(OCC5(CN6CCC(CN7CCN(c8ccc9c(c8)CN([C@H]8CCC(=O)NC8=O)C9=O)CC7)CC6)CC5)nc4c3F)c12]<br>(S)-3-chloro-5-(2-((1-((4-((4-(2-(2,6-dioxopiperidin-3-yl)-1-oxoisoindolin-5-yl)piperazin-1-yl)methyl)piperidin-1-yl)methyl)cyclopropyl)methoxy)-7-(8-ethyl-7-fluoro-3-hydroxynaphthalen-1-yl)-8-fluoropyrido[4,3-d]pyrimidin-4-yl)-N,N-dimethyl-5,6,7,8-tetrahydro-4H-pyrazolo[1,5-a][1,4]diazepine-2-carboxamide |

TABLE 1-continued

Exemplary Compounds of the Present Disclosure

| Cpd # | Structure and IUPAC Name |
|---|---|
| 109 | 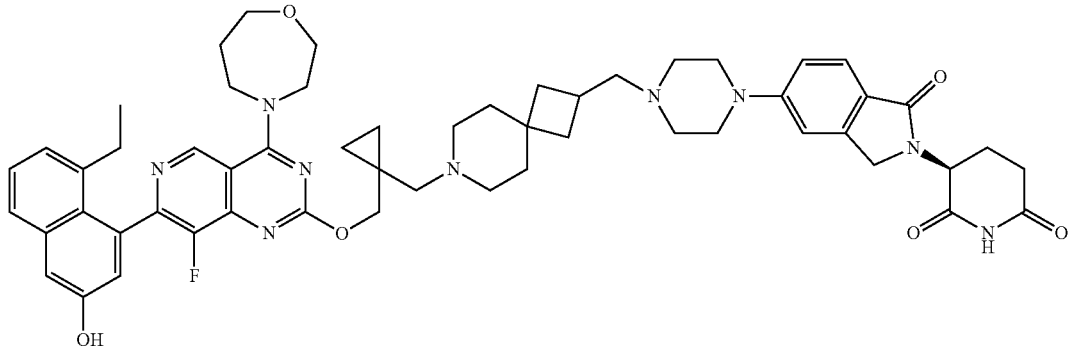 [SMILES: CCc1cccc2cc(O)cc(-c3ncc4c(N5CCCOCC5)nc(OCC5(CN6CCC7(CC6)CC(CN6CCN(c8ccc9c(c8)CN([C@H]8CCC(=O)NC8=O)C9=O)CC6)C7)CC5)nc4c3F)c12]<br>(S)-3-(5-(4-((7-(((1-(((7-(8-ethyl-3-hydroxynaphthalen-1-yl)-8-fluoro-4-(1,4-oxazepan-4-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |
| 110 | 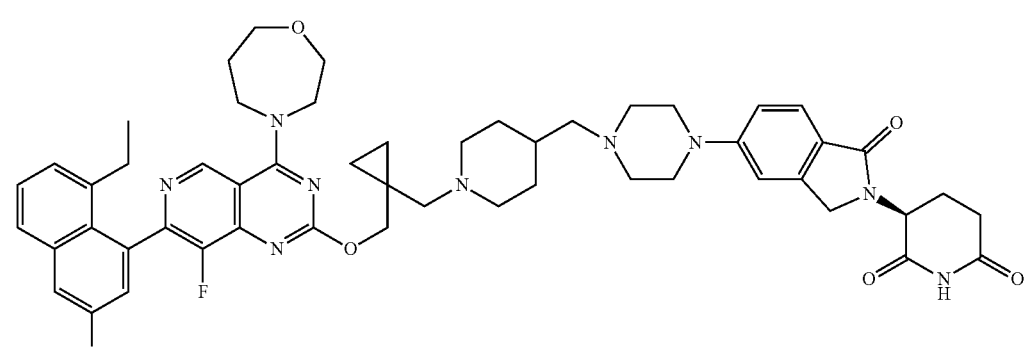<br>(S)-3-(5-(4-((1-((1-(((7-(8-ethyl-3-hydroxynaphthalen-1-yl)-8-fluoro-4-(1,4-oxazepan-4-yl)pyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione |
| 111 | 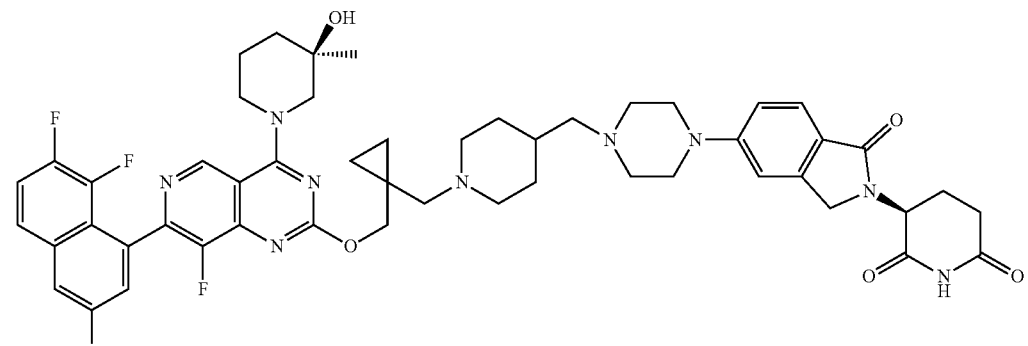<br>(S)-3-(5-(4-((1-((1-(((7-(7,8-difluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione |

TABLE 1-continued

Exemplary Compounds of the Present Disclosure

| Cpd # | Structure and IUPAC Name |
|---|---|
| 112 | 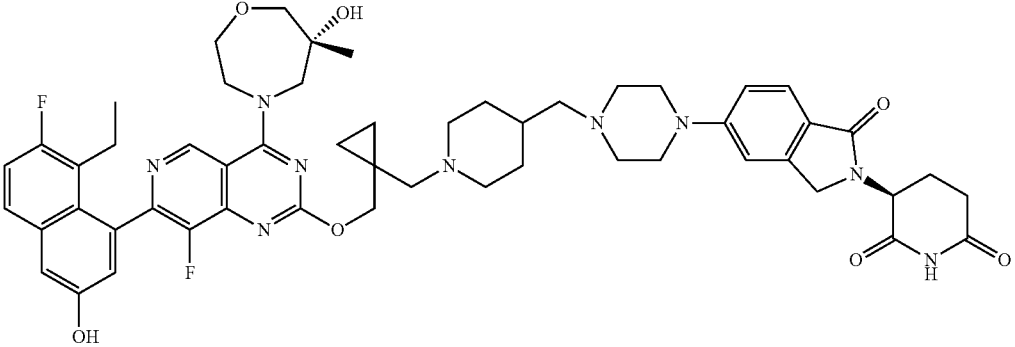 [SMILES: CCc1c(F)ccc2cc(O)cc(-c3ncc4c(N5CCOC[C@](C)(O)C5)nc(OCC5(CN6CCC(CN7CCN(c8ccc9c(c8)CN([C@H]8CCC(=O)NC8=O)C9=O)CC7)CC6)CC5)nc4c3F)c12] (S)-3-(5-(4-(((1-(((7-(8-ethyl-7-fluoro-3-hydroxynaphthalen-1-yl)-8-fluoro-4-((R)-6-hydroxy-6-methyl-1,4-oxazepan-4-yl)pyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione |
| 113 | 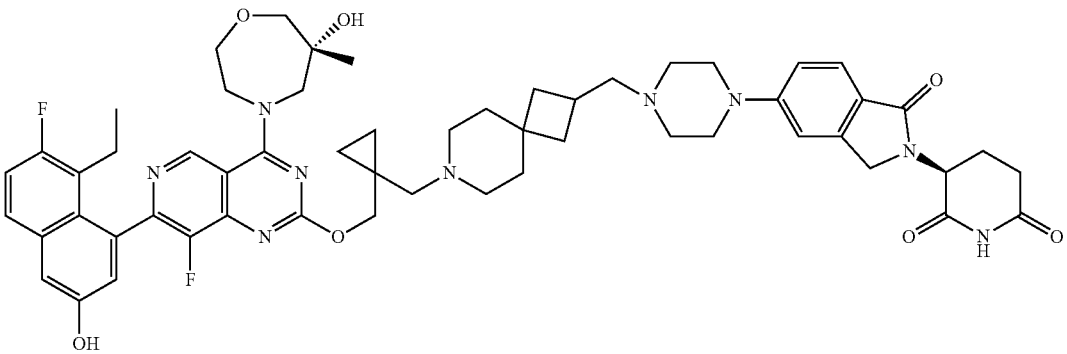 [SMILES: CCc1c(F)ccc2cc(O)cc(-c3ncc4c(N5CCOC[C@](C)(O)C5)nc(OCC5(CN6CCC7(CC6)CC(CN6CCN(c8ccc9c(c8)CN([C@H]8CCC(=O)NC8=O)C9=O)CC6)C7)CC5)nc4c3F)c12] (S)-3-(5-(4-((7-((1-(((7-(8-ethyl-7-fluoro-3-hydroxynaphthalen-1-yl)-8-fluoro-4-((R)-6-hydroxy-6-methyl-1,4-oxazepan-4-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |
| 114 | 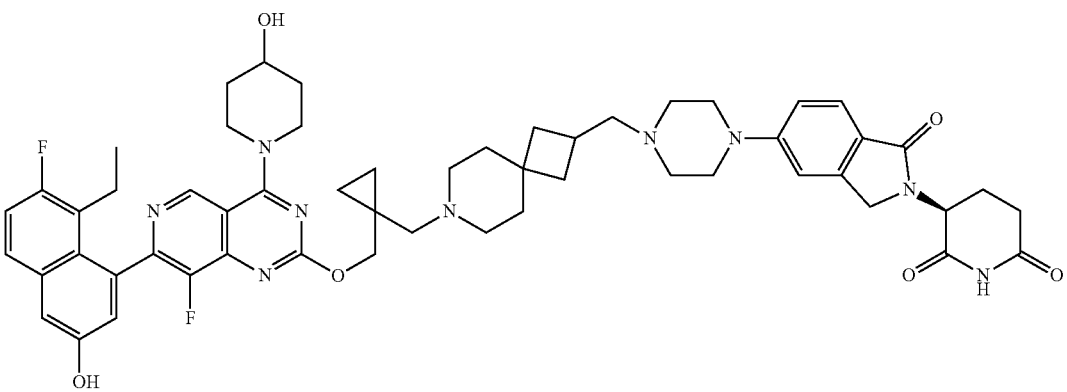 [SMILES: CCc1c(F)ccc2cc(O)cc(-c3ncc4c(N5CCC(O)CC5)nc(OCC5(CN6CCC7(CC6)CC(CN6CCN(c8ccc9c(c8)CN([C@H]8CCC(=O)NC8=O)C9=O)CC6)C7)CC5)nc4c3F)c12] (S)-3-(5-(4-((7-((1-(((7-(8-ethyl-7-fluoro-3-hydroxynaphthalen-1-yl)-8-fluoro-4-(4-hydroxypiperidin-1-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |

TABLE 1-continued

Exemplary Compounds of the Present Disclosure

| Cpd # | Structure and IUPAC Name |
|---|---|
| 115 | 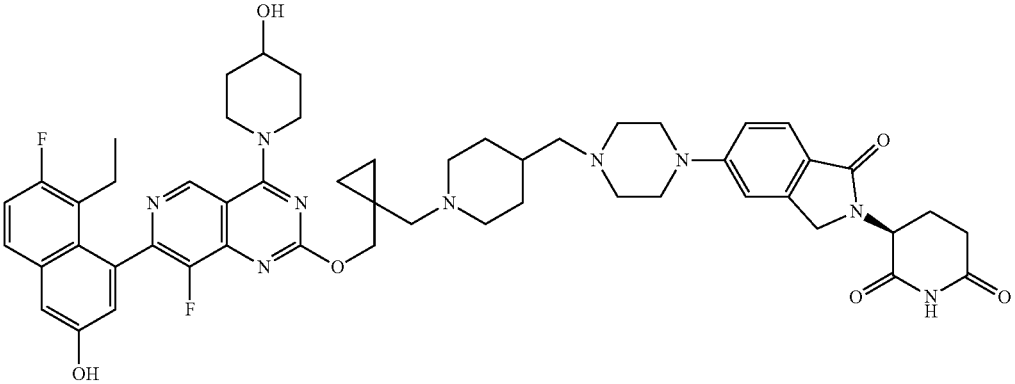 [SMILES: CCc1c(F)ccc2cc(O)cc(-c3ncc4c(N5CCC(O)CC5)nc(OCC5(CN6CCC(CN7CCN(c8ccc9c(c8)CN([C@H]8CCC(=O)NC8=O)C9=O)CC7)CC6)CC5)nc4c3F)c12]<br>(S)-3-(5-(4-((1-((1-(((7-(8-ethyl-7-fluoro-3-hydroxynaphthalen-1-yl)-8-fluoro-4-(4-hydroxypiperidin-1-yl)pyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione |
| 116 | 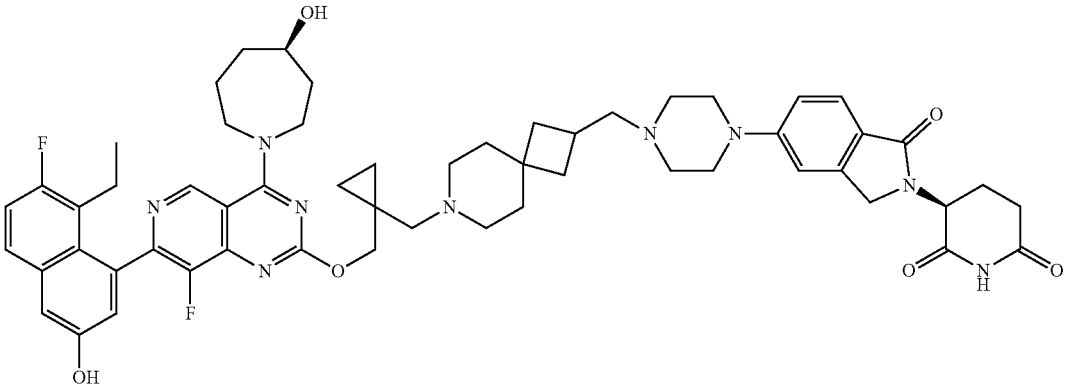 [SMILES: CCc1c(F)ccc2cc(O)cc(-c3ncc4c(N5CCC[C@@H](O)CC5)nc(OCC5(CN6CCC7(CC6)CC(CN6CCN(c8ccc9c(c8)CN([C@H]8CCC(=O)NC8=O)C9=O)CC6)C7)CC5)nc4c3F)c12]<br>(S)-3-(5-(4-((7-((1-(((7-(8-ethyl-7-fluoro-3-hydroxynaphthalen-1-yl)-8-fluoro-4-((R)-4-hydroxyazepan-1-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |
| 117 | 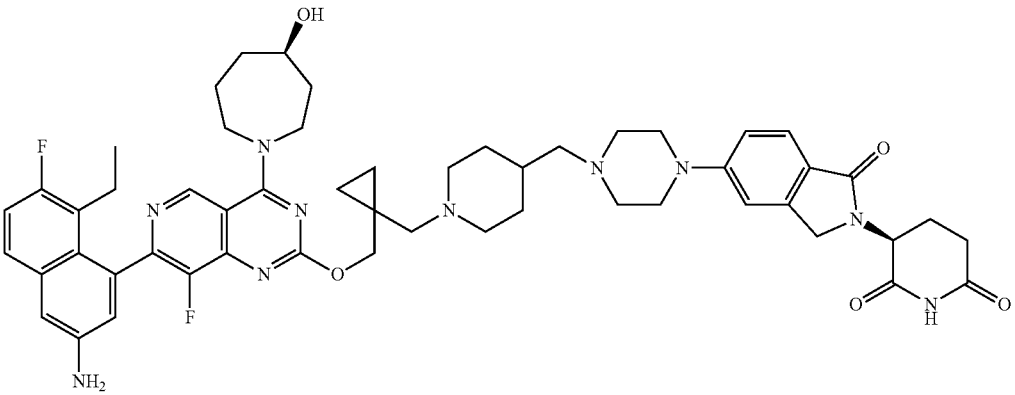 [SMILES: CCc1c(F)ccc2cc(N)cc(-c3ncc4c(N5CCC[C@@H](O)CC5)nc(OCC5(CN6CCC(CN7CCN(c8ccc9c(c8)CN([C@H]8CCC(=O)NC8=O)C9=O)CC7)CC6)CC5)nc4c3F)c12]<br>(S)-3-(5-(4-((1-((1-(((7-(8-ethyl-7-fluoro-3-hydroxynaphthalen-1-yl)-8-fluoro-4-((R)-4-hydroxyazepan-1-yl)pyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione |

TABLE 1-continued

Exemplary Compounds of the Present Disclosure

| Cpd # | Structure and IUPAC Name |
|---|---|
| 118 | 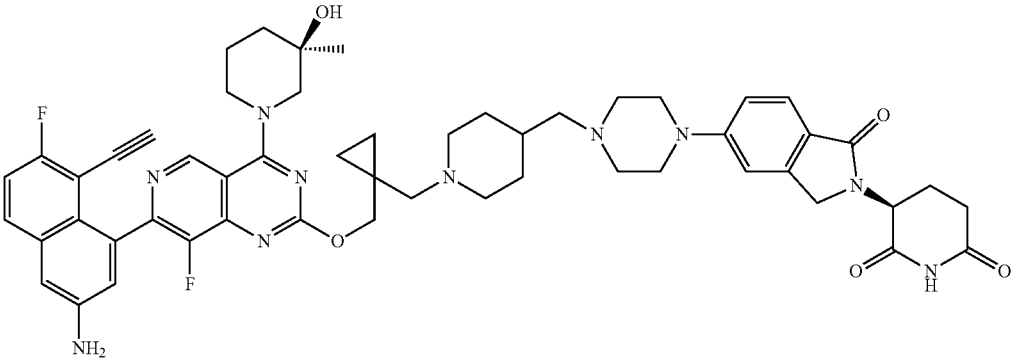 [SMILES: C#Cc1c(F)ccc2cc(N)cc(-c3ncc4c(N5CCC[C@@](C)(O)C5)nc(OCC5(CN6CCC(CN7CCN(c8ccc9c(c8)CN([C@H]8CCC(=O)NC8=O)C9=O)CC7)CC6)CC5)nc4c3F)c12]<br>(S)-3-(5-(4-((1-((1-(((7-(3-amino-8-ethynyl-7-fluoronaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione |
| 119 | 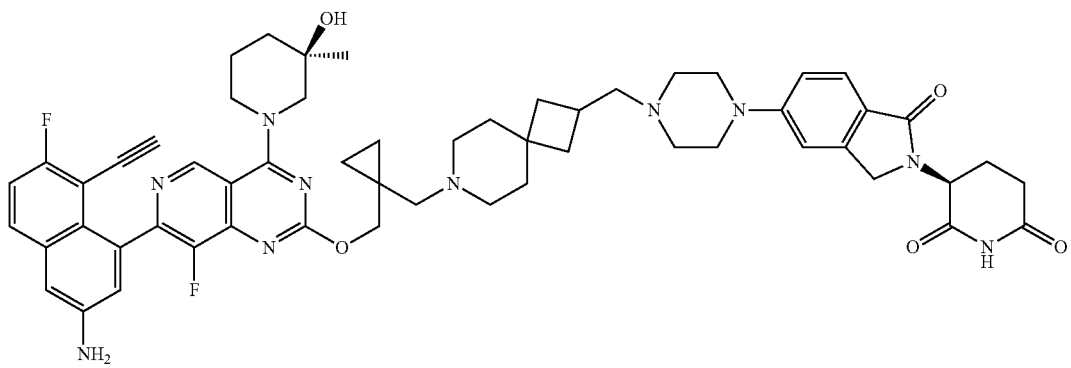 [SMILES: C#Cc1c(F)ccc2cc(N)cc(-c3ncc4c(N5CCC[C@@](C)(O)C5)nc(OCC5(CN6CCC7(CC6)CC(CN6CCN(c8ccc9c(c8)CN([C@H]8CCC(=O)NC8=O)C9=O)CC6)C7)CC5)nc4c3F)c12]<br>(S)-3-(5-(4-((7-((1-(((7-(3-amino-8-ethynyl-7-fluoronaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |
| 120 | 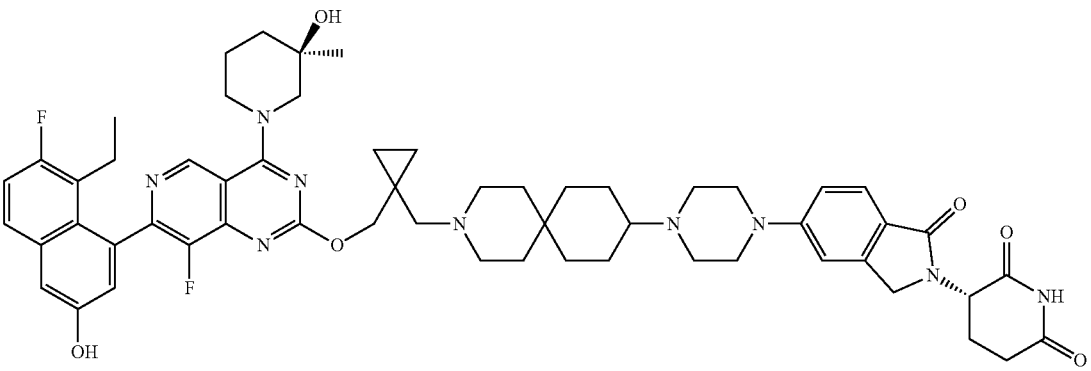 [SMILES: CCc1c(F)ccc2cc(O)cc(-c3ncc4c(N5CCC[C@@](C)(O)C5)nc(OCC5(CN6CCC7(CCC(N8CCN(c9ccc%10c(c9)CN([C@H]9CCC(=O)NC9=O)C%10=O)CC8)CC7)CC6)CC5)nc4c3F)c12]<br>(S)-3-(5-(4-(3-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-3-azaspiro[5.5]undecan-9-yl)piperazin-1-yl)-1-oxoisoindolin-2-yl)piperidine-2,6-dione |

TABLE 1-continued

Exemplary Compounds of the Present Disclosure

| Cpd # | Structure and IUPAC Name |
|---|---|
| 121 | 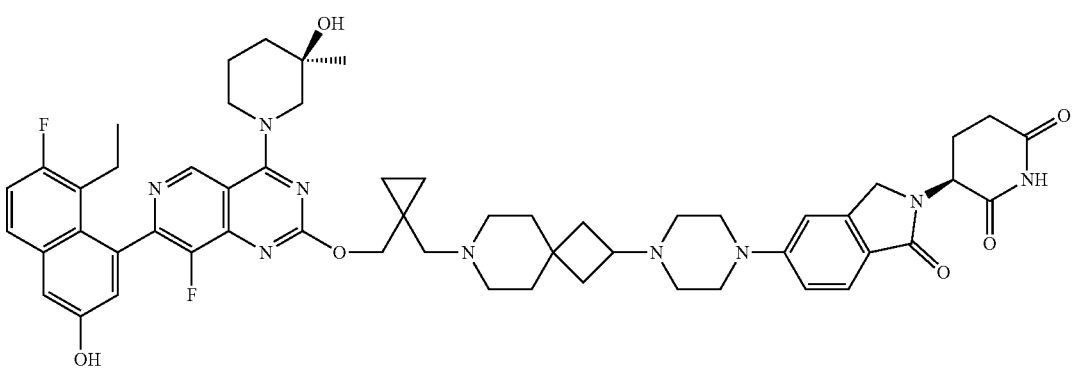 [SMILES: CCc1c(F)ccc2cc(O)cc(-c3ncc4c(N5CCC[C@@](C)(O)C5)nc(OCC5(CN6CCC7(CC6)CC(N6CCN(c8ccc9c(c8)CN([C@H]8CCC(=O)NC8=O)C9=O)CC6)C7)CC5)nc4c3F)c12]<br>(S)-3-(5-(4-(7-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-azaspiro[3.5]nonan-2-yl)piperazin-1-yl)-1-oxoisoindolin-2-yl)piperidine-2,6-dione |
| 122 | 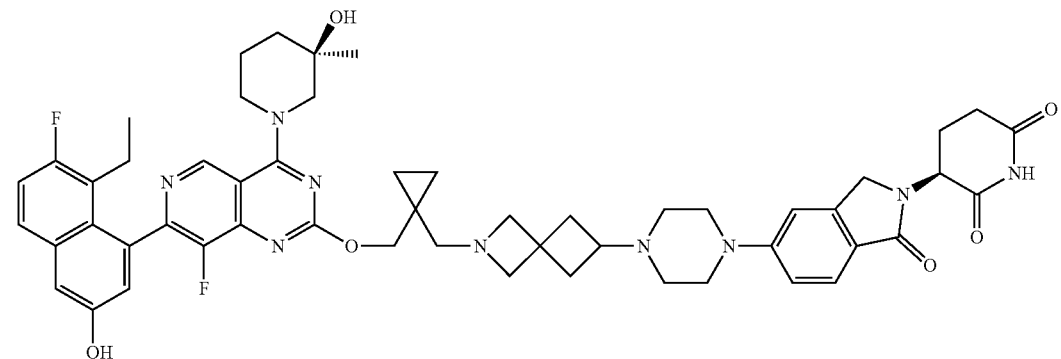 [SMILES: CCc1c(F)ccc2cc(O)cc(-c3ncc4c(N5CCC[C@@](C)(O)C5)nc(OCC5(CN6CC7(CC(N8CCN(c9ccc%10c(c9)CN([C@H]9CCC(=O)NC9=O)C%10=O)CC8)C7)C6)CC5)nc4c3F)c12]<br>(S)-3-(5-(4-(2-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-2-azaspiro[3.3]heptan-6-yl)piperazin-1-yl)-1-oxoisoindolin-2-yl)piperidine-2,6-dione |
| 123 | 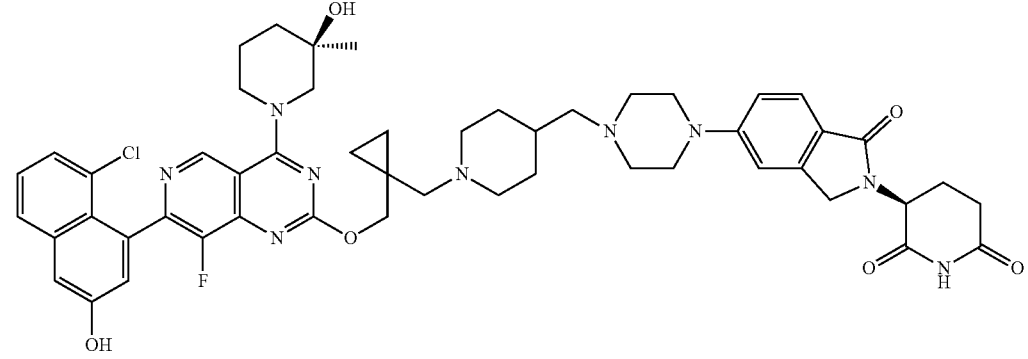 [SMILES: C[C@@]1(O)CCCN(c2nc(OCC3(CN4CCC(CN5CCN(c6ccc7c(c6)CN([C@H]6CCC(=O)NC6=O)C7=O)CC5)CC4)CC3)nc3c(F)c(-c4cc(O)cc5cccc(Cl)c45)ncc23)C1]<br>(S)-3-(5-(4-((1-((1-(((7-(8-chloro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione |

TABLE 1-continued

Exemplary Compounds of the Present Disclosure

| Cpd # | Structure and IUPAC Name |
|---|---|
| 124 | 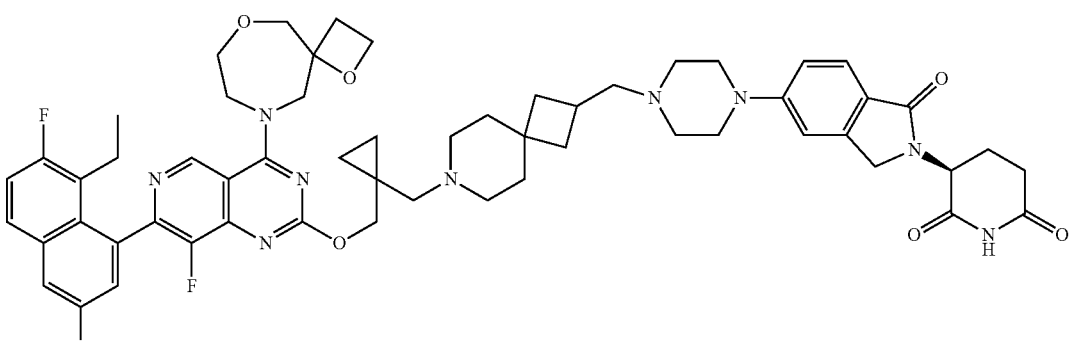<br>(3S)-3-(5-(4-((7-((1-(((7-(8-ethyl-7-fluoro-3-hydroxynaphthalen-1-yl)-8-fluoro-4-(1,6-dioxa-9-azaspiro[3.6]decan-9-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |
| 125 | 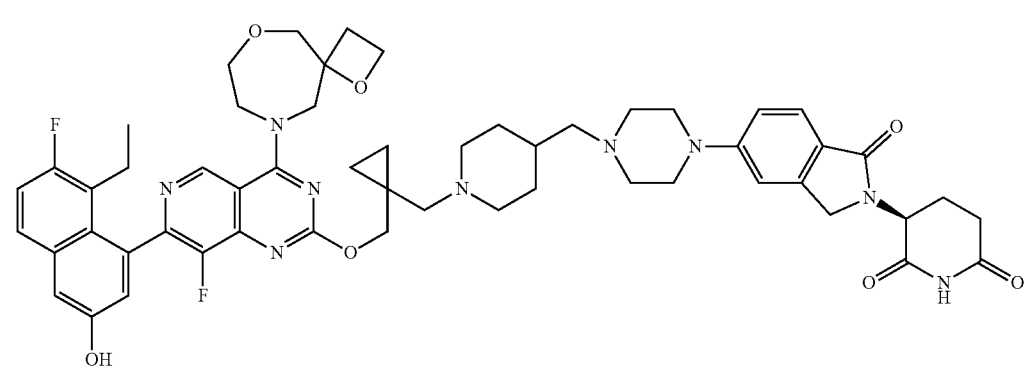 [SMILES: CCc1c(F)ccc2cc(O)cc(-c3ncc4c(N5CCOCC6(CCO6)C5)nc(OCC5(CN6CCC(CN7CCN(c8ccc9c(c8)CN([C@H]8CCC(=O)NC8=O)C9=O)CC7)CC6)CC5)nc4c3F)c12]<br>(3S)-3-(5-(4-((1-((1-(((7-(8-ethyl-7-fluoro-3-hydroxynaphthalen-1-yl)-8-fluoro-4-(1,6-dioxa-9-azaspiro[3.6]decan-9-yl)pyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione |
| 126 | 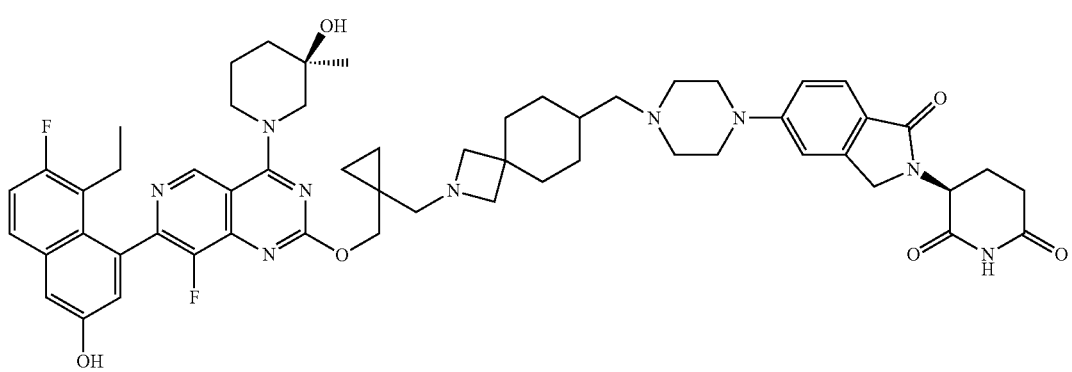 [SMILES: CCc1c(F)ccc2cc(O)cc(-c3ncc4c(N5CCC[C@@](C)(O)C5)nc(OCC5(CN6CC7(CCC(CN8CCN(c9ccc%10c(c9)CN([C@H]9CCC(=O)NC9=O)C%10=O)CC8)CC7)C6)CC5)nc4c3F)c12]<br>(S)-3-(5-(4-((2-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-2-azaspiro[3.5]nonan-7-yl)methyl)piperazin-1-yl)-1-oxoisoindolin-2-yl)piperidine-2,6-dione |

TABLE 1-continued

Exemplary Compounds of the Present Disclosure

| Cpd # | Structure and IUPAC Name |
|---|---|
| 127 | 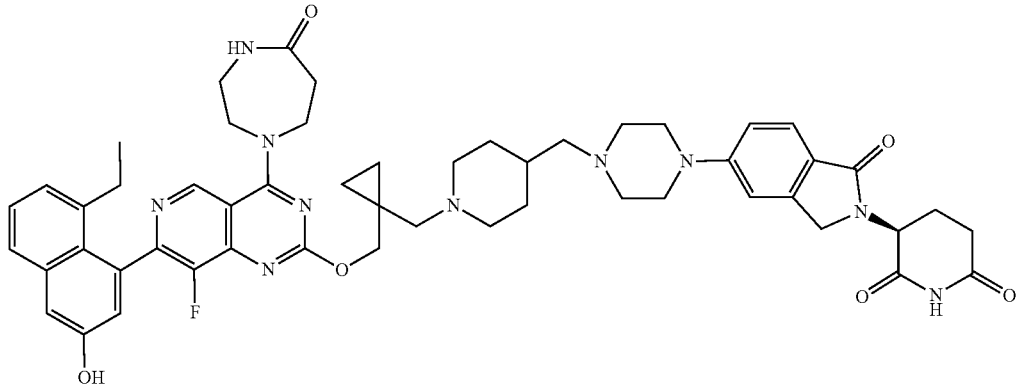 [SMILES: CCc1cccc2cc(O)cc(-c3ncc4c(N5CCNC(=O)CC5)nc(OCC5(CN6CCC(CN7CCN(c8ccc9c(c8)CN([C@H]8CCC(=O)NC8=O)C9=O)CC7)CC6)CC5)nc4c3F)c12]<br>(S)-3-(5-(4-((1-((1-(((7-(8-ethyl-3-hydroxynaphthalen-1-yl)-8-fluoro-4-(5-oxo-1,4-diazepan-1-yl)pyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione |
| 128 | 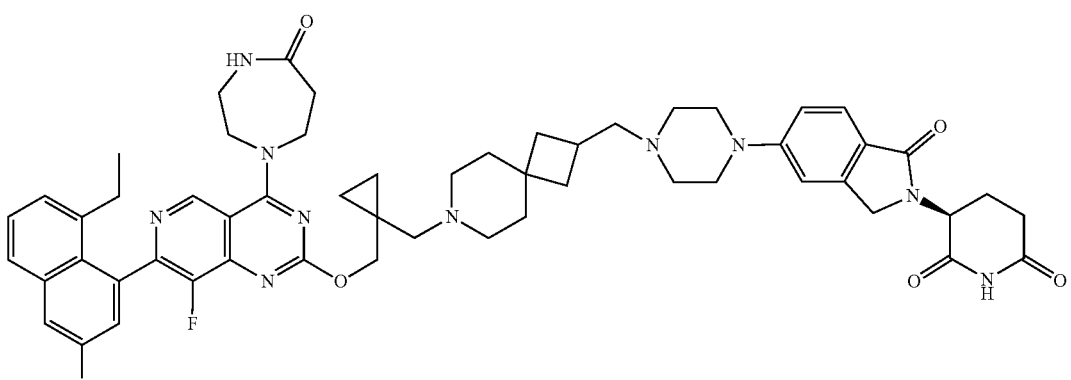<br>(S)-3-(5-(4-((7-((1-(((7-(8-ethyl-3-hydroxynaphthalen-1-yl)-8-fluoro-4-(5-oxo-1,4-diazepan-1-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |
| 129 | 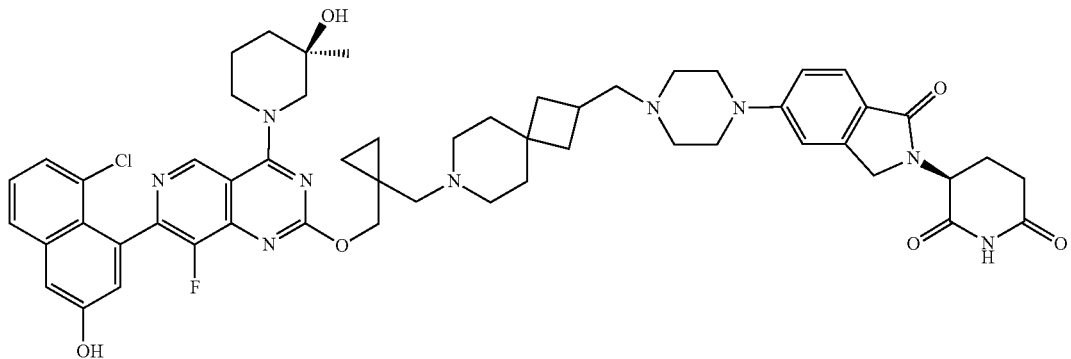 [SMILES: C[C@@]1(O)CCCN(c2nc(OCC3(CN4CCC5(CC4)CC(CN4CCN(c6ccc7c(c6)CN([C@H]6CCC(=O)NC6=O)C7=O)CC4)C5)CC3)nc3c(F)c(-c4cc(O)cc5cccc(Cl)c45)ncc23)C1]<br>(S)-3-(5-(4-((7-((1-(((7-(8-chloro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |

| Cpd # | Structure and IUPAC Name |
|---|---|
| 130 | 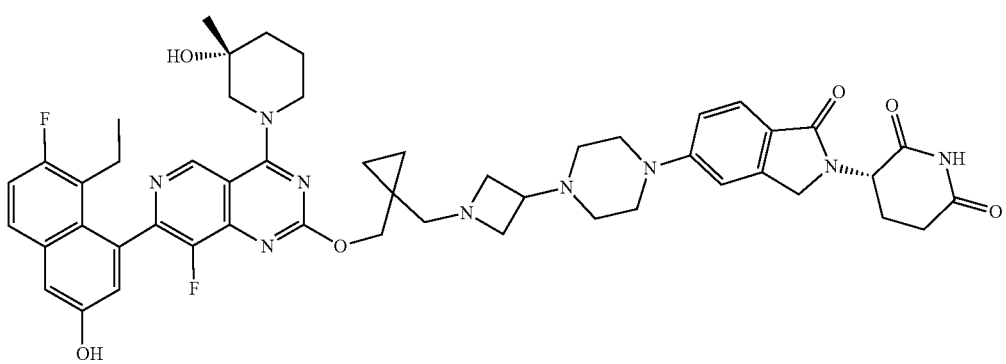 [SMILES: CCc1c(F)ccc2cc(O)cc(-c3ncc4c(N5CCC[C@@](C)(O)C5)nc(OCC5(CN6CC(N7CCN(c8ccc9c(c8)CN([C@H]8CCC(=O)NC8=O)C9=O)CC7)C6)CC5)nc4c3F)c12]
(S)-3-(5-(4-(1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)azetidin-3-yl)piperazin-1-yl)-1-oxoisoindolin-2-yl)piperidine-2,6-dione |
| 131 | 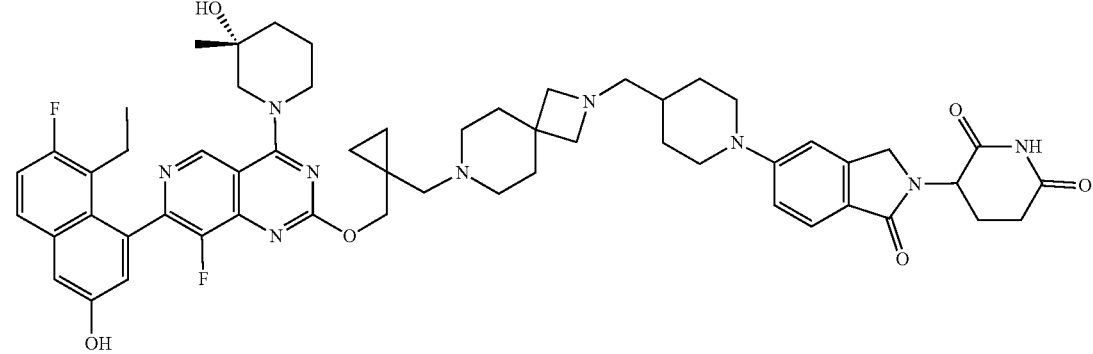 [SMILES: CCc1c(F)ccc2cc(O)cc(-c3ncc4c(N5CCC[C@@](C)(O)C5)nc(OCC5(CN6CCC7(CC6)CN(CC6CCN(c8ccc9c(c8)CN(C8CCC(=O)NC8=O)C9=O)CC6)C7)CC5)nc4c3F)c12]
3-(5-(4-((7-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-2,7-diazaspiro[3.5]nonan-2-yl)methyl)piperidin-1-yl)-1-oxoisoindolin-2-yl)piperidine-2,6-dione |
| 132 | 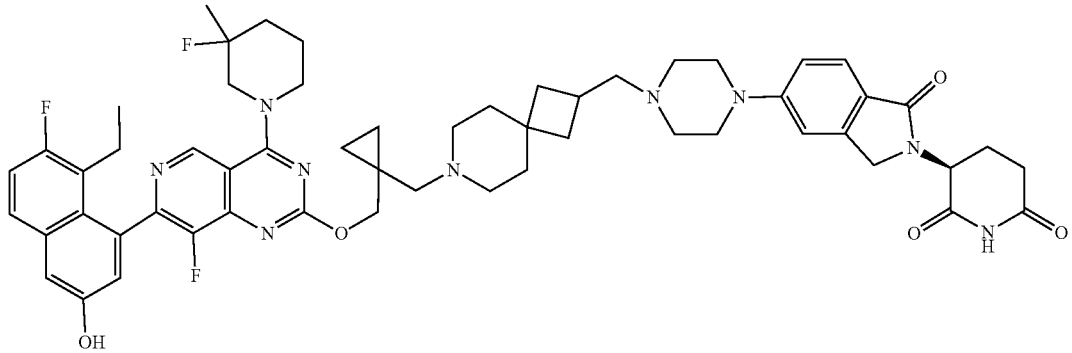 [SMILES: CCc1c(F)ccc2cc(O)cc(-c3ncc4c(N5CCCC(C)(F)C5)nc(OCC5(CN6CCC7(CC6)CC(CN6CCN(c8ccc9c(c8)CN([C@H]8CCC(=O)NC8=O)C9=O)CC6)C7)CC5)nc4c3F)c12]
(3S)-3-(5-(4-((7-((1-(((7-(8-ethyl-7-fluoro-3-hydroxynaphthalen-1-yl)-8-fluoro-4-(3-fluoro-3-methylpiperidin-1-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |

TABLE 1-continued

Exemplary Compounds of the Present Disclosure

| Cpd # | Structure and IUPAC Name |
|---|---|
| 133 | 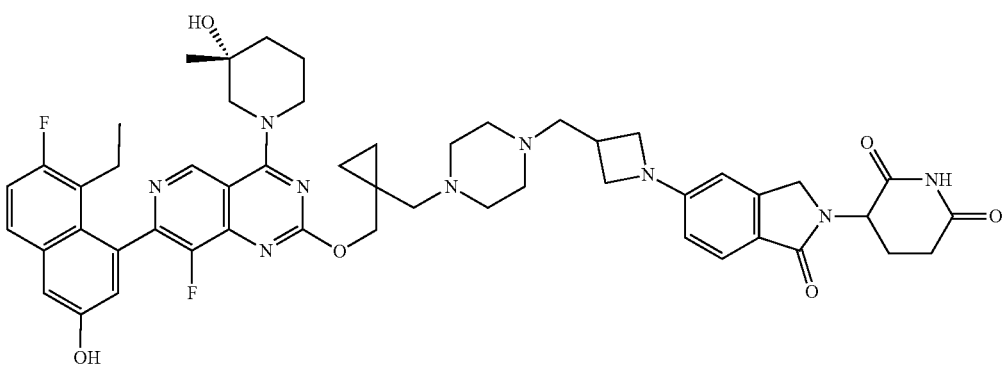 [SMILES: CCc1c(F)ccc2cc(O)cc(-c3ncc4c(N5CCC[C@@](C)(O)C5)nc(OCC5(CN6CCN(CC7CN(c8ccc9c(c8)CN(C8CCC(=O)NC8=O)C9=O)C7)CC6)CC5)nc4c3F)c12]<br>3-(5-(3-((4-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperazin-1-yl)methyl)azetidin-1-yl)-1-oxoisoindolin-2-yl)piperidine-2,6-dione |
| 134 | 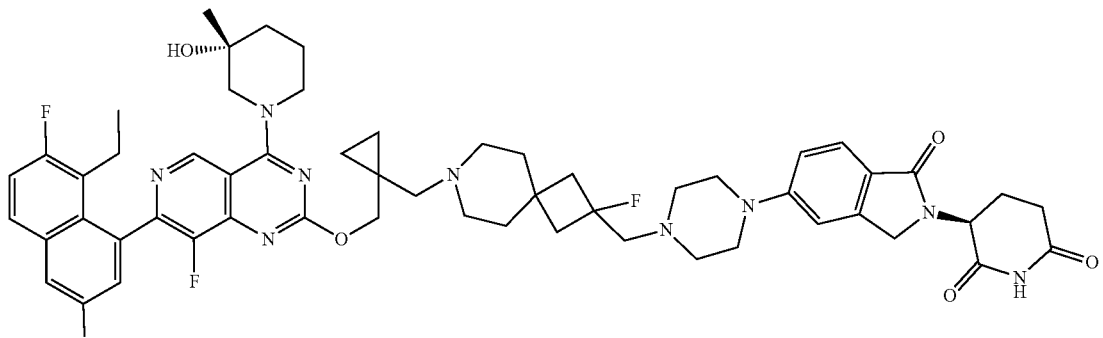<br>(S)-3-(5-(4-((7-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-2-fluoro-7-azaspiro[3.5]nonan-2-yl)methyl)piperazin-1-yl)-1-oxoisoindolin-2-yl)piperidine-2,6-dione |
| 135 | 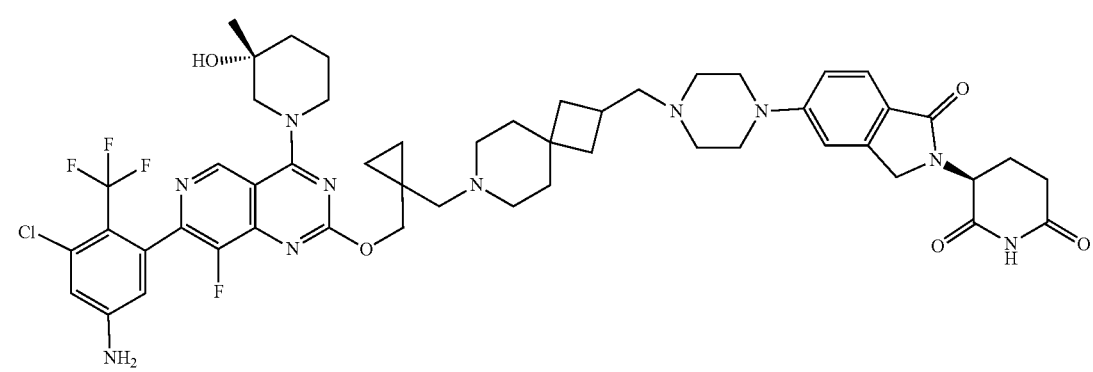 [SMILES: C[C@@]1(O)CCCN(c2nc(OCC3(CN4CCC5(CC4)CC(CN4CCN(c6ccc7c(c6)CN([C@H]6CCC(=O)NC6=O)C7=O)CC4)C5)CC3)nc3c(F)c(-c4cc(N)cc(Cl)c4C(F)(F)F)ncc23)C1]<br>(S)-3-(5-(4-((7-((1-(((7-(5-amino-3-chloro-2-(trifluoromethyl)phenyl)-8-fluoro-4-((R)-3-hydroxy-3-methylpiperidin-1-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |

TABLE 1-continued

Exemplary Compounds of the Present Disclosure

| Cpd # | Structure and IUPAC Name |
|---|---|
| 136 | 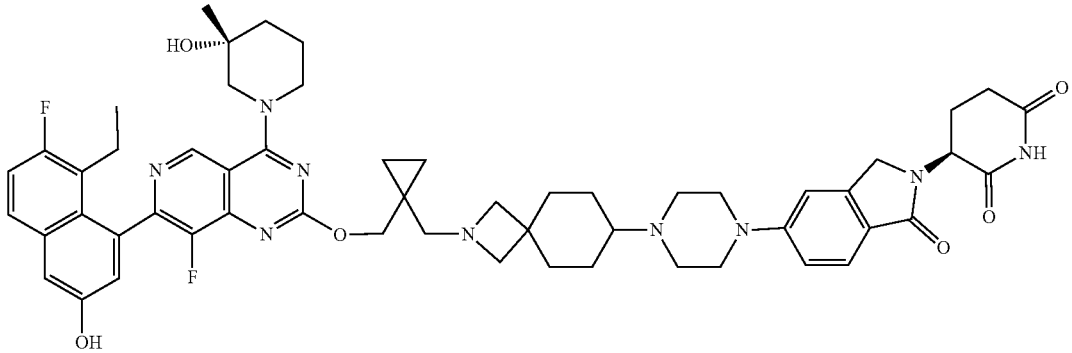 [SMILES: CCc1c(F)ccc2cc(O)cc(-c3ncc4c(N5CCC[C@@](C)(O)C5)nc(OCC5(CN6CC7(CCC(N8CCN(c9ccc%10c(c9)CN([C@H]9CCC(=O)NC9=O)C%10=O)CC8)CC7)C6)CC5)nc4c3F)c12]<br>(S)-3-(5-(4-(2-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-2-azaspiro[3.5]nonan-7-yl)piperazin-1-yl)-1-oxoisoindolin-2-yl)piperidine-2,6-dione |
| 137 | 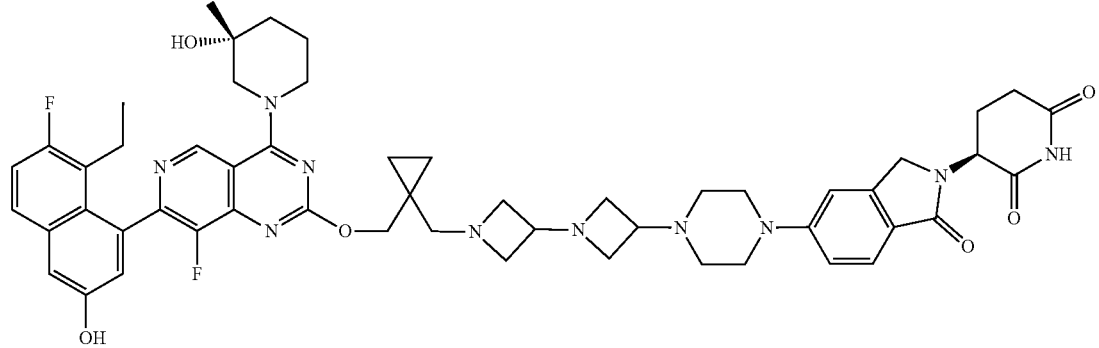 [SMILES: CCc1c(F)ccc2cc(O)cc(-c3ncc4c(N5CCC[C@@](C)(O)C5)nc(OCC5(CN6CC(N7CC(N8CCN(c9ccc%10c(c9)CN([C@H]9CCC(=O)NC9=O)C%10=O)CC8)C7)C6)CC5)nc4c3F)c12]<br>(S)-3-(5-(4-(1'-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-[1,3'-biazetidin]-3-yl)piperazin-1-yl)-1-oxoisoindolin-2-yl)piperidine-2,6-dione |
| 138 | 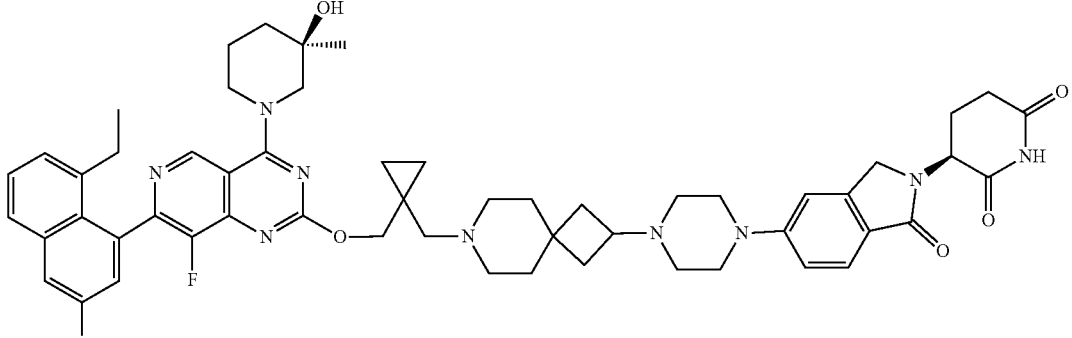<br>(S)-3-(5-(4-(7-((1-(((7-(8-ethyl-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-azaspiro[3.5]nonan-2-yl)piperazin-1-yl)-1-oxoisoindolin-2-yl)piperidine-2,6-dione |

TABLE 1-continued

Exemplary Compounds of the Present Disclosure

| Cpd # | Structure and IUPAC Name |
|---|---|
| 139 | 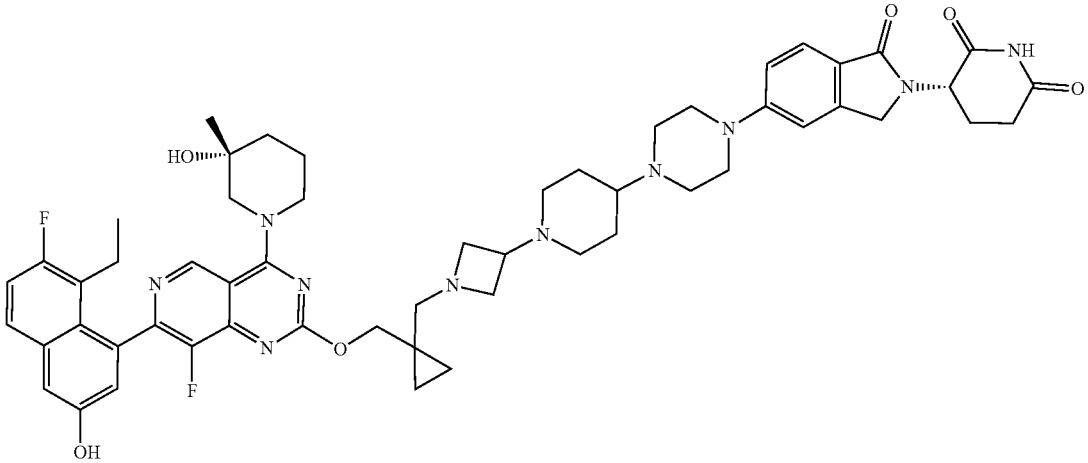 [SMILES: CCc1c(F)ccc2cc(O)cc(-c3ncc4c(N5CCC[C@@](C)(O)C5)nc(OCC5(CN6CC(N7CCC(N8CCN(c9ccc%10c(c9)CN([C@H]9CCC(=O)NC9=O)C%10=O)CC8)CC7)C6)CC5)nc4c3F)c12]<br>(S)-3-(5-(4-(1-(1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)azetidin-3-yl)piperidin-4-yl)piperazin-1-yl)-1-oxoisoindolin-2-yl)piperidine-2,6-dione |
| 140 | 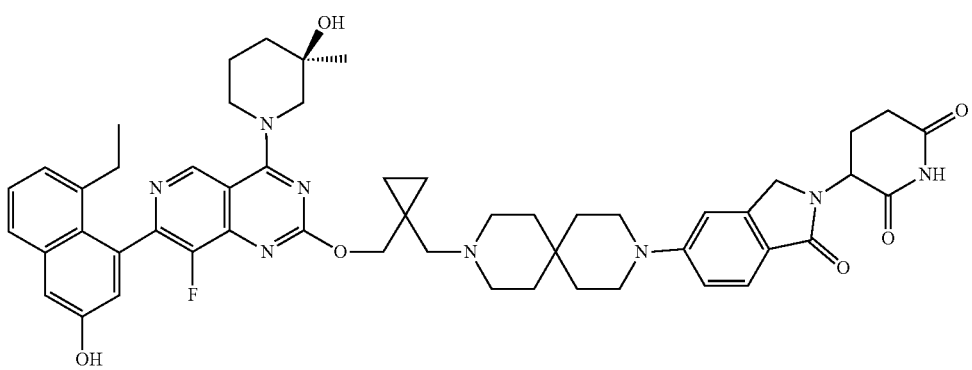 [SMILES: CCc1cccc2cc(O)cc(-c3ncc4c(N5CCC[C@@](C)(O)C5)nc(OCC5(CN6CCC7(CC6)CCN(c6ccc8c(c6)CN(C6CCC(=O)NC6=O)C8=O)CC7)CC5)nc4c3F)c12]<br>3-(5-(9-((1-(((7-(8-ethyl-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-3,9-diazaspiro[5.5]undecan-3-yl)-1-oxoisoindolin-2-yl)piperidine-2,6-dione |
| 141 | 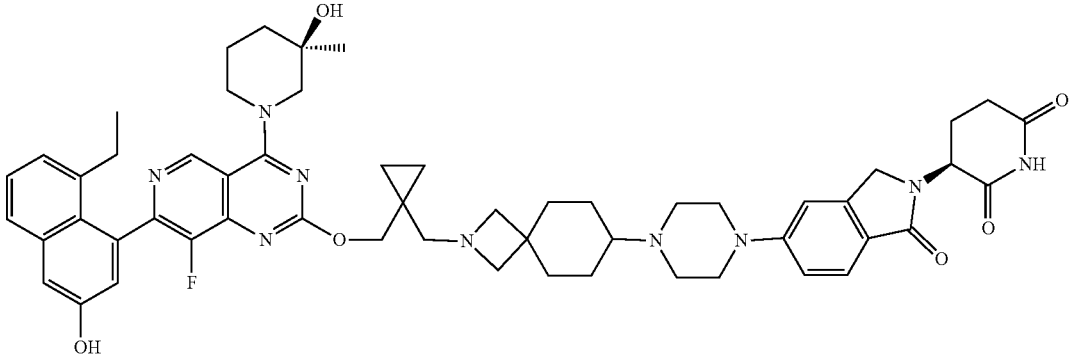 [SMILES: CCc1cccc2cc(O)cc(-c3ncc4c(N5CCC[C@@](C)(O)C5)nc(OCC5(CN6CC7(CCC(N8CCN(c9ccc%10c(c9)CN([C@H]9CCC(=O)NC9=O)C%10=O)CC8)CC7)C6)CC5)nc4c3F)c12]<br>(S)-3-(5-(4-(2-((1-(((7-(8-ethyl-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-2-azaspiro[3.5]nonan-7-yl)piperazin-1-yl)-1-oxoisoindolin-2-yl)piperidine-2,6-dione |

TABLE 1-continued

Exemplary Compounds of the Present Disclosure

| Cpd # | Structure and IUPAC Name |
|---|---|
| 142 | 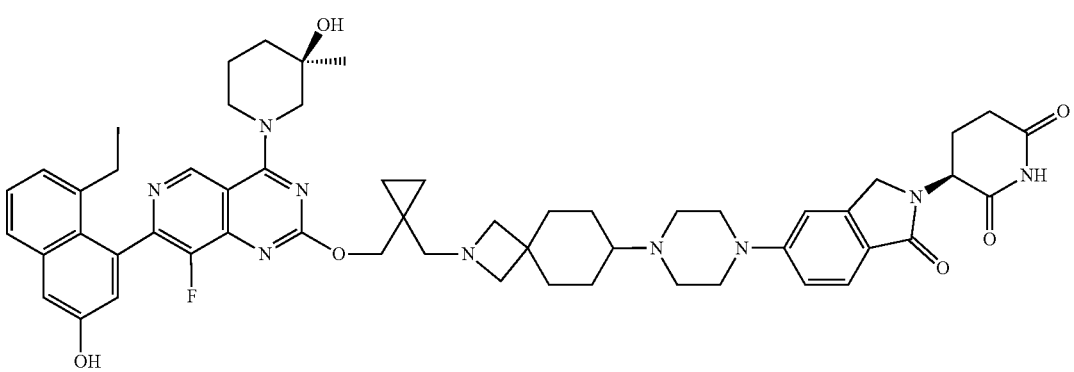 [SMILES: CCc1cccc2cc(O)cc(-c3ncc4c(N5CCC[C@@](C)(O)C5)nc(OCC5(CN6CC7(CCC(N8CCN(c9ccc%10c(c9)CN([C@H]9CCC(=O)NC9=O)C%10=O)CC8)CC7)C6)CC5)nc4c3F)c12]<br>(S)-3-(5-(4-(2-((1-(((7-(8-ethyl-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-2-azaspiro [3.5]nonan-7-yl)piperazin-1-yl)-1-oxoisoindolin-2-yl)piperidine-2,6-dione |
| 143 | 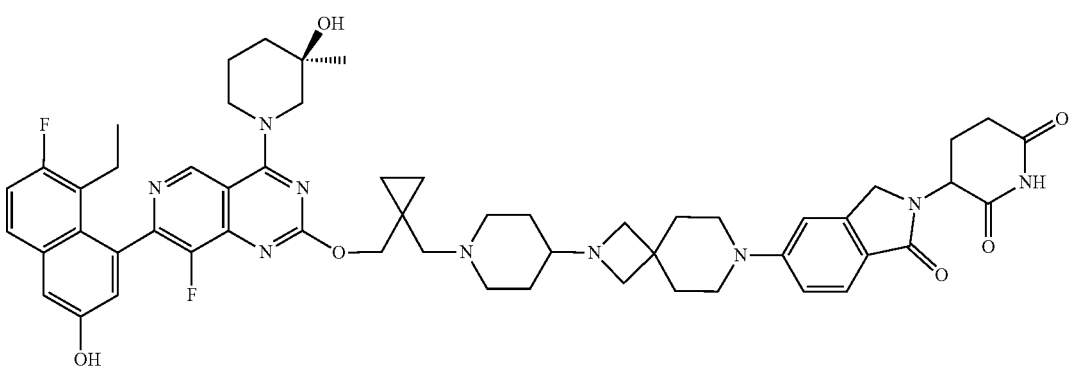 [SMILES: CCc1c(F)ccc2cc(O)cc(-c3ncc4c(N5CCC[C@@](C)(O)C5)nc(OCC5(CN6CCC(N7CC8(CCN(c9ccc%10c(c9)CN(C9CCC(=O)NC9=O)C%10=O)CC8)C7)CC6)CC5)nc4c3F)c12]<br>3-(5-(2-(1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)-2, 7-diazaspiro[3.5]nonan-7-yl)-1-oxoisoindolin-2-yl)piperidine-2,6-dione |
| 144 | 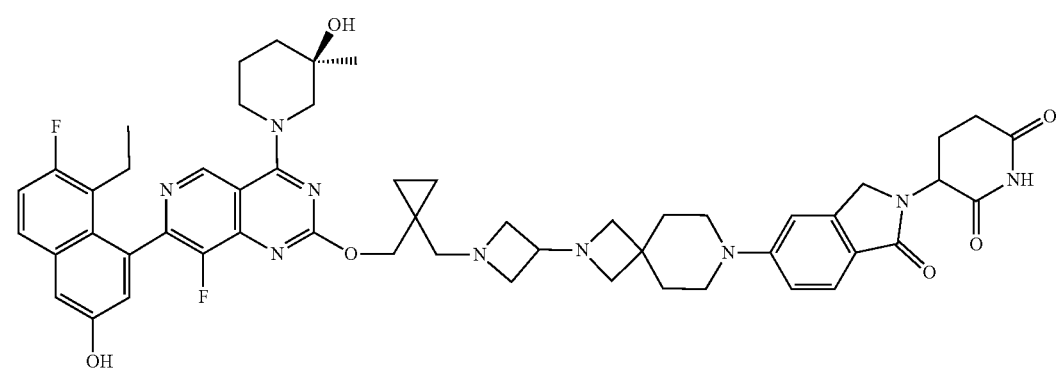 [SMILES: CCc1c(F)ccc2cc(O)cc(-c3ncc4c(N5CCC[C@@](C)(O)C5)nc(OCC5(CN6CC(N7CC8(CCN(c9ccc%10c(c9)CN(C9CCC(=O)NC9=O)C%10=O)CC8)C7)C6)CC5)nc4c3F)c12]<br>3-(5-(2-(1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)azetidin-3-yl)-2,7-diazaspiro[3.5]nonan-7-yl)-1-oxoisoindolin-2-yl)piperidine-2,6-dione |

TABLE 1-continued

Exemplary Compounds of the Present Disclosure

| Cpd # | Structure and IUPAC Name |
|---|---|
| 145 | 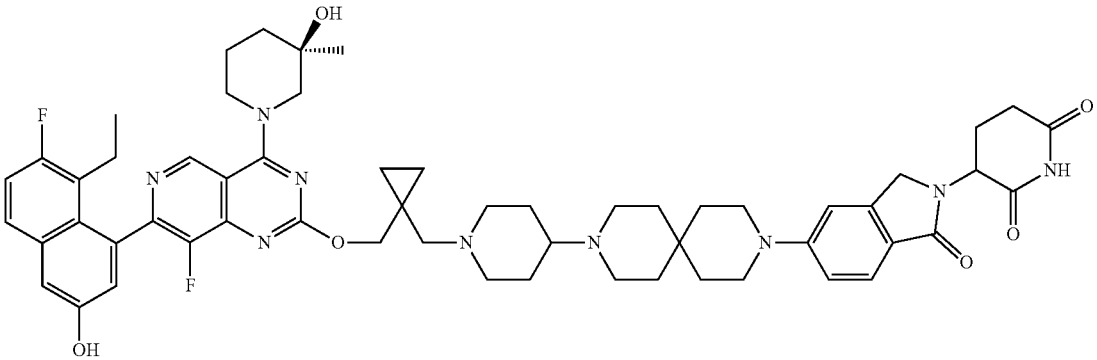
3-(5-(9-(1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)-3,9-diazaspiro[5.5]undecan-3-yl)-1-oxoisoindolin-2-yl)piperidine-2,6-dione |
| 146 | 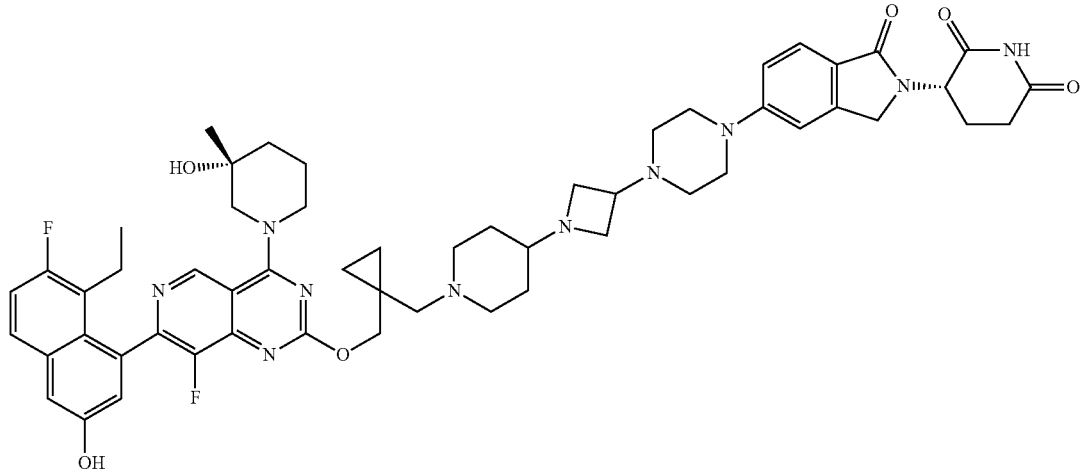 [SMILES: CCc1c(F)ccc2cc(O)cc(-c3ncc4c(N5CCC[C@@](C)(O)C5)nc(OCC5(CN6CCC(N7CC(N8CCN(c9ccc%10c(c9)CN([C@H]9CCC(=O)NC9=O)C%10=O)CC8)C7)CC6)CC5)nc4c3F)c12]
(S)-3-(5-(4-(1-(1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)azetidin-3-yl)piperazin-1-yl)-1-oxoisoindolin-2-yl)piperidine-2,6-dione |
| 147 | 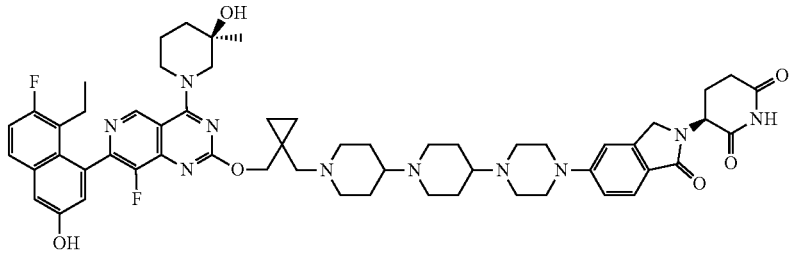 [SMILES: CCc1c(F)ccc2cc(O)cc(-c3ncc4c(N5CCC[C@@](C)(O)C5)nc(OCC5(CN6CCC(N7CCC(N8CCN(c9ccc%10c(c9)CN([C@H]9CCC(=O)NC9=O)C%10=O)CC8)CC7)CC6)CC5)nc4c3F)c12]
(S)-3-(5-(4-(1'-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-[1,4'-bipiperidin]-4-yl)piperazin-1-yl)-1-oxoisoindolin-2-yl)piperidine-2,6-dione |

TABLE 1-continued

Exemplary Compounds of the Present Disclosure

| Cpd # | Structure and IUPAC Name |
|---|---|
| 148 | 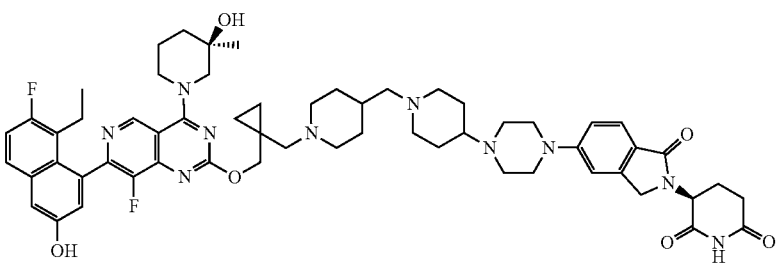 [SMILES: CCc1c(F)ccc2cc(O)cc(-c3ncc4c(N5CCC[C@@](C)(O)C5)nc(OCC5(CN6CCC(CN7CCC(N8CCN(c9ccc%10c(c9)CN([C@H]9CCC(=O)NC9=O)C%10=O)CC8)CC7)CC6)CC5)nc4c3F)c12]<br>(S)-3-(5-(4-(1-((1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)methyl)piperidin-4-yl)piperazin-1-yl)-1-oxoisoindolin-2-yl)piperidine-2,6-dione |
| 149 | 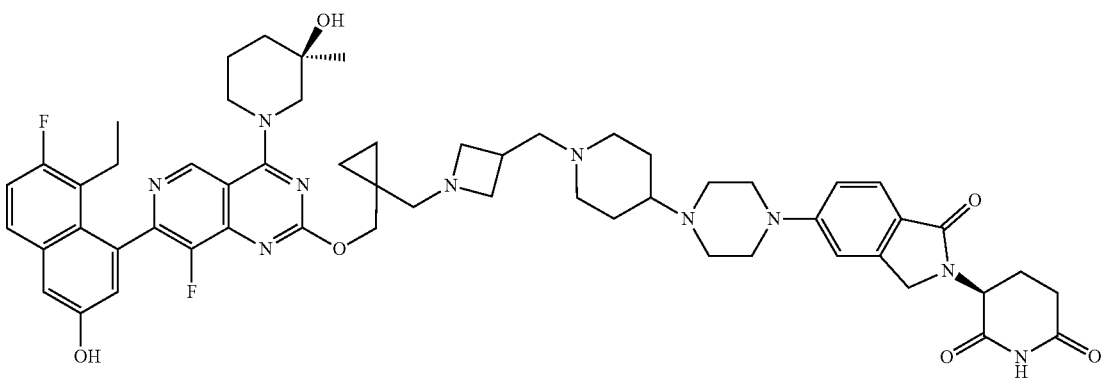 [SMILES: CCc1c(F)ccc2cc(O)cc(-c3ncc4c(N5CCC[C@@](C)(O)C5)nc(OCC5(CN6CC(CN7CCC(N8CCN(c9ccc%10c(c9)CN([C@H]9CCC(=O)NC9=O)C%10=O)CC8)CC7)C6)CC5)nc4c3F)c12]<br>(S)-3-(5-(4-(1-((1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)azetidin-3-yl)methyl)piperidin-4-yl)piperazin-1-yl)-1-oxoisoindolin-2-yl)piperidine-2,6-dione |
| 150 | 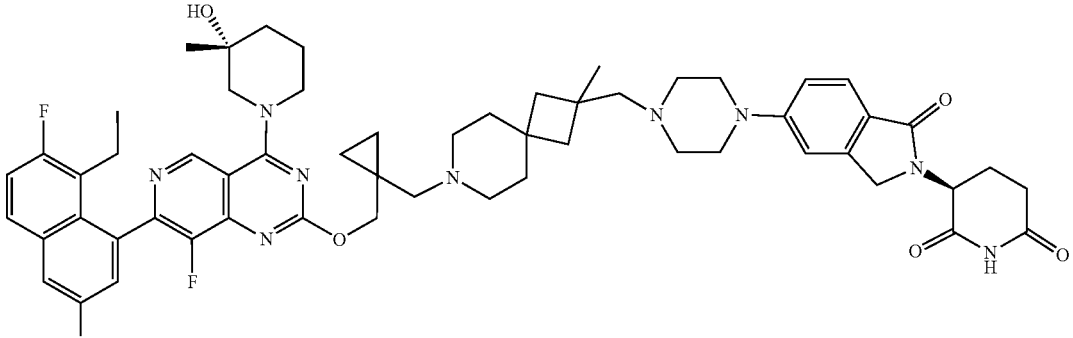<br>(S)-3-(5-(4-((7-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-2-methyl-7-azaspiro[3.5]nonan-2-yl)methyl)piperazin-1-yl)-1-oxoisoindolin-2-yl)piperidine-2,6-dione |

TABLE 1-continued

Exemplary Compounds of the Present Disclosure

| Cpd # | Structure and IUPAC Name |
|---|---|
| 151 | 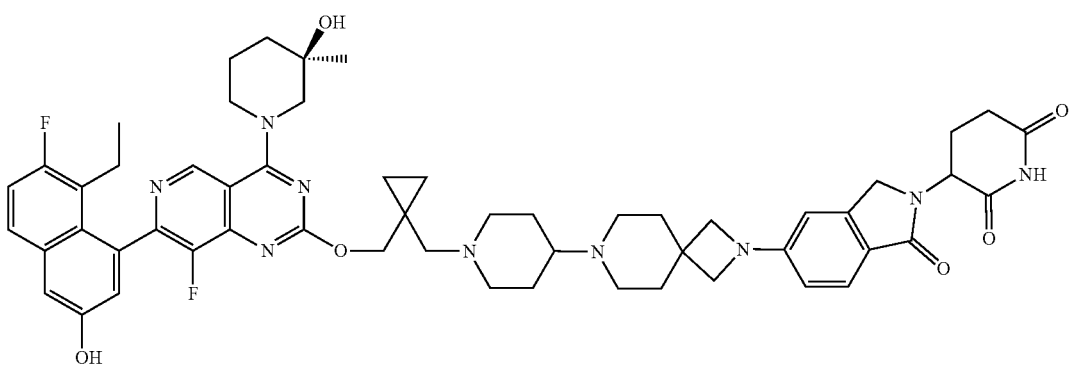 [SMILES: CCc1c(F)ccc2cc(O)cc(-c3ncc4c(N5CCC[C@@](C)(O)C5)nc(OCC5(CN6CCC(N7CCC8(CC7)CN(c7ccc9c(c7)CN(C7CCC(=O)NC7=O)C9=O)C8)CC6)CC5)nc4c3F)c12]

3-(5-(7-(1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)-2,7-diazaspiro[3.5]nonan-2-yl)-1-oxoisoindolin-2-yl)piperidine-2,6-dione |
| 152 | 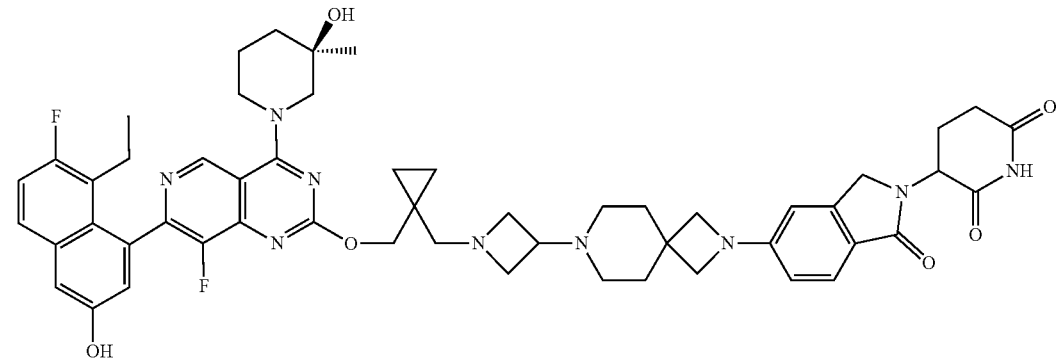 [SMILES: CCc1c(F)ccc2cc(O)cc(-c3ncc4c(N5CCC[C@@](C)(O)C5)nc(OCC5(CN6CC(N7CCC8(CC7)CN(c7ccc9c(c7)CN(C7CCC(=O)NC7=O)C9=O)C8)C6)CC5)nc4c3F)c12]

3-(5-(7-(1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)azetidin-3-yl)-2, 7-diazaspiro[3.5]nonan-2-yl)-1-oxoisoindolin-2-yl)piperidine-2,6-dione |
| 153 | 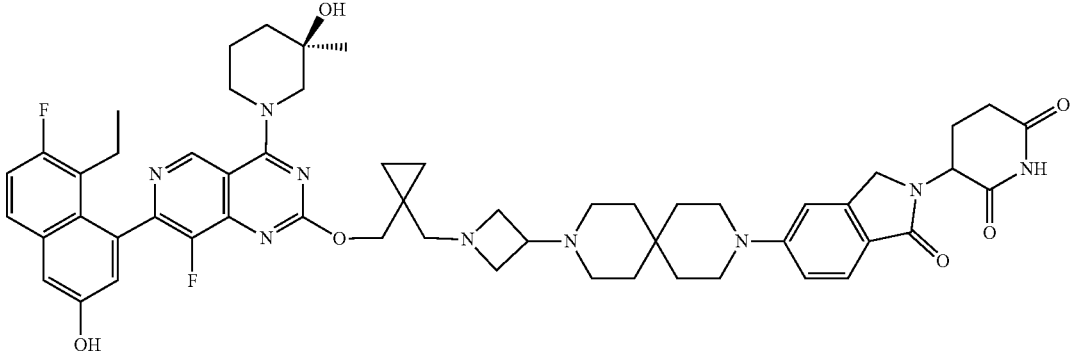 [SMILES: CCc1c(F)ccc2cc(O)cc(-c3ncc4c(N5CCC[C@@](C)(O)C5)nc(OCC5(CN6CC(N7CCC8(CCN(c9ccc%10c(c9)CN(C9CCC(=O)NC9=O)C%10=O)CC8)CC7)C6)CC5)nc4c3F)c12]

3-(5-(9-(1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)azetidin-3-yl)-3,9-diazaspiro[5.5]undecan-3-yl)-1-oxoisoindolin-2-yl)piperidine-2,6-dione |

TABLE 1-continued

Exemplary Compounds of the Present Disclosure

| Cpd # | Structure and IUPAC Name |
|---|---|
| 154 | 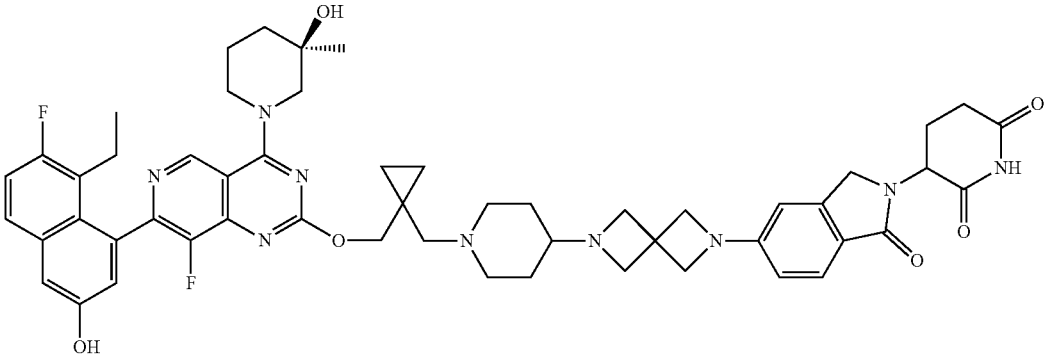 [SMILES: CCc1c(F)ccc2cc(O)cc(-c3ncc4c(N5CCC[C@@](C)(O)C5)nc(OCC5(CN6CCC(N7CC8(CN(c9ccc%10c(c9)CN(C9CCC(=O)NC9=O)C%10=O)C8)C7)CC6)CC5)nc4c3F)c12]<br>3-(5-(6-(1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)-2,6-diazaspiro[3.3]heptan-2-yl)-1-oxoisoindolin-2-yl)piperidine-2,6-dione |
| 155 | 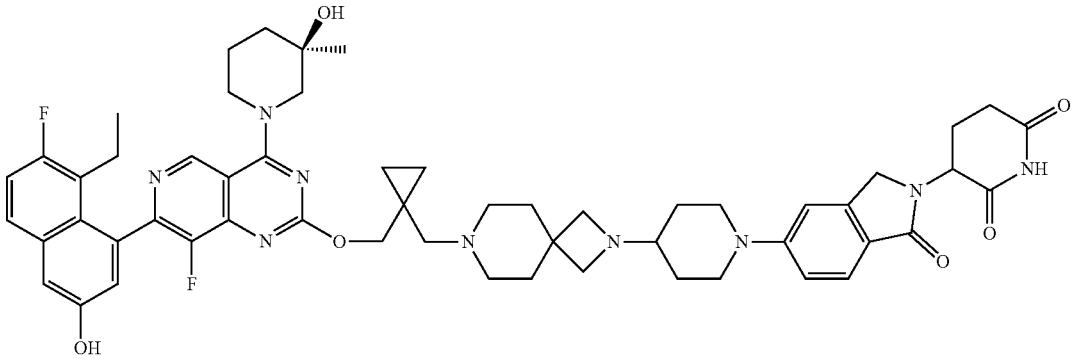 [SMILES: CCc1c(F)ccc2cc(O)cc(-c3ncc4c(N5CCC[C@@](C)(O)C5)nc(OCC5(CN6CCC7(CC6)CN(C6CCN(c8ccc9c(c8)CN(C8CCC(=O)NC8=O)C9=O)CC6)C7)CC5)nc4c3F)c12]<br>3-(5-(4-(7-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-2,7-diazaspiro[3.5]nonan-2-yl)piperidin-1-yl)-1-oxoisoindolin-2-yl)piperidine-2,6-dione |
| 156 | 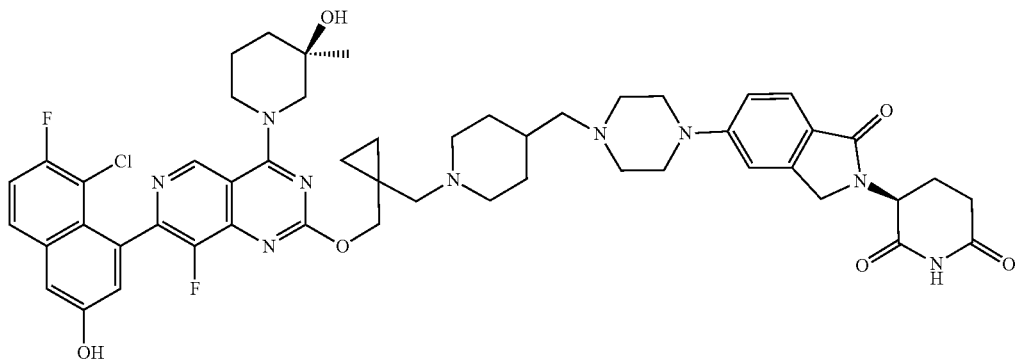 [SMILES: C[C@@]1(O)CCCN(c2nc(OCC3(CN4CCC(CN5CCN(c6ccc7c(c6)CN([C@H]6CCC(=O)NC6=O)C7=O)CC5)CC4)CC3)nc3c(F)c(-c4cc(O)cc5ccc(F)c(Cl)c45)ncc23)C1]<br>(S)-3-(5-(4-((1-((1-(((7-(8-chloro-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione |

TABLE 1-continued

Exemplary Compounds of the Present Disclosure

| Cpd # | Structure and IUPAC Name |
|---|---|
| 157 | 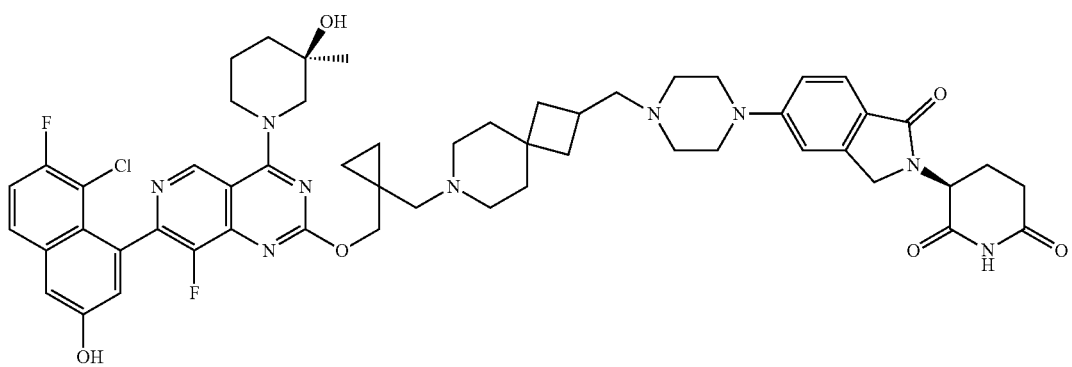<br>(S)-3-(5-(4-((7-((1-(((7-(8-chloro-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |
| 158 | 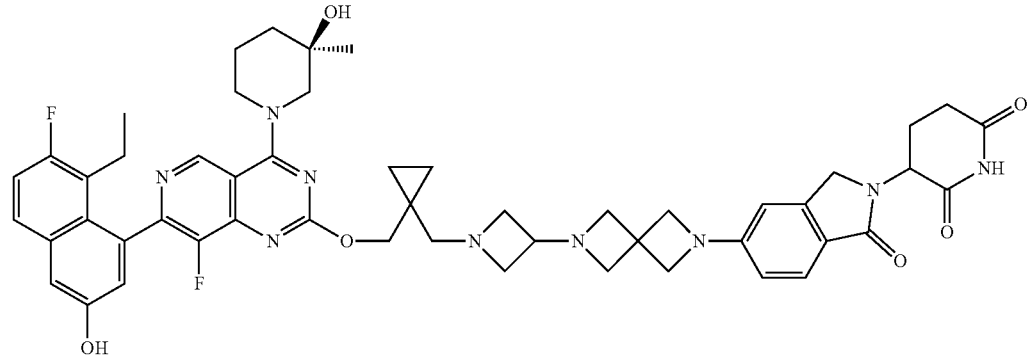 [SMILES: CCc1c(F)ccc2cc(O)cc(-c3ncc4c(N5CCC[C@@](C)(O)C5)nc(OCC5(CN6CC(N7CC8(CN(c9ccc%10c(c9)CN(C9CCC(=O)NC9=O)C%10=O)C8)C7)C6)CC5)nc4c3F)c12]<br>3-(5-(6-(1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)azetidin-3-yl)-2,6-diazaspiro[3.3]heptan-2-yl)-1-oxoisoindolin-2-yl)piperidine-2,6-dione |
| 159 | 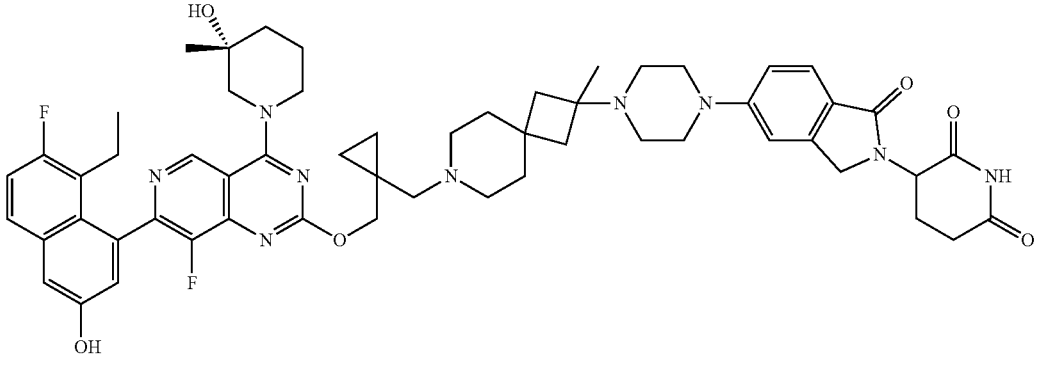 [SMILES: CCc1c(F)ccc2cc(O)cc(-c3ncc4c(N5CCC[C@@](C)(O)C5)nc(OCC5(CN6CCC7(CC6)CC(C)(N6CCN(c8ccc9c(c8)CN(C8CCC(=O)NC8=O)C9=O)CC6)C7)CC5)nc4c3F)c12]<br>3-(5-(4-(7-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-2-methyl-7-azaspiro[3.5]nonan-2-yl)piperazin-1-yl)-1-oxoisoindolin-2-yl)piperidine-2,6-dione |

TABLE 1-continued

Exemplary Compounds of the Present Disclosure

| Cpd # | Structure and IUPAC Name |
|---|---|
| 160 | 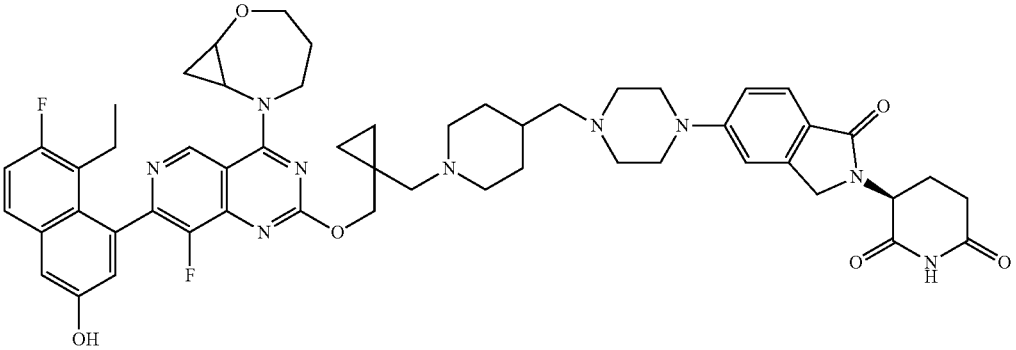 [SMILES: CCc1c(F)ccc2cc(O)cc(-c3ncc4c(N5CCCOC6CC65)nc(OCC5(CN6CCC(CN7CCN(c8ccc9c(c8)CN([C@H]8CCC(=O)NC8=O)C9=O)CC7)CC6)CC5)nc4c3F)c12]<br>(3S)-3-(5-(4-((1-(((4-(2-oxa-6-azabicyclo[5.1.0]octan-6-yl)-7-(8-ethyl-7-fluoro-3-hydroxynaphthalen-1-yl)-8-fluoropyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione |
| 161 | 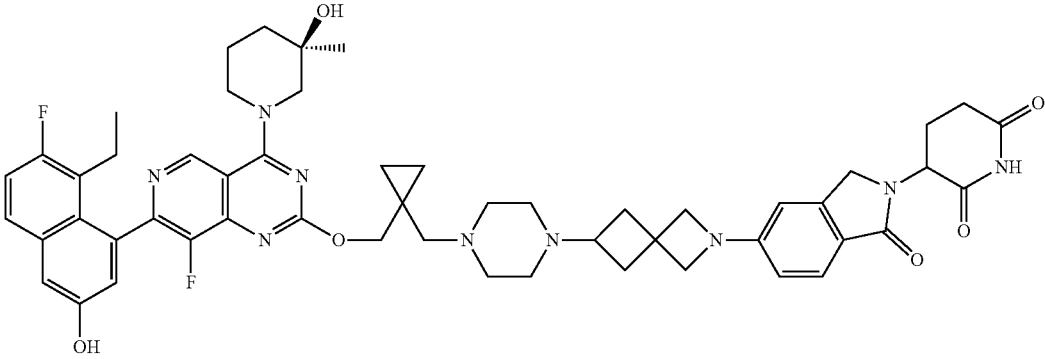<br>3-(5-(6-(4-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperazin-1-yl)-2-azaspiro[3.3]heptan-2-yl)-1-oxoisoindolin-2-yl)piperidine-2,6-dione |
| 162 | 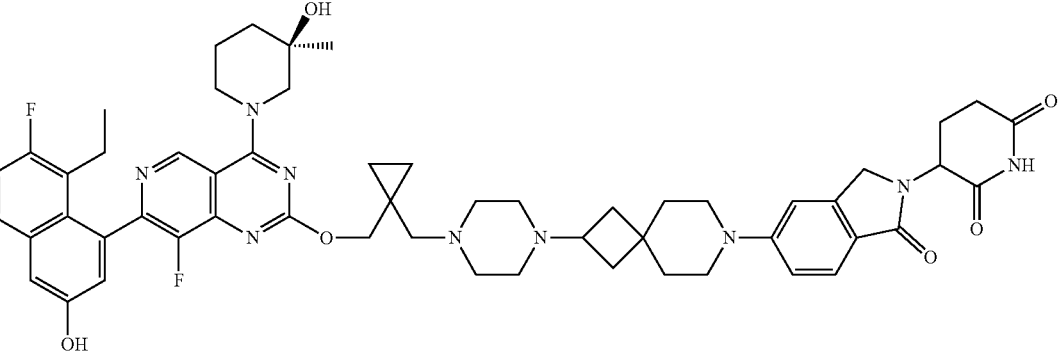<br>3-(5-(2-(4-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperazin-1-yl)-7-azaspiro[3.5]nonan-7-yl)-1-oxoisoindolin-2-yl)piperidine-2,6-dione |

TABLE 1-continued

Exemplary Compounds of the Present Disclosure

| Cpd # | Structure and IUPAC Name |
|---|---|
| 163 | 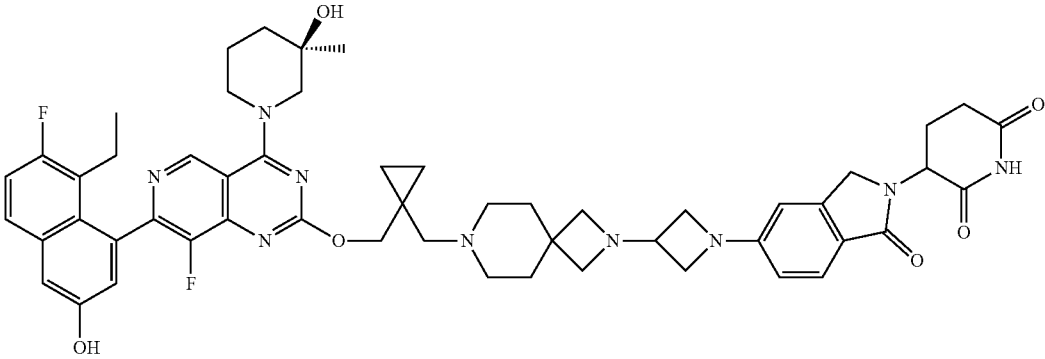 [SMILES: CCc1c(F)ccc2cc(O)cc(-c3ncc4c(N5CCC[C@@](C)(O)C5)nc(OCC5(CN6CCC7(CC6)CN(C6CN(c8ccc9c(c8)CN(C8CCC(=O)NC8=O)C9=O)C6)C7)CC5)nc4c3F)c12]<br>3-(5-(3-(7-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-2,7-diazaspiro[3.5]nonan-2-yl)azetidin-1-yl)-1-oxoisoindolin-2-yl)piperidine-2,6-dione |
| 164 | 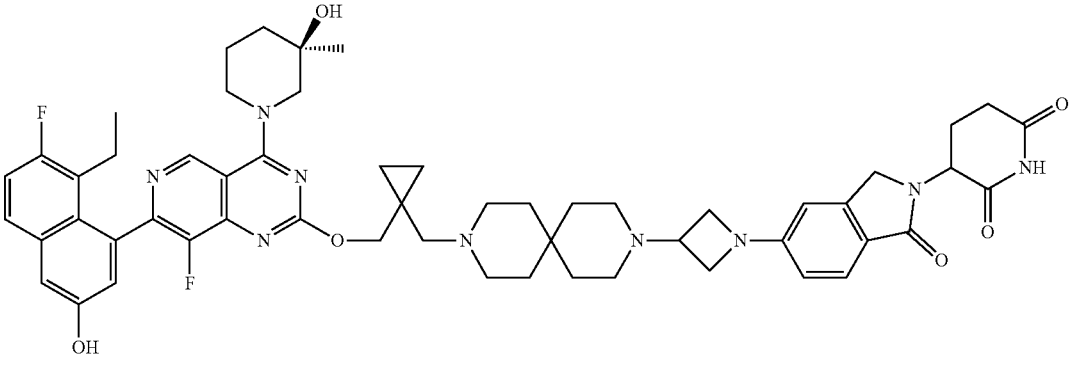 [SMILES: CCc1c(F)ccc2cc(O)cc(-c3ncc4c(N5CCC[C@@](C)(O)C5)nc(OCC5(CN6CCC7(CC6)CCN(C6CN(c8ccc9c(c8)CN(C8CCC(=O)NC8=O)C9=O)C6)CC7)CC5)nc4c3F)c12]<br>3-(5-(3-(9-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-3,9-diazaspiro[5.5]undecan-3-yl)azetidin-1-yl)-1-oxoisoindolin-2-yl)piperidine-2,6-dione |
| 165 | 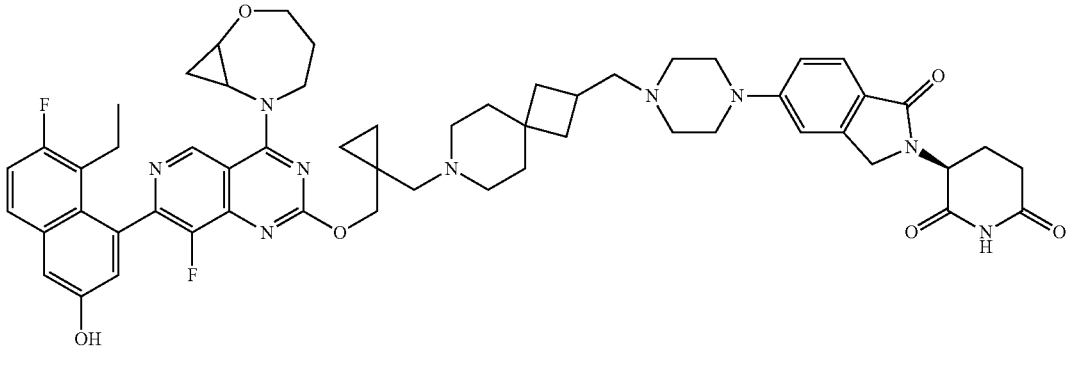 [SMILES: CCc1c(F)ccc2cc(O)cc(-c3ncc4c(N5CCCOC6CC65)nc(OCC5(CN6CCC7(CC6)CC(CN6CCN(c8ccc9c(c8)CN([C@H]8CCC(=O)NC8=O)C9=O)CC6)C7)CC5)nc4c3F)c12]<br>(3S)-3-(5-(4-((7-((1-(((4-(2-oxa-6-azabicyclo[5.1.0]octan-6-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |

TABLE 1-continued

Exemplary Compounds of the Present Disclosure

| Cpd # | Structure and IUPAC Name |
|---|---|
| 166 | 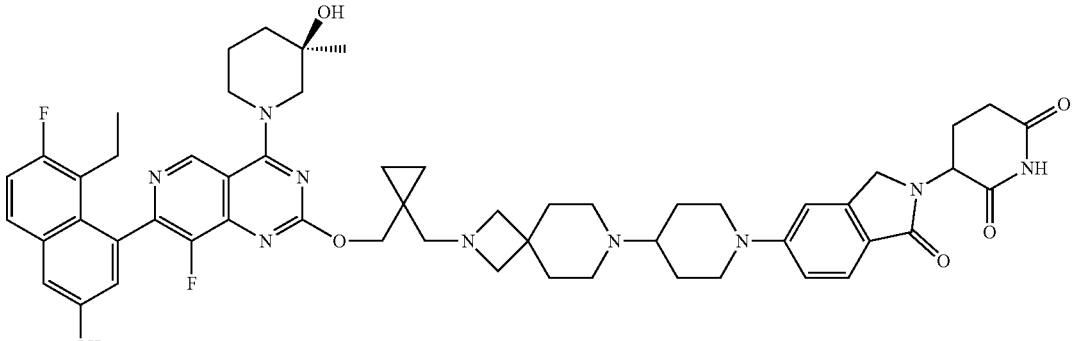<br>3-(5-(4-(2-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-2,7-diazaspiro[3.5]nonan-7-yl)piperidin-1-yl)-1-oxoisoindolin-2-yl)piperidine-2,6-dione |
| 167 | 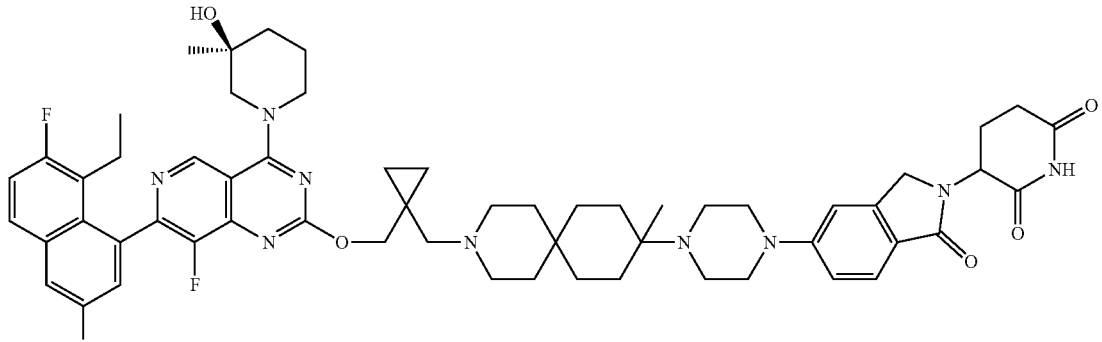<br>3-(5-(4-(3-((1-(((7-(8-ethyl-7-fluoro-3-hydroxynaphthalen-1-yl)-8-fluoro-4-((S)-3-hydroxy-3-methylpiperidin-1-yl)pyrido[4,3-d]pyrimidin-2-yl)oxy)methyl)cyclopropyl)methyl)-9-methyl-3-azaspiro[5.5]undecan-9-yl)piperazin-1-yl)-1-oxoisoindolin-2-yl)piperidine-2,6-dione |
| 168 | 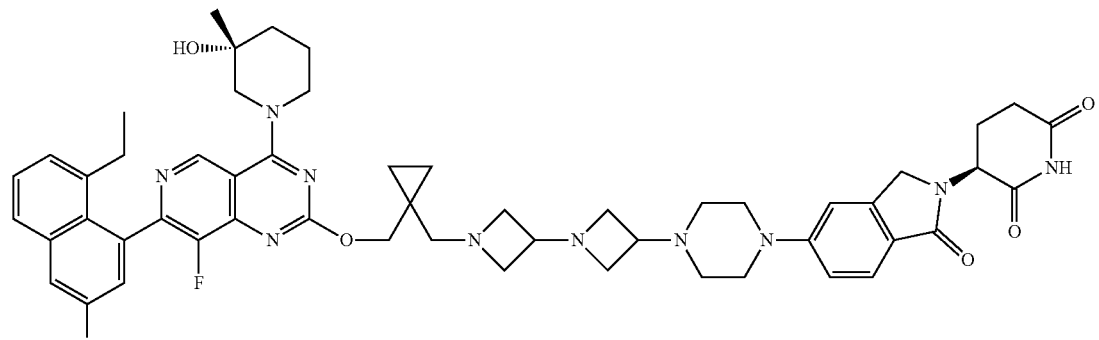<br>(S)-3-(5-(4-(1'-((1-(((7-(8-ethyl-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-[1,3'-biazetidin]-3-yl)piperazin-1-yl)-1-oxoisoindolin-2-yl)piperidine-2,6-dione |

TABLE 1-continued

Exemplary Compounds of the Present Disclosure

| Cpd # | Structure and IUPAC Name |
|---|---|
| 169 | 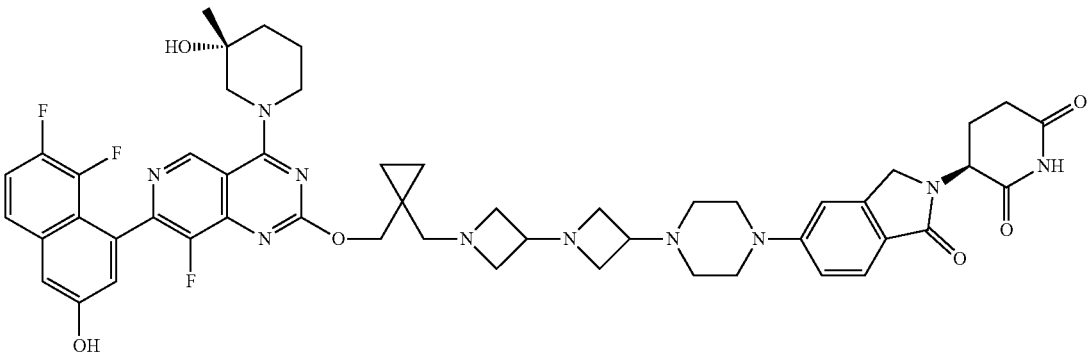 [SMILES: C[C@@]1(O)CCCN(c2nc(OCC3(CN4CC(N5CC(N6CCN(c7ccc8c(c7)CN([C@H]7CCC(=O)NC7=O)C8=O)CC6)C5)C4)CC3)nc3c(F)c(-c4cc(O)cc5ccc(F)c(F)c45)ncc23)C1]<br>(S)-3-(5-(4-(1'-((1-(((7-(7,8-difluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-[1,3'-biazetidin]-3-yl)piperazin-1-yl)-1-oxoisoindolin-2-yl)piperidine-2,6-dione |
| 170 | 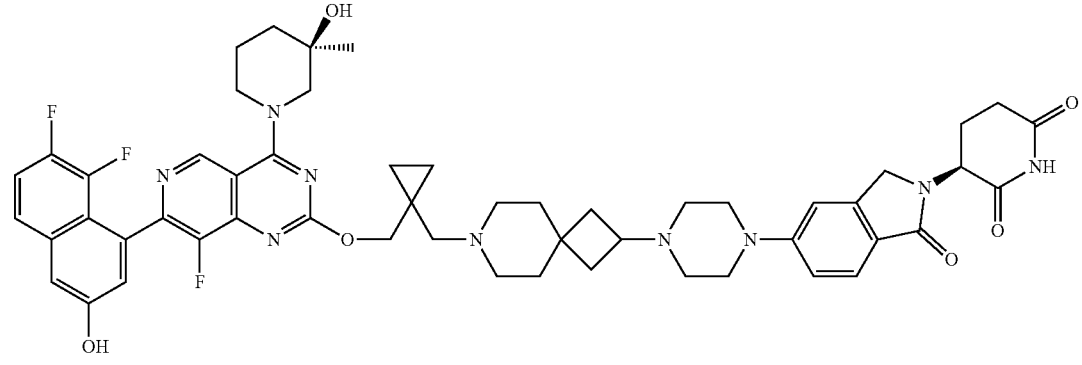 [SMILES: C[C@@]1(O)CCCN(c2nc(OCC3(CN4CCC5(CC4)CC(N4CCN(c6ccc7c(c6)CN([C@H]6CCC(=O)NC6=O)C7=O)CC4)C5)CC3)nc3c(F)c(-c4cc(O)cc5ccc(F)c(F)c45)ncc23)C1]<br>(S)-3-(5-(4-(7-((1-(((7-(7,8-difluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-azaspiro[3.5]nonan-2-yl)piperazin-1-yl)-1-oxoisoindolin-2-yl)piperidine-2,6-dione |
| 171 | 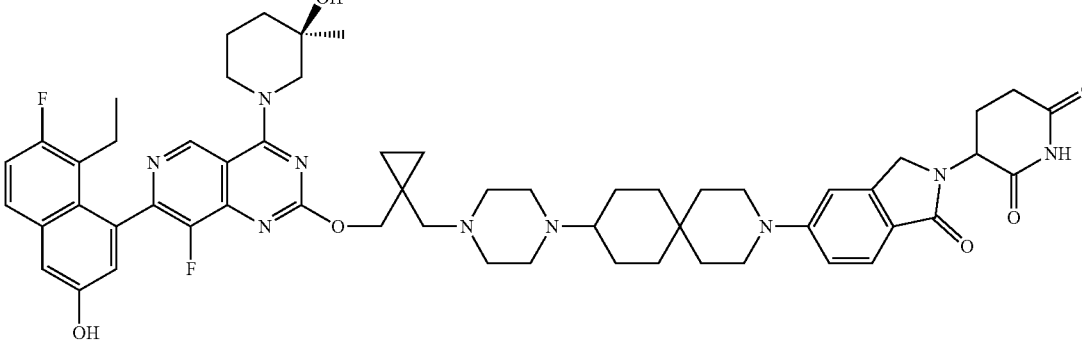<br>3-(5-(9-(4-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperazin-1-yl)-3-azaspiro[5.5]undecan-3-yl)-1-oxoisoindolin-2-yl)piperidine-2,6-dione |

TABLE 1-continued

Exemplary Compounds of the Present Disclosure

| Cpd # | Structure and IUPAC Name |
|---|---|
| 172 | 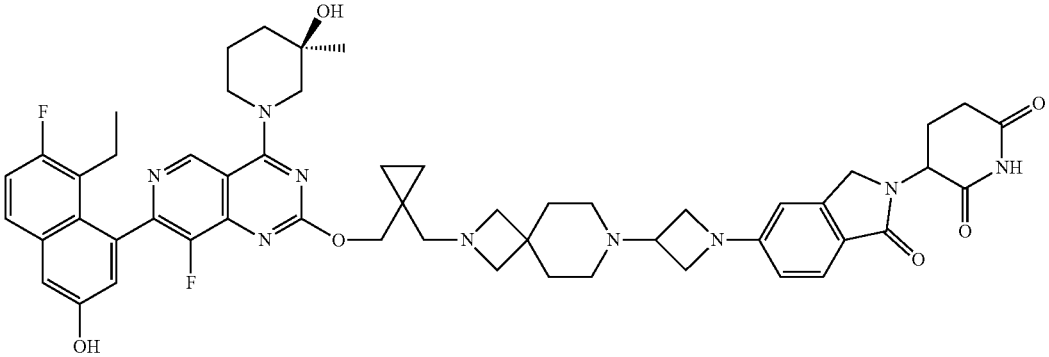 [SMILES: CCc1c(F)ccc2cc(O)cc(-c3ncc4c(N5CCC[C@@](C)(O)C5)nc(OCC5(CN6CC7(CCN(C8CN(c9ccc%10c(c9)CN(C9CCC(=O)NC9=O)C%10=O)C8)CC7)C6)CC5)nc4c3F)c12]<br>3-(5-(3-(2-(((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-2,7-diazaspiro[3.5]nonan-7-yl)azetidin-1-yl)-1-oxoisoindolin-2-yl)piperidine-2,6-dione |
| 173 | 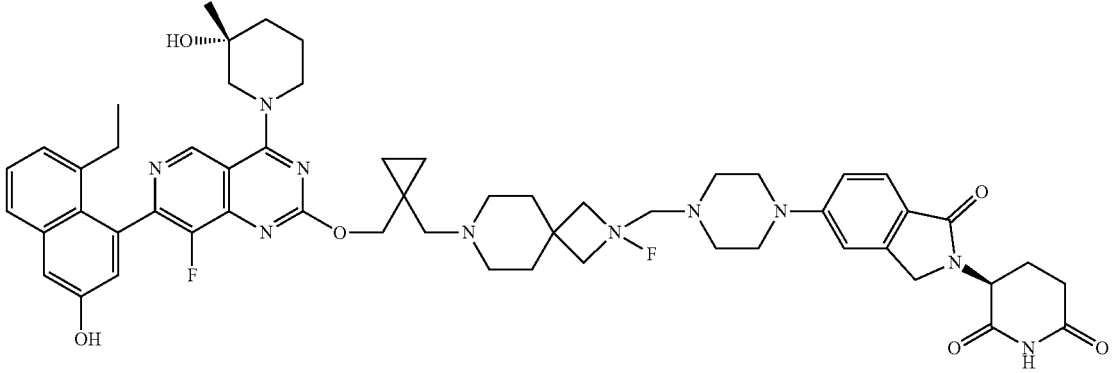<br>(S)-3-(5-(4-((7-((1-(((7-(8-ethyl-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-2-fluoro-7-azaspiro[3.5]nonan-2-yl)methyl)piperazin-1-yl)-1-oxoisoindolin-2-yl)piperidine-2,6-dione |
| 174 | 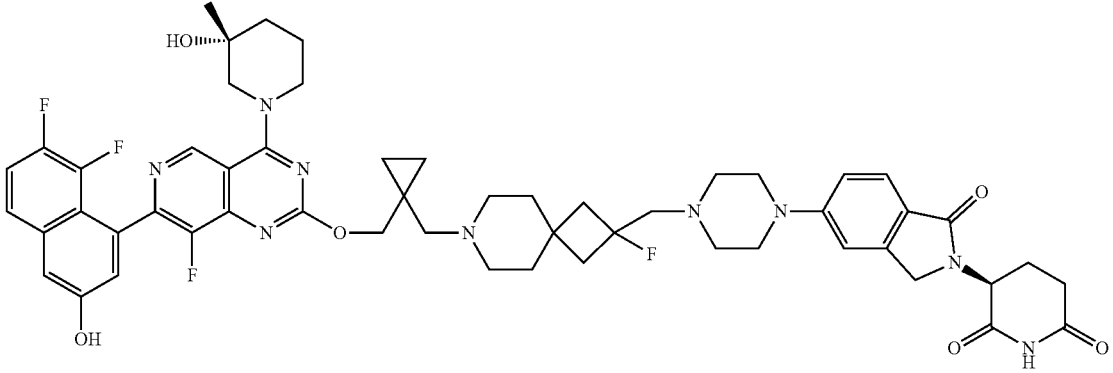 [SMILES: C[C@@]1(O)CCCN(c2nc(OCC3(CN4CCC5(CC4)CC(F)(CN4CCN(c6ccc7c(c6)CN([C@H]6CCC(=O)NC6=O)C7=O)CC4)C5)CC3)nc3c(F)c(-c4cc(O)cc5ccc(F)c(F)c45)ncc23)C1]<br>(S)-3-(5-(4-((7-((1-(((7-(7,8-difluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-2-fluoro-7-azaspiro[3.5]nonan-2-yl)methyl)piperazin-1-yl)-1-oxoisoindolin-2-yl)piperidine-2,6-dione |

TABLE 1-continued

Exemplary Compounds of the Present Disclosure

| Cpd # | Structure and IUPAC Name |
|---|---|
| 175 | 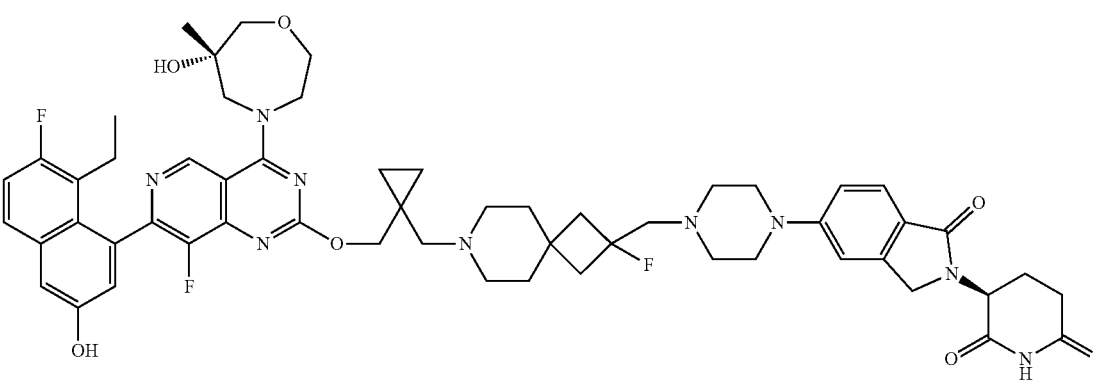 (S)-3-(5-(4-((7-((1-(((7-(8-ethyl-7-fluoro-3-hydroxynaphthalen-1-yl)-8-fluoro-4-((S)-6-hydroxy-6-methyl-1,4-oxazepan-4-yl)pyrido[4,3-d]pyrimidin-2-yl)oxy)methyl)cyclopropyl)methyl)-2-fluoro-7-azaspiro[3.5]nonan-2-yl)methyl)piperazin-1-yl)-1-oxoisoindolin-2-yl)piperidine-2,6-dione |
| 176 | 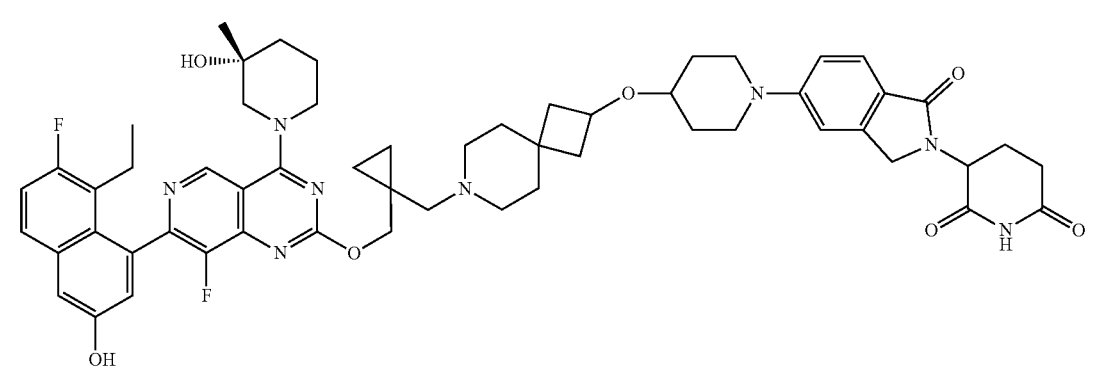 [SMILES: CCc1c(F)ccc2cc(O)cc(-c3ncc4c(N5CCC[C@@](C)(O)C5)nc(OCC5(CN6CCC7(CC6)CC(OC6CCN(c8ccc9c(c8)CN(C8CCC(=O)NC8=O)C9=O)CC6)C7)CC5)nc4c3F)c12] 3-(5-(4-((7-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-azaspiro[3.5]nonan-2-yl)oxy)piperidin-1-yl)-1-oxoisoindolin-2-yl)piperidine-2,6-dione |
| 177 | 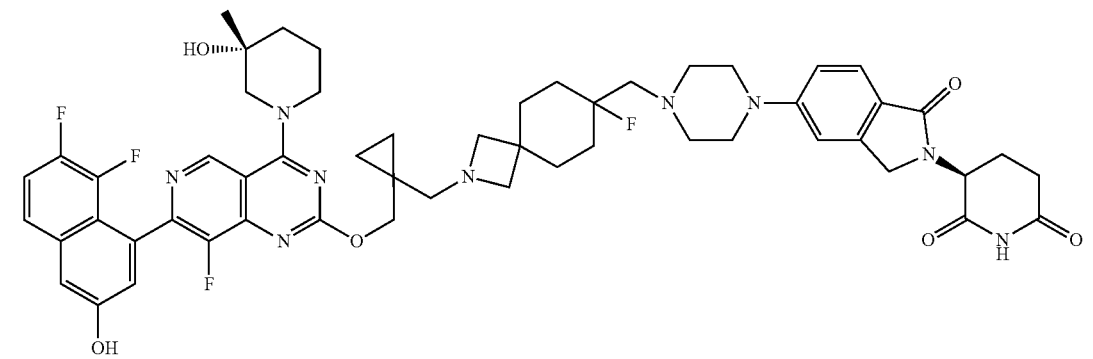 [SMILES: C[C@@]1(O)CCCN(c2nc(OCC3(CN4CC5(CCC(F)(CN6CCN(c7ccc8c(c7)CN([C@H]7CCC(=O)NC7=O)C8=O)CC6)CC5)C4)CC3)nc3c(F)c(-c4cc(O)cc5ccc(F)c(F)c45)ncc23)C1] (S)-3-(5-(4-((2-((1-(((7-(7,8-difluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-fluoro-2-azaspiro[3.5]nonan-7-yl)methyl)piperazin-1-yl)-1-oxoisoindolin-2-yl)piperidine-2,6-dione |

TABLE 1-continued

Exemplary Compounds of the Present Disclosure

| Cpd # | Structure and IUPAC Name |
|---|---|
| 178 | 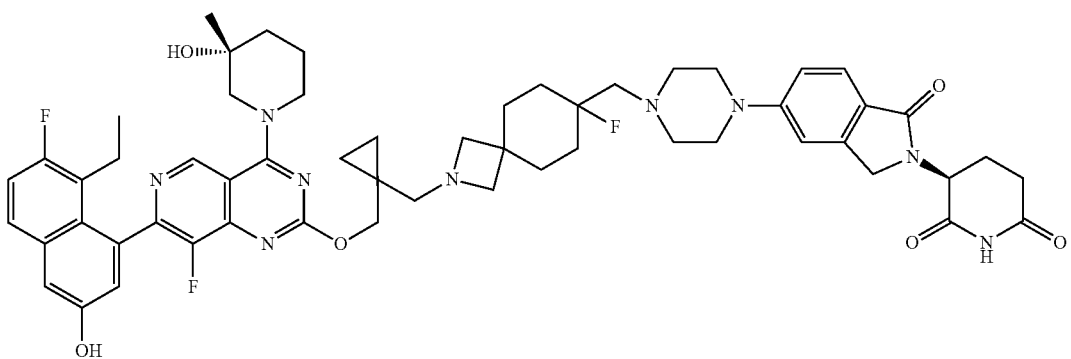 [SMILES: CCc1c(F)ccc2cc(O)cc(-c3ncc4c(N5CCC[C@@](C)(O)C5)nc(OCC5(CN6CC7(CCC(F)(CN8CCN(c9ccc%10c(c9)CN([C@H]9CCC(=O)NC9=O)C%10=O)CC8)CC7)C6)CC5)nc4c3F)c12]<br>(S)-3-(5-(4-((2-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-fluoro-2-azaspiro[3.5]nonan-7-yl)methyl)piperazin-1-yl)-1-oxoisoindolin-2-yl)piperidine-2,6-dione |
| 179 | 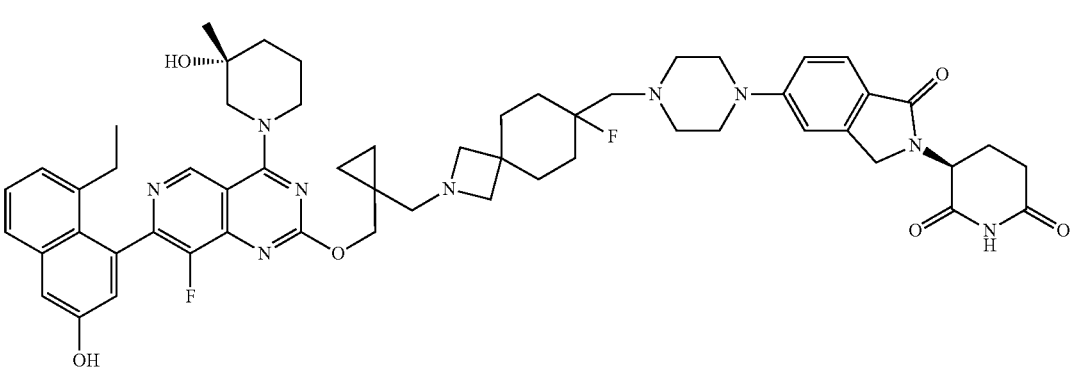 [SMILES: CCc1cccc2cc(O)cc(-c3ncc4c(N5CCC[C@@](C)(O)C5)nc(OCC5(CN6CC7(CCC(F)(CN8CCN(c9ccc%10c(c9)CN([C@H]9CCC(=O)NC9=O)C%10=O)CC8)CC7)C6)CC5)nc4c3F)c12]<br>(S)-3-(5-(4-((2-((1-(((7-(8-ethyl-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-fluoro-2-azaspiro[3.5]nonan-7-yl)methyl)piperazin-1-yl)-1-oxoisoindolin-2-yl)piperidine-2,6-dione |
| 180 | 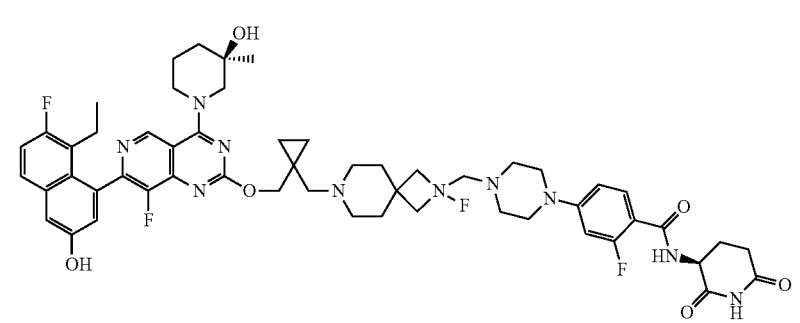<br>N-((S)-2,6-dioxopiperidin-3-yl)-4-(4-((7-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-2-fluoro-7-azaspiro[3.5]nonan-2-yl)methyl)piperazin-1-yl)-2-fluorobenzamide |

TABLE 1-continued

Exemplary Compounds of the Present Disclosure

| Cpd # | Structure and IUPAC Name |
|---|---|
| 181 | 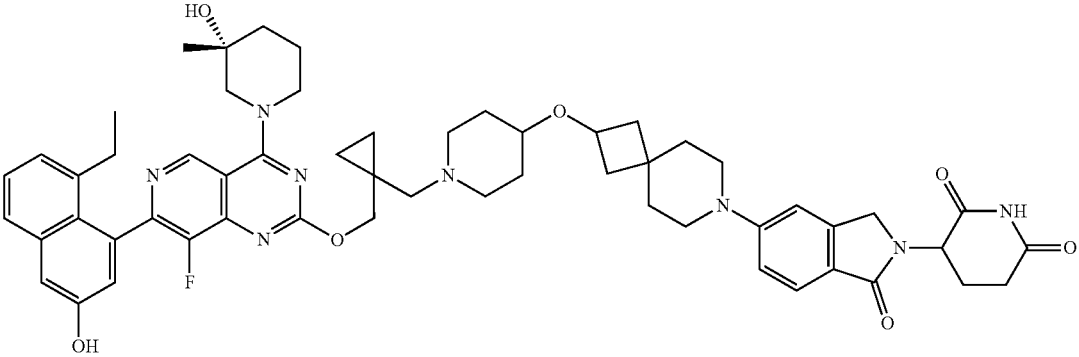 [SMILES: CCc1cccc2cc(O)cc(-c3ncc4c(N5CCC[C@@](C)(O)C5)nc(OCC5(CN6CCC(OC7CC8(CCN(c9ccc%10c(c9)CN(C9CCC(=O)NC9=O)C%10=O)CC8)C7)CC6)CC5)nc4c3F)c12]<br>3-(5-(2-((1-((1-(((7-(8-ethyl-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)oxy)-7-azaspiro[3.5]nonan-7-yl)-1-oxoisoindolin-2-yl)piperidine-2,6-dione |
| 182 | 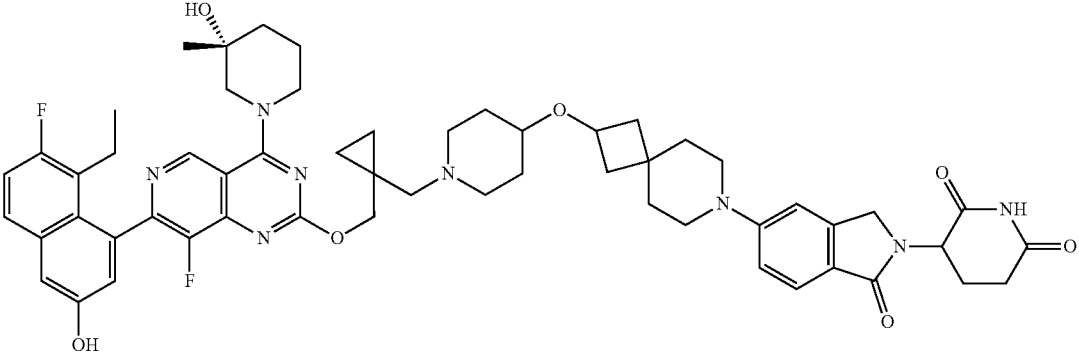 [SMILES: CCc1c(F)ccc2cc(O)cc(-c3ncc4c(N5CCC[C@@](C)(O)C5)nc(OCC5(CN6CCC(OC7CC8(CCN(c9ccc%10c(c9)CN(C9CCC(=O)NC9=O)C%10=O)CC8)C7)CC6)CC5)nc4c3F)c12]<br>3-(5-(2-((1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)oxy)-7-azaspiro[3.5]nonan-7-yl)-1-oxoisoindolin-2-yl)piperidine-2,6-dione |
| 183 | 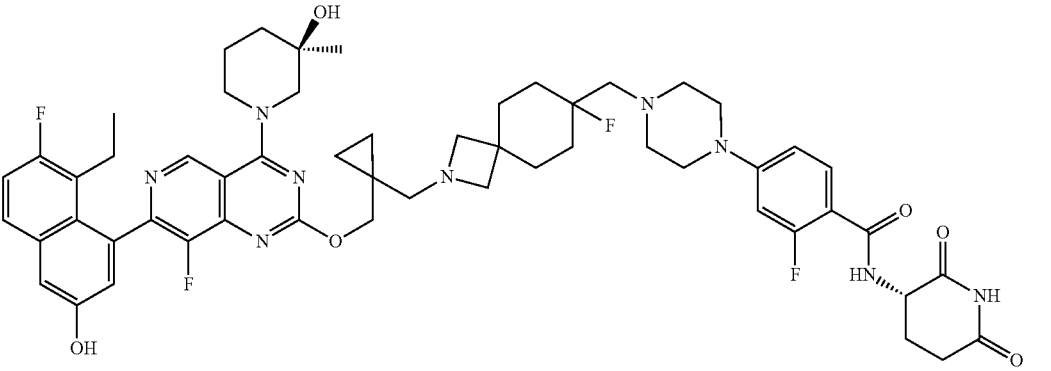 [SMILES: CCc1c(F)ccc2cc(O)cc(-c3ncc4c(N5CCC[C@@](C)(O)C5)nc(OCC5(CN6CC7(CCC(F)(CN8CCN(c9ccc(C(=O)N[C@H]%10CCC(=O)NC%10=O)c(F)c9)CC8)CC7)C6)CC5)nc4c3F)c12]<br>N-((S)-2,6-dioxopiperidin-3-yl)-4-(4-((2-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-fluoro-2-azaspiro[3.5]nonan-7-yl)methyl)piperazin-1-yl)-2-fluorobenzamide |

TABLE 1-continued

Exemplary Compounds of the Present Disclosure

| Cpd # | Structure and IUPAC Name |
|---|---|
| 184 | 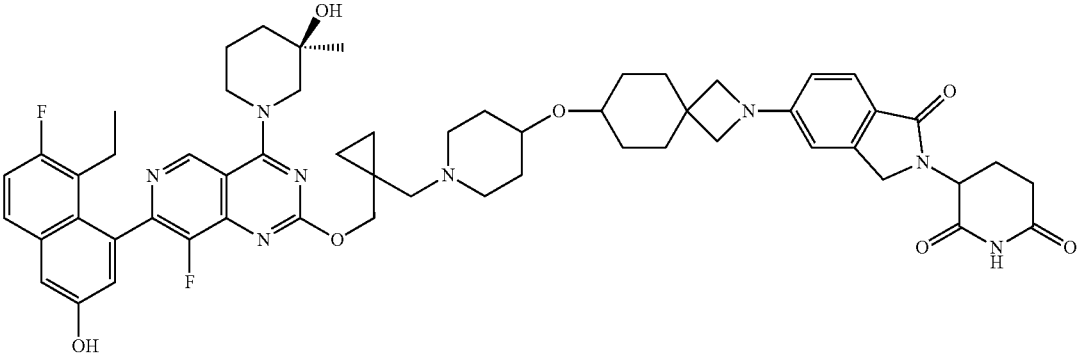 [SMILES: CCc1c(F)ccc2cc(O)cc(-c3ncc4c(N5CCC[C@@](C)(O)C5)nc(OCC5(CN6CCC(OC7CCC8(CC7)CN(c7ccc9c(c7)CN(C7CCC(=O)NC7=O)C9=O)C8)CC6)CC5)nc4c3F)c12]<br>3-(5-(7-((1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)oxy)-2-azaspiro[3.5]nonan-2-yl)-1-oxoisoindolin-2-yl)piperidine-2,6-dione |
| 185 | 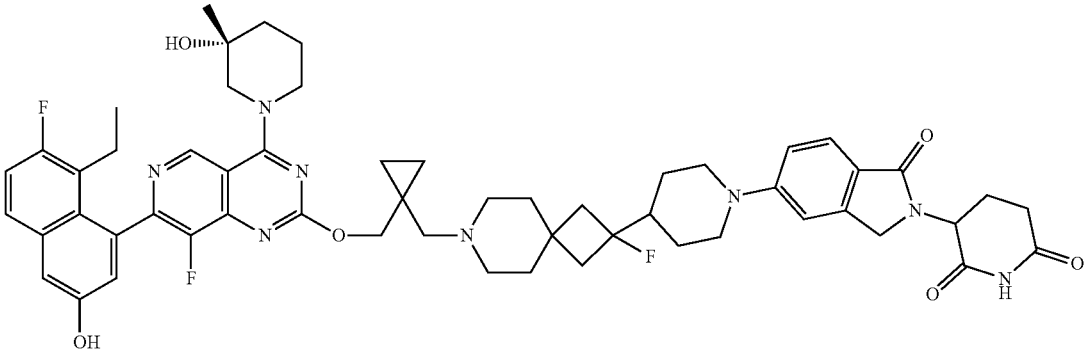 [SMILES: CCc1c(F)ccc2cc(O)cc(-c3ncc4c(N5CCC[C@@](C)(O)C5)nc(OCC5(CN6CCC7(CC6)CC(F)(C6CCN(c8ccc9c(c8)CN(C8CCC(=O)NC8=O)C9=O)CC6)C7)CC5)nc4c3F)c12]<br>3-(5-(4-(7-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-2-fluoro-7-azaspiro[3.5]nonan-2-yl)piperidin-1-yl)-1-oxoisoindolin-2-yl)piperidine-2,6-dione |
| 186 | 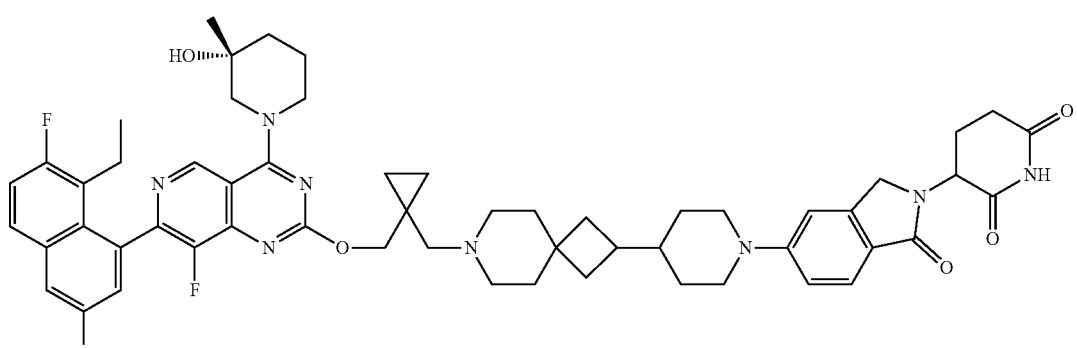<br>3-(5-(4-(7-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-azaspiro[3.5]nonan-2-yl)piperidin-1-yl)-1-oxoisoindolin-2-yl)piperidine-2,6-dione |

TABLE 1-continued

Exemplary Compounds of the Present Disclosure

| Cpd # | Structure and IUPAC Name |
|---|---|
| 187 | 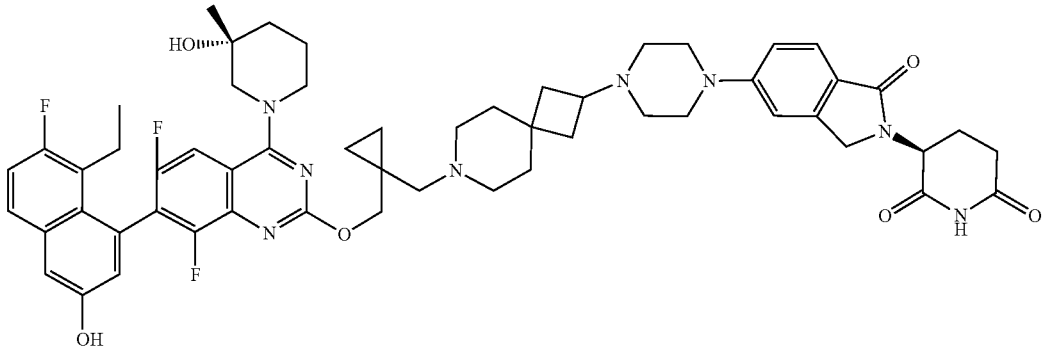 [SMILES: CCc1c(F)ccc2cc(O)cc(C3=C(F)c4nc(OCC5(CN6CCC7(CC6)CC(N6CCN(c8ccc9c(c8)CN([C@H]8CCC(=O)NC8=O)C9=O)CC6)C7)CC5)nc(N5CCC[C@@](C)(O)C5)c4C=C(F)C3)c12]<br>(3S)-3-(5-(4-(7-(((1-(((7-(8-ethyl-7-fluoro-3-hydroxynaphthalen-1-yl)-6,8-difluoro-4-((R)-3-hydroxy-3-methylpiperidin-1-yl)quinazolin-2-yl)oxy)methyl)cyclopropyl)methyl)-7-azaspiro[3.5]nonan-2-yl)piperazin-1-yl)-1-oxoisoindolin-2-yl)piperidine-2,6-dione |
| 188 | 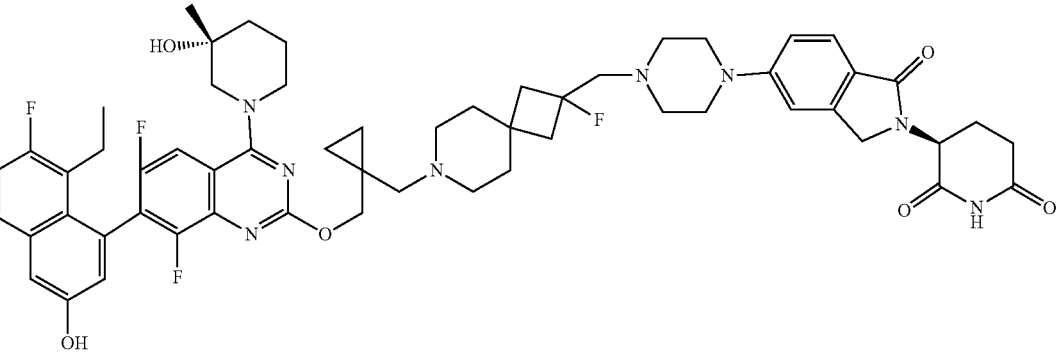 [SMILES: CCc1c(F)ccc2cc(O)cc(-c3c(F)cc4c(N5CCC[C@@](C)(O)C5)nc(OCC5(CN6CCC7(CC6)CC(F)(CN6CCN(c8ccc9c(c8)CN([C@H]8CCC(=O)NC8=O)C9=O)CC6)C7)CC5)nc4c3F)c12]<br>(3S)-3-(5-(4-((7-(((1-(((7-(8-ethyl-7-fluoro-3-hydroxynaphthalen-1-yl)-6,8-difluoro-4-((R)-3-hydroxy-3-methylpiperidin-1-yl)quinazolin-2-yl)oxy)methyl)cyclopropyl)methyl)-2-fluoro-7-azaspiro[3.5]nonan-2-yl)methyl)piperazin-1-yl)-1-oxoisoindolin-2-yl)piperidine-2,6-dione |
| 189 | 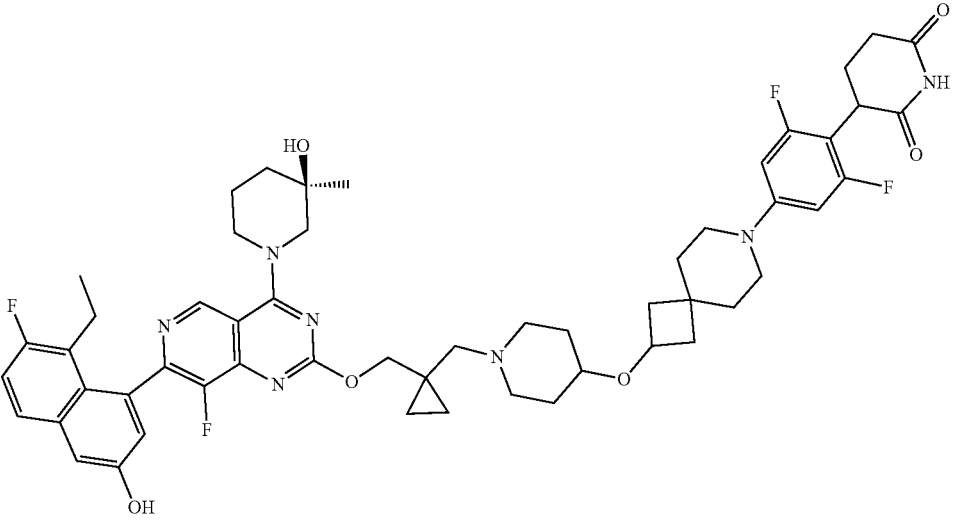 [SMILES: CCc1c(F)ccc2cc(O)cc(-c3ncc4c(N5CCC[C@@](C)(O)C5)nc(OCC5(CN6CCC(OC7CC8(CCN(c9cc(F)c(C%10CCC(=O)NC%10=O)c(F)c9)CC8)C7)CC6)CC5)nc4c3F)c12]<br>3-(4-(2-((1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)oxy)-7-azaspiro[3.5]nonan-7-yl)-2,6-difluorophenyl)piperidine-2,6-dione |

TABLE 1-continued

Exemplary Compounds of the Present Disclosure

| Cpd # | Structure and IUPAC Name |
|---|---|

190

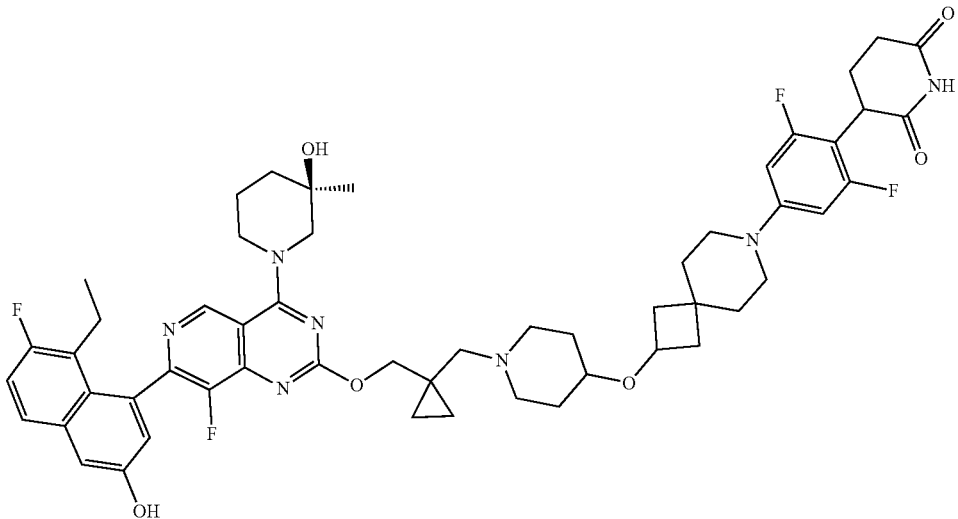 [SMILES: CCc1c(F)ccc2cc(O)cc(-c3ncc4c(N5CCC[C@@](C)(O)C5)nc(OCC5(CN6CCC(OC7CC8(CCN(c9cc(F)c(C%10CCC(=O)NC%10=O)c(F)c9)CC8)C7)CC6)CC5)nc4c3F)c12]

3-(4-(2-((1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)oxy)-7-azaspiro[3.5]nonan-7-yl)-2,6-difluorophenyl)piperidine-2,6-dione

191

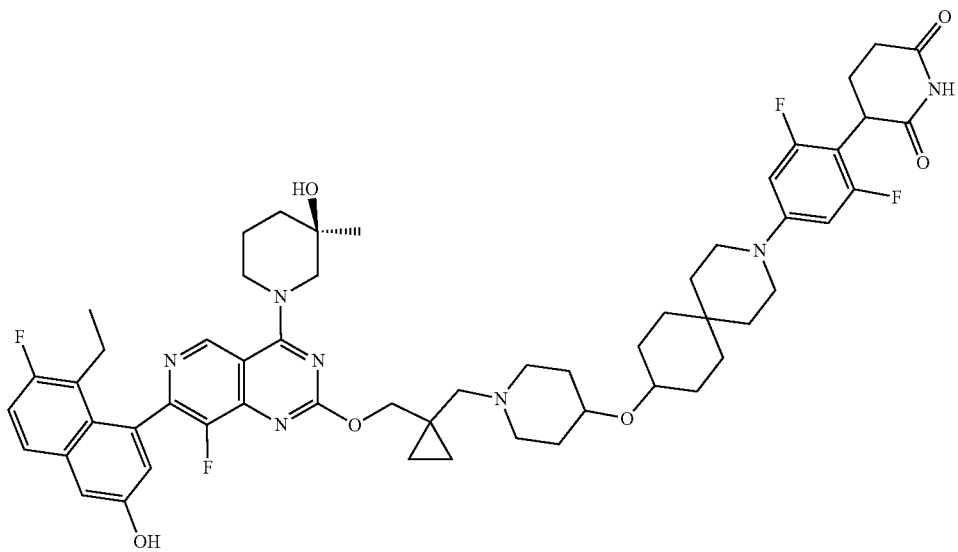

3-(4-(9-((1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)oxy)-3-azaspiro[5.5]undecan-3-yl)-2,6-difluorophenyl)piperidine-2,6-dione TABLE 1-continued Exemplary Compounds of the Present Disclosure

| Cpd # | Structure and IUPAC Name |
|---|---|
| 192 | 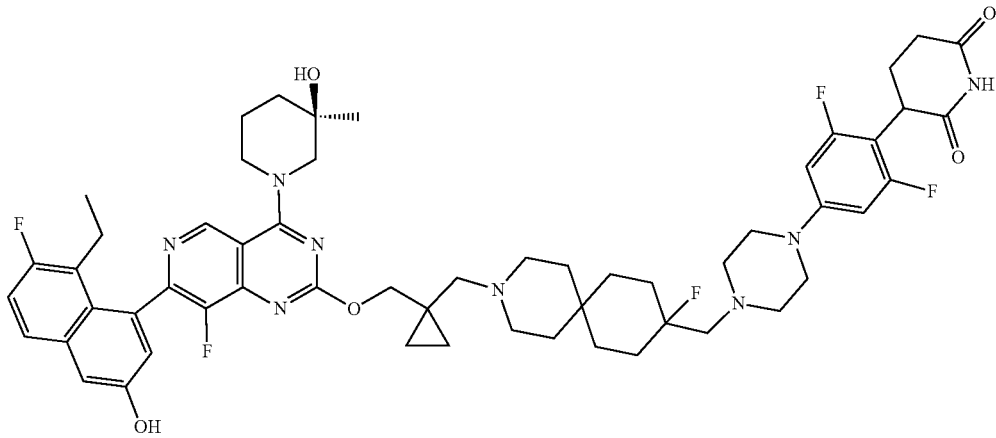 [SMILES: CCc1c(F)ccc2cc(O)cc(-c3ncc4c(N5CCC[C@@](C)(O)C5)nc(OCC5(CN6CCC7(CC6)CCC(F)(CN6CCN(c8cc(F)c(C9CCC(=O)NC9=O)c(F)c8)CC6)CC7)CC5)nc4c3F)c12]<br>3-(4-(4-((3-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-9-fluoro-3-azaspiro[5.5]undecan-9-yl)methyl)piperazin-1-yl)-2,6-difluorophenyl)piperidine-2,6-dione |
| 193 | 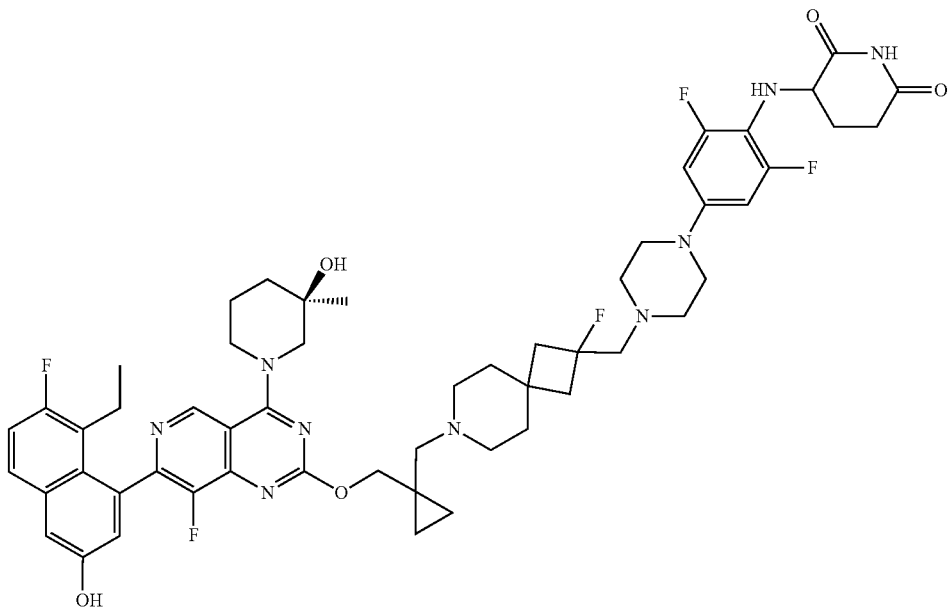 [SMILES: CCc1c(F)ccc2cc(O)cc(-c3ncc4c(N5CCC[C@@](C)(O)C5)nc(OCC5(CN6CCC7(CC6)CC(F)(CN6CCN(c8cc(F)c(NC9CCC(=O)NC9=O)c(F)c8)CC6)C7)CC5)nc4c3F)c12]<br>3-((4-(4-((7-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-2-fluoro-7-azaspiro[3.5]nonan-2-yl)methyl)piperazin-1-yl)-2,6-difluorophenyl)amino)piperidine-2,6-dione |

TABLE 1-continued

Exemplary Compounds of the Present Disclosure

| Cpd # | Structure and IUPAC Name |
|---|---|
| 194 | 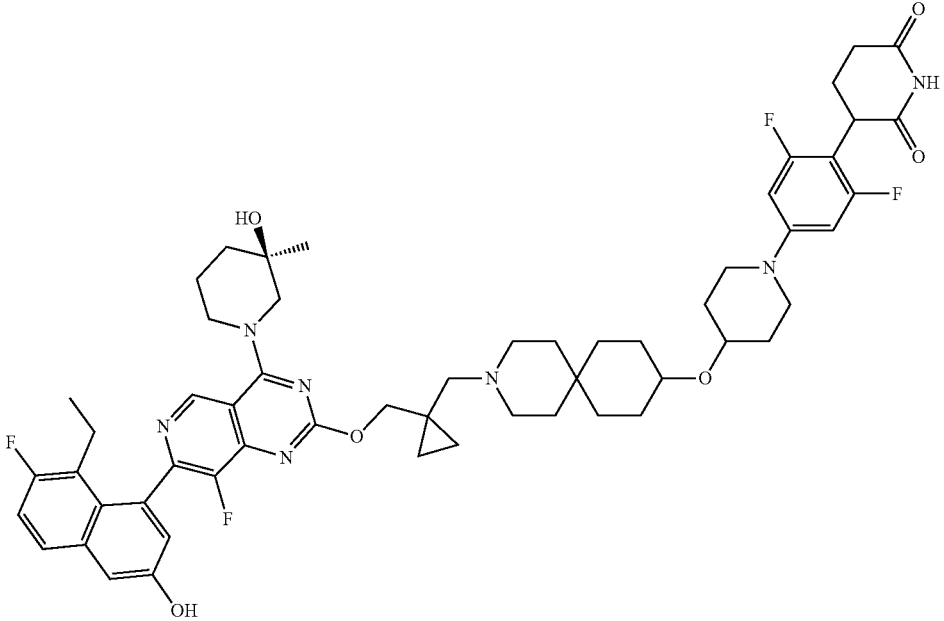 [SMILES: CCc1c(F)ccc2cc(O)cc(-c3ncc4c(N5CCC[C@@](C)(O)C5)nc(OCC5(CN6CCC7(CCC(OC8CCN(c9cc(F)c(C%10CCC(=O)NC%10=O)c(F)c9)CC8)CC7)CC6)CC5)nc4c3F)c12]<br>3-(4-(4-((3-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-3-azaspiro[5.5]undecan-9-yl)oxy)piperidin-1-yl)-2,6-difluorophenyl)piperidine-2,6-dione |
| 195 | 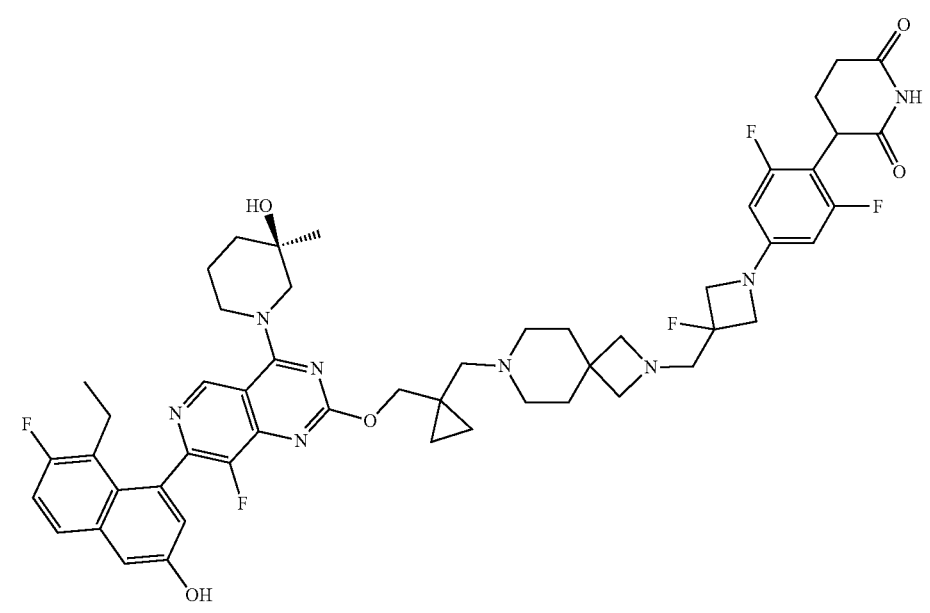 [SMILES: CCc1c(F)ccc2cc(O)cc(-c3ncc4c(N5CCC[C@@](C)(O)C5)nc(OCC5(CN6CCC7(CC6)CN(CC6(F)CN(c8cc(F)c(C9CCC(=O)NC9=O)c(F)c8)C6)C7)CC5)nc4c3F)c12]<br>3-(4-(3-((7-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-2,7-diazaspiro[3.5]nonan-2-yl)methyl)-3-fluoroazetidin-1-yl)-2,6-difluorophenyl)piperidine-2,6-dione |

TABLE 1-continued

Exemplary Compounds of the Present Disclosure

| Cpd # | Structure and IUPAC Name |
|---|---|

196

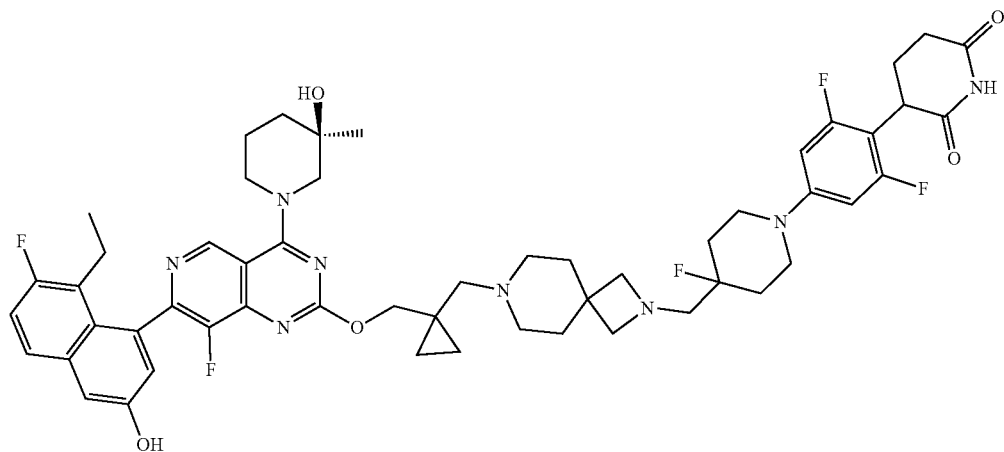 [SMILES: CCc1c(F)ccc2cc(O)cc(-c3ncc4c(N5CCC[C@@](C)(O)C5)nc(OCC5(CN6CCC7(CC6)CN(CC6(F)CCN(c8cc(F)c(C9CCC(=O)NC9=O)c(F)c8)CC6)C7)CC5)nc4c3F)c12]

3-(4-(4-((7-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-2,7-diazaspiro[3.5]nonan-2-yl)methyl)-4-fluoropiperidin-1-yl)-2,6-difluorophenyl)piperidine-2,6-dione

197

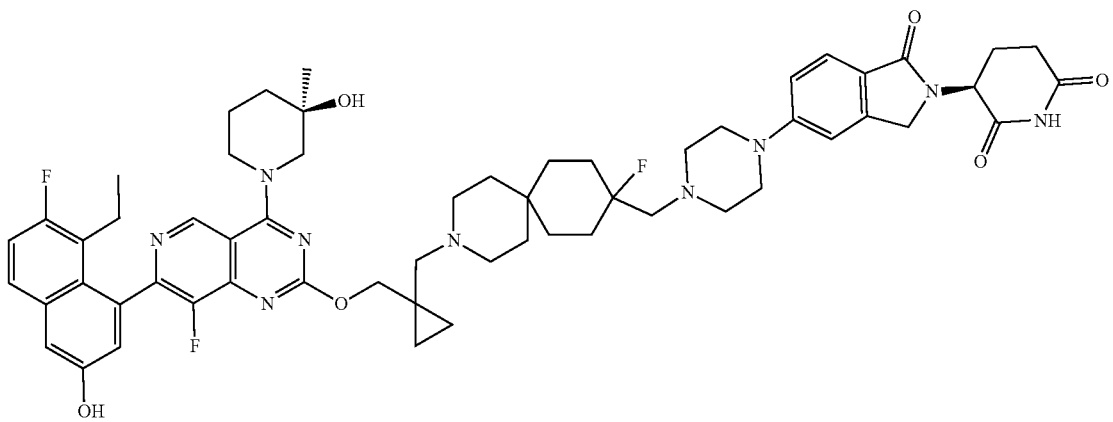 [SMILES: CCc1c(F)ccc2cc(O)cc(-c3ncc4c(N5CCC[C@@](C)(O)C5)nc(OCC5(CN6CCC7(CC6)CCC(F)(CN6CCN(c8ccc9c(c8)CN([C@H]8CCC(=O)NC8=O)C9=O)CC6)CC7)CC5)nc4c3F)c12]

(S)-3-(5-(4-((3-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-9-fluoro-3-azaspiro[5.5]undecan-9-yl)methyl)piperazin-1-yl)-1-oxoisoindolin-2-yl)piperidine-2,6-dione

| Cpd # | Structure and IUPAC Name |
|---|---|
| 198 | 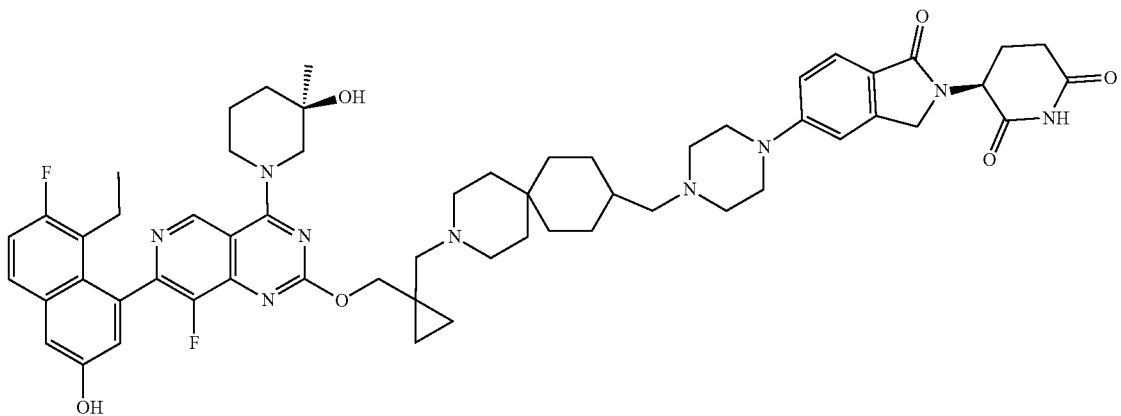 [SMILES: CCc1c(F)ccc2cc(O)cc(-c3ncc4c(N5CCC[C@@](C)(O)C5)nc(OCC5(CN6CCC7(CCC(CN8CCN(c9ccc%10c(c9)CN([C@H]9CCC(=O)NC9=O)C%10=O)CC8)CC7)CC6)CC5)nc4c3F)c12]<br>(S)-3-(5-(4-((3-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-3-azaspiro[5.5]undecan-9-yl)methyl)piperazin-1-yl)-1-oxoisoindolin-2-yl)piperidine-2,6-dione |
| 199 | 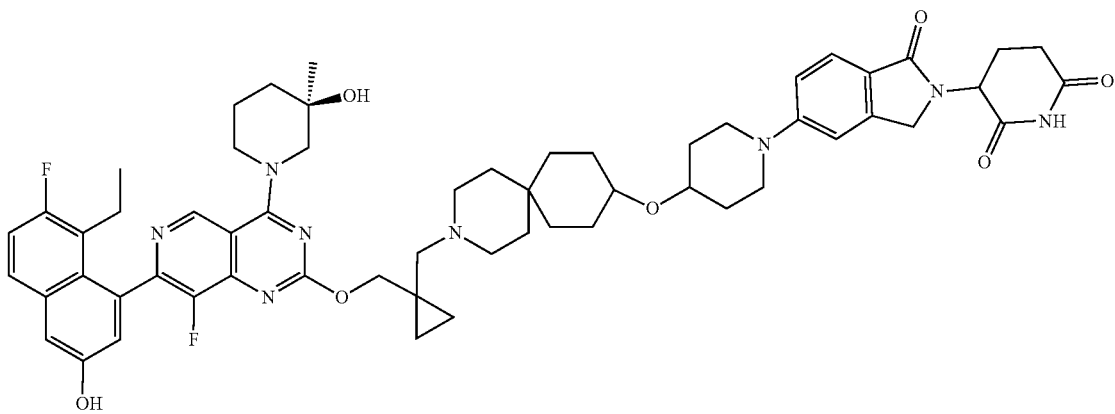 [SMILES: CCc1c(F)ccc2cc(O)cc(-c3ncc4c(N5CCC[C@@](C)(O)C5)nc(OCC5(CN6CCC7(CCC(OC8CCN(c9ccc%10c(c9)CN(C9CCC(=O)NC9=O)C%10=O)CC8)CC7)CC6)CC5)nc4c3F)c12]<br>3-(5-(4-((3-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-3-azaspiro[5.5]undecan-9-yl)oxy)piperidin-1-yl)-1-oxoisoindolin-2-yl)piperidine-2,6-dione |

TABLE 1-continued

Exemplary Compounds of the Present Disclosure

| Cpd # | Structure and IUPAC Name |
|---|---|
| 200 | 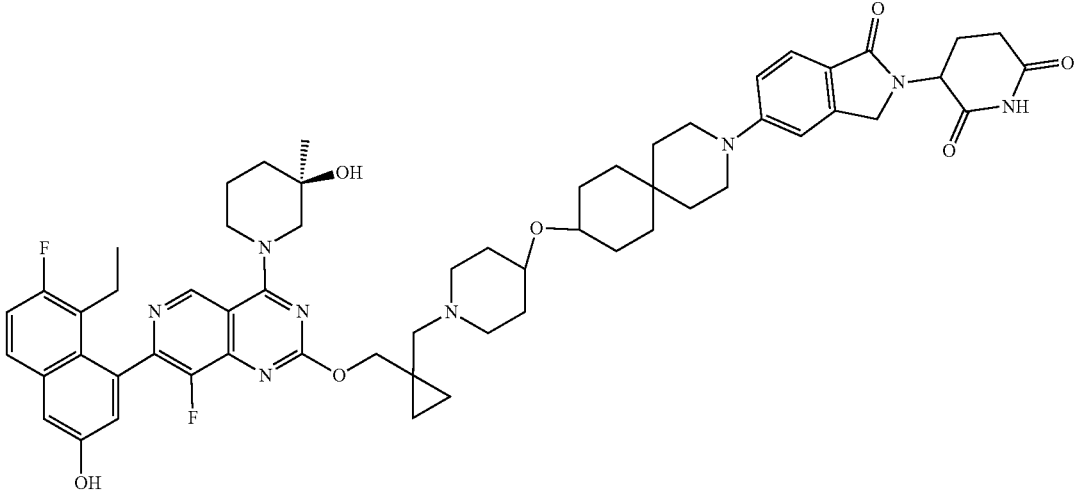 [SMILES: CCc1c(F)ccc2cc(O)cc(-c3ncc4c(N5CCC[C@@](C)(O)C5)nc(OCC5(CN6CCC(OC7CCC8(CC7)CCN(c7ccc9c(c7)CN(C7CCC(=O)NC7=O)C9=O)CC8)CC6)CC5)nc4c3F)c12] 3-(5-(9-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)oxy)-3-azaspiro[5.5]undecan-3-yl)-1-oxoisoindolin-2-yl)piperidine-2,6-dione |
| 201 | 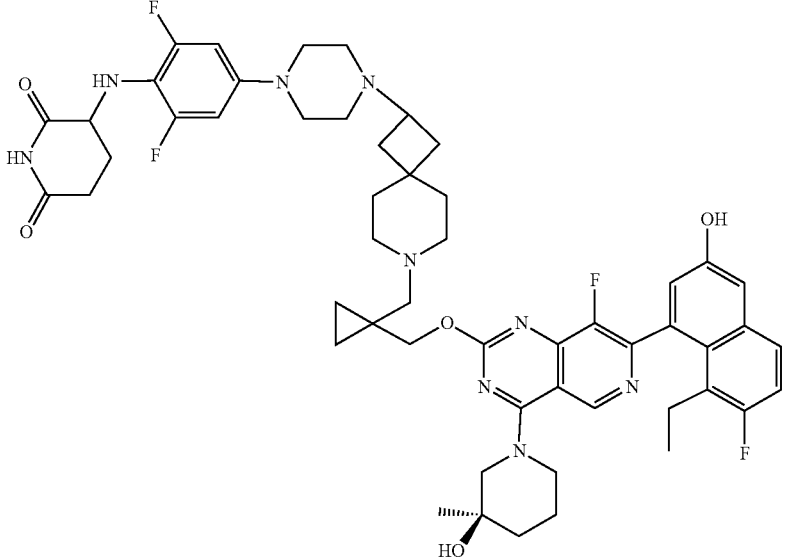 [SMILES: CCc1c(F)ccc2cc(O)cc(-c3ncc4c(N5CCC[C@@](C)(O)C5)nc(OCC5(CN6CCC7(CC6)CC(N6CCN(c8cc(F)c(NC9CCC(=O)NC9=O)c(F)c8)CC6)C7)CC5)nc4c3F)c12] 3-((4-(4-(7-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-azaspiro[3.5]nonan-2-yl)piperazin-1-yl)-2,6-difluorophenyl)amino)piperidine-2,6-dione |

TABLE 1-continued

Exemplary Compounds of the Present Disclosure

| Cpd # | Structure and IUPAC Name |
|---|---|
| 202 | 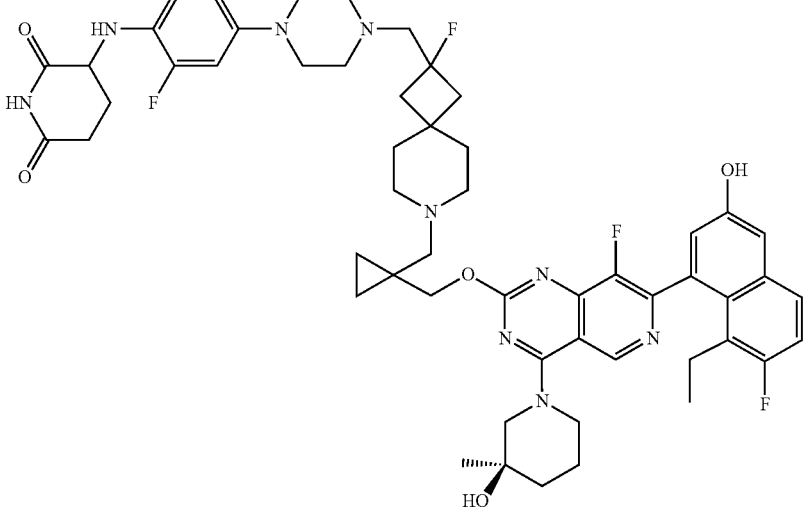<br>3-((4-(4-((7-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-2-fluoro-7-azaspiro[3.5]nonan-2-yl)methyl)piperazin-1-yl)-2-fluorophenyl)amino)piperidine-2,6-dione |
| 203 | 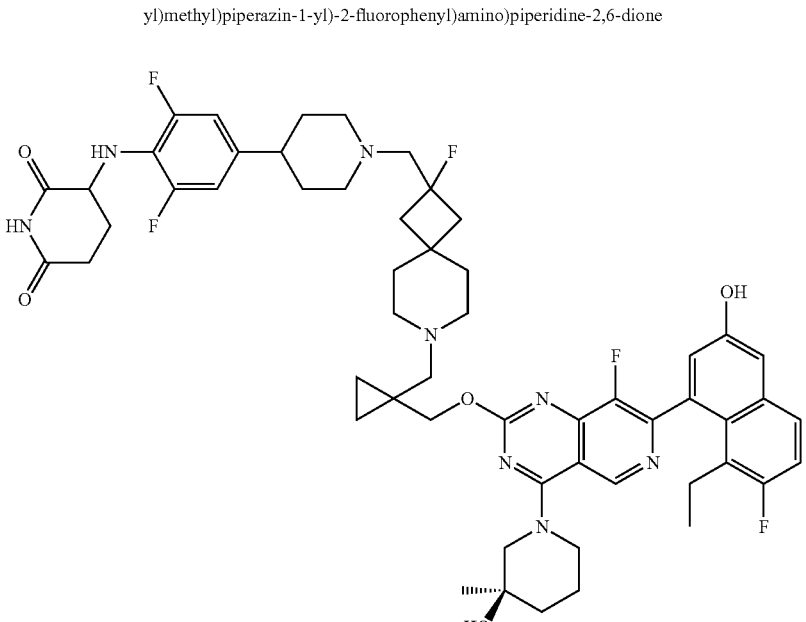<br>3-((4-(1-((7-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-2-fluoro-7-azaspiro[3.5]nonan-2-yl)methyl)piperidin-4-yl)-2,6-difluorophenyl)amino)piperidine-2,6-dione |

TABLE 1-continued

Exemplary Compounds of the Present Disclosure

| Cpd # | Structure and IUPAC Name |
|---|---|
| 204 | 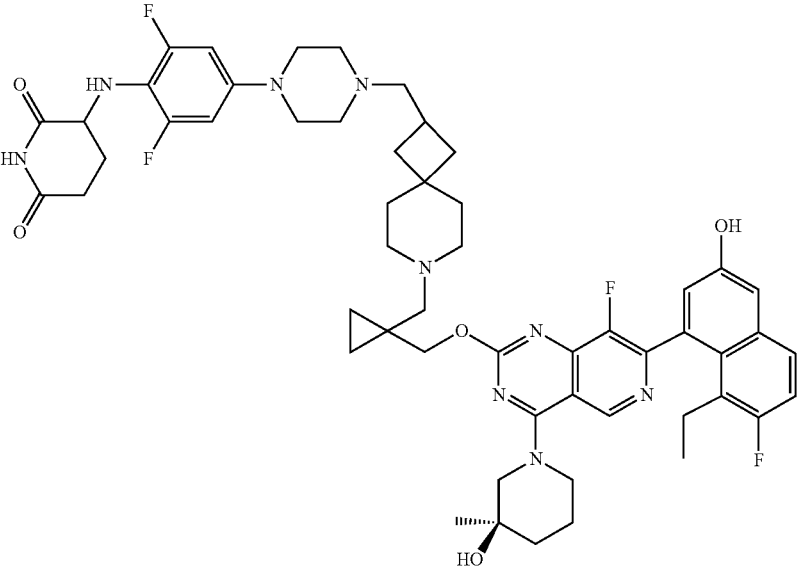<br>3-((4-(4-((7-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-azaspiro[3.5]nonan-2-yl)methyl)piperazin-1-yl)-2,6-difluorophenyl)amino)piperidine-2,6-dione |
| 205 | 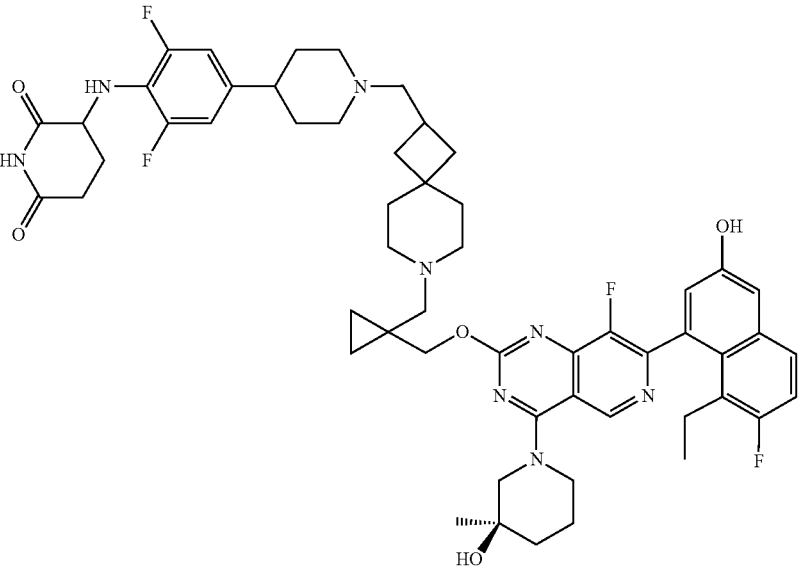 [SMILES: CCc1c(F)ccc2cc(O)cc(-c3ncc4c(N5CCC[C@@](C)(O)C5)nc(OCC5(CN6CCC7(CC6)CC(CN6CCN(c8cc(F)c(NC9CCC(=O)NC9=O)c(F)c8)CC6)C7)CC5)nc4c3F)c12]<br>3-((4-(1-((7-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-azaspiro[3.5]nonan-2-yl)methyl)piperidin-4-yl)-2,6-difluorophenyl)amino)piperidine-2,6-dione |

TABLE 1-continued

Exemplary Compounds of the Present Disclosure

| Cpd # | Structure and IUPAC Name |
|---|---|
| 206 | 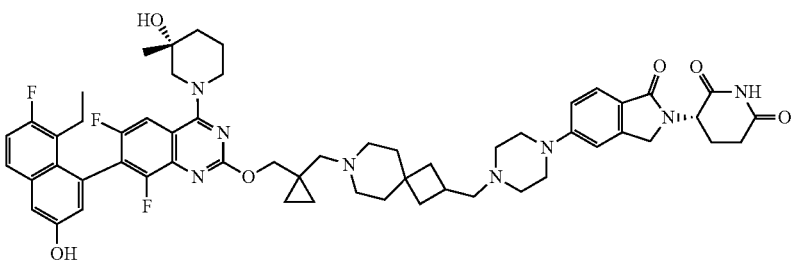 [SMILES: CCc1c(F)ccc2cc(O)cc(-c3c(F)cc4c(N5CCC[C@@](C)(O)C5)nc(OCC5(CN6CCC7(CC6)CC(CN6CCN(c8ccc9c(c8)CN([C@H]8CCC(=O)NC8=O)C9=O)CC6)C7)CC5)nc4c3F)c12]

(3S)-3-(5-(4-((7-((1-(((7-(8-ethyl-7-fluoro-3-hydroxynaphthalen-1-yl)-6,8-difluoro-4-((R)-3-hydroxy-3-methylpiperidin-1-yl)quinazolin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |
| 207 | 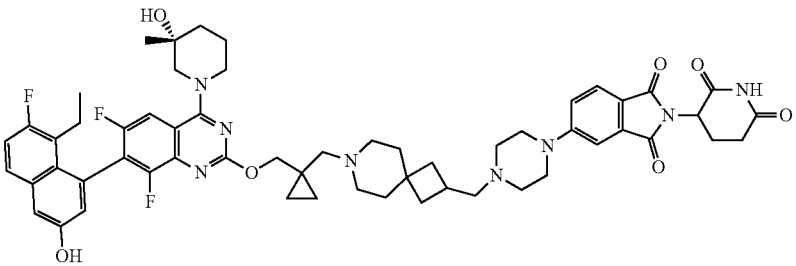 [SMILES: CCc1c(F)ccc2cc(O)cc(-c3c(F)cc4c(N5CCC[C@@](C)(O)C5)nc(OCC5(CN6CCC7(CC6)CC(CN6CCN(c8ccc9c(c8)C(=O)N(C8CCC(=O)NC8=O)C9=O)CC6)C7)CC5)nc4c3F)c12]

2-(2,6-dioxopiperidin-3-yl)-5-(4-((7-((1-(((7-(8-ethyl-7-fluoro-3-hydroxynaphthalen-1-yl)-6,8-difluoro-4-((R)-3-hydroxy-3-methylpiperidin-1-yl)quinazolin-2-yl)oxy)methyl)cyclopropyl)methyl)-7-azaspiro[3.5]nonan-2-yl)methyl)piperazin-1-yl)isoindoline-1,3-dione |
| 208 | 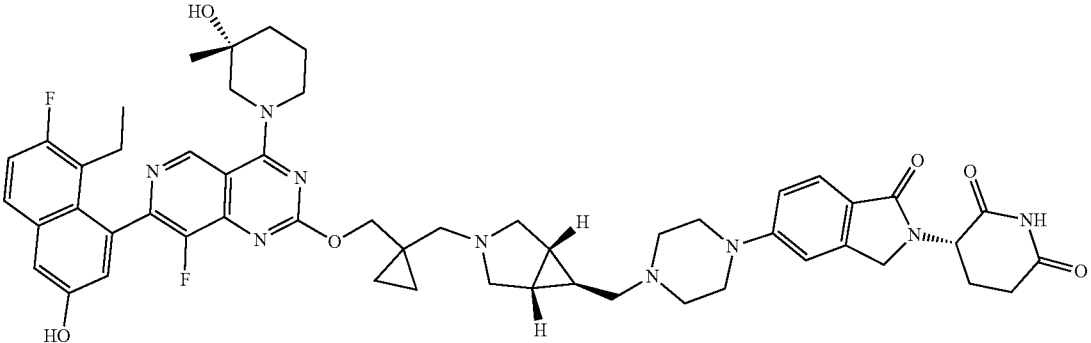 [SMILES: CCc1c(F)ccc2cc(O)cc(-c3ncc4c(N5CCC[C@@](C)(O)C5)nc(OCC5(CN6C[C@@H]7[C@@H](CN8CCN(c9ccc%10c(c9)CN([C@H]9CCC(=O)NC9=O)C%10=O)CC8)[C@@H]7C6)CC5)nc4c3F)c12]

(S)-3-(5-(4-(((1R,5S,6R)-3-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-3-azabicyclo[3.1.0]hexan-6-yl)methyl)piperazin-1-yl)-1-oxoisoindolin-2-yl)piperidine-2,6-dione |

TABLE 1-continued

Exemplary Compounds of the Present Disclosure

| Cpd # | Structure and IUPAC Name |
|---|---|
| 209 | 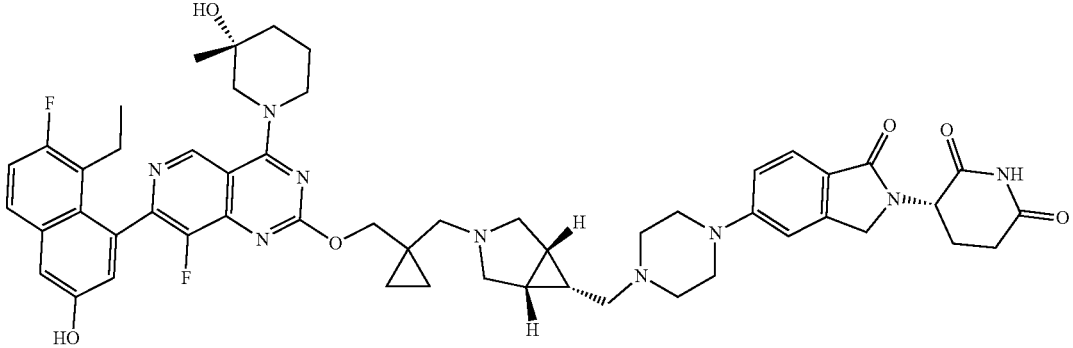 [SMILES: CCc1c(F)ccc2cc(O)cc(-c3ncc4c(N5CCC[C@@](C)(O)C5)nc(OCC5(CN6C[C@@H]7[C@H](CN8CCN(c9ccc%10c(c9)CN([C@H]9CCC(=O)NC9=O)C%10=O)CC8)[C@@H]7C6)CC5)nc4c3F)c12]<br>(S)-3-(5-(4-(((1R,5S,6S)-3-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-3-azabicyclo[3.1.0]hexan-6-yl)methyl)piperazin-1-yl)-1-oxoisoindolin-2-yl)piperidine-2,6-dione |
| 210 | 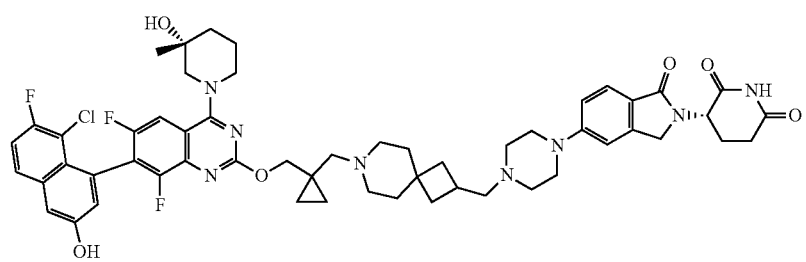 [SMILES: C[C@@]1(O)CCCN(c2nc(OCC3(CN4CCC5(CC4)CC(CN4CCN(c6ccc7c(c6)CN([C@H]6CCC(=O)NC6=O)C7=O)CC4)C5)CC3)nc3c(F)c(-c4cc(O)cc5ccc(F)c(Cl)c45)c(F)cc23)C1]<br>(3S)-3-(5-(4-((7-((1-(((7-(8-chloro-7-fluoro-3-hydroxynaphthalen-1-yl)-6,8-difluoro-4-((R)-3-hydroxy-3-methylpiperidin-1-yl)quinazolin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione |
| 211 | 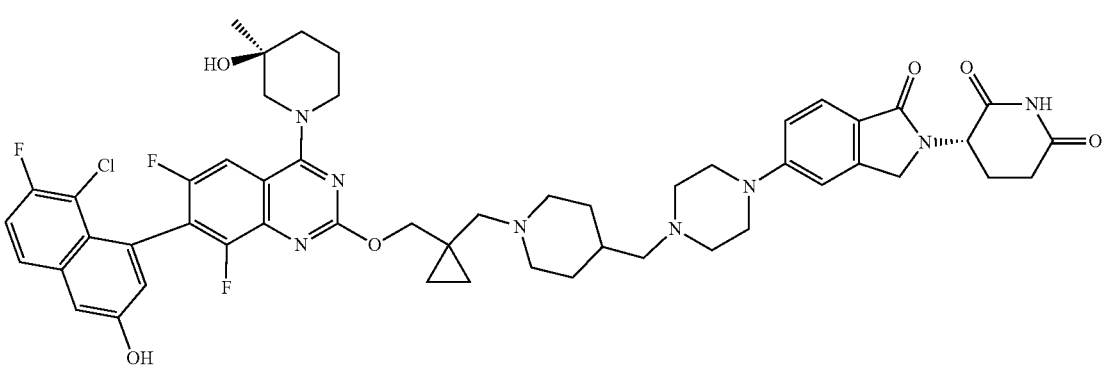 [SMILES: C[C@]1(O)CCCN(c2nc(OCC3(CN4CCC(CN5CCN(c6ccc7c(c6)CN([C@H]6CCC(=O)NC6=O)C7=O)CC5)CC4)CC3)nc3c(F)c(-c4cc(O)cc5ccc(F)c(Cl)c45)c(F)cc23)C1]<br>(3S)-3-(5-(4-((1-((1-(((7-(8-chloro-7-fluoro-3-hydroxynaphthalen-1-yl)-6,8-difluoro-4-((S)-3-hydroxy-3-methylpiperidin-1-yl)quinazolin-2-yl)oxy)methyl)cyclopropyl)methyl)piperidin-4-yl)methyl)piperazin-1-yl)-1-oxoisoindolin-2-yl)piperidine-2,6-dione |

TABLE 1-continued

Exemplary Compounds of the Present Disclosure

| Cpd # | Structure and IUPAC Name |
|---|---|
| 212 | 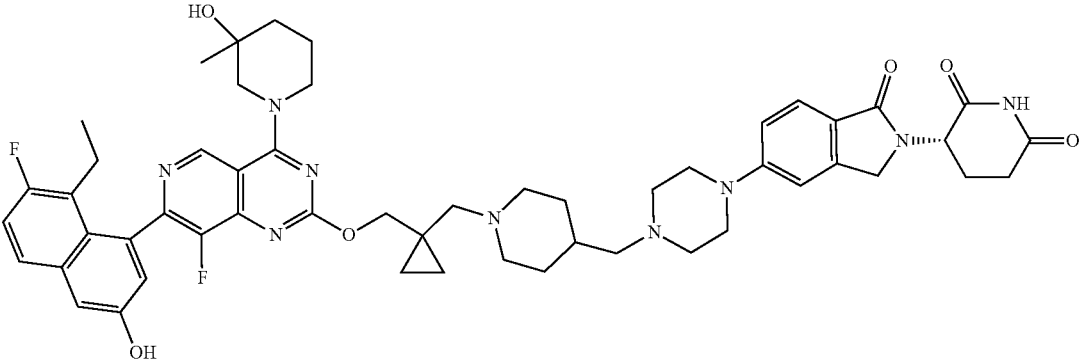 [SMILES: CCc1c(F)ccc2cc(O)cc(-c3ncc4c(N5CCCC(C)(O)C5)nc(OCC5(CN6CCC(CN7CCN(c8ccc9c(c8)CN([C@H]8CCC(=O)NC8=O)C9=O)CC7)CC6)CC5)nc4c3F)c12]<br>(3S)-3-(5-(4-((1-((1-(((7-(8-ethyl-7-fluoro-3-hydroxynaphthalen-1-yl)-8-fluoro-4-(3-hydroxy-3-methylpiperidin-1-yl)pyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione |
| 213 | 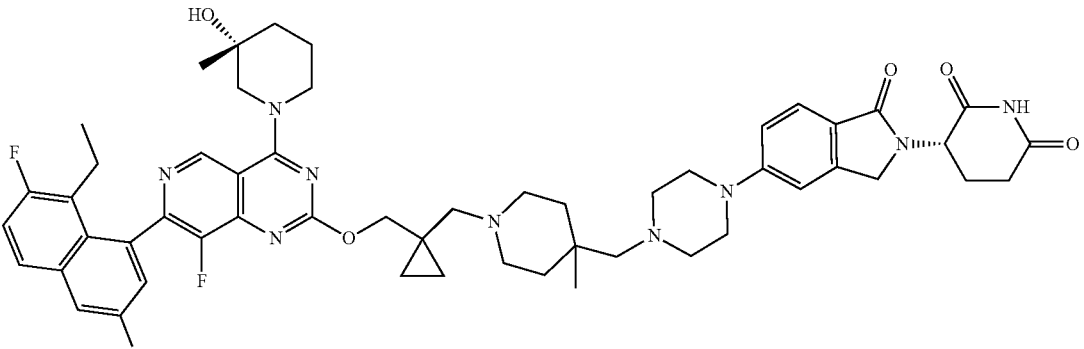<br>(S)-3-(5-(4-(1-((1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-4-methylpiperidin-4-yl)methyl)piperidin-4-yl)piperazin-1-yl)-1-oxoisoindolin-2-yl)piperidine-2,6-dione |
| 214 | 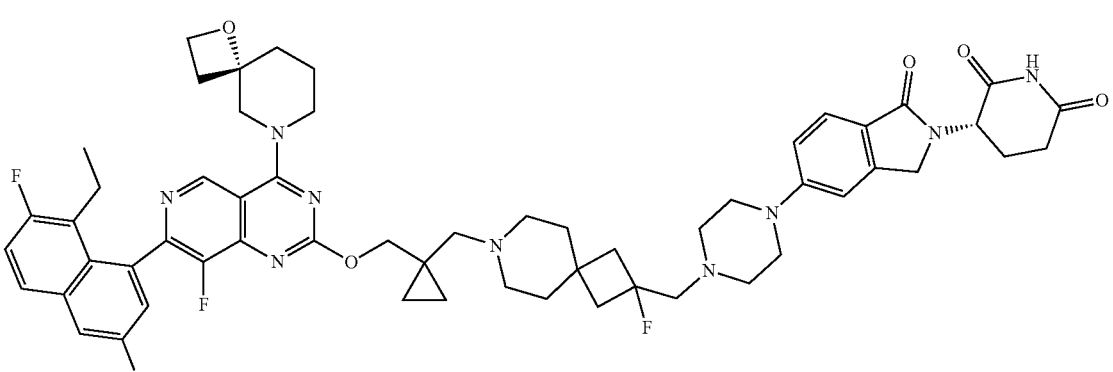<br>(S)-3-(5-(4-((7-((1-(((7-(8-ethyl-7-fluoro-3-hydroxynaphthalen-1-yl)-8-fluoro-4-((S)-1-oxa-6-azaspiro[3.5]nonan-6-yl)pyrido[4,3-d]pyrimidin-2-yl)oxy)methyl)cyclopropyl)methyl)-2-fluoro-7-azaspiro[3.5]nonan-2-yl)methyl)piperazin-1-yl)-1-oxoisoindolin-2-yl)piperidine-2,6-dione |

TABLE 1-continued

Exemplary Compounds of the Present Disclosure

| Cpd # | Structure and IUPAC Name |
|---|---|
| 215 | 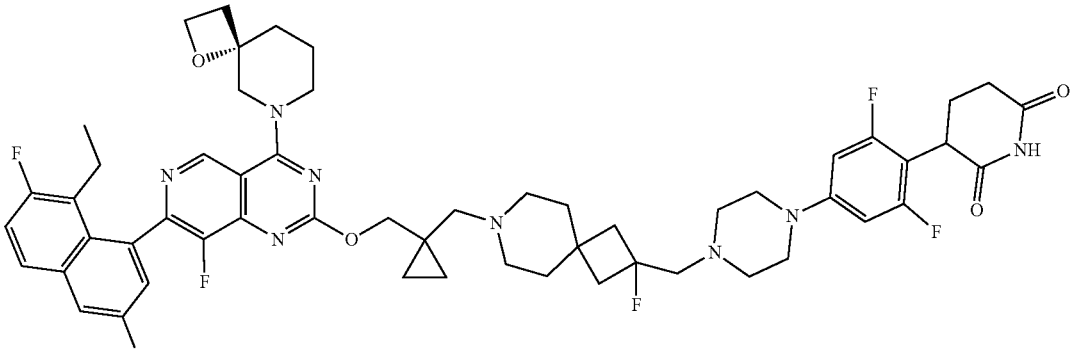 3-(4-(4-((7-((1-(((7-(8-ethyl-7-fluoro-3-hydroxynaphthalen-1-yl)-8-fluoro-4-((S)-1-oxa-6-azaspiro[3.5]nonan-6-yl)pyrido[4,3-d]pyrimidin-2-yl)oxy)methyl)cyclopropyl)methyl)-2-fluoro-7-azaspiro[3.5]nonan-2-yl)methyl)piperazin-1-yl)-2,6-difluorophenyl)piperidine-2,6-dione |
| 216 | 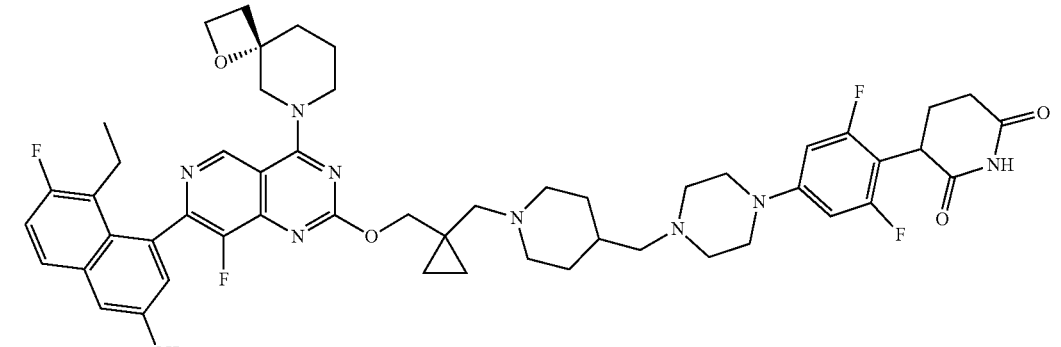 3-(4-(4-((1-((1-(((7-(8-ethyl-7-fluoro-3-hydroxynaphthalen-1-yl)-8-fluoro-4-((S)-1-oxa-6-azaspiro[3.5]nonan-6-yl)pyrido[4,3-d]pyrimidin-2-yl)oxy)methyl)cyclopropyl)methyl)piperidin-4-yl)methyl)piperazin-1-yl)-2,6-difluorophenyl)piperidine-2,6-dione |
| 217 | 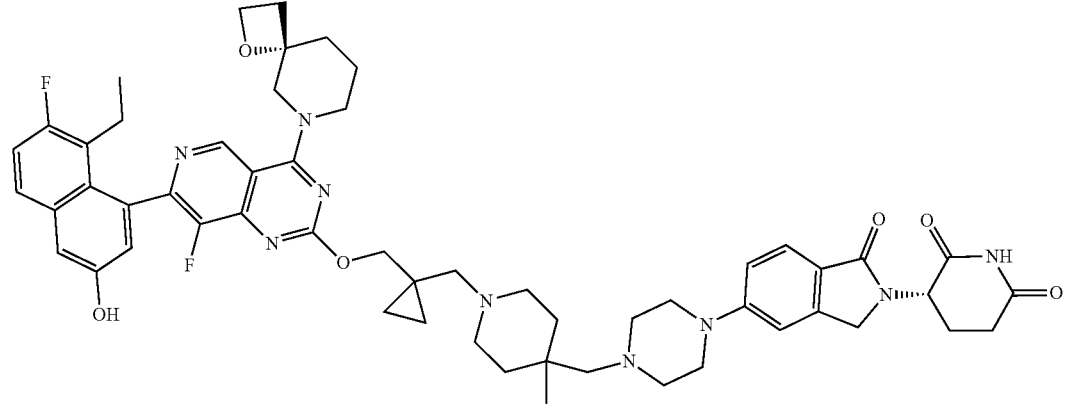 [SMILES: CCc1c(F)ccc2cc(O)cc(-c3ncc4c(N5CCC[C@]6(CCO6)C5)nc(OCC5(CN6CCC(C)(CN7CCN(c8ccc9c(c8)CN([C@H]8CCC(=O)NC8=O)C9=O)CC7)CC6)CC5)nc4c3F)c12] (S)-3-(5-(4-((1-((1-(((7-(8-ethyl-7-fluoro-3-hydroxynaphthalen-1-yl)-8-fluoro-4-((S)-1-oxa-6-azaspiro[3.5]nonan-6-yl)pyrido[4,3-d]pyrimidin-2-yl)oxy)methyl)cyclopropyl)methyl)-4-methylpiperidin-4-yl)methyl)piperazin-1-yl)-1-oxoisoindolin-2-yl)piperidine-2,6-dione |

TABLE 1-continued

Exemplary Compounds of the Present Disclosure

| Cpd # | Structure and IUPAC Name |
|---|---|
| 218 | 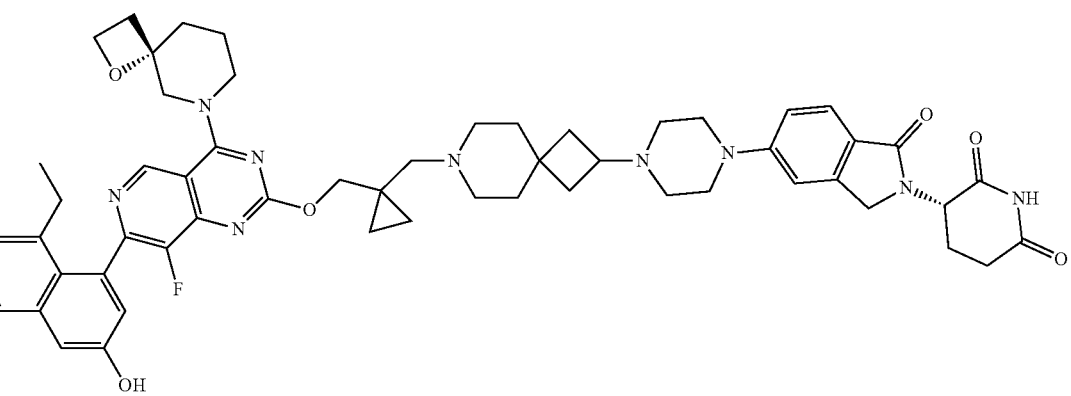<br>(S)-3-(5-(4-(7-((1-(((7-(8-ethyl-7-fluoro-3-hydroxynaphthalen-1-yl)-8-fluoro-4-((S)-1-oxa-6-azaspiro[3.5]nonan-6-yl)pyrido[4,3-d]pyrimidin-2-yl)oxy)methyl)cyclopropyl)methyl)-7-azaspiro[3.5]nonan-2-yl)piperazin-1-yl)-1-oxoisoindolin-2-yl)piperidine-2,6-dione |
| 219 | 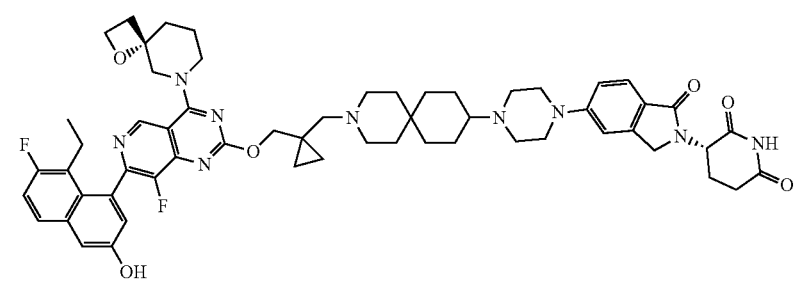 [SMILES: CCc1c(F)ccc2cc(O)cc(-c3ncc4c(N5CCC[C@]6(CCO6)C5)nc(OCC5(CN6CCC7(CCC(N8CCN(c9ccc%10c(c9)CN([C@H]9CCC(=O)NC9=O)C%10=O)CC8)CC7)CC6)CC5)nc4c3F)c12]<br>(S)-3-(5-(4-(3-((1-(((7-(8-ethyl-7-fluoro-3-hydroxynaphthalen-1-yl)-8-fluoro-4-((S)-1-oxa-6-azaspiro[3.5]nonan-6-yl)pyrido[4,3-d]pyrimidin-2-yl)oxy)methyl)cyclopropyl)methyl)-3-azaspiro[5.5]undecan-9-yl)piperazin-1-yl)-1-oxoisoindolin-2-yl)piperidine-2,6-dione |
| 220 | 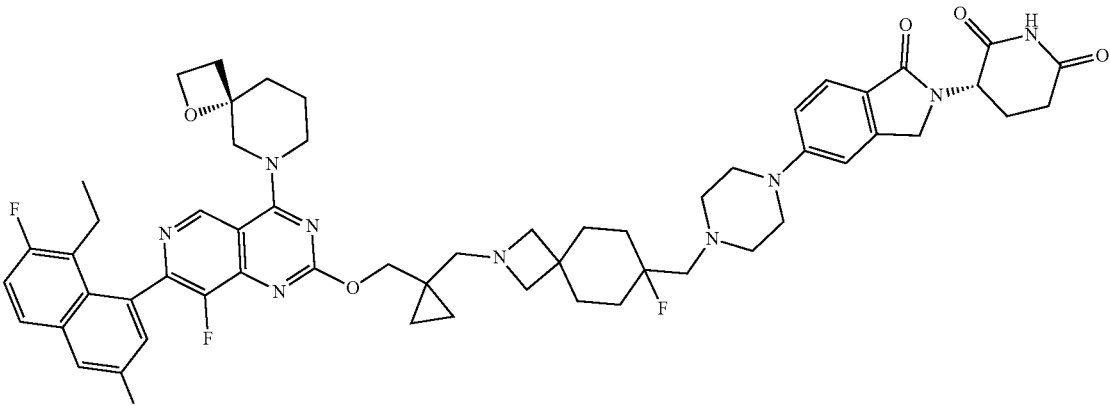<br>(S)-3-(5-(4-((2-((1-(((7-(8-ethyl-7-fluoro-3-hydroxynaphthalen-1-yl)-8-fluoro-4-((S)-1-oxa-6-azaspiro[3.5]nonan-6-yl)pyrido[4,3-d]pyrimidin-2-yl)oxy)methyl)cyclopropyl)methyl)-7-fluoro-2-azaspiro[3.5]nonan-7-yl)methyl)piperazin-1-yl)-1-oxoisoindolin-2-yl)piperidine-2,6-dione |

TABLE 1-continued

Exemplary Compounds of the Present Disclosure

| Cpd # | Structure and IUPAC Name |
|---|---|
| 221 | 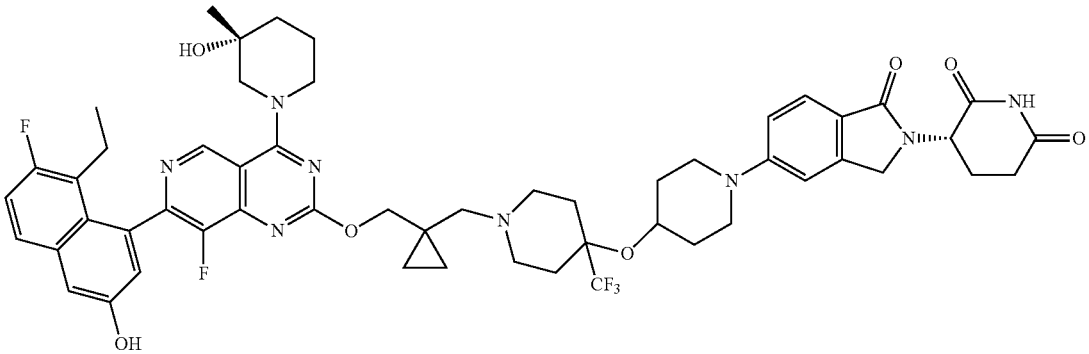 [SMILES: CCc1c(F)ccc2cc(O)cc(-c3ncc4c(N5CCC[C@@](C)(O)C5)nc(OCC5(CN6CCC(OC7CCN(c8ccc9c(c8)CN([C@H]8CCC(=O)NC8=O)C9=O)CC7)(C(F)(F)F)CC6)CC5)nc4c3F)c12]<br>(S)-3-(5-(4-((1-(((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-4-(trifluoromethyl)piperidin-4-yl)oxy)piperidin-1-yl)-1-oxoisoindolin-2-yl)piperidine-2,6-dione |
| 222 | 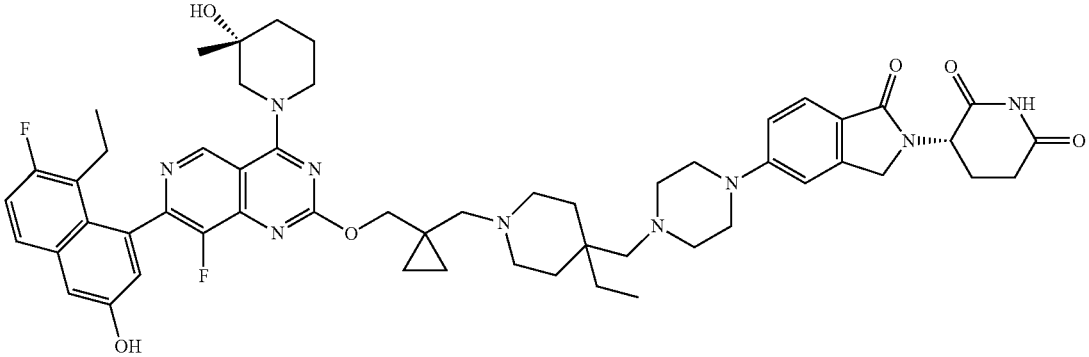 [SMILES: CCc1c(F)ccc2cc(O)cc(-c3ncc4c(N5CCC[C@@](C)(O)C5)nc(OCC5(CN6CCC(CC)(CN7CCN(c8ccc9c(c8)CN([C@H]8CCC(=O)NC8=O)C9=O)CC7)CC6)CC5)nc4c3F)c12]<br>(S)-3-(5-(4-((4-ethyl-1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione |
| 223 | 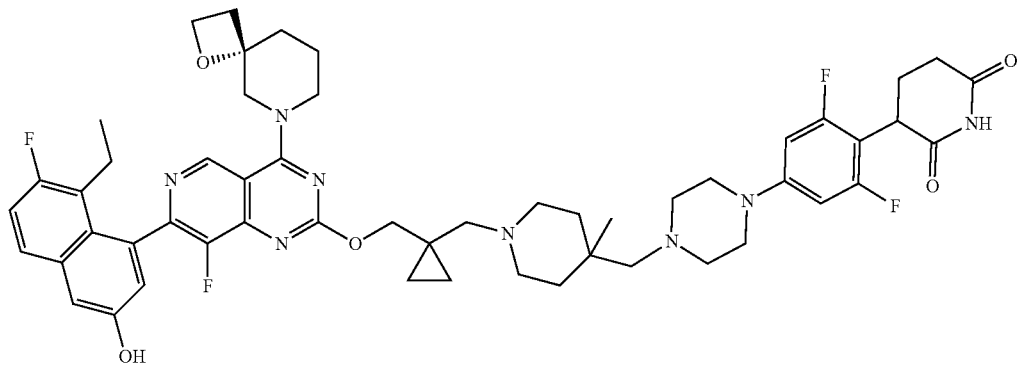 [SMILES: CCc1c(F)ccc2cc(O)cc(-c3ncc4c(N5CCC[C@]6(CCO6)C5)nc(OCC5(CN6CCC(C)(CN7CCN(c8cc(F)c(C9CCC(=O)NC9=O)c(F)c8)CC7)CC6)CC5)nc4c3F)c12]<br>3-(4-(4-((1-(((1-(((7-(8-ethyl-7-fluoro-3-hydroxynaphthalen-1-yl)-8-fluoro-4-((S)-1-oxa-6-azaspiro[3.5]nonan-6-yl)pyrido[4,3-d]pyrimidin-2-yl)oxy)methyl)cyclopropyl)methyl)-4-methylpiperidin-4-yl)methyl)piperazin-1-yl)-2,6-difluorophenyl)piperidine-2,6-dione |

TABLE 1-continued

Exemplary Compounds of the Present Disclosure

| Cpd # | Structure and IUPAC Name |
|---|---|
| 224 | 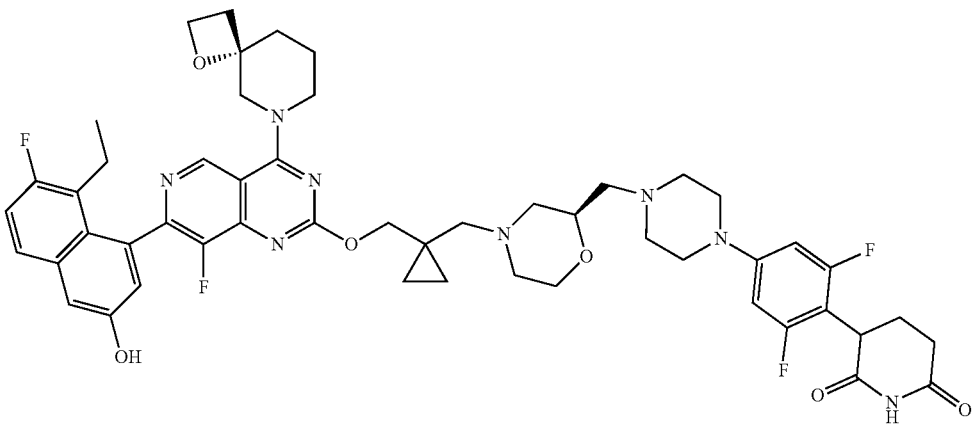 [SMILES: CCc1c(F)ccc2cc(O)cc(-c3ncc4c(N5CCC[C@]6(CCO6)C5)nc(OCC5(CN6CCO[C@H](CN7CCN(c8cc(F)c(C9CCC(=O)NC9=O)c(F)c8)CC7)C6)CC5)nc4c3F)c12]
3-(4-(4-(((R)-4-((1-(((7-(8-ethyl-7-fluoro-3-hydroxynaphthalen-1-yl)-8-fluoro-4-((S)-1-oxa-6-azaspiro[3.5]nonan-6-yl)pyrido[4,3-d]pyrimidin-2-yl)oxy)methyl)cyclopropyl)methyl)morpholin-2-yl)methyl)piperazin-1-yl)-2,6-difluorophenyl)piperidine-2,6-dione |
| 225 | 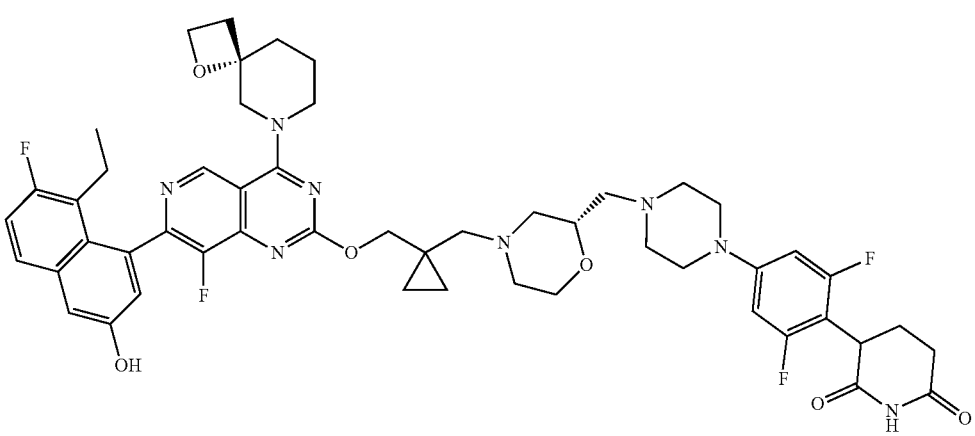 [SMILES: CCc1c(F)ccc2cc(O)cc(-c3ncc4c(N5CCC[C@]6(CCO6)C5)nc(OCC5(CN6CCO[C@@H](CN7CCN(c8cc(F)c(C9CCC(=O)NC9=O)c(F)c8)CC7)C6)CC5)nc4c3F)c12]
3-(4-(4-(((S)-4-((1-(((7-(8-ethyl-7-fluoro-3-hydroxynaphthalen-1-yl)-8-fluoro-4-((S)-1-oxa-6-azaspiro[3.5]nonan-6-yl)pyrido[4,3-d]pyrimidin-2-yl)oxy)methyl)cyclopropyl)methyl)morpholin-2-yl)methyl)piperazin-1-yl)-2,6-difluorophenyl)piperidine-2,6-dione |
| 226 | 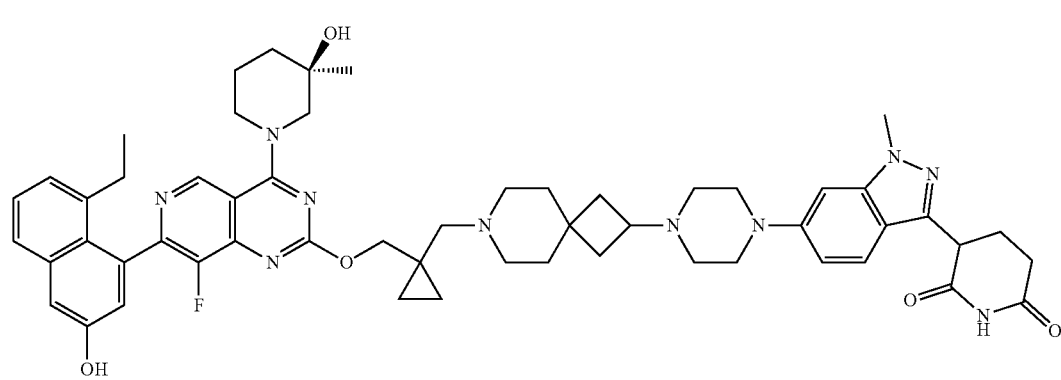 [SMILES: CCc1cccc2cc(O)cc(-c3ncc4c(N5CCC[C@@](C)(O)C5)nc(OCC5(CN6CCC7(CC6)CC(N6CCN(c8ccc9c(C%10CCC(=O)NC%10=O)nn(C)c9c8)CC6)C7)CC5)nc4c3F)c12]
3-(6-(4-(7-((1-(((7-(8-ethyl-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-azaspiro[3.5]nonan-2-yl)piperazin-1-yl)-1-methyl-1H-indazol-3-yl)piperidine-2,6-dione |

TABLE 1-continued

Exemplary Compounds of the Present Disclosure

| Cpd # | Structure and IUPAC Name |
|---|---|
| 227 | 3-(6-(4-((7-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-azaspiro[3.5]nonan-2-yl)methyl)piperazin-1-yl)-1-methyl-1H-indazol-3-yl)piperidine-2,6-dione |
| 228 | 3-(6-(4-((7-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-2-fluoro-7-azaspiro[3.5]nonan-2-yl)methyl)piperazin-1-yl)-1-methyl-1H-indazol-3-yl)piperidine-2,6-dione |
| 229 | 3-(6-(4-((1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)methyl)piperazin-1-yl)-1-methyl-1H-indazol-3-yl)piperidine-2,6-dione |

TABLE 1-continued

Exemplary Compounds of the Present Disclosure

| Cpd # | Structure and IUPAC Name |
|---|---|
| 230 | 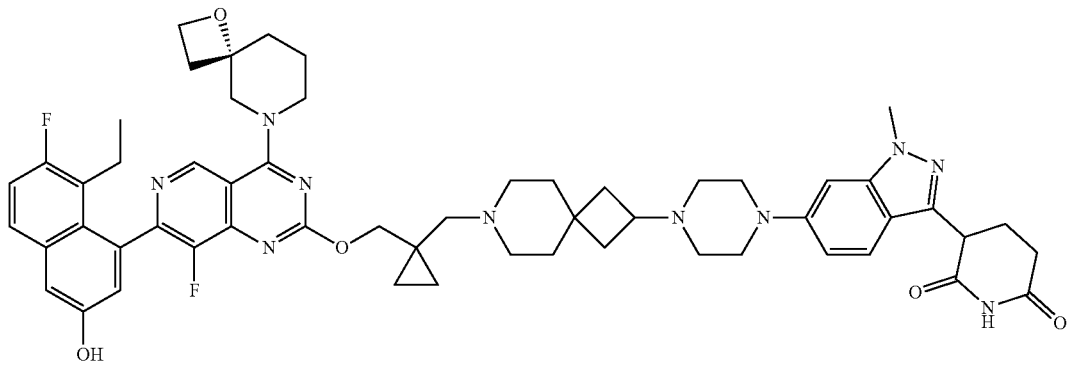 [SMILES: CCc1c(F)ccc2cc(O)cc(-c3ncc4c(N5CCC[C@]6(CCO6)C5)nc(OCC5(CN6CCC7(CC6)CC(N6CCN(c8ccc9c(C%10CCC(=O)NC%10=O)nn(C)c9c8)CC6)C7)CC5)nc4c3F)c12]<br>3-(6-(4-(7-((1-(((7-(8-ethyl-7-fluoro-3-hydroxynaphthalen-1-yl)-8-fluoro-4-((S)-1-oxa-6-azaspiro[3.5]nonan-6-yl)pyrido[4,3-d]pyrimidin-2-yl)oxy)methyl)cyclopropyl)methyl)-7-azaspiro[3.5]nonan-2-yl)piperazin-1-yl)-1-methyl-1H-indazol-3-yl)piperidine-2,6-dione |
| 231 | 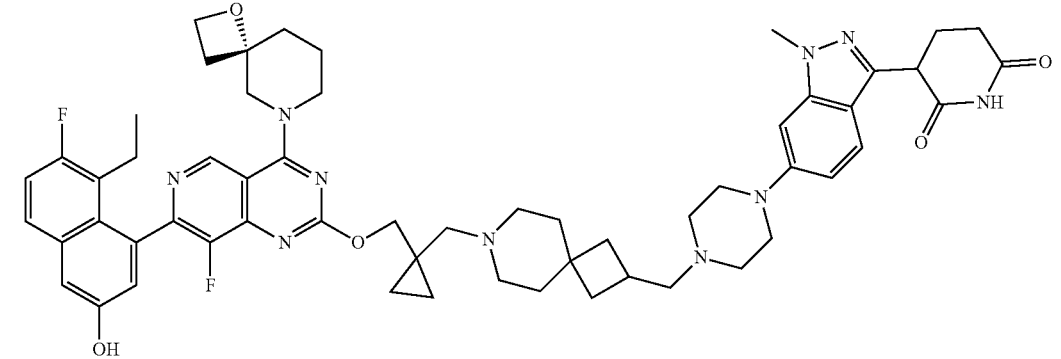 [SMILES: CCc1c(F)ccc2cc(O)cc(-c3ncc4c(N5CCC[C@]6(CCO6)C5)nc(OCC5(CN6CCC7(CC6)CC(CN6CCN(c8ccc9c(C%10CCC(=O)NC%10=O)nn(C)c9c8)CC6)C7)CC5)nc4c3F)c12]<br>3-(6-(4-((7-((1-(((7-(8-ethyl-7-fluoro-3-hydroxynaphthalen-1-yl)-8-fluoro-4-((S)-1-oxa-6-azaspiro[3.5]nonan-6-yl)pyrido[4,3-d]pyrimidin-2-yl)oxy)methyl)cyclopropyl)methyl)-7-azaspiro[3.5]nonan-2-yl)methyl)piperazin-1-yl)-1-methyl-1H-indazol-3-yl)piperidine-2,6-dione |
| 232 | 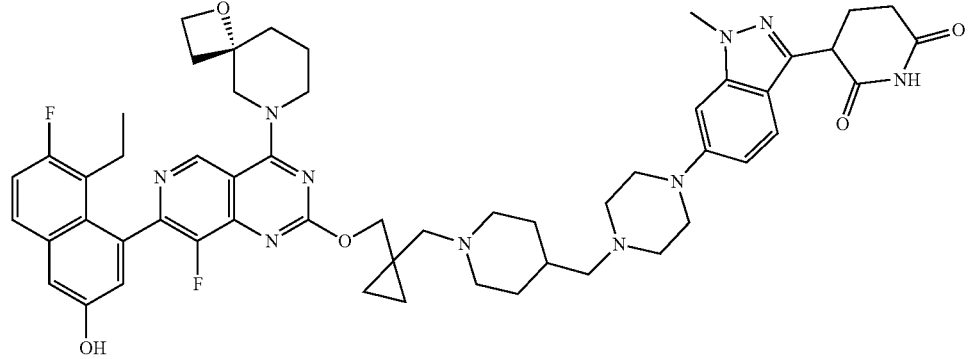 [SMILES: CCc1c(F)ccc2cc(O)cc(-c3ncc4c(N5CCC[C@]6(CCO6)C5)nc(OCC5(CN6CCC(CN7CCN(c8ccc9c(C%10CCC(=O)NC%10=O)nn(C)c9c8)CC7)CC6)CC5)nc4c3F)c12]<br>3-(6-(4-((1-((1-(((7-(8-ethyl-7-fluoro-3-hydroxynaphthalen-1-yl)-8-fluoro-4-((S)-1-oxa-6-azaspiro[3.5]nonan-6-yl)pyrido[4,3-d]pyrimidin-2-yl)oxy)methyl)cyclopropyl)methyl)piperidin-4-yl)methyl)piperazin-1-yl)-1-methyl-1H-indazol-3-yl)piperidine-2,6-dione |

TABLE 1-continued

Exemplary Compounds of the Present Disclosure

| Cpd # | Structure and IUPAC Name |
|---|---|
| 233 | 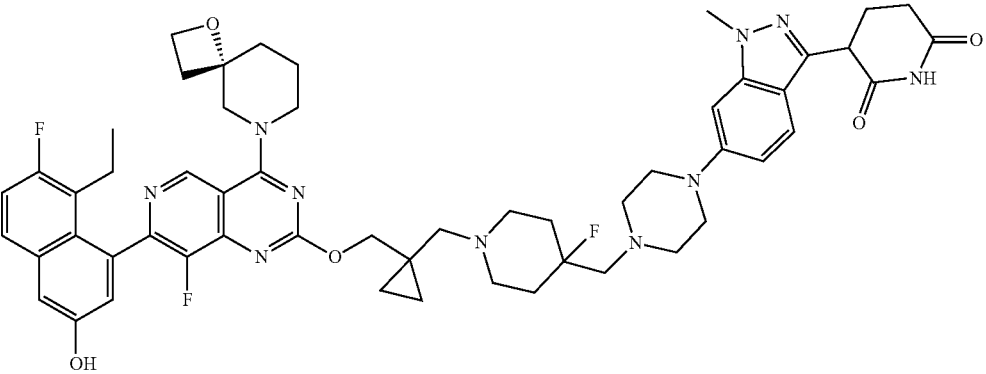 [SMILES: CCc1c(F)ccc2cc(O)cc(-c3ncc4c(N5CCC[C@]6(CCO6)C5)nc(OCC5(CN6CCC(F)(CN7CCN(c8ccc9c(C%10CCC(=O)NC%10=O)nn(C)c9c8)CC7)CC6)CC5)nc4c3F)c12]<br>3-(6-(4-((1-(((7-(8-ethyl-7-fluoro-3-hydroxynaphthalen-1-yl)-8-fluoro-4-((S)-1-oxa-6-azaspiro[3.5]nonan-6-yl)pyrido[4,3-d]pyrimidin-2-yl)oxy)methyl)cyclopropyl)methyl)-4-fluoropiperidin-4-yl)methyl)piperazin-1-yl)-1-methyl-1H-indazol-3-yl)piperidine-2,6-dione |
| 234 | 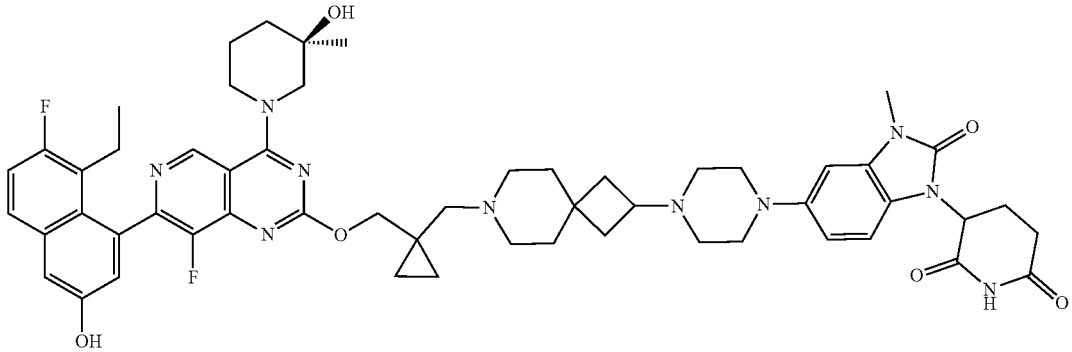 [SMILES: CCc1c(F)ccc2cc(O)cc(-c3ncc4c(N5CCC[C@@](C)(O)C5)nc(OCC5(CN6CCC7(CC6)CC(N6CCN(c8ccc9c(c8)n(C)c(=O)n9C8CCC(=O)NC8=O)CC6)C7)CC5)nc4c3F)c12]<br>3-(5-(4-(7-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-azaspiro[3.5]nonan-2-yl)piperazin-1-yl)-3-methyl-2-oxo-2,3-dihydro-1H-benzo[d]imidazol-1-yl)piperidine-2,6-dione |
| 235 | 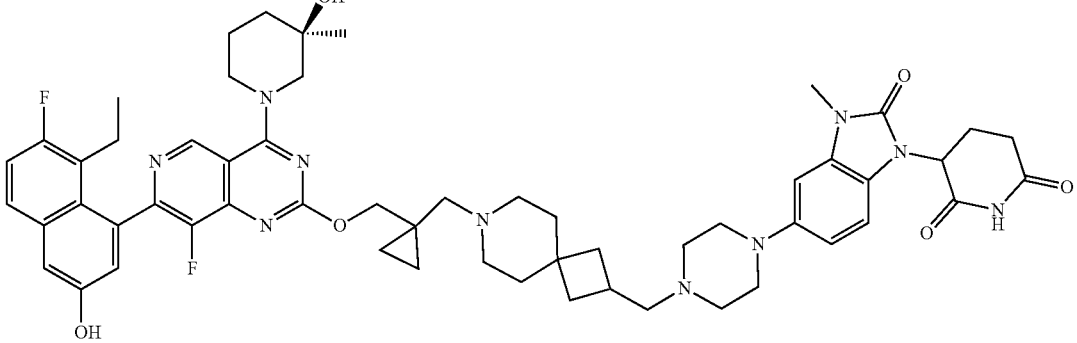<br>3-(5-(4-((7-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-azaspiro[3.5]nonan-2-yl)methyl)piperazin-1-yl)-3-methyl-2-oxo-2,3-dihydro-1H-benzo[d]imidazol-1-yl)piperidine-2,6-dione |

TABLE 1-continued

Exemplary Compounds of the Present Disclosure

| Cpd # | Structure and IUPAC Name |
|---|---|
| 236 | 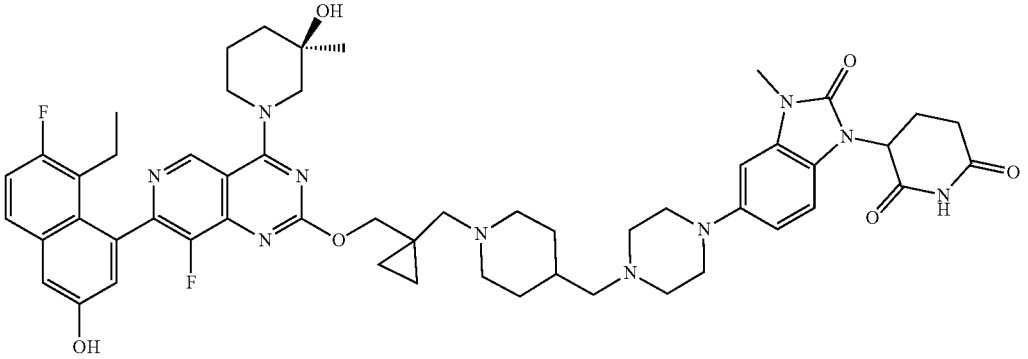 [SMILES: CCc1c(F)ccc2cc(O)cc(-c3ncc4c(N5CCC[C@@](C)(O)C5)nc(OCC5(CN6CCC(CN7CCN(c8ccc9c(c8)n(C)c(=O)n9C8CCC(=O)NC8=O)CC7)CC6)CC5)nc4c3F)c12]<br>3-(5-(4-((1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)methyl)piperazin-1-yl)-3-methyl-2-oxo-2,3-dihydro-1H-benzo[d]imidazol-1-yl)piperidine-2,6-dione |
| 237 | 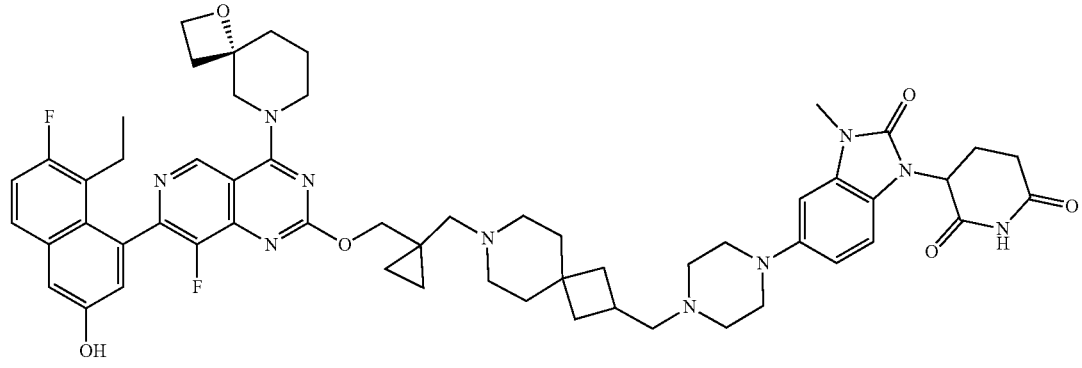 [SMILES: CCc1c(F)ccc2cc(O)cc(-c3ncc4c(N5CCC[C@]6(CCO6)C5)nc(OCC5(CN6CCC7(CC6)CC(CN6CCN(c8ccc9c(c8)n(C)c(=O)n9C8CCC(=O)NC8=O)CC6)C7)CC5)nc4c3F)c12]<br>3-(5-(4-((7-((1-(((7-(8-ethyl-7-fluoro-3-hydroxynaphthalen-1-yl)-8-fluoro-4-((S)-1-oxa-6-azaspiro[3.5]nonan-6-yl)pyrido[4,3-d]pyrimidin-2-yl)oxy)methyl)cyclopropyl)methyl)-7-azaspiro[3.5]nonan-2-yl)methyl)piperazin-1-yl)-3-methyl-2-oxo-2,3-dihydro-1H-benzo[d]imidazol-1-yl)piperidine-2,6-dione |
| 238 | 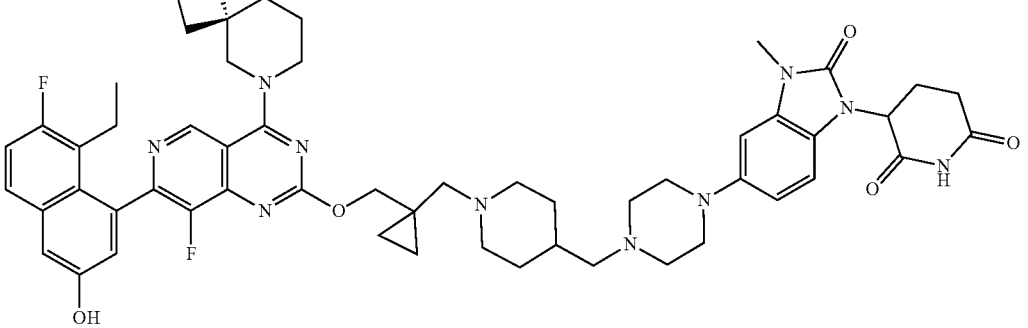<br>3-(5-(4-((1-((1-(((7-(8-ethyl-7-fluoro-3-hydroxynaphthalen-1-yl)-8-fluoro-4-((S)-1-oxa-6-azaspiro[3.5]nonan-6-yl)pyrido[4,3-d]pyrimidin-2-yl)oxy)methyl)cyclopropyl)methyl)piperidin-4-yl)methyl)piperazin-1-yl)-3-methyl-2-oxo-2,3-dihydro-1H-benzo[d]imidazol-1-yl)piperidine-2,6-dione |

TABLE 1-continued

Exemplary Compounds of the Present Disclosure

| Cpd # | Structure and IUPAC Name |
|---|---|
| 239 | 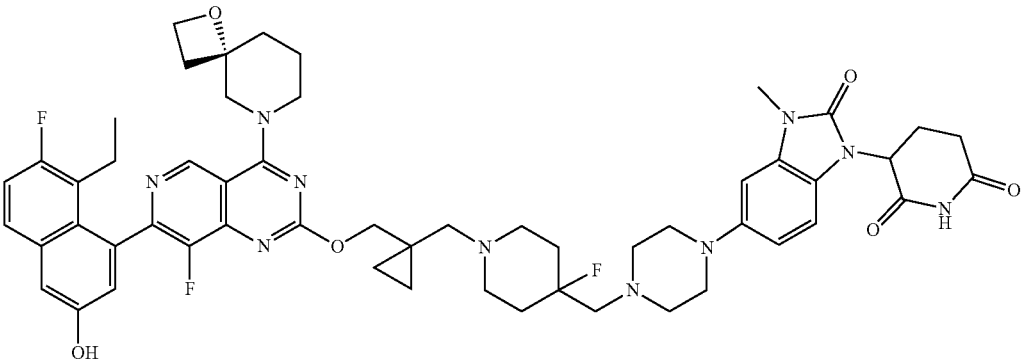 [SMILES: CCc1c(F)ccc2cc(O)cc(-c3ncc4c(N5CCC[C@]6(CCO6)C5)nc(OCC5(CN6CCC(F)(CN7CCN(c8ccc9c(c8)n(C)c(=O)n9C8CCC(=O)NC8=O)CC7)CC6)CC5)nc4c3F)c12]<br>3-(5-(4-((1-(((7-(8-ethyl-7-fluoro-3-hydroxynaphthalen-1-yl)-8-fluoro-4-((S)-1-oxa-6-azaspiro[3.5]nonan-6-yl)pyrido[4,3-d]pyrimidin-2-yl)oxy)methyl)cyclopropyl)methyl)-4-fluoropiperidin-4-yl)methyl)piperazin-1-yl)-3-methyl-2-oxo-2,3-dihydro-1H-benzo[d]imidazol-1-yl)piperidine-2,6-dione |
| 240 | 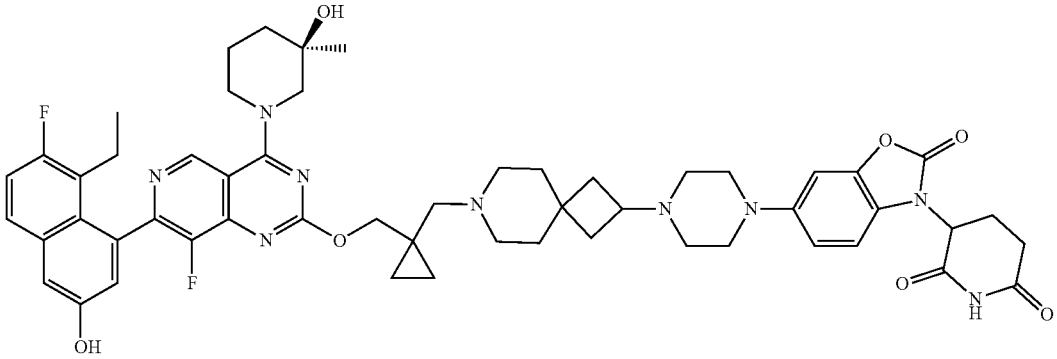 [SMILES: CCc1c(F)ccc2cc(O)cc(-c3ncc4c(N5CCC[C@@](C)(O)C5)nc(OCC5(CN6CCC7(CC6)CC(N6CCN(c8ccc9c(c8)oc(=O)n9C8CCC(=O)NC8=O)CC6)C7)CC5)nc4c3F)c12]<br>3-(6-(4-(7-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-azaspiro[3.5]nonan-2-yl)piperazin-1-yl)-2-oxobenzo[d]oxazol-3(2H)-yl)piperidine-2,6-dione |
| 241 | 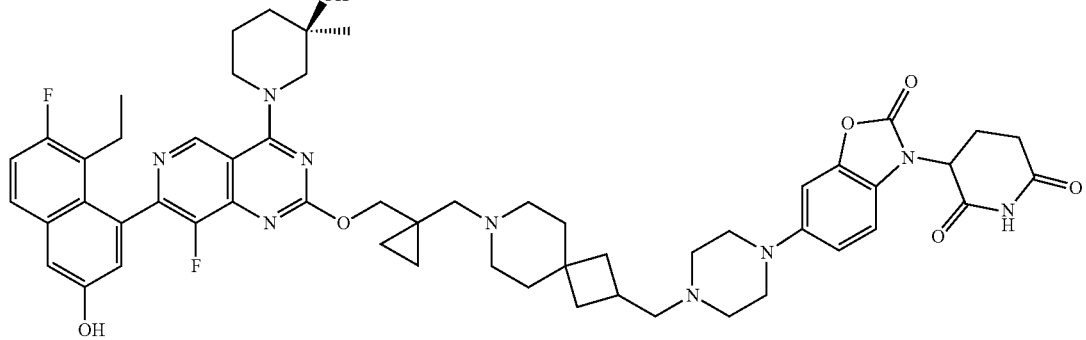<br>3-(6-(4-((7-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-azaspiro[3.5]nonan-2-yl)methyl)piperazin-1-yl)-2-oxobenzo[d]oxazol-3(2H)-yl)piperidine-2,6-dione |

TABLE 1-continued

Exemplary Compounds of the Present Disclosure

| Cpd # | Structure and IUPAC Name |
|---|---|
| 242 | 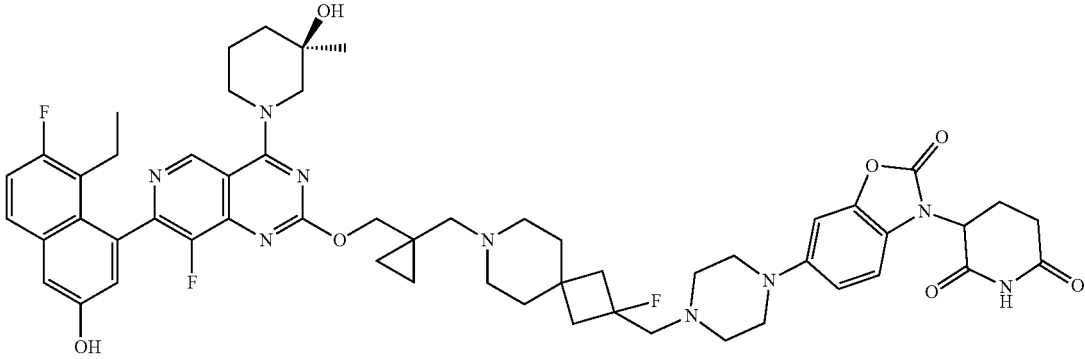 [SMILES: CCc1c(F)ccc2cc(O)cc(-c3ncc4c(N5CCC[C@@](C)(O)C5)nc(OCC5(CN6CCC7(CC6)CC(F)(CN6CCN(c8ccc9c(c8)oc(=O)n9C8CCC(=O)NC8=O)CC6)C7)CC5)nc4c3F)c12]

3-(6-(4-((7-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-2-fluoro-7-azaspiro[3.5]nonan-2-yl)methyl)piperazin-1-yl)-2-oxobenzo[d]oxazol-3(2H)-yl)piperidine-2,6-dione |
| 243 | 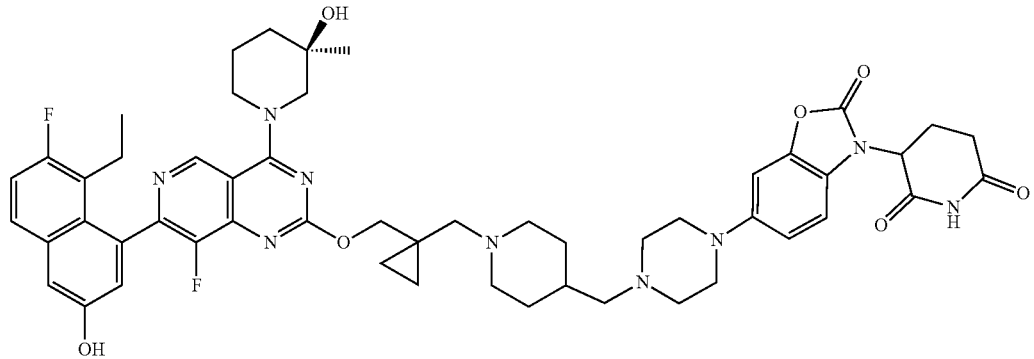 [SMILES: CCc1c(F)ccc2cc(O)cc(-c3ncc4c(N5CCC[C@@](C)(O)C5)nc(OCC5(CN6CCC(CN7CCN(c8ccc9c(c8)oc(=O)n9C8CCC(=O)NC8=O)CC7)CC6)CC5)nc4c3F)c12]

3-(6-(4-((1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)methyl)piperazin-1-yl)-2-oxobenzo[d]oxazol-3(2H)-yl)piperidine-2,6-dione |
| 244 | 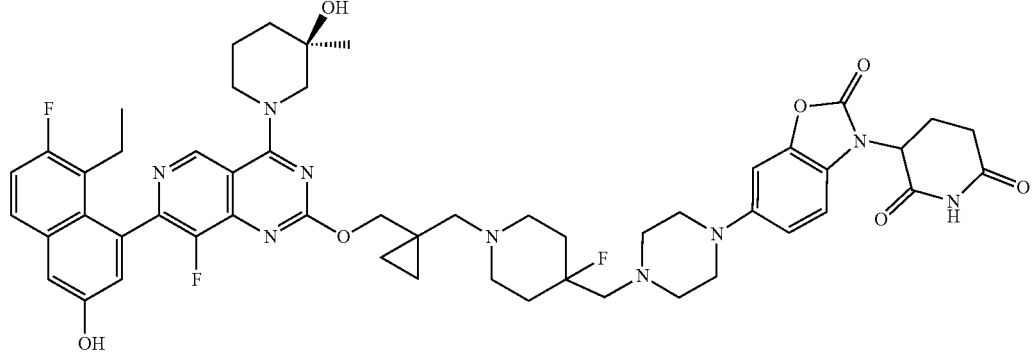 [SMILES: CCc1c(F)ccc2cc(O)cc(-c3ncc4c(N5CCC[C@@](C)(O)C5)nc(OCC5(CN6CCC(F)(CN7CCN(c8ccc9c(c8)oc(=O)n9C8CCC(=O)NC8=O)CC7)CC6)CC5)nc4c3F)c12]

3-(6-(4-((1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-4-fluoropiperidin-4-yl)methyl)piperazin-1-yl)-2-oxobenzo[d]oxazol-3(2H)-yl)piperidine-2,6-dione |

TABLE 1-continued

Exemplary Compounds of the Present Disclosure

| Cpd # | Structure and IUPAC Name |
|---|---|

245

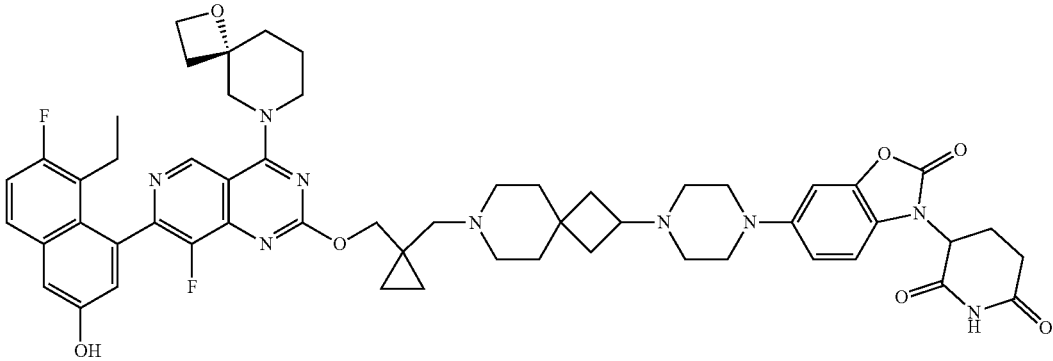 [SMILES: CCc1c(F)ccc2cc(O)cc(-c3ncc4c(N5CCC[C@]6(CCO6)C5)nc(OCC5(CN6CCC7(CC6)CC(N6CCN(c8ccc9c(c8)oc(=O)n9C8CCC(=O)NC8=O)CC6)C7)CC5)nc4c3F)c12]

3-(6-(4-(7-((1-(((7-(8-ethyl-7-fluoro-3-hydroxynaphthalen-1-yl)-8-fluoro-4-((S)-1-oxa-
6-azaspiro[3.5]nonan-6-yl)pyrido[4,3-d]pyrimidin-2-
yl)oxy)methyl)cyclopropyl)methyl)-7-azaspiro[3.5]nonan-2-yl)piperazin-1-yl)-2-
oxobenzo[d]oxazol-3(2H)-yl)piperidine-2,6-dione

246

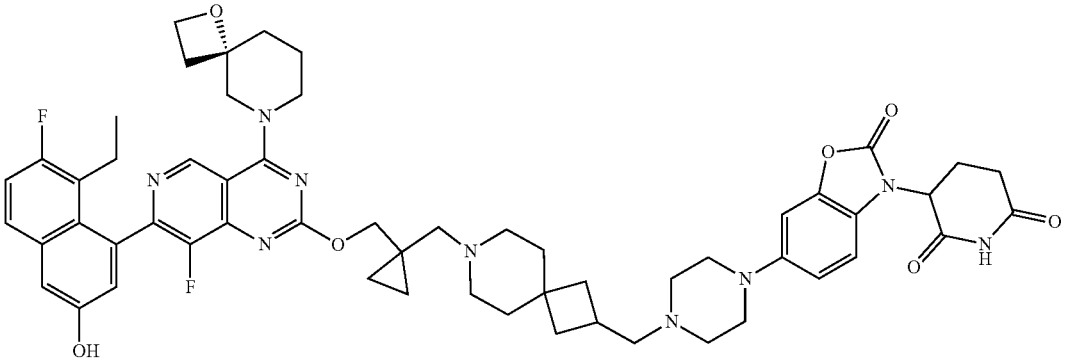 [SMILES: CCc1c(F)ccc2cc(O)cc(-c3ncc4c(N5CCC[C@]6(CCO6)C5)nc(OCC5(CN6CCC7(CC6)CC(CN6CCN(c8ccc9c(c8)oc(=O)n9C8CCC(=O)NC8=O)CC6)C7)CC5)nc4c3F)c12]

3-(6-(4-((7-((1-(((7-(8-ethyl-7-fluoro-3-hydroxynaphthalen-1-yl)-8-fluoro-4-((S)-1-oxa-
6-azaspiro[3.5]nonan-6-yl)pyrido[4,3-d]pyrimidin-2-
yl)oxy)methyl)cyclopropyl)methyl)-7-azaspiro[3.5]nonan-2-yl)methyl)piperazin-1-yl)-
2-oxobenzo[d]oxazol-3(2H)-yl)piperidine-2,6-dione

247

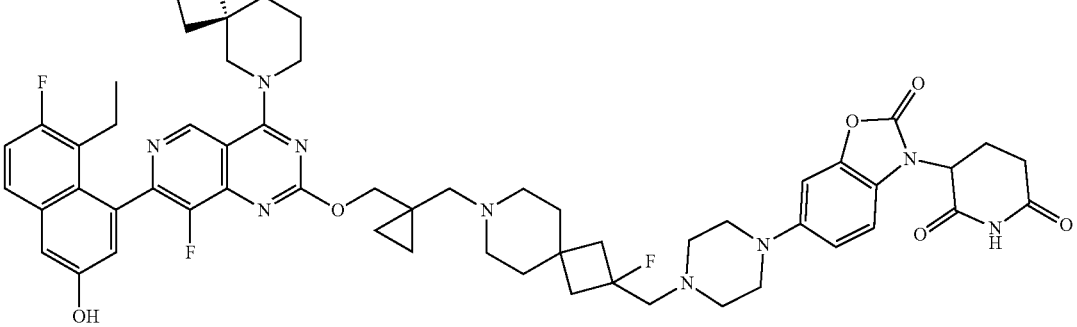

3-(6-(4-((7-((1-(((7-(8-ethyl-7-fluoro-3-hydroxynaphthalen-1-yl)-8-fluoro-4-((S)-1-oxa-
6-azaspiro[3.5]nonan-6-yl)pyrido[4,3-d]pyrimidin-2-
yl)oxy)methyl)cyclopropyl)methyl)-2-fluoro-7-azaspiro[3.5]nonan-2-
yl)methyl)piperazin-1-yl)-2-oxobenzo[d]oxazol-3(2H)-yl)piperidine-2,6-dione TABLE 1-continued Exemplary Compounds of the Present Disclosure

| Cpd # | Structure and IUPAC Name |
|---|---|
| 248 | 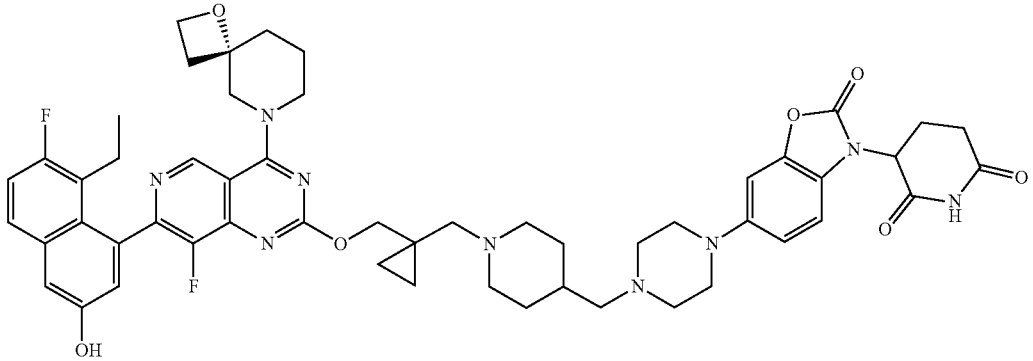 [SMILES: CCc1c(F)ccc2cc(O)cc(-c3ncc4c(N5CCC[C@]6(CCO6)C5)nc(OCC5(CN6CCC(CN7CCN(c8ccc9c(c8)oc(=O)n9C8CCC(=O)NC8=O)CC7)CC6)CC5)nc4c3F)c12]<br>3-(6-(4-((1-(((1-(((7-(8-ethyl-7-fluoro-3-hydroxynaphthalen-1-yl)-8-fluoro-4-((S)-1-oxa-6-azaspiro[3.5]nonan-6-yl)pyrido[4,3-d]pyrimidin-2-yl)oxy)methyl)cyclopropyl)methyl)piperidin-4-yl)methyl)piperazin-1-yl)-2-oxobenzo[d]oxazol-3(2H)-yl)piperidine-2,6-dione |
| 249 | 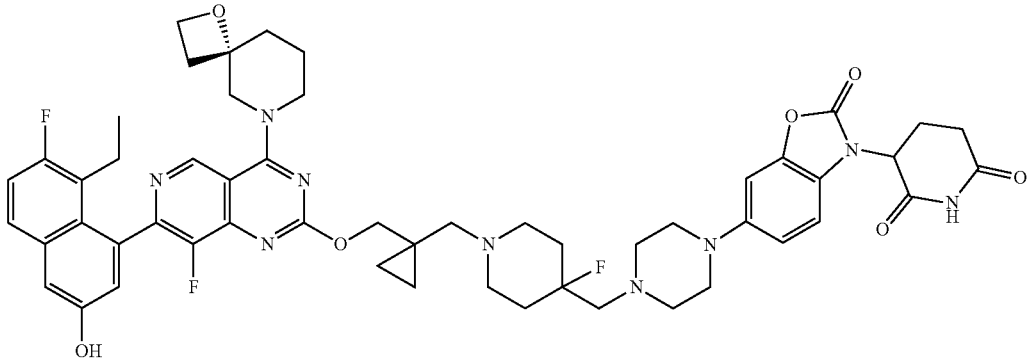 [SMILES: CCc1c(F)ccc2cc(O)cc(-c3ncc4c(N5CCC[C@]6(CCO6)C5)nc(OCC5(CN6CCC(F)(CN7CCN(c8ccc9c(c8)oc(=O)n9C8CCC(=O)NC8=O)CC7)CC6)CC5)nc4c3F)c12]<br>3-(6-(4-((1-(((1-(((7-(8-ethyl-7-fluoro-3-hydroxynaphthalen-1-yl)-8-fluoro-4-((S)-1-oxa-6-azaspiro[3.5]nonan-6-yl)pyrido[4,3-d]pyrimidin-2-yl)oxy)methyl)cyclopropyl)methyl)-4-fluoropiperidin-4-yl)methyl)piperazin-1-yl)-2-oxobenzo[d]oxazol-3(2H)-yl)piperidine-2,6-dione |
| 250 | 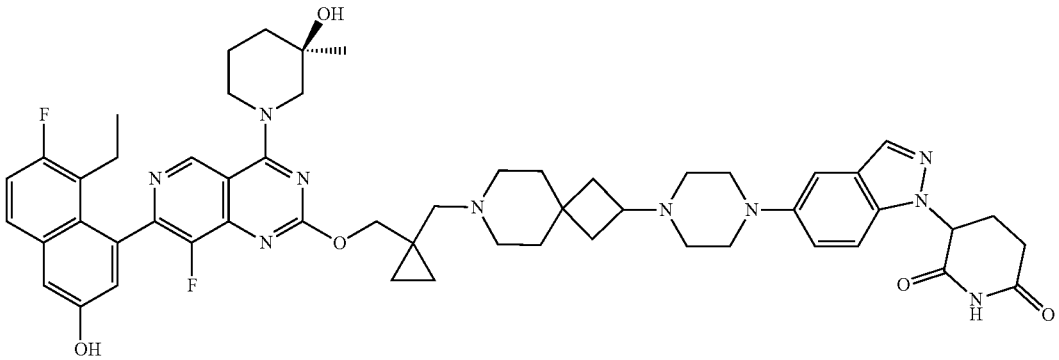 [SMILES: CCc1c(F)ccc2cc(O)cc(-c3ncc4c(N5CCC[C@@](C)(O)C5)nc(OCC5(CN6CCC7(CC6)CC(N6CCN(c8ccc9c(cnn9C9CCC(=O)NC9=O)c8)CC6)C7)CC5)nc4c3F)c12]<br>3-(5-(4-(7-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-azaspiro[3.5]nonan-2-yl)piperazin-1-yl)-1H-indazol-1-yl)piperidine-2,6-dione |

TABLE 1-continued

Exemplary Compounds of the Present Disclosure

| Cpd # | Structure and IUPAC Name |
|---|---|
| 251 | 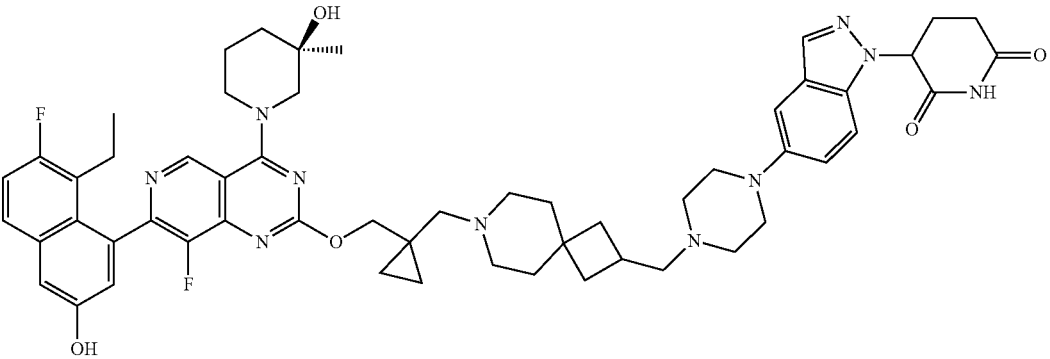
3-(5-(4-((7-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-azaspiro[3.5]nonan-2-yl)methyl)piperazin-1-yl)-1H-indazol-1-yl)piperidine-2,6-dione |
| 252 | 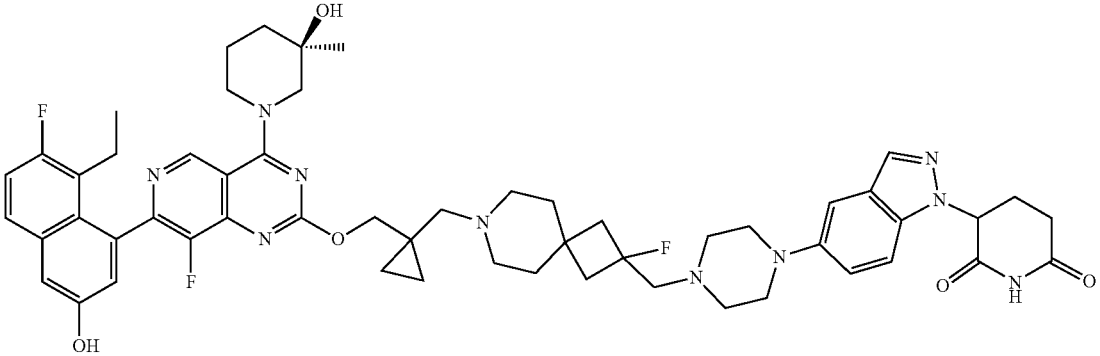 [SMILES: CCc1c(F)ccc2cc(O)cc(-c3ncc4c(N5CCC[C@@](C)(O)C5)nc(OCC5(CN6CCC7(CC6)CC(F)(CN6CCN(c8ccc9c(cnn9C9CCC(=O)NC9=O)c8)CC6)C7)CC5)nc4c3F)c12]
3-(5-(4-((7-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-2-fluoro-7-azaspiro[3.5]nonan-2-yl)methyl)piperazin-1-yl)-1H-indazol-1-yl)piperidine-2,6-dione |
| 253 | 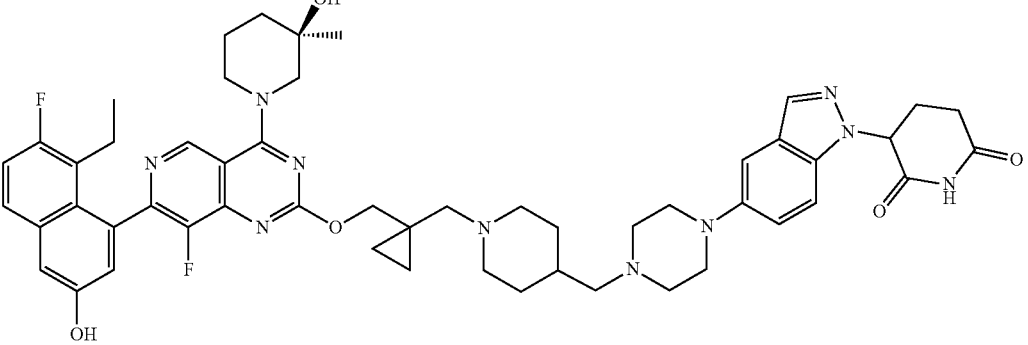
3-(5-(4-((1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)methyl)piperazin-1-yl)-1H-indazol-1-yl)piperidine-2,6-dione |

TABLE 1-continued

Exemplary Compounds of the Present Disclosure

| Cpd # | Structure and IUPAC Name |
|---|---|
| 254 | 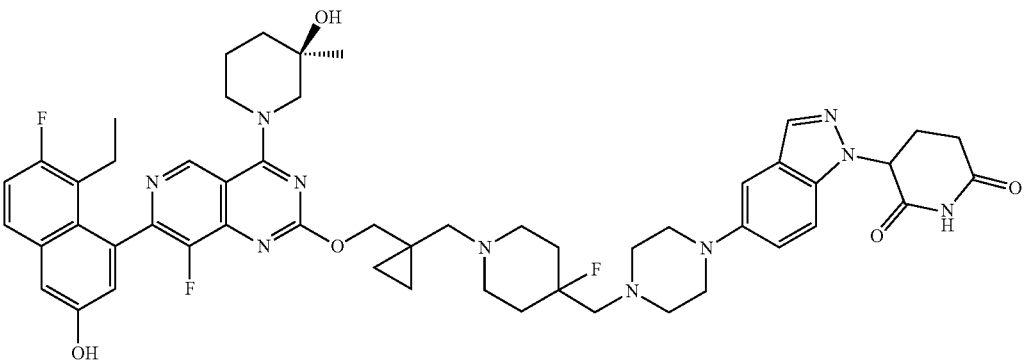 [SMILES: CCc1c(F)ccc2cc(O)cc(-c3ncc4c(N5CCC[C@@](C)(O)C5)nc(OCC5(CN6CCC(F)(CN7CCN(c8ccc9c(cnn9C9CCC(=O)NC9=O)c8)CC7)CC6)CC5)nc4c3F)c12]<br>3-(5-(4-((1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-4-fluoropiperidin-4-yl)methyl)piperazin-1-yl)-1H-indazol-1-yl)piperidine-2,6-dione |
| 255 | 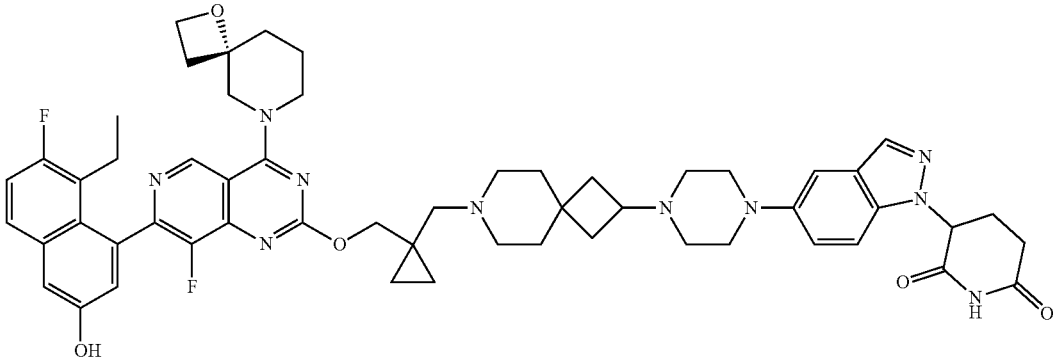 [SMILES: CCc1c(F)ccc2cc(O)cc(-c3ncc4c(N5CCC[C@]6(CCO6)C5)nc(OCC5(CN6CCC7(CC6)CC(N6CCN(c8ccc9c(cnn9C9CCC(=O)NC9=O)c8)CC6)C7)CC5)nc4c3F)c12]<br>3-(5-(4-(7-((1-(((7-(8-ethyl-7-fluoro-3-hydroxynaphthalen-1-yl)-8-fluoro-4-((S)-1-oxa-6-azaspiro[3.5]nonan-6-yl)pyrido[4,3-d]pyrimidin-2-yl)oxy)methyl)cyclopropyl)methyl)-7-azaspiro[3.5]nonan-2-yl)piperazin-1-yl)-1H-indazol-1-yl)piperidine-2,6-dione |
| 256 | 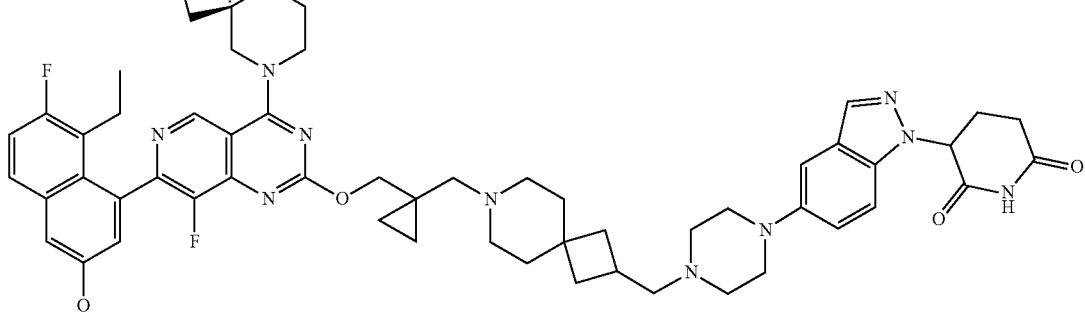<br>3-(5-(4-((7-((1-(((7-(8-ethyl-7-fluoro-3-hydroxynaphthalen-1-yl)-8-fluoro-4-((S)-1-oxa-6-azaspiro[3.5]nonan-6-yl)pyrido[4,3-d]pyrimidin-2-yl)oxy)methyl)cyclopropyl)methyl)-7-azaspiro[3.5]nonan-2-yl)methyl)piperazin-1-yl)-1H-indazol-1-yl)piperidine-2,6-dione |

| Cpd # | Structure and IUPAC Name |
|---|---|
| 257 | 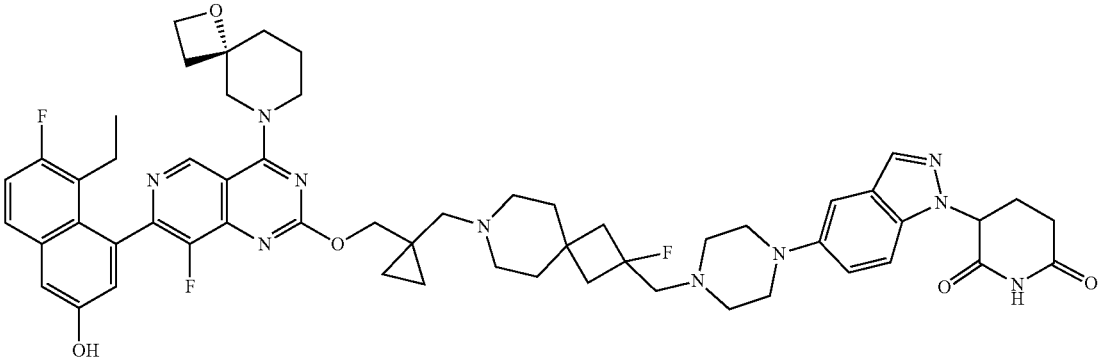 [SMILES: CCc1c(F)ccc2cc(O)cc(-c3ncc4c(N5CCC[C@]6(CCO6)C5)nc(OCC5(CN6CCC7(CC6)CC(F)(CN6CCN(c8ccc9c(cnn9C9CCC(=O)NC9=O)c8)CC6)C7)CC5)nc4c3F)c12]<br>3-(5-(4-((7-((1-(((7-(8-ethyl-7-fluoro-3-hydroxynaphthalen-1-yl)-8-fluoro-4-((S)-1-oxa-6-azaspiro[3.5]nonan-6-yl)pyrido[4,3-d]pyrimidin-2-yl)oxy)methyl)cyclopropyl)methyl)-2-fluoro-7-azaspiro[3.5]nonan-2-yl)methyl)piperazin-1-yl)-1H-indazol-1-yl)piperidine-2,6-dione |
| 258 | 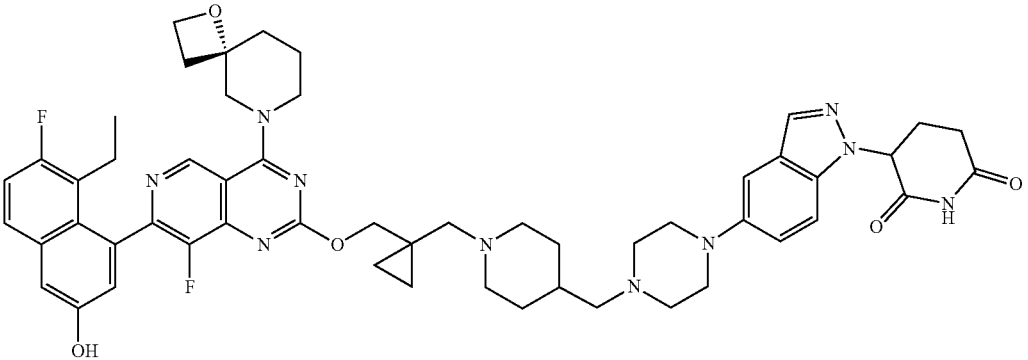 [SMILES: CCc1c(F)ccc2cc(O)cc(-c3ncc4c(N5CCC[C@]6(CCO6)C5)nc(OCC5(CN6CCC(CN7CCN(c8ccc9c(cnn9C9CCC(=O)NC9=O)c8)CC7)CC6)CC5)nc4c3F)c12]<br>3-(5-(4-((1-((1-(((7-(8-ethyl-7-fluoro-3-hydroxynaphthalen-1-yl)-8-fluoro-4-((S)-1-oxa-6-azaspiro[3.5]nonan-6-yl)pyrido[4,3-d]pyrimidin-2-yl)oxy)methyl)cyclopropyl)methyl)piperidin-4-yl)methyl)piperazin-1-yl)-1H-indazol-1-yl)piperidine-2,6-dione |
| 259 | 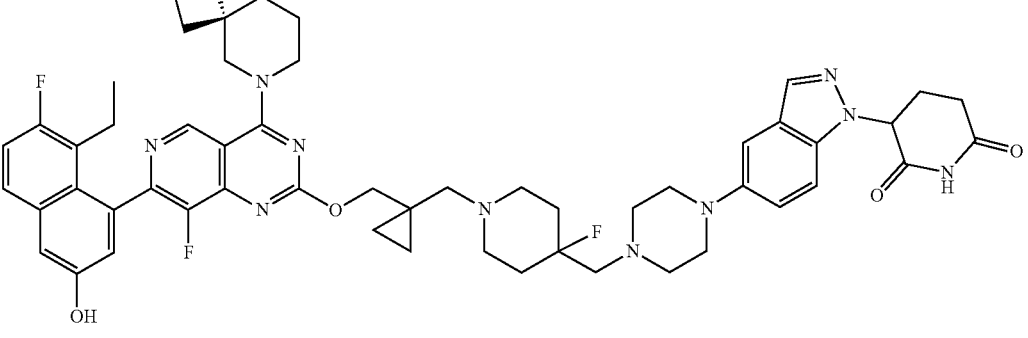<br>3-(5-(4-((1-((1-(((7-(8-ethyl-7-fluoro-3-hydroxynaphthalen-1-yl)-8-fluoro-4-((S)-1-oxa-6-azaspiro[3.5]nonan-6-yl)pyrido[4,3-d]pyrimidin-2-yl)oxy)methyl)cyclopropyl)methyl)-4-fluoropiperidin-4-yl)methyl)piperazin-1-yl)-1H-indazol-1-yl)piperidine-2,6-dione |

TABLE 1-continued

Exemplary Compounds of the Present Disclosure

| Cpd # | Structure and IUPAC Name |
|---|---|
| 260 | 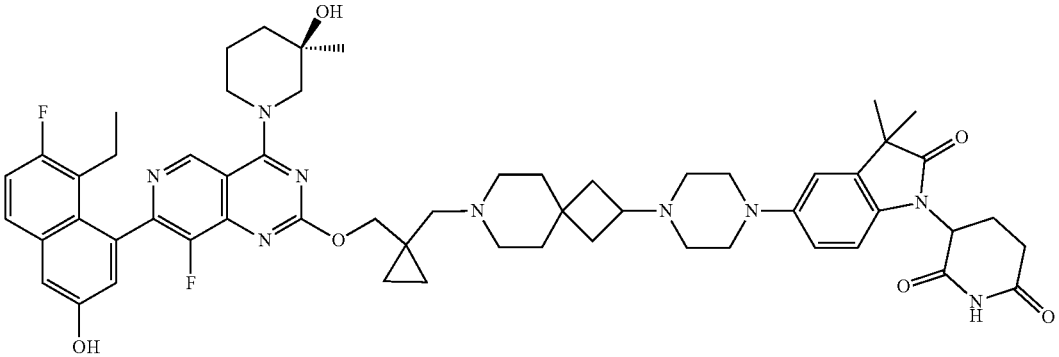

3-(5-(4-(7-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-azaspiro[3.5]nonan-2-yl)piperazin-1-yl)-3,3-dimethyl-2-oxoindolin-1-yl)piperidine-2,6-dione |
| 261 | 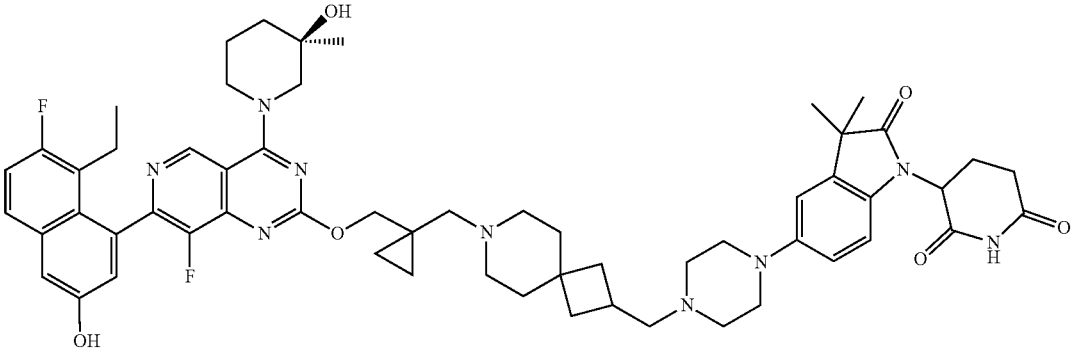

3-(5-(4-((7-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-azaspiro[3.5]nonan-2-yl)methyl)piperazin-1-yl)-3,3-dimethyl-2-oxoindolin-1-yl)piperidine-2,6-dione |
| 262 | 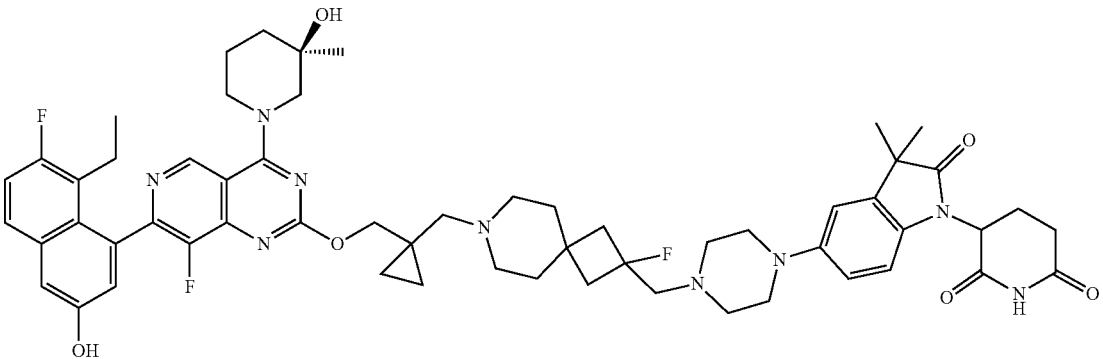 [SMILES: CCc1c(F)ccc2cc(O)cc(-c3ncc4c(N5CCC[C@@](C)(O)C5)nc(OCC5(CN6CCC7(CC6)CC(F)(CN6CCN(c8ccc9c(c8)C(C)(C)C(=O)N9C8CCC(=O)NC8=O)CC6)C7)CC5)nc4c3F)c12]

3-(5-(4-((7-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-2-fluoro-7-azaspiro[3.5]nonan-2-yl)methyl)piperazin-1-yl)-3,3-dimethyl-2-oxoindolin-1-yl)piperidine-2,6-dione |

TABLE 1-continued

Exemplary Compounds of the Present Disclosure

| Cpd # | Structure and IUPAC Name |
|---|---|
| 263 | 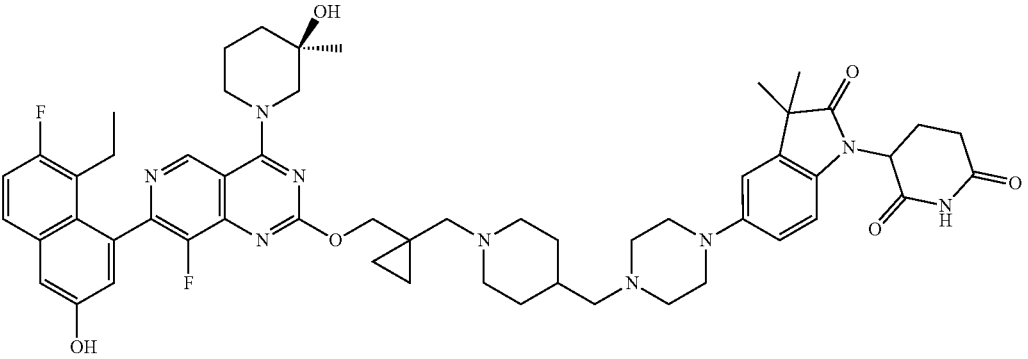 [SMILES: CCc1c(F)ccc2cc(O)cc(-c3ncc4c(N5CCC[C@@](C)(O)C5)nc(OCC5(CN6CCC(CN7CCN(c8ccc9c(c8)C(C)(C)C(=O)N9C8CCC(=O)NC8=O)CC7)CC6)CC5)nc4c3F)c12]<br>3-(5-(4-((1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)methyl)piperazin-1-yl)-3,3-dimethyl-2-oxoindolin-1-yl)piperidine-2,6-dione |
| 264 | 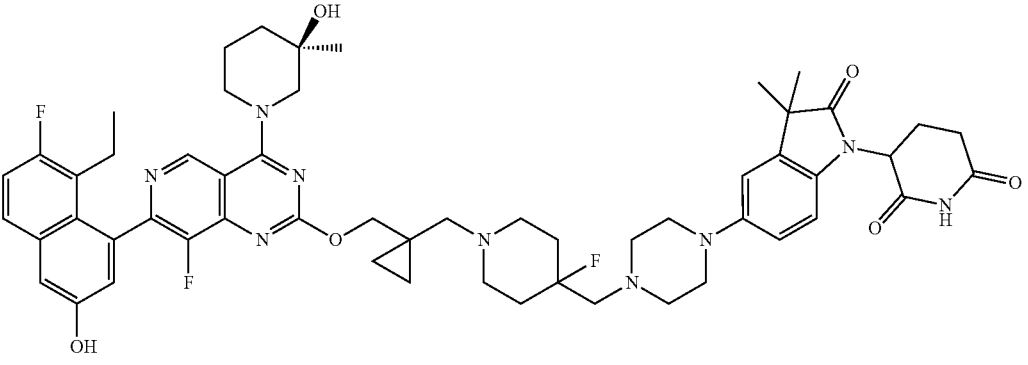 [SMILES: CCc1c(F)ccc2cc(O)cc(-c3ncc4c(N5CCC[C@@](C)(O)C5)nc(OCC5(CN6CCC(F)(CN7CCN(c8ccc9c(c8)C(C)(C)C(=O)N9C8CCC(=O)NC8=O)CC7)CC6)CC5)nc4c3F)c12]<br>3-(5-(4-((1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-4-fluoropiperidin-4-yl)methyl)piperazin-1-yl)-3,3-dimethyl-2-oxoindolin-1-yl)piperidine-2,6-dione |
| 265 | 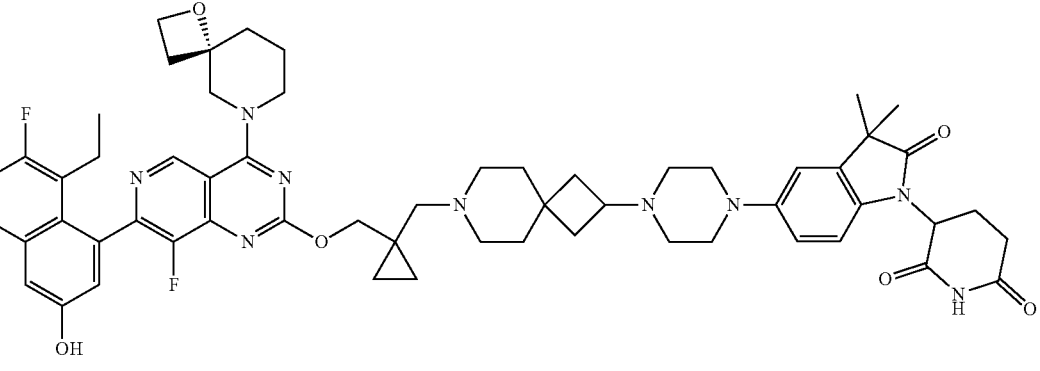<br>3-(5-(4-(7-((1-(((7-(8-ethyl-7-fluoro-3-hydroxynaphthalen-1-yl)-8-fluoro-4-((S)-1-oxa-6-azaspiro[3.5]nonan-6-yl)pyrido[4,3-d]pyrimidin-2-yl)oxy)methyl)cyclopropyl)methyl)-7-azaspiro[3.5]nonan-2-yl)piperazin-1-yl)-3,3-dimethyl-2-oxoindolin-1-yl)piperidine-2,6-dione |

TABLE 1-continued

Exemplary Compounds of the Present Disclosure

| Cpd # | Structure and IUPAC Name |
|---|---|
| 266 | 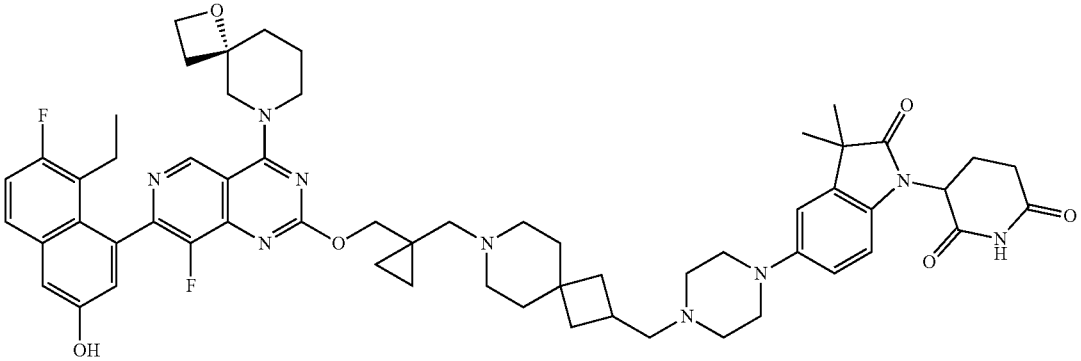 [SMILES: CCc1c(F)ccc2cc(O)cc(-c3ncc4c(N5CCC[C@]6(CCO6)C5)nc(OCC5(CN6CCC7(CC6)CC(CN6CCN(c8ccc9c(c8)C(C)(C)C(=O)N9C8CCC(=O)NC8=O)CC6)C7)CC5)nc4c3F)c12]<br>3-(5-(4-((7-((1-(((7-(8-ethyl-7-fluoro-3-hydroxynaphthalen-1-yl)-8-fluoro-4-((S)-1-oxa-6-azaspiro[3.5]nonan-6-yl)pyrido[4,3-d]pyrimidin-2-yl)oxy)methyl)cyclopropyl)methyl)-7-azaspiro[3.5]nonan-2-yl)methyl)piperazin-1-yl)-3,3-dimethyl-2-oxoindolin-1-yl)piperidine-2,6-dione |
| 267 | 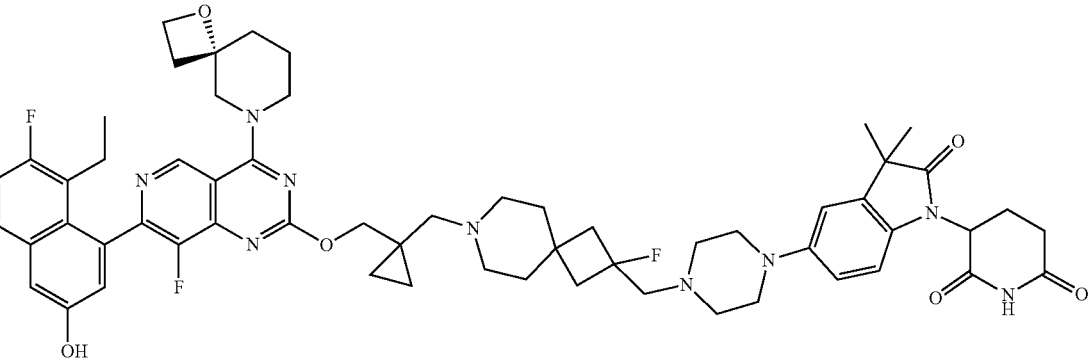 [SMILES: CCc1c(F)ccc2cc(O)cc(-c3ncc4c(N5CCC[C@]6(CCO6)C5)nc(OCC5(CN6CCC7(CC6)CC(F)(CN6CCN(c8ccc9c(c8)C(C)(C)C(=O)N9C8CCC(=O)NC8=O)CC6)C7)CC5)nc4c3F)c12]<br>3-(5-(4-((7-((1-(((7-(8-ethyl-7-fluoro-3-hydroxynaphthalen-1-yl)-8-fluoro-4-((S)-1-oxa-6-azaspiro[3.5]nonan-6-yl)pyrido[4,3-d]pyrimidin-2-yl)oxy)methyl)cyclopropyl)methyl)-2-fluoro-7-azaspiro[3.5]nonan-2-yl)methyl)piperazin-1-yl)-3,3-dimethyl-2-oxoindolin-1-yl)piperidine-2,6-dione |
| 268 | 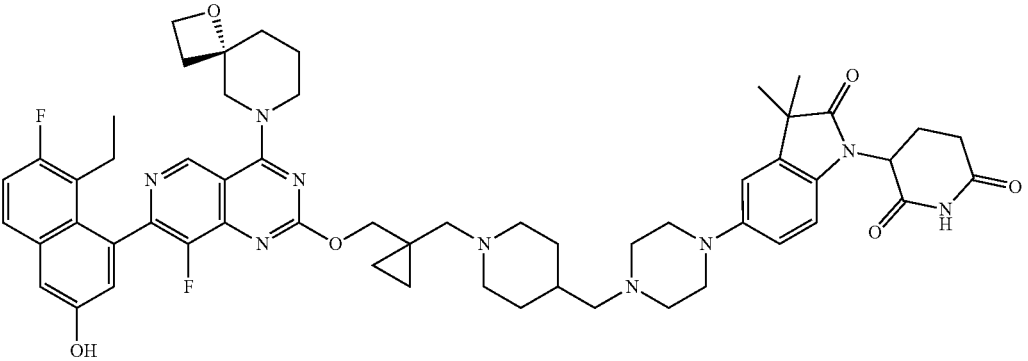 [SMILES: CCc1c(F)ccc2cc(O)cc(-c3ncc4c(N5CCC[C@]6(CCO6)C5)nc(OCC5(CN6CCC(CN7CCN(c8ccc9c(c8)C(C)(C)C(=O)N9C8CCC(=O)NC8=O)CC7)CC6)CC5)nc4c3F)c12]<br>3-(5-(4-((1-((1-(((7-(8-ethyl-7-fluoro-3-hydroxynaphthalen-1-yl)-8-fluoro-4-((S)-1-oxa-6-azaspiro[3.5]nonan-6-yl)pyrido[4,3-d]pyrimidin-2-yl)oxy)methyl)cyclopropyl)methyl)piperidin-4-yl)methyl)piperazin-1-yl)-3,3-dimethyl-2-oxoindolin-1-yl)piperidine-2,6-dione |

TABLE 1-continued

Exemplary Compounds of the Present Disclosure

| Cpd # | Structure and IUPAC Name |
|---|---|
| 269 | 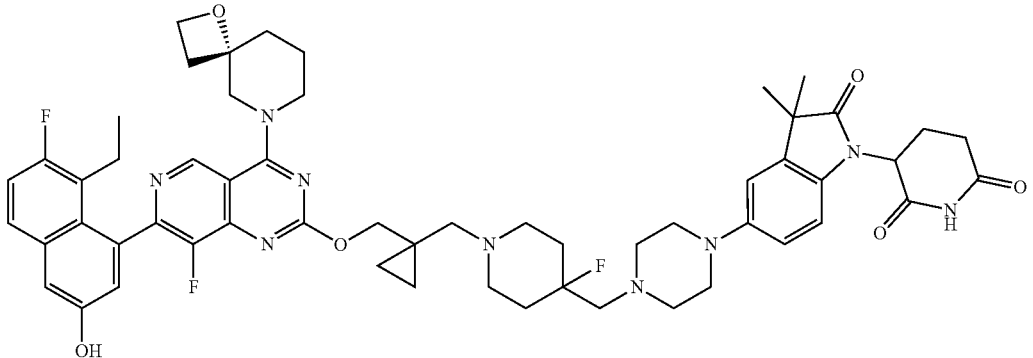 [SMILES: CCc1c(F)ccc2cc(O)cc(-c3ncc4c(N5CCC[C@]6(CCO6)C5)nc(OCC5(CN6CCC(F)(CN7CCN(c8ccc9c(c8)C(C)(C)C(=O)N9C8CCC(=O)NC8=O)CC7)CC6)CC5)nc4c3F)c12]<br>3-(5-(4-((1-(((1-(((7-(8-ethyl-7-fluoro-3-hydroxynaphthalen-1-yl)-8-fluoro-4-((S)-1-oxa-6-azaspiro[3.5]nonan-6-yl)pyrido[4,3-d]pyrimidin-2-yl)oxy)methyl)cyclopropyl)methyl)-4-fluoropiperidin-4-yl)methyl)piperazin-1-yl)-3,3-dimethyl-2-oxoindolin-1-yl)piperidine-2,6-dione |
| 270 | 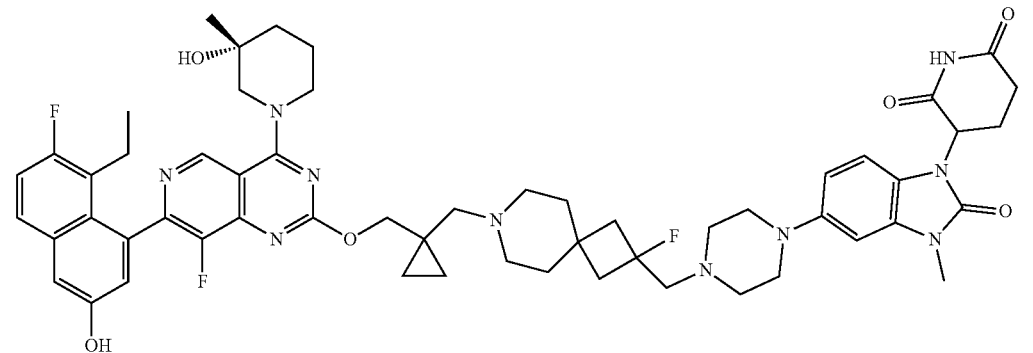 [SMILES: CCc1c(F)ccc2cc(O)cc(-c3ncc4c(N5CCC[C@@](C)(O)C5)nc(OCC5(CN6CCC7(CC6)CC(F)(CN6CCN(c8ccc9c(c8)n(C)c(=O)n9C8CCC(=O)NC8=O)CC6)C7)CC5)nc4c3F)c12]<br>3-(5-(4-((7-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-2-fluoro-7-azaspiro[3.5]nonan-2-yl)methyl)piperazin-1-yl)-3-methyl-2-oxo-2,3-dihydro-1H-benzo[d]imidazol-1-yl)piperidine-2,6-dione |
| 271 | 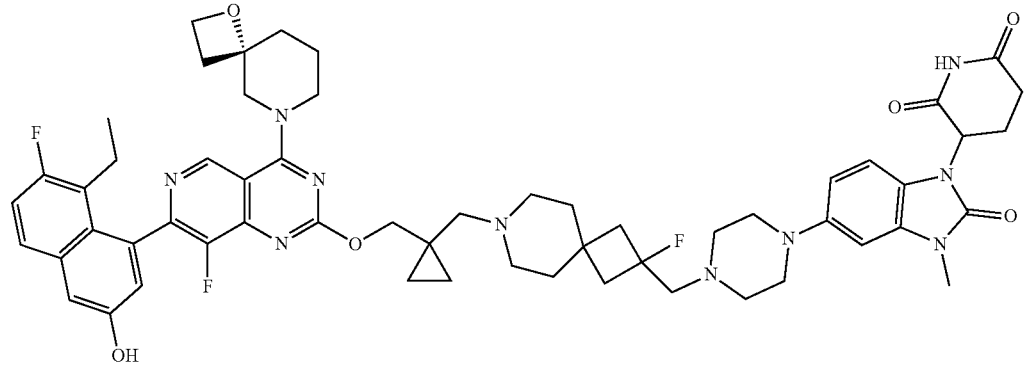 [SMILES: CCc1c(F)ccc2cc(O)cc(-c3ncc4c(N5CCC[C@]6(CCO6)C5)nc(OCC5(CN6CCC7(CC6)CC(F)(CN6CCN(c8ccc9c(c8)n(C)c(=O)n9C8CCC(=O)NC8=O)CC6)C7)CC5)nc4c3F)c12]<br>3-(5-(4-((7-((1-(((7-(8-ethyl-7-fluoro-3-hydroxynaphthalen-1-yl)-8-fluoro-4-((S)-1-oxa-6-azaspiro[3.5]nonan-6-yl)pyrido[4,3-d]pyrimidin-2-yl)oxy)methyl)cyclopropyl)methyl)-2-fluoro-7-azaspiro[3.5]nonan-2-yl)methyl)piperazin-1-yl)-3-methyl-2-oxo-2,3-dihydro-1H-benzo[d]imidazol-1-yl)piperidine-2,6-dione |

TABLE 1-continued

Exemplary Compounds of the Present Disclosure

| Cpd # | Structure and IUPAC Name |
|---|---|
| 272 | 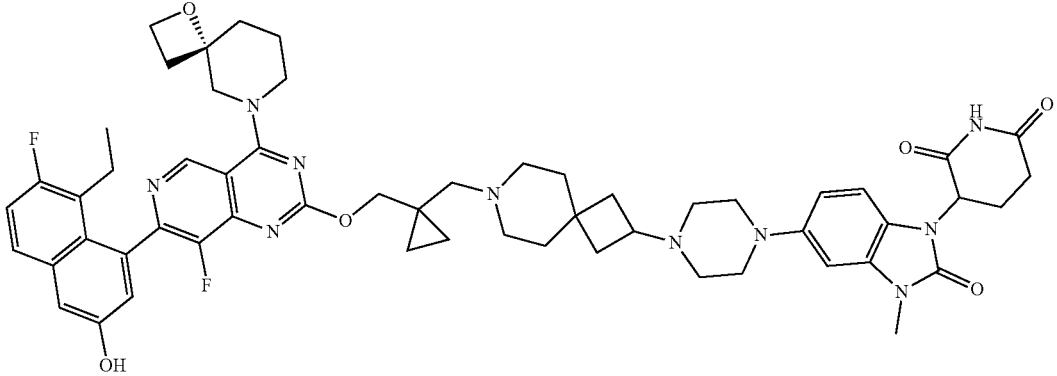 [SMILES: CCc1c(F)ccc2cc(O)cc(-c3ncc4c(N5CCC[C@]6(CCO6)C5)nc(OCC5(CN6CCC7(CC6)CC(N6CCN(c8ccc9c(c8)n(C)c(=O)n9C8CCC(=O)NC8=O)CC6)C7)CC5)nc4c3F)c12]<br>3-(5-(4-(7-((1-(((7-(8-ethyl-7-fluoro-3-hydroxynaphthalen-1-yl)-8-fluoro-4-((S)-1-oxa-6-azaspiro[3.5]nonan-6-yl)pyrido[4,3-d]pyrimidin-2-yl)oxy)methyl)cyclopropyl)methyl)-7-azaspiro[3.5]nonan-2-yl)piperazin-1-yl)-3-methyl-2-oxo-2,3-dihydro-1H-benzo[d]imidazol-1-yl)piperidine-2,6-dione |
| 273 | 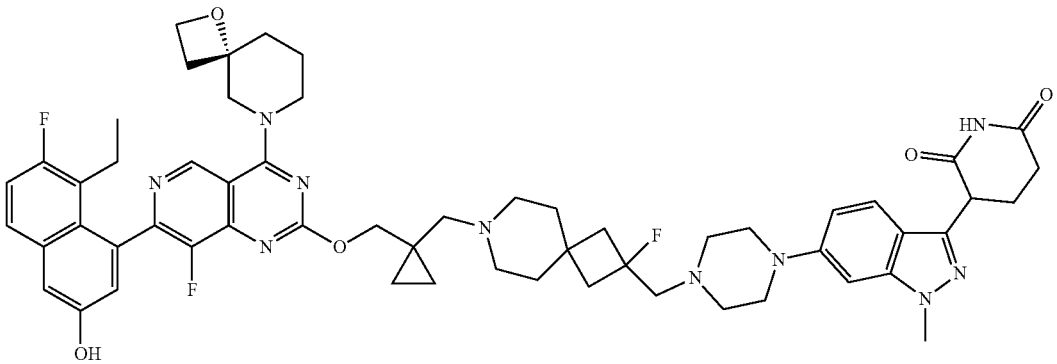 [SMILES: CCc1c(F)ccc2cc(O)cc(-c3ncc4c(N5CCC[C@]6(CCO6)C5)nc(OCC5(CN6CCC7(CC6)CC(F)(CN6CCN(c8ccc9c(C%10CCC(=O)NC%10=O)nn(C)c9c8)CC6)C7)CC5)nc4c3F)c12]<br>3-(6-(4-((7-((1-(((7-(8-ethyl-7-fluoro-3-hydroxynaphthalen-1-yl)-8-fluoro-4-((S)-1-oxa-6-azaspiro[3.5]nonan-6-yl)pyrido[4,3-d]pyrimidin-2-yl)oxy)methyl)cyclopropyl)methyl)-2-fluoro-7-azaspiro[3.5]nonan-2-yl)methyl)piperazin-1-yl)-1-methyl-1H-indazol-3-yl)piperidine-2,6-dione |
| 274 | 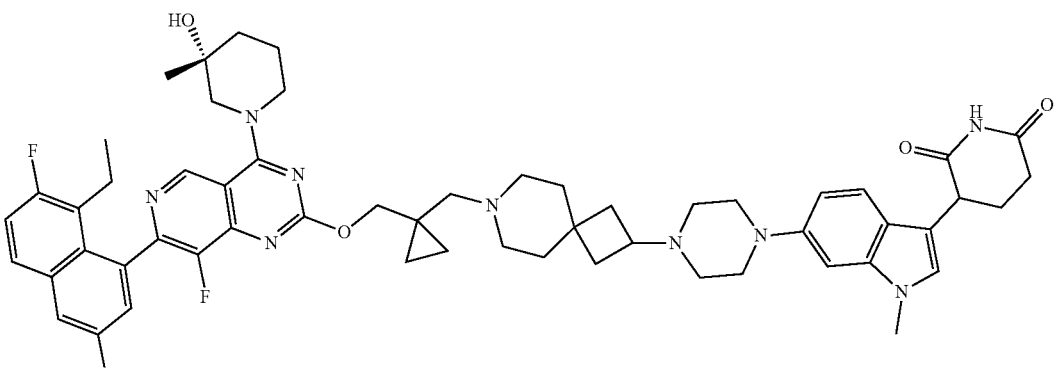<br>3-(6-(4-(7-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-azaspiro[3.5]nonan-2-yl)piperazin-1-yl)-1-methyl-1H-indazol-3-yl)piperidine-2,6-dione |

TABLE 1-continued

Exemplary Compounds of the Present Disclosure

| Cpd # | Structure and IUPAC Name |
|---|---|
| 275 | 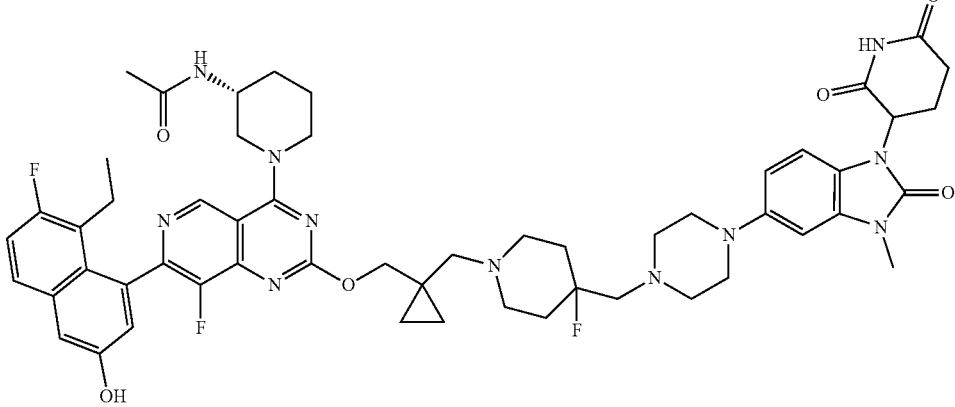<br>N-((3R)-1-(2-((1-((4-((4-(1-(2,6-dioxopiperidin-3-yl)-3-methyl-2-oxo-2,3-dihydro-1H-benzo[d]imidazol-5-yl)piperazin-1-yl)methyl)-4-fluoropiperidin-1-yl)methyl)cyclopropyl)methoxy)-7-(8-ethyl-7-fluoro-3-hydroxynaphthalen-1-yl)-8-fluoropyrido[4,3-d]pyrimidin-4-yl)piperidin-3-yl)acetamide |
| 276 | 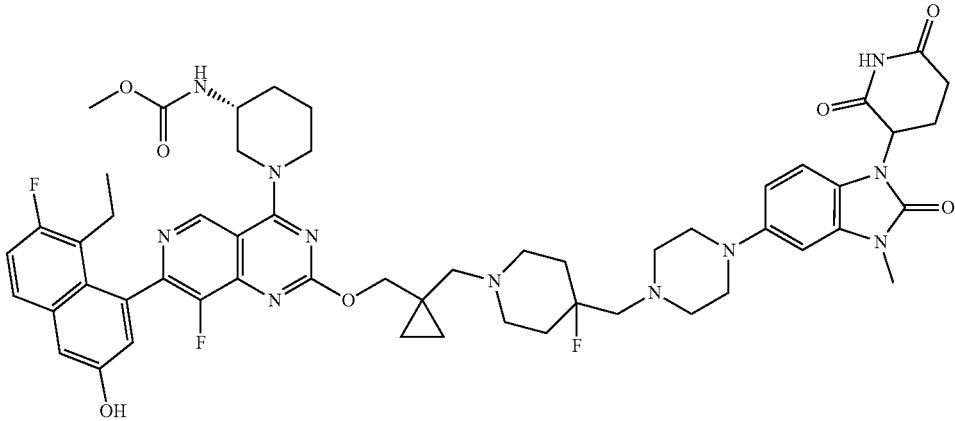 [SMILES: CCc1c(F)ccc2cc(O)cc(-c3ncc4c(N5CCC[C@@H](NC(=O)OC)C5)nc(OCC5(CN6CCC(F)(CN7CCN(c8ccc9c(c8)n(C)c(=O)n9C8CCC(=O)NC8=O)CC7)CC6)CC5)nc4c3F)c12]<br>methyl ((3R)-1-(2-((1-((4-((4-(1-(2,6-dioxopiperidin-3-yl)-3-methyl-2-oxo-2,3-dihydro-1H-benzo[d]imidazol-5-yl)piperazin-1-yl)methyl)-4-fluoropiperidin-1-yl)methyl)cyclopropyl)methoxy)-7-(8-ethyl-7-fluoro-3-hydroxynaphthalen-1-yl)-8-fluoropyrido[4,3-d]pyrimidin-4-yl)piperidin-3-yl)carbamate |

Pharmaceutical Compositions

Pharmaceutical compositions of the present disclosure comprise at least one compound of Formula (I), or a tautomer, stereoisomer or a mixture of stereoisomers, or a pharmaceutically acceptable salt, or hydrate, or deuterated derivative thereof formulated together with one or more pharmaceutically acceptable carriers. These formulations include those suitable for oral, rectal, topical, buccal and parenteral (e.g., subcutaneous, intramuscular, intradermal, or intravenous) administration. The most suitable form of administration in any given case will depend on the degree and severity of the condition being treated and on the nature of the particular compound being used.

Formulations suitable for oral administration may be presented in discrete units, such as capsules, cachets, lozenges, or tablets, each containing a predetermined amount of a compound of the present disclosure as powder or granules; as a solution or a suspension in an aqueous or non-aqueous liquid; or as an oil-in-water or water-in-oil emulsion. As indicated, such formulations may be prepared by any suitable method of pharmacy which includes the step of bringing into association at least one compound of the present disclosure as the active compound and a carrier or excipient (which may constitute one or more accessory ingredients). The carrier must be acceptable in the sense of being compatible with the other ingredients of the formulation and must not be deleterious to the recipient. The carrier may be a solid or a liquid, or both, and may be formulated with at least one compound described herein as the active compound in a unit-dose formulation, for example, a tablet, which may contain from 0.05% to 95% by weight of the at least one active compound. Other pharmacologically active substances may also be present including other compounds. The formulations of the present disclosure may be prepared by any of the well-known techniques of pharmacy consisting essentially of admixing the components.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmacologically administrable compositions can, for example, be prepared by, for example, dissolving or dispersing, at least one active compound of the present disclosure as described herein and optional pharmaceutical adjuvants in an excipient, such as, for example, water, saline, aqueous dextrose, glycerol, ethanol, and the like, to thereby form a solution or suspension. In general, suitable formulations may be prepared by uniformly and intimately admixing the at least one active compound of the present disclosure with a liquid or finely divided solid carrier, or both, and then, if necessary, shaping the product. For example, a tablet may be prepared by compressing or molding a powder or granules of at least one compound of the present disclosure, which may be optionally combined with one or more accessory ingredients. Compressed tablets may be prepared by compressing, in a suitable machine, at least one compound of the present disclosure in a free-flowing form, such as a powder or granules, which may be optionally mixed with a binder, lubricant, inert diluent and/or surface active/dispersing agent(s). Molded tablets may be made by molding, in a suitable machine, where the powdered form of at least one compound of the present disclosure is moistened with an inert liquid diluent.

Compounds of the present disclosure can be prepared and administered in a wide variety of oral, parenteral, and topical dosage forms. Thus, the compounds of the present disclosure can be administered by injection (e.g., intravenously, intramuscularly, intracutaneously, subcutaneously, intraduodenally, or intraperitoneally). In some embodiments, compounds of the present disclosure are administered orally. Also, the compounds described herein can be administered by inhalation, for example, intranasally. Additionally, the compounds of the present disclosure can be administered transdermally. It is also envisioned that multiple routes of administration (e.g., intramuscular, oral, transdermal) can be used to administer compounds of the disclosure. Accordingly, the present disclosure also provides pharmaceutical compositions comprising pharmaceutically acceptable carrier or excipient and one or more compounds of the disclosure.

For preparing pharmaceutical compositions from the compounds of the present disclosure, pharmaceutically acceptable carriers can be either solid or liquid. Solid form preparations include powders, tablets, pills, capsules, cachets, suppositories, and dispersible granules. A solid carrier can be one or more substances that may also act as diluents, flavoring agents, binders, preservatives, tablet disintegrating agents, or an encapsulating material.

In powders, the carrier is finely divided solid in a mixture with the finely divided active component. In tablets, the active component is mixed with the carrier having the necessary binding properties in suitable proportions and compacted in the shape and size desired.

Formulations suitable for buccal (sub-lingual) administration include lozenges comprising at least one compound of the present disclosure in a flavored base, usually sucrose and acacia or tragacanth, and pastilles comprising the at least one compound in an inert base such as gelatin and glycerin or sucrose and acacia.

Formulations of the present disclosure suitable for parenteral administration comprise sterile aqueous preparations of at least one compound of Formula (I), or tautomers, stereoisomers, pharmaceutically acceptable salts, and hydrates thereof, which are approximately isotonic with the blood of the intended recipient. These preparations are administered intravenously, although administration may also be affected by means of subcutaneous, intramuscular, or intradermal injection. Such preparations may conveniently be prepared by admixing at least one compound described herein with water and rendering the resulting solution sterile and isotonic with the blood. Injectable compositions according to the present disclosure may contain from 0.1% to 5% w/w of the active compound.

Formulations suitable for rectal administration are presented as unit-dose suppositories. These may be prepared by admixing at least one compound as described herein with one or more conventional solid carriers, for example, cocoa butter, and then shaping the resulting mixture.

Formulations suitable for topical application to the skin may take the form of an ointment, cream, lotion, paste, gel, spray, aerosol, or oil. Carriers and excipients which may be used include Vaseline, lanoline, polyethylene glycols, alcohols, and combinations of two or more thereof. The active compound (i.e., at least one compound of Formula (I), or tautomers, stereoisomers, pharmaceutically acceptable salts, and hydrates thereof) is generally present at a concentration of from 0.1% to 15% w/w of the composition, for example, from 0.5 to 2%.

Effective Dosages

Pharmaceutical compositions provided by the present disclosure include compositions wherein the active ingredient is contained in a therapeutically effective amount, i.e., in an amount effective to achieve its intended purpose. The actual amount effective for a particular application will depend, inter alia, on the condition being treated. For example, when administered in methods to treat cancer, such compositions will contain an amount of active ingredient effective to achieve the desired result (e.g., degrading KRAS and/or decreasing an amount of KRAS in a subject).

The dosage and frequency (single or multiple doses) of compound administered can vary depending upon a variety of factors, including route of administration; size, age, sex, health, body weight, body mass index, and diet of the recipient; nature and extent of the symptoms of the disease being treated (e.g., the disease responsive treatment; and complications from any disease or treatment regimen. Other therapeutic regimens or agents can be used in conjunction with the methods and compounds of the disclosure.

For any provided compound or test agent, the therapeutically effective amount can be initially determined from cell culture assays. Target concentrations will be those concentrations of active compound(s) that are capable of decreasing KRAS and KRAS mutants expressed in a subject.

Therapeutically effective amounts for use in humans may be determined from animal models. For example, a dose for humans can be formulated to achieve a concentration that has been found to be effective in animals. The dosage in humans can be adjusted by monitoring biomarkers associated with cancer and adjusting the dosage upwards or downwards, as described above.

Dosages may be varied depending upon the requirements of the patient and the compound being employed. The dose administered to a patient, in the context of the present disclosure, should be sufficient to affect a beneficial therapeutic response in the patient over time. The size of the dose also will be determined by the existence, nature, and extent of any adverse side effects.

In some embodiments, a compound of the disclosure or a pharmaceutical composition comprising the same is provided as a unit dose.

The amount of active compound administered may be dependent on the subject being treated, the subject's weight, the manner of administration and the judgment of the prescribing physician. For example, a dosing schedule may involve the daily or semi-daily administration of the encapsulated compound at a perceived dosage of 1 µg to 1000 mg. In another embodiment, intermittent administration, such as on a monthly or yearly basis, of a dose of the encapsulated compound may be employed. Encapsulation facilitates access to the site of action and allows the administration of the active ingredients simultaneously, in theory producing a synergistic effect. In accordance with standard dosing regimens, physicians will readily determine optimum dosages and will be able to readily modify administration to achieve such dosages.

A therapeutically effective amount of a compound or composition disclosed herein can be measured by the therapeutic effectiveness of the compound. The dosages, however, may be varied depending upon the requirements of the patient, the severity of the condition being treated, and the compound being used. In one embodiment, the therapeutically effective amount of a disclosed compound is sufficient to establish a maximal plasma concentration. Preliminary doses as, for example, determined according to animal tests, and the scaling of dosages for human administration is performed according to art-accepted practices.

Toxicity and therapeutic efficacy can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$.

Data obtained from the cell culture assays or animal studies can be used in formulating a range of dosage for use in humans. Therapeutically effective dosages achieved in one animal model may be converted for use in another animal, including humans, using conversion factors known in the art (see, e.g., Freireich et al., *Cancer Chemother. Reports* 50(4):219-244 (1966) and the following Table for Equivalent Surface Area Dosage Factors).

TABLE 2

Equivalent Surface Area Dosage Factors.

| From: | To: | | | | |
|---|---|---|---|---|---|
| | Mouse (20 g) | Rat (150 g) | Monkey (3.5 kg) | Dog (8 kg) | Human (60 kg) |
| Mouse | 1 | ½ | ¼ | ⅙ | 1/12 |
| Rat | 2 | 1 | ½ | ¼ | 1/7 |
| Monkey | 4 | 2 | 1 | ⅗ | ⅓ |
| Dog | 6 | 4 | ⅗ | 1 | ½ |
| Human | 12 | 7 | 3 | 2 | 1 |

The dosage of such compounds lies, for example, within a range of circulating concentrations that include the ED50 with little or no toxicity. The dosage may vary within this range depending upon the dosage form employed and the route of administration utilized. Generally, a therapeutically effective amount may vary with the subject's age, condition, and gender, as well as the severity of the medical condition in the subject. The dosage may be determined by a physician and adjusted, as necessary, to suit observed effects of the treatment.

In some embodiments, the disclosure provides a pharmaceutical composition comprising a therapeutically effective amount of a compound of Formula (I), or a tautomer, stereoisomer or a mixture of stereoisomers, or a pharmaceutically acceptable salt, or hydrate, or deuterated derivative thereof, and one or more of a pharmaceutically acceptable carrier, a pharmaceutically acceptable vehicle, a pharmaceutically acceptable excipient, or combinations thereof.

The compounds of the disclosure can be administered alone or can be co-administered to the subject. Co-administration is meant to include simultaneous or sequential administration of the compounds individually or in combination (more than one compound). The preparations can also be combined, when desired, with other active substances (e.g., to reduce metabolic degradation).

In some embodiments, a compound as described herein can be incorporated into a pharmaceutical composition for administration by methods known to those skilled in the art and described herein for provided compounds.

Methods of Treatment

In some embodiments, a compound of Formula (I), or a tautomer, stereoisomer or a mixture of stereoisomers, or a pharmaceutically acceptable salt, or hydrate, or deuterated derivative thereof, is administered to treat cancer in a subject in need thereof. In some embodiments, the cancer is a KRAS mutant-associated cancer. In some embodiments, the KRAS mutant-associated cancer is chosen from breast cancer, lung cancer, pancreatic cancer, small bowel cancer, colorectal cancer, gall bladder cancer, thyroid cancer, liver cancer, bile duct cancer, ovarian cancer, endometrial cancer, cervical cancer, bladder cancer, prostate cancer, esophageal cancer, and blood cancer. In some embodiments, the cancer is breast cancer. In some embodiments, the cancer is lung cancer. In some embodiments, the lung cancer is non-small cell lung cancer. In some embodiments, the cancer is pancreatic cancer. In some embodiments, the pancreatic cancer is pancreatic adenocarcinoma. In some embodiments, the cancer is small bowel cancer. In some embodiments, the cancer is colorectal cancer. In some embodiments, the cancer is gall bladder cancer. In some embodiments, the cancer is thyroid cancer. In some embodiments, the cancer is liver cancer. In some embodiments, the cancer is bile duct cancer. In some embodiments, the cancer is ovarian cancer. In some embodiments, the cancer is endometrial cancer. In some embodiments, the cancer is cervical cancer. In some embodiments, the cancer is bladder cancer. In some embodiments, the cancer is prostate cancer. In some embodiments, the cancer is esophageal cancer. In some embodiments, the cancer is blood cancer. In some embodiments, the therapeutic treatment is for the treatment of pan-KRAS-associated diseases and conditions.

In some embodiments, a compound of Formula (I), or a tautomer, stereoisomer or a mixture of stereoisomers, or a pharmaceutically acceptable salt, or hydrate, or deuterated derivative thereof, is administered as a pharmaceutical composition.

In some embodiments, the disclosure provides for methods for treating cancer in a subject (e.g., patient) in need thereof, comprising (a) determining that the cancer is associated with one or more KRAS mutations (such as KRAS (G12C), KRAS (G12D), KRAS (G12S), KRAS (G12V)); and (b) administering to the subject a therapeutically effective amount of at least one compound of Formula (I) or a tautomer, stereoisomer or a mixture of stereoisomers, or a pharmaceutically acceptable salt, or hydrate, or deuterated derivative thereof, or a pharmaceutical composition comprising at least one compound of Formula (I) or a tautomer, stereoisomer or a mixture of stereoisomers, or a pharmaceutically acceptable salt, or hydrate, or deuterated derivative thereof.

In some embodiments, the disclosure provides for methods for treating a cancer associated with one or more KRAS mutations in a subject (e.g., patient) in need thereof, comprising administering to the subject a therapeutically effective amount of at least one compound of Formula (I) or a tautomer, stereoisomer or a mixture of stereoisomers, or a pharmaceutically acceptable salt, or hydrate, or deuterated derivative thereof, or a pharmaceutical composition comprising at least one compound of Formula (I) or a tautomer, stereoisomer or a mixture of stereoisomers, or a pharmaceutically acceptable salt, or hydrate, or deuterated derivative thereof. In certain of such embodiments, the cancer has been determined to be associated with one or more KRAS mutations (e.g., KRAS (G12C), KRAS (G12D), KRAS (G12S), KRAS (G12V)) and/or the patient has been diagnosed as suffering from a cancer associated with one or more KRAS mutations.

In some embodiments, the disclosure provides for methods for degrading KRAS (such as KRAS (G12C), KRAS (G12D), KRAS (G12S), KRAS (G12V), and/or KRAS (WT)) in a cell, comprising contacting the cell with at least one compound of Formula (I) or a tautomer, stereoisomer or a mixture of stereoisomers, or a pharmaceutically acceptable salt, or hydrate, or deuterated derivative thereof, or a pharmaceutical composition comprising at least one compound of Formula (I) or a tautomer, stereoisomer or a mixture of stereoisomers, or a pharmaceutically acceptable salt, or hydrate, or deuterated derivative thereof.

In some embodiments, the disclosure provides for methods for degrading KRAS (such as KRAS (G12C), KRAS (G12D), KRAS (G12S), KRAS (G12V), and/or KRAS (WT)) in a cell or subject, comprising contacting the cell in which degradation of KRAS is desired with an effective amount of a compound of Formula (I), pharmaceutically acceptable salts thereof or pharmaceutical compositions containing the compound or pharmaceutically acceptable salt thereof. In one embodiment, the contacting is in vitro. In one embodiment, the contacting is in vivo.

As used herein, the term "contacting" refers to the bringing together of indicated moieties in an in vitro system or an in vivo system. For example, "contacting" a KRAS protein with a compound provided herein includes the administration of a compound provided herein to an individual or patient.

In one embodiment, a cell in which degradation of KRAS is desired is contacted with an effective amount of a compound of Formula (I) to negatively modulate KRAS (such as KRAS (G12C), KRAS (G12D), KRAS (G12S), KRAS (G12V), and/or KRAS (WT)). In other embodiments, a therapeutically effective amount of pharmaceutically acceptable salt or pharmaceutical compositions containing the compound of Formula (I) may be used.

By negatively modulating KRAS (e.g., by degradation), the methods described herein are designed to halt undesired cellular proliferation resulting from enhanced KRAS presence within the cell. The cells may be contacted in a single dose or multiple doses in accordance with a particular treatment regimen to affect the desired negative modulation of KRAS.

The concentration and route of administration to the patient will vary depending on the cancer to be treated.

In one embodiment, a compound of Formula (I), or a tautomer, stereoisomer or a mixture of stereoisomers, or a pharmaceutically acceptable salt, or hydrate, or deuterated derivative thereof, is administered in combination with another therapeutic agent, e.g., chemotherapy, or used in combination with other treatments, such as radiation or surgical intervention, either as an adjuvant prior to surgery or post-operatively.

In some embodiments, a compound of Formula (I), or a tautomer, stereoisomer or a mixture of stereoisomers, or a pharmaceutically acceptable salt, or hydrate, or deuterated derivative thereof, is administered with an additional anti-cancer agent. In some embodiments, the compound of Formula (I) and/or the pharmaceutical composition comprising the compound of Formula (I), and the additional anti-cancer agent are administered concomitantly. In some embodiments, the compound of Formula (I) and/or the pharmaceutical composition comprising the compound of Formula (I), and the additional anti-cancer agent are administered sequentially.

Also provided herein is a compound of Formula (I), or a pharmaceutically acceptable salt or solvate thereof, or a pharmaceutical composition thereof as defined herein for use in therapy.

Also provided herein is a compound of Formula (I), or a pharmaceutically acceptable salt or solvate/hydrate thereof or a pharmaceutical composition thereof as defined herein for use in the treatment of cancer.

Also provided herein is a compound of Formula (I), or a pharmaceutically acceptable salt or solvate thereof for use in the degradation of KRAS (pan-KRAS, such as KRAS (G12C), KRAS (G12D), KRAS (G12S), KRAS (G12V), and/or KRAS (WT)).

Also provided herein is a compound of Formula (I), or a pharmaceutically acceptable salt or solvate thereof or a pharmaceutical composition thereof as defined herein, for use in the treatment of a KRAS-associated disease or disorder.

Also provided herein is the use of a compound of Formula (I), or a pharmaceutically acceptable salt or solvate thereof, as defined herein in the manufacture of a medicament for the treatment of cancer.

Also provided herein is a use of a compound of Formula (I), or a pharmaceutically acceptable salt or solvate thereof, as defined herein in the manufacture of a medicament for the degradation of various KRAS forms, such as KRAS (G12C), KRAS (G12D), KRAS (G12S), KRAS (G12V), and/or KRAS (WT).

Also provided herein is the use of a compound of Formula (I), or a pharmaceutically acceptable salt or solvate thereof, as defined herein, in the manufacture of a medicament for the treatment of a KRAS-associated disease or disorder.

One skilled in the art will recognize that, both in vivo and in vitro trials using suitable, known and generally accepted cell and/or animal models are predictive of the ability of a test compound to treat or prevent a given disorder.

EXAMPLES

The examples and preparations provided below further illustrate and exemplify the compounds as disclosed herein and methods of preparing such compounds. It is to be understood that the scope of the present disclosure is not limited in any way by the scope of the following examples and preparations.

The chemical entities described herein can be synthesized according to one or more illustrative schemes herein and/or techniques well known in the art. Unless specified to the contrary, the reactions described herein take place at atmospheric pressure, generally within a temperature range from −10° C. to 200° C. Further, except as otherwise specified, reaction times and conditions are intended to be approximate, e.g., taking place at atmospheric pressure within a temperature range of −10° C. to 200° C. over a period that can be, for example, 1 to 24 hours; reactions left to run overnight in some embodiments can average a period of 16 hours.

Isolation and purification of the chemical entities and intermediates described herein can be affected, if desired, by any suitable separation or purification procedure such as, for example, filtration, extraction, crystallization, column chromatography, thin-layer chromatography or thick-layer chromatography, or a combination of these procedures. See, e.g., Carey et al. Advanced Organic Chemistry, $3^{rd}$ Ed., 1990 New York: Plenum Press; Mundy et al., Name Reaction and Reagents in Organic Synthesis, $2^{nd}$ Ed., 2005 Hoboken, NJ: J. Wiley & Sons. Specific illustrations of suitable separation and isolation procedures are given by reference to the examples hereinbelow. However, other equivalent separation or isolation procedures can also be used.

In all of the methods, it is well understood that protecting groups for sensitive or reactive groups may be employed where necessary, in accordance with general principles of chemistry. Protecting groups are manipulated according to standard methods of organic synthesis (T. W. Greene and P. G. M. Wuts (1999) Protective Groups in Organic Synthesis, $3^{rd}$ Ed., John Wiley & Sons). These groups may be removed at a convenient stage of the compound synthesis using methods that are readily apparent to those skilled in the art.

When desired, the (R)- and (S)-isomers of the nonlimiting exemplary compounds, if present, can be resolved by methods known to those skilled in the art, for example, by formation of diastereoisomeric salts or complexes which can be separated, e.g., by crystallization; via formation of diastereoisomeric derivatives which can be separated, e.g., by crystallization, gas-liquid or liquid chromatography; selective reaction of one enantiomer with an enantiomer-specific reagent, e.g., enzymatic oxidation or reduction, followed by separation of the modified and unmodified enantiomers; or gas-liquid or liquid chromatography in a chiral environment, e.g., on a chiral support, such as silica with a bound chiral ligand or in the presence of a chiral solvent. Alternatively, a specific enantiomer can be synthesized by asymmetric synthesis using optically active reagents, substrates, catalysts, or solvents, or by converting one enantiomer to the other by asymmetric transformation.

The compounds described herein can be optionally contacted with a pharmaceutically acceptable acid to form the corresponding acid addition salts. Also, the compounds described herein can be optionally contacted with a pharmaceutically acceptable base to form the corresponding basic addition salts.

In some embodiments, disclosed compounds can generally be synthesized by an appropriate combination of generally well-known synthetic methods. Techniques useful in synthesizing these chemical entities are both readily apparent and accessible to those of skill in the relevant art, based on the instant disclosure. Many of the optionally substituted starting compounds and other reactants are commercially available, e.g., from Millipore Sigma or can be readily prepared by those skilled in the art using commonly employed synthetic methodology.

The discussion below is offered to illustrate certain of the diverse methods available for use in making the disclosed compounds and is not intended to limit the scope of reactions or reaction sequences that can be used in preparing the compounds provided herein. The skilled artisan will understand that standard atom valences apply to all compounds disclosed herein in genus or named compound for unless otherwise specified.

HPLC spectra for all compounds were acquired using an Agilent 1200 Series system with DAD detector. Chromatography was performed on a 2.1×150 mm Zorbax 300SB-C18 5 µm column with water containing 0.1% formic acid as solvent A and acetonitrile containing 0.1% formic acid as solvent B at a flow rate of 0.4 mL/min. The gradient program was as follows: 1% B (0-1 min), 1-99% B (1-4 min), and 99% B (4-8 min). High-resolution mass spectra (HRMS) data were acquired in positive ion mode using an Agilent G1969A API-TOF with an electrospray ionization (ESI) source. Nuclear Magnetic Resonance (NMR) spectra were acquired on a Bruker spectrometer with 600 MHz or 400 MHz for proton ($^1$H NMR) and 150 MHz for carbon ($^{13}$C NMR); chemical shifts are reported in (δ). Preparative HPLC was performed on Agilent Prep 1200 series with UV detector set to 254 nm and 220 nm. Samples were injected onto a Phenomenex Luna 75×30 mm, 5 µm, $C_{18}$ column at room temperature. The flow rate was 40 mL/min. A linear gradient was used with 10% (or 50%) of MeOH (A) in $H_2O$ (with 0.1% TFA) (B) to 100% of MeOH (A). HPLC was used to establish the purity of target compounds. All final compounds were determined to be >95% purity when analyzed according to the HPLC methods described above.

General Synthetic Schemes

The disclosed compounds can be prepared according to the following schemes. The following schemes represent the general methods used in preparing these compounds. However, the synthesis of these compounds is not limited to these representative methods, as they can also be prepared through various other methods by those skilled in the art of synthetic chemistry.

General Synthetic Scheme 1

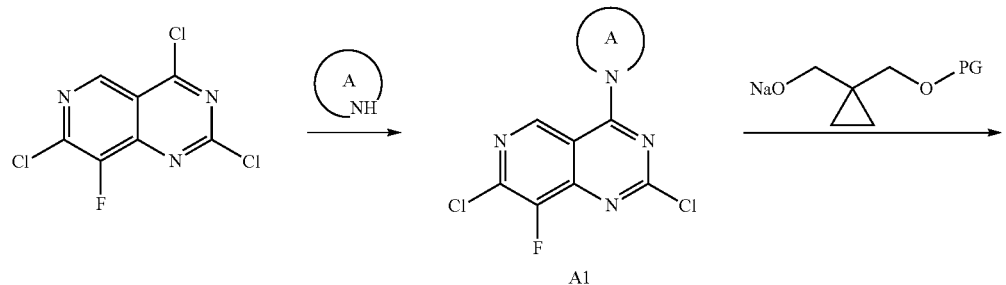

A1

-continued
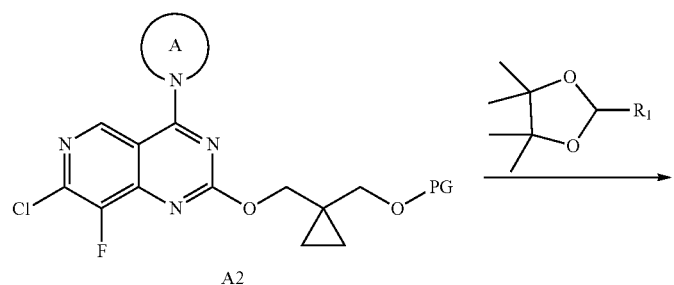
A2
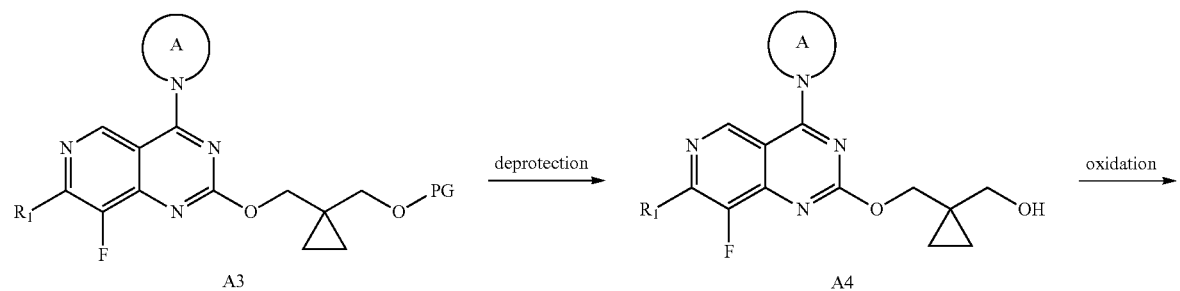
A3 → deprotection → A4 → oxidation
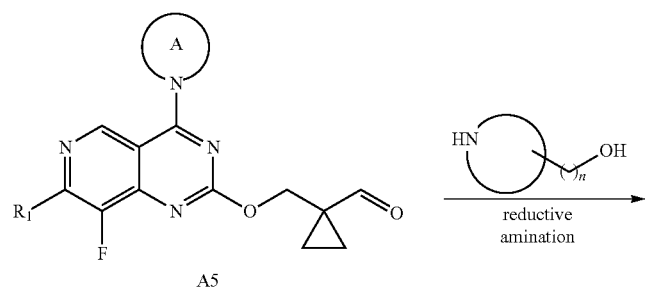
A5 → reductive amination →
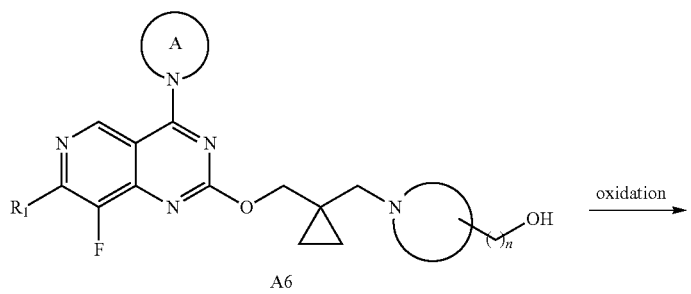
A6 → oxidation -continued
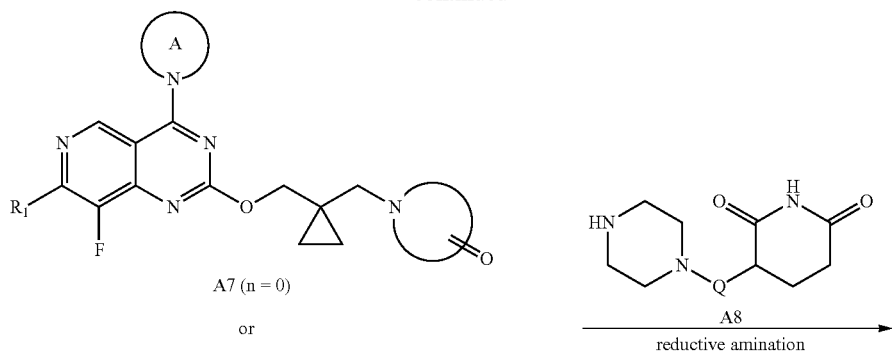
A7 (n = 0)
or
A7 (n = 1)
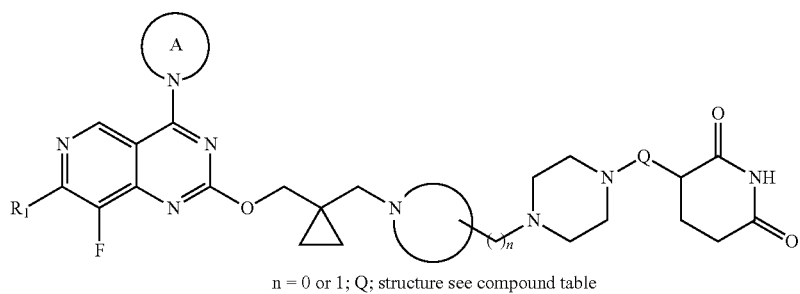
n = 0 or 1; Q: structure see compound table
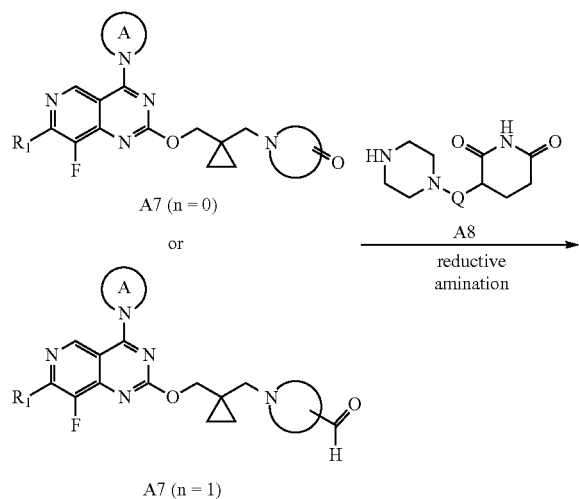
A7 (n = 0)
or
A7 (n = 1)
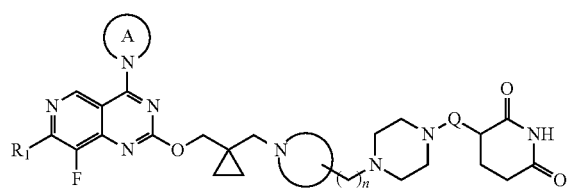
n = 0 or 1; Q: structure see compound table

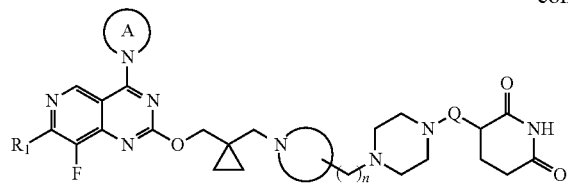

n = 0 or 1; Q: structure see compound table

In General Synthetic Scheme 1, commercially available 2,4,7-trichloro-8-fluoropyrido[4,3-d]pyrimidine can react with a cyclic amine, such as (R)-3-methylpiperidin-3-ol, or (S)-1-oxa-6-azaspiro[3.5]nonane to form intermediate A1. In the second step, mono-protected 1,1-cyclopropyldimethanol in the presence of base such as sodium hydride can react with intermediate A1 to form the ether intermediate A2. The coupling of intermediate A2 with an aryl boronic acid pinacol ester under Suzuki coupling conditions can give intermediate A3, which can undergo the deprotection of the hydroxyl protecting group to generate A4. The hydroxyl group can be oxidized to an aldehyde intermediate A5. The aldehyde intermediate A5 can undergo a reductive amination with a cyclic amine bearing a hydroxyl group to form an intermediate A6. The hydroxyl group in A6 can be oxidized to form an aldehyde or ketone intermediate A7. The reductive amination of A7 with a glutarimide derivative A8 followed by deprotection of protective groups will provide the desired final compound of Formula I. It should be noticed that the cyclic amine used in the reductive amination to convert A5 to A6 can be monocyclic, bicyclic or spirocyclic amines. It should further be noticed that the piperazine in A8 is just an example. The piperazine moiety in A8 can be monocyclic amine or spirocyclic amine and the ring size can be 3, 4, 5, 6 and 7.

General Synthetic Scheme 2

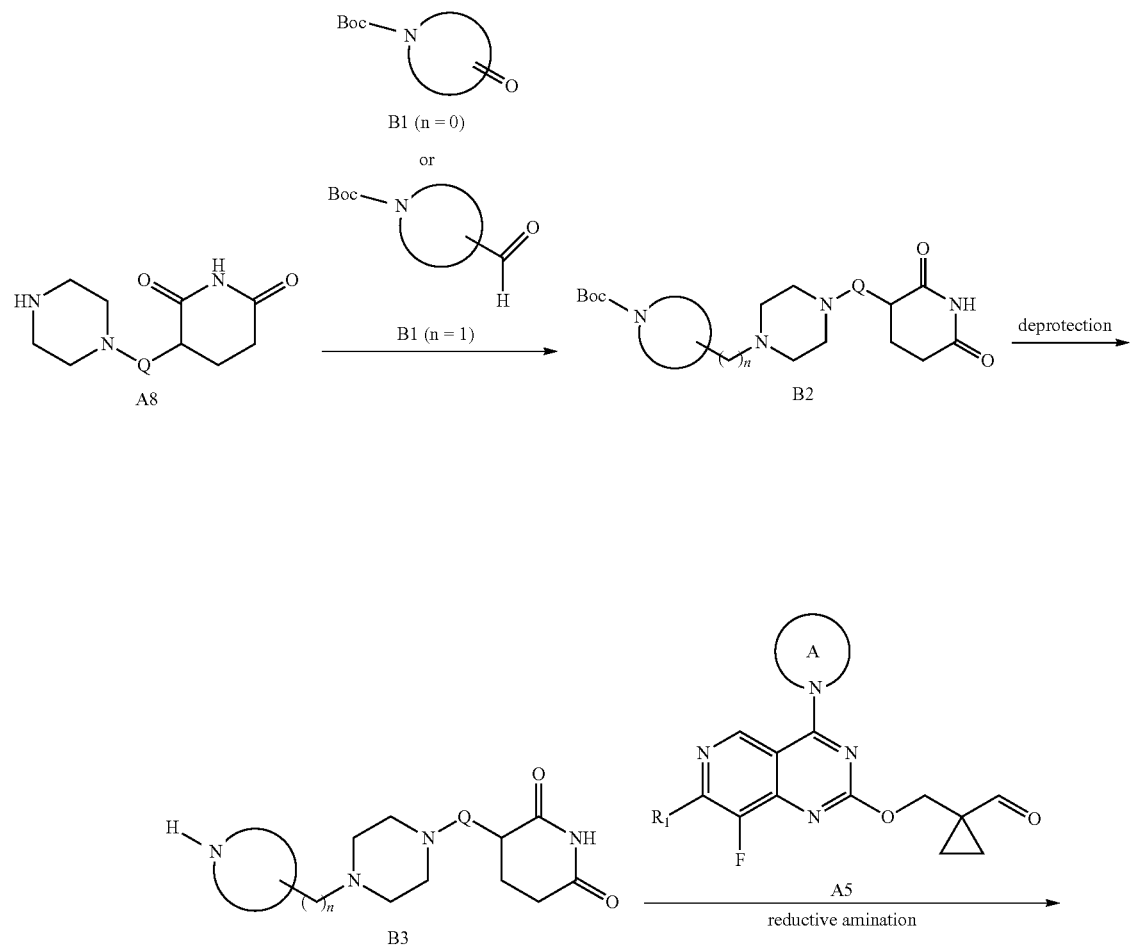

-continued

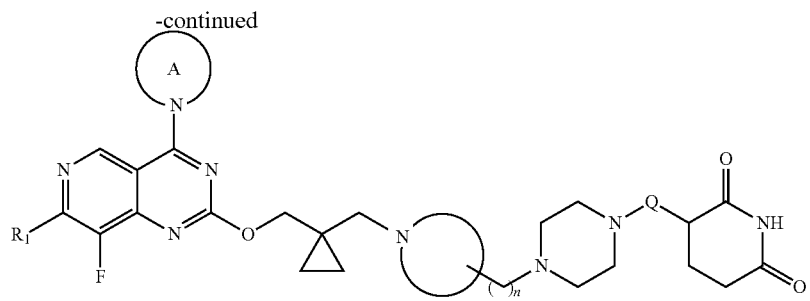

n = 0 or 1; Q: structure see compound table

Alternatively, compounds of Formula I can also be prepared according to General Synthetic Scheme 2. Reductive amination of A8 with an aldehyde or a ketone B1 can form B2, which can be deprotected to release the free amine B3. It should be noticed that B1 can be monocyclic, bicyclic, or spirocyclic aldehyde or ketone. The reductive amination of B3 with the key intermediate aldehyde A5 followed by the deprotection of protective groups will generate the desired compound with structure of Formula I. It should also be noticed that the piperazine in A8 is just an example. The piperazine moiety in A8 can be monocyclic amine or spirocyclic amine and the ring size can be 3, 4, 5, 6 and 7. The Boc-protected cyclic amine B1 can also be monocyclic or spirocyclic amines.

General Synthetic Scheme 3

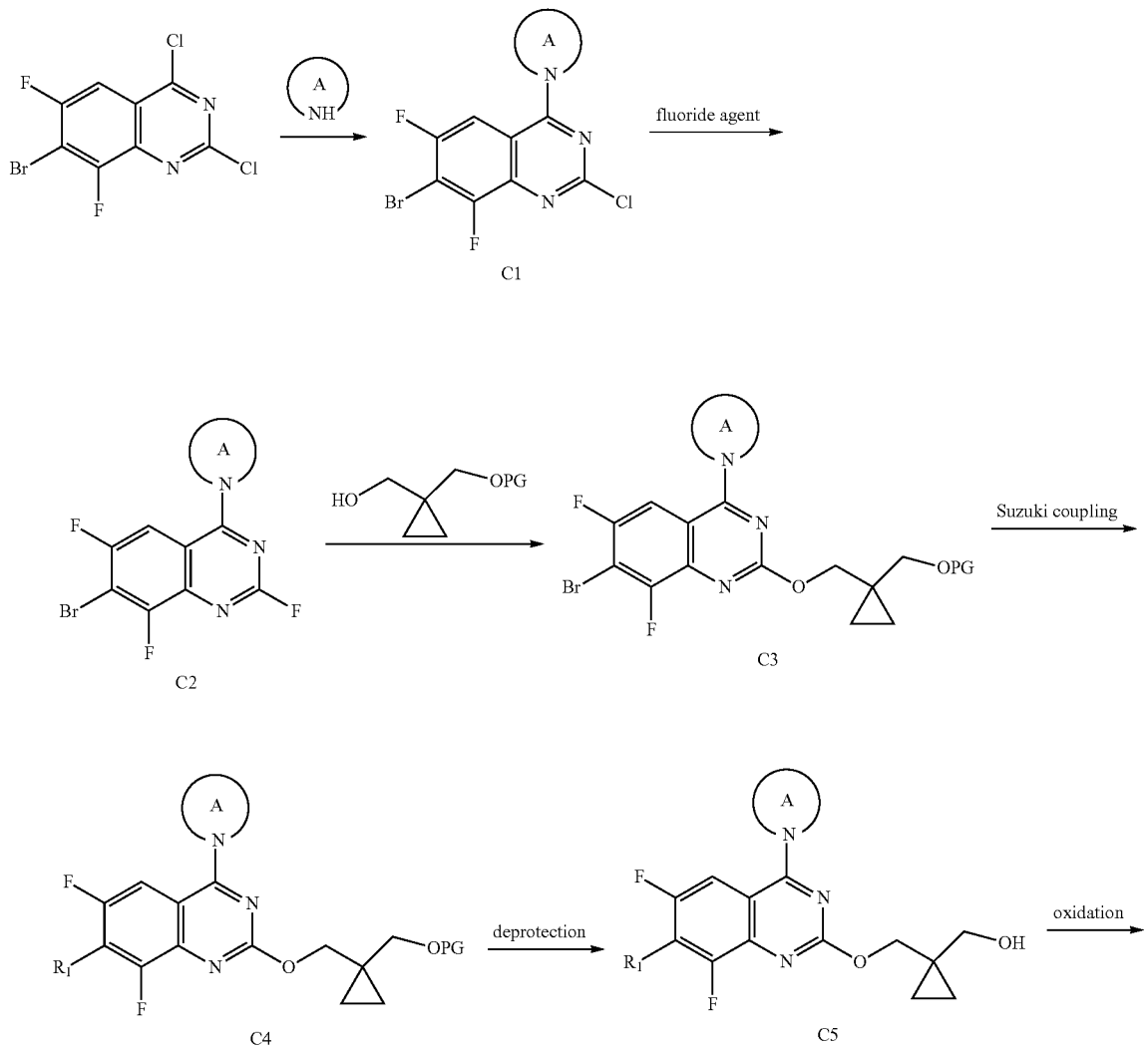

-continued

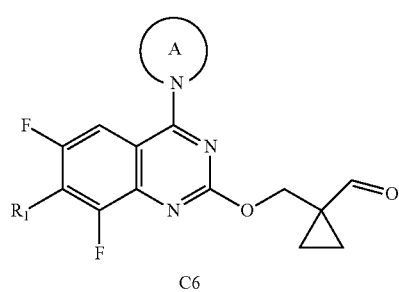

C6

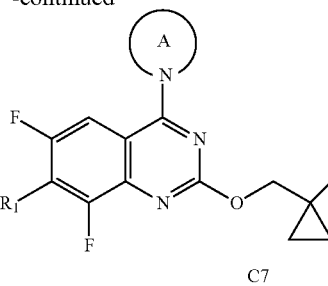

C7 reductive amination → oxidation →

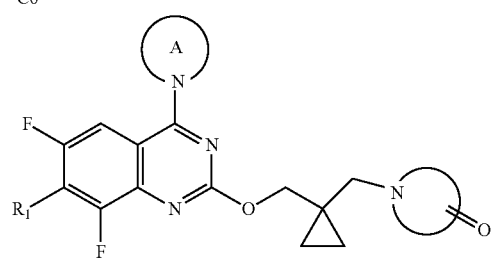

C8 (n = 0)

or

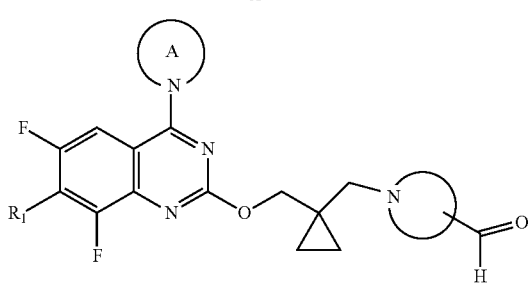

C8 (n = 1)

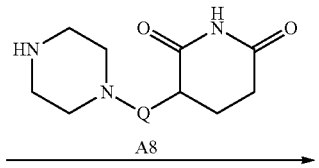

A8

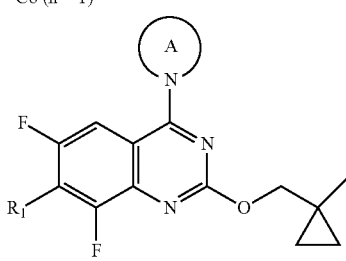

n = 0 or 1; Q: structure see compound table

For compounds of Formula I with a 6,8-difluoroquinazoline moiety, they can be synthesized according to General Synthetic Scheme 3. The commercially available 7-bromo-2,4-dichloro-6,8-difluoroquinazoline can react with a cyclic amine such as (R)-3-methylpiperidin-3-ol, or (S)-1-oxa-6-azaspiro[3.5]nonane to form intermediate C1. In the second step, the 2-chloro substituent can be converted to 2-fluoro substituent using fluoride agent such as potassium fluoride. The mono-protected 1,1-cyclopropyldimethanol in the presence of base such as sodium hydride can react with intermediate C2 to form the ether intermediate C3. By following similar sequences as described in General Synthetic Scheme 1, compounds of formula I with 6,8-difluoroquinazoline moiety can be prepared from intermediate C3 through intermediates C4 to C8. It should be noticed that the cyclic amine used in the reductive amination to convert C6 to C7 can be monocyclic, bicyclic or spirocyclic amines. It should further be noticed that the piperazine moiety in A8 can be monocyclic amine or spirocyclic amine and the ring size can be 3, 4, 5, 6 and 7.

The following abbreviations have the definitions set forth below:
ACN acetonitrile
AcOH acetic acid
Boc tert-butyloxycarbonyl
Bpin boronic pinacolinate
DABCO 1,4-diazabicyclo[2.2.2]octane
dba Dibenzylideneacetone
DBU 1,8-Diazabicyclo[5.4.0]undec-7-ene
DCM dichloromethane
DIAD diisopropyl azodicarboxylate
DIBAL-H diisobutylaluminium hydride
DIEA N,N-Diisopropylethylamine
DIPEA N,N-Diisopropylethylamine DME dimethyl ether
DMF dimethylformamide
DMP 2,2-dimethoxypropane
DMSO dimethyl sulfoxide
DNP 2,4-Dinitrophenol
dppf 1,1'-bis(diphenylphosphino)ferrocene
dtbpy,dtbbpy 4,4'-Di-tert-butyl-2,2'-bipyridine
EA ethyl acetate
ee enantiomeric excess
FA Formic Acid
HATU hexafluorophosphate azabenzotriazole tetramethyl uronium
LC/MS (LCMS) liquid chromatography/mass spectrometry
m-CPBA meta-chloroperbenzoic acid
MeCN (methyl cyanide
MeOH methanol
MOM methoxymethyl ether
MTBE methyl tert-butyl ether
n-Bu butan-1-yl
NMP N-methylpyrrolidone
NMR nuclear magnetic resonance
PE petroleum ether
ppy phenylpyridine
prep-HPLC preparative high-performance liquid chromatography
preparative thin layer chromatography
Prep-TLC
RF retention factors
SEM 2-(Trimethylsilyl)ethoxymethyl
SFC Supercritical fluid chromatography
TBAB tetrabutylammonium bromide
TBAF tetrabutylammonium fluoride
TBS tert-Butyldimethylsilyl
t-Bu Tert-butyl
TEA triethylamine
TFA trifluoroacetic acid
TFAA trifluoroacetic anhydride
THF tetrahydrofuran
TLC thin layer chromatography
TMS tetramethylsilane
Tos toluenesulfonyl group
TsOH p-toluenesulfonic acid
TTMSS tris(trimethylsilyl)silane
XantPhos (9,9-Dimethyl-9H-xanthene-4,5-diyl)bis(diphenylphosphane)

PREPARATION OF INTERMEDIATES

Preparation of (3S)-3-(1-oxo-5-piperazin-1-yl-isoindolin-2-yl) piperidine-2,6-dione (Intermediate 1)
Three methods were carried out for the synthesis of Intermediate 1 as described in Method A, B, and C.

Method A

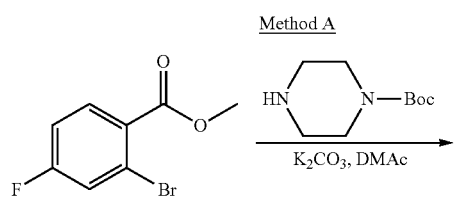

-continued

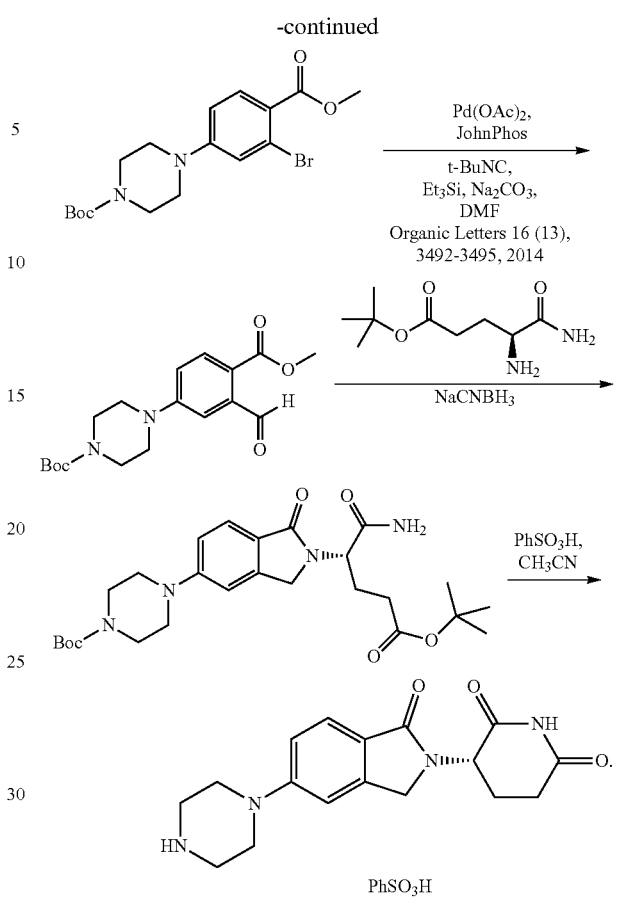

Method B

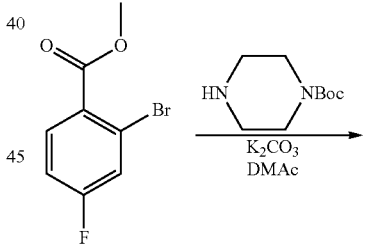

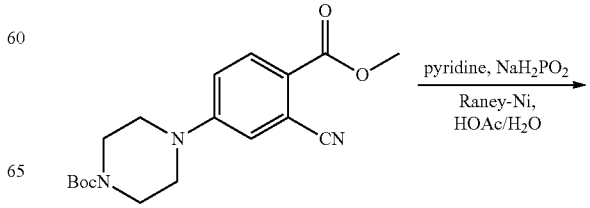

339
-continued

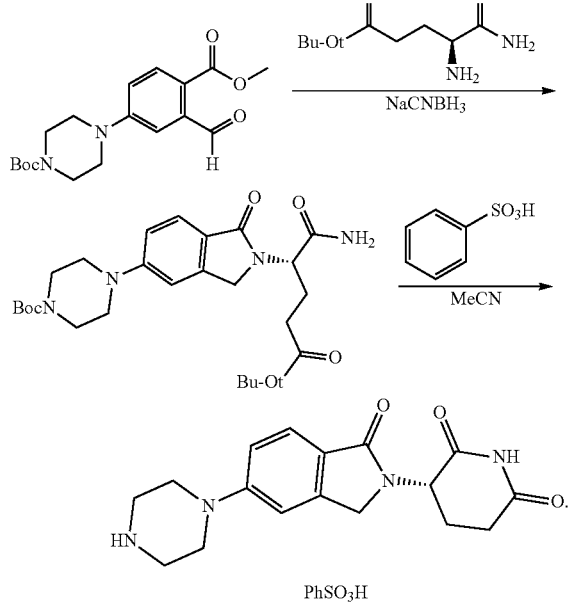

340
-continued

Intermediate 1

Details of using method C in the preparation of Int-1 were described in the following.

Step 1: Preparation of tert-butyl 4-(1-oxo-3H-isobenzofuran-5-yl)piperazine-1-carboxylate The mixture of 5-fluoro-3H-isobenzofuran-1-one (4 g, 26.29 mmol, 1 eq) and tert-butyl piperazine-1-carboxylate (5.88 g, 31.55 mmol, 1.2 eq) in DMSO (40 mL) was stirred at 110° C. for 48 hours. LCMS showed 5-fluoro-3H-isobenzofuran-1-one was consumed and the desired MS was detected. The reaction solution was poured into water (200 mL), then filtered to give tert-butyl 4-(1-oxo-3H-isobenzofuran-5-yl)piperazine-1-carboxylate (7 g, 21.99 mmol, 83.6% yield) as a light yellow solid. LCMS: m/z [M+H]$^+$=319.3.

Step 2: Preparation of 4-(4-tert-butoxycarbonylpiperazin-1-yl)-2-(hydroxymethyl)benzoic acid To a solution of tert-butyl 4-(1-oxo-3H-isobenzofuran-5-yl)piperazine-1-carboxylate (3.2 g, 10.05 mmol, 1 eq) in MeOH (20 mL), THF (20 mL) and H$_2$O (20 mL) was added NaOH (1.61 g, 40.21 mmol, 4 eq). The mixture was stirred at 20° C. for 4 h. TLC (PE:EA=2:1, Rf=0.4)) and LCMS indicated tert-butyl 4-(1-oxo-3H-isobenzofuran-5-yl)piperazine-1-carboxylate was consumed completely and one new spot formed. The reaction mixture was diluted with 20 mL of water. Then the mixture was acidized to pH=4-5 and extracted with EA (20 mL×3). The combined organic layers were washed with brine (20 mL×2), dried over Na$_2$SO$_4$, filtered and concentrated under reduced pressure to give compound 4-(4-tert-butoxycarbonylpiperazin-1-yl)-2-(hydroxymethyl)benzoic acid (3.1 g, 9.22 mmol, 91.7% yield) as an off-white solid. LCMS: m/z [M+H]$^+$=263.0; $^1$H NMR (DMSO-d$_6$, 400 MHZ) δ=7.79 (d, J=8.8 Hz, 1H), 7.23 (d, J=2.4 Hz, 1H), 6.82 (dd, J=2.4, 8.8 Hz, 1H), 4.80 (s, 2H), 3.48-3.45 (m, 4H), 3.30-3.28 (m, 4H), 1.43 (s, 9H).

Step 3: General Procedure for Preparation of tert-butyl 4-[3-(hydroxymethyl)-4-methoxycarbonyl-phenyl]piperazine-1-carboxylate To a solution of 4-(4-tert-butoxycarbonylpiperazin-1-yl)-2-(hydroxymethyl)benzoic acid (3.1 g, 9.22 mmol, 1 eq) in MeOH (30 mL) and EtOAc (30 mL) was added diazomethyl (trimethyl)silane (2 M, 13.82 mL, 3 eq) at −10° C. The mixture was stirred at −10° C. for 0.5 h. TLC (Petroleum ether:Ethyl acetate=2:1, R$_f$=0.55) indicated the reactant was consumed completely and one new spot formed. The reaction mixture was diluted with water (50 mL) and extracted with EA (30 mL×2). The combined organic layers were washed with brine (40 mL), dried over $Na_2SO_4$, filtered and concentrated to afford compound tert-butyl 4-[3-(hydroxymethyl)-4-methoxycarbonyl-phenyl]piperazine-1-carboxylate (3 g, 8.56 mmol, 92.9% yield) as a yellow oil. $^1$H NMR (DMSO-$d_6$, 400 MHZ) δ=7.77 (d, J=8.8 Hz, 1H), 7.22 (d, J=2.0 Hz, 1H), 6.82 (dd, J=2.4, 8.8 Hz, 1H), 5.16-5.09 (m, 1H), 4.79-4.78 (m, 2H), 3.73 (s, 3H), 3.46-3.44 (m, 4H), 3.30-3.28 (m, 3H), 1.41 (s, 9H).

Step 4: General Procedure for Preparation of tert-butyl 4-[3-(bromomethyl)-4-methoxycarbonyl-phenyl]piperazine-1-carboxylate To a solution of tert-butyl 4-[3-(hydroxymethyl)-4-methoxycarbonyl-phenyl]piperazine-1-carboxylate (3 g, 8.56 mmol, 1 eq) in THF (50 mL) was added $PPh_3$ (3.37 g, 12.84 mmol, 1.5 eq) and $CBr_4$ (4.26 g, 12.84 mmol, 1.5 eq). The mixture was stirred at 25° C. for 1 h. TLC (Petroleum ether:Ethyl acetate=2:1, $R_f$=0.65) indicated the reactant was consumed. The reaction mixture was diluted with water 100 mL and extracted with EA (50 mL×2). The combined organic layers were washed with brine (50 mL×2), dried over $Na_2SO_4$, filtered and concentrated under reduced pressure to give a residue which was purified by column chromatography (Petroleum ether/Ethyl acetate=50/1 to 15/1) to afford compound tert-butyl 4-[3-(bromomethyl)-4-methoxycarbonyl-phenyl]piperazine-1-carboxylate (2 g, 4.84 mmol, 56.5% yield) as a yellow solid. $^1$H NMR ($CDCl_3$, 400 MHZ) δ=7.86 (d, J=8.8 Hz, 1H), 6.81 (d, J=2.4 Hz, 1H), 6.71 (dd, J=2.4, 8.8 Hz, 1H), 4.89 (s, 2H), 3.82 (s, 3H), 3.53-3.50 (m, 4H), 3.26-3.24 (m, 4H), 1.42 (s, 9H).

Step 5: Preparation of tert-butyl 4-[2-[(3S)-2,6-dioxo-3-piperidyl]-1-oxo-isoindolin-5-yl]piperazine-1-carboxylate To a solution of tert-butyl 4-[3-(bromomethyl)-4-methoxycarbonyl-phenyl]piperazine-1-carboxylate (650 mg, 1.57 mmol, 1 eq) and (3S)-3-aminopiperidine-2,6-dione (388.27 mg, 2.36 mmol, 1.5 eq, HCl) in ACN (20 mL) was added DIEA (609.78 mg, 4.72 mmol, 821.80 uL, 3 eq). The mixture was stirred at 80° C. for 12 h. LC-MS showed that the reactant was consumed completely. LC-MS indicated 42.5% of desired compound was detected. The mixture was concentrated to give a crude product which was purified by reverse perp-HPLC (Column: 330 g Flash Column Welch Ultimate XB_C18 20-40 μm; Flow rate: 100 mL/min; Mobile phase: MeCN/$H_2O$; Gradient B % 10-100% in 60 min; Instrument: TELEDYNE ISCO CombiFlash Rf150) to afford compound tert-butyl 4-[2-[(3S)-2,6-dioxo-3-piperidyl]-1-oxo-isoindolin-5-yl]piperazine-1-carboxylate (1 g, 2.33 mmol, 48.50% yield) as a blue solid. LCMS: m/z [M+H]$^+$=429.3; $^1$H NMR (DMSO-$d_6$, 400 MHZ) δ=10.96 (s, 1H), 7.54 (d, J=8.4 Hz, 1H), 7.09-7.06 (m, 2H), 5.06 (dd, J=5.2, 13.2 Hz, 1H), 4.36-4.32 (m, 1H), 4.24-4.20 (m, 1H), 3.47 (br d, J=5.2 Hz, 4H), 3.30-3.26 (m, 4H), 2.97-2.83 (m, 1H), 2.59 (br d, J=17.2 Hz, 1H), 2.40-2.35 (m, 1H), 1.98-1.94 (m, 1H), 1.43 (s, 9H).

Step 6: Preparation of (3S)-3-(1-oxo-5-piperazin-1-yl-isoindolin-2-yl) piperidine-2,6-dione (Intermediate 1)

To a solution of tert-butyl 4-[2-[(3S)-2,6-dioxo-3-piperidyl]-1-oxo-isoindolin-5-yl]piperazine-1-carboxylate (1 g, 2.33 mmol, 1 eq) in THF (20 mL) was added HCl/EtOAc (4 M, 20 mL, 34.28 eq) at 20° C. The mixture was stirred at 20° C. for 1 h. LC-MS showed that the reactant was consumed completely. LC-MS indicated 96.57% of desired compound was detected. The mixture was concentrated to give compound (3S)-3-(1-oxo-5-piperazin-1-yl-isoindolin-2-yl) piperidine-2,6-dione hydrochloride salt (850 mg, 2.33 mmol, 99.83% yield, HCl) as off-white solid. LCMS: m/z [M+H]$^+$=329.1; 1H NMR (DMSO-$d_6$, 400 MHZ) δ=10.83 (s, 1H), 9.38 (br s, 2H), 7.45 (d, J=8.4 Hz, 1H), 7.03-6.99 (m, 2H), 4.94 (dd, J=5.0, 13.3 Hz, 1H), 4.26-4.22 (m, 1H), 4.13-4.09 (m, 1H), 3.44-3.41 (m, 4H), 3.08 (br s, 4H), 2.78-2.75 (m, 1H), 2.47 (br d, J=16.1 Hz, 1H), 2.26 (dq, J=4.3, 13.1 Hz, 1H), 1.84 (br d, J=4.6 Hz, 1H).

Preparation of tert-butyl 2-fluoro-2-formyl-7-azaspiro[3.5]nonane-7-carboxylate (Intermediate 2)

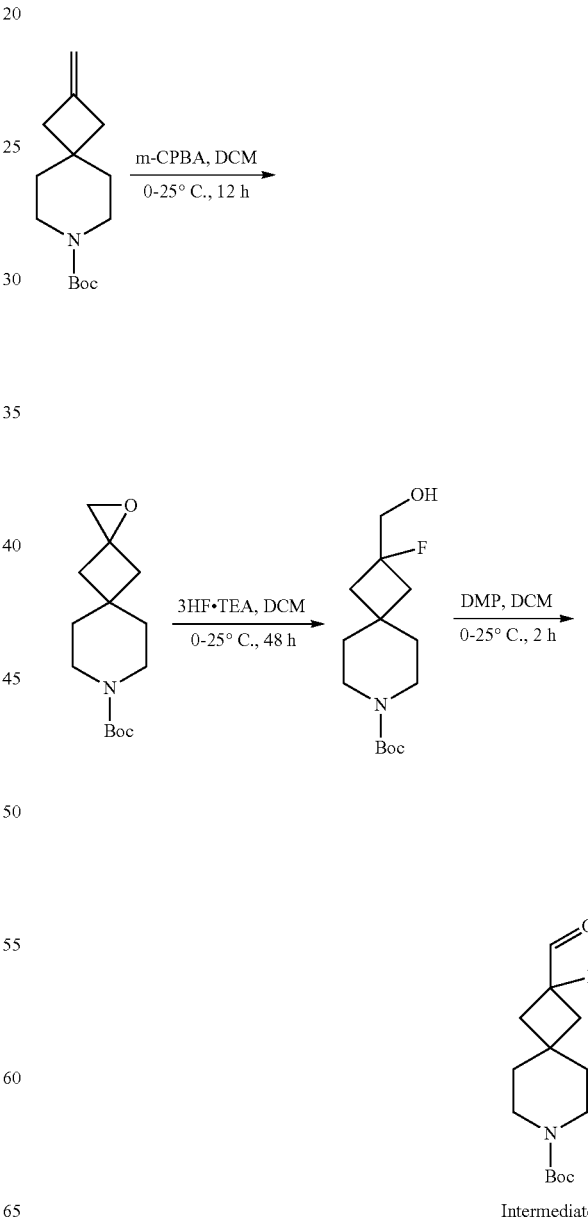

Intermediate 2

Step 1: preparation of tert-butyl 1-oxa-8-azadispiro[2.1.5⁵.1³]undecane-8-carboxylate To a solution of tert-butyl 2-methylene-7-azaspiro[3.5]nonane-7-carboxylate (1.80 g, 7.58 mmol, 1.00 eq) in DCM (20.0 mL) was added m-CPBA (3.08 g, 15.2 mmol, 85% purity, 2.00 eq) at 0° C. The mixture was stirred at 25° C. for 12 hours. TLC (PE:EA=8:1, DNP) indicated complete consumption of the reactant and formation of one new spot. The residue was poured into saturated aqueous Na$_2$SO$_3$ (20.0 mL) at 0° C. and the mixture was stirred for 5 minutes. The aqueous phase was extracted with DCM (20.0 mL*3). The combined organic layers were washed with saturated aqueous NaHCO$_3$ (50.0 mL*2). The combined organic layers were then washed with brine (50.0 mL), dried over anhydrous Na$_2$SO$_4$, filtered and concentrated under reduced pressure to afford the desired compound (2.10 g, 8.29 mmol, 99.36% yield) as a yellow oil. ¹H NMR (400 MHZ, CHLOROFORM-d) δ=3.36 (td, J=5.6, 11.6 Hz, 4H), 2.72 (s, 2H), 2.26-2.16 (m, 4H), 1.66-1.61 (m, 4H), 1.46 (s, 9H).

Step 2: Preparation of tert-butyl 2-fluoro-2-(hydroxymethyl)-7-azaspiro[3.5]nonane-7-carboxylate To a solution of tert-butyl 1-oxa-8-azadispiro[2.1.5⁵.1³]undecane-8-carboxylate (1.90 g, 7.50 mmol, 1.00 eq) in DCM (20.0 mL) was added N,N-diethylethanamine; trihydrofluoride (12.1 g, 75.0 mmol, 12.2 mL, 10.0 eq) at 0° C. The mixture was stirred at 25° C. for 48 hours. TLC (PE:EA=2:1) indicated that complete consumption of the reactant and the formation of one new spot. The reaction mixture was poured into ice-water (200 mL) and the reaction mixture was stirred for 5 minutes. The aqueous phase was extracted with DCM (50.0 mL×3). The combined organic layers were washed with brine (100 mL×2), dried over anhydrous Na$_2$SO$_4$, filtered and concentrated under reduced pressure to give the desired compound (1.80 g, 6.59 mmol, 87.8% yield) as a yellow oil. ¹H NMR (400 MHZ, CHLOROFORM-d) δ=3.73-3.62 (m, 2H), 3.36-3.29 (m, 4H), 2.14-2.04 (m, 4H), 1.70-1.64 (m, 2H), 1.50-1.46 (m, 3H), 1.45 (s, 9H).

Step 3: Preparation of tert-butyl 2-fluoro-2-formyl-7-azaspiro[3.5]nonane-7-carboxylate (Intermediate 2)

To a solution of tert-butyl 2-fluoro-2-(hydroxymethyl)-7-azaspiro[3.5]nonane-7-carboxylate (1.60 g, 5.85 mmol, 1.00 eq) in DCM (10.0 mL) was added DMP (4.97 g, 11.7 mmol, 3.63 mL, 2.00 eq) at 0° C. The reaction mixture was stirred at 25° C. for 2 hours. The residue was poured into saturated aqueous Na$_2$SO$_3$ (100 mL) at 0° C. and stirred for 5 minutes. The aqueous phase was extracted with DCM (30.0 mL×3). The combined organic layers were washed with brine (10.0 mL×2), dried over anhydrous Na$_2$SO$_4$, filtered and concentrated under reduced pressure. The residue was purified by column chromatography (SiO$_2$, Petroleum ether/Ethyl acetate=20/1 to 1/1) to give the desired product (550 mg, crude) as a yellow oil. ¹H NMR (400 MHZ, CHLOROFORM-d) δ=9.82 (d, J=4.4 Hz, 1H), 3.39-3.27 (m, 4H), 2.22-1.89 (m, 4H), 1.73-1.69 (m, 2H), 1.65-1.51 (m, 3H), 1.46 (s, 9H).

Preparation of 1-[[7-[8-ethyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropanecarbaldehyde (Intermediate 3)

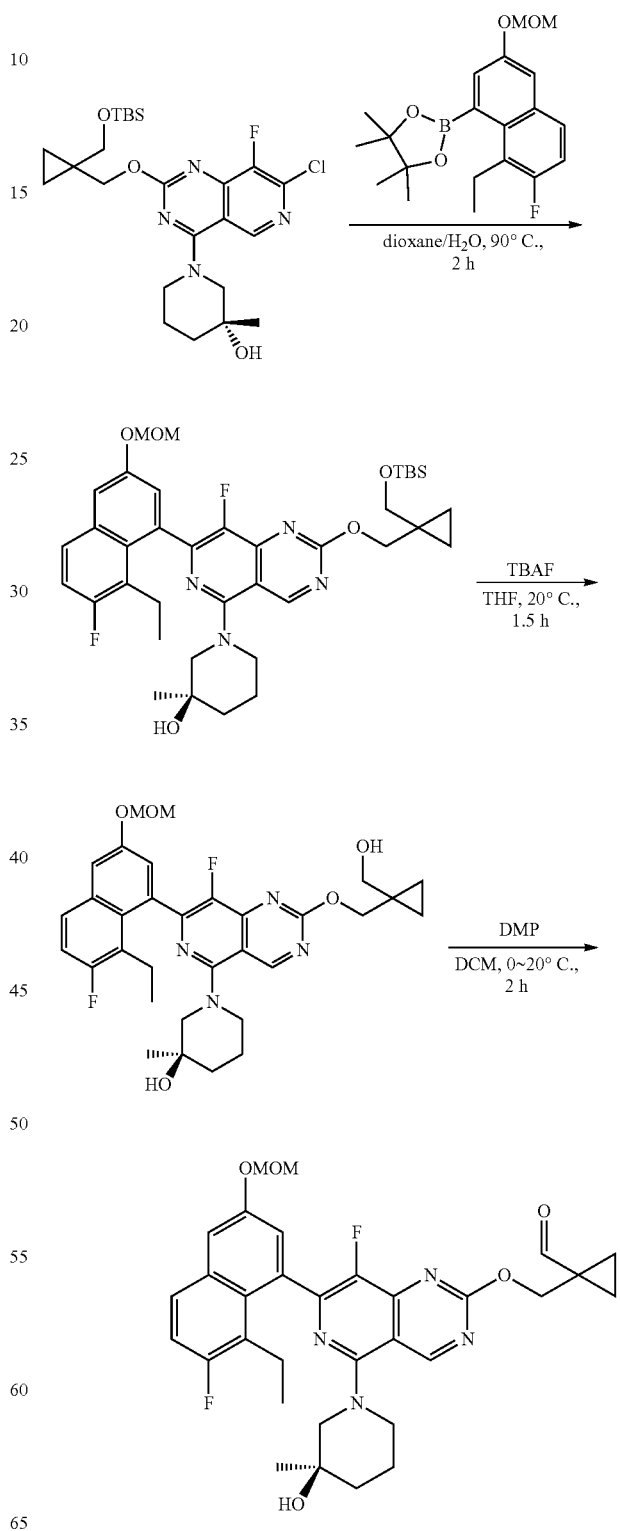

Intermediate 3

Step 1: Preparation of (3R)-1-[2-[[1-[[tert-butyl(dimethyl)silyl]oxymethyl]cyclopropyl]methoxy]-7-[8-ethyl-7-fluoro-3-(methoxymethoxy)-1-naphthyl]-8-fluoro-pyrido[4,3-d]pyrimidin-4-yl]-3-methyl-piperidin-3-ol To a solution of (3R)-1-[2-[1-[[tert-butyl(dimethyl)silyl]oxymethyl]cyclopropyl]methoxy]-7-chloro-8-fluoro-pyrido[4,3-d]pyrimidin-4-yl]-3-methyl-piperidin-3-ol (5.2 g, 10.17 mmol, 1 eq) and 2-[8-ethyl-7-fluoro-3-(methoxymethoxy)-1-naphthyl]-4,4,5,5-tetramethyl-1,3,2-dioxaborolane (4.03 g, 11.19 mmol, 1.1 eq) in dioxane (160 mL) and H₂O (16 mL) was added K₃PO₄ (6.48 g, 30.52 mmol, 3 eq) and [2-(2-aminophenyl)phenyl]palladium(1+); bis(1-adamantyl)-butyl-phosphane; methanesulfonate (740.95 mg, 1.02 mmol, 0.1 eq) under N₂ atmosphere. The reaction mixture was stirred at 90° C. for 2 hours. LCMS indicated that a new peak with desired mass was detected. The organic layers were concentrated to give a residue, which was purified by silica column chromatography (PE/EA=1/0 to 0/1) to afford the desired compound (4.9 g, 6.91 mmol, 67.94% yield) as a yellow oil. ¹H NMR (DMSO-d₆, 400 MHZ) δ=9.23 (d, J=10.4 Hz, 1H), 7.92-7.88 (m, 1H), 7.67 (d, J=2.0 Hz, 1H), 7.44 (t, J=9.2 Hz, 1H), 7.22 (d, J=2.0 Hz, 1H), 5.35 (s, 1H), 4.40-4.33 (m, 3H), 4.29-4.25 (m, 1H), 3.63-3.56 (m, 3H), 3.42 (s, 3H), 2.38-2.36 (m, 1H), 2.30-2.26 (m, 1H), 1.90-1.88 (m, 1H), 1.69-1.67 (m, 1H), 1.66-1.63 (m, 1H), 1.37 (s, 3H), 0.81 (s, 9H), 0.76-0.74 (m, 3H), 0.72-0.70 (m, 2H), 0.52-0.50 (m, 2H), −0.016 (s, 6H).

Step 2: Preparation of (3R)-1-[7-[8-ethyl-7-fluoro-3-(methoxymethoxy)-1-naphthyl]-8-fluoro-2-[[1-(hydroxymethyl)cyclopropyl]methoxy]pyrido[4,3-d]pyrimidin-4-yl]-3-methyl-piperidin-3-ol To a solution of (3R)-1-[2-[[1-[tert-butyl(dimethyl)silyl]oxymethyl]cyclopropyl]methoxy]-7-[8-ethyl-7-fluoro-3-(methoxymethoxy)-1-naphthyl]-8-fluoro-pyrido[4,3-d]pyrimidin-4-yl]-3-methyl-piperidin-3-ol (4.8 g, 6.77 mmol, 1 eq) in THF (60 mL) was added TBAF (1 M, 20.31 mL, 3 eq) at 20° C. The mixture was stirred at 20° C. for 1.5 hours. LCMS indicated complete consumption of the reactant and the desired mass was detected. The mixture was extracted with EA (100 mL*2) and H₂O (200 mL). The combined organic layers were washed with brine 200 mL (100 mL*2), dried over anhydrous Na₂SO₄, filtered and concentrated under reduced pressure to give a residue. The residue was purified by silica column chromatography (PE/EA=I/O to 0/1) to afford the desired product (3.5 g, 5.89 mmol, 86.93% yield) as a yellow solid. ¹H NMR (CDCl₃, 400 MHZ) δ=9.19 (d, J=9.6 Hz, 1H), 7.72-7.66 (m, 1H), 7.52 (d, J=2.4 Hz, 1H), 7.26-7.21 (m, 2H), 5.32-5.27 (m, 2H), 4.70-4.60 (m, 1H), 4.56-4.43 (m, 2H), 4.41-4.32 (m, 1H), 3.57-3.52 (m, 1H), 3.52 (s, 3H), 3.49-3.41 (m, 2H), 2.58-2.42 (m, 1H), 2.28-2.07 (m, 3H), 1.96-1.87 (m, 2H), 1.37 (s, 3H), 0.90-0.82 (m, 4H), 0.73-0.66 (m, 2H), 0.64-0.57 (m, 2H).

Step 3: Preparation of 1-[[7-[8-ethyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropanecarbaldehyde (Intermediate 3)

To a solution of (3R)-1-[7-[8-ethyl-7-fluoro-3-(methoxymethoxy)-1-naphthyl]-8-fluoro-2-[[1-(hydroxymethyl)cyclopropyl]methoxy]pyrido[4,3-d]pyrimidin-4-yl]-3-methyl-piperidin-3-ol (3.4 g, 5.72 mmol, 1 eq) in DCM (70 mL) was added DMP (3.15 g, 7.43 mmol, 2.30 mL, 1.3 eq) at 0° C. and the reaction mixture was stirred for 2 hours at 20° C. LCMS indicated complete consumption of the reactant and a new peak with the desired mass was detected. The mixture was filtered and concentrated to get a residue, which was purified by silica gel column chromatography (PE/EA=0/1 to 1/1) to afford the desired compound (2.7 g, 4.15 mmol, 72.51% yield, 91% purity) as a yellow solid. ¹H NMR (CDCl₃, 400 MHz) δ=9.25-9.21 (m, 1H), 9.20-9.15 (m, 1H), 7.72-7.64 (m, 1H), 7.54-7.51 (m, 1H), 7.26-7.21 (m, 2H), 5.34-5.27 (m, 2H), 4.82-4.68 (m, 2H), 4.50-4.38 (m, 2H), 3.56-3.53 (m, 1H), 3.49-3.39 (m, 1H), 3.37-3.25 (m, 1H), 2.81-2.65 (m, 1H), 2.58-2.46 (m, 1H), 2.28-2.18 (m, 1H), 2.15-2.08 (m, 1H), 1.93-1.84 (m, 1H), 1.82-1.61 (m, 3H), 1.41-1.37 (m, 2H), 1.36 (s, 3H), 1.34-1.30 (m, 2H), 0.89-0.82 (m, 3H).

Preparation of (3S)-3-[5-[4-(7-azaspiro[3.5]nonan-2-ylmethyl)piperazin-1-yl]-1-oxo-isoindolin-2-yl]piperidine-2,6-dione (Intermediate 4)

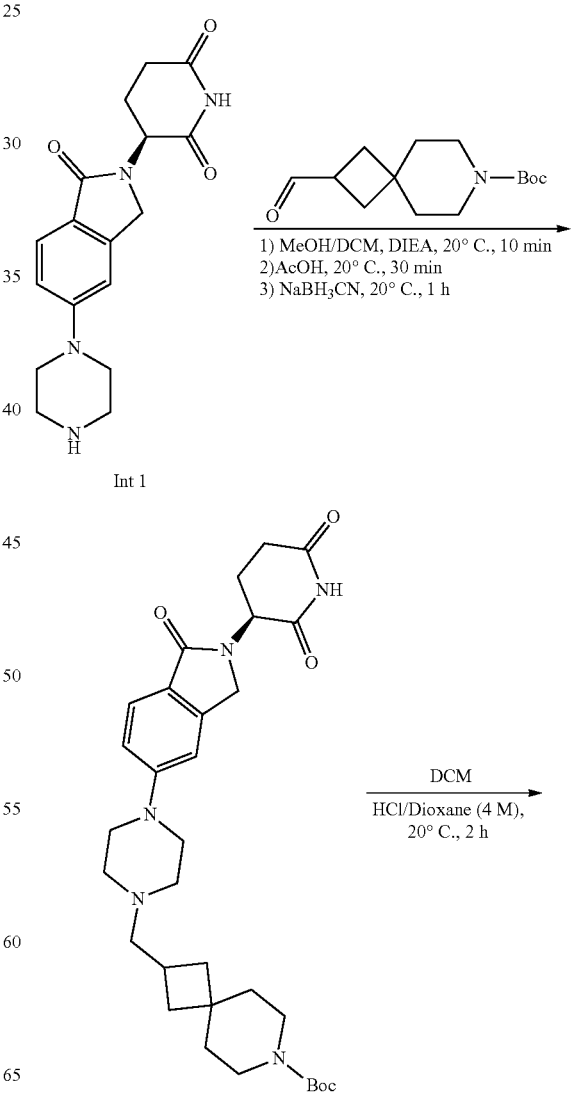

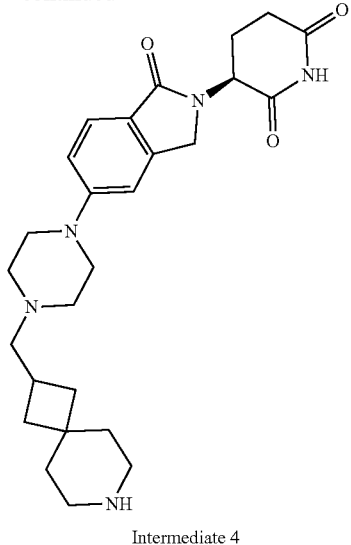

Intermediate 4

Step 1: Preparation of tert-butyl 2-[[4-[2-[(3S)-2,6-dioxo-3-piperidyl]-1-oxo-isoindolin-5-yl]piperazin-1-yl]methyl]-7-azaspiro[3.5]nonane-7-carboxylate DIEA (3.45 g, 26.6 mmol, 4.65 mL, 0.58 eq) was added to a mixture of (3S)-3-(1-oxo-5-piperazin-1-yl-isoindolin-2-yl)piperidine-2,6-dione (15 g, 45.6 mmol, 1 eq) in DCM (100 mL) and MeOH (100 mL). After 1 minute, tert-butyl 2-formyl-7-azaspiro[3.5]nonane-7-carboxylate (6.75 g, 26.6 mmol, 0.58 eq) and AcOH (4.80 g, 79.9 mmol, 4.58 mL, 1.75 eq) were added. The reaction mixture was stirred 20° C. for 30 minutes. NaBH$_3$CN (2.02 g, 32.2 mmol) was then added, and the mixture was stirred for another 1 hour. LCMS indicated that a new peak with peak area of ~92.9% with the desired mass was detected. The mixture was diluted with ethyl acetate (500 mL), washed with saturated bicarbonate sodium solution (300 mL*2), dried over anhydrous sodium sulfate and concentrated under reduced pressure to give tert-butyl 2-[[4-[2-[(3S)-2,6-dioxo-3-piperidyl]-1-oxo-isoindolin-5-yl]piperazin-1-yl]methyl]-7-azaspiro[3.5]nonane-7-carboxylate (15 g, 25.7 mmol, 56.3% yield, 97% purity) as a white solid.

Step 2: Preparation of (3S)-3-[5-[4-(7-azaspiro[3.5]nonan-2-ylmethyl)piperazin-1-yl]-1-oxo-isoindolin-2-yl]piperidine-2,6-dione (Intermediate 4)

To a solution of tert-butyl 2-[[4-[2-[(3S)-2,6-dioxo-3-piperidyl]-1-oxo-isoindolin-5-yl]piperazin-1-yl]methyl]-7-azaspiro[3.5]nonane-7-carboxylate (12.3 g, 21.7 mmol, 1 eq) in dioxane (100 mL) was added HCl solution (4 M in dioxane, 100 mL, 18.4 eq). The mixture was stirred at 20° C. for 1 hour. LCMS showed a new peak of 86% peak area with the desired mass. The mixture was concentrated to afford (3S)-3-[5-[4-(7-azaspiro[3.5]nonan-2-ylmethyl)piperazin-1-yl]-1-oxo-isoindolin-2-yl]piperidine-2,6-dione (11.7 g, 21.7 mmol, 99.9% yield, 2HCl) as a white solid. $^1$H NMR (CD$_3$OD, 400 MHZ) δ=7.68 (d, J=8.4 Hz, 1H), 7.22-7.12 (m, 2H), 5.14-5.07 (m, 1H), 4.50-4.37 (m, 2H), 4.03 (br d, J=12.4 Hz, 2H), 3.65-3.59 (m, 2H), 3.34 (br d, J=7.2 Hz, 2H), 3.30-3.23 (m, 2H), 3.22 (br s, 5H), 2.96-2.84 (m, 2H), 2.82-2.72 (m, 1H), 2.54-2.41 (m, 1H), 2.28-2.19 (m, 2H), 2.19-2.11 (m, 1H), 1.98-1.92 (m, 2H), 1.91-1.70 (m, 5H).

Preparation of (3S)-3-[5-[4-[(2-fluoro-7-azaspiro[3.5]nonan-2-yl)methyl]piperazin-1-yl]-1-oxo-isoindolin-2-yl]piperidine-2,6-dione (Intermediate 5)

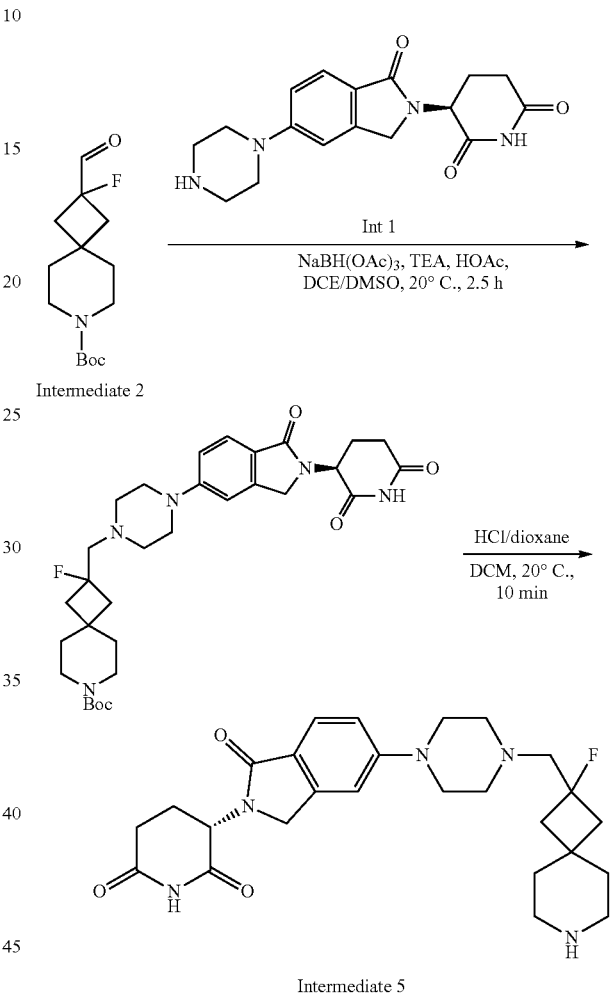

Intermediate 5

Step 1: Preparation of tert-butyl 2-[[4-[2-[(3S)-2,6-dioxo-3-piperidyl]-1-oxo-isoindolin-5-yl]piperazin-1-yl]methyl]-2-fluoro-7-azaspiro[3.5]nonane-7-carboxylate The solution of (3S)-3-(1-oxo-5-piperazin-1-yl-isoindolin-2-yl)piperidine-2,6-dione (4.9 g, 10.45 mmol, 1 eq) and DIEA (1.35 g, 10.45 mmol, 1.82 mL, 1 eq) in DMSO (30 mL) and DCE (70 mL) was stirred at 20° C. for 10 minutes. Then, AcOH (1.25 g, 20.89 mmol, 1.20 mL, 2 eq) and tert-butyl 2-fluoro-2-formyl-7-azaspiro[3.5]nonane-7-carboxylate (3.27 g, 12.04 mmol, 1.15 eq) was added and the mixture was stirred at 20° C. for 20 minutes followed by addition of NaBH(OAc)$_3$ (6.64 g, 31.34 mmol, 3 eq). The reaction mixture was stirred at 20° C. for 2 hours. LCMS showed the reactant was fully consumed and a new peak with desired mass was detected. The reaction mixture was concentrated under reduced pressure to give a residue. The residue was purified by reversed-phase HPLC (0.1% FA condition) afford the desired compound (3.2 g, 5.48 mmol, 52.48% yield) as a white solid. $^1$H NMR (CD$_3$OD, 400 MHZ) δ=7.68 (d, J=9.2 Hz, 1H), 7.26-7.00 (m, 2H), 5.14-5.07 (m, 1H), 4.82-4.69 (m, 2H), 4.42 (d, J=6.4 Hz, 2H), 3.53 (br s, 4H), 3.39 (br s, 2H), 3.36-3.33 (m, 2H), 3.19 (br d, J=12.8 Hz, 4H), 2.89 (br d, J=13.2 Hz, 1H), 2.82-2.73 (m, 1H), 2.53-2.40 (m, 1H), 2.35-2.10 (m, 5H), 1.75-1.66 (m, 2H), 1.58-1.52 (m, 2H), 1.45 (s, 9H).

Step 2: Preparation of (3S)-3-[5-[4-[(2-fluoro-7-azaspiro[3.5]nonan-2-yl)methyl]piperazin-1-yl]-1-oxo-isoindolin-2-yl]piperidine-2,6-dione (Intermediate 5)

To a solution of tert-butyl 2-[[4-[2-[(3S)-2,6-dioxo-3-piperidyl]-1-oxo-isoindolin-5-yl]piperazin-1-yl]methyl]-2-fluoro-7-azaspiro[3.5]nonane-7-carboxylate (3.1 g, 5.31 mmol, 1 eq) in DCM (10 mL) was added and HCl solution (4 M in dioxane, 20.00 mL, 15.06 eq). The mixture was stirred at 20° C. for 10 minutes. LCMS showed the reactant was fully consumed and desired mass was detected. The reaction mixture was concentrated under reduced pressure to afford the desired product as a white solid. $^1$H NMR (CD$_3$OD, 400 MHZ) δ=7.68 (d, J=9.2 Hz, 1H), 7.26-7.00 (m, 2H), 5.14-5.07 (m, 1H), 4.82-4.69 (m, 2H), 4.42 (d, J=6.4 Hz, 2H), 3.53 (br s, 4H), 3.39 (br s, 2H), 3.36-3.33 (m, 2H), 3.19 (br d, J=12.8 Hz, 4H), 2.89 (br d, J=13.2 Hz, 1H), 2.82-2.73 (m, 1H), 2.53-2.40 (m, 1H), 2.35-2.10 (m, 5H), 1.75-1.66 (m, 2H), 1.58-1.52 (m, 2H), 1.45 (s, 9H).

Preparation of 1-[[7-[8-ethyl-7-fluoro-3-(methoxymethoxy)-1-naphthyl]-8-fluoro-4-[(6S)-6-hydroxy-6-methyl-1,4-oxazepan-4-yl]pyrido[4,3-d]pyrimidin-2-yl]oxymethyl] cyclopropanecarbaldehyde (Intermediate 6)

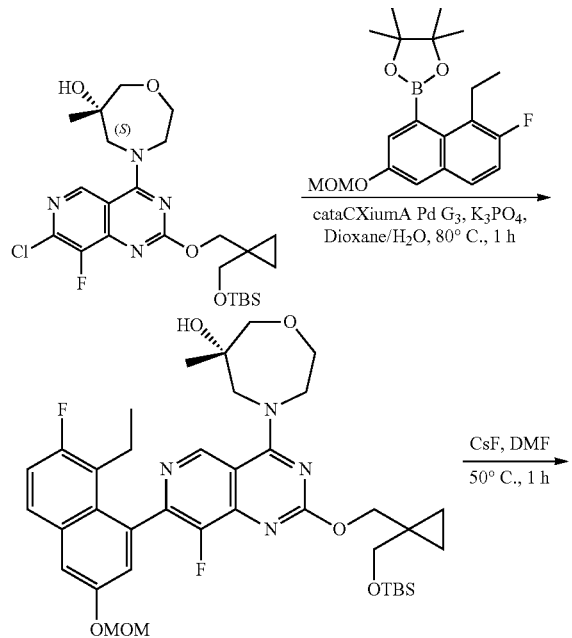

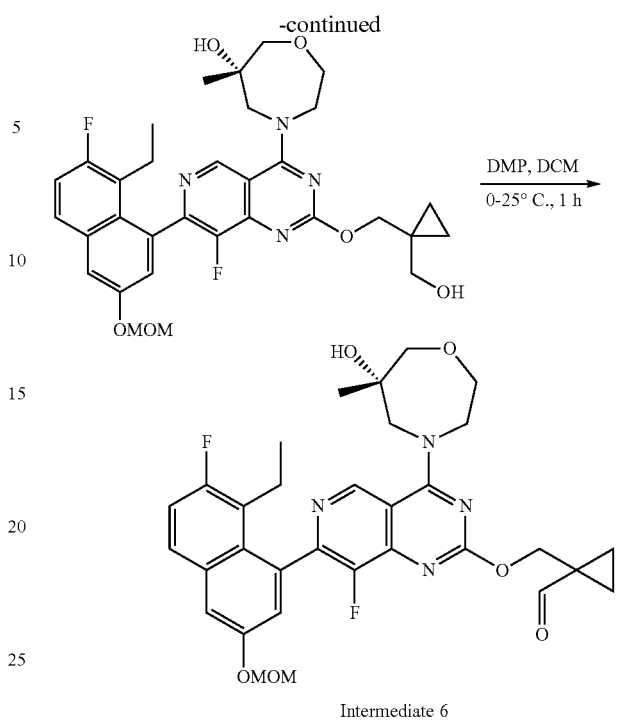

Intermediate 6

Step 1: Preparation of (6S)-4-[2-[[1-[tert-butyl(dimethyl)silyl]oxymethyl]cyclopropyl]methoxy]-7-[8-ethyl-7-fluoro-3-(methoxymethoxy)-1-naphthyl]-8-fluoro-pyrido[4,3-d]pyrimidin-4-yl]-6-methyl-1,4-oxazepan-6-ol A mixture of (6S)-4-[2-[[1-[[tert-butyl(dimethyl)silyl]oxymethyl]cyclopropyl]methoxy]-7-chloro-8-fluoro-pyrido[4,3-d]pyrimidin-4-yl]-6-methyl-1,4-oxazepan-6-ol (400 mg, 758 μmol, 1.00 eq), 2-[8-ethyl-7-fluoro-3-(methoxymethoxy)-1-naphthyl]-4,4,5,5-tetramethyl-1,3,2-dioxaborolane (273 mg, 758 μmol, 1.00 eq), [2-(2-aminophenyl)phenyl]palladium(1+); bis(1-adamantyl)-butyl-phosphane; methanesulfonate (110 mg, 151 μmol, 0.20 eq) and K$_3$PO$_4$ (483 mg, 2.28 mmol, 3.00 eq) in dioxane (7 mL) and H$_2$O (1 mL) was degassed and purged with N$_2$ for 3 times, and then the mixture was stirred at 80° C. for 1 hour under N$_2$ atmosphere. LCMS showed complete consumption of the reactant and a new peak with peak area of 61.0% with the desired mass was detected. The reaction mixture was quenched by water 50 mL at 0° C., and then diluted with EA (10 mL) and extracted with EA (20 mL*2). The combined organic layers were washed with water 60 mL (30 mL*2), dried over anhydrous Na$_2$SO$_4$, filtered and concentrated under reduced pressure to give a residue. The residue was purified by prep-TLC (SiO2, PE:EA=1:1) to give (6S)-4-[2-[[1-[tert-butyl(dimethyl)silyl]oxymethyl]cyclopropyl]methoxy]-7-[8-ethyl-7-fluoro-3-(methoxymethoxy)-1-naphthyl]-8-fluoro-pyrido[4,3-d]pyrimidin-4-yl]-6-methyl-1,4-oxazepan-6-ol (500 mg, 689 μmol, 90.9% yield) as a yellow oil.

Step 2: Preparation of (6S)-4-[7-[8-ethyl-7-fluoro-3-(methoxymethoxy)-1-naphthyl]-8-fluoro-2-[[1-(hydroxymethyl)cyclopropyl]methoxy]pyrido[4,3-d]pyrimidin-4-yl]-6-methyl-1,4-oxazepan-6-ol To a solution of (6S)-4-[2-[[1-[[tert-butyl(dimethyl)silyl]oxymethyl]cyclopropyl]methoxy]-7-[8-ethyl-7-fluoro-3-

(methoxymethoxy)-1-naphthyl]-8-fluoro-pyrido[4,3-d]pyrimidin-4-yl]-6-methyl-1,4-oxazepan-6-ol (490 mg, 675 umol, 1.00 eq) in DMF (5 mL) was added CsF (2.05 g, 13.5 mmol, 499 μL, 20.0 eq). The mixture was stirred at 50° C. for 1 hour. LCMS showed complete consumption of the reactant and a new peak with peak area of 82.9% with the desired mass was detected. The reaction mixture was quenched by water (100 mL) at 0° C., and then diluted with EA 10 mL and extracted with EA 100 mL (50 mL*2). The combined organic layers were washed with water (50 mL*2), dried over anhydrous Na$_2$SO$_4$, filtered and concentrated under reduced pressure to give (6S)-4-[7-[8-ethyl-7-fluoro-3-(methoxymethoxy)-1-naphthyl]-8-fluoro-2-[[1-(hydroxymethyl)cyclopropyl]methoxy]pyrido[4,3-d]pyrimidin-4-yl]-6-methyl-1,4-oxazepan-6-ol (410 mg, 671 μmol, 99.3% yield) as a yellow oil.

Step 3: Preparation of 1-[[7-[8-ethyl-7-fluoro-3-(methoxymethoxy)-1-naphthyl]-8-fluoro-4-[(6S)-6-hydroxy-6-methyl-1,4-oxazepan-4-yl]pyrido[4,3-d]pyrimidin-2-yl]oxymethyl] cyclopropanecarbaldehyde (Intermediate 6)

To a solution of (6S)-4-[[7-[8-ethyl-7-fluoro-3-(methoxymethoxy)-1-naphthyl]-8-fluoro-2-[1-(hydroxymethyl)cyclopropyl]methoxy]pyrido[4,3-d]pyrimidin-4-yl]-6-methyl-1,4-oxazepan-6-ol (400 mg, 655 μmol, 1.00 eq) in DCM (5 mL) was added DMP (600 mg, 1.41 mmol, 438 μL, 2.16 eq) at 0° C. The mixture was stirred at 25° C. for 1 hour. LCMS showed complete consumption of the reactant and a new peak with peak area of 77.7% with the desired mass was detected. The reaction mixture was quenched by saturated aqueous Na$_2$S203 (50 mL) at 0° C., and then diluted with DCM (10 mL) and extracted with DCM (20 mL*2). The combined organic layers were washed with water (30 mL*2), dried over anhydrous Na$_2$SO$_4$, filtered and concentrated under reduced pressure to give a crude residue. The residue was purified by prep-TLC (SiO$_2$, PE:EA=0:1) to give 1-[[7-[8-ethyl-7-fluoro-3-(methoxymethoxy)-1-naphthyl]-8-fluoro-4-[(6S)-6-hydroxy-6-methyl-1,4-oxazepan-4-yl]pyrido[4,3-d]pyrimidin-2-yl]oxymethyl]cyclopropanecarbaldehyde (320 mg, 525 μmol, 80.2% yield) as a yellow solid. Preparation of (R)-1-(((7-(7,8-difluoro-3-(methoxymethoxy)naphthalen-1-yl)-8-fluoro-4-(3-hydroxy-3-methylpiperidin-1-yl)pyrido[4,3-d]pyrimidin-2-yl)oxy) methyl)cyclopropane-1-carbaldehyde (Intermediate 7)

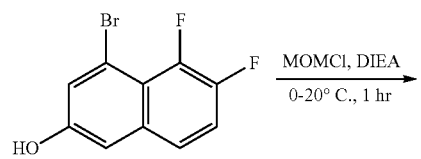

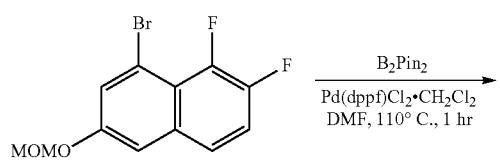

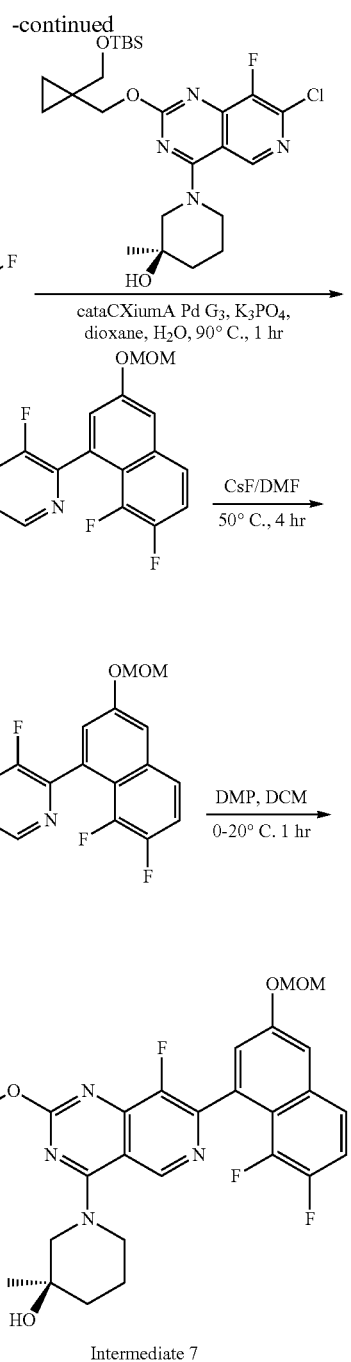

Intermediate 7

Step 1: Preparation of 8-bromo-1,2-difluoro-6-(methoxymethoxy)naphthalene

To a mixture of 4-bromo-5,6-difluoro-naphthalen-2-ol (1.6 g, 6.18 mmol, 1 eq), DIPEA (2.39 g, 18.5 mmol, 3.23 mL, 3 eq) in DCM (30 mL) was added bromo(methoxy)methane (1.54 g, 12.35 mmol, 1.01 mL, 2 eq) dropwise at 0° C. Then the mixture was stirred at 20° C. for 1 hour. LCMS showed complete consumption of the reactant and detection of the desired product. The reaction mixture was poured into water (40 mL) and extracted with DCM (20 mL*3). Then the organic layers were combined and washed with brine (30 mL), dried over anhydrous Na$_2$SO$_4$, concentrated under reduced pressure to afford the crude residue. The crude residue was purified by column chromatography (SiO$_2$, PE:EA=20:1 to PE:EA=10:1). 8-bromo-1,2-difluoro-6-(methoxymethoxy)naphthalene (1.8 g, 5.94 mmol, 96.2% yield) as yellow solid. $^1$H NMR (400 MHZ, CHLOROFORM-d) δ=7.62-7.57 (m, 1H), 7.52-7.44 (m, 1H), 7.36-7.29 (m, 2H), 5.27 (s, 2H), 3.52 (s, 3H).

Step 2: Preparation of 2-(7,8-difluoro-3-(methoxymethoxy)naphthalen-1-yl)-4,4,5,5-tetramethyl-1,3,2-dioxaborolane To a mixture of 8-bromo-1,2-difluoro-6-(methoxymethoxy)naphthalene (1.6 g, 5.28 mmol, 1 eq), 4,4,5,5-tetramethyl-2-(4,4,5,5-tetramethyl-1,3,2-dioxaborolan-2-yl)-1,3,2-dioxaborolane (2.68 g, 10.6 mmol, 2 eq) in DMF (45 mL) was added KOAc (1.30 g, 13.2 mmol, 2.5 eq), and Pd(dppf)Cl$_2$·CH$_2$Cl$_2$ (431 mg, 528 µmol, 0.1 eq). The reaction mixture was stirred at 110° C. for 1 hour under N$_2$ atmosphere. TLC (Rf=0.4, PE:EA=10:1) showed that complete consumption of the reactant and a new spot was formed. The reaction mixture was poured into water (450 mL) and extracted with EA (50 mL*3). Then the organic layers were combined and washed with brine (100 mL), dried over anhydrous Na$_2$SO$_4$, concentrated under reduced pressure to afford the crude residue, which was purified by column chromatography (SiO$_2$, PE:EA=1:0 to PE:EA=100:1) to afford 2-(7,8-difluoro-3-(methoxymethoxy)naphthalen-1-yl)-4,4,5,5-tetramethyl-1,3,2-dioxaborolane (1.7 g, 4.85 mmol, 92.0% yield) as a white solid. $^1$H NMR (400 MHz, CHLOROFORM-d) δ=7.47 (ddd, J=1.6, 4.8, 9.2 Hz, 1H), 7.43 (d, J=2.4 Hz, 1H), 7.41-7.39 (m, 1H), 7.33-7.27 (m, 1H), 5.29 (s, 2H), 3.51 (s, 3H), 1.45 (s, 12H).

Step 3: Preparation of (R)-1-(2-((1-(((tert-butyldimethylsilyl)oxy)methyl)cyclopropyl)methoxy)-7-(7,8-difluoro-3-(methoxymethoxy)naphthalen-1-yl)-8-fluoropyrido[4,3-d]pyrimidin-4-yl)-3-methylpiperidin-3-ol To a mixture of (3R)-1-[2-[[1-[[tert-butyl(dimethyl)silyl]oxymethyl]cyclopropyl]methoxy]-7-chloro-8-fluoro-pyrido[4,3-d]pyrimidin-4-yl]-3-methyl-piperidin-3-ol (1.8 g, 3.52 mmol, 1 eq), 2-[7,8-difluoro-3-(methoxymethoxy)-1-naphthyl]-4,4,5,5-tetramethyl-1,3,2-dioxaborolane (1.5 g, 4.28 mmol, 1.22 eq) in dioxane (30 mL) was added [2-(2-aminophenyl)phenyl]palladium(1+) bis(1-adamantyl)-butyl-phosphane; methanesulfonate (256 mg, 352 µmol, 0.1 eq), K$_3$PO$_4$ (2.24 g, 10.6 mmol, 3 eq) in H$_2$O (3 mL). The reaction mixture was stirred at 90° C. for 1 hour. LCMS indicated complete consumption of the reactant and detection of the desired product. The reaction mixture was poured into water (50 mL) and extracted with EA (30 mL×3). The organic layers were combined and washed with brine (30 mL), dried over anhydrous Na$_2$SO$_4$, concentrated under reduced pressure to afford the crude residue. The crude was purified by column chromatography (SiO$_2$, PE:EA=10:1 to PE:EA=2:1) to afford (R)-1-(2-((1-(((tert-butyldimethylsilyl)oxy)methyl)cyclopropyl)methoxy)-7-(7,8-difluoro-3-(methoxymethoxy)naphthalen-1-yl)-8-fluoropyrido[4,3-d]pyrimidin-4-yl)-3-methylpiperidin-3-ol (2 g, 2.63 mmol, 67.96% yield, 92% purity) as a yellow oil. $^1$H NMR (400 MHZ, DMSO-d$_6$) δ=9.24 (d, J=2.8 Hz, 1H), 7.87 (dd, J=5.0, 8.8 Hz, 1H), 7.75 (s, 1H), 7.70-7.63 (m, 1H), 7.44 (s, 1H), 5.39 (s, 2H), 4.72 (d, J=18.6 Hz, 1H), 4.40-4.22 (m, 3H), 3.63-3.54 (m, 7H), 3.44 (s, 3H), 3.42-3.34 (m, 2H), 1.75-1.62 (m, 3H), 1.15-1.13 (m, 1H), 0.82 (s, 9H), 0.61-0.58 (m, 2H), 0.56-0.49 (m, 2H), −0.01 (s, 6H).

Step 4: Preparation of (R)-1-(7-(7,8-difluoro-3-(methoxymethoxy)naphthalen-1-yl)-8-fluoro-2-((1-(hydroxymethyl)cyclopropyl)methoxy)pyrido[4,3-d]pyrimidin-4-yl)-3-methylpiperidin-3-ol To a mixture of (3R)-1-[2-[[1-[tert-butyl(dimethyl)silyl]oxymethyl]cyclopropyl]methoxy]-7-[7,8-difluoro-3-(methoxymethoxy)-1-naphthyl]-8-fluoro-pyrido[4,3-d]pyrimidin-4-yl]-3-methyl-piperidin-3-ol (1.8 g, 2.58 mmol, 1 eq) in DMF (30 mL) was added CsF (1.96 g, 12.9 mmol, 4759 µL, 5 eq). The reaction mixture was stirred at 50° C. for 4 hours. LCMS showed complete consumption of the reactant and detection of the desired product. The reaction mixture was poured into water (300 mL) and extracted with DCM:MeOH (10:1, 50 mL*3). The organic layers were combined and washed with brine (30 mL), dried over anhydrous Na$_2$SO$_4$, concentrated under reduced pressure to afford the crude residue, which was purified by column chromatography (SiO$_2$, PE:EA=5:1 to PE: EA=1:2). The desired compound (1.1 g, 1.80 mmol, 63.5% yield, 95.6% purity) as a white solid. $^1$H NMR (400 MHZ, CHLOROFORM-d) δ=9.20 (d, J=7.8 Hz, 1H), 8.03 (s, 1H), 7.58 (ddd, J=1.5, 4.8, 9.2 Hz, 1H), 7.52 (t, J=2.0 Hz, 1H), 7.43-7.38 (m, 1H), 7.38-7.32 (m, 1H), 5.34-5.30 (m, 2H), 4.70 (br d, J=12.2 Hz, 1H), 4.55-4.43 (m, 2H), 4.32 (br d, J=11.8 Hz, 1H), 3.56-3.50 (m, 4H), 3.46 (br t, J=11.6 Hz, 1H), 3.39-3.28 (m, 2H), 2.20-2.08 (m, 1H), 1.91 (br d, J=13.8 Hz, 1H), 1.84-1.76 (m, 1H), 1.70 (dt, J=4.4, 12.8 Hz, 2H), 1.37 (s, 3H), 0.74-0.65 (m, 2H), 0.64-0.56 (m, 2H).

Step 5: Preparation of (R)-1-(((7-(7,8-difluoro-3-(methoxymethoxy)naphthalen-1-yl)-8-fluoro-4-(3-hydroxy-3-methylpiperidin-1-yl)pyrido[4,3-d]pyrimidin-2-yl)oxy)methyl)cyclopropane-1-carbaldehyde (Intermediate 7)

To a mixture of (3R)-1-[7-[7,8-difluoro-3-(methoxymethoxy)-1-naphthyl]-8-fluoro-2-[[1-(hydroxymethyl)cyclopropyl]methoxy]pyrido[4,3-d]pyrimidin-4-yl]-3-methyl-piperidin-3-ol (1 g, 1.71 mmol, 1 eq) in DCM (10 mL) was added DMP (1.45 g, 3.42 mmol, 1.06 mL, 2 eq) at 0° C. The reaction mixture was stirred at 20° C. for 1 hour. LCMS showed complete consumption of the reactant and detection of the desired product. The reaction was quenched by saturated Na$_2$SO$_3$ aqueous solution (50 mL) and extracted with DCM (30 mL*3). The organic layers were combined and washed with brine (30 mL), dried over anhydrous Na$_2$SO$_4$, concentrated under reduced pressure to afford the crude residue, which was purified by column chromatography (SiO$_2$, PE:EA=5:1 to PE:EA=1:2). (R)-1-(((7-(7,8-difluoro-3-(methoxymethoxy)naphthalen-1-yl)-8-fluoro-4-(3-hydroxy-3-methylpiperidin-1-yl)pyrido[4,3-d]pyrimidin-2-yl)oxy)methyl)cyclopropane-1-carbaldehyde (710 mg, 1.22 mmol, 71.25% yield) as a white solid. $^1$H NMR (400 MHZ, CHLOROFORM-d) δ=9.26 (d, J=4.2 Hz, 1H), 9.19 (d, J=7.8 Hz, 1H), 7.62-7.55 (m, 1H), 7.53 (s, 1H), 7.43-7.31 (m, 2H), 5.37-5.26 (m, 2H), 4.89-4.62 (m, 2H), 4.53-4.36 (m, 2H), 3.53 (s, 3H), 3.49-3.39 (m, 1H), 3.31 (d, J=13.4 Hz, 1H), 3.04-2.69 (m, 1H), 2.16-2.06 (m, 1H), 1.90 (br d, J=13.8 Hz, 1H), 1.79-1.68 (m, 2H).

Preparation of (R)-1-(((7-(8-ethyl-3-(methoxymethoxy)naphthalen-1-yl)-8-fluoro-4-(3-hydroxy-3-methylpiperidin-1-yl)pyrido[4,3-d]pyrimidin-2-yl)oxy)methyl)cyclopropane-1-carbaldehyde (Intermediate 8)

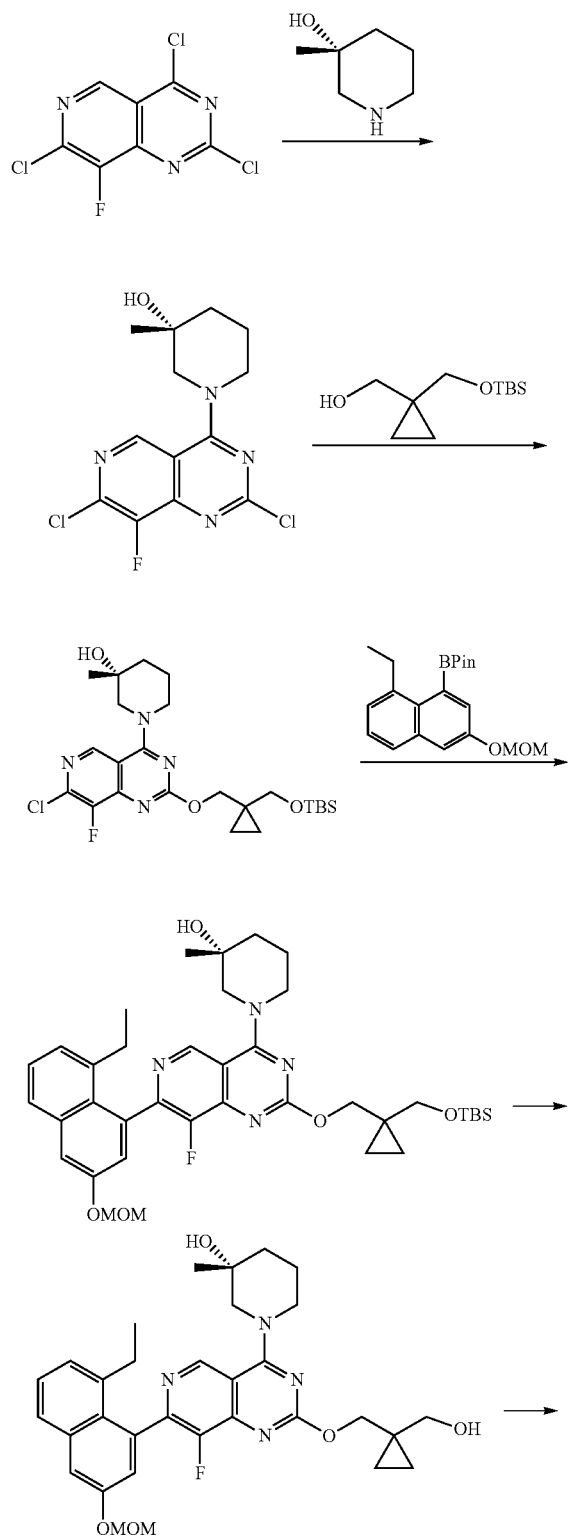

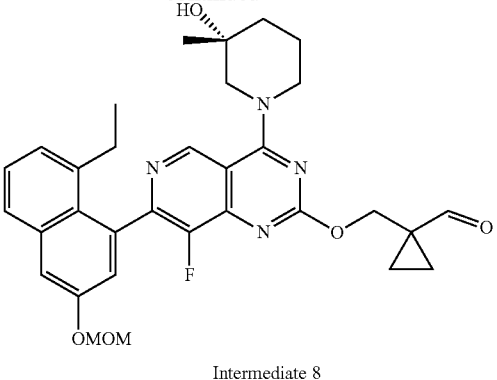

Intermediate 8

Step 1: Preparation of (R)-1-(2,7-dichloro-8-fluoro-pyrido[4,3-d]pyrimidin-4-yl)-3-methyl piperidin-3-ol To a solution of 2,4,7-trichloro-8-fluoropyrido[4,3-d]pyrimidine (6 g, 23.8 mmol) in DCM (20 mL) was added DIEA (10.1 g, 78.5 mmol) and (3R)-3-methylpiperidin-3-ol hydrochloride (3.97 g, 26.2 mmol) under nitrogen at 0° C. The reaction mixture was stirred at 0° C. for 2 hours. The reaction was quenched with water and extracted with EA. The organic phase was washed with brine and dried over $Na_2SO_4$. The solution was concentrated in vacuum and the residue was purified by flash chromatography on silica gel with PE:EA=2:1 to give the desired compound (7.3 g, 92.6% yield) as a white solid. LC/MS: 330.8 $[M+H]^+$.

Step 2: Preparation of (R)-1-(2-((1-(((tert-butyldimethylsilyl)oxy)methyl)cyclopropyl)methoxy)-7-chloro-8-fluoropyrido[4,3-d]pyrimidin-4-yl)-3-methylpiperidin-3-ol To a solution of (1-{[(tert-butyldimethylsilyl)oxy]methyl}cyclopropyl)methanol (5.4 g, 24.7 mmol) in THF (50 mL) was added NaH (1.9 g, 60%, 47.5 mmol) at 0° C. The mixture was stirred at 0° C. for 15 minutes and (R)-1-(2,7-dichloro-8-fluoropyrido[4,3-d]pyrimidin-4-yl)-3-methylpiperidin-3-ol (6.3 g, 19.0 mmol) was added. The reaction mixture was stirred at 25° C. for 2 hours. The reaction was quenched with water and extracted with EA. The organic phase was washed with brine and dried over $Na_2SO_4$. The solution was concentrated in vacuum and the residue was purified by flash chromatography on silica gel with PE:EA=1:1 to give the desired compound (7.8 g, 80.5% yield) as a white solid. LC/MS: 510.8 $[M+H]^+$.

Step 3: Preparation of (R)-1-(2-((1-(((tert-butyldimethylsilyl)oxy)methyl)cyclopropyl)methoxy)-7-(8-ethyl-3-(methoxymethoxy)naphthalen-1-yl)-8-fluoropyrido[4,3-d]pyrimidin-4-yl)-3-methyl piperidin-3-ol To a solution of (R)-1-(2-((1-(((tert-butyldimethylsilyl)oxy)methyl)cyclopropyl)methoxy)-7-chloro-8-fluoropyrido[4,3-d]pyrimidin-4-yl)-3-methylpiperidin-3-ol (2 g, 3.9 mmol) and 2-(8-ethyl-3-(methoxymethoxy)naphthalen-1-yl)-4,4,5,5-tetramethyl-1,3,2-dioxaborolane (1.74 g, 5.1 mmol) in dioxane (15 mL) and $H_2O$ (4 mL) was added $K_2CO_3$ (1.35 g, 9.75 mmol) and Catacxium A-Pd-G3 (0.28 g, 0.30 mmol). The mixture was stirred under $N_2$ at 95° C.

for 12 hours. The reaction was quenched with water and extracted with EA. The organic phase was washed with brine and dried over Na₂SO₄. The solution was concentrated in vacuum and the residue was purified by flash chromatography on silica gel with MeOH:DCM=1:20 to give the desired compound (1.9 g, 69.2% yield) as a yellow solid. LC/MS: 691.1 [M+H]⁺.

Step 4: Preparation of (R)-1-(7-(8-ethyl-3-(methoxymethoxy)naphthalen-1-yl)-8-fluoro-2-((1-(hydroxymethyl)cyclopropyl)methoxy)pyrido[4,3-d]pyrimidin-4-yl)-3-methylpiperidin-3-ol To a solution of (R)-1-(2-((1-(((tert-butyldimethylsilyl)oxy)methyl)cyclopropyl)methoxy)-7-(8-ethyl-3-(methoxymethoxy)naphthalen-1-yl)-8-fluoropyrido[4,3-d]pyrimidin-4-yl)-3-methyl piperidin-3-ol (1.9 g, 2.74 mmol) in DMF (10 mL) was added CsF (3.52 g, 23.2 mmol) at room temperature. The mixture was stirred under N₂ at 40° C. for 4 hours. The reaction was quenched with water and extracted with EA. The organic phase was washed with brine and dried over Na₂SO₄. The solution was concentrated in vacuum and the residue was purified by flash chromatography on silica gel with MeOH:DCM=1:20 to give the desired compound (1.42 g, 86.1% yield) as a colorless oil. LC/MS: 577.3 [M+H]⁺.

Step 5: Preparation of (R)-1-(((7-(8-ethyl-3-(methoxymethoxy)naphthalen-1-yl)-8-fluoro-4-(3-hydroxy-3-methylpiperidin-1-yl)pyrido[4,3-d]pyrimidin-2-yl)oxy)methyl)cyclopropane-1-carbaldehyde (Intermediate 8)

To a solution of (R)-1-(7-(8-ethyl-3-(methoxymethoxy)naphthalen-1-yl)-8-fluoro-2-((1-(hydroxymethyl)cyclopropyl)methoxy)pyrido[4,3-d]pyrimidin-4-yl)-3-methylpiperidin-3-ol (1.4 g, 2.43 mmol) in DCM (20 mL) was added a solution of Dess-Martin reagent (6.69 g, 15.8 mmol) in DCM (50 mL) dropwise at 0° C. The mixture was stirred at 25° C. for 2 hours. The reaction was quenched with water and extracted with DCM. The organic phase was washed with brine and dried over Na₂SO₄. The solution was concentrated in vacuum and the residue was purified by flash chromatography on silica gel with MeOH: DCM=1:20 to give the desired compound (0.7 g, 50.1% yield) as a white solid. LC/MS: 575.2 [M+H]⁺.

Preparation of 1-(((7-(8-ethyl-7-fluoro-3-(methoxymethoxy)naphthalen-1-yl)-8-fluoro-4-(1-oxa-6-azaspiro[3.5]nonan-6-yl)pyrido[4,3-d]pyrimidin-2-yl)oxy)methyl)cyclopropane-1-carbaldehyde (Intermediate 9)

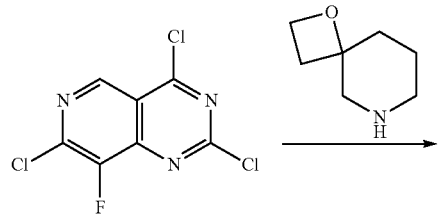

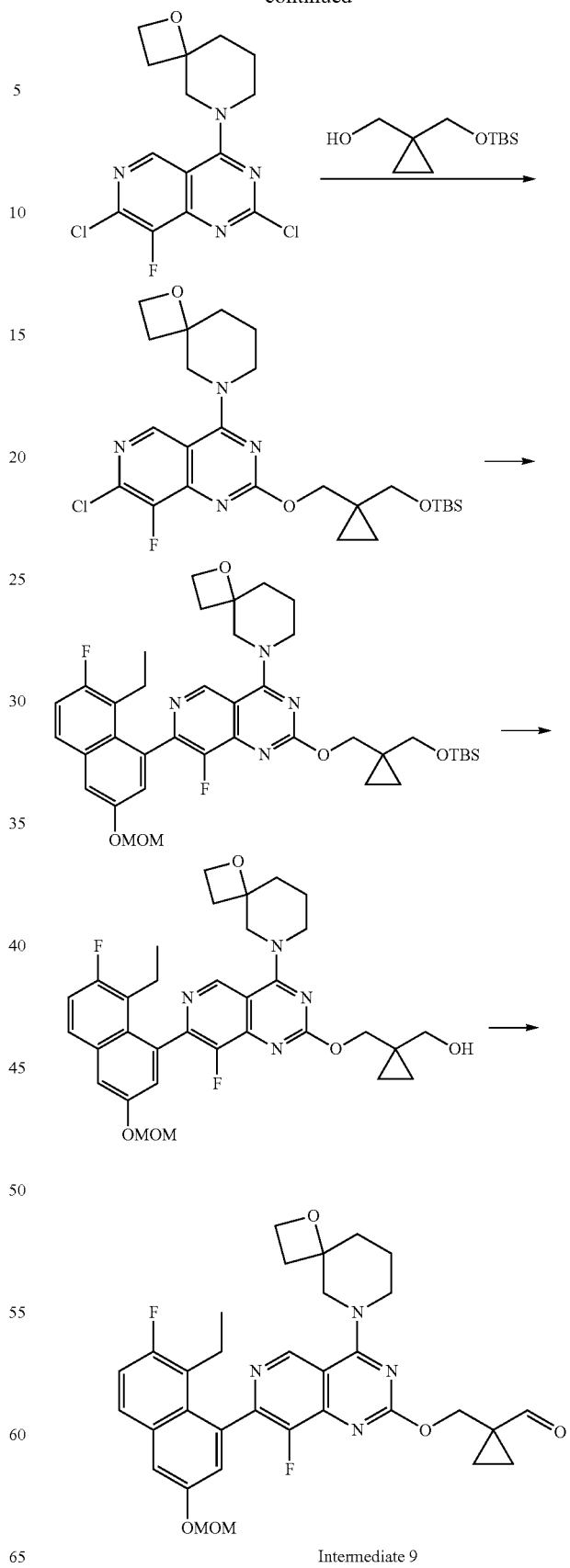

Intermediate 9

Step 1: Preparation of 6-(2,7-dichloro-8-fluoropyrido[4,3-d]pyrimidin-4-yl)-1-oxa-6-azaspiro[3.5]nonane To a solution of 2,4,7-trichloro-8-fluoropyrido[4,3-d]pyrimidine (1.3 g, 5.15 mmol) in DCM (20 mL) was added DIEA (1996 mg, 15.44 mmol) and 1-Oxa-6-azaspiro[3.5]nonane ethanedioate (2:1) (1064 mg, 3.09 mmol) under nitrogen at −40° C. The reaction mixture was stirred at −40° C. for 1 hour. The reaction was quenched with water and extracted with EA. The organic phase was washed with brine and dried over Na$_2$SO$_4$. The solution was concentrated in vacuum and the residue was purified by flash chromatography on silica gel with PE:EA=4:1 to give the desired compound (1 g, 57% yield) as a white solid. LC/MS: 342.8 [M+H]$^+$.

Step 2: Preparation of 6-(2-((1-(((tert-butyldimethylsilyl)oxy)methyl)cyclopropyl)methoxy)-7-chloro-8-fluoropyrido[4,3-d]pyrimidin-4-yl)-1-oxa-6-azaspiro[3.5]nonane To a solution of (1-(((tert-butyldimethylsilyl)oxy)methyl)cyclopropyl)methanol (1419 mg, 6.56 mmol) in THF (12 mL) was added NaH (115 mg, 60% purity, 2.88 mmol) at 0° C. The mixture was stirred at 0° C. for 15 minutes then (3R)-1-{2,7-dichloro-8-fluoropyrido[4,3-d]pyrimidin-4-yl}-3-methylpiperidin-3-ol (900 mg, 2.62 mmol) was added. The reaction mixture was stirred at 25° C. for 2 hours. The reaction was quenched with water and extracted with EA. The organic phase was washed with brine and dried over Na$_2$SO$_4$. The solution was concentrated in vacuum and the residue was purified by flash chromatography on silica gel with PE:EA=3:1 to give the desired compound (500 mg, 29% yield) as a white solid. LC/MS: 532.3 [M+H]$^+$.

Step 3: Preparation of 6-(2-((1-(((tert-butyldimethylsilyl)oxy)methyl)cyclopropyl)methoxy)-7-(8-ethyl-7-fluoro-3-(methoxymethoxy)naphthalen-1-yl)-8-fluoropyrido[4,3-d]pyrimidin-4-yl)-1-oxa-6-azaspiro[3.5]nonane To a solution of 6-(2-((1-(((tert-butyldimethylsilyl)oxy)methyl)cyclopropyl)methoxy)-7-chloro-8-fluoropyrido[4,3-d]pyrimidin-4-yl)-1-oxa-6-azaspiro[3.5]nonane (500 mg, 0.96 mmol) and 2-(8-ethyl-7-fluoro-3-(methoxymethoxy)naphthalen-1-yl)-4,4,5,5-tetramethyl-1,3,2-dioxaborolane (516 mg, 1.43 mmol) in dioxane (3 mL) and H$_2$O (1 mL) was added potassium carbonate (609 mg, 2.87 mmol) and Catacxium A-Pd-G3 (70 mg, 0.10 mmol). The mixture was stirred under N$_2$ at 90° C. for 2 hours. The reaction was quenched with water and extracted with EA. The organic phase was washed with brine and dried over Na$_2$SO$_4$. The solution was concentrated in vacuum and the residue was purified by flash chromatography on silica gel with PE:EA=1:1 to give the desired compound (510 mg, 74% yield) as a yellow solid. LC/MS: 721.2 [M+H]$^+$.

Step 4: Preparation of (1-(((7-(8-ethyl-7-fluoro-3-(methoxymethoxy)naphthalen-1-yl)-8-fluoro-4-(1-oxa-6-azaspiro[3.5]nonan-6-yl)pyrido[4,3-d]pyrimidin-2-yl)oxy)methyl)cyclopropyl)methanol To a solution of 6-(2-((1-(((tert-butyldimethylsilyl)oxy)methyl)cyclopropyl)methoxy)-7-(8-ethyl-7-fluoro-3-(methoxymethoxy)naphthalen-1-yl)-8-fluoropyrido[4,3-d]pyrimidin-4-yl)-1-oxa-6-azaspiro[3.5]nonane (500 mg, 0.69 mmol) in THF (9 mL) was added TBAF-THF (1 M, 3 mL). the mixture was stirred at room temperature for 1 hour. The reaction was quenched with water and extracted with EA. The organic phase was washed with brine and dried over Na$_2$SO$_4$. The solution was concentrated in vacuum and the residue was purified by flash chromatography on silica gel with PE:EA=1:1 to give the desired compound (340 mg, 81% yield) as a colorless oil. LC/MS: 606.8 [M+H]$^+$.

Step 5: Preparation of 1-(((7-(8-ethyl-7-fluoro-3-(methoxymethoxy)naphthalen-1-yl)-8-fluoro-4-(1-oxa-6-azaspiro[3.5]nonan-6-yl)pyrido[4,3-d]pyrimidin-2-yl)oxy)methyl)cyclopropane-1-carbaldehyde (Intermediate 9)

To a solution of (1-(((7-(8-ethyl-7-fluoro-3-(methoxymethoxy)naphthalen-1-yl)-8-fluoro-4-(1-oxa-6-azaspiro[3.5]nonan-6-yl)pyrido[4,3-d]pyrimidin-2-yl)oxy)methyl)cyclopropyl)methanol (330 mg, 0.54 mmol) in DCM (8 mL) was added Dess-Martin reagent (461 mg, 1.01 mmol). The mixture was stirred at 25° C. for 1 hour. The reaction was quenched with saturated Na$_2$S2O3 solution and extracted with DCM. The organic phase was washed with brine and dried over Na$_2$SO$_4$. The solution was concentrated in vacuum and the residue was purified by flash chromatography on silica gel with PE:EA=1:1 to give the desired compound (300 mg, 91% yield) as a white solid. LC/MS: 605.2 [M+H]$^+$.

Preparation of (S)-1-(((7-(8-ethyl-7-fluoro-3-(methoxymethoxy)naphthalen-1-yl)-8-fluoro-4-(1-oxa-6-azaspiro[3.5]nonan-6-yl)pyrido[4,3-d]pyrimidin-2-yl)oxy)methyl)cyclopropane-1-carbaldehyde (Intermediate 10) and (R)-1-(((7-(8-ethyl-7-fluoro-3-(methoxymethoxy)naphthalen-1-yl)-8-fluoro-4-(1-oxa-6-azaspiro[3.5]nonan-6-yl)pyrido[4,3-d]pyrimidin-2-yl)oxy)methyl)cyclopropane-1-carbaldehyde (Intermediate 11)

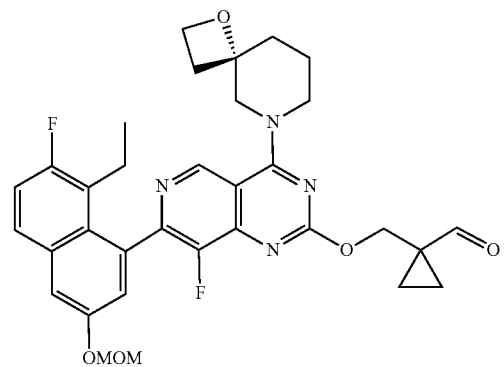

Intermediate 10

Intermediate 11

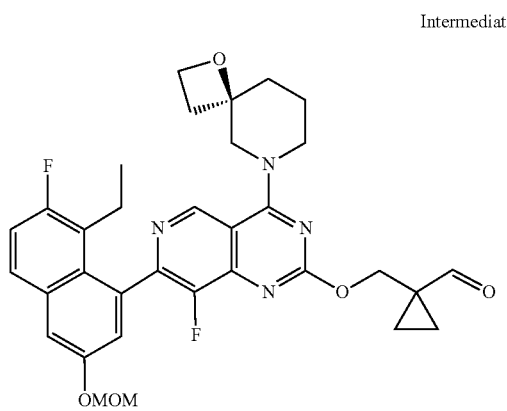

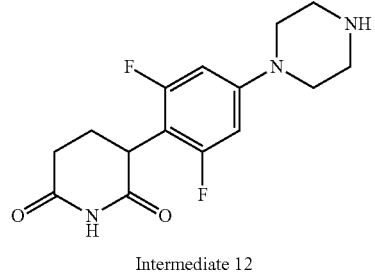

Intermediate 12

Intermediates 10 and Intermediate 11 were prepared with the procedure described for Intermediate 9 by using (S)-1-oxa-6-azaspiro[3.5]nonane and (R)-1-oxa-6-azaspiro[3.5]nonane in step 1 respectively.

Preparation of 3-(2,6-difluoro-4-(piperazin-1-yl)phenyl)piperidine-2,6-dione (Intermediate 12)

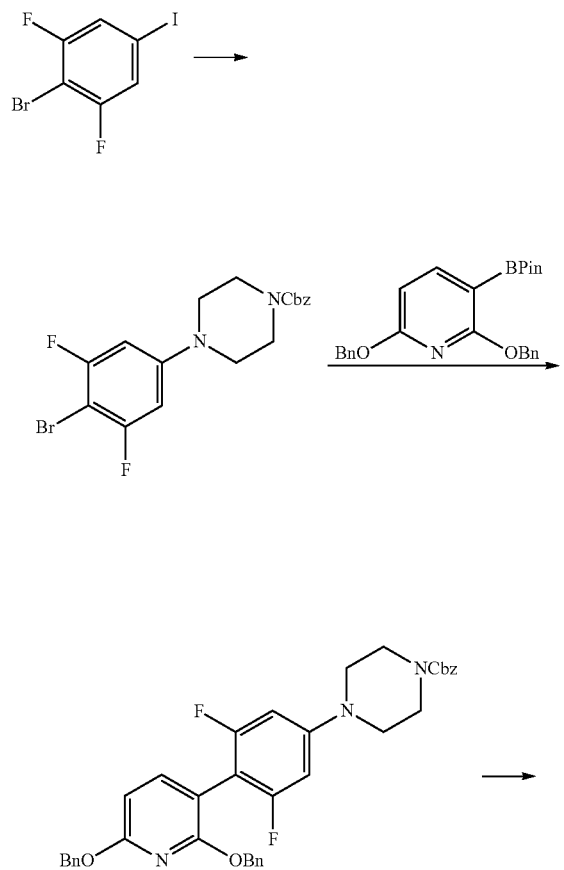

Step 1: Preparation of benzyl 4-(4-bromo-3,5-difluorophenyl)piperazine-1-carboxylate To a solution of 2-bromo-1,3-difluoro-5-iodobenzene (1.5 g, 4.7 mmol), benzyl piperazine-1-carboxylate (1.24 g, 5.64 mmol) and t-BuONa (0.9 g, 9.4 mmol) in toluene (15 mL) were added $Pd_2(dba)_3$ (0.43 g, 0.47 mmol) and Xantphos (0.54 g, 0.94 mmol). The mixture was stirred under $N_2$ at 80° C. for 20 minutes. The reaction mixture was diluted with $H_2O$ (20 mL) and extracted with EtOAc (20 mL×3). The organic phase was washed with brine and dried over $Na_2SO_4$. The solution was concentrated in vacuum and the residue was purified by flash column chromatography (PE:EA=5:1) to give the desired compound (1 g, 51.7% yield) as a yellow solid. LC/MS: 411.0 $[M+H]^+$.

Step 2: Preparation of benzyl 4-(4-(2,6-bis(benzyloxy)pyridin-3-yl)-3,5-difluorophenyl)piperazine-1-carboxylate To a mixture of benzyl 4-(4-bromo-3,5-difluorophenyl)piperazine-1-carboxylate (3 g, 7.3 mmol), 2,6-bis(benzyloxy)-3-(4,4,5,5-tetramethyl-1,3,2-dioxaborolan-2-yl)pyridine (3.96 g, 9.49 mmol) and $K_2CO_3$ (2.52 g, 18.25 mmol) in dioxane (30 mL) and $H_2O$ (6 mL) was added $Pd(PPh_3)_4$ (1.27 g, 1.09 mmol). The resulting mixture was stirred under $N_2$ at 100° C. for 12 hours. The reaction mixture was diluted with $H_2O$ (20 mL) and extracted with EtOAc (20 mL×3). The organic phase was washed with brine and dried over $Na_2SO_4$. The solution was concentrated in vacuum and the residue was purified by flash column chromatography (PE:EA=5:1) to give the desired compound (2.25 g, 49.3% yield) as a yellow oil. LC/MS: 622.2 $[M+H]^+$.

Step 3: Preparation of 3-(2,6-difluoro-4-(piperazin-1-yl)phenyl)piperidine-2,6-dione (Intermediate 12)

To a solution of benzyl 4-(4-(2,6-bis(benzyloxy)pyridin-3-yl)-3,5-difluorophenyl)piperazine-1-carboxylate (1 g, 1.60 mmol) in AcOH (1 mL) and trifluoroethanol (10 mL) was added Pd/C (0.2 g, 10% purity) at 25° C. under the protection of N2. The resulting mixture was stirred at 50° C. for 14 hours under $H_2$ atmosphere (balloon). The reaction mixture was filtered and washed with THF/IPA (100 mL; 1/1) and the filtrate was concentrated to give the desired compound (0.5 g) as yellow oil. LC/MS: 310.1 $[M+H]^+$.

Preparation of Exemplary Compounds
Example 1: Preparation of (S)-3-(5-(4-((1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione (Compound 1)
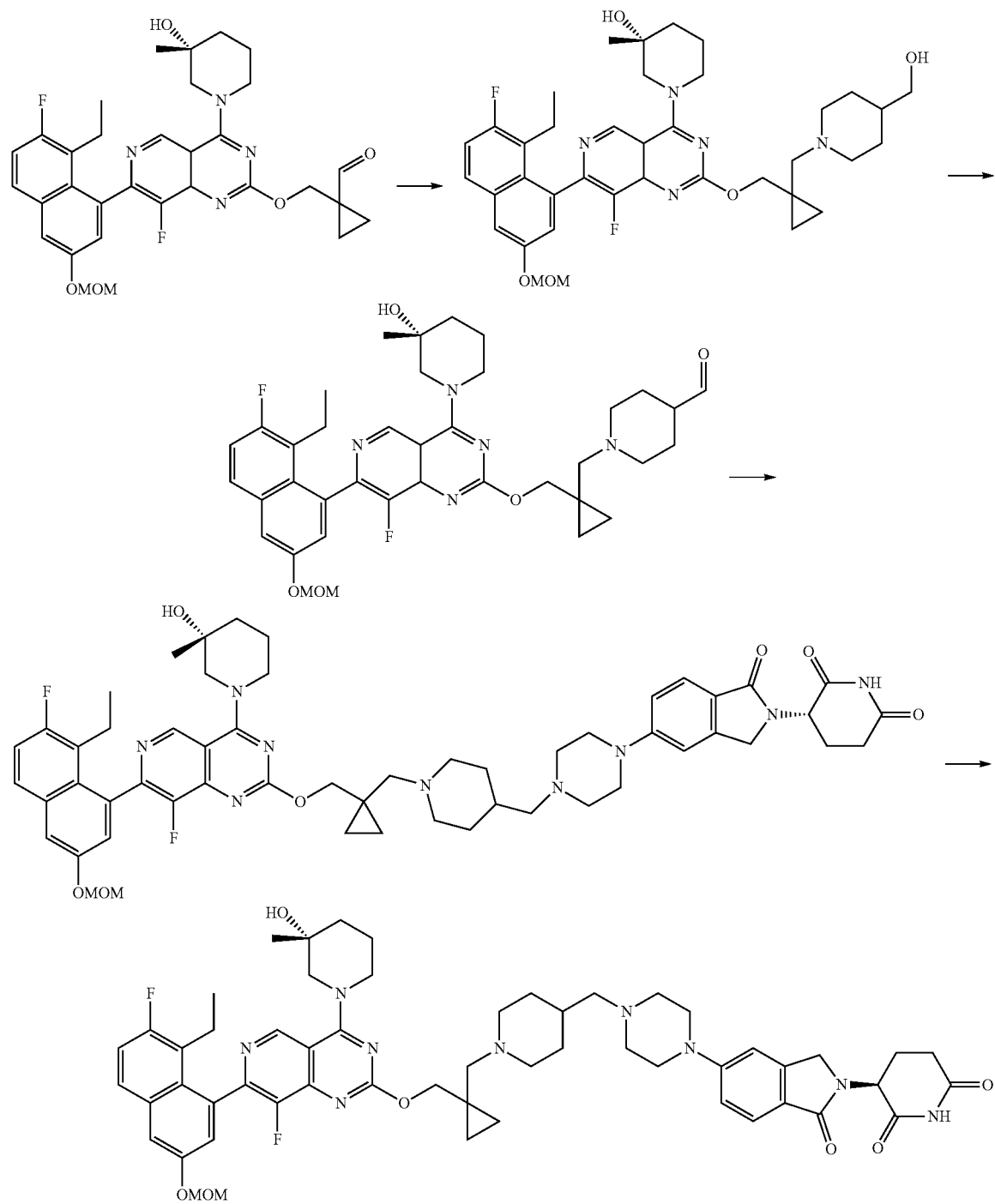

Step 1: Preparation of (R)-1-(((7-(8-ethyl-7-fluoro-3-(methoxymethoxy)naphthalen-1-yl)-8-fluoro-4-(3-hydroxy-3-methylpiperidin-1-yl)pyrido[4,3-d]pyrimidin-2-yl)oxy)methyl)cyclo propane-1-carbaldehyde To a solution of (R)-1-(((7-(8-ethyl-7-fluoro-3-(methoxymethoxy)naphthalen-1-yl)-8-fluoro-4-(3-hydroxy-3-methylpiperidin-1-yl)pyrido[4,3-d]pyrimidin-2-yl)oxy)methyl)cyclopropane-1-carbaldehyde (1.9 g, 3.2 mmol) and piperidin-4-ylmethanol (1.84 g, 16 mmol) in DCM (20 mL) was added NaBH$_3$CN (0.6 g, 9.6 mmol) and NaOAc (0.79 g, 9.6 mmol). The reaction mixture was stirred at 25° C. for 2 hours. The reaction was quenched with water and extracted with DCM. The organic phase was washed with brine and dried over Na$_2$SO$_4$. The solution was concentrated in vacuum and the residue was purified by flash chromatography on silica gel with MeOH (1% NH$_3$H$_2$O added): DCM=1:15 to give the desired compound (1 g, 40.6% yield). LC/MS: 692.3[M+H]$^+$.

Step 2: Preparation of (R)-1-((1-(((7-(8-ethyl-7-fluoro-3-(methoxymethoxy)naphthalen-1-yl)-8-fluoro-4-(3-hydroxy-3-methylpiperidin-1-yl)pyrido[4,3-d]pyrimidin-2-yl)oxy)methyl)cyclopropyl)methyl)piperidine-4-carbaldehyde To a solution of (3R)-1-{7-[8-ethyl-7-fluoro-3-(methoxymethoxy)naphthalen-1-yl]-8-fluoro-2-[(1-{[4-(hydroxymethyl)piperidin-1-yl]methyl}cyclopropyl)methoxy]pyrido[4,3-d]pyrimidin-4-yl}-3-methylpiperidin-3-ol (680 mg, 0.98 mmol) in DCM (20 mL) was added a solution of Dess-Martin periodinane (1.25 g, 2.95 mmol) in DCM (10 mL) dropwise at 0° C. The mixture was stirred at 25° C. for 15 hours. The reaction was quenched with NaHCO$_3$ solution and extracted with DCM. The organic phase was washed with brine and dried over Na$_2$SO$_4$. The solution was concentrated in vacuum and the residue was purified by flash chromatography on silica gel with MeOH (1% NH$_3$H$_2$O added): DCM=1:10 to give the desired compound (600 mg, 70% purity, 61.9% yield) as a white solid. LC/MS: 690.2 [M+H]$^+$.

Step 3: Preparation of (S)-3-(5-(4-((1-((1-(((7-(8-ethyl-7-fluoro-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione To a solution of 1-({1-[({7-[8-ethyl-7-fluoro-3-(methoxymethoxy)naphthalen-1-yl]-8-fluoro-4-[(3R)-3-hydroxy-3-methylpiperidin-1-yl]pyrido[4,3-d]pyrimidin-2-yl}oxy)methyl]cyclopropyl}methyl)piperidine-4-carbaldehyde (680 mg, 0.98 mmol) and (3S)-3-[1-oxo-5-(piperazin-1-yl)-3H-isoindol-2-yl]piperidine-2,6-dione benzenesulfonic acid (959 mg, 1.97 mmol) in DCM (20 mL) was added NaOAc (485 mg, 5.91 mmol) and NaBH$_3$CN (186 mg, 2.96 mmol) under Ar. The reaction mixture was stirred at 25° C. for 2 hours. The reaction was quenched with water and extracted with DCM. The organic phase was washed with brine and dried over Na$_2$SO$_4$. The solution was concentrated in vacuum and the residue was purified by flash chromatography on silica gel with MeOH (1% NH$_3$H$_2$O added): DCM=1:10 to give the desired compound (600 mg, 90% purity, 54.6% yield) as a yellow oil. LC/MS: 1002.4 [M+H]$^+$.

Step 4: Preparation of (S)-3-(5-(4-((1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione (Compound 1)

A solution of (3S)-3-[5-(4-{[1-({1-[({7-[8-ethyl-7-fluoro-3-(methoxymethoxy)naphthalen-1-yl]-8-fluoro-4-[(3R)-3-hydroxy-3-methylpiperidin-1-yl]pyrido[4,3-d]pyrimidin-2-yl}oxy)methyl]cyclopropyl}methyl)piperidin-4-yl]methyl}piperazin-1-yl)-1-oxo-3H-isoindol-2-yl]piperidine-2,6-dione (580 mg, 0.58 mmol) in HCl in dioxane (4 M, 1 mL) and THF (1 mL) was stirred under nitrogen at room temperature for 0.5 hours. The reaction mixture was concentrated in vacuum and the residue was purified by Prep-HPLC (0.1% FA in H$_2$O/ACN=10~40%) to obtain the desired compound (200 mg, 35.9% yield) as a yellow solid. LC/MS: 958.4 [M+H]$^+$; $^1$H NMR (400 MHZ, DMSO) δ 10.96 (s, 1H), 10.00-9.96 (m, 1H), 9.26 (s, 1H), 8.62 (brs, 1H), 7.80-7.74 (m, 1H), 7.54 (d, J=7.9 Hz, 1H), 7.38-7.32 (m, 2H), 7.13-7.03 (m, 2H), 7.02-7.00 (m, 1H), 5.05 (dd, J=13.0, 4.8 Hz, 1H), 4.72 (d, J=7.8 Hz, 1H), 4.40-4.29 (m, 4H), 4.21 (d, J=17.1 Hz, 1H), 4.14-4.05 (m, 1H), 3.79-3.66 (m, 2H), 3.64-3.52 (m, 2H), 3.29-3.13 (m, 6H), 2.99-2.85 (m, 3H), 2.64-2.54 (m, 2H), 2.45-2.25 (m, 4H), 2.23-2.07 (m, 3H), 2.07-1.97 (m, 4H), 1.73-1.63 (m, 3H), 1.49-1.33 (m, 2H), 1.23 (s, 3H), 1.17 (d, J=10.4 Hz, 3H), 0.91-0.85 (m, 2H), 0.77-0.72 (m, 4H).

Example 2: Preparation of (S)-3-(5-(4-((7-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione (Compound 2)

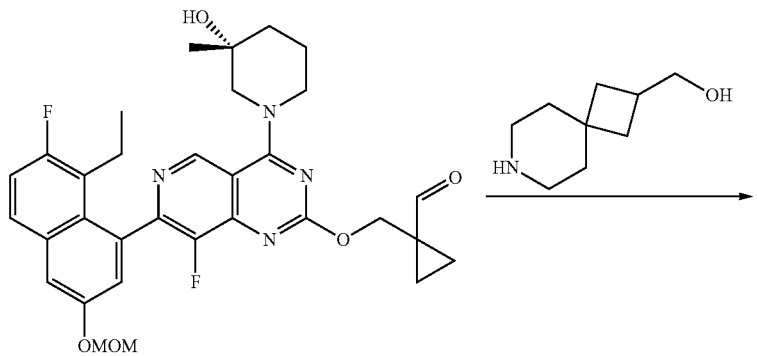

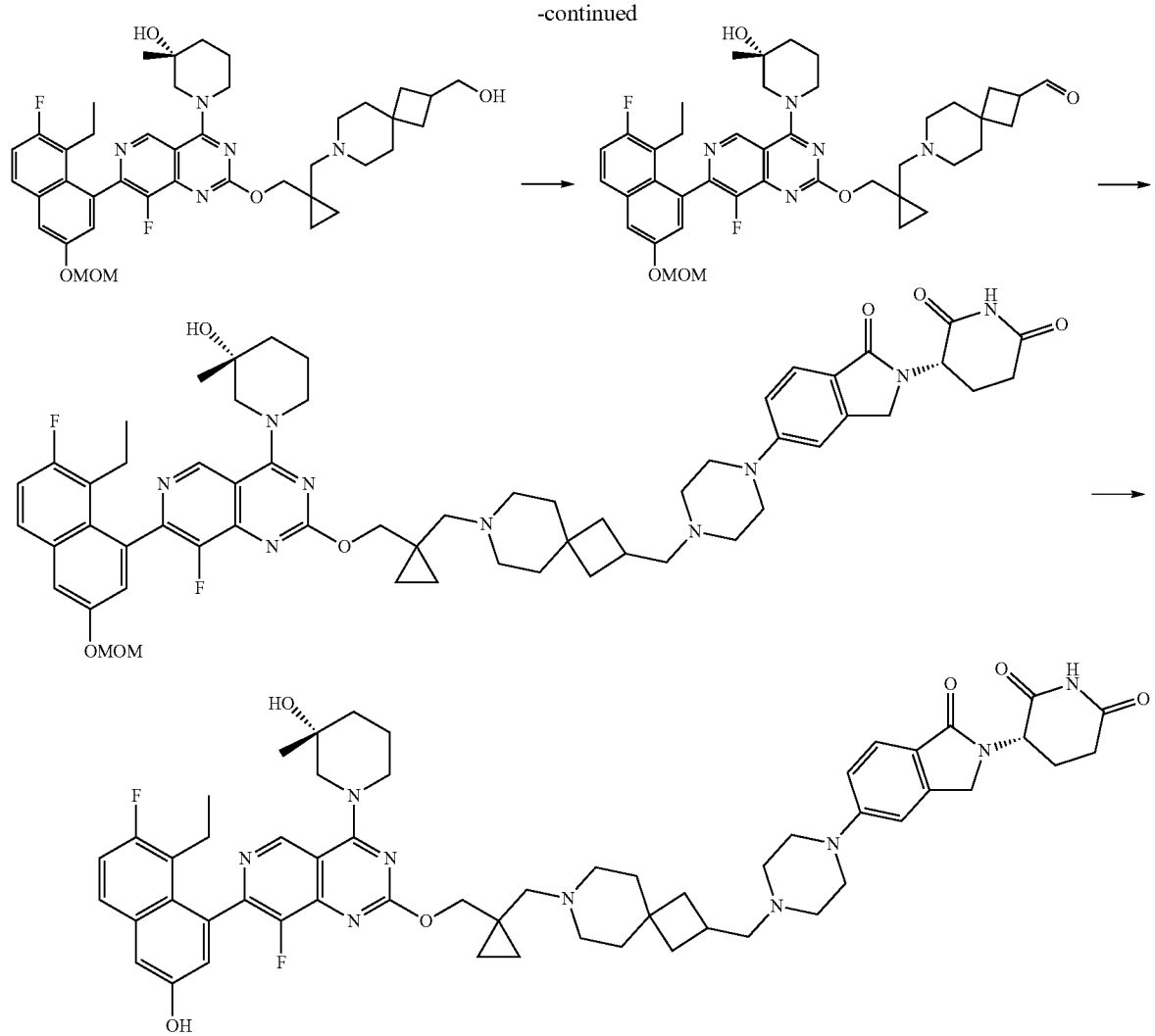

Step 1: Preparation of (R)-1-(7-(8-ethyl-7-fluoro-3-(methoxymethoxy)naphthalen-1-yl)-8-fluoro-2-((1-((2-(hydroxymethyl)-7-azaspiro[3.5]nonan-7-yl)methyl)cyclopropyl)methoxy)pyrido[4,3-d]pyrimidin-4-yl)-3-methylpiperidin-3-ol To a solution of (R)-1-(((7-(8-ethyl-7-fluoro-3-(methoxymethoxy)naphthalen-1-yl)-8-fluoro-4-(3-hydroxy-3-methylpiperidin-1-yl)pyrido[4,3-d]pyrimidin-2-yl)oxy)methyl)cyclopropane-1-carbaldehyde (300 mg, 0.50 mmol) in DCM (5 mL) was added 7-azaspiro[3.5]nonan-2-ylmethanol hydrochloride (291 mg, 1.52 mmol), NaOAc (250 mg, 3.04 mmol) and NaBH$_3$CN (95 mg, 1.52 mmol). The mixture was stirred at 25° C. for 2 hours. The reaction was quenched with NaHCO$_3$ solution and extracted with DCM. The organic phase was washed with brine and dried over Na$_2$SO$_4$. The solution was concentrated in vacuum and the residue was purified by flash chromatography on silica gel with MeOH (1% NH$_3$H$_2$O added): DCM=1:15 to give the desired compound (270 mg, 72.8% yield) as a yellow solid. LC/MS: 732.4 [M+H]$^+$.

Step 2: Preparation of (R)-7-((1-(((7-(8-ethyl-7-fluoro-3-(methoxymethoxy)naphthalen-1-yl)-8-fluoro-4-(3-hydroxy-3-methylpiperidin-1-yl)pyrido[4,3-d]pyrimidin-2-yl)oxy)methyl)cyclo propyl)methyl)-7-azaspiro[3.5]nonane-2-carbaldehyde To a solution of (3R)-1-{7-[8-ethyl-7-fluoro-3-(methoxymethoxy)naphthalen-1-yl]-8-fluoro-2-[(1-{[2-(hydroxymethyl)-7-azaspiro[3.5]nonan-7-yl]methyl}cyclopropyl)methoxy]pyrido[4,3-d]pyrimidin-4-yl}-3-methylpiperidin-3-ol (130 mg, 0.18 mmol) in DCM (5 mL) was added a solution of Dess-Martin periodinae (226 mg, 0.53 mmol) in DCM (2 mL) dropwise at 0° C. The mixture was stirred at 25° C. for 2 hours. The reaction was quenched with NaHCO$_3$ solution and extracted with DCM. The organic phase was washed with brine and dried over Na$_2$SO$_4$. The solution was concentrated in vacuum and the residue was purified by flash chromatography on silica gel with MeOH (1% NH$_3$H$_2$O added): DCM=1:10 to give the desired compound (100 mg, 90% purity, 69.4% yield) as a white solid. LC/MS: 730.3 [M+H]$^+$.

Step 3: Preparation of (S)-3-(5-(4-((7-((1-(((7-(8-ethyl-7-fluoro-3-(methoxymethoxy)naphthalen-1-yl)-8-fluoro-4-((R)-3-hydroxy-3-methylpiperidin-1-yl)pyrido[4,3-d]pyrimidin-2-yl)oxy) methyl) cyclopropyl)methyl)-7-azaspiro[3.5]nonan-2-yl) methyl)piperazin-1-yl)-1-oxoisoindolin-2-yl) piperidine-2,6-dione To a solution of 7-({1-[({7-[8-ethyl-7-fluoro-3-(methoxymethoxy)naphthalen-1-yl]-8-fluoro-4-[(3R)-3-hydroxy-3-methylpiperidin-1-yl]pyrido[4,3-d]pyrimidin-2-yl}oxy)methyl]cyclopropyl}methyl)-7-azaspiro[3.5] nonane-2-carbaldehyde (130 mg. 0.17 mmol) and (3S)-3-[1-oxo-5-(piperazin-1-yl)-3H-isoindol-2-yl]piperidine-2,6-dione; benzenesulfonic acid (174 mg, 0.35 mmol) in DCM (8 mL) was added NaOAc (88 mg, 1.07 mmol) and NaBH₃CN (34 mg, 0.54 mmol). The reaction mixture was stirred at 25° C. for 2 hours. The reaction was quenched with water and extracted with EA. The organic phase was washed with brine and dried over Na₂SO₄. The solution was concentrated in vacuum and the residue was purified by flash chromatography on silica gel with MeOH (1% NH₃H₂O added): DCM=1:10 to give the desired compound (135 mg, 72.7% yield) as a yellow solid. LC/MS: 1042.4 [M+H]⁺.

Step 4: Preparation of (S)-3-(5-(4-((7-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclo propyl) methyl)-7-azaspiro[3.5]nonan-2-yl)methyl) piperazin-1-yl)-1-oxoisoindolin-2-yl)piperidine-2,6-dione (Compound 2)

A solution of (3S)-3-[5-(4-{[7-({1-[({7-[8-ethyl-7-fluoro-3-(methoxymethoxy)naphthalen-1-yl]-8-fluoro-4-[(3R)-3-hydroxy-3-methylpiperidin-1-yl]pyrido[4,3-d]pyrimidin-2-yl}oxy)methyl]cyclopropyl}methyl)-7-azaspiro[3.5]nonan-2-yl]methyl}piperazin-1-yl)-1-oxo-3H-isoindol-2-yl] piperidine-2,6-dione (65 mg, 0.062 mmol) in HCl in dioxane (4 M, 1 mL) and THF (1 mL) was stirred under nitrogen at room temperature for 0.5 hours. The solution was concentrated in vacuum and the residue was purified by Prep-HPLC (0.1% FA in H2O/ACN=10~40%) to obtain the desired compound (35 mg, 54.0% yield) as a yellow solid. LC/MS: 998.4 [M+H]⁺; ¹H NMR (400 MHZ, DMSO) δ 10.94 (s, 1H), 9.93 (brs, 1H), 9.21 (s, 1H), 8.13 (s, 1H), 7.76 (dd, J=9.1, 6.0 Hz, 1H), 7.50 (d, J=8.9 Hz, 1H), 7.37-7.31 (m, 2H), 7.04-6.99 (m, 3H), 5.06-5.01 (m, 1H), 4.76-4.69 (m, 1H), 4.34-4.23 (m, 5H), 4.07-3.98 (m, 1H), 3.65-3.45 (m, 2H), 3.26-3.20 (m, 6H), 2.93-2.87 (m, 1H), 2.59-2.55 (m, 1H), 2.38-2.32 (m, 6H), 2.01-1.94 (m, 3H), 1.89-1.82 (m, 2H), 1.70-1.64 (m, 3H), 1.59-1.53 (m, 2H), 1.46-1.42 (m, 2H), 1.38-1.33 (m, 2H), 1.22 (s, 6H), 1.17-1.13 (m, 3H), 0.86-0.82 (m, 1H), 0.75-0.70 (m, 3H), 0.66 (s, 2H), 0.43 (s, 2H).

Example 3: Preparation of (S)-3-(5-(4-((7-((1 (((4-(((1-(dimethylamino)cyclobutyl)methyl) amino)-7-(8-ethyl-7-fluoro-3-hydroxynaphthalen-1-yl)-8-fluoropyrido[4,3-d]pyrimidin-2-yl)oxy)methyl) cyclopropyl)methyl)-7-azaspiro[3.5]nonan-2-yl) methyl)piperazin-1-yl)-1-oxoisoindolin-2-yl) piperidine-2,6-dione (Compound 3)

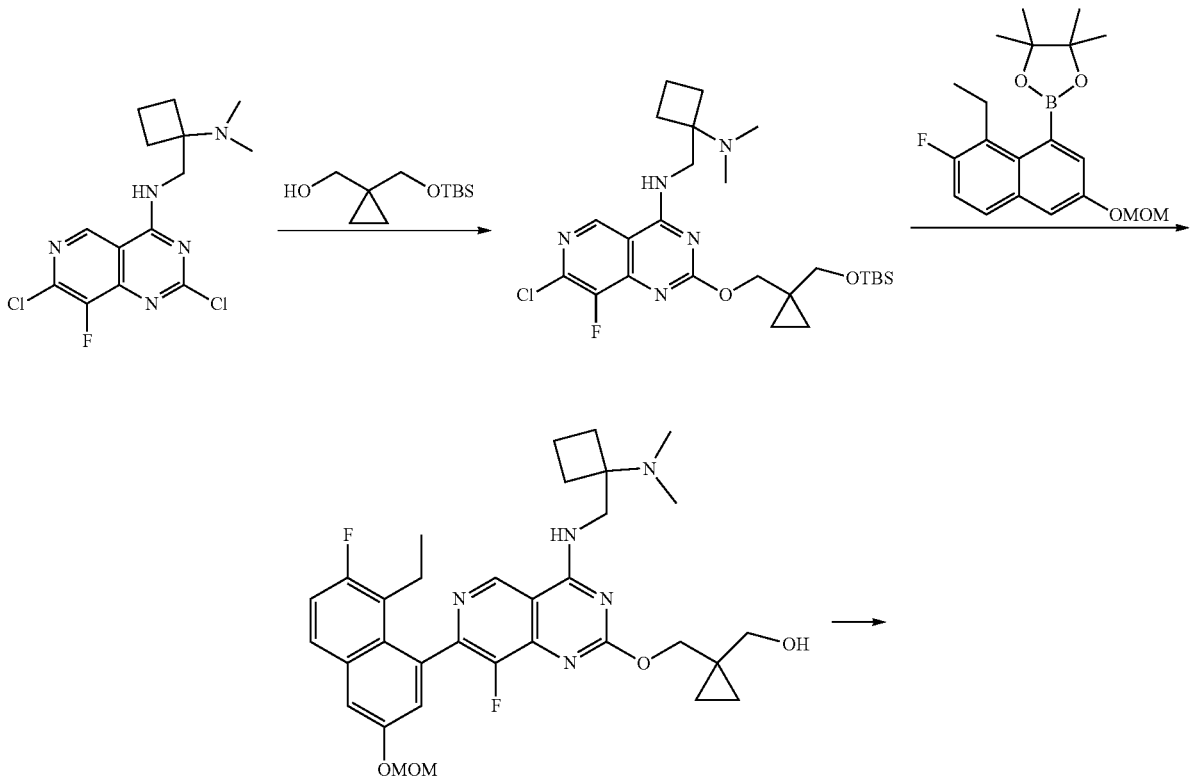

-continued

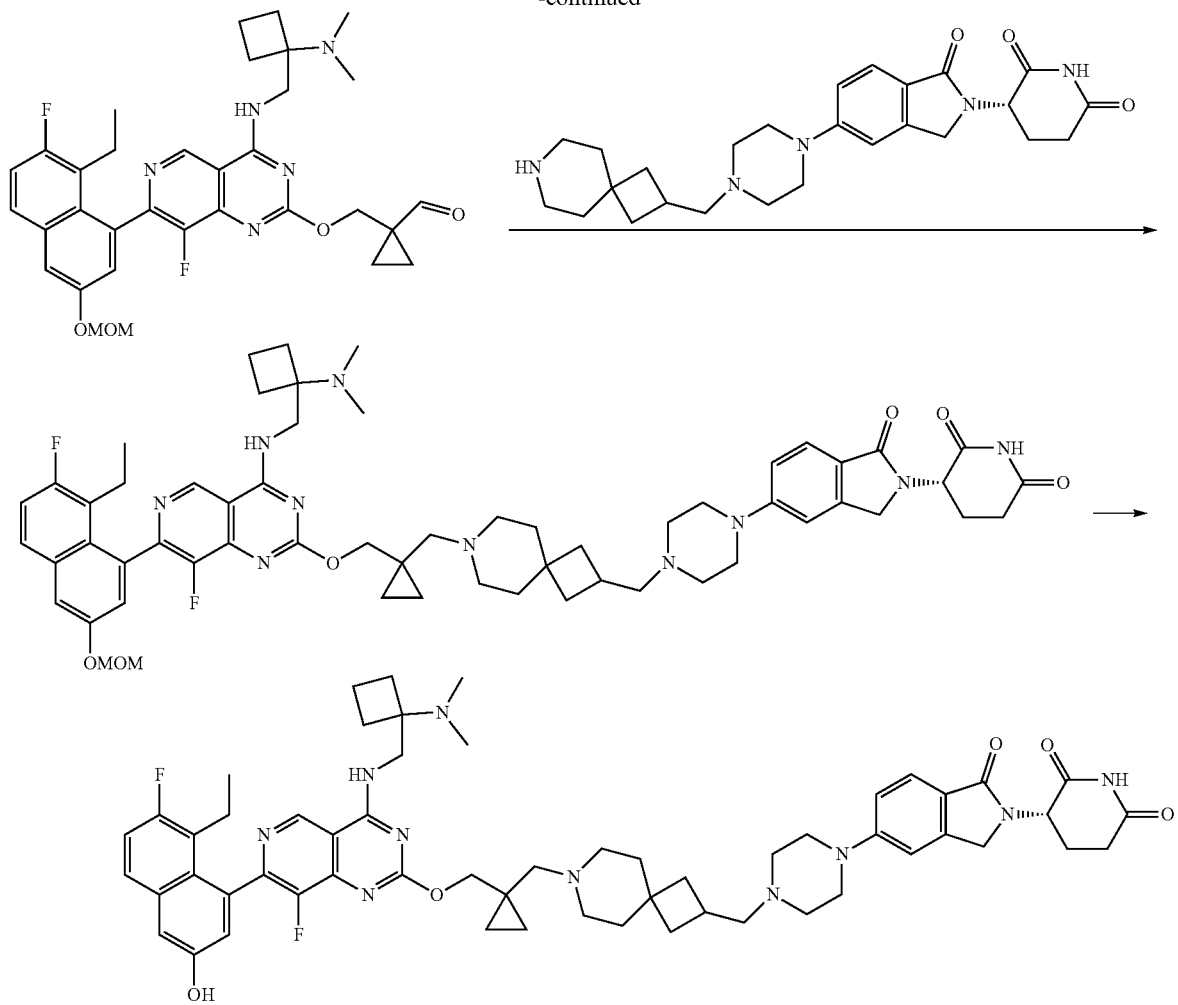

Step 1: Preparation of 2-((1-(((tert-butyldimethylsilyl)oxy)methyl)cyclopropyl)methoxy)-7-chloro-N-((1-(dimethylamino)cyclobutyl)methyl)-8-fluoropyrido[4,3-d]pyrimidin-4-amine To a solution of 2,7-dichloro-N-((1-(dimethylamino)cyclobutyl)methyl)-8-fluoropyrido[4,3-d]pyrimidin-4-amine (300 mg, 0.87 mmol) in dioxane (8 mL) was added (1-(((tert-butyldimethylsilyl)oxy)methyl)cyclopropyl)methanol (1.13 g, 5.22 mmol) and Cs$_2$CO$_3$ (1.7 g, 5.22 mmol). The mixture was stirred at 95° C. for 16 hours. The reaction mixture was poured into water and extracted with EA. The organic phase was washed with brine and dried over Na$_2$SO$_4$. The solvent was removed and the residue was purified by flash column chromatography with PE:EA=5:1 to give the title compound as a white solid (54 mg, 11.8% yield). LC/MS: 524.3 [M+H]$^+$.

Step 2: Preparation of (1-(((4-(((1-(dimethylamino)cyclobutyl)methyl)amino)-7-(8-ethyl-7-fluoro-3-(methoxymethoxy)naphthalen-1-yl)-8-fluoropyrido[4,3-d]pyrimidin-2-yl)oxy)methyl)cyclo-propyl)methanol To a solution of 2-((1-(((tert-butyldimethylsilyl)oxy)methyl)cyclopropyl)methoxy)-7-chloro-N-((1-(dimethylamino)cyclobutyl)methyl)-8-fluoropyrido[4,3-d]pyrimidin-4-amine (35 mg, 0.058 mmol) in dioxane (2.5 mL) and H$_2$O (0.5 mL) was added 2-[8-ethyl-7-fluoro-3-(methoxymethoxy)naphthalen-1-yl]-4,4,5,5-tetramethyl-1,3,2-dioxaborolane (30 mg, 0.083 mmol), Catacxium A-Pd-G3 (12 mg, 0.016 mmol) and potassium carbonate (35 mg, 0.24 mmol). The reaction mixture was stirred at 90° C. for 16 hours. The reaction mixture was poured into water and extracted with EA. The organic phase was washed with brine and dried over Na$_2$SO$_4$. The solvent was removed and the residue was purified by flash column chromatography with PE: EA=1:1 to give the title compound (30 mg, 45.2% yield) as a white solid. LC/MS: 608.3 [M+H]$^+$.

Step 3: Preparation of 1-(((4-(((1-(dimethylamino)cyclobutyl)methyl)amino)-7-(8-ethyl-7-fluoro-3-(methoxymethoxy)naphthalen-1-yl)-8-fluoropyrido[4,3-d]pyrimidin-2-yl)oxy)methyl)cyclopropane-1-carbaldehyde To a solution of (1-(((4-(((1-(dimethylamino)cyclobutyl)methyl)amino)-7-(8-ethyl-7-fluoro-3-(methoxymethoxy)naphthalen-1-yl)-8-fluoropyrido[4,3-d]pyrimidin-2-yl)oxy)methyl)cyclopropyl)methanol (28 mg, 0.046 mmol) in DCM (3 mL) stirred under nitrogen at 0° C. was added Dess-Martin periodinane (39 mg, 0.092 mmol). The reaction mixture was stirred at 25° C. for 2 hours. The reaction mixture was poured into water and extracted with EA. The organic phase was washed with brine and dried over Na$_2$SO$_4$. The solvent was removed and the residue was purified by flash column chromatography with PE:EA=1:1 to give the title compound (20 mg, 71.5% yield) as a white solid. LC/MS: 606.3 [M+H]$^+$.

Step 4: Preparation of (S)-3-(5-(4-((7-((1-(((4-(((1-(dimethylamino)cyclobutyl)methyl)amino)-7-(8-ethyl-7-fluoro-3-(methoxymethoxy)naphthalen-1-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione To a solution of 1-(((4-(((1-(dimethylamino)cyclobutyl)methyl)amino)-7-(8-ethyl-7-fluoro-3-(methoxymethoxy)naphthalen-1-yl)-8-fluoropyrido[4,3-d]pyrimidin-2-yl)oxy)methyl)cyclopropane-1-carbaldehyde (18 mg, 0.029 mmol) in DMA (1 mL) and THF (1 mL) was added (3S)-3-[5-(4-{7-azaspiro[3.5]nonan-2-ylmethyl}piperazin-1-yl)-1-oxo-3H-isoindol-2-yl]piperidine-2,6-dione (82 mg, 0.118 mmol) and DIEA (61 mg, 0.47 mmol). The mixture was stirred under nitrogen at room temperature for 0.5 hours. Sodium triacetoxyborohydride (50 mg, 0.23 mmol) was added and the mixture was stirred at 25° C. for 16 hours. The reaction mixture was poured into water and extracted with EA. The organic phase was washed with brine and dried over Na$_2$SO$_4$. The solvent was removed and the residue was purified by flash column chromatography with DCM: MeOH=10:1 to give the title compound (10 mg, 31.9% yield) as a white solid. LC/MS: 1055.6 [M+H]$^+$.

Step 5: Preparation of (S)-3-(5-(4-((7-((1-(((4-(((1-(dimethylamino)cyclobutyl)methyl)amino)-7-(8-ethyl-7-fluoro-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione (Compound 3)

A solution of (S)-3-(5-(4-((7-((1-(((4-(((1-(dimethylamino)cyclobutyl)methyl)amino)-7-(8-ethyl-7-fluoro-3-(methoxymethoxy)naphthalen-1-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione (10 mg, 0.0095 mmol) in HCl in dioxane (4 M, 1 mL) and THF (1 mL) was stirred under nitrogen at room temperature for 1 hour. The solvent was removed under vacuum and the residue was purified by Prep-TLC with DCM: MeOH=8:1 to give the title compound (3.7 mg, 35.7% yield) as a white solid. LC/MS: 1011.5 [M+H]$^+$; $^1$H NMR (400 MHZ,) δ 10.96 (s, 1H), 9.37 (s, 1H), 8.77 (brs, 1H), 8.23 (s, 3H), 7.76 (dd, J=9.0, 6.1 Hz, 1H), 7.56-7.48 (m, 1H), 7.39-7.31 (m, 2H), 7.09-7.00 (m, 3H), 5.05 (dd, J=13.3, 5.0 Hz, 1H), 4.34-4.30 (m, 2H), 4.22-4.17 (m, 1H), 4.01-3.96 (m, 1H), 3.82-3.78 (m, 1H), 3.26-3.22 (m, 4H), 2.97-2.82 (m, 2H), 2.58 (d, J=17.9 Hz, 2H), 2.48-2.43 (m, 6H), 2.39-2.33 (m, 5H), 2.32-2.34 (m, 10H), 2.17-2.08 (m, 1H), 2.03 (t, J=7.7 Hz, 3H), 1.98-1.93 (m, 1H), 1.85 (t, J=8.9 Hz, 2H), 1.77-1.66 (m, 2H), 1.57-1.50 (m, 2H), 1.43-1.32 (m, 4H), 0.72 (t, J=7.3 Hz, 3H), 0.67-0.61 (m, 2H), 0.44-0.36 (m, 2H).

Example 4: Preparation of (S)-3-(5-(4-((7-((1-(((7-(8-ethyl-7-fluoro-3-hydroxynaphthalen-1-yl)-8-fluoro-4-(2,3,6,7-tetrahydro-1H-azepin-1-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione (Compound 4)

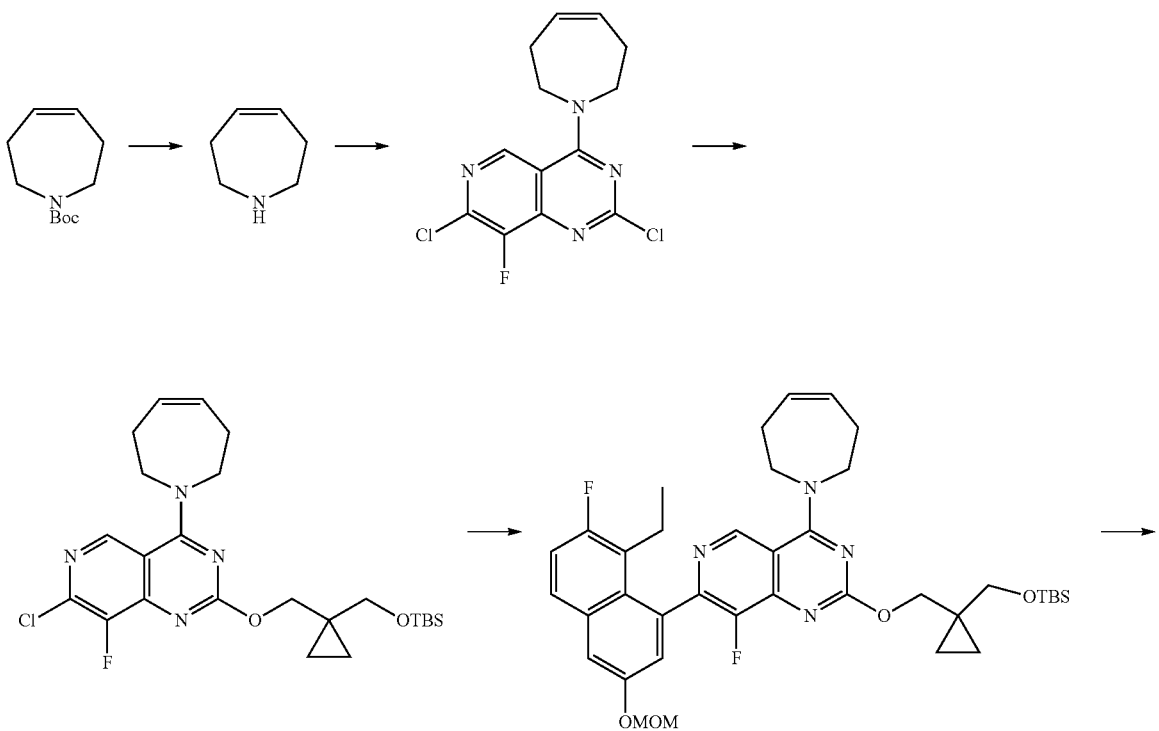

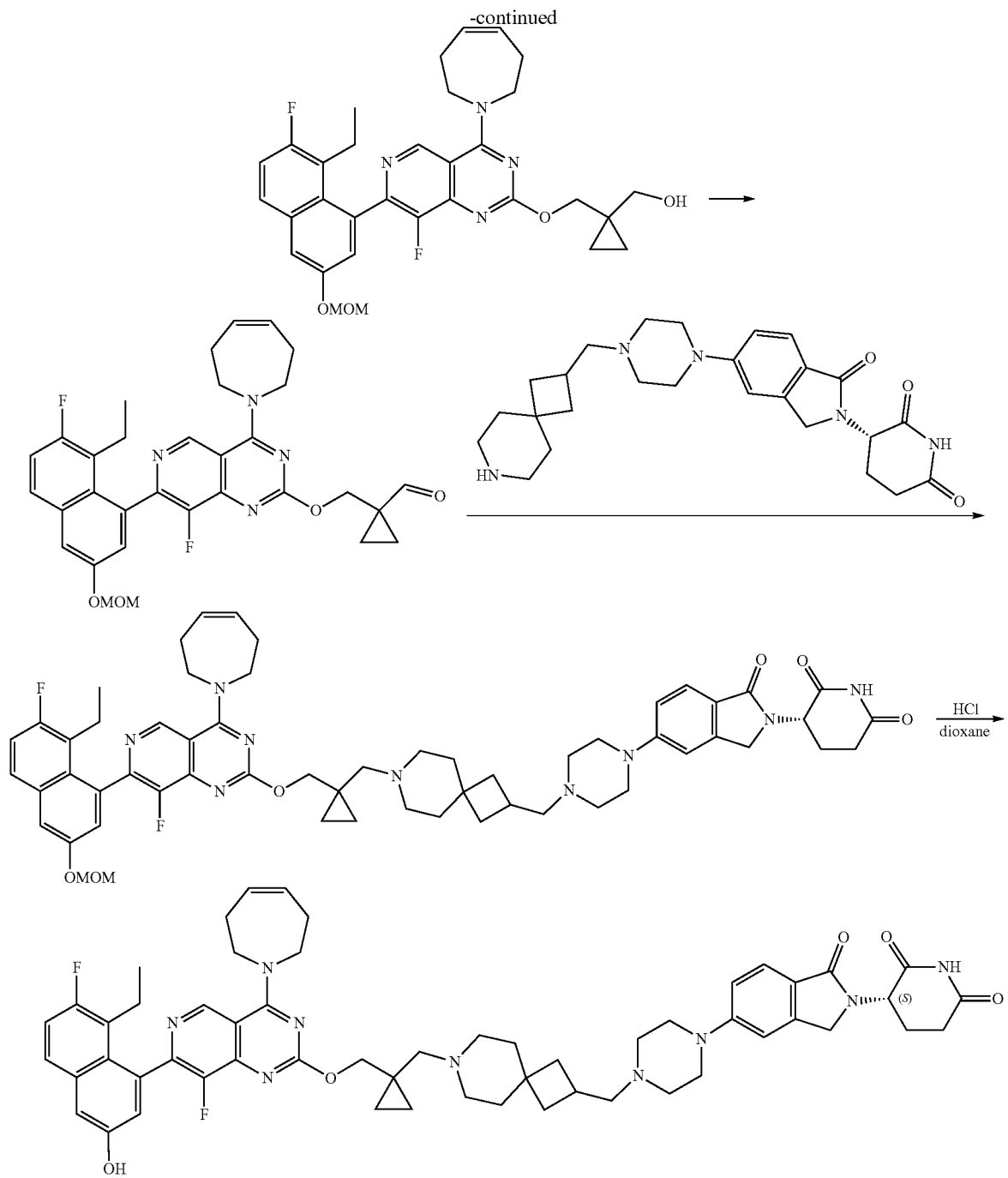

Step 1: Preparation of 2,3,6,7-tetrahydro-1H-azepine

A solution of tert-butyl 2,3,6,7-tetrahydroazepine-1-carboxylate (240 mg, 1.22 mmol) in HCl/dioxane (5 mL) was stirred at room temperature for 1 hour. The mixture was concentrated in vacuum to give the desired compound (100 mg, 95% purity, 80.3% yield) as a white solid. LC/MS: 98.2 [M+H]$^+$.

Step 2: Preparation of 2,7-dichloro-8-fluoro-4-(2,3,6,7-tetrahydro-1H-azepin-1-yl)pyrido[4,3-d]pyrimidine To a solution of 2,3,6,7-tetrahydro-1H-azepine (100 mg, 1.02 mmol) and DIEA (665 mg, 5.14 mmol) in DCM (6 mL) was added 2,4,7-trichloro-8-fluoropyrido[4,3-d]pyrimidine (260 mg, 1.02 mmol) under nitrogen at −40° C. The reaction mixture was stirred at room temperature for 1 hour. The reaction was quenched with water and extracted with EA. The organic phase was washed with brine and dried over Na$_2$SO$_4$. The solution was concentrated in vacuum and the residue was purified by Prep-TLC with PE:EA=2:1 to afford the desired compound (150 mg, 95% purity, 44.2% yield) as a white solid. LC/MS: 312.8 [M+H]$^+$.

Step 3: Preparation of 2-((1-(((tert-butyldimethylsilyl)oxy)methyl)cyclopropyl)methoxy)-7-chloro-8-fluoro-4-(2,3,6,7-tetrahydro-1H-azepin-1-yl)pyrido[4,3-d]pyrimidine To a solution of (1-{[(tert-butyldimethylsilyl)oxy]methyl}cyclopropyl)methanol (104 mg, 0.47 mmol) in THF (10 mL) was added NaH (23 mg, 0.57 mmol, 60%) under nitrogen at 0° C. The mixture was stirred at 0° C. for 1 hour then a solution of 1-{2,7-dichloro-8-fluoropyrido[4,3-d]-pyrimidin-4-yl}-2,3,6,7-tetrahydroazepine (150 mg, 0.48 mmol) was added. The reaction mixture was stirred at room temperature for 1 hour. The reaction was quenched with water and extracted with EA. The organic phase was washed with brine and dried over Na$_2$SO$_4$. The solution was concentrated in vacuum and the residue was purified by Prep-TLC with PE:EA=2:1 to afford the desired compound (175 mg, 70% purity, 51.8% yield) as a white solid. LC/MS: 493.3 [M+H]$^+$.

Step 4: Preparation of 2-((1-(((tert-butyldimethylsilyl)oxy)methyl)cyclopropyl)methoxy)-7-(8-ethyl-7-fluoro-3-(methoxymethoxy)naphthalen-1-yl)-8-fluoro-4-(2,3,6,7-tetrahydro-1H-azepin-1-yl)pyrido[4,3-d]pyrimidine To a solution of 1-{2-[(1-{[(tert-butyldimethylsilyl)oxy]methyl}cyclopropyl)methoxy]-7-chloro-8-fluoropyrido[4,3-d]pyrimidin-4-yl}-2,3,6,7-tetrahydroazepine (175 mg, 0.35 mmol) and 2-[8-ethyl-7-fluoro-3-(methoxymethoxy)naphthalen-1-yl]-4,4,5,5-tetramethyl-1,3,2-dioxaborolane (192 mg, 0.53 mmol) in dioxane (5 mL) and H$_2$O (1 mL) was added Catacxium A-Pd-G3 (26 mg, 0.035 mmol) and K$_2$CO$_3$ (147 mg, 1.06 mmol). The reaction mixture was stirred under N$_2$ at 90° C. for 2 hours. The reaction was quenched with water and extracted with EA. The organic phase was washed with brine and dried over Na$_2$SO$_4$. The solution was concentrated in vacuum and the residue was purified by Prep-TLC with PE:EA=3:1 to afford the desired compound (170 mg, 95% purity, 65.8% yield) as a white solid. LC/MS: 691.4 [M+H]$^+$.

Step 5: Preparation of (1-(((7-(8-ethyl-7-fluoro-3-(methoxymethoxy)naphthalen-1-yl)-8-fluoro-4-(2,3,6,7-tetrahydro-1H-azepin-1-yl)pyrido[4,3-d]pyrimidin-2-yl)oxy)methyl)cyclopropyl)methanol To a solution of 1-{2-[(1-{[(tert-butyldimethylsilyl)oxy]methyl}cyclopropyl)methoxy]-7-[8-ethyl-7-fluoro-3-(methoxymethoxy)naphthalen-1-yl]-8-fluoropyrido[4,3-d]pyrimidin-4-yl}-2,3,6,7-tetrahydroazepine (170 mg, 0.24 mmol) in DMF (3 mL) was added CsF (374 mg, 2.4 mmol). The reaction mixture was stirred at room temperature for 16 hours. The reaction was quenched with water and extracted with EA. The organic phase was washed with brine and dried over Na$_2$SO$_4$. The solution was concentrated in vacuum and the residue was purified by Prep-TLC with PE:EA=1:1 to afford the desired compound (120 mg, 95% purity, 80.3% yield) as a white solid. LC/MS: 577.2 [M+H]$^+$.

Step 6: Preparation of 1-(((7-(8-ethyl-7-fluoro-3-(methoxymethoxy)naphthalen-1-yl)-8-fluoro-4-(2,3,6,7-tetrahydro-1H-azepin-1-yl)pyrido[4,3-d]pyrimidin-2-yl)oxy)methyl)cyclopropane-1-carbaldehyde To a solution of {1-[({7-[8-ethyl-7-fluoro-3-(methoxymethoxy)naphthalen-1-yl]-8-fluoro-4-(2,3,6,7-tetrahydroazepin-1-yl)pyrido[4,3-d]pyrimidin-2-yl}oxy)methyl]cyclopropyl}methanol (120 mg, 0.20 mmol) in DCM (3 mL) was added Dess-Martin periodinane (132 mg, 0.31 mmol) at 0° C. The reaction mixture was stirred at room temperature for 1 hour. The reaction was quenched with water and extracted with DCM. The organic phase was washed with brine and dried over Na$_2$SO$_4$. The solution was concentrated in vacuum and the residue was purified by Prep-TLC with PE:EA=2:1 to afford the desired compound (110 mg, 95% purity, 87.4% yield) as a white solid. LC/MS: 575.2 [M+H]$^+$.

Step 7: Preparation of (S)-3-(5-(4-((7-((1-(((7-(8-ethyl-7-fluoro-3-(methoxymethoxy)naphthalen-1-yl)-8-fluoro-4-(2,3,6,7-tetrahydro-1H-azepin-1-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl) piperidine-2,6-dione To a solution of 1-[({7-[8-ethyl-7-fluoro-3-(methoxymethoxy)naphthalen-1-yl]-8-fluoro-4-(2,3,6,7-tetrahydroazepin-1-yl)pyrido[4,3-d]pyrimidin-2-yl}oxy)methyl]cyclopropane-1-carbaldehyde (110 mg, 0.19 mmol) and (3S)-3-[5-(4-{7-azaspiro[3.5]nonan-2-ylmethyl}piperazin-1-yl)-1-oxo-3H-isoindol-2-yl]piperidine-2,6-dione (89 mg, 0.19 mmol) in DMF (6 mL) was added DIEA (124 mg, 0.95 mmol). The mixture was stirred at room temperature for 30 minutes and sodium triacetoxyborohydride (81 mg, 0.38 mmol) was added.

The reaction mixture was stirred at room temperature for 1 hour. The reaction was quenched with water and extracted with EA. The organic phase was washed with brine and dried over Na$_2$SO$_4$. The solution was concentrated in vacuum and the residue was purified by Prep-TLC with DCM:MeOH=10:1 to afford the desired compound (40 mg, 95% purity, 19.3% yield) as a white solid. LC/MS: 1024.5 [M+H]$^+$.

Step 8: Preparation of (S)-3-(5-(4-((7-((1-(((7-(8-ethyl-7-fluoro-3-hydroxynaphthalen-1-yl)-8-fluoro-4-(2,3,6,7-tetrahydro-1H-azepin-1-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione (Compound 4)

A solution of (3S)-3-[5-(4-{[7-({1-[({7-[8-ethyl-7-fluoro-3-(methoxymethoxy)naphthalen-1-yl]-8-fluoro-4-(2,3,6,7-tetrahydroazepin-1-yl)pyrido[4,3-d]pyrimidin-2-yl}oxy)methyl]cyclopropyl}methyl)-7-azaspiro[3.5]nonan-2-yl]methyl}piperazin-1-yl)-1-oxo-3H-isoindol-2-yl]piperidine-2,6-dione (30 mg, 0.03 mmol) in HCl/dioxane (4 M, 1 mL) and THF (1 mL) was stirred under nitrogen at 25° C. for 2 hours. The mixture was concentrated in vacuum and the residue was purified by Prep-HPLC (Gemini-C18:150×21.2 mm, 5 μm; ACN-H$_2$O (0.1% FA) 23-23%) to give the desired product (10 mg, 99.6% purity in 214 nm, 34.7% yield) as a white solid. LC/MS: 980.4 [M+H]$^+$; $^1$H NMR (400 MHZ) δ10.92 (s, 1H), 9.15 (s, 1H), 8.11 (s, 1H), 7.73

(dd, J=9.1, 6.0 Hz, 1H), 7.49 (d, J=8.6 Hz, 1H), 7.33-7.29 (m, 2H), 7.03-6.99 (m, 3H), 5.67 (t, J=2.6 Hz, 2H), 5.01 (dd, J=13.3, 5.1 Hz, 1H), 4.32-4.25 (m, 3H), 4.19-4.09 (m, 5H), 3.30-3.20 (m, 6H), 2.92-2.70 (m, 6H), 2.61-2.50 (m, 9H), 2.38-2.26 (m, 3H), 2.19-2.02 (m, 2H), 1.94-1.85 (m, 3H), 1.75-1.64 (m, 3H), 1.61-1.54 (m, 2H), 1.44-1.37 (m, 2H), 0.75-0.66 (m, 5H), 0.59 (s, 2H).
Example 5: Preparation of (S)-3-(5-(4-((1-((1-(((7-(8-ethyl-3-hydroxynaphthalen-1-yl)-8-fluoro-4-((R)-3-hydroxy-3-methylpiperidin-1-yl)pyrido[4,3-d]pyrimidin-2-yl)oxy)methyl) cyclopropyl)methyl) piperidin-4-yl)methyl)piperazin-1-yl)-1-oxoisoindolin-2-yl)piperidine-2,6-dione (Compound 6)
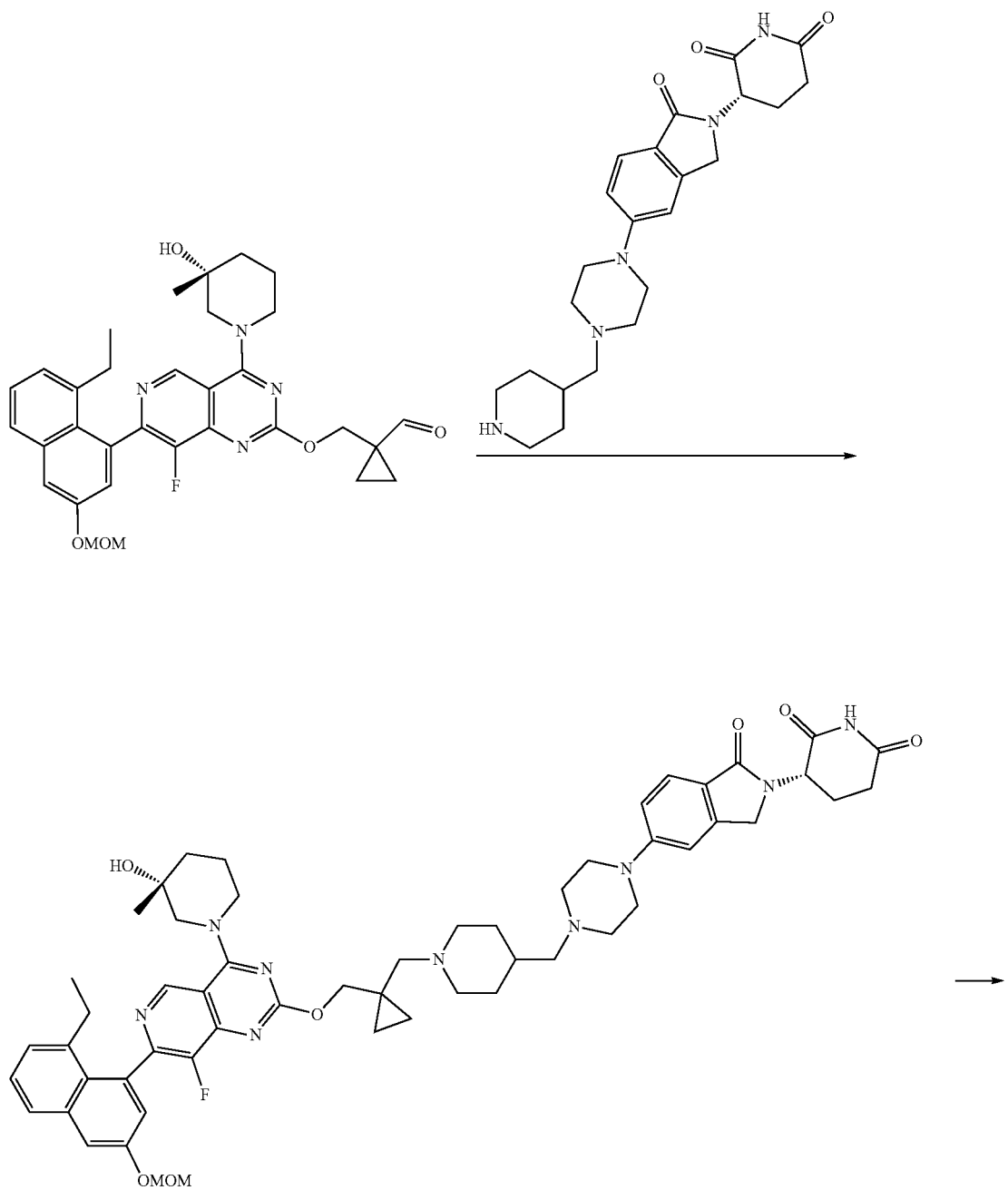

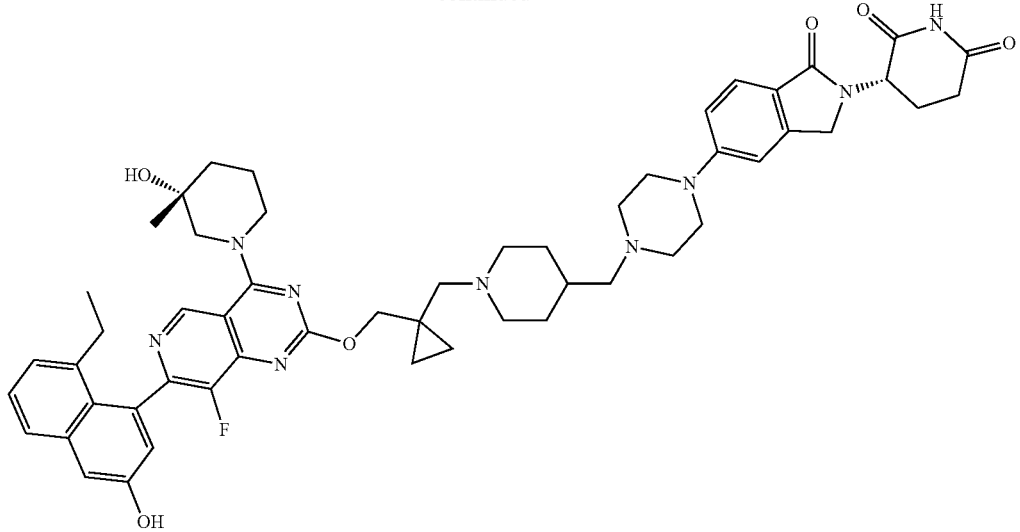

Step 1: Preparation of (S)-3-(5-(4-((1-((1-(((7-(8-ethyl-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione To a solution of (R)-1-(((7-(8-ethyl-3-(methoxymethoxy)naphthalen-1-yl)-8-fluoro-4-(3-hydroxy-3-methylpiperidin-1-yl)pyrido[4,3-d]pyrimidin-2-yl)oxy)methyl)cyclopropane-1-carbaldehyde (500 mg, 0.87 mmol) and (S)-3-(1-oxo-5-(4-(piperidin-4-ylmethyl)piperazin-1-yl)isoindolin-2-yl)piperidine-2,6-dione (651 mg, 1.30 mmol) in DMA (5 mL) and THF (5 mL) was added DIEA (562 mg, 4.35 mmol). The mixture was stirred at room temperature for 1 hour and STAB (553 mg, 2.61 mmol) was added. The reaction mixture was stirred at 40° C. for 16 hours. The reaction mixture was poured into water (10 mL) and extracted with DCM (10 mL×3). The combined organic layer was dried over $Na_2SO_4$ and concentrated in vacuum. The residue was purified by Prep-TLC (DCM:MeOH=10:1) to give the desired compound (350 mg, 40.8% yield) as a white solid. LC/MS: 984.5 [M+H]+

Step 2: Preparation of (S)-3-(5-(4-((1-((1-(((7-(8-ethyl-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl) methyl)piperidin-4-yl)methyl)piperazin-1-yl)-1-oxoisoindolin-2-yl)piperidine-2,6-dione (Compound 6)

A solution of (S)-3-(5-(4-((1-((1-(((7-(8-ethyl-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione (350 mg, 0.35 mmol) in HCl/dioxane (4 M, 2 ml) and THF (2 mL) was stirred at room temperature for 1 hour. The mixture was concentrated in vacuum to give a crude product. The crude product was purified by Prep-HPLC (0.1% FA in $H_2O$/ACN=5~95%) to give the desired product (200 mg, 59.8%) as a white solid. LC/MS: 940.5 [M+H]+; $^1$H NMR (400 MHZ, DMSO) δ 10.96 (s, 1H), 9.22 (d, J=8.0 Hz, 1H), 8.17 (s, 2H), 7.67 (d, J=8.2 Hz, 1H), 7.52 (d, J=8.7 Hz, 1H), 7.37 (t, J=7.6 Hz, 1H), 7.29 (d, J=2.5 Hz, 1H), 7.12 (d, J=7.0 Hz, 1H), 7.07-7.01 (m, 2H), 6.98 (d, J=2.6 Hz, 1H), 5.05 (dd, J=13.6, 5.2 Hz, 1H), 4.35-4.27 (m, 5H), 4.24-4.15 (m, 2H), 4.05 (dd, J=19.2, 13.1 Hz, 2H), 3.63 (d, J=13.0 Hz, 1H), 3.51 (d, J=13.3 Hz, 1H), 3.42-3.33 (m, 2H), 3.29-3.21 (m, 2H), 3.08-2.98 (m, 3H), 2.93-2.85 (m, 1H), 2.47-2.40 (m, 4H), 2.38-2.32 (m, 2H), 2.14 (d, J=7.1 Hz, 2H), 2.02-1.95 (m, 4H), 1.73-1.63 (m, 5H), 1.54-1.48 (m, 1H), 1.21-1.07 (m, 6H), 0.86-0.78 (m, 3H), 0.71-0.64 (m, 2H), 0.48-0.42 (m, 2H).

Example 6: Preparation of (S)-3-(5-(4-((1-((1-(((7-(8-ethyl-7-fluoro-3-hydroxynaphthalen-1-yl)-8-fluoro-4-((R)-3-hydroxy-3-methylpiperidin-1-yl) pyrido[4,3-d]pyrimidin-2-yl)oxy)methyl) cyclopropyl)methyl)-4-fluoropiperidin-4-yl)methyl) piperazin-1-yl)-1-oxoisoindolin-2-yl)piperidine-2,6-dione (Compound 8)

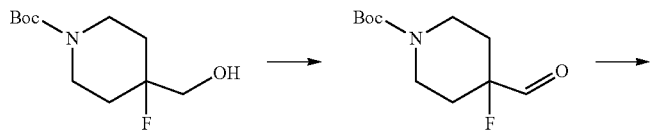

383                                                                                        384
-continued
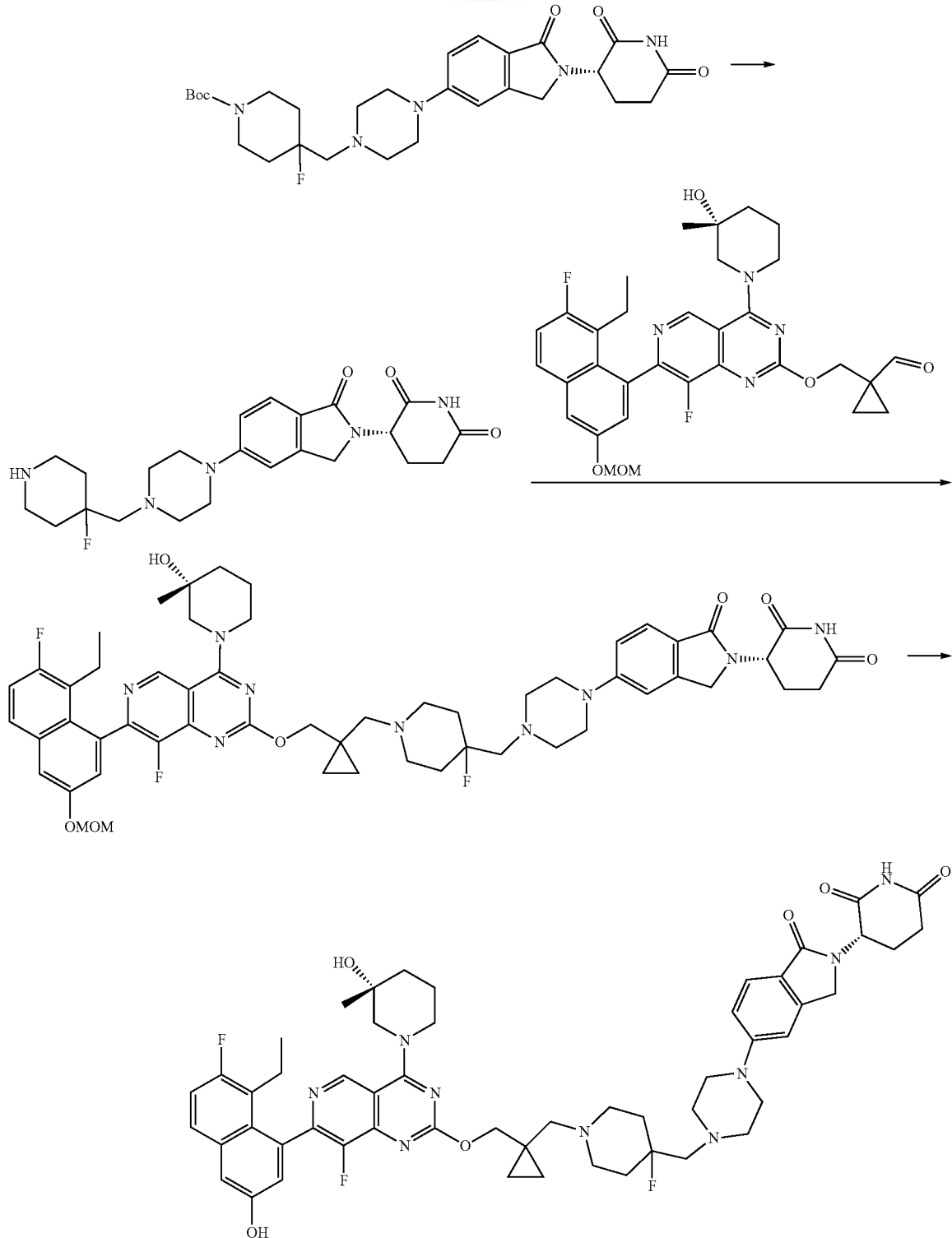
Step 1: Preparation of tert-butyl
4-fluoro-4-formylpiperidine-1-carboxylate
To a solution of tert-butyl 4-fluoro-4-(hydroxymethyl)piperidine-1-carboxylate (10 g, 42.9 mmol) in EA (200 mL) was added IBX (24 g, 85.8 mmol). The reaction was stirred at 80° C. for 24 hours. The mixture was filtered and the filtrate was concentrated to afford the desired product (9 g, 86% yield) as a yellow oil.

Step 2: Preparation of tert-butyl (S)-4-((4-(2-(2,6-dioxopiperidin-3-yl)-1-oxoisoindolin-5-yl)piperazin-1-yl)methyl)-4-fluoropiperidine-1-carboxylate To a solution of (S)-3-(1-oxo-5-(piperazin-1-yl)isoindolin-2-yl)piperidine-2,6-dione benzenesulfonate (5 g, 15.2 mmol) in DMA (50 mL) was added DIEA (1.96 g, 15.2 mmol). The mixture was stirred at room temperature for 20 minutes and tert-butyl (4-fluoro-4-formylpiperidin-1-yl)formate (5.3 g, 22.8 mmol) and HOAc (2 mL) were added. The mixture was stirred at room temperature for 2 hours and STAB (9.66 g, 45.6 mmol) was added. The reaction mixture was stirred at room temperature for 16 hours. The mixture was diluted with EA (300 mL) and washed with water (100 mL×3). The organic phase was washed with brine and dried over $Na_2SO_4$. The solution was concentrated in vacuum and the residue was purified by Flash (PE:EA=100:1~1:1) to give the desired compound (5 g, 61% yield) as a brown solid. LC/MS: 487.8 [M−56+H]+.

Step 3: Preparation of (S)-3-(5-(4-((4-fluoropiperidin-4-yl)methyl)piperazin-1-yl)-1-oxoisoindolin-2-yl)piperidine-2,6-dione To a solution of tert-butyl {4-[(4-{2-[(3S)-2,6-dioxopiperidin-3-yl]-1-oxo-3H-isoindol-5-yl}piperazin-1-yl)methyl]-4-fluoropiperidin-1-yl}formate (5 g, 8.7 mmol) in dioxane (50 mL) was added HCl/dioxane (4 M, 50 mL). The reaction was stirred at room temperature for 2 hours. The mixture was concentrated in vacuum and the residue was triturated with ACN (15 mL). The solid was filtered and dried to give the title product (4.8 g, HCl salt, crude) as a white solid. LC/MS: 443.9 [M+H]+.

Step 4: Preparation of (S)-3-(5-(4-((1-((1-(((7-(8-ethyl-7-fluoro-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-4-fluoropiperidin-4-yl)methyl)piperazin-1-yl)-1-oxoisoindolin-2-yl)piperidine-2,6-dione The mixture of (R)-1-(((7-(8-ethyl-7-fluoro-3-(methoxymethoxy)naphthalen-1-yl)-8-fluoro-4-(3-hydroxy-3-methylpiperidin-1-yl)pyrido[4,3-d]pyrimidin-2-yl)oxy)methyl)cyclopropane-1-carbaldehyde (3 g, 5.06 mmol), (S)-3-(5-(4-((4-fluoropiperidin-4-yl)methyl)piperazin-1-yl)-1-oxoisoindolin-2-yl)piperidine-2,6-dione hydrochloride (2.92 g, 6.08 mmol) and DIEA (6.55 g, 50.68 mmol) in DMA (60 mL) was stirred at 40° C. for 0.5 h and STAB (3.22 g, 15.19 mmol) was added. The mixture was stirred at 40° C. for 16 hours. The reaction was quenched with water (30 mL) and extracted with DCM (30 mL×3). The organic phase was concentrated in vacuum and the residue was purified by flash chromatography on silica gel (DCM:MeOH=10:1) to afford the desired product (1.9 g, 37% yield). LC/MS: 1020.4 [M+H]+.

Step 5: Preparation of (S)-3-(5-(4-((1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-4-fluoropiperidin-4-yl)methyl)piperazin-1-yl)-1-oxoisoindolin-2-yl)piperidine-2,6-dione (Compound 8)

To the solution of (S)-3-(5-(4-((1-((1-(((7-(8-ethyl-7-fluoro-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-4-fluoropiperidin-4-yl)methyl)piperazin-1-yl)-1-oxoisoindolin-2-yl)piperidine-2,6-dione (1.9 g, 1.86 mmol) in DCM (25 mL) was added HCl/dioxane (4 M, 6 mL). The mixture was stirred at room temperature for 1 hour. The mixture was concentrated in vacuum and the residue was purified by Prep-HPLC (Gemini-C18: 150×21.2 mm, 5 μm, ACN-$H_2O$ (0.05% $NH_3$) 20~50%) to give the desired product (1.182 g, 65% yield). LC/MS: 976.3 [M+H]+; $^1$H NMR (400 MHZ, DMSO) δ 10.95 (s, 1H), 9.95 (s, 1H), 9.22 (d, J=2.0 Hz, 1H), 7.76 (dd, J=9.2, 6.0 Hz, 1H), 7.51 (d, J=8.8 Hz, 1H), 7.39-7.31 (m, 2H), 7.07-6.99 (m, 3H), 5.05 (dd, J=13.2, 5.2 Hz, 1H), 4.74 (d, J=7.2 Hz, 1H), 4.39-4.27 (m, 4H), 4.22-4.17 (m, 1H), 4.10-3.99 (m, 1H), 3.65-3.48 (m, 1H), 3.24 (s, 4H), 2.95-2.85 (m, 1H), 2.76-2.53 (m, 7H), 2.43-2.09 (m, 9H), 2.02-1.92 (m, 2H), 1.83-1.54 (m, 8H), 1.17 (d, J=9.6 Hz, 3H), 0.74 (q, J=7.2 Hz, 3H), 0.65 (s, 2H), 0.42 (s, 2H).

Example 7: Preparation of (S)-3-(5-(4-((1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-4-methylpiperidin-4-yl)methyl)piperazin-1-yl)-1-oxoisoindolin-2-yl)piperidine-2,6-dione (Compound 12)

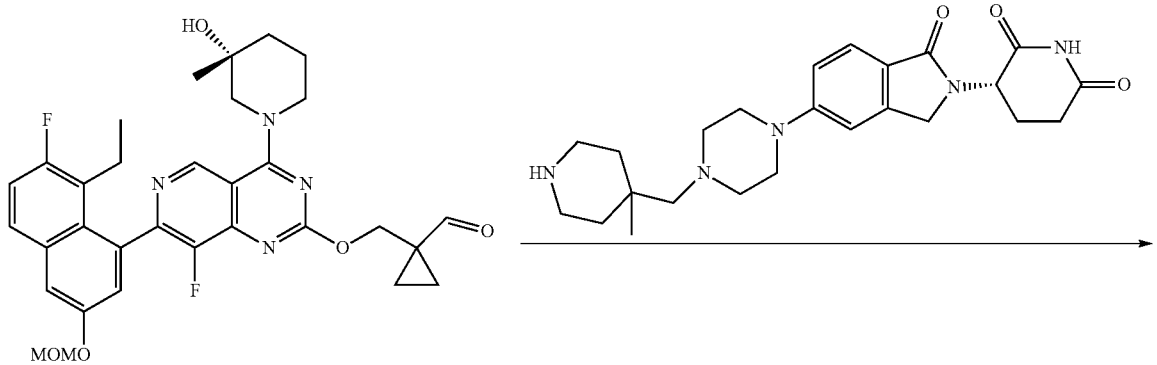

-continued
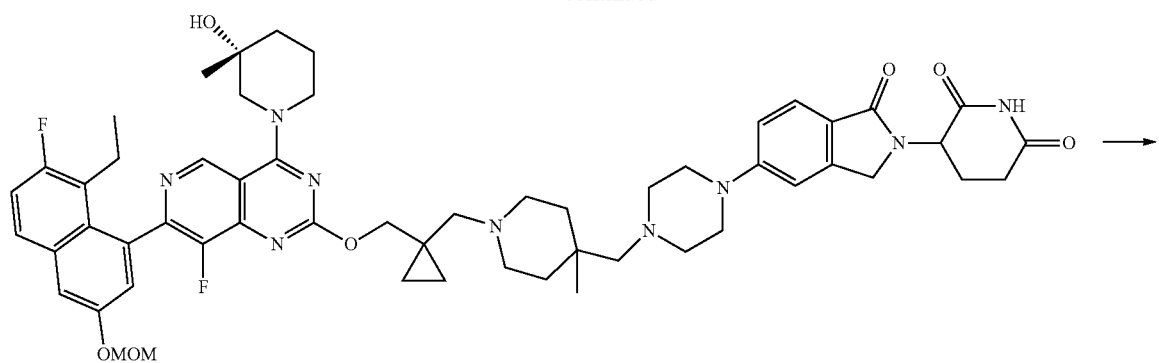
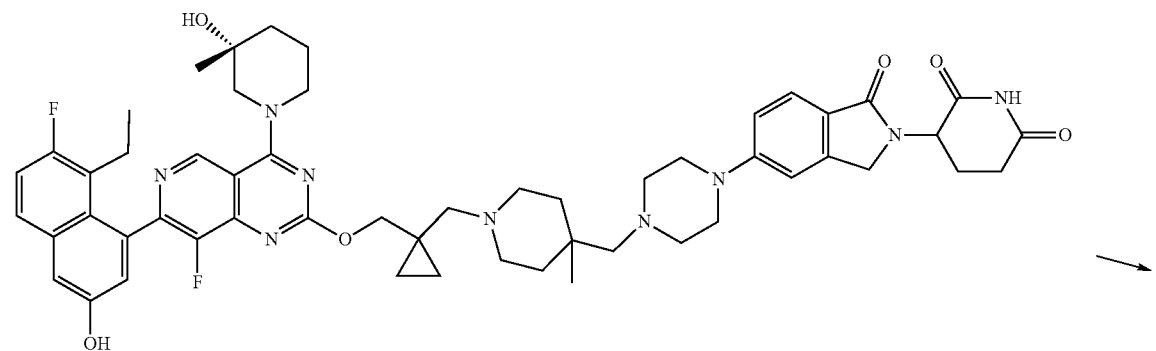
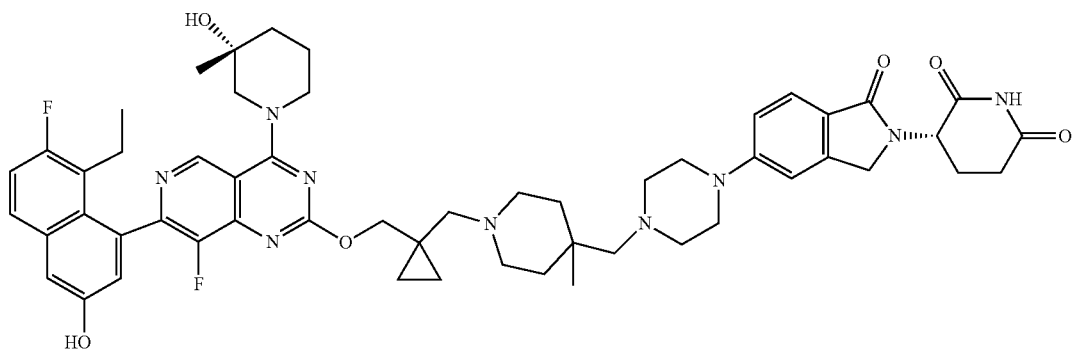
12
+
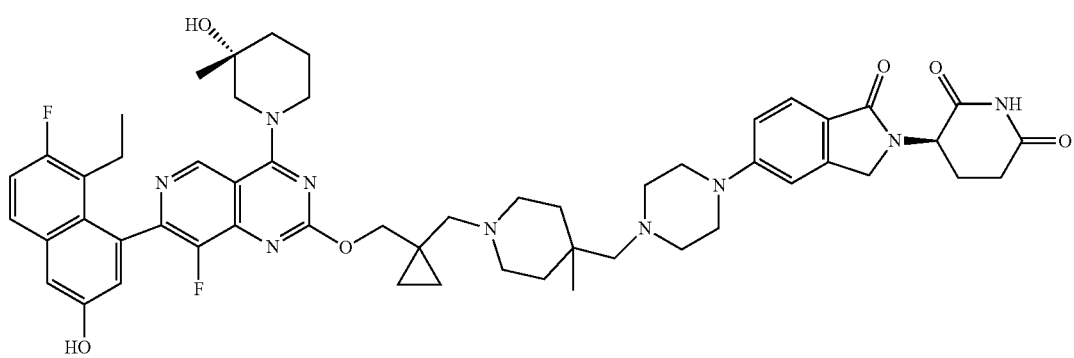

Step 1: Preparation of 3-(5-(4-((1-((1-(((7-(8-ethyl-7-fluoro-3-(methoxymethoxy)naphthalen-1-yl)-8-fluoro-4-((R)-3-hydroxy-3-methylpiperidin-1-yl) pyrido[4,3-d]pyrimidin-2-yl)oxy)methyl) cyclopropyl)methyl)-4-methylpiperidin-4-yl)methyl) piperazin-1-yl)-1-oxoisoindolin-2-yl)piperidine-2,6-dione To a solution of (R)-1-(((7-(8-ethyl-7-fluoro-3-(methoxymethoxy)naphthalen-1-yl)-8-fluoro-4-(3-hydroxy-3-methylpiperidin-1-yl)pyrido[4,3-d]pyrimidin-2-yl)oxy)methyl)cyclopropane-1-carbaldehyde (2.4 g, 4.05 mmol) in DMA/i-PrOH (1:1, 30 mL) stirred at room temperature was added (S)-3-(5-(4-((4-methylpiperidin-4-yl)methyl)piperazin-1-yl)-1-oxoisoindolin-2-yl)piperidine-2,6-dione hydrochloride (2.31 g, 4.86 mmol), DIEA (7.1 mL, 40.5 mmol) and Ti(i-PrO)$_4$ (12 ml, 40.5 mmol). The mixture was stirred at 45° C. for 16 hours and STAB (2.58 g, 12.15 mmol) was added. The reaction mixture was stirred at 45° C. for 3 hours and NaBH$_3$CN (764 mg, 12.15 mmol) was added. The reaction mixture was stirred at 45° C. for 16 hours. The reaction was poured into water (100 mL) and extracted with DCM (100 mL×2). The combined organic layer was dried over Na$_2$SO$_4$ and concentrated in vacuum. The solution was concentrated in vacuum and the residue was purified by Flash (DCM:MeOH=10:1) to give the desired compound (2.4 g, 58% yield) as a yellow solid. LC/MS: 1016.3 [M+H]$^+$.

Step 2: Preparation of (S)-3-(5-(4-((1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-4-methylpiperidin-4-yl)methyl)piperazin-1-yl)-1-oxoisoindolin-2-yl)piperidine-2,6-dione (Compound 12)

To a solution of 3-(5-(4-((1-((1-(((7-(8-ethyl-7-fluoro-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-4-methylpiperidin-4-yl)methyl)piperazin-1-yl)-1-oxoisoindolin-2-yl)piperidine-2,6-dione (2.4 g, 2.36 mmol) in DCM (25 mL) was added HCl/dioxane (4 M, 5 mL). The mixture was stirred at room temperature for 1 hour. The mixture was concentrated in vacuum to give a crude product. The crude product was purified by Prep-HPLC (Xbridge-C18: 150×19 mm, 5 μm, ACN-H$_2$O (0.05% NH$_3$) 65~80%) to give 3-(5-(4-((1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-4-methylpiperidin-4-yl)methyl)piperazin-1-yl)-1-oxoisoindolin-2-yl)piperidine-2,6-dione (0.9 g, 82.8% purity).

The obtained 3-(5-(4-((1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-4-methylpiperidin-4-yl)methyl)piperazin-1-yl)-1-oxoisoindolin-2-yl)piperidine-2,6-dione (50 mg) was separated by chiral HPLC to obtain Compound 12-P1 (4.6 mg), LC/MS: 972.4 [M+H]$^+$; $^1$H NMR (400 MHZ, DMSO) δ 10.94 (s, 1H), 9.96 (s, 0.5H), 9.21 (d, J=5.2 Hz, 1H), 8.22 (s, 0.5H), 7.76 (dd, J=8.8, 6.0 Hz, 1H), 7.50 (d, J=8.4 Hz, 1H), 7.38-7.30 (m, 2H), 7.05-6.97 (m, 3H), 5.04 (dd, J=13.2, 5.2 Hz, 1H), 4.80-4.64 (m, 1H), 4.37-4.17 (m, 5H), 4.08-3.97 (m, 1H), 3.61-3.52 (m, 1H), 3.22 (s, 4H), 2.93-2.85 (m, 1H), 2.61-2.53 (m, 7H), 2.41-2.14 (m, 9H), 2.02-1.92 (m, 2H), 1.71-1.61 (m, 3H), 1.45-1.38 (m, 2H), 1.22-1.10 (m, 6H), 0.87 (s, 3H), 0.76-0.70 (m, 3H), 0.64 (s, 2H), 0.41 (s, 2H) and Compound 12-P2 (5.7 mg), LC/MS: 972.3 [M+H]$^+$; $^1$H NMR (400 MHZ, DMSO) δ 10.94 (s, 1H), 9.97 (s, 1H), 9.21 (d, J=4.4 Hz, 1H), 7.76 (dd, J=9.2, 6.0 Hz, 1H), 7.50 (d, J=8.8 Hz, 1H), 7.37-7.30 (m, 2H), 7.05-6.97 (m, 3H), 5.04 (dd, J=13.2, 5.2 Hz, 1H), 4.73 (d, J=8.4 Hz, 1H), 4.38-4.17 (m, 5H), 4.08-3.96 (m, 1H), 3.65-3.50 (m, 1H), 3.21 (s, 4H), 2.95-2.83 (m, 1H), 2.63-2.52 (m, 7H), 2.42-2.13 (m, 9H), 2.04-1.92 (m, 2H), 1.72-1.62 (m, 3H), 1.46-1.38 (m, 2H), 1.22-1.11 (m, 6H), 0.86 (s, 3H), 0.76-0.71 (m, 3H), 0.63 (s, 2H), 0.40 (s, 2H).

Example 8: Preparation of 3-(5-(2-((1-((1-(((7-(8-ethyl-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl) piperidin-4-yl)methyl)-2,7-diazaspiro[3.5]nonan-7-yl)-1-oxoisoindolin-2-yl)piperidine-2,6-dione (Compound 19)

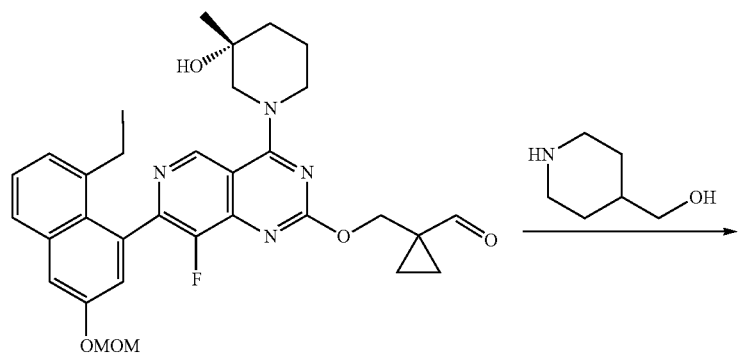

391
392
-continued
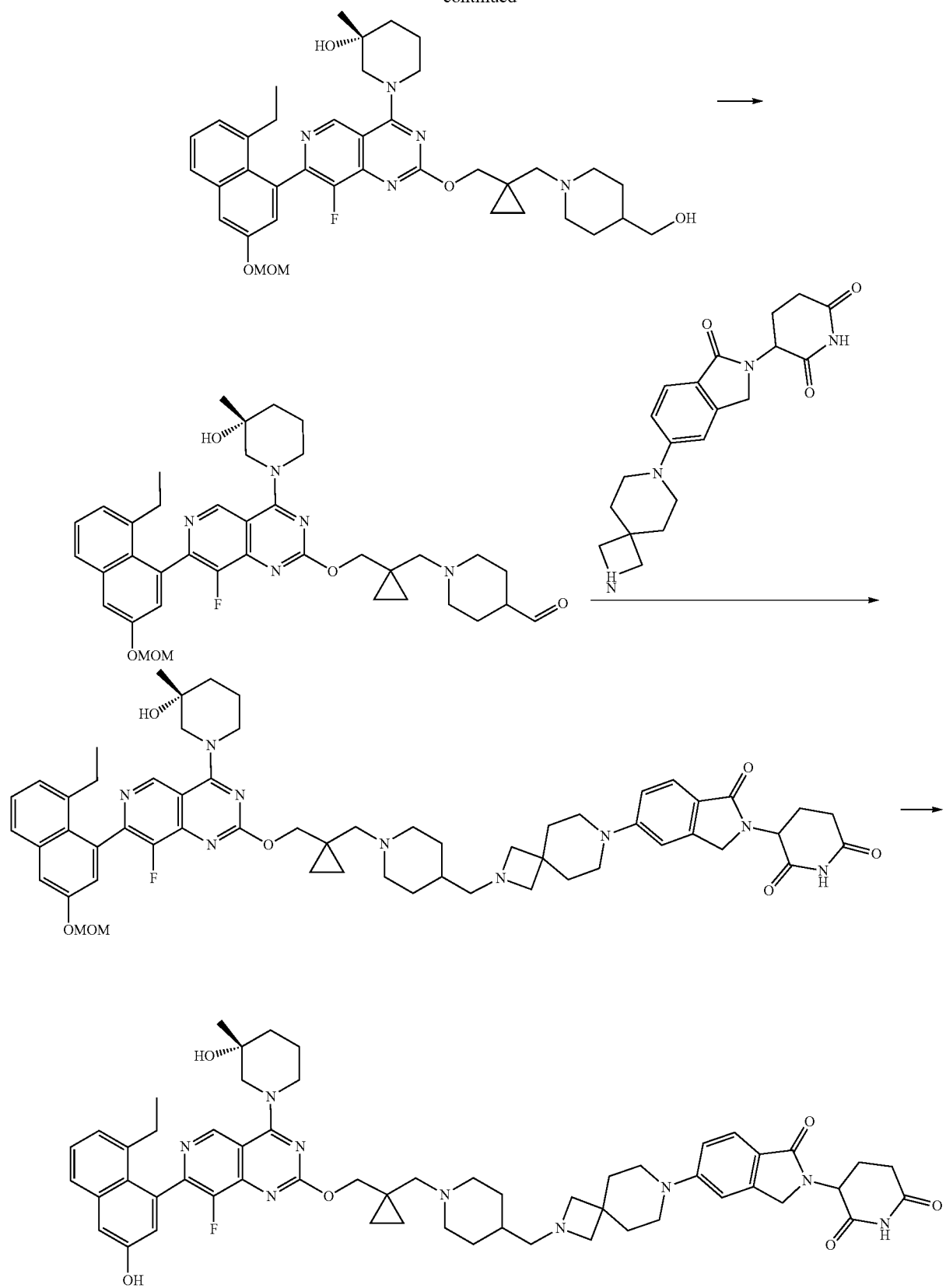

Step 1: Preparation of (R)-1-(7-(8-ethyl-3-(methoxymethoxy)naphthalen-1-yl)-8-fluoro-2-((1-((4-(hydroxymethyl)piperidin-1-yl)methyl)cyclopropyl)methoxy)pyrido[4,3-d]pyrimidin-4-yl)-3-methylpiperidin-3-ol To a solution of (R)-1-(((7-(8-ethyl-3-(methoxymethoxy)naphthalen-1-yl)-8-fluoro-4-(3-hydroxy-3-methylpiperidin-1-yl)pyrido[4,3-d]pyrimidin-2-yl)oxy)methyl)cyclopropane-1-carbaldehyde (242 mg, 2.1 mmol) in DCM (5 mL) was added TEA (212 mg, 2.1 mmol) and piperidin-4-ylmethanol (242 mg, 2.1 mmol). The mixture was stirred at 25° C. for 30 minutes and STAB (267 mg, 1.26 mmol) was added. The mixture was stirred at 25° C. for 2 hours. The reaction was quenched with NaHCO$_3$ solution and extracted with DCM. The organic phase was washed with brine and dried over Na$_2$SO$_4$. The solution was concentrated in vacuum and the residue was purified by flash chromatography on silica gel with MeOH (1% NH$_3$H$_2$O added): DCM=1:15 to give the desired compound (150 mg, 52.3% yield) as a white solid. LC/MS: 674.32 [M+H]$^+$.

Step 2: Preparation of (R)-1-((1-(((7-(8-ethyl-3-(methoxymethoxy)naphthalen-1-yl)-8-fluoro-4-(3-hydroxy-3-methylpiperidin-1-yl)pyrido[4,3-d]pyrimidin-2-yl)oxy)methyl)cyclopropyl)methyl)piperidine-4-carbaldehyde To a solution of ((R)-1-{7-[8-ethyl-3-(methoxymethoxy)naphthalen-1-yl]-8-fluoro-2-[(1-{[4-(hydroxymethyl)piperidin-1-yl]methyl}cyclopropyl)methoxy]pyrido[4,3-d]pyrimidin-4-yl}-3-methylpiperidin-3-ol (150 mg, 0.22 mmol) in DCM (5 mL) was added a solution of Dess-Martin periodinane (187 mg, 0.44 mmol) in DCM (2 mL) dropwise at 0° C. The mixture was stirred at 25° C. for 2 hours. The reaction was quenched with NaHCO$_3$ solution and extracted with DCM. The organic phase was washed with brine and dried over Na$_2$SO$_4$. The solution was concentrated in vacuum and the residue was purified by flash chromatography on silica gel with MeOH (1% NH$_3$H$_2$O added): DCM=1:10 to give the desired compound (100 mg, 68.1% yield) as a white solid. LC/MS: 672.3 [M+H]$^+$.

Step 3: Preparation of 3-(5-(2-((1-((1-(((7-(8-ethyl-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclo propyl)methyl)piperidin-4-yl)methyl)-2,7-diazaspiro[3.5]nonan-7-yl)-1-oxoisoindolin-2-yl)piperidine-2,6-dione To a solution of (R)-1-((1-(((7-(8-ethyl-3-(methoxymethoxy)naphthalen-1-yl)-8-fluoro-4-(3-hydroxy-3-methylpiperidin-1-yl)pyrido[4,3-d]pyrimidin-2-yl)oxy)methyl)cyclopropyl)methyl) piperidine-4-carbaldehyde (50 mg, 0.074 mmol) and 3-(5-{2,7-diazaspiro[3.5]nonan-7-yl}-1-oxo-3H-isoindol-2-yl)piperidine-2,6-dione (82 mg, 0.222 mmol) in DCM (8 mL) was added DIEA (29 mg, 0.222 mmol). The mixture was stirred at 25° C. for 30 minutes and STAB (47 mg, 0.222 mmol) was added. The reaction mixture was stirred at 25° C. for 2 hours. The reaction was quenched with water and extracted with EA. The organic phase was washed with brine and dried over Na$_2$SO$_4$. The solution was concentrated in vacuum and the residue was purified by flash column chromatography on silica gel with MeOH (1% NH$_3$H$_2$O added): DCM=1:10 to give the desired compound (45 mg, 59.4% yield) as a yellow solid. LC/MS: 1024.5 [M+H]$^+$.

Step 4: Preparation of 3-(5-(2-((1-((1-(((7-(8-ethyl-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl) piperidin-4-yl)methyl)-2,7-diazaspiro[3.5]nonan-7-yl)-1-oxoisoindolin-2-yl)piperidine-2,6-dione (Compound 19)

A solution of 3-(5-(2-((1-((1-(((7-(8-ethyl-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclopropyl)methyl) piperidin-4-yl)methyl)-2,7-diazaspiro[3.5]nonan-7-yl)-1-oxoisoindolin-2-yl)piperidine-2,6-dione (45 mg, 0.044 mmol) in HCl/dioxane (4 M, 1 mL) and THF (1 mL) was stirred under nitrogen at room temperature for 0.5 hour. The solution was concentrated in vacuum and the residue was purified by Prep-HPLC (0.1% FA in H2O/ACN=10~40%) to obtain the desired compound (8.7 mg, 20.4% yield) as a white solid. LC/MS: 980.2 [M+H]$^+$; $^1$H NMR (400 MHZ, DMSO) δ 10.94 (s, 1H), 9.94 (s, 1H), 9.21 (d, J=6.8 Hz, 1H), 8.18 (s, 1H), 7.67 (d, J=8.4 Hz, 1H), 7.49 (d, J=8.4 Hz, 1H), 7.37 (t, J=7.6 Hz, 1H), 7.28 (d, J=2.4 Hz, 1H), 7.12 (d, J=6.4 Hz, 1H), 7.07-7.01 (m, 2H), 6.98 (d, J=2.4 Hz, 1H), 5.04 (dd, J=13.2, 5.2 Hz, 1H), 4.75 (s, 1H), 4.37-4.16 (m, 5H), 4.09-4.00 (m, 1H), 3.63 (d, J=12.8 Hz, 1H), 3.51 (d, J=13.2 Hz, 1H), 3.26 (s, 6H), 3.12 (s, 4H), 3.00-2.86 (m, 3H), 2.60-2.55 (m, 1H), 2.43-2.38 (m, 1H), 2.34-2.16 (m, 4H), 2.02-1.93 (m, 2H), 1.85 (t, J=10.0 Hz, 2H), 1.75-1.58 (m, 7H), 1.64-1.54 (m, 2H), 1.17 (d, J=10.8 Hz, 3H), 1.08 (t, J=10.0 Hz, 2H), 0.85-0.80 (m, 3H), 0.65 (s, 2H), 0.41 (s, 2H).

Example 9: Preparation of 3-(5-(4-((1-((1-(((7-(8-ethyl-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl) piperidin-4-yl)oxy)piperidin-1-yl)-1-oxoisoindolin-2-yl)piperidine-2,6-dione (Compound 24)

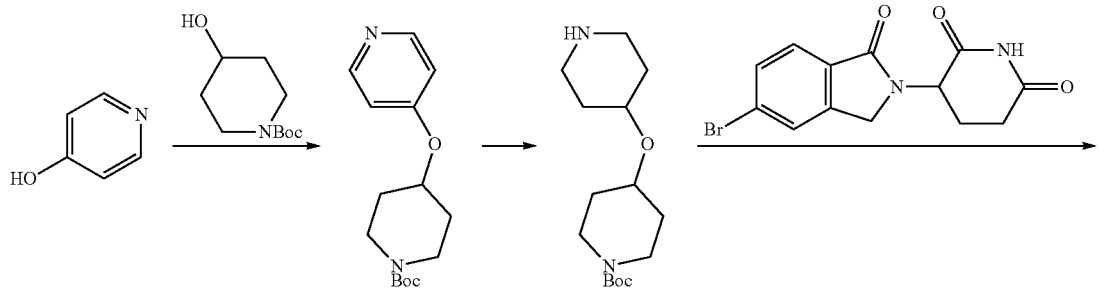

-continued
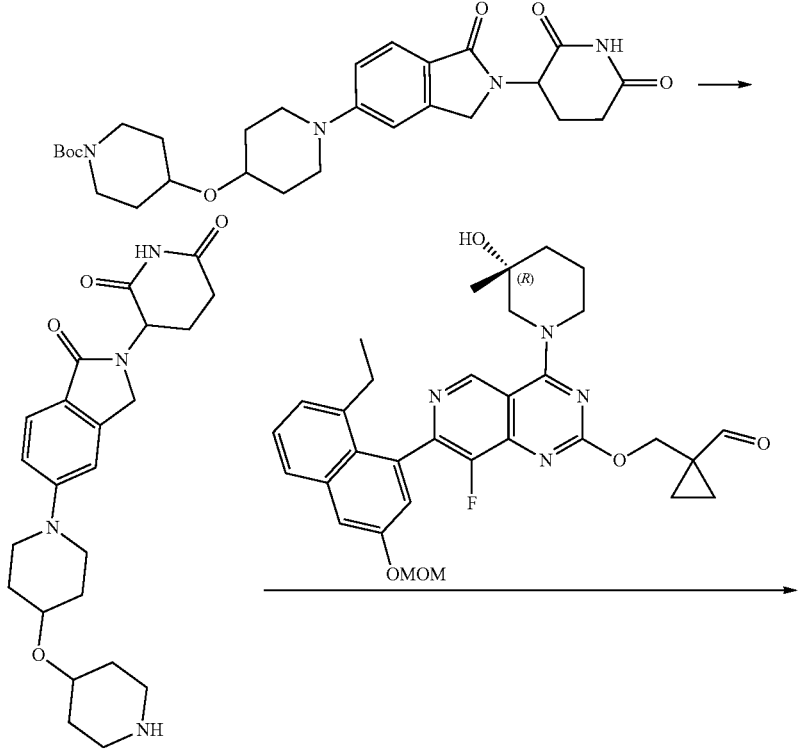
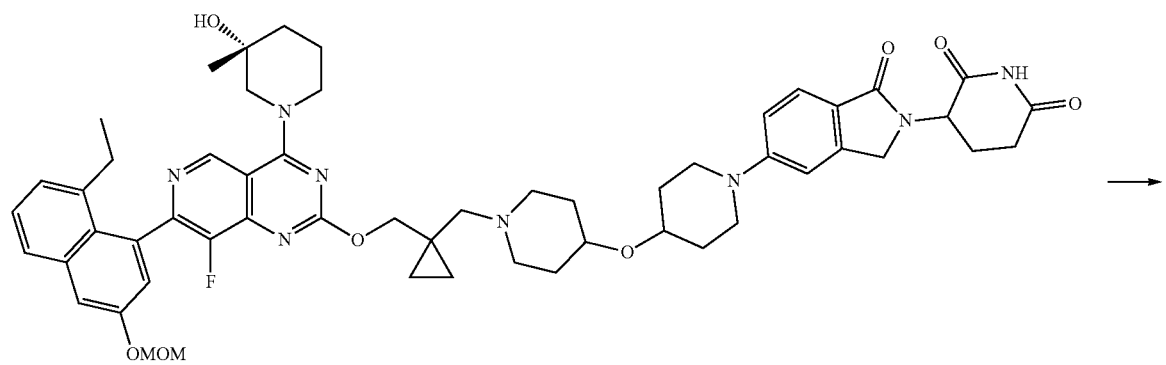
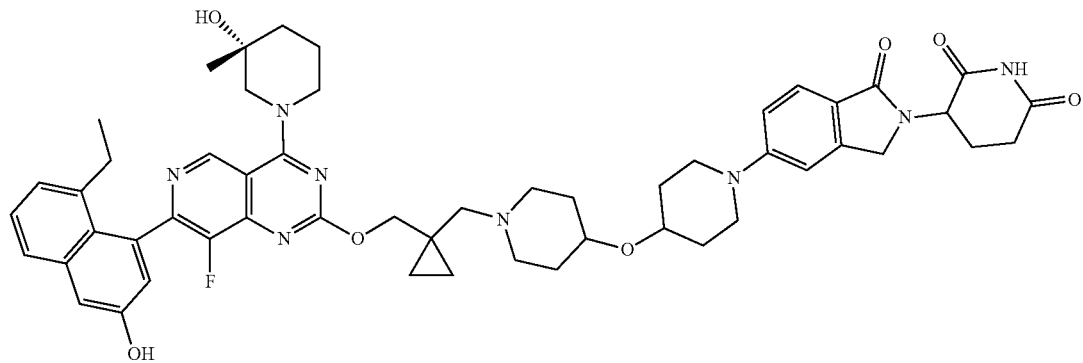

Step 1: Preparation of tert-butyl 4-(pyridin-4-yloxy)piperidine-1-carboxylate To a solution of pyridin-4-ol (9 g, 0.10 mol), tert-butyl 4-hydroxypiperidine-1-carboxylate (32 g, 0.12 mol) and PPh$_3$ (32.2 g, 0.12 mol) in THF (500 mL) was added DEAD (21.4 g, 0.12 mol) dropwise. The mixture was stirred at room temperature for 2 hours. The reaction was quenched with water (1 L) and extracted with EA (1 L×3). The organic phase was washed with brine and dried over Na$_2$SO$_4$. The solution was concentrated in vacuum. The residue was purified by flash chromatography on silica gel with PE:EA=5:1 to give the desired compound (12 g, 40.9% yield) as a yellow oil. LC/MS: 279.2 [M+H]+

Step 2: Preparation of tert-butyl 4-(piperidin-4-yloxy)piperidine-1-carboxylate To a solution of tert-butyl [4-(pyridin-4-yloxy)piperidin-1-yl] formate (3 g, 0.01 mol) in EtOH (50 mL) and HOAc (5 mL) was added Pd/C (0.45 g, 10%). The mixture was stirred under hydrogen atmosphere at 80° C. for 24 hours. The catalyst was filtered off and the filtrate was concentrated in vacuum. The residue was purified by flash column chromatography on silica gel with MeOH:DCM=1:10 to give the desired compound (1 g, 29.9% yield) as a white solid. LC/MS: 285.2 [M+H]$^+$.

Step 3: Preparation of tert-butyl 4-((1-(2-(2,6-dioxopiperidin-3-yl)-1-oxoisoindolin-5-yl)piperidin-4-yl)oxy)piperidine-1-carboxylate To a solution of tert-butyl [4-(piperidin-4-yloxy)piperidin-1-yl]formate (238 mg, 0.84 mmol) and 3-(5-bromo-1-oxo-3H-isoindol-2-yl)piperidine-2,6-dione (1000 mg, 3.09 mmol) in dioxane (20 mL) was added X-Phos (442 mg, 0.93 mmol), Pd(OAc)$_2$ (139 mg, 0.62 mmol) and Cs$_2$CO$_3$ (3024 mg, 9.28 mmol). The mixture was stirred at 100° C. for 15 hours. The reaction was quenched with water and extracted with EA (10 mL×3). The organic phase was washed with brine and dried over Na$_2$SO$_4$. The solution was concentrated in vacuum. The residue was purified by flash column chromatography on silica gel with PE:EA=2:1 to give the desired compound (800 mg, 39.3% yield) as a white solid. LC/MS: 526.8 [M+H]$^+$.

Step 4: Preparation of 3-(1-oxo-5-(4-(piperidin-4-yloxy)piperidin-1-yl)isoindolin-2-yl)piperidine-2,6-dione A solution of tert-butyl {4-[(1-{2-[(3S)-2,6-dioxopiperidin-3-yl]-1-oxo-3H-isoindol-5-yl}piperidin-4-yl)oxy]piperidin-1-yl}formate (800 mg, 1.52 mmol) in HCl/dioxane (4 M, 1 mL) and THF (1 mL) was stirred at room temperature for 0.5 hours. The solution was concentrated in vacuum and the residue was purified by flash column chromatography on silica gel with MeOH:DCM=1:20 to give the title compound (600 mg, 74.2% yield) as a yellow solid. LC/MS: 958.4[M+H]$^+$.

Step 5: Preparation of 3-(5-(4-((1-((1-(((7-(8-ethyl-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclopropyl)methyl) piperidin-4-yl)oxy)piperidin-1-yl)-1-oxoisoindolin-2-yl)piperidine-2,6-dione To a solution of (3S)-3-{1-oxo-5-[4-(piperidin-4-yloxy) piperidin-1-yl]-3H-isoindol-2-yl}piperidine-2,6-dione (200 mg, 0.47 mmol) in DCM (2 mL) was added DIEA (363 mg, 2.81 mmol), STAB (298 mg, 1.41 mmol) and (R)-1-(((7-(8-ethyl-3-(methoxymethoxy)naphthalen-1-yl)-8-fluoro-4-(3-hydroxy-3-methylpiperidin-1-yl)pyrido[4,3-d]pyrimidin-2-yl)oxy)methyl)cyclopropane-1-carbaldehyde (134 mg, 0.23 mmol). The mixture was stirred at room temperature for 2 hours. The reaction was quenched with water (5 mL) and extracted with DCM (5 mL×3). The organic phase was washed with brine and dried over Na$_2$SO$_4$. The solution was concentrated in vacuum and the residue was purified by flash column chromatography on silica gel with MeOH:DCM=1:10 to give the desired compound (50 mg, 10.8% yield) as a yellow oil. LC/MS: 985.4[M+H]$^+$.

Step 6: Preparation of 3-(5-(4-((1-((1-(((7-(8-ethyl-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)oxy)piperidin-1-yl)-1-oxoisoindolin-2-yl) piperidine-2,6-dione (Compound 24)

A solution of 3-(5-(4-((1-((1-(((7-(8-ethyl-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclopropyl)methyl) piperidin-4-yl)oxy) piperidin-1-yl)-1-oxoisoindolin-2-yl)piperidine-2,6-dione (40 mg, 0.019 mmol) in HCl/dioxane (4 M, 1 mL) and THF (1 mL) was stirred under nitrogen at room temperature for 0.5 hours. The solution was concentrated in vacuum and the residue was purified by Prep-HPLC (0.1% FA in H$_2$O/ACN=10~40%) to obtain the desired compound (18 mg, 49.2% yield) as a yellow solid. LC/MS: 941.4 [M+H]; $^1$H NMR (400 MHZ, DMSO) δ 10.94 (s, 1H), 10.14-9.64 (m, 1H), 9.20 (d, J=7.2 Hz, 1H), 7.67 (d, J=8.3 Hz, 1H), 7.50 (d, J=8.5 Hz, 1H), 7.37 (t, J=8.0 Hz, 1H), 7.28 (d, J=2.5 Hz, 1H), 7.12 (d, J=7.2 Hz, 1H), 7.06-7.02 (m, 2H), 6.98 (d, J=2.6 Hz, 1H), 5.04 (dd, J=13.2, 5.0 Hz, 1H), 4.74 (d, J=14.9 Hz, 1H), 4.33-4.27 (m, 3H), 4.22-4.17 (m, 1H), 4.03 (dd, J=19.3, 13.0 Hz, 1H), 3.66-3.60 (m, 3H), 3.43-3.40 (m, 1H), 3.09-3.02 (m, 2H), 2.94-2.86 (m, 1H), 2.83-2.68 (m, 2H), 2.67-2.55 (m, 1H), 2.38 (d, J=4.6 Hz, 1H), 2.35-2.32 (m, 1H), 2.31-2.28 (m, 2H), 2.27-2.15 (m, 3H), 2.10-2.04 (m, 2H), 2.01-1.92 (m, 2H), 1.87-1.81 (m, 2H), 1.79-1.74 (m, 2H), 1.72-1.63 (m, 3H), 1.50-1.44 (m, 2H), 1.42-1.36 (m, 2H), 1.31-1.23 (m, 1H), 1.21-1.14 (m, 3H), 0.83 (dt, J=7.3, 3.7 Hz, 3H), 0.67-0.60 (m, 2H), 0.42-0.36 (m, 2H).

Example 10: Preparation of (S)-3-(5-(4-((1-((1-(((7-(8-ethyl-3-hydroxynaphthalen-1-yl)-8-fluoro-4-(((1R,2R)-2-fluorocyclopropyl)(methyl)amino) pyrido[4,3-d]pyrimidin-2-yl)oxy) methyl) cyclopropyl)methyl)piperidin-4-yl)methyl)piperazin-1-yl)-1-oxoisoindolin-2-yl)piperidine-2,6-dione (Compound 29)
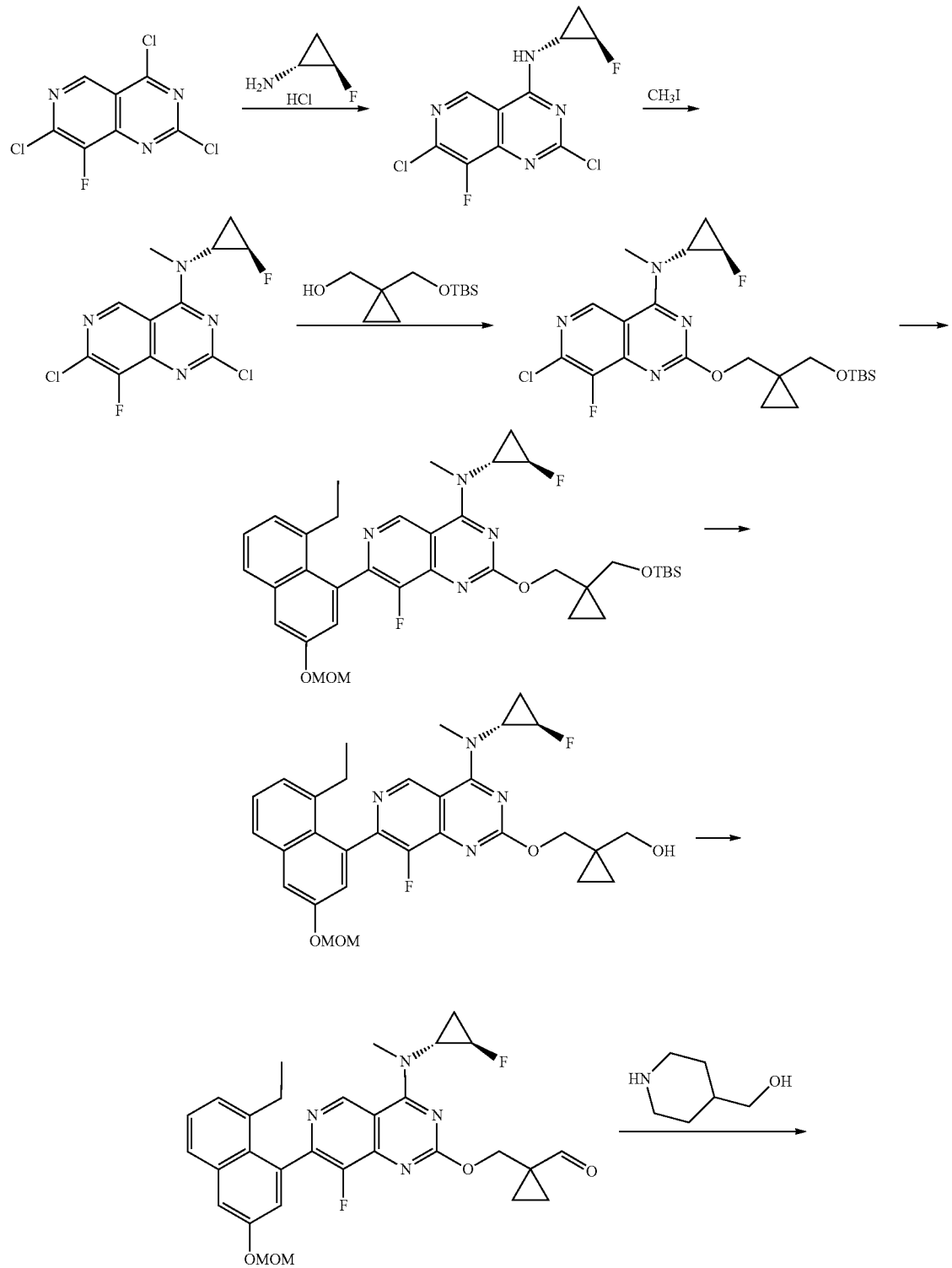

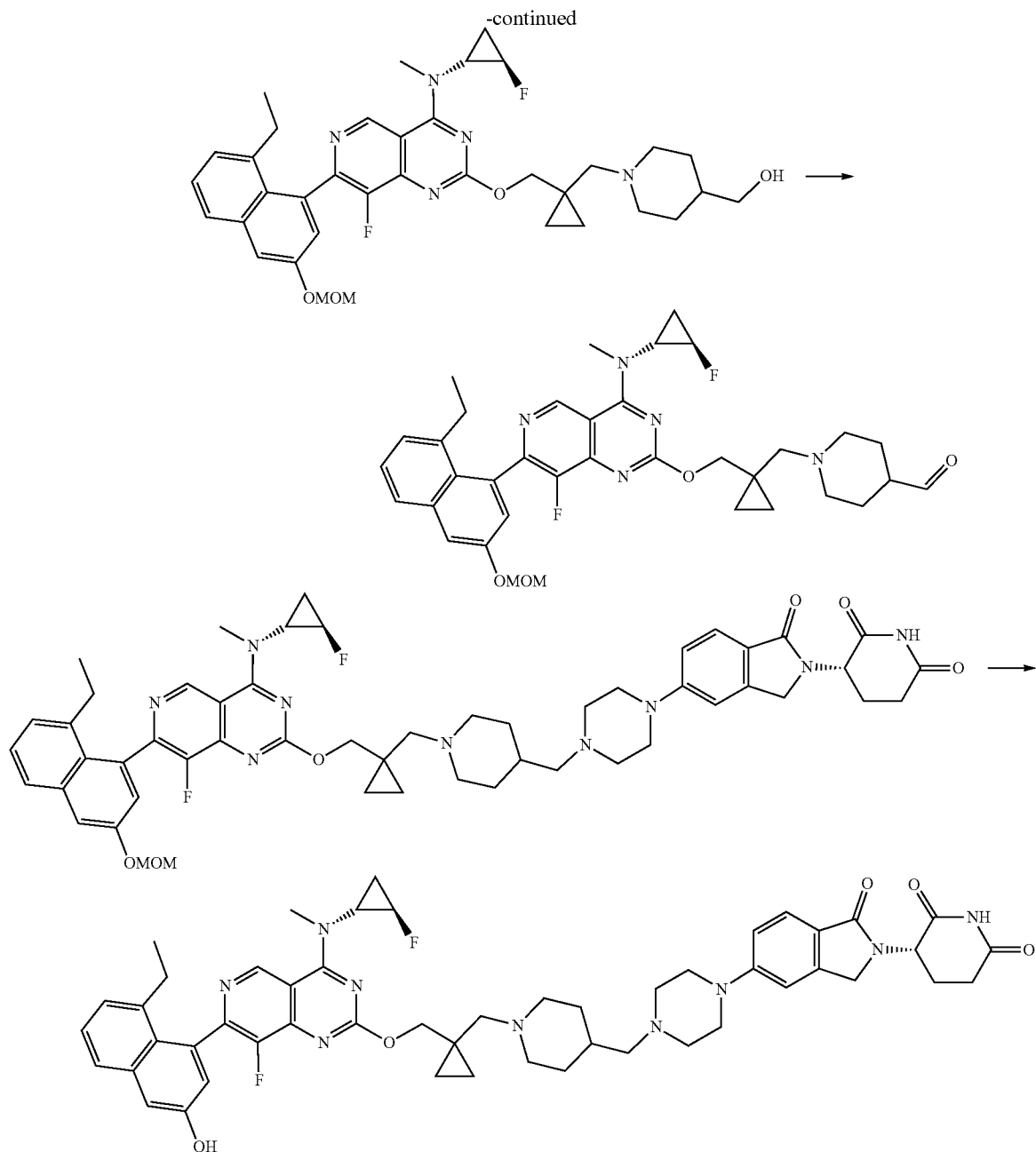

Step 1: Preparation of 2,7-dichloro-8-fluoro-N-((1R, 2R)-2-fluorocyclopropyl)pyrido[4,3-d]pyrimidin-4-amine To the solution of 2,4,7-trichloro-8-fluoropyrido[4,3-d]pyrimidine (1 g, 3.96 mmol) and DIEA (2.05 g, 15.85 mmol) in DCM (15 mL) was added (1R,2R)-2-fluorocyclopropan-1-amine hydrochloride (442 mg, 3.96 mmol) at 0° C. The mixture was stirred at room temperature for 1 hour. The reaction was quenched with water and extracted with DCM. The combined organic phase was washed with brine and dried over Na$_2$SO$_4$. The solution was concentrated in vacuum and the residue was purified by flash chromatography on silica gel (PE:EA=2:1) to give the target product (1 g, 87% yield) as a yellow solid. LC/MS: 209.9 [M+H]$^+$.

Step 2: Preparation of 2,7-dichloro-8-fluoro-N-((1R, 2R)-2-fluorocyclopropyl)-N-methylpyrido[4,3-d] pyrimidin-4-amine The mixture of 2,7-dichloro-8-fluoro-N-((1R,2R)-2-fluorocyclopropyl)pyrido[4,3-d] pyrimidin-4-amine (1 g, 3.44 mmol) and NaH (60%, 275 mg, 6.87 mmol) in DMF (10 mL) was stirred at 0° C. for 0.5 hour and CH$_3$I (1.95 g, 13.74 mmol) was added. The reaction mixture was stirred at room temperature for 16 hours. The reaction was quenched with water and extracted with DCM. The combined organic phase was washed with brine and dried over Na₂SO₄. The solution was concentrated in vacuum and the residue was purified by flash chromatography on silica gel (PE:EA=1:1) to give the desired compound (750 mg, 72% yield) as a yellow solid. LC/MS: 305.0 [M+H]⁺.

Step 3: Preparation of 2-((1-(((tert-butyldimethylsilyl)oxy)methyl)cyclopropyl) methoxy)-7-chloro-8-fluoro-N-((1R,2R)-2-fluorocyclopropyl)-N-methylpyrido[4,3-d]pyrimidin-4-amine To a solution of (1-(((tert-butyldimethylsilyl)oxy)methyl) cyclopropyl)methanol (461 mg, 2.13 mol) in THF (10 mL) was added NaH (60%, 128 mg, 3.20 mol) at 0° C. for 0.5 hours and 2,7-dichloro-8-fluoro-N-((1R,2R)-2-fluorocyclopropyl)-N-methyl pyrido[4,3-d]pyrimidin-4-amine (650 mg, 2.13 mmol) was added. The reaction mixture was stirred at room temperature for 4 hours. The reaction was quenched with water and extracted with DCM. The combined organic phase was washed with brine and dried over Na₂SO₄. The solution was concentrated in vacuum and the residue was purified by flash chromatography on silica gel (DCM: MeOH=10:1) to give the desired compound (550 mg, 53% yield) as a brown solid. LC/MS: 484.8 [M+H]⁺

Step 4: Preparation of 2-((1-(((tert-butyldimethylsilyl)oxy)methyl)cyclopropyl) methoxy)-7-(8-ethyl-3-(methoxymethoxy)naphthalen-1-yl)-8-fluoro-N-((1R,2R)-2-fluorocyclopropyl)-N-methylpyrido[4,3-d]pyrimidin-4-amine The mixture of 2-((1-(((tert-butyldimethylsilyl)oxy) methyl)cyclopropyl)methoxy)-7-chloro-8-fluoro-N-((1R, 2R)-2-fluorocyclopropyl)-N-methylpyrido[4,3-d]pyrimidin-4-amine (550 mg, 1.13 mmol), 2-(8-ethyl-3-(methoxymethoxy)naphthalen-1-yl)-4,4,5,5-tetramethyl-1, 3,2-dioxaborolane (582 mg, 1.70 mmol), CataCXium A-Pd-G3 (83 mg, 0.11 mmol) and K₃PO₄ (722 mg, 3.40 mmol) in dioxane/H₂O (5/1, 12 mL) was stirred at 90° C. for 2 hours. The reaction was quenched with water and extracted with EA. The combined organic phase was washed with brine and dried over Na₂SO₄. The solvent was removed in vacuum and the residue was purified by flash chromatography on silica gel (DCM:MeOH=10:1) to give the desired compound (500 mg, 66% yield) as a brown solid. LC/MS: 665.2 [M+H]⁺.

Step 5: Preparation of (1-(((7-(8-ethyl-3-(methoxymethoxy)naphthalen-1-yl)-8-fluoro-4-(((1R,2R)-2-fluorocyclopropyl)(methyl)amino) pyrido[4,3-d]pyrimidin-2-yl)oxy) methyl) cyclopropyl)methanol A solution of 2-((1-(((tert-butyldimethylsilyl)oxy)methyl) cyclopropyl)methoxy)-7-(8-ethyl-3-(methoxymethoxy) naphthalen-1-yl)-8-fluoro-N-((1R,2R)-2-fluorocyclopropyl)-N-methylpyrido[4,3-d]pyrimidin-4-amine (490 mg, 0.74 mmol) in THF (6 mL) and TBAF (0.8 mL, 1 M in THF) was stirred at room temperature under nitrogen for 1 hour. The solution was concentrated under vacuum, diluted with water and extracted with DCM. The organic phase was dried over Na₂SO₄ and concentrated in vacuum and the residue was purified by flash chromatography on silica gel (DCM: MeOH=10:1) to give the desired compound (370 mg, 91% yield) as a brown solid. LC/MS: 551.2 [M+H]⁺.

Step 6: Preparation of 1-(((7-(8-ethyl-3-(methoxymethoxy)naphthalen-1-yl)-8-fluoro-4-(((1R,2R)-2-fluorocyclopropyl)(methyl)amino) pyrido[4,3-d]pyrimidin-2-yl)oxy) methyl) cyclopropane-1-carbaldehyde The mixture of (1-(((7-(8-ethyl-3-(methoxymethoxy) naphthalen-1-yl)-8-fluoro-4-(((1R,2R)-2-fluorocyclopropyl)(methyl)amino)pyrido[4,3-d]pyrimidin-2-yl)oxy)methyl)cyclopropyl)methanol (360 mg, 0.65 mmol) and DMP (555 mg, 1.31 mmol) in DCM (10 mL) were stirred under N₂ at room temperature for 2 hours. The reaction was quenched with saturated Na₂S₂O₃ solution and extracted with DCM. The solution was concentrated in vacuum and the residue was purified by Prep-TLC (DCM:MeOH=10:1) to give the desired compound (300 mg, 84% yield) as a brown solid. LC/MS: 548.8 [M+H]⁺.

Step 7: Preparation of (1-((1-(((7-(8-ethyl-3-(methoxymethoxy)naphthalen-1-yl)-8-fluoro-4-(((1R,2R)-2-fluorocyclopropyl)(methyl)amino) pyrido[4,3-d]pyrimidin-2-yl)oxy)methyl) cyclopropyl)methyl)piperidin-4-yl)methanol The mixture of 1-(((7-(8-ethyl-3-(methoxymethoxy) naphthalen-1-yl)-8-fluoro-4-(((1R,2R)-2-fluorocyclopropyl)(methyl)amino)pyrido[4,3-d]pyrimidin-2-yl)oxy) methyl) cyclopropane-1-carbaldehyde (90 mg, 0.16 mmol), piperidin-4-ylmethanol (95 mg, 0.82 mmol) and TEA (83 mg, 0.82 mmol) in DCM (10 mL) was stirred at room temperature for 0.5 hours and STAB (104 mg, 0.49 mmol) was added. The reaction mixture was stirred at room temperature for 16 hours. The reaction was quenched with water and extracted with DCM. The organic phase was washed with brine and dried over Na₂SO₄. The solution was concentrated in vacuum and the residue was purified by Prep-TLC (DCM:MeOH=10:1) to give the desired compound (90 mg, 85% yield) as a yellow solid. LC/MS: 648.3 [M+H]⁺.

Step 8: Preparation of 1-((1-(((7-(8-ethyl-3-(methoxymethoxy)naphthalen-1-yl)-8-fluoro-4-(((1R,2R)-2-fluorocyclopropyl)(methyl)amino) pyrido[4,3-d]pyrimidin-2-yl) oxy)methyl) cyclopropyl)methyl)piperidine-4-carbaldehyde To a solution of (1-((1-(((7-(8-ethyl-3-(methoxymethoxy) naphthalen-1-yl)-8-fluoro-4-(((1R,2R)-2-fluorocyclopropyl)(methyl)amino)pyrido[4,3-d]pyrimidin-2-yl)oxy) methyl)cyclopropyl)methyl)piperidin-4-yl)methanol (85 mg, 0.13 mmol) in DCM (5 mL) was added DMP (111 mg, 0.26 mmol). The reaction was stirred at room temperature for 1 hour. The reaction was quenched with saturated Na₂S₂O₃ solution and extracted with DCM. The organic phase was washed with brine and dried over Na₂SO₄. The solution was concentrated in vacuum and the residue was purified by Pre-TLC (DCM:MeOH=10:1) to afford the desired compound (60 mg, 71% yield) as a brown solid. LC/MS: 646.2 [M+H]⁺.

Step 9: Preparation of (S)-3-(5-(4-((1-((1-(((7-(8-ethyl-3-(methoxymethoxy)Naphthalen-1-yl)-8-fluoro-4-(((1R,2R)-2-fluorocyclopropyl)(methyl) amino)pyrido[4,3-d]pyrimidin-2-yl)oxy)methyl) cyclopropyl)methyl)piperidin-4-yl)methyl)piperazin-1-yl)-1-oxoisoindolin-2-yl)piperidine-2,6-dione The mixture of 1-((1-(((7-(8-ethyl-3-(methoxymethoxy) naphthalen-1-yl)-8-fluoro-4-(((1R,2R)-2-fluorocyclopropyl)(methyl)amino)pyrido[4,3-d]pyrimidin-2-yl)oxy)methyl)cyclopropyl)methyl)piperidine-4-carbaldehyde (55 mg, 0.085 mmol), (S)-3-(1-oxo-5-(piperazin-1-yl)isoindolin-2-yl)piperidine-2,6-dione (83 mg, 0.17 mmol), and NaOAc (21 mg, 0.26 mmol) in DCM/MeOH (3:1, 8 mL) was stirred at room temperature for 0.5 hour and STAB (54 mg, 0.26 mmol) was added. The reaction mixture was stirred at room temperature for 2 hours. The reaction was quenched with water and extracted with DCM. The organic phase was washed with brine and dried over Na$_2$SO$_4$. The solution was concentrated in vacuum and the residue was purified by Pre-TLC (DCM:MeOH=10:1) to afford the desired compound (50 mg, 61% yield) as a brown solid. LC/MS: 957.6 [M+H]$^+$.

Step 10: Preparation of (S)-3-(5-(4-((1-(((7-(8-ethyl-3-hydroxynaphthalen-1-yl)-8-fluoro-4-(((1R,2R)-2-fluorocyclopropyl)(methyl)amino)pyrido[4,3-d]pyrimidin-2-yl)oxy)methyl)cyclopropyl)methyl) piperidin-4-yl)methyl)piperazin-1-yl)-1-oxoisoindolin-2-yl)piperidine-2,6-dione (Compound 29)

To a solution of (S)-3-(5-(4-((1-(((1-(((7-(8-ethyl-3-(methoxymethoxy)naphthalen-1-yl)-8-fluoro-4-(((1R,2R)-2-fluorocyclopropyl)(methyl)amino)pyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione (45 mg, 0.047 mmol) in DCM (3 mL) was added HCl/dioxane (4 M, 0.5 mL). The mixture was stirred at room temperature for 1 hour. The mixture was concentrated in vacuum and the residue was purified by Prep-HPLC (AQ-C18, ACN-H$_2$O (0.1% FA), 15~30%) to give the desired product (15 mg, 35% yield) as a white solid. LC/MS: 914.4 [M+H]$^+$; $^1$HNMR (400 MHZ) δ10.91 (s, 1H), 9.47 (d, J=1.2 Hz, 1H), 8.13 (s, 1H), 7.63 (d, J=8.4 Hz, 1H), 7.47 (d, J=8.8 Hz, 1H), 7.33 (t, J=7.6 Hz, 1H), 7.25 (d, J=2.4 Hz, 1H), 7.08 (d, J=7.2 Hz, 1H), 7.03-6.94 (m, 3H), 5.01 (dd, J=13.2, 5.2 Hz, 1H), 4.32-4.03 (m, 5H), 3.29-3.18 (m, 8H), 2.98-2.82 (m, 3H), 2.59-2.51 (m, 1H), 2.43-2.06 (m, 11H), 1.99-1.78 (m, 3H), 1.68-1.40 (m, 4H), 1.25-1.16 (m, 1H), 1.10-0.94 (m, 2H), 0.79 (t, J=7.2 Hz, 3H), 0.61 (s, 2H), 0.38 (s, 2H).

Example 11: Preparation of (S)-3-(5-(4-((1-((1-(((7-(8-ethyl-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-4-fluoropiperidin-4-yl)methyl)piperazin-1-yl)-1-oxoisoindolin-2-yl)piperidine-2,6-dione (Compound 33)

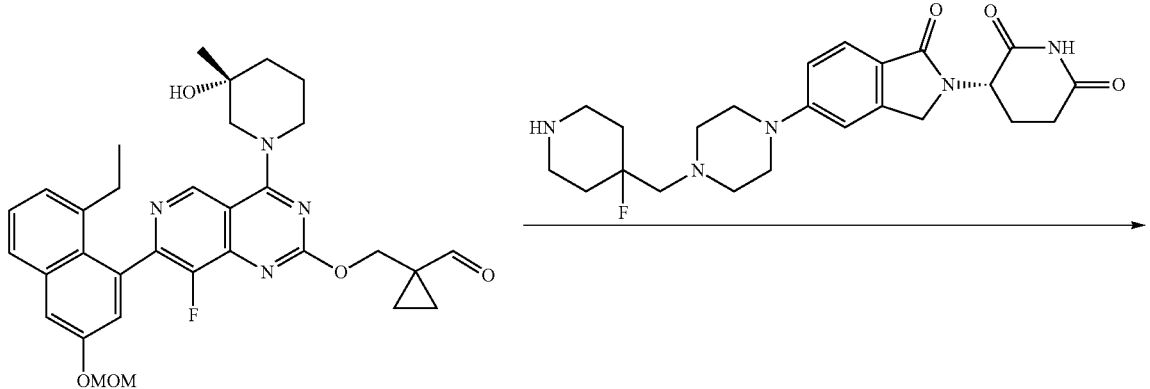

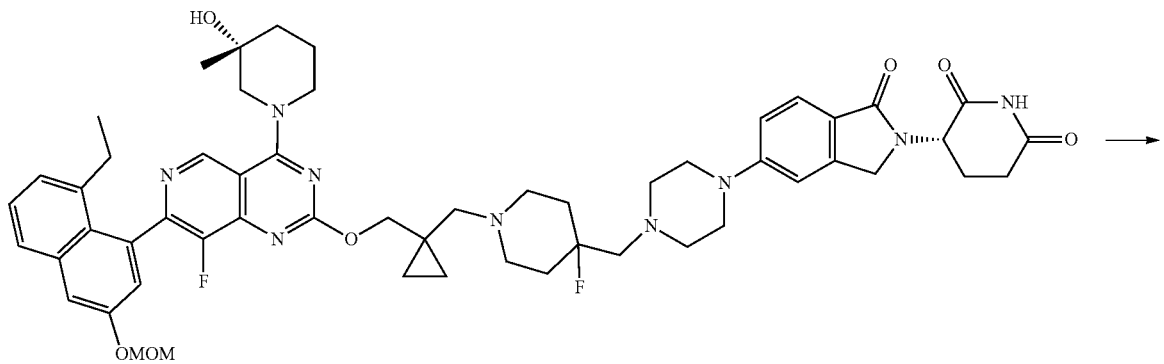

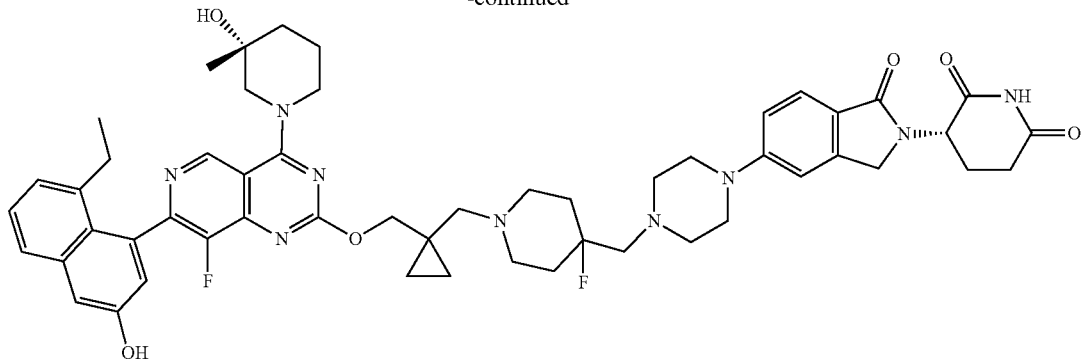

33

Step 1: Preparation of (S)-3-(5-(4-((1-((1-(((7-(8-ethyl-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-4-fluoropiperidin-4-yl)methyl)piperazin-1-yl)-1-oxoisoindolin-2-yl)piperidine-2,6-dione To a solution of (R)-1-(((7-(8-ethyl-3-(methoxymethoxy)naphthalen-1-yl)-8-fluoro-4-(3-hydroxy-3-methylpiperidin-1-yl)pyrido[4,3-d]pyrimidin-2-yl)oxy)methyl)cyclopropane-1-carbaldehyde (160 mg, 0.27 mmol) in DMA (5 mL) was added (S)-3-(5-(4-((4-fluoropiperidin-4-yl)methyl)piperazin-1-yl)-1-oxoisoindolin-2-yl)piperidine-2,6-dione (186.96 mg, 2 TFA salt, 0.27 mmol) and DIEA (360 mg, 2.78 mmol) at room temperature. The mixture was stirred at 40° C. for 2 hours and STAB (177.01 mg, 0.83 mmol) was added. The reaction mixture was stirred at 40° C. for 16 hours. The reaction was quenched by adding water and extracted with EA. The organic phase was washed with brine and dried over $Na_2SO_4$. The solvent was removed and the residue was purified by column chromatography with DCM/MeOH=10:1 to give the product (60 mg, 90% purity, 19.9% yield) as a white solid. LC/MS: 1002.5 [M+H]$^+$.

Step 2: Preparation of (S)-3-(5-(4-((1-((1-(((7-(8-ethyl-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-4-fluoropiperidin-4-yl)methyl)piperazin-1-yl)-1-oxoisoindolin-2-yl)piperidine-2,6-dione (Compound 33)

A solution of (S)-3-(5-(4-((1-((1-(((7-(8-ethyl-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-4-fluoropiperidin-4-yl)methyl)piperazin-1-yl)-1-oxoisoindolin-2-yl)piperidine-2,6-dione (57 mg, 0.05 mmol) in DCM/TFA (2 mL, 3/1) was stirred under nitrogen at room temperature for 1 hour. The mixture was concentrated in vacuum and the residue was purified by Prep-HPLC (Gemini-C18:150×21.2 mm, 5 μm. ACN-H$_2$O (0.1% FA) 15-30%) to give the desired product (19.4 mg, 40.1% yield) as a white solid. LC/MS: 958.5 [M+H]$^+$; $^1$H NMR (400 MHZ, DMSO) δ 10.96 (s, 1H), 9.94 (d, J=2.6 Hz, 1H), 9.25 (d, J=9.9 Hz, 1H), 8.14 (s, 1H), 7.67 (d, J=7.9 Hz, 1H), 7.53 (d, J=8.9 Hz, 1H), 7.37 (t, J=7.6 Hz, 1H), 7.29 (d, J=2.6 Hz, 1H), 7.11 (d, J=6.8 Hz, 1H), 7.08-7.00 (m, 2H), 6.97 (d, J=2.6 Hz, 1H), 5.04 (dd, J=13.3, 5.1 Hz, 1H), 4.37-4.26 (m, 4H), 4.19 (d, J=17.0 Hz, 1H), 4.04 (dd, J=19.4, 13.3 Hz, 1H), 3.75-3.59 (m, 2H), 3.51 (d, J=13.2 Hz, 1H), 3.44-3.30 (m, 1H), 3.26 (s, 4H), 3.18-3.04 (m, 2H), 2.96-2.85 (m, 1H), 2.69-2.55 (m, 6H), 2.44-2.11 (m, 7H), 2.09-1.83 (m, 5H), 1.77-1.59 (m, 4H), 1.17 (d, J=10.9 Hz, 3H), 0.91-0.71 (m, 7H).

Example 12: Preparation of 3-(2-((7-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-azaspiro[3.5]nonan-2-yl)methyl)isoindolin-5-yl)piperidine-2,6-dione (Compound 34)

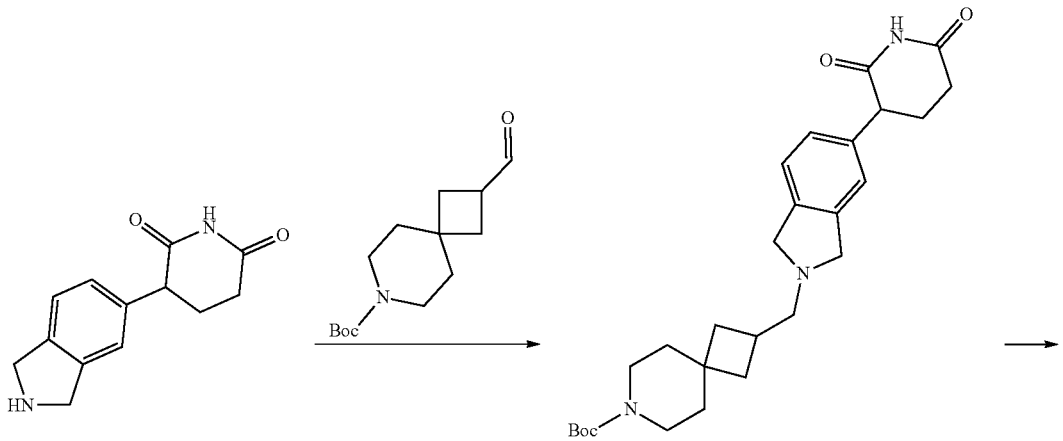

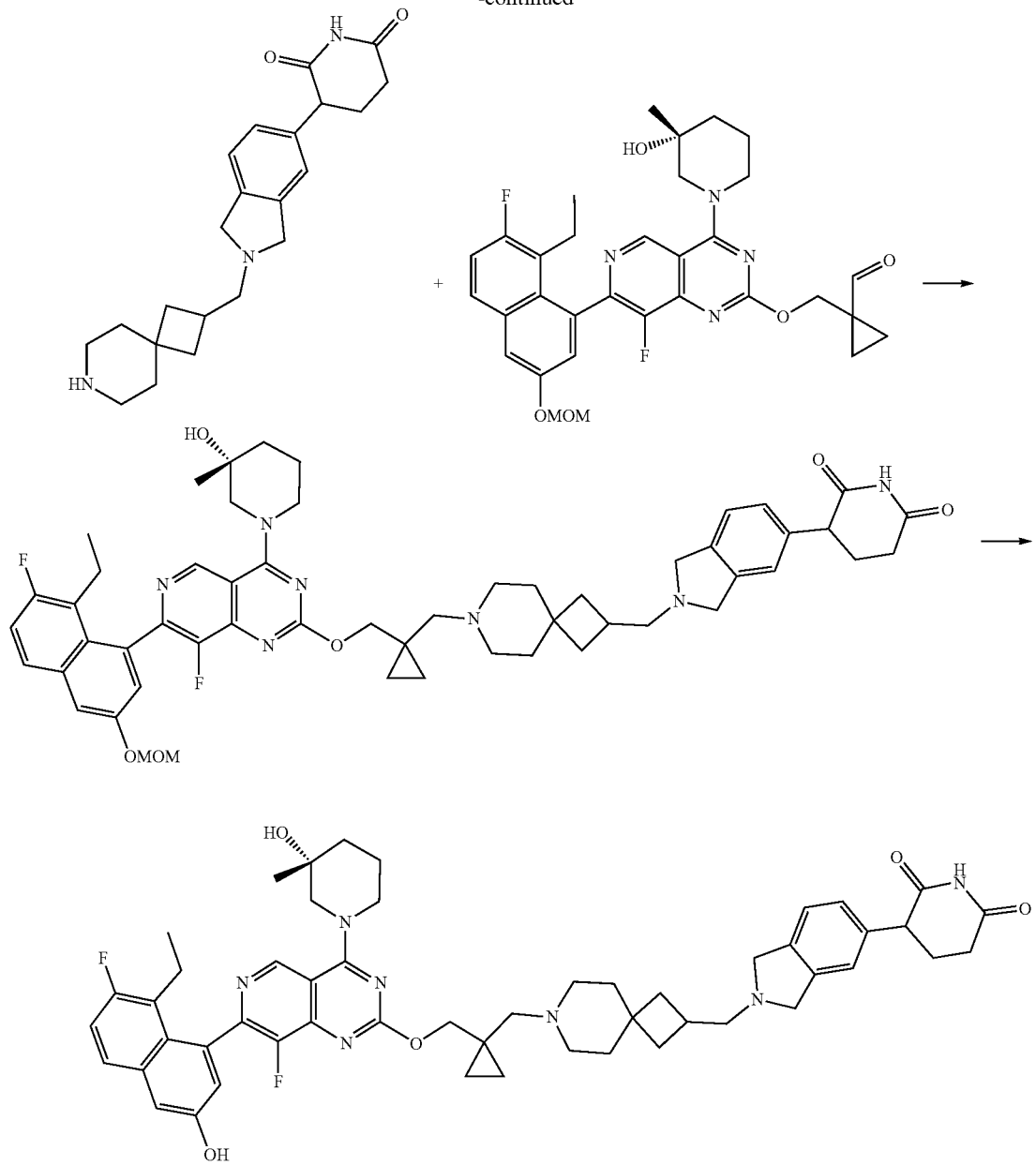

Step 1: Preparation of tert-butyl 2-((5-(2,6-dioxopiperidin-3-yl)isoindolin-2-yl)methyl)-7-azaspiro[3.5]nonane-7-carboxylate To a solution of 3-(2,3-dihydro-1H-isoindol-5-yl)piperidine-2,6-dione (130 mg, 0.57 mmol) in DCM (2 mL) was added DIEA (438 mg, 3.39 mmol), STAB (358 mg, 1.70 mmol) and tert-butyl {2-formyl-7-azaspiro[3.5]nonan-7-yl}formate (288 mg, 1.13 mmol). The reaction mixture was stirred at room temperature for 2 hours. The reaction was quenched with water (10 mL) and extracted with DCM (10 mL×3). The organic phase was washed with brine and dried over Na$_2$SO$_4$. The solution was concentrated in vacuum and the residue was purified by flash chromatography on silica gel (MeOH: DCM=1:20) to give the desired compound (200 mg, 68.0% yield) as a yellow oil. LC/MS: 468.3 [M+H]$^+$.

Step 2: Preparation of 3-(2-((7-azaspiro[3.5]nonan-2-yl)methyl)isoindolin-5-yl)piperidine-2,6-dione A solution of tert-butyl (2-{[5-(2,6-dioxopiperidin-3-yl)-1,3-dihydroisoindol-2-yl]methyl}-7-aza spiro[3.5]nonan-7-yl) formate (200 mg, 0.43 mmol) in HCl/dioxane (4 M, 1 mL) and THF (1 mL) was stirred at room temperature for 0.5 hour. The mixture was concentrated in vacuum to give the desired compound (100 mg) as a yellow solid. LC/MS: 368.3[M+H]$^+$.

Step 3: Preparation of 3-(2-((7-((1-(((7-(8-ethyl-7-fluoro-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclopropyl)methy)-7-azaspiro[3.5]nonan-2-yl)methyl)isoindolin-5-yl)piperidine-2,6-dione To a solution of 3-(2-{7-azaspiro[3.5]nonan-2-ylmethyl}-1,3-dihydroisoindol-5-yl)piperidine-2,6-dione (93 mg, 0.25 mmol) in DCM (6 mL) was added DIEA (66 mg, 0.51 mmol), (R)-1-(((7-(8-ethyl-7-fluoro-3-(methoxymethoxy)naphthalen-1-yl)-8-fluoro-4-(3-hydroxy-3-methylpiperidin-1-yl)pyrido[4,3-d]pyrimidin-2-yl)oxy)methyl)cyclopropane-1-carbaldehyde (100 mg, 0.17 mmol) and STAB (179 mg, 0.84 mmol). The reaction mixture was stirred at room temperature for 2 hours. The reaction was quenched with water (10 mL) and extracted with DCM (10 mL×3). The organic phase was washed with brine and dried over Na₂SO₄. The mixture was concentrated in vacuum. The residue was purified by flash chromatography on silica gel with MeOH: DCM=1:10 to give the desired compound (80 mg, 80% purity, 23.1% yield) as a yellow oil. LC/MS: 943.7[M+H]⁺.

Step 4: Preparation of 3-(2-((7-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-azaspiro[3.5]nonan-2-yl)methyl)isoindolin-5-yl)piperidine-2,6-dione (Compound 34)

A solution of 3-(2-{7-({1-[({7-[8-ethyl-7-fluoro-3-(methoxymethoxy)naphthalen-1-yl]-8-fluoro-4-[(3R)-3-hydroxy-3-methylpiperidin-1-yl]pyrido[4,3-d]pyrimidin-2-yl}oxy)methyl]cyclopropyl}methyl)-7-azaspiro[3.5]nonan-2-yl]methyl}-1,3-dihydroisoindol-5-yl)piperidine-2,6-dione (20 mg, 0.021 mmol) in HCl/dioxane (4 M, 1 mL) and THF (1 mL) was stirred at room temperature for 0.5 hour. The solution was concentrated in vacuum. The residue was purified by Prep-HPLC (0.1% FA in H₂O/ACN=10~40%) to obtain the desired compound (8 mg, 39.62% yield) as a yellow solid. LC/MS: 900.4 [M+H]⁺; ¹H NMR (400 MHZ, DMSO) δ 10.81 (s, 1H), 10.05-9.94 (brs, 1H), 9.21 (s, 1H), 8.23 (s, 1H), 7.79-7.72 (m, 1H), 7.42-7.29 (m, 1H), 7.33-7.26 (m, 2H), 7.15 (d, J=8.1 Hz, 1H), 7.05-6.98 (m, 2H), 5.75 (s, 1H), 4.78-4.74 (m, 1H), 4.37-4.23 (m, 4H), 4.11-3.95 (m, 4H), 3.84-3.77 (m, 3H), 3.64 (s, 3H), 2.70-2.57 (m, 3H), 2.44-2.20 (m, 5H), 2.19-2.05 (m, 2H), 2.04-1.94 (m, 2H), 1.91-1.73 (m, 2H), 1.72-1.59 (m, 2H), 1.58-1.46 (m, 2H), 1.45-1.32 (m, 3H), 1.30-1.24 (m, 2H), 1.23 (s, 3H), 1.16 (d, J=10.0 Hz, 2H), 0.87-0.82 (m, 1H), 0.78-0.67 (m, 2H), 0.65-0.60 (m, 1H), 0.41-0.36 (m, 1H).

Example 13: Preparation of (S)-3-(5-(4-((7-((1-(((7-(8-ethyl-7-fluoro-3-hydroxynaphthalen-1-yl)-8-fluoro-4-((R)-3-methoxy-3-methylpiperidin-1-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione (Compound 36)

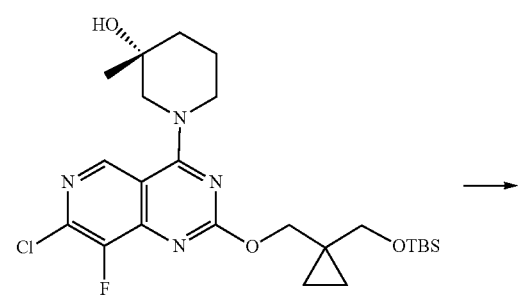

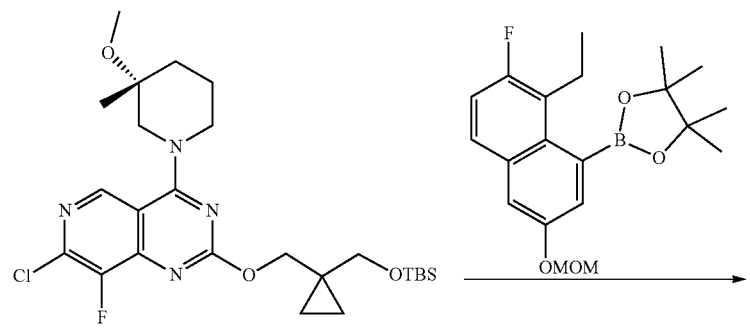

413                                          414
-continued
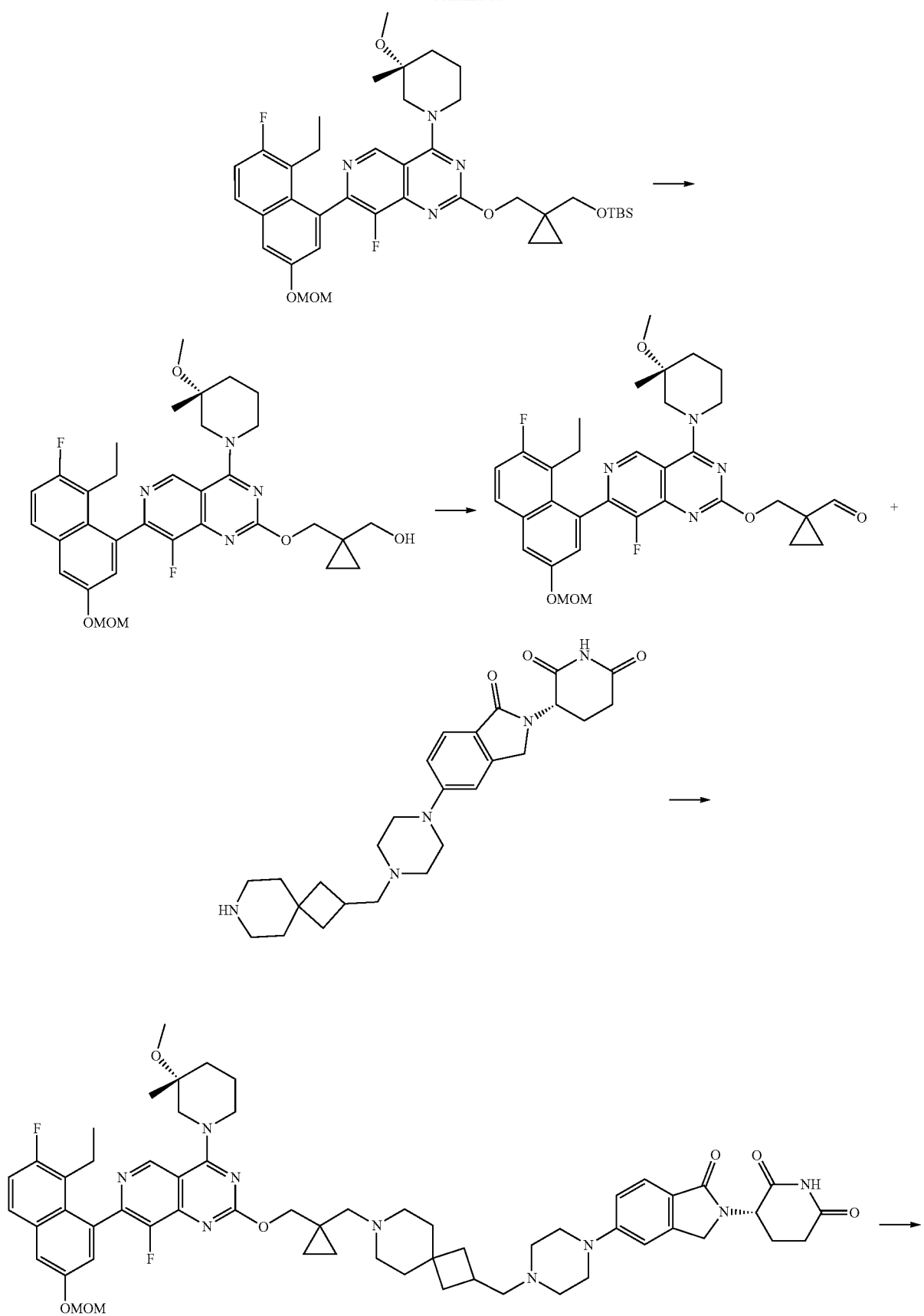

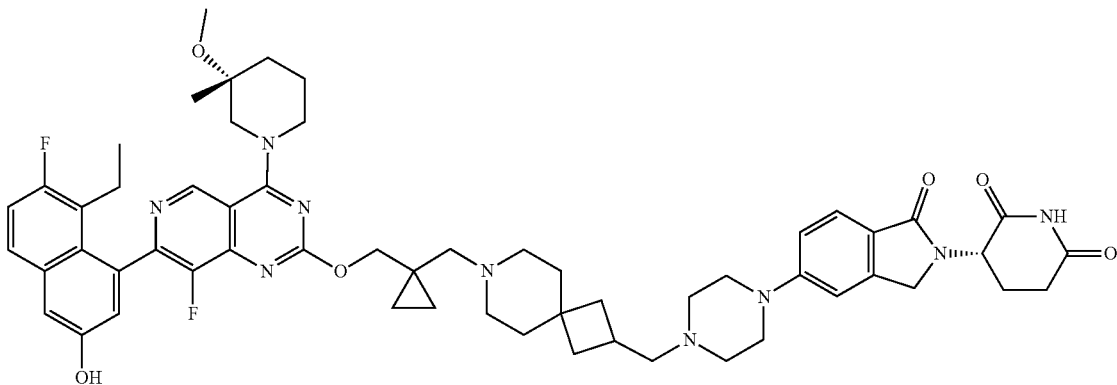

36

Step 1: Preparation of (R)-2-((1-(((tert-butyldimethylsilyl)oxy)methyl)cyclopropyl)methoxy)-7-chloro-8-fluoro-4-(3-methoxy-3-methylpiperidin-1-yl)pyrido[4,3-d]pyrimidine The mixture of (R)-1-(2-((1-(((tert-butyldimethylsilyl)oxy)methyl)cyclopropyl)methoxy)-7-chloro-8-fluoropyrido[4,3-d]pyrimidin-4-yl)-3-methylpiperidin-3-ol (600 mg, 1.17 mmol) and NaH (70 mg, 1.76 mmol) in DMF (10 mL) was stirred at 0° C. for 0.5 hours. $CH_3I$ (666 mg, 4.69 mmol) was added. The mixture was stirred at room temperature for 2 h. LCMS showed the reaction is completed. The reaction was quenched with water and extracted with DCM. The organic phase was washed with brine and dried over $Na_2SO_4$. The solution was concentrated in vacuum and the residue was purified by flash column chromatography on silica gel (PE:EA=2:1) to give the desired compound (200 mg. 32% yield) as a brown solid. LC/MS: 525.2 [M+H]$^+$.

Step 2: Preparation of (R)-2-((1-(((tert-butyldimethylsilyl)oxy)methyl)cyclopropyl)methoxy)-7-(8-ethyl-7-fluoro-3-(methoxymethoxy)naphthalen-1-yl)-8-fluoro-4-(3-methoxy-3-methylpiperidin-1-yl)pyrido[4,3-d]pyrimidine To a solution of (R)-2-((1-(((tert-butyldimethylsilyl)oxy)methyl)cyclopropyl)methoxy)-7-chloro-8-fluoro-4-(3-methoxy-3-methylpiperidin-1-yl)pyrido[4,3-d]pyrimidine (200 mg, 0.38 mmol) in dioxane/water (12 mL, 5:1) was added 2-[8-ethyl-7-fluoro-3-(methoxymethoxy)naphthalen-1-yl]-4,4,5,5-tetramethyl-1,3,2-dioxaborolane (206 mg, 0.57 mmol), CataCXium A-Pd-G3 (28 mg, 0.038 mmol) and $K_3PO4$ (243 mg, 1.14 mmol) under nitrogen. The reaction mixture was stirred at 90° C. for 2 hours. The reaction mixture was diluted with water and extracted with EA. The organic phase was washed with brine and dried over $Na_2SO_4$. The solvent was concentrated in vacuum and the residue was purified by Pre-TLC (PE:EA=1:1) to afford the desired compound (200 mg, 73% yield) as brown solid. LC/MS: 723.3 [M+H]$^+$.

Step 3: Preparation of (R)-(1-(((7-(8-ethyl-7-fluoro-3-(methoxymethoxy)naphthalen-1-yl)-8-fluoro-4-(3-methoxy-3-methylpiperidin-1-yl)pyrido[4,3-d]pyrimidin-2-yl)oxy)methyl)cyclopropyl)methanol The mixture of (R)-2-((1-(((tert-butyldimethylsilyl)oxy)methyl)cyclopropyl)methoxy)-7-(8-ethyl-7-fluoro-3-(methoxymethoxy)naphthalen-1-yl)-8-fluoro-4-(3-methoxy-3-methylpiperidin-1-yl)pyrido[4,3-d]pyrimidine (190 mg, 0.26 mmol) and TBAF (1.5 mL, 1 M in THF) in THF (4.5 mL) was stirred at room temperature under nitrogen for 1 hour. The reaction mixture was concentrated under vacuum, diluted with water and extracted with DCM. The organic phase was dried over $Na_2SO_4$ and concentrated in vacuum to give crude product which was used in the next step without further purification (130 mg, 81% yield) as brown solid. LC/MS: 609.3 [M+H]$^+$.

Step 4: Preparation of (R)-1-(((7-(8-ethyl-7-fluoro-3-(methoxymethoxy)naphthalen-1-yl)-8-fluoro-4-(3-methoxy-3-methylpiperidin-1-yl)pyrido[4,3-d]pyrimidin-2-yl)oxy)methyl)cyclopropane-1-carbaldehyde The mixture of (R)-(1-(((7-(8-ethyl-7-fluoro-3-(methoxymethoxy)naphthalen-1-yl)-8-fluoro-4-(3-methoxy-3-methylpiperidin-1-yl)pyrido[4,3-d]pyrimidin-2-yl)oxy)methyl)cyclopropyl)methanol (120 mg, 0.20 mmol) and DMP (167 mg, 0.39 mmol) in DCM (6 mL) was stirred under $N_2$ at room temperature for 1 hour. The reaction was quenched with saturated $Na_2S_2O_3$ solution, extracted with DCM and concentrated under vacuum. The residue was purified by Prep-TLC (DCM:MeOH=10:1) to give the desired compound (100 mg, 84% yield) as a brown solid. LC/MS: 607.3 [M+H]$^+$.

Step 5: Preparation of (S)-3-(5-(4-((7-((1-(((7-(8-ethyl-7-fluoro-3-(methoxymethoxy)naphthalen-1-yl)-8-fluoro-4-((R)-3-methoxy-3-methylpiperidin-1-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione The mixture of (R)-1-(((7-(8-ethyl-7-fluoro-3-(methoxymethoxy)naphthalen-1-yl)-8-fluoro-4-(3- methoxy-3-methylpiperidin-1-yl)pyrido[4,3-d]pyrimidin-2-yl)oxy)methyl)cyclopropane-1-carbaldehyde (90 mg, 0.15 mmol), (S)-3-(5-(4-((7-azaspiro[3.5]nonan-2-yl)methyl)piperazin-1-yl)-1-oxoisoindolin-2-yl)piperidine-2,6-dione 2,2,2-trifluoroacetate (129 mg, 0.22 mmol) and TEA (60 mg, 0.59 mmol) in DCM (8 mL) was stirred at room temperature for 0.5 h, and STAB (94 mg, 0.45 mmol) was added. The reaction mixture was stirred at room temperature for 16 hours. The reaction was quenched with water and extracted with DCM. The organic phase was washed with brine and dried over $Na_2SO_4$. The solution was concentrated in vacuum and the residue was purified by Pre-TLC with DCM:MeOH=10:1 to afford the desired compound (90 mg, 57% yield) as yellow solid. LC/MS: 1055.6 [M+H]$^+$.

Step 6: Preparation of (S)-3-(5-(4-((7-((1-(((7-(8-ethyl-7-fluoro-3-hydroxynaphthalen-1-yl)-8-fluoro-4-((R)-3-methoxy-3-methylpiperidin-1-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione (Compound 36)

A solution of (S)-3-(5-(4-((7-((7-(8-ethyl-7-fluoro-3-(methoxymethoxy)naphthalen-1-yl)-8-fluoro-4-((R)-3-methoxy-3-methylpiperidin-1-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione (85 mg, 0.081 mmol) in DCM (5 mL) and HCl/dioxane (4 M, 0.8 mL) was stirred under nitrogen at room temperature for 1 hour. The mixture was concentrated in vacuum and the residue was purified by Prep-HPLC to give the desired product (25.2 mg, 31% yield) as a colorless solid. LC/MS: 1012.4 [M+H]$^+$; $^1$H NMR (400 MHz, DMSO) δ 10.97 (s, 1H), 10.53 (s, 1H), 9.23 (d, J=5.6 Hz, 1H), 8.87 (s, 1H), 7.78 (dd, J=9.2, 6.0 Hz, 1H), 7.60 (d, J=8.4 Hz, 1H), 7.41-7.30 (m, 2H), 7.18-7.02 (m, 3H), 5.07 (dd, J=13.2, 5.2 Hz, 1H), 4.54-4.22 (m, 6H), 4.05-3.94 (m, 2H), 3.64-3.42 (m, 5H), 3.32-3.02 (m, 10H), 2.99-2.69 (m, 6H), 2.41-2.28 (m, 2H), 2.21-1.56 (m, 15H), 1.15 (d, J=3.6 Hz, 3H), 0.92-0.70 (m, 7H).

Example 14: Preparation of (3S)-3-(5-{2-[(1-{[1-({[7-(8-ethyl-7-fluoro-3-hydroxynaphthalen-1-yl)-8-fluoro-4-[(3R)-3-hydroxy-3-methylpiperidin-1-yl]pyrido[4,3-d]pyrimidin-2-yl]oxy}methyl)cyclopropyl]methyl}-4-methylpiperidin-4-yl)methyl]-2,7-diazaspiro[3.5]nonan-7-yl}-1-oxo-3H-isoindol-2-yl)piperidine-2,6-dione (Compound 40)

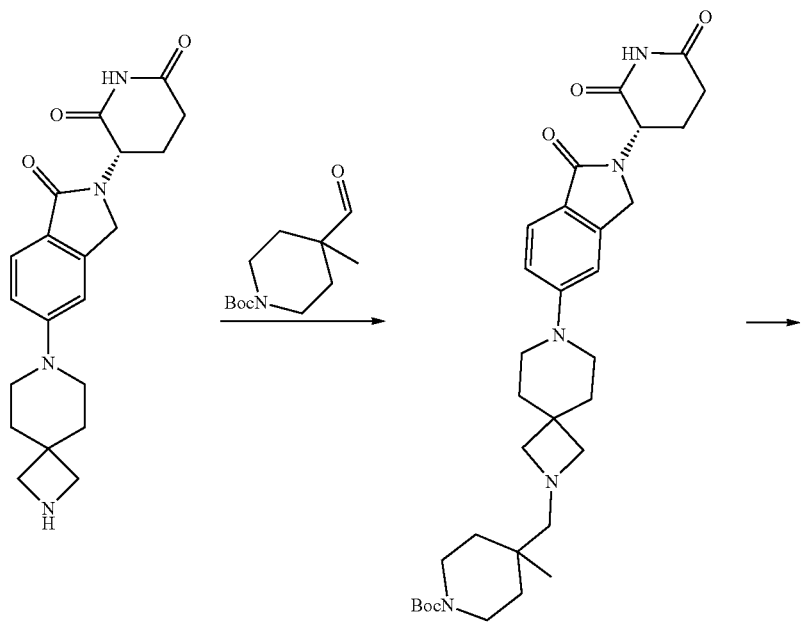

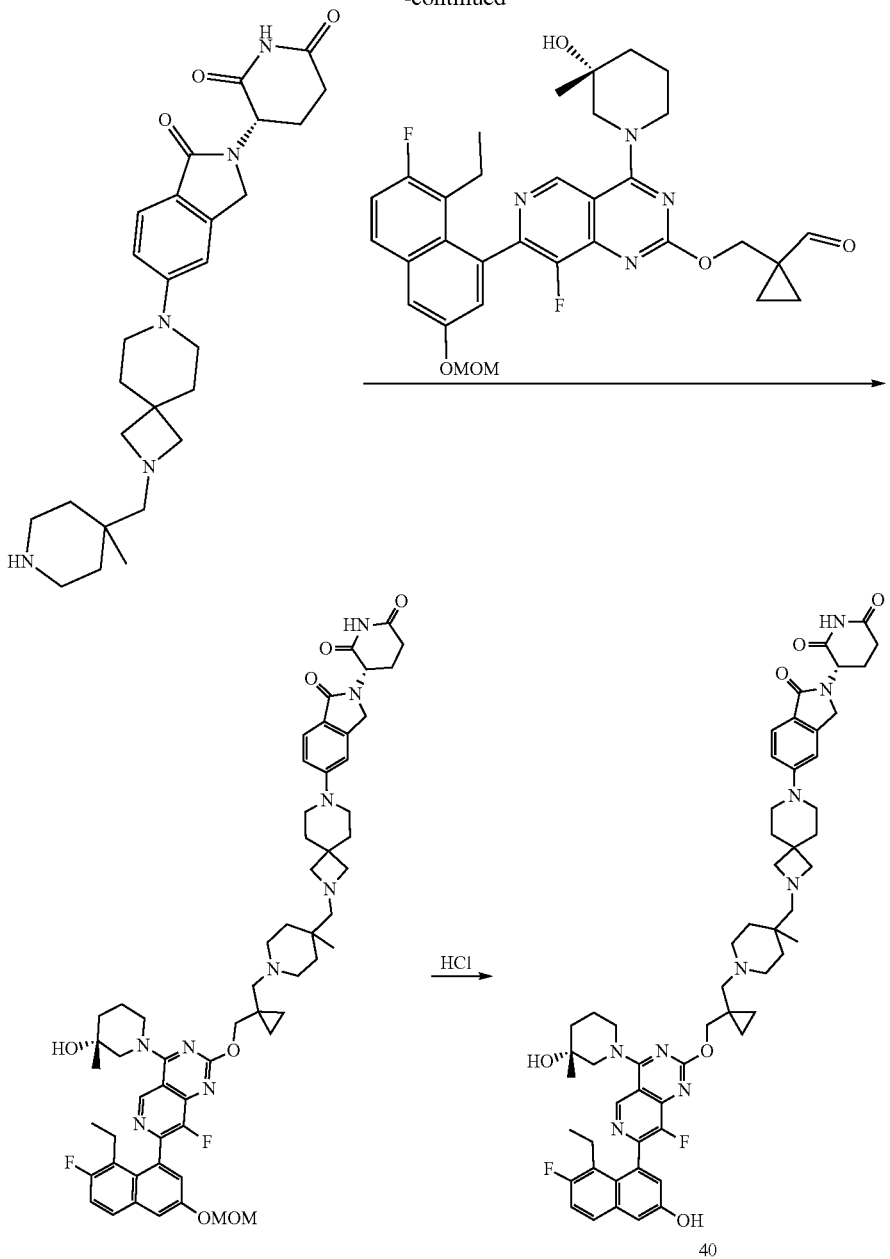

Step 1: Preparation of tert-butyl {4-[(7-{2-[(3S)-2,6-dioxopiperidin-3-yl]-1-oxo-3H-isoindol-5-yl}-2,7-diazaspiro[3.5]nonan-2-yl)methyl]-4-methylpiperidin-1-yl}formate A mixture of tert-butyl (4-formyl-4-methylpiperidin-1-yl)formate (100 mg, 0.43 mmol), (S)-3-(1-oxo-5-(2,7-diazaspiro[3.5]nonan-7-yl)isoindolin-2-yl)piperidine-2,6-dione (242 mg, 0.43 mmol) and TEA (133 mg, 1.31 mmol) in DMA (1 mL) and THF (1 mL) was stirred at room temperature for 30 minutes. AcOH (0.5 mL) and sodium triacetoxyborohydride (STAB) (186 mg, 0.87 mmol) were added and the mixture was stirred at room temperature for 1 hour. NaBH₃CN (55 mg, 0.87 mmol) was added and the mixture was stirred at room temperature for 12 hours. The resulting mixture was diluted with water (10 mL) and extracted with EA (5 mL×3). The organic phase was washed with brine and dried over Na₂SO₄. The solution was concentrated in vacuum and the residue was purified by flash chromatography (DCM:MeOH=15:1) to give the desired compound (200 mg, 82.1% yield) as a yellow solid. LC/MS: 580.3 [M+H]⁺.

Step 2: Preparation of (3S)-3-(5-{2-[(4-methylpiperidin-4-yl)methyl]-2,7-diazaspiro[3.5]nonan-7-yl}-1-oxo-3H-isoindol-2-yl)piperidine-2,6-dione The solution of tert-butyl {4-[(7-{2-[(3S)-2,6-dioxopiperidin-3-yl]-1-oxo-3H-isoindol-5-yl}-2,7-diazaspiro[3.5]nonan-2-yl)methyl]-4-methylpiperidin-1-yl}formate (200 mg, 0.34 mmol) in HCl/dioxane (4M, 2 mL) and DCM (2 mL) was stirred at room temperature for 2 hours. The solution was concentrated in vacuum to give the desired compound as HCl salt (200 mg, crude) as a white solid. LC/MS: 480.4 [M+H]⁺.

Step 3: Preparation of (3S)-3-[5-(2-{[1-({1-[({7-[8-ethyl-7-fluoro-3-(methoxymethoxy)naphthalen-1-yl]-8-fluoro-4-[(3R)-3-hydroxy-3-methylpiperidin-1-yl]pyrido[4,3-d]pyrimidin-2-yl}oxy)methyl]cyclopropyl}methyl)-4-methylpiperidin-4-yl]methyl}-2,7-diazaspiro[3.5]nonan-7-yl)-1-oxo-3H-isoindol-2-yl]piperidine-2,6-dione A solution of (3S)-3-(5-{2-[(4-methylpiperidin-4-yl)methyl]-2,7-diazaspiro[3.5]nonan-7-yl}-1-oxo-3H-isoindol-2-yl)piperidine-2,6-dione (301 mg, 0.58 mmol), (R)-1-(((7-(8-ethyl-7-fluoro-3-(methoxymethoxy)naphthalen-1-yl)-8-fluoro-4-(3-hydroxy-3-methylpiperidin-1-yl)pyrido[4,3-d]pyrimidin-2-yl)oxy)methyl)cyclopropane-1-carbaldehyde (115 mg, 0.19 mmol) and DIEA (150 mg, 1.16 mmol) in DMA (5 mL) and DCM (5 mL) was stirred at room temperature for 1 hour. STAB (123 mg, 0.58 mmol) was added and the mixture was stirred at room temperature for 15 hours. The reaction mixture was diluted with water (20 mL) and extracted with EA (10 mL×3). The organic phase was washed with brine and dried over Na₂SO₄. The solution was concentrated in vacuum and the residue was purified by Flash (DCM:MeOH=10:1) to give the desired compound (50 mg, 23.2% yield) as a yellow solid. LC/MS: 1056.5 [M+H]⁺.

Step 4: Preparation of (3S)-3-(5-{2-[(1-{[1-({[7-(8-ethyl-7-fluoro-3-hydroxynaphthalen-1-yl)-8-fluoro-4-[(3R)-3-hydroxy-3-methylpiperidin-1-yl]pyrido[4,3-d]pyrimidin-2-yl]oxy}methyl)cyclopropyl]methyl}-4-methylpiperidin-4-yl)methyl]-2,7-diazaspiro[3.5]nonan-7-yl}-1-oxo-3H-isoindol-2-yl)piperidine-2,6-dione (Compound 40)

A solution of (3S)-3-[5-(2-{[1-({1-[({7-[8-ethyl-7-fluoro-3-(methoxymethoxy)naphthalen-1-yl]-8-fluoro-4-[(3R)-3-hydroxy-3-methylpiperidin-1-yl]pyrido[4,3-d]pyrimidin-2-yl}oxy)methyl]cyclopropyl}methyl)-4-methylpiperidin-4-yl]methyl}-2,7-diazaspiro[3.5]nonan-7-yl)-1-oxo-3H-isoindol-2-yl]piperidine-2,6-dione (50 mg, 0.047 mmol) in HCl/dioxane (4M, 1 mL) and THF (1 mL) was stirred at room temperature for 30 minutes. The mixture was concentrated in vacuum to give a crude product. The crude product was purified by Prep-HPLC (0.1% FA in H₂O/ACN=10~40%) to give the desired product (17 mg, 35.4%). LC/MS: 1012.4 [M+H]⁺; ¹H NMR (400 MHZ, DMSO) δ 10.95 (s, 1H), 9.97 (brs, 1H), 9.21 (d, J=4.8 Hz, 1H), 8.17 (s, 1H), 7.75 (dd, J=9.1, 6.1 Hz, 1H), 7.48 (d, J=8.5 Hz, 1H), 7.36-7.29 (m, 2H), 7.11-6.93 (m, 3H), 5.03 (dd, J=13.5, 5.1 Hz, 1H), 4.79-4.70 (m, 1H), 4.39-4.22 (m, 4H), 4.21-4.12 (m, 1H), 4.10-3.96 (m, 2H), 3.64-3.59 (m, 1H), 3.57-3.49 (m, 1H), 3.26-3.13 (m, 7H), 3.01 (s, 4H), 2.95-2.80 (m, 2H), 2.69-2.53 (m, 2H), 2.47-2.21 (m, 8H), 2.14-2.05 (m, 1H), 2.04-1.89 (m, 2H), 1.76-1.62 (m, 6H), 1.40-1.28 (m, 2H), 1.16 (d, J=9.5 Hz, 4H), 0.80 (s, 2H), 0.73 (dd, J=13.0, 7.2 Hz, 2H), 0.63 (s, 2H), 0.40 (s, 2H).

Example 15: Preparation of (3S)-3-(5-(4-((1-(((1-(((7-(8-ethyl-7-fluoro-3-hydroxynaphthalen-1-yl)-8-fluoro-4-(1-oxa-6-azaspiro[3.5]nonan-6-yl)pyrido[4,3-d]pyrimidin-2-yl)oxy)methyl)cyclopropyl)methyl)-4-fluoropiperidin-4-yl)methyl)piperazin-1-yl)-1-oxoisoindolin-2-yl)piperidine-2,6-dione (Compound 41)

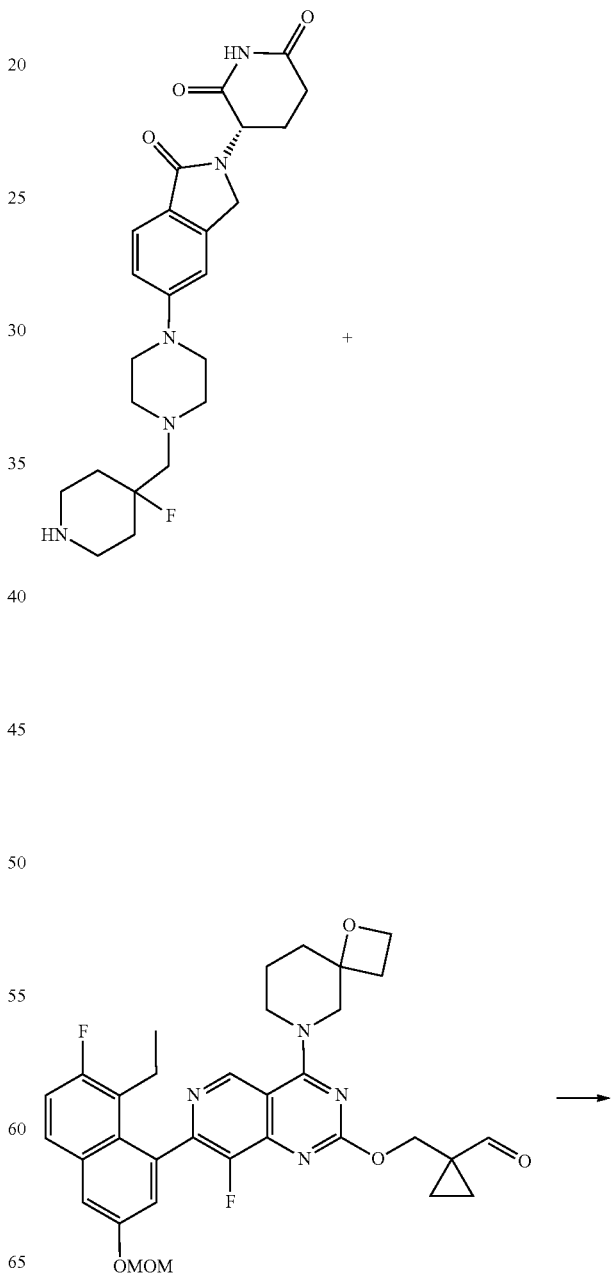

-continued

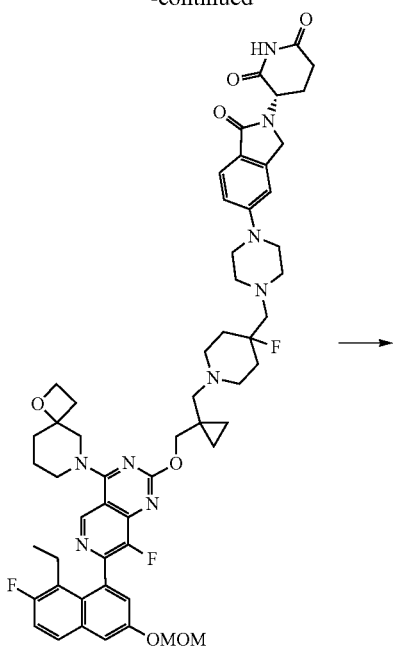

Step 1: Preparation of (3S)-3-(5-(4-((1-((1-(((7-(8-ethyl-7-fluoro-3-(methoxymethoxy) naphthalen-1-yl)-8-fluoro-4-(1-oxa-6-azaspiro[3.5]nonan-6-yl) pyrido[4,3-d]pyrimidin-2-yl)oxy)methyl) cyclopropyl)methyl)-4-fluoropiperidin-4-yl)methyl) piperazin-1-yl)-1-oxo isoindolin-2-yl)piperidine-2,6-dione The mixture of (S)-3-(5-(4-((4-fluoropiperidin-4-yl) methyl)piperazin-1-yl)-1-oxoisoindolin-2-yl)piperidine-2,6-dione (194 mg, 80% purity, 0.35 mmol), 1-(((7-(8-ethyl-7-fluoro-3-(methoxymethoxy)naphthalen-1-yl)-8-fluoro-4-(1-oxa-6-azaspiro[3.5]nonan-6-yl)pyrido[4,3-d]pyrimidin-2-yl)oxy)methyl)cyclopropane-1-carbaldehyde (130 mg, 0.22 mmol) and TEA (87 mg, 0.86 mmol) in DCM:MeOH (3:1, 8 mL) was stirred at room temperature for 0.5 hour and STAB (137 mg, 0.65 mmol) was added. After stirring for 0.5 hour, NaBH$_3$CN (27 mg, 0.43 mmol) was added. The reaction mixture was stirred at room temperature for 16 hours. The reaction was quenched with H$_2$O (5 mL) and extracted with DCM (10 mL×3). The organic phase was washed with brine and dried over Na$_2$SO$_4$. The solution was concentrated in vacuum and the residue was purified by Pre-TLC (DCM:MeOH=10:1) to afford the desired compound (73 mg crude) as a brown solid. LC/MS: 1032.5 [M+H]$^+$.

Step 2: Preparation of (3S)-3-(5-(4-((1-((1-(((7-(8-ethyl-7-fluoro-3-hydroxynaphthalen-1-yl)-8-fluoro-4-(1-oxa-6-azaspiro[3.5]nonan-6-yl)pyrido[4,3-d] pyrimidin-2-yl)oxy)methyl)cyclopropyl)methyl)-4-fluoropiperidin-4-yl)methyl)piperazin-1-yl)-1-oxoisoindolin-2-yl)piperidine-2,6-dione (Compound 41)

A solution of (3S)-3-(5-(4-((1-((1-(((7-(8-ethyl-7-fluoro-3-(methoxymethoxy)naphthalen-1-yl)-8-fluoro-4-(1-oxa-6-azaspiro[3.5]nonan-6-yl)pyrido[4,3-d]pyrimidin-2-yl)oxy) methyl)cyclopropyl)methyl)-4-fluoropiperidin-4-yl)methyl) piperazin-1-yl)-1-oxoisoindolin-2-yl)piperidine-2,6-dione (68 mg crude) in DCM:TFA (3:1, 4 mL) was stirred under nitrogen at room temperature for 2 hours. The mixture was concentrated in vacuum and the residue was purified by Prep-HPLC (Gemini-C18: 150×21.2 mm, 5 µm, ACN-H$_2$O (0.1% TFA) 10~40%) to give the desired product (11.4 mg, 5% yield for 2 steps) as a yellow solid. LC/MS: 988.5 [M+H]$^+$; $^1$H NMR (400 MHZ, DMSO) δ 10.97 (s, 1H), 10.00 (s, 1H), 9.26 (d, J=3.2 Hz, 1H), 7.78 (dd, J=9.2, 6.0 Hz, 1H), 7.57 (d, J=8.4 Hz, 1H), 7.40-7.33 (m, 2H), 7.15-7.02 (m, 3H), 5.06 (dd, J=13.2, 4.8 Hz, 1H), 4.57-4.53 (m, 1H), 4.41-4.19 (m, 12H), 3.96-3.91 (m, 1H), 3.86-3.81 (m, 1H), 3.77-3.71 (m, 2H), 3.66-3.59 (m, 1H), 3.54-3.48 (m, 1H), 3.42-3.23 (m, 6H), 3.18-3.11 (m, 2H), 2.96-2.86 (m, 2H), 2.42-2.26 (m, 6H), 2.17-2.06 (m, 3H), 2.00-1.83 (m, 4H), 1.75-1.68 (m, 1H), 0.94-0.77 (m, 5H).

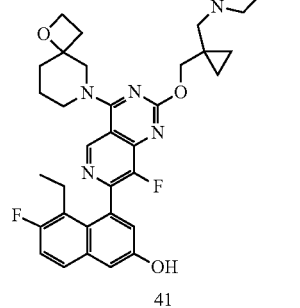

41

Example 16: Preparation of 3-(5-(4-((1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy) methyl)cyclopropyl) methyl)piperidin-4-yl)oxy)-[1,4'-bipiperidin]-1'-yl)-1-oxoisoindolin-2-yl)piperidine-2,6-dione (Compound 43)
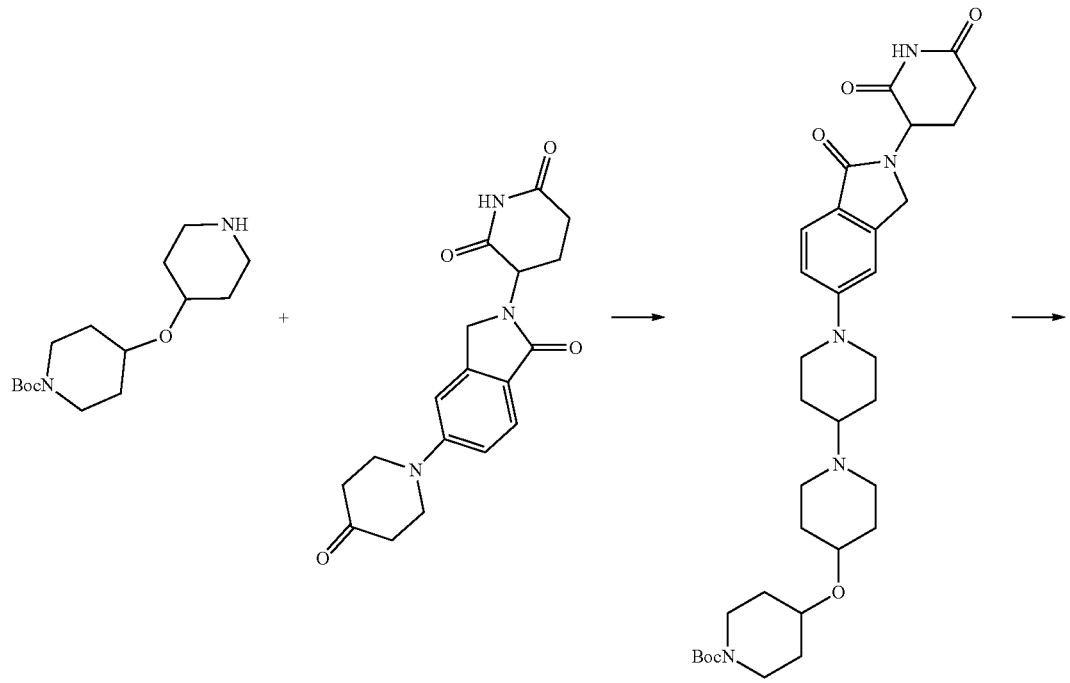
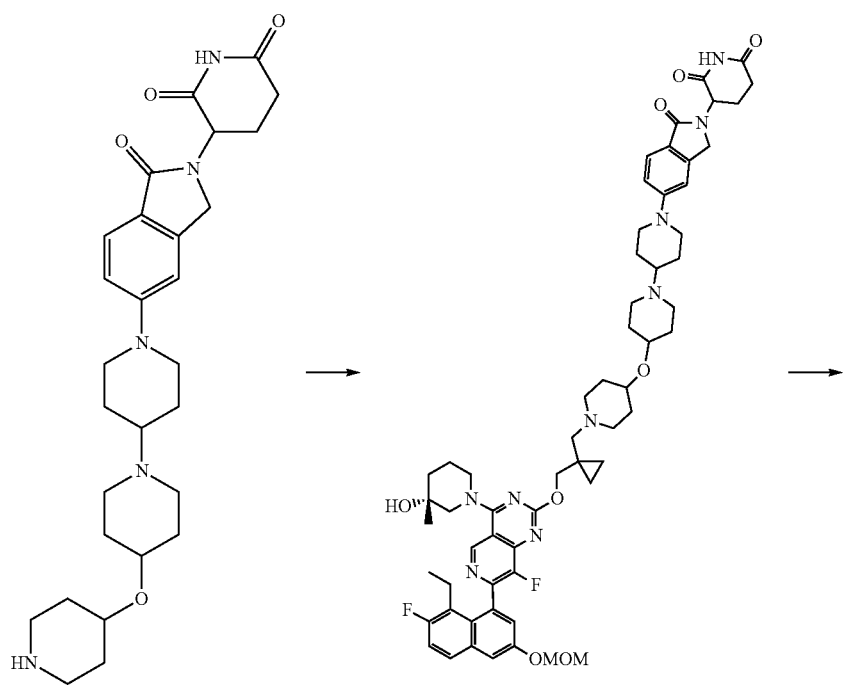

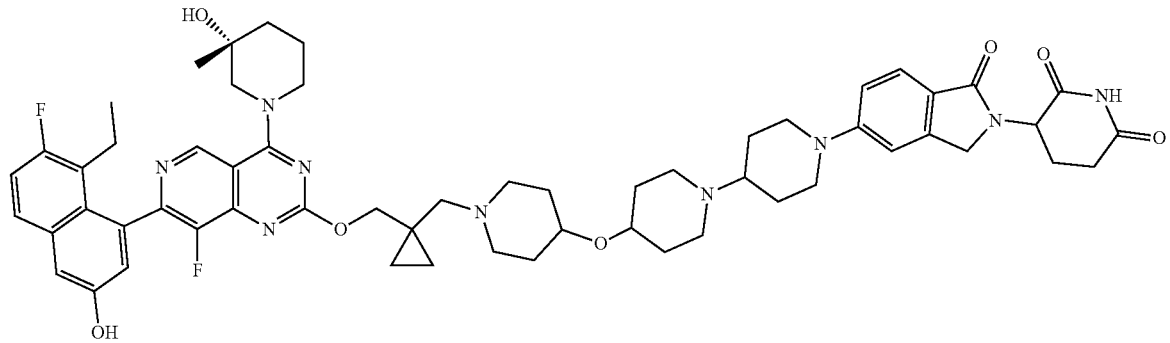

43

Step 1: Preparation of tert-butyl 4-((1'-(2-(2,6-di-oxopiperidin-3-yl)-1-oxoisoindolin-5-yl)-[1,4'-bipip-eridin]-4-yl)oxy)piperidine-1-carboxylate The mixture of tert-butyl [4-(piperidin-4-yloxy)piperidin-1-yl]formate (200 mg, 0.70 mmol), 3-(1-oxo-5-(4-oxopip-eridin-1-yl)isoindolin-2-yl)piperidine-2,6-dione (239 mg, 0.70 mmol), Ti(Oi-Pr)$_4$ (597 mg, 2.10 mmol) and STAB (440 mg, 7.00 mmol) in DMA (5 mL) was stirred at 45° C. for 16 hours. The reaction was quenched with water (20 mL) and extracted with EA (20 mL×3). The organic phase was washed with brine and dried over Na$_2$SO$_4$. The solution was concentrated in vacuum and the residue was purified by flash column chromatography (DCM: MeOH=15:1) to give the desired compound (150 mg, 35.0% yield) as a white solid. LC/MS: 610.3 [M+H]$^+$.

Step 2: Preparation of 3-(1-oxo-5-(4-(piperidin-4-yloxy)-[1,4'-bipiperidin]-1'-yl)isoindolin-2-yl) piperidine-2,6-dione The solution of tert-butyl 4-((1'-(2-(2,6-dioxopiperidin-3-yl)-1-oxoisoindolin-5-yl)-[1,4'-bipiperidin]-4-yl)oxy)piperidine-1-carboxylate (150 mg, 0.24 mmol) in HCl/dioxane (4 M)/DCM (6 mL, 1:1) was stirred at 25° C. for 2 hours. The solvent was removed in vacuum to afford the desired compound (120 mg, 90.9% yield) as a white solid. LC/MS: 510.3 [M+H]$^+$.

Step 3: Preparation of 3-(5-(4-((1-((1-(((7-(8-ethyl-7-fluoro-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)oxy)-[1,4'-bipip-eridin]-1'-yl)-1-oxoisoindolin-2-yl)piperidine-2,6-dione The mixture of (R)-1-(((7-(8-ethyl-7-fluoro-3-(methoxymethoxy)naphthalen-1-yl)-8-fluoro-4-(3-hydroxy-3-methylpiperidin-1-yl)pyrido[4,3-d]pyrimidin-2-yl)oxy)methyl)cyclopropane-1-carbaldehyde (150 mg, 0.25 mmol), 3-(1-oxo-5-(4-(piperidin-4-yloxy)-[1,4'-bipiperidin]-1'-yl) isoindolin-2-yl)piperidine-2,6-dione (130 mg, 0.25 mmol), Ti(Oi-Pr)$_4$ (360 mg, 1.26 mmol), TEA (153 mg, 1.51 mmol) and STAB (536 mg, 2.53 mmol) in DMA (5 mL) was stirred at 25° C. for 16 hours. The reaction mixture was poured into water (10 mL) and extracted with DCM (10 mL×3). The combined organic layer was dried over Na$_2$SO$_4$ and concentrated in vacuum. The residue was purified by Prep-TLC (DCM:MeOH=10:1) to give the desired compound (60 mg, 20.7% yield) as a white solid. LC/MS: 1086.6 [M+H]$^+$.

Step 4: Preparation of 3-(5-(4-((1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl) methyl) piperidin-4-yl)oxy)-[1,4'-bipiperidin]-1'-yl)-1-oxoisoindolin-2-yl)piperidine-2,6-dione (Compound 43)

The solution of 3-(5-(4-((1-((1-(((7-(8-ethyl-7-fluoro-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclo propyl)methyl)piperidin-4-yl)oxy)-[1,4'-bipiperidin]-1'-yl)-1-oxoisoindolin-2-yl)piperidine-2,6-dione (60 mg, 0.05 mmol) was stirred in HCl/dioxane (4 M)/THF (4 mL, 1:1) was stirred at room temperature for 1 hour. The mixture was concentrated in vacuum to give a crude product. The crude product was purified by Prep-HPLC (0.1% FA in H$_2$O/ACN=10~40%) to give the desired product (16.9 mg, 27.9%). LC/MS: 1042.4 [M+H]$^+$; $^1$H NMR (400 MHz, DMSO)δ 10.93 (s, 1H), 9.21 (s, 1H), 8.16 (s, 1H), 7.78-7.74 (m, 1H), 7.49 (d, J=8.5 Hz, 1H), 7.37-7.32 (m, 2H), 7.08-6.99 (m, 3H), 5.04 (dd, J=13.3, 5.1 Hz, 1H), 4.73 (brs, 1H), 4.36-4.24 (m, 4H), 4.19 (d, J=16.9 Hz, 1H), 4.03 (dd, J=21.3, 13.2 Hz, 1H), 3.91 (d, J=12.7 Hz, 2H), 3.62 (d, J=13.2 Hz, 1H), 3.54-3.50 (m, 1H), 2.94-2.85 (m, 2H), 2.78 (d, J=11.0 Hz, 6H), 2.60-2.56 (m, 1H), 2.38-2.29 (m, 6H), 2.19-1.94 (m, 6H), 1.82-1.65 (m, 10H), 1.53-1.45 (m, 2H), 1.38-1.34 (m, 4H), 1.17 (d, J=9.6 Hz, 3H), 0.76-0.71 (m, 3H), 0.64 (s, 2H), 0.40 (s, 2H).

Example 17: Preparation of (S)-3-(5-(4-((1-(((1-(((7-(8-ethyl-7-fluoro-3-hydroxynaphthalen-1-yl)-8-fluoro-4-((S)-1-oxa-6-azaspiro[3.5]nonan-6-yl) pyrido[4,3-d]pyrimidin-2-yl)oxy) methyl) cyclopropyl)methyl) piperidin-4-yl)methyl) piperazin-1-yl)-1-oxoisoindolin-2-yl)piperidine-2,6-dione (Compound 44)
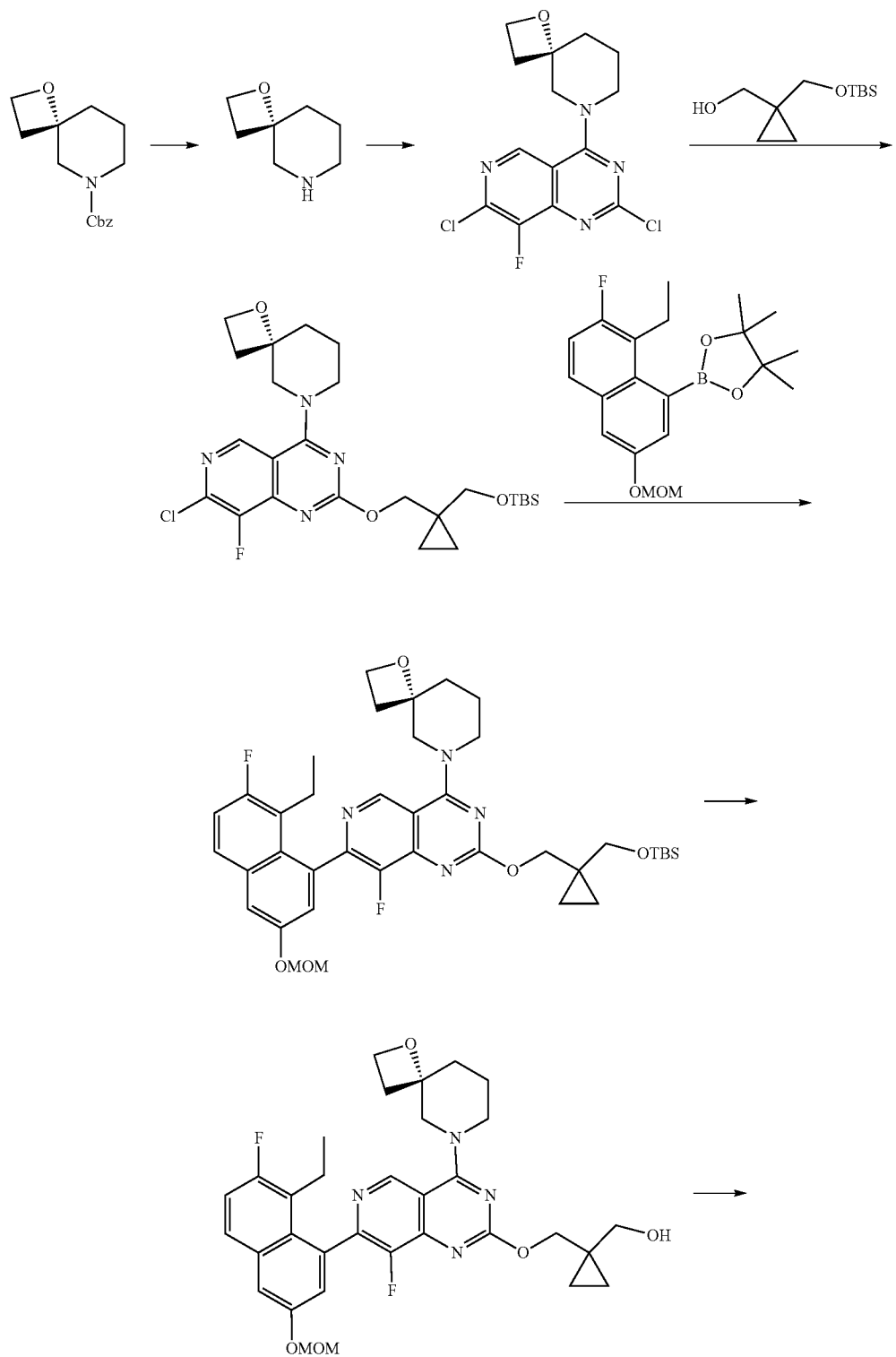

431

-continued

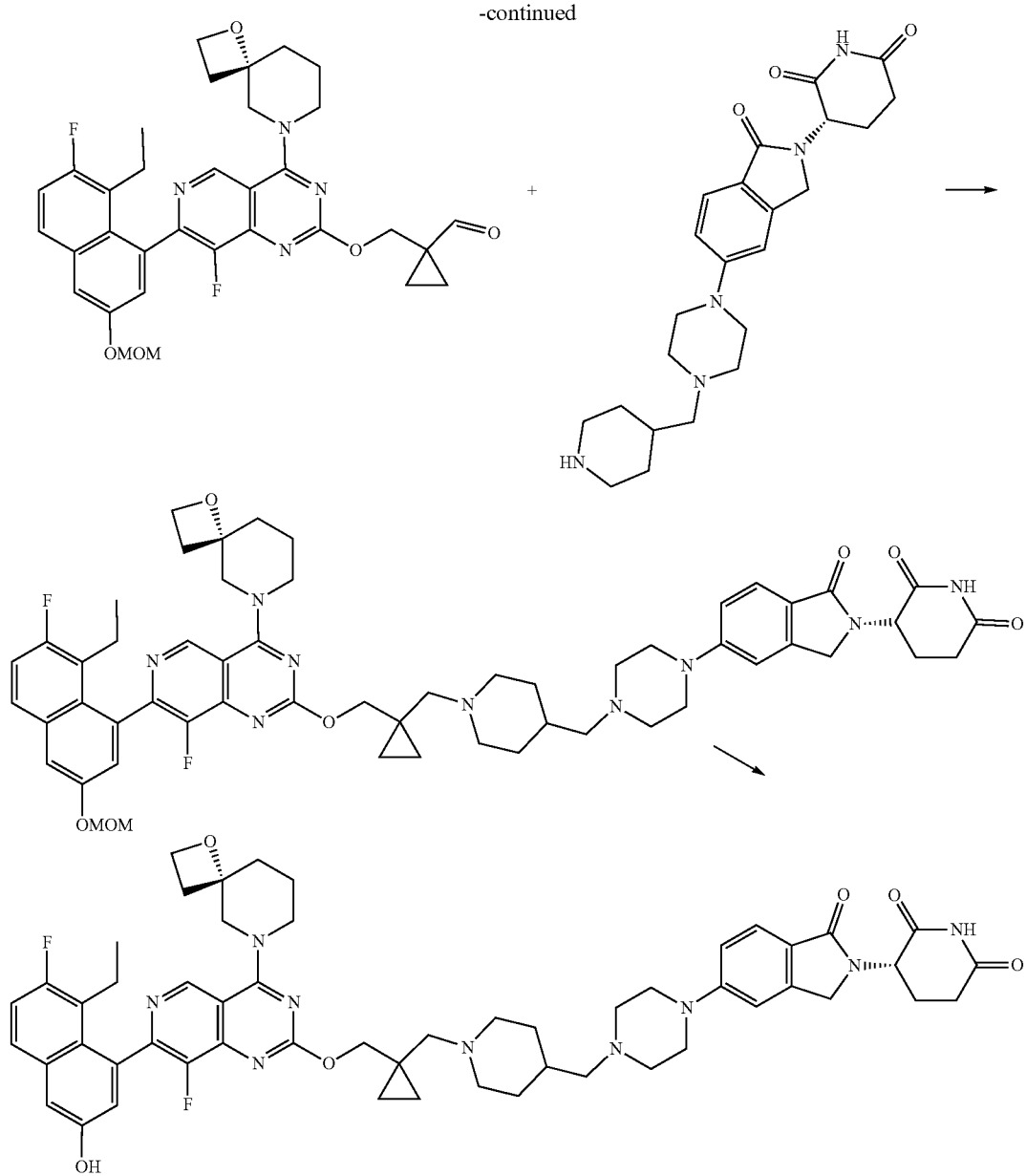

Step 1: Preparation of (S)-1-oxa-6-azaspiro[3.5]nonane

To a solution of benzyl (S)-1-oxa-6-azaspiro[3.5]nonane-6-carboxylate (5.0 g, 19.10 mmol) in EtOH (50 mL) was added Pd/C (1 g, 10%). The mixture was stirred under hydrogen atmosphere at room temperature for 16 hours. The mixture was filtered through a Celite pad. The filtrate was concentrated under vacuum to give the desired compound (2.2 g, 90.9% yield) as a yellow oil. LC/MS: 128.1 [M+H]+

Step 2: Preparation of (S)-6-(2,7-dichloro-8-fluoro-pyrido[4,3-d]pyrimidin-4-yl)-1-oxa-6-azaspiro[3.5]nonane To a solution of (S)-1-oxa-6-azaspiro[3.5]nonane (2.2 g, 17.29 mmol) in DCM (35 mL) was added DIEA (6.7 g, 51.89 mmol) and 2,4,7-trichloro-8-fluoropyrido[4,3-d]pyrimidine (4.2 g, 17.29 mmol) at −40° C. under nitrogen atmosphere. The mixture was stirred at −40° C. for 1 hour. The reaction mixture was poured into water (50 mL) and extracted with DCM (50 mL×3). The organic layers were combined, dried over Na₂SO₄ and concentrated in vacuum. The residue was purified by flash chromatography on silica gel (25% EA in PE) to give the desired compound (3.6 g, 56% yield) as a yellow solid. LC/MS: 343.0 [M+H]+.

Step 3: Preparation of (S)-6-(2-((1-(((tert-butyldimethylsilyl)oxy)methyl)cyclopropyl)methoxy)-7-chloro-8-fluoropyrido[4,3-d]pyrimidin-4-yl)-1-oxa-6-azaspiro[3.5]nonane A solution of butyldimethylsilyl)oxy)methyl)cyclopropyl)methanol (5.67 g, 26.22 mmol) in THF (45 mL) was added NaH (460 mg, 11.54 mmol) at 0° C. The mixture was stirred at 0° C. for 15 minutes and (S)-6-(2,7-dichloro-8-fluoropyrido[4,3-d]pyrimidin-4-yl)-1-oxa-6-azaspiro[3.5]nonane (3.6 g, 10.49 mmol) was added at 0° C. The mixture was stirred at room temperature for 2 hours. The reaction mixture was poured into water (100 mL) and extracted with EA (100 mL×3). The combined organic layers were dried over $Na_2SO_4$ and concentrated in vacuum. The residue was purified by flash column chromatography on silica gel (20% EA in PE) to give the desired compound (4.17 g, 76% yield) as a yellow solid. LC/MS: 523.2 [M+H]$^+$.

Step 4: Preparation of (S)-6-(2-((1-(((tert-butyldimethylsilyl)oxy)methyl)cyclopropyl)methoxy)-7-(8-ethyl-7-fluoro-3-(methoxymethoxy)naphthalen-1-yl)-8-fluoropyrido[4,3-d]pyrimidin-4-yl)-1-oxa-6-azaspiro[3.5]nonane To a solution of (S)-6-(2-((1-(((tert-butyldimethylsilyl)oxy)methyl)cyclopropyl)methoxy)-7-chloro-8-fluoropyrido[4,3-d]pyrimidin-4-yl)-1-oxa-6-azaspiro[3.5]nonane (4.17 g, 7.97 mmol) in dioxane (40 mL) and $H_2O$ (10 mL) was added 2-[8-ethyl-7-fluoro-3-(methoxymethoxy)naphthalen-1-yl]-4,4,5,5-tetramethyl-1,3,2-dioxaborolane (3.45 g, 9.56 mmol), Catacxium A-Pd-G3 (1.16 g, 1.59 mmol) and $K_2CO_3$ (3.3 g, 23.91 mmol). The mixture was stirred at 90° C. for 16 hours under nitrogen atmosphere. The reaction mixture was poured into water (100 mL) and extracted with DCM (100 mL×3). The combined organic layers were dried over $Na_2SO_4$ and concentrated in vacuum. The residue was purified by flash chromatography on silica gel (7% MeOH in DCM) to give the desired compound (5.6 g, 97% yield) as a yellow solid. LC/MS: 721.4 [M+H]$^+$.

Step 5: Preparation of (S)-(1-(((7-(8-ethyl-7-fluoro-3-(methoxymethoxy)naphthalen-1-yl)-8-fluoro-4-(1-oxa-6-azaspiro[3.5]nonan-6-yl)pyrido[4,3-d]pyrimidin-2-yl)oxy)methyl)cyclopropyl) methanol To a solution of (S)-6-(2-((1-(((tert-butyldimethylsilyl)oxy)methyl)cyclopropyl)methoxy)-7-(8-ethyl-7-fluoro-3-(methoxymethoxy)naphthalen-1-yl)-8-fluoropyrido[4,3-d]pyrimidin-4-yl)-1-oxa-6-azaspiro[3.5]nonane (5.6 g, 7.90 mmol) in DMF (50 mL) was added CsF (18.10 g, 118.59 mmol). The mixture was stirred at 40° C. for 16 hours. The reaction mixture was poured into water (100 mL) and extracted with EA (100 mL×3). The combined organic layers were dried over $Na_2SO_4$ and concentrated in vacuum. The residue was purified by flash chromatography on silica gel (30% EA in PE) to give the desired compound (3.2 g, 70% yield) as a yellow solid. LC/MS: 607.3 [M+H]$^+$.

Step 6: Preparation of (S)-1-(((7-(8-ethyl-7-fluoro-3-(methoxymethoxy)naphthalen-1-yl)-8-fluoro-4-(1-oxa-6-azaspiro[3.5]nonan-6-yl)pyrido[4,3-d]pyrimidin-2-yl)oxy)methylcyclopropane-1-carbaldehyde A solution of (S)-(1-(((7-(8-ethyl-7-fluoro-3-(methoxymethoxy)naphthalen-1-yl)-8-fluoro-4-(1-oxa-6-azaspiro[3.5]nonan-6-yl)pyrido[4,3-d]pyrimidin-2-yl)oxy)methyl)cyclopropyl)methanol (200 mg, 0.33 mmol) in DCM (4 mL) was added Dess-Martin periodinane (280 mg, 0.65 mmol) at 0° C. under nitrogen atmosphere. The mixture was stirred at room temperature for 2 hours. The reaction mixture was diluted with EA (10 mL) and quenched with saturated aqueous $Na_2S_2O_3$:$NaHCO_3$:$H_2O$=1:1:1 (10 mL). The organic layer was dried over $Na_2SO_4$ and concentrated under vacuum to give a crude product (180 mg, 94.% yield) as a yellow solid. LC/MS: 605.3 [M+H]$^+$.

Step 7: Preparation of (S)-3-(5-(4-((1-((1-(((7-(8-ethyl-7-fluoro-3-(methoxymethoxy)naphthalen-1-yl)-8-fluoro-4-((S)-1-oxa-6-azaspiro[3.5]nonan-6-yl)pyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione To a solution of (S)-1-(((7-(8-ethyl-7-fluoro-3-(methoxymethoxy)naphthalen-1-yl)-8-fluoro-4-(1-oxa-6-azaspiro[3.5]nonan-6-yl)pyrido[4,3-d]pyrimidin-2-yl)oxy)methyl)cyclopropane-1-carbaldehyde (180 mg, 0.33 mmol) in DCM (4 mL) was added 3-(1-oxo-5-(4-(piperidin-4-ylmethyl)piperazin-1-yl)isoindolin-2-yl)piperidine-2,6-dione (521 mg, 0.99 mmol), DIEA (128 mg, 0.99 mmol) and STAB (350 mg, 1.65 mmol). The mixture was stirred at room temperature for 16 hours. The reaction mixture was poured into water (10 mL) and extracted with DCM (10 mL×3). The combined organic layers were dried over $Na_2SO_4$ and concentrated in vacuum. The residue was purified by PTLC (5% MeOH in DCM) to give the desired compound (100 mg, 29.8% yield) as a yellow solid. LC/MS: 1014.5 [M+H]$^+$.

Step 8: Preparation of (S)-3-(5-(4-((1-((1-(((7-(8-ethyl-7-fluoro-3-hydroxynaphthalen-1-yl)-8-fluoro-4-((S)-1-oxa-6-azaspiro[3.5]nonan-6-yl)pyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione (Compound 44)

A solution of (S)-3-(5-(4-((1-((1-(((7-(8-ethyl-7-fluoro-3-(methoxymethoxy)naphthalen-1-yl)-8-fluoro-4-((S)-1-oxa-6-azaspiro[3.5]nonan-6-yl)pyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione (100 mg, 0.098 mmol) in DCM (4 mL) was added TFA (1 mL). The mixture was stirred at room temperature for 1 hour. The mixture was concentrated in vacuum and the residue was purified by Prep-HPLC (0.1% FA in $H_2O$/ACN=22~25%) to give the desired product (14 mg, 14.7% yield). LC/MS: 970.5 [M+H]$^+$; $^1$H NMR (400 MHZ, DMSO) δ 10.96 (s, 1H), 10.00 (s, 1H), 9.26 (d, J=4.6 Hz, 1H), 9.00-8.55 (m, 1H), 7.78 (dd, J=9.0, 5.9 Hz, 1H), 7.61-7.50 (m, 1H), 7.40-7.32 (m, 2H), 7.20-7.01 (m, 3H), 5.06 (dd, J=13.1, 4.9 Hz, 1H), 4.58-4.19 (m, 8H), 3.86-3.83 (m, 1H), 3.78-3.72 (m, 1H), 3.32-3.18 (m, 8H), 3.14-2.84 (m, 4H), 2.62-2.56 (m, 1H), 2.48-2.32 (m, 7H), 2.28-2.06 (m, 4H), 2.04-1.84 (m, 6H), 1.74-1.67 (m, 1H), 1.56-1.34 (m, 2H), 0.95-0.85 (m, 2H), 0.80-0.76 (m, 2H), 0.76-0.70 (m, 3H).

Example 18: Preparation of (S)-3-(5-(4-((1-(((1-(((7-(8-ethyl-7-fluoro-3-hydroxynaphthalen-1-yl)-8-fluoro-4-((R)-1-oxa-6-azaspiro[3.5]nonan-6-yl)pyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione (Compound 45)
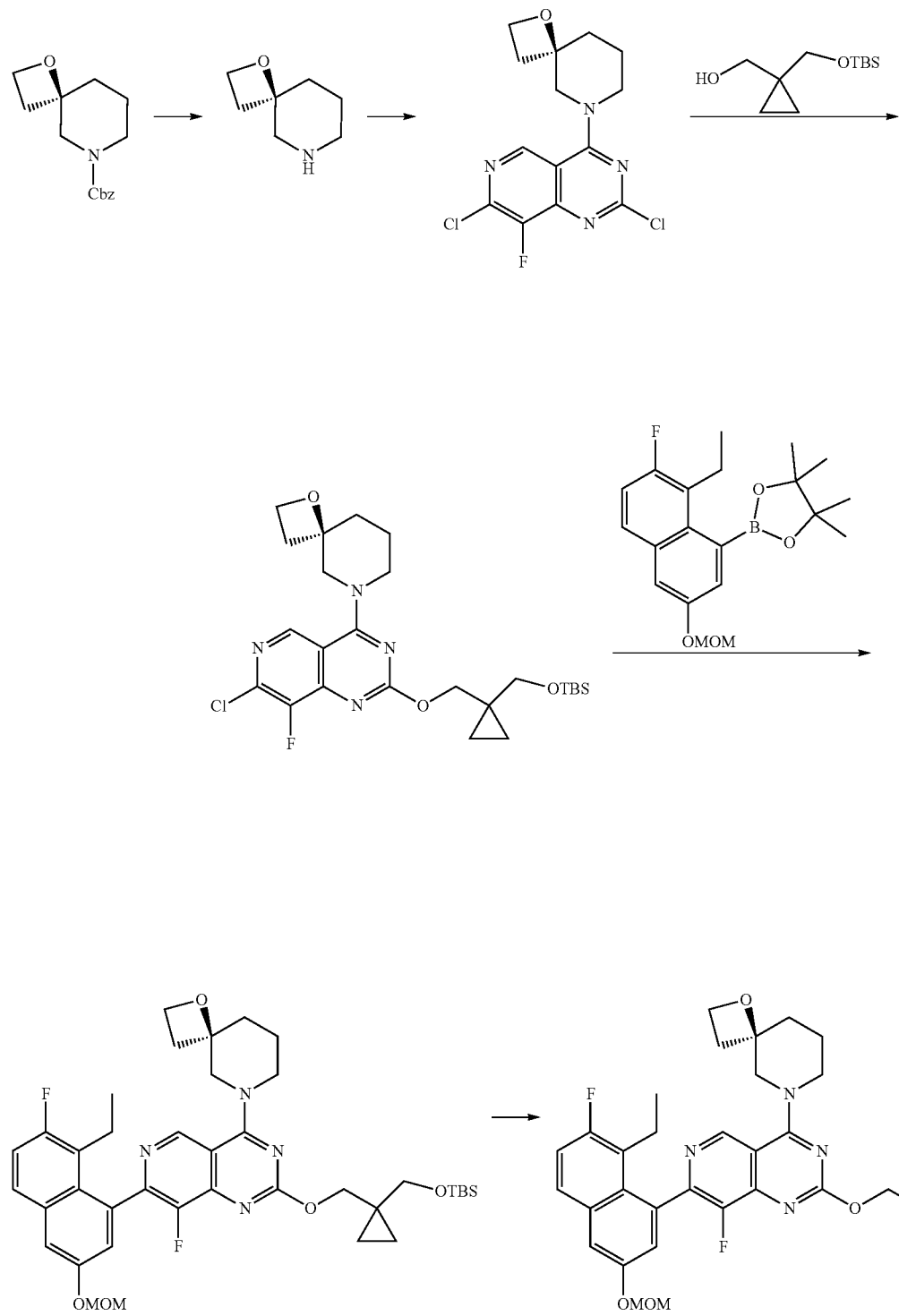

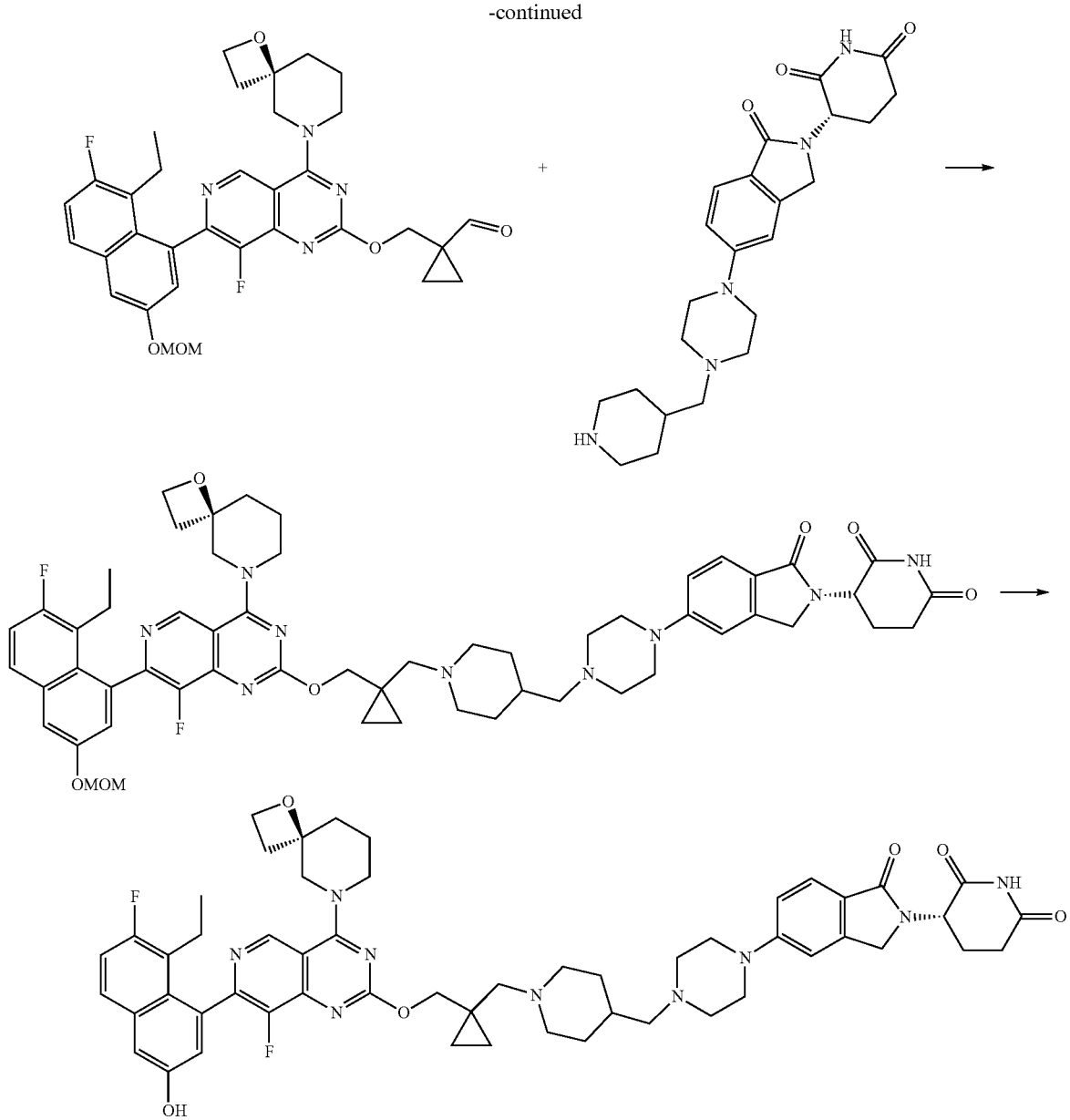

Step 1: Preparation of (R)-1-oxa-6-azaspiro[3.5]nonane

To a solution of (R)-1-oxa-6-azaspiro[3.5]nonane-6-carboxylate (1.0 g, 3.83 mmol) in EtOH (20 mL) was added Pd/C (0.2 g, 10%). The mixture was stirred under hydrogen atmosphere at room temperature for 16 hours. The mixture was filtered through a Celite pad. The filtrate was concentrated under vacuum to give the desired compound (400 mg, 82.2% yield) as a yellow oil. LC/MS: 128.1 [M+H]+.

Step 2: Preparation of (R)-6-(2,7-dichloro-8-fluoropyrido[4,3-d]pyrimidin-4-yl)-1-oxa-6-azaspiro[3.5]nonane To a solution of (R)-1-oxa-6-azaspiro[3.5]nonane (101 mg, 0.79 mmol) in DCM (5 mL) was added 2,4,7-trichloro-8-fluoropyrido[4,3-d]pyrimidine (340 mg, 0.79 mmol) and DIEA (307 mg, 2.38 mmol) at −40° C. under nitrogen atmosphere. The mixture was stirred at −40° C. for 1 hour. The reaction mixture was poured into water (10 mL) and extracted with DCM (10 mL×3). The organic layers were combined and dried over Na₂SO₄. The solution was concentrated in vacuum and the residue was purified by flash column chromatography on silica gel (25% EA in PE) to give the desired compound (220 mg, 80.9% yield) as a yellow solid. LC/MS: 343.0 [M+H]+.

Step 3: Preparation of (R)-6-(2-((1-(((tert-butyldimethylsilyl)oxy)methyl)cyclopropyl)methoxy)-7-chloro-8-fluoropyrido[4,3-d]pyrimidin-4-yl)-1-oxa-6-azaspiro[3.5]nonane To a solution of butyldimethylsilyl)oxy)methyl)cyclopropyl)methanol (488 mg, 2.25 mmol) in THF (5 mL) was added NaH (39.7 mg, 0.99 mmol) at 0° C. The mixture was stirred at 0° C. for 15 minutes and (R)-6-(2,7-dichloro-8-fluoropyrido[4,3-d]pyrimidin-4-yl)-1-oxa-6-azaspiro[3.5]nonane (310 mg, 0.90 mmol) was added at 0° C. The mixture was stirred at room temperature for 2 hours. The reaction mixture was poured into water (10 mL) and extracted with EA (10 mL×3). The combined organic layers were dried over $Na_2SO_4$ and concentrated in vacuum. The residue was purified by flash chromatography on silica gel (20% EA in PE) to give the desired compound (320 mg, 67.6% yield) as a yellow solid. LC/MS: 523.2 [M+H]$^+$.

Step 4: Preparation of (R)-6-(2-((1-(((tert-butyldimethylsilyl)oxy)methyl)cyclopropyl)methoxy)-7-(8-ethyl-7-fluoro-3-(methoxymethoxy)naphthalen-1-yl)-8-fluoropyrido[4,3-d]pyrimidin-4-yl)-1-oxa-6-azaspiro[3.5]nonane To a solution of (R)-6-(2-((1-(((tert-butyldimethylsilyl)oxy)methyl)cyclopropyl)methoxy)-7-chloro-8-fluoropyrido[4,3-d]pyrimidin-4-yl)-1-oxa-6-azaspiro[3.5]nonane (310 mg, 0.59 mmol) in dioxane (8 mL) and $H_2O$ (2 mL) was added 2-[8-ethyl-7-fluoro-3-(methoxymethoxy) naphthalen-1-yl]-4,4,5,5-tetramethyl-1,3,2-dioxaborolane (256 mg, 0.71 mmol), Catacxium A-Pd-G3 (86.32 mg, 0.11 mmol) and $K_2CO_3$ (245.7 mg, 1.77 mmol). The mixture was stirred at 90° C. for 16 hours under nitrogen atmosphere. The reaction mixture was poured into water (10 mL) and extracted with DCM (10 mL×3). The combined organic layers were dried over $Na_2SO_4$ and concentrated in vacuum. The residue was purified by flash chromatography on silica gel (7% MeOH in DCM) to give the desired compound (350 mg, 79.4% yield) as a yellow solid. LC/MS: 721.4 [M+H]$^+$.

Step 5: Preparation of (R)-(1-(((7-(8-ethyl-7-fluoro-3-(methoxymethoxy)naphthalen-1-yl)-8-fluoro-4-(1-oxa-6-azaspiro[3.5]nonan-6-yl)pyrido[4,3-d]pyrimidin-2-yl)oxy)methyl)cyclopropyl) methanol To a solution of (R)-6-(2-((1-(((tert-butyldimethylsilyl)oxy)methyl)cyclopropyl)methoxy)-7-(8-ethyl-7-fluoro-3-(methoxymethoxy)naphthalen-1-yl)-8-fluoropyrido[4,3-d]pyrimidin-4-yl)-1-oxa-6-azaspiro[3.5]nonane (350 mg, 0.48 mmol) in DMF (6 mL) was added CsF (1.16 g, 7.28 mmol). The reaction mixture was stirred at 40° C. for 16 hours. The reaction mixture was poured into water (10 mL) and extracted with EA (10 mL×3). The combined organic layers were dried over $Na_2SO_4$ and concentrated in vacuum. The residue was purified by flash chromatography on silica gel (30% EA in PE) to give the desired compound (200 mg, 70% yield) as a yellow solid. LC/MS: 607.3 [M+H]$^+$.

Step 6: Preparation of (R)-1-(((7-(8-ethyl-7-fluoro-3-(methoxymethoxy)naphthalen-1-yl)-8-fluoro-4-(1-oxa-6-azaspiro[3.5]nonan-6-yl)pyrido[4,3-d]pyrimidin-2-yl)oxy)methyl)cyclopropane-1-carbaldehyde A solution of (R)-(1-(((7-(8-ethyl-7-fluoro-3-(methoxymethoxy)naphthalen-1-yl)-8-fluoro-4-(1-oxa-6-azaspiro[3.5]nonan-6-yl)pyrido[4,3-d]pyrimidin-2-yl)oxy)methyl)cyclopropyl)methanol (200 mg, 0.33 mmol) in DCM (4 mL) was added Dess-Martin periodinane (280 mg, 0.65 mmol) at 0° C. under nitrogen atmosphere. The mixture was stirred at room temperature for 2 hours. The reaction mixture was diluted with EA (10 mL) and quenched with saturated aqueous $Na_2S_3O_3$: $NaHCO_3$:$H_2O$=1:1:1 (10 mL). The organic layer was dried over $Na_2SO_4$ and concentrated under vacuum to give a crude product (180 mg, 94.7% yield) as a yellow solid. LC/MS: 605.3 [M+H]$^+$.

Step 7: Preparation of (S)-3-(5-(4-((1-((1-(((7-(8-ethyl-7-fluoro-3-(methoxymethoxy)naphthalen-1-yl)-8-fluoro-4-((R)-1-oxa-6-azaspiro[3.5]nonan-6-yl)pyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione To a solution of (R)-1-(((7-(8-ethyl-7-fluoro-3-(methoxymethoxy)naphthalen-1-yl)-8-fluoro-4-(1-oxa-6-azaspiro[3.5]nonan-6-yl)pyrido[4,3-d]pyrimidin-2-yl)oxy)methyl)cyclopropane-1-carbaldehyde (180 mg, 0.33 mmol) in DCM (4 mL) was added 3-(1-oxo-5-(4-(piperidin-4-ylmethyl)piperazin-1-yl)isoindolin-2-yl)piperidine-2,6-dione (521 mg, 0.99 mmol), DIEA (128 mg, 0.99 mmol) and STAB (350 mg, 1.65 mmol). The mixture was stirred at room temperature for 16 hours. The reaction mixture was poured into water (10 mL) and extracted with DCM (10 mL×3). The combined organic layers were dried over $Na_2SO_4$ and concentrated in vacuum. The residue was purified by Prep-TLC (5% MeOH in DCM) to give the desired compound (100 mg, 29.8% yield) as a yellow solid. LC/MS: 1014.5 [M+H]$^+$.

Step 8: Preparation of (S)-3-(5-(4-((1-((1-(((7-(8-ethyl-7-fluoro-3-hydroxynaphthalen-1-yl)-8-fluoro-4-((R)-1-oxa-6-azaspiro[3.5]nonan-6-yl)pyrido[4,3-d]pyrimidin-2-yl)oxy)methyl) cyclopropyl)methyl)piperidin-4-yl)methyl)piperazin-1-yl)-1-oxoisoindolin-2-yl)piperidine-2,6-dione (Compound 45)

A solution of (S)-3-(5-(4-((1-((1-(((7-(8-ethyl-7-fluoro-3-(methoxymethoxy)naphthalen-1-yl)-8-fluoro-4-((R)-1-oxa-6-azaspiro[3.5]nonan-6-yl)pyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione (100 mg, 0.098 mmol) in DCM (4 mL) was added TFA (1 mL). The mixture was stirred at room temperature for 1 hour. The mixture was concentrated in vacuum and the residue was purified by Prep-HPLC (0.1% FA in $H_2O$/ACN=22~25%) to give the desired product (20 mg, 20.9% yield) as a white solid. LC/MS: 970.5 [M+H]$^+$; $^1$H NMR (400 MHZ, DMSO) δ 10.96 (s, 1H), 10.10-9.75 (m, 2H), 9.30-9.16 (m, 1H), 9.05-8.70 (m, 1H), 7.82-7.73 (m, 1H), 7.60 (d, J=8.4 Hz, 1H), 7.40-7.32 (m, 2H), 7.25-6.97 (m, 4H), 5.07 (dd, J=13.2, 5.1 Hz, 1H), 4.58-4.53 (m, 1H), 4.40-4.26 (m, 7H), 3.86-3.83 (m, 1H), 3.78-3.76 (m, 1H), 3.35-3.05 (m, 9H), 3.00-2.86 (m, 3H), 2.63-2.58 (m, 1H), 2.48-2.35 (m, 7H), 2.21-2.03 (m, 4H), 2.03-1.77 (m, 6H), 1.75-1.68 (m, 1H), 1.56-1.46 (m, 2H), 0.94-0.86 (m, 2H), 0.79 (s, 2H), 0.76-0.70 (m, 3H).

Example 19: Preparation of 3-(4-(4-((1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-4-methylpiperidin-4-yl)methyl)piperazin-1-yl)-2,6-difluorophenyl)piperidine-2,6-dione (Compound 48)
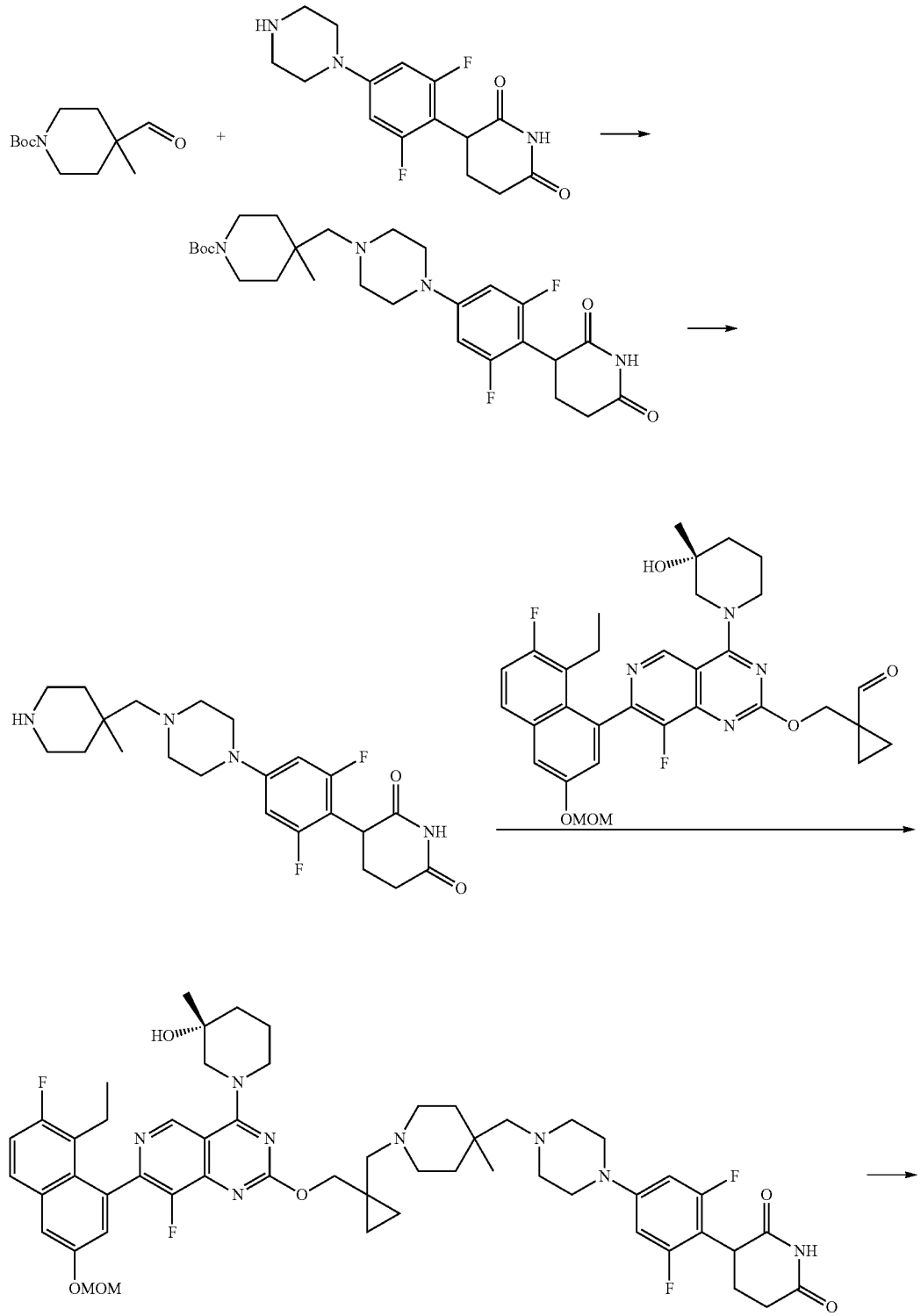

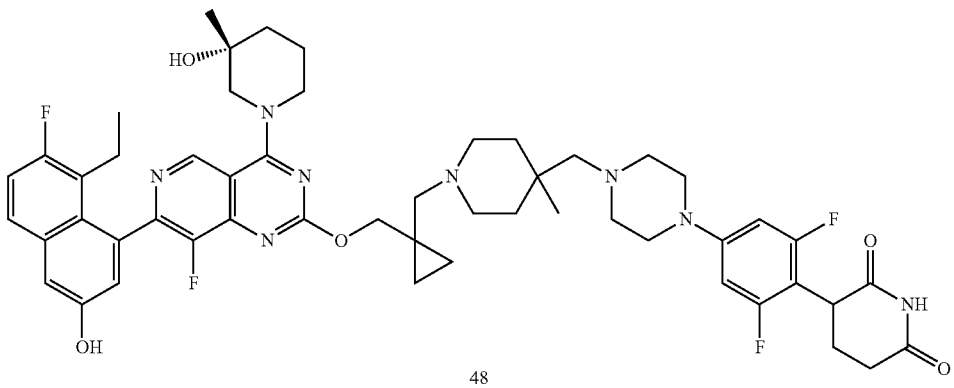

48

Step 1: Preparation of tert-butyl 4-((4-(4-(2,6-dioxopiperidin-3-yl)-3,5-difluorophenyl)piperazin-1-yl)methyl)-4-methylpiperidine-1-carboxylate To a solution of tert-butyl (4-formyl-4-methylpiperidin-1-yl) formate (200 mg, 0.88 mmol) and 3-[2,6-difluoro-4-(piperazin-1-yl)phenyl]piperidine-2,6-dione (270 mg, 0.88 mmol) in DMA (8 mL) was added TEA (450 mg, 3.51 mmol). The mixture was stirred for 1 hour at 25° C. Sodium triacetoxyborohydride (742 mg, 3.51 mmol) was added and the mixture was stirred at room temperature for 16 hours. The mixture was diluted with EtOAc (200 mL) and washed with water (80 mL×3). The organic layer was washed with brine, dried over $Na_2SO_4$, and concentrated in vacuum. The residue was purified by Prep-TLC with DCM:MeOH=95:5 to give the title compound (120 mg, 24.9% yield) as a white solid. LC/MS: 520.9 [M+H]$^+$.

Step 2: Preparation of 3-(2,6-difluoro-4-(4-((4-methylpiperidin-4-yl)methyl)piperazin-1-yl)phenyl)piperidine-2,6-dione A solution of tert-butyl4-((4-(4-(2,6-dioxopiperidin-3-yl)-3,5-difluorophenyl)piperazin-1-yl) methyl)-4-methylpiperidine-1-carboxylate (110 mg, 0.21 mmol) in DCM (2 mL) and TFA (2 mL) was stirred at 25° C. for 1 hour. The solvent was removed under vacuum to give the title compound (120 mg, crude) as a yellow oil. LC/MS: 421.2 [M+H]$^+$.

Step 3: Preparation of 3-(4-(4-((1-(((7-(8-ethyl-7-fluoro-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-4-methylpiperidin-4-yl)methyl)piperazin-1-yl)-2,6-difluorophenyl)piperidine-2,6-dione A solution of 1-[({7-[8-ethyl-7-fluoro-3-(methoxymethoxy)naphthalen-1-yl]-8-fluoro-4-[(3R)-3-hydroxy-3-methylpiperidin-1-yl]pyrido[4,3-d]pyrimidin-2-yl}oxy)methyl]cyclopropane-1-carbaldehyde (110 mg, 0.18 mmol) and 3-(2,6-difluoro-4-{4-[(4-methylpiperidin-4-yl)methyl] piperazin-1-yl}phenyl)piperidine-2,6-dione (93.6 mg, 0.22 mmol) in DMA (5 mL) was added DIPEA (120 mg, 0.9 mmol). The mixture was stirred for 1 hour at 25° C. Sodium triacetoxyborohydride (157 mg, 0.74 mmol) was added. The mixture was stirred for 2 hours. $NaBH_3CN$ (12 mg, 0.2 mmol) was added. The reaction mixture was stirred at 25° C. for 12 hours. The mixture was diluted with EtOAc (200 mL) and washed with water (80 mL×3). The organic layer was washed with brine, dried over $Na_2SO_4$, and concentrated in vacuum. The residue was purified by Pre-TLC with DCM:MeOH=95:5 to give the title compound (50 mg, 25.6% yield) as a white solid. LC/MS: 996.6 [M+H]$^+$.

Step 4: Preparation of 3-(4-(4-((1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-4-methylpiperidin-4-yl)methyl)piperazin-1-yl)-2,6-difluorophenyl)piperidine-2,6-dione (Compound 48)

A solution of 3-(4-(4-((1-((1-(((7-(8-ethyl-7-fluoro-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-4-methylpiperidin-4-yl)methyl)piperazin-1-yl)-2,6-difluorophenyl)piperidine-2,6-dione in HCl/dioxane (4 M, 1 mL) and THF (1 mL) was stirred at 25° C. for 1 hour. The solvent was removed under vacuum to give a crude product. The crude product was purified by Prep-HPLC (ACN-H$_2$O (0.1% FA) 22~25%) to give the desired product (10.3 mg, 25.6% yield) as a white solid. LC/MS: 953.7 [M+H]$^+$; $^1$H NMR (400 MHZ, DMSO) δ10.88 (s, 1H), 9.97 (s, 1H), 9.24 (s, 1H), 8.14 (s, 1H), 7.78-7.75 (m, 1H), 7.37-7.33 (m, 2H), 7.02 (d, J=2.4 Hz, 1H), 6.60 (d, J=12.8 Hz, 2H), 4.74 (d, J=7.3 Hz, 1H), 4.43-4.20 (m, 3H), 4.05 (dd, J=12.5, 5.0 Hz, 2H), 3.63 (d, J=13.2 Hz, 1H), 3.53 (d, J=13.0 Hz, 1H), 3.18-3.10 (m, 4H), 3.08 (d, J=5.6 Hz, 1H), 2.95-2.92 (m, 1H), 2.84-2.68 (m, 2H), 2.57-2.52 (m, 3H), 2.36-2.30 (m, 1H), 2.22-2.13 (m, 3H), 2.09-2.06 (m, 1H), 2.03-1.96 (m, 2H), 1.75-1.51 (m, 6H), 1.48-1.38 (m, 3H), 1.29-1.20 (m, 3H), 1.17 (d, J=10.1 Hz, 3H), 0.93 (s, 3H), 0.88-0.82 (m, 1H), 0.83-0.70 (m, 5H), 0.68-0.51 (m, 2H).

Example 20: Preparation of 3-{4-[4-(3-{[1-({[7-(8-ethyl-7-fluoro-3-hydroxynaphthalen-1-yl)-8-fluoro-4-[(3R)-3-hydroxy-3-methylpiperidin-1-yl]pyrido[4,3-d]pyrimidin-2-yl]oxy}methyl) cyclopropyl] methyl}-3-azaspiro[5.5]undecan-9-yl)piperazin-1-yl]-2,6-difluorophenyl}piperidine-2,6-dione (Compound 51)
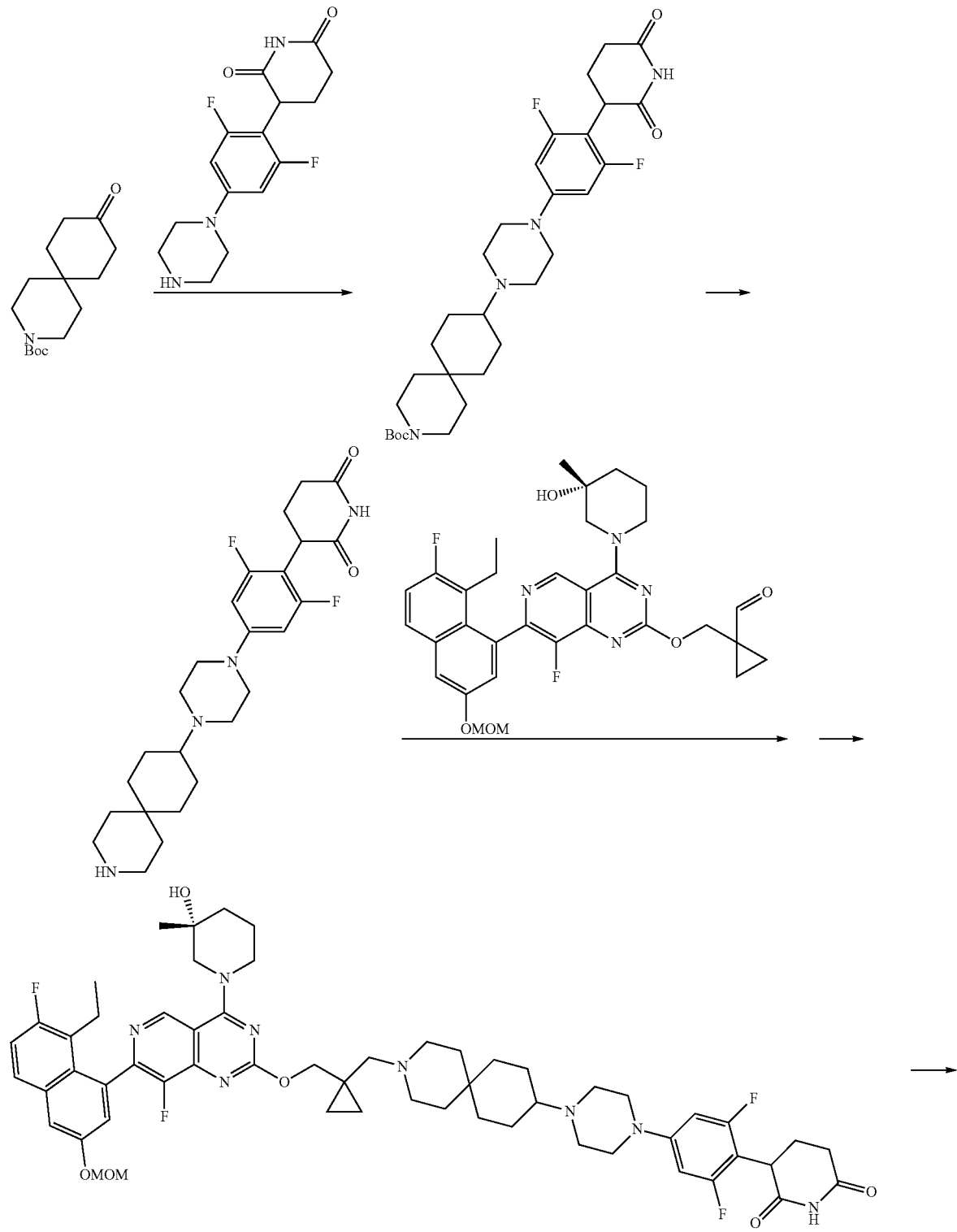

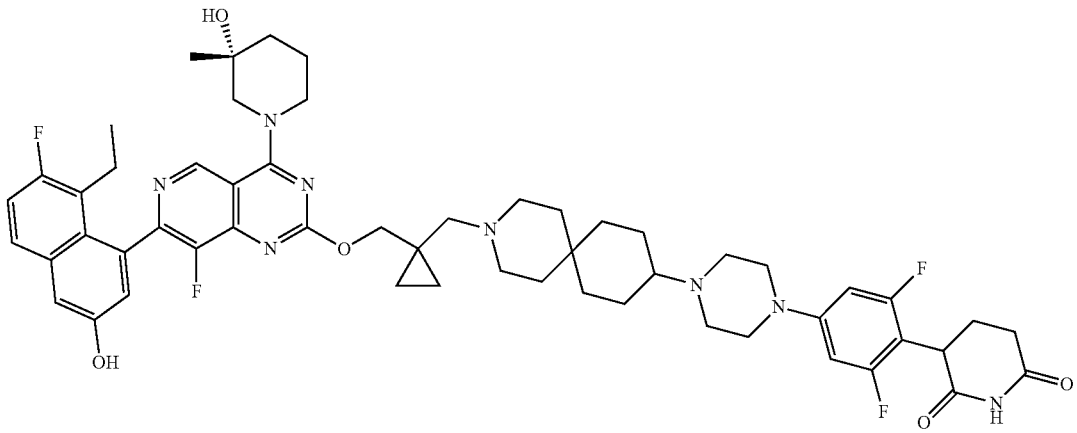

51

Step 1: Preparation of tert-butyl (9-{4-[4-(2,6-di-oxopiperidin-3-yl)-3,5-difluorophenyl]piperazin-1-yl}-3-azaspiro[5.5]undecan-3-yl)formate The mixture of tert-butyl {9-oxo-3-azaspiro[5.5]undecan-3-yl}formate (200 mg, 0.74 mmol), 3-(2,6-difluoro-4-(piperazin-1-yl)phenyl)piperidine-2,6-dione (288 mg, 0.74 mmol), DIEA (289 mg, 2.23 mmol) and STAB (474 mg, 2.23 mmol) in DCM (5 mL) was stirred at 45° C. for 16 hours. The reaction was quenched with water (20 mL) and extracted with EA (20 mL×3). The organic phase was washed with brine and dried over Na₂SO₄. The solution was concentrated in vacuum and the residue was purified by Prep-TLC (PE:EA=1:3) to give the desired compound (180 mg, 42.9% yield) as a white solid. LC/MS: 561.3 [M+H]⁺.

Step 2: Preparation of 3-[4-(4-{3-azaspiro[5.5]undecan-9-yl}piperazin-1-yl)-2,6-difluorophenyl] piperidine-2,6-dione The solution of tert-butyl (9-{4-[4-(2,6-dioxopiperidin-3-yl)-3,5-difluorophenyl]piperazin-1-yl}-3-azaspiro[5.5]undecan-3-yl) formate (180 mg, 0.32 mmol) in DCM/TFA (10 ml, 1/1) was stirred at 25° C. for 2 hours. The solvent was removed in vacuum to afford the desired compound (150 mg, 96.5% yield) as a yellow solid. LC/MS: 461.3 [M+H]⁺.

Step 3: Preparation of 3-(4-{4-[3-({1-[({7-[8-ethyl-7-fluoro-3-(methoxymethoxy)naphthalen-1-yl]-8-fluoro-4-[(3R)-3-hydroxy-3-methylpiperidin-1-yl]pyrido[4,3-d]pyrimidin-2-yl}oxy)methyl]cyclopropyl}methyl)-3-azaspiro[5.5]undecan-9-yl]piperazin-1-yl}-2,6-difluorophenyl)piperidine-2,6-dione The mixture of 3-[4-(4-{3-azaspiro[5.5]undecan-9-yl}piperazin-1-yl)-2,6-difluorophenyl]piperidine-2,6-dione (150 mg, 0.32 mmol), (R)-1-(((7-(8-ethyl-7-fluoro-3-(methoxymethoxy)naphthalen-1-yl)-8-fluoro-4-(3-hydroxy-3-methylpiperidin-1-yl)pyrido[4,3-d]pyrimidin-2-yl)oxy) methyl)cyclopropane-1-carbaldehyde (96 mg, 0.16 mmol), DIEA (126.3 mg, 0.97 mmol) and STAB (207 mg, 0.98 mmol) in DMA (1 mL) was stirred at room temperature for 16 hours. The reaction mixture was poured into water (10 mL) and extracted with DCM (10 mL×3). The combined organic layer was dried over Na₂SO₄ and concentrated in vacuum. The residue was purified by Prep-TLC (DCM:MeOH=10:1) to give the desired compound (60 mg, 17.7% yield) as a white solid. LC/MS: 1037.5 [M+H]⁺.

Step 4: Preparation of 3-{4-[4-(3-{[1-({[7-(8-ethyl-7-fluoro-3-hydroxynaphthalen-1-yl)-8-fluoro-4-[(3R)-3-hydroxy-3-methylpiperidin-1-yl]pyrido[4,3-d]pyrimidin-2-yl]oxy}methyl)cyclopropyl] methyl}-3-azaspiro[5.5]undecan-9-yl)piperazin-1-yl]-2,6-difluorophenyl}piperidine-2,6-dione (Compound 51)

The solution of 3-(4-{4-[3-({1-[({7-[8-ethyl-7-fluoro-3-(methoxymethoxy)naphthalen-1-yl]-8-fluoro-4-[(3R)-3-hydroxy-3-methylpiperidin-1-yl]pyrido[4,3-d]pyrimidin-2-yl}oxy)methyl] cyclopropyl}methyl)-3-azaspiro[5.5] undecan-9-yl]piperazin-1-yl}-2,6-difluorophenyl) piperidine-2,6-dione (60 mg, 0.06 mmol) in HCl-dioxane (4 M)/THF (4 mL, 1:1) was stirred at room temperature for 1 hour. The mixture was concentrated in vacuum to give a crude product. The crude product was purified by Prep-HPLC (0.1% FA in H₂O/ACN=12~30%) to give the desired product (23.7 mg, 39.2%). LC/MS: 993.3 [M+H]⁺; ¹H NMR (400 MHz, DMSO) δ 10.86 (s, 1H), 9.94 (brs, 1H), 9.22 (s, 1H), 7.76 (dd, J=9.0, 6.1 Hz, 1H), 7.37-7.30 (m, 2H), 7.02 (d, J=2.4 Hz, 1H), 6.61 (d, J=12.7 Hz, 2H), 4.73 (s, 1H), 4.38-4.25 (m, 3H), 4.09-4.00 (m, 2H), 3.63 (d, J=13.2 Hz, 1H), 3.53 (d, J=13.3 Hz, 1H), 3.15 (s, 4H), 2.88-2.69 (m, 2H), 2.58 (s, 5H), 2.39-2.28 (m, 2H), 2.25-1.92 (m, 6H), 1.78-1.52 (m, 8H), 1.47 (s, 2H), 1.38-1.22 (m, 6H), 1.17 (d, J=9.8 Hz, 3H), 1.03 (t, J=24 Hz, 2H), 0.77-0.66 (m, 5H), 0.47 (s, 2H).

Example 21: Preparation of 3-(4-(2-(9-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl) cyclopropyl) methyl)-3,9-diazaspiro[5.5]undecan-3-yl)ethyl)-2,6-difluorophenyl) piperidine-2,6-dione (Compound 56)
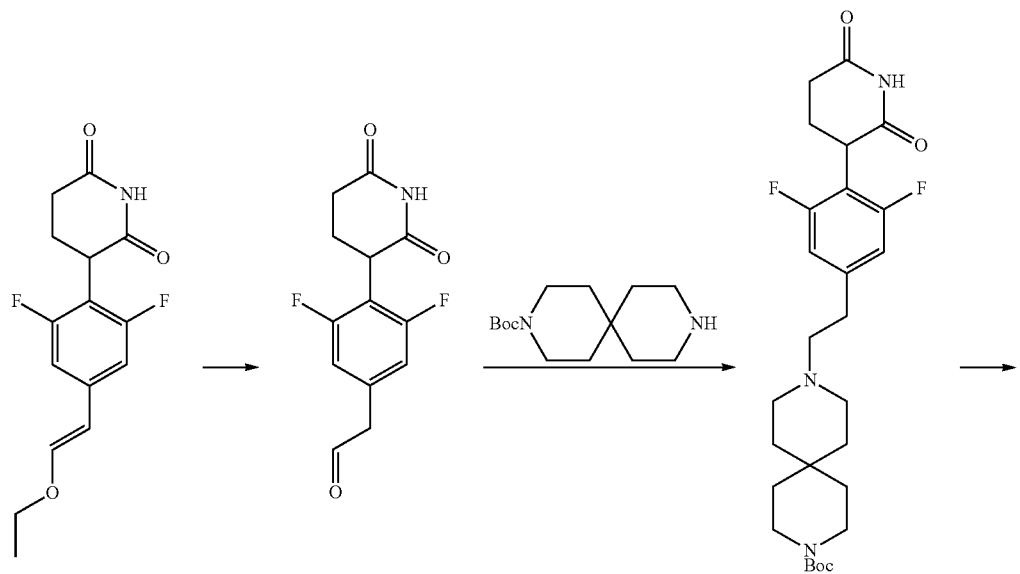
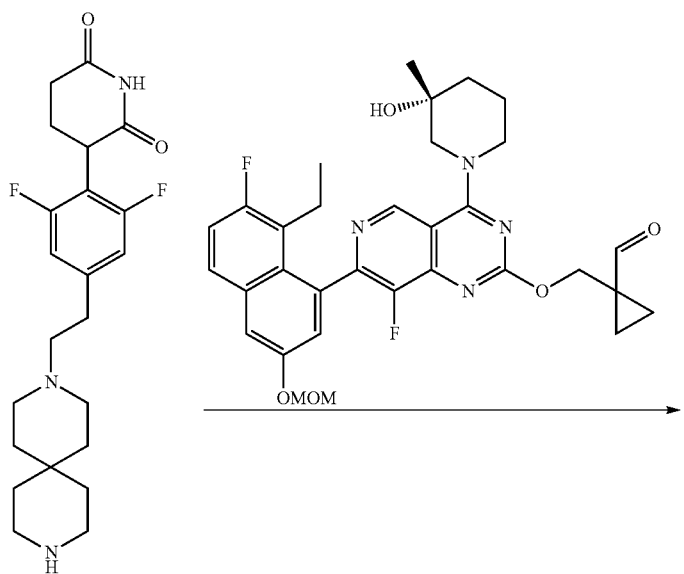

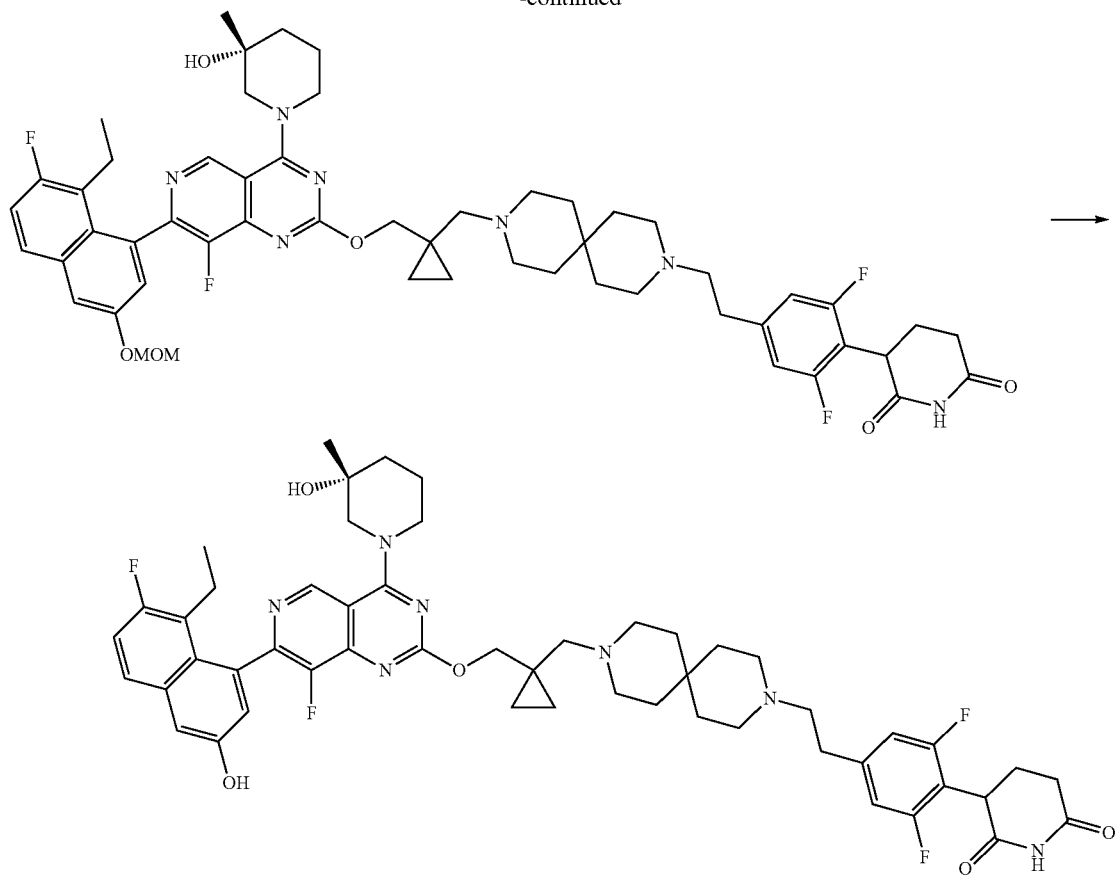

56

Step 1: Preparation of 2-(4-(2,6-dioxopiperidin-3-yl)-3,5-difluorophenyl) acetaldehyde A solution of (E)-3-(4-(2-ethoxyvinyl)-2,6-difluorophenyl)piperidine-2,6-dione (600 mg, 2.033 mmol) in formic acid (4 mL) was stirred in air at room temperature for 2 hours. The mixture was concentrated in vacuum and the residue was purified by Prep-HPLC (ACN-H₂O (0.1% FA) 20-35%) to give the desired product (380 mg, 69.9% yield) as a yellow solid. LC/MS: 268.1 [M+H]⁺.

Step 2: Preparation of tert-butyl 9-(4-(2,6-dioxopiperidin-3-yl)-3,5-difluorophenethyl)-3,9-diaza spiro [5.5]undecane-3-carboxylate To a solution of 2-(4-(2,6-dioxopiperidin-3-yl)-3,5-difluorophenyl)acetaldehyde (150 mg, 0.561 mmol) and tert-butyl 3,9-diazaspiro[5.5]undecane-3-carboxylate (143 mg, 0.561 mmol) in DCM (5 mL) was added STAB (357 mg, 1.683 mmol). The reaction mixture was stirred at room temperature for 4 hours. The reaction mixture was quenched with water and extracted with DCM. The solution was concentrated in vacuum and the residue was purified by Prep-HPLC (ACN-H₂O (0.1% FA) 20-35%) to give the desired product (150 mg, 80% purity, 42.3% yield) as a white solid. LC/MS: 506.2 [M+H]⁺.

Step 3: Preparation of 3-(4-(2-(3,9-diazaspiro[5.5] undecan-3-yl)ethyl)-2,6-difluorophenyl)piperidine-2, 6-dione A solution of tert-butyl 9-(4-(2,6-dioxopiperidin-3-yl)-3, 5-difluorophenethyl)-3,9-diazaspiro[5.5] undecane-3-carboxylate (150 mg, 0.296 mmol) in HCl/dioxane (4 M, 10 mL) was stirred at 25° C. for 2 hours. The solution was concentrated in vacuum to afford the desired compound (105 mg, HCl salt, 74.5% yield) as a white solid. LC/MS: 405.9 [M+H]⁺.

Step 4: Preparation of 3-(4-(2-(9-((1-(((7-(8-ethyl-7-fluoro-3-(methoxymethoxy)naphthalen-1-yl)-8-fluoro-4-((R)-3-hydroxy-3-methylpiperidin-1-yl) pyrido[4,3-d]pyrimidin-2-yl)oxy)methyl) cyclopropyl)methyl)-3,9-diazaspiro[5.5]undecan-3-yl)ethyl)-2,6-difluorophenyl)piperidine-2,6-dione To a solution of 3-(4-(2-(3,9-diazaspiro[5.5]undecan-3-yl)ethyl)-2,6-difluorophenyl)piperidine-2,6-dione (140 mg, 0.292 mmol) and (R)-1-(((7-(8-ethyl-7-fluoro-3-(methoxymethoxy)naphthalen-1-yl)-8-fluoro-4-(3-hydroxy-3-methylpiperidin-1-yl)pyrido[4,3-d]pyrimidin-2-yl)oxy) methyl)cyclopropane-1-carbaldehyde (204 mg, 0.344 mmol) in DMA (5 mL) was added DIPEA (223 mg, 1.725 mmol) and STAB (219 mg, 1.035 mmol). The mixture was stirred at 45° C. for 16 hours. The reaction was quenched with water (20 mL) and extracted with EA (20 mL×3). The organic phase was washed with brine and dried over Na$_2$SO$_4$. The solution was concentrated in vacuum and the residue was purified by Prep-TLC (DCM:MeOH=10:1) to give the desired compound (50 mg, 17.4% yield) as a yellow solid. LC/MS: 982.4 [M+H]$^+$.

Step 5: Preparation of 3-(4-(2-(9-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy) methyl)cyclopropyl) methyl)-3,9-diazaspiro[5.5]undecan-3-yl)ethyl)-2,6-difluorophenyl)piperidine-2,6-dione (Compound 56)

A solution of 3-(4-{2-[9-({1-[({7-[8-ethyl-7-fluoro-3-(methoxymethoxy)naphthalen-1-yl]-8-fluoro-4-[(3R)-3-hydroxy-3-methylpiperidin-1-yl]pyrido[4,3-d]pyrimidin-2-yl}oxy)methyl]cyclopropyl}methyl)-3,9-diazaspiro[5.5]undecan-3-yl]ethyl}-2,6-difluorophenyl)piperidine-2,6-dione (45 mg, 0.045 mmol) in DCM (3 mL) and TFA (1 mL) was stirred at room temperature for 1 hour. The mixture was concentrated in vacuum and the residue was purified by Prep-HPLC (Gemini-C18:150×21.2 mm, 5 μm. ACN-H$_2$O (0.1% FA) 23-23%) to give the desired product (22.5 mg, 98.1% purity in 214 nm, 49.7% yield) as a white solid. LC/MS: 938.4 [M+H]$^+$; $^1$H NMR (400 MHZ, DMSO) & 10.95 (s, 1H), 9.96 (s, 1H), 9.96 (brs, 1H), 9.23 (s, 1H), 8.14 (s, 1H), 7.76 (dd, J=9.1, 6.0 Hz, 1H), 7.38-7.32 (m, 2H), 7.05-7.01 (m, 3H), 4.72 (s, 1H), 4.38-4.28 (m, 3H), 4.20 (dd, J=12.7, 5.2 Hz, 1H), 4.10-4.01 (m, 1H), 3.66-3.51 (m, 3H), 2.87-2.78 (m, 6H), 2.70-2.58 (m, 6H), 2.35-2.30 (m, 1H), 2.18-2.09 (m, 2H), 2.03-1.96 (m, 2H), 1.77-1.61 (m, 4H), 1.50 (s, 8H), 1.26-1.11 (m, 4H), 0.87-0.62 (m, 6H), 0.55 (s, 2H).

Example 22: Preparation of (S)-3-(5-(4-((7-((1-(((7-(8-ethyl-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione (Compound 87)

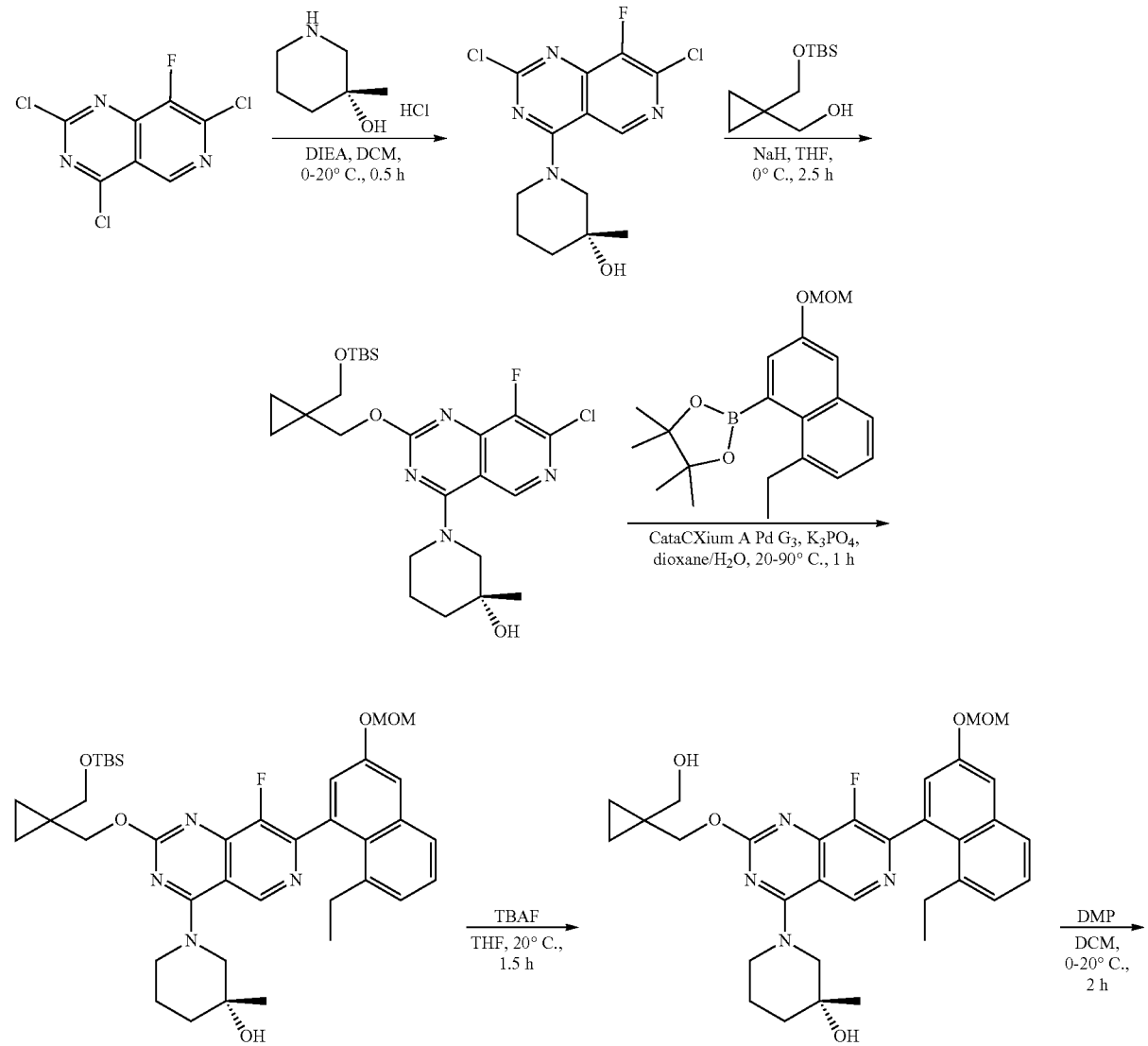

-continued
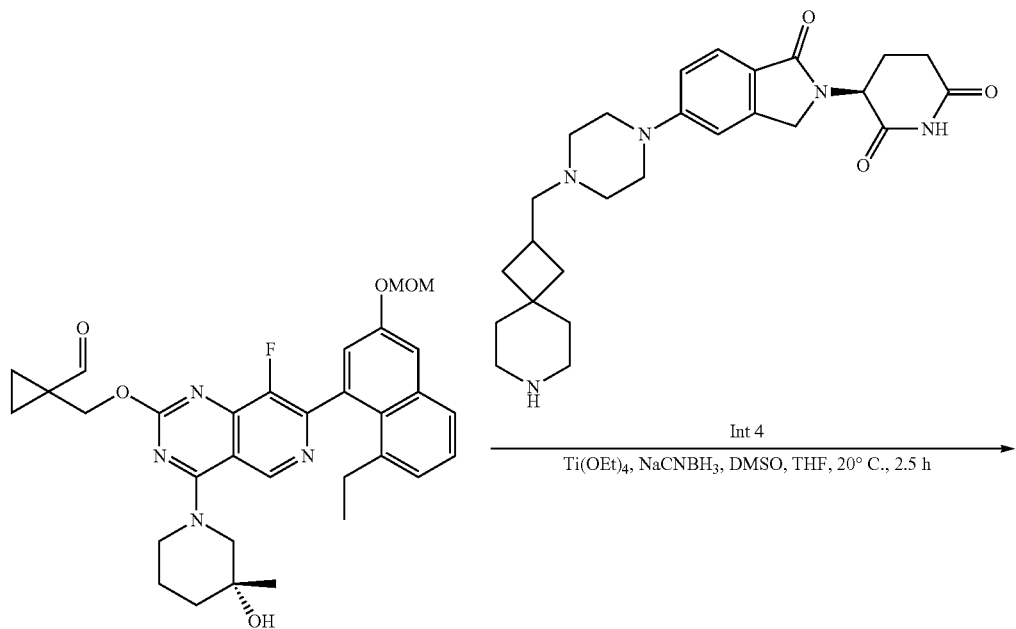
Int 4
Ti(OEt)₄, NaCNBH₃, DMSO, THF, 20° C., 2.5 h
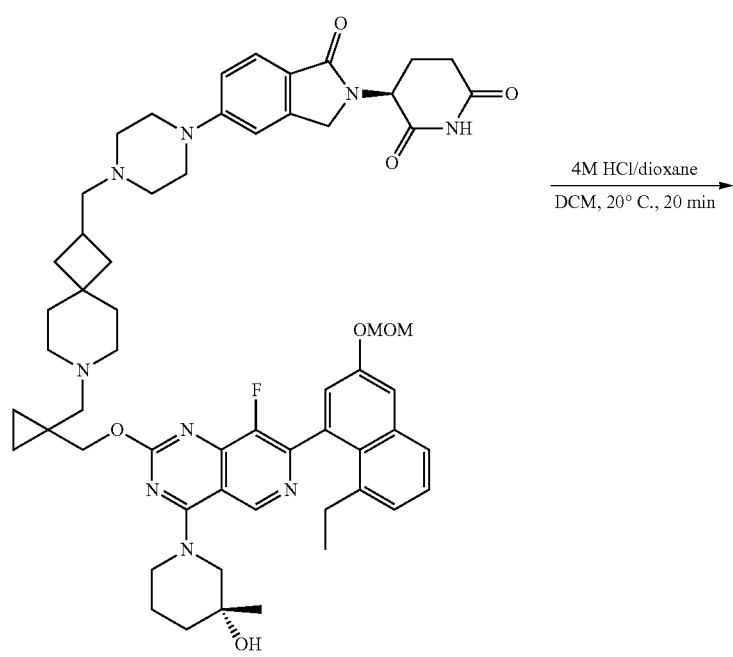
4M HCl/dioxane
DCM, 20° C., 20 min

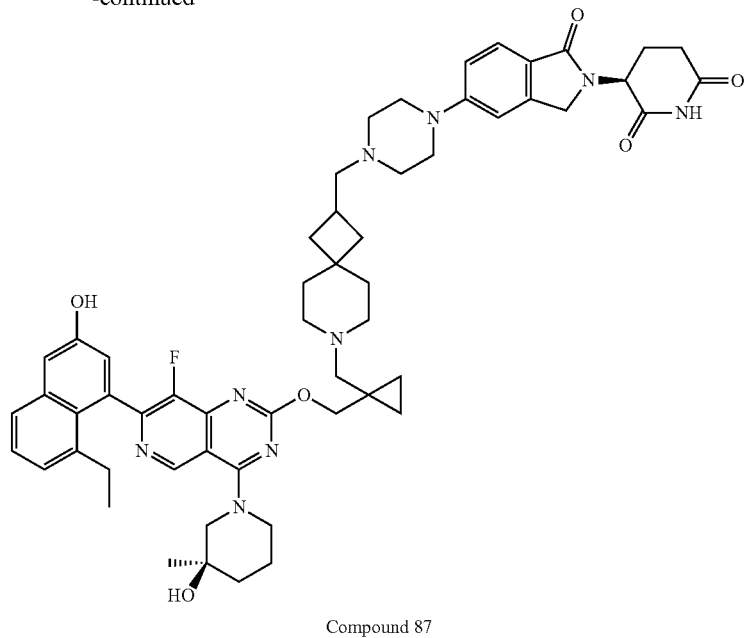

Compound 87

Step 1: Preparation of (R)-1-(2,7-dichloro-8-fluoro-pyrido[4,3-d]pyrimidin-4-yl)-3-methylpiperidin-3-ol To a solution of 2,4,7-trichloro-8-fluoro-pyrido[4,3-d]pyrimidine (15 g, 59.4 mmol, 1 eq) and (3R)-3-methylpiperidin-3-ol (9.01 g, 59.4 mmol, 1 eq, HCl) in DCM (200 mL) was added DIEA (23.0 g, 178 mmol, 31.0 mL, 3 eq) at 0° C. The reaction mixture was stirred for 0.5 hours at 20° C. LCMS showed complete consumption of the reactant and detection of the desired product. The reaction mixture was concentrated under reduced pressure to afford a crude residue, which was purified by column chromatography (SiO$_2$, Petroleum ether/Ethyl acetate=1/0 to 0/1) to give (R)-1-(2,7-dichloro-8-fluoropyrido[4,3-d]pyrimidin-4-yl)-3-methylpiperidin-3-ol (15 g, 45.2 mmol, 76.2% yield) as a yellow solid. $^1$H NMR (400 MHZ, DMSO-d$_6$) δ=9.17 (s, 1H), 4.74 (s, 1H), 4.46 (d, J=12.4 Hz, 1H), 4.10 (d, J=13.6 Hz, 1H), 3.55 (d, J=13.6 Hz, 1H), 3.32-3.23 (m, 1H), 2.02-1.89 (m, 1H), 1.72-1.60 (m, 3H), 1.16 (s, 3H).

Step 2: Preparation of (R)-1-(2-((1-(((tert-butyldimethylsilyl)oxy)methyl)cyclopropyl)methoxy)-7-chloro-8-fluoropyrido[4,3-d]pyrimidin-4-yl)-3-methylpiperidin-3-ol To a solution of [1-[[tert-butyl(dimethyl)silyl]oxymethyl]cyclopropyl]methanol (3.27 g, 15.1 mmol, 1 eq) in THF (50 mL) was added NaH (724 mg, 18.1 mmol, 60% purity, 1.2 eq) at 0° C. and the reaction mixture was stirred for 0.5 hours. Then (3R)-1-(2,7-dichloro-8-fluoro-pyrido[4,3-d]pyrimidin-4-yl)-3-methyl-piperidin-3-ol (5 g, 15.1 mmol, 1 eq) was added at 0° C. The mixture was stirred for 2 hours at 0° C. LCMS showed complete consumption of the reactant and detection of the desired product. The reaction mixture was quenched with saturated NH$_4$Cl (500 mL) at 0° C. and extracted with EA (150 mL*2). The combined organic layers were washed with brine (100 mL), dried over anhydrous Na$_2$SO$_4$, filtered and concentrated under reduced pressure to give a crude residue, which was purified by column chromatography (SiO$_2$, Petroleum ether/Ethyl acetate=1/0 to 1/1) to afford (R)-1-(2-((1-(((tert-butyldimethylsilyl)oxy)methyl)cyclopropyl)methoxy)-7-chloro-8-fluoropyrido[4,3-d]pyrimidin-4-yl)-3-methylpiperidin-3-ol (19 g, 37.1 mmol, 82.0% yield) as a yellow oil. $^1$H NMR (400 MHZ, DMSO-d$_6$) δ=9.00 (s, 1H), 4.62 (s, 1H), 4.37-4.20 (m, 3H), 3.99-3.94 (m, 1H), 3.59-3.51 (m, 3H), 3.30-3.21 (m, 1H), 1.96-1.88 (m, 1H), 1.71-1.53 (m, 3H), 1.12 (s, 3H), 0.81 (s, 9H), 0.62-0.57 (m, 2H), 0.54-0.49 (m, 2H), 0.02 (s, 6H).

Step 3: Preparation of (R)-1-(2-((1-(((tert-butyldimethylsilyl)oxy)methyl)cyclopropyl)methoxy)-7-(8-ethyl-3-(methoxymethoxy)naphthalen-1-yl)-8-fluoropyrido[4,3-d]pyrimidin-4-yl)-3-methylpiperidin-3-ol To a solution of (3R)-1-[2-[[1-[[tert-butyl(dimethyl)silyl]oxymethyl]cyclopropyl]methoxy]-7-chloro-8-fluoro-pyrido[4,3-d]pyrimidin-4-yl]-3-methyl-piperidin-3-ol (3 g, 5.87 mmol, 1 eq) and 2-[8-ethyl-3-(methoxymethoxy)-1-naphthyl]-4,4,5,5-tetramethyl-1,3,2-dioxaborolane (2.21 g, 6.46 mmol, 1.1 eq) in dioxane (60 mL) and H$_2$O (6 mL) was added K$_3$PO$_4$ (3.74 g, 17.6 mmol, 3 eq) and [2-(2-aminophenyl)phenyl]palladium(1+); bis(1-adamantyl)-butylphosphane; methanesulfonate (854 mg, 1.17 mmol, 0.2 eq) at 20° C. under N$_2$ atmosphere. The mixture was stirred for 1 hour at 90° C. under N$_2$ atmosphere. LCMS showed detection of desired product. The mixture was concentrated to get a residue under reduced pressure. The residue was purified by column chromatography (SiO$_2$, Petroleum ether/Ethyl acetate=1/0 to 0/1) to give (R)-1-(2-((1-(((tert-butyldimethylsilyl)oxy)methyl)cyclopropyl)methoxy)-7-(8-ethyl-3-(methoxymethoxy)naphthalen-1-yl)-8-fluoropyrido[4,3-d]pyrimidin-4-yl)-3-methylpiperidin-3-ol (11 g, crude) as a yellow oil. $^1$H NMR (400 MHZ, DMSO-d$_6$) δ=9.23-9.19 (m, 1H), 7.83-7.74 (m, 1H), 7.63-7.57 (m, 1H), 7.44 (t, J=7.6 Hz, 1H), 7.26-7.21 (m, 1H), 7.18-7.15 (m, 1H), 5.39-5.30 (m, 2H), 4.80-4.67 (m, 1H), 4.44-4.19 (m, 3H), 4.01-3.98 (m, 1H), 3.94 (s, 1H), 3.68-3.48 (m, 6H), 3.43 (s, 5H), 3.40

(br s, 1H), 2.36-2.14 (m, 2H), 1.76-1.59 (m, 3H), 1.19 (s, 2H), 0.83-0.79 (m, 9H), 0.60 (br s, 2H), 0.54-0.49 (m, 2H), −0.02 (d, J=1.4 Hz, 5H).

Step 4: Preparation of (R)-1-(7-(8-ethyl-3-(methoxymethoxy)naphthalen-1-yl)-8-fluoro-2-((1-(hydroxymethyl)cyclopropyl)methoxy)pyrido[4,3-d]pyrimidin-4-yl)-3-methylpiperidin-3-ol To a solution of (3R)-1-[2-[[1-[[tert-butyl(dimethyl)silyl]oxymethyl]cyclopropyl]methoxy]-7-[8-ethyl-3-(methoxymethoxy)-1-naphthyl]-8-fluoro-pyrido[4,3-d]pyrimidin-4-yl]-3-methyl-piperidin-3-ol (10 g, 14.4 mmol, 1 eq) in THF (200 mL) was added TBAF (1 M, 43.4 mL, 3 eq) at 20° C. The mixture was stirred for 1.5 hours at 20° C. LCMS showed complete consumption of the reactant and detection of the desired product. The mixture was extracted with EA (100 mL*2) and H$_2$O (200 mL). The combined organic layers were washed with brine (100 mL*2), dried over anhydrous Na$_2$SO$_4$, filtered and concentrated under reduced pressure to give a residue. The residue was purified by column chromatography (SiO$_2$, Petroleum ether/Ethyl acetate=1/0 to 0/1) to afford (R)-1-(7-(8-ethyl-3-(methoxymethoxy)naphthalen-1-yl)-8-fluoro-2-((1-(hydroxymethyl)cyclopropyl)methoxy)pyrido[4,3-d]pyrimidin-4-yl)-3-methylpiperidin-3-ol (7.2 g, 12.4 mmol, 79.1% yield) as a yellow solid. $^1$H NMR (400 MHZ, DMSO-d$_6$) δ=9.21 (d, J=9.4 Hz, 1H), 7.79 (d, J=8.2 Hz, 1H), 7.61 (d, J=2.4 Hz, 1H), 7.45 (t, J=7.6 Hz, 1H), 7.24 (d, J=7.0 Hz, 1H), 7.17 (d, J=2.6 Hz, 1H), 5.35 (s, 2H), 4.79-4.68 (m, 1H), 4.65 (t, J=5.6 Hz, 1H), 4.41-4.22 (m, 3H), 4.14-3.96 (m, 1H), 3.67-3.47 (m, 1H), 3.43 (s, 3H), 3.41-3.36 (m, 2H), 2.35-2.15 (m, 2H), 2.00 (br s, 1H), 1.81-1.58 (m, 3H), 1.20-1.17 (m, 2H), 1.15 (s, 2H), 0.91-0.78 (m, 3H), 0.60-0.46 (m, 4H).

Step 5: Preparation of (R)-1-(((7-(8-ethyl-3-(methoxymethoxy)naphthalen-1-yl)-8-fluoro-4-(3-hydroxy-3-methylpiperidin-1-yl)pyrido[4,3-d]pyrimidin-2-yl)oxy)methyl)cyclopropane-1-carbaldehyde To a solution of (3R)-1-[7-[8-ethyl-3-(methoxymethoxy)-1-naphthyl]-8-fluoro-2-[[1-(hydroxymethyl)cyclopropyl]methoxy]pyrido[4,3-d]pyrimidin-4-yl]-3-methyl-piperidin-3-ol (7 g, 12.1 mmol, 1 eq) in DCM (100 mL) was added DMP (7.72 g, 18.2 mmol, 5.64 mL, 1.5 eq) at 0° C. The mixture was stirred for 2 hours at 20° C. LCMS showed complete consumption of the reactant and detection of the desired product. The mixture was concentrated under reduced pressure to give a crude residue, which was purified by column chromatography (SiO$_2$, Petroleum ether/Ethyl acetate=1/0 to 0/1) to afford (R)-1-(((7-(8-ethyl-3-(methoxymethoxy)naphthalen-1-yl)-8-fluoro-4-(3-hydroxy-3-methylpiperidin-1-yl)pyrido[4,3-d]pyrimidin-2-yl)oxy)methyl)cyclopropane-1-carbaldehyde (6.2 g, 10.7 mmol, 88.8% yield) as a yellow solid. $^1$H NMR (400 MHZ, DMSO-d$_6$) δ=9.23 (d, J=8.8 Hz, 1H), 8.93 (s, 1H), 7.80 (d, J=8.4 Hz, 1H), 7.61 (d, J=2.4 Hz, 1H), 7.45 (t, J=7.6 Hz, 1H), 7.28-7.22 (m, 1H), 7.20-7.13 (m, 1H), 5.35 (s, 2H), 4.78-4.65 (m, 1H), 4.57-4.51 (m, 2H), 4.39-4.25 (m, 1H), 4.13-4.06 (m, 1H), 3.64-3.47 (m, 1H), 3.45-3.41 (m, 3H), 3.37 (br s, 1H), 2.31-2.16 (m, 2H), 2.07-2.00 (m, 1H), 1.76-1.61 (m, 3H), 1.38-1.34 (m, 2H), 1.33-1.29 (m, 2H), 1.15-1.13 (m, 2H), 0.87-0.80 (m, 3H).

Step 6: Preparation of (S)-3-(5-(4-((7-((1-(((7-(8-ethyl-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione To a solution of 1-[[7-[8-ethyl-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropanecarbaldehyde (3 g, 5.22 mmol, 1 eq) and (3S)-3-[5-[4-(7-azaspiro[3.5]nonan-2-ylmethyl)piperazin-1-yl]-1-oxo-isoindolin-2-yl]piperidine-2,6-dione (3.15 g, 5.84 mmol, 1.12 eq, 2 HCl) in THF (60 mL) and DMSO (10 mL) was added Ti(OEt)$_4$ (11.9 g, 52.2 mmol, 10.8 mL, 10 eq) and the reaction mixture was stirred at 20° C. for 2 hours, Then NaBH$_3$CN (656 mg, 10.4 mmol, 2 eq) was added and the reaction mixture was stirred at 20° C. for 0.5 hours. LCMS showed complete consumption of the reactant and detection of desired product. The mixture was extracted with EA (300 mL*2) and washed with H$_2$O (200 mL). The combined organic layers were washed with brine (100 mL), dried over anhydrous Na$_2$SO$_4$, filtered and concentrated under reduced pressure to give a crude residue, which was purified by column chromatography (SiO$_2$, PE:EA=0:1 to DCM: MeOH=1:1) to give (S)-3-(5-(4-((7-((1-(((7-(8-ethyl-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione (9.2 g, 6.29 mmol, 60.2% yield, 70% purity) as a yellow solid. $^1$H NMR (400 MHZ, MeOD-d$_4$) δ=9.22 (d, J=4.4 Hz, 1H), 7.74 (br d, J=8.2 Hz, 1H), 7.64 (d, J=9.2 Hz, 1H), 7.60 (d, J=2.6 Hz, 1H), 7.43 (t, J=7.6 Hz, 1H), 7.26 (d, J=7.2 Hz, 1H), 7.21-7.18 (m, 1H), 7.12-7.05 (m, 2H), 5.33 (s, 2H), 5.12-5.03 (m, 1H), 4.70-4.51 (m, 5H), 4.46-4.27 (m, 5H), 3.67-3.54 (m, 3H), 3.52-3.49 (m, 3H), 3.45-3.40 (m, 3H), 3.35-3.35 (m, 3H), 3.35 (s, 2H), 2.95-2.70 (m, 6H), 2.51-2.25 (m, 4H), 2.19-2.08 (m, 3H), 1.91-1.73 (m, 9H), 1.29 (br d, J=11.0 Hz, 3H), 0.96 (br s, 2H), 0.94-0.88 (m, 3H), 0.86 (br s, 2H).

Step 7: Preparation of (S)-3-(5-(4-((7-((1-(((7-(8-ethyl-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione (Compound 87)

To a mixture of (3S)-3-[5-[4-[[7-[[1-[[7-[8-ethyl-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropyl]methyl]-7-azaspiro[3.5]nonan-2-yl]methyl]piperazin-1-yl]-1-oxo-isoindolin-2-yl]piperidine-2,6-dione (9 g, 8.79 mmol, 1 eq) in DCM (30 mL) was added HCl (4 M in dioxane, 30 mL, 13.6 eq) and the reaction mixture was stirred at 20° C. for 20 minutes. LCMS showed complete consumption of the reactant and detection of the desired product. The mixture was concentrated under reduced pressure to afford a crude residue, which was purified by prep-HPLC (FA Phenomenex Synergi Max-RP 250*50 mm 10 μm; mobile phase: [water (FA)-ACN]; gradient: 5%-35% B over 20 minutes) to afford (S)-3-(5-(4-((7-((1-(((7-(8-ethyl-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione (100 mg, 102 µmol, 1.16% yield) as a white solid. LCMS: [M+H]⁺=980.7 ¹H NMR (400 MHZ, MeOD-d₄) δ=9.21 (d, J=5.8 Hz, 1H), 8.46 (s, 1H), 7.68-7.61 (m, 2H), 7.37 (t, J=7.6 Hz, 1H), 7.30 (d, J=2.4 Hz, 1H), 7.19-7.15 (m, 1H), 7.11-7.06 (m, 2H), 7.01 (t, J=2.8 Hz, 1H), 5.14-5.06 (m, 1H), 4.61-4.51 (m, 1H), 4.46 (br t, J=7.2 Hz, 2H), 4.40 (d, J=5.8 Hz, 2H), 4.36-4.28 (m, 1H), 3.67-3.54 (m, 2H), 3.47-3.35 (m, 6H), 3.25-3.19 (m, 2H), 2.96-2.84 (m, 3H), 2.69 (br d, J=3.6 Hz, 4H), 2.61 (br s, 3H), 2.52-2.23 (m, 4H), 2.20-1.98 (m, 6H), 1.91-1.74 (m, 5H), 1.67-1.60 (m, 2H), 1.29 (d, J=11.4 Hz, 3H), 0.97 (s, 2H), 0.94-0.87 (m, 3H), 0.84 (s, 2H). LCMS: [M+H]⁺=980.7.

Compounds 88, 89, 90, 93, 95, 96, 97, 98, 101, 103, 109, 110, 111, 114, 115, 116, 117, 118, 119, 123, 127, 128, 129, 132, 135, 177, 178, 179, 180, and 183 were prepared via similar synthetic procedures as example 22.

| Cpd # | Characterization |
|---|---|
| 88 | LCMS: [M + H]⁺ = 997.6<br>¹H NMR (400 MHz, METHANOL-d₄) δ = 9.22 (d, J = 2.4 Hz, 1H), 8.37 (s, 2H), 7.65 (d, J = 8.8 Hz, 1H), 7.59 (dd, J = 6.0, 9.2 Hz, 1H), 7.22-7.16 (m, 2H), 7.11-7.07 (m, 2H), 6.99 (dd, J = 2.8, 4.0 Hz, 1H), 5.10 (dd, J = 5.2, 13.2 Hz, 1H), 4.65-4.53 (m, 2H), 4.53-4.28 (m, 6H), 3.68-3.55 (m, 2H), 3.44-3.34 (m, 6H), 3.25 (br s, 2H), 2.98-2.82 (m, 2H), 2.81-2.76 (m, 1H), 2.74-2.69 (m, 4H), 2.63 (br s, 3H), 2.51-2.38 (m, 2H), 2.15 (dtd, J = 2.8, 5.2, 10.4 Hz, 4H), 1.93-1.72 (m, 6H), 1.69-1.58 (m, 2H), 1.29 (d, J = 9.2 Hz, 4H), 0.98 (s, 2H), 0.83 (br s, 2H), 0.83-0.76 (m, 3H). |
| 89 | LCMS: [M + H]⁺ = 957.6<br>¹H NMR (400 MHz, METHANOL-d₄) δ = 9.23 (d, J = 2.4 Hz, 1H), 7.65 (d, J = 9.6 Hz, 1H), 7.59 (dd, J = 6.0, 8.8 Hz, 1H), 7.21-7.15 (m, 2H), 7.11-7.05 (m, 2H), 7.02-6.98 (m, 1H), 5.11 (dd, J = 5.2, 13.6 Hz, 1H), 4.54-4.55 (m, 1H), 4.54-4.45 (m, 2H), 4.45-4.36 (m, 2H), 4.36-4.29 (m, 1H), 3.96-3.80 (m, 2H), 3.67-3.56 (m, 1H), 3.46-3.33 (m, 6H), 3.08-2.96 (m, 2H), 2.88 (dd, J = 5.2, 13.2 Hz, 1H), 2.81-2.75 (m, 4H), 2.46 (dq, J = 4.8, 13.2 Hz, 4H), 2.20-2.10 (m, 5H), 2.07-1.74 (m, 5H), 1.71-1.53 (m, 2H), 1.30 (d, J = 8.8 Hz, 4H), 1.03-0.98 (m, 2H), 0.87 (s, 2H), 0.80 (q, J = 7.2 Hz, 3H). |
| 90 | LCMS: [M + H]⁺ = 1009.9<br>¹H NMR (400 MHz, MeOD) δ = 9.30-9.18 (m, 1H), 7.73-7.60 (m, 2H), 7.31 (d, J = 2.8 Hz, 1H), 7.29-7.22 (m, 1H), 7.11-7.02 (m, 3H), 5.14-5.06 (m, 1H), 4.98 (br d, J = 12.4 Hz, 1H), 4.75 (br d, J = 14.4 Hz, 1H), 4.67-4.48 (m, 2H), 4.43-4.29 (m, 4H), 3.85-3.74 (m, 1H), 3.53-3.41 (m, 2H), 3.38 (br s, 4H), 3.24 (br t, J = 9.6 Hz, 2H), 2.92-2.85 (m, 1H), 2.82-2.78 (m, 1H), 2.77-2.73 (m, 1H), 2.70 (br s, 4H), 2.62 (br s, 3H), 2.52-2.37 (m, 3H), 2.31-2.08 (m, 6H), 2.05-1.77 (m, 6H), 1.63 (br s, 2H), 1.44-1.36 (m, 1H), 1,29 (br s, 1H), 0.97 (br s, 2H), 0.89-0.70 (m, 5H). |
| 93 | LCMS: [M + H]⁺ = 957.5<br>¹H NMR (400 MHz, METHANOL-d₄) δ ppm 0.80 (br t, J = 7.27 Hz, 5H), 0.96 (br s, 2 H), 1.30 (br s, 1H), 1.58-1.65 (m, 2H), 1.84 (br s, 2H), 1.93-2.02 (m, 2H), 2.08-2.22 (m, 4H), 2.29 (br d, J = 5.38 Hz, 2H), 2.42-2.51 (m, 2H), 2.58 (br s, 3H), 2.55-2.69 (m, 4H), 2.74-2.81 (m, 1H), 2.84-2.97 (m, 2H), 3.11-3.24 (m, 3H), 3.25-3.29 (m, 2H), 3.36 (br s, 4H), 3.60 (br s, 1H), 3.57 (dt, J = 5.32, 2.23 Hz, 1H), 4.30-4.36 (m, 2H), 4.40 (d, J = 6.24 Hz, 2H), 4.45 (s, 1H), 4.46-4.47 (m, 1H), 4.48 (s, 1H), 4.59 (d, J = 3.55 Hz, 1H), 4.60-4.68 (m, 1H), 4.61-4.69 (m, 1H), 4.65 (br d, J = 12.84 Hz, 1H), 5.10 (dd, J = 13.33, 5.14 Hz, 1H), 7.05-7.10 (m, 3H), 7.23-7.33 (m, 2H), 7.61-7.73 (m, 1H), 8.47-8.53 (m, 1H), 9.26-9.35 (m, 1H). |
| 95 | LCMS: [M + H]⁺ = 997.5<br>¹H NMR (400 MHz, METHANOL-d₄) δ ppm 0.73 (br s, 2H), 0.80 (t, J = 7.46 Hz, 3H), 0.91 (br s, 2H), 1.30 (br s, 1H), 1.41-1.54 (m, 2H), 1.76-1.87 (m, 1H), 1.93-2.03 (m, 2H), 2.11-2.25 (m, 3H), 2.29 (br d, J = 6.48 Hz, 4H), 2.39-2.52 (m, 3H), 2.55-2.62 (m, 5H), 2.72-2.83 (m, 1H), 2.77-2.77 (m, 1H), 2.90 (ddd, J = 18.03, 13.20, 5.32 Hz, 2H), 3.27 (br d, J = 2.32 Hz, 3H), 3.34-3.36 (m, 1H), 3.46-3.62 (m, 2H), 4.29-4.35 (m, 2H), 4.39 (d, J = 5.99 Hz, 2H), 4.49 (br d, J = 3.30 Hz, 2H), 4.52-4.61 (m, 1H), 4.54 (s, 1H), 4.61-4.69 (m, 1H), 5.10 (dd, J = 13.39, 5.07 Hz, 1H), 7.03-7.09 (m, 3H) 7.22-7.29 (m, 1H), 7.29-7.35 (m, 1H), 7.61-7.65 (m, 1H), 7.65-7.72 (m, 1H), 8.50-8.57 (m, 1H), 9.27-9.32 (m, 1H). |
| 96 | LCMS: [M + H]⁺ = 970.5<br>¹H NMR (400 MHz, METHANOL-d₄) δ = 9.30-9.21 (m, 1H), 7.68 (dd, J = 6.0, 9.2 Hz, 1H), 7.64 (d, J = 8.8 Hz, 1H), 7.31 (d, J = 2.4 Hz, 1H), 7.28-7.21 (m, 1H), 7.10-7.02 (m, 3H), 5.10 (dd, J = 5.2, 13.2 Hz, 1H), 4.96 (br s, 2H), 4.81 (br d, J = 13.6 Hz, 2H), 4.55 (br d, J = 12.0 Hz, 1H), 4.46-4.31 (m, 4H), 3.96-3.72 (m, 3H), 3.54-3.44 (m, 1H), 3.33 (br s, 4H), 3.10-2.93 (m, 2H), 2.92-2.85 (m, 1H), 2.82-2.74 (m, 1H), 2.63 (br s, 4H), 2.51-2.43 (m, 2H), 2.42-2.30 (m, 3H), 2.30-2.15 (m, 4H), 2.14-2.06 (m, 2H), 2.00-1.90 (m, 2H), 1.82 (br d, J = 11,6 Hz, 1H), 1,69-1.51 (m, 2H), 1.45-1.33 (m, 1H), 0.99 (s, 2H), 0.86 (s, 2H), 0.83-0.76 (m, 3H). |
| 97 | LCMS: [M + H]⁺ = 1025.0<br>¹H NMR (400 MHz, METHANOL-d₄) δ ppm 0.81 (br t, J = 6.17 Hz, 5H), 0.95 (br s, 2 H), 1.22-1.35 (m, 2H), 1.56-1.66 (m, 2H), 1.66-1.77 (m, 2H), 1.78-1.88 (m, 6H), 2.00-2.26 (m, 7H), 2.31 (br d, J = 4.28 Hz, 1H), 2.46 (br dd, J = 13.08, 4.77 Hz, 2H), 2.53-2.68 (m, 7H), 2.71-2.83 (m, 1H), 2.75 (br s, 1H), 2.88 (br dd, J = 13.27, 5.20 Hz, 2H), 3.35 (br d, J = 4.65 Hz, 3H), 3.84-4.16 (m, 5H), 4.18-4.36 (m, 1H), 4.37-4.52 (m, 4H), 4.65 (s, 1H), 5.11 (dd, J = 13.39, 5.07 Hz, 1H), 7.02-7.11 (m, 3H), 7.24-7.36 (m, 2H), 7.61-7.72 (m, 2H), 8.48-8.55 (m, 1H), 9.06-9.10 (m, 1H). |
| 98 | LCMS: [M + H]⁺ = 984.8<br>¹H NMR (400 MHz, METHANOL-d₄) δ ppm 0.77-0.84 (m, 3H), 0.88 (br s, 2H), 0.95-1.03 (m, 2H), 1.57-1.89 (m, 9H), 1.99-2.35 (m, 8H), 2.39-2.56 (m, 4H), 2.78 (br d, J = 5.75 Hz, 5H), 2.84-3.08 (m, 3H), 3.37-3.48 (m, 4H), 3.77-4.15 (m, 6H), 4.22- |

| Cpd # | Characterization |
|---|---|
| | 4.33 (m, 1H), 4.34-4.42 (m, 2H), 4.44-4.54 (m, 2H), 5.11 (dd, J = 13.33, 5.14 Hz, 1 H), 7.07 (br d, J = 5.75 Hz, 3H), 7.22-7.37 (m, 2H), 7.43-7.49 (m, 1H), 7.62-7.71 (m, 2H), 8.43 (s, 1H), 9.07-9.12 (m, 1H). |
| 101 | LCMS: [M + H]$^+$ = 992.5<br>$^1$H NMR (400 MHz, METHANOL-d$_4$) δ = 9.24 (d, J = 12.8 Hz, 1H), 8.41 (br s, 1H), 7.68-7.61 (m, 2H), 7.40-7.33 (m, 1H), 7.29 (d, J = 2.4 Hz, 1H), 7.16 (d, J = 7.6 Hz, 1H), 7.12-7.06 (m, 2H), 7.01 (dd, J = 2.8, 15.6 Hz, 1H), 5.10 (dd, J = 5.2, 13.2 Hz, 1H), 4.78 (br d, J = 12.4 Hz, 3H), 4.53-4.48 (m, 1H), 4.42-4.31 (m, 4H), 3.81 (br d, J = 14.8 Hz, 1H), 3.54-3.38 (m, 6H), 3.25 (br s, 2H), 2.95-2.81 (m, 2H), 2.80-2.69 (m, 5H), 2.66 (br s, 3H), 2.53-2.29 (m, 4H), 2.29-2.20 (m, 3H), 2.19-2.02 (m, 4H), 1.99-1.74 (m, 5H), 1.69-1.58 (m, 2H), 1.43-1.35 (m, 1H), 0.97 (br s, 2H), 0.92-0.83 (m, 5H). |
| 103 | LCMS: [M + H]$^+$ = 987.9<br>$^1$H NMR (400 MHz, METHANOL-d$_4$) δ = 9.25-9.20 (m, 1H), 8.37 (br s, 1H), 7.67-7.60 (m, 2H), 7.41 (br d, J = 8.0 Hz, 1H), 7.34 (s, 1H), 7.25 (br d, J = 12.0 Hz, 1H), 7.13-7.06 (m, 2H), 5.14-5.05 (m, 1H), 4.82-4.75 (m, 1H), 4.61-4.44 (m, 3H), 3.67-3.59 (m, 1H), 3.43 (br s, 5H), 3.27-3.24 (m, 2H), 2.91-2.74 (m, 8H), 2.49-2.41 (m, 1H), 2.21-1.60 (m, 14H) 1.29 (d, J = 2.8 Hz, 3H), 0.98 (br s, 2H), 0.85 (br s, 2H). |
| 109 | LCMS: [M + H]$^+$ = 966.5<br>$^1$H NMR (400 MHz, MeOD-d$_4$) δ = 9.16 (s, 1H), 8.48 (s, 1H), 7.64 (d, J = 8.4 Hz, 2H), 7.40-7.34 (m, 1H), 7.30 (d, J = 2.8 Hz, 1H), 7.17 (d, J = 7.2 Hz, 1H), 7.11-7.06 (m, 2H), 7.01 (d, J = 2.6 Hz, 1H), 5.12 (br d, J = 5.2 Hz, 1H), 4.59 (br s, 3H), 4.46 (d, J = 8.0 Hz, 2H), 4.43-4.38 (m, 2H), 4.32-4.21 (m, 4H), 4.09-4.02 (m, 2H), 3.90-3.83 (m, 2H), 3.36 (br d, J = 5.0 Hz, 6H), 3.21-3.16 (m, 2H), 2.92-2.85 (m, 1H), 2.80 (br d, J = 2.1 Hz, 1H), 2.66 (br d, J = 4.4 Hz, 4H), 2.60-2.54 (m, 3H), 2.51-2.43 (m, 1H), 2.37-2.25 (m, 2H), 2.23-2.15 (m, 3H), 2.13 (br s, 2H), 2.01-1.97 (m, 1H), 1.85 (br d, J = 4.8 Hz, 2H), 1.63 (br d, J = 8.8 Hz, 2H), 0.95 (s, 2H), 0.90 (t, J = 7.6 Hz, 3H), 0.85-0.81 (m, 2H). |
| 110 | LCMS: [M + H]$^+$ = 926.4<br>$^1$H NMR (400 MHz, MeOD-d$_4$) δ = 9.17 (s, 1H), 8.30 (s, 1H), 7.64 (dd, J = 2.8, 8.4 Hz, 1H), 7.37 (t, J = 7.6 Hz, 1H), 7.31 (d, J = 2.8 Hz, 1H), 7.17 (d, J = 7.2 Hz, 1H), 7.08-7.01 (m, 1H), 5.10 (dd, J = 5.2, 13.2 Hz, 1H), 4.53-4.44 (m, 1H), 4.41-4.34 (m, 1H), 4.32-4.23 (m, 1H), 4.09-4.00 (m, 1H), 3.93-3.83 (m, 1H), 3.80 (br s, 1H), 3.28 (br s, 1H), 3.10-2.92 (m, 1H), 2.88 (br d, J = 5.2, 13.2 Hz, 1H), 2.83-2.73 (m, 1H), 2.58 (br s, 1H), 2.46 (br dd, J = 4.8, 13.2 Hz, 1H), 2.42-2.05 (m, 1H), 1.95 (br d, J = 2.1 Hz, 1H), 1.59 (br d, J = 12.4 Hz, 1H), 1.02-0.95 (m, 2H), 0.94-0.82 (m, 5H). |
| 111 | LCMS: [M + H]$^+$ = 948.5<br>$^1$H NMR (400 MHz, METHANOL-d$_4$) δ = 9.30-9.22 (m, 1H), 8.50 (s, 1H), 8.55-8.44 (m, 1H), 7.70-7.61 (m, 2H), 7.46-7.35 (m, 2H), 7.30-7.25 (m, 1H), 7.10-7.04 (m, 2H), 5.12 (br dd, J = 5.2, 13.2 Hz, 2H), 4.67-4.31 (m, 9H), 3.80 (br dd, J = 2.4, 5.2 Hz, 2H), 3.65 (d, J = 13.2 Hz, 1H), 3.54-3.39 (m, 2H), 3.25 (br d, J = 4.0 Hz, 2H), 2.92 (ddd, J = 5.2, 13.0, 18.0 Hz, 2H), 2.84-2.76 (m, 1H), 2.58 (br s, 4H), 2.48 (dd, J = 4.8, 12.8 Hz, 1H), 2.31 (br d, J = 6.0 Hz, 2H), 2.23-2.07 (m, 4H), 1.95-1.75 (m, 4H), 1.67-1.54 (m, 2H), 1.32 (d, J = 3.6 Hz, 3H), 1.00 (br s, 2H), 0.86 (br s, 2H). |
| 114 | LCMS: [M + H]$^+$ = 984.6<br>$^1$H NMR (400 MHz, DMSO-d$_6$) δ = 10.94 (s, 1H), 10.30-9.47 (m, 1H), 9.06 (s, 1H), 8.16 (s, 1H), 7.76 (dd, J = 6.1,9.1 Hz, 1H), 7.51 (d, J = 9.0 Hz, 1H), 7.39-7.29 (m, 2H), 7.08-6.98 (m, 3H), 5.04 (dd, J = 5.1, 13.3 Hz, 1H), 4.98-4.76 (m, 1H), 4.35-4.27 (m, 3H), 4.21 (s, 3H), 3.88 (br dd, J = 3.6, 7.5 Hz, 1H), 3.73-3.63 (m, 3H), 3.25 (br d, J =3.4 Hz, 4H), 2.98-2.82 (m, 2H), 2.46 (br d, J = 3.8 Hz, 4H), 2.40-2.34 (m, 5H), 2.31-2.25 (m, 3H), 2.14 (dt, J =2.4, 7.3 Hz, 2H), 1.99-1.91 (m, 3H), 1.84 (br t, J = 9.2 Hz, 2H), 1,68-1.46 (m, 5H), 1.43-1.30 (m, 4H), 0.73 (t, J =7.4 Hz, 3H), 0.64 (br s, 2H), 0.40 (br s, 2H). |
| 115 | LCMS: [M + H]$^+$ = 944.6<br>H NMR (400 MHz, DMSO-d$_6$) δ = 10.94 (s, 1H), 9.96 (s, 1H), 9.10 (s, 1H), 7.77 (dd, J = 6.0 Hz, 1H), 7.52 (d, J = 8.8 Hz, 1H), 7.42-7.27 (m, 2H), 7.09-6.96 (m, 3H), 5.05 (dd, J = 5.2, 13.2 Hz, 1H), 4.92 (br d, J = 3.2 Hz, 1H), 4.39-4.29 (m, 3H), 4.28-4.19 (m, 3H), 3.90 (br d, J = 2.4 Hz, 1H), 3.75-3.66 (m, 2H), 3.27 (br s, 4H), 2.96-2.83(m, 2H), 2.72-2.51 (m, 6H), 2.44-2.26 (m, 4H), 2.25-2.01 (m, 4H), 2.00-1.93 (m, 3H), 1.92-1.49 (m, 6H), 1.46-1.17 (m, 2H), 0.80 (br s, 2H), 0.73 (br t, J = 7.4 Hz, 3H), 0.63 (br s, 2H). |
| 116 | LCMS: [M + H]$^+$ = 998.5<br>$^1$H NMR (400 MHz, DMSO-d$_6$) δ = 10.94 (s, 1H), 9.96 (s, 1H), 9.17 (s, 1H), 7.77 (dd, J = 6.0, 9.2 Hz, 1H), 7.52 (d, J = 8.8 Hz, 1H), 7.40-7.31 (m, 2H), 7.06 (m, 2H), 7.01 (d, J = 2.4 Hz, 1H), 5.04 (dd, J = 5.2, 13.2 Hz, 1H), 4.67 (br d, J = 3.2 Hz, 1H), 4.39-4.19 (m, 5H), 4.12-3.95 (m, 4H), 3.94-3.73 (m, 3H), 2.93-2.84 (m, 2H), 2.60 (br d, J = 2.4 Hz, 5H), 2.43-2.27 (m, 5H), 2.24-2.04 (m, 5H), 2.03-1.77 (m, 8H), 1.76-1.54 (m, 6H), 1.53-1.32 (m, 3H), 0.87-0.78 (m, 2H), 0.73 (brt, J = 7.2 Hz, 3H), 0.71-0.52 (m, 2H). |
| 117 | LCMS: [M + H]$^+$ = 958.4<br>$^1$H NMR (400 MHz, DMSO-d$_6$) δ = 10.97 (s, 1H), 9.98 (s, 1H), 9.19 (s, 1H), 7.80 (dd, J = 6.0, 9.2 Hz, 1H), 7.55 (d, J = 8.8 Hz, 1H), 7.43-7.33 (m, 2H), 7.13-7.00 (m, 3H), 5.08 (dd, J = 5.2, 13.2Hz, 1H), 4.70 (br s, 1H), 4.43-4.29 (m,3H), 4.28-4.18 (m, 1H), 4.13-4.00 (m, 3H), 3.94-3.80 (m, 2H), 3.29 (br s, 4H), 3.03-2.80 (m, 2H), 2.74-2.58 (m, 4H), 2.50 (br s, 4H), 2.45-2.32 (m, 3H), 2.27-2.05 (m, 6H), 2.02-1.92 (m, 2H), 1.90-1.71 (m, 4H), 1.71-1.55 (m, 2H), 1.30-1.15 (m, 2H), 0.77 (br t, J = 7.4 Hz, 5H), 0.57 (br s, 2H). |
| 118 | LCMS: [M + H]$^+$ = 953.3<br>$^1$H NMR (400 MHz, DMSO-d$_6$) δ = 10.93 (s, 1H), 9.22-9.17 (m, 1H), 9.04 (s, 1H), 8.22-8.09 (m, 1H), 7.81-7.72 (m, 1H), 7.51 (d, J = 8.8 Hz, 1H), 7.38-7.28 (m, 1H), 7.10-7.01 (m, 4H), 5,72-5.55 (m, 2H), 5.07-5.01 (m, 1H), 4.82-4.64 (m, 1H), 4.37-4.20 |

| Cpd # | Characterization |
|---|---|
| | (m, 5H), 4.11-3.95 (m, 1H), 3.88-3.83 (m, 1H), 3.61-3.55 (m, 1H), 3.25 (br s, 4H), 3.03-2.83 (m, 4H), 2.60 (br d, J = 1.6 Hz, 1H), 2.58-2.56 (m, 1H), 2.45 (br d, J = 3.2 Hz, 5H), 2.35 (br s, 2H), 2.33 (br d, J = 1.6 Hz, 1H), 2.14 (br d, J = 6.8 Hz, 2H), 1.98-1.89 (m, 3H), 1.67 (br d, J = 10.8 Hz, 4H), 1.54-1.47 (m, 1H), 1.17 (br d, J = 16.0 Hz, 3H), 1.13-1.04 (m, 2H), 0.65 (br s, 2H), 0.43 (br s, 2H). |
| 119 | LCMS: $[M + H]^+$ = 993.5<br>$^1$H NMR (400 MHz, DMSO-d$_6$) δ = 10.94 (s, 1H), 9.21-9.17 (m, 1H), 9.03 (s, 1H), 8.19-8.14 (m, 1H), 7.77 (dd, J = 6.0, 9.6 Hz, 1H), 7.51 (d, J = 8.8 Hz, 1H), 7.35-7.29 (m, 1H), 7.09-7.02 (m, 4H), 5.63 (br s, 2H), 5.06-5.00 (m, 1H), 4.80-4.68 (m, 1H), 4.34-4.17 (m, 5H), 4.11-3.93 (m, 1H), 3.88-3.84 (m, 1H), 3.60-3.56 (m, 1H), 3.26-3.24 (m, 4H), 2.94-2.86 (m, 1H), 2.63-2.59 (m, 1H), 2.55-2.54 (m, 1H), 2.47-2.45 (m, 4H), 2.37 (br d, J = 4.8 Hz, 4H), 2.34-2.28 (m, 5H), 2.04-1.91 (m, 3H), 1.88-1.83 (m, 2H), 1.75-1.65 (m, 3H), 1.59-1.53 (m, 2H), 1.46-1.41 (m, 2H), 1.38-1.33 (m, 2H), 1.18 (s, 3H), 0.66-0.61 (m, 2H), 0.41 (br s, 2H). |
| 123 | LCMS: $[M + H]^+$ = 946.5<br>$^1$H NMR (400 MHz, METHANOL-d$_4$) δ = 9.20 (d, J = 2.4 Hz, 1H), 8.53 (br s, 1H), 7.76 (dd, J = 1.6, 7.6 Hz, 1H), 7.63 (d, J = 8.4 Hz, 1H), 7.43-7.30 (m, 3H), 7.17 (t, J = 3.2 Hz, 1H), 7.10-7.02 (m, 2H), 5.10 (dd, J = 5.2, 13.2 Hz, 1H), 4.64-4.44 (m, 4H), 4.44-4.26 (m, 4H), 3.80-3.57 (m, 3H), 3.48-3.41 (m, 1H), 3.30-3.26 (m, 2H), 3.12 (br d, J = 4.4 Hz, 2H), 2.97-2.72 (m, 4H), 2.54 (br s, 4H), 2.50-2.40 (m, 1H), 2.25 (br d, J = 6.4 Hz, 2H), 2.20-2.11 (m, 2H), 2.03 (br d, J = 11.2 Hz, 2H), 1.91-1.83 (m, 2H), 1.82-1.73 (m, 2H), 1.52 (br d, J = 10.8 Hz, 2H), 1.30 (d, J = 9.6 Hz, 3H), 0.94 (br s, 2H), 0.79 (br s, 2H). |
| 127 | LCMS: $[M + H]^+$ = 939.4<br>$^1$H NMR (400 MHz, METHANOL-d$_4$) δ ppm 0.68-0.81 (m, 2H), 0.85-0.95 (m, 5H), 1.37-1.57 (m, 2H), 1.76-1.88 (m, 1H), 1.92-2.05 (m, 2H), 2.15 (ddt, J = 10.15, 5.26, 2.45, 2.45 Hz, 1H), 2.19-2.52 (m, 6H), 2.56 (br d, J = 4.40 Hz, 5H), 2.74-2.81 (m, 1H), 2.82-2.98 (m, 2H), 3.07 (brt, J = 6.17 Hz, 3H), 3.47-3.78 (m, 1H), 3.65-3.69 (m, 1H), 4.18-4.24 (m, 3H), 4.34 (s, 2H), 4.44-4.54 (m, 2H), 4.82 (br s, 4H), 5.10 (dd, J = 13.27, 5.07 Hz, 1H), 7.00-7.09 (m, 3H), 7.14-7.20 (m, 1H), 7.28-7.41 (m, 2H), 7.60-7.66 (m, 2H), 8.52-8.55 (m, 1H), 9.08 (s, 1H). |
| 128 | LCMS: $[M + H]^+$ = 979.4<br>$^1$H NMR (400 MHz, METHANOL-d$_4$) δ ppm 0.97 (s, 6H), 0.93-1.01 (m, 1H), 1.58-1.66 (m, 2H), 1.86 (br s, 2H), 1.96-2.18 (m, 5H), 2.23-2.38 (m, 2H), 2.40-2.51 (m, 1H), 2.57-2.69 (m, 6H), 2.74-2.81 (m, 1H), 2.86-2.94 (m, 1H), 3.02-3.15 (m, 3H), 3.15-3.30 (m, 5H), 3.37 (br s, 4H), 3.68 (br t, J = 4.77 Hz, 2H), 4.09-4.30 (m, 4H), 4.32-4.44 (m, 2H), 4.45-4.52 (m, 2H), 5.07-5.12 (m, 1H), 6.99-7.11 (m, 2H), 7.05-7.11 (m, 1H), 7.17 (d, J = 6.85 Hz, 1H), 7.30 (d, J = 2.57 Hz, 1H), 7.37 (t, J = 7.70 Hz, 1H), 7.64 (d. J = 8.44 Hz, 2H), 8.46-8.50 (m, 1H), 9.06-9.11 (m, 1H). |
| 129 | LCMS: $[M + H]^+$ = 986.8<br>$^1$H NMR (400 MHz, DMSO-d$_6$) δ = 10.95 (br s, 1H), 10.50-10.04 (m, 1H), 9.19 (s, 1H), 7.85 (d, J = 7.6 Hz, 1H), 7.51 (d, J = 8.8 Hz, 1H), 7.46-7.34 (m, 3H), 7.15 (d, J = 2.4 Hz, 1H), 7.08-7.01 (m, 2H), 5.05 (dd, J = 5.2, 13.2 Hz, 1H), 4.75 (br d, J = 7.6 Hz, 1H), 4.45-4.18 (m, 5H), 4.02 (br t, J = 12.4 Hz, 1H), 3.66-3.51 (m, 1H), 3.25 (br s, 4H), 2.98-2.84 (m, 1H), 2.46 (br d, J = 3.6 Hz, 4H), 2.40-2.32 (m, 6H), 2.30-2.15 (m, 5H), 1.98 (br dd, J = 5.2, 6.4Hz, 2H), 1.88-1.81 (m, 2H), 1.77-1.58 (m, 4H), 1.52 (br s, 2H), 1.42-1.32 (m, 4H), 1.18 (d, J = 11.2 Hz, 3H), 0.63 (br s, 2H), 0.39 (s, 2H). |
| 132 | LCMS: $[M + H]^+$ = 1000.5<br>$^1$H NMR (400 MHz, METHANOL-d$_4$) δ = 9.10 (d, J = 5.4 Hz, 1H), 7.68 (dd, J = 5.8, 8.8 Hz, 1H), 7.64 (d, J = 8.4 Hz, 1H), 7.31 (d, J = 2.6 Hz, 1H), 7.25 (d, J = 9.2 Hz, 1H), 7.12-7.03 (m, 3H), 5.10 (dd, J = 5.2, 13.2 Hz, 1H), 4.73-4.64 (m, 2H), 4.50 (s, 2H), 4.42-4.33 (m, 2H), 3.73-3.59 (m, 1H), 3.38-3.33 (m, 5H), 2.95-2.81 (m, 2H), 2.81-2.73 (m, 2H), 2.71-2.59 (m, 6H), 2.57 (br s, 4H), 2.47-2.35 (m, 2H), 2.25 (br s, 4H), 2.09-1.91 (m, 3H), 1.89-1.75 (m, 3H), 1.73 (br s, 2H), 1.61-1.48 (m, 3H), 1.47-1.39 (m, 3H), 0.81 (br t, J = 7.2 Hz, 5H), 0.71-0.54 (m, 2H). |
| 135 | LCMS: $[M + H]^+$ = 1003.5<br>$^1$H NMR (400 MHz, CD$_3$OD) δ = 9.15 (s, 1H), 8.53 (s, 1H), 7.64 (d, J = 8.8 Hz, 1H), 7.15-7.03 (m, 2H), 6.91 (d, J = 1.6 Hz, 1H), 6.50 (s, 1H), 5.12-5.06 (m, 1H), 4.58 (s, 2H), 4.56-4.48 (m, 1H), 4.47-4.43 (m, 1H), 4.40 (d, J = 6.0 Hz, 2H), 4.26 (d, J = 13.2 Hz, 1H), 3.66-3.54 (m, 1H), 3.46-3.34 (m, 5H), 3.07-2.71 (m, 6H), 2.67-2.58 (m, 5H), 2.58-2.37 (m, 4H), 2.22-2.05 (m, 4H), 2.01-1.83 (m, 3H), 1.82-1.69 (m, 4H), 1.65-1.55 (m, 2H), 1.28 (s, 3H), 0.90 (s, 2H), 0.75 (br s, 2H). |
| 177 | LCMS: $[M + H]^+$ = 1006.5<br>$^1$H NMR (400 MHz, DMSO-d$_6$) δ = 10.94 (s, 1H), 9.22 (s, 1H), 8.18 (d, J = 2.4 Hz, 1H), 7.77-7.70 (m, 1H), 7.61-7.48 (m, 2H), 7.39 (s, 1H), 7.28-7.23 (m, 1H), 7.06-7.00 (m, 2H), 5.08-5.01 (m, 1H), 4.81-4.65 (m, 1H), 4.39-4.16 (m, 6H), 4.05 (br d, J = 13.4 Hz, 1H), 3.62-3.55 (m, 2H), 3.38-3.34 (m, 3H), 3.10-2.97 (m, 5H), 2.92-2.85 (m, 1H), 2.57 (br d, J = 4.0 Hz, 6H), 2.46-2.42 (m, 1H), 2.40-2.30 (m, 1H), 2.04-1.92 (m, 2H), 1.80-1.56 (m, 10H), 1.54-1.39 (m, 2H), 1.17 (br d, J = 4.8 Hz, 3H), 0.55 (br s, 2H), 0.51-0.44 (m, 2H). |
| 178 | LCMS: $[M + H]^+$ = 1016.6<br>$^1$H NMR(400 MHz, METHANOL-d$_4$) δ = 9.25-9.22 (m, 1H), 8.50 (s, 1H), 7.70-7.63 (m, 2H), 7.33-7.21 (m, 2H), 7.08-6.99 (m, 3H), 5.16-5.03 (m, 2H), 4.57-4.53 (m, 1H) 4.42-4.30 (m, 5H), 4.23-4.11 (m, 2H), 4.04-3.93 (m, 2H), 3.67-3.58 (m, 1H), 3.49-3.34 (m, 6H), 3.23 (br s, 4H), 2.96-2.95 (m, 1H), 2.91-2.91 (m, 1H), 2.96-2.88 (m, 1H), 2.82-2.74 (m, 1H), 2.63 (br s, 4H), 2.53-2.45 (m, 4H), 2.26-2.10 (m, 4H), 2.02-1.94 (m, 4H), 1.93-1.83 (m, 5H), 1.82-1.75 (m, 2H), 1.66-1.63 (m, 1H), 1.65-1.44 (m, 3H), 1.30 (d, J = 10.0 Hz, 3H), 0.92-0.89 (m, 2H), 0.87-0.79 (m, 5H). |

| Cpd # | Characterization |
|---|---|
| 179 | LCMS: [M + H]⁺ = 998.6<br>¹H NMR (400 MHz, MeOD-d₄) δ = 9.19 (d, J = 14.0 Hz, 1H), 8.54 (s, 1H), 7.65-7.59 (m, 2H), 7.36 (t, J = 7.6 Hz, 1H), 7.28 (t, J = 2.4 Hz, 1H), 7.17 (d, J = 7.2 Hz, 1H), 7.05-6.98 (m, 3H), 5.10 (dd, J = 5.2, 13.2 Hz, 1H), 4.61-4.52 (m, 4H), 4.41-4.37 (m, 3H), 4.29 (br dd, J = 9.2, 13.2 Hz, 1H), 3.93-3.84 (m, 1H), 3,77-3.69 (m, 1H), 3.68-3.61 (m, 1H), 3.48-3.40 (m, 1H), 3.23 (br s, 4H), 3.17-3.13 (m, 1H), 2.94-2.85 (m, 1H), 2.81-2.73 (m, 1H), 2.62 (br s, 4H), 2.51-2.48 (m, 1H), 2.48-2.40 (m, 2H), 2.39-2.32 (m, 1H), 2.31-2.24 (m, 1H), 2.20-2.03 (m, 3H), 1.96-1.74 (m, 9H), 1.61-1.45 (m, 2H), 1.29 (d, J = 12.0 Hz, 3H), 0.91 (dt, J = 4.0, 7.2 Hz, 3H), 0.86-0.73 (m, 4H). |
| 180 | LCMS: [M + H]⁺ = 1022.4<br>¹H NMR (400 MHz, DMSO-d₆) δ = 10.84 (s, 1H), 9.21 (s, 1H), 8.16 (s, 1H), 8.04 (t, J = 7.2 Hz, 1H), 7.80-7.73 (m, 1H), 7.62 (t, J = 9.2 Hz, 1H), 7.39-7.30 (m, 2H), 7.02 (d, J = 2.4 Hz, 1H), 6.83-6.71 (m, 2H), 4.75-4.69 (m, 1H), 4.35-4.24 (m, 3H), 4.09-3.99 (m, 1H), 3.62 (br d, J = 13.2 Hz, 1H), 3.53-3.50 (m, 1H), 3.38 (br d, J = 11.6 Hz, 3H), 3.27 (br s, 4H), 2.81-2.73 (m, 1H), 2.56 (br d, J = 4.2 Hz, 5H), 2.38-2.26 (m, 6H), 2.18-2.05 (m, 4H), 2.04-1.99 (m, 2H), 1.96 (br s, 1H), 1.92 (br d, J = 10.8 Hz, 1H), 1.76-1.63 (m, 3H), 1.58 (br s, 2H), 1.47 (br s, 2H), 1.16 (d, J = 10.0 Hz, 3H), 0.78-0.69 (m, 3H), 0.65 (s, 2H), 0.41 (s, 2H). |
| 183 | LCMS: [M + H]⁺ = 1022.6<br>¹H NMR (400 MHz, MeOD-d₄) δ = 9.23 (s, 1H), 8.48 (s, 1H), 7.76 (t, J = 9.2 Hz, 1H), 7.67 (dd, J = 5.6, 8.8 Hz, 1H), 7.30 (d, J = 2.4 Hz, 1H), 7.25 (t, J = 9.2 Hz, 1H), 7.06 (t, J = 2.4 Hz, 1H), 6.75 (dd, J = 1.6, 8.8 Hz, 1H), 6.63 (dd, J = 1.6, 15.6 Hz, 1H), 4.78 (br d, J = 5.2 Hz, 1H), 4.57 (br d, J = 12.8 Hz, 2H), 4.47-4.37 (m, 2H), 4.31 (br dd, J = 10.8, 11.6 Hz, 1H), 4.21-4.12 (m, 1H), 3.98 (br s, 2H), 3.69-3.56 (m, 1H), 3.49-3.34 (m, 3H), 3.22 (br s, 4H), 2.88-2.76 (m, 1H), 2.76-2.66 (m, 1H), 2.59 (br s, 4H), 2.53-2.41 (m, 3H), 2.37-2.28 (m, 1H), 2.26-2.10 (m, 3H), 2.01-1.74 (m, 9H), 1.64-1.42 (m, 2H), 1.29 (d, J = 9.6 Hz, 3H), 0.95-0.77 (m, 7H). |

Example 23: Preparation of (3S)-3-(5-(4-((7-(((7-(8-ethyl-7-fluoro-3-hydroxynaphthalen-1-yl)-8-fluoro-4-(6-hydroxy-6-methyl-1,4-oxazepan-4-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione (Compound 91)

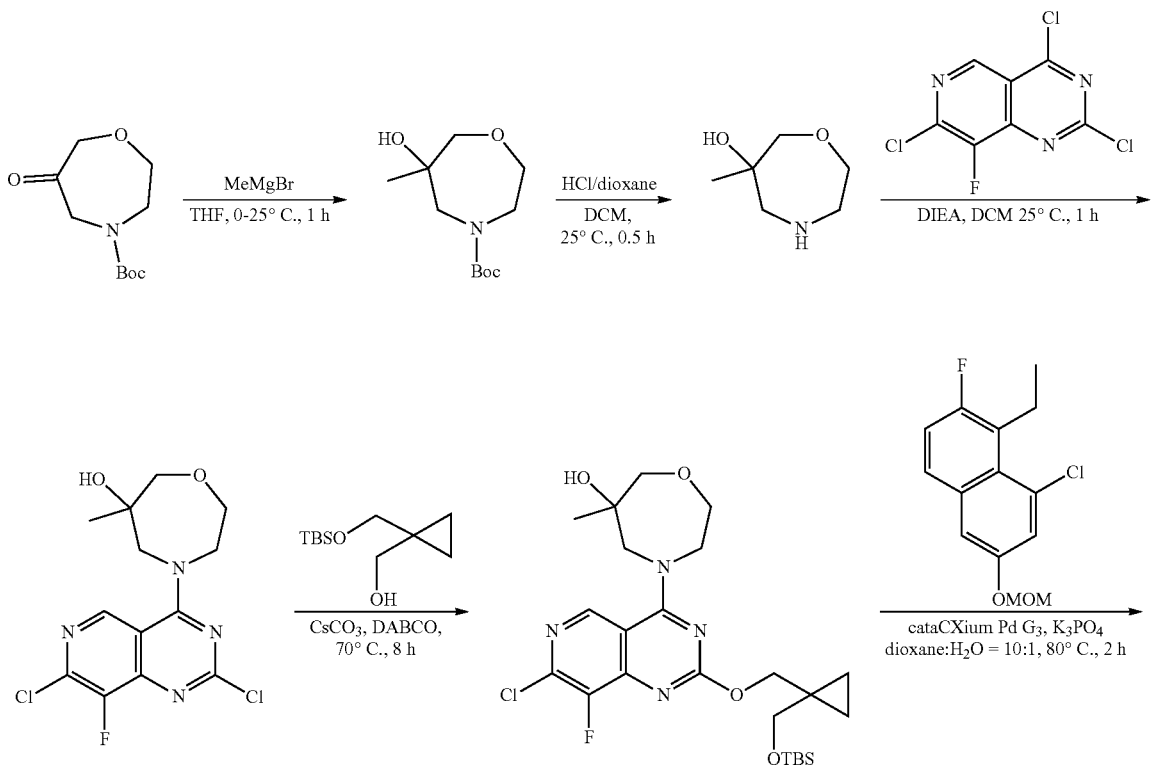

469
470
-continued
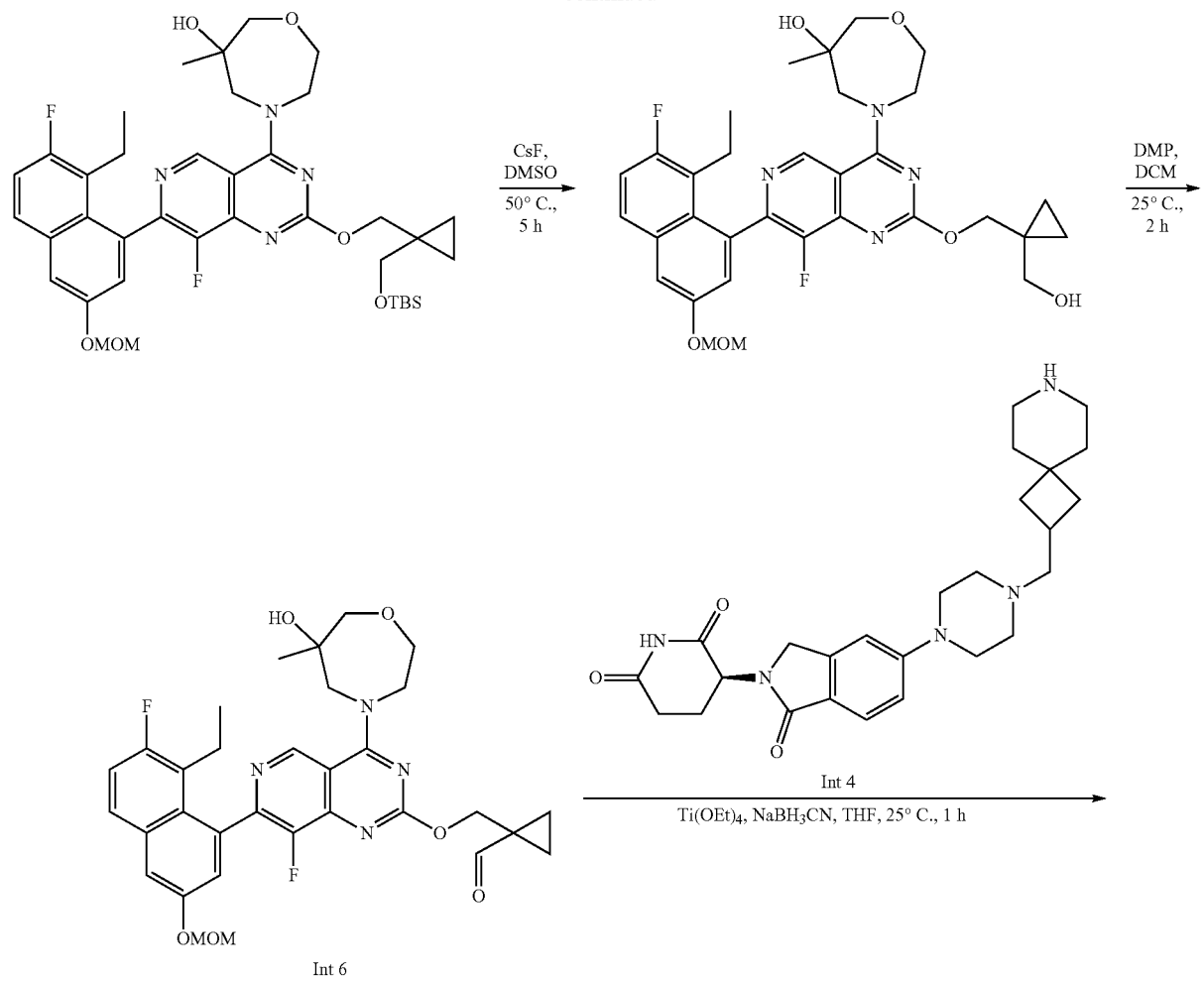
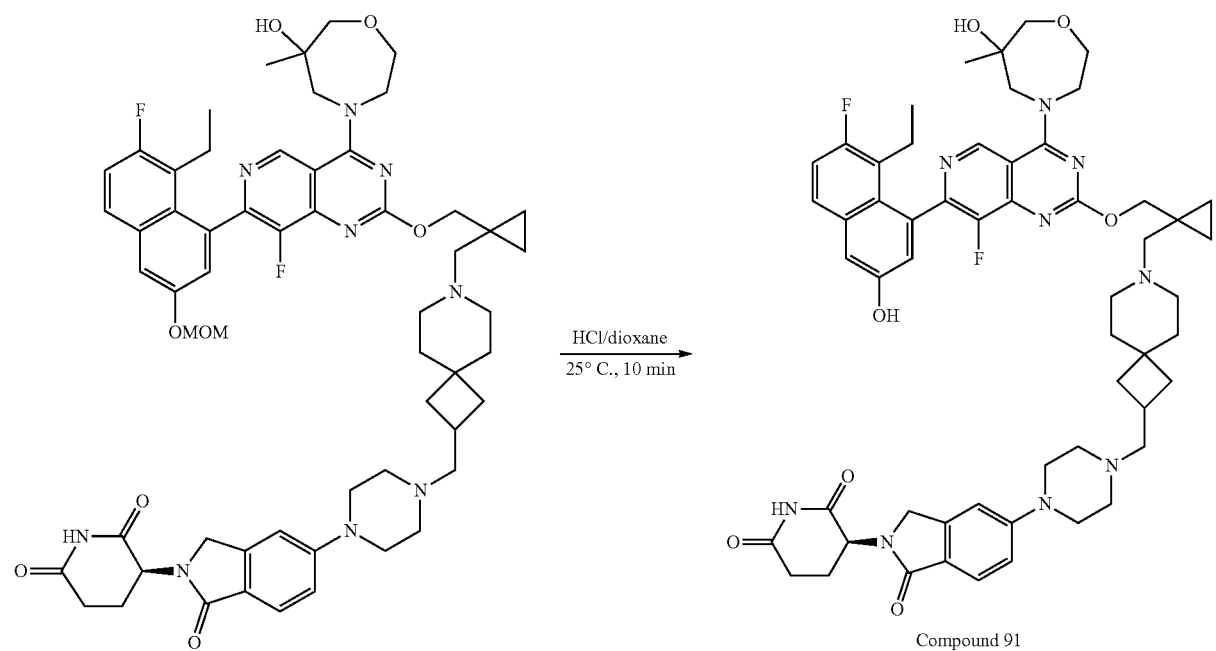

Step 1: Preparation of tert-butyl 6-hydroxy-6-methyl-1,4-oxazepane-4-carboxylate To a solution of MeMgBr (3 M, 4.18 mL, 3 eq) in THF (10 mL) was added tert-butyl 6-oxo-1,4-oxazepane-4-carboxylate (900 mg, 4.18 mmol, 1 eq) at 0° C. under $N_2$ atmosphere. The reaction mixture was stirred at 25° C. for 1 hour. TLC (PE:EA=3:1) indicated complete consumption of the reactant and one major new spot was formed. The mixture was diluted with $NH_4Cl$ (10 mL) and extracted with EA (10 mL*3). The combined organic layers were washed with brine (10 mL*2), dried over anhydrous $Na_2SO_4$, filtered and concentrated under reduced pressure to give a crude residue, which was purified by column chromatography ($SiO_2$, Petroleum ether/Ethyl acetate=10/1 to 3/1, Rf=0.2) to give tert-butyl 6-hydroxy-6-methyl-1,4-oxazepane-4-carboxylate (840 mg, 3.63 mmol, 86.8% yield) as a white solid. $^1$H NMR (400 MHz, DMSO-d$_6$) δ=4.63 (br d, J=11.2 Hz, 1H), 3.72-3.52 (m, 4H), 3.38-3.23 (m, 2H), 3.17-3.02 (m, 2H), 1.40 (s, 9H), 1.06 (br d, J=9.8 Hz, 3H).

Step 2: Preparation of 6-methyl-1,4-oxazepan-6-ol

To a solution of tert-butyl 6-hydroxy-6-methyl-1,4-oxazepane-4-carboxylate (830 mg, 3.59 mmol, 1 eq) in DCM (8 mL) was added HCl (4 M in dioxane, 16.6 mL, 18.5 eq). The mixture was stirred at 25° C. for 0.5 hours. TLC indicated complete consumption of the reactant and one new spot (PE:EA=3:1, Rf=0.1) was formed. The reaction mixture was filtered and concentrated under reduced pressure to give 6-methyl-1,4-oxazepan-6-ol (510 mg, 3.04 mmol, 84.7% yield, HCl) as a white solid without further purification. $^1$H NMR (400 MHz, DMSO-d$_6$) δ=9.93-9.66 (m, 1H), 5.46 (br s, 1H), 3.98-3.88 (m, 1H), 3.82-3.71 (m, 1H), 3.66-3.55 (m, 2H), 3.46 (d, J=12.8 Hz, 1H), 3.30-3.24 (m, 1H), 3.15-3.04 (m, 1H), 2.98 (br d, J=13.6 Hz, 1H), 1.10 (s, 3H).

Step 3: Preparation of 4-(2,7-dichloro-8-fluoro-pyrido[4,3-d]pyrimidin-4-yl)-6-methyl-1,4-oxazepan-6-ol To a solution of 6-methyl-1,4-oxazepan-6-ol (500 mg, 2.98 mmol, 1 eq, HCl) in DCM (5 mL) was added DIEA (770 mg, 5.97 mmol, 1.04 mL, 2 eq) and 2,4,7-trichloro-8-fluoro-pyrido[4,3-d]pyrimidine (753 mg, 2.98 mmol, 1 eq). The mixture was stirred at 25° C. for 1 hour. LCMS indicated complete consumption of the reactant. A major new peak of 98% peak area with the desired mass was detected on LCMS. The reaction mixture was filtered and concentrated under reduced pressure to give a crude residue, which further purified after trituration with MTBE (5 mL) at 25° C. for 5 minutes to give 4-(2,7-dichloro-8-fluoropyrido[4,3-d]pyrimidin-4-yl)-6-methyl-1,4-oxazepan-6-ol (800 mg, 2.30 mmol, 77.2% yield) as a yellow solid. $^1$H NMR (400 MHZ, DMSO-d$_6$) δ=9.50 (br s, 1H), 5.22 (s, 1H), 4.42-4.32 (m, 1H), 4.26 (br d, J=14.8 Hz, 1H), 4.07-3.99 (m, 2H), 3.98-3.90 (m, 1H), 3.88-3.76 (m, 1H), 3.63-3.49 (m, 2H), 1.16 (s, 3H).

Step 4: Preparation of 4-(2-((1-(((tert-butyldimethylsilyl)oxy)methyl)cyclopropyl)methoxy)-7-chloro-8-fluoropyrido[4,3-d]pyrimidin-4-yl)-6-methyl-1,4-oxazepan-6-ol To a solution of (6S)-4-(2,7-dichloro-8-fluoro-pyrido[4,3-d]pyrimidin-4-yl)-6-methyl-1,4-oxazepan-6-ol (200 mg, 576 μmol, 1 eq) in THF (8 mL) was added $Cs_2CO_3$ (375 mg, 1.15 mmol, 2 eq) and DABCO (12.2 mg, 115 μmol, 12.6 μL, 0.2 eq) and [1-[[tert-butyl(dimethyl)silyl]oxymethyl]cyclopropyl]methanol (124 mg, 576 μmol, 1 eq). The reaction mixture was stirred at 70° C. for 8 hours. LCMS showed complete consumption of the reactant. A peak of 47% peak area with the desired mass was detected on LCMS. The reaction mixture was diluted with water (10 mL) and extracted with EA (10 mL*3). The combined organic layers were washed with brine (10 mL*2), dried over anhydrous $Na_2SO_4$, filtered and concentrated under reduced pressure to give a crude residue, which was purified by column chromatography by prep-TLC ($SiO_2$, PE:EA=1:1, Rf=0.4) to give 4-(2-((1-(((tert-butyldimethylsilyl)oxy)methyl)cyclopropyl)methoxy)-7-chloro-8-fluoropyrido[4,3-d]pyrimidin-4-yl)-6-methyl-1,4-oxazepan-6-ol (120 mg, 227 μmol, 39.5% yield) as a white solid. $^1$H NMR (400 MHZ, DMSO-d$_6$) δ=9.31 (s, 1H), 5.13 (s, 1H), 4.39-4.24 (m, 3H), 4.16 (br d, J=14.6 Hz, 1H), 4.01-3.88 (m, 3H), 3.83-3.73 (m, 1H), 3.62-3.48 (m, 4H), 1.13 (s, 3H), 0.82 (s, 9H), 0.68-0.41 (m, 4H), −0.01 (s, 6H).

Step 5: Preparation of 4-(2-((1-(((tert-butyldimethylsilyl)oxy)methyl)cyclopropyl)methoxy)-7-(8-ethyl-7-fluoro-3-(methoxymethoxy)naphthalen-1-yl)-8-fluoropyrido[4,3-d]pyrimidin-4-yl)-6-methyl-1,4-oxazepan-6-ol To a solution of (6S)-4-[2-[[1-[[tert-butyl(dimethyl)silyl]oxymethyl]cyclopropyl]methoxy]-7-chloro-8-fluoro-pyrido[4,3-d]pyrimidin-4-yl]-6-methyl-1,4-oxazepan-6-ol (310 mg, 588.12 μmol, 1 eq) and 2-[8-ethyl-7-fluoro-3-(methoxymethoxy)-1-naphthyl]-4,4,5,5-tetramethyl-1,3,2-dioxaborolane (211 mg, 588 μmol, 1 eq) in dioxane (5 mL) and $H_2O$ (1 mL) was added [2-(2-aminophenyl)phenyl]palladium(1+);bis(1-adamantyl)-butyl-phosphane; methanesulfonate (42.8 mg, 58.8 μmol, 0.1 eq) and $K_3PO_4$ (374 mg, 1.76 mmol, 3 eq). The reaction mixture was stirred at 80° C. for 2 hours. LCMS showed complete consumption of the reactant. A peak of 60% peak area with the desired mass was detected on LCMS. The reaction mixture was diluted with water (10 mL) and extracted with EA (10 mL*3). The combined organic layers were washed with brine (10 mL*2), dried over anhydrous $Na_2SO_4$, filtered and concentrated under reduced pressure to give a residue, which was purified by column chromatography ($SiO_2$, Petroleum ether/Ethyl acetate=10/1 to 0/1, Rf=0.3) to give 4-(2-((1-(((tert-butyldimethylsilyl)oxy)methyl)cyclopropyl)methoxy)-7-(8-ethyl-7-fluoro-3-(methoxymethoxy)naphthalen-1-yl)-8-fluoropyrido[4,3-d]pyrimidin-4-yl)-6-methyl-1,4-oxazepan-6-ol (290 mg, 400 μmol, 68.0% yield) as a yellow solid.

Step 6: Preparation of 4-(7-(8-ethyl-7-fluoro-3-(methoxymethoxy)naphthalen-1-yl)-8-fluoro-2-((1-(hydroxymethyl)cyclopropyl)methoxy)pyrido[4,3-d]pyrimidin-4-yl)-6-methyl-1,4-oxazepan-6-ol To a solution of (6S)-4-[2-[[1-[[tert-butyl(dimethyl)silyl]oxymethyl]cyclopropyl]methoxy]-7-[8-ethyl-7-fluoro-3-(methoxymethoxy)-1-naphthyl]-8-fluoro-pyrido[4,3-d]pyrimidin-4-yl]-6-methyl-1,4-oxazepan-6-ol (280 mg, 386 μmol, 1 eq) in DMF (5 mL) was added CsF (176 mg, 1.16 mmol, 42.7 μL, 3 eq). The reaction mixture was stirred at 50° C. for 5 hours. LCMS showed complete consumption of the reactant. A new peak of ~83% peak area with the desired mass was detected on LCMS. The mixture was diluted with water (10 mL) and extracted with EA (10 mL*3). The combined organic layers were washed with brine (10 mL*2), dried over anhydrous Na₂SO₄, filtered and concentrated under reduced pressure to give 4-(7-(8-ethyl-7-fluoro-3-(methoxymethoxy)naphthalen-1-yl)-8-fluoro-2-((1-(hydroxymethyl)cyclopropyl)methoxy)pyrido[4,3-d]pyrimidin-4-yl)-6-methyl-1,4-oxazepan-6-ol (230 mg, 376 µmol, 97.5% yield) as a yellow oil. $^1$H NMR (400 MHZ, DMSO-d₆) δ=9.49 (s, 1H), 7.93-7.87 (m, 1H), 7.67 (d, J=2.4 Hz, 1H), 7.44 (s, 1H), 7.25-7.18 (m, 1H), 5.35 (s, 2H), 5.18 (s, 1H), 4.72-4.58 (m, 1H), 4.40-4.34 (m, 1H), 4.34-4.30 (m, 2H), 4.21 (br d, J=14.8 Hz, 1H), 4.03 (br d, J=7.2 Hz, 5H), 3.59-3.54 (m, 2H), 3.43 (s, 3H), 3.41-3.36 (m, 3H), 1.26-1.10 (m, 6H), 0.74 (br d, J=3.4 Hz, 2H), 0.55 (br s, 2H).

Step 7: Preparation of 1-(((7-(8-ethyl-7-fluoro-3-(methoxymethoxy)naphthalen-1-yl)-8-fluoro-4-(6-hydroxy-6-methyl-1,4-oxazepan-4-yl)pyrido[4,3-d]pyrimidin-2-yl)oxy)methyl)cyclopropane-1-carbaldehyde To a solution of (6S)-4-[7-[8-ethyl-7-fluoro-3-(methoxymethoxy)-1-naphthyl]-8-fluoro-2-[[1-(hydroxymethyl)cyclopropyl]methoxy]pyrido[4,3-d]pyrimidin-4-yl]-6-methyl-1,4-oxazepan-6-ol (230 mg, 376 µmol, 1 eq) in DCM (3 mL) was added DMP (479 mg, 1.13 mmol, 350.0 µL, 3 eq). The mixture was stirred at 25° C. for 2 hours. LCMS showed complete consumption of the reactant. A new peak of ~40% peak area with the desired mass was detected on LCMS. The reaction mixture was filtered and concentrated under reduced pressure to give a residue, which was purified by column chromatography by prep-TLC (SiO₂, PE:EA=0:1, Rf=0.5) to give 1-(((7-(8-ethyl-7-fluoro-3-(methoxymethoxy)naphthalen-1-yl)-8-fluoro-4-(6-hydroxy-6-methyl-1,4-oxazepan-4-yl)pyrido[4,3-d]pyrimidin-2-yl)oxy)methyl)cyclopropane-1-carbaldehyde (130 mg, 213 µmol, 56.7% yield) as a white solid.

Step 8: Preparation of (3S)-3-(5-(4-((7-((1-(((7-(8-ethyl-7-fluoro-3-(methoxymethoxy)naphthalen-1-yl)-8-fluoro-4-(6-hydroxy-6-methyl-1,4-oxazepan-4-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione To a solution of 1-(((7-(8-ethyl-7-fluoro-3-(methoxymethoxy)naphthalen-1-yl)-8-fluoro-4-(6-hydroxy-6-methyl-1,4-oxazepan-4-yl)pyrido[4,3-d]pyrimidin-2-yl)oxy)methyl)cyclopropane-1-carbaldehyde (60 mg, 98.5 µmol, 1 eq) and (3S)-3-[5-[4-(7-azaspiro[3.5]nonan-2-ylmethyl)piperazin-1-yl]-1-oxo-isoindolin-2-yl]piperidine-2,6-dione (49.49 mg, 98.58 µmol, 1 eq, HCl) in THF (0.5 mL) was added Ti(OEt)₄ (224 mg, 985 µmol, 204 µL, 10 eq). The reaction mixture was stirred at 25° C. for 0.5 hours. Then NaBH₃CN (61.9 mg, 985 µmol, 10 eq) was added and the reaction mixture was stirred at 25° C. for 0.5 hours. LCMS showed complete consumption of the reactant. A new peak of ~50% peak area with the desired mass was detected on LCMS. The reaction mixture was added to water dropwise. The resulting mixture was filtered. The mother liquor was collected, diluted with water (5 mL), and extracted with EA (5 mL*3). The combined organic layers were washed with brine (5 mL*2), dried over anhydrous Na₂SO₄, filtered and concentrated under reduced pressure to give a residue, which was purified by column chromatography by prep-TLC (SiO₂, DCM: MeOH=8:1Rf=0.2) to give (3S)-3-(5-(4-((7-((1-(((7-(8-ethyl-7-fluoro-3-(methoxymethoxy)naphthalen-1-yl)-8-fluoro-4-(6-hydroxy-6-methyl-1,4-oxazepan-4-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione (32 mg, 30.2 µmol, 30.6% yield) as a yellow solid.

Step 9: Preparation of (3S)-3-(5-(4-((7-((1-(((7-(8-ethyl-7-fluoro-3-hydroxynaphthalen-1-yl)-8-fluoro-4-(6-hydroxy-6-methyl-1,4-oxazepan-4-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione (Compound 91)

HCl (4 M in dioxane, 2 mL, 282 eq) was added to (3S)-3-[5-[4-[[7-[[1-[[7-[8-ethyl-7-fluoro-3-(methoxymethoxy)-1-naphthyl]-8-fluoro-4-[(6S)-6-hydroxy-6-methyl-1,4-oxazepan-4-yl]pyrido[4,3-d]pyrimidin-2-yl]oxymethyl]cyclopropyl]methyl]-7-azaspiro[3.5]nonan-2-yl]methyl]piperazin-1-yl]-1-oxo-isoindolin-2-yl]piperidine-2,6-dione (30 mg, 28.35 µmol, 1 eq). The reaction mixture was stirred at 25° C. for 10 minutes. LCMS showed complete consumption of the reactant. A new peak of ~90% peak area with the desired mass was detected on LCMS. The reaction was filtered and concentrated under reduced pressure to give a residue, which was purified by prep-HPLC (FA condition; column: Phenomenex Luna C18 150*25 mm*10 µm; mobile phase: [water (FA)-ACN]; gradient: 10%-40% B over 10 minutes) to give (3S)-3-(5-(4-((7-((1-(((7-(8-ethyl-7-fluoro-3-hydroxynaphthalen-1-yl)-8-fluoro-4-(6-hydroxy-6-methyl-1,4-oxazepan-4-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione (9 mg, 8.74 µmol, 30.8% yield, 98.5% purity) as a white solid. LCMS: [M+H]⁺=1014.5. $^1$H NMR (400 MHZ, METHANOL-d₄) δ=9.57 (d, J=5.0 Hz, 1H), 7.71-7.61 (m, 2H), 7.34-7.22 (m, 2H), 7.13-7.01 (m, 3H), 5.14-5.07 (m, 1H), 4.62-4.57 (m, 1H), 4.57-4.51 (m, 1H), 4.47 (br t, J=4.6 Hz, 2H), 4.40 (d, J=5.6 Hz, 2H), 4.25-4.15 (m, 1H), 4.08-3.82 (m, 3H), 3.75-3.64 (m, 2H), 3.42-3.33 (m, 5H), 3.22-3.09 (m, 3H), 3.00-2.83 (m, 2H), 2.81-2.74 (m, 1H), 2.69-2.53 (m, 7H), 2.51-2.40 (m, 2H), 2.26-2.05 (m, 4H), 2.02-1.90 (m, 2H), 1.88-1.78 (m, 2H), 1.66-1.56 (m, 2H), 1.35-1.22 (m, 5H), 1.01-0.90 (m, 2H), 0.84-0.78 (m, 4H).

Compound 92 was prepared via a similar synthetic procedure as example 23.

| Cpd # | Characterization |
|---|---|
| 92 | LCMS: [M + H]+ = 974.5<br>$^1$H NMR (400 MHz, METHANOL-d₄) δ = 9.58 (br s, 1H), 7.63 (d, J = 8.6 Hz, 2H), 7.38-7.20 (m, 2H), 7.15-7.00 (m, 3H), 5.13-5.07 (m, 1H), 4.92-4.88 (m, 4H), 4.62-4.53 (m, 2H), 4.53-4.47 (m, 2H), 4.45-4.34 (m, 2H), 4.25-4.15 (m, 1H), 4.08-4.01 (m, 1H), 4.01-3.82 (m, 2H), 3.77-3.63 (m, 3H), 3.35-3.32 (m, 2H), 3.28-3.17 (m, |

| Cpd # | Characterization |
|---|---|
| | 1H), 3.16-3.09 (m, 1H), 2.95-2.74 (m, 3H), 2.57 (br s, 4H), 2.51-2.38 (m, 2H), 2.27 (br d, J = 4.2 Hz, 2H), 2.24-2.10 (m, 2H), 2.08-1.97 (m, 2H), 1.93-1.78 (m, 1H), 1.64-1.39 (m, 2H), 1.28 (d, J = 2.8 Hz, 4H), 0.99-0.89 (m, 2H), 0.83-0.76 (m, 4H). |
Example 24: Preparation of (3S)-3-[5-[4-[[1-[[1-[[7-(8-ethyl-7-fluoro-3-hydroxy-1-naphthyl)-8-fluoro-4-[(6S)-6-hydroxy-6-methyl-1,4-oxazepan-4-yl]pyrido[4,3-d]pyrimidin-2-yl]oxymethyl]cyclopropyl]methyl]-4-piperidyl]methyl]piperazin-1-yl]-1-oxo-isoindolin-2-yl]piperidine-2,6-dione (Compound 104)
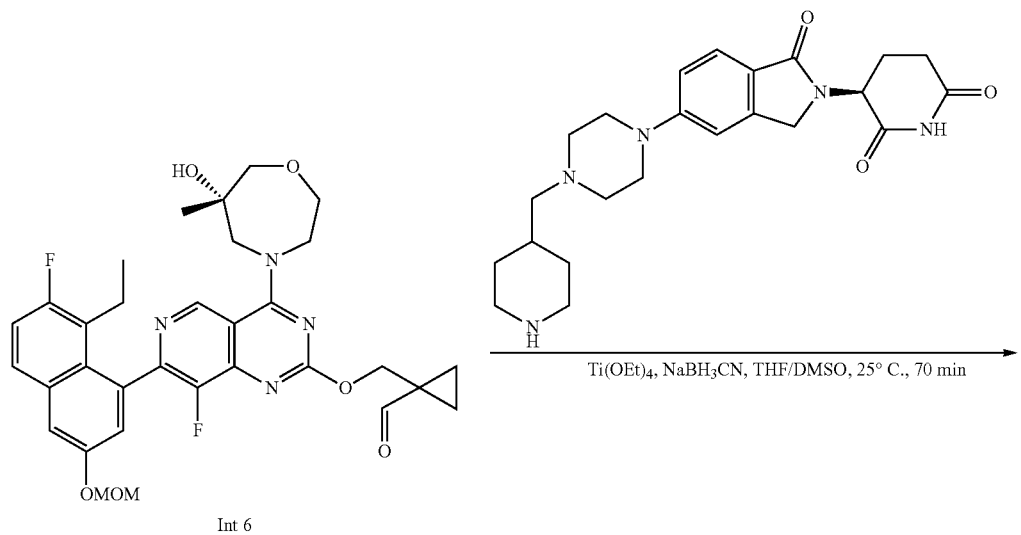
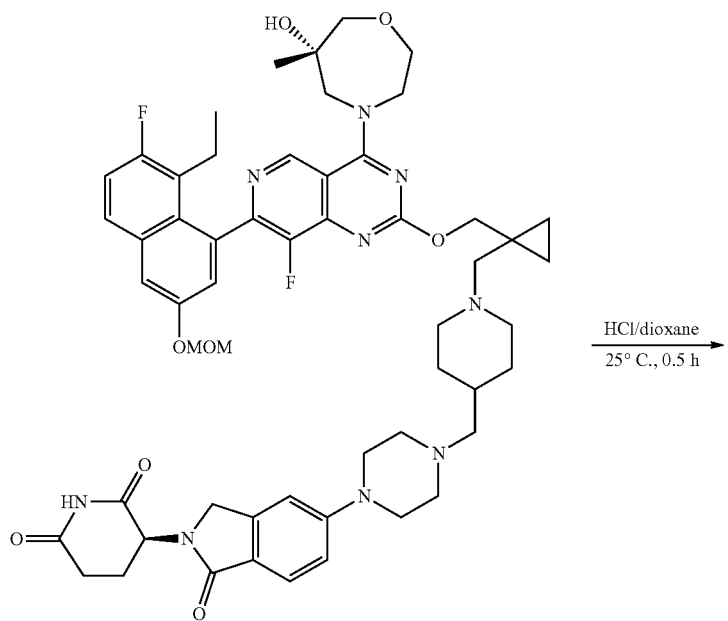

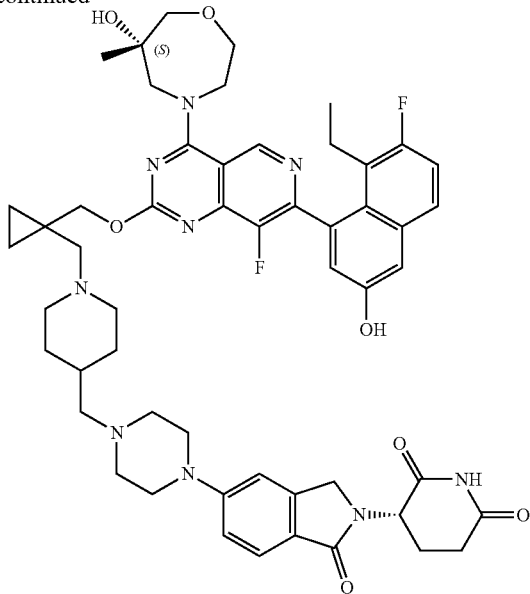

Compound 104

Step 1: Preparation of (3S)-3-[5-[4-[[1-[[1-[[7-[8-ethyl-7-fluoro-3-(methoxymethoxy)-1-naphthyl]-8-fluoro-4-[(6S)-6-hydroxy-6-methyl-1,4-oxazepan-4-yl]pyrido[4,3-d]pyrimidin-2-yl]oxymethyl]cyclopropyl]methyl]-4-piperidyl]methyl]piperazin-1-yl]-1-oxo-isoindolin-2-yl]piperidine-2,6-dione To a solution of 1-[[7-[8-ethyl-7-fluoro-3-(methoxymethoxy)-1-naphthyl]-8-fluoro-4-[(6S)-6-hydroxy-6-methyl-1,4-oxazepan-4-yl]pyrido[4,3-d]pyrimidin-2-yl]oxymethyl]cyclopropanecarbaldehyde (100 mg, 164 μmol, 1.00 eq) and (3S)-3-[1-oxo-5-[4-(4-piperidylmethyl)piperazin-1-yl]isoindolin-2-yl]piperidine-2,6-dione (151 mg, 328 μmol, 2.00 eq, HCl) in THF (3 mL) and DMSO (1 mL) was added Ti(OEt)$_4$ (2.20 g, 9.64 mmol, 2.00 mL, 58.7 eq). The mixture was stirred at 25° C. for 1 hour. Then NaBH$_3$CN (20.7 mg, 329 μmol, 2.00 eq) was added to the mixture and the mixture was stirred at 25° C. for 10 minutes. LCMS showed complete consumption of the reactant and a new peak of 80.3% peak area with desired mass. The reaction mixture was quenched with water (100 mL) at 0° C. The reaction mixture was diluted with EA (10 mL) and extracted with EA (50 mL*2). The combined organic layers were washed with water (50 mL*2), dried over anhydrous Na$_2$SO$_4$, filtered and concentrated under reduced pressure to give a residue, which was purified by prep-TLC (SiO$_2$, DCM: MeOH=8:1) to give (3S)-3-[5-[4-[[1-[[1-[[7-[8-ethyl-7-fluoro-3-(methoxymethoxy)-1-naphthyl]-8-fluoro-4-[(6S)-6-hydroxy-6-methyl-1,4-oxazepan-4-yl]pyrido[4,3-d]pyrimidin-2-yl]oxymethyl]cyclopropyl]methyl]-4-piperidyl]methyl]piperazin-1-yl]-1-oxo-isoindolin-2-yl]piperidine-2,6-dione (160 mg, 157 μmol, 95.6% yield) as a yellow solid.

Step 2: Preparation of (3S)-3-[5-[4-[1-[1-[[7-(8-ethyl-7-fluoro-3-hydroxy-1-naphthyl)-8-fluoro-4-[(6S)-6-hydroxy-6-methyl-1,4-oxazepan-4-yl]pyrido[4,3-d]pyrimidin-2-yl]oxymethyl]cyclopropyl]methyl]-4-piperidyl]methyl]piperazin-1-yl]-1-oxo-isoindolin-2-yl]piperidine-2,6-dione (Compound 104)

A mixture of (3S)-3-[5-[4-[1-[1-[[7-[8-ethyl-7-fluoro-3-(methoxymethoxy)-1-naphthyl]-8-fluoro-4-[(6S)-6-hydroxy-6-methyl-1,4-oxazepan-4-yl]pyrido[4,3-d]pyrimidin-2-yl]oxymethyl]cyclopropyl]methyl]-4-piperidyl]methyl]piperazin-1-yl]-1-oxo-isoindolin-2-yl]piperidine-2,6-dione (150 mg, 147 μmol, 1.00 eq) in HCl solution (4 M in dioxane, 4.00 mL, 108 eq) was stirred at 25° C. for 0.5 hours. LCMS showed complete consumption of the reactant and a new peak of 83.8% peak area with desired mass. The reaction mixture was concentrated under reduced pressure to give a residue, which was purified by prep-HPLC (FA condition; column: Phenomenex Luna C18 150*25 mm 10 μm; mobile phase: [water (FA)-ACN]; gradient: 6%-36% B over 10 minutes) to give (3S)-3-[5-[4-[1-[1-[7-(8-ethyl-7-fluoro-3-hydroxy-1-naphthyl)-8-fluoro-4-[(6S)-6-hydroxy-6-methyl-1,4-oxazepan-4-yl]pyrido[4,3-d]pyrimidin-2-yl]oxymethyl]cyclopropyl]methyl]-4-piperidyl]methyl]piperazin-1-yl]-1-oxo-isoindolin-2-yl]piperidine-2,6-dione (76.0 mg, 73.5 μmol, 49.9% yield, 98.7% purity, FA) as a white solid. LCMS: [M+H]$^+$=974.4. $^1$H NMR (400 MHZ, METHANOL-d$_4$) δ=9.57 (d, J=2.8 Hz, 1H), 8.52 (s, 1H), 7.68 (dd, J=5.6, 8.8 Hz, 1H), 7.63 (d, J=8.8 Hz, 1H), 7.31 (d, J=2.8 Hz, 1H), 7.29-7.22 (m, 1H), 7.09-7.06 (m, 1H), 7.04 (s, 2H), 5.10 (dd, J=5.2, 13.2 Hz, 1H), 4.95 (br d, J=6.0 Hz, 2H), 4.64-4.53 (m, 3H), 4.52-4.46 (m, 2H), 4.45-4.34 (m, 2H), 4.24-4.16 (m, 1H), 4.08-3.84 (m, 3H), 3.76-3.56 (m, 4H), 3.20-3.03 (m, 2H), 2.96-2.70 (m, 4H), 2.57 (br s, 4H), 2.53-2.40 (m, 2H), 2.31-2.25 (m, 2H), 2.24-2.11 (m, 2H), 2.03 (br d, J=11.2 Hz, 2H), 1.93-1.80 (m, 1H), 1.64-1.43 (m, 2H), 1.28 (d, J=2.8 Hz, 4H), 0.94 (br s, 2H), 0.86-0.76 (m, 5H).

Example 25: Preparation of (S)-3-chloro-5-(2-((1-((4-((4-(2-(2,6-dioxopiperidin-3-yl)-1-oxoisoindolin-5-yl)piperazin-1-yl)methyl)piperidin-1-yl)methyl)cyclopropyl)methoxy)-7-(8-ethyl-7-fluoro-3-hydroxynaphthalen-1-yl)-8-fluoropyrido[4,3-d]pyrimidin-4-yl)-N,N-dimethyl-5,6,7,8-tetrahydro-4H-pyrazolo[1,5-a][1,4]diazepine-2-carboxamide (Compound 108)
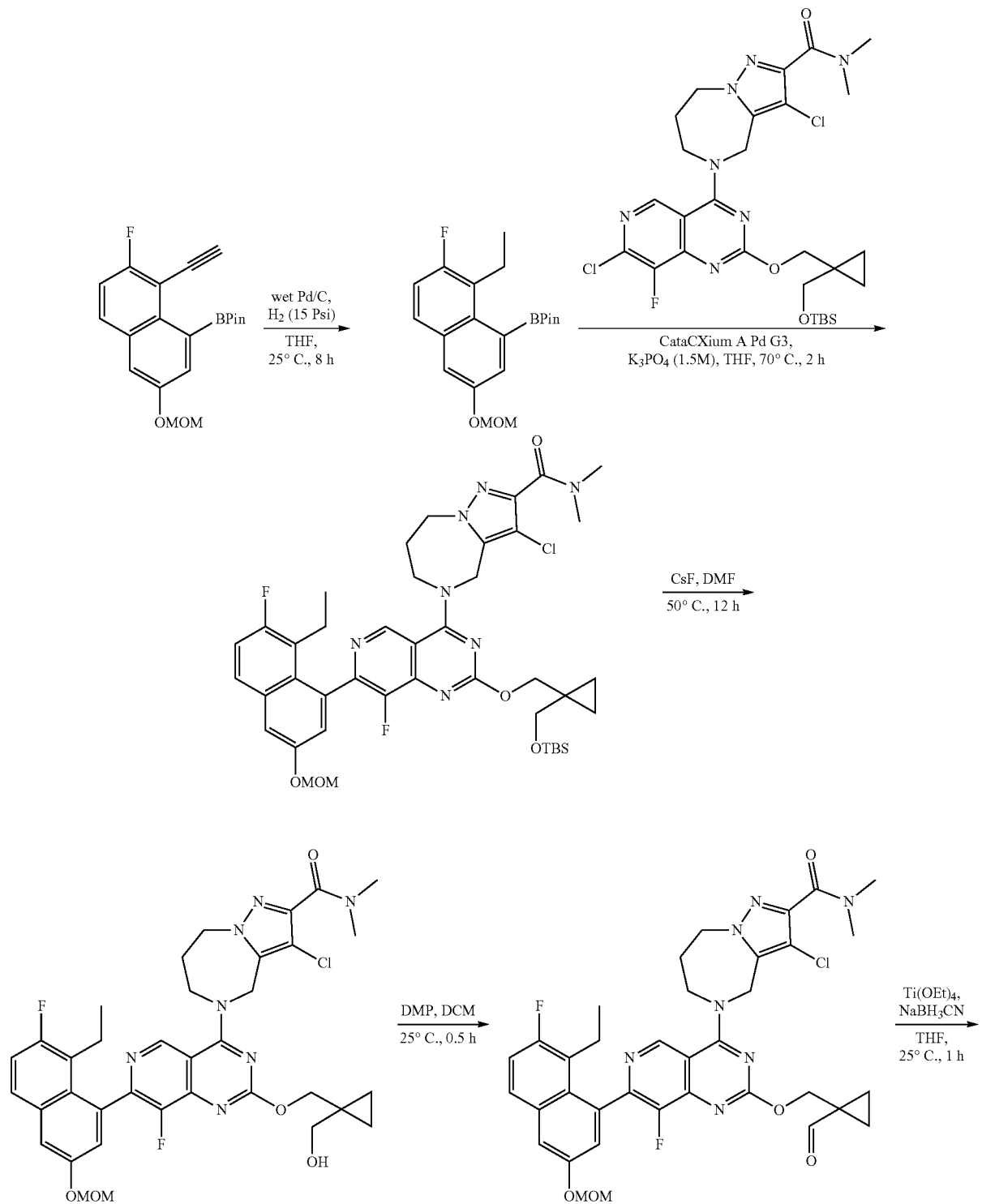

-continued

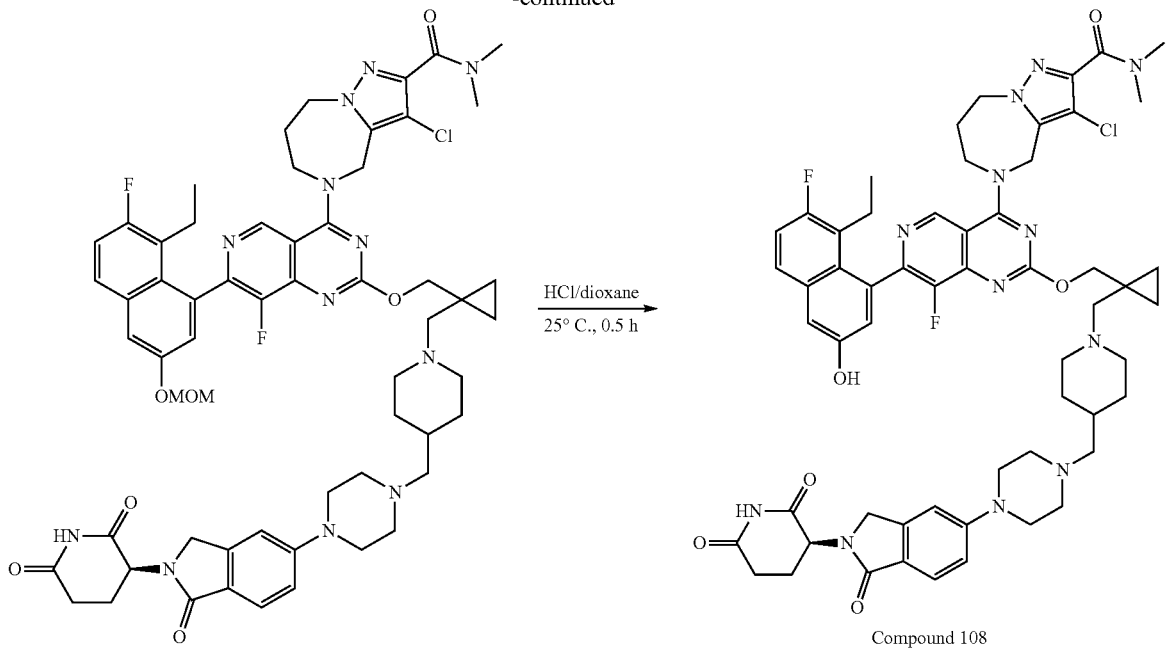

Compound 108

Step 1: Preparation of 2-(8-ethyl-7-fluoro-3-(methoxymethoxy)naphthalen-1-yl)-4,4,5,5-tetramethyl-1,3,2-dioxaborolane To a suspension of Pd/C (3 g, 2.82 mmol, 10% purity, 0.33 eq) in THF (60 mL) was added 2-[8-ethynyl-7-fluoro-3-(methoxymethoxy)-1-naphthyl]-4,4,5,5-tetramethyl-1,3,2-dioxaborolane (3 g, 8.42 mmol, 1 eq). The reaction mixture was stirred at 25° C. for 8 hours under H$_2$ atmosphere (15 Psi). LCMS showed complete consumption of the reactant and a new peak of ~70% peak area with desired mass. The reaction mixture was filtered and concentrated under reduced pressure to give a crude residue, which was purified by column chromatography (SiO$_2$, Petroleum ether/Ethyl acetate=1/0 to 50/1, Rf=0.3) to give 2-(8-ethyl-7-fluoro-3-(methoxymethoxy)naphthalen-1-yl)-4,4,5,5-tetramethyl-1,3,2-dioxaborolane (2.5 g, 6.94 mmol, 82.4% yield) as a white oil.

Step 2: Preparation of 5-(2-((1-(((tert-butyldimethylsilyl)oxy)methyl)cyclopropyl)methoxy)-7-(8-ethyl-7-fluoro-3-(methoxymethoxy)naphthalen-1-yl)-8-fluoropyrido[4,3-d]pyrimidin-4-yl)-3-chloro-N,N-dimethyl-5,6,7,8-tetrahydro-4H-pyrazolo[1,5-a][1,4]diazepine-2-carboxamide To a solution of 5-[2-[[1-[[tert-butyl(dimethyl)silyl]oxymethyl]cyclopropyl]methoxy]-7-chloro-8-fluoro-pyrido[4,3-d]pyrimidin-4-yl]-3-chloro-N,N-dimethyl-4,6,7,8-tetrahydropyrazolo[1,5-a][1,4]diazepine-2-carboxamide (160 mg, 250 µmol, 1 eq) and 2-[8-ethyl-7-fluoro-3-(methoxymethoxy)-1-naphthyl]-4,4,5,5-tetramethyl-1,3,2-dioxaborolane (180 mg, 501 µmol, 2 eq) in THF (5 mL) and H$_2$O (0.1 mL) was added [2-(2-aminophenyl)phenyl]palladium(1+);bis(1-adamantyl)-butyl-phosphane;methanesulfonate (18.2 mg, 25.0 µmol, 0.1 eq) and K$_3$PO$_4$ (1.5 M, 501 µL, 3 eq). The reaction mixture was stirred at 70° C. for 2 hours. LCMS showed complete consumption of the reactant and a new peak with ~44% peak area with desired mass.

The reaction mixture was diluted with water (10 mL) and extracted with EA (10 mL*3). The combined organic layers were washed with brine (10 mL*2), dried over anhydrous Na$_2$SO$_4$, filtered and concentrated under reduced pressure to give a residue, which was purified by column chromatography (SiO$_2$, Petroleum ether/Ethyl acetate=1/0 to 0/1, Rf=0.3) to give 5-(2-((1-(((tert-butyldimethylsilyl)oxy)methyl)cyclopropyl)methoxy)-7-(8-ethyl-7-fluoro-3-(methoxymethoxy)naphthalen-1-yl)-8-fluoropyrido[4,3-d]pyrimidin-4-yl)-3-chloro-N,N-dimethyl-5,6,7,8-tetrahydro-4H-pyrazolo[1,5-a][1,4]diazepine-2-carboxamide (440 mg, crude) as a yellow oil. $^1$H NMR (400 MHZ, DMSO-d$_6$) δ=9.18 (s, 1H), 7.98-7.86 (m, 1H), 7.71 (d, J=2.8 Hz, 1H), 7.47 (t, J=9.4 Hz, 1H), 7.22 (d, J=2.6 Hz, 1H), 5.37 (s, 2H), 5.24 (br d, J=9.0 Hz, 2H), 4.50 (br d, J=6.2 Hz, 2H), 4.38-4.30 (m, 4H), 3.96 (s, 2H), 3.62 (s, 2H), 3.45 (s, 3H), 3.01 (d, J=14.8 Hz, 6H), 1.20 (t, J=7.2 Hz, 3H), 0.84 (s, 9H), 0.77-0.74 (m, 2H), 0.59 (br s, 2H), 0.55 (br d, J=2.8 Hz, 2H), 0.01--0.01 (m, 6H).

Step 3: Preparation of 3-chloro-5-(7-(8-ethyl-7-fluoro-3-(methoxymethoxy)naphthalen-1-yl)-8-fluoro-2-((1-(hydroxymethyl)cyclopropyl)methoxy)pyrido[4,3-d]pyrimidin-4-yl)-N,N-dimethyl-5,6,7,8-tetrahydro-4H-pyrazolo[1,5-a][1,4]diazepine-2-carboxamide To a solution of 5-[2-[[1-[[tert-butyl(dimethyl)silyl]oxymethyl]cyclopropyl]methoxy]-7-[8-ethyl-7-fluoro-3-(methoxymethoxy)-1-naphthyl]-8-fluoro-pyrido[4,3-d]pyrimidin-4-yl]-3-chloro-N,N-dimethyl-4,6,7,8-tetrahydropyrazolo[1,5-a][1,4]diazepine-2-carboxamide (420 mg, 502 µmol, 1 eq) in DMF (5 mL) was added CsF (228 mg, 1.51 mmol, 55.6 µL, 3 eq). The mixture was stirred at 50° C. for 12 hours. LCMS showed full consumption of the reactant and a new peak of ~63% peak area with desired mass. The reaction mixture was diluted with water (10 mL) and extracted with EA (10 mL*3). The combined organic layers were washed with brine (10 mL*2), dried over anhydrous Na$_2$SO$_4$, filtered and concentrated under reduced pressure to give a residue, which was purified by column chromatography by prep-TLC (SiO$_2$, DCM:MeOH=9:1, Rf=0.4) to give 3-chloro-5-(7-(8-ethyl-7-fluoro-3-(methoxymethoxy)naphthalen-1-yl)-8-fluoro-2-((1-(hydroxymethyl)cyclopropyl)methoxy)pyrido[4,3-d]pyrimidin-4-yl)-N,N-dimethyl-5,6,7,8-tetrahydro-4H-pyrazolo[1,5-a][1,4]diazepine-2-carboxamide (200 mg, 193 µmol, 38.6% yield, 70% purity) as a yellow oil.

Step 4: Preparation of 3-chloro-5-(7-(8-ethyl-7-fluoro-3-(methoxymethoxy)naphthalen-1-yl)-8-fluoro-2-((1-formylcyclopropyl)methoxy)pyrido[4,3-d]pyrimidin-4-yl)-N,N-dimethyl-5,6,7,8-tetrahydro-4H-pyrazolo[1,5-a][1,4]diazepine-2-carboxamide To a solution of 3-chloro-5-[7-[8-ethyl-7-fluoro-3-(methoxymethoxy)-1-naphthyl]-8-fluoro-2-[[1-(hydroxymethyl)cyclopropyl]methoxy]pyrido[4,3-d]pyrimidin-4-yl]-N,N-dimethyl-4,6,7,8-tetrahydropyrazolo[1,5-a][1,4]diazepine-2-carboxamide (200 mg, 193.86 µmol, 1 eq) in DCM (5 mL) was added DMP (164 mg, 387 µmol, 120 µL, 2 eq). The reaction mixture was stirred at 25° C. for 0.5 hours. LCMS showed full consumption of the reactant and a new peak of ~80% peak area with desired mass. The mixture was diluted with water (5 mL) and extracted with DCM (5 mL*3). The combined organic layers were washed with brine (5 mL*2), dried over anhydrous Na$_2$SO$_4$, filtered and concentrated under reduced pressure to give a residue, which was purified by prep-TLC (SiO$_2$, DCM: MeOH=10:1, Rf=0.4) to give 3-chloro-5-(7-(8-ethyl-7-fluoro-3-(methoxymethoxy)naphthalen-1-yl)-8-fluoro-2-((1-formylcyclopropyl)methoxy)pyrido[4,3-d]pyrimidin-4-yl)-N,N-dimethyl-5,6,7,8-tetrahydro-4H-pyrazolo[1,5-a][1,4]diazepine-2-carboxamide (135 mg, 187 µmol, 96.7% yield) as a white solid.

Step 5: Preparation of (S)-3-chloro-5-(2-((1-((4-((4-(2-(2,6-dioxopiperidin-3-yl)-1-oxoisoindolin-5-yl)piperazin-1-yl)methyl)piperidin-1-yl)methyl)cyclopropyl)methoxy)-7-(8-ethyl-7-fluoro-3-(methoxymethoxy)naphthalen-1-yl)-8-fluoropyrido[4,3-d]pyrimidin-4-yl)-N,N-dimethyl-5,6,7,8-tetrahydro-4H-pyrazolo[1,5-a][1,4]diazepine-2-carboxamide To a solution of 3-chloro-5-[7-[8-ethyl-7-fluoro-3-(methoxymethoxy)-1-naphthyl]-8-fluoro-2-[(1-formylcyclopropyl)methoxy]pyrido[4,3-d]pyrimidin-4-yl]-N,N-dimethyl-4,6,7,8-tetrahydropyrazolo[1,5-a][1,4]diazepine-2-carboxamide (125 mg, 173 µmol, 1 eq) and (3S)-3-[1-oxo-5-[4-(4-piperidylmethyl)piperazin-1-yl]isoindolin-2-yl]piperidine-2,6-dione (73.8 mg, 159 µmol, 0.921 eq, HCl) in THF (4 mL) was added Ti(OEt)$_4$ (395 mg, 1.74 mmol, 359 µL, 10 eq) and the reaction mixture was stirred for 0.5 hours at 25° C. Then NaBH$_3$CN (109 mg, 1.74 mmol, 10 eq) was added and the reaction mixture stirred at 25° C. for 0.5 hours. A new peak of ~70% peak area with desired mass was detected on LCMS. The mixture was diluted with water (10 mL) and extracted with EA (10 mL*3). The combined organic layers were washed with brine (10 mL*2), dried over anhydrous Na$_2$SO$_4$, filtered and concentrated under reduced pressure to give a crude residue, which was purified by prep-TLC (SiO$_2$, DCM: MeOH=9:1) to give (S)-3-chloro-5-(2-((1-((4-((4-(2-(2,6-dioxopiperidin-3-yl)-1-oxoisoindolin-5-yl)piperazin-1-yl)methyl)piperidin-1-yl)methyl)cyclopropyl)methoxy)-7-(8-ethyl-7-fluoro-3-(methoxymethoxy)naphthalen-1-yl)-8-fluoropyrido[4,3-d]pyrimidin-4-yl)-N,N-dimethyl-5,6,7,8-tetrahydro-4H-pyrazolo[1,5-a][1,4]diazepine-2-carboxamide (60 mg, 53.1 µmol, 30.6% yield) as a white solid.

Step 6: preparation of (S)-3-chloro-5-(2-((1-((4-((4-(2-(2,6-dioxopiperidin-3-yl)-1-oxoisoindolin-5-yl)piperazin-1-yl)methyl)piperidin-1-yl)methyl)cyclopropyl)methoxy)-7-(8-ethyl-7-fluoro-3-hydroxynaphthalen-1-yl)-8-fluoropyrido[4,3-d]pyrimidin-4-yl)-N,N-dimethyl-5,6,7,8-tetrahydro-4H-pyrazolo[1,5-a][1,4]diazepine-2-carboxamide (Compound 108)

To a solution of 3-chloro-5-[2-[[1-[[4-[[4-[2-[(3S)-2,6-dioxo-3-piperidyl]-1-oxo-isoindolin-5-yl]piperazin-1-yl]methyl]-1-piperidyl]methyl]cyclopropyl]methoxy]-7-[8-ethyl-7-fluoro-3-(methoxymethoxy)-1-naphthyl]-8-fluoro-pyrido[4,3-d]pyrimidin-4-yl]-N,N-dimethyl-4,6,7,8-tetrahydropyrazolo[1,5-a][1,4]diazepine-2-carboxamide (55 mg, 48.6 µmol, 1 eq) was added HCl solution (4 M in dioxane, 1.00 eq). The mixture was stirred at 25° C. for 0.5 hours. LCMS showed complete consumption of the reactant and a new peak of ~97% peak area with desired mass. The reaction mixture was filtered and concentrated under reduced pressure to give a crude residue, which was purified by prep-HPLC (FA condition; column: Phenomenex Luna C18 150*25 mm*10 µm; mobile phase: [water (FA)-ACN]; gradient: 12%-42% B over 10 minutes) to give (S)-3-chloro-5-(2-((1-((4-((4-(2-(2,6-dioxopiperidin-3-yl)-1-oxoisoindolin-5-yl)piperazin-1-yl)methyl)piperidin-1-yl)methyl)cyclopropyl)methoxy)-7-(8-ethyl-7-fluoro-3-hydroxynaphthalen-1-yl)-8-fluoropyrido[4,3-d]pyrimidin-4-yl)-N,N-dimethyl-5,6,7,8-tetrahydro-4H-pyrazolo[1,5-a][1,4]diazepine-2-carboxamide (23 mg, 20.9 µmol, 43.0% yield, 99% purity) as a white solid. LCMS: [M+H]$^+$=1085.5. $^1$H NMR (400 MHZ, DMSO-d$_6$) δ=10.95 (s, 1H), 10.12-9.75 (m, 1H), 9.20-9.07 (m, 1H), 8.15 (s, 1H), 7.80-7.75 (m, 1H), 7.52 (d, J=8.6 Hz, 1H), 7.39-7.32 (m, 2H), 7.07-7.02 (m, 2H), 7.00 (d, J=2.6 Hz, 1H), 5.29-5.14 (m, 2H), 5.08-5.02 (m, 1H), 4.48 (br d, J=5.8 Hz, 2H), 4.37-4.26 (m, 5H), 4.24-4.17 (m, 1H), 3.29-3.24 (m, 7H), 3.00 (d, J=17.8 Hz, 8H), 2.63-2.56 (m, 3H), 2.46-2.44 (m, 3H), 2.40-2.35 (m, 3H), 2.17-2.08 (m, 3H), 2.00-1.86 (m, 3H), 1.69-1.60 (m, 2H), 1.54-1.45 (m, 1H), 1.11-0.98 (m, 2H), 0.74 (t, J=7.4 Hz, 3H), 0.62 (br s, 2H), 0.42 (br s, 2H).

Compounds 94 and 102 were prepared via similar synthetic procedures as example 25.

| Cpd #. | Characterization |
| --- | --- |
| 94 | LCMS: [M + H]$^+$ = 1125.7<br>$^1$H NMR (400 MHz, MeOD-d$_4$) δ = 9.21-9.14 (m, 1H), 7.71-7.66 (m, 1H), 7.62-7.62 (m, 1H), 7.65-7.62 (m, 1H), 7.31 (d, J = 2.4 Hz, 1H), 7.29-7.22 (m, 1H), 7.10-7.02 (m, 3H), 5.36-5.28 (m, 2H), 5.25-5.15 (m, 2H), 5.14-5.04 (m, 3H), 4.51-4.42 (m, 4H), |

| Cpd #. | Characterization |
|---|---|
| | 4.40 (br d, J = 4.8 Hz, 3H), 3.35 (br d, J = 4.4 Hz, 5H), 3.13 (s, 3H), 3.11 (s, 3H), 2.96-2.71 (m, 5H), 2.66-2.58 (m, 5H), 2.56-2.42 (m, 7H), 2.25-2.11 (m, 3H), 2.10-1.97 (m, 3H), 1.91-1.79 (m, 2H), 1.75-1.66 (m, 2H), 1.62-1.49 (m, 2H), 1.37-1.25 (m, 3H), 0.83-0.75 (m, 4H).<br>LCMS: [M + H]⁺ = 1107.5 |
| 102 | ¹H NMR (400 MHz, MeOD-d₄) δ = 9.21-9.16 (m, 1H), 8.54-8.48 (m, 1H), 7.66-7.61 (m, 2H), 7.37 (t, J = 7.6 Hz, 1H), 7.30 (d, J = 2.6 Hz, 1H), 7.17 (d, J = 7.2 Hz, 1H), 7.10-7.05 (m, 2H), 6.98 (s, 1H), 5.35-5.16 (m, 2H), 5.13-5.07 (m, 1H), 4.61-4.56 (m, 2H), 4.50-4.42 (m, 4H), 4.39 (br d, J = 6.2 Hz, 3H), 4.36-4.33 (m, 1H), 3.35 (br d, J = 2.8 Hz, 4H), 3.13 (s, 3H), 3.11 (s, 3H), 2.96-2.85 (m, 2H), 2.81-2.73 (m, 1H), 2.63 (br s, 4H), 2.58-2.49 (m, 5H), 2.49-2.24 (m, 4H), 2.18-2.04 (m, 3H), 1.98-1.89 (m, 2H), 1.78 (br s, 2H), 1.63-1.55 (m, 2H), 1.35-1.26 (m, 1H), 0.90 (t, J = 7.2 Hz, 5H), 0.80-0.75 (m, 2H). |

Example 26: Preparation of 3-(5-(4-((7-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-2,7-diazaspiro[3.5]nonan-2-yl)methyl)piperidin-1-yl)-1-oxoisoindolin-2-yl)piperidine-2,6-dione (Compound 131)

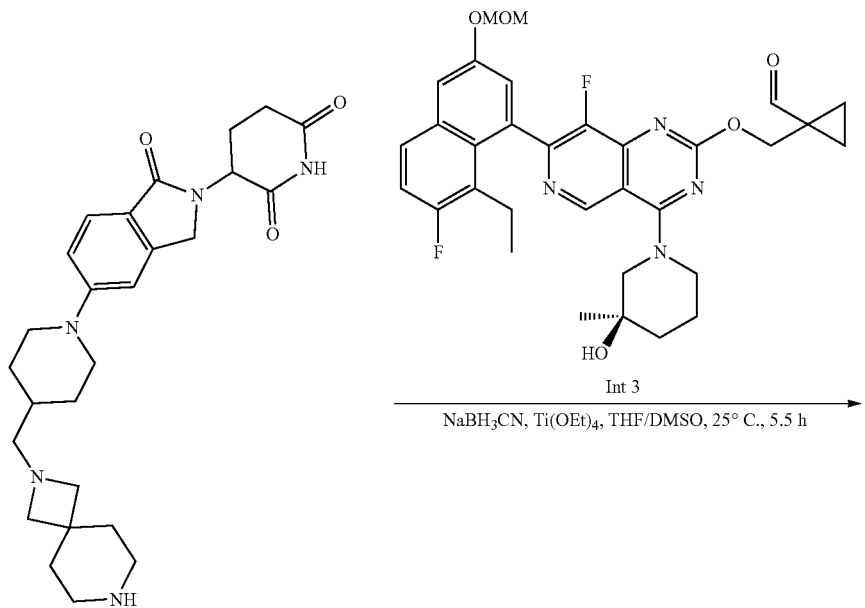

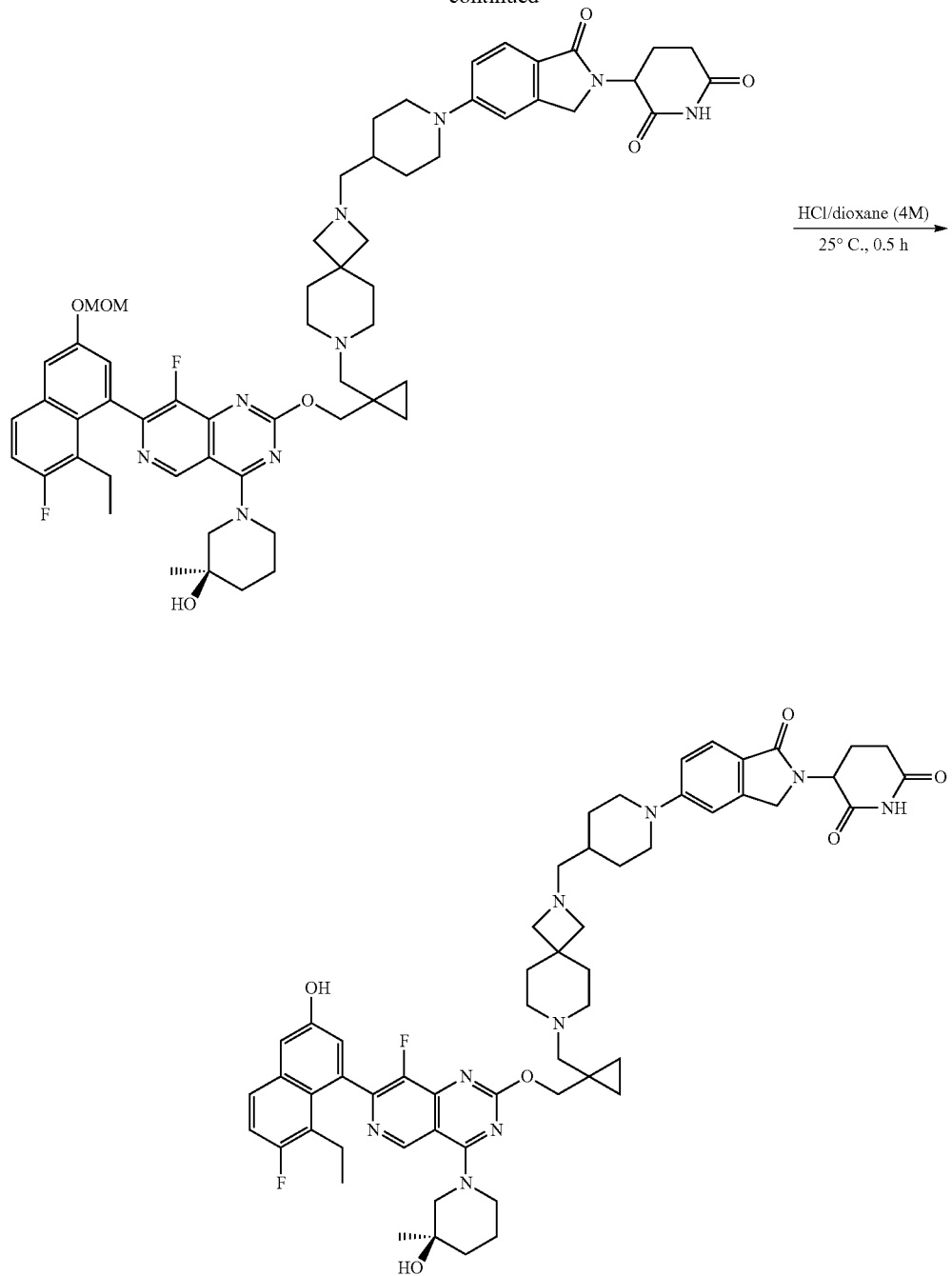

Compound 131

Step 1: Preparation of 3-(5-(4-((7-(((1-(((7-(8-ethyl-7-fluoro-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-2,7-diazaspiro[3.5]nonan-2-yl)methyl)piperidin-1-yl)-1-oxoisoindolin-2-yl)piperidine-2,6-dione To a solution of 3-[5-[4-(2,7-diazaspiro[3.5]nonan-2-ylmethyl)-1-piperidyl]-1-oxo-isoindolin-2-yl]piperidine-2,6-dione (40 mg, 79.6 μmol, 1 eq, HCl) and 1-[7-[8-ethyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropanecarbaldehyde (47.2 mg, 79.6 μmol, 1 eq) in THF (2 mL) and DMSO (1 mL) was added Ti(OEt)$_4$ (90.8 mg, 398 μmol, 82.6 μL, 5 eq) at 25° C. The mixture was stirred for 5 hours. Then NaBH$_3$CN (15.0 mg, 239 μmol, 3 eq) was added and the reaction mixture was stirred for 0.5 hours at 25° C. LCMS showed complete consumption of the reactant and a new peak of ~33% peak area with desired mass. The reaction mixture was diluted with water (10 mL) and extracted with EA (10 mL×3). The combined organic layers were washed with brine (10 mL×2), dried over anhydrous Na$_2$SO$_4$, filtered and concentrated under reduced pressure to give a residue, which was purified by prep-TLC (SiO$_2$, DCM: MeOH=10:1Rf=0.2) to give 3-(5-(4-((7-((1-(((7-(8-ethyl-7-fluoro-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-2,7-diazaspiro[3.5]nonan-2-yl)methyl)piperidin-1-yl)-1-oxoisoindolin-2-yl)piperidine-2,6-dione (15 mg, 12.9 µmol, 16.2% yield, 90% purity) as a white solid.

Step 2: Preparation of 3-(5-(4-((7-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-2,7-diazaspiro[3.5]nonan-2-yl)methyl)piperidin-1-yl)-1-oxoisoindolin-2-yl)piperidine-2,6-dione (Compound 131)

To a solution of 3-[5-[4-[7-[[1-[[7-[8-ethyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropyl]methyl]-2,7-diazaspiro[3.5]nonan-2-yl]methyl]-1-piperidyl]-1-oxo-isoindolin-2-yl]piperidine-2,6-dione (15 mg, 12.9 µmol, 1 eq) in DCM (1 mL) was added HCl solution (4 M in dioxane, 45.0 µL, 13.9 eq). The mixture was stirred at 25° C. for 0.5 hours. LCMS showed full consumption of the reactant a new peak of ~95% peak area with desired mass. The reaction mixture was filtered and concentrated under reduced pressure to give a residue, which was purified by prep-HPLC (FA condition; column: Phenomenex Luna C18 150*25 mm*10 µm; mobile phase: [water (FA)-ACN]; gradient: 10%-40% B over 10 minutes) to give 3-(5-(4-((7-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-2,7-diazaspiro[3.5]nonan-2-yl)methyl)piperidin-1-yl)-1-oxoisoindolin-2-yl)piperidine-2,6-dione (6 mg, 6.01 µmol, 46.4% yield, 100% purity) as a white solid. LCMS: [M+H]$^+$=998.5. $^1$H NMR (400 MHZ, METHANOL-d$_4$) δ=9.21 (d, J=3.8 Hz, 1H), 7.71-7.64 (m, 1H), 7.62 (d, J=8.4 Hz, 1H), 7.33-7.22 (m, 2H), 7.08-7.04 (m, 3H), 5.12-5.07 (m, 1H), 4.53-4.48 (m, 1H), 4.44 (br d, J=4.8 Hz, 2H), 4.38 (d, J=5.8 Hz, 2H), 4.26 (br t, J=13.4 Hz, 1H), 3.92 (br d, J=12.6 Hz, 2H), 3.68-3.59 (m, 2H), 3.56-3.52 (m, 2H), 3.46-3.42 (m, 1H), 2.92-2.74 (m, 9H), 2.71-2.54 (m, 5H), 2.51-2.42 (m, 3H), 2.17-2.12 (m, 2H), 1.88-1.79 (m, 8H), 1.29 (d, J=10.6 Hz, 6H), 0.85-0.78 (m, 5H), 0.57 (br s, 2H).

Example 27: Preparation of 3-[5-[3-[[4-[1-[[7-(8-ethyl-7-fluoro-3-hydroxy-1-naphthyl)-8-fluoro-4-[(3R)-3-hydroxy-3-methyl-1-piperidyl]pyrido[4,3-d]pyrimidin-2-yl]oxymethyl]cyclopropyl methyl]piperazin-1-yl]methyl]azetidin-1-yl]-1-oxo-isoindolin-2-yl]piperidine-2,6-dione (Compound 133)

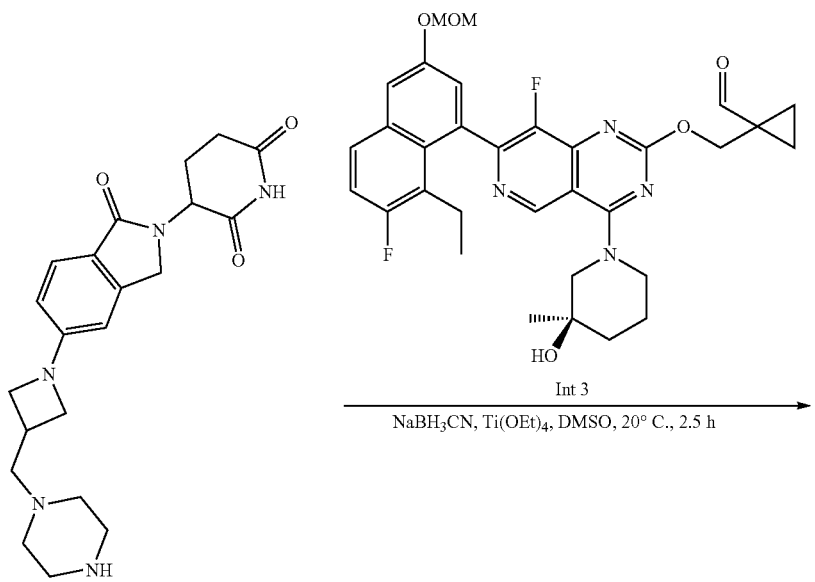
Int 3
NaBH$_3$CN, Ti(OEt)$_4$, DMSO, 20° C., 2.5 h

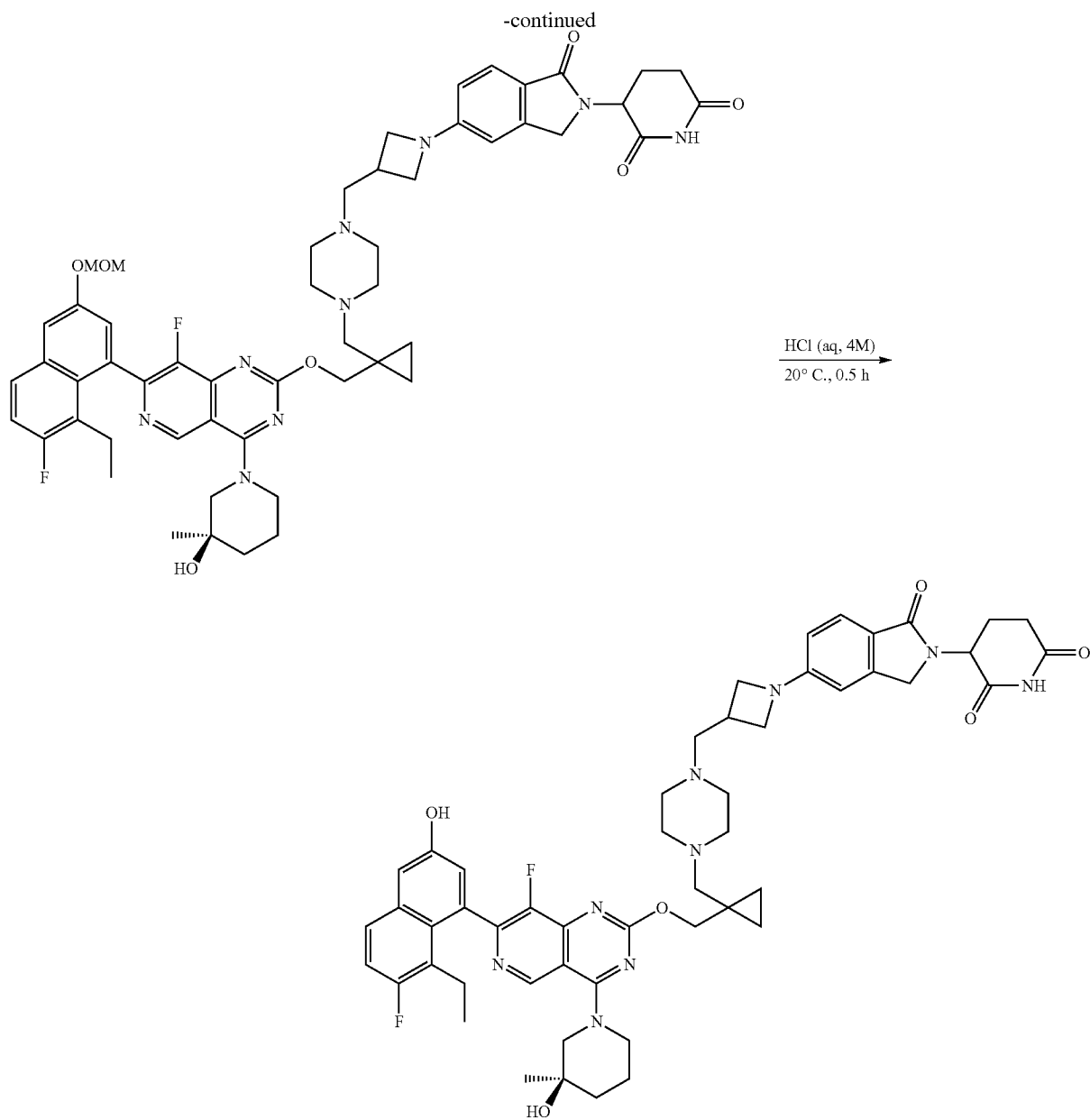

Compound 133

Step 1: Preparation of 3-[5-[3-[[4-[1-[[7-[8-ethyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropyl]methyl]piperazin-1-yl]methyl]azetidin-1-yl]-1-oxo-isoindolin-2-yl]piperidine-2,6-dione To a solution of 1-[7-[8-ethyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropanecarbaldehyde (52.1 mg, 87.8 μmol, 1 eq) and 3-[1-oxo-5-[3-(piperazin-1-ylmethyl)azetidin-1-yl]isoindolin-2-yl]piperidine-2,6-dione (45 mg, 87.9 μmol, 1 eq, TFA) in DMSO (1 mL) was added Ti(OEt)$_4$ (200 mg, 879 μmol, 182.44 μL, 10 eq) and the reaction mixture was stirred at 20° C. for 2 hours. Then NaBH$_3$CN (11.0 mg, 175 μmol, 2 eq) was added and the reaction mixture was stirred at 20° C. for 0.5 hours. LCMS showed a new peak of 54% peak area with desired mass. The reaction mixture was diluted with ethyl acetate (50 mL), washed with saturated bicarbonate solution (50 mL*2), dried over anhydrous sodium sulfate and concentrated under reduced pressure to give a residue, which was purified by prep-TLC (SiO$_2$, DCM: MeOH=10:1) to give 3-[5-[3-[4-[1-[[7-[8-ethyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropyl]methyl]piperazin-1-yl]methyl]azetidin-1-yl]-1-oxo-isoindolin-2-yl]piperidine-2,6-dione (50 mg, 42.8 μmol, 48.7% yield, 83.5% purity) as a yellow solid.

Step 2: Preparation of 3-[5-[3-[4-[[1-[[7-(8-ethyl-7-fluoro-3-hydroxy-1-naphthyl)-8-fluoro-4-[(3R)-3-hydroxy-3-methyl-1-piperidyl]pyrido[4,3-d]pyrimidin-2-yl]oxymethyl]cyclopropyl]methyl]piperazin-1-yl]methyl]azetidin-1-yl]-1-oxo-isoindolin-2-yl]piperidine-2,6-dione (Compound 133)

To a solution of 3-[5-[3-[[4-[1-[7-[8-ethyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropyl]methyl]piperazin-1-yl]methyl]azetidin-1-yl]-1-oxo-isoindolin-2-yl]piperidine-2,6-dione (48 mg, 49.2 µmol, 1 eq) in HCl (4 M in dioxane, 2 mL). The reaction mixture was stirred at 20° C. for 0.5 hours. LCMS showed a new peak of 73% peak area with desired mass. The reaction mixture concentrated under reduced pressure to give a crude residue, which was purified by prep-HPLC (column: Phenomenex Luna C18 150*25 mm*10 µm; mobile phase: [water (FA)-ACN]; gradient: 18%-48% B over 10 minutes) to give 30 mg yellow solid, which was further purified by Pre-HPLC (column: Phenomenex Luna C18 150*25 mm*10 µm; mobile phase: [water (FA)-ACN]; gradient: 17%-47% B over 10 minutes) to give 3-[5-[3-[[4-[[1-[7-(8-ethyl-7-fluoro-3-hydroxy-1-naphthyl)-8-fluoro-4-[(3R)-3-hydroxy-3-methyl-1-piperidyl]pyrido[4,3-d]pyrimidin-2-yl]oxymethyl]cyclopropyl]methyl]piperazin-1-yl]methyl]azetidin-1-yl]-1-oxo-isoindolin-2-yl]piperidine-2,6-dione (15 mg, 15.7 µmol, 31.8% yield, 97.4% purity) as a light yellow solid. LCMS: [M+H]$^+$=930.4. $^1$H NMR (400 MHZ, MeOD-d$_4$) δ=9.21 (d, J=7.2 Hz, 1H), 8.46 (s, 1H), 7.69-7.61 (m, 1H), 7.55 (d, J=8.8 Hz, 1H), 7.29-7.18 (m, 2H), 7.05 (t, J=2.8 Hz, 1H), 6.49-6.42 (m, 2H), 5.11-5.04 (m, 1H), 4.53-4.40 (m, 4H), 4.32 (br t, J=4.0 Hz, 2H), 4.29-4.24 (m, 1H), 4.08 (br t, J=7.6 Hz, 2H), 3.71-3.53 (m, 4H), 3.50-3.45 (m, 1H), 3.04-3.00 (m, 1H), 2.95-2.87 (m, 2H), 2.84-2.78 (m, 4H), 2.77-2.64 (m, 6H), 2.49-2.41 (m, 2H), 2.27-2.20 (m, 1H), 2.18-2.09 (m, 2H), 1.90-1.77 (m, 3H), 1.29 (d, J=10.0 Hz, 3H), 0.85-0.78 (m, 5H), 0.61 (s, 2H).

Example 28: Preparation of (3S)-3-(5-(4-((7-(((1-(((4-(2-oxa-6-azabicyclo[5.1.0]octan-6-yl)-7-(8-ethyl-7-fluoro-3-hydroxynaphthalen-1-yl)-8-fluoro-pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione (Compound 165)

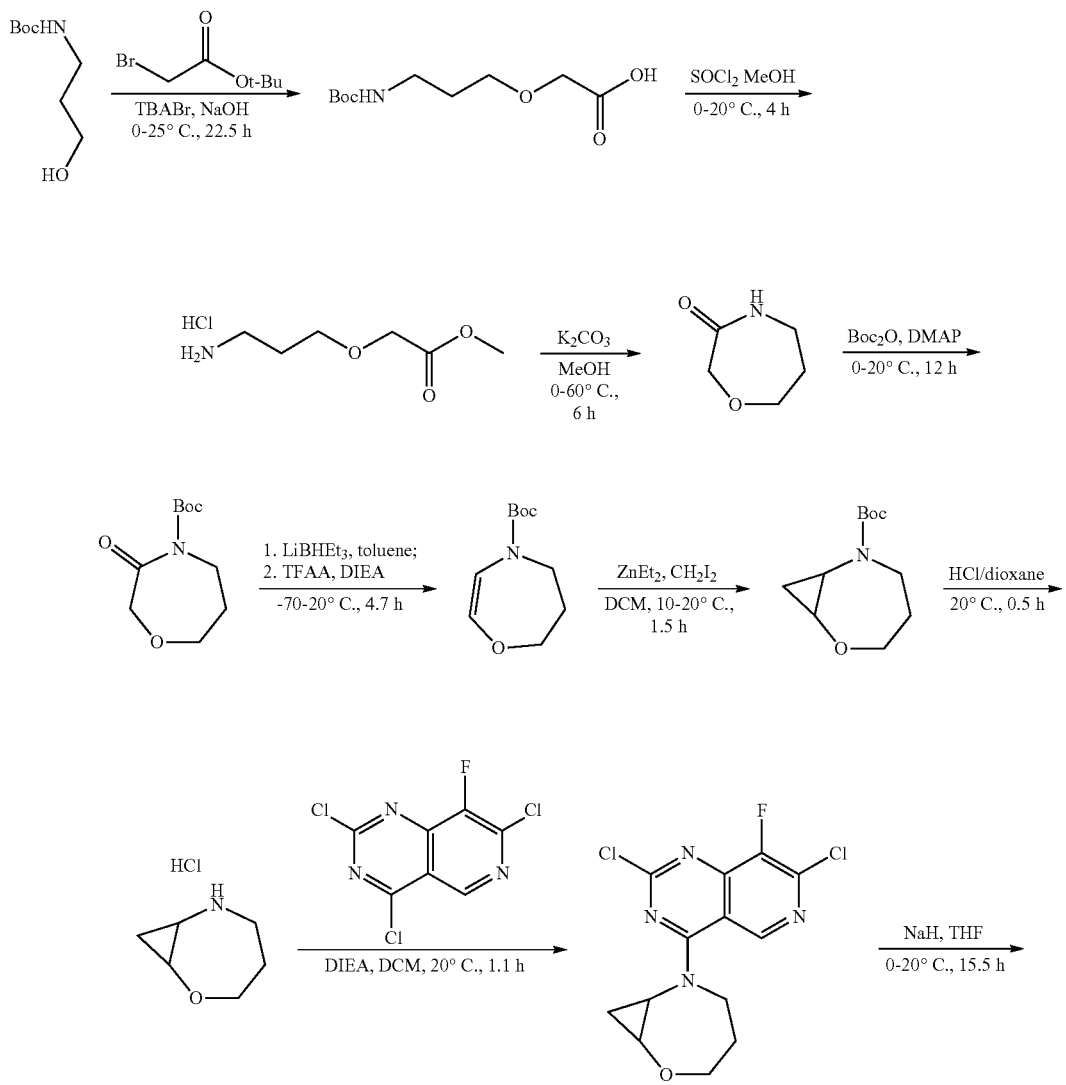

495
496
-continued
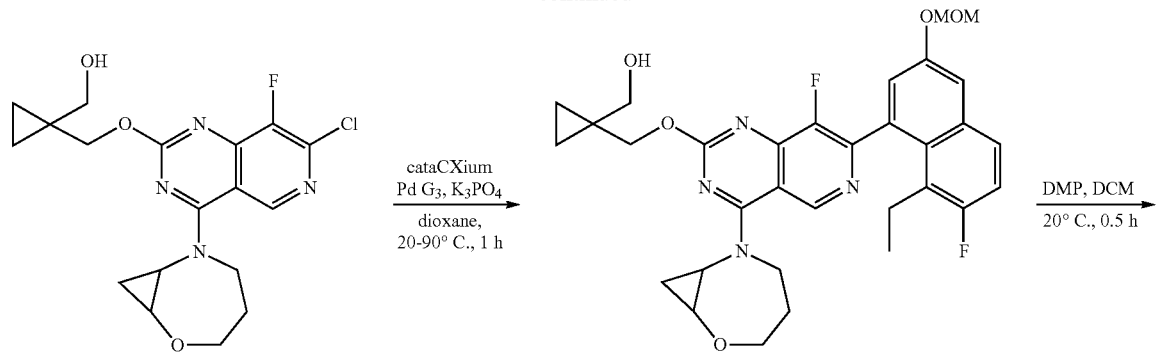
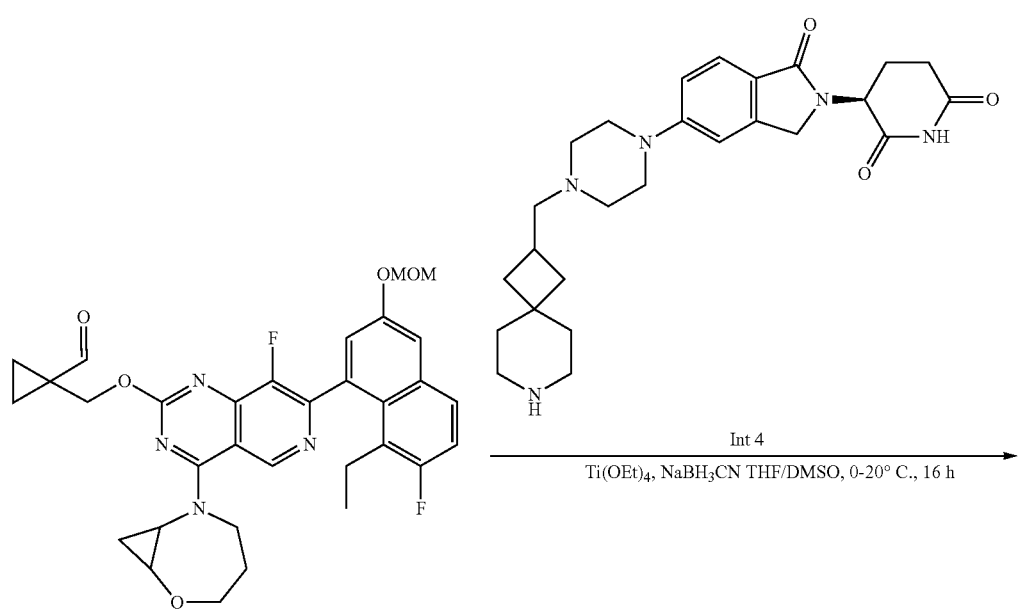
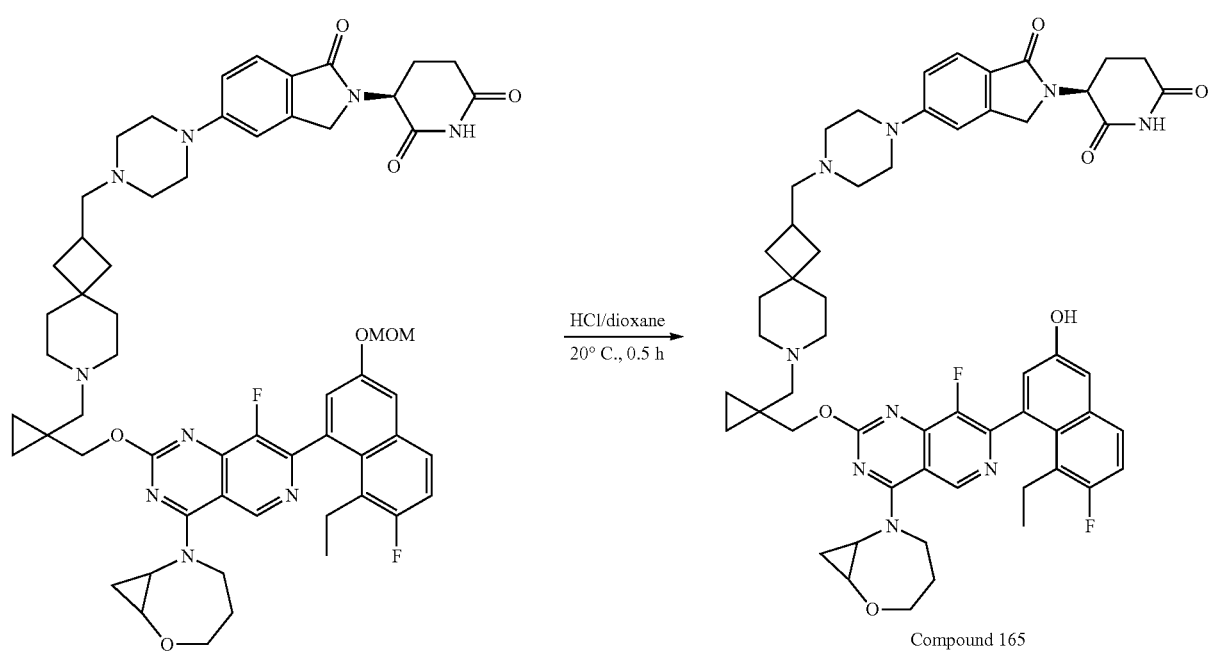
Compound 165

Step 1: Preparation of 2-(3-((tert-butoxycarbonyl)amino)propoxy)acetic acid

To a solution of tert-butyl N-(3-hydroxypropyl)carbamate (12 g, 68.5 mmol, 11.7 mL, 1 eq) and TBAB (1.1 g, 3.4 mmol, 0.05 eq) in toluene (120 mL) was added NaOH (6 M, 57.1 mL, 5 eq) at 0-5° C. The mixture was stirred at 20° C. for 0.5 hours. A solution of tert-butyl 2-bromoacetate (16 g, 82.2 mmol, 12.1 mL, 1.2 eq) in toluene (16 mL) was added dropwise to the mixture at 0-10° C. Then, the mixture was stirred at 20° C. for 12 hours. And the reaction mixture was stirred at 60° C. for another 10 hours. The aqueous phase was washed with MTBE (100 mL×2) and was carefully acidified with 1 N HCl to pH=2-3. The resulting mixture was extracted with EA (250 mL×3). The combined organic layers were washed with brine (100 mL), dried over anhydrous $Na_2SO_4$, filtered, and concentrated under reduced pressure to give 2-(3-((tert-butoxycarbonyl)amino)propoxy) acetic acid as a light yellow oil. $^1$H NMR (400 MHZ, MeOD-$d_6$) δ=4.06 (s, 2H), 3.56 (t, J=6 Hz, 1H), 3.16 (t, J=6.4 Hz, 2H), 1.77-1.71 (m, 2H), 1.43 (s, 9H).

Step 2: Preparation of preparation of methyl 2-(3-aminopropoxy)acetate

To a solution of 2-[3-(tert-butoxycarbonylamino) propoxy]acetic acid (36.2 g, 155 mmol, 1 eq) in MeOH (360 mL) was added $SOCl_2$ (49.9 g, 419 mmol, 30.4 mL, 2.7 eq) dropwise at 0-5° C. Then the mixture was stirred at 20° C. for 4 hours. LCMS showed complete consumption of the reactant. The reaction mixture was concentrated under reduced pressure to give methyl 2-(3-aminopropoxy)acetate as a light yellow oil. $^1$H NMR (400 MHZ, DMSO-$d_6$) δ=8.07 (s, 3H), 4.11 (s, 2H), 3.65 (s, 3H), 3.53 (t, J=6 Hz, 2H), 2.88-2.8 (m, 2H), 1.86-1.8 (m, 2H).

Step 3: Preparation of 1,4-oxazepan-3-one

To a solution of methyl 2-(3-aminopropoxy)acetate (31 g, 169 mmol, 1 eq, HCl) in MeOH (310 mL) was added $K_2CO_3$ (49 g, 355 mmol, 2.1 eq) at 20° C. The reaction mixture was stirred at 60° C. for 6 hours. The reaction mixture was concentrated under reduced pressure to give a residue, which was purified by silica gel chromatography (PE/EA=1/1 to 0/1, then EA/MeOH=10/1) to give 1,4-oxazepan-3-one as a light yellow oil. $^1$H NMR (400 MHZ, DMSO-$d_6$) δ=7.66 (s, 1H), 4.00 (s, 2H), 3.76 (t, J=5.6 Hz, 2H), 3.20-3.17 (m, 2H), 1.78-1.73 (m, 2H).

Step 4: Preparation of preparation of tert-butyl 3-oxo-1,4-oxazepane-4-carboxylate To a solution of 1,4-oxazepan-3-one (10 g, 86.9 mmol, 1 eq) and DMAP (1.06 g, 8.69 mmol, 0.1 eq) in THF (100 mL) was added (Boc)$_2$O (26.5 g, 122 mmol, 27.9 mL, 1.4 eq) at 0-10° C. portion wise. The reaction mixture was stirred at 20° C. for 12 hours. LCMS showed a new peak of 97.3% peak area with desired mass. The reaction mixture was poured into water (400 mL) and the mixture was extracted with EtOAc (100 mL×3). The combined organic layers were washed with brine (50 mL), dried over anhydrous $Na_2SO_4$, filtered, and concentrated under reduced pressure to give a residue. The residue was purified by column chromatography (PE/EA=20/1 to 2/1) to give tert-butyl 3-oxo-1,4-oxazepane-4-carboxylate as a light yellow oil. $^1$H NMR (400 MHZ, DMSO-$d_6$) δ=4.26 (s, 2H), 3.87-3.85 (m, 2H), 3.81-3.8 (s, 2H), 1.8-1.74 (m, 2H), 1.44 (s, 9H).

Step 5: Preparation of tert-butyl 6,7-dihydro-1,4-oxazepine-4(5H)-carboxylate To a solution of tert-butyl 3-oxo-1,4-oxazepane-4-carboxylate (1 g, 4.65 mmol, 1 eq) in toluene (10 mL) was added LiBHEt$_3$ (1 M, 5.11 mL, 1.1 eq) dropwise at −70° C. under $N_2$ atmosphere. Then the mixture was stirred at −70° C. for 0.5 hours. A solution of DIPEA (1.50 g, 11.6 mmol, 2.02 mL, 2.5 eq) and DMAP (56.8 mg, 465 µmol, 0.1 eq) in toluene (2 mL) was added dropwise to the mixture at −70° C. After that, the reaction mixture was stirred at −70° C. for another 10 minutes. TFAA (1.95 g, 9.29 mmol, 1.29 mL, 2 eq) was added dropwise at −70° and the reaction mixture was stirred at 20° C. for 2 hours. DIPEA (600 mg, 4.65 mmol, 809 µL, 1 eq) was added dropwise to the mixture at −70° C. and the reaction mixture was stirred at −70° C. for 0.1 hour under $N_2$ atmosphere. The reaction mixture was quenched with slow addition of saturated aqueous NaHCO$_3$ solution (30 mL) under stirring at 0-5°. EtOAc (100 mL) and water (100 mL) were added to the mixture and the organic layers were separated. The aqueous phase was extracted with EtOAc (100 mL×2). The organic layers were combined and washed with brine (50 mL), dried over anhydrous $Na_2SO_4$, filtered, and concentrated under reduced pressure to give a residue, which was purified by column chromatography (PE/EA=100/1) to give tert-butyl 6,7-dihydro-1,4-oxazepine-4(5H)-carboxylate as a light yellow oil. $^1$H NMR (400 MHZ, CDCl$_3$) δ=5.91-5.71 (m, 2H), 4.01 (s, 2H), 3.78 (t, J=5.6 Hz, 2H), 1.99-1.95 (m, 2H), 1.49 (s, 9H).

Step 6: Preparation of tert-butyl 2-oxa-6-azabicyclo[5.1.0]octane-6-carboxylate To a solution of tert-butyl 6,7-dihydro-1,4-oxazepine-4 (5H)-carboxylate (1 g, 5.02 mmol, 1 eq) in DCM (10 mL) was added ZnEt$_2$ (1 M, 12.6 mL, 2.5 eq) dropwise at 20° C. under $N_2$ atmosphere. The reaction mixture was stirred at 20° C. for 0.5 hours. A solution of CH$_2$I$_2$ (5.38 g, 20.1 mmol, 1.62 mL, 4 eq) in DCM (4 mL) was added dropwise to the mixture at 10-20° C. and the reaction mixture was stirred at 20° C. for 1 hour. The reaction mixture was quenched with slow addition of saturated aqueous NH$_4$Cl solution (30 mL) under stirring at 0-5° C. DCM (50 mL) and water (50 mL) were added to the mixture. The aqueous phase was extracted with DCM (50 mL×2). The organic layers were combined, washed with brine (30 mL), dried over anhydrous $Na_2SO_4$, filtered, and concentrated under reduced pressure to give a residue, which was purified by column chromatography (PE/EA=10/1 to 2/1) to give tert-butyl 2-oxa-6-azabicyclo [5.1.0]octane-6-carboxylate as a light yellow oil. $^1$H NMR (400 MHZ, CDCl$_3$) δ=4.13-3.93 (m, 2H), 3.69-3.65 (t, J=12.8 Hz, 1H), 3.41-3.39 (m, 1H), 3.4-3.0 (m, 1H), 2.36 (d, J=5.2 Hz, 1H), 1.91-1.86 (m, 1H), 1.74 (d, J=14 Hz, 1H), 1.595 (s, 9H), 1.17-1.08 (m, 2H).

Step 7: Preparation of 2-oxa-6-azabicyclo[5.1.0]octane

To a solution of tert-butyl 2-oxa-6-azabicyclo[5.1.0]octane-6-carboxylate (1.6 g, 7.50 mmol, 1 eq) in DCM (15 mL) was added dropwise HCl solution (4 M in dioxane, 15 mL, 8.00 eq) at 20° C. The reaction mixture was stirred at 20° C. for 0.5 hours. TLC (PE/EA=3/1, 12) showed full consumption of the starting material. The reaction mixture was concentrated under reduced pressure below 35° C. to give 2-oxa-6-azabicyclo[5.1.0]octane as a light yellow solid. $^1$H NMR (400 MHZ, DMSO-$d_6$) δ=10.46 (s, 1H), 8.81 (s, 1H), 3.92 (d, J=12.4 Hz, 1H), 3.66-3.64 (m, 1H), 3.54-3.50 (m, 1H), 3.35 (s, 1H), 3.31 (s, 1H), 2.68 (s, 1H), 1.91-1.87 (m, 2H), 1.30-1.27 (m, 1H), 1.25-1.07 (m, 1H).

Step 8: Preparation of 6-(2,7-dichloro-8-fluoro-pyrido[4,3-d]pyrimidin-4-yl)-2-oxa-6-azabicyclo [5.1.0]octane To a solution of 2-oxa-6-azabicyclo[5.1.0]octane (900 mg, 6.02 mmol, 1 eq, HCl) in DCM (20 mL) was added DIPEA (1.94 g, 15 mmol, 2.62 mL, 2.5 eq) at 20° C. The mixture was stirred at 20° C. for 6 minutes. 2,4,7-trichloro-8-fluoro-pyrido[4,3-d]pyrimidine (1.52 g, 6.02 mmol, 1 eq) was added to the mixture portion wise at 20° C. and the reaction mixture was stirred at 20° C. for another hour. LCMS showed a new peak of 89.543% peak area with desired mass. The reaction mixture was poured into water (60 mL). The organic layers were collected, and the aqueous layer was extracted with DCM (30 mL×3). The organic layers were combined, washed with brine (20 mL), dried over anhydrous $Na_2SO_4$, filtered, and concentrated under reduced pressure to give a residue, which was purified by column chromatography (PE/EA=4/1 to 0/1) to give 6-(2,7-dichloro-8-fluoropyrido[4,3-d]pyrimidin-4-yl)-2-oxa-6-azabicyclo[5.1.0]octane as a light yellow solid. $^1$H NMR (400 MHZ, DMSO-$d_6$) δ=9.33 (s, 1H), 4.46 (br d, J=13.6 Hz, 1H), 3.90-3.81 (m, 1H), 3.79-3.69 (m, 2H), 3.62 (br t, J=11.6 Hz, 1H), 3.50-3.41 (m, 1H), 2.12-1.99 (m, 1H), 1.96-1.82 (m, 1H), 1.28 (q, J=6.8 Hz, 1H), 0.84-0.68 (m, 1H).

Step 9: Preparation of (1-(((4-(2-oxa-6-azabicyclo [5.1.0]octan-6-yl)-7-chloro-8-fluoropyrido[4,3-d] pyrimidin-2-yl)oxy)methyl)cyclopropyl)methanol To a solution of [1-(hydroxymethyl)cyclopropyl]methanol (450 mg, 4.41 mmol, 1 eq) in THF (5 mL) was added NaH (176 mg, 4.41 mmol, 60% purity, 1 eq) portion wise at 0-5° C. under $N_2$ atmosphere. The reaction mixture was stirred at 0-5° C. for 0.5 hours. A solution of 6-(2,7-dichloro-8-fluoropyrido[4,3-d]pyrimidin-4-yl)-2-oxa-6-azabicyclo [5.1.0]octane (1.45 g, 4.41 mmol, 1 eq) in THF (10 mL) was added dropwise to the mixture at 0-5° C. and the reaction mixture was stirred at 0-10° C. for 6 hours. LCMS showed a new peak of 32.691% peak area with desired mass and another major peak of 57.108% peak area with mass signal of the reactant. The reaction mixture was warmed to 20° C. and stirred for 12 hours. LCMS showed the peak area of the desired product increased to 51.814%. The reaction mixture was quenched by slow addition of saturated aqueous $NH_4Cl$ solution (30 mL) under stirring at 0-5° C. EtOAc (40 mL) and water (80 mL) were added to the mixture, and the organic layer was collected. The aqueous phase was extracted with EtOAc (40 mL×2). The organic layers were collected, washed with brine (20 mL), dried over anhydrous $Na_2SO_4$, filtered, and concentrated under reduced pressure to give a residue, which was purified by normal phase HPLC (Welch Ultimate XB-SiOH 250*700 μm; mobile phase: [Hexane-EtOH]; gradient: 1%-40% B over 15 minutes) to give (1-(((4-(2-oxa-6-azabicyclo[5.1.0]octan-6-yl)-7-chloro-8-fluoropyrido[4,3-d]pyrimidin-2-yl)oxy)methyl)cyclopropyl)methanol as a light yellow solid. $^1$H NMR (400 MHZ, $CDCl_3$) δ=9.14 (s, 1H), 4.69 (d, J=13.6 Hz, 1H), 4.61 (d, J=11.6 Hz, 1H), 4.36 (d, J=12 Hz, 1H), 3.77 (d, J=3.6 Hz, 1H), 3.75-3.73 (m, 2H), 3.56-3.53 (m, 2H), 3.38 (d, J=12 Hz, 1H), 3.36-3.14 (m, 1H), 2.43-2.40 (m, 1H), 1.93 (d, J=14.8 Hz, 1H), 1.39-1.37 (m, 1H), 0.82-0.81 (m, 1H), 0.71-0.69 (m, 2H), 0.62-0.61 (m, 2H).

Step 10: Preparation of (1-(((4-(2-oxa-6-azabicyclo [5.1.0]octan-6-yl)-7-(8-ethyl-7-fluoro-3-(methoxymethoxy)naphthalen-1-yl)-8-fluoropyrido [4,3-d]pyrimidin-2-yl)oxy)methyl)cyclopropyl) methanol To a solution of [1-[7-chloro-8-fluoro-4-(2-oxa-6-azabicyclo[5.1.0]octan-6-yl)pyrido[4,3-d]pyrimidin-2-yl]oxymethyl]cyclopropyl]methanol (500 mg, 1.27 mmol, 1 eq), 2-[8-ethyl-7-fluoro-3-(methoxymethoxy)-1-naphthyl]-4,4,5,5-tetramethyl-1,3,2-dioxaborolane (502 mg, 1.39 mmol, 1.1 eq) and $K_3PO_4$ (1.5 M, 2.53 mL, 3 eq) in dioxane (15 mL) was added [2-(2-aminophenyl)phenyl]palladium(1+); bis(1-adamantyl)-butyl-phosphane; methanesulfonate (184 mg, 253 μmol, 0.2 eq) at 20° C. under $N_2$ atmosphere. The reaction mixture was stirred at 90° C. for 1 hour. LCMS showed a new peak of 50.071% peak area with desired mass. The reaction mixture was poured into water (40 mL) and the organic layer was collected. The aqueous phase was extracted with EtOAc (20 mL×3). The organic layers were combined, washed with brine (20 mL), dried over anhydrous $Na_2SO_4$, filtered, and concentrated under reduced pressure to give a residue, which was purified by column chromatography (PE/EA=1/3 to 0/1) and further purified by preparative TLC to give (1-(((4-(2-oxa-6-azabicyclo[5.1.0]octan-6-yl)-7-(8-ethyl-7-fluoro-3-(methoxymethoxy) naphthalen-1-yl)-8-fluoropyrido[4,3-d]pyrimidin-2-yl)oxy) methyl)cyclopropyl)methanol as a light yellow solid. $^1$H NMR (400 MHZ, DMSO-$d_6$) δ=9.40 (d, J=19.2 Hz, 1H), 7.7-7.66 (m, 1H), 7.52 (d, J=2.4 Hz, 1H), 7.27 (s, 1H), 7.25-7.23 (m, 1H), 5.31 (s, 2H), 4.82-4.79 (m, 1H), 4.53-4.70 (m, 1H), 3.81-3.78 (m, 1H), 3.77-3.76 (m, 1H), 3.76-3.75 (m, 2H), 3.53-3.52 (m, 1H), 3.49 (s, 3H), 3.48-3.44 (m, 2H), 3.44-3.20 (m, 1H), 2.51-2.5 (m, 2H), 2.49-2.47 (m, 1H), 1.85-1.95 (m, 1H), 1.44-1.39 (m, 1H), 0.88-0.83 (m, 4H), 0.69-0.61 (m, 4H).

Step 11: Preparation of 1-(((4-(2-oxa-6-azabicyclo [5.1.0]octan-6-yl)-7-(8-ethyl-7-fluoro-3-(methoxymethoxy)naphthalen-1-yl)-8-fluoropyrido [4,3-d]pyrimidin-2-yl)oxy)methyl)cyclopropane-1-carbaldehyde To a solution of [1-[7-[8-ethyl-7-fluoro-3-(methoxymethoxy)-1-naphthyl]-8-fluoro-4-(2-oxa-6-azabicyclo[5.1.0]octan-6-yl)pyrido[4,3-d]pyrimidin-2-yl]oxymethyl]cyclopropyl]methanol (300 mg, 506.22 μmol, 1 eq) in DCM (3 mL) was added DMP (279 mg, 658 μmol, 204 μL, 1.3 eq) at 20° C. The reaction mixture was stirred at 20° C. for 0.5 hours. LCMS showed a new peak of 67.484% peak area with desired mass and complete consumption of starting material. The reaction mixture was quenched by slow addition of saturated aqueous $Na_2SO_3$ solution (5 mL) under stirring at 0-10° C. DCM (5 mL) and water (5 mL) were added to the mixture and the organic layer was separated. The aqueous phase was extracted with DCM (5 mL×2). The organic layers were combined, washed with brine (3 mL), dried over anhydrous $Na_2SO_4$, filtered, and concentrated under reduced pressure to give a residue, which was purified by preparative TLC (PE/EA=1/2) to give 1-(((4-(2-oxa-6-azabicyclo[5.1.0]octan-6-yl)-7-(8-ethyl-7-fluoro-3-(methoxymethoxy)naphthalen-1-yl)-8-fluoropyrido[4,3-d]

pyrimidin-2-yl)oxy)methyl)cyclopropane-1-carbaldehyde as a light yellow solid. ¹H NMR (400 MHZ, CDCl₃) δ=9.37 (d, J=21.2 Hz, 1H), 9.26 (s, 1H), 7.7-7.66 (m, 1H), 7.52 (d, J=2.8 Hz, 1H), 7.26-7.23 (m, 2H), 5.31 (s, 2H), 4.78-4.72 (m, 3H), 4.05-3.81 (m, 1H), 3.77-3.76 (m, 2H), 3.58-3.48 (m, 4H), 3.21-3.20 (m, 1H), 2.52-2.50 (m, 2H), 2.50-2.49 (m, 1H), 1.95-1.90 (m, 1H), 1.43-1.33 (m, 5H), 0.85-0.81 (m, 4H).

Step 12: Preparation of (3S)-3-(5-(4-((7-((1-(((4-(2-oxa-6-azabicyclo[5.1.0]octan-6-yl)-7-(8-ethyl-7-fluoro-3-(methoxymethoxy)naphthalen-1-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione To a solution of 1-[7-[8-ethyl-7-fluoro-3-(methoxymethoxy)-1-naphthyl]-8-fluoro-4-(2-oxa-6-azabicyclo[5.1.0]octan-6-yl)pyrido[4,3-d]pyrimidin-2-yl]oxymethyl]cyclopropanecarbaldehyde (115 mg, 195 μmol, 1 eq) and (3S)-3-[5-[4-(7-azaspiro[3.5]nonan-2-ylmethyl)piperazin-1-yl]-1-oxo-isoindolin-2-yl]piperidine-2,6-dione (90.7 mg, 181 μmol, 0.927 eq, HCl) in THF (3 mL) and DMSO (1 mL) was added Ti(OEt)₄ (550 mg, 2.41 mmol, 0.5 mL, 12.4 eq) at 20° C. The reaction mixture was stirred at 20° C. for 2 hours. (3S)-3-[5-[4-(7-azaspiro[3.5]nonan-2-ylmethyl)piperazin-1-yl]-1-oxo-isoindolin-2-yl]piperidine-2,6-dione (45.33 mg, 90.29 μmol, 0.464 eq, HCl) was added to the mixture at 20° C. and the mixture was stirred at 20° C. for 12 hours. (3S)-3-[5-[4-(7-azaspiro[3.5]nonan-2-ylmethyl)piperazin-1-yl]-1-oxo-isoindolin-2-yl]piperidine-2,6-dione (97.8 mg, 195 μmol, 1 eq, HCl) was added to the mixture at 20° C. and the mixture was stirred at 20° C. for 1 hour. NaBH₃CN (122 mg, 1.95 mmol, 10 eq) was added to the mixture at 0-5° C. and the mixture was stirred at 20° C. for 1 hour. LCMS showed a new peak of 83.873% peak area with desired mass. EtOAc (10 mL) and water (30 mL) were added to the mixture and the mixture was carefully basified with a saturated solution of NaHCO₃ to pH=8. The mixture was filtered, and the filtrate was extracted with EtOAc (10 mL×3). The combined organic layers were washed with brine (5 mL), dried over anhydrous Na₂SO₄, and concentrated under reduced pressure to give a residue, which was purified by preparative reversed phase liquid (FA; ACN/H₂O: 30% to 40%) and further purified by another round of preparative HPLC (Waters Xbridge C18 150*50 mm*10 μm; mobile phase: [water (NH₄HCO₃)-ACN]; gradient: 40%-70% B over 10 minutes) to give (3S)-3-(5-(4-((7-((1-(((4-(2-oxa-6-azabicyclo[5.1.0]octan-6-yl)-7-(8-ethyl-7-fluoro-3-(methoxymethoxy)naphthalen-1-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione as a light yellow solid. ¹H NMR (400 MHZ, CDCl₃) δ=10.94 (s, 1H), 9.41 (d, J=23.2 Hz, 1H), 7.89-7.88 (m, 1H), 7.66 (s, 1H), 7.52-7.42 (m, 1H), 7.23-7.22 (m, 1H), 7.20-7.15 (m, 1H), 7.04-7.02 (m, 2H), 5.34-5.32 (m, 2H), 5.05-5.02 (m, 1H), 4.50-4.30 (m, 6H), 3.75-3.5 (m, 8H), 3.48 (s, 3H), 3.23 (s, 4H), 2.80-2.75 (m, 1H), 2.46-2.30 (m, 17H), 1.95-1.85 (m, 3H), 1.55-1.51 (m, 2H), 1.34-1.31 (m, 7H), 0.75-0.71 (m, 4H).

Step 13: Preparation of (3S)-3-(5-(4-((7-((1-(((4-(2-oxa-6-azabicyclo[5.1.0]octan-6-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione (Compound 165)

To a solution of (3S)-3-(5-(4-((7-((1-(((4-(2-oxa-6-azabicyclo[5.1.0]octan-6-yl)-7-(8-ethyl-7-fluoro-3-(methoxymethoxy)naphthalen-1-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione (80 mg, 76.9 μmol, 1 eq) in DCM (0.3 mL) was added HCl solution (2 M in dioxane, 38.5 μL, 1 eq) at 20° C. and the reaction mixture was stirred at 20° C. for 0.5 hours. LCMS showed a major new peak of near 100% peak area with desired mass and full consumption of the starting material. The reaction mixture was concentrated under reduced pressure below 30° C. to give a residue, which was purified by preparative HPLC (Phenomenex Luna C18 150*25 mm*10 μm; mobile phase: [water (FA)-ACN]; gradient: 11%-41% B over 10 minutes) to give (3S)-3-(5-(4-((7-((1-(((4-(2-oxa-6-azabicyclo[5.1.0]octan-6-yl)-7-(8-ethyl-7-fluoro-3-hydroxynaphthalen-1-yl)-8-fluoropyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione as a white solid. LCMS: [M+H]⁺=996.5. ¹H NMR (400 MHz, CDCl₃) δ=9.44 (d, J=19.6 Hz, 1H), 8.49 (m, 1H), 7.71-7.63 (m, 2H), 7.32 (m, 1H), 7.31-7.26 (m, 1H), 7.09-7.07 (m, 3H), 5.12-5.09 (m, 1H), 4.86-4.51 (m, 3H), 4.48-4.4 (m, 4H), 3.85-3.84 (m, 1H), 3.84-3.83 (m, 2H), 3.83-3.82 (m, 1H), 3.40-3.36 (m, 6H), 3.31-3.19 (m, 3H), 3.02-2.95 (m, 1H), 2.67-2.65 (m, 1H), 2.67-2.58 (m, 7H), 2.47-2.43 (m, 3H), 2.35-2.03 (m, 4H), 1.86-1.84 (m, 3H), 1.80-1.73 (m, 2H), 1.62-1.60 (m, 2H), 1.51-1.46 (m, 1H), 0.96-0.76 (m, 8H).

Compound 160 was prepared via a similar synthetic procedure as example 28.

| Cpd # | Characterization |
|---|---|
| 160 | LCMS: [M + H]⁺ = 956.4<br>¹H NMR (400 MHz, CDCl₃) δ = 9.43 (d, J = 21,2 Hz, 1H), 8.53 (m, 1H), 7.68-7.66 (m, 1H), 7.64-7.62 (m, 1H), 7.32 (m, 1H), 7.31-7.26 (m, 1H), 7.09-7.07 (m, 3H), 5.12-5.09 (m, 1H), 4.86-4.81 (m, 1H), 4.75-4.51 (m, 2H), 4.45-4.38 (m, 4H), 3.85-3.84 (m, 1H), 3.84-3.83 (m, 2H), 3.73-3.51 (m, 3H), 3.48-3.41 (m, 2H), 3.23-2.79 (m, 3H), 2.78-2.66 (m, 3H), 2.62-2.53 (m, 4H), 2.51-2.33 (m, 3H), 2.31-2.23 (m, 4H), 2.06-1.77 (m, 4H), 1.52-1.41 (m, 3H), 0.85-0.62 (m, 9H). |

Example 29: Preparation of (S)-3-(5-(4-((7-(((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-2-fluoro-7-azaspiro[3.5]nonan-2-yl)methyl)piperazin-1-yl)-1-oxoisoindolin-2-yl)piperidine-2,6-dione (Compound 134)
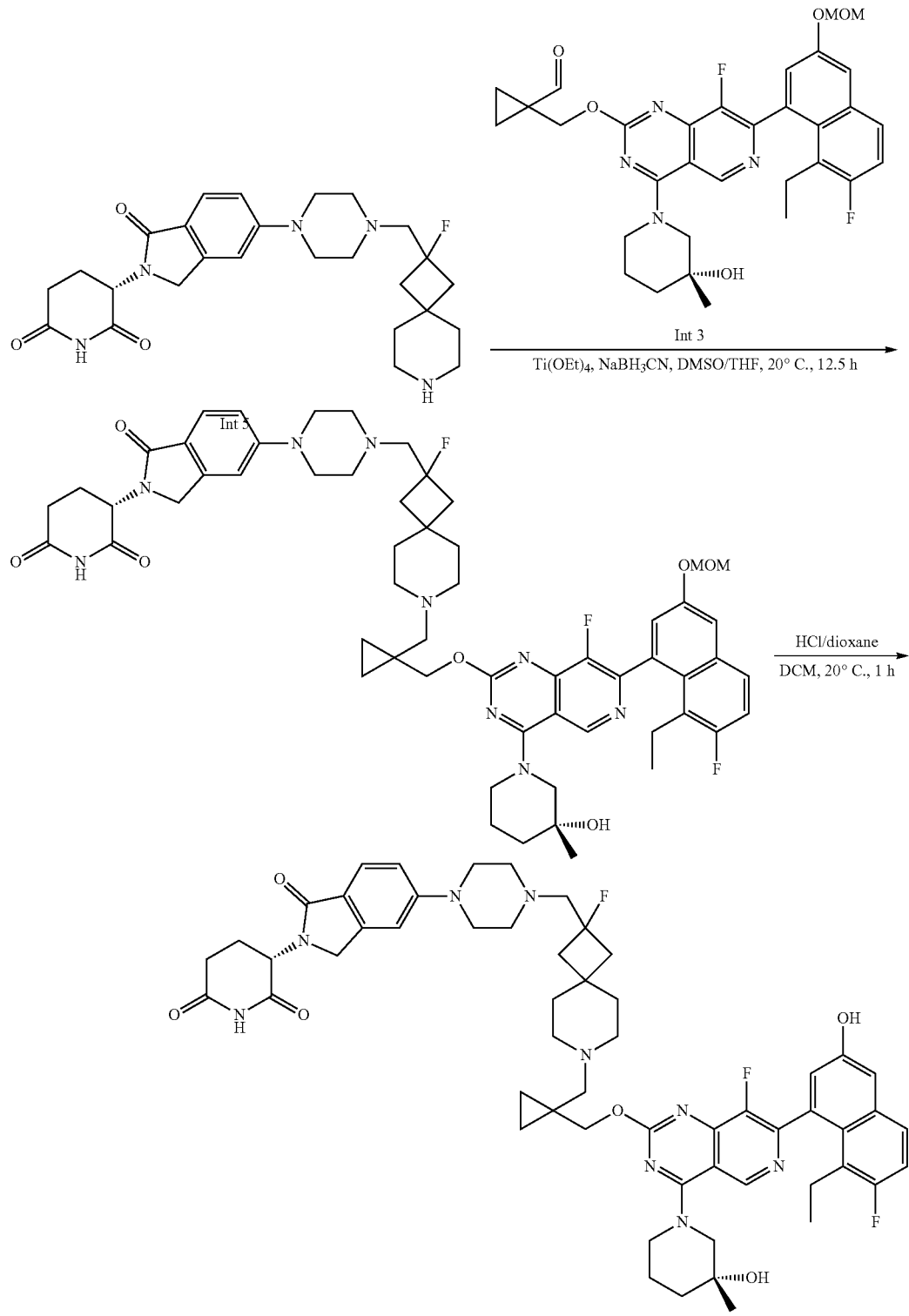
Compound 134

Step 1: Preparation of (3S)-3-[5-[4-[[7-[[1-[[7-[8-ethyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropyl]methyl]-2-fluoro-7-azaspiro[3.5]nonan-2-yl]methyl]piperazin-1-yl]-1-oxo-isoindolin-2-yl]piperidine-2,6-dione To a solution of 1-[[7-[8-ethyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropanecarbaldehyde (3.17 g, 4.62 mmol, 1 eq) and (3S)-3-[5-[4-[(2-fluoro-7-azaspiro[3.5]nonan-2-yl)methyl]piperazin-1-yl]-1-oxo-isoindolin-2-yl]piperidine-2,6-dione (2.4 g, 4.62 mmol, 1 eq, HCl) in DMSO (20 mL) and THF (40 mL) was added Ti(OEt)$_4$ (10.53 g, 46.15 mmol, 9.57 mL, 10 eq) and the reaction mixture was stirred at 20° C. for 12 hours. Then NaBH$_3$CN (870.03 mg, 13.85 mmol, 3 eq) was added, the mixture was stirred at 20° C. for 0.5 hours. LCMS showed that the reactant was fully consumed and a peak with desired mass was detected. The reaction mixture was diluted with EA (100 mL) and THF (100 mL), then poured into water (200 mL). The resulting mixture was filtered, and the filtrate was extracted with EA/THF=1/1 (100 mL*5). The organic layers were combined and washed with brine (200 mL), dried over anhydrous Na$_2$SO$_4$, filtered and concentrated under reduced pressure to give a residue, which was purified by column chromatography (PE/EA=1/0 to 0/1, then DCM/MeOH=1/0 to 8/1) to afford the desired compound (3.4 g, 3.12 mmol, 67.54% yield, 97.2% purity) as a light yellow solid. $^1$H NMR (CD$_3$OD, 400 MHZ) δ=9.24 (s, 1H), 7.84-7.77 (m, 1H), 7.66-7.60 (m, 2H), 7.32 (t, J=9.2 Hz, 1H), 7.25-7.20 (m, 1H), 7.08-7.04 (m, 2H), 5.33 (s, 2H), 5.12-5.06 (m, 1H), 4.64-4.51 (m, 3H), 4.47 (br t, J=5.2 Hz, 2H), 4.39 (d, J=5.6 Hz, 2H), 4.36-4.28 (m, 1H), 3.68-3.55 (m, 2H), 3.50 (s, 3H), 3.44 (s, 2H), 3.35 (s, 2H), 3.34 (br s, 2H), 3.26 (br s, 2H), 2.96-2.83 (m, 2H), 2.81-2.68 (m, 8H), 2.54-2.40 (m, 2H), 2.35-2.21 (m, 4H), 2.20-2.03 (m, 6H), 2.00-1.92 (m, 2H), 1.91-1.74 (m, 3H), 1.29 (d, J=10.0 Hz, 3H), 0.98 (s, 2H), 0.86 (br s, 2H).

Step 2: Preparation of (3S)-3-[5-[4-[7-[1-[[7-(8-ethyl-7-fluoro-3-hydroxy-1-naphthyl)-8-fluoro-4-[(3R)-3-hydroxy-3-methyl-1-piperidyl]pyrido[4,3-d]pyrimidin-2-yl]oxymethyl]cyclopropyl]methyl]-2-fluoro-7-azaspiro[3.5]nonan-2-yl]methyl]piperazin-1-yl]-1-oxo-isoindolin-2-yl]piperidine-2,6-dione (Compound 134)

To a solution of (3S)-3-[5-[4-[7-[[1-[[7-[8-ethyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropyl]methyl]-2-fluoro-7-azaspiro[3.5]nonan-2-yl]methyl]piperazin-1-yl]-1-oxo-isoindolin-2-yl]piperidine-2,6-dione (3.2 g, 3.02 mmol, 1 eq) in DCM (20 mL) was added HCl solution (2 M in dioxane, 20 mL, 13.25 eq) at 20° C. The mixture was stirred at 20° C. for 1 hour. LCMS showed that the starting material was fully consumed and a new peak with desired mass was detected. The reaction mixture was concentrated under reduced pressure to give a residue, which was purified by prep-HPLC(FA): column: column: Phenomenex Synergi Max-RP 250*50 mm 0 um; mobile phase: [water (FA)-ACN]; gradient: 5%-35% B over 20 minutes and further purified by column: Phenomenex Luna C18 (250*70 mm, 10 um); mobile phase: [water (FA)-ACN]; gradient: 15%-45% B over 20 minutes to afford the desired compound (1.39 g, 1.36 mmol, 45.09% yield, 99.5% purity) as a white solid. LCMS: [M+H]$^+$=1016.5. $^1$H NMR (CD$_3$OD, 400 MHZ) δ=9.23 (s, 1H), 8.50-8.38 (m, 1H), 7.71-7.61 (m, 2H), 7.31 (d, J=2.4 Hz, 1H), 7.26 (t, J=9.6 Hz, 1H), 7.05 (br s, 3H), 5.13-5.07 (m, 1H), 4.57 (br d, J=12.0 Hz, 2H), 4.49-4.42 (m, 2H), 4.39 (br d, J=5.2 Hz, 2H), 4.35-4.26 (m, 1H), 3.66-3.56 (m, 1H), 3.50-3.38 (m, 2H), 3.38-3.33 (m, 4H), 3.26-3.12 (m, 3H), 2.95-2.78 (m, 2H), 2.78-2.59 (m, 7H), 2.50-2.39 (m, 2H), 2.34-2.19 (m, 4H), 2.19-2.12 (m, 3H), 2.06 (br s, 2H), 1.93 (br s, 2H), 1.88-1.73 (m, 3H), 1.29 (d, J=9.6 Hz, 3H), 0.97 (s, 2H), 0.86-0.77 (m, 5H).

Example 30: Preparation of (S)-3-(5-(4-((7-((1-(((7-(8-ethyl-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-2-fluoro-7-azaspiro[3.5]nonan-2-yl)methyl)piperazin-1-yl)-1-oxoisoindolin-2-yl)piperidine-2,6-dione (Compound 188)

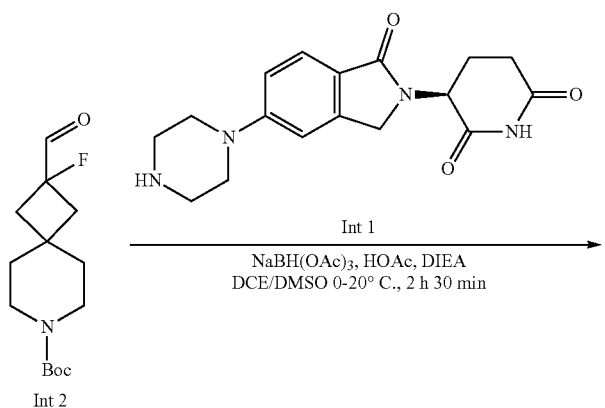

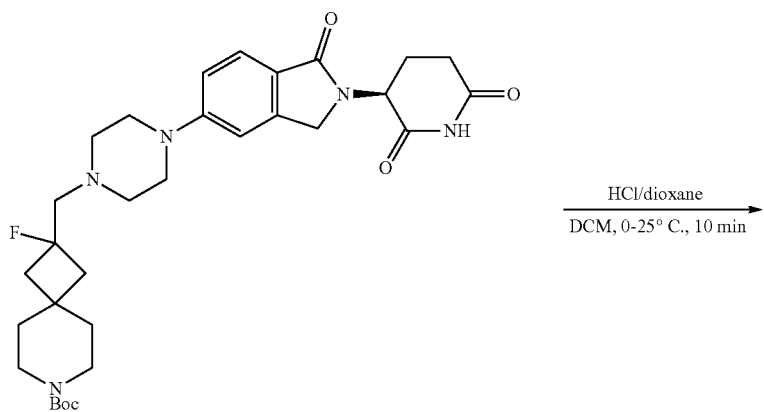
-continued
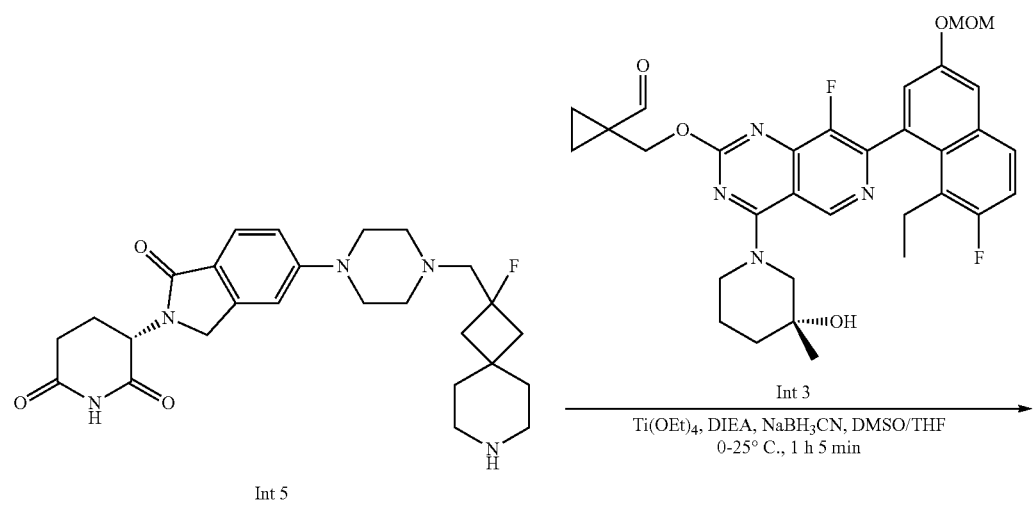
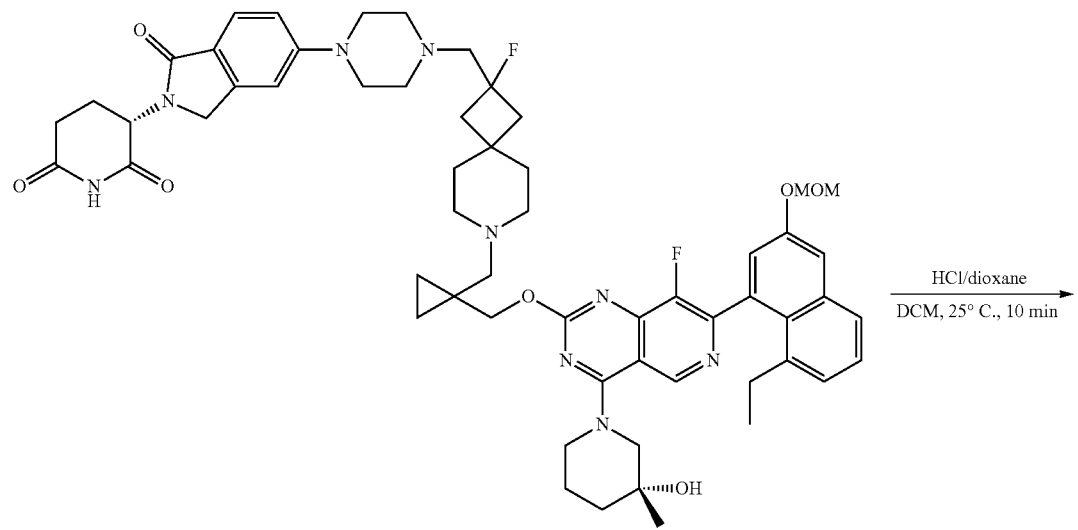

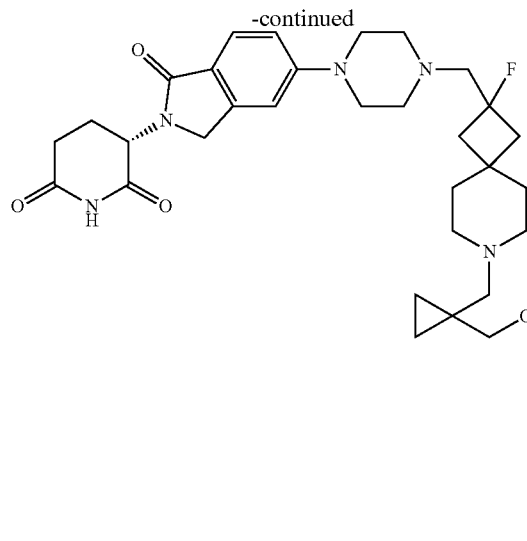

Compound 188

Step 1: Preparation of tert-butyl (S)-2-((4-(2-(2,6-dioxopiperidin-3-yl)-1-oxoisoindolin-5-yl)piperazin-1-yl)methyl)-2-fluoro-7-azaspiro[3.5]nonane-7-carboxylate A solution of (3S)-3-(1-oxo-5-piperazin-1-yl-isoindolin-2-yl)piperidine-2,6-dione (924 mg, 1.69 mmol, 1.00 eq) and DIEA (218 mg, 1.69 mmol, 294 μL, 1 eq) in DCE (3.00 mL) and DMSO (3.00 mL) was stirred at 20° C. for 10 minutes. Then AcOH (203 mg, 3.38 mmol, 193 μL, 2.00 eq) and tert-butyl 2-fluoro-2-formyl-7-azaspiro[3.5]nonane-7-carboxylate (550 mg, 2.03 mmol, 1.20 eq) were added and the reaction mixture was stirred at 20° C. for 20 minutes. Then NaBH(OAc)$_3$ (1.07 g, 5.07 mmol, 3.00 eq) was added at 0° C. and the mixture was stirred at 20° C. for 2 hours. LCMS showed complete consumption of the starting material and detection of the desired product. MeOH (5.00 mL) was added, and the reaction mixture was concentrated under reduced pressure. The resulting residue was purified by reverse phase flash column chromatography (FA 0.1%) to give the desired product (120 mg, 206 μmol, 12.2% yield) as a white solid. $^1$H NMR (400 MHZ, CHLOROFORM-d) δ=7.95 (s, 1H), 7.75 (d, J=8.8 Hz, 1H), 7.03-6.96 (m, 1H), 6.88 (s, 1H), 5.21 (dd, J=5.2, 13.2 Hz, 1H), 4.47-4.22 (m, 2H), 3.40-3.29 (m, 7H), 2.95-2.69 (m, 7H), 2.40-2.08 (m, 6H), 1.69 (br d, J=5.2 Hz, 4H), 1.54-1.49 (m, 2H), 1.46 (s, 9H).

Step 2: Preparation of (S)-3-(5-(4-((2-fluoro-7-azaspiro[3.5]nonan-2-yl)methyl)piperazin-1-yl)-1-oxoisoindolin-2-yl)piperidine-2,6-dione To a solution of tert-butyl 2-[4-[2-[(3S)-2,6-dioxo-3-piperidyl]-1-oxo-isoindolin-5-yl]piperazin-1-yl]methyl]-2-fluoro-7-azaspiro[3.5]nonane-7-carboxylate (100 mg, 171 μmol, 1.00 eq) in DCM (2.00 mL) was added HCl solution (2 M in dioxane, 5.00 mL, 58.4 eq) at 0° C. The reaction mixture was stirred at 25° C. for 10 minutes. LCMS showed complete consumption of the starting material and detection of the desired product as a major peak. The reaction mixture was concentrated under reduced pressure to give the desired product (89.0 mg, 171 μmol, 99.9% yield, HCl) as a yellow solid without further purification. $^1$H NMR (400 MHZ, DMSO-d$_6$) δ=10.95 (s, 1H), 8.93 (br d, J=1.6 Hz, 1H), 7.59 (br d, J=8.4 Hz, 1H), 7.19-7.09 (m, 2H), 5.06 (br dd, J=4.8, 13.6 Hz, 1H), 4.39-4.34 (m, 1H), 4.25 (br s, 1H), 3.98 (br d, J=12.4 Hz, 2H), 3.67 (br s, 1H), 3.61 (br s, 2H), 3.47 (br d, J=10.8 Hz, 3H), 3.29-3.20 (m, 2H), 2.97-2.86 (m, 4H), 2.59 (br d, J=15.6 Hz, 2H), 2.44-2.32 (m, 2H), 2.30-2.18 (m, 2H), 1.99-1.93 (m, 1H), 1.81 (br dd, J=5.2, 7.6 Hz, 4H), −0.07 (br s, 2H).

Step 3: Preparation of (S)-3-(5-(4-((7-((1-(((7-(8-ethyl-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-2-fluoro-7-azaspiro[3.5]nonan-2-yl)methyl)piperazin-1-yl)-1-oxoisoindolin-2-yl)piperidine-2,6-dione To a solution of (3S)-3-[5-[4-[(2-fluoro-7-azaspiro[3.5]nonan-2-yl)methyl]piperazin-1-yl]-1-oxo-isoindolin-2-yl]piperidine-2,6-dione (40.0 mg, 76.9 μmol, 1.20 eq, HCl) in DMSO (1.00 mL) and THF (2.00 mL) and was added DIEA (8.28 mg, 64.1 μmol, 11.2 μL, 1.00 eq) at 0° C. 1-[7-[8-ethyl-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropanecarbaldehyde (36.8 mg, 64.1 μmol, 1.00 eq) and Ti(OEt)$_4$ (1.10 g, 4.82 mmol, 1.00 mL, 75.2 eq) were added. The reaction mixture was stirred at 25° C. for 1 hour and NaBH$_3$CN (40.3 mg, 641 μmol, 10.0 eq) was added at 0° C. The mixture was stirred at 25° C. for another 5 minutes. LCMS indicated complete consumption of the starting material and detection of the desired product as a major peak. The reaction mixture was poured into ice-water (50.0 mL) and the reaction mixture was stirred for 5 minutes. The mixture was filtered and extracted with ethyl acetate (30.0 mL*3). The combined organic layers were washed with brine (50.0 mL), dried over anhydrous Na$_2$SO$_4$, filtered and concentrated under reduced pressure. The resulting residue was redissolved in DCM:MeOH=1:1 (100 mL), filtered and concentrated under reduced pressure to give a crude residue, which was purified by prep-TLC (SiO$_2$, DCM: MeOH=9:1) to give the desired product (66.0 mg, 55.1 µmol, 85.9% yield, 87% purity) as a yellow oil.

Step 4: Preparation of (S)-3-(5-(4-((7-((1-(((7-(8-ethyl-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-2-fluoro-7-azaspiro[3.5]nonan-2-yl)methyl)piperazin-1-yl)-1-oxoisoindolin-2-yl)piperidine-2,6-dione (Compound 188)

To a solution of (3S)-3-[5-[4-[7-[1-[[7-[8-ethyl-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropyl]methyl]-2-fluoro-7-azaspiro[3.5]nonan-2-yl]methyl]piperazin-1-yl]-1-oxo-isoindolin-2-yl]piperidine-2,6-dione (60.0 mg, 50.1 µmol, 1.00 eq) in DCM (4.00 mL) was added HCl solution (2 M in dioxane, 2.00 mL, 79.9 eq). The mixture was stirred at 25° C. for 10 minutes. LCMS showed complete consumption of the starting material and detection of the desired product as a major peak. The reaction mixture was concentrated under reduced pressure to give a crude residue, which was purified by prep-HPLC (FA condition; column: Phenomenex Luna C18 150*25 mm*10 µm; mobile phase: [water (FA)-ACN]; gradient: 15%-35% B over 10 minutes) to give the desired compound (23.9 mg, 22.7 µmol, 45.3% yield, 99% purity, FA) as a white solid. LCMS: [M+H]$^+$=998.5. $^1$H NMR (400 MHZ, METHANOL-$d_4$) δ=9.20 (d, J=6.4 Hz, 1H), 8.51 (s, 1H), 7.63 (d, J=8.4 Hz, 2H), 7.36 (t, J=7.6 Hz, 1H), 7.29 (d, J=2.8 Hz, 1H), 7.17 (d, J=6.8 Hz, 1H), 7.10-6.99 (m, 3H), 5.10 (dd, J=5.2, 13.6 Hz, 1H), 4.56-4.42 (m, 3H), 4.42-4.34 (m, 2H), 4.30 (br dd, J=9.6, 13.2 Hz, 1H), 3.69-3.50 (m, 2H), 3.49-3.36 (m, 2H), 3.34 (br s, 3H), 3.12-2.97 (m, 3H), 2.96-2.81 (m, 2H), 2.77-2.60 (m, 7H), 2.51-2.43 (m, 1H), 2.42-2.23 (m, 4H), 2.22-2.07 (m, 5H), 2.04-1.96 (m, 2H), 1.88-1.73 (m, 5H), 1.29 (d, J=11.6 Hz, 3H), 0.94-0.86 (m, 5H), 0.76 (br s, 2H).

Example 31: Preparation of (S)-3-(5-(4-((7-((1-(((7-(7,8-difluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-2-fluoro-7-azaspiro[3.5]nonan-2-yl)methyl)piperazin-1-yl)-1-oxoisoindolin-2-yl)piperidine-2,6-dione (Compound 174)

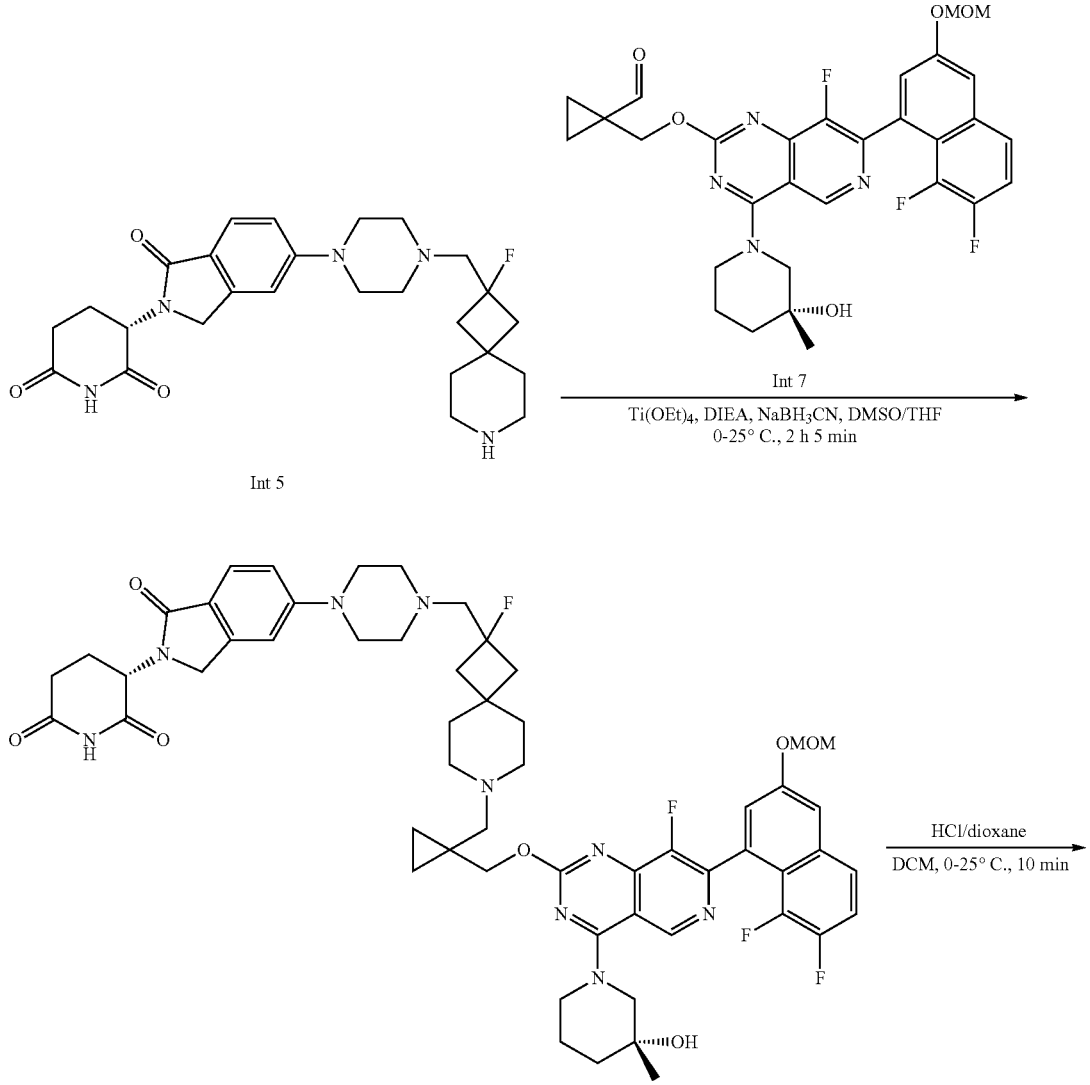

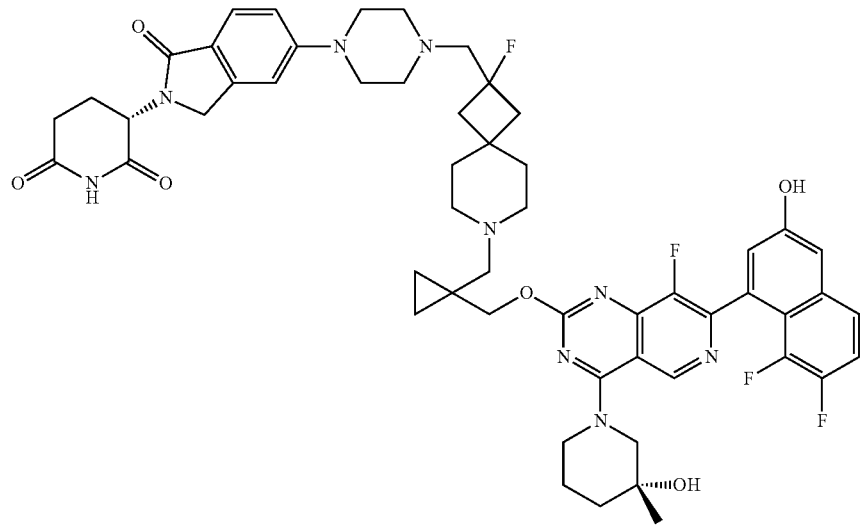

Compound 174

Step 1: Preparation of (S)-3-(5-(4-((7-((1-(((7-(7,8-difluoro-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-2-fluoro-7-azaspiro[3.5]nonan-2-yl)methyl)piperazin-1-yl)-1-oxoisoindolin-2-yl)piperidine-2,6-dione To a solution of (3S)-3-[5-[4-[(2-fluoro-7-azaspiro[3.5]nonan-2-yl)methyl]piperazin-1-yl]-1-oxo-isoindolin-2-yl]piperidine-2,6-dione (40.0 mg, 76.9 μmol, 1.20 eq, HCl) in THF (4.00 mL) and DMSO (2.00 mL) and was added DIEA (8.28 mg, 64.1 μmol, 11.2 μL, 1.00 eq) at 0° C. 1-[7-[7,8-difluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropanecarbaldehyde (37.3 mg, 64.1 μmol, 1.00 eq) and Ti(OEt)₄ (1.65 g, 7.23 mmol, 1.50 mL, 113 eq) were added. The reaction mixture was stirred at 25° C. for 2 hours. NaBH₃CN (40.3 mg, 641 μmol, 10.0 eq) was added at 0° C. and the reaction mixture was stirred at 25° C. for 5 minutes. LCMS showed complete consumption of the starting material and detection of the desired compound as a major peak. The reaction mixture was poured into ice-water (50.0 mL) and the reaction mixture was stirred for 5 minutes. The mixture was filtered, extracted with ethyl acetate (30.0 mL*3). The combined organic layers were washed with brine (50.0 mL), dried over anhydrous Na₂SO₄, filtered and concentrated under reduced pressure. The resulting residue was redissolved in DCM:MeOH (1:1, 100 mL), flittered and concentrated under reduced pressure. The resulting residue was purified by prep-TLC (SiO₂, DCM:MeOH=10:1) to give the desired product (60.0 mg, 51.4 μmol, 80.2% yield, 90% purity) as a yellow oil.

Step 2: Preparation of (S)-3-(5-(4-((7-((1-(((7-(7,8-difluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-2-fluoro-7-azaspiro[3.5]nonan-2-yl)methyl)piperazin-1-yl)-1-oxoisoindolin-2-yl)piperidine-2,6-dione (Compound 174)

To a solution of (3S)-3-[5-[4-[[7-[[1-[[7-[7,8-difluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropyl]methyl]-2-fluoro-7-azaspiro[3.5]nonan-2-yl]methyl]piperazin-1-yl]-1-oxo-isoindolin-2-yl]piperidine-2,6-dione (55.0 mg, 47.1 μmol, 1.00 eq) in DCM (2.00 mL) was added HCl solution (2 M in dioxane, 1.00 mL, 42.4 eq) at 0° C. The mixture was stirred at 25° C. for 10 minutes. LCMS showed complete consumption of the starting material and detection of the desired product as a major product. The reaction mixture was concentrated under reduced pressure and the resulting residue was purified by prep-HPLC (FA condition; column: Phenomenex Luna C18 150*25 mm*10 μm; mobile phase: [water (FA)-ACN]; gradient: 11%-38% B over 9 minutes) to give the desired product (22.3 mg, 20.7 μmol, 44.0% yield, 98% purity, FA) as a white solid. LCMS: [M+H]⁺=1006.5. ¹H NMR (400 MHZ, METHANOL-d₄) δ=9.25-9.19 (m, 1H), 8.41-8.32 (m, 1H), 7.63 (br d, J=8.4 Hz, 2H), 7.41 (q, J=9.2 Hz, 1H), 7.34 (br d, J=1.6 Hz, 1H), 7.29-7.22 (m, 1H), 7.09-7.03 (m, 2H), 5.10 (dd, J=5.2, 13.2 Hz, 1H), 4.61-4.49 (m, 2H), 4.42 (br s, 3H), 4.32 (br d, J=16.4 Hz, 1H), 3.62 (br dd, J=5.4, 13.2 Hz, 1H), 3.45-3.36 (m, 2H), 3.33 (br d, J=5.2 Hz, 4H), 3.30-3.21 (m, 3H), 3.04-2.81 (m, 2H), 2.81-2.77 (m, 1H), 2.75-2.67 (m, 6H), 2.51-2.41 (m, 1H), 2.35-2.20 (m, 3H), 2.20-2.10 (m, 4H), 2.09-1.93 (m, 4H), 1.89-1.75 (m, 3H), 1.29 (d, J=2.4 Hz, 3H), 0.98 (br s, 2H), 0.85 (br s, 2H).

Example 32: Preparation of (S)-3-(5-(4-((1-(((1-(((7-(8-chloro-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione (Compound 156)
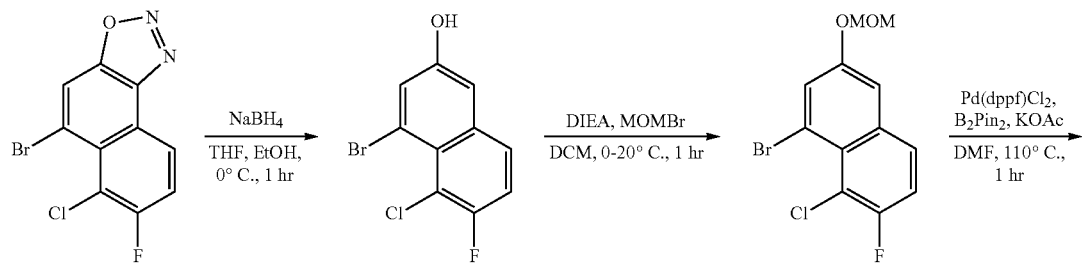
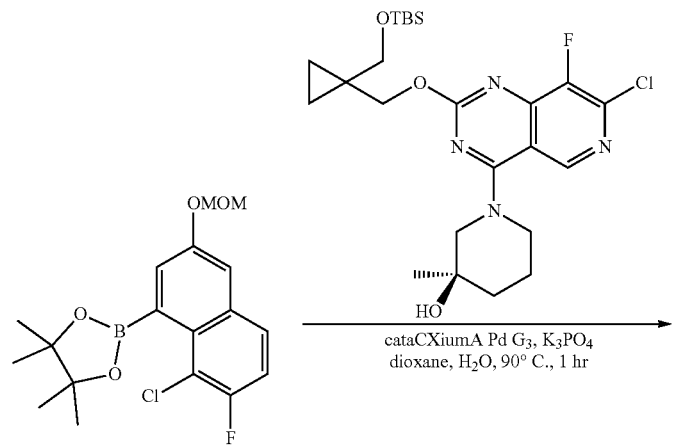
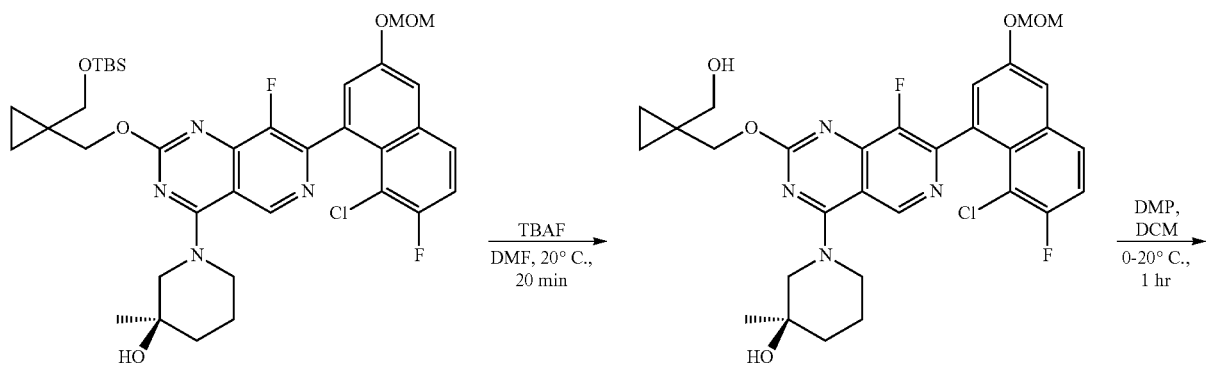

517
518
-continued
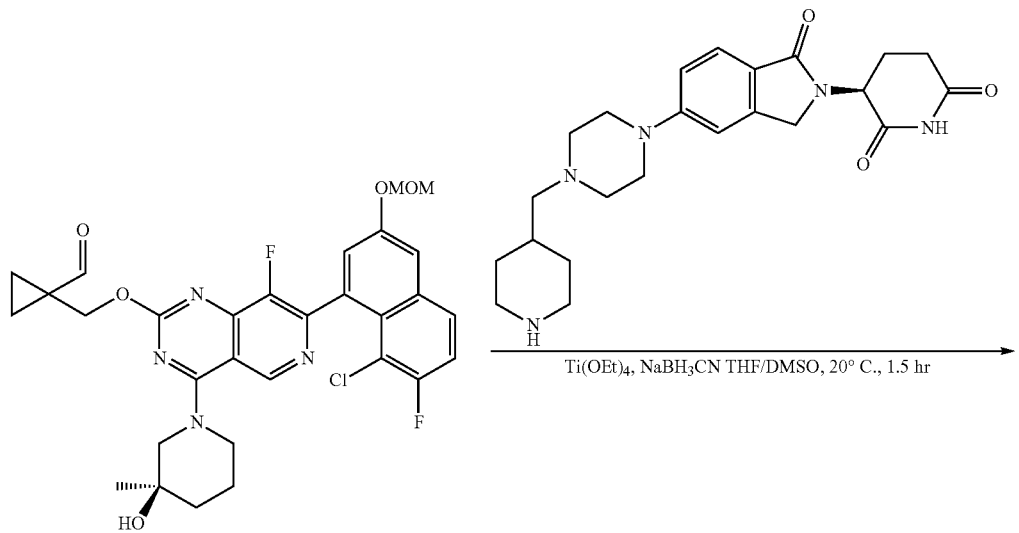
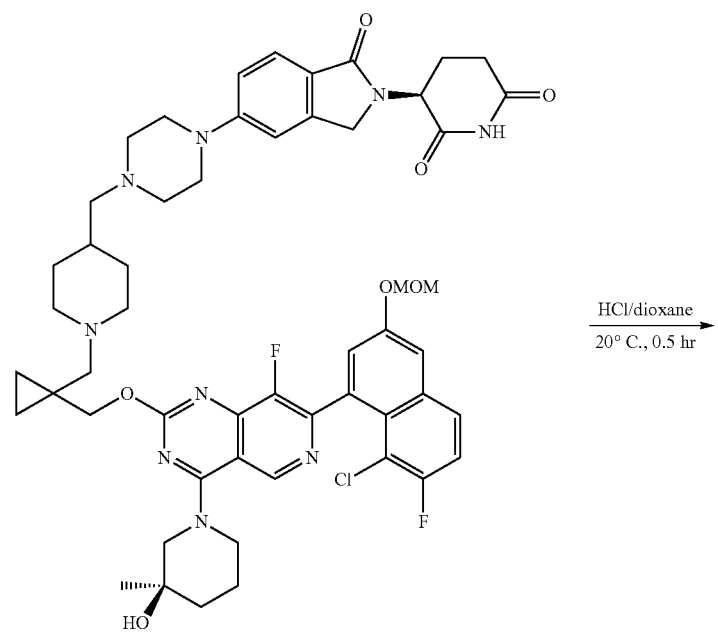

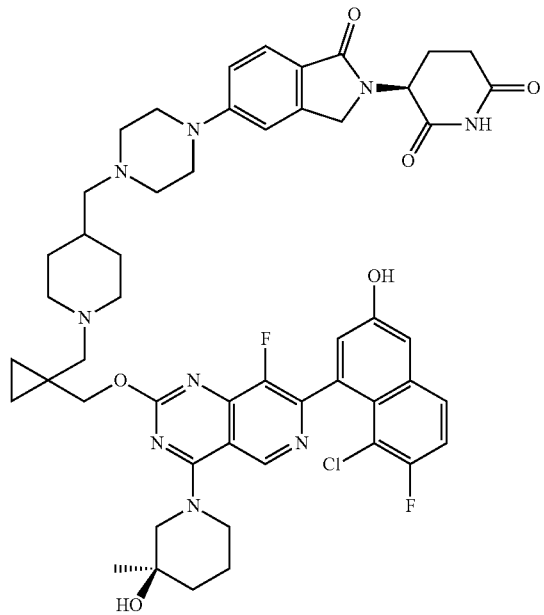

Compound 156

Step 1: Preparation of 4-bromo-5-chloro-6-fluoronaphthalen-2-ol

The mixture of 5-bromo-6-chloro-7-fluoro-benzo[e] [1,2,3] benzoxadiazole (5 g, 15.1 mmol, 1 eq) in THF (16 mL) and EtOH (40 mL) was cooled to 0° C. NaBH$_4$ (1.21 g, 32.0 mmol, 2.12 eq) was added to the mixture slowly and the mixture was stirred at 0° C. for 1 hour. LCMS showed complete consumption of the starting material and detection of the desired product. The reaction mixture was poured into saturated NH$_4$Cl aqueous solution (300 mL) at 0° C. The mixture was extracted with EA (50 mL*3). Then the organic layers were combined and washed with brine (50 mL), dried over anhydrous Na$_2$SO$_4$, concentrated under reduced pressure to afford the crude residue, which was purified by column chromatography (SiO$_2$, PE:EA=1:0, PE:EA=2:1, Rf=0.6) to give 4-bromo-5-chloro-6-fluoronaphthalen-2-ol (2.8 g, 10.2 mmol, 67.4% yield) as a brown solid. $^1$H NMR (400 MHZ, DMSO-d$_6$) δ=10.34 (s, 1H), 7.87 (dd, J=6.0, 9.2 Hz, 1H), 7.61 (d, J=2.4 Hz, 1H), 7.55 (t, J=8.8 Hz, 1H), 7.32 (d, J=2.4 Hz, 1H).

Step 2: Preparation of 8-bromo-1-chloro-2-fluoro-6-(methoxymethoxy)naphthalene A mixture of 4-bromo-5-chloro-6-fluoro-naphthalen-2-ol (2.1 g, 7.62 mmol, 1 eq) in DCM (40 mL) was added DIPEA (2.96 g, 22.9 mmol, 3 eq) at 0° C. Then bromo (methoxy) methane (1.91 g, 15.2 mmol, 2 eq) was added to the mixture at 0° C. The mixture was stirred at 20° C. for 12 hours. The LCMS showed complete consumption of the starting material. The reaction mixture was poured into saturated NaHCO$_3$ aqueous solution (100 mL), and the resulting mixture was extracted with DCM (30 mL*3). The organic layers were combined and washed with brine (50 mL), dried over anhydrous Na$_2$SO$_4$, concentrated under reduced pressure to afford the crude residue, which was purified by column chromatography (SiO$_2$, PE:EA=1:0 to PE:EA=10:1) to afford 8-bromo-1-chloro-2-fluoro-6-(methoxymethoxy) naphthalene (2.67 g, 8.36 mmol, 87.7% yield) as a brown solid. $^1$H NMR (400 MHZ, CHLOROFORM-d) δ=8.96 (s, 1H), 4.74-4.56 (m, 2H), 3.48-3.32 (m, 1H), 3.28-3.15 (m, 1H), 2.26-2.10 (m, 2H), 1.90-1.66 (m, 2H), 1.52-1.43 (m, 3H).

Step 3: Preparation of 2-(8-chloro-7-fluoro-3-(methoxymethoxy)naphthalen-1-yl)-4,4,5,5-tetramethyl-1,3,2-dioxaborolane To a mixture of 8-bromo-1-chloro-2-fluoro-6-(methoxymethoxy)naphthalene (2.3 g, 7.20 mmol, 1 eq), 4,4,5,5-tetramethyl-2-(4,4,5,5-tetramethyl-1,3,2-dioxaborolan-2-yl)-1,3,2-dioxaborolane (3.66 g, 14.4 mmol, 2 eq) in DMF (60 mL) was added KOAc (1.77 g, 18.0 mmol, 2.5 eq), Pd(dppf)Cl$_2$·CH$_2$Cl$_2$ (588 mg, 720 μmol, 0.1 eq). The reaction mixture was stirred at 110° C. for 1 hour under N$_2$ atmosphere. TLC (Rf=0.4, PE:EA=10:1) showed complete consumption of the starting material and formation of a major new spot. The mixture was poured into water (600 mL) and was extracted with EA (200 mL*3). The organic layers were combined and washed with brine (200 mL), dried over anhydrous Na$_2$SO$_4$, concentrated under reduced pressure to afford the residue as brown oil. The crude residue was purified by column chromatography (SiO$_2$, PE:EA=1:0 to PE:EA=80:1) to give 2-(8-chloro-7-fluoro-3-(methoxymethoxy)naphthalen-1-yl)-4,4,5,5-tetramethyl-1,3,2-dioxaborolane (2.2 g, 6.00 mmol, 83.4% yield) as a white solid. $^1$H NMR (400 MHZ, CHLOROFORM-d) δ=7.64 (dd, J=5.4, 9.0 Hz, 1H), 7.41 (s, 2H), 7.32-7.27 (m, 1H), 5.29 (s, 2H), 3.51 (s, 3H), 1.46 (s, 12H).

Step 4: Preparation of (R)-1-(2-((1-(((tert-butyldimethylsilyl)oxy)methyl)cyclopropyl)methoxy)-7-(8-chloro-7-fluoro-3-(methoxymethoxy)naphthalen-1-yl)-8-fluoropyrido[4,3-d]pyrimidin-4-yl)-3-methylpiperidin-3-ol To a mixture of (3R)-1-[2-[[1-[[tert-butyl(dimethyl)silyl] oxymethyl]cyclopropyl]methoxy]-7-chloro-8-fluoro-pyrido

[4,3-d]pyrimidin-4-yl]-3-methyl-piperidin-3-ol (1.2 g, 2.35 mmol, 1 eq), 2-[8-chloro-7-fluoro-3-(methoxymethoxy)-1-naphthyl]-4,4,5,5-tetramethyl-1,3,2-dioxaborolane (1.03 g, 2.82 mmol, 1.2 eq) in dioxane (20 mL) and H$_2$O (2 mL) was added K$_3$PO$_4$ (1.50 g, 7.04 mmol, 3 eq), [2-(2-aminophenyl)phenyl]palladium(1+);bis(1-adamantyl)-butyl-phosphane; methanesulfonate (171 mg, 235 µmol, 0.1 eq). The reaction mixture was stirred at 90° C. for 1 hour under N$_2$ atmosphere. LCMS showed complete consumption of the reactant and detection of the desired product. The reaction mixture was poured into water (50 mL) and extracted with EA (20 mL*3). The organic layers were combined and washed with brine (30 mL), dried over anhydrous Na$_2$SO$_4$, concentrated under reduced pressure to afford the crude residue. The crude residue was purified by column chromatography (SiO$_2$, PE:EA=5:1 to PE:EA=1:1) to afford (R)-1-(2-((1-(((tert-butyldimethylsilyl)oxy)methyl)cyclopropyl)methoxy)-7-(8-chloro-7-fluoro-3-(methoxymethoxy)naphthalen-1-yl)-8-fluoropyrido[4,3-d]pyrimidin-4-yl)-3-methylpiperidin-3-ol (460 mg, 601 µmol, 25.6% yield, 93.4% purity) as a white solid. $^1$H NMR (400 MHZ, CHLOROFORM-d) δ=9.14 (s, 1H), 7.75 (dd, J=5.4, 9.2 Hz, 1H), 7.55 (d, J=2.4 Hz, 1H), 7.39-7.31 (m, 2H), 5.31 (s, 2H), 4.47-4.41 (m, 3H), 3.69 (d, J=3.6 Hz, 2H), 3.52 (s, 3H), 3.49-3.41 (m, 1H), 3.35-3.27 (m, 1H), 2.89 (br d, J=16.0 Hz, 1H), 2.16-2.07 (m, 1H), 1.91 (br d, J=12.4 Hz, 1H), 1.82-1.62 (m, 3H), 1.36 (s, 3H), 0.88 (s, 9H), 0.62 (br d, J=10.8 Hz, 4H), 0.03 (s, 6H).

Step 5: Preparation of (R)-1-(7-(8-chloro-7-fluoro-3-(methoxymethoxy)naphthalen-1-yl)-8-fluoro-2-((1-(hydroxymethyl)cyclopropyl)methoxy)pyrido[4,3-d]pyrimidin-4-yl)-3-methylpiperidin-3-ol(R)-1-(7-(8-chloro-7-fluoro-3-(methoxymethoxy)naphthalen-1-yl)-8-fluoro-2-((1-(hydroxymethyl)cyclopropyl)methoxy)pyrido[4,3-d]pyrimidin-4-yl)-3-methylpiperidin-3-ole To a mixture of (3R)-1-[2-[[1-[[tert-butyl(dimethyl)silyl]oxymethyl]cyclopropyl]methoxy]-7-[8-chloro-7-fluoro-3-(methoxymethoxy)-1-naphthyl]-8-fluoro-pyrido[4,3-d]pyrimidin-4-yl]-3-methyl-piperidin-3-ol (430 mg, 561 µmol, 1 eq) in DMF (5 mL) was added tetrabutylammonium; fluoride; trihydrate (1 M, 1.68 mL, 3 eq). The reaction mixture stirred at 20° C. for 20 minutes. LCMS showed complete consumption of the reactant and detection of the desired product. The reaction mixture was poured into water (50 mL) and extracted with EA (30 mL*3). The organic layers were combined and washed with brine (30 mL), dried over anhydrous Na$_2$SO$_4$, concentrated under reduced pressure to afford the crude residue. The crude residue was purified by Prep-HPLC (column: Welch Ultimate XB-SiOH 250*700 um; mobile phase: [Hexane-EtOH]; gradient: 1%-40% B over 15 minutes) to afford (R)-1-(7-(8-chloro-7-fluoro-3-(methoxymethoxy)naphthalen-1-yl)-8-fluoro-2-((1-(hydroxymethyl)cyclopropyl)methoxy)pyrido[4,3-d]pyrimidin-4-yl)-3-methylpiperidin-3-ol(R)-1-(7-(8-chloro-7-fluoro-3-(methoxymethoxy)naphthalen-1-yl)-8-fluoro-2-((1-(hydroxymethyl)cyclopropyl)methoxy)pyrido[4,3-d]pyrimidin-4-yl)-3-methylpiperidin-3-ole (280 mg, 457 µmol, 81.3% yield, 98% purity) as a white solid. $^1$H NMR (400 MHZ, CHLOROFORM-d) δ=9.19 (d, J=2.0 Hz, 1H), 7.76 (dd, J=5.4, 9.0 Hz, 1H), 7.55 (d, J=2.4 Hz, 1H), 7.42-7.31 (m, 2H), 5.35-5.28 (m, 2H), 4.70 (d, J=12.0 Hz, 1H), 4.56-4.44 (m, 2H), 4.31 (dd, J=3.2, 12.0 Hz, 1H), 3.98 (br d, J=1.1 Hz, 1H), 3.54 (br s, 1H), 3.52 (s, 3H), 3.50-3.40 (m, 1H), 3.40-3.27 (m, 2H), 2.84-2.68 (m, 1H), 2.22-2.08 (m, 1H), 1.90 (br d, J=12.2 Hz, 1H), 1.83-1.67 (m, 2H), 1.36 (s, 3H), 0.77-0.56 (m, 4H).

Step 6: Preparation of 1-[[7-[8-chloro-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropanecarbaldehyde To a mixture of (3R)-1-[7-[8-chloro-7-fluoro-3-(methoxymethoxy)-1-naphthyl]-8-fluoro-2-[[1-(hydroxymethyl)cyclopropyl]methoxy]pyrido[4,3-d]pyrimidin-4-yl]-3-methyl-piperidin-3-ol (250 mg, 408 µmol, 1 eq) in DCM (5 mL) was added DMP (259 mg, 611 µmol, 189 µL, 1.5 eq) at 0° C. The reaction mixture was stirred at 20° C. for 1 hour. LCMS showed complete consumption of the reactant and detection of the desired product. The reaction mixture was poured into saturated Na$_2$SO$_3$ aqueous solution (30 mL) and neutralized with NaHCO$_3$ to pH=7. Then the solution was extracted with DCM (30 mL*3). The organic layers were combined and washed with brine (30 mL), dried over anhydrous Na$_2$SO$_4$, concentrated under reduced pressure to afford the crude residue. The crude residue was purified by column chromatography (SiO$_2$, PE:EA=5:1 to PE:EA=1:1) to afford 1-[7-[8-chloro-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropanecarbaldehyde (210 mg, 351 µmol, 86.0% yield) as a brown solid. $^1$H NMR (400 MHZ, CHLOROFORM-d) δ=9.25 (d, J=3.6 Hz, 1H), 9.17 (s, 1H), 7.76 (dd, J=5.4, 9.0 Hz, 1H), 7.55 (d, J=2.4 Hz, 1H), 7.40-7.32 (m, 2H), 5.37-5.29 (m, 2H), 4.85-4.65 (m, 2H), 4.53-4.39 (m, 2H), 3.53 (s, 3H), 3.51-3.42 (m, 1H), 3.31 (dd, J=11.6, 13.6 Hz, 1H), 2.15-2.07 (m, 1H), 1.95-1.86 (m, 1H), 1.80-1.63 (m, 3H), 1.41-1.32 (m, 7H).

Step 7: Preparation of (S)-3-(5-(4-((1-((1-(((7-(8-chloro-7-fluoro-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione To a mixture of 1-[[7-[8-chloro-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropanecarbaldehyde (80 mg, 134 µmol, 1 eq), (3S)-3-[1-oxo-5-[4-(4-piperidylmethyl)piperazin-1-yl]isoindolin-2-yl]piperidine-2,6-dione (100 mg, 195 µmol, 1.46 eq, HCl) in DMSO (2 mL) and THF (1 mL) was added Ti(OEt)$_4$ (305 mg, 1.34 mmol, 277 µL, 10 eq). The reaction mixture was stirred for 1 hour at 20° C. Then NaBH$_3$CN (25.18 mg, 400.65 µmol, 3 eq) was added and the reaction mixture was stirred for 0.5 hours at 20° C. LCMS showed complete consumption of the reactant and detection of the desired product. The reaction mixture was poured into water (30 mL), filtered and extracted with DCM (30 mL*3). Then the organic layers were combined and washed with brine (30 mL), dried over anhydrous Na$_2$SO$_4$, concentrated under reduced pressure to afford the crude residue. The crude residue was purified by reversed phase HPLC (0.1% FA condition) to afford (S)-3-(5-(4-((1-((1-(((7-(8-chloro-7-fluoro-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione (75 mg, 74.4 μmol, 55.7% yield) as a white solid. $^1$H NMR (400 MHZ, METHANOL-$d_4$) δ=9.23 (s, 1H), 8.48 (s, 1H), 7.99-7.90 (m, 1H), 7.71 (s, 1H), 7.67-7.60 (m, 1H), 7.50-7.42 (m, 1H), 7.39 (br d, J=3.2 Hz, 1H), 7.10-7.00 (m, 2H), 5.37 (s, 2H), 5.10 (br dd, J=5.2, 13.6 Hz, 1H), 4.96-4.91 (m, 2H), 4.82 (br d, J=11.3 Hz, 1H), 4.62-4.51 (m, 3H), 4.45-4.37 (m, 3H), 4.33 (br d, J=14.0 Hz, 1H), 3.92-3.71 (m, 2H), 3.61 (br t, J=13.4 Hz, 1H), 3.51 (s, 3H), 3.47-3.40 (m, 1H), 3.27-3.16 (m, 2H), 3.03-2.83 (m, 3H), 2.80-2.73 (m, 1H), 2.56 (br s, 4H), 2.48-2.38 (m, 1H), 2.28 (br d, J=6.0 Hz, 2H), 2.18-2.02 (m, 4H), 1.93-1.73 (m, 4H), 1.63-1.50 (m, 2H), 1.30 (d, J=8.6 Hz, 3H), 0.97 (br s, 2H), 0.90-0.79 (m, 2H).

Step 8: Preparation of (S)-3-(5-(4-((1-((1-(((7-(8-chloro-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione (Compound 156)

To a mixture of (3S)-3-[5-[4-[1-[1-[7-[8-chloro-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropyl]methyl]-4-piperidyl]methyl]piperazin-1-yl]-1-oxo-isoindolin-2-yl]piperidine-2,6-dione (70 mg, 69.4 μmol, 1 eq) in DCM (1 mL) was added HCl solution (2 M in dioxane, 1 mL, 28.8 eq). The reaction mixture was stirred at 20° C. for 0.5 hours. LCMS showed complete consumption of the reactant and detection of the desired product. The reaction mixture was concentrated under reduced pressure to afford the crude residue. The crude residue was purified by Prep-HPLC (column: Phenomenex Luna C18 150*25 mm*10 μm; mobile phase: [water (FA)-ACN]; gradient: 10%-40% B over 10 minutes) to afford (S)-3-(5-(4-((1-((1-(((7-(8-chloro-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)methyl)piperazin-1-yl)-1-oxoisoindolin-2-yl)piperidine-2,6-dione (42.5 mg, 41.7 μmol, 60.1% yield, 94.8% purity) as an off-white solid. LCMS: [M+H]$^+$=964.3. $^1$H NMR (400 MHZ, METHANOL-$d_4$) δ=9.22 (s, 1H), 8.46 (s, 1H), 7.87-7.79 (m, 1H), 7.63 (d, J=8.3 Hz, 1H), 7.43-7.37 (m, 2H), 7.22 (dd, J=2.4, 4.4 Hz, 1H), 7.09-7.01 (m, 2H), 5.10 (dd, J=5.2, 13.6 Hz, 1H), 4.56 (br d, J=12.2 Hz, 3H), 4.45 (s, 1H), 4.43-4.40 (m, 1H), 4.39 (s, 1H), 4.33 (br d, J=14.4 Hz, 1H), 3.73 (br s, 2H), 3.61 (t, J=13.6 Hz, 1H), 3.52-3.34 (m, 2H), 3.30-3.17 (m, 4H), 3.10 (br s, 1H), 2.92-2.82 (m, 1H), 2.81-2.73 (m, 1H), 2.67-2.51 (m, 4H), 2.50-2.39 (m, 1H), 2.32-2.21 (m, 2H), 2.21-2.12 (m, 2H), 2.08 (br d, J=13.4 Hz, 2H), 1.98-1.85 (m, 2H), 1.84-1.73 (m, 2H), 1.66-1.49 (m, 2H), 1.30 (d, J=8.4 Hz, 3H), 0.98 (br s, 2H), 0.85 (br s, 2H).

Example 33: Preparation of (S)-3-(5-(4-((7-((1-(((7-(8-chloro-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione (Compound 157)

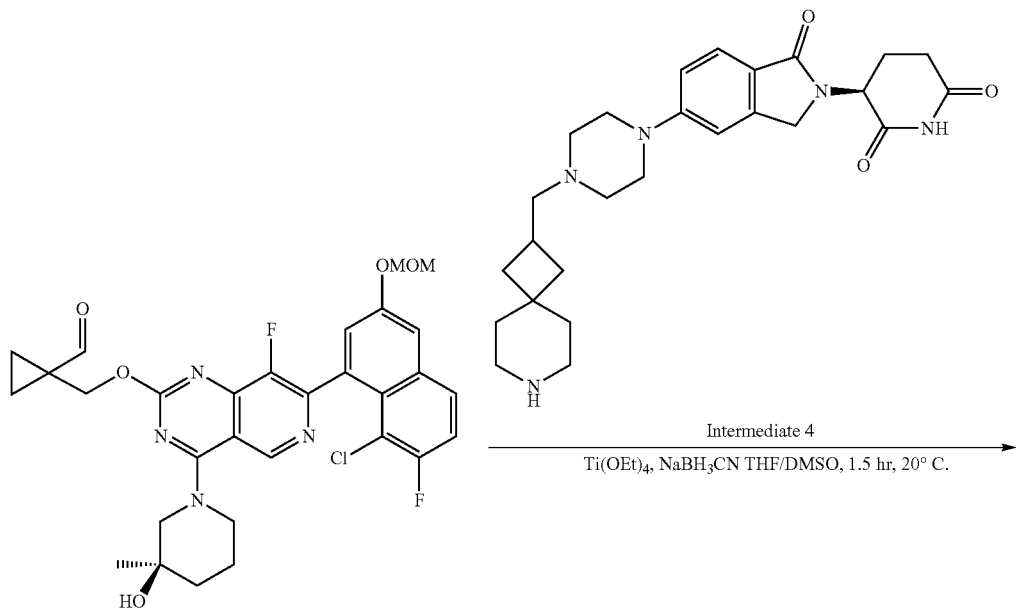

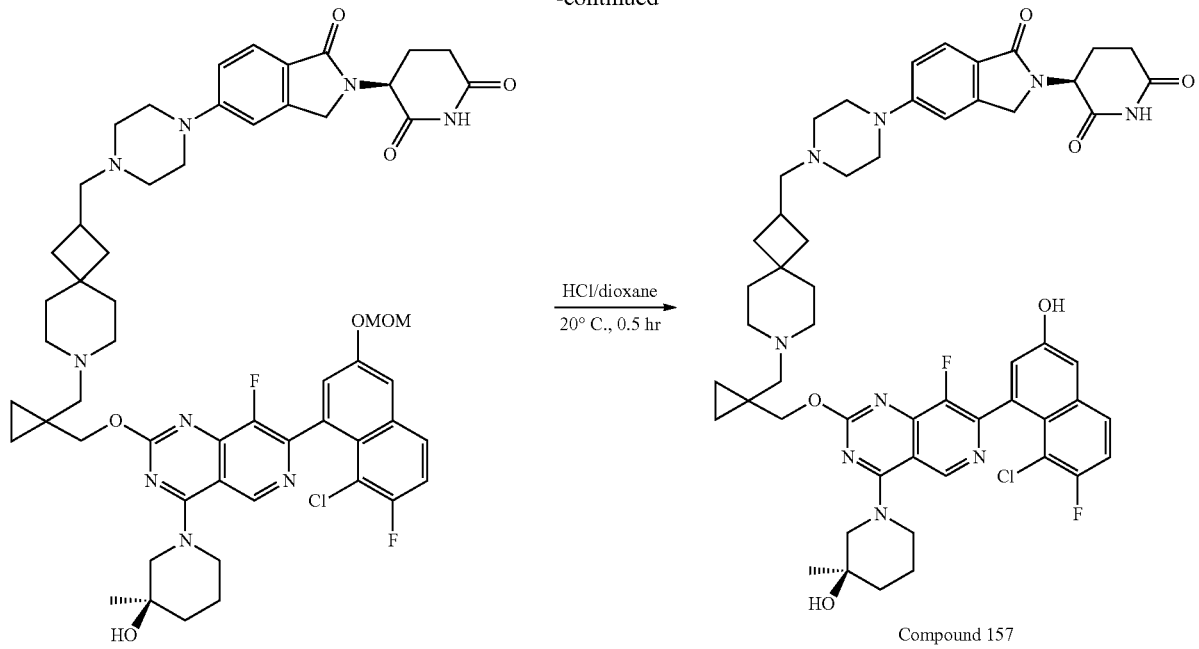

Step 1: Preparation of (S)-3-(5-(4-((7-((1-(((7-(8-chloro-7-fluoro-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione To a mixture of 1-[[7-[8-chloro-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropanecarbaldehyde (80 mg, 134 µmol, 1 eq), (3S)-3-[5-[4-(7-azaspiro[3.5]nonan-2-ylmethyl)piperazin-1-yl]-1-oxo-isoindolin-2-yl]piperidine-2,6-dione (100 mg, 168 µmol, 1.26 eq, 2HCl) in DMSO (2 mL) and THF (1 mL) was added Ti(OEt)$_4$ (305 mg, 1.34 mmol, 277 µL, 10 eq). The reaction mixture was stirred at 20° C. for 1 hour. Then NaBH$_3$CN (16.8 mg, 267 µmol, 2 eq) was added and the reaction mixture was stirred at 20° C. for 0.5 hours. LCMS showed complete consumption of the reactant and detection of the desired product. The reaction mixture was poured into water (20 mL), filtered and extracted with DCM (20 mL*3). Then the organic layers were combined and washed with brine (30 mL), dried over anhydrous Na$_2$SO$_4$, concentrated under reduced pressure to afford the crude residue. The crude residue was purified by reversed phased HPLC (0.1% FA condition) to afford (S)-3-(5-(4-((7-((1-(((7-(8-chloro-7-fluoro-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione (70 mg, 64.8 µmol, 48.5% yield, 97% purity) as a white solid. $^1$H NMR (400 MHZ, METHANOL-d$_4$) δ=9.23 (s, 1H), 8.52 (s, 1H), 7.95 (dd, J=5.6, 9.6 Hz, 1H), 7.71 (d, J=2.4 Hz, 1H), 7.64 (d, J=8.6 Hz, 1H), 7.47 (dt, J=1.4, 8.8 Hz, 1H), 7.42-7.35 (m, 1H), 7.12-7.01 (m, 2H), 5.37 (s, 2H), 5.10 (dd, J=4.8, 13.4 Hz, 1H), 4.59-4.54 (m, 1H), 4.50 (br d, J=12.2 Hz, 1H), 4.43 (s, 1H), 4.40 (br d, J=2.6 Hz, 1H), 4.39-4.35 (m, 1H), 4.34-4.27 (m, 1H), 3.63 (br d, J=14.4 Hz, 1H), 3.52 (s, 3H), 3.46-3.40 (m, 1H), 3.38-3.33 (m, 4H), 3.24-3.00 (m, 4H), 2.95-2.83 (m, 2H), 2.82-2.77 (m, 1H), 2.77-2.67 (m, 1H), 2.66-2.60 (m, 4H), 2.59-2.50 (m, 3H), 2.49-2.43 (m, 1H), 2.20-2.03 (m, 4H), 2.02-1.91 (m, 2H), 1.90-1.73 (m, 6H), 1.71-1.50 (m, 3H), 1.30 (d, J=9.2 Hz, 3H), 0.99-0.86 (m, 2H), 0.79 (br s, 2H).

Step 2: Preparation of (S)-3-(5-(4-((7-((1-(((7-(8-chloro-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione (Compound 157)

To a mixture of (3S)-3-[5-[4-[7-[1-[[7-[8-chloro-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropyl]methyl]-7-azaspiro[3.5]nonan-2-yl]methyl]piperazin-1-yl]-1-oxo-isoindolin-2-yl]piperidine-2,6-dione (65 mg, 62.0 µmol, 1 eq) in DCM (1 mL) was added HCl solution (2 M in dioxane, 1 mL, 32.3 eq) and the reaction mixture was stirred at 20° C. for 0.5 hours. LCMS showed complete consumption of the reactant and detection of the desired product. The reaction mixture was concentrated under reduced pressure to afford the crude residue. The crude residue was purified by Prep-HPLC (column: Phenomenex Luna C18 150*25 mm*10 µm; mobile phase: [water (FA)-ACN]; gradient: 10%-40% B over 10 minutes) to afford (S)-3-(5-(4-((7-((1-(((7-(8-chloro-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione (30.7 mg, 29.2 µmol, 47.1% yield, 95.6% purity) as a white solid. LCMS: [M+H]$^+$=1004.4 $^1$H NMR (400 MHZ, METHANOL-d$_4$) δ=9.21 (d, J=2.4 Hz, 1H), 8.52 (s, 1H), 7.82 (dd, J=5.6, 9.2 Hz, 1H), 7.64 (d, J=8.6 Hz, 1H), 7.44-7.36 (m, 2H), 7.22 (dd, J=2.4, 4.6 Hz, 1H), 7.12-7.04

(m, 2H), 5.10 (dd, J=4.8, 13.6 Hz, 1H), 4.59-4.50 (m, 3H), 4.49-4.38 (m, 3H), 4.36-4.25 (m, 1H), 3.62 (t, J=13.6 Hz, 1H), 3.47-3.40 (m, 1H), 3.40-3.34 (m, 4H), 3.30-2.95 (m, 5H), 2.94-2.86 (m, 1H), 2.81-2.73 (m, 1H), 2.70-2.61 (m, 4H), 2.60-2.50 (m, 3H), 2.50-2.36 (m, 1H), 2.15 (m, 2H), 2.12-2.01 (m, 2H), 1.95 (br s, 2H), 1.87-1.70 (m, 5H), 1.58 (br t, J=8.0 Hz, 2H), 1.30 (d, J=8.8 Hz, 3H), 0.93 (br s, 2H), 0.78 (br s, 2H).
Example 34: Preparation of (3S)-3-(5-(4-((7-((1-(((7-(8-ethyl-7-fluoro-3-hydroxynaphthalen-1-yl)-8-fluoro-4-(1,6-dioxa-9-azaspiro[3.6]decan-9-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione (Compound 124)
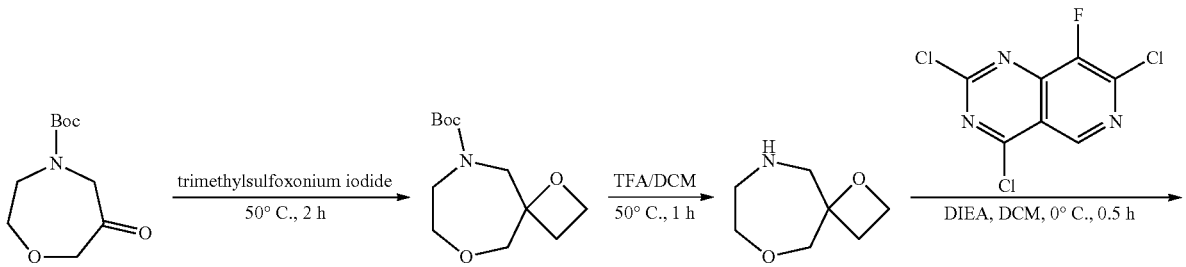
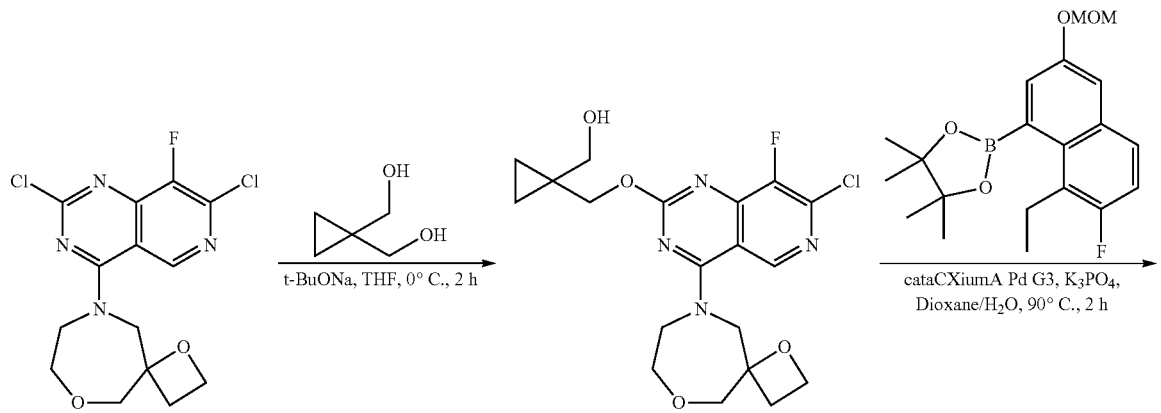
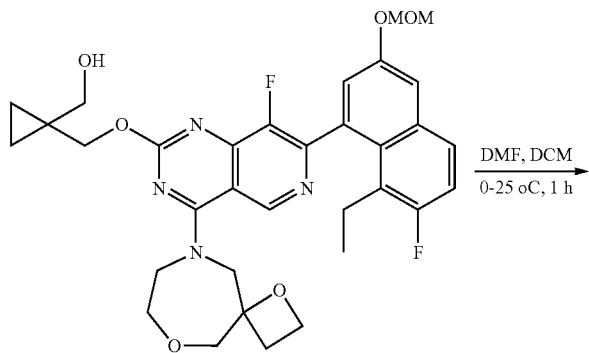

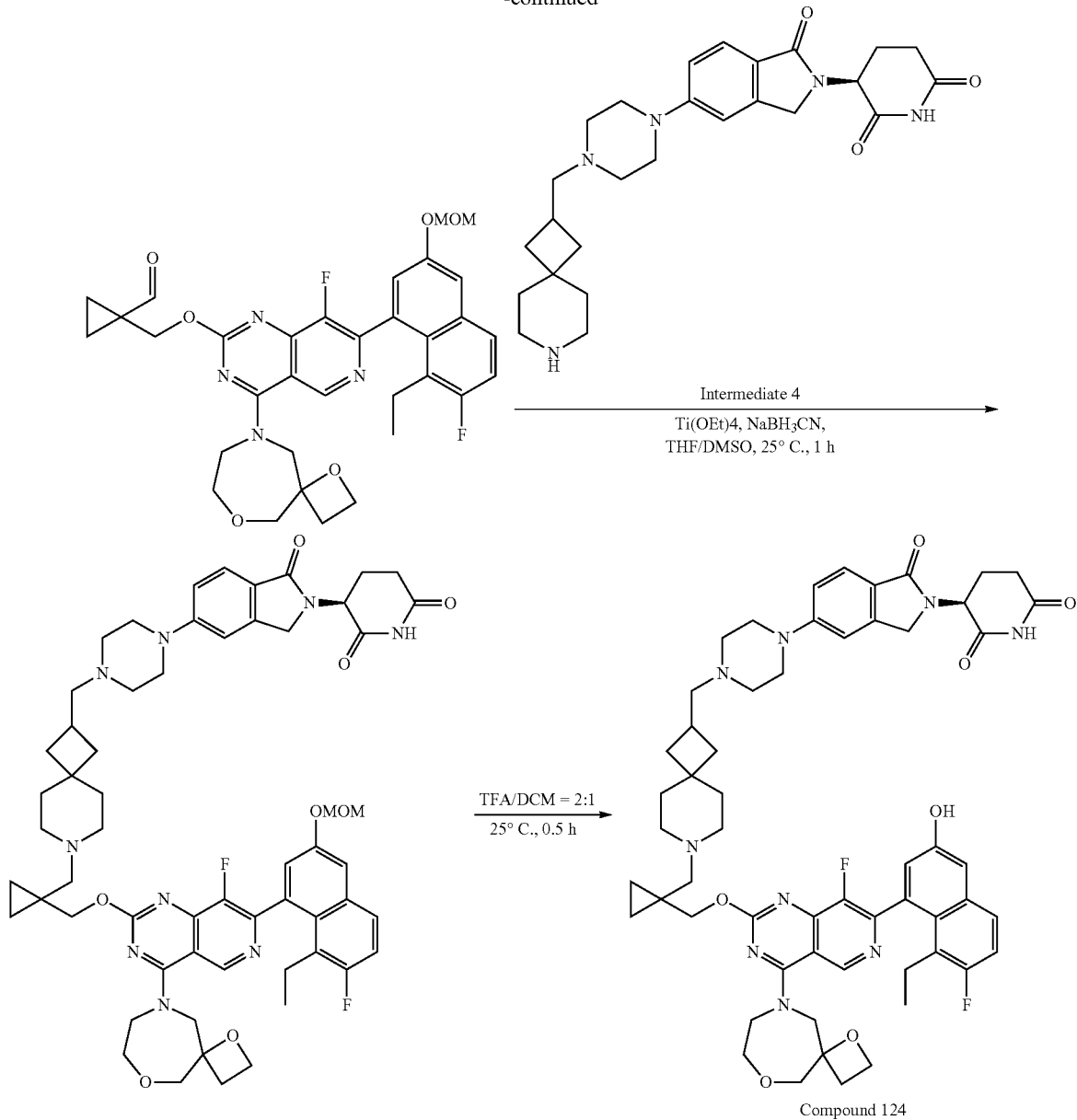

Compound 124

Step 1: Preparation of tert-butyl 1,6-dioxa-9-azaspiro[3.6]decane-9-carboxylate To a suspension of trimethylsulfoxonium iodide (5.11 g, 23.23 mmol, 2.5 eq) in t-BuOH (50 mL) was added t-BuOK (2.61 g, 23.23 mmol, 2.5 eq) at 50° C. The mixture was stirred at 50° C. for 1 hour. Then tert-butyl 6-oxo-1,4-oxazepane-4-carboxylate (2 g, 9.29 mmol, 1 eq) was added at 50° C. and the mixture stirred at 50° C. for another 1 hour. LCMS indicated complete consumption of the reactant. A new peak of 46% peak area with desired mass was detected on LCMS. The residue was diluted with EA (200 mL) and washed with H$_2$O (200 mL). The combined organic layers were washed with brine (100 mL), dried over anhydrous Na$_2$SO$_4$, filtered and concentrated under reduced pressure to give a residue. The residue was purified by column chromatography (SiO$_2$, Petroleum ether/Ethyl acetate=1/0 to 2/1) to afford tert-butyl 1,6-dioxa-9-azaspiro[3.6]decane-9-carboxylate (940 mg, crude) as a light yellow oil. $^1$H NMR (400 MHz, CHLOROFORM-d) δ=4.58-4.38 (m, 2H), 4.24 (br s, 2H), 3.88-3.79 (m, 2H), 3.63-3.56 (m, 2H), 3.46-3.39 (m, 1H), 3.30-3.16 (m, 1H), 2.78-2.69 (m, 1H), 2.49-2.28 (m, 1H), 1.48 (s, 9H).

Step 2: Preparation of 1,6-dioxa-9-azaspiro[3.6]decane

To a solution of tert-butyl 1,6-dioxa-9-azaspiro[3.6]decane-9-carboxylate (940 mg, 3.86 mmol, 1 eq) in DCM (10 mL) was added TFA (3.07 g, 26.9 mmol, 2 mL, 6.97 eq). The mixture was stirred at 25° C. for 1 hour. LCMS indicated complete consumption of the reactant and detection of the desired product. The reaction mixture was concentrated under reduced pressure to afford the desired compound without further purification.

Step 3: Preparation of 9-(2,7-dichloro-8-fluoro-pyrido[4,3-d]pyrimidin-4-yl)-1,6-dioxa-9-azaspiro[3.6]decane To a solution of 2,4,7-trichloro-8-fluoro-pyrido[4,3-d]pyrimidine (750 mg, 2.97 mmol, 1 eq) in DCM (12 mL) was added DIEA (1.15 g, 8.91 mmol, 1.55 mL, 3 eq) and 1,6-dioxa-9-azaspiro[3.6]decane (1.28 g, 8.91 mmol, 3 eq) at 0° C. The mixture was stirred at 0° C. for 0.5 hours. LCMS showed a peak of 52% peak area with desired mass. The reaction mixture was diluted with DCM (50 mL) and extracted with H$_2$O (50 mL). The combined organic layers were washed with brine (20 mL), dried over anhydrous Na$_2$SO$_4$, filtered and concentrated under reduced pressure to give a residue. The residue was purified by column chromatography (SiO$_2$, Petroleum ether/Ethyl acetate=1/0 to 3/1) to give 9-(2,7-dichloro-8-fluoropyrido[4,3-d]pyrimidin-4-yl)-1,6-dioxa-9-azaspiro[3.6]decane (730 mg, 1.48 mmol, 49.9% yield, 73% purity) as a white solid.

Step 4: Preparation of (1-(((7-chloro-8-fluoro-4-(1,6-dioxa-9-azaspiro[3.6]decan-9-yl)pyrido[4,3-d]pyrimidin-2-yl)oxy)methyl)cyclopropyl)methanol To a solution of [1-(hydroxymethyl)cyclopropyl]methanol (207 mg, 2.03 mmol, 1 eq) in THF (10 mL) was added t-BuONa (175 mg, 1.83 mmol, 0.9 eq) and a solution of 6-(2,7-dichloro-8-fluoro-pyrido[4,3-d]pyrimidin-4-yl)-1,9-dioxa-6-azaspiro[3.6]decane (730 mg, 2.03 mmol, 1 eq) in THF (10 mL). The mixture was stirred at 0° C. for 2 hours. The reaction mixture was diluted with EA (20 mL) and extracted with H$_2$O (20 mL). The combined organic layers were washed with brine (10 mL), dried over anhydrous Na$_2$SO$_4$, filtered and concentrated under reduced pressure to give a residue. The residue was purified by prep-TLC (SiO$_2$, DCM:MeOH=10:1) to afford (1-(((7-chloro-8-fluoro-4-(1,6-dioxa-9-azaspiro[3.6]decan-9-yl)pyrido[4,3-d]pyrimidin-2-yl)oxy)methyl)cyclopropyl)methanol (350 mg, 782 µmol, 38.5% yield, 95% purity) as a white solid.

Step 5: Preparation of (1-(((7-(8-ethyl-7-fluoro-3-(methoxymethoxy)naphthalen-1-yl)-8-fluoro-4-(1,6-dioxa-9-azaspiro[3.6]decan-9-yl)pyrido[4,3-d]pyrimidin-2-yl)oxy)methyl)cyclopropyl)methanol To a solution of (1-(((7-chloro-8-fluoro-4-(1,6-dioxa-9-azaspiro[3.6]decan-9-yl)pyrido[4,3-d]pyrimidin-2-yl)oxy)methyl)cyclopropyl)methanol (470 mg, 1.11 mmol, 1 eq) and 2-[8-ethyl-7-fluoro-3-(methoxymethoxy)-1-naphthyl]-4,4,5,5-tetramethyl-1,3,2-dioxaborolane (597 mg, 1.66 mmol, 1.5 eq) in dioxane (8 mL) was added [2-(2-aminophenyl)phenyl]palladium(1+);bis(1-adamantyl)-butyl-phosphane; methanesulfonate (80.5 mg, 110 µmol, 0.1 eq) and K$_3$PO$_4$ (1.5 M, 2.21 mL, 3 eq). The mixture was stirred at 90° C. for 1 hour. LCMS showed a new peak of 40% peak area with desired mass. The residue was diluted with EA (20 mL) and extracted with H$_2$O (20 mL). The combined organic layers were washed with brine (10 mL), dried over anhydrous Na$_2$SO$_4$, filtered and concentrated under reduced pressure to give a residue. The residue was purified by column chromatography (SiO$_2$, Petroleum ether/Ethyl acetate=0/1 to 1/0) to afford (1-(((7-(8-ethyl-7-fluoro-3-(methoxymethoxy)naphthalen-1-yl)-8-fluoro-4-(1,6-dioxa-9-azaspiro[3.6]decan-9-yl)pyrido[4,3-d]pyrimidin-2-yl)oxy)methyl)cyclopropyl)methanol (475 mg, 556 µmol, 50.3% yield, 73% purity) as a yellow gum.

Step 6: Preparation of 1-(((7-(8-ethyl-7-fluoro-3-(methoxymethoxy)naphthalen-1-yl)-8-fluoro-4-(1,6-dioxa-9-azaspiro[3.6]decan-9-yl)pyrido[4,3-d]pyrimidin-2-yl)oxy)methyl)cyclopropane-1-carbaldehyde To a solution (1-(((7-(8-ethyl-7-fluoro-3-(methoxymethoxy)naphthalen-1-yl)-8-fluoro-4-(1,6-dioxa-9-azaspiro[3.6]decan-9-yl)pyrido[4,3-d]pyrimidin-2-yl)oxy)methyl)cyclopropyl)methanol (465 mg, 746 µmol, 1 eq) in DCM (4 mL) was added DMP (475 mg, 1.12 mmol, 347 µL, 1.5 eq) at 0° C. Then the mixture was stirred at 25° C. for 1 hour. LCMS showed complete consumption of the reactant and detection of the desired product. The reaction mixture was concentrated under reduced pressure to give a crude residue, which was purified by column chromatography (SiO$_2$, Petroleum ether/Ethyl acetate=0/1 to 1/1) to 1-(((7-(8-ethyl-7-fluoro-3-(methoxymethoxy)naphthalen-1-yl)-8-fluoro-4-(1,6-dioxa-9-azaspiro[3.6]decan-9-yl)pyrido[4,3-d]pyrimidin-2-yl)oxy)methyl)cyclopropane-1-carbaldehyde (380 mg, 520 µmol, 69.6% yield, 85% purity) as a yellow solid.

Step 7: Preparation of (3S)-3-(5-(4-((7-((1-(((7-(8-ethyl-7-fluoro-3-(methoxymethoxy)naphthalen-1-yl)-8-fluoro-4-(1,6-dioxa-9-azaspiro[3.6]decan-9-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione To a solution of 1-(((7-(8-ethyl-7-fluoro-3-(methoxymethoxy)naphthalen-1-yl)-8-fluoro-4-(1,6-dioxa-9-azaspiro[3.6]decan-9-yl)pyrido[4,3-d]pyrimidin-2-yl)oxy)methyl)cyclopropane-1-carbaldehyde (120 mg, 193 µmol, 1 eq) and (3S)-3-[5-[4-(7-azaspiro[3.5]nonan-2-ylmethyl)piperazin-1-yl]-1-oxo-isoindolin-2-yl]piperidine-2,6-dione (108 mg, 232 µmol, 1.2 eq) in THF (2 mL) and DMSO (0.5 mL) was added Ti(OEt)$_4$ (1.10 g, 4.83 mmol, 1.00 mL, 25 eq). The mixture was stirred at 25° C. for 1 hour. Then NaBH$_3$CN (60.5 mg, 966 µmol, 5 eq) was added at 0° C., and the mixture was stirred at 25° C. for 1 hour. LCMS showed complete consumption of the reactant and detection of the desired product. The reaction mixture was poured into a mixture of THF (200 mL) and ethyl acetate (100 mL). The combined organic layers were washed with water (20 mL), dried over anhydrous Na$_2$SO$_4$, filtered and concentrated under reduced pressure. The residue was purified by prep-TLC (SiO$_2$, DCM:MeOH=5:1) to afford (3S)-3-(5-(4-((7-((1-(((7-(8-ethyl-7-fluoro-3-(methoxymethoxy)naphthalen-1-yl)-8-fluoro-4-(1,6-dioxa-9-azaspiro[3.6]decan-9-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione (80 mg, 68.7 µmol, 35.5% yield, 92% purity) as an off-white solid. $^1$H NMR (400 MHZ, CHLOROFORM-d) δ=9.51-9.36 (m, 1H), 7.98-7.90 (m, 1H), 7.76-7.72 (m, 1H), 7.71-7.65 (m, 1H), 7.52 (d, J=2.6 Hz, 1H), 7.24-7.20 (m, 1H), 7.01-6.96 (m, 1H), 6.90-6.83 (m, 1H), 5.32-5.30 (m, 2H), 5.30-5.27 (m, 1H), 5.24-5.15 (m, 1H), 4.85-4.68 (m, 1H), 4.66-4.52 (m, 4H), 4.48-4.35 (m, 2H), 4.16 (br d, J=17.6 Hz, 2H), 4.11-3.73 (m, 6H), 3.52 (s, 3H), 3.38-3.22 (m, 4H), 2.93-2.64 (m, 4H), 2.60-2.44 (m, 9H), 2.41-2.14 (m, 6H), 2.09-1.90 (m, 3H), 1.26 (s, 5H), 1.00-0.92 (m, 2H), 0.89-0.81 (m, 5H), 0.15--0.02 (m, 1H).

Step 8: preparation of (3S)-3-(5-(4-((7-((1-(((7-(8-ethyl-7-fluoro-3-hydroxynaphthalen-1-yl)-8-fluoro-4-(1,6-dioxa-9-azaspiro[3.6]decan-9-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione (Compound 124)

To a solution of (3S)-3-(5-(4-((7-((1-(((7-(8-ethyl-7-fluoro-3-(methoxymethoxy)naphthalen-1-yl)-8-fluoro-4-(1,6-dioxa-9-azaspiro[3.6]decan-9-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione (76 mg, 71.01 μmol, 1 eq) in DCM (2 mL) was added TFA (1 mL). The mixture was stirred at 25° C. for 0.5 hour. LCMS showed complete consumption of the reactant and a new peak of 95% peak area with desired mass. The reaction mixture was concentrated to give a residue, which was purified by prep-HPLC (column: Phenomenex Luna C18 150*25 mm 10 μm; mobile phase: [water (FA)-ACN]; gradient: 9%-39% B over 10 minutes) to afford (3S)-3-(5-(4-((7-((1-(((7-(8-ethyl-7-fluoro-3-hydroxynaphthalen-1-yl)-8-fluoro-4-(1,6-dioxa-9-azaspiro[3.6]decan-9-yl)pyrido[4,3-d]pyrimidin-2-yl)oxy)methyl)cyclopropyl)methyl)-7-azaspiro[3.5]nonan-2-yl)methyl)piperazin-1-yl)-1-oxoisoindolin-2-yl)piperidine-2,6-dione (25.48 mg, 24.3 μmol, 34.2% yield, 98% purity) as a white solid. LCMS: [M+H]$^+$=1026.7. $^1$H NMR (400 MHZ, DMSO-d$_6$) δ=10.94 (s, 1H), 10.15-9.81 (m, 1H), 9.41 (d, J=11.2 Hz, 1H), 8.17 (s, 1H), 7.87-7.64 (m, 1H), 7.51 (d, J=9.2 Hz, 1H), 7.42-7.26 (m, 2H), 7.12-6.99 (m, 3H), 5.09-5.01 (m, 1H), 4.74-4.49 (m, 1H), 4.49-4.37 (m, 3H), 4.37-4.27 (m, 4H), 4.22 (s, 1H), 4.02-3.85 (m, 5H), 3.25 (br d, J=3.6 Hz, 4H), 2.95-2.86 (m, 1H), 2.70-2.58 (m, 2H), 2.46 (br s, 6H), 2.39-2.33 (m, 5H), 2.31-2.22 (m, 4H), 2.21-2.04 (m, 2H), 1.99-1.92 (m, 1H), 1.89-1.80 (m, 2H), 1.56-1.47 (m, 2H), 1.43-1.32 (m, 4H), 0.78-0.70 (m, 3H), 0.65 (s, 2H), 0.40 (s, 2H).

Compound 125 was prepared via a similar synthetic procedure as example 34.

Example 35: Preparation of (S)-3-(5-(4-(3-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-3-azaspiro[5.5]undecan-9-yl)piperazin-1-yl)-1-oxoisoindolin-2-yl)piperidine-2,6-dione (Compound 120)

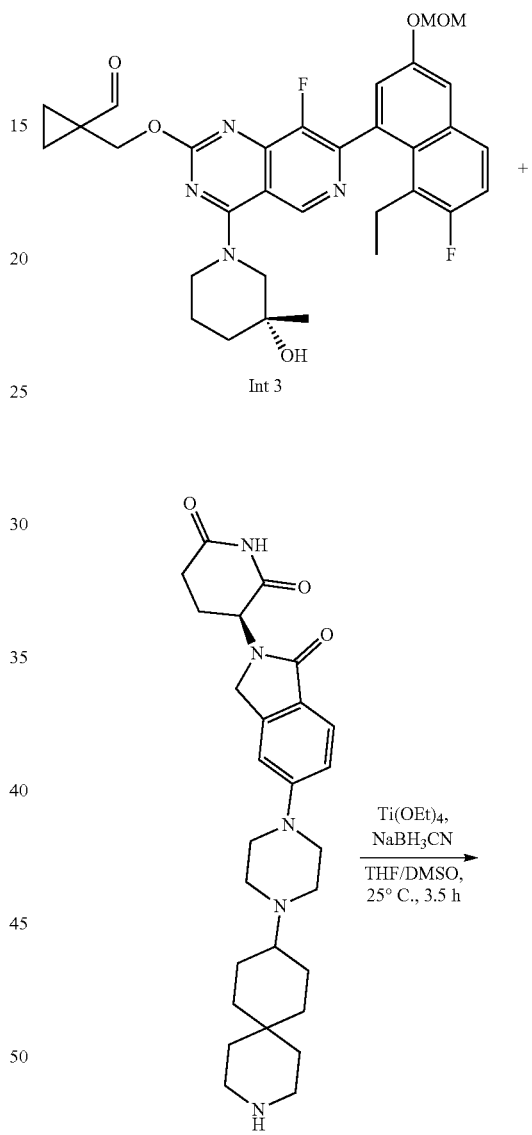

| Cpd # | Characterization |
|---|---|
| 125 | LCMS: [M + H]$^+$ = 986.4<br>$^1$H NMR (400 MHz, DMSO-d$_6$) δ = 10.94 (s, 1H), 10.26-9.67 (m, 1H), 9.42 (d, J = 11.6 Hz, 1H), 8.17 (s, 1H), 7.86-7.68 (m, 1H), 7.52 (d, J = 8.8 Hz, 1H), 7.41-7.30 (m, 2H), 7.11-6.98 (m, 3H), 5.08-5.01 (m, 1H), 4.74-4.53 (m, 1H), 4.53-4.36 (m, 4H), 4.36-4.24 (m, 4H), 4.23 (s, 1H), 4.00-3.85 (m, 5H), 3.26 (br s, 4H), 3.03-2.81 (m, 4H), 2.60 (br s, 2H), 2.45 (br s, 4H), 2.40-2.25 (m, 4H), 2.12 (br d, J = 5.2 Hz, 2H), 2.01-1.84 (m, 3H), 1.65 (br d, J = 10.8 Hz, 2H), 1.53-1.43 (m, 1H), 1.12-0.99 (m, 2H), 0.78-0.70 (m, 3H), 0.66 (br s, 2H), 0.42 (s, 2H). |

-continued

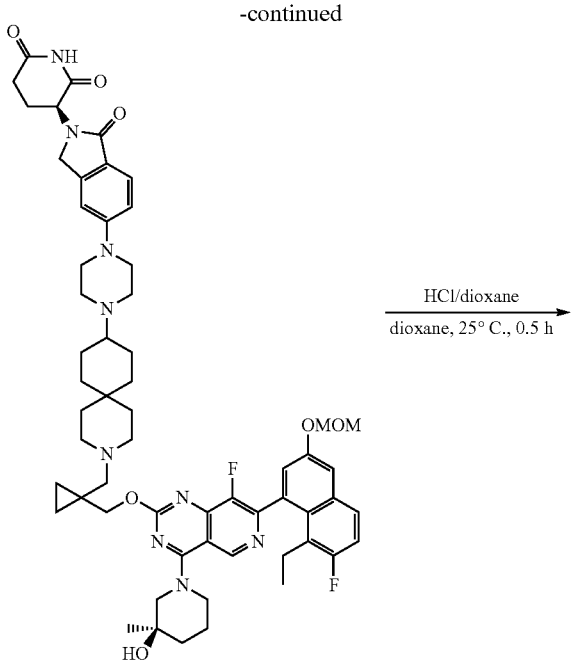

HCl/dioxane
───────────────→
dioxane, 25° C., 0.5 h

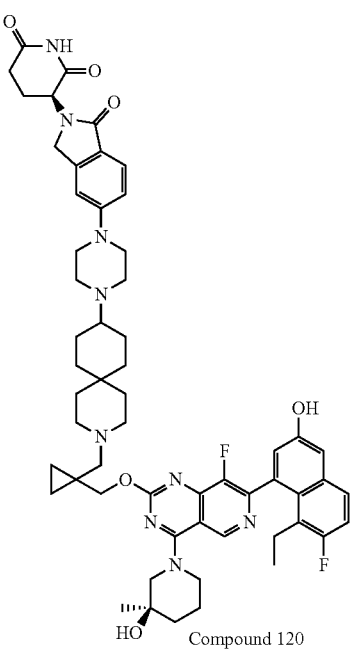 [SMILES: CCc1c(F)ccc2cc(O)cc(-c3ncc4c(N5CCC[C@@](C)(O)C5)nc(OCC5(CN6CCC7(CCC(N8CCN(c9ccc%10c(c9)CN([C@H]9CCC(=O)NC9=O)C%10=O)CC8)CC7)CC6)CC5)nc4c3F)c12]

Compound 120

Step 1: Preparation of (S)-3-(5-(4-(3-((1-(((7-(8-ethyl-7-fluoro-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl) cyclopropyl)methyl)-3-azaspiro[5.5]undecan-9-yl) piperazin-1-yl)-1-oxoisoindolin-2-yl)piperidine-2,6-dione To a solution of 1-[[7-[8-ethyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl] oxymethyl]cyclopropanecarbaldehyde (150 mg, 253.11 µmol, 1 eq) and (3S)-3-[5-[4-(3-azaspiro[5.5]undecan-9-yl) piperazin-1-yl]-1-oxo-isoindolin-2-yl]piperidine-2,6-dione (130 mg, 253 µmol, 1 eq, HCl) in DMSO (2 mL) and THF (5 mL) was added Ti(OEt)$_4$ (288 mg, 1.27 mmol, 262 µL, 5 eq) and the reaction mixture was stirred at 25° C. for 3 hours. Then NaBH$_3$CN (47.7 mg, 759 µmol, 3 eq) was added and the reaction mixture was stirred at 25° C. for 0.5 hours. LCMS showed complete consumption of the reactant and detection of the desired product. The mixture was diluted with water (5 mL) and extracted with EA (5 mL×3). The combined organic layers were washed with brine (5 mL×2), dried over anhydrous Na$_2$SO$_4$, filtered and concentrated under reduced pressure to give a residue. The residue (DCM:MeOH=8:1) was purified by prep-TLC (SiO$_2$, DCM: MeOH=8:1, Rf=0.2) to give (S)-3-(5-(4-(3-((1-(((7-(8-ethyl-7-fluoro-3-(methoxymethoxy)naphthalen-1-yl)-8-fluoro-4-((R)-3-hydroxy-3-methylpiperidin-1-yl)pyrido[4, 3-d]pyrimidin-2-yl)oxy)methyl)cyclopropyl)methyl)-3-azaspiro[5.5]undecan-9-yl)piperazin-1-yl)-1-oxoisoindolin-2-yl)piperidine-2,6-dione (60 mg, 48.2 µmol, 19.0% yield, 85% purity) as a yellow solid.

Step 2: preparation of (S)-3-(5-(4-(3-((1-(((7-(8-ethyl-7-fluoro-3-hydroxynaphthalen-1-yl)-8-fluoro-4-((R)-3-hydroxy-3-methylpiperidin-1-yl)pyrido[4, 3-d]pyrimidin-2-yl)oxy)methyl)cyclopropyl) methyl)-3-azaspiro[5.5]undecan-9-yl)piperazin-1-yl)-1-oxoisoindolin-2-yl)piperidine-2,6-dione (Compound 120)

To a solution of (S)-3-(5-(4-(3-((1-(((7-(8-ethyl-7-fluoro-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-3-azaspiro[5.5] undecan-9-yl)piperazin-1-yl)-1-oxoisoindolin-2-yl) piperidine-2,6-dione (55 mg, 44.2 µmol, 1 eq) in dioxane (0.5 mL) was added HCl solution (4 M in dioxane, 0.1 mL, 9.04 eq). The mixture was stirred at 25° C. for 0.5 hours. LCMS showed complete consumption of the reactant and detection of the desired product. The reaction mixture was filtered and concentrated under reduced pressure to give a residue. The residue was purified by prep-HPLC (FA condition; column: Phenomenex Luna C18 150*25 mm*10 µm; mobile phase: [water (FA)-ACN]; gradient: 12%-42% B over 10 minutes) to give (S)-3-(5-(4-(3-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl) oxy)methyl)cyclopropyl)methyl)-3-azaspiro[5.5]undecan-9-yl)piperazin-1-yl)-1-oxoisoindolin-2-yl)piperidine-2,6-dione (12 mg, 11.1 µmol, 25.1% yield, 94% purity) as a white solid. LCMS: [M+H]$^+$=1012.6. $^1$H NMR (400 MHZ, DMSO-d$_6$) δ=10.94 (s, 1H), 9.22 (s, 1H), 8.18 (s, 1H), 7.81-7.72 (m, 1H), 7.51 (d, J=9.0 Hz, 1H), 7.38-7.32 (m, 2H), 7.07-7.01 (m, 3H), 5.11-4.98 (m, 1H), 4.74 (br d, J=1.2 Hz, 1H), 4.38-4.26 (m, 4H), 4.24-4.17 (m, 1H), 4.10-3.98 (m, 1H), 3.67-3.58 (m, 1H), 3.25 (br s, 6H), 2.90 (br d, J=1.6 Hz, 2H), 2.36-2.32 (m, 4H), 2.26-2.08 (m, 4H), 2.07-1.92 (m, 3H), 1.77-1.55 (m, 9H), 1.42 (br s, 2H), 1.37-1.30 (m, 2H), 1.25 (br d, J=1.6 Hz, 2H), 1.22-1.12 (m, 4H), 1.02 (br s, 3H), 0.78-0.71 (m, 3H), 0.68-0.62 (m, 2H), 0.42 (br s, 2H).

Example 36: Preparation of (3S)-3-[5-[4-[[2-[[1-[[7-(8-ethyl-7-fluoro-3-hydroxy-1-naphthyl)-8-fluoro-4-[(3R)-3-hydroxy-3-methyl-1-piperidyl]pyrido[4,3-d]pyrimidin-2-yl]oxymethyl]cyclopropyl]methyl]-2-azaspiro[3.5]nonan-7-yl]methyl]piperazin-1-yl]-1-oxo-isoindolin-2-yl]piperidine-2,6-dione (Compound 126)
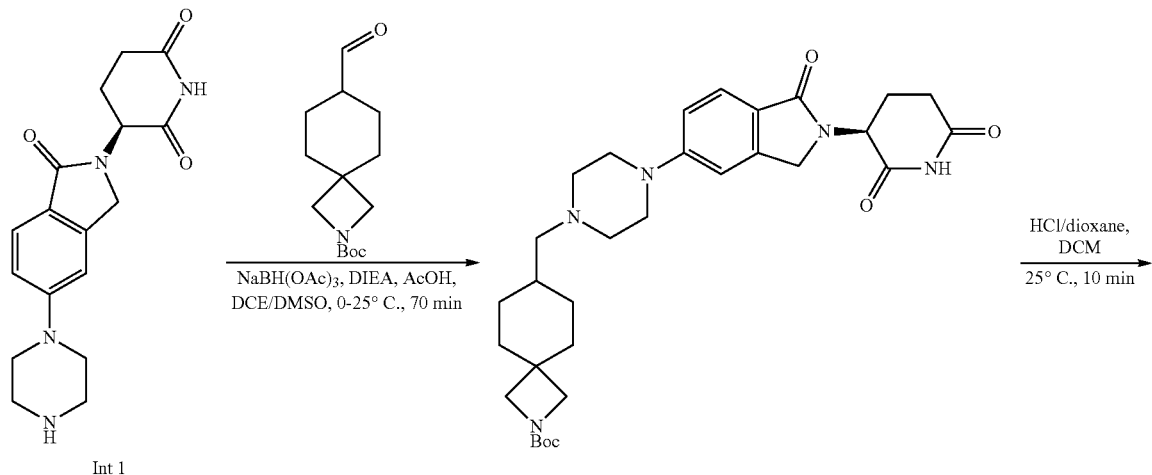
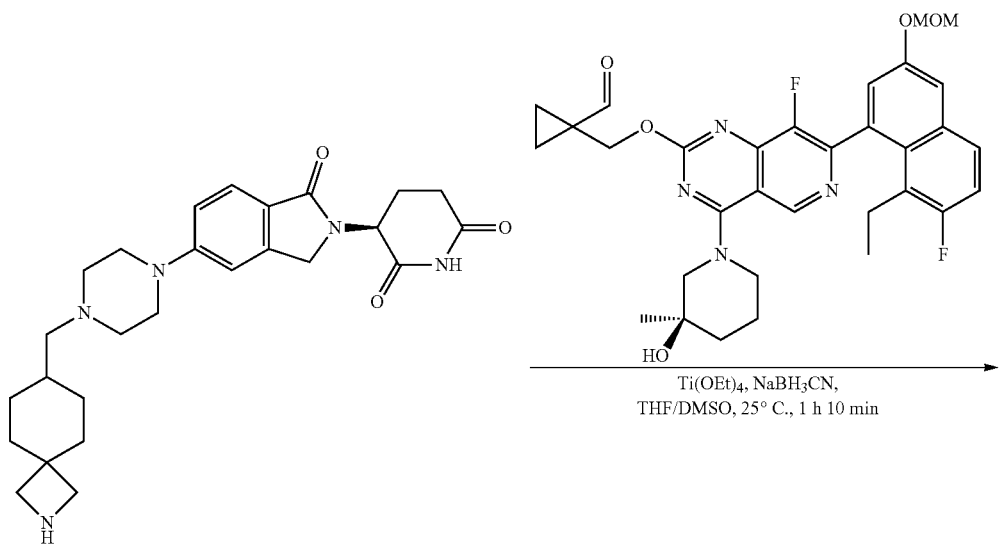

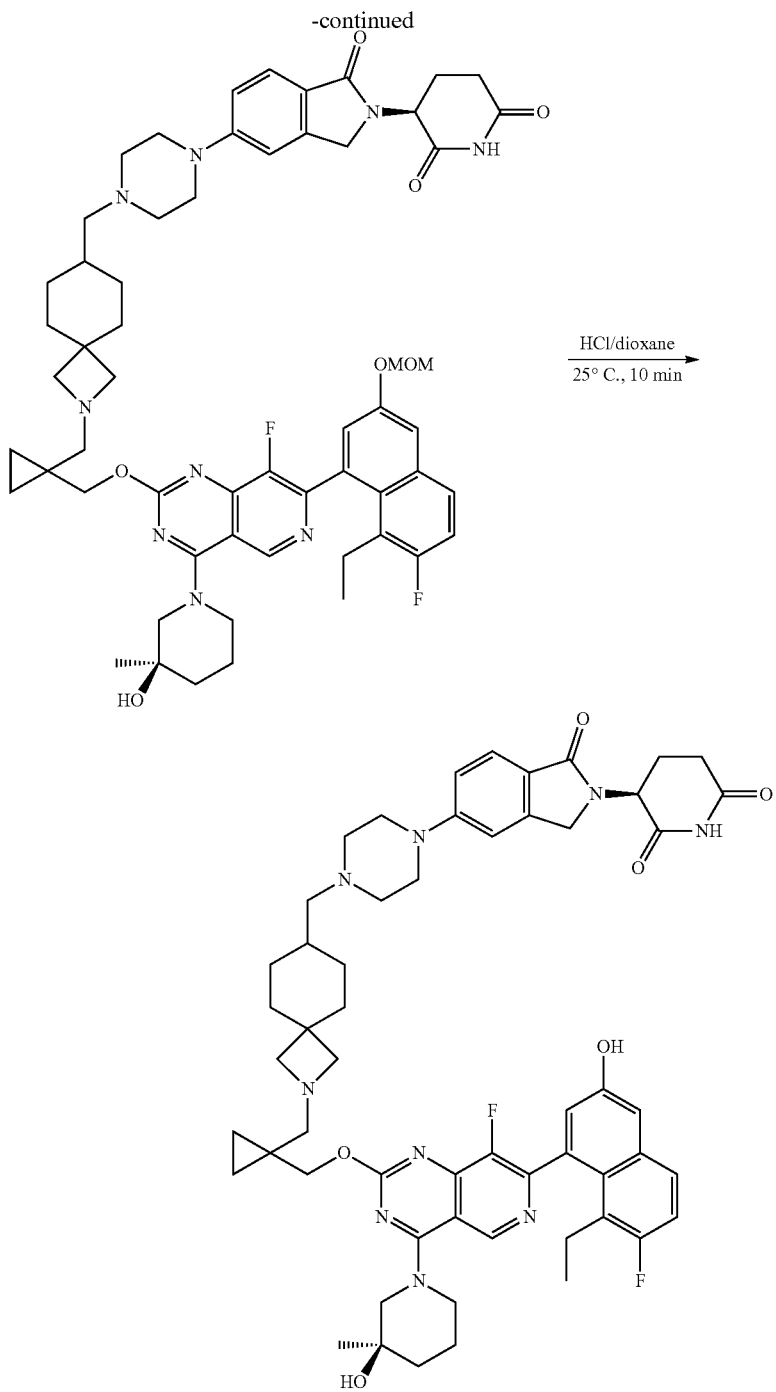

Compound 126

Step 1: Preparation of tert-butyl 7-[4-[2-[(3S)-2,6-dioxo-3-piperidyl]-1-oxo-isoindolin-5-yl]piperazin-1-yl]methyl]-2-azaspiro[3.5]nonane-2-carboxylate To a solution of (3S)-3-(1-oxo-5-piperazin-1-yl-isoindolin-2-yl)piperidine-2,6-dione (1 g, 1.83 mmol, 1 eq) in DCE (12 mL) and DMSO (4 mL) was added DIPEA (236 mg, 1.83 mmol, 318 μL, 1 eq) and the reaction mixture was stirred at 25° C. for 10 minutes. Then tert-butyl 7-formyl-2-azaspiro[3.5]nonane-2-carboxylate (500 mg, 1.97 mmol, 1.08 eq) and AcOH (219 mg, 3.65 mmol, 209 μL, 2 eq) were added and the reaction mixture was stirred at 25° C. for 0.5 hours. NaBH(OAc)$_3$ (774 mg, 3.65 mmol, 2 eq) was added to the mixture at 0° C. and stirred at 25° C. for 0.5 hours. LCMS showed complete consumption of the reactant and a new peak of 88.4% peak area with desired mass. The reaction mixture was quenched by water (100 mL) and extracted with dichloromethane (300 mL). The combined organic layers were washed with brine (500 mL) and dried over anhydrous sodium sulfate, filtered and concentrated under reduced pressure to give tert-butyl 7-[[4-[2-[(3S)-2,6-dioxo-3-piperidyl]-1-oxo-isoindolin-5-yl]piperazin-1-yl]

methyl]-2-azaspiro[3.5]nonane-2-carboxylate (1 g, 1.77 mmol, 96.74% yield) as a yellow oil. $^1$H NMR (400 MHz, DMSO-d$_6$) δ=10.93 (br s, 1H), 7.51 (d, J=8.8 Hz, 1H), 7.11-6.99 (m, 2H), 5.04 (dd, J=5.2, 13.2 Hz, 1H), 4.39-4.13 (m, 2H), 3.52-3.43 (m, 4H), 3.26 (br s, 4H), 2.95-2.82 (m, 1H), 2.63-2.56 (m, 1H), 2.46 (br d, J=4.0 Hz, 4H), 2.42-2.26 (m, 2H), 2.11 (br d, J=7.2 Hz, 2H), 1.99-1.92 (m, 1H), 1.79 (br d, J=13.2 Hz, 2H), 1.71-1.63 (m, 2H), 1.54-1.41 (m, 2H), 1.37 (s, 9H), 0.92-0.82 (m, 2H).

Step 2: Preparation of (3S)-3-[5-[4-(2-azaspiro[3.5] nonan-7-ylmethyl)piperazin-1-yl]-1-oxo-isoindolin-2-yl]piperidine-2,6-dione To a solution of tert-butyl 7-[4-[2-[(3S)-2,6-dioxo-3-piperidyl]-1-oxo-isoindolin-5-yl]piperazin-1-yl]methyl]-2-azaspiro[3.5]nonane-2-carboxylate (300 mg, 530 μmol, 1 eq) in DCM (1 mL) was added HCl solution (4 M in dioxane, 4 mL, 30.1 eq) at 25° C. The mixture was stirred at 25° C. for 10 minutes. LCMS showed complete consumption of the reactant and a new peak of 90.3% peak with desired mass. The reaction mixture was concentrated under reduced pressure to give (3S)-3-[5-[4-(2-azaspiro[3.5]nonan-7-ylmethyl)piperazin-1-yl]-1-oxo-isoindolin-2-yl]piperidine-2,6-dione (260 mg, 517 μmol, 97.6% yield, HCl) as a white solid. $^1$H NMR (400 MHZ, DMSO-d$_6$) δ=10.95 (s, 2H), 9.32 (br s, 2H), 7.58 (d, J=8.4 Hz, 1H), 7.22-7.05 (m, 2H), 5.06 (dd, J=5.2, 13.2 Hz, 1H), 4.39-4.21 (m, 2H), 3.95 (br s, 2H), 3.65-3.57 (m, 4H), 3.55-3.43 (m, 4H), 3.14-3.02 (m, 2H), 3.01-2.83 (m, 3H), 2.58 (br d, J=17.6 Hz, 2H), 2.48-2.30 (m, 2H), 2.06-1.98 (m, 2H), 1.81 (br d, J=12.0 Hz, 2H), 1.47-1.38 (m, 2H), 1.06-0.93 (m, 2H).

Step 3: Preparation of (3S)-3-[5-[4-[2-[[1-[7-[8-ethyl-7-fluoro-3-(methoxymethoxy)-1-naphthyl]-8-fluoro-4-[(3R)-3-hydroxy-3-methyl-1-piperidyl] pyrido[4,3-d]pyrimidin-2-yl]oxymethyl]cyclopropyl] methyl]-2-azaspiro[3.5]nonan-7-yl]methyl] piperazin-1-yl]-1-oxo-isoindolin-2-yl]piperidine-2,6-dione To a solution of (3S)-3-[5-[4-(2-azaspiro[3.5]nonan-7-ylmethyl)piperazin-1-yl]-1-oxo-isoindolin-2-yl]piperidine-2,6-dione (50 mg, 99.5 μmol, 1 eq, HCl) and 1-[7-[8-ethyl-7-fluoro-3-(methoxymethoxy)-1-naphthyl]-8-fluoro-4-[(3R)-3-hydroxy-3-methyl-1-piperidyl]pyrido[4,3-d] pyrimidin-2-yl]oxymethyl]cyclopropanecarbaldehyde (59.0 mg, 99.5 μmol, 1 eq) in THF (6 mL) and DMSO (2 mL) was added Ti(OEt)$_4$ (1.10 g, 4.82 mmol, 1.00 mL, 48.4 eq). The mixture was stirred at 25° C. for 1 hour. Then NaBH$_3$CN (18.7 mg, 298 μmol, 3 eq) was added to the mixture and the mixture was stirred at 25° C. for 10 minutes. LCMS showed complete consumption of the reactant and a new peak of 70% peak area with desired mass. The reaction mixture was quenched by addition of water (50 mL) at 0° C., diluted with EA (10 mL) and extracted with EA 40 mL (20 mL*2). The combined organic layers were washed with water 100 mL (50 mL*2), dried over anhydrous Na$_2$SO$_4$, filtered and concentrated under reduced pressure to give a residue. The residue was purified by prep-TLC (SiO$_2$, DCM:MeOH=8:1) to give (3S)-3-[5-[4-[2-[[1-[7-[8-ethyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl] oxymethyl]cyclopropyl]methyl]-2-azaspiro[3.5]nonan-7-yl] methyl]piperazin-1-yl]-1-oxo-isoindolin-2-yl]piperidine-2, 6-dione (60 mg, 50.66 μmol, 50.8% yield, 88.0% purity) as a yellow oil.

Step 4: Preparation of (3S)-3-[5-[4-[2-[[1-[[7-(8-ethyl-7-fluoro-3-hydroxy-1-naphthyl)-8-fluoro-4-[(3R)-3-hydroxy-3-methyl-1-piperidyl]pyrido[4,3-d] pyrimidin-2-yl]oxymethyl]cyclopropyl]methyl]-2-azaspiro[3.5]nonan-7-yl]methyl]piperazin-1-yl]-1-oxo-isoindolin-2-yl]piperidine-2,6-dione (Compound 126)

A mixture of (3S)-3-[5-[4-[2-[[1-[[7-[8-ethyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl] oxymethyl]cyclopropyl]methyl]-2-azaspiro[3.5]nonan-7-yl] methyl]piperazin-1-yl]-1-oxo-isoindolin-2-yl]piperidine-2, 6-dione (60 mg, 50.6 μmol, 1 eq) in HCl solution (4 M in dioxane, 4 mL, 315 eq) was stirred at 25° C. for 10 minutes. LCMS showed complete consumption of the reactant and a new peak of 82.8% peak area with desired mass. The reaction mixture was concentrated under reduced pressure to give a residue. The residue was purified by prep-HPLC (FA condition; column: Phenomenex Luna C18 150*25 mm*10 μm; mobile phase: [water (FA)-ACN]; gradient: 16%-36% B over 10 minutes) to give (3S)-3-[5-[4-[2-[[1-[[7-(8-ethyl-7-fluoro-3-hydroxy-1-naphthyl)-8-fluoro-4-[(3R)-3-hydroxy-3-methyl-1-piperidyl]pyrido[4,3-d]pyrimidin-2-yl]oxymethyl]cyclopropyl]methyl]-2-azaspiro[3.5]nonan-7-yl] methyl]piperazin-1-yl]-1-oxo-isoindolin-2-yl]piperidine-2, 6-dione (28 mg, 25.9 μmol, 51.2% yield, 96.8% purity, FA) as a white solid. LCMS: [M+H]$^+$=998.5 $^1$H NMR (400 MHZ, METHANOL-d$_4$) δ=9.24 (s, 1H), 8.53 (s, 1H), 7.68 (dd, J=6.0, 9.2 Hz, 1H), 7.64 (d, J=8.8 Hz, 1H), 7.31 (d, J=2.8 Hz, 1H), 7.29-7.21 (m, 1H), 7.09-7.04 (m, 3H), 5.18-5.07 (m, 2H), 4.60-4.54 (m, 4H), 4.40 (br d, J=5.6 Hz, 3H), 4.38-4.25 (m, 1H), 4.12-3.81 (m, 3H), 3.68-3.56 (m, 1H), 3.46-3.38 (m, 2H), 2.95-2.85 (m, 1H), 2.82-2.74 (m, 1H), 2.53 (br s, 4H), 2.51-2.43 (m, 2H), 2.29-2.01 (m, 8H), 1.96-1.69 (m, 6H), 1.60-1.51 (m, 3H), 1.29 (d, J=10.0 Hz, 3H), 1.06-0.92 (m, 2H), 0.91-0.77 (m, 8H).

Example 37: Preparation of (S)-3-(5-(4-(7-((1-(((7-(8-ethyl-7-fluoro-3-hydroxynaphthalen-1-yl)-8-fluoro-4-((R)-3-hydroxy-3-methylpiperidin-1-yl) pyrido[4,3-d]pyrimidin-2-yl)oxy)methyl) cyclopropyl)methyl)-7-azaspiro[3.5]nonan-2-yl) piperazin-1-yl)-1-oxoisoindolin-2-yl)piperidine-2,6-dione (Compound 121)

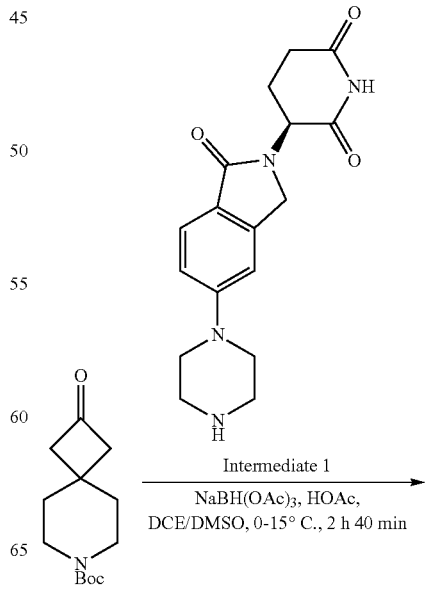

Intermediate 1

NaBH(OAc)$_3$, HOAc, DCE/DMSO, 0-15° C., 2 h 40 min

543
-continued

544
-continued

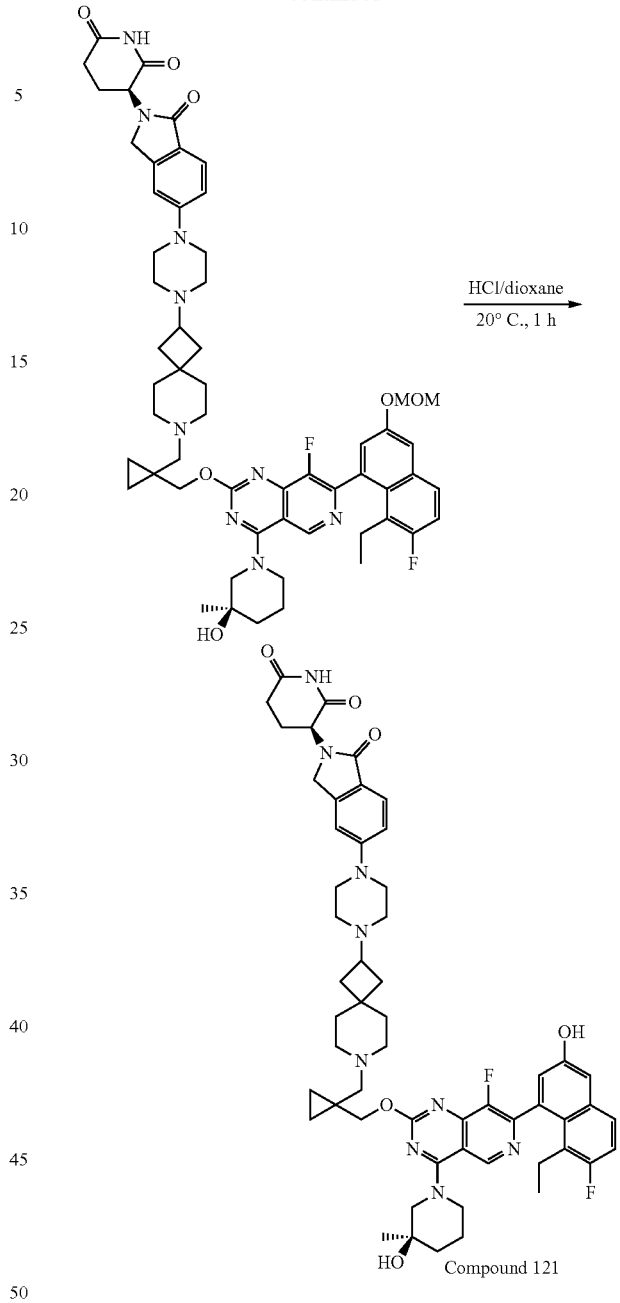

Step 1: Preparation of tert-butyl (S)-2-(4-(2-(2,6-dioxopiperidin-3-yl)-1-oxoisoindolin-5-yl)piperazin-1-yl)-7-azaspiro[3.5]nonane-7-carboxylate To a solution of (3S)-3-(1-oxo-5-piperazin-1-yl-isoindolin-2-yl)piperidine-2,6-dione (503 mg, 919 μmol, 1 eq) in DCE (10 mL) was added DIEA (119 mg, 919 μmol, 160 μL, 1 eq) and the reaction mixture was stirred at 15° C. for 10 minutes. Then tert-butyl 2-oxo-7-azaspiro[3.5]nonane-7-carboxylate (330 mg, 1.38 mmol, 1.5 eq) and AcOH (110 mg, 1.84 mmol, 105 μL, 2 eq) were added and the reaction mixture was stirred at 15° C. for 0.5 hours. NaBH(OAc)$_3$ (390 mg, 1.84 mmol, 2 eq) was added to the mixture at 0° C. and the mixture stirred at 15° C. for 2 hours. LCMS showed a new peak of ~81% peak area with desired mass.

The mixture was diluted with water (20 mL) and extracted with DCM (20 mL*3). The combined organic layers were washed with brine (20 mL*3), dried over anhydrous Na$_2$SO$_4$, concentrated under reduced pressure to give a residue. The residue was purified by column chromatography (SiO$_2$, Dichloromethane:Methanol=1/0 to 10/1) to give tert-butyl (S)-2-(4-(2-(2,6-dioxopiperidin-3-yl)-1-oxoisoindolin-5-yl)piperazin-1-yl)-7-azaspiro[3.5]nonane-7-carboxylate (700 mg, crude) as a white solid.

Step 2: Preparation of (S)-3-(5-(4-(7-azaspiro[3.5]nonan-2-yl)piperazin-1-yl)-1-oxoisoindolin-2-yl)piperidine-2,6-dione A mixture of tert-butyl 2-[4-[2-[(3S)-2,6-dioxo-3-piperidyl]-1-oxo-isoindolin-5-yl]piperazin-1-yl]-7-azaspiro[3.5]nonane-7-carboxylate (655 mg, 1.19 mmol, 1 eq) in HCl solution (4 M in dioxane, 3 mL, 10.11 eq) was stirred at 20° C. for 1 hour. LCMS showed a new peak of ~100% peak area with desired mass. The reaction mixture was concentrated under reduced pressure to give (S)-3-(5-(4-(7-azaspiro[3.5]nonan-2-yl)piperazin-1-yl)-1-oxoisoindolin-2-yl)piperidine-2,6-dione (550 mg, crude) as a white solid.

Step 3: Preparation of (S)-3-(5-(4-(7-((1-(((7-(8-ethyl-7-fluoro-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-azaspiro[3.5]nonan-2-yl)piperazin-1-yl)-1-oxoisoindolin-2-yl)piperidine-2,6-dione To a mixture of (3S)-3-[5-[4-(7-azaspiro[3.5]nonan-2-yl)piperazin-1-yl]-1-oxo-isoindolin-2-yl]piperidine-2,6-dione (100 mg, 205 µmol, 1.2 eq, HCl), 1-[7-[8-ethyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropanecarbaldehyde (101 mg, 171 µmol, 1 eq) in THF (3 mL) and DMSO (1 mL) was added Ti(OEt)$_4$ (195 mg, 854 µmol, 177 µL, 5 eq) and the reaction mixture was stirred at 20° C. for 1 hour. NaBH$_3$CN (32.19 mg, 512.27 µmol, 3 eq) was added and the reaction mixture was stirred at 20° C. for 0.5 hours. LCMS showed a new peak of 40% peak area with desired mass. The mixture was diluted with water (2 mL) and filtered. The filter cakes were washed with (DCM:MeOH=1:1, 10 mL). The combined organic layers were concentrated under reduced pressure to give the crude residue. The residue was purified by prep-HPLC (column: Phenomenex Luna C18 150*25 mm*10 µm; mobile phase: [water (FA)-ACN]; gradient: 17%-47% B over 10 minutes) to give (S)-3-(5-(4-(7-((1-(((7-(8-ethyl-7-fluoro-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-azaspiro[3.5]nonan-2-yl)piperazin-1-yl)-1-oxoisoindolin-2-yl)piperidine-2,6-dione (42 mg, 40.9 µmol, 23.9% yield) as a white solid.

Step 4: Preparation of (S)-3-(5-(4-(7-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-azaspiro[3.5]nonan-2-yl)piperazin-1-yl)-1-oxoisoindolin-2-yl)piperidine-2,6-dione
(Compound 121)

A mixture of (3S)-3-[5-[4-[[7-[[1-[[7-[8-ethyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropyl]methyl]-7-azaspiro[3.5]nonan-2-yl]piperazin-1-yl]-1-oxo-isoindolin-2-yl]piperidine-2,6-dione (32 mg, 31.1 µmol, 1 eq) in HCl solution (4 M in dioxane, 4 mL) was stirred at 20° C. for 1 hour. LCMS showed a new peak of ~94% peak area with desired mass. The reaction mixture was concentrated under reduced pressure to give a residue. The residue was purified by prep-HPLC (column: Phenomenex Luna C18 150*25 mm*10 µm; mobile phase: [water (FA)-ACN]; gradient: 12%-32% B over 10 minutes) to give the desired compound (16.19 mg, 16.1 µmol, 51.6% yield, 97.6% purity) as a white solid. LCMS: [M+H]$^+$ =984.4. $^1$H NMR (400 MHZ, DMSO-d$_6$) δ=0.81 (q, J=7.6 Hz, 5H). 0.95 (s, 2H). 1.29 (d, J=9.6 Hz, 3H). 1.75-1.97 (m, 9H). 2.08-2.27 (m, 5H). 2.46 (br dd, J=13.2, 5.2 Hz, 2H). 2.50-2.58 (m, 4H). 2.74-2.81 (m, 1H). 2.83-2.94 (m, 2H). 3.02-3.27 (m, 4H). 3.34-3.51 (m, 6H). 3.57-3.67 (m, 1H). 4.28-4.36 (m, 1H). 4.40 (br d, J=5.6 Hz, 2H). 4.47 (br t, J=7.6 Hz, 2H). 4.51-4.62 (m, 2H). 5.10 (dd, J=13.20, 5.2 Hz, 1H). 6.99-7.15 (m, 3H). 7.26 (t, J=9.2 Hz, 1H). 7.31 (d, J=2.4 Hz, 1H). 7.58-7.77 (m, 2H). 8.50 (s, 1H). 9.23 (d, J=1.6 Hz, 1H).

Compounds 136, 141, 143, 144, 145, 151, 152, 153, 154, 155, and 158 were prepared via similar synthetic procedures as example 37.

| Cpd # | Characterization |
|---|---|
| 136 | LCMS: [M + H]$^+$ = 984.6 <br> 1H NMR (400 MHz, MeOD-d$_4$) δ = 9.24 (s, 1H), 8.45 (br s, 1H), 7.69-7.62 (m, 1H), 7.32-7.29 (m, 1H), 7.33-7.28 (m, 1H), 7.24 (dt, J = 2.0, 9.2 Hz, 1H), 7.05 (br d, J = 9.2 Hz, 1H), 5.10 (dd, J = 5.2, 13.2 Hz, 1H), 4.57 (br d, J = 12.8 Hz, 1H), 4.47-4.37 (m, 1H), 4.35-4.28 (m, 1H), 4.14 (br s, 1H), 3.98 (br s, 2H), 3.67-3.57 (m, 1H), 3.49-3.39 (m, 1H), 3.37 (br s, 1H), 3.35-3.33 (m, 2H), 2.88 (br dd, J = 5.1, 13.1 Hz, 1H), 2.79 (br s, 1H), 2.52-2.38 (m, 1H), 2.26-2.10 (m, 1H), 1.98-1.74 (m, 1H), 1.60 (br t, J = 12.0 Hz, 1H), 1.34 (br d, J = 8.0 Hz, 1H), 1.29 (d, J = 9.6 Hz, 1H), 0.92-0.79 (m, 7H). |
| 141 | LCMS: [M + H]$^+$ = 966.6 <br> $^1$H NMR (400 MHz, METHANOL-d$_4$) δ ppm 0.86-0.94 (m, 7 H). 1.23-1.36 (m, 4 H). 1.47-1.66 (m, 4 H). 1.71-1.90 (m, 4 H). 2.02-2.18 (m, 4 H). 2.22-2.48 (m, 5 H). 2.71-2.82 (m, 2 H). 2.88 (br dd, J = 13.33, 5.01 Hz, 1 H). 3.04 (br s, 5 H). 3.34-3.50 (m, 5 H). 3.55-3.69 (m, 2 H). 3.94-4.09 (m, 2 H). 4.26-4.42 (m, 5 H). 4.55 (br d, J = 11.13 Hz, 2 H). 5.10 (dd, J = 13.20, 5.14 Hz, 1 H). 7.02-7.10 (m, 3 H). 7.14-7.19 (m, 1 H). 7.27-7.31 (m, 1 H). 7.36 (t, J = 7.76 Hz, 1 H). 7.59-7.68 (m, 2 H). 8.33-8.36 (m, 1 H). 9.19-9.24 (m, 1 H). |

| Cpd # | Characterization |
|---|---|
| 143 | LCMS: [M + H]⁺ = 984.5<br>¹H NMR (400 MHz, METHANOL-d₄) δ ppm 0.62-0.70 (m, 2 H). 0.78-0.87 (m, 5 H). 1.29 (d, J = 9.66 Hz, 3 H). 1.54-1.66 (m, 2 H). 1.75-1.83 (m, 2 H). 1.86 (br s, 1 H). 1.92 (br s, 4 H). 1.99-2.06 (m, 2 H). 2.11-2.26 (m, 3 H). 2.39-2.56 (m, 4 H). 2.74-2.96 (m, 5 H). 3.32 (br s, 4 H). 3.45 (br t, J = 12.10 Hz, 3 H). 3.56-3.73 (m, 5 H). 4.24-4.34 (m, 1 H). 4.34-4.41 (m, 2 H). 4.42-4.48 (m, 2 H). 4.53 (br d, J = 12.84 Hz, 1 H). 5.09 (dd, J = 13.27, 5.20 Hz, 1 H). 7.03-7.10 (m, 3 H). 7.21-7.34 (m, 2 H). 7.59-7.72 (m, 2 H). 8.39 (s, 2 H). 9.22 (d, J = 4.52 Hz, 1 H). |
| 144 | LCMS: [M + H]⁺ = 956.4<br>¹H NMR (400 MHz, METHANOL-d₄) δ = 9.23 (d, J = 2.0 Hz, 1H), 8.52 (s, 1H), 7.69-7.63 (m, 1H), 7.60 (d, J = 9.2 Hz, 1H), 7.32-7.28 (m, 1H), 7.27-7.19 (m, 1H), 7.06 (s, 1H), 7.02-6.96 (m, 2H), 5.10 (dd, J = 5.2, 13.2 Hz, 1H), 4.54 (br s, 2H), 4.42-4.34 (m, 4H), 4.34-4.26 (m, 1H), 4.06-3.91 (m, 2H), 3.75-3.50 (m, 4H), 3.49-3.38 (m, 1H), 3.26-3.21 (m, 4H), 3.20 (s, 3H), 3.07 (br s, 2H), 2.95-2.85 (m, 1H), 2.82-2.73 (m, 1H), 2.45 (br dd, J = 5.2, 12.8 Hz, 2H), 2.28-2.10 (m, 3H), 1.90-1.75 (m, 7H), 1.29 (d, J = 9.6 Hz, 3H), 0.86-0.79 (m, 5H), 0.74 (br s, 2H). |
| 145 | LCMS: [M + H]⁺ = 1012.6<br>¹H NMR(400 MHz, METHANOL-d₄) δ = 9.21 (d, J = 5.2 Hz, 1H), 8.54 (s, 1H), 7.65-7.58 (m, 2H), 7.29-7.19 (m, 2H), 7.08-6.98 (m, 3H), 5.13-5.06 (m, 1H), 4.62-4.45 (m, 3H), 4.44-4.32 (m, 3H), 4.30-4.22 (m, 1H), 3.69-3.56 (m, 1H), 3.50-3.42 (m, 1H), 2.96-2.72 (m, 7H), 2.65-2.42 (m, 4H), 2.29-1.88 (m, 8H), 1.88-1,71 (m, 4H), 1.70-1.55 (m, 10H), 1.29 (d, J = 9.6 Hz, 3H), 0.86-0.70 (m, 5H), 0.58-0.49 (m, 2H). |
| 151 | LCMS: [M + H]⁺ = 984.6<br>¹H NMR (400 MHz, MeOD-d₄) δ = 9.25-9.16 (m, 1H), 7.64 (ddd, J = 2.8, 6.0, 8.8 Hz, 1H), 4.54-4.46 (m, 2H), 4.44-4.33 (m, 3H), 4.30-4.22 (m, 1H), 3.68-3.61 (m, 5H), 3.49-3.43 (m, 1H), 3.22-3.12 (m, 2H), 2.94-2.85 (m, 1H), 2.81-2.73 (m, 1H), 2.58-2.41 (m, 7H), 2.38-2.11 (m, 6H), 1.99-1.91 (m, 2H), 1.87-1.79 (m, 8H), 1.59-1.47 (m, 2H), 1.29 (d, J = 9.6 Hz, 3H), 0.82 (q, J = 7.2 Hz, 3H), 0.72 (br d, J = 2.8 Hz, 2H), 0.52-0.47 (m, 2H). |
| 152 | LCMS: [M + H]⁺ = 956.5<br>¹H NMR (400 MHz, CD₃OD) δ = 9.23 (d, J = 2.0 Hz, 1H), 8.51 (s, 1H), 7.71-7.65 (m, 1H), 7.57 (d, J = 8.8 Hz, 1H), 7.31 (d, J = 2.4 Hz, 1H), 7.25 (t, J = 9.2 Hz, 1H), 7.06 (t, J = 2.0 Hz, 1H), 6.53-6.48 (m, 2H), 5.11-5.06 (m, 1H), 4.54 (d, J = 3.6 Hz, 1H), 4.41-4.34 (m, 4H), 4.33-4.26 (m, 1H), 4.10-4.05 (m, 1H), 3.71-3.66 (m, 5H), 3.59 (d, J = 13.2 Hz, 1H), 3.47-3.42 (m, 1H), 3.20-3.13 (m, 1H), 3.08 (s, 2H), 2.98-2.83 (m, 2H), 2.81-2.72 (m, 2H), 2.53-2.42 (m, 2H), 2.41-2.41 (m, 1H), 2.42-2.29 (m, 2H), 2.29-2.22 (m, 1H), 2.21-2.05 (m, 2H), 1.85 (s, 2H), 1.84 (s, 3H), 1.79 (d, J = 1.2 Hz, 2H), 1.29 (d, J = 9.6 Hz, 3H), 0.93-0.70 (m, 7H). |
| 153 | LCMS: [M + H]⁺ = 984.5<br>¹H NMR (400 MHz, MeOD-d₄) δ = 9.24 (d, J = 3.2 Hz, 1H), 8.50-8.43 (m, 1H), 7.70-7.65 (m, 1H), 7.61 (d, J = 8.6 Hz, 1H), 7.31 (d, J = 2.6 Hz, 1H), 7.28-7.20 (m, 1H), 7.08-7.00 (m, 3H), 5.12-5.06 (m, 1H), 4.56 (br d, J = 14.2 Hz, 1H), 4.43-4.36 (m, 4H), 4.35-4.27 (m, 1H), 4.26-4.18 (m, 2H), 3.93-3.86 (m, 2H), 3.68-3.55 (m, 1H), 3.49-3.39 (m, 1H), 3.36-3.33 (m, 2H), 3.24-3.19 (m, 2H), 2.91-2.84 (m, 1H), 2.81-2.73 (m, 1H), 2.51-2.38 (m, 6H), 2.29-2.19 (m, 1H), 2.18-2.08 (m, 2H), 1.91-1.73 (m, 3H), 1.64-1.53 (m, 8H), 1.32-1.26 (m, 3H), 0.86-0.78 (m, 7H). |
| 154 | LCMS: [M + H]⁺ = 956.6<br>¹H NMR (400 MHz, METHANOL-d₄) δ = 9.23 (d, J = 3.2 Hz, 1H), 7.68 (dd, J = 6.0, 9.2 Hz, 1H), 7.60 (d, J = 8.4 Hz, 1H), 7.33-7.21 (m, 2H), 7.05 (t, J = 2.8 Hz, 1H), 6.57-6.49 (m, 2H), 5.09 (br d, J = 8.4 Hz, 1H), 4.92 (br s, 4H), 4.62-4.41 (m, 4H), 4.38-4.18 (m, 2H), 4.06 (s, 3H), 3.75-3.56 (m, 5H), 3.55-3.40 (m, 1H), 3.18-3.07 (m, 2H), 2.94-2.73 (m, 3H), 2.71-2.61 (m, 1H), 2.51-2.37 (m, 2H), 2.28-1.96 (m, 5H), 1.93-1.59 (m, 5H), 1.30 (d, J = 9.6 Hz, 3H), 0.94 (s, 2H), 0.85-0.75 (m, 5H). |
| 155 | LCMS: [M + H]⁺ = 984.4<br>¹H NMR (400 MHz, METHANOL-d₄) δ ppm 0.72 (br s, 2 H). 0.81 (q, J = 7.59 Hz, 3 H). 0.85-0.93 (m, 2 H). 1.29 (d, J = 9.38 Hz, 3 H). 1.44-1.57 (m, 2 H). 1.75-1.89 (m, 3 H). 1.98 (br d, J = 11.76 Hz, 2 H). 2.04-2.27 (m, 7 H). 2.38-2.51 (m, 2 H). 2.64-2.83 (m, 1 H). 2.65-2.67 (m, 1 H). 2.84-2.96 (m, 5 H). 2.98-3.11 (m, 4 H). 3.39-3.49 (m, 1 H). 3.57-3.66 (m, 1 H). 3.73 (s, 3 H). 3.94-4.02 (m, 2 H). 4.26-4.33 (m, 1 H). 4.35-4.57 (m, 6 H). 5.09 (dd, J = 13.26, 5.13 Hz, 1 H). 7.03-7.10 (m, 3 H). 7.22-7.32 (m, 2 H). 7.59-7.72 (m, 2 H). 8.40 (s, 1 H). 9.22 (d, J = 5.38 Hz, 1 H). |
| 158 | LCMS: [M + H]⁺ = 928.3<br>¹H NMR (400 MHz, METHANOL-d₄) δ = 9.23 (d, J = 2.8 Hz, 1H), 8.57-8.47 (m, 1H), 7.69-7.63 (m, 1H), 7.56 (d, J = 8.0 Hz, 1H), 7.31-7.20 (m, 2H), 7.06 (t, J = 2.8 Hz, 1H), 6.50-6.43 (m, 2H), 5.08 (dd, J = 5.2, 13.2 Hz, 1H), 4.60-4.52 (m, 2H), 4.40-4.26 (m, 5H), 3.98 (s, 6H), 3.71-3.57 (m, 3H), 3.49 (s, 5H), 3.07 (br s, 2H), 2.95-2.85 (m, 1H), 2.82-2.73 (m, 1H), 2.52-2.39 (m, 2H), 2.27-2.09 (m, 3H), 1.89-1.74 (m, 3H), 1.29 (d, J = 9.6 Hz, 3H), 0.85-0.78 (m, 5H), 0.74 (br s, 2H). |

Example 38: Preparation of (S)-3-(5-(4-(2-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-2-azaspiro[3.3]heptan-6-yl)piperazin-1-yl)-1-oxoisoindolin-2-yl)piperidine-2,6-dione (Compound 122)

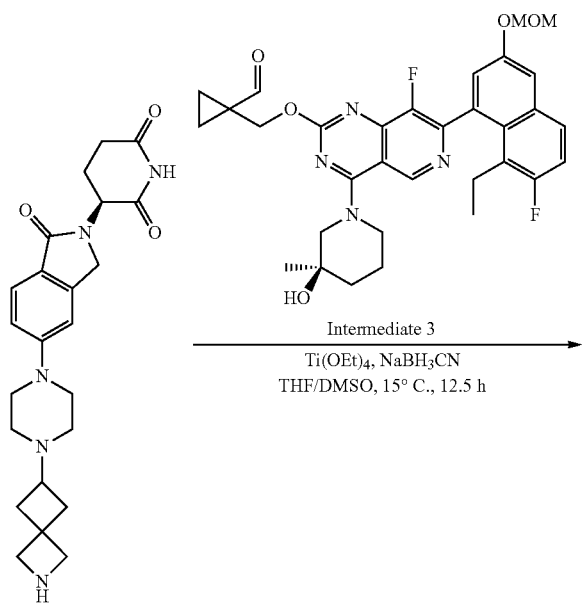

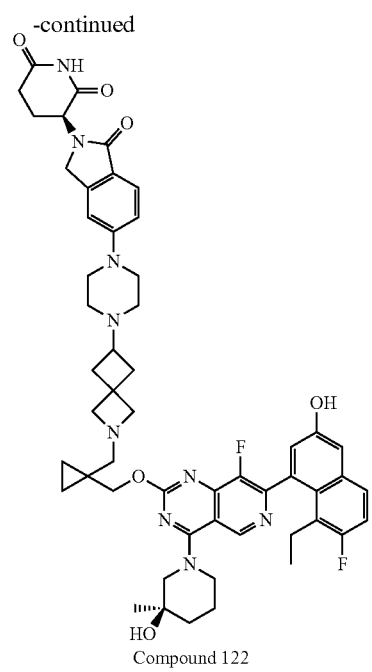

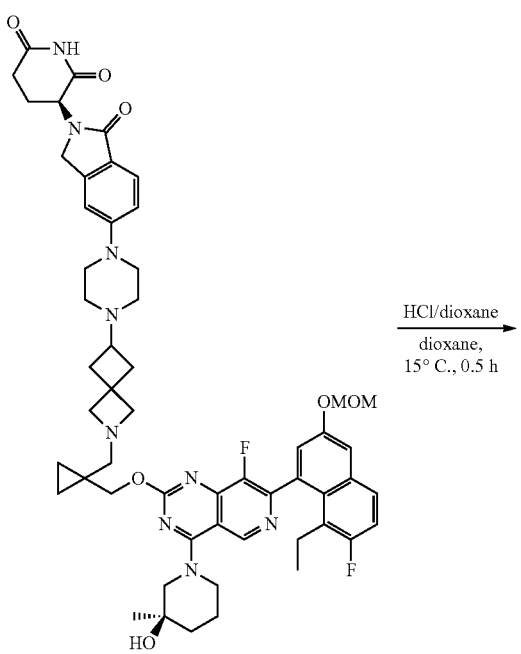

Step 1: Preparation of (S)-3-(5-(4-(2-((1-(((7-(8-ethyl-7-fluoro-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-2-azaspiro[3.3]heptan-6-yl)piperazin-1-yl)-1-oxoisoindolin-2-yl)piperidine-2,6-dione A mixture of (3S)-3-[5-[4-(2-azaspiro[3.3]heptan-6-yl)piperazin-1-yl]-1-oxo-isoindolin-2-yl]piperidine-2,6-dione (95 mg, 164 μmol, 1 eq, TFA), 1-[7-[8-ethyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropanecarbaldehyde (97.4 mg, 164 μmol, 1 eq), Ti(OEt)$_4$ (2.20 g, 9.64 mmol, 2.00 mL, 58.6 eq) in THF (4 mL) and DMSO (1 mL) was stirred at 15° C. for 12 hours. Then sodium cyanoborohydride (103 mg, 1.64 mmol, 10 eq) was added to the reaction mixture and stirred at 15° C. for 0.5 hours. LCMS showed that the reactant was fully consumed. The reaction mixture was poured into water (100 mL). The mixture was filtered, and the cake was washed with THF (10 mL*4) and EA (10 mL*3). The aqueous phase was extracted with EA (30 mL*3). The organic layers were combined, washed with brine (120 mL), dried over anhydrous Na$_2$SO$_4$, filtered and concentrated under reduced pressure to give a residue. The residue was purified by prep-TLC (SiO$_2$, DCM:MeOH=8:1) to give (S)-3-(5-(4-(2-((1-(((7-(8-ethyl-7-fluoro-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-2-azaspiro[3.3]heptan-6-yl)piperazin-1-yl)-1-oxoisoindolin-2-yl)piperidine-2,6-dione (120 mg, 119 μmol, 73.0% yield) as a light yellow solid.

Step 2: Preparation of (S)-3-(5-(4-(2-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-2-azaspiro[3.3]heptan-6-yl)piperazin-1-yl)-1-oxoisoindolin-2-yl)piperidine-2,6-dione (Compound 122)

To a solution of (3S)-3-[5-[4-[2-[[1-[7-[8-ethyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropyl]methyl]-2-azaspiro[3.3]heptan-6-yl]piperazin-1-yl]-1-oxo-isoindolin-2-yl]piperidine-2,6-dione (100 mg, 99.9 μmol, 1 eq) in dioxane (2 mL) was added HCl solution (4 M in dioxane, 2 mL, 80.0 eq) and the mixture was stirred at 15° C. for 0.5 hours. LCMS showed near full consumption of the reactant and detection of the desired product. The reaction mixture was concentrated under reduced pressure to give a residue. The residue was purified by prep-HPLC (FA condition) column: Phenomenex Luna C18 150*25 mm*10 μm; mobile phase: [water (FA)-ACN]; gradient: 10%-40% B over 9 minutes to give (S)-3-(5-(4-(2-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-2-azaspiro[3.3]heptan-6-yl)piperazin-1-yl)-1-oxoisoindolin-2-yl)piperidine-2,6-dione (28.4 mg, 28.2 μmol, 28.2% yield, 95.6% purity) as a white solid. LCMS: [M+H]$^+$=956.5 $^1$H NMR (400 MHZ, MeOD-d$_4$) δ=9.25 (d, J=2.4 Hz, 1H), 8.47 (s, 1H), 7.69 (dd, J=6.0, 9.2 Hz, 1H), 7.65 (d, J=8.4 Hz, 1H), 7.32 (d, J=2.8 Hz, 1H), 7.27 (t, J=9.6 Hz, 1H), 7.11-7.04 (m, 1H), 7.12-7.03 (m, 1H), 5.11 (dd, J=5.2, 13.2 Hz, 1H), 4.83-4.82 (m, 1H), 4.64-4.54 (m, 1H), 4.40 (br d, J=5.2 Hz, 1H), 4.37-4.29 (m, 1H), 4.22 (br s, 1H), 3.68-3.57 (m, 1H), 3.51-3.40 (m, 1H), 3.37-3.34 (m, 1H), 2.88 (br dd, J=5.2, 13.2 Hz, 1H), 2.80 (br d, J=2.8 Hz, 1H), 2.75 (br t, J=7.2 Hz, 1H), 2.56-2.42 (m, 1H), 2.30-2.10 (m, 1H), 1.92-1.76 (m, 1H), 1.34-1.26 (m, 1H), 0.91-0.79 (m, 1H).

Example 39: Preparation of (S)-3-(5-(4-(1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)azetidin-3-yl)piperazin-1-yl)-1-oxoisoindolin-2-yl)piperidine-2,6-dione (Compound 130)

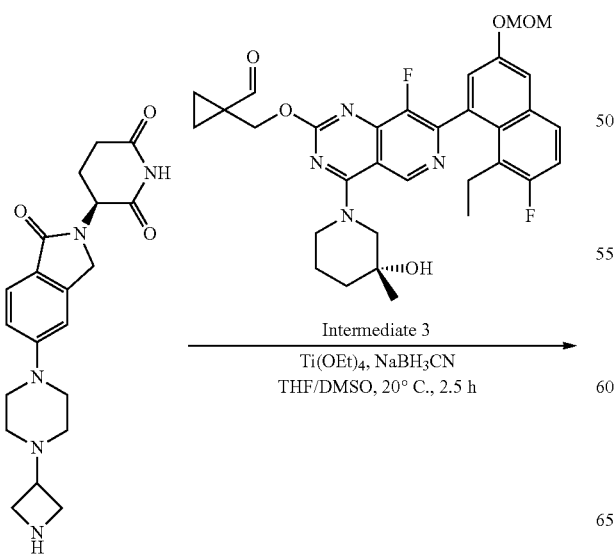

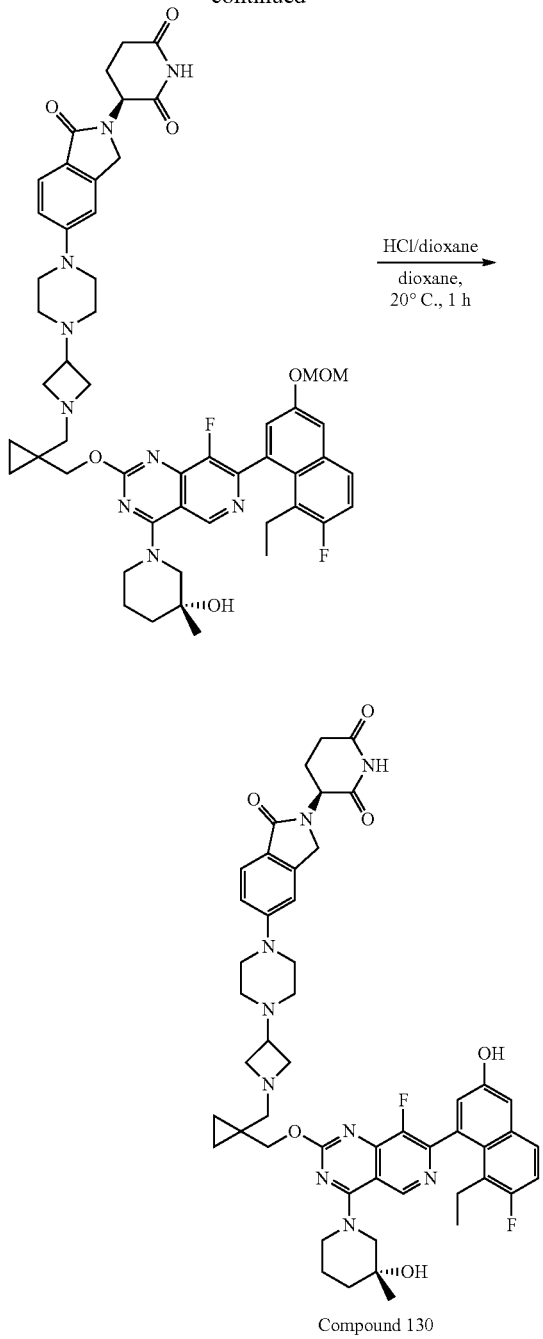

Compound 130

Step 1: Preparation of (S)-3-(5-(4-(1-((1-(((7-(8-ethyl-7-fluoro-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)azetidin-3-yl)piperazin-1-yl)-1-oxoisoindolin-2-yl)piperidine-2,6-dione To a solution of 1-[[7-[8-ethyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropanecarbaldehyde (95.3 mg, 160 μmol, 1 eq) and (3S)-3-[5-[4-(azetidin-3-yl)piperazin-1-yl]-1-oxo-isoindolin-2-yl]piperidine-2,6-dione (120 mg, 241 μmol, 1.5 eq, TFA) was added Ti(OEt)₄ (2.20 g, 9.64 mmol, 2 mL, 59.9 eq) in THF (4 mL) and DMSO (1 mL), and the mixture was stirred at 20° C. for 2 hours. Then NaBH₃CN (101 mg, 1.61 mmol, 10 eq) was added and the reaction mixture was stirred at 20° C. for 30 minutes. LCMS showed full consumption of reactant and a new peak of ~65% peak area with desired mass. The reaction mixture was poured into water (100 mL). The mixture was filtered, and the cake was washed with THF (10 mL*4) and EA (10 mL*3). The filtrate was extracted with EA (30 mL*3). The combined organic layers were washed with brine (120 mL), dried over anhydrous Na₂SO₄, filtered and concentrated under reduced pressure to give a residue. The residue was purified by prep-TLC (SiO₂, DCM: MeOH=8:1) to give (S)-3-(5-(4-(1-((1-(((7-(8-ethyl-7-fluoro-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)azetidin-3-yl)piperazin-1-yl)-1-oxoisoindolin-2-yl)piperidine-2,6-dione (90 mg, 85.3 μmol, 53.0% yield, 91.9% purity) as a white solid.

Step 2: Preparation of (S)-3-(5-(4-(1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)azetidin-3-yl)piperazin-1-yl)-1-oxoisoindolin-2-yl) piperidine-2,6-dione (Compound 130)

To a solution of (S)-3-(5-(4-(1-((1-(((7-(8-ethyl-7-fluoro-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)azetidin-3-yl)piperazin-1-yl)-1-oxoisoindolin-2-yl)piperidine-2,6-dione (85 mg, 88.5 μmol, 1 eq) in dioxane (1 mL) was added HCl solution (4 M in dioxane, 14.1 mL, 640 eq) and the mixture was stirred at 20° C. for 1 hour. LCMS showed that the reactant was fully consumed and a new peak with desired mass was detected. The reaction mixture was concentrated under reduced pressure to give a residue. The residue was purified by prep-HPLC (FA condition)column: Phenomenex Luna C18 150*25 mm*10 μm; mobile phase: [water (FA)-ACN]; gradient: 20%-40% B over 10 minutes to give (S)-3-(5-(4-(1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)azetidin-3-yl)piperazin-1-yl)-1-oxoisoindolin-2-yl)piperidine-2,6-dione (15.3 mg, 15.5 μmol, 17.5% yield, 97.5% purity, FA) as a white solid. LCMS: [M+H]⁺=916.5. ¹H NMR (400 MHZ, MeOD-d₄) δ=9.24 (s, 1H), 8.53 (br s, 1H), 7.70-7.61 (m, 1H), 7.30 (t, J=2.0 Hz, 1H), 7.29-7.21 (m, 1H), 7.09-7.02 (m, 1H), 5.18 (s, 1H), 5.14-5.07 (m, 1H), 5.06-4.98 (m, 1H), 4.55 (br d, J=4.8 Hz, 1H), 4.42-4.37 (m, 1H), 4.36-4.26 (m, 1H), 4.09 (br dd, J=6.0, 12.4 Hz, 1H), 3.82-3.71 (m, 1H), 3.69-3.57 (m, 1H), 3.51-3.44 (m, 1H), 3.43-3.36 (m, 1H), 3.28-3.20 (m, 1H), 3.18-3.04 (m, 1H), 2.96-2.86 (m, 1H), 2.84-2.75 (m, 1H), 2.57-2.50 (m, 1H), 2.50-2.40 (m, 1H), 2.29-2.12 (m, 1H), 1.92-1.76 (m, 1H), 1.30 (d, J=9.6 Hz, 1H), 0.88-0.73 (m, 1H).

Example 40: Preparation of (3S)-3-[5-[4-[[1-(azetidin-3-yl)azetidin-3-yl]methyl]piperazin-1-yl]-1-oxo-isoindolin-2-yl]piperidine-2,6-Dione (Compound 138)

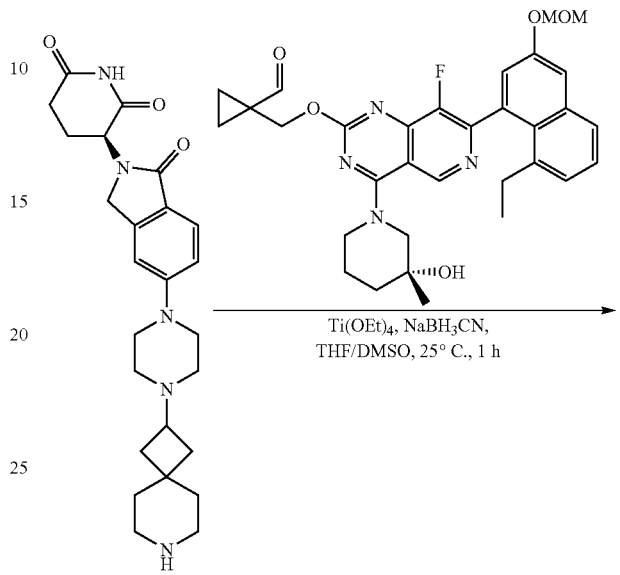

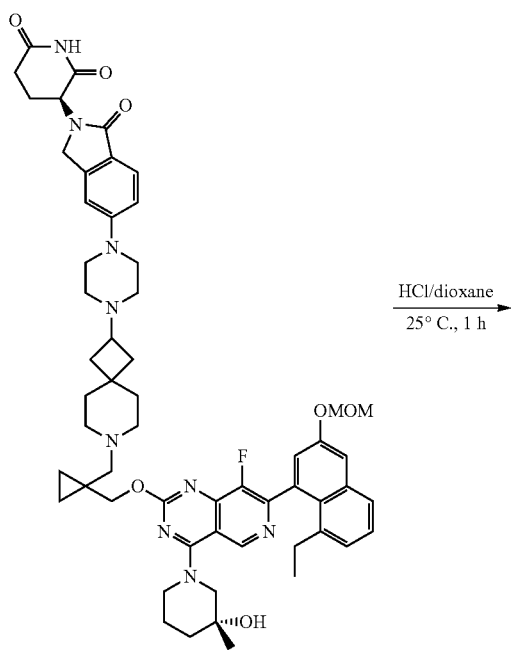

-continued

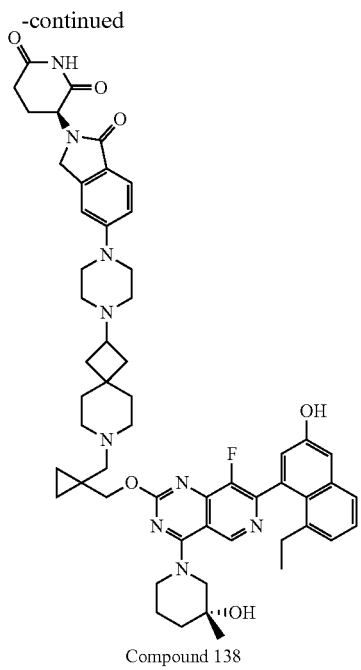

Compound 138

Step 1: Preparation of (3S)-3-[5-[4-[7-[[1-[[7-[8-ethyl-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropyl]methyl]-7-azaspiro[3.5]nonan-2-yl]piperazin-1-yl]-1-oxo-isoindolin-2-yl]piperidine-2,6-dione To a solution of 1-[7-[8-ethyl-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropanecarbaldehyde (126 mg, 219 μmol, 1 eq) and (3S)-3-[5-[4-(7-azaspiro[3.5]nonan-2-yl)piperazin-1-yl]-1-oxo-isoindolin-2-yl]piperidine-2,6-dione (115 mg, 219 μmol, 1 eq, 2HCl) in THF (4 mL) DMSO (1 mL) was added tetraethoxytitanium (1.50 g, 6.58 mmol, 1.36 mL, 30 eq). The mixture was stirred for 0.2 hours. Then sodium cyanoborohydride (68.8 mg, 1.10 mmol, 5 eq) was added. The mixture was stirred at 25° C. for 0.8 hours. LCMS showed complete consumption of the reactant and one main peak with desired mass. The reaction mixture was concentrated under reduced pressure to give a residue, which was purified by reversed-phase flash column chromatography (0.1% FA condition) to afford (3S)-3-[5-[4-[7-[[1-[[7-[8-ethyl-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropyl]methyl]-7-azaspiro[3.5]nonan-2-yl]piperazin-1-yl]-1-oxo-isoindolin-2-yl]piperidine-2,6-dione (95 mg, 94.0 μmol, 42.9% yield) as a white solid.

Step 2: Preparation of (3S)-3-[5-[4-[7-[[1-[7-(8-ethyl-3-hydroxy-1-naphthyl)-8-fluoro-4-[(3R)-3-hydroxy-3-methyl-1-piperidyl]pyrido[4,3-d]pyrimidin-2-yl]oxymethyl]cyclopropyl]methyl]-7-azaspiro[3.5]nonan-2-yl]piperazin-1-yl]-1-oxo-isoindolin-2-yl]piperidine-2,6-dione (Compound 138)

To a solution of (3S)-3-[5-[4-[7-[[1-[[7-[8-ethyl-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropyl]methyl]-7-azaspiro[3.5]nonan-2-yl]piperazin-1-yl]-1-oxo-isoindolin-2-yl]piperidine-2,6-dione (80 mg, 79.1 μmol, 1 eq) was added HCl solution (4 M in dioxane, 8.00 mL, 404 eq). The mixture was stirred at 25° C. for 15 minutes. LCMS showed complete consumption of the reactant and one main peak with desired mass. The reaction mixture was concentrated under reduced pressure to remove solvent. The residue was purified by prep-HPLC (FA condition) to give (3S)-3-[5-[4-[7-[[1-[7-(8-ethyl-3-hydroxy-1-naphthyl)-8-fluoro-4-[(3R)-3-hydroxy-3-methyl-1-piperidyl]pyrido[4,3-d]pyrimidin-2-yl]oxymethyl]cyclopropyl]methyl]-7-azaspiro[3.5]nonan-2-yl]piperazin-1-yl]-1-oxo-isoindolin-2-yl]piperidine-2,6-dione (10 mg, 9.88 μmol, 12.5% yield, IFA) as a white solid. LCMS: [M+H]⁺=966.0. $^1$H NMR (400 MHZ, METHANOL-$d_4$) δ=9.23 (d, J=4.8 Hz, 1H), 8.55-8.50 (m, 1H), 7.69-7.63 (m, 2H), 7.38 (t, J=7.4 Hz, 1H), 7.31 (d, J=2.8 Hz, 1H), 7.21-7.17 (m, 1H), 7.13-7.08 (m, 2H), 7.05-7.01 (m, 1H), 5.16-5.08 (m, 1H), 4.64-4.44 (m, 5H), 4.42 (d, J=5.6 Hz, 2H), 4.37-4.29 (m, 1H), 3.69-3.57 (m, 1H), 3.51-3.43 (m, 1H), 3.41-3.41 (m, 1H), 3.39 (br s, 5H), 3.17-3.07 (m, 3H), 2.97-2.74 (m, 4H), 2.55 (br s, 4H), 2.48 (dd, J=4.8, 13.3 Hz, 1H), 2.44-2.22 (m, 3H), 2.21-2.07 (m, 4H), 1.98-1.86 (m, 5H), 1.85-1.73 (m, 5H), 1.31 (d, J=11.2 Hz, 4H), 1.00-0.85 (m, 6H), 0.83-0.76 (m, 2H).

Example 41: Preparation of (S)-3-(5-(4-(7-((1-(((7-(7,8-difluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-azaspiro[3.5]nonan-2-yl)piperazin-1-yl)-1-oxoisoindolin-2-yl)piperidine-2,6-dione (Compound 170)

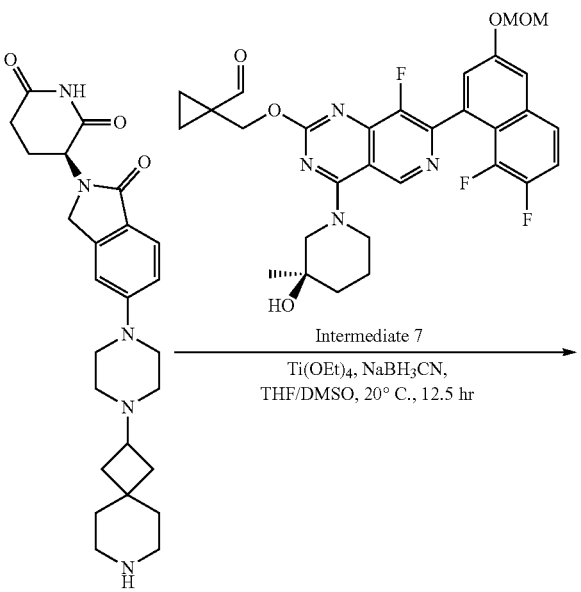

Intermediate 7

Ti(OEt)₄, NaBH₃CN,
THF/DMSO, 20° C., 12.5 hr

-continued

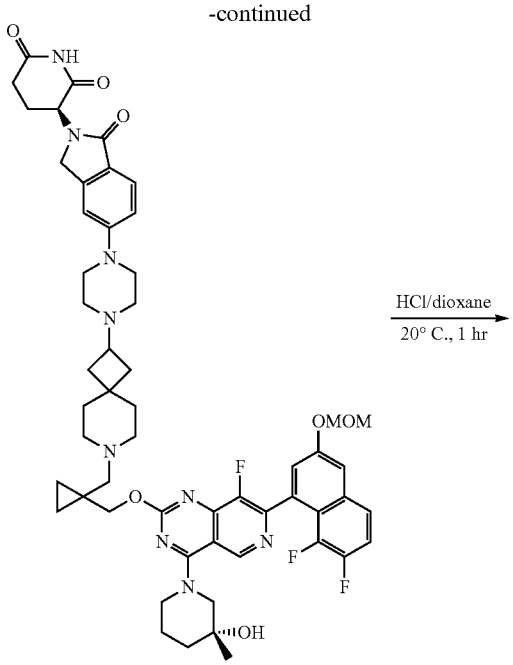

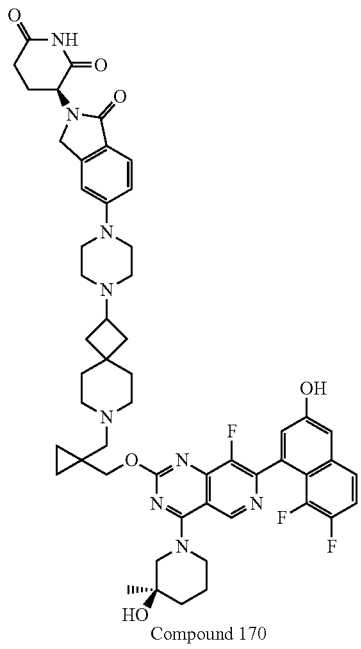

Compound 170

Step 1: Preparation of (S)-3-(5-(4-(7-((1-(((7-(7,8-difluoro-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-azaspiro[3.5]nonan-2-yl)piperazin-1-yl)-1-oxoisoindolin-2-yl)piperidine-2,6-dione To a solution of 1-[[7-[7,8-difluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropanecarbaldehyde (80 mg, 137 μmol, 1 eq) in DMSO (1 mL) and THF (1 mL) was added (3S)-3-[5-[4-(7-azaspiro[3.5]nonan-2-yl)piperazin-1-yl]-1-oxo-isoindolin-2-yl]piperidine-2,6-dione (101 mg, 206 μmol, 1.5 eq, HCl) and Ti(OEt)$_4$ (313 mg, 1.37 mmol, 285 μL, 10 eq). The reaction mixture was stirred at 20° C. for 12 hours. Then NaBH$_3$CN (17.3 mg, 275 μmol, 2 eq) was added and the mixture was stirred at 20° C. for 0.5 hours. LCMS showed complete consumption of the reactant and detection of the desired product. Water (30 mL) was added and the mixture was filtered to afford the crude, which was purified by reversed phase-HPLC (0.1% FA condition) to afford (S)-3-(5-(4-(7-((1-(((7-(7,8-difluoro-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-azaspiro[3.5]nonan-2-yl)piperazin-1-yl)-1-oxoisoindolin-2-yl)piperidine-2,6-dione (100 mg, 98.2 μmol, 71.5% yield) as a white solid.

Step 2: Preparation of (S)-3-(5-(4-(7-((1-(((7-(7,8-difluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-azaspiro[3.5]nonan-2-yl)piperazin-1-yl)-1-oxoisoindolin-2-yl)piperidine-2,6-dione (Compound 170)

To a mixture of (3S)-3-[5-[4-[7-[1-[[7-[7,8-difluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropyl]methyl]-7-azaspiro[3.5]nonan-2-yl]piperazin-1-yl]-1-oxo-isoindolin-2-yl]piperidine-2,6-dione (100 mg, 98.2 μmol, 1 eq) in DCM (2 mL) was added HCl solution (2 M in dioxane, 2 mL, 40.7 eq) and the reaction mixture was stirred at 20° C. for 1 hour. LCMS showed complete consumption of the reactant and detection of the desired product. The reaction was concentrated under reduced pressure to afford the crude. The crude product was purified by preparative HPLC (column: Waters xbridge 150*25 mm 10 μm; mobile phase: [water (NH$_4$HCO$_3$)-ACN]; gradient: 36%-56% B over 8 minutes) to afford (S)-3-(5-(4-(7-((1-(((7-(7,8-difluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-azaspiro[3.5]nonan-2-yl)piperazin-1-yl)-1-oxoisoindolin-2-yl)piperidine-2,6-dione (20.7 mg, 20.5 μmol, 20.8% yield, 96.3% purity) as an off-white solid. LCMS: [M+H]$^+$=974.5; $^1$H NMR (400 MHZ, METHANOL-d$_4$) δ=9.22 (d, J=7.6 Hz, 1H), 7.67-7.60 (m, 2H), 7.46-7.38 (m, 1H), 7.34 (s, 1H), 7.26 (dd, J=2.3, 6.6 Hz, 1H), 7.13-7.07 (m, 2H), 5.12 (dd, J=5.3, 13.3 Hz, 1H), 4.58-4.50 (m, 2H), 4.46 (s, 2H), 4.42 (d, J=5.9 Hz, 2H), 4.30-4.24 (m, 1H), 3.71-3.65 (m, 1H), 3.52-3.48 (m, 1H), 3.38 (br s, 4H), 2.93-2.86 (m, 1H), 2.81 (br dd, J=2.0, 4.9 Hz, 1H), 2.79-2.74 (m, 1H), 2.54-2.44 (m, 8H), 2.20-2.13 (m, 2H), 2.06-2.00 (m, 2H), 1.92-1.85 (m, 1H), 1.84-1.78 (m, 2H), 1.73-1.64 (m, 4H), 1.61-1.52 (m, 3H), 1.35-1.28 (m, 4H), 0.82-0.72 (m, 2H), 0.61-0.49 (m, 2H).

Example 42: Preparation of 3-(5-(6-(4-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperazin-1-yl)-2-azaspiro[3.3]heptan-2-yl)-1-oxoisoindolin-2-yl)piperidine-2,6-dione (Compound 161)

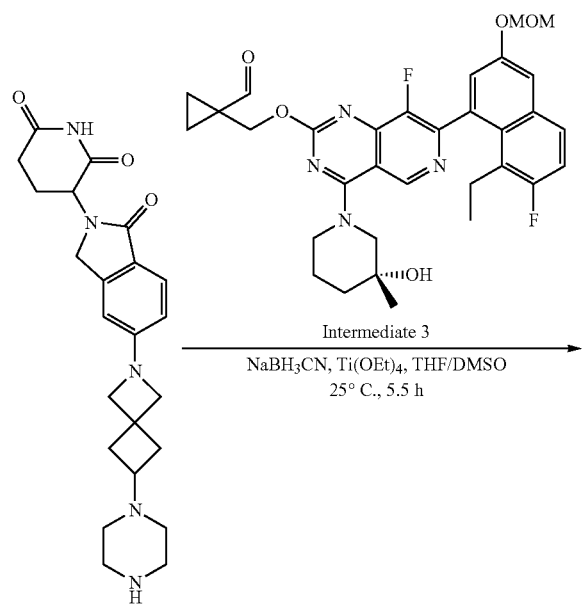

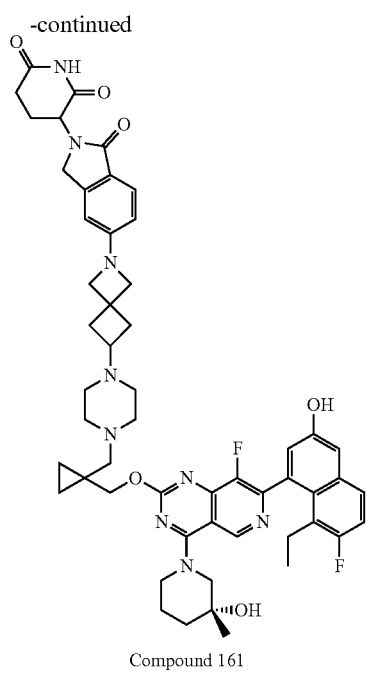

Compound 161

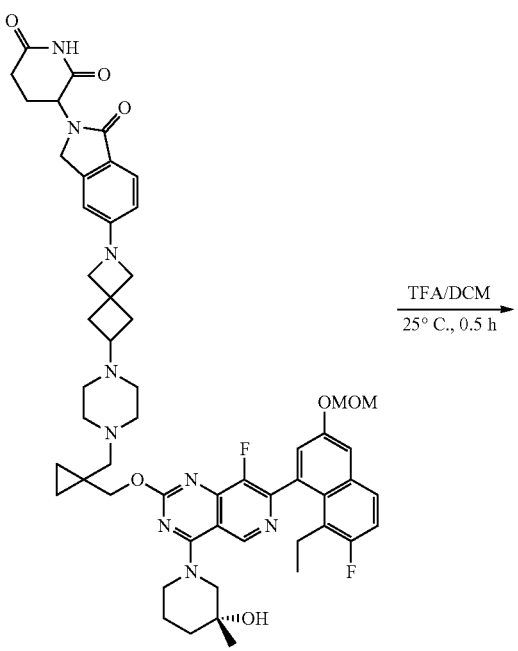

Step 1: Preparation of 3-(5-(6-(4-((1-(((7-(8-ethyl-7-fluoro-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperazin-1-yl)-2-azaspiro[3.3]heptan-2-yl)-1-oxoisoindolin-2-yl)piperidine-2,6-dione To a solution of 3-[1-oxo-5-(6-piperazin-1-yl-2-azaspiro[3.3]heptan-2-yl)isoindolin-2-yl]piperidine-2,6-dione (70 mg, 149 μmol, 1 eq) and 1-[[7-[8-ethyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropanecarbaldehyde (88.4 mg, 149 μmol, 1 eq) in THF (3 mL) and DMSO (1 mL) was added Ti(OEt)$_4$ (102 mg, 447 μmol, 92.7 μL, 3 eq) and the reaction mixture was stirred at 25° C. for 5 hours. Then NaBH$_3$CN (18.7 mg, 298 μmol, 2 eq) was added and the mixture was stirred at 25° C. for 0.5 hours. The mixture was diluted with water (10 mL) and extracted with EA (10 mL*3). The combined organic layers were washed with brine (10 mL*2), dried over anhydrous Na$_2$SO$_4$, filtered and concentrated under reduced pressure to give a residue. The residue was purified by prep-TLC (SiO$_2$, DCM:MeOH=10:1, Rf=0.2) to give 3-(5-(6-(4-((1-(((7-(8-ethyl-7-fluoro-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperazin-1-yl)-2-azaspiro[3.3]heptan-2-yl)-1-oxoisoindolin-2-yl)piperidine-2,6-dione (85 mg, 76.4 μmol, 51.3% yield, 90% purity) as a white solid. 1H NMR (400 MHZ, DMSO-d$_6$) δ=10.92 (br s, 1H), 9.22 (s, 1H), 7.95-7.83 (m, 1H), 7.67 (d, J=1.4 Hz, 1H), 7.46 (t, J=8.2 Hz, 2H), 7.23 (d, J=2.6 Hz, 1H), 6.50-6.40 (m, 2H), 5.34 (s, 2H), 5.08-4.97 (m, 1H), 4.74 (d, J=6.8 Hz, 1H), 4.37-4.25 (m, 4H), 4.21-4.05 (m, 5H), 3.90 (s, 2H), 3.79 (s, 2H), 3.67-3.59 (m, 1H), 3.51 (br s, 1H), 2.62-2.56 (m, 3H), 2.45-2.13 (m, 13H), 2.06-1.90 (m, 5H), 1.77-1.60 (m, 3H), 1.25-1.13 (m, 4H), 0.79-0.71 (m, 3H), 0.64 (s, 2H), 0.44-0.37 (m, 2H).

Step 2: Preparation of 3-(5-(6-(4-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperazin-1-yl)-2-azaspiro[3.3]heptan-2-yl)-1-oxoisoindolin-2-yl)piperidine-2,6-dione (Compound 161)

To a solution of 3-[5-[6-[4-[[1-[[7-[8-ethyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropyl]methyl]piperazin-1-yl]-2-azaspiro[3.3]heptan-2-yl]-1-oxo-isoindolin-2-yl]piperidine-2,6-dione (80 mg, 71.99 μmol, 1 eq) in DCM (5 mL) was added TFA (0.5 mL). The mixture was stirred at 25° C. for 0.5 hours. The reaction mixture was filtered and concentrated under reduced pressure to give a residue. The residue was purified by prep-HPLC (FA condition; column: Phenomenex Luna C18 150*25 mm*10 μm; mobile phase: [water (FA)-ACN]; gradient: 18%-48% B over 10 minutes) to give 3-(5-(6-(4-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperazin-1-yl)-2-azaspiro[3.3]heptan-2-yl)-1-oxoisoindolin-2-yl)piperidine-2,6-dione (10 mg, 9.62 μmol, 13.3% yield, 92% purity) as a yellow solid. LCMS: [M+H]$^+$ =956.0. $^1$H NMR (400 MHZ, DMSO-$d_6$) δ=10.93 (s, 1H), 10.23-9.64 (m, 1H), 9.21 (s, 1H), 8.16 (s, 1H), 7.81-7.73 (m, 1H), 7.47 (d, J=8.2 Hz, 1H), 7.41-7.29 (m, 2H), 7.03 (d, J=2.4 Hz, 1H), 6.47 (s, 2H), 5.06-4.99 (m, 1H), 4.81-4.68 (m, 1H), 4.36-4.25 (m, 4H), 4.20-4.13 (m, 1H), 4.09-3.98 (m, 1H), 3.91 (s, 2H), 3.79 (s, 2H), 3.68-3.58 (m, 1H), 3.57-3.49 (m, 1H), 2.93-2.83 (m, 1H), 2.62-2.53 (m, 2H), 2.44-2.38 (m, 2H), 2.37-2.23 (m, 9H), 2.20-2.09 (m, 3H), 2.07-1.89 (m, 5H), 1.73-1.62 (m, 3H), 1.17 (d, J=9.8 Hz, 3H), 0.78-0.69 (m, 3H), 0.64 (s, 2H), 0.45-0.37 (m, 2H).

Example 43: Preparation of 3-[5-[2-[4-[[1-[[7-(8-ethyl-7-fluoro-3-hydroxy-1-naphthyl)-8-fluoro-4-[(3R)-3-hydroxy-3-methyl-1-piperidyl]pyrido[4,3-d]pyrimidin-2-yl]oxymethyl]cyclopropyl]methyl]piperazin-1-yl]-7-azaspiro[3.5]nonan-7-yl]-1-oxo-isoindolin-2-yl]piperidine-2,6-dione (Compound 162)

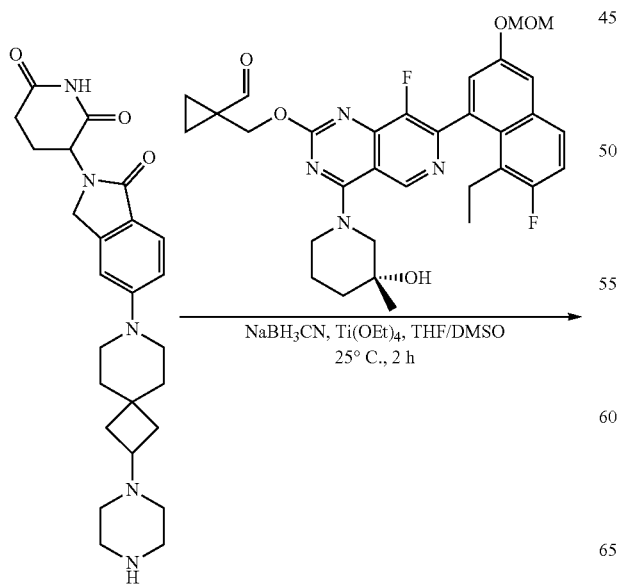

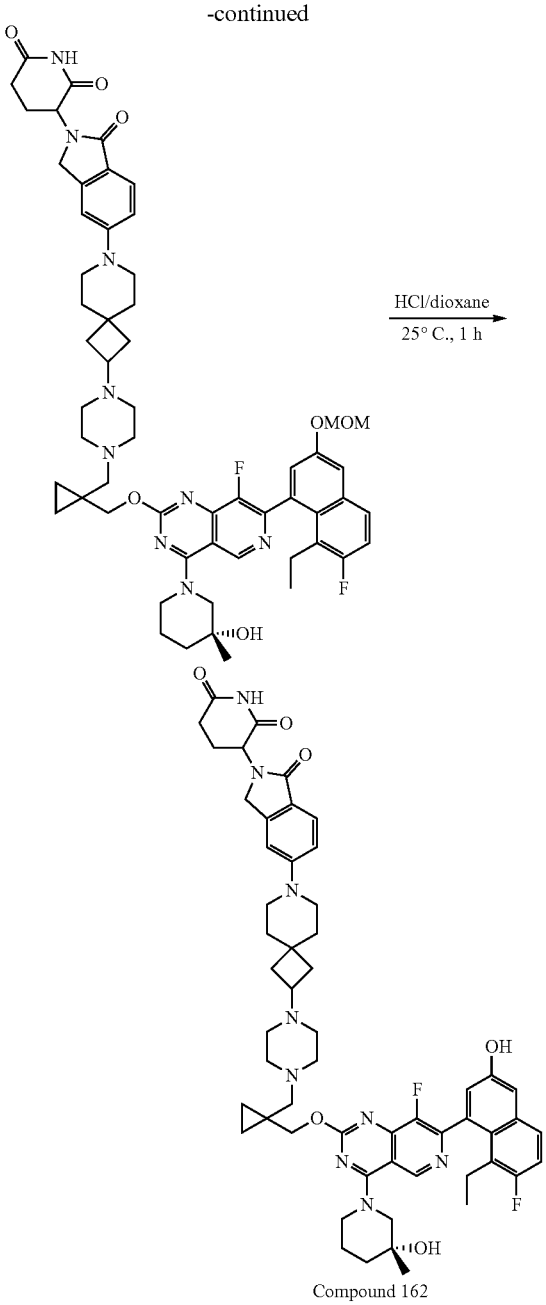

Compound 162

Step 1: Preparation of 3-[5-[2-[4-[1-[7-[8-ethyl-7-fluoro-3-(methoxymethoxy)-1-naphthyl]-8-fluoro-4-[(3R)-3-hydroxy-3-methyl-1-piperidyl] pyrido[4,3-d]pyrimidin-2-yl] oxymethyl] cyclopropyl] methyl] piperazin-1-yl]-7-azaspiro[3.5]nonan-7-yl]-1-oxo-isoindolin-2-yl]piperidine-2,6-dione To a solution of 1-[7-[8-ethyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropanecarbaldehyde (101 mg, 170 μmol, 1.1 eq) 3-[1-oxo-5-(2-piperazin-1-yl-7-azaspiro[3.5]nonan-7-yl)isoindolin-2-yl]piperidine-2,6-dione (70 mg, 155 μmol, 1 eq) in DMSO (3 mL) THF (3 mL) was added tetraethoxytitanium (1.06 g, 4.65 mmol, 964 μL, 30 eq). The mixture was stirred for 1 hour. Then sodium cyanoborohydride (9.74 mg, 155 µmol, 1 eq) was added. The mixture was stirred at 25° C. for 1 hours. LCMS showed complete consumption of the reactant and one main peak with desired mass. The reaction mixture was poured into water (30 mL), filtered and then extracted with EA (30 mL*3), the organic layers were combined and washed with brine (60 mL), dried over anhydrous $Na_2SO_4$, filtered and concentrated under vacuum. The residue was purified by reversed-phase flash (0.1% FA condition). Then solution was lyophilized to give a white solid. Compound 3-[5-[2-[4-[1-[7-[8-ethyl-7-fluoro-3-(methoxymethoxy)-1-naphthyl]-8-fluoro-4-[(3R)-3-hydroxy-3-methyl-1-piperidyl] pyrido[4,3-d] pyrimidin-2-yl]oxymethyl] cyclopropyl] methyl] piperazin-1-yl]-7-azaspiro[3.5]nonan-7-yl]-1-oxo-isoindolin-2-yl]piperidine-2,6-dione (80 mg, 77.8 µmol, 50.2% yield) to give a white solid. $^1H$ NMR (400 MHZ, CHLOROFORM-d) δ=9.23-9.13 (m, 1H), 8.00-7.95 (m, 1H), 7.78-7.67 (m, 2H), 7.55 (d, J=2.8 Hz, 1H), 7.03-6.84 (m, 2H), 5.37-5.18 (m, 3H), 4.59-4.22 (m, 7H), 3.42-3.17 (m, 9H), 2.99-2.79 (m, 5H), 2.43-2.13 (m, 8H), 1.93-1.87 (m, 5H), 1.80-1.61 (m, 16H), 1.43-1.35 (m, 4H), 0.93-0.84 (m, 4H), 0.55-0.48 (m, 1H).

Step 2: Preparation of 3-[5-[2-[4-[1-[[7-(8-ethyl-7-fluoro-3-hydroxy-1-naphthyl)-8-fluoro-4-[(3R)-3-hydroxy-3-methyl-1-piperidyl]pyrido[4,3-d]pyrimidin-2-yl]oxymethyl]cyclopropyl]methyl]piperazin-1-yl]-7-azaspiro[3.5]nonan-7-yl]-1-oxo-isoindolin-2-yl]piperidine-2,6-dione (Compound 162)

To a solution of 3-[5-[2-[4-[1-[7-[8-ethyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropyl]methyl]piperazin-1-yl]-7-azaspiro[3.5]nonan-7-yl]-1-oxo-isoindolin-2-yl]piperidine-2,6-dione (50 mg, 48.6 µmol, 1 eq) in DCM (3 mL) was added HCl solution (2 M in dioxane, 24.3 µL, 1 eq). The mixture was stirred at 25° C. for 1 hours. LCMS showed complete consumption of the reactant and one main peak with desired mass. The reaction mixture was concentrated under reduced pressure to remove solvent. The residue was purified by prep-HPLC (FA condition)column: column: Phenomenex Luna C18 150*25 mm*10 µm; mobile phase: [water (FA)-ACN]; gradient: 24%-44% B over 10 minutes. Then solution was lyophilized to give white solid. Compound 3-[5-[2-[4-[[1-[[7-(8-ethyl-7-fluoro-3-hydroxy-1-naphthyl)-8-fluoro-4-[(3R)-3-hydroxy-3-methyl-1-piperidyl]pyrido[4,3-d]pyrimidin-2-yl]oxymethyl]cyclopropyl]methyl]piperazin-1-yl]-7-azaspiro[3.5]nonan-7-yl]-1-oxo-isoindolin-2-yl] piperidine-2,6-dione (20.8 mg, 19.9 µmol, 40.9% yield, 98.2% purity, FA) as a white solid. LCMS: [M+H]$^+$=984.8; $^1H$ NMR (400 MHZ, METHANOL-d$_4$) δ=9.28-9.22 (m, 1H), 7.73-7.67 (m, 1H), 7.66-7.61 (m, 1H), 7.35-7.31 (m, 1H), 7.27 (t, J=9.2 Hz, 1H), 7.08 (br d, J=3.2 Hz, 1H), 5.11 (dd, J=5.2, 13.2 Hz, 1H), 4.61 (br s, 9H), 4.55-4.43 (m, 3H), 4.40 (d, J=6.0 Hz, 2H), 4.37-4.25 (m, 1H), 3.71-3.60 (m, 1H), 3.47 (br t, J=12.0 Hz, 1H), 3.29 (br s, 3H), 3.08-2.95 (m, 2H), 2.93-2.86 (m, 2H), 2.83-2.75 (m, 2H), 2.74-2.65 (m, 2H), 2.54-2.41 (m, 3H), 2.30-2.20 (m, 3H), 2.19-2.12 (m, 2H), 1.94-1.79 (m, 5H), 1.78-1.69 (m, 4H), 1.31 (d, J=10.0 Hz, 4H), 0.89-0.77 (m, 5H), 0.64-0.51 (m, 2H).

Example 44: Preparation of (S)-3-(5-(4-(1-(1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)azetidin-3-yl)piperazin-1-yl)-1-oxoisoindolin-2-yl)piperidine-2,6-dione (Compound 146)

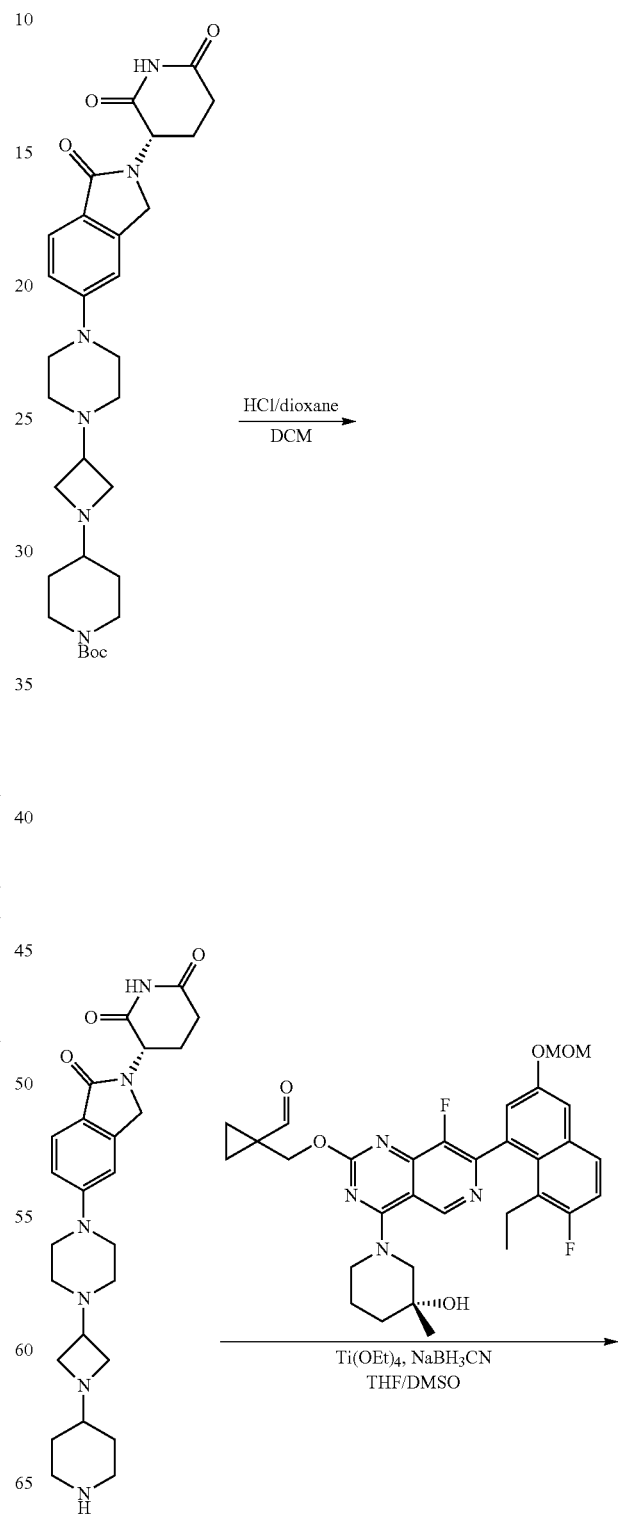

-continued

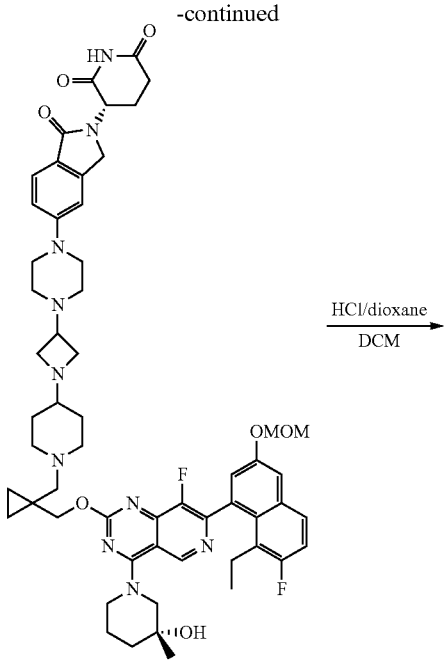

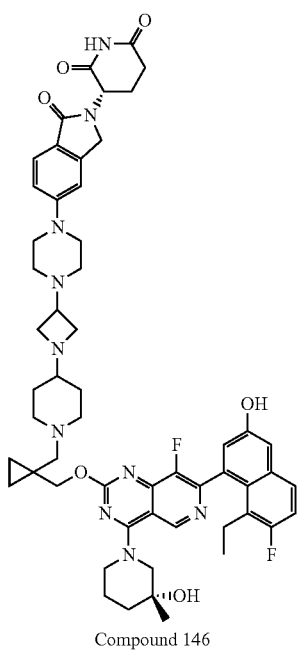 [SMILES: CCc1c(F)ccc2cc(O)cc(-c3ncc4c(N5CCC[C@@](C)(O)C5)nc(OCC5(CN6CCC(N7CC(N8CCN(c9ccc%10c(c9)CN([C@H]9CCC(=O)NC9=O)C%10=O)CC8)C7)CC6)CC5)nc4c3F)c12]

Compound 146

Step 1: Preparation of (S)-3-(1-oxo-5-(4-(1-(piperidin-4-yl)azetidin-3-yl)piperazin-1-yl)isoindolin-2-yl)piperidine-2,6-dione HCl solution (4 M in dioxane, 6.00 mL, 113 eq) was added to a solution of tert-butyl 4-[3-[4-[2-[(3S)-2,6-dioxo-3-piperidyl]-1-oxo-isoindolin-5-yl]piperazin-1-yl]azetidin-1-yl]piperidine-1-carboxylate (120 mg, 212 µmol, 1.00 eq) in DCM (2.00 mL). The mixture was stirred at 25° C. for 10 minutes. LCMS indicated complete consumption of the reactant and a new peak of ~98% peak area with desired mass. The reaction mixture was concentrated under reduced pressure to give (S)-3-(1-oxo-5-(4-(1-(piperidin-4-yl)azetidin-3-yl)piperazin-1-yl)isoindolin-2-yl)piperidine-2,6-dione (106 mg, 211 µmol, 99.5% yield, HCl) as a white solid. $^1$H NMR (400 MHZ, DMSO-$d_6$) δ=10.96-10.93 (m, 1H), 9.31-9.15 (m, 1H), 8.91-8.68 (m, 1H), 7.58 (d, J=8.4 Hz, 1H), 7.20-7.14 (m, 2H), 5.06 (br dd, J=5.2, 13.2 Hz, 1H), 4.75-4.59 (m, 3H), 4.42-4.30 (m, 4H), 4.28-4.19 (m, 2H), 3.87-3.81 (m, 1H), 3.45-3.38 (m, 3H), 3.26-3.12 (m, 3H), 2.97-2.81 (m, 4H), 2.59 (br d, J=16.8 Hz, 1H), 2.38 (br dd, J=4.4, 13.2 Hz, 1H), 2.10 (br d, J=10.4 Hz, 2H), 2.00-1.94 (m, 1H), 1.83-1.74 (m, 2H), 1.32-1.20 (m, 1H).

Step 2: Preparation of (S)-3-(5-(4-(1-(1-((1-(((7-(8-ethyl-7-fluoro-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)azetidin-3-yl)piperazin-1-yl)-1-oxoisoindolin-2-yl)piperidine-2,6-dione To a solution of (3S)-3-[1-oxo-5-[4-[1-(4-piperidyl)azetidin-3-yl]piperazin-1-yl]isoindolin-2-yl]piperidine-2,6-dione (90.0 mg, 179 µmol, 1.00 eq, HCl) and 1-[7-[8-ethyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropanecarbaldehyde (100.00 mg, 169 µmol, 0.943 eq) in THF (6.00 mL) and DMSO (2.00 mL) was added Ti(OEt)$_4$ (5.50 g, 24.1 mmol, 5.00 mL, 135 eq) and the reaction mixture was stirred at 25° C. for 2 hours. The mixture was added NaBH$_3$CN (125 mg, 1.99 mmol, 11.1 eq) at 25° C. The mixture was stirred at 25° C. for 10 minutes. LCMS indicated complete consumption of the reactant and a new peak of ~55% peak area with desired mass. The residue was poured into ice-water (50.0 mL). The reaction mixture was stirred for 5 minutes and filtered. The aqueous phase was extracted with ethyl acetate (30.0 mL*3). The combined organic layers were washed with brine (50.0 mL), dried over anhydrous Na$_2$SO$_4$, filtered and concentrated under reduced pressure. The residue was redissolved in DCM:MeOH=1:1 (100 mL), filtered and concentrated under reduced pressure. The residue was purified by prep-TLC (SiO$_2$, DCM:MeOH=8:1) to give (S)-3-(5-(4-(1-(1-((1-(((7-(8-ethyl-7-fluoro-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)azetidin-3-yl)piperazin-1-yl)-1-oxoisoindolin-2-yl)piperidine-2,6-dione (100 mg, 86.3 µmol, 48.2% yield, 90.0% purity) as a yellow solid.

Step 3: Preparation of (S)-3-(5-(4-(1-(1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)azetidin-3-yl)piperazin-1-yl)-1-oxoisoindolin-2-yl)piperidine-2,6-dione (Compound 146)

To a solution of (S)-3-(5-(4-(1-(1-((1-(((7-(8-ethyl-7-fluoro-3-(methoxymethoxy)naphthalen-1-yl)-8-fluoro-4-

((R)-3-hydroxy-3-methylpiperidin-1-yl)pyrido[4,3-d]pyrimidin-2-yl)oxy)methyl)cyclopropyl)methyl)piperidin-4-yl)azetidin-3-yl)piperazin-1-yl)-1-oxoisoindolin-2-yl)piperidine-2,6-dione (95.0 mg, 82.0 μmol, 1.00 eq) in DCM (1.00 mL) was added HCl solution (4 M in dioxane, 3.00 mL, 146 eq). The mixture was stirred at 25° C. for 30 minutes. LCMS indicated complete consumption of the reactant and a new peak with ~99% peak area with desired mass. The reaction mixture was concentrated under reduced pressure. The residue was purified by prep-HPLC (FA condition; column: Phenomenex Luna C18 150*25 mm*10 μm; mobile phase: [water (FA)-ACN]; gradient: 7%-37% B over 10 minutes) to give the desired product (20.0 mg, 18.6 μmol, 22.7% yield, 97.3% purity, FA) as a white solid. LCMS: [M+H]$^+$=999.5; $^1$H NMR (400 MHZ, METHANOL-d$_4$) δ=9.14-9.12 (m, 1H), 8.44-8.37 (m, 3H), 7.69-7.64 (m, 2H), 7.30 (t, J=2.4 Hz, 1H), 7.25 (t, J=9.6 Hz, 1H), 7.07-7.04 (m, 3H), 5.11 (br d, J=8.0 Hz, 1H), 4.74 (br t, J=14.4 Hz, 2H), 4.46-4.38 (m, 4H), 4.16-4.13 (m, 1H), 4.03 (br s, 2H), 3.98-3.84 (m, 4H), 3.37 (br d, J=4.4 Hz, 6H), 2.95-2.74 (m, 7H), 2.48 (dt, J=4.8, 13.2 Hz, 3H), 2.23-2.12 (m, 4H), 2.07-1.95 (m, 6H), 1.60 (br t, J=12.4 Hz, 2H), 1.43-1.32 (m, 2H), 0.91-0.86 (m, 4H), 0.80 (t, J=7.2 Hz, 3H).

Compounds 137, 147, 168, and 169 were prepared via similar synthetic procedures as example 44.

| Cpd # | Characterization |
|---|---|
| 137 | LCMS: [M + H]$^+$ = 971.4<br>$^1$H NMR (400 MHz, METHANOL-d$_4$) δ = 9.23 (d, J = 1.6 Hz, 1H), 8.60-8.46 (m, 1H), 7.69-7.62 (m, 2H), 7.32-7.29 (m, 1H), 7.27-7.21 (m, 1H), 7.08-7.03 (m, 3H), 5.12-5.08 (m, 1H), 4.60-4.49 (m, 5H), 4.44-4.36 (m, 4H), 4.34-4.26 (m, 1H), 4.01-3.84 (m, 2H), 3.67-3.52 (m, 6H), 3.49-3.42 (m, 1H), 3.16-3.12 (m, 2H), 3.08-2.98 (m, 3H), 2.93-2.85 (m, 1H), 2.81-2.74 (m, 1H), 2.51-2.42 (m, 6H), 2.24-2.10 (m, 3H), 1.88-1.75 (m, 3H), 1.29 (d, J = 9.6 Hz, 3H), 0.85-0.77 (m, 5H), 0.74-0.70 (m, 2H). |
| 147 | LCMS: [M + H]$^+$ = 1027.6<br>$^1$H NMR (400 MHz, MeOD-d$_4$) δ = 9.23 (d, J = 3.2 Hz, 1H), 8.47 (s, 1H), 7.72-7.62 (m, 1H), 7.31 (d, J = 2.8 Hz, 1H), 7.26 (t, J = 9.2 Hz, 1H), 7.12-7.04 (m, 1H), 5.10 (dd, J = 5.2, 13.2 Hz, 1H), 4.92-4.90 (m, 1H), 4.92-4.89 (m, 1H), 4.58-4.51 (m, 1H), 4.51-4.42 (m, 1H), 4.40 (d, J = 5.6 Hz, 1H), 4.36-4.24 (m, 1H), 3.68-3.56 (m, 1H), 3.53-3.41 (m, 1H), 3.36 (br s, 1H), 2.95-2.85 (m, 1H), 2.82-2.77 (m, 2H), 2.74 (br s, 5H), 2.70 (br d, J = 6.0 Hz, 1H), 2.52-2.34 (m, 1H), 2.29-2.20 (m, 1H), 2.20-2.11 (m, 1H), 2.05 (br d, J = 12.0 Hz, 1H), 1.90-1.67 (m, 1H), 1.30 (d, J = 9.6 Hz, 1H), 0.82 (q, J = 7.2 Hz, 5H), 0.65-0.61 (m, 2H). |
| 168 | LCMS: [M + H]$^+$ = 953.5<br>$^1$H NMR (400 MHz, METHANOL-d$_4$) δ = 9.22 (d, J = 7.4 Hz, 1H), 8.48 (s, 1H), 7.66-7.60 (m, 2H), 7.35 (t, J = 7.6 Hz, 1H), 7.29 (d, J = 2.4 Hz, 1H), 7.16 (br d, J = 7.4 Hz, 1H), 7.08-7.00 (m, 3H), 5.13-5.07 (m, 1H), 4.63-4.50 (m, 2H), 4.44-4.34 (m, 4H), 4.33-4.27 (m, 1H), 4.13 (br s, 2H), 3.88 (br d, J = 5.4 Hz, 2H), 3.67-3.61 (m, 1H), 3.61-3.55 (m, 3H), 3.49-3.40 (m, 1H), 3.30-3.26 (m, 2H), 3.20 (s, 2H), 3.15 (br t, J = 6.8 Hz, 2H), 3.08-3.01 (m, 1H), 2.96-2.85 (m, 1H), 2.82-2.73 (m, 1H), 2.51-2.40 (m, 5H), 2.39-2.26 (m, 2H), 2.19-2.09 (m, 2H), 1.92-1.74 (m, 3H), 1.29 (d, J = 10.6 Hz, 3H), 1.18 (t, J = 7.2 Hz, 1H), 0.94-0.88 (m, 3H), 0.87-0.77 (m, 4H). |
| 169 | LCMS: [M + H]$^+$ = 961.3<br>$^1$H NMR (400 MHz, DMSO-d$_6$) δ = 10.94 (s, 1H), 9.22 (s, 1H), 8.17 (s, 1H), 7.74 (br dd, J = 5.2, 8.4 Hz, 1H), 7.61-7.48 (m, 2H), 7.39 (s, 1H), 7.29-7.22 (m, 1H), 7.14-6.90 (m, 2H), 5.04 (dd, J = 5.2, 13.2 Hz, 1H), 4.87-4.60 (m, 1H), 4.31 (br d, J = 16.8 Hz, 2H), 4.21 (s, 2H), 4.06 (br d, J = 13,2 Hz, 1H), 3.56 (br dd, J = 4.8, 13.2 Hz, 2H), 3.25 (br s, 9H), 2.90 (br d, J = 5.2 Hz, 6H), 2.68-2.55 (m, 1H), 2.44 (br s, 2H), 2.34 (br d, J = 3.6 Hz, 6H), 2.05-1.91 (m, 2H), 1.74-1.61 (m, 3H), 1.17 (br d, J = 4.4 Hz, 3H), 0.54 (br s, 2H), 0.45 (br s, 2H). |

Example 45: Preparation of (S)-3-(5-(4-(1-(1-(((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)azetidin-3-yl)piperidin-4-yl)piperazin-1-yl)-1-oxoisoindolin-2-yl)piperidine-2,6-dione (Compound 139)

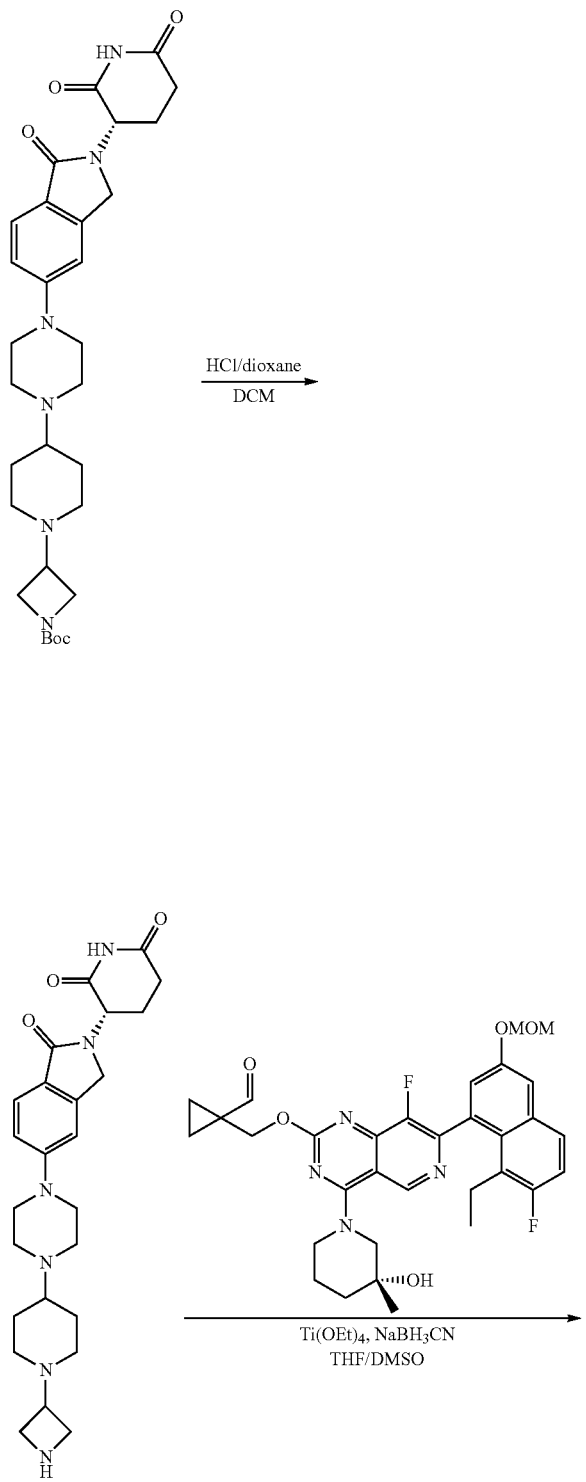

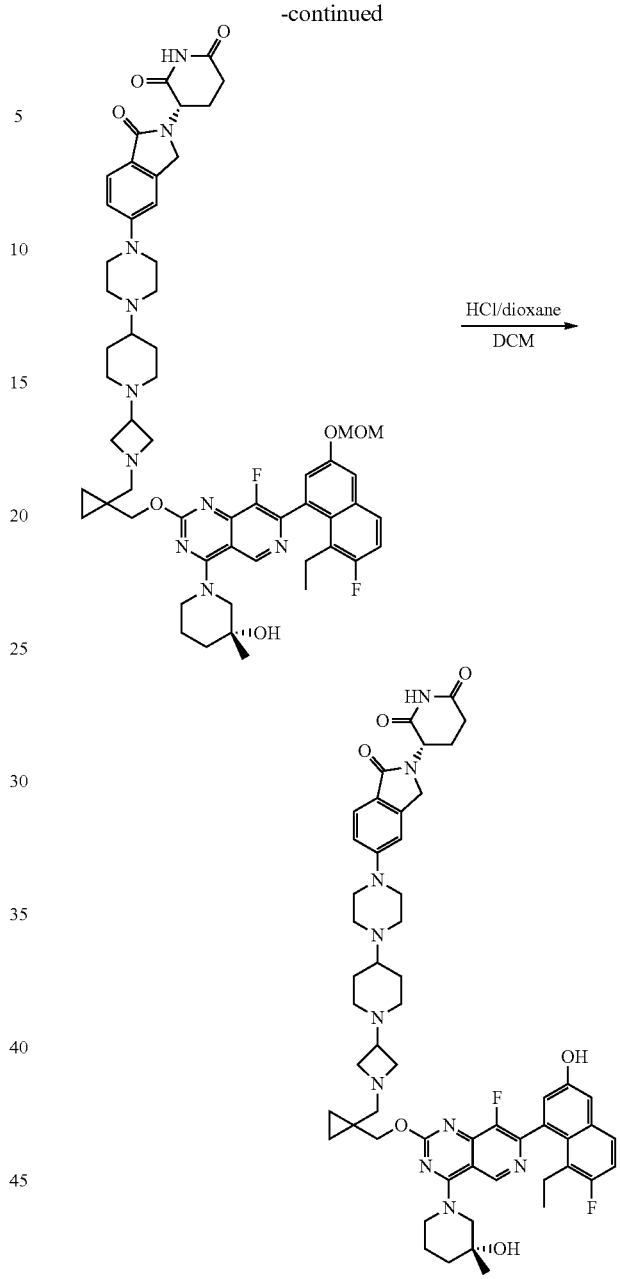

Compound 139

Step 1: Preparation of (S)-3-(5-(4-(1-(azetidin-3-yl)piperidin-4-yl)piperazin-1-yl)-1-oxoisoindolin-2-yl)piperidine-2,6-dione To a solution of tert-butyl 3-[4-[4-[2-[(3S)-2,6-dioxo-3-piperidyl]-1-oxo-isoindolin-5-yl]piperazin-1-yl]-1-piperidyl]azetidine-1-carboxylate (200 mg, 352 μmol, 1 eq) in DCM (2 mL) was added HCl solution (4 M in dioxane, 2 mL, 22.6 eq). The mixture was stirred at 25° C. for 0.5 hours. LCMS showed a new peak of 90% peak area with desired mass. The reaction mixture was filtered and concentrated under reduced pressure to give (S)-3-(5-(4-(1-(azetidin-3-yl)piperidin-4-yl)piperazin-1-yl)-1-oxoisoindolin-2-yl)piperidine-2,6-dione (170 mg, 337 μmol, 95.7% yield, HCl) as a white solid.

Step 2: Preparation of (S)-3-(5-(4-(1-(1-((1-(((7-(8-ethyl-7-fluoro-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)azetidin-3-yl)piperidin-4-yl)piperazin-1-yl)-1-oxoisoindolin-2-yl)piperidine-2,6-dione To a solution of (3S)-3-[5-[4-[1-(azetidin-3-yl)-4-piperidyl]piperazin-1-yl]-1-oxo-isoindolin-2-yl]piperidine-2,6-dione (80 mg, 159 μmol, 1 eq, HCl) and 1-[7-[8-ethyl-7-fluoro-3-(methoxymethoxy)-1-naphthyl]-8-fluoro-5-[(3R)-3-hydroxy-3-methyl-1-piperidyl]pyrido[4,3-d]pyrimidin-2-yl]oxymethyl]cyclopropanecarbaldehyde (109 mg, 159 μmol, 1 eq) in THF (5 mL) and DMSO (1 mL) was added Ti(OEt)₄ (181 mg, 795 μmol, 164 μL, 5 eq) and the reaction mixture was stirred at 25° C. for 5 hours. Then NaBH₃CN (29.9 mg, 477 μmol, 3 eq) was added and the reaction mixture was stirred at 25° C. for 0.5 hours. LCMS showed a new peak of 60% peak area with desired mass. The mixture was diluted with water (10 mL) and extracted with EA (10 mL*3). The combined organic layers were washed with brine (10 mL*2), dried over anhydrous Na₂SO₄, filtered and concentrated under reduced pressure to give a residue. The residue was purified by column chromatography by prep-TLC (SiO₂, DCM:MeOH=9:1, Rf=0.2) to give (S)-3-(5-(4-(1-(1-((1-(((7-(8-ethyl-7-fluoro-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)azetidin-3-yl)piperidin-4-yl)piperazin-1-yl)-1-oxoisoindolin-2-yl)piperidine-2,6-dione (40 mg, 36.8 μmol, 23.1% yield, 96% purity) as a yellow solid.

Step 3: Preparation of (S)-3-(5-(4-(1-(1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)azetidin-3-yl)piperidin-4-yl)piperazin-1-yl)-1-oxoisoindolin-2-yl)piperidine-2,6-dione (Compound 139)

To a solution of (S)-3-(5-(4-(1-(1-((1-(((7-(8-ethyl-7-fluoro-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)azetidin-3-yl)piperidin-4-yl)piperazin-1-yl)-1-oxoisoindolin-2-yl)piperidine-2,6-dione (40 mg, 36.8 μmol, 1 eq) in DCM (2 mL) was added HCl solution (4 M in dioxane, 2 mL, 217 eq). The mixture was stirred at 25° C. for 0.5 hours. LCMS showed a new peak of 90% peak area with desired mass. The reaction mixture was filtered and concentrated under reduced pressure to give a residue. The residue was purified by prep-HPLC (FA condition; column: Phenomenex Luna C18 150*25 mm*10 μm; mobile phase: [water (FA)-ACN]; gradient: 10%-40% B over 10 minutes) to give (S)-3-(5-(4-(1-(1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)azetidin-3-yl)piperidin-4-yl)piperazin-1-yl)-1-oxoisoindolin-2-yl)piperidine-2,6-dione (19 mg, 18.2 μmol, 49.5% yield, 96% purity) as a white solid. LCMS: [M+H]⁺ =999.6. ¹H NMR (400 MHZ, METHANOL-d₄) δ=9.29-9.18 (m, 1H), 8.47 (s, 1H), 7.65 (d, J=8.2 Hz, 2H), 7.36-7.18 (m, 2H), 7.07 (d, J=2.4 Hz, 3H), 5.13-5.08 (m, 1H), 4.60-4.54 (m, 1H), 4.28 (br s, 5H), 4.24 (br d, J=1.8 Hz, 1H), 4.01-3.85 (m, 2H), 3.69-3.56 (m, 1H), 3.48-3.41 (m, 1H), 3.40-3.33 (m, 5H), 3.25 (br s, 3H), 2.98-2.84 (m, 3H), 2.84-2.69 (m, 5H), 2.53-2.08 (m, 6H), 2.00-1.74 (m, 7H), 1.63-1.44 (m, 2H), 1.29 (d, J=9.4 Hz, 3H), 0.90-0.76 (m, 7H).

Example 46: Preparation of (S)-3-(5-(4-(1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)methyl)piperidin-4-yl)piperazin-1-yl)-1-oxoisoindolin-2-yl)piperidine-2,6-dione (Compound 148)

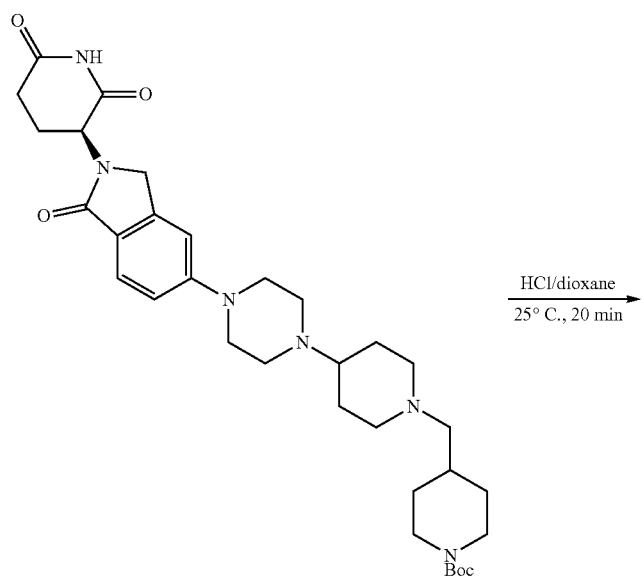

HCl/dioxane
25° C., 20 min

573
-continued
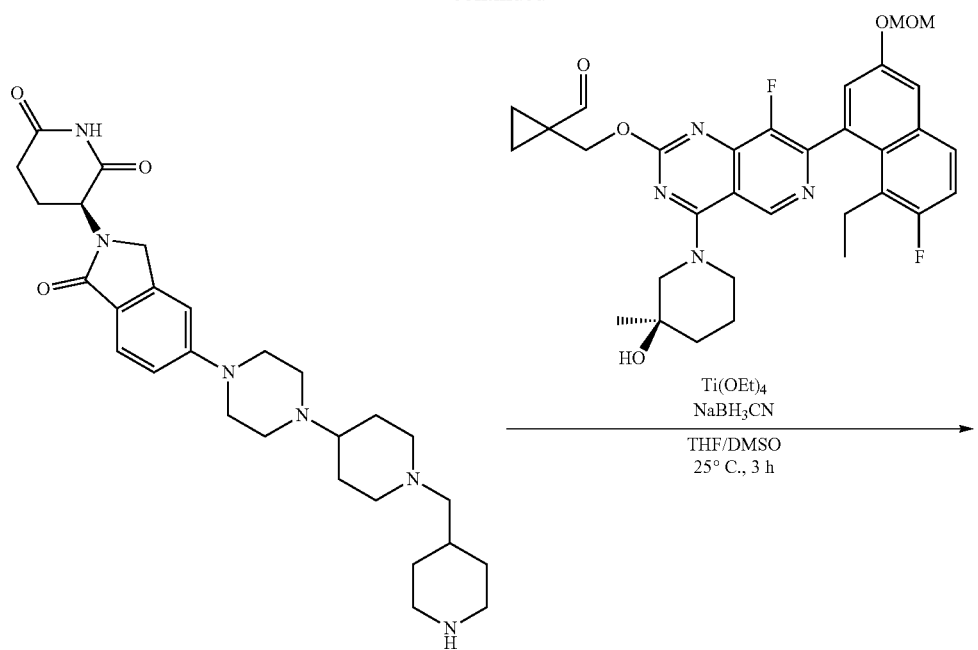
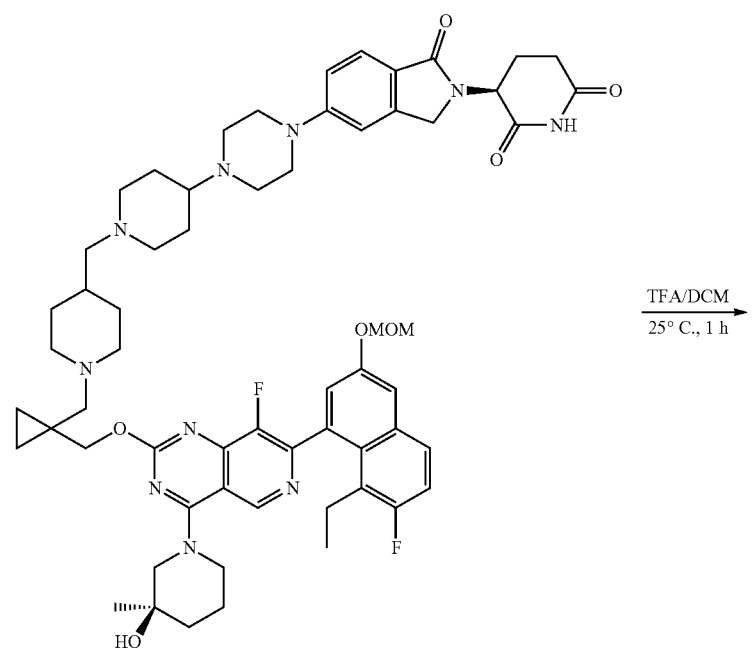

-continued

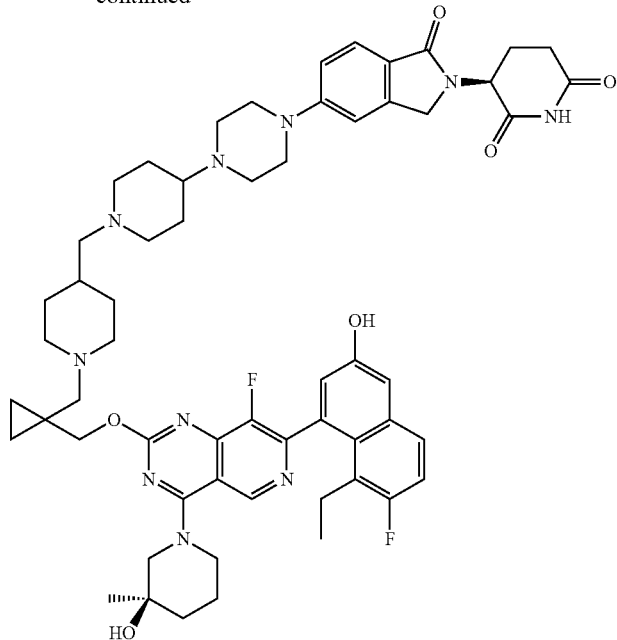 [SMILES: CCc1c(F)ccc2cc(O)cc(-c3ncc4c(N5CCC[C@@](C)(O)C5)nc(OCC5(CN6CCC(CN7CCC(N8CCN(c9ccc%10c(c9)CN([C@H]9CCC(=O)NC9=O)C%10=O)CC8)CC7)CC6)CC5)nc4c3F)c12]

Step 1: Preparation of (S)-3-(1-oxo-5-(4-(1-(piperidin-4-ylmethyl)piperidin-4-yl)piperazin-1-yl)isoindolin-2-yl)piperidine-2,6-dione To a solution of tert-butyl 4-[[4-[4-[2-[(3S)-2,6-dioxo-3-piperidyl]-1-oxo-isoindolin-5-yl]piperazin-1-yl]-1-piperidyl]methyl]piperidine-1-carboxylate (210 mg, 344 μmol, 1 eq) in DCM (1 mL) was added HCl/dioxane (3 mL). The mixture was stirred at 25° C. for 20 minutes. LCMS showed complete consumption of the reactant and a major new peak with desired mass. The reaction mixture was concentrated to give (S)-3-(1-oxo-5-(4-(1-(piperidin-4-ylmethyl)piperidin-4-yl)piperazin-1-yl)isoindolin-2-yl)piperidine-2,6-dione (240 mg, crude, HCl) as a white solid, which was used in the next step without further purification.

Step 2: Preparation of (S)-3-(5-(4-(1-((1-((1-(((7-(8-ethyl-7-fluoro-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)methyl)piperidin-4-yl)piperazin-1-yl)-1-oxoisoindolin-2-yl)piperidine-2,6-dione To a solution of (3S)-3-[1-oxo-5-[4-[1-(4-piperidylmethyl)-4-piperidyl]piperazin-1-yl]isoindolin-2-yl]piperidine-2,6-dione (109 mg, 200 μmol, 1.4 eq, HCl) and 1-[7-[8-ethyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropanecarbaldehyde (85.0 mg, 143 μmol, 1 eq) in DMSO (0.5 mL) and THF (2 mL) was added Ti(OEt)$_4$ (981 mg, 4.30 mmol, 892 μL, 30 eq). The mixture was stirred at 25° C. for 20 minutes. Then NaBH$_3$CN (45.1 mg, 717 μmol, 5 eq) was added at 0° C. and the mixture was stirred at 25° C. for 10 minutes. The reaction mixture was poured into a mixture of THF (100 mL) and ethyl acetate (50 mL). The combined organic layers were washed with water (20 mL), dried over anhydrous Na$_2$SO$_4$, filtered and concentrated under reduced pressure. The residue was purified by prep-HPLC (column: Phenomenex Luna C18 150*25 mm*10 μm; mobile phase: [water (FA)-ACN]; gradient: 5%-35% B over 10 min) to afford (S)-3-(5-(4-(1-((1-((1-(((7-(8-ethyl-7-fluoro-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)piperazin-1-yl)-1-oxoisoindolin-2-yl)piperidine-2,6-dione (35 mg, 32.2 μmol, 22.4% yield, 100% purity) as a white solid.

Step 3: Preparation of (S)-3-(5-(4-(1-((1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)methyl)piperidin-4-yl)piperazin-1-yl)-1-oxoisoindolin-2-yl)piperidine-2,6-dione
(Compound 148)

A solution of (S)-3-(5-(4-(1-((1-((1-(((7-(8-ethyl-7-fluoro-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)methyl)piperidin-4-yl)piperazin-1-yl)-1-oxoisoindolin-2-yl)piperidine-2,6-dione (75 mg, 69.1 μmol, 1 eq) in TFA (1 mL) and DCM (2 mL) was stirred at 25° C. for 1 hour. LCMS showed full consumption of the reactant and detection of the desired product. The reaction mixture was concentrated under reduced pressure to give a crude residue, which was purified by prep-HPLC (column: Phenomenex Luna C18 150*25 mm 10 μm; mobile phase: [water (FA)-ACN]; gradient: 4%-34% B over 10 min) to afford (S)-3-(5-(4-(1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)methyl)piperidin-4-yl)piperazin-1-yl)-1-oxoisoindolin-2-yl)piperidine-2,6-dione (30 mg, 28.5 μmol, 41.2% yield, 99% purity) as a white solid. LCMS: [M+H]$^+$=1041.6. $^1$H NMR (400 MHZ, DMSO-d$_6$) δ=9.20-9.13 (m, 1H), 8.28 (s, 1H), 7.73 (dd, J=6.0, 9.2 Hz, 1H), 7.54 (d, J=9.0 Hz, 1H), 7.37-7.28 (m, 2H), 7.09-6.96 (m, 3H), 4.96 (dd, J=5.2, 13.2 Hz, 1H), 4.37-4.23 (m, 4H), 4.23-4.17 (m, 1H), 4.09-4.00 (m, 1H), 3.62-3.49 (m, 1H), 3.43 (br s, 1H), 3.26 (br s, 6H), 3.06-2.94 (m, 2H), 2.92-2.74 (m, 2H), 2.73-2.64 (m, 2H), 2.62 (br s, 4H), 2.45-2.35 (m, 2H), 2.35-2.23 (m, 5H), 2.20-2.05 (m, 3H), 2.02-1.94 (m, 2H), 1.85-1.63 (m, 8H), 1.55-1.42 (m, 2H), 1.30-1.18 (m, 2H), 1.14 (d, J=10.8 Hz, 3H), 0.76-0.63 (m, 5H), 0.62-0.50 (m, 2H).

Compound 149 was prepared via a similar synthetic procedure as example 46.

| Cpd # | Characterization |
|---|---|
| 149 | LCMS: [M + H]$^+$ = 1013.6<br>$^1$H NMR (400 MHz, DMSO-d$_6$) δ = 9.22 (d, J = 2.0 Hz, 1H), 7.75 (dd, J = 6.0, 9.2 Hz, 1H), 7.55 (d, J = 9.2 Hz, 1H), 7.40-7.28 (m, 2H), 7.10-7.00 (m, 3H), 5.00 (dd, J = 4.8, 13.2 Hz, 1H), 4.44-4.13 (m, 6H), 4.11-4.00(m, 2H), 3.53-3.38 (m, 2H), 3.32-3.23 (m, 3H), 3.15-3.03 (m, 2H), 2.96-2.84 (m, 4H), 2.71-2.60 (m, 5H),2.41-2.27 (m, 4H), 2.13 (ddd, J = 6.8, 13.2, 15.2 Hz, 2H), 2.05-1.91 (m, 3H), 1.87-1.78 (m, 2H), 1.75-1.59(m, 4H), 1.51-1.40 (m, 2H), 1.27-1.08 (m, 5H), 0.76-0.65 (m, 7H). |

Example 47: Preparation of 3-[5-[3-[7-[[1-[[7-(8-ethyl-7-fluoro-3-hydroxy-1-naphthyl)-8-fluoro-4-[(3R)-3-hydroxy-3-methyl-1-piperidyl]pyrido[4,3-d]pyrimidin-2-yl]oxymethyl]cyclopropyl]methyl]-2,7-diazaspiro[3.5]nonan-2-yl]azetidin-1-yl]-1-oxo-isoindolin-2-yl]piperidine-2,6-dione (Compound 163)

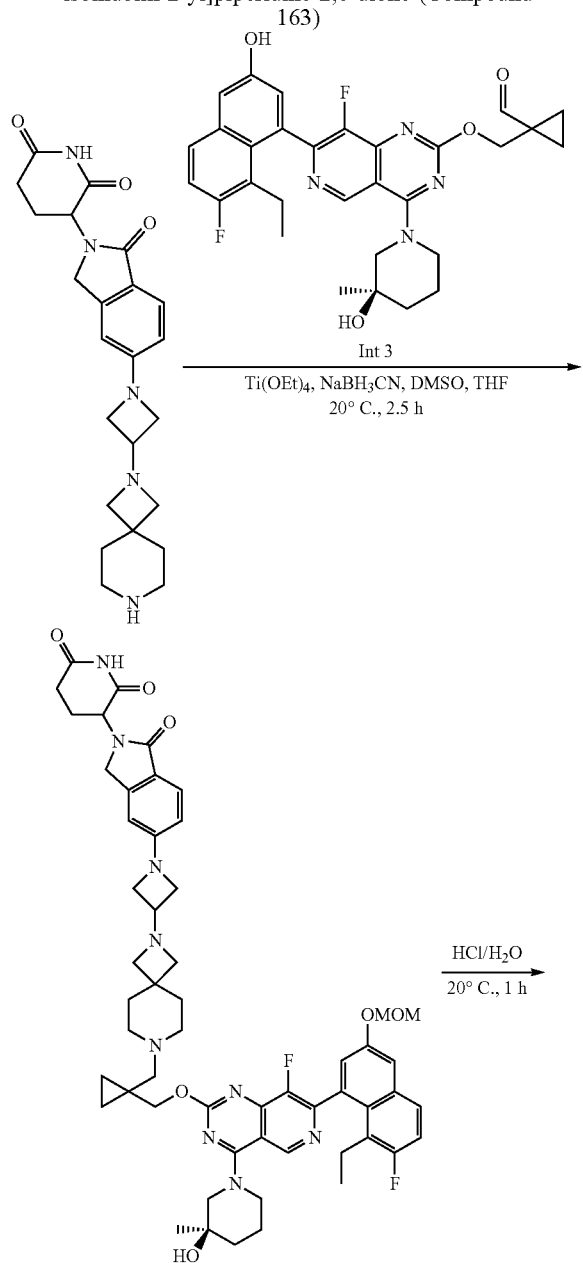

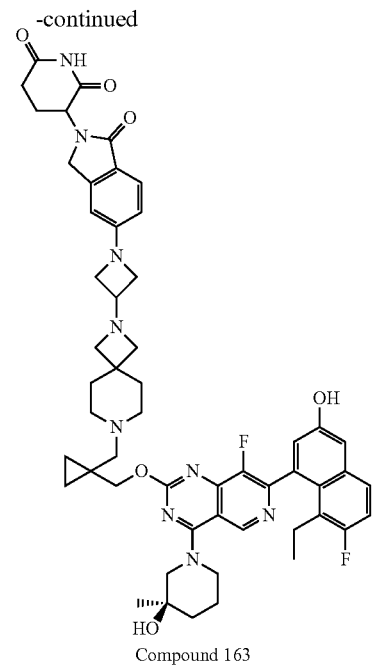

Compound 163

Step 1: Preparation of 3-[5-[3-[7-[1-[[7-[8-ethyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropyl]methyl]-2,7-diazaspiro[3.5]nonan-2-yl]azetidin-1-yl]-1-oxo-isoindolin-2-yl]piperidine-2,6-dione To a solution of 3-[5-[3-(2,7-diazaspiro[3.5]nonan-2-yl) azetidin-1-yl]-1-oxo-isoindolin-2-yl]piperidine-2,6-dione (100 mg, 186 μmol, 1 eq, TFA) and 1-[[7-[8-ethyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl] oxymethyl]cyclopropanecarbaldehyde (110 mg, 186 μmol, 1 eq) in DMSO (5 mL) and THF (5 mL) was added Ti(OEt)$_4$ (424 mg, 1.86 mmol, 385 μL, 10 eq) at 20° C. over 2 hours. NaBH$_3$CN (23.3 mg, 372 μmol, 2 eq) was added and the reaction mixture was stirred at 20° C. for 0.5 hours. LCMS showed a new peak of 45% peak area with desired mass. The mixture was diluted with ethyl acetate (50 mL), washed with saturated bicarbonate sodium solution (50 mL*2), dried over anhydrous sodium sulfate and concentrated under reduced pressure to give a residue. The residue was purified by reversed-phase HPLC (0.1% FA condition) to give 3-[5-[3-[7-[[1-[[7-[8-ethyl-7-fluoro-3-(methoxymethoxy)-1-naphthyl]-8-fluoro-4-[(3R)-3-hydroxy-3-methyl-1-piperidyl] pyrido[4,3-d]pyrimidin-2-yl]oxymethyl]cyclopropyl] methyl]-2,7-diazaspiro[3.5]nonan-2-yl]azetidin-1-yl]-1-oxo-isoindolin-2-yl]piperidine-2,6-dione (35 mg, 35.0 μmol, 18.8% yield, 100% purity) as a white solid. $^1$H NMR (400 MHZ, CDCl₃) δ=9.14 (d, J=4.4 Hz, 1H), 8.84-8.47 (m, 1H), 8.45-8.19 (m, 1H), 7.75-7.62 (m, 2H), 7.51 (d, J=2.8 Hz, 1H), 7.27-7.20 (m, 2H), 6.46-6.39 (m, 1H), 6.35 (s, 1H), 5.34-5.22 (m, 2H), 5.22-5.06 (m, 1H), 4.53-4.29 (m, 5H), 4.25-4.16 (m, 1H), 3.94 (br t, J=7.6 Hz, 2H), 3.82-3.71 (m, 2H), 3.70-3.62 (m, 1H), 3.51 (s, 3H), 3.46-3.39 (m, 1H), 3.35-3.26 (m, 1H), 3.11 (s, 4H), 2.88-2.73 (m, 4H), 2.56-2.44 (m, 3H), 2.34-2.02 (m, 5H), 1.96-1.59 (m, 8H), 1.34 (s, 3H), 0.89-0.80 (m, 3H), 0.75 (br s, 2H), 0.53 (br s, 2H).

Step 2: Preparation of 3-[5-[3-[7-[1-[7-(8-ethyl-7-fluoro-3-hydroxy-1-naphthyl)-8-fluoro-4-[(3R)-3-hydroxy-3-methyl-1-piperidyl]pyrido[4,3-d]pyrimidin-2-yl]oxymethyl]cyclopropyl]methyl]-2,7-diazaspiro[3.5]nonan-2-yl]azetidin-1-yl]-1-oxo-isoindolin-2-yl]piperidine-2,6-dione (Compound 163)

To a solution of 3-[5-[3-[7-[[1-[[7-[8-ethyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropyl]methyl]-2,7-diazaspiro[3.5]nonan-2-yl]azetidin-1-yl]-1-oxo-isoindolin-2-yl]piperidine-2,6-dione (33 mg, 33 μmol, 1 eq) in H₂O (1.5 mL) was added HCl (4 M in dioxane, 0.5 mL, 60.6 eq) and the reaction mixture was stirred at 20° C. for 1 hour. LCMS showed a new peak of 69.8% peak area with desired mass. The mixture was purified by prep-HPLC (column: Phenomenex Luna C18 150*25 mm*10 μm; mobile phase: [water (FA)-ACN]; gradient: 10%-40% B over 10 minutes) to give 3-[5-[3-[7-[1-[7-(8-ethyl-7-fluoro-3-hydroxy-1-naphthyl)-8-fluoro-4-[(3R)-3-hydroxy-3-methyl-1-piperidyl]pyrido[4,3-d]pyrimidin-2-yl]oxymethyl]cyclopropyl]methyl]-2,7-diazaspiro[3.5]nonan-2-yl]azetidin-1-yl]-1-oxo-isoindolin-2-yl]piperidine-2,6-dione (15 mg, 15.56 μmol, 47.1% yield, 99.2% purity) as a white solid. LCMS: [M+H]⁺=956.3. ¹H NMR (400 MHZ, DMSO-d₆) δ=10.93 (s, 1H), 9.21 (s, 1H), 8.16 (s, 1H), 7.81-7.71 (m, 1H), 7.47 (d, J=8.4 Hz, 1H), 7.39-7.29 (m, 2H), 7.02 (d, J=2.4 Hz, 1H), 6.48 (s, 1H), 6.47-6.43 (m, 1H), 5.08-4.96 (m, 1H), 4.37-4.24 (m, 4H), 4.20-4.14 (m, 1H), 4.03 (br d, J=9.2 Hz, 1H), 3.89 (br d, J=7.2 Hz, 2H), 3.67-3.63 (m, 3H), 2.93 (s, 4H), 2.91-2.81 (m, 2H), 2.59 (br s, 1H), 2.40-2.23 (m, 8H), 2.22-2.07 (m, 2H), 2.02-1.90 (m, 2H), 1.75-1.59 (m, 7H), 1.16 (d, J=10.0 Hz, 3H), 0.77-0.69 (m, 3H), 0.64 (br s, 2H), 0.40 (s, 2H).

Example 48: Preparation of 3-(5-(3-(2-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-2,7-diazaspiro[3.5]nonan-7-yl)azetidin-1-yl)-1-oxoisoindolin-2-yl)piperidine-2,6-dione (Compound 172)

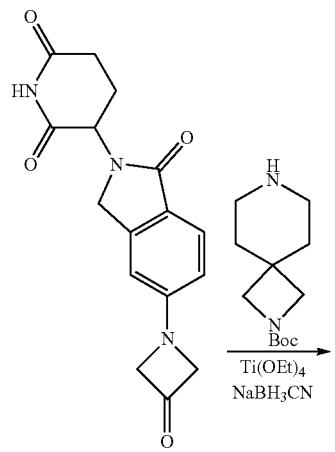

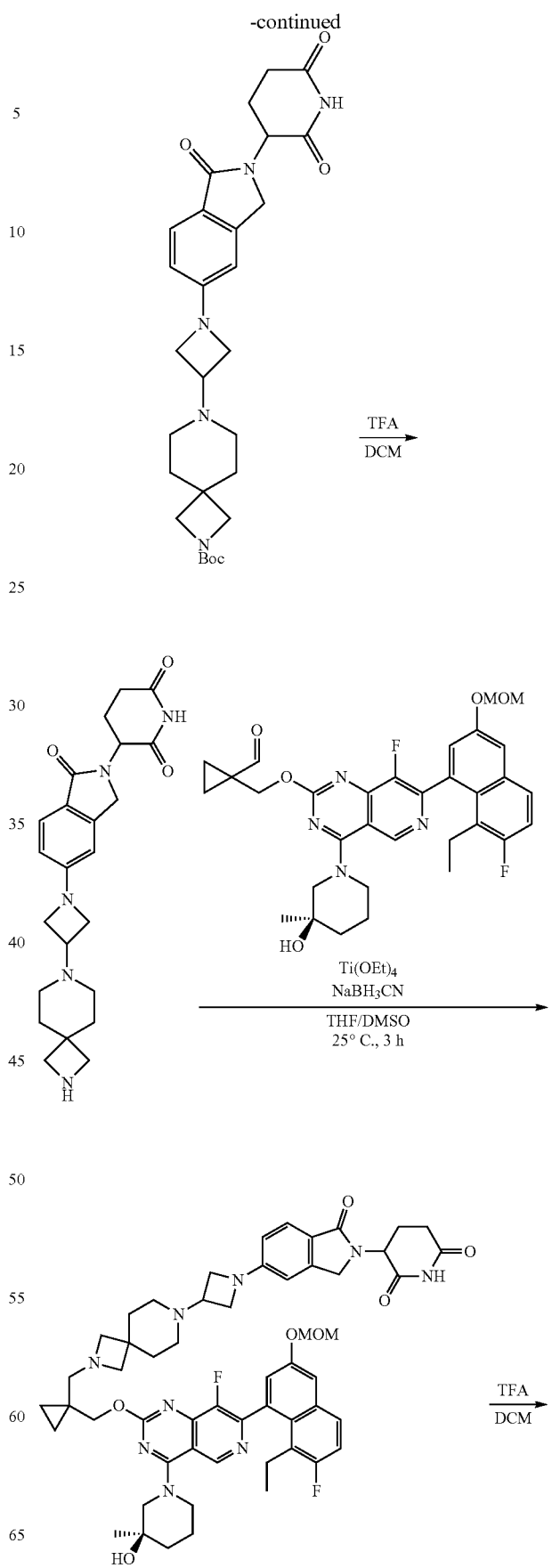

-continued

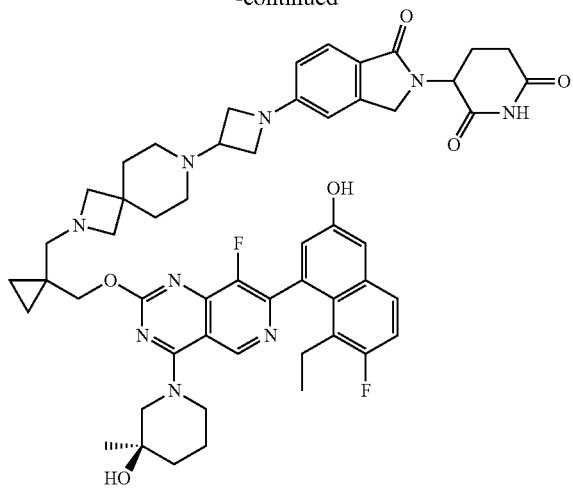

172

Step 1: Preparation of tert-butyl 7-(1-(2-(2,6-di-oxopiperidin-3-yl)-1-oxoisoindolin-5-yl)azetidin-3-yl)-2,7-diazaspiro[3.5]nonane-2-carboxylate To a solution of tert-butyl 2,7-diazaspiro[3.5]nonane-2-carboxylate (86.6 mg, 383 μmol, 1.2 eq) in DMSO (2 mL) and THF (2 mL) was added Ti(OEt)₄ (364 mg, 1.60 mmol, 330 μL, 5 eq), NaBH₃CN (100 mg, 1.60 mmol, 5 eq) and 3-[1-oxo-5-(3-oxoazetidin-1-yl)isoindolin-2-yl]piperidine-2,6-dione (100 mg, 319 μmol, 1 eq). The mixture was stirred at 25° C. for 2 hours. LCMS indicate complete consumption of the reactant and a new peak of 50% peak area with desired mass. The residue was poured into a mixture of THF (50 mL) and DCM (50 mL). The combined organic layers were washed with water (10 mL), dried over anhydrous Na₂SO₄, filtered and concentrated under reduced pressure. The crude product was purified by reversed-phase HPLC (0.1% FA condition) to afford tert-butyl 7-(1-(2-(2,6-dioxopiperidin-3-yl)-1-oxoisoindolin-5-yl)azetidin-3-yl)-2,7-diazaspiro[3.5]nonane-2-carboxylate (57 mg, 82.7 μmol, 25.9% yield, 76% purity) as a yellow solid.

Step 2: Preparation of 3-(5-(3-(2,7-diazaspiro[3.5]nonan-7-yl)azetidin-1-yl)-1-oxoisoindolin-2-yl)piperidine-2,6-dione To a solution of tert-butyl 7-[1-[2-(2,6-dioxo-3-piperidyl)-1-oxo-isoindolin-5-yl]azetidin-3-yl]-2,7-diazaspiro[3.5]nonane-2-carboxylate (57 mg, 108 μmol, 1 eq) in DCM (2 mL) was added TFA (0.4 mL). The mixture was stirred at 0° C. for 3 hours. LCMS showed full consumption of the reactant and a major new peak with desired mass. The reaction mixture was concentrated under reduced pressure to give a residue. The crude residue was purified by reversed-phase HPLC (0.1% FA condition) to afford 3-(5-(3-(2,7-diazaspiro[3.5]nonan-7-yl)azetidin-1-yl)-1-oxoisoindolin-2-yl)piperidine-2,6-dione (35 mg, 65.1 μmol, 59.8% yield, TFA) as a white solid.

Step 3: Preparation of 3-(5-(3-(2-((1-(((7-(8-ethyl-7-fluoro-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-2,7-diazaspiro[3.5]nonan-7-yl)azetidin-1-yl)-1-oxoisoindolin-2-yl)piperidine-2,6-dione To a solution of 3-[5-[3-(2,7-diazaspiro[3.5]nonan-7-yl)azetidin-1-yl]-1-oxo-isoindolin-2-yl]piperidine-2,6-dione (30 mg, 55.8 μmol, 1.2 eq, TFA), 1-[7-[8-ethyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropanecarbaldehyde (27.5 mg, 46.5 μmol, 1 eq) in THF (2 mL) and DMSO (2 mL) was added Ti(OEt)₄ (212 mg, 930 μmol, 192 μL, 20 eq) and NaBH₃CN (14.61 mg, 232 μmol, 5 eq). The mixture was stirred at 25° C. for 12 hours. The residue was poured into a mixture of THF (50 mL) and DCM (50 mL). The combined organic layers were washed with water (10 mL), dried over anhydrous Na₂SO₄, filtered and concentrated under reduced pressure. The crude product was purified by reversed-phase HPLC (0.1% FA condition) to afford 3-(5-(3-(2-((1-(((7-(8-ethyl-7-fluoro-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-2,7-diazaspiro[3.5]nonan-7-yl)azetidin-1-yl)-1-oxoisoindolin-2-yl)piperidine-2,6-dione (30 mg, 29.1 μmol, 62.5% yield, 97% purity) as a white solid.

Step 4: Preparation of 3-(5-(3-(2-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-2,7-diazaspiro[3.5]nonan-7-yl)azetidin-1-yl)-1-oxoisoindolin-2-yl)piperidine-2,6-dione (Compound 172)

To a solution of 3-[5-[3-[2-[[1-[7-[8-ethyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropyl]methyl]-2,7-diazaspiro[3.5]nonan-7-yl]azetidin-1-yl]-1-oxo-isoindolin-2-yl]piperidine-2,6-dione (30 mg, 30.0 μmol, 1 eq) in DCM (2 mL) was added TFA (0.4 mL) at 0° C. The mixture was stirred at 25° C. for 1 hour. LCMS showed complete consumption of the reactant and a major peak with desired mass. The reaction mixture was concentrated under reduced pressure to give a residue. The residue was purified by prep-HPLC (Phenomenex Luna C18 150*25 mm*10 μm; mobile phase: [water (FA)-ACN]; gradient: 8%-38% B over 10 minutes) to afford 3-(5-(3-(2-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-2,7-diazaspiro[3.5]nonan-7-yl)azetidin-1-yl)-1-oxoisoindolin-2-yl)piperidine-2,6-dione (12.3 mg, 12.7 μmol, 42.6% yield, 99% purity) as a white solid. LCMS: [M+H]⁺=956.4; ¹H NMR (400 MHZ, METHANOL-d₄) δ=9.23 (d, J=3.2 Hz, 1H), 8.53 (s, 1H), 7.68 (dd, J=6.0, 9.2 Hz, 1H), 7.5 (d, J=9.2 Hz, 1H), 7.31 (d, J=2.4 Hz, 1H), 7.25 (s, 1H), 7.06 (s, 1H), 6.55-6.49 (m, 2H), 5.08 (br d, J=8.4 Hz, 1H), 4.58-4.51 (m, 2H), 4.40 (s, 2H), 4.38-4.25 (m, 3H), 4.04 (dt, J=3.6, 7.2 Hz, 2H), 3.96-3.52 (m, 7H), 3.51-3.39 (m, 2H), 3.24-3.14 (m, 1H), 2.98-2.72 (m, 2H), 2.53-2.35 (m, 5H), 2.32-2.09 (m, 4H), 1.94-1.75 (m, 7H), 1.31-1.28 (m, 3H), 0.87-0.76 (m, 7H).

Compounds 166 and 171 were prepared via similar synthetic procedures as example 48.

| Cpd # | Characterization |
|---|---|
| 166 | LCMS: [M + H]⁺ = 984.5<br>¹H NMR (400 MHz, DMSO-d₆) δ = 11.10-10.74 (m, 1H), 9.22 (s, 1H), 8.23-8.07 (m, 1H), 7.76 (br dd, J = 6.0, 9.2 Hz, 1H), 7.59-7.46 (m, 1H), 7.40-7.29 (m, 2H), 7.13-6.97 (m, 3H), 5.08-5.01 (m, 1H), 4.38-4.15 (m, 6H), 4.13-3.96 (m, 3H), 3.93-3.87 (m, 2H), 3.63 (br s, 2H), 3.60 (br s, 1H), 3.26 (br s, 2H), 2.83-2.74 (m, 4H), 2.65-2.59 (m, 2H), 2.54 (s, 4H), 2.39-2.29 (m, 2H), 2.21-1.90 (m, 5H), 1.87-1.60 (m, 9H), 1.54-1.48 (m, 1H), 1.16 (br d, J = 9.6 Hz, 3H), 0.73 (q, J = 7.2 Hz, 3H), 0.66-0.50 (m, 4H). |
| 171 | LCMS: [M + H]⁺ = 1012.6<br>¹H NMR (400 MHz, METHANOL-d₄) δ = 9.20 (d, J = 6.0 Hz, 1H), 7.67-7.54 (m, 2H), 7.27-7.19 (m, 2H), 7.08-6.99 (m, 3H), 5.11-5.07 (m, 1H), 4.58 (br s, 6H), 4.38 (br d, J = 5.2 Hz, 2H), 4.35-4.20 (m, 1H), 3.72-3.56 (m, 1H), 3.52-3.45 (m, 1H), 3.28-3.21 (m, 3H), 2.94-2.85 (m, 1H), 2.82-2.75 (m, 1H), 2.64-2.55 (m, 4H), 2.55-2.50 (m, 2H), 2.49-2.43 (m, 2H), 2.40-2.06 (m, 6H), 1.80 (br d, J = 11.0 Hz, 4H), 1.75-1.69 (m, 2H), 1.67-1.61 (m, 2H), 1.50-1.46 (m, 2H), 1.45-1.35 (m, 2H), 1.32-1.29 (m, 2H), 1.29-1.26 (m, 2H), 1.21-1.13 (m, 2H), 0.86-0.78 (m, 3H), 0.76-0.66 (m, 2H), 0.54-0.46 (m, 2H). |

Example 49: Preparation of 3-(5-(3-(9-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-3,9-diazaspiro[5.5]undecan-3-yl)azetidin-1-yl)-1-oxoisoindolin-2-yl)piperidine-2,6-dione (Compound 164)

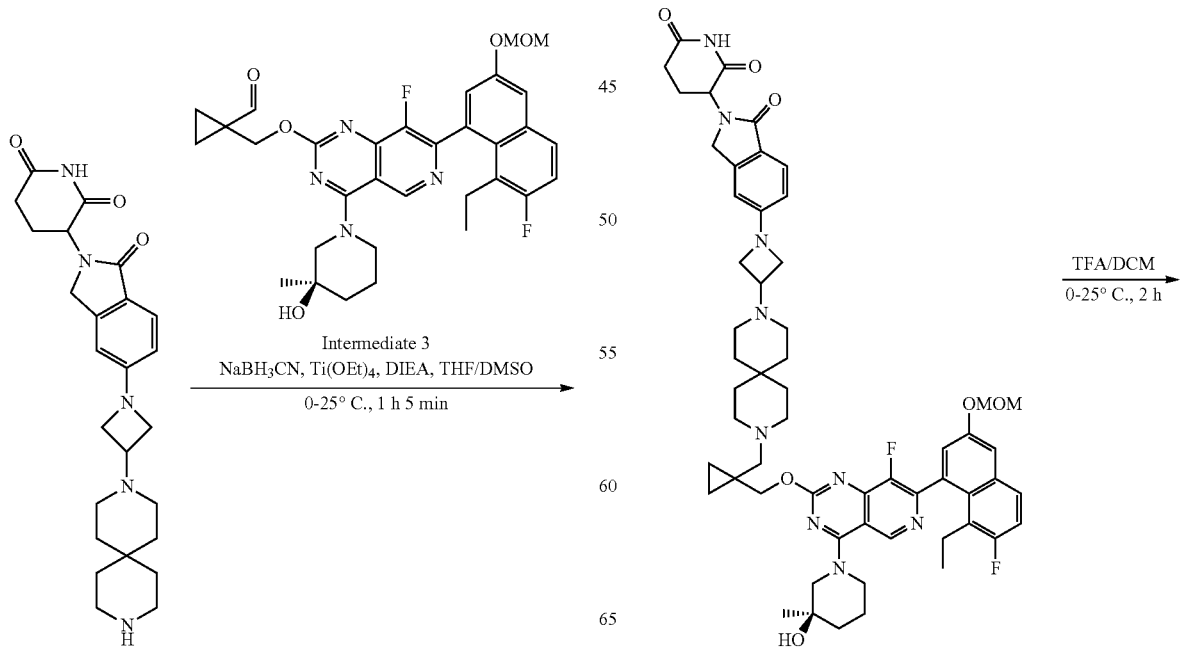

-continued

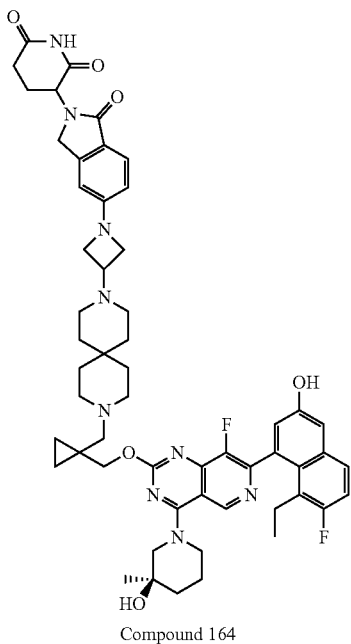

Compound 164

Step 1: Preparation of 3-(5-(3-(9-((1-(((7-(8-ethyl-7-fluoro-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-3,9-diazaspiro[5.5]undecan-3-yl)azetidin-1-yl)-1-oxoisoindolin-2-yl)piperidine-2,6-dione To a solution of 3-[5-[3-(3,9-diazaspiro[5.5]undecan-3-yl]azetidin-1-yl]-1-oxo-isoindolin-2-yl]piperidine-2,6-dione (200 mg, 294 μmol, 1.16 eq, 2TFA) in THF (6.00 mL) and DMSO (2.00 mL) was added DIEA (32.7 mg, 253 μmol, 44.1 μL, 1.00 eq) at 0° C. and the mixture was then added 1-[[7-[8-ethyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropanecarbaldehyde (150 mg, 253 μmol, 1.00 eq) and Ti(OEt)$_4$ (2.20 g, 9.64 mmol, 2.00 mL, 38.1 eq) and stirred at 25° C. for 1 hour. The mixture was then added NaBH$_3$CN (159 mg, 2.53 mmol, 10.0 eq) and stirred at 25° C. for 5 minutes. The residue was poured into ice-water (50.0 mL), and the mixture was stirred for 5 minutes and filtered. The aqueous phase was extracted with ethyl acetate (30.0 mL*3). The combined organic layers were washed with brine (50.0 mL), dried over anhydrous Na$_2$SO$_4$, filtered and concentrated under reduced pressure. The solid was added DCM:MeOH=1:1 (100 mL), filtered and concentrated under reduced pressure. The residue was purified by prep-TLC (SiO$_2$, DCM:MeOH=10:1) to give 3-(5-(3-(9-((1-(((7-(8-ethyl-7-fluoro-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-3,9-diazaspiro[5.5]undecan-3-yl)azetidin-1-yl)-1-oxoisoindolin-2-yl)piperidine-2,6-dione (260 mg, 202 μmol, 79.9% yield, 80.0% purity) as a yellow oil. $^1$H NMR (400 MHZ, DMSO-d$_6$) δ=10.93 (s, 1H), 9.25 (s, 1H), 7.93-7.86 (m, 1H), 7.68 (d, J=1.6 Hz, 1H), 7.51-7.41 (m, 2H), 7.21 (d, J=2.4 Hz, 1H), 6.52-6.45 (m, 2H), 5.35 (s, 2H), 5.06-5.00 (m, 1H), 4.72 (d, J=8.4 Hz, 1H), 4.38-4.26 (m, 4H), 4.21-4.14 (m, 1H), 4.12-3.98 (m, 4H), 3.70-3.50 (m, 4H), 3.43 (s, 3H), 3.37 (br s, 2H), 3.17 (d, J=4.8 Hz, 4H), 2.96-2.84 (m, 2H), 2.38-2.27 (m, 6H), 2.24-2.12 (m, 2H), 2.07-1.91 (m, 3H), 1.74-1.62 (m, 4H), 1.25 (br d, J=6.4 Hz, 3H), 1.17 (br d, J=10.0 Hz, 3H), 0.79-0.72 (m, 4H), 0.60-0.18 (m, 3H), 0.10--0.14 (m, 1H).

Step 2: Preparation of 3-(5-(3-(9-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-3,9-diazaspiro[5.5]undecan-3-yl)azetidin-1-yl)-1-oxoisoindolin-2-yl)piperidine-2,6-dione (Compound 164)

To a solution of 3-[5-[3-[9-[[1-[[7-[8-ethyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropyl]methyl]-3,9-diazaspiro[5.5]undecan-3-yl]azetidin-1-yl]-1-oxo-isoindolin-2-yl]piperidine-2,6-dione (255 mg, 198 μmol, 1.00 eq) in DCM (5.00 mL) was added TFA (1.54 g, 13.5 mmol, 1.00 mL, 67.9 eq) at 0° C. The mixture was stirred at 25° C. for 2 hours. LCMS indicated complete consumption of the reactant and a new peak of ~89% peak area with desired mass. The reaction mixture was concentrated under reduced pressure. The residue was purified by prep-HPLC (FA condition; column: Phenomenex Luna C18 150*25 mm*10 μm; mobile phase: [water (FA)-ACN]; gradient: 16%-36% B over 10 minutes) to give the desired product (60.1 mg, 59.6 μmol, 30.0% yield, 97.6% purity) as a white solid. LCMS: [M+H]$^+$=984.5; $^1$H NMR (400 MHZ, METHANOL-d$_4$) δ=9.24 (d, J=2.4 Hz, 1H), 8.32 (s, 1H), 7.69 (dd, J=6.0, 9.2 Hz, 1H), 7.60 (d, J=8.8 Hz, 1H), 7.32 (d, J=2.4 Hz, 1H), 7.26 (t, J=9.6 Hz, 1H), 7.05 (t, J=3.2 Hz, 1H), 6.57-6.52 (m, 2H), 5.09 (dd, J=5.2, 13.6 Hz, 1H), 4.64-4.54 (m, 3H), 4.51-4.42 (m, 2H), 4.40-4.28 (m, 3H), 4.10 (br t, J=7.6 Hz, 2H), 3.82-3.77 (m, 2H), 3.69-3.53 (m, 2H), 3.50-3.37 (m, 3H), 3.28 (br s, 4H), 2.95-2.85 (m, 1H), 2.81-2.73 (m, 1H), 2.50-2.38 (m, 6H), 2.29-2.12 (m, 3H), 1.90-1.76 (m, 6H), 1.69-1.55 (m, 3H), 1.29 (d, J=9.2 Hz, 3H), 0.99 (s, 2H), 0.87-0.78 (m, 5H).

Example 50: Preparation of (3S)-3-[5-[4-[[7-[1-[7-(8-ethyl-7-fluoro-3-hydroxy-1-naphthyl)-8-fluoro-4-[(3R)-3-hydroxy-3-methyl-1-piperidyl]pyrido[4,3-d]pyrimidin-2-yl]oxymethyl]cyclopropyl]methyl]-2-methyl-7-azaspiro[3.5]nonan-2-yl]methyl]piperazin-1-yl]-1-oxo-isoindolin-2-yl]piperidine-2,6-dione (Compound 150)
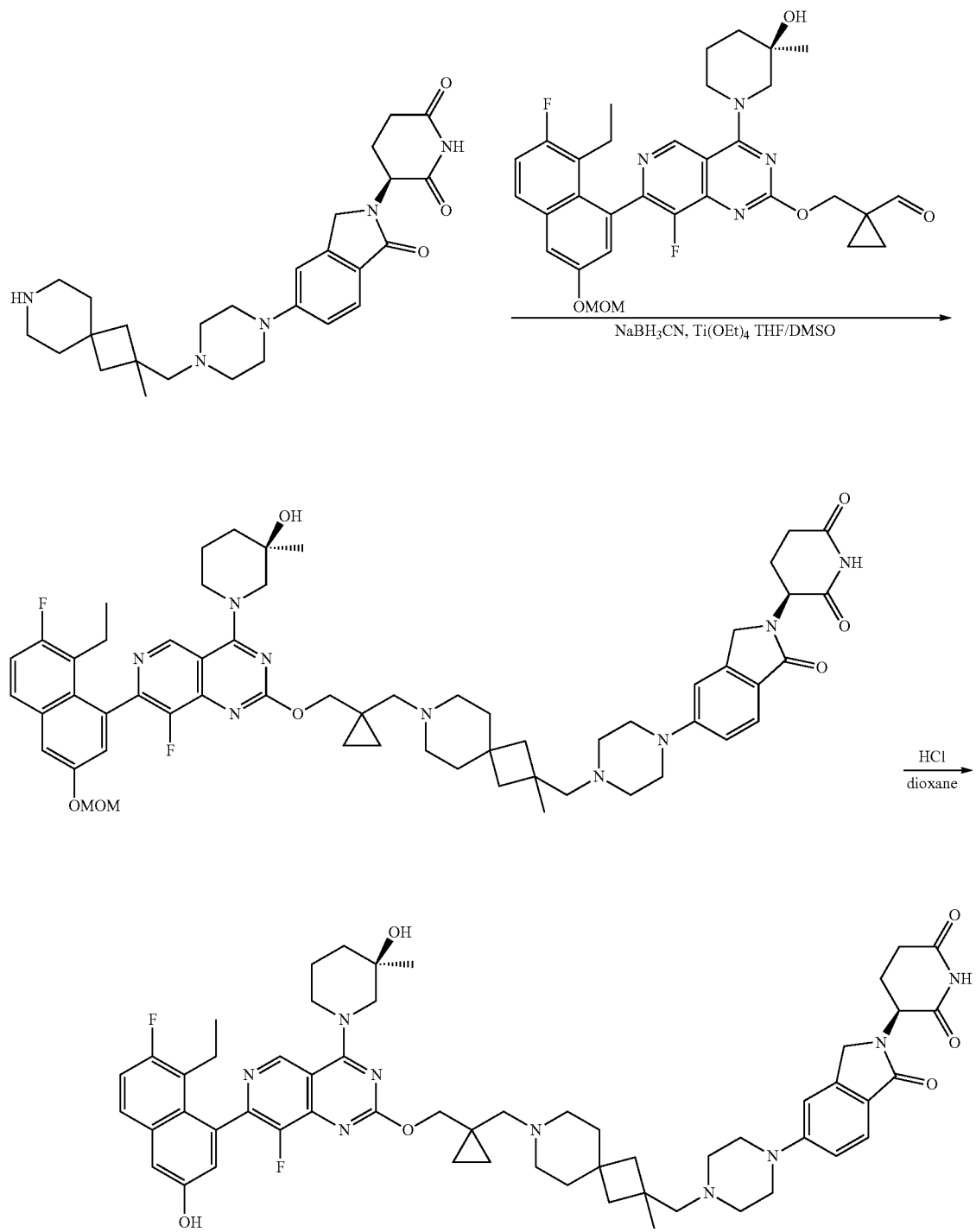

Step 1: Preparation of (3S)-3-[5-[4-[[7-[[1-[[7-[8-ethyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropyl]methyl]-2-methyl-7-azaspiro[3.5]nonan-2-yl]methyl]piperazin-1-yl]-1-oxo-isoindolin-2-yl]piperidine-2,6-dione To a solution of 3-[5-[4-[(2-methyl-7-azaspiro[3.5]nonan-2-yl)methyl]piperazin-1-yl]-1-oxo-isoindolin-2-yl]piperidine-2,6-dione (93.2 mg, 168 μmol, 1 eq, 2HCl) and 1-[7-[8-ethyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropanecarbaldehyde (100 mg, 168 μmol, 1 eq) in THF (4 mL) and DMSO (2 mL) was added Ti(OEt)$_4$ (220 mg, 964 μmol, 0.2 mL, 5.72 eq). The mixture was stirred at 25° C. for 1 hour. NaBH$_3$CN (53.0 mg, 843 μmol, 5 eq) was added to the mixture and the mixture was stirred at 25° C. for 10 minutes. LCMS showed a new peak of 63.5% peak area with desired mass. The reaction mixture was quenched by water (50 mL) at 0° C., and then diluted with EA (10 mL) and extracted with EA (20 mL*2). The combined organic layers were washed with water (50 mL*2), dried over anhydrous Na$_2$SO$_4$, filtered and concentrated under reduced pressure to give a residue. The residue was purified by prep-TLC (SiO$_2$, DCM:MeOH=10:1) to give (3S)-3-[5-[4-[7-[1-[[7-[8-ethyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropyl]methyl]-2-methyl-7-azaspiro[3.5]nonan-2-yl]methyl]piperazin-1-yl]-1-oxo-isoindolin-2-yl]piperidine-2,6-dione (160 mg, 135 μmol, 80.4% yield, 89.6% purity) as a yellow solid.

Step 2: Preparation of (3S)-3-[5-[4-[7-[1-[[7-(8-ethyl-7-fluoro-3-hydroxy-1-naphthyl)-8-fluoro-4-[(3R)-3-hydroxy-3-methyl-1-piperidyl]pyrido[4,3-d]pyrimidin-2-yl]oxymethyl]cyclopropyl]methyl]-2-methyl-7-azaspiro[3.5]nonan-2-yl]methyl]piperazin-1-yl]-1-oxo-isoindolin-2-yl]piperidine-2,6-dione (Compound 150)

To a solution of (3S)-3-[5-[4-[[7-[[1-[[7-[8-ethyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropyl]methyl]-2-methyl-7-azaspiro[3.5]nonan-2-yl]methyl]piperazin-1-yl]-1-oxo-isoindolin-2-yl]piperidine-2,6-dione (160 mg, 135 μmol, 1 eq) in DCM (2 mL) was added HCl solution (4 M in dioxane, 4 mL, 117 eq). The mixture was stirred at 25° C. for 0.5 hours. LCMS showed complete consumption of the reactant and a new peak of 67.6% peak area with desired mass. The reaction mixture was concentrated under reduced pressure to give a residue. The residue was purified by prep-HPLC (FA condition; column: Phenomenex Luna C18 150*25 mm*10 μm; mobile phase: [water (FA)-ACN]; gradient: 12%-42% B over 10 minutes) to give (3S)-3-[5-[4-[7-[1-[7-(8-ethyl-7-fluoro-3-hydroxy-1-naphthyl)-8-fluoro-4-[(3R)-3-hydroxy-3-methyl-1-piperidyl]pyrido[4,3-d]pyrimidin-2-yl]oxymethyl]cyclopropyl]methyl]-2-methyl-7-azaspiro[3.5]nonan-2-yl]methyl]piperazin-1-yl]-1-oxo-isoindolin-2-yl]piperidine-2,6-dione (75 mg, 68.3 μmol, 50.3% yield, 96.5% purity, FA) as a white solid. LCMS: [M+H]$^+$=1012.4; $^1$H NMR (400 MHZ, METHANOL-d$_4$) δ=9.22 (s, 1H), 8.52 (s, 1H), 7.68 (dd, J=6.0, 9.2 Hz, 1H), 7.63 (d, J=8.4 Hz, 1H), 7.31 (d, J=2.8 Hz, 1H), 7.29-7.22 (m, 1H), 7.09-7.02 (m, 3H), 5.10 (dd, J=5.2, 13.2 Hz, 1H), 4.62-4.49 (m, 4H), 4.49-4.43 (m, 2H), 4.39 (d, J=5.6 Hz, 2H), 4.35-4.25 (m, 1H), 3.67-3.55 (m, 1H), 3.49-3.35 (m, 2H), 3.18-3.00 (m, 3H), 2.92-2.85 (m, 1H), 2.81-2.74 (m, 1H), 2.64-2.57 (m, 4H), 2.51-2.42 (m, 2H), 2.38 (s, 2H), 2.27-2.09 (m, 3H), 1.94 (br d, J=4.4 Hz, 2H), 1.90-1.81 (m, 5H), 1.81-1.69 (m, 4H), 1.29 (d, J=10.0 Hz, 3H), 1.26 (s, 3H), 0.93 (br s, 2H), 0.85-0.74 (m, 5H).

Example 51: Preparation of 3-[5-[4-[7-[[1-[[7-(8-ethyl-7-fluoro-3-hydroxy-1-naphthyl)-8-fluoro-4-[(3R)-3-hydroxy-3-methyl-1-piperidyl]pyrido[4,3-d]pyrimidin-2-yl]oxymethyl]cyclopropyl]methyl]-2-methyl-7-azaspiro[3.5]nonan-2-yl]piperazin-1-yl]-1-oxo-isoindolin-2-yl]piperidine-2,6-dione (Compound 159)

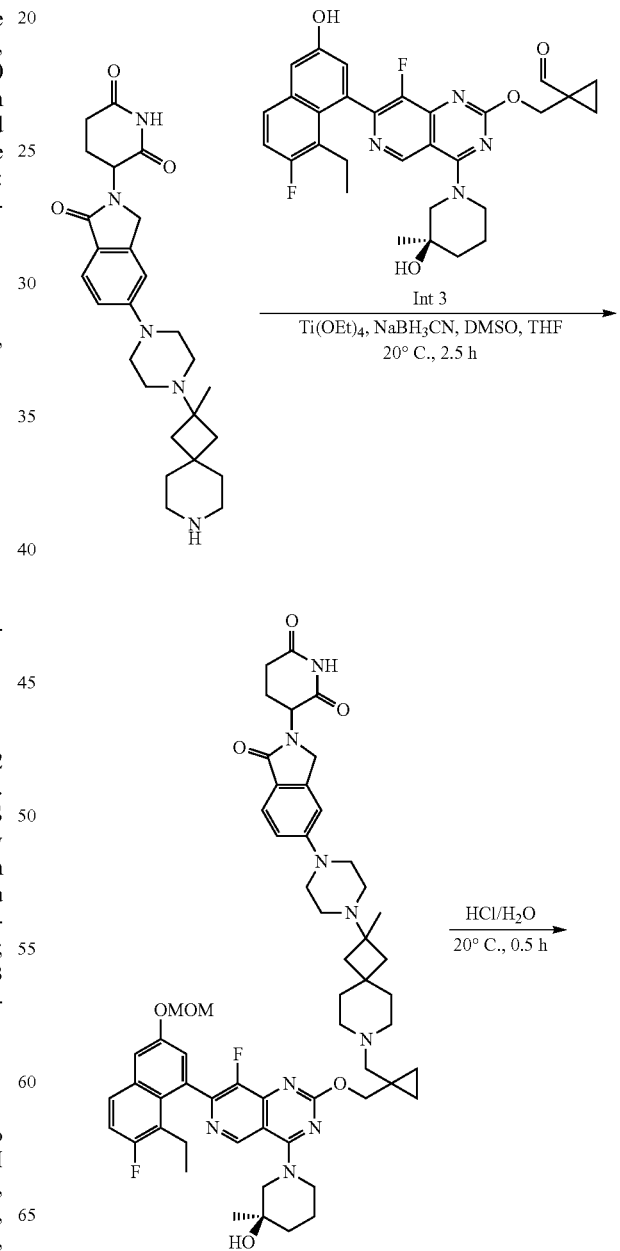

591

-continued

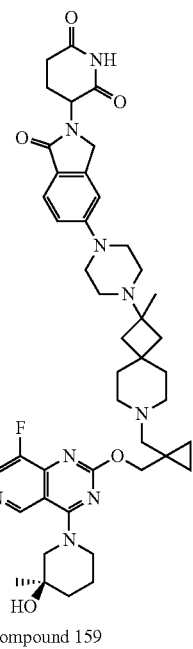

Compound 159

Step 1: Preparation of 3-[5-[4-[[7-[[1-[[7-[8-ethyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropyl]methyl]-2-methyl-7-azaspiro[3.5]nonan-2-yl]piperazin-1-yl]-1-oxo-isoindolin-2-yl]piperidine-2,6-dione To a solution of 1-[7-[8-ethyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropanecarbaldehyde (118.04 mg, 199.18 μmol, 1 eq) and 3-[5-[4-(2-methyl-7-azaspiro[3.5]nonan-2-yl)piperazin-1-yl]-1-oxo-isoindolin-2-yl]piperidine-2,6-dione (100 mg, 199.18 μmol, 1 eq, HCl) in DMSO (5 mL) and THF (5 mL) was added Ti(OEt)$_4$ (454.36 mg, 1.99 mmol, 413.05 μL, 10 eq) and the reaction mixture was stirred at 20° C. for 2 hours. NaBH$_3$CN (25.03 mg, 398.37 μmol, 2 eq) was added to the above mixture and the mixture was stirred at 20° C. for 0.5 hours. The mixture was diluted with ethyl acetate (50 mL), washed with saturated bicarbonate sodium solution (50 mL*2), dried over anhydrous sodium sulfate and concentrated under reduced pressure to give a residue. The crude residue was purified by reversed-phase HPLC (0.1% FA condition) to give 3-[5-[4-[7-[1-[[7-[8-ethyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropyl]methyl]-2-methyl-7-azaspiro[3.5]nonan-2-yl]piperazin-1-yl]-1-oxo-isoindolin-2-yl]piperidine-2,6-dione (100 mg, 91.89 μmol, 46.13% yield, 100% purity, FA) as a white solid. $^1$H NMR (400 MHZ, DMSO-d$_6$) δ=10.94 (s, 1H), 9.22 (s, 1H), 8.17 (s, 1H), 7.93-7.85 (m, 1H), 7.67 (d, J=2.0 Hz, 1H), 7.51 (d, J=9.2 Hz, 1H), 7.43 (t, J=9.2 Hz, 1H), 7.22 (d, J=2.4 Hz, 1H), 7.06-7.00 (m, 2H), 5.34 (s, 2H), 5.09-4.99 (m, 1H), 4.35-4.25 (m, 4H), 4.23-4.17 (m, 1H), 4.08-3.98 (m, 1H), 3.62 (br d, J=13.6 Hz, 1H), 3.52 (br d, J=13.2 Hz, 1H), 3.43 (s, 3H), 3.24 (br s, 4H), 2.94-2.86 (m, 1H), 2.61-2.55 (m, 1H), 2.46 (br s, 4H), 2.42-2.22 (m, 8H), 2.22-1.90 (m, 4H), 1.74-1.62 (m, 5H), 1.57-1.44 (m, 6H), 1.16 (d, J=9.6 Hz, 3H), 1.04 (s, 3H), 0.79-0.70 (m, 3H), 0.64 (s, 2H), 0.41 (s, 2H).

592

Step 2: Preparation of 3-[5-[4-[7-[1-[[7-(8-ethyl-7-fluoro-3-hydroxy-1-naphthyl)-8-fluoro-4-[(3R)-3-hydroxy-3-methyl-1-piperidyl]pyrido[4,3-d]pyrimidin-2-yl]oxymethyl]cyclopropyl]methyl]-2-methyl-7-azaspiro[3.5]nonan-2-yl]piperazin-1-yl]-1-oxo-isoindolin-2-yl]piperidine-2,6-dione (Compound 159)

To a solution of 3-[5-[4-[7-[[1-[7-[8-ethyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropyl]methyl]-2-methyl-7-azaspiro[3.5]nonan-2-yl]piperazin-1-yl]-1-oxo-isoindolin-2-yl]piperidine-2,6-dione (90 mg, 86.35 μmol, 1 eq) in H$_2$O (1 mL) was added HCl (4 M, 1 mL, 46.32 eq) and the reaction mixture was stirred at 20° C. for 0.5 hours. LCMS indicated a new peak of 90% peak area with desired mass. The residue was purified by prep-HPLC (column: Phenomenex Luna C18 150*25 mm*10 μm; mobile phase: [water (FA)-ACN]; gradient: 12%-42% B over 10 minutes) to give 3-[5-[4-[7-[1-[7-(8-ethyl-7-fluoro-3-hydroxy-1-naphthyl)-8-fluoro-4-[(3R)-3-hydroxy-3-methyl-1-piperidyl]pyrido[4,3-d]pyrimidin-2-yl]oxymethyl]cyclopropyl]methyl]-2-methyl-7-azaspiro[3.5]nonan-2-yl]piperazin-1-yl]-1-oxo-isoindolin-2-yl]piperidine-2,6-dione (35 mg, 34.78 μmol, 40.28% yield, 99.2% purity) as a white solid. LCMS: [M+H]$^+$=998.4; $^1$H NMR (400 MHZ, DMSO-d$_6$) δ=10.94 (s, 1H), 10.10-9.87 (m, 1H), 9.23 (s, 1H), 8.14 (s, 1H), 7.82-7.72 (m, 1H), 7.52 (br d, J=8.8 Hz, 1H), 7.40-7.28 (m, 2H), 7.11-6.97 (m, 3H), 5.09-4.96 (m, 1H), 4.74 (br s, 1H), 4.41-4.26 (m, 4H), 4.24-4.16 (m, 1H), 4.12-4.01 (m, 1H), 3.63 (br d, J=12.8 Hz, 1H), 3.52 (br d, J=13.2 Hz, 1H), 3.27 (br s, 8H), 2.97-2.84 (m, 2H), 2.81-2.65 (m, 3H), 2.58 (br d, J=18.4 Hz, 2H), 2.40-2.30 (m, 2H), 2.20-2.10 (m, 1H), 2.05-1.92 (m, 2H), 1.82 (br d, J=10.0 Hz, 2H), 1.78-1.56 (m, 9H), 1.17 (br d, J=10.0 Hz, 3H), 1.07 (br s, 3H), 0.82-0.68 (m, 5H), 0.61 (br s, 2H).

Example 52: Preparation of 3-[5-[4-[3-[[1-[[7-(8-ethyl-7-fluoro-3-hydroxy-1-naphthyl)-8-fluoro-4-[(3R)-3-hydroxy-3-methyl-1-piperidyl]pyrido[4,3-d]pyrimidin-2-yl]oxymethyl]cyclopropyl]methyl]-9-methyl-3-azaspiro[5.5]undecan-9-yl]piperazin-1-yl]-1-oxo-isoindolin-2-yl]piperidine-2,6-dione (Compound 167)

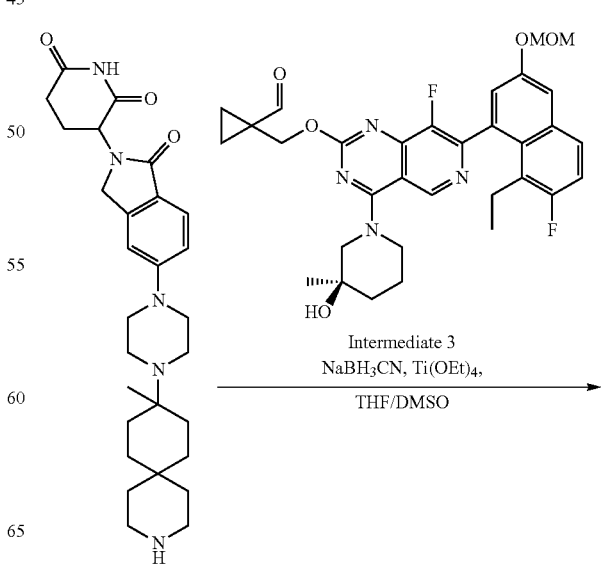

Intermediate 3
NaBH$_3$CN, Ti(OEt)$_4$,
THF/DMSO

-continued

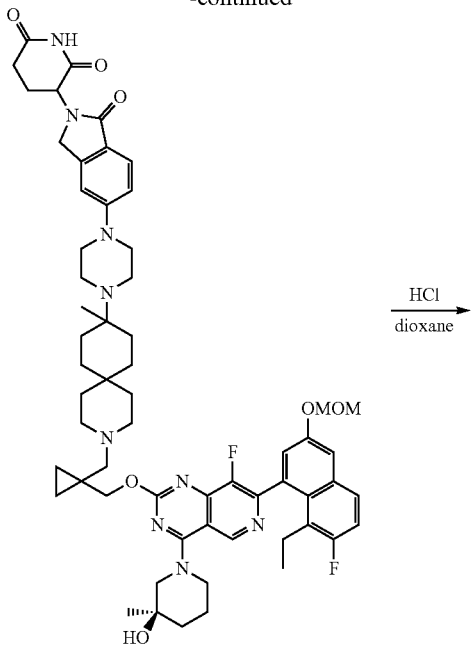

→ HCl / dioxane →

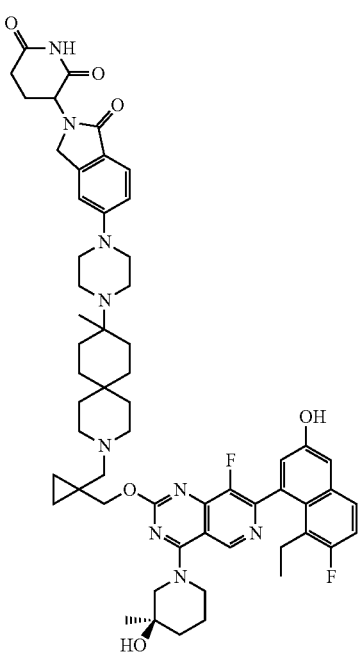

Step 1: Preparation of 3-[5-[4-[3-[1-[7-[8-ethyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropyl]methyl]-9-methyl-3-azaspiro[5.5]undecan-9-yl]piperazin-1-yl]-1-oxo-isoindolin-2-yl]piperidine-2,6-dione To a solution of 3-[5-[4-(9-methyl-3-azaspiro[5.5]undecan-9-yl)piperazin-1-yl]-1-oxo-isoindolin-2-yl]piperidine-2,6-dione (80 mg, 162.1 µmol, 1 eq) 1-[7-[8-ethyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl] oxymethyl]cyclopropanecarbaldehyde (105.7 mg, 178.3 µmol, 1.1 eq) in DMSO (2.5 mL) and THF (2.5 mL) was added tetraethoxytitanium (1.11 g, 4.86 mmol, 1.01 mL, 30 eq) and the mixture was stirred for 0.2 hours. Then sodium cyanoborohydride (10.18 mg, 162.1 µmol, 1 eq) was added. The mixture was stirred at 25° C. for 0.8 hours. LCMS showed complete consumption of the reactant and one main peak with desired mass. The reaction mixture was poured into water (30 mL), filtered and then extracted with EA (30 mL*3). The organic layers were combined and washed with brine (60 mL), dried over anhydrous $Na_2SO_4$, filtered and concentrated under vacuum. The residue was purified by reversed-phase flash (0.1% FA condition). Then the solution was lyophilized to give 3-[5-[4-[3-[1-[7-[8-ethyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropyl]methyl]-9-methyl-3-azaspiro[5.5]undecan-9-yl]piperazin-1-yl]-1-oxo-isoindolin-2-yl] piperidine-2,6-dione (95 mg, 88.8 µmol, 54.8% yield) as a white solid.

Step 2: Preparation of 3-[5-[4-[3-[1-[[7-(8-ethyl-7-fluoro-3-hydroxy-1-naphthyl)-8-fluoro-4-[(3R)-3-hydroxy-3-methyl-1-piperidyl]pyrido[4,3-d]pyrimidin-2-yl]oxymethyl]cyclopropyl]methyl]-9-methyl-3-azaspiro[5.5]undecan-9-yl]piperazin-1-yl]-1-oxo-isoindolin-2-yl]piperidine-2,6-dione (Compound 167)

To a solution of 3-[5-[4-[3-[1-[[7-[8-ethyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl] oxymethyl]cyclopropyl]methyl]-9-methyl-3-azaspiro[5.5]undecan-9-yl]piperazin-1-yl]-1-oxo-isoindolin-2-yl] piperidine-2,6-dione (50.0 mg, 46.7 µmol, 1 eq) in DCM (5 mL) was added HCl solution (2 M in dioxane, 2.5 mL, 107.0 eq). The mixture was stirred at 25° C. for 10 minutes. LCMS showed complete consumption of the reactant and one main peak with desired mass. The reaction mixture was concentrated under reduced pressure to remove solvent. The residue was purified by prep-HPLC (FA condition)column: Phenomenex Luna C18 150*25 mm*10 µm; mobile phase: [water (FA)-ACN]; gradient: 15%-35% B over 10 minutes; column: Phenomenex Luna C18 150*25 mm 10 µm; mobile phase: [water (FA)-ACN]; gradient: 15%-35% B over 10 minutes Then solution was lyophilized to give 3-[5-[4-[3-[1-[7-(8-ethyl-7-fluoro-3-hydroxy-1-naphthyl)-8-fluoro-4-[(3R)-3-hydroxy-3-methyl-1-piperidyl]pyrido[4,3-d]pyrimidin-2-yl]oxymethyl]cyclopropyl]methyl]-9-methyl-3-azaspiro[5.5]undecan-9-yl]piperazin-1-yl]-1-oxo-isoindolin-2-yl]piperidine-2,6-dione (19.6 mg, 18.7 µmol, 39.9% yield, 97.7% purity) as a white solid. LCMS: [M+H]$^+$=1026.6; $^1$H NMR (400 MHZ, METHANOL-$d_4$) δ=9.26 (s, 1H), 8.48-8.42 (m, 1H), 7.75-7.64 (m, 2H), 7.38-7.24 (m, 2H), 7.16-7.06 (m, 3H), 5.18-5.06 (m, 3H), 4.59 (br dd, J=2.0, 11.8 Hz, 2H), 4.48-4.29 (m, 4H), 3.70-3.61 (m, 1H), 3.59-3.47 (m, 5H), 3.27-3.16 (m, 2H), 3.16-3.02 (m, 4H), 2.97-2.69 (m, 3H), 2.54-2.38 (m, 2H), 2.32-2.12 (m, 4H), 1.99-1.86 (m, 4H), 1.84-1.74 (m, 5H), 1.72-1.60 (m, 3H), 1.47-1.28 (m, 6H), 1.18 (br s, 3H), 1.03-0.94 (m, 3H), 0.91-0.78 (m, 6H).

Example 53: Preparation of (S)-3-(5-(4-((7-((1-(((7-(8-ethyl-7-fluoro-3-hydroxynaphthalen-1-yl)-8-fluoro-4-((S)-6-hydroxy-6-methyl-1,4-oxazepan-4-yl)pyrido[4,3-d]pyrimidin-2-yl)oxy)methyl)cyclopropyl)methyl)-2-fluoro-7-azaspiro[3.5]nonan-2-yl)methyl)piperazin-1-yl)-1-oxoisoindolin-2-yl)piperidine-2,6-dione (Compound 175)
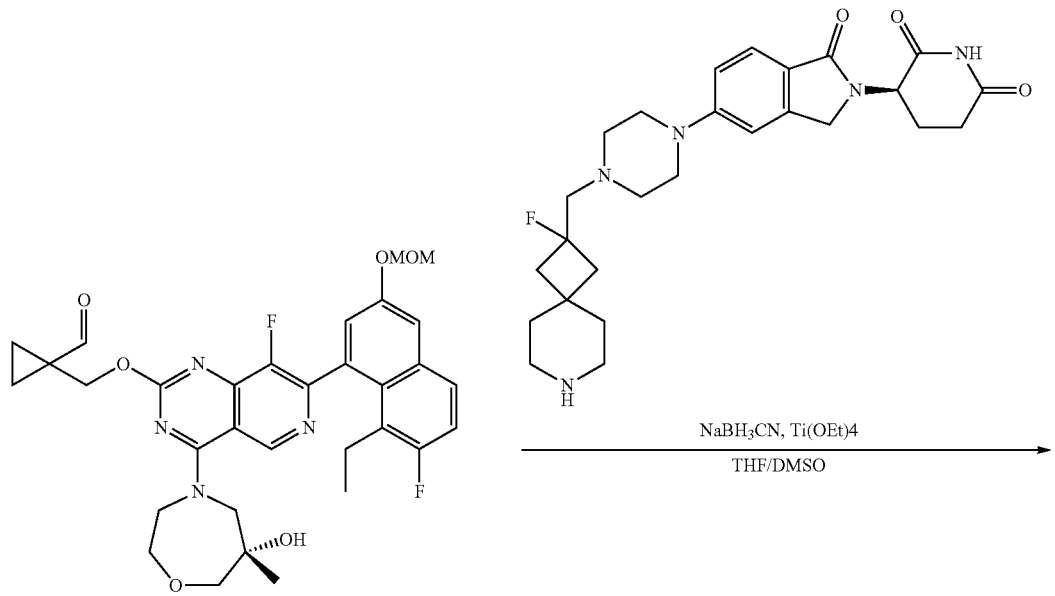
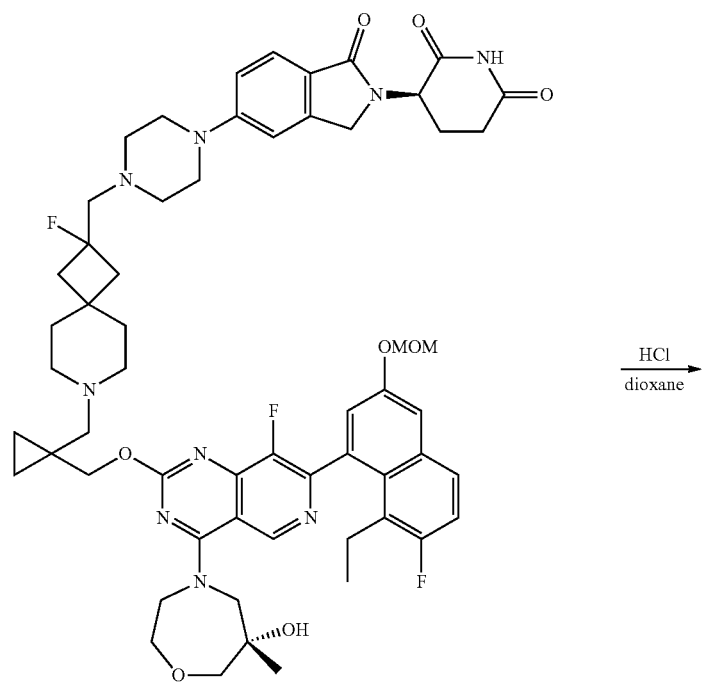

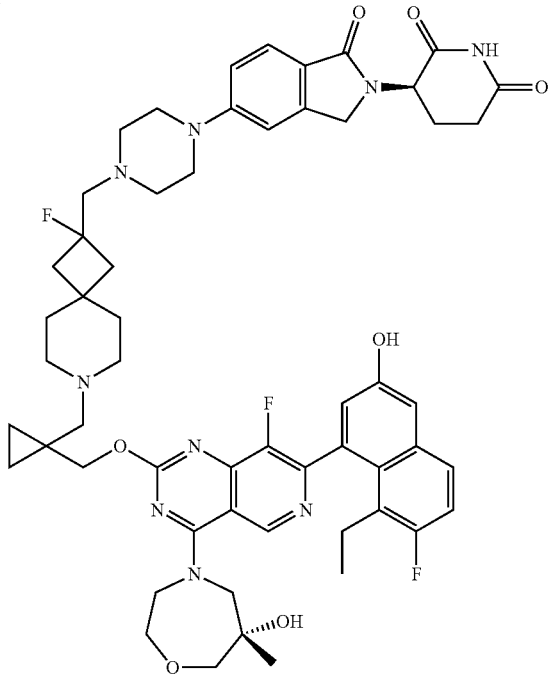

Step 1: Preparation of (S)-3-(5-(4-((7-((1-(((7-(8-ethyl-7-fluoro-3-(methoxymethoxy)naphthalen-1-yl)-8-fluoro-4-((S)-6-hydroxy-6-methyl-1,4-oxazepan-4-yl)pyrido[4,3-d]pyrimidin-2-yl)oxy)methyl)cyclopropyl)methyl)-2-fluoro-7-azaspiro[3.5]nonan-2-yl)methyl)piperazin-1-yl)-1-oxoisoindolin-2-yl)piperidine-2,6-dione To a solution of 1-[7-[8-ethyl-7-fluoro-3-(methoxymethoxy)-1-naphthyl]-8-fluoro-4-[(6S)-6-hydroxy-6-methyl-1,4-oxazepan-4-yl]pyrido[4,3-d]pyrimidin-2-yl]oxymethyl]cyclopropanecarbaldehyde (60 mg, 98.5 μmol, 1 eq) and (3S)-3-[5-[4-[(2-fluoro-7-azaspiro[3.5]nonan-2-yl)methyl]piperazin-1-yl]-1-oxo-isoindolin-2-yl]piperidine-2,6-dione (51.2 mg, 98.5 μmol, 1 eq, HCl) in DMSO (1 mL) and THF (3 mL) was added Ti(OEt)$_4$ (44.9 mg, 197 μmol, 40.8 μL, 2 eq) and the reaction mixture was stirred at 25° C. for 0.5 hours. NaBH$_3$CN (6.20 mg, 98.5 μmol, 1 eq) was added and the mixture was stirred at 25° C. for another 0.5 hours. LCMS showed a peak of 55% peak area of desired mass. The mixture was diluted with water (10 mL) and extracted with EA (10 mL*3). The combined organic layers were washed with brine (10 mL*2), dried over anhydrous Na$_2$SO$_4$, filtered and concentrated under reduced pressure to give a residue. The residue was purified by prep-TLC (SiO$_2$, DCM:MeOH=10:1, Rf=0.3) to give (S)-3-(5-(4-((7-((1-(((7-(8-ethyl-7-fluoro-3-(methoxymethoxy)naphthalen-1-yl)-8-fluoro-4-((S)-6-hydroxy-6-methyl-1,4-oxazepan-4-yl)pyrido[4,3-d]pyrimidin-2-yl)oxy)methyl)cyclopropyl)methyl)-2-fluoro-7-azaspiro[3.5]nonan-2-yl)methyl)piperazin-1-yl)-1-oxoisoindolin-2-yl)piperidine-2,6-dione (100 mg, 92.9 μmol, 94.6% yield) as a white solid.

Step 2: Preparation of (S)-3-(5-(4-((7-((1-(((7-(8-ethyl-7-fluoro-3-hydroxynaphthalen-1-yl)-8-fluoro-4-((S)-6-hydroxy-6-methyl-1,4-oxazepan-4-yl)pyrido[4,3-d]pyrimidin-2-yl)oxy)methyl)cyclopropyl)methyl)-2-fluoro-7-azaspiro[3.5]nonan-2-yl)methyl)piperazin-1-yl)-1-oxoisoindolin-2-yl)piperidine-2,6-dione (Compound 175)

To a solution of (3S)-3-[5-[4-[7-[1-[[7-[8-ethyl-7-fluoro-3-(methoxymethoxy)-1-naphthyl]-8-fluoro-4-[(6S)-6-hydroxy-6-methyl-1,4-oxazepan-4-yl]pyrido[4,3-d]pyrimidin-2-yl]oxymethyl]cyclopropyl]methyl]-2-fluoro-7-azaspiro[3.5]nonan-2-yl]methyl]piperazin-1-yl]-1-oxo-isoindolin-2-yl]piperidine-2,6-dione (80 mg, 74.3 μmol, 1 eq) in DCM (4 mL) was added HCl solution (2 M in dioxane, 1 mL, 26.9 eq). The mixture was stirred at 25° C. for 0.5 hours. LCMS showed a new peak of 78% peak area with desired mass. The reaction mixture was concentrated under reduced pressure to give a residue. The residue was purified by prep-HPLC (FA condition; column: Phenomenex Luna C18 150*25 mm*10 μm; mobile phase: [water (FA)-ACN]; gradient: 10%-40% B over 10 minutes) to give (S)-3-(5-(4-((7-((1-(((7-(8-ethyl-7-fluoro-3-hydroxynaphthalen-1-yl)-8-fluoro-4-((S)-6-hydroxy-6-methyl-1,4-oxazepan-4-yl)pyrido[4,3-d]pyrimidin-2-yl)oxy)methyl)cyclopropyl)methyl)-2-fluoro-7-azaspiro[3.5]nonan-2-yl)methyl)piperazin-1-yl)-1-oxoisoindolin-2-yl)piperidine-2,6-dione (20 mg, 18.8 μmol, 25.2% yield, 97% purity) as a white solid, LCMS: [M+H]$^+$=1032.5; $^1$H NMR (400 MHZ, DMSO-d$_6$) δ=10.94 (s, 1H), 10.20-9.65 (m, 1H), 9.47 (s, 1H), 8.17 (s, 1H), 7.80-7.72 (m, 1H), 7.51 (d, J=8.2 Hz, 1H), 7.39-7.31 (m, 2H), 7.09-6.98 (m, 3H), 5.15 (br d, J=13.4 Hz, 1H), 5.09-5.00 (m, 1H), 4.39-4.24 (m, 5H), 4.23-4.12 (m, 2H), 4.08-3.93 (m, 3H), 3.58-3.53 (m, 2H), 3.28-3.25 (m, 5H), 2.94-2.84 (m, 1H), 2.66-2.63 (m, 1H), 2.62-2.56 (m, 6H), 2.39-2.30 (m, 4H), 2.30-2.24 (m, 3H), 2.13-2.01 (m, 3H), 1.98-1.86 (m, 3H), 1.57 (br d, J=1.6 Hz, 2H), 1.46 (br d, J=1.8 Hz, 2H), 1.15 (d, J=6.4 Hz, 3H), 0.77-0.70 (m, 3H), 0.63 (br s, 2H), 0.40 (s, 2H).

Example 54: Preparation of 3-(5-(4-((7-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-azaspiro[3.5]nonan-2-yl)oxy)piperidin-1-yl)-1-oxoisoindolin-2-yl)piperidine-2,6-dione (Compound 176)
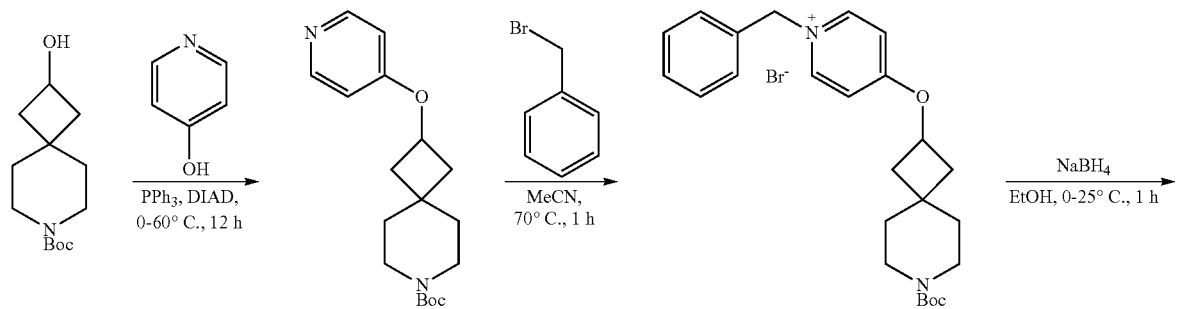
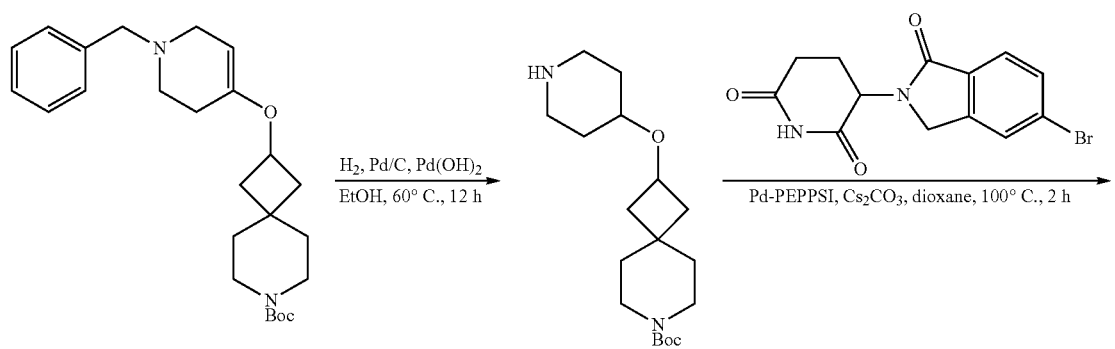
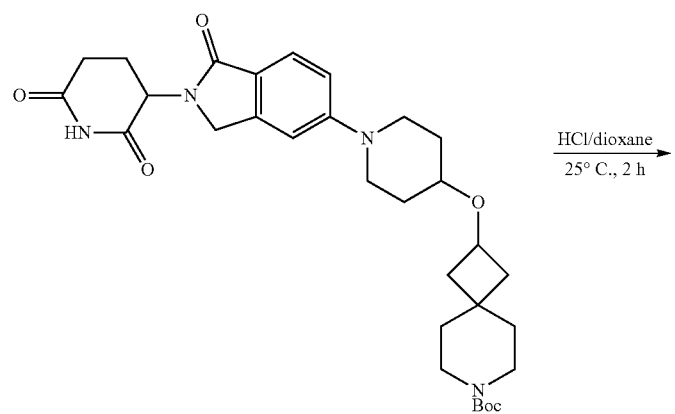

601
602
-continued
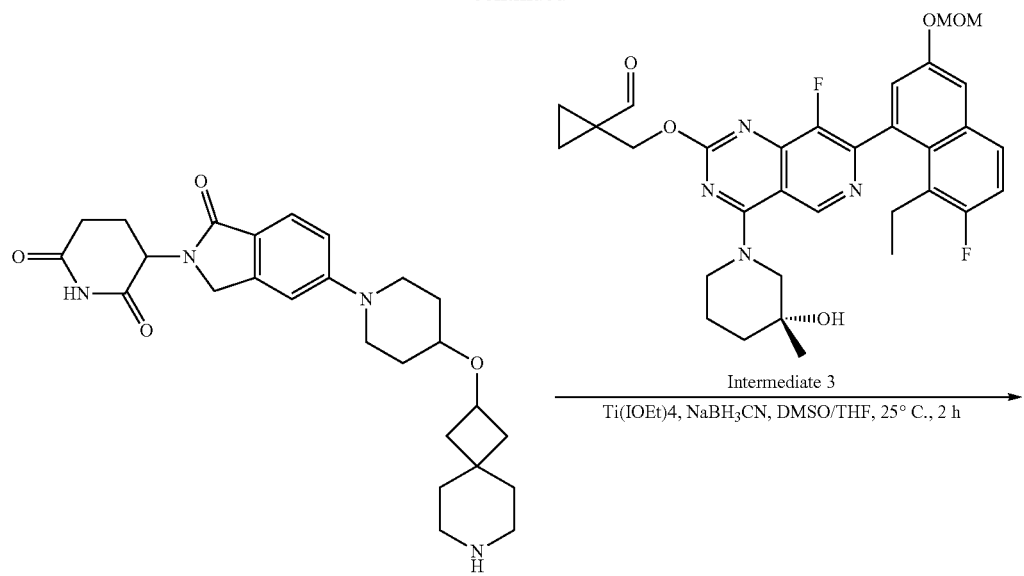
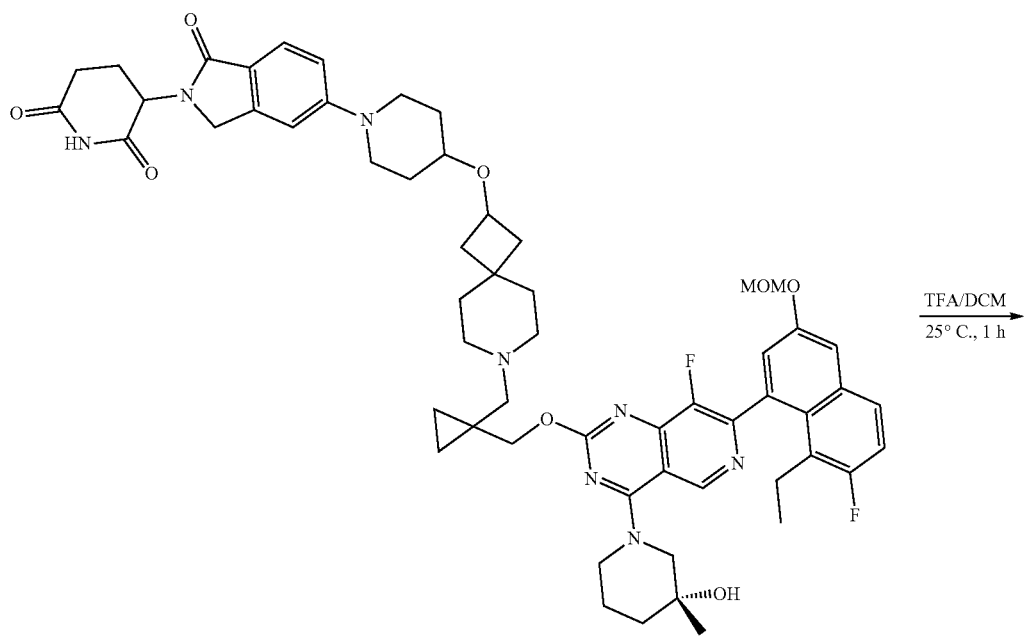

-continued

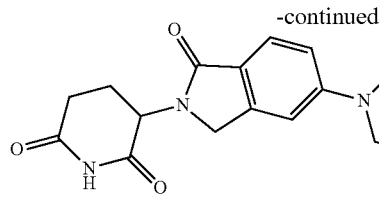
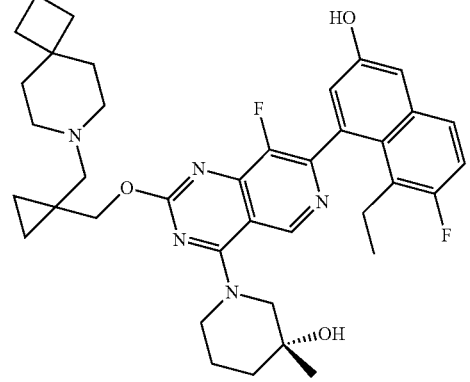

Compound 176

Step 1: Preparation of tert-butyl 2-(pyridin-4-yloxy)-7-azaspiro[3.5]nonane-7-carboxylate To a solution of tert-butyl 2-hydroxy-7-azaspiro[3.5]nonane-7-carboxylate (2 g, 8.29 mmol, 1 eq) and pyridin-4-ol (788 mg, 8.29 mmol, 1 eq) in THF (20 mL) was added $PPh_3$ (2.61 g, 9.95 mmol, 1.2 eq) and DIAD (2.01 g, 9.95 mmol, 1.93 mL, 1.2 eq) at 0° C. The mixture was stirred at 60° C. for 12 hours. LCMS showed complete consumption of the reactant and a major peak with desired mass. The reaction mixture was concentrated under reduced pressure to give a residue. The crude residue was purified by reversed-phase HPLC (0.1% FA condition) to afford tert-butyl 2-(pyridin-4-yloxy)-7-azaspiro[3.5]nonane-7-carboxylate (2.5 g, 7.85 mmol, 94.7% yield, 100% purity) as a light yellow solid.

Step 2: Preparation of 1-benzyl-4-((7-(tert-butoxycarbonyl)-7-azaspiro[3.5]nonan-2-yl)oxy)pyridin-1-ium bromide To a solution of tert-butyl 2-(pyridin-4-yloxy)-7-azaspiro[3.5]nonane-7-carboxylate (900 mg, 2.83 mmol, 1 eq) in ACN (9 mL) was added bromomethylbenzene (580 mg, 3.39 mmol, 402 µL, 1.2 eq). The mixture was stirred at 70° C. for 1 hour. LCMS showed complete consumption of the reactant and a major peak with desired mass. The reaction mixture was concentrated under reduced pressure to give a residue. The crude product was triturated with ethyl acetate (5 mL) at 25° C. for 10 minutes. Two batches of this reaction afforded 1-benzyl-4-((7-(tert-butoxycarbonyl)-7-azaspiro[3.5]nonan-2-yl)oxy)pyridin-1-ium bromide (4.1 g, 2.45 mmol, 86.7% yield, 100% purity) as a white solid. $^1H$ NMR (400 MHZ, DMSO-$d_6$) δ=8.99 (br d, J=7.2 Hz, 2H), 7.57 (br d, J=7.2 Hz, 2H), 7.52-7.46 (m, 2H), 7.46-7.32 (m, 3H), 5.69 (s, 2H), 5.15 (br t, J=6.8 Hz, 1H), 3.29 (br d, J=4.6 Hz, 2H), 3.21 (br s, 2H), 2.57-2.51 (m, 2H), 1.96-1.85 (m, 2H), 1.57-1.51 (m, 2H), 1.51-1.46 (m, 2H), 1.38 (s, 9H).

Step 3: Preparation of tert-butyl 2-((1-benzyl-1,2,3,6-tetrahydropyridin-4-yl)oxy)-7-azaspiro[3.5]nonane-7-carboxylate To a solution of 1-benzyl-4-((7-(tert-butoxycarbonyl)-7-azaspiro[3.5]nonan-2-yl)oxy)pyridin-1-ium bromide (4.1 g, 8.38 mmol, 1 eq) in EtOH (40 mL) was added $NaBH_4$ (1.90 g, 50.2 mmol, 6 eq). The mixture was stirred at 0-25° C. for 1 hour under $N_2$ atmosphere. LCMS showed complete consumption of the reactant and a major peak with desired mass. The residue was poured into ice-water (50 mL) and the reaction mixture was stirred for 2 minutes. The aqueous phase was extracted with ethyl acetate (50 mL*3). The combined organic layers were washed with brine (30 mL*2), dried over anhydrous $Na_2SO_4$, filtered and concentrated under reduced pressure. The crude product tert-butyl 2-((1-benzyl-1,2,3,6-tetrahydropyridin-4-yl)oxy)-7-azaspiro[3.5]nonane-7-carboxylate (3.4 g, crude) was used in the next step without further purification as a light yellow gum.

Step 4: Preparation of tert-butyl 2-(piperidin-4-yloxy)-7-azaspiro[3.5]nonane-7-carboxylate To a suspension of Pd/C (10 g, 9.40 mmol, 10% purity, 1.14 eq), Pd(OH)$_2$ (5 g, 7.12 mmol, 20% purity, 0.864 eq) in EtOH (30 mL) was added tert-butyl 2-((1-benzyl-1,2,3,6-tetrahydropyridin-4-yl)oxy)-7-azaspiro[3.5]nonane-7-carboxylate (3.4 g, 8.24 mmol, 1 eq) under $N_2$ atmosphere at 60° C. for 12 hours. The suspension was degassed under reduced pressure and purged with $H_2$ (50 PSI) several times. LCMS showed complete consumption of the reactant and a major peak with desired mass. The mixture was filtered, and the filtrate was concentrated under reduced pressure. The crude product tert-butyl 2-(piperidin-4-yloxy)-7-azaspiro[3.5]nonane-7-carboxylate (2.4 g, crude) was used in the next step without further purification as a yellow gum. $^1H$ NMR (400 MHZ, DMSO-$d_6$) δ=4.35 (t, J=5.2 Hz, 1H), 4.06 (t, J=7.2 Hz, 1H), 3.44 (br dd, J=4.8, 6.8 Hz, 2H), 3.23 (br d, J=4.4 Hz, 2H), 3.20-3.16 (m, 2H), 2.86 (td, J=4.0, 12.4 Hz, 2H), 2.42-2.34 (m, 2H), 2.16-2.10 (m, 2H), 1.76-1.68 (m, 2H), 1.62-1.54 (m, 2H), 1.43-1.40 (m, 3H), 1.38 (s, 9H), 1.25-1.17 (m, 2H).

Step 5: Preparation of tert-butyl 2-((1-(2-(2,6-dioxopiperidin-3-yl)-1-oxoisoindolin-5-yl)piperidin-4-yl)oxy)-7-azaspiro[3.5]nonane-7-carboxylate A mixture of tert-butyl 2-(4-piperidyloxy)-7-azaspiro[3.5]nonane-7-carboxylate (2.2 g, 6.78 mmol, 1.3 eq), 3-(5- bromo-1-oxoisoindolin-2-yl)piperidine-2,6-dione (1.69 g, 5.22 mmol, 1 eq), [1,3-bis[2,6-bis(1-ethylpropyl)phenyl]-4,5-dichloro-imidazol-2-ylidene]-dichloro-(2-methylpyridin-1-ium-1-yl)palladium (219 mg, 260 μmol, 0.05 eq), Cs$_2$CO$_3$ (5.10 g, 15.6 mmol, 3 eq) in dioxane (20 mL) was degassed and purged with N$_2$ for 3 times, and then the mixture was stirred at 100° C. for 2 hours under N$_2$ atmosphere. The crude product was quenched with 10% acetic acid solution and the reaction mixture was stirred for 2 minutes. The aqueous phase was extracted with DCM (10 mL*3). The combined organic layers were washed with brine (10 mL*2), dried over anhydrous Na$_2$SO$_4$, filtered and concentrated under reduced pressure. The crude product was purified by reversed-phase HPLC (0.1% FA condition) to afford tert-butyl 2-((1-(2-(2,6-dioxopiperidin-3-yl)-1-oxoisoindolin-5-yl)piperidin-4-yl)oxy)-7-azaspiro[3.5]nonane-7-carboxylate (1.6 g, 2.00 mmol, 38.4% yield, 71% purity) as a gray solid.

Step 6: Preparation of 3-(5-(4-((7-azaspiro[3.5]nonan-2-yl)oxy)piperidin-1-yl)-1-oxoisoindolin-2-yl)piperidine-2,6-dione To a solution of tert-butyl 2-[[1-[2-(2,6-dioxo-3-piperidyl)-1-oxo-isoindolin-5-yl]-4-piperidyl]oxy]-7-azaspiro[3.5]nonane-7-carboxylate (300 mg, 529 μmol, 1 eq) in DCM (1 mL) was added HCl/dioxane (3 mL). The mixture was stirred at 25° C. for 2 hours. LCMS showed complete consumption of the reactant and a major peak with desired mass. The reaction mixture was concentrated under reduced pressure to give a residue. The crude residue was purified to afford 3-(5-(4-((7-azaspiro[3.5]nonan-2-yl)oxy)piperidin-1-yl)-1-oxoisoindolin-2-yl)piperidine-2,6-dione (320 mg, crude) as a yellow solid.

Step 7: Preparation of 3-(5-(4-((7-((1-(((7-(8-ethyl-7-fluoro-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-azaspiro[3.5]nonan-2-yl)oxy)piperidin-1-yl)-1-oxoisoindolin-2-yl)piperidine-2,6-dione To a solution of 1-[[7-[8-ethyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropanecarbaldehyde (145 mg, 244 μmol, 1 eq), 3-[5-[4-(7-azaspiro[3.5]nonan-2-yloxy)-1-piperidyl]-1-oxo-isoindolin-2-yl]piperidine-2,6-dione (160 mg, 318 μmol, 1.3 eq, HCl) in THF (3 mL) and DMSO (0.5 mL) was added Ti(OEt)$_4$ (1.12 g, 4.89 mmol, 1.01 mL, 20 eq) and NaBH$_3$CN (76.8 mg, 1.22 mmol, 5 eq). The mixture was stirred at 25° C. for 1 hour. LCMS showed complete consumption of reactant and a new peak of 70% peak area of desired mass. The residue was poured into a mixture of THF (100 mL) and DCM (100 mL). The combined organic layers were washed with water (20 mL), dried over anhydrous Na$_2$SO$_4$, filtered and concentrated under reduced pressure. The crude product was purified by reversed-phase HPLC (0.1% FA condition) to afford 3-(5-(4-((7-((1-(((7-(8-ethyl-7-fluoro-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-azaspiro[3.5]nonan-2-yl)oxy)piperidin-1-yl)-1-oxoisoindolin-2-yl)piperidine-2,6-dione (135 mg, 120 μmol, 49.1% yield, 93% purity) as a white solid.

Step 8: Preparation of 3-(5-(4-((7-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-azaspiro[3.5]nonan-2-yl)oxy)piperidin-1-yl)-1-oxoisoindolin-2-yl)piperidine-2,6-dione (Compound 176)

To a solution of 3-[5-[4-[[7-[1-[7-[8-ethyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropyl]methyl]-7-azaspiro[3.5]nonan-2-yl]oxy]-1-piperidyl]-1-oxo-isoindolin-2-yl]piperidine-2,6-dione (130 mg, 124 μmol, 1 eq) in DCM (4 mL) was added TFA (0.8 mL) at 0° C. The mixture was stirred at 25° C. for 1 hour. LCMS showed complete consumption of the reactant and a major peak with desired mass. The reaction mixture was concentrated under reduced pressure to give a residue. The residue was purified by prep-HPLC (Phenomenex Luna C18 150*25 mm*10 μm; mobile phase: [water (FA)-ACN]; gradient: 18%-48% B over 10 minutes) to afford 3-(5-(4-((7-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-7-azaspiro[3.5]nonan-2-yl)oxy)piperidin-1-yl)-1-oxoisoindolin-2-yl)piperidine-2,6-dione (54.0 mg, 51.9 μmol, 41.6% yield, 96% purity) as a white solid. LCMS: [M+H]$^+$=999.5; $^1$H NMR (400 MHZ, METHANOL-d$_4$) δ=9.24 (d, J=2.4 Hz, 1H), 8.54 (s, 1H), 7.70 (dd, J=6.0, 9.2 Hz, 1H), 7.63 (d, J=8.8 Hz, 1H), 7.33 (d, J=2.8 Hz, 1H), 7.27 (t, J=9.6 Hz, 1H), 7.11-7.05 (m, 3H), 5.11 (dd, J=5.2, 13.2 Hz, 1H), 4.64-4.42 (m, 4H), 4.40 (d, J=5.2 Hz, 2H), 4.30 (br d, J=12.0 Hz, 1H), 4.20 (br t, J=7.2 Hz, 1H), 3.80-3.69 (m, 2H), 3.69-3.61 (m, 1H), 3.60-3.55 (m, 1H), 3.49-3.41 (m, 1H), 3.15-3.05 (m, 4H), 3.03 (br s, 2H), 2.97-2.85 (m, 2H), 2.83-2.76 (m, 1H), 2.52-2.42 (m, 2H), 2.41-2.07 (m, 6H), 2.00-1.93 (m, 2H), 1.85 (br s, 4H), 1.82-1.74 (m, 4H), 1.67-1.59 (m, 2H), 1.30 (d, J=9.6 Hz, 3H), 0.92 (br s, 2H), 0.83 (q, J=7.6 Hz, 3H), 0.76 (br s, 2H).

Example 55: Preparation of 3-(5-(2-((1-((((7-(8-ethyl-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)oxy)-7-azaspiro[3.5]nonan-7-yl)-1-oxoisoindolin-2-yl)piperidine-2,6-dione (Compound 181)

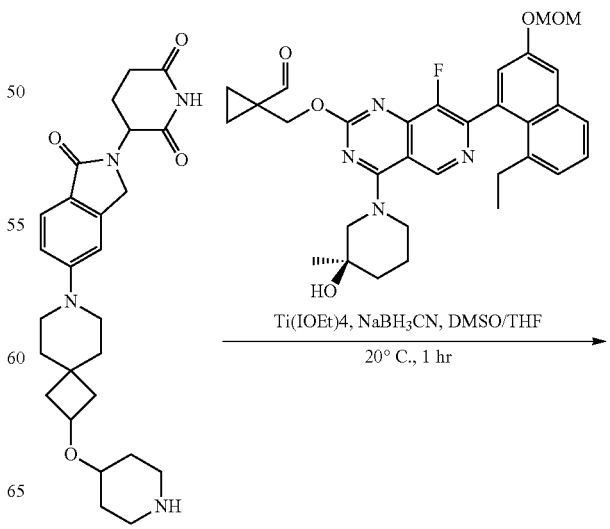

-continued

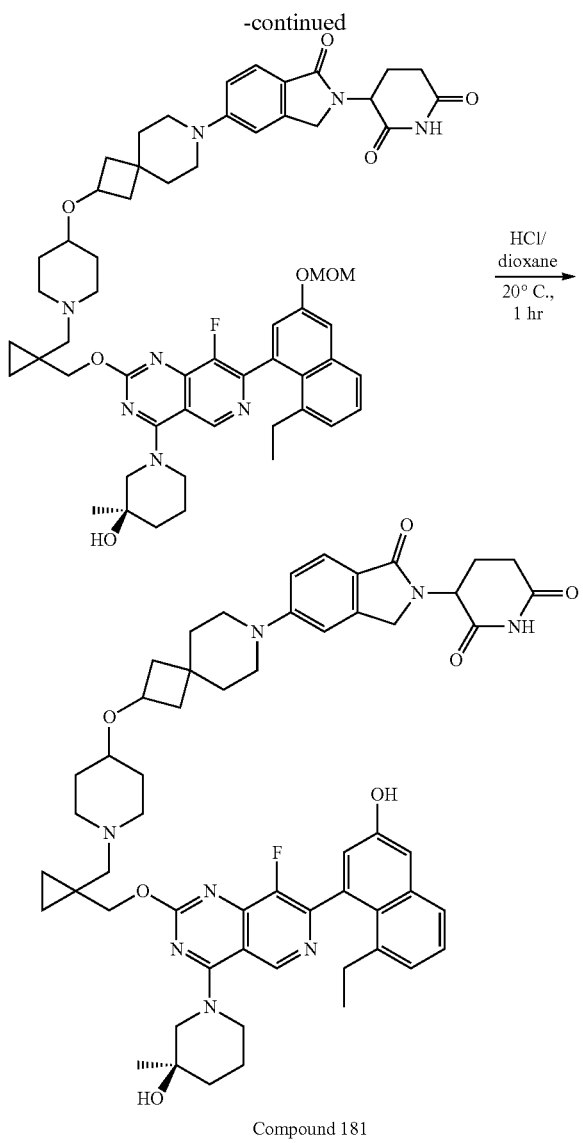

Compound 181

Step 1: Preparation of 3-(5-(2-((1-((1-(((7-(8-ethyl-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)oxy)-7-azaspiro[3.5]nonan-7-yl)-1-oxoisoindolin-2-yl)piperidine-2,6-dione To a mixture of 1-[[7-[8-ethyl-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropanecarbaldehyde (98.5 mg, 171 μmol, 1 eq), 3-[1-oxo-5-[2-(4-piperidyloxy)-7-azaspiro[3.5]nonan-7-yl]isoindolin-2-yl]piperidine-2,6-dione (80 mg, 171 μmol, 1 eq) in DMSO (2 mL) and THF (1 mL) was added Ti(OEt)$_4$ (391 mg, 1.71 mmol, 356 μL, 10 eq). The reaction mixture was stirred for 0.5 hours. Then NaBH$_3$CN (32.3 mg, 514 μmol, 3 eq) was added and the mixture was stirred for 0.5 hours at 20° C. LCMS showed full consumption of the reactant and detection of the desired product. The reaction mixture was concentrated under reduced pressure to give a crude residue, which was purified by reversed phase HPLC (0.1% FA condition) to afford 3-(5-(2-((1-((1-(((7-(8-ethyl-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)oxy)-7-azaspiro[3.5]nonan-7-yl)-1-oxoisoindolin-2-yl)piperidine-2,6-dione (0.1 g, 95.9 μmol, 55.9% yield, 98.3% purity) as a white solid.

Step 2: Preparation of 3-(5-(2-((1-((1-(((7-(8-ethyl-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)oxy)-7-azaspiro[3.5]nonan-7-yl)-1-oxoisoindolin-2-yl)piperidine-2,6-dione (Compound 181)

The mixture of 3-[5-[2-[[1-[[1-[7-[8-ethyl-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropyl]methyl]-4-piperidyl]oxy]-7-azaspiro[3.5]nonan-7-yl]-1-oxo-isoindolin-2-yl]piperidine-2,6-dione (80 mg, 78.0 μmol, 1 eq) in HCl (3 M, 2 mL, 76.9 eq) and MeCN (1 mL) was stirred at 20° C. for 1 hour. LCMS showed complete consumption of the reactant and detection of the desired product. The crude product was purified by preparative HPLC: column: Phenomenex Luna C18 150*25 mm*10 μm; mobile phase: [water (FA)-ACN]; gradient: 25%-45% B over 10 minutes to afford 3-(5-(2-((1-((1-(((7-(8-ethyl-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)piperidin-4-yl)oxy)-7-azaspiro[3.5]nonan-7-yl)-1-oxoisoindolin-2-yl)piperidine-2,6-dione (35.1 mg, 34.7 μmol, 44.5% yield, 97% purity) as a white solid. LCMS: [M+H]$^+$=981.5; $^1$H NMR (400 MHZ, DMSO-d$_6$) δ=10.93 (s, 1H), 9.89 (br s, 1H), 9.20 (d, J=7.4 Hz, 1H), 7.66 (d, J=8.2 Hz, 1H), 7.48 (d, J=8.6 Hz, 1H), 7.36 (t, J=7.6 Hz, 1H), 7.28 (d, J=2.4 Hz, 1H), 7.12 (d, J=7.2 Hz, 1H), 7.05-6.99 (m, 2H), 6.98 (d, J=2.6 Hz, 1H), 5.03 (dd, J=5.2, 13.4 Hz, 1H), 4.74 (br d, J=14.8 Hz, 1H), 4.38-4.24 (m, 4H), 4.22-4.14 (m, 1H), 4.10-3.97 (m, 2H), 3.64-3.49 (m, 1H), 3.27 (br d, J=3.8 Hz, 5H), 2.97-2.75 (m, 3H), 2.62-2.55 (m, 1H), 2.40-2.31 (m, 3H), 2.30-2.19 (m, 2H), 2.18-2.10 (m, 3H), 2.09-2.02 (m, 1H), 2.02-1.89 (m, 2H), 1.70 (br dd, J=11.4, 12.4 Hz, 4H), 1.66-1.53 (m, 7H), 1.43-1.31 (m, 2H), 1.17 (d, J=10.8 Hz, 3H), 0.82 (dt, J=4.6, 7.4 Hz, 3H), 0.66 (br s, 2H), 0.42 (br s, 2H).

Example 56: Preparation of 3-[5-[2-[[1-[[1-[[7-(8-ethyl-7-fluoro-3-hydroxy-1-naphthyl)-8-fluoro-4-[(3R)-3-hydroxy-3-methyl-1-piperidyl]pyrido[4,3-d]pyrimidin-2-yl)oxymethyl]cyclopropyl]methyl]-4-piperidyl]oxy]-7-azaspiro[3.5]nonan-7-yl]-1-oxo-isoindolin-2-yl]piperidine-2,6-dione (Compound 182)

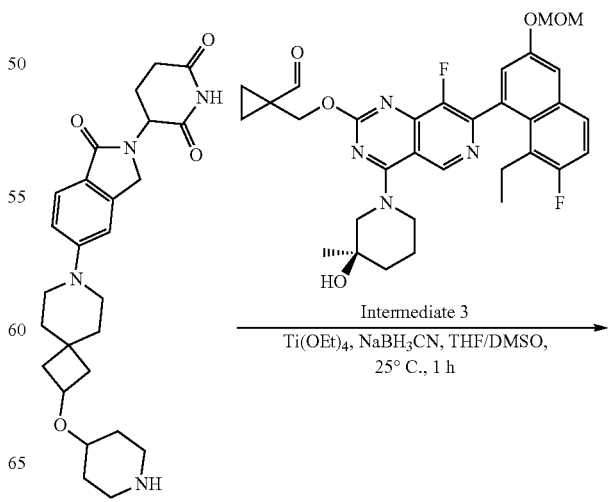

Intermediate 3
Ti(OEt)$_4$, NaBH$_3$CN, THF/DMSO, 25° C., 1 h

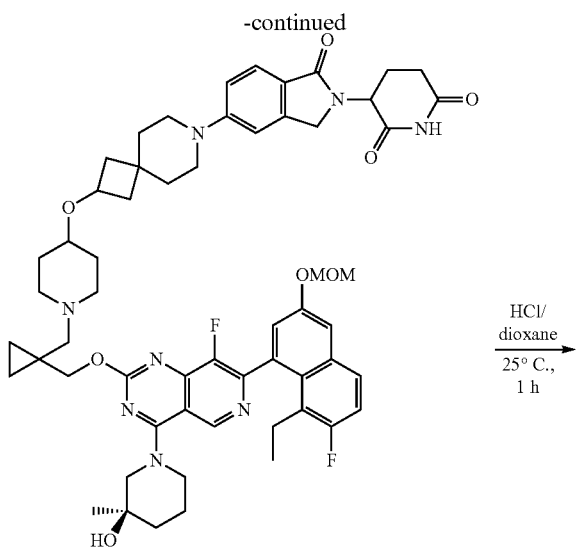

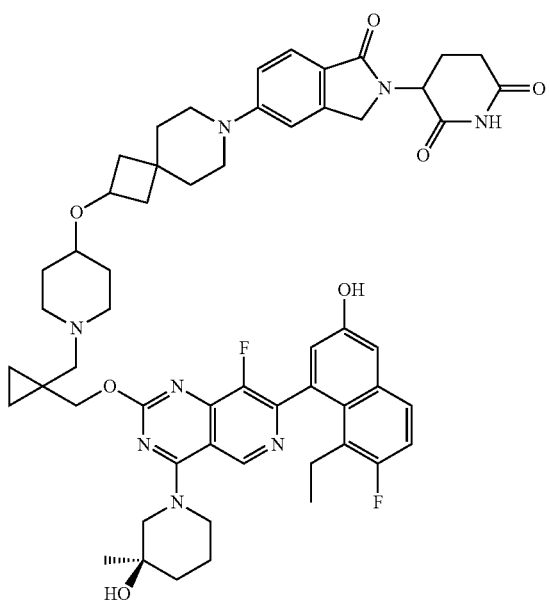

Compound 182

Step 1: Preparation of 3-[5-[2-[[1-[[1-[[7-[8-ethyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropyl]methyl]-4-piperidyl]oxy]-7-azaspiro[3.5]nonan-7-yl]-1-oxo-isoindolin-2-yl]piperidine-2,6-dione To a solution of 3-[1-oxo-5-[2-(4-piperidyloxy)-7-azaspiro[3.5]nonan-7-yl]isoindolin-2-yl]piperidine-2,6-dione (70 mg, 150.0 μmol, 1 eq) 1-[[7-[8-ethyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropanecarbaldehyde (97.8 mg, 165.0 μmol, 1.1 eq) in THF (2.5 mL) and DMSO (2.5 mL) was added tetraethoxytitanium (1.03 g, 4.50 mmol, 933.4 μL, 30 eq). Then the solution was stirred for 0.5 hours. The mixture was added sodium cyanoborohydride (9.43 mg, 150.0 μmol, 1 eq). The mixture was stirred at 25° C. for 1.5 hours. LCMS showed 3-[1-oxo-5-[2-(4-piperidyloxy)-7-azaspiro[3.5]nonan-7-yl]isoindolin-2-yl]piperidine-2,6-dione was consumed completely and one main peak with desired mass. The reaction mixture was poured into water (30 mL), filtered and then extracted with EA (30 mL*3), the organic layers were combined and washed with brine (60 mL), dried over anhydrous $Na_2SO_4$, filtered and concentrated under vacuum. The residue was purified by reversed-phase flash (0.1% FA condition). The resulting solution was lyophilized to give 3-[5-[2-[[1-[[1-[[7-[8-ethyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropyl]methyl]-4-piperidyl]oxy]-7-azaspiro[3.5]nonan-7-yl]-1-oxo-isoindolin-2-yl]piperidine-2,6-dione (100 mg, 92.9 μmol, 61.9% yield, 97% purity) as a white solid.

Step 2: Preparation of 3-[5-[2-[[1-[1-[7-(8-ethyl-7-fluoro-3-hydroxy-1-naphthyl)-8-fluoro-4-[(3R)-3-hydroxy-3-methyl-1-piperidyl]pyrido[4,3-d]pyrimidin-2-yl]oxymethyl]cyclopropyl]methyl]-4-piperidyl]oxy]-7-azaspiro[3.5]nonan-7-yl]-1-oxo-isoindolin-2-yl]piperidine-2,6-dione (Compound 182)

To a solution of 3-[5-[2-[[1-[1-[7-[8-ethyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropyl]methyl]-4-piperidyl]oxy]-7-azaspiro[3.5]nonan-7-yl]-1-oxo-isoindolin-2-yl]piperidine-2,6-dione (80.0 mg, 76.7 μmol, 1 eq) in ACN (1 mL) was added HCl (3 M in $H_2O$, 2 mL, 78.2 eq). The mixture was stirred at 25° C. for 20 minutes. LCMS showed 3-[5-[2-[[1-[[1-[[7-[8-ethyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropyl]methyl]-4-piperidyl]oxy]-7-azaspiro[3.5]nonan-7-yl]-1-oxo-isoindolin-2-yl]piperidine-2,6-dione was consumed completely and one main peak with desired mass. The reaction mixture was concentrated under reduced pressure to remove solvent. The residue was purified by prep-HPLC column: Phenomenex Luna C18 150*25 mm*10 μm; mobile phase: [water (FA)-ACN]; gradient: 22%-52% B over 10 minutes. Then solution was lyophilized to give 3-[5-[2-[[1-[[1-[[7-(8-ethyl-7-fluoro-3-hydroxy-1-naphthyl)-8-fluoro-4-[(3R)-3-hydroxy-3-methyl-1-piperidyl]pyrido[4,3-d]pyrimidin-2-yl]oxymethyl]cyclopropyl]methyl]-4-piperidyl]oxy]-7-azaspiro[3.5]nonan-7-yl]-1-oxo-isoindolin-2-yl]piperidine-2,6-dione (58 mg, 53.9 μmol, 70.3% yield, 97.1% purity, FA) as a white solid. LCMS: $[M+H]^+$=999.6; $^1H$ NMR: (400 MHz, METHANOL-$d_4$) δ=9.24 (s, 1H), 8.52 (s, 1H), 7.73-7.60 (m, 2H), 7.35-7.22 (m, 2H), 7.11-7.03 (m, 3H), 5.13-5.08 (m, 1H), 4.69-4.52 (m, 3H), 4.48 (br t, J=5.6 Hz, 2H), 4.42-4.30 (m, 3H), 4.22-4.13 (m, 1H), 3.67-3.58 (m, 2H), 3.51-3.36 (m, 3H), 3.27-3.22 (m, 2H), 3.11 (br d, J=3.2 Hz, 3H), 3.00-2.75 (m, 3H), 2.54-2.40 (m, 2H), 2.32-2.02 (m, 8H), 1.96-1.64 (m, 12H), 1.31 (d, J=9.8 Hz, 3H), 0.94 (br s, 2H), 0.89-0.76 (m, 5H).

Example 57: Preparation of 3-[5-[7-[[1-[[1-[[7-(8-ethyl-7-fluoro-3-hydroxy-1-naphthyl)-8-fluoro-4-[(3R)-3-hydroxy-3-methyl-1-piperidyl]pyrido[4,3-d]pyrimidin-2-yl]oxymethyl]cyclopropyl]methyl]-4-piperidyl]oxy]-2-azaspiro[3.5]nonan-2-yl]-1-oxo-isoindolin-2-yl]piperidine-2,6-dione (Compound 184)

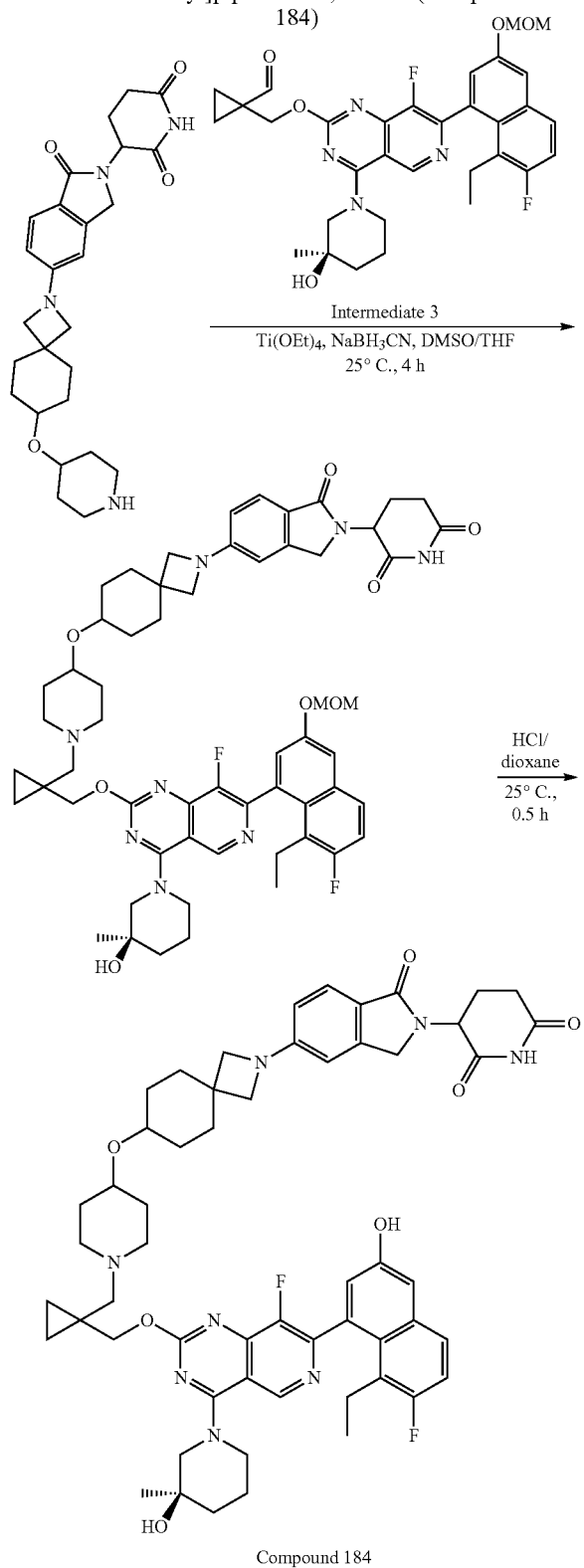

Compound 184

Step 1: Preparation of 3-[5-[7-[1-[[1-[7-[8-ethyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropyl]methyl]-4-piperidyl]oxy]-2-azaspiro[3.5]nonan-2-yl]-1-oxo-isoindolin-2-yl]piperidine-2,6-dione To a solution of 1-[7-[8-ethyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropanecarbaldehyde (81.7 mg, 138 µmol, 1 eq) and 3-[1-oxo-5-[7-(4-piperidyloxy)-2-azaspiro[3.5]nonan-2-yl]isoindolin-2-yl]piperidine-2,6-dione (80.0 mg, 138 µmol, 1 eq, TFA) in THF (2 mL) and DMSO (2 mL) was added Ti(OEt)$_4$ (314 mg, 1.38 mmol, 286 µL, 10 eq), and the mixture was stirred at 25° C. for 2 hours, followed by the addition of NaBH$_3$CN (43.2 mg, 689 µmol, 5 eq). The resulting mixture was stirred at 25° C. for another 2 hours. LCMS showed full consumption of the reactant and detection of the desired product. The reaction mixture was diluted with EA (30 mL) and washed with water 20 mL then extracted with EA (15 mL*3). The combined organic layers were washed with brine (40 mL*2), dried over anhydrous Na$_2$SO$_4$, filtered and concentrated under reduced pressure to give a residue. The residue was purified by prep-HPLC (FA condition) to afford the 3-[5-[7-[1-[1-[7-[8-ethyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropyl]methyl]-4-piperidyl]oxy]-2-azaspiro[3.5]nonan-2-yl]-1-oxo-isoindolin-2-yl]piperidine-2,6-dione (40 mg, 37.58 µmol, 27.27% yield, 98% purity) as a white solid.

Step 2: Preparation of 3-[5-[7-[1-[1-[[7-(8-ethyl-7-fluoro-3-hydroxy-1-naphthyl)-8-fluoro-4-[(3R)-3-hydroxy-3-methyl-1-piperidyl]pyrido[4,3-d]pyrimidin-2-yl]oxymethyl]cyclopropyl]methyl]-4-piperidyl]oxy]-2-azaspiro[3.5]nonan-2-yl]-1-oxo-isoindolin-2-yl]piperidine-2,6-dione (Compound 184)

To a solution of 3-[5-[7-[1-[1-[7-[8-ethyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropyl]methyl]-4-piperidyl]oxy]-2-azaspiro[3.5]nonan-2-yl]-1-oxo-isoindolin-2-yl]piperidine-2,6-dione (40.0 mg, 38.3 µmol, 1 eq) in ACN (1 mL) was added HCl (3 M in H$_2$O, 2 mL, 156 eq). The mixture was stirred at 25° C. for 0.5 hours. LCMS showed complete consumption of the reactant and detection of the desired product. The residue was purified by prep-HPLC (column: Phenomenex Luna C18 150*25 mm*10 µm; mobile phase: [water (FA)-ACN]; gradient: 23%-53% B over 10 minutes) to give 3-[5-[7-[[1-[1-[7-(8-ethyl-7-fluoro-3-hydroxy-1-naphthyl)-8-fluoro-4-[(3R)-3-hydroxy-3-methyl-1-piperidyl]pyrido[4,3-d]pyrimidin-2-yl]oxymethyl]cyclopropyl]methyl]-4-piperidyl]oxy]-2-azaspiro[3.5]nonan-2-yl]-1-oxo-isoindolin-2-yl]piperidine-2,6-dione (10.16 mg, 9.97 µmol, 25.99% yield, 98% purity) as a white solid. LCMS: [M+H]$^+$=999.5; $^1$H NMR (400 MHZ, DMSO-d$_6$) δ=11.00-10.81 (m, 1H), 10.03-9.84 (m, 1H), 9.21 (s, 1H), 8.20 (s, 1H), 7.80-7.72 (m, 1H), 7.47 (d, J=8.0 Hz, 1H), 7.39-7.28 (m, 2H), 7.03 (d, J=2.4 Hz, 1H), 6.52-6.42 (m, 2H), 5.06-4.98 (m, 1H), 4.78-4.70 (m, 1H), 4.31 (br d, J=4.4 Hz, 2H), 4.27 (s, 1H), 4.19-4.13 (m, 1H), 4.08-3.98 (m, 1H), 3.59 (br d, J=8.0 Hz, 4H), 2.97-2.83 (m, 3H), 2.80-2.69 (m, 3H), 2.29 (br s, 2H), 2.12-2.00 (m, 4H), 1.98-1.89 (m, 2H), 1.87-1.81 (m, 2H), 1.76-1.63 (m, 8H), 1.59-1.45 (m, 3H), 1.42-1.25 (m, 5H), 1.17 (br d, J=9.6 Hz, 3H), 0.74 (q, J=6.8 Hz, 3H), 0.64 (br s, 2H), 0.39 (br s, 2H).

Example 58: Preparation of 3-(5-(4-((1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-4-fluoropiperidin-4-yl)methyl)piperazin-1-yl)-3-methyl-2-oxo-2,3-dihydro-1H-benzo[d]imidazol-1-yl)piperidine-2,6-dione (Compound 64)
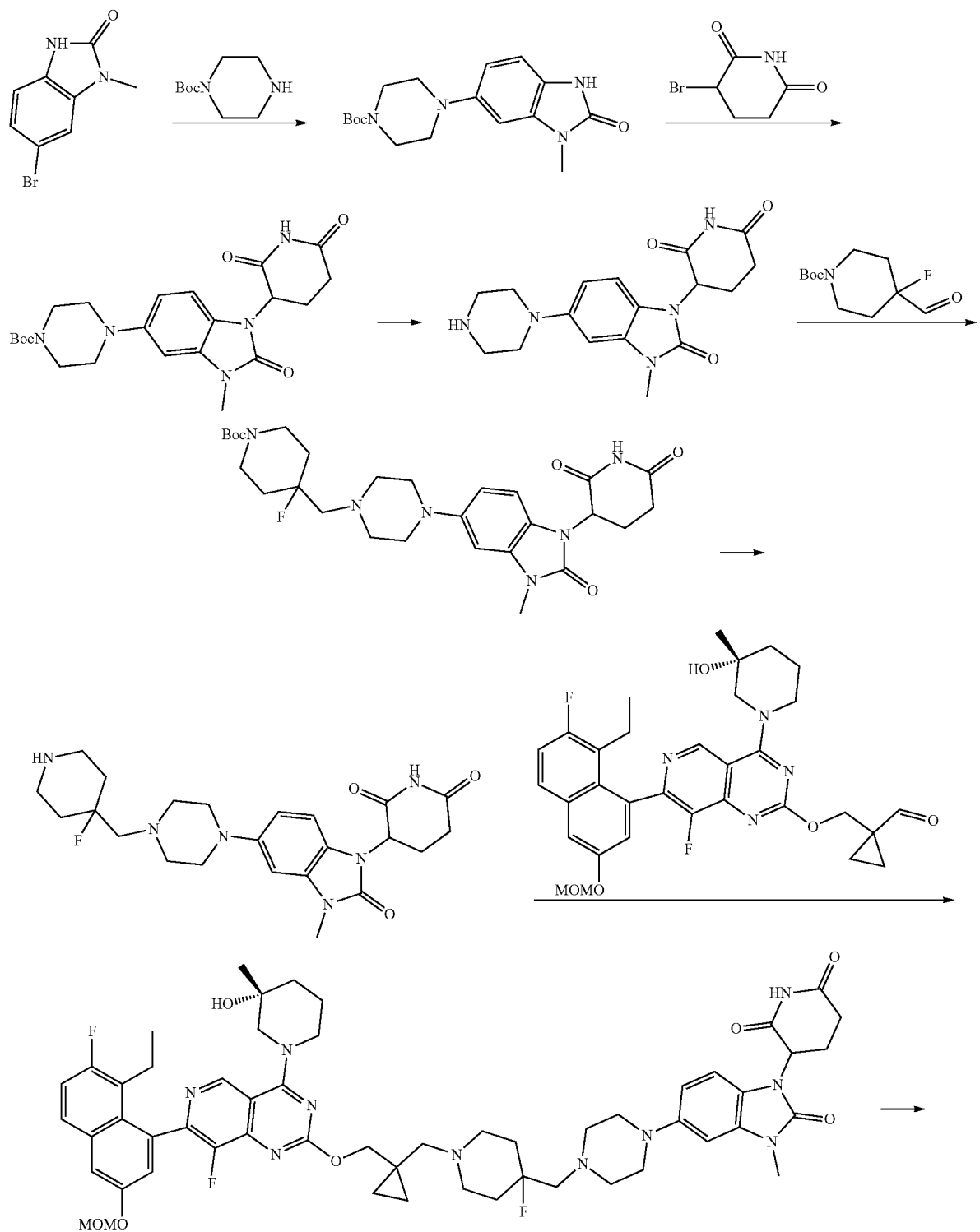

-continued

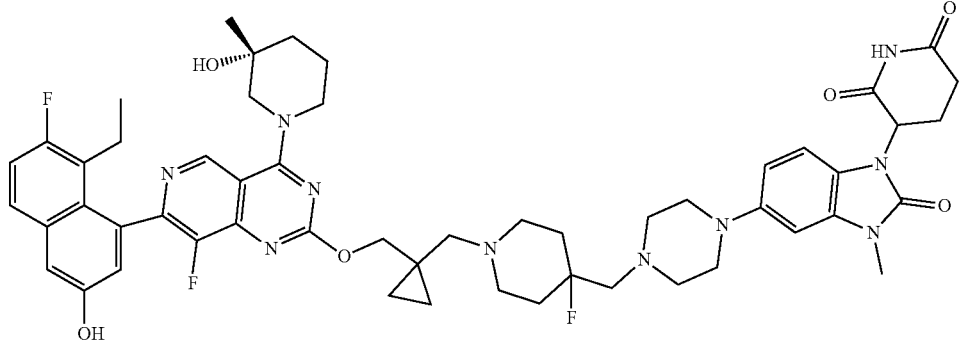

64

Step 1: Preparation of tert-butyl 4-(3-methyl-2-oxo-2,3-dihydro-1H-benzo[d]imidazol-5-yl)piperazine-1-carboxylate To a solution of 6-bromo-1-methyl-1,3-dihydro-2H-benzo[d]imidazol-2-one (1.0 g, 4.4 mmol) in dioxane (10 mL) was added tert-butyl piperazine-1-carboxylate (1.64 g, 8.8 mmol), $Pd_2(dba)_3$ (201 mg, 0.22 mmol), Xantphos (255 mg, 0.44 mmol) and t-BuONa (1.27 g, 13.2 mmol). The reaction mixture was stirred at 80° C. for 16 hours. The reaction mixture was quenched with water and extracted with EA. The organic phase was washed with brine and dried over $Na_2SO_4$. The solution was concentrated in vacuum and the residue was purified by flash chromatography on silica gel with DCM:MeOH=10:1 to afford the desired compound (1.0 g, 68.% yield) as a white solid. LC/MS: 333.1 [M+H]+.

Step 2: Preparation of tert-butyl 4-(1-(2,6-dioxopiperidin-3-yl)-3-methyl-2-oxo-2,3-dihydro-1H-benzo[d]imidazol-5-yl)piperazine-1-carboxylate To a solution of tert-butyl 4-(3-methyl-2-oxo-2,3-dihydro-1H-benzo[d]imidazol-5-yl)piperazine-1-carboxylate (750 mg, 2.26 mmol) and 3-bromopiperidine-2,6-dione (868 mg, 4.52 mmol) in THF (10 mL) was added LiHMDS (13.6 ml, 13.56 mmol) at room temperature. The reaction mixture was stirred at 90° C. for 12 hours. The reaction mixture was quenched with water and extracted with EA. The organic phase was washed with brine and dried over $Na_2SO_4$. The solution was concentrated in vacuum and the residue was purified by Prep-HPLC (Gemini-C18:150×21.2 mm, 5 μm. ACN-$H_2O$ (0.1% FA)) to afford the desired compound (160 mg, 15.9% yield) as a yellow solid. LC/MS: 444.2 [M+H]+.

Step 3: Preparation of 3-(3-methyl-2-oxo-5-(piperazin-1-yl)-2,3-dihydro-1H-benzo[d]imidazol-1-yl)piperidine-2,6-dione A solution of tert-butyl 4-(1-(2,6-dioxopiperidin-3-yl)-3-methyl-2-oxo-2,3-dihydro-1H-benzo[d]imidazol-5-yl)piperazine-1-carboxylate (200 mg, 0.45 mmol) in HCl/dioxane (4 M, 5 mL) and DCM (5 mL) was stirred at room temperature for 1 hour. The solution was concentrated in vacuum to afford the desired compound (180 mg, crude) as a brown oil. LC/MS: 344.2 [M+H]+.

Step 4: Preparation of tert-butyl 4-((4-(1-(2,6-dioxopiperidin-3-yl)-3-methyl-2-oxo-2,3-dihydro-1H-benzo[d]imidazol-5-yl)piperazin-1-yl)methyl)-4-fluoropiperidine-1-carboxylate To a solution of 3-(3-methyl-2-oxo-5-(piperazin-1-yl)-2,3-dihydro-1H-benzo[d]imidazol-1-yl)piperidine-2,6-dione (170 mg, crude) in DMA (10 mL) was added DIEA (646 mg, 5 mmol) and tert-butyl 4-fluoro-4-formylpiperidine-1-carboxylate (578 mg, 2.5 mmol). The mixture was stirred at room temperature for 2 hours and then STAB (318 mg, 1.5 mmol) was added. The reaction mixture was stirred at 40° C. for 12 hours. The reaction mixture was quenched with water and extracted with EA. The organic phase was washed with brine, dried over $Na_2SO_4$, and concentrated in vacuum. The residue was purified by flash chromatography on silica gel with DCM:MeOH=10:1 to afford the desired compound (200 mg, 80% yield of two steps) as a white solid. LC/MS: 559.3 [M+H]+.

Step 5: Preparation of 3-(5-(4-((4-fluoropiperidin-4-yl)methyl)piperazin-1-yl)-3-methyl-2-oxo-2,3-dihydro-1H-benzo[d]imidazol-1-yl)piperidine-2,6-dione A solution of tert-butyl 4-((4-(1-(2,6-dioxopiperidin-3-yl)-3-methyl-2-oxo-2,3-dihydro-1H-benzo[d]imidazol-5-yl)piperazin-1-yl)methyl)-4-fluoropiperidine-1-carboxylate (200 mg, 0.36 mmol) in HCl/dioxane (4 M, 5 mL) and DCM (5 mL) was stirred at room temperature for 2 hours. The solution was concentrated in vacuum to afford the desired compound (200 mg, crude) as a brown oil. LC/MS: 458.9 [M+H]+.

Step 6: Preparation of 3-(5-(4-((1-(((7-(8-ethyl-7-fluoro-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-4-fluoropiperidin-4-yl)methyl)piperazin-1-yl)-3-methyl-2-oxo-2,3-dihydro-1H-benzo[d]imidazol-1-yl)piperidine-2,6-dione To a solution of 3-(5-(4-((4-fluoropiperidin-4-yl)methyl)piperazin-1-yl)-3-methyl-2-oxo-2,3-dihydro-1H-benzo[d]imidazol-1-yl)piperidine-2,6-dione (100 mg, crude) in DMA (10 mL) was added $Na_2SO_4$ (312 mg, 2.2 mmol), DIEA (284 mg, 2.2 mmol) and (R)-1-(((7-(8-ethyl-7-fluoro-3-(methoxymethoxy)naphthalen-1-yl)-8-fluoro-4-(3-hydroxy-3-methylpiperidin-1-yl)pyrido[4,3-d]pyrimidin-2-yl)oxy)

methyl)cyclopropane-1-carbaldehyde (107 mg, 0.18 mmol) at room temperature. The mixture was stirred at room temperature for 0.5 hours and then STAB (140 mg, 0.66 mmol) was added. The reaction mixture was stirred at room temperature for 2 hours. And then quenched with water. The reaction mixture was extracted with EA. The organic phase was washed with brine and dried over Na$_2$SO$_4$. The solution was concentrated in vacuum and the residue was purified by Prep-TLC with DCM:MeOH=10:1 to afford the desired compound (40 mg, 22.2% yield of two steps) as a white solid. LC/MS: 1035.5 [M+H]$^+$.

Step 7: Preparation of 3-(5-(4-((1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-4-fluoropiperidin-4-yl)methyl)piperazin-1-yl)-3-methyl-2-oxo-2,3-dihydro-1H-benzo[d]imidazol-1-yl)piperidine-2,6-dione (Compound 64)

A solution of 3-(5-(4-((1-((1-(((7-(8-ethyl-7-fluoro-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-4-fluoropiperidin-4-yl)methyl)piperazin-1-yl)-3-methyl-2-oxo-2,3-dihydro-1H-benzo[d]imidazol-1-yl)piperidine-2,6-dione (40 mg, 0.04 mmol) in in HCl/dioxane (4 M, 2 mL) and DCM (2 mL) was stirred at room temperature for 1 hour. The mixture was concentrated in vacuum and the residue was purified by Prep-HPLC (Gemini-C18:150×21.2 mm, 5 μm. ACN-H$_2$O (0.1% FA)) to give the desired product (6 mg, 15% yield) as a white solid. LC/MS: 991.3 [M+H]$^+$;

$^1$HNMR (400 MHZ, DMSO) δ 11.07 (s, 1H), 9.21 (d, J=2.8 Hz, 1H), 8.23 (s, 1H), 7.81-7.71 (m, 1H), 7.37-7.32 (m, 2H), 7.03 (s, 1H), 6.92 (d, J=8.8 Hz, 1H), 6.82 (s, 1H), 6.60 (d, J=8.4 Hz, 1H), 5.28 (dd, J=12.8, 5.2 Hz, 1H), 4.36-4.26 (m, 3H), 4.04 (dd, J=21.4, 13.1 Hz, 1H), 3.64-3.59 (m, 2H), 3.52-3.50 (m, 2H), 3.29 (s, 3H), 3.06-3.02 (m, 4H), 2.92-2.85 (m, 1H), 2.70-2.66 (m, 2H), 2.63-2.59 (m, 4H), 2.46 (s, 2H), 2.37-2.28 (m, 4H), 2.24-2.14 (m, 3H), 2.02-1.94 (m, 2H), 1.79 (t, J=12.0 Hz, 2H), 1.71-1.63 (m, 4H), 1.59-1.53 (m, 1H), 1.16 (d, J=9.6 Hz, 3H), 0.73 (q, J=7.2 Hz, 3H), 0.65 (s, 2H), 0.42 (s, 2H).

Example 59: Preparation of 3-(4-(4-((1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-4-fluoropiperidin-4-yl)methyl)piperazin-1-yl)-3-methyl-2-oxo-2,3-dihydro-1H-benzo[d]imidazol-1-yl)piperidine-2,6-dione (Compound 65)

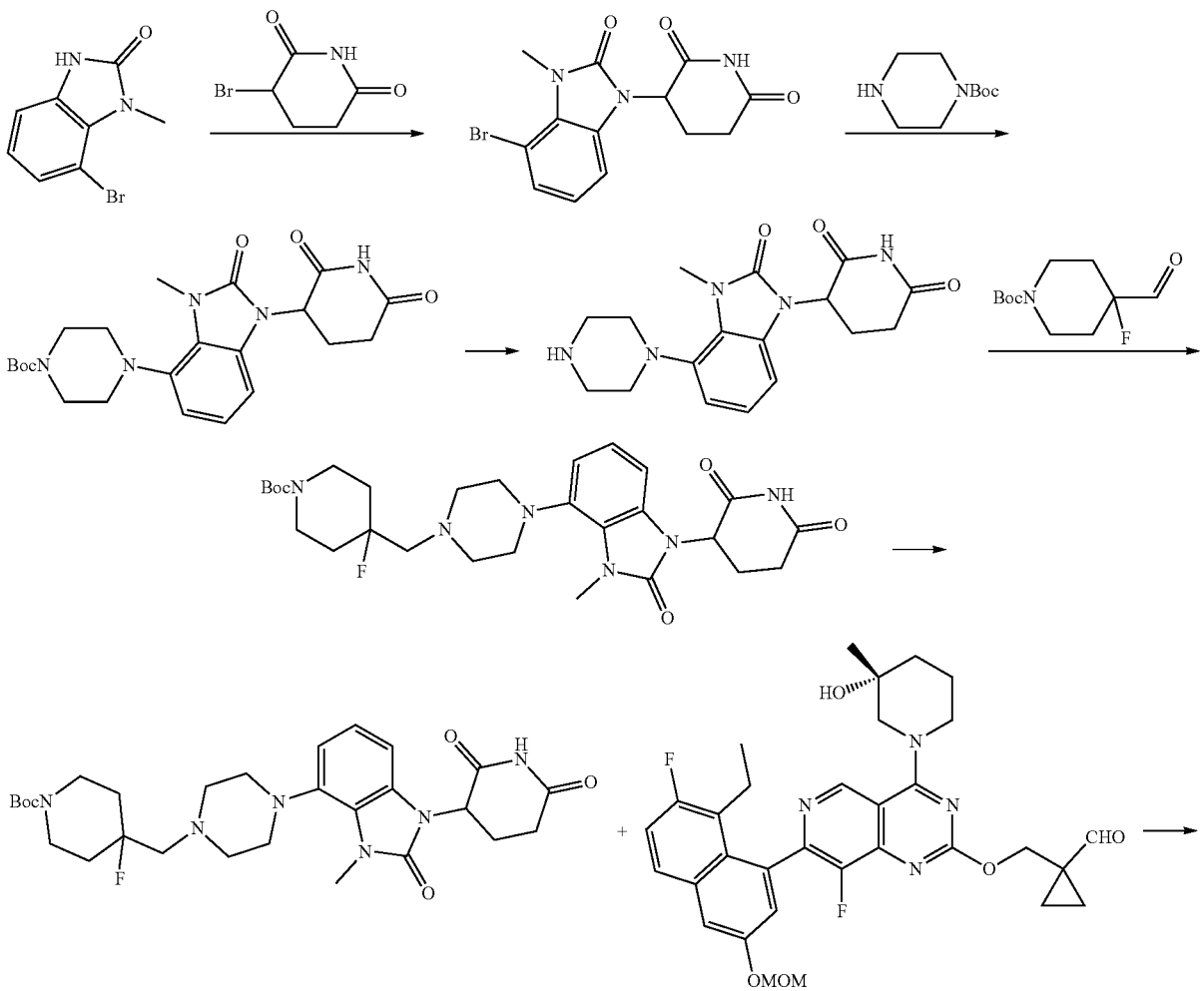

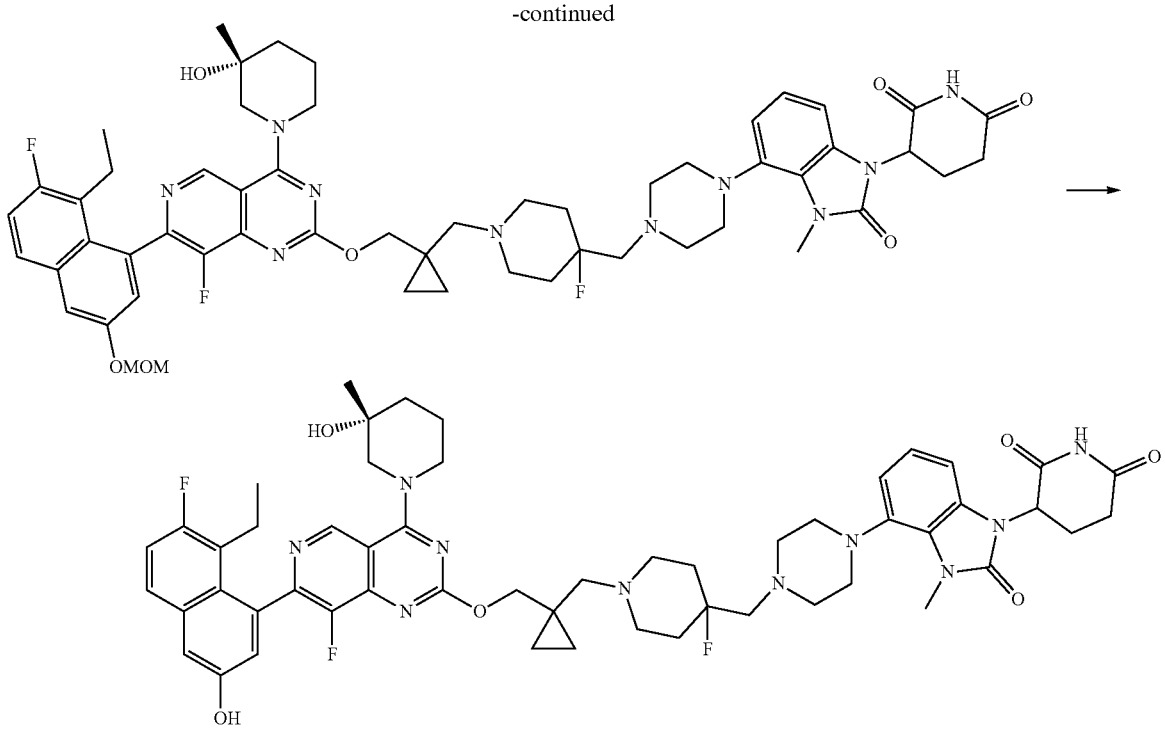

Step 1: Preparation of 3-(4-bromo-3-methyl-2-oxo-2,3-dihydro-1H-benzo[d]imidazol-1-yl)piperidine-2,6-dione To a solution of 7-bromo-1-methyl-3H-1,3-benzodiazol-2-one (2 g, 8.81 mmol) in DMF (20 mL) stirred at room temperature was added 3-bromopiperidine-2,6-dione (3.38 g, 17.62 mmol) and LiHMDS (26.5 ml, 26.43 mmol). The reaction mixture was stirred at 70° C. for 12 hours. The reaction mixture was quenched with water and extracted with EA. The organic phase was washed with brine and dried over $Na_2SO_4$. The solution was concentrated in vacuum and the residue was purified by flash chromatography on silica gel with DCM:MeOH=10:1 to afford the desired compound (600 mg, 20% yield) as a white solid. LC/MS: 338.2 [M+H]$^+$.

Step 2: Preparation of tert-butyl 4-(1-(2,6-dioxopiperidin-3-yl)-3-methyl-2-oxo-2,3-dihydro-1H-benzo[d]imidazol-4-yl)piperazine-1-carboxylate To a solution of 3-(4-bromo-3-methyl-2-oxo-2,3-dihydro-1H-benzo[d]imidazol-1-yl)piperidine-2,6-dione (890 mg, 2.63 mmol) in dioxane (10 mL) was added tert-butyl piperazine-1-carboxylate (980 mg, 5.26 mmol), $Pd_2(dba)_3$ (119 mg, 0.13 mmol), Xantphos (150 mg, 0.26 mmol) and t-BuONa (758 mg, 7.89 mmol). The reaction mixture was stirred at 80° C. for 16 hours. After cooling down to room temperature, the reaction mixture was quenched with water and extracted with EA. The organic phase was washed with brine and dried over $Na_2SO_4$. The solution was concentrated in vacuum and the residue was purified by flash chromatography on silica gel with DCM:MeOH=10:1 to afford the desired compound (750 mg, 64.2% yield) as a white solid. LC/MS: 444.1 [M+H]$^+$.

Step 3: Preparation of 3-(3-methyl-2-oxo-4-(piperazin-1-yl)-2,3-dihydro-1H-benzo[d]imidazol-1-yl)piperidine-2,6-dione A solution of tert-butyl 4-(1-(2,6-dioxopiperidin-3-yl)-3-methyl-2-oxo-2,3-dihydro-1H-benzo[d]imidazol-4-yl)piperazine-1-carboxylate (740 mg, 1.67 mmol) in HCl/dioxane (4 M, 5 mL) and DCM (5 mL) was stirred at room temperature for 1 hour. The solution was concentrated in vacuum and the residue was purified by Prep-HPLC (Gemini-C18:150×21.2 mm, 5 μm. ACN-$H_2O$ (0.1% FA) to afford the desired compound (350 mg, 60.3% yield) as a yellow solid. LC/MS: 344.2 [M+H]$^+$.

Step 4: Preparation of tert-butyl 4-((4-(1-(2,6-dioxopiperidin-3-yl)-3-methyl-2-oxo-2,3-dihydro-1H-benzo[d]imidazol-4-yl)piperazin-1-yl)methyl)-4-fluoropiperidine-1-carboxylate To a solution of 3-(3-methyl-2-oxo-4-(piperazin-1-yl)-2,3-dihydro-1H-benzo[d]imidazol-1-yl)piperidine-2,6-dione (280 mg, 0.82 mmol) in DMA (10 mL) was added DIEA (1.06 g, 8.2 mmol) and tert-butyl 4-fluoro-4-formylpiperidine-1-carboxylate (569 mg, 2.46 mmol). The mixture was stirred at room temperature for 2 hours and then STAB (522 mg, 2.46 mmol) was added. The reaction mixture was stirred at 40° C. for 12 hours. The reaction mixture was quenched with water and extracted with EA. The organic phase was washed with brine, dried over $Na_2SO_4$ and concentrated in vacuum. The residue was purified by flash chromatography on silica gel with DCM:MeOH=10:1 to afford the desired compound (220 mg, 47.5% yield) as a white solid. LC/MS: 559.3 [M+H]$^+$.

Step 5: Preparation of 3-(4-(4-((4-fluoropiperidin-4-yl)methyl)piperazin-1-yl)-3-methyl-2-oxo-2,3-dihydro-1H-benzo[d]imidazol-1-yl)piperidine-2,6-dione A solution of tert-butyl 4-((4-(1-(2,6-dioxopiperidin-3-yl)-3-methyl-2-oxo-2,3-dihydro-1H-benzo[d]imidazol-4-yl)piperazin-1-yl)methyl)-4-fluoropiperidine-1-carboxylate (200 mg, 0.36 mmol) in HCl/dioxane (4 M, 5 mL) and DCM (5 mL) was stirred at room temperature for 2 hours. The solution was concentrated in vacuum and the residue was purified by Prep-HPLC (Gemini-C18:150×21.2 mm, 5 μm. ACN-H$_2$O (0.1% FA) to afford the desired compound (120 mg, 72.2% yield) as a yellow solid. LC/MS: 459.1 [M+H]$^+$.

Step 6: Preparation of 3-(4-(4-((1-((1-(((7-(8-ethyl-7-fluoro-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-4-fluoropiperidin-4-yl)methyl)piperazin-1-yl)-3-methyl-2-oxo-2,3-dihydro-1H-benzo[d]imidazol-1-yl)piperidine-2,6-dione To a solution of 3-(4-(4-((4-fluoropiperidin-4-yl)methyl)piperazin-1-yl)-3-methyl-2-oxo-2,3-dihydro-1H-benzo[d]imidazol-1-yl)piperidine-2,6-dione (90 mg, 0.2 mmol) in DMA (10 mL) was added Na$_2$SO$_4$ (284 mg, 2 mmol), DIEA (259 mg, 2 mmol) and (R)-1-(((7-(8-ethyl-7-fluoro-3-(methoxymethoxy)naphthalen-1-yl)-8-fluoro-4-(3-hydroxy-3-methylpiperidin-1-yl)pyrido[4,3-d]pyrimidin-2-yl)oxy)methyl)cyclopropane-1-carbaldehyde (101 mg, 0.17 mmol) at room temperature. The mixture was stirred at room temperature for 0.5 hours and then STAB (127 mg, 0.6 mmol) was added. The reaction mixture was stirred at 45° C. for 12 hours. The reaction was quenched with water and extracted with EA. The organic phase was washed with brine, dried over Na$_2$SO$_4$, and concentrated in vacuum. The residue was purified by Prep-TLC with DCM:MeOH=10:1 to afford the desired compound (40 mg, 20% yield) as a white solid. LC/MS: 1035.5 [M+H]$^+$.

Step 7: Preparation of 3-(4-(4-((1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-4-fluoropiperidin-4-yl)methyl)piperazin-1-yl)-3-methyl-2-oxo-2,3-dihydro-1H-benzo[d]imidazol-1-yl)piperidine-2,6-dione (Compound 65)

A solution of 3-(4-(4-((1-((1-(((7-(8-ethyl-7-fluoro-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-4-fluoropiperidin-4-yl)methyl)piperazin-1-yl)-3-methyl-2-oxo-2,3-dihydro-1H-benzo[d]imidazol-1-yl)piperidine-2,6-dione (40 mg, 0.04 mmol) in HCl/dioxane (4 M, 2 mL) and DCM (2 mL) was stirred at room temperature for 1 hour. The mixture was concentrated in vacuum and the residue was purified by Prep-HPLC (Gemini-C18:150×21.2 mm, 5 μm. ACN-H$_2$O (0.1% FA)) to give the desired product (30 mg, 75% yield) as a white solid. LC/MS: 991.3 [M+H]$^+$; $^1$HNMR (400 MHZ, DMSO) δ 11.10 (s, 1H), 9.26 (s, 1H), 7.79-7.66 (m, 2H), 7.39-7.29 (m, 2H), 7.04-6.97 (m, 2H), 6.96-6.82 (m, 2H), 5.38-5.32 (m, 1H), 4.57 (q, J=7.2 Hz, 3H), 4.35 (s, 3H), 3.82 (s, 2H), 3.74 (s, 3H), 3.63 (s, 4H), 3.54 (d, J=13.6 Hz, 2H), 3.32 (s, 2H), 3.17-3.08 (m, 3H), 2.93-2.86 (m, 2H), 2.72-2.58 (m, 3H), 2.37-2.28 (m, 3H), 2.18-2.11 (m, 2H), 2.00 (q, J=7.6 Hz, 3H), 1.73-1.64 (m, 3H), 1.52 (d, J=7.2 Hz, 5H), 1.18 (d, J=10.4 Hz, 3H), 0.85 (t, J=6.8 Hz, 2H), 0.74 (q, J=7.2 Hz, 2H).

Example 60: Preparation of 3-(6-(4-((1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-4-fluoropiperidin-4-yl)methyl)piperazin-1-yl)-1-methyl-1H-indazol-3-yl)piperidine-2,6-dione (Compound 66)

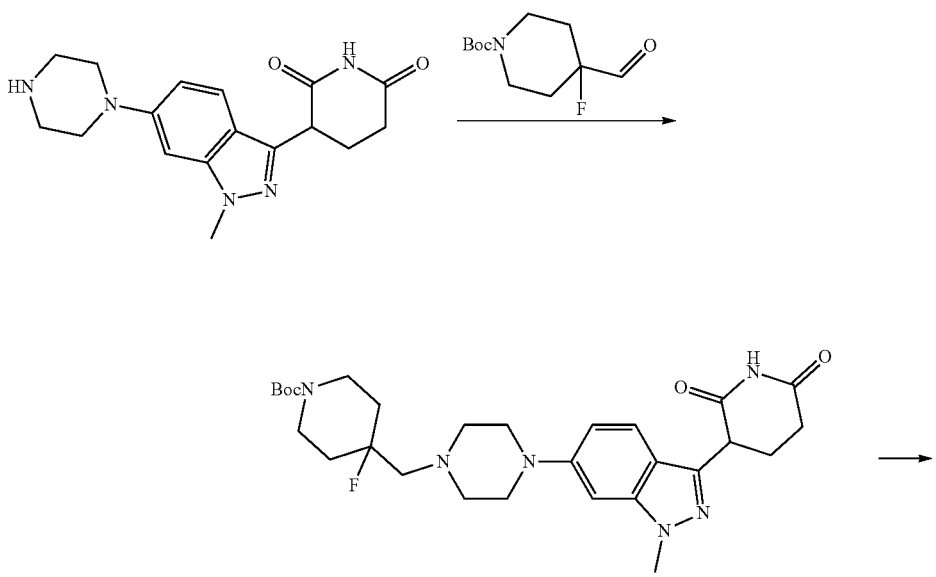

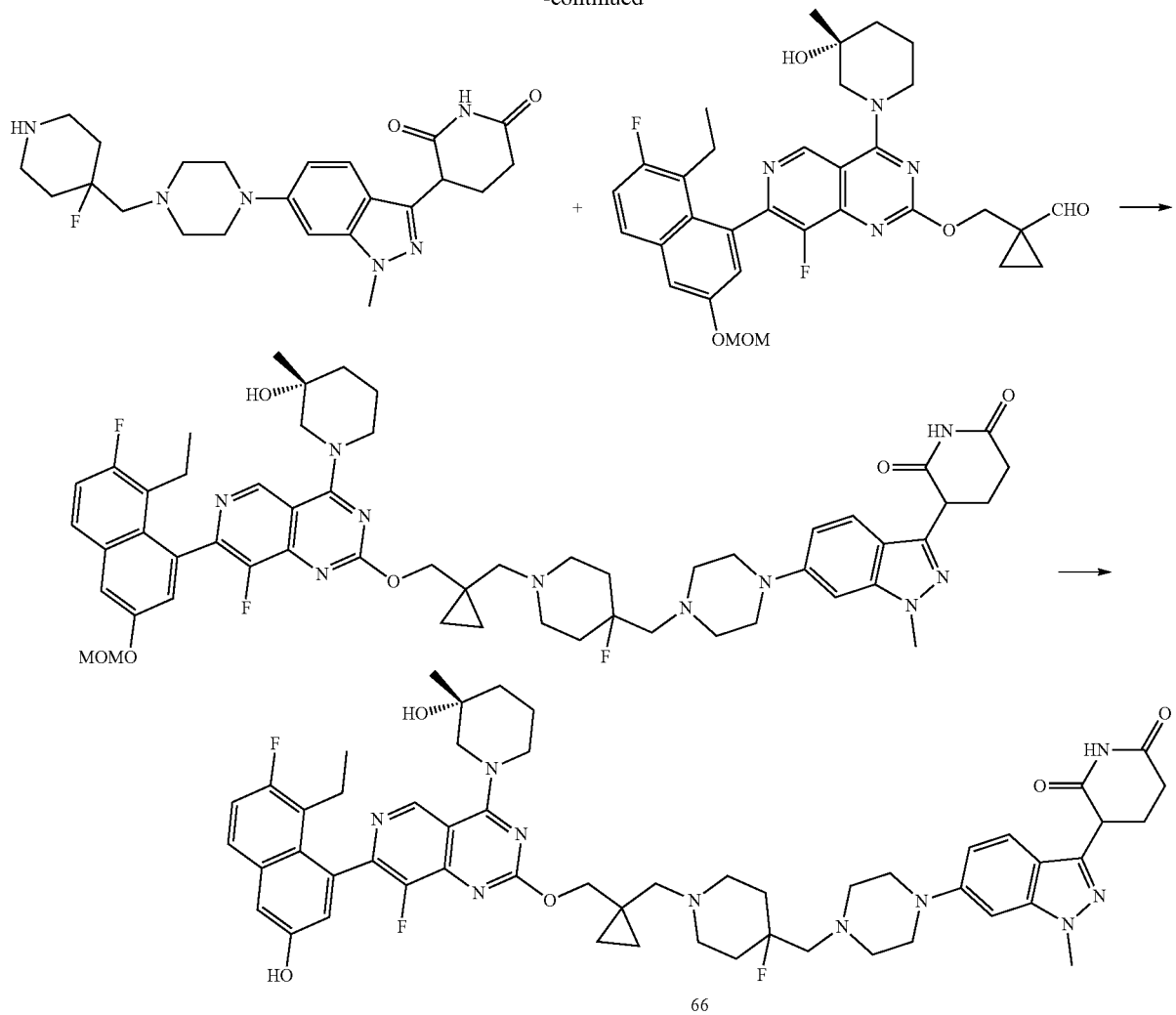

66

Step 1: Preparation of tert-butyl 4-((4-(3-(2,6-di-oxopiperidin-3-yl)-1-methyl-1H-indazol-6-yl)piper-azin-1-yl)methyl)-4-fluoropiperidine-1-carboxylate To a solution of 3-(1-methyl-6-(piperazin-1-yl)-1H-indazol-3-yl)piperidine-2,6-dione prepared according to the procedure described in WO2023083194 (page 322, intermediate 106-4) (120 mg, 0.33 mmol) in DCM (2 mL) was added DIEA (213 mg, 1.65 mmol), STAB (139 mg, 0.66 mmol) and tert-butyl 4-fluoro-4-formylpiperidine-1-carboxylate (305 mg, 0.66 mmol). The mixture was stirred at room temperature for 2 hours. The reaction mixture was poured into water (20 mL) and extracted with EA (10 mL×3). The organic phase was washed with brine and dried over Na$_2$SO$_4$. The solution was concentrated in vacuum and the residue was purified by Prep-TLC (PE:EA=1:1) to give the desired compound (75 mg, 41.8% yield) as a white solid. LC/MS: 543.3 [M+H]$^+$.

Step 2: Preparation of 3-(6-(4-((4-fluoropiperidin-4-yl)methyl)piperazin-1-yl)-1-methyl-1H-indazol-3-yl)piperidine-2,6-dione A solution of tert-butyl 4-((4-(3-(2,6-dioxopiperidin-3-yl)-1-methyl-1H-indazol-6-yl)piperazin-1-yl)methyl)-4-fluoropiperidine-1-carboxylate (75 mg, 0.14 mmol) in HCl/dioxane (4 M, 1 mL) and DCM (1 mL) was stirred at room temperature for 1 hour. The mixture was concentrated in vacuum to give the desired compound (90 mg, crude) as a yellow solid. LC/MS: 443.3 [M+H]$^+$.

Step 3: Preparation of 3-(6-(4-((1-(((1-(((7-(8-ethyl-7-fluoro-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-4-fluoropiperidin-4-yl)methyl)piperazin-1-yl)-1-methyl-1H-indazol-3-yl)piperidine-2,6-dione To a solution of 3-(6-(4-((4-fluoropiperidin-4-yl)methyl)piperazin-1-yl)-1-methyl-1H-indazol-3-yl)piperidine-2,6-dione (90 mg, crude) in DMA (2 mL) was added DIEA (88 mg, 0.68 mmol), STAB (57 mg, 0.27 mmol) and (R)-1-(((7-(8-ethyl-7-fluoro-3-(methoxymethoxy)naphthalen-1-yl)-8-fluoro-4-(3-hydroxy-3-methylpiperidin-1-yl)pyrido[4,3-d]pyrimidin-2-yl)oxy)methyl) cyclopropane-1-carbaldehyde (70 mg, 0.14 mmol). The mixture was stirred at room temperature for 16 hours. The reaction mixture was poured into water (20 mL) and extracted with DCM (10 mL×3). The Step 4: Preparation of 3-(6-(4-((1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-4-fluoropiperidin-4-yl)methyl)piperazin-1-yl)-1-methyl-1H-indazol-3-yl)piperidine-2,6-dione (Compound 66)

A solution of 3-(6-(4-((1-((1-(((7-(8-ethyl-7-fluoro-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-4-fluoropiperidin-4-yl)methyl)piperazin-1-yl)-1-methyl-1H-indazol-3-yl)piperidine-2,6-dione (35 mg, 0.034 mmol) in TFA (1 mL) and DCM (3 mL) was stirred at room temperature for 1 hour. The mixture was concentrated in vacuum and the residue was purified by Prep-HPLC (0.1% FA in H₂O/ACN=22% to 25%) to give the desired product (14 mg, 41.9% yield) as a white solid. LC/MS: 975.3 [M+H]⁺; ¹H NMR (400 MHZ, DMSO) δ 10.87 (s, 1H), 9.99 (s, 1H), 9.26 (s, 1H), 9.08-8.89 (m, 1H), 7.79-7.65 (m, 2H), 7.50 (d, J=9.0 Hz, 1H), 7.37-7.29 (m, 2H), 7.04-6.98 (m, 1H), 6.90 (d, J=8.5 Hz, 1H), 6.83 (s, 1H), 4.77-4.69 (m, 1H), 4.39-4.30 (m, 3H), 4.28-4.23 (m, 1H), 4.14-4.04 (m, 1H), 3.89 (s, 3H), 3.82 (s, 1H), 3.71 (s, 1H), 3.30-3.28 (m, 2H), 3.21 (s, 5H), 2.64-2.59 (m, 2H), 2.54 (s, 5H), 2.36-2.27 (m, 3H), 2.22-2.10 (m, 4H), 2.08-1.95 (m, 4H), 1.77-1.61 (m, 5H), 1.50 (d, J=7.0 Hz, 2H), 1.41-1.34 (m, 1H), 1.17 (d, J=10.3 Hz, 3H), 0.92-0.87 (m, 2H), 0.74-0.71 (m, 2H).

Example 61: Preparation of 3-(7-(4-((1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-4-fluoropiperidin-4-yl)methyl)piperazin-1-yl)-1-methyl-1H-indazol-3-yl)piperidine-2,6-dione (Compound 67)

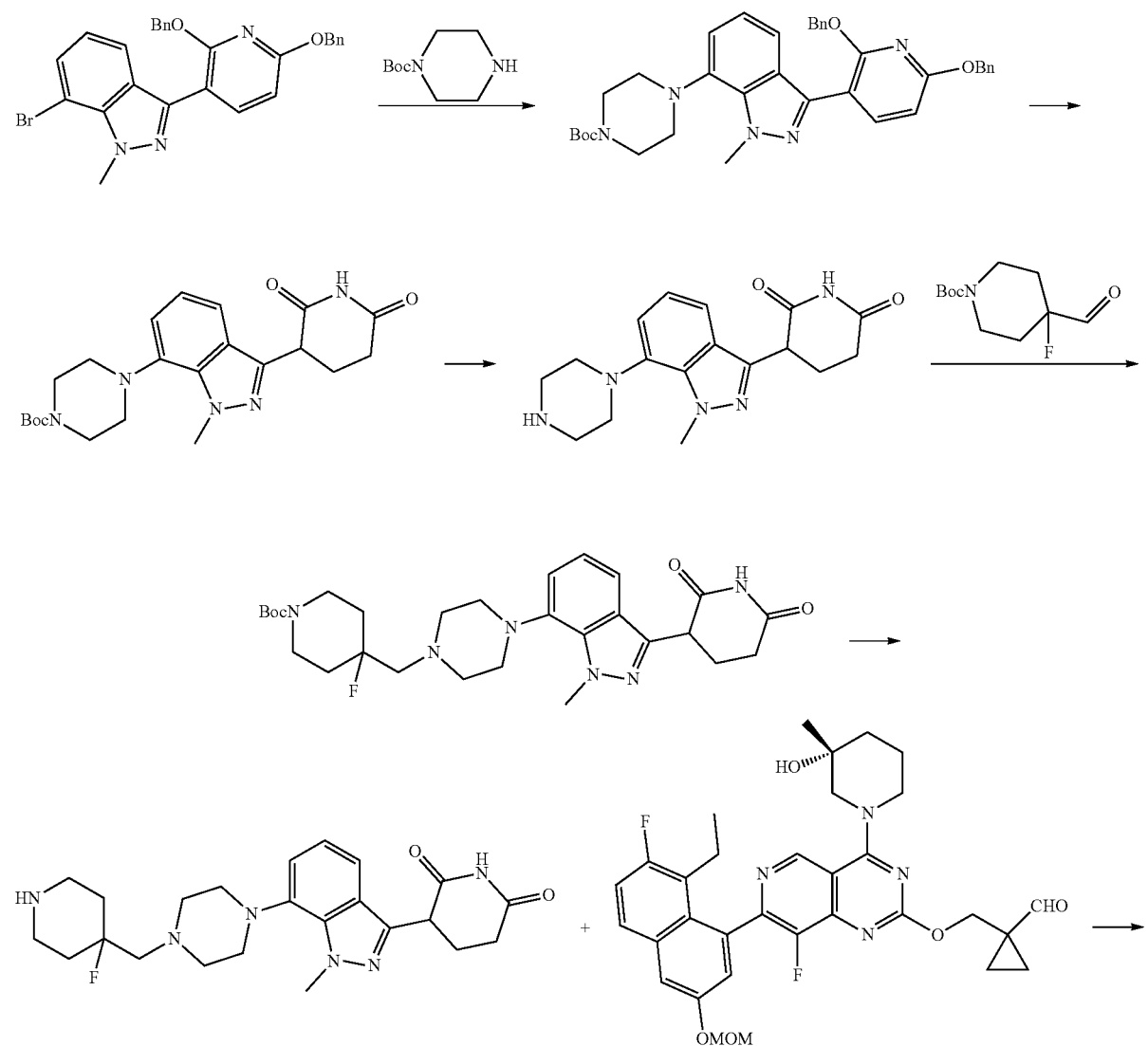

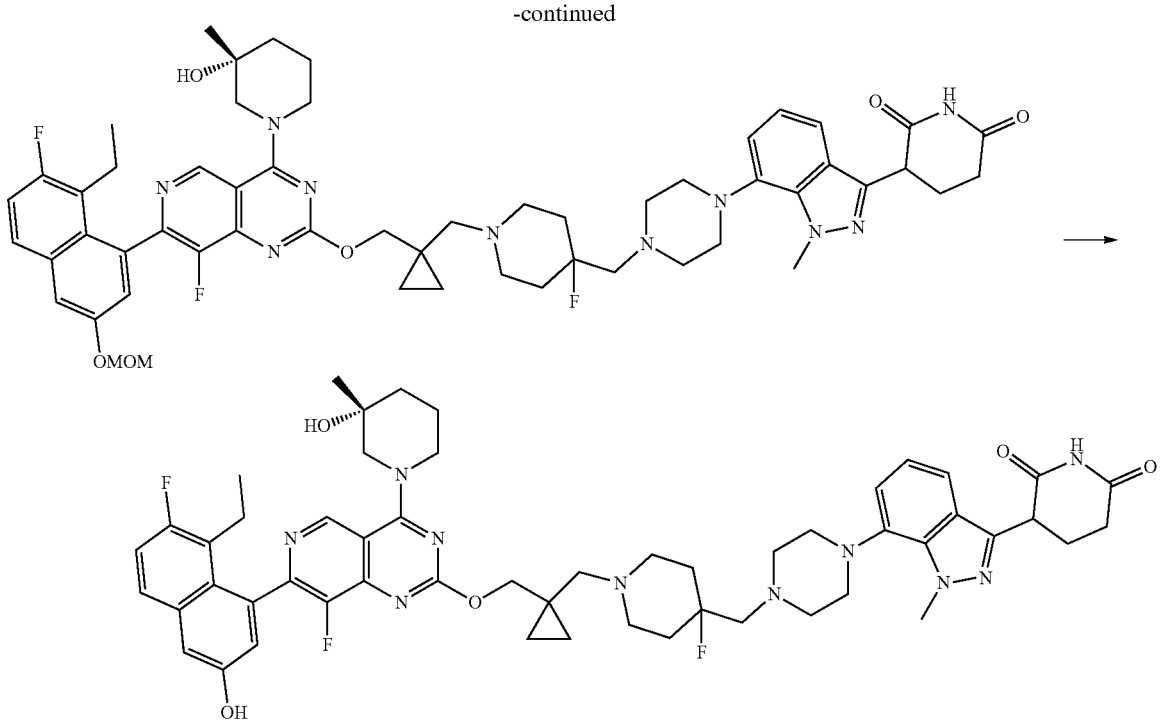

67

Step 1: Preparation of tert-butyl 4-(3-(2,6-bis(benzyloxy)pyridin-3-yl)-1-methyl-1H-indazol-7-yl)piperazine-1-carboxylate To a solution 3-(2,6-bis(benzyloxy)pyridin-3-yl)-7-bromo-1-methyl-1H-indazole prepared according to the procedure described in WO2021262812 (page 48) (500 mg, 1.0 mmol) in dioxane (20 mL) was added tert-butyl piperazine-1-carboxylate (187 mg, 1.0 mmol), Pd$_2$(dba)$_3$ (183 mg, 0.2 mmol), X-PHOS (190 mg, 0.4 mmol) and Cs$_2$CO$_3$ (977 mg, 3.0 mmol). The mixture was stirred at 90° C. for 16 hours under argon atmosphere. After cooling down to room temperature, the reaction was quenched with water (20 mL) and extracted with EA (20 mL×3). The organic phase was washed with brine and dried over Na$_2$SO$_4$. The solution was concentrated in vacuum and the residue was purified by Prep-TLC (PE:EA=3:1) to give the desired compound (590 mg, 97.3% yield) as a white solid. LC/MS: 606.3 [M+H]$^+$.

Step 2: Preparation of tert-butyl 4-(3-(2,6-dioxopiperidin-3-yl)-1-methyl-1H-indazol-7-yl)piperazine-1-carboxylate To a solution of 3-(2,6-bis(benzyloxy)pyridin-3-yl)-7-bromo-1-methyl-1H-indazole (500 mg, 0.82 mmol) in THF (20 mL) was added Pd/C (880 mg, 10%, 0.82 mmol) and Pd(OH)$_2$ (116 mg, 0.82 mmol). The mixture was stirred at room temperature for 1 hour under hydrogen atmosphere (0.4 MPa). The catalyst was filtered off and the filtrate was concentrated in vacuum to give the title compound (70 mg, 19.8% yield). LC/MS: 428.2 [M+H]$^+$.

Step 3: Preparation of 3-(1-methyl-7-(piperazin-1-yl)-1H-indazol-3-yl)piperidine-2,6-dione A solution of tert-butyl 4-(3-(2,6-dioxopiperidin-3-yl)-1-methyl-1H-indazol-7-yl)piperazine-1-carboxylate (70 mg, 0.16 mmol) in HCl/dioxane (4 M, 5 mL) and DCM (5 mL) was stirred at 25° C. for 0.5 hour. The mixture was concentrated in vacuum to afford the desired compound (50 mg, 93.3% yield) as a white solid. LC/MS: 328.2 [M+H]$^+$.

Step 4: Preparation of tert-butyl 4-((4-(3-(2,6-dioxopiperidin-3-yl)-1-methyl-1H-indazol-7-yl)piperazin-1-yl)methyl)-4-fluoropiperidine-1-carboxylate To a solution of 3-(1-methyl-7-(piperazin-1-yl)-1H-indazol-3-yl)piperidine-2,6-dione (50 mg, 0.15 mmol) and tert-butyl 4-fluoro-4-formylpiperidine-1-carboxylate (35 mg, 0.15 mmol) in DCM (5 mL) was added DIEA (197 mg, 1.53 mmol) and STAB (162 mg, 0.76 mmol). The mixture was stirred at 45° C. for 1 hour. The reaction mixture was quenched with water (20 mL) and extracted with EA (20 mL×3). The organic phase was washed with brine, dried over Na$_2$SO$_4$ and concentrated in vacuum. The residue was purified by Prep-TLC (PE:EA=3:1) to give the desired compound (80 mg, 96.5% yield) as a white solid. LC/MS: 543.3 [M+H]$^+$.

Step 5: Preparation of 3-(7-{4-[(4-fluoropiperidin-4-yl)methyl]piperazin-1-yl}-1-methylindazol-3-yl)piperidine-2,6-dione A solution of tert-butyl 4-((4-(3-(2,6-dioxopiperidin-3-yl)-1-methyl-1H-indazol-7-yl)piperazin-1-yl)methyl)-4-fluoropiperidine-1-carboxylate (80 mg, 0.18 mmol) in HCl/dioxane (4 M, 5 mL) and DCM (5 mL) was stirred at 25° C. for 0.5 hour. The mixture was concentrated in vacuum to afford the desired compound (50 mg, 81.6% yield) as a white solid. LC/MS: 443.2 [M+H]$^+$.

Step 6: Preparation of 3-(7-(4-((1-((1-(((7-(8-ethyl-7-fluoro-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-4-fluoropiperidin-4-yl)methyl)piperazin-1-yl)-1-methyl-1H-indazol-3-yl)piperidine-2,6-dione To a solution of 3-(7-{4-[(4-fluoropiperidin-4-yl)methyl]piperazin-1-yl}-1-methylindazol-3-yl) piperidine-2,6-dione (50 mg, 0.11 mmol) and (R)-1-(((7-(8-ethyl-7-fluoro-3-(methoxymethoxy)naphthalen-1-yl)-8-fluoro-4-(3-hydroxy-3-methylpiperidin-1-yl)pyrido[4,3-d]pyrimidin-2-yl)oxy)methyl)cyclopropane-1-carbaldehyde (134 mg, 0.23 mmol) in DCM/DMA (5 mL, 4/1) was added DIEA (146 mg, 1.13 mmol), MgSO₄ (68 mg, 0.57 mmol) and STAB (120 mg, 0.57 mmol). The mixture was stirred at room temperature for 1 hour. The reaction mixture was poured into water (10 mL) and extracted with DCM (10 mL×3). The combined organic layer was dried over Na₂SO₄ and concentrated in vacuum. The residue was purified by Prep-TLC (DCM:MeOH=10:1) to give the desired compound (25 mg, 21.7% yield) as a yellow solid. LC/MS: 1019.4 [M+H]⁺.

Step 7: Preparation of 3-(7-(4-((1-((1-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)cyclopropyl) methyl)-4-fluoropiperidin-4-yl)methyl)piperazin-1-yl)-1-methyl-1H-indazol-3-yl)piperidine-2,6-dione (Compound 67)

A solution of 3-(7-(4-((1-((1-(((7-(8-ethyl-7-fluoro-3-(methoxymethoxy)naphthalen-1-yl)-8-fluoro-4-((R)-3-hydroxy-3-methylpiperidin-1-yl)pyrido[4,3-d]pyrimidin-2-yl)oxy)methyl)cyclopropyl)methyl)-4-fluoropiperidin-4-yl)methyl)piperazin-1-yl)-1-methyl-1H-indazol-3-yl) piperidine-2,6-dione (30 mg, 0.03 mmol) in DCM/TFA (4 mL, 3/1) was stirred at room temperature for 0.5 hour. The reaction mixture was quenched with saturated NaHCO₃ solution (10 mL) at 0° C. and extracted with EA (10 mL×3). The solution was concentrated in vacuum to give a crude compound. The crude product was purified by Prep-HPLC (0.1% TFA in H₂O/ACN=10% to 40%) to give the desired product (13.2 mg, 45.2% yield). LC/MS: 975.3 [M+H]⁺; ¹H NMR (400 MHZ, DMSO) δ 11.09 (s, 1H), 10.45-9.85 (m, 1H), 9.56-9.33 (m, 1H), 9.26 (s, 1H), 7.77 (dd, J=9.0, 6.0 Hz, 1H), 7.40-7.30 (m, 2H), 7.20-7.10 (m, 1H), 7.02 (d, J=2.3 Hz, 1H), 6.88 (t, J=7.7 Hz, 1H), 6.56-6.43 (m, 1H), 4.70 (d, J=8.0 Hz, 1H), 4.45-4.30 (m, 6H), 4.15-4.05 (m, 5H), 3.78-3.72 (m, 2H), 3.63 (d, J=13.1 Hz, 2H), 3.55-3.35 (m, 4H), 3.30-3.10 (m, 4H), 2.85-2.75 (m, 1H), 2.65-2.53 (m, 2H), 2.45-2.25 (m, 4H), 2.24-1.95 (m, 6H), 1.75-1.60 (m, 3H), 1.18 (d, J=10.4 Hz, 3H), 0.95-0.80 (m, 4H), 0.79-0.69 (m, 4H).

Example 62: Preparation of (S)-3-(5-(4-((7-((1-(((7-(8-ethyl-7-fluoro-3-hydroxynaphthalen-1-yl)-8-fluoro-4-((S)-1-oxa-6-azaspiro[3.5]nonan-6-yl)pyrido[4,3-d]pyrimidin-2-yl)oxy)methyl)cyclopropyl)methyl)-2-fluoro-7-azaspiro[3.5]nonan-2-yl)methyl)piperazin-1-yl)-1-oxoisoindolin-2-yl)piperidine-2,6-dione (Compound 214)

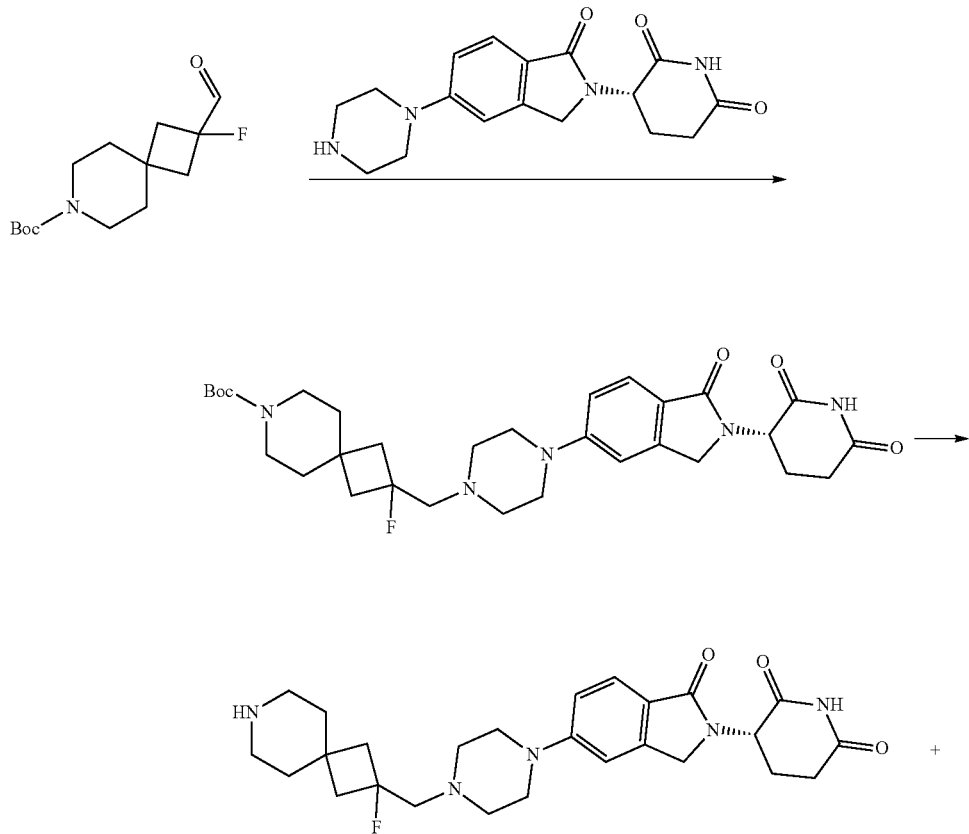

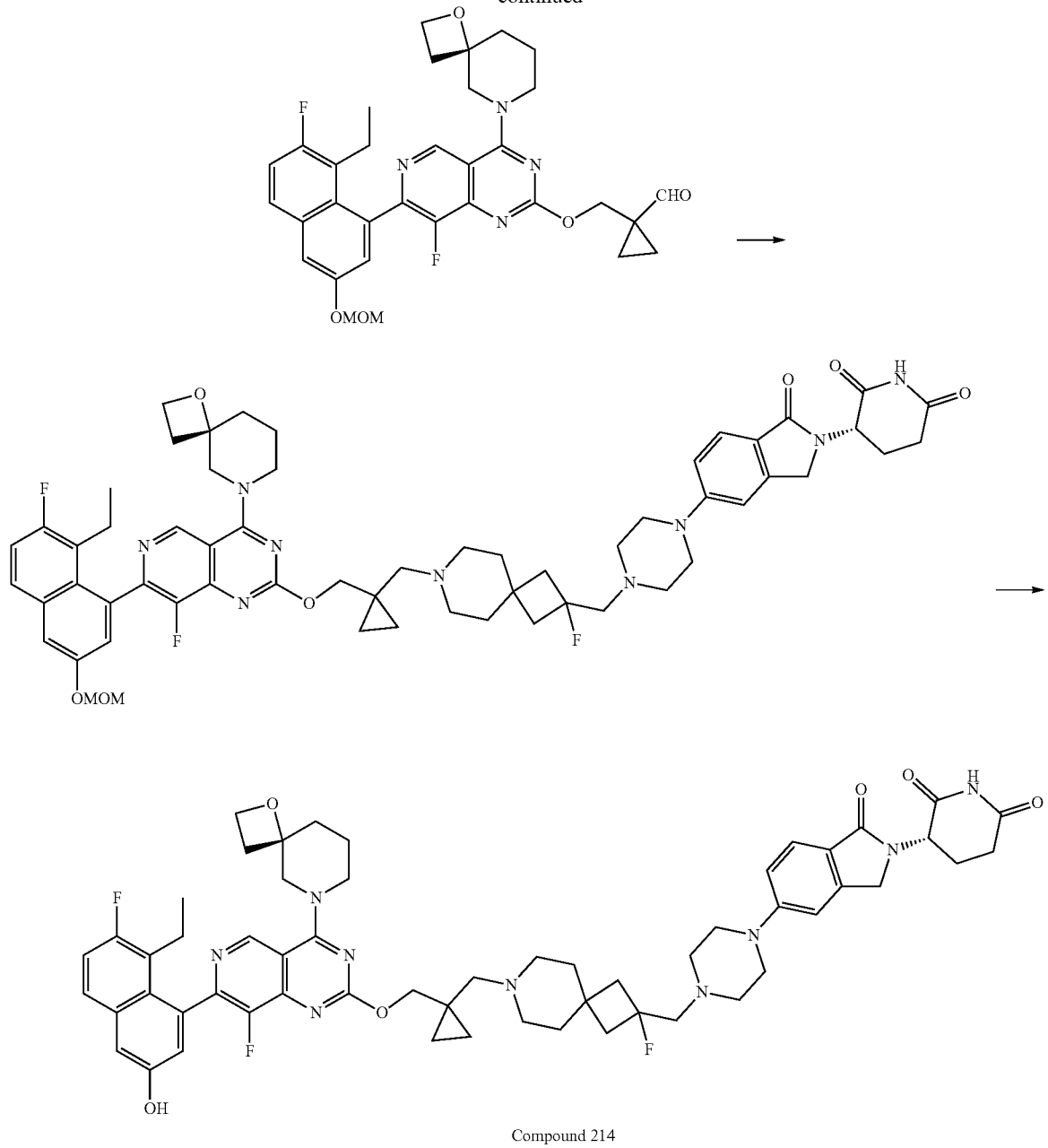

Compound 214

Step 1: Preparation of tert-butyl (S)-2-((4-(2-(2,6-dioxopiperidin-3-yl)-1-oxoisoindolin-5-yl)piperazin-1-yl)methyl)-2-fluoro-7-azaspiro[3.5]nonane-7-carboxylate To a solution of tert-butyl 2-fluoro-2-formyl-7-azaspiro[3.5]nonane-7-carboxylate (500 mg, 1.836 mmol) in DMA (10 mL) was added (S)-3-(1-oxo-5-(piperazin-1-yl)isoindolin-2-yl)piperidine-2,6-dione (783.74 mg, 2.387 mmol) and NaOAc (602.46 mg, 7.344 mmol). The mixture was stirred at room temperature for 1 hour. NaBH$_3$CN was added and the mixture was stirred at room temperature for 16 hours. The reaction mixture was quenched with water (20 mL) and extracted with EA (20 mL×3). The organic phase was washed with brine and dried over Na$_2$SO$_4$. The solution was concentrated in vacuum and the residue was purified by flash chromatography on silica gel with EA:PE=1:1 to afford the desired compound (430 mg, 38.1% yield) as a yellow solid. LC/MS: 584.4 [M+H]$^+$.

Step 2: Preparation of (S)-3-(5-(4-((2-fluoro-7-azaspiro[3.5]nonan-2-yl)methyl)piperazin-1-yl)-1-oxoisoindolin-2-yl)piperidine-2,6-dione To a solution of tert-butyl (S)-2-((4-(2-(2,6-dioxopiperidin-3-yl)-1-oxoisoindolin-5-yl)piperazin-1-yl)methyl)-2-fluoro-7-azaspiro[3.5]nonane-7-carboxylate (430 mg, 0.7354 mmol) in TFA (2 mL) and DCM (4 mL) was stirred at room temperature for 1 hour. The solution was concentrated in vacuum to afford the desired compound (450 mg, crude, TFA salt) as a brown solid. LC/MS: 484.2 [M+H]$^+$.

Step 3: Preparation of (S)-3-(5-(4-((7-((1-(((7-(8-ethyl-7-fluoro-3-(methoxymethoxy)naphthalen-1-yl)-8-fluoro-4-((S)-1-oxa-6-azaspiro[3.5]nonan-6-yl)pyrido[4,3-d]pyrimidin-2-yl)oxy)methyl)cyclopropyl)methyl)-2-fluoro-7-azaspiro[3.5]nonan-2-yl)methyl)piperazin-1-yl)-1-oxoisoindolin-2-yl)piperidine-2,6-dione To a solution of (S)-3-(5-(4-((2-fluoro-7-azaspiro[3.5]nonan-2-yl)methyl)piperazin-1-yl)-1-oxoisoindolin-2-yl)piperidine-2,6-dione (120 mg, 0.2481 mmol), (S)-1-(((7-(8-ethyl-7-fluoro-3-(methoxymethoxy)naphthalen-1-yl)-8-fluoro-4-(1-oxa-6-azaspiro[3.5]nonan-6-yl)pyrido[4,3-d]pyrimidin-2-yl)oxy)methyl)cyclopropane-1-carbaldehyde (50 mg, 0.0827 mmol) and DIEA (53.44 mg, 0.4135 mmol) in DMA (5 mL) was stirred at room temperature for 1 hour. STAB (87.64 mg, 0.4135 mmol) was added and the mixture was stirred at 45° C. for 16 hours. The reaction mixture was quenched with water (10 mL) and extracted with EA (10 mL×3). The organic phase was washed with brine and dried over $Na_2SO_4$. The solution was concentrated in vacuum and the residue was purified by Prep-TLC (DCM:MeOH=10:1) to give the desired compound (70 mg, 79.01% yield) as a yellow solid. LC/MS: 1073.3 $[M+H]^+$.

Step 4: Preparation of (S)-3-(5-(4-((7-((1-(((7-(8-ethyl-7-fluoro-3-hydroxynaphthalen-1-yl)-8-fluoro-4-((S)-1-oxa-6-azaspiro[3.5]nonan-6-yl)pyrido[4,3-d]pyrimidin-2-yl)oxy)methyl)cyclopropyl)methyl)-2-fluoro-7-azaspiro[3.5]nonan-2-yl)methyl)piperazin-1-yl)-1-oxoisoindolin-2-yl)piperidine-2,6-dione (Compound 214)

To a solution of (S)-3-(5-(4-((7-((1-(((7-(8-ethyl-7-fluoro-3-(methoxymethoxy)naphthalen-1-yl)-8-fluoro-4-((S)-1-oxa-6-azaspiro[3.5]nonan-6-yl)pyrido[4,3-d]pyrimidin-2-yl)oxy)methyl)cyclopropyl)methyl)-2-fluoro-7-azaspiro[3.5]nonan-2-yl)methyl)piperazin-1-yl)-1-oxoisoindolin-2-yl)piperidine-2,6-dione (70 mg, 0.0653 mmol) in DCM (2 mL) was added TFA (1 mL). The mixture was stirred at room temperature for 1 hour. The solution was concentrated in vacuum to give a crude compound. The crude product was purified by Prep-HPLC (0.1% FA in $H_2O$/ACN=10~40%) to give the desired product (21.5 mg, 33.5% yield). LC/MS: 1029.3 $[M+H]^+$.

$^1$H NMR (400 MHZ, DMSO-$d_6$) δ 10.91 (s, 1H), 9.97-9.82 (m, 1H), 9.23-9.15 (m, 1H), 8.10 (s, 1H), 7.73 (dd, J=9.2, 6.1 Hz, 1H), 7.48 (d, J=8.9 Hz, 1H), 7.31 (dd, J=11.2, 6.0 Hz, 2H), 7.05-6.97 (m, 3H), 5.01 (dd, J=13.1, 5.1 Hz, 1H), 4.51-4.09 (m, 8H), 3.84 (dd, J=42.5, 13.0 Hz, 1H), 3.23 (s, 6H), 2.92-2.81 (m, 1H), 2.67-2.50 (m, 11H), 2.42-2.23 (m, 5H), 2.08 (t, J=14.8 Hz, 4H), 1.99-1.76 (m, 5H), 1.59 (d, J=41.5 Hz, 5H), 0.70 (q, J=6.9 Hz, 5H), 0.48 (s, 2H).

The following compounds were prepared according the general schemes 1-3 with similar methods as described in examples 1-62: Compound #7, 9, 10, 11, 13, 14, 15, 16, 17, 18, 20, 21, 22, 23, 25, 26, 27, 28, 30, 31, 32, 35, 37, 38, 39, 46, 49, 50, 57, 58, 59, 60, 61, 62, 63, 64, 65, 66, 68, 69, 72, 76, 84, 85, 86, 214, 215, 216, 217, 218, 219, 220. All of them showed purity higher than 95% based on LC/MS and HPLC analysis. The corresponding data of LC/MS and $^1$H-NMR are listed below.

| Cpd # | Characterization |
|---|---|
| 7 | LC/MS: 944.30 $[M + H]^+$;<br>1H NMR (400 MHz, DMSO) δ 10.95 (s, 1H), 9.93 (s, 1H), 9.22 (s, 1H), 8.16 (s, 1H), 7.79-7.74 (m, 1H), 7.51 (d, J = 9.0 Hz, 1H), 7.36-7.31 (m, 2H), 7.03 (s, 3H), 5.04 (dd, J = 13.2, 5.1 Hz, 1H), 4.75 (d, J = 8.1 Hz, 1H), 4.39-4.26 (m, 5H), 4.19 (d, J = 17.1 Hz, 1H), 4.06-3.98 (m, 1H), 3.23 (s, 4H), 3.05-2.96 (m, 2H), 2.95-2.82 (m, 2H), 2.58 (s, 7H), 2.19 (s, 2H), 2.07-1.79 (m, 5H), 1.70 (s, 6H), 1.40-1.31 (m, 2H), 1,17 (d, J = 9.4 Hz, 3H), 0.77-0.71 (m, 3H), 0.65 (s, 2H), 0.41 (s, 2H). |
| 9 | LC/MS: 985.50 $[M + H]^+$;<br>1H NMR (400 MHz, DMSO) δ 10.96 (s, 1H), 9.21 (d, J = 1,9 Hz, 1H), 8.32 (s, 3H), 7.76 (dd, J = 8.9, 6.1 Hz, 1H), 7.51 (d, J = 8.9 Hz, 1H), 7.34 (dd, J = 12.3, 5.9 Hz, 2H), 7.05-7.01 (m, 2H), 5.05 (dd, J = 13.2, 4.9 Hz, 1H), 4.32 (d, J = 16.7 Hz, 2H), 4.21 (s, 2H), 4.05 (dd, J = 19.5, 13.2 Hz, 2H), 3.61 (d, J = 13.2 Hz, 1H), 3.52-3.49 (m, 1H), 3.39-3.34 (m, 1H), 3.28-3.14 (m, 9H), 2.90-2.77 (m, 5H), 2.63-2.53 (m, 3H), 2.48-2.38 (m, 8H), 2.37-2.30 (m, 2H), 2.15-1.92 (m, 3H), 1.73-1.62 (m, 3H), 1.16 (d, J = 9.3 Hz, 3H), 0.77-0.70 (m, 3H), 0.56-0.49 (m, 2H), 0.46-0.39 (m, 2H). |
| 10 | LC/MS: 958.30 $[M + H]^+$;<br>1H NMR (400 MHz, DMSO) δ 10.94 (s, 1H), 9.94 (d, J = 3.1 Hz, 1H), 9.21 (s, 1H), 7.76 (dd, J = 9.1, 6.0 Hz, 1H), 7.48 (d, J = 8.8 Hz, 1H), 7.38-7.34 (m, 1H), 7.33-7.32 (m, 1H), 7.05-7.01 (m, 3H), 5.03 (dd, J = 12.9, 4.7 Hz, 1H), 4.74 (d, J = 4.8 Hz, 1H), 4.35-4.25 (m, 4H), 4.21-4.14 (m, 1H), 4.08-3.99 (m, 1H), 3.85 (d, J = 11.7 Hz, 2H), 3.68-3.45 (m, 1H), 2.92-2.85 (m, 1H), 2.79 (t, J = 11.5 Hz, 2H), 2.38-2.27 (m, 8H), 2.18-2.10 (m, 3H), 2.07 (s, 3H), 2.00-1.87 (m, 3H), 1.75-1.64 (m, 6H), 1.16 (d, J = 9.6 Hz, 5H), 0.88-0.78 (m, 2H), 0.76-0.70 (m, 3H), 0.67-0.61 (m, 2H), 0.46-0.37 (m, 2H). |
| 11 | LC/MS: 970.30 $[M + H]^+$;<br>1H NMR (400 MHz, DMSO) δ 10.97 (s, 1H), 10.06-9.86 (m, 3H), 9.27 (s, 1H), 7.77 (d, J = 11.2, 7.6 Hz, 1H), 7.60 (d, J = 8.4 Hz, 1H), 7.40-7.33 (m, 2H), 7.17-7.11 (m, 2H), 7.02 (d, J = 2.4 Hz, 1H), 5.07 (dd, J = 13.2, 5.2 Hz, 1H), 4.38-4.32 (m, 2H), 4.26-4.20 (m, 3H), 4.17-4.13 (m, 2H), 4.09-3.95 (m, 6H), 3.66-3.62 (m, 1H), 3.56-3.51 (m, 1H), 3.49-3.32 (m, 4H), 3.29-3.24 (m, 2H), 3.21-3.01 (m, 7H), 2.94-2.87 (m, 1H), 2.67-2.55 (m, 2H), 2.37-2.28 (m, 3H), 2.15-2.05 (m, 2H), 2.01-1.90 (m, 3H), 1.74-1.65 (m, 3H), 1.18 (d, J = 9.6 Hz, 3H), 0.78-0.71 (m, 6H). |
| 13 | LC/MS: 974.30 $[M + H]^+$;<br>1H NMR (400 MHz, DMSO) δ 10.95 (s, 1H), 9.21 (d, J = 4.4 Hz, 1H), 8.21 (s, 1H), 7.76 (dd, J = 9.2, 6.4 Hz, 1H), 7.50 (d, J = 8.4 Hz, 1H), 7.37-7.29 (m, 2H), 7.06- |

| Cpd # | Characterization |
|---|---|
| | 6.96 (m, 3H), 5.05 (dd, J = 13.2, 5.2 Hz, 1H), 4.38-4.25 (m, 4H), 4.21-4.16 (m, 1H), 4.11-3.97 (m, 2H), 3.65-3.57 (m, 1H), 3.54-3.47 (m, 1H), 3.38-3.29 (m, 6H), 3.25-3.18 (m, 4H), 2.91-2.85 (m, 1H), 2.69-2.57 (m, 5H), 2.41-2.20 (m, 8H), 2.01-1.90 (m, 2H), 1.74-1.62 (m, 3H), 1.53-1.43 (m, 3H), 1.16 (d, J = 10.0 Hz, 3H), 0.73 (q, J = 6.8 Hz, 2H), 0.64 (s, 2H), 0.41 (s, 2H). |
| 14 | LC/MS: 903.50 [M + H]$^+$;<br>1H NMR (400 MHz, DMSO) δ 10.77 (s, 1H), 9.22 (d, J = 1.6 Hz, 1H), 8.19 (s, 1H), 7.76 (dd, J = 9.0, 6.0 Hz, 1H), 7.34 (dd, J = 12.4, 6.0 Hz, 2H), 7.04 (d, J = 8.8 Hz, 3H), 6.87 (d, J = 8.7 Hz, 2H), 4.37-4.25 (m, 3H), 4.04 (dd, J = 21.4, 13.4 Hz, 1H), 3.74-3.70 (m, 1H), 3.63 (d, J = 13.3 Hz, 1H), 3.52 (d, J = 13.2 Hz, 1H), 3.43-3.32 (m, 2H), 3.14-3.04 (m, 4H), 3.02-2.95 (m, 2H), 2.68-2.59 (m, 1H), 2.47 (d, J = 5.1 Hz, 1H), 2.46-2.41 (m, 4H), 2.39-2.29 (m, 3H), 2.19-2.06 (m, 4H), 2.05-1.88 (m, 4H), 1.71-1.62 (m, 4H), 1.50 (s, 1H), 1.17 (d, J = 9.7 Hz, 3H), 1.12-1.01 (m, 2H), 0.74 (q, J = 7.1 Hz, 3H), 0.68-0.61 (m, 2H), 0.46-0.37 (m, 2H). |
| 15 | LC/MS: 896.40 [M + H]$^+$;<br>1H NMR (400 MHz, DMSO) δ 10.95 (s, 1H), 9.59 (s, 1H), 8.24 (s, 1H), 7.67 (d, J = 8.0 Hz, 1H), 7.51 (d, J = 8.4 Hz, 1H), 7.36 (t, J = 7.6 Hz, 1H), 7.28 (d, J = 2.8 Hz, 1H), 7.12 (d, J = 6.8 Hz, 1H), 7.06-7.02 (m, 2H), 7.01 (d, J = 2.8 Hz, 1H), 5.05 (dd, J = 13.2, 5.2 Hz, 1H), 4.34-4.18 (m, 4H), 3.67-3.62 (m, 2H), 3.33 (s, 3H), 3.27-3.23 (m, 4H), 3.00-2.83 (m, 4H), 2.47-2.42 (m, 4H), 2.39-2.16 (m, 6H), 2.12 (d, J = 7.2 Hz, 2H), 1.99-1.94 (m, 1H), 1.89-1.80 (m, 2H), 1.68-1.61 (m, 2H), 1.50-1.44 (m, 1H), 1.05-0.97 (m, 3H), 0.83 (t, J = 7.6 Hz, 4H), 0.71-0.61 (m, 3H), 0.40 (s, 2H). |
| 16 | LC/MS: 883.30 [M + H]$^+$;<br>1HNMR (400 MHz, ) δ 10.94 (s, 1H), 9.89 (s, J = 22.0 Hz, 1H), 9.21 (d, J = 8.6 Hz. 1H), 8.16 (s, 1H), 7.67 (d, J = 8.0 Hz, 1H), 7.48 (d, J = 8.6 Hz, 1H), 7.39-7.34 (m, 1H), 7.29 (d, J = 3.8 Hz, 1H), 7.12 (d, J = 7.0 Hz, 1H), 7.05-6.99 (m, 2H), 6.98 (d, J = 2.6 Hz, 1H), 5.03 (dd, J = 13.3, 5.0 Hz, 1H), 4.74 (d, J = 19.2 Hz, 1H), 4.37-4.14 (m, 5H), 4.10-3.98 (m, 1H), 3.63-3.51 (m, 1H), 3.25 (s, 7H), 3.10 (s, 4H), 2.95-2.85 (m, 1H), 2.62-2.57 (m, 1H), 2.35 (dd, J = 14.6, 3.7 Hz, 1H), 2.31-2.14 (m, 2H), 2.08-1.90 (m, 2H), 1.70 (dd, J = 32.8, 8.5 Hz, 7H), 1.17 (d, J = 11.0 Hz, 3H), 0.82 (td, J = 7.4, 5.0 Hz, 3H), 0.60-0.46 (m, 4H). |
| 17 | LC/MS: 951.60 [M + H]$^+$;<br>1H NMR (400 MHz, DMSO) δ 10.94 (s, 1H), 9.20 (d, J = 9.6 Hz, 1H), 8.27 (s, 1H), 7.66 (d, J = 7.6 Hz, 1H), 7.48 (d, J = 8.0 Hz, 1H), 7.36 (t, J = 7.6 Hz, 1H), 7.28 (d, J = 2.4 Hz, 1H), 7.12 (d, J = 6.8 Hz, 1H), 7.07-7.0 (m, 2H), 6.98 (d, J = 2.4 Hz, 1H), 5.03 (dd, J = 13.2, 5.2 Hz, 1H), 4.85-4.71 (m, 1H), 4.36-4.17 (m, 5H), 4.08-4.00 (m, 1H), 3.61 (d, J = 13.2 Hz, 1H), 3.52 (d, J = 13.2 Hz, 1H), 3.29-3.16 (m, 6H), 2.97 (s, 4H), 2.83-2.76 (m, 2H), 2.58 (d, J = 7.6 Hz, 2H), 2.40 (s, 2H), 2.38-2.32 (m, 2H), 2.30-2.12 (m, 3H), 2.04-1.96 (m, 2H), 1.81-1.59 (m, 7H), 1.17 (d, J = 10.8 Hz, 3H), 0.85-0.80 (m, 3H), 0.53 (s, 2H), 0.43 (s, 2H). |
| 18 | LC/MS: 966.40 [M + H]$^+$;<br>1H NMR (400 MHz, DMSO) δ 10.94 (s, 1H), 9.20 (d, J = 8.2 Hz, 1H), 8.20 (s, 2H), 7.66 (d, J = 8.0 Hz, 1H), 7.48 (d, J = 9.1 Hz, 1H), 7.38-7.33 (m, 1H), 7.29-7.25 (m, 1H), 7.12 (d, J = 7.0 Hz, 1H), 7.05-6.94 (m, J = 17.1 Hz, 3H), 5.08-5.01 (m, 1H), 4.32-4.21 ( m, 4H), 4.23-4.12 (m, H), 4.08-3.96 (m, 2H), 3.64-3.54 (m, 2H), 3.24-3.19 (m, 4H), 2.95 (s, 3H), 2.62-2.53 (m, 2H), 2.39-2.32 (m, 4H), 2.20-2.14 (m, 2H), 2.10-1.88 (m, 6H), 1.72-1.67 (m, 4H), 1.23 (s, 6H), 1.16 (d, J = 10.9 Hz, 3H), 0.86-0.77 (m, 4H), 0.62 (s, 2H), 0.41 (s, 2H). |
| 20 | LC/MS: 983.30 [M + H]$^+$;<br>1H NMR (400 MHz, DMSO) δ 10.96 (s, 1H), 9.96 (s, 1H), 9.22 (s, 1H), 7.76 (d, J = 6.2 Hz, 1H), 7.51 (d, J = 8.3 Hz, 1H), 7.41-7.27 (m, 2H), 7.14-6.92 (m, 3H), 5.05 (d, J = 8.5 Hz, 1H), 4.74 (d, J = 5.5 Hz, 1H), 4.41-4.26 (m, 4H), 4.25-4.17 (m, 1H), 4.09-3.99 (m, 1H), 3.61 (d, J = 13.2 Hz, 1H), 3.51 (d, J = 12.9 Hz, 1H), 3.25 (s, 4H), 3.09-2.80 (m, 4H), 2.69 (s, 4H), 2.59-2.54 (m, 2H), 2.45-2.27 (m, 4H), 2.25-1.91 (m, 7H), 1.90-1.81 (m, 2H), 1.67 (s, 3H), 1.48 (s, 2H), 1.17 (d, J = 9.0 Hz, 3H), 0.80-0.58 (m, 5H). |
| 21 | LC/MS: 958.50 [M + H]$^+$;<br>1H NMR (400 MHz, DMSO) δ 10.78 (s, 1H), 9.21 (s, 1H), 8.20 (s, 2H), 7.77 (dd, J = 8.9, 6.1 Hz, 1H), 7.35 (dd, J = 12.6, 5.8 Hz, 2H), 7.04 (dd, J = 5.5, 2.7 Hz, 3H), 6.87 (d, J = 8.6 Hz, 2H), 4.35-4.25 (m, 3H), 4.04 (dd, J = 21.4, 13.3 Hz, 1H), 3.74-3.70 (m, 1H), 3.64-3.62 (m, 1H), 3.59-3.55 (m, 2H), 3.53-3.50 (m, 1H), 3.38-3.34 (m, 2H), 3.11-3.02 (m, 7H), 2.90 (s, 2H), 2.70-2.59 (m, 3H), 2.47-2.43 (m, 4H), 2.39-2.29 (m, 4H), 2.13 (dd, J = 19.9, 10.6 Hz, 2H), 2.05-1.90 (m, 4H), 1.74-1.62 (m, 5H), 1.24-1.16 (m, 5H), 0.77-0.72 (m, 3H), 0.68-0.62 (m, 2H), 0.46-0.38 (m, 2H). |
| 22 | LC/MS: 967.40 [M + H]$^+$;<br>1H NMR (400 MHz, DMSO) δ 10.95 (s, 1H), 9.20 (d, J = 8.4 Hz, 1H), 8.23 (s, 1H), 7.66 (d, J = 8.0 Hz, 1H), 7.48 (d, J = 8.9 Hz, 1H), 7.36 (t, J = 7.6 Hz, 1H), 7.28 (d, J = 2.3 Hz, 1H), 7.12 (d, J = 7.2 Hz, 1H), 7.02 (s, 2H), 6.97 (d, J = 2.4 Hz, 1H), 5.03 (dd, J = 13.2, 5.2 Hz, 1H), 4.35-4.22 (m, 4H), 4.17 (d, J = 17.4 Hz, 1H), 4.08-3.97 (m, 1H), 3.61 (d, J = 13.7 Hz, 2H), 3.52-3.46 (s, 2H), 3.22 (s, 4H), 2.95 (s, 3H), 2.88 (d, J = 11.9 Hz, 1H), 2.57 (d, J = 12.6 Hz, 2H), 2.37-2.31 (m, 4H), 2.21-2.14 (m, 2H), 2.04-1.90 (m, 4H), 1.83-1.62 (m, 9H), 1.32-1.24 (m, 2H), 1.16 (d, J = 10.7 Hz, 3H), 0.88-0.78 (m, 4H), 0.61 (s, 2H), 0.41 (s, 2H). |

-continued

| Cpd # | Characterization |
|---|---|
| 23 | LC/MS: 970.30 [M + H]⁺;<br>1H NMR (400 MHz, DMSO) δ 10.95 (s, 1H), 9.97 (s, 1H), 9.22 (d, J = 5.0 Hz, 1H), 8.19 (s, 1H), 7.77 (dd, J = 9.1, 6.0 Hz, 1H), 7.51 (d, J = 8.5 Hz, 1H), 7.35 (d, J = 12.8, 6.1 Hz, 2H), 7.08-7.01 (m, 3H), 5.05 (dd, J = 13.2, 4.8 Hz, 1H), 4.46-4.17 (m, 8H), 3.94-3.79 (m, 1H), 3.50 (s, 1H), 3.25 (s, 4H), 3.00-2.84 (m, J = 25.8 Hz, 4H), 2.60 (s, 1H), 2.44 (s, 5H), 2.39-2.30 (m, 4H), 2.11 (d, J = 7.6 Hz, 4H), 1.95 (s, 1H), 1.85 (d, J = 8.4 Hz, 4H), 1.73 (s, 1H), 1.67-1.60 (m, 2H), 1.50-1.44 (m, 1H), 1.04 (s, 2H), 0.74 (d, J = 6.3 Hz, 3H), 0.65 (s, 2H), 0.41 (s, 2H). |
| 25 | LC/MS: 988.50 [M + H]⁺;<br>1H NMR (400 MHz, DMSO) δ 10.96 (s, 1H), 9.29-9.24 (m, 1H), 7.80-7.76 (m, 1H), 7.55 (d, J = 8.4 Hz, 1H), 7.39-7.34 (m, 2H), 7.12-7.08 (m, 2H), 7.06-6.95 (m, 2H), 5.06 (dd, J = 13.2, 5.2 Hz, 2H), 4.59-4.51 (m, 2H), 4.37-4.30 (m, 5H), 4.24-4.18 (m, 3H), 3.87-3.81 (m, 2H), 3.77-3.71 (m, 3H), 3.58-3.51 (m, 3H), 3.38-3.30 (m, 5H), 3.24-3.20 (m, 2H), 3.16-3.10 (m, 2H), 2.94-2.86 (m, 3H), 2.69-2.65 (m, 1H), 2.45-2.28 (m, 5H), 2.24-2.10 (m, 3H), 1.98-1.86 (m, 4H), 1.54-1.41 (m, 3H), 0.95-0.84 (m, 3H), 0.79-0.70 (m, 5H). |
| 26 | LC/MS: 984.50 [M + H]⁺;<br>¹H NMR (400 MHz, DMSO) δ 10.95 (s, 1H), 9.20 (s, 1H), 8.14 (s, 1H), 7.53 (d, J = 8.6 Hz, 1H), 7.10-7.03 (m, 2H), 6.86 (s, 2H), 6.25 (s, 1H), 5.05 (dd, J = 13.2, 5.0 Hz, 1H), 4.69 (s, 1H), 4.42-4.25 (m, 4H), 4.16-4.24 (m, 1H), 4.04 (d, J = 13.1 Hz, 1H), 3.56 (d, J = 13.2 Hz, 2H), 3.43-3.15 (m, 10H), 3.06-2.87 (m, 4H), 2.69-2.58 (m, 3H), 2.56-2.53 (m, 2H), 2.48-2.44 (m, 3H), 2.43-2.29 (m, 1H), 2.05-1.90 (m, 4H), 1.85-1.76 (m, 2H), 1.75-1.59 (m, 5H), 1.53-1.42 (m, 2H), 1.16 (s, 3H), 0.85-0.76 (m, 2H), 0.72-0.61 (m, 2H). |
| 27 | LC/MS: 954.40 [M + H]⁺;<br>1H NMR (400 MHz, DMSO) δ 10.96 (s, 1H), 10.01 (s, 1H), 9.55 (s, 1H), 8.86 (s, 1H), 7.68 (d, J = 8.0 Hz, 1H), 7.60 (d, J = 8.4 Hz, 1H), 7.37 (t, J = 7.6 , 1H), 7.30 (d, J = 2.4 Hz, 1H), 7.18-7.11 (m, 3H), 6.99 (s, 1H), 5.07 (dd, J = 13.2, 5.2 Hz, 1H), 4.38-4.30 (m, 4 H), 4.27-4.21 (m, 3H), 4.17-4.10 (m, 3H), 4.02-3.96 (m, 2H), 3.62-3.46 (m, 4H), 3.27-3.06 (m, 8H), 2.95-2.57 (m, 5H), 2.40-2.11 (m, 4H), 2.04-1.92 (m, 3H), 1.81-1.55 (m, 6H), 0.89-0.74 (m, 7H). |
| 28 | LC/MS: 999.40 [M + H]⁺;<br>1HNMR (400 MHz, DMSO) δ 10.94 (s, 1H), 9.89 (s, 1H), 9.20 (d, J = 8.0 Hz, 1H), 8.14 (s, 1H), 7.66 (d, J = 8.4 Hz, 1H), 7.49 (d, J = 8.4 Hz, 1H), 7.36 (t, J = 7.6 Hz, 1H), 7.28 (d, J = 2.4 Hz, 1H), 7.12 (d, J = 7.1 Hz, 1H), 7.04-7.00 (m, 2H), 6.98 (d, J = 2.5 Hz, 1H), 5.24-5.02 (m, 1H), 4.74 (d, J = 16.2 Hz, 1H), 4.35-4.25 (m, 4H), 4.18 (d, J = 16.9 Hz, 1H), 4.07-3.99 (m, 1H), 3.50 (t, J = 6.3 Hz, 1H), 3.42 (s, 1H), 3.24 (s, 5H), 3.05 (s, 4H), 2.93-2.85 (m, 1H), 2.80-2.67 (m, 2H), 2.61 (s, 1H), 2.56 (s, 1H), 2.35 (dd, J = 13.8, 4.1 Hz, 3H), 2.28-2.16 (m, 4H), 2.05-1.91 (m, 3H), 1.75-1.64 (m, 10H), 1.17 (d, J = 10.8 Hz, 3H), 0.86-0.79 (m, 4H), 0.66 (s, 2H), 0.43 (s, 2H). |
| 30 | LC/MS: 967.40 [M + H]⁺;<br>1H NMR (400 MHz, DMSO) δ 10.96 (s, 1H), 9.20 (d, J = 7.0 Hz, 1H), 8.20 (s, 1H), 8.07 (s, 1H), 7.71 (s, 1H), 7.67 (d, J = 7.9 Hz, 1H), 7.49 (d, J = 7.8 Hz, 1H), 7.35 (d, J = 7.1 Hz, 1H), 7.28 (s, 1H), 7.12 (d, J = 6.5 Hz, 1H), 7.05 (s, 1H), 6.98 (s, 1H), 5.04 (d, J = 8.3 Hz, 1H), 4.65 (s, 1H), 4.28 (s, 2H), 4.21 (d, J = 7.4 Hz, 2H), 4.08-3.99 (m, 2H), 3.82 (s, 1H), 3.09 (s, 3H), 2.89 (s, 3H), 2.35-2.30 (m, 2H), 2.28-2.17 (m, 5H), 2.07 (s, 1H), 2.00-1.89 (m, 5H), 1.73 (s, 5H), 1.64 (s, 4H), 1.57-1.45 (m, 4H), 1.42-1.33 (m, 2H), 1.23 (s, 2H), 1.17 (d, J = 10.3 Hz, 3H), 0.92 (d, J = 7.3 Hz, 1H), 0.64 (s, 2H), 0.40 (s, 2H). |
| 31 | LC/MS: 980.40 [M + H]⁺;<br>1H NMR (400 MHz, ) δ 11.11 (s, 1H), 9.25 (d, J = 9.5 Hz, 1H), 8.80 (s, 1H), 7.78 (d, J = 8.5 Hz, 1H), 7.68 (d, J = 8.4 Hz, 1H), 7.50 (s, 1H), 7.38 (t, J = 7.6 Hz, 2H), 7.29 (d, J = 2.4 Hz, 1H), 7.13 (d, J = 7.4 Hz, 1H), 6.97 (d, J = 2.6 Hz, 1H), 5.10 (dd, J = 12.8, 5.3 Hz, 1H), 4.33-4.25 (m, 4H), 4.13-4.04 (m, 4H), 3.78 (s, 2H), 3.67-3.58 (m, 3H), 3.50-3.30 (m, 3H), 3.22 (s, 4H), 3.08-2.80 (m, 5H), 2.33 (s, 2H), 2.26-2.09 (m, 4H), 2.05-1.98 (m, 2H), 1.93-1.77 (m, 4H), 1.74-1.61 (m, 3H), 1.17 (d, J = 12.6 Hz, 3H), 0.92-0.73 (m, 7H). |
| 32 | LC/MS: 994.40 [M + H]⁺;<br>1H NMR (400 MHz, ) δ 11.11 (s, 1H), 9.25 (d, J = 9.7 Hz, 1H), 8.69 (s, 1H), 7.77 (d, J = 8.5 Hz, 1H), 7.68 (d, J = 8.2 Hz, 1H), 7.49 (s, 1H), 7.43-7.32 (m, 2H), 7.29 (d, J = 2.4 Hz, 1H), 7.13 (d, J = 7.0 Hz, 1H), 6.97 (d, J = 2.5 Hz, 1H), 5.10 (dd, J = 12.8, 5.3 Hz, 1H), 4.44-4.16 (m, 8H), 4.16-4.02 (m, 2H), 3,70-3.54 (m, 3H), 3.53-3.42 (m, 2H), 3.41-3.33 (m, 1H), 3.23 (d, J = 15.2 Hz, 6H), 3.12 (s, 2H), 3.02-2.78 (m, 3H), 2.76-2.67 (m, 1H), 2.29-2.11 (m, 3H), 2.01 (dd, J = 19.8, 14.2 Hz, 3H), 1.83-1.57 (m, 8H), 1.17 (d, J = 12.8 Hz, 3H), 0.94-0.70 (m, 7H). |
| 35 | LC/MS: 1001.40 [M + H]⁺;<br>1H NMR (400 MHz, DMSO) δ 10.95 (s, 1H), 9.21 (s, 1H), 8.24 (s, 2H), 7.54-7.40 (m, 3H), 7.14-7.00 (m, 4H), 5.74 (s, 2H), 5.04 (dd, J = 13.2, 5.0 Hz, 1H), 4.82-4.68 (m, 1H), 4.42-4.16 (m, 6H), 4.06-4.00 (m, 1H), 3.60-3.56 (m, 1H), 3.38-3.33 (m, 2H), 3.24 (s, 3H), 2.97-2.83 (m, 2H), 2.65-2.58 (m, 4H), 2.39-2.31 (m, 6H), 2.25-2.14 (m, 2H), 2.07-1.89 (m, 3H), 1.77-1.52 (m, 8H), 1.46-1.21 (m, 8H), 0.64 (s, 2H), 0.41 (s, 2H). |
| 37 | LC/MS: 1025.30 [M + H]⁺;<br>1H NMR (400 MHz, DMSO) δ 10.96 (s, 1H), 9.29-9.24 (m, 1H), 7.80-7.76 (m, 1H), 7.55 (d, J = 8.4 Hz, 1H), 7.39-7.34 (m, 2H), 7.12-7.08 (m, 2H), 7.06-6.95 (m, 2H), 5.06 (dd, J = 13.2, 5.2 Hz, 2H), 4.59-4.51 (m, 2H), 4.37-4.30 (m, 5H), |

| Cpd # | Characterization |
|---|---|
| | 4.24-4.18 (m, 3H), 3.87-3.81 (m, 2H), 3.77-3.71 (m, 3H), 3.58-3.51 (m, 3H), 3.38-3.30 (m, 5H), 3.24-3.20 (m, 2H), 3.16-3.10 (m, 2H), 2.94-2.86 (m, 3H), 2.69-2.65 (m, 1H), 2.45-2.28 (m, 5H), 2.24-2.10 (m, 3H), 1.98-1.86 (m, 4H), 1.54-1.41 (m, 3H), 0.95-0.84 (m, 3H), 0,79-0.70 (m, 5H). |
| 38 | LC/MS: 1053.50 [M + H]⁺; 1H NMR (400 MHz, DMSO) δ 10.95 (s, 1H), 9.95 (s, 1H), 9.27 (d, J = 2.8 Hz, 1H), 9.05 (s, 1H), 7.78 (dd, J = 9.2, 6.2 Hz, 1H), 7.61 (d, J = 8.4 Hz, 1H), 7.38-7.33 (m, 2H), 7.21-7.14 (m, 2H), 7.06-7.02 (m, 1H), 5.07 (dd, J = 13.2, 5.1 Hz, 1H), 4.58-4.52 (m, 1H), 4.40-4.25 (m, 10H), 4.22-4.17 (m, 2H), 4.15-3.98 (m, 6H), 3.79-3.69 (m, 4H), 3.46-3.37 (m, 2H), 3.29-3.19 (m, 4H), 3.02-2.87 (m, 6H), 2.43-2.29 (m, 6H), 2.17-2.09 (m, 2H), 2.07-1.93 (m, 6H), 1.91-1.82 (m, 2H), 1.77-1.69 (m, 1H), 1.56-1.42 (m, 2H), 0.80-0.71 (m, 5H). |
| 39 | LC/MS: 1055.50 [M + H]⁺; 1H NMR (400 MHz, DMSO) δ 10.95 (s, 1H), 9.26 (s, 1H), 8.84-8.64 (m, 1H), 7.77 (d, J = 8.8, 6.0 Hz, 1H), 7.55 (d, J = 8.4 Hz, 1H), 7.39-7.32 (m, 2H), 7.14-7.08 (m, 2H), 7.02 (d, J = 2.4 Hz, 1H), 5.05 (dd, J = 13.2, 5.2 Hz, 1H), 4.41-4.29 (m, 9H), 4.24-4.21 (m, 2H), 4.19-4.17 (m, 1H), 4.07-4.02 (m, 3H), 3.68-3.60 (m, 1H), 3.56-3.50 (m, 2H), 3.43-3.35 (m, 3H), 3.25-3.18 (m, 2H), 3.09-3.03 (m, 2H), 2.93-2.84 (m, 4H), 2.68-2.60 (m, 2H), 2.38-2.32 (m, 2H), 2.23 (s, 1H), 2.14-2.04 (m, 3H), 1.98-1.94 (m, 1H), 1.78-1.60 (m, 8H), 1.57-1.47 (m, 2H), 1.17 (d, J = 10.4 Hz, 3H), 1.01 (s, 2H), 0.94-0.87 (m, 3H), 0.79-0.69 (m, 5H). |
| 49 | LC/MS: 979.30 [M + H]⁺; 1H NMR (400 MHz, ) δ 10.87 (s, 1H), 9.97 (brs, 1H), 9.21 (s, 1H), 7.76 (dd, J = 9.0, 6.1 Hz, 1H), 7.37-7.32 (m, 2H), 7.02 (d, J = 2.4 Hz, 1H), 6.61 (d, J = 12.6 Hz, 2H), 4.74 (s, 1H), 4.34-4.27 (m, 3H), 4.09-3.97 (m, 2H), 3.62 (d, J = 13.2 Hz, 1H), 3.52 (d, J = 13.3 Hz, 1H), 3.44-3.38 (m, 2H), 3.14 (s, 4H), 2.83-2.73 (m, 1H), 2.45-2.38 (m, 5H), 2.36-2.33 (m, 4H), 2.30-2.24 (m, 4H), 2.19-1.92 (m, 4H), 1.84 (t, J = 8.9 Hz, 2H), 1.75-1.60 (m, 3H), 1,52 (s, 2H), 1.40 (s, 2H), 1.38-1.29 (m, 2H), 1.16 (d, J = 9.9 Hz, 3H), 0.73 (d, J = 6.9 Hz, 3H), 0.64 (s, 2H), 0.40 (s, 2H). |
| 46 | LC/MS: 997.30 [M + H]⁺; 1H NMR (400 MHz, ) δ 10.87 (s, 1H), 9.93 (s, 1H), 9.21 (s, 1H), 8.17 (s, 1H), 7.80-7.76 (m, 1H), 7.41-7.27 (m, 2H), 7.02 (d, J = 2.7 Hz, 1H), 6.62 (d, J = 13.1 Hz, 2H), 4.74 (d, J = 4.8 Hz, 1H), 4.35-4.25 (m, 3H), 4.09-3.97 (m, 2H), 3.16 (s, 5H), 2.68-2.65 (m, 4H), 2.35-2.31 (m, 6H), 2.30-2.25 (m, 4H), 2.10-2.01 (m, 4H), 1.97-1.84 (m, 4H), 1.71-1.64 (m, 3H), 1.58-1.54 (m, 2H), 1.47-1.43 (m, 2H), 1.16 (d, J = 9.9 Hz, 4H), 0.80-0.66 (m, 4H), 0.64 (s, 2H), 0.39 (s, 2H). |
| 50 | LC/MS: 966.40 [M + H]⁺; 1H NMR (400 MHz, DMSO) δ 10.86 (s, 1H), 9.93 (brs, 1H), 9.22 (s, 1H), 7.79-7.75 (m, 1H), 7.38-7.33 (m, 2H), 7.06-7.02 (m, 1H), 6.62 (d, J = 12.7 Hz, 2H), 4.77-4.71 (m, 1H), 4.37-4.25 (m, 4H), 4.10-3.96 (m, 4H), 3.64-3.61 (m, 2H), 3.54-3.51 (m, 2H), 3.18-3.15 (m, 5H), 2.81-2.73 (m, 2H), 2.67-2.61 (m, 2H), 2.34-2.28 (m, 4H), 2.16-1.95 (m, 6H), 1.93-1.89 (m, 2H), 1.75-1.67 (m, 4H), 1.53-1.45 (m, 4H), 1.17 (d, J = 9.9 Hz, 2H), 0.73 (dd, J = 13.9, 7.1 Hz, 3H), 0.66-0.43 (m, 4H). |
| 57 | LC/MS: 965.20 [M + H]⁺; 1H NMR (400 MHz, DMSO) δ 10.83 (s, 1H), 9.93 (brs, 1H), 9.18 (s, 1H), 8.11 (s, 1H), 7.73 (dd, J = 8.8, 6.0 Hz, 1H), 7.33-7.29 (m, 2H), 7.00 (s, 1H), 6.60 (d, J = 12.8 Hz, 2H), 4.73 (brs, 1H), 4.33-4.25 (m, 3H), 4.05-3.97 (m, 2H), 3.58 (d, J = 12.8 Hz, 2H), 3.48 (d, J = 12.8 Hz, 3H), 3.15 (s, 4H), 2.97 (s, 1H), 2.77-2.69 (m, 1H), 2.63 (s, 1H), 2.39-2.27 (m, 2H), 2.17-1.99 (m, 2H), 1.97-1.87 (m, 4H), 1.72 (s, 6H), 1.64 (s, 2H), 1.20 (s, 6H), 1.13 (d, J = 8.8 Hz, 3H), 0.81 (t, J = 6.8 Hz, 1H), 0.70 (q, J = 6.8 Hz, 3H), 0.63 (s, 2H), 0.40 (s, 2H). |
| 58 | LC/MS: 1006.30 [M + H]⁺; 1H NMR (400 MHz, DMSO) δ 10.87 (s, 1H), 9.21 (s, 1H), 8.31 (s, 1H), 7.76 (dd, J = 8.8, 6.0 Hz, 1H), 7.38-7.31 (m, 2H), 7.03 (d, J = 2.4 Hz, 1H), 6.72-6.60 (m, 2H), 4.35-4.23 (m, 3H), 4.08-4.00 (m, 2H), 3.74-3.68 (m, 2H), 3.62 (d, J = 13.2 Hz, 3H), 3.18-3.13 (m, 4H), 2.90 (s, 3H), 2.81-2.74 (m, 1H), 2.70-2.65 (m, 1H), 2.28-2.22 (m, 2H), 2.17-2.07 (m, 2H), 2.04-1.91 (m, 4H), 1.77-1.72 (m, 2H), 1.70-1.62 (m, 5H), 1.48-1.41 (m, 4H), 1.23 (s, 6H), 1.16 (d, J = 10.0 Hz, 3H), 0.85 (t, J = 6.8 Hz, 1H), 0.73 (q, J = 7.2 Hz, 3H), 0.63 (s, 2H), 0.39 (s, 2H). |
| 59 | LC/MS: 1005.30 [M + H]⁺; 1H NMR (400 MHz, DMSO) δ 10.89 (s, 1H), 9.05 (s, 1H), 8.48 (s, 1H), 7.75-7.66 (m, 1H), 7.36-7.25 (m, 2H), 7.08-6.98 (m, 1H), 6.68 (d, J = 13.2 Hz, 1H), 6.49 (d, J = 14.0 Hz, 1H), 4.98-4.68 (m, 2H), 4.50-4.35 (m, 2H), 4.32-4.16 (m, 2H), 4.15-3.98 (m, 3H), 3.97-3.80 (m, 3H), 3.67-3.49 (m, 3H), 3.47-3.40 (m, 2H), 3.25 (s, 3H), 3.20-3.15 (m, 1H), 3.13-3.04 (m, 2H), 2.98-2.91 (m, 2H), 2.84-2.75 (m, 2H), 2.42-2.32 (m, 1H), 2.09-1.89 (m, 5H), 1.82-1.63 (m, 6H), 1.59-1.41 (m, 4H), 1.28-1.22 (m, 4H), 1.21-1.17 (m, 2H), 0.90-0.84 (m, 1H), 0.83-0.72 (m, 3H), 0.66-0.55 (m, 1H), 0.54-0.42 (m, 2H), 0.41-0.32 (m, 1H). |
| 60 | LC/MS: 965.30 [M + H]⁺; 1H NMR (400 MHz, DMSO) δ 10.88 (s, 1H), 9.94 (brs, 1H), 9.22 (s, 1H), 8.15 (s, 1H), 7.78-7.74 (m, 1H), 7.38-7.32 (m, 2H), 7.04-7.01 (m, 1H), 6.61 (d, J = 12.6 Hz, 2H), 4.74 (d, J = 6.8 Hz, 1H), 4.35-4.29 (m, 1H), 4.27-4.19 (m, 2H), 4.07-4.00 (m, 2H), 3.44-3.37 (m, 2H), 3.13 (s, 5H), 3.05-2.90 (m, 4H), 2.80-2.73 (m, 1H), 2.63-2.56 (m, 5H), 2.22-2.13 (m, 2H), 2.12-2.03 (m, 2H), 2.02-1.93 (m, 2H), 1.91-1.84 (m, 2H), 1.74-1.61 (m, 6H), 1.36-1.29 (m, 2H), 1.28-1,20 (m, 2H), 1.17 (d, J = 9.5 Hz, 3H), 0.74 (d, J = 7.3 Hz, 3H), 0.57 (s, 2H), 0.48 (s, 2H). |

| Cpd # | Characterization |
|---|---|
| 61 | LC/MS: 993.30 [M + H]+;<br>1H NMR (400 MHz, DMSO) δ 10.86 (s, 1H), 10.03-9.85 (m, 1H), 9.21 (s, 1H), 8.16 (s, 1H), 7.78-7.65 (m, 2H), 7.37-7.30 (m, 2H), 7.03-7.00 (m, 2H), 6.59 (d, J = 13.1 Hz, 2H), 4.77-4.72 (m, 1H), 4.36-4.20 (m, 6H), 4.06-4.01 (m, 2H), 3.82 (s, 1H), 3.62 (d, J = 12.9 Hz, 2H), 3.54-3.50 (m, 2H), 3.19-3.14 ( m, 6H), 3.06-2.98 (m, 4H), 2.69-2.64 (m, 1H), 2.61-2.56 (m, SH), 2.55-2.52 (m, 2H), 2.11-2.07 (m,2H), 2.01-1.97 (m, 2H), 1.87-1.83 (m, 2H), 1.42-1.34 (m, 4H), 1.17 (d, J = 9.2 Hz, 4H), 0.92-0.83 (m,2H), 0.74 (q, J = 6.7 Hz, 3H), 0.67-0.63 (m, 2H), 0.43 0.38 (m, 2H). |
| 62 | LC/MS: 993.40 [M + H]+;<br>1H NMR (400 MHz, DMSO) δ 10.93 (s, 1H), 9.21 (s, 1H), 8.37-8.21 (m, 3H), 7.76 (dd, J = 9.0, 6.0 Hz, 1H), 7.38-7.30 (m, 2H), 7.02 (d, J = 2.5 Hz, 1H), 7.00 (d, J = 10.0 Hz, 2H), 4.74 (brs, 1H), 4.35-4.25 (m, 3H), 4.18 (dd, J = 12.7, 5.1 Hz, 1H), 4.07-3.99 (m, 1H), 3.62 (d, J = 13.2 Hz, 1H), 3.52 (d, J = 13.3 Hz, 1H), 3.42-3.35 (m, 2H), 2.89 (s, 4H), 2.85-2.69 (m, 6H), 2.54-2.52 (m, 2H), 2.31-2.23 (m, 4H), 2.21-1.91 (m, 8H), 1.73-1.60 (m, 4H), 1.59-1.55 (m, 4H), 1.19-1.16 (m, 3H), 1.15-1.07 (m, 2H), 0.73 (q, J = 7.1 Hz, 3H), 0.68-0.59 (m, 2H), 0.45-0.33 (m, 2H). |
| 63 | LC/MS: 972.40 [M + H]+;<br>1H NMR (400 MHz, DMSO) δ 10.91 (s, 1H), 9.17 (d, J = 4.8 Hz, 1H), 8.16 (s, 1H), 7.72 (dd, J = 9.2, 6.0 Hz, 1H), 7.46 (d, J = 8.8 Hz, 1H), 7.38-7.25 (m, 2H), 7.00-6.95 (m, 3H), 5.00 (dd, J = 13.2, 4.8 Hz, 1H), 4.33-4.23 (m, 4H), 4.18-4.12 (m, 1H), 4.04-3.95 (m, 1H), 3.59-3.57 (m, 0.5H), 3.48-3.46 (m, 0.5H), 3.34-3.31 (m, 1H), 3.20-3.16 (m, 4H), 2.89-2.81 (m, 1H), 2.58-2.52 (m, 7H), 2.37-2.21 (m, 6H), 2.10 (s, 3H), 2.01-1.88 (m, 2H), 1,70-1.58 (m, 3H), 1.46-1.35 (m, 2H), 1.25-1.09 (m, 6H), 0.83 (s, 3H),0.73-0.66 (m, 3H), 0.61 (s, 2H), 0.38 (s, 2H). |
| 64 | LC/MS: 991.30 [M + H]+;<br>1H NMR (400 MHz, DMSO) δ 11.07 (s, 1H), 9.21 (d, J = 2.8 Hz, 1H), 8.23 (s, 1H), 7.81-7.71 (m, 1H), 7.37-7.32 (m, 2H), 7.03 (s, 1H), 6.92 (d, J = 8.8 Hz, 1H), 6.82 (s, 1H), 6.60 (d, J = 8.4 Hz, 1H), 5.28 (dd, J = 12.8, 5.2 Hz, 1H), 4.36-4.26 (m, 3H), 4.04 (dd, J = 21.4, 13.1 Hz, 1H), 3.64-3.59 (m, 2H), 3.52-3.50 (m, 2H), 3.29 (s, 3H), 3.06-3.02 (m, 4H), 2.92-2.85 (m, 1H), 2.70-2.66 (m, 2H), 2.63-2.59 (m, 4H), 2.46 (s, 2H), 2.37-2.28 (m, 4H), 2.24-2.14 (m, 3H), 2.02-1,94 (m, 2H), 1.79 (t, J = 12.0 Hz, 2H), 1.71-1.63 (m, 4H), 1.59-1.53 (m, 1H), 1.16 (d, J = 9.6 Hz, 3H), 0.73 (q, J = 7.2 Hz, 3H), 0.65 (s, 2H), 0.42 (s, 2H). |
| 65 | LC/MS: 991.30 [M + H]+;<br>1H NMR (400 MHz, DMSO) δ 11.10 (s, 1H), 9.26 (s, 1H), 7.79-7.66 (m, 2H), 7.39-7.29 (m, 2H), 7.04-6.97 (m, 2H), 6.96-6.82 (m, 2H), 5.38-5.32 (m, 1H), 4.57 (q, J = 7.2 Hz, 3H), 4.35 (s, 3H), 3.82 (s, 2H), 3.74 (s, 3H), 3.63 (s, 4H), 3.54 (d, J = 13.6 Hz, 2H), 3.32 (s, 2H), 3.17-3.08 (m, 3H), 2.93-2.86 (m, 2H), 2.72-2.58 (m, 3H), 2.37-2.28 (m, 3H), 2.18-2.11 (m, 2H), 2.00 (q, J = 7.6 Hz, 3H), 1.73-1.64 (m, 3H), 1.52 (d, J = 7.2 Hz, 5H), 1.18 (d, J = 10.4 Hz, 3H), 0.85 (t, J = 6.8 Hz, 2H), 0.74 (q, J = 7.2 Hz, 2H). |
| 66 | LC/MS: 975.30 [M + H]+;<br>1H NMR (400 MHz, DMSO) δ 10.87 (s, 1H), 9.99 (s, 1H), 9.26 (s, 1H), 9.00 (brs, 1H), 7.79-7.65 (m, 2H), 7.50 (d, J = 9.0 Hz, 1H), 7.37-7.29 (m, 2H), 7.04-6.98 (m, 1H), 6.90 (d, J = 8.5 Hz, 1H), 6.83 (s, 1H), 4.77-4.69 (m, 1H), 4.39-4.30 (m, 3H), 4.28-4.23 (m, 1H), 4.14-4.04 (m, 1H), 3.89 (s, 3H), 3.82 (s, 1H), 3.75-3.68 (m, 1H), 3.30-3.28 (m, 2H), 3.25-3.15 (m, 5H), 2.64-2.59 (m, 2H), 2.58-2.54 (m, 5H), 2.36-2.27 (m, 3H), 2.22-2.10 (m, 4H), 2.08-1.95 (m, 4H), 1.77-1.61 (m, 5H), 1.54-1.46 (m, 2H), 1.41-1.34 (m, 1H), 1.17 (d, J = 10.3 Hz, 3H), 0.92-0.87 (m, 2H), 0.74-0.71 (m, 2H). |
| 68 | LC/MS: 987,60 [M + H]+;<br>1H NMR (400 MHz, DMSO) δ 10.96 (s, 1H), 9.22 (s, 1H), 8.17 (s, 1H), 7.76 (s, 1H), 7.53-7.46 (m, 1H), 7.40-7.30 (m, 2H), 7.09-6.97 (m, 3H), 5.04 (d, J = 9.2 Hz. 1H), 4.41-4.12 (m, 6H), 4.08-4.01 (m, 1H), 3.41 (s, 4H), 3.22 (s, 4H), 3.12-3.01 (m, 6H), 2.91-2.78 (m, 3H), 2.55 (s, 4H), 2.39-2.31 (m, 2H), 2.20-1.91 (m, 4H), 1.76-1.61 (m, 7H), 1.20-1.12 (m, 3H), 0.74 (s, 3H), 0.59-0.43 (m, 4H). |
| 69 | LC/MS: 948.30 [M + H]+;<br>1H NMR (400 MHz, DMSO) δ 10.96 (s, 1H), 10.84-10.66 (m, 0.5H), 10.12-9.85 (m, 0.5H), 9.27 (s, 1H), 7.77 (dd, J = 9.2, 6.0 Hz, 1H), 7.56 (d, J = 8.4 Hz, 1H), 7.40-7.30 (m, 2H), 7.12-6.99 (m, 3H), 5.06 (dd, J = 13.2, 5.2 Hz, 1H), 4.80-3.95 (m, 11H), 3.74-3.17 (m, 10H), 3.14-2.86 (m, 4H), 2.63-2.55 (m, 1H), 2.45-2.25 (m, 3H), 2.20-2.10 (m, 1H), 2.05-1.92 (m, 2H), 1.77-1.59 (m, 3H), 1.17 (d, J = 9.2 Hz, 3H), 0.81 (s, 4H), 0.76-0.69 (m, 3H). |
| 72 | LC/MS: 1059.40 [M + H]+;<br>1H NMR (400 MHz, DMSO) δ 10.97 (s, 1H), 9.47 (brs, 1H), 9.26 (s, 1H), 7.77 (dd, J = 8.8, 6.4 Hz, 1H), 7.60 (d, J = 8.4 Hz, 1H), 7.39-7.33 (m, 2H), 7.21-7.15 (m, 2H), 7.02 (s, 1H), 5.07 (dd, J = 13.2, 4.8 Hz, 1H), 4.40-4.31 (m, 4H), 4.27-4.21 (m, 2H), 4.12-4.04 (m, 4H), 3.63 (d, J = 12.8 Hz, 2H), 3.53 (d, J = 13.6 Hz, 2H), 3.44-3.25 (m, 8H), 3.21-3.06 (m, 5H), 2.97-2.84 (m, 2H), 2.68-2.56 (m, 2H), 2.41-2.32 (m, 2H), 2.31-1.89 (m, 12H), 1.76-1.64 (m, 3H), 1.27-1.23 (m, 1H), 1.18 (d, J = 10.4 Hz, 3H), 0.92-0.85 (m, 2H), 0.82-0,69 (m, 5H). |
| 76 | LC/MS: 1037.40 [M + H]+;<br>1H NMR (400 MHz, DMSO) δ 10.90 (s, 1H), 9.99 (brs, 1H), 9.26 (s, 1H), 7.77 (dd, J = 8.8, 6.2 Hz, 1H), 7.39-7.31 (m, 2H), 7.02 (d, J = 2.0 Hz, 1H), 6.79 (d, J = 12.5 Hz, 2H), 4.31 (s, 3H), 4.12-4.04 (m, 4H), 3.65-3.52 (m, 7H), 3.43-3.32 (m, 4H), 3.28-3.24 (m, 4H), 3.17-3.05 (m, 6H), 2.87-2.71 (m, 2H), 2.36-2.29 (m, 2H), |

| Cpd # | Characterization |
|---|---|
| | 2.22-2.05 (m, 5H), 2.06-1.91 (m, 4H), 1.80-1.60 (m, 7H), 1.25-1.08 (m, 5H), 0.91-0.87 (m, 2H), 0.80-0.76 (m, 2H), 0.74-0.69 (m, 3H). |
| 84 | LC/MS: 939.40 [M + H]$^+$;<br>1H NMR (400 MHz, DMSO) δ 10.82 (s, 1H), 9.59 (brs, 1H), 9.26 (s, 1H), 7.77 (dd, J = 9.0, 6.1 Hz, 1H), 7.39-7.32 (m, 2H), 7.15 (t, J = 8.7 Hz, 1H), 7.02 (d, J = 2.0 Hz, 1H), 6.85-6.76 (m, 2H), 4.42-4.32 (m, 3H), 4.14-4.03 (m, 1H), 3.92 (dd, J = 12.4, 4.8 Hz, 1H), 3.75 (s, 2H), 3.63 (d, J = 13.0 Hz, 1H), 3.53 (d, J = 13.3 Hz, 1H), 3.47-3.05 (m, 13H), 2.78-2.65 (m, 1H), 2.53 (d, J = 3.6 Hz, 1H), 2.40-2.24 (m, 3H), 2.23-1.90 (m, 7H), 1.78-1.62 (m, 3H), 1.18 (d, J = 10.3 Hz, 3H), 0.99-0.56 (m, 8H). |
| 85 | LC/MS: 977.30 [M + H]$^+$;<br>1H NMR (400 MHz, DMSO) δ 10.91 (s, 1H), 10.06-9.96 (m, 1H), 9.89-9.72 (m, 2H), 9.26 (d, J = 3.9 Hz, 1H), 7.82-7.73 (m, 1H), 7.39-7.31 (m, 2H), 7.06-7.00 (m, 1H), 6.79 (d, J = 12.2 Hz, 2H), 4.62-4.48 (m, 1H), 4.44-4.34 (m, 2H), 4.31-4.19 (m, 3H), 4.15-4.04 (m, 3H), 4.01-3.79 (m, 8H), 3.41-3.36 (m, 2H), 3.34-3.16 (m, 4H), 3.15-2.98 (m, 5H), 2.83-2.73 (m, 1H), 2.43-2.35 (m, 2H), 2.31-2.25 (m, 1H), 2.18-2.07 (m, 4H), 2.05-1.90 (m, 4H), 1.89-1.82 (m, 1H), 1.77-1.68 (m, 1H), 1.56-1.45 (m, 3H), 1.40-1.31 (m, 1H), 0.84-0.70 (m, 7H). |
| 86 | LC/MS: 988.30 [M + H]$^+$;<br>1H NMR (400 MHz, DMSO) δ 10.93 (brs, 1H), 9.21 (d, J = 4.4 Hz, 0.5H), 9.11 (s, 0.5H), 8.26 (s, 2H), 7.80-7.72 (m, 1H), 7.51 (d, J = 8.8 Hz, 1H), 7.39-7.29 (m, 2H), 7.08-6.98 (m, 3H), 5.04 (dd, J = 13.2, 5.2 Hz, 1H), 4.42-4.15 (m, 7H), 4.06-3.89 (m, 2H), 3.55-3.50 (m, 2H), 3.24 (s, 4H), 2.94-2.85 (m, 1H), 2.74-2.56 (m, 7H), 2.42-2.27 (m, 7H), 2.24-2.07 (m, 5H), 1.97-1.56 (m, 7H), 0.78-0.70 (m, 3H), 0.66 (s, 2H), 0.42 (s, 2H). |
| 214 | LC/MS: 1028.30 [M + H]$^+$;<br>1H NMR (400 MHz, DMSO) δ 10.91 (s, 1H), 9.90 (brs, 1H), 9.21-9.18 (m, 1H), 8.10 (s, 1H), 7.73 (dd, J = 9.2, 6.1 Hz, 1H), 7.48 (d, J = 8.9 Hz, 1H), 7.34-7.30 (m, 2H), 7.01-6.98 (m, 3H), 5.01 (dd, J = 13.1, 5.1 Hz, 1H), 4.53-4.09 (m, 8H), 3.91-3.77 (m, 1H), 3.26-3.18 (m, 6H), 2.93-2.80 (m, 1H), 2.62-2.52 (m, 11H), 2.41-2.24 (m, 5H), 2.14-2.03 (m, 4H), 1.99-1.77 (m, 5H), 1.70-1.48 (m, 5H), 0.74-0.66 (m, 5H), 0.51-0.44 (m, 2H). |
| 215 | LC/MS: 1009.30 [M + H]$^+$;<br>1H NMR (400 MHz, DMSO) δ 10.83 (s, 1H), 9.17 (d, J = 3.3 Hz, 1H), 8.16 (s, 1H), 7.73 (dd, J = 9.0, 6.0 Hz, 1H), 7.33-7.29 (m, 2H), 7.05-7.00 (m, 1H), 6.58 (d, J = 12.6 Hz, 2H), 4.48-4.18 (m, 6H), 4.01 (dd, J = 12.5, 4.9 Hz, 1H), 3.90-3.75 (m, 1H), 3.51-3.46 (m, 1H), 3.40-3.31 (m, 1H), 3.15-3.11 (m, 5H), 2.81-2.68 (m, 1H), 2.61-2.56 (m, 1H), 2.55-2.53 (m, 5H), 2.39-2.19 (m, 9H), 2.12-1.98 (m, 6H), 1.94-1.80 (m, 5H), 1.73-1.62 (m, 1H), 1.56-1.49 (m, 2H), 1.43-1.38 (m, 2H), 0.75-0.67 (m, 3H), 0.61-0.58 (m, 2H), 0.38-0.35 (m, 2H). |
| 216 | LC/MS: 951.40 [M + H]$^+$;<br>1H NMR (400 MHz, DMSO) δ 10.87 (s, 1H), 9.98-9.88 (m, 1H), 7.82-7.67 (m, 1H), 7.35-7.28 (m, 2H), 7.03-6.95 (m, 1H), 6.75 (d, J = 12.4 Hz, 2H), 4.34-4.21 (m, 3H), 4.09-4.01 (m, 2H), 3.95-3.85 (m, 4H), 3.75-3.70 (m, 3H), 3.23-3.18 (m, 3H), 3.12-3.09 (m, 3H), 3.08-2.99 (m, 4H), 2.91-2.85 (m, 2H), 2.82-2.71 (m, 1H), 2.38-2.27 (m, 2H), 2.24-2.17 (m, 3H), 2.12-2.04 (m, 3H), 2.03-1.97 (m, 3H), 1.93-1.89 (m, 1H), 1.75-1.64 (m, 1H), 1.57-1.41 (m, 2H), 1.36-1.33 (m, 2H), 1.25-1.19 (m, 2H), 0.86-0.75 (m, 5H), 0.73-0.65 (m, 4H). |
| 217 | LC/MS: 984.30 [M + H]$^+$;<br>1H NMR (400 MHz, DMSO) δ 10.94 (s, 1H), 9.95 (brs, 1H), 9.26-9.18 (m, 1H), 8.15 (s, 1H), 7.77 (dd, J = 9.2, 6.4 Hz, 1H), 7.50 (d, J = 8.4 Hz, 1H), 7.40-7.31 (m, 2H), 7.05-6.98 (m, 3H), 5.04 (dd, J = 13.2, 5.2 Hz, 1H), 4.64-4.05 (m, 8H), 3.97-3.77 (m, 1H), 3.58-3.49 (m, 3H), 3.24-3.18 (m, 4H), 2.94-2.86 (m, 1H), 2.83-2.67 (m, 2H), 2.62-2.54 (m, 6H), 2.46-2.30 (m, 6H), 2.25-2.06 (m, 5H), 2.01-1.82 (m, 3H), 1.75-1.65 (m, 1H), 1.56-1.44 (m, 2H), 1.33-1.24 (m, 2H), 0.89 (s, 3H), 0.76-0.64 (m, 5H), 0.50 (s, 2H). |
| 218 | LC/MS: 996.30 [M + H]$^+$;<br>1H NMR (400 MHz, DMSO) δ 10.98 (s, 1H), 9.33-9.21 (m, 1H), 8.87 (brs, 1H), 7.78 (dd, J = 9.2, 6.0 Hz, 1H), 7.61 (d, J = 8.4 Hz, 1H), 7.41-7.33 (m, 2H), 7.20-7.11 (m, 2H), 7.06-7.00 (m, 1H), 5.10-5.05 (m, 1H), 4.43-4.20 (m, 7H), 4.09-3.92 (m, 3H), 3.90-3.74 (m, 2H), 3.69-3.59 (m, 2H), 3.56-3.39 (m, 3H), 3.26-3.07 (m, 4H), 3.04-2.82 (m, 5H), 2.67-2.57 (m, 1H), 2.45-2.27 (m, 5H), 2.20-2.02 (m, 5H), 2.00-1.64 (m, 8H), 0.95-0.85 (s, 2H), 0.82-0.65 (m, 5H). |
| 219 | LC/MS: 1024.40 [M + H]$^+$;<br>1H NMR (400 MHz, DMSO) δ 10.95 (s, 1H), 9.21 (d, J = 3.2 Hz, 1H), 8.28 (s, 1H), 7.77 (dd, J = 8.8, 6.0 Hz, 1H), 7.51 (d, J = 9.2 Hz, 1H), 7.35 (dd, J = 12.0, 6.0 Hz, 2H), 7.04 (d, J = 7.2 Hz, 3H), 5.05 (dd, J = 13.2, 5.2 Hz, 1H), 4.48 (d, J = 14.0 Hz, 1H), 4.43-4.38 (m, 1H), 4.36-4.27 (m, 4H), 4.22 (s, 1H), 3.94 (d, J = 13.2 Hz, 1H), 3.82 (d, J = 13.6 Hz, 1H), 3.58-3.48 (m, 3H), 3.43-3.34 (m, 2H), 3.27-3.20 (m, 4H), 2.97-2.81 (m, 2H), 2.65-2.58 (m, 4H), 2.43-2.30 (m, 8H), 2.23-2.08 (m, 3H), 1.99-1.83 (m, 3H), 1.76-1.67 (m, 1H), 1.65-1.56 (m, 3H), 1.44-1.35 (m, 2H), 1.23 (s, 3H), 1.02 (t, J = 11.8 Hz, 2H), 0.83-0.71 (m, 3H), 0.65 (s, 2H), 0.41 (s, 2H). |
| 220 | LC/MS: 1028.30 [M + H]$^+$;<br>1H NMR (400 MHz, DMSO) δ 10.96 (s, 1H), 9.87 (brs, 1H), 9.34-9.17 (m, 1H), 7.81-7.75 (m, 1H), 7.60 (d, J = 8.4 Hz, 1H), 7.39-7.32 (m, 2H), 7.17-7.10 (m, 2H), 7.03 (d, J = 12.0 Hz, 1H), 5.07 (dd, J = 13.2, 5.2 Hz, 1H), 4.60-4.50 (m, 1H), |

| Cpd # | Characterization |
|---|---|
| | 4.38 (s, 1H), 4.34 (s, 1H), 4.32-4.21 (m, 3H), 4.17-3.99 (m, 3H), 3.97-3.80 (m, 4H), 3.65-3.52 (m, 2H), 3.50-3.36 (m, 5H), 3.34-3.23 (m, 4H), 2.96-2.85 (m, 1H), 2.63-2.55 (m, 2H), 2.46-2.31 (m, 3H), 2.30-2.19 (m, 1H), 2.18-2.10 (m, 1H), 2.09-1.82 (m, 7H), 1.80-1.60 (m, 4H), 1.58-1.41 (m, 1H), 1.29-1.22 (m, 2H), 0.89-0.82 (m, 1H), 0.79 (s, 3H), 0.77-0.70 (m, 3H). |

KRAS/RAF1 Binding Inhibition Assay

Binding affinity against GTP-bound KRAS of the compounds disclosed herein was measured by monitoring the interaction of guanosine 5'-[β,γ-imido]triphosphate-bound (GppNHp-bound) KRAS with the RBD domain of RAF1 in the presence of the test compound. Briefly, for the KRAS-G12V/RAF1 binding assay, 2 nM GppNHp-bound 6*His tagged KRAS-G12V proteins or 2 nM GDP-bound 6*His tagged KRAS-G12V proteins (final concentration) were pre-incubated with 2.5 nM GST tagged RAF1 proteins (final concentration, amino acids 54-131) in an assay buffer containing 20 mM 4-(2-hydroxyethyl)-1-piperazineethanesulfonic acid (HEPES), pH 7.5, 150 mM NaCl, 1 mM $MgCl_2$, 0.05% Tween-20, 0.5 mM DTT, and 0.05% BSA for 90 minutes. The test compounds in 2% DMSO (final concentration) at various concentrations were then added to the reaction mixture and incubated for 60 minutes at 4° C. 5 ug/ml GSH ALphaScreen donor beads (PerkinElmer, 6765300) and 5 µg/mL nickel chelate (Ni-NTA) ALphaScreen acceptor beads (PerkinElmer, 6760619C) (final concentrations) were then added to the mixture. After an incubation of 1 hour at 4° C. and then 30 minutes at room temperature, the fluorescent signals were obtained on the En Vision® 2105 Multilabel Plate Reader (PerkinElmer).

Raw ALphaScreen data were converted to a percentage of inhibition (relative to DMSO) using the following equations:

a) For a given test compound concentration X:

Signal (X)=Signal (GppNHp-bound KRAS & RAF1 & compound)–Signal (GDP-bound KRAS & RAF1 & compound)

b) Percentage of inhibition at concentration X=[1–Signal (X)/Signal (DMSO)]*100%

The $IC_{50}$ values were determined by nonlinear regression of plots of [inhibitor] vs. percentage of inhibition with variable slope, analyzed using GraphPad Prism (Version 9). The results are shown in Table 3, which summarizes the inhibition results of binding ($IC_{50}$) between KRAS G12V mutant and RAFI with exemplary compounds of the present disclosure.

Example 63: KRAS Degradation in Cells Carrying Endogenous KRAS Mutants or Wildtype (WT) KRAS and KRAS cells growth inhibition SW620 (KRAS G12V homozygous), AsPC1 (KRAS G12D homozygous), MIA PaCa2 (KRAS G12C homozygous), A549 (KRAS G12S homozygous) and MCF7 (KRAS WT) cells were obtained from American Type Culture Collection (ATCC). Cells were plated in 24-well plates in the RPMI1640 growth medium containing 10% FBS and 1% Penicillin Streptomycin at the density of $1.5 \times 10^5$ (SW620, AsPC1, A549, MCF7) or $2 \times 10^5$ (MIA PACa2) cells/well, and then incubated at 37° C. overnight. The following day, the test compound was administered to the cells by using 1000× compound stock solution prepared in DMSO at various concentrations. After administration of the compound, the cells were then incubated at 37° C. for 24 hours. Upon completion, the cells were washed with PBS and protein was collected in Laemmli sample buffer (1×; VWR International). Proteins in cell lysate were separated by SDS-PAGE and transferred to Odyssey nitrocellulose membranes (Licor) with iblot® dry blotting transfer system (ThermoFisher). Nonspecific binding was blocked by incubating membranes with Intercept Blocking Buffer (Licor) for 1 hour at room temperature with gentle shaking. The membranes were then incubated overnight at 4° C. with Primary antibodies rabbit anti-KRAS (1:1,000, Abcam, ab 191595) and mouse anti-GAPDH (1:5,000, Santa Cruz Biotechnology, sc-47724) diluted in Intercept Blocking Buffer containing 0.1% Tween 20. After washing 3 times with TBS-T, the membranes were incubated with IRDye® 800CW goat anti-rabbit IgG (1:20,000, Licor) and IRDye® 680RD goat anti-mouse IgG (1:20,000, Licor) for 1 hour. After TBS-T washes, membranes were rinsed in TBS and Western blot images were acquired by Odyssey CLx (LI-COR Biosciences).

The results are shown in FIGS. 1-5, which illustrate the pan-KRAS degradative activity of exemplary compound 1 of the present disclosure in cancer cell lines with various KRAS forms 24 hours after administration.

The signal intensity of target proteins was calculated using ImageStudio software. KRAS fluorescent intensity (FLU) from DMSO (vehicle) treatment was set as 100%. Relative KRAS expression level was determined by the following formula:

KRAS expression (%)="$FLU_{compound}$"/"$FLU_{DMSO}$"×100

The percentage of KRAS expression was calculated using Microsoft Excel. The half-maximal degradation concentration ($DC_{50}$) values were generated by GraphPad Prism (Version 9) using the dose-response equation of variable slope (four parameters).

The results in SW620 cells are shown in Table 3, which summarizes KRAS G12V degradation $DC_{50}$ of exemplary compounds.

3D cell growth inhibition of SW620 cells carrying endogenous KRAS G12V mutation SW620 cells were obtained from American Type Culture Collection (ATCC) and maintained in the RPMI1640 growth medium containing 10% FBS and 1% Penicillin Streptomycin. For cell growth assay, SW620 cells were seeded in round bottom ultra-low attachment 96-well plates (Corning 4520) at 3000 cells/well in 90 µL of DMEM growth medium containing 10% FBS and 1% Penicillin Streptomycin, and then incubated at 37° C. overnight. The following day, the test compound was administered to the cells by using 1000× compound stock solution prepared in DMSO at various concentrations. 1000× compound stock solution was first diluted in culturing medium to 10×, then 10 µL compound medium was added to each well in the cell plates. After administration of the compound, the cells were then incubated at 37° C. for 6 days. Upon completion, the plates were equilibrated at room temperature for approximately 10 minutes. 100 μL of CellTiter-Glo® 3D Reagent (Promega) was added to each well. The plates were then incubated at room temperature for 30 minutes and luminescence was recorded by EnSpire plate reader (PerkinElmer). The results are shown in Table 3, which summarizes the growth inhibition ($GI_{50}$) in SW620 cells with exemplary compounds of the present disclosure.

TABLE 3

Biological activities of exemplified compounds in KRAS G12V/RAF1 binding assay, KRAS G12V cellular degradation assay, and cellular growth inhibition assay

| Cpd # | KRAS G12V/RAF1 binding assay $IC_{50}$ | SW620 KRAS G12V $DC_{50}$ | SW620 3D cell growth $GI_{50}$ |
|---|---|---|---|
| 1 | B | A | A |
| 2 | B | A | B |
| 3 | C | C | C |
| 4 | C | C | C |
| 5 | — | C | C |
| 6 | B | A | A |
| 7 | — | A | — |
| 8 | B | A | A |
| 9 | A | B | B |
| 10 | B | A | A |
| 11 | A | B | B |
| 12 | B | A | A |
| 13 | A | B | B |
| 14 | A | C | B |
| 15 | C | C | C |
| 16 | B | C | C |
| 17 | B | C | C |
| 18 | A | C | B |
| 19 | B | B | B |
| 20 | C | C | A |
| 21 | — | C | C |
| 22 | A | C | B |
| 23 | B | B | A |
| 24 | B | A | A |
| 25 | A | A | A |
| 26 | C | C | C |
| 27 | C | B | B |
| 28 | B | A | A |
| 29 | C | B | B |
| 30 | A | B | A |
| 31 | B | B | A |
| 32 | B | B | A |
| 33 | B | A | A |
| 34 | — | C | C |
| 35 | — | C | C |
| 36 | — | C | C |
| 37 | — | B | A |
| 38 | — | B | A |
| 39 | A | A | A |
| 40 | A | A | A |
| 41 | B | B | A |
| 43 | A | A | A |
| 44 | B | B | A |
| 45 | C | C | C |
| 46 | — | B | A |
| 48 | B | B | A |
| 49 | B | A | A |
| 50 | B | A | A |
| 51 | B | B | A |
| 56 | A | B | A |
| 57 | A | B | A |
| 60 | B | A | A |
| 63 | B | B | A |
| 68 | C | B | A |
| 72 | A | A | A |
| 85 | — | B | A |
| 86 | B | A | A |
| 87 | B | B | A |
| 88 | C | C | B |
| 89 | C | C | C |
| 90 | C | B | A |
| 91 | B | B | A |
| 92 | B | B | A |
| 93 | B | C | C |
| 94 | C | B | — |
| 95 | C | C | — |
| 96 | C | A | — |
| 97 | C | C | — |
| 98 | C | B | — |
| 99 | B | C | — |
| 100 | B | C | — |
| 101 | C | A | — |
| 102 | C | A | — |
| 103 | B | A | — |
| 104 | B | 2 | A |
| 105 | B | C | C |
| 106 | B | B | — |
| 107 | C | C | — |
| 108 | C | B | A |
| 109 | C | C | C |
| 110 | C | C | C |
| 111 | B | B | — |
| 112 | C | C | — |
| 113 | C | C | — |
| 114 | C | C | C |
| 115 | C | C | C |
| 116 | C | B | C |
| 117 | C | B | C |
| 118 | C | C | C |
| 119 | C | C | C |
| 120 | A | B | A |
| 121 | A | A | A |
| 122 | — | B | A |
| 123 | B | B | B |
| 124 | B | B | A |
| 125 | B | — | — |
| 126 | B | B | A |
| 127 | — | C | — |
| 128 | C | C | C |
| 129 | B | A | B |
| 130 | B | B | A |
| 131 | A | A | A |
| 132 | C | C | — |
| 133 | B | A | A |
| 134 | B | A | A |
| 135 | B | B | A |
| 136 | A | A | B |
| 137 | B | B | A |
| 138 | B | A | A |
| 139 | A | A | A |
| 140 | B | A | A |
| 141 | A | C | C |
| 142 | B | B | C |
| 143 | A | A | A |
| 144 | A | A | A |
| 145 | A | B | A |
| 146 | A | A | A |
| 147 | A | A | A |
| 148 | A | A | A |
| 149 | B | C | B |
| 150 | B | A | A |
| 151 | B | A | A |
| 152 | B | A | A |
| 153 | B | A | A |
| 154 | A | A | A |
| 155 | A | A | A |
| 156 | — | A | A |
| 157 | — | A | A |
| 158 | — | B | A |
| 159 | — | A | A |
| 160 | B | C | — |
| 161 | B | A | A |
| 162 | B | A | A |
| 163 | A | A | A |
| 164 | B | B | A |

TABLE 3-continued

Biological activities of exemplified compounds in KRAS G12V/RAF1 binding assay, KRAS G12V cellular degradation assay, and cellular growth inhibition assay

| Cpd # | KRAS G12V/RAF1 binding assay $IC_{50}$ | SW620 KRAS G12V $DC_{50}$ | SW620 3D cell growth $GI_{50}$ |
|---|---|---|---|
| 165 | — | B | B |
| 166 | A | B | C |
| 167 | A | B | A |
| 168 | B | B | C |
| 169 | B | C | C |
| 170 | B | B | A |
| 171 | B | C | B |
| 172 | A | B | A |
| 173 | B | A | A |
| 174 | B | A | A |
| 175 | A | A | A |
| 176 | B | A | A |
| 177 | C | C | B |
| 178 | B | A | A |
| 179 | B | — | — |
| 180 | B | C | B |
| 181 | C | A | A |
| 182 | B | A | A |
| 183 | C | C | B |
| 184 | C | A | A |
| 185 | B | C | — |
| 186 | C | A | A |
| 213 | A | A | A |
| 214 | B | A | A |
| 215 | B | A | A |
| 216 | C | B | A |
| 217 | B | A | A |
| 218 | B | A | A |
| 219 | A | A | A |

KRAS G12V/RAF1 binding assay $IC_{50}$ (nM): A ≤ 20 nM; B > 20 nM and ≤ 200 nM; C > 200 nM.
SW620 KRAS G12D $DC_{50}$ (nM): A ≤ 1 nM; B > 1 nM and ≤ 10 nM; C > 100 nM.
SW620 3D cell growth $GI_{50}$ (nM): A ≤ 10 nM; B > 10 nM and ≤ 100 nM; C > 100 nM.

Example 64: Evaluation of Tolerability and Bioavailability of Compounds of the Present Disclosure in Animals Following Intravenous and Oral Administration Compounds disclosed herein were studied for animal tolerability and pharmacokinetics following single intravenous (iv) and oral gavage (po) dosing to male CD-1 mice. For each compound in each dosing route, 3 mice were used with iv dosing volume of 5 mL/kg and po dosing volume of 10 mL/kg. The compounds were formulated in 10% DMSO, 30% PEG400, 60% aqueous solution containing 20%2-hydroxypropyl-β-cyclodextrin. Blood sampling time points for iv dosing were 0.083, 0.25, 0.5, 1, 2, 4, 8 and 24 h. The sampling time points for po dosing were 0.25, 0.5, 1, 2, 4, 6, 8 and 24 h. Mice activities were monitored and recorded immediately following the dosing. The prepared plasma samples were analyzed using LC/MS/MS on AB Sciex Triple Quad 5500+ system. The PK parameters were determined by non-compartmental analysis using WinNonlin (Version 8.0). Table 4 shows the average exposure ($AUC_{0-24h}$) in animals of compounds disclosed herein following single oral administration at different doses.

TABLE 4

The average of area under the curve ($AUC_{0-24h}$) following single oral dosing of selected compounds.

| Cpd # | Single Oral Dose (mg/Kg) | $AUC_{0-last}$ (hr * ng/mL) |
|---|---|---|
| 1 | 30 | 220 |
| 8 | 30 | 3423 |
| 12 | 30 | 3251 |
| 23 | 30 | 783 |
| 25 | 25 | 525 |
| 28 | 30 | 539 |
| 33 | 30 | 509 |
| 38 | 30 | 170 |
| 39 | 30 | 399 |
| 40 | 30 | 652 |
| 41 | 30 | 1854 |
| 46 | 30 | 9128 |
| 48 | 30 | 17231 |
| 49 | 30 | 3168 |
| 50 | 30 | 3897 |
| 51 | 30 | 2278 |
| 60 | 30 | 1785 |
| 65 | 30 | 10712 |
| 66 | 30 | 7420 |
| 68 | 30 | 901 |
| 84 | 30 | 11884 |
| 86 | 30 | 1322 |
| 120 | 50 | 255 |
| 121 | 50 | 598 |
| 134 | 50 | 1945 |
| 134 | 30 | 982 |
| 182 | 30 | 4901 |
| 184 | 30 | 12495 |
| 213 | 30 | 1364 |
| 214 | 30 | 1463 |
| 215 | 30 | 4706 |
| 216 | 15 | 2137 |
| 217 | 15 | 977 |
| 219 | 30 | 718 |

Figure 6:
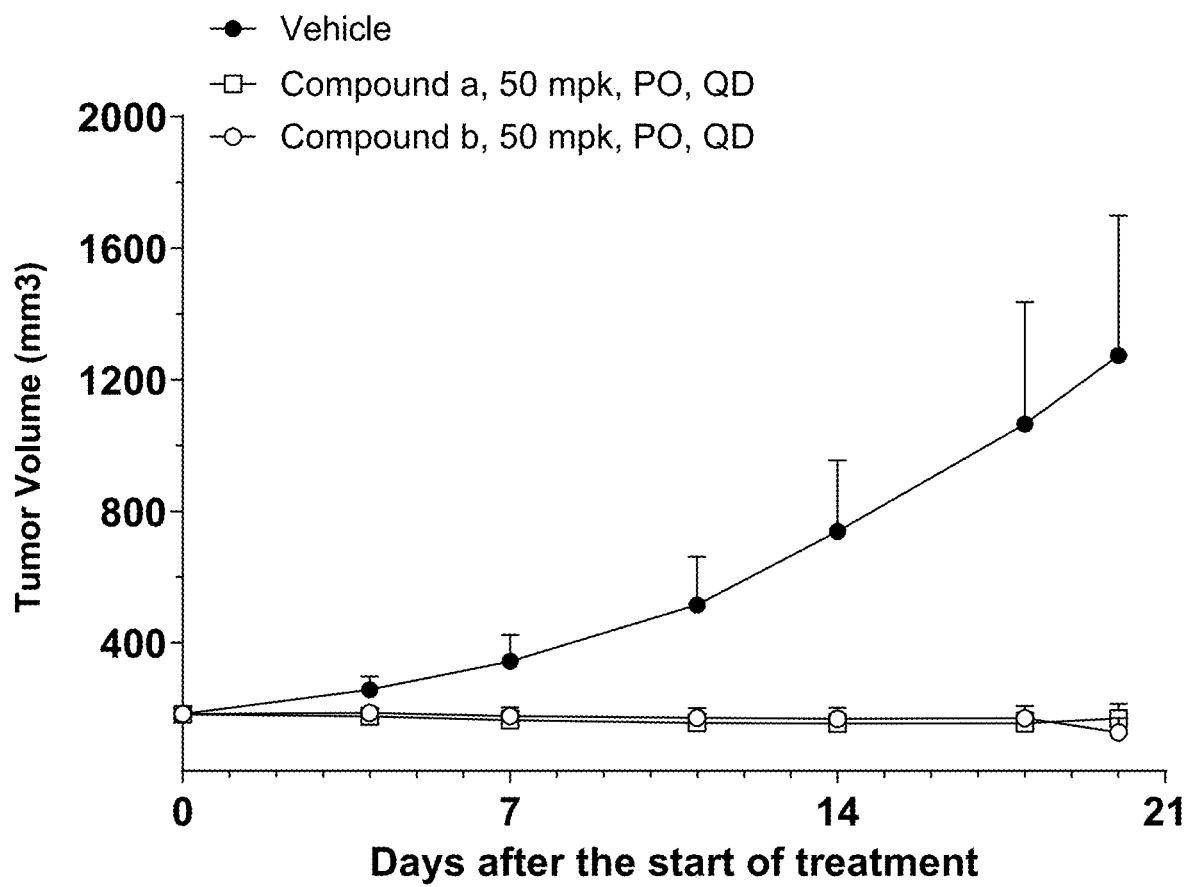
FIG. 6 illustrates a tumor volume trace after orally administering compounds of Table 4 and vehicle to MIA PaCa-2 tumor-bearing female BALB/c Nude mice. Data points represent group mean values and the error bars represent standard error of the mean (SEM).

Example 65: Study of Tumor Growth Inhibition of Compounds of the Present Disclosure in MIA Paca-2 (KRAS G12C) Xenograft Efficacy Model The MIA PaCa-2 tumor cells were obtained from ATCC and maintained in vitro as monolayer culture in DMEM/F-12 medium supplemented with 10% fetal bovine serum and 1% 100 U/mL penicillin and 100 μg/mL streptomycin at 37° C. in an atmosphere of 5% $CO_2$ in air. The tumor cells were routinely sub-cultured twice weekly. For MIA PaCa-2 tumor generation in mice, $10 \times 10^6$ MIA PaCa-2 cells in 0.1 mL of PBS mixed with 0.1 mL matrigel (total 0.2 mL) was introduced subcutaneously at the armpit of the right flank of each female BALB/c Nude mouse. The treatment started when the average tumor volume reached approximately 182 $mm^3$. The first day of treatment was denoted as Day 0. The compounds tested, compounds listed in Table 4, were formulated in 10% DMSO/30% PEG400/60% aqueous solution containing 20% HP-β-CD (pH=5), and then administrated daily (QD) for 21 days to the mice according to the predetermined regimen shown in FIG. 6. Tumor volume was determined twice weekly. As can be seen from FIG. 6, there was almost no tumor growth observed for compounds a and b of the present disclosure (listed in Tables 1 and 4) during the study when compared to the vehicle.

Example 66: Cryogenic-Electron Microscopy (Cryo-EM) to Determine the Ternary Complex of a Chimeric Degrader Disclosed Herein Bound to Mutant KRAS-G12V and Cereblon and to Show Protein-Protein Interactions Between KRAS-G12V and Cereblon Induced by the Chimeric Degrader Constructs, Protein Expression and Purification:

Genes encoding KRAS (UniProt P01116, 1-169) mutants (G12V) were codon-optimized and sub-cloned into pRSF-Duet1 vector with N-terminal 6×His tag and thrombin protease recognition sequence. KRAS mutants were expressed in E. coli T7 competent cells. When OD of E. coli cells reached ~0.6, 0.5 mM IPTG was added to the medium and the cells were grown for 18 h at 18° C. with shaking (220 rpm). Cells were harvested by centrifugation and stored at −80° C. until purification.

Genes encoding CRBN (UniProt Q96SW2, 1-442) and DDB1 (UniProt Q16531, 1-395-GNGNSG-706-1140, E898D, L899V) were codon-optimized and sub-cloned into pFastBacHTb and pFastBac1 vectors, respectively, resulting in expressing of N-terminal 6×His-TEV tagged CRBN and no-tagged DDB1. CRBN-DDB1 was expressed in Sf9 insect cells. 10 mL P2 viruses of each protein were added to 1 L Sf9 cells of $1.5\times10^6$/mL density in medium with 50 mM $Zn(OAc)_2$. Virus-infected cells were grown at 27° C. for 72 h with shaking (130 rpm). Cells were harvested by centrifugation and stored at −80° C. until purification.

E. coli cells expressing KRAS mutant protein were resuspended in Lysis 1 buffer (25 mM Tris-HCl pH 8.0, 500 mM NaCl, 10 mM imidazole, 1 mM PMSF) and lysed by high-pressure homogenization. Sf9 cells expressing CRBN and DDB1 were resuspended in Lysis 2 buffer (25 mM Tris-HCl pH 8.0, 300 mM NaCl, 1 mM TCEP, 10 mM Imidazole, 5% glycerol, 1 mM PMSF, 1× Protease inhibitor cocktail (Yeasen), 0.5% Triton X-100) and lysed by sonication. After centrifugation at 17,000 rpm for 1 h, the supernatants were collected for further purification. His-tagged KRAS mutant protein were purified by Ni-NTA affinity chromatography, Hitrap Q ion-exchange chromatography and size-exclusion chromatography (SEC) with Superdex 75 Increase 10/300 GL column pre-equilibrated in SEC 1 buffer (50 mM Tris-HCl pH 7.5, 100 mM NaCl, 1 mM $MgCl_2$, 1 mM DTT). SEC fractions containing His-KRAS were pooled and concentrated by ultrafiltration. His-KRAS was mixed with 2× molar ration of GppNHp and the mixture was incubated at 4° C. overnight. Excess GppNHp was removed by desalting in SEC 1 buffer. His-KRAS-GppNHp was concentrated, flash-frozen in liquid $N_2$ and stored at −80° C. for further use.

CRBN-DDB1 complex was purified by Ni-NTA and Resource-Q. Q fractions containing CRBN-DDB1 were collected and mixed with homemade His-tagged TEV protease at 4° C. overnight. After His-tag cleavage, the sample was passed through Ni-NTA column to remove TEV protease and cleaved His-tag. CRBN-DDB1 complex was further purified by SEC with Superdex 200 Increase 10/300 GL column pre-equilibrated in SEC 2 buffer (20 mM HEPES-Na pH 7.5, 150 mM NaCl, 1 mM TCEP). SEC fractions containing CRBN-DDB1 complex were pooled and concentrated by ultrafiltration. Concentrated protein was flash-frozen by liquid $N_2$ and stored at −80° C. for further use.

Ternary Complex Preparation:

His-KRAS-GppNHp was mixed with 5× molar ratio degrader B (selected from Table 4) in SEC 3 buffer (20 mM HEPES-Na pH 7.5, 100 mM NaCl, 1 mM $MgCl_2$, 1 mM TCEP) and incubated at 4° C. overnight. Excess compounds were removed by SEC purification with Superdex 75 Increase 10/300 GL column pre-equilibrated in SEC 3 buffer. Fractions containing His-KRAS-GppNHp-compound were pooled and concentrated.

CRBN-DDB1 of 7.5 μM and His-KRAS-GppNHp-compound of 30 μM were mixed and incubated at room temperature for 1 h and then further incubated at 4° C. overnight. The mixture was purified by SEC with Superdex 200 Increase 10/300 GL column pre-equilibrated in SEC 3 buffer. Fractions containing CRBN-DDB1-His-KRAS-GppNHp-compound complex were collected and concentrated for cryo-EM grid preparation.

Cryo-EM Grid Preparation and Data Collection:

Freshly prepared CRBN-DDB1-His-KRAS-GppNHp-compound complex was diluted to A280 nm ~0.6 right before grid preparation. 300-mesh R1.2/1.3 Quantifoil gold grids were glow-discharged in Pleco EasiGlow at 20 mA for 90 s. Three microliters of the sample were applied onto the glow-discharged grids. After waiting for 5 s, the grids were blotted for 3 s and rapidly cryocooled in liquid ethane using Vitrobot Mark IV at 7° C. and 100% humidity.

The grids were imaged at Titan Krios G4 cryo-electron microscope operated at 300 kV equipped with Falcon 4 direct electron detector and Selectris X energy filter (Shuimu Inc., Hangzhou). Movies were recorded by EPU software at a magnification of 130,000× corresponding to a calibrated sampling of 0.95 Å per pixel (0.475 Å per pixel in super-resolution mode). Each movie was composed of 32 frames with an exposure time of 6.541 s and total dose of 47.47 e−/Å2. A total of 5426 movie stacks were collected for Degrader B complex.

Cryo-EM Data Processing:

All moves stacks were motion-corrected using MotionCor2. Motion-corrected micrographs were imported into CryoSPARC for processing. The contrast transfer function (CTF) was determined using Patch CTF estimation in CryoSPARC. The micrographs were manually curated according to CTF fit resolution and Relative ice thickness. After curation, 5332 micrographs were selected for further processing.

Particles were initially selected by Blot Picker from 500 micrographs with diameter parameter set from 240 to 280 Å. The particles were extracted and used to perform one round of 2D classification. Good classes were selected as templates for Template Picker to pick particles from all micrographs in the two datasets. After inspection and extraction, 1,649,185 particles with data size of 200 pixels×1.90 Å/pixel were obtained for Degrader B. After several rounds of 2D and 3D classifications, 466,068 particles were selected for 3D reconstruction. These particles were re-extracted with data size of 400 pixels×0.95 Å/pixel. The 3D Homogenous Refinement and Non-uniform Refinement were performed with D2 symmetry, resulting in 2.97-Å resolution maps. The resolution for the final maps was estimated with the 0.143 criterion of the Fourier shell correlation curve. Local resolution map was calculated using the "Local Resolution Estimation" option in CryoSPARC.

Figure 7:
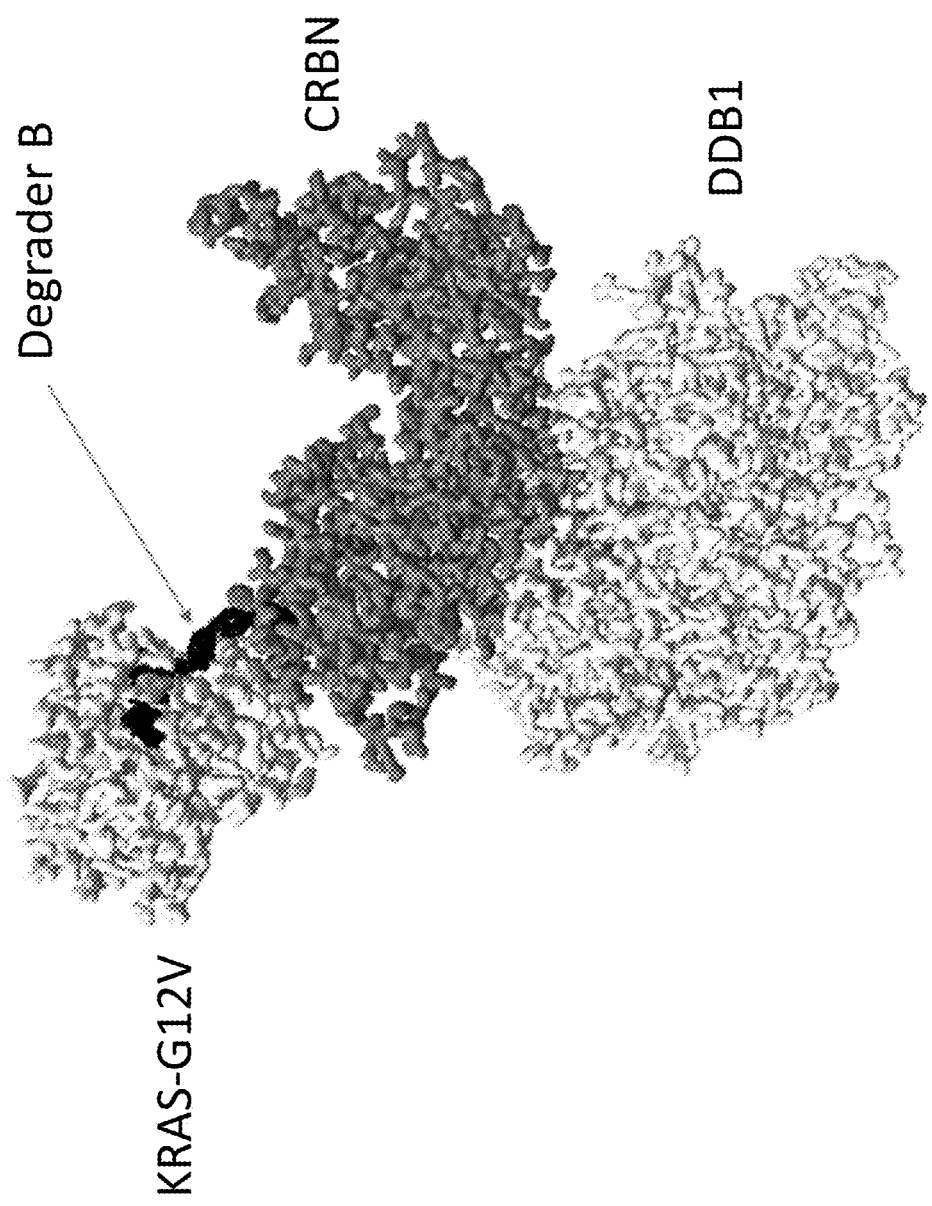
FIG. 7 illustrates the cryo-EM structure of Degrader B bound to KRAS-G12V and CRBN-DDB1 and further shows the induced protein-protein interactions between KRAS-G12V and cereblon at the interface.

Model Building and Structural Analysis:

The maps were sharpened using DeepEMhancer wrapper in CryoSPARC and the sharpened maps were used for model building. For model building, crystal structures of CRBN-DDB1 and KRAS-GppNHp-compound were initially fitted into the EM maps in ChimeraX. The resulting models were manually checked and adjusted in Coot for several rounds. Final models were obtained after refinement using real-space-refine in Phenix. All structural analysis and figure preparation were performed using ChimeraX. FIG. 7 shows the cryo-EM structure of Degrader B bound to KRAS-G12V and CRBN-DDB1 and further shows the induced protein-protein interactions between KRAS-G12V and cereblon at the interface.

EQUIVALENTS AND INCORPORATION BY REFERENCE

While aspects of the present disclosure have been particularly shown and described with reference to certain embodiments and various alternate embodiments, it will be understood by persons skilled in the relevant art that various changes in form and details can be made therein without departing from the spirit and scope of the present disclosure.

All references, issued patents, and patent applications cited within the body of the instant specification are hereby incorporated by reference in their entirety, for all purposes. In particular, U.S. Provisional Patent Application No. 63/385,453, filed Nov. 30, 2022, and U.S. Provisional Patent Application No. 63/593,528, filed Oct. 26, 2023, are hereby incorporated by reference in their entirety.

What is claimed is:

1. A compound, wherein the compound is represented by Formula IC or is a pharmaceutically acceptable salt thereof:

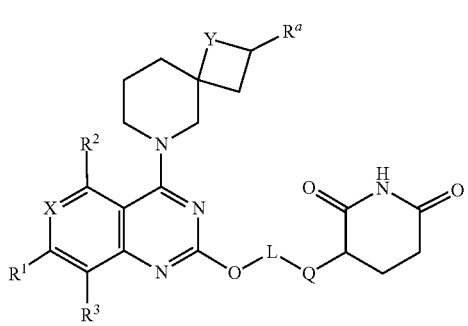

(IC)

wherein:
  each $R^a$ is independently selected from hydrogen, halogen, cyano, hydroxy, and $C_1$-$C_6$ alkyl;
  $R^1$ is a monocyclic or bicyclic aryl or heteroaryl, wherein the monocyclic or bicyclic aryl and heteroaryl are independently substituted with 0, 1, 2, 3, or 4 $R^b$; each $R^b$ is independently selected from halogen, cyano, hydroxy, amino, and $C_1$-$C_4$ alkyl;
  X is N;
  Y is O or $CH_2$;
  $R^2$ is H or halogen;
  $R^3$ is halogen;
  L is selected from

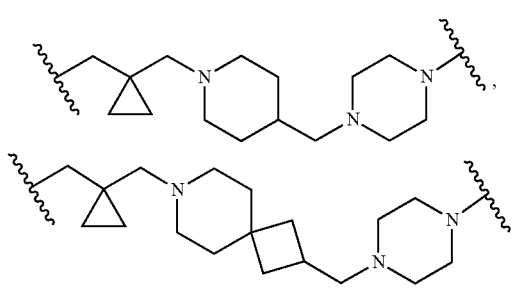

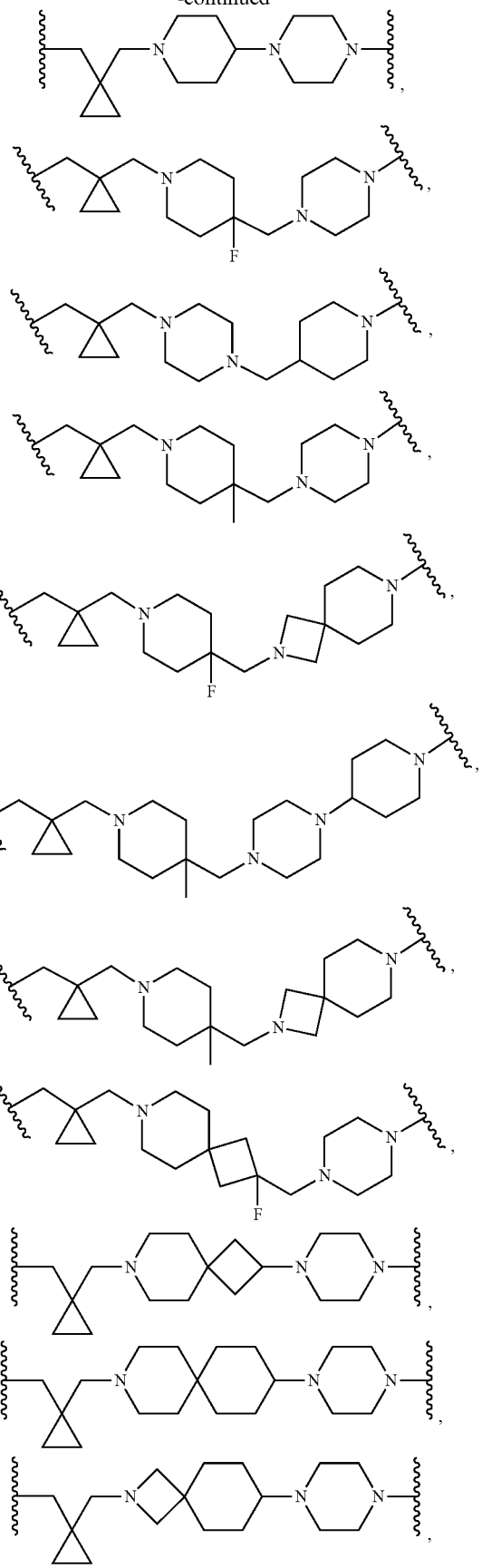

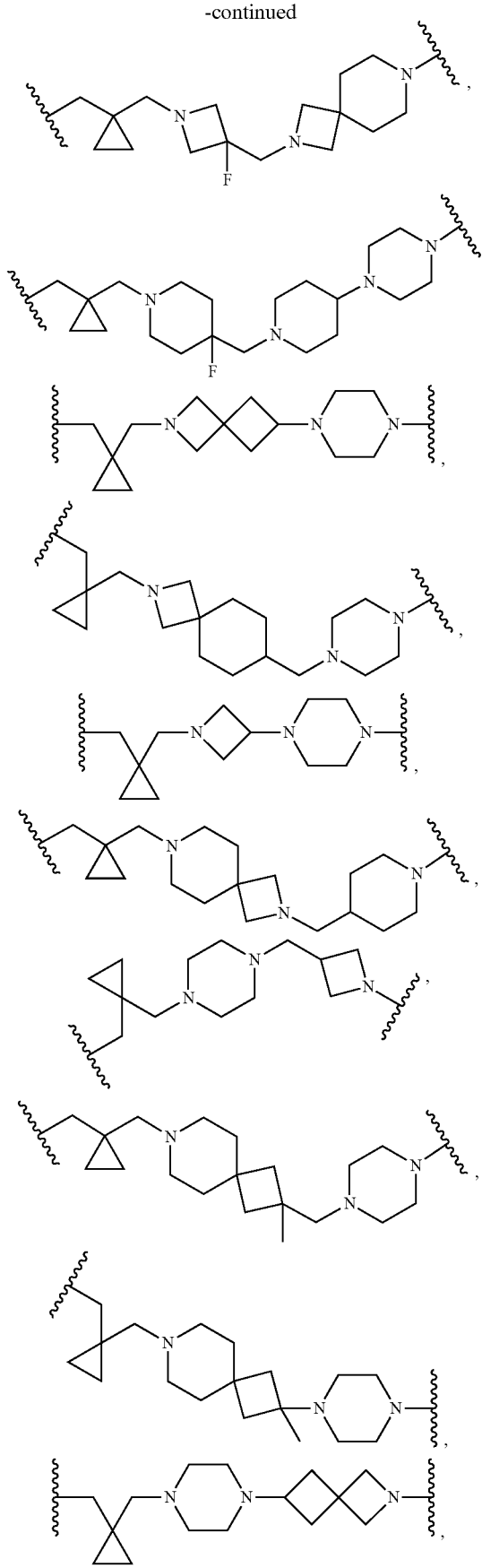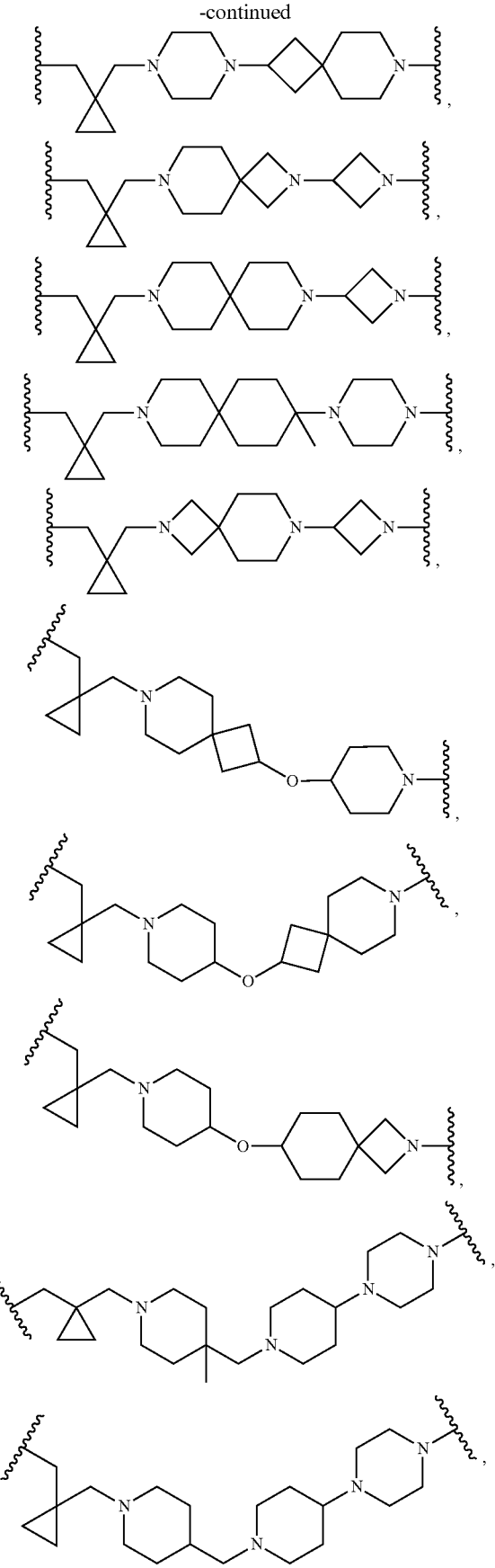

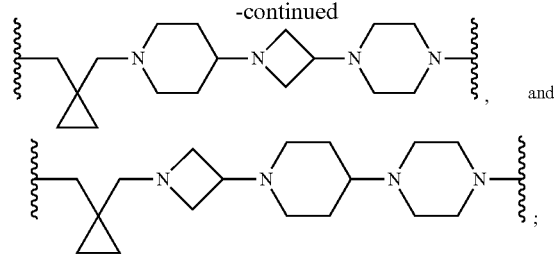

Q is 1 to 5 carbon atoms in length, wherein one or more carbon atoms are replaced by a divalent group selected from heterocyclyl, aryl, heteroaryl, —NH—, —C(=O)—, and —C(=O)—NH—, and wherein each of the heterocyclyl, aryl, and heteroaryl is independently substituted with 0, 1, 2, 3, 4, or 5 $R^f$; and each $R^f$ is independently selected from halogen, hydroxy, $C_1$-$C_3$ alkyl, $C_1$-$C_3$ haloalkyl, $C_1$-$C_5$ alkoxy, and an oxo group.

2. The compound of claim 1, wherein L is selected from

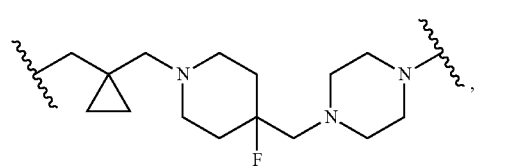

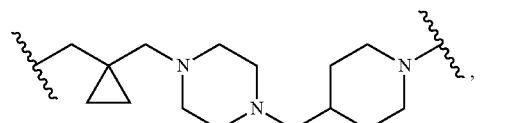

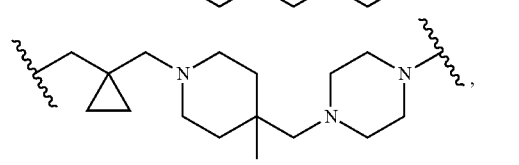

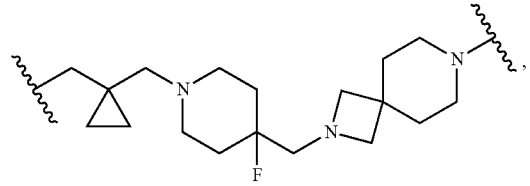

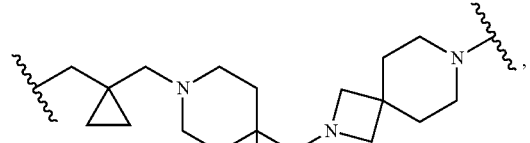

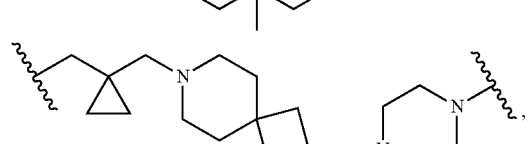

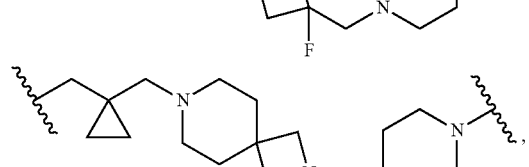

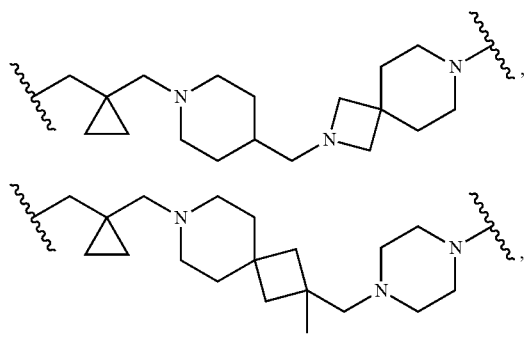

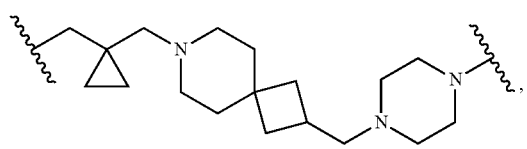

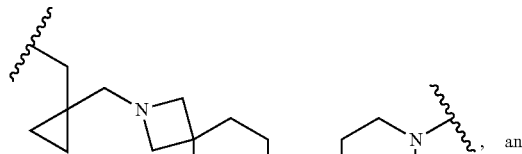

3. The compound of claim 1, wherein L is selected from

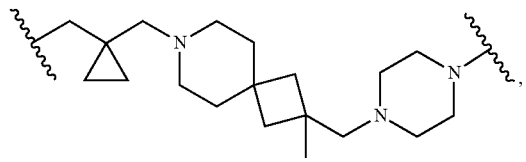

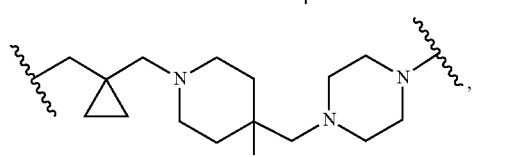

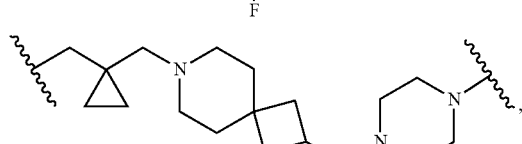

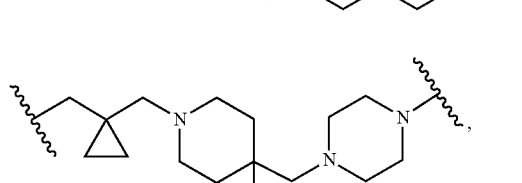

-continued
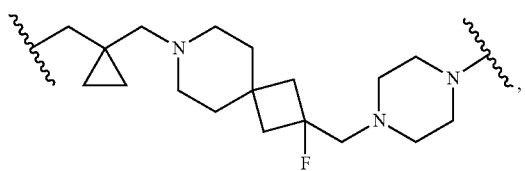
and
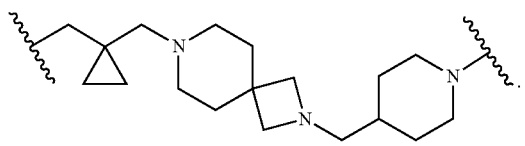
4. The compound of claim 1, wherein L is selected from
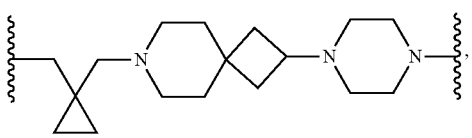
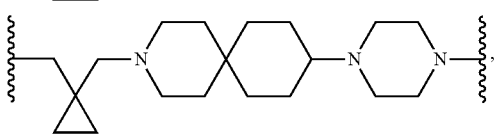
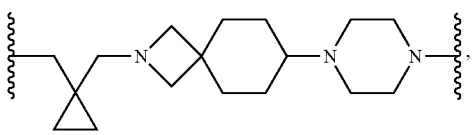
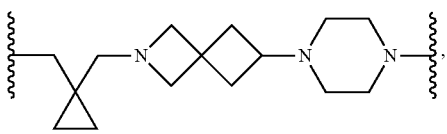
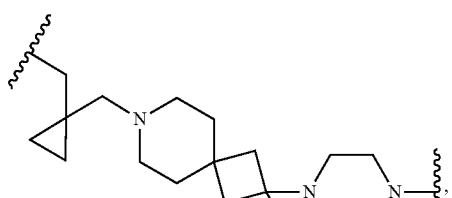
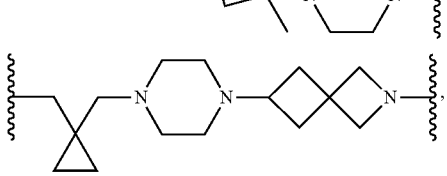
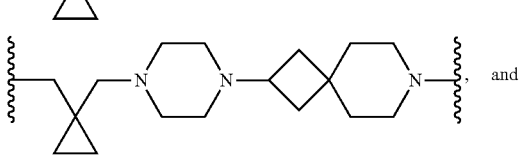, and
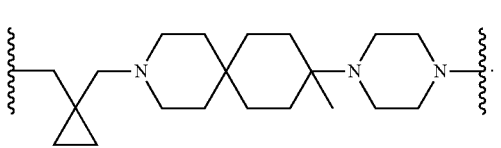
5. The compound of claim 1, wherein Q is selected from
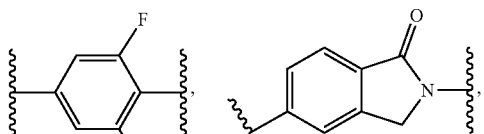
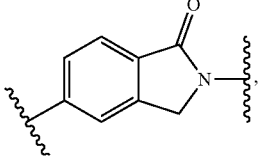
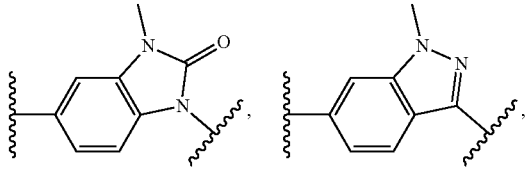
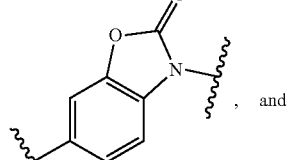, and
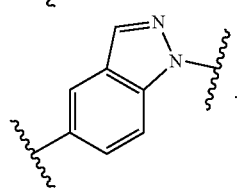
6. The compound of claim 1, wherein Q is selected from
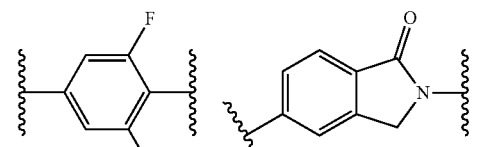
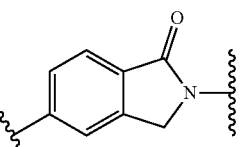
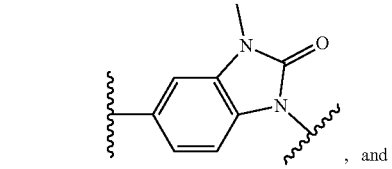, and
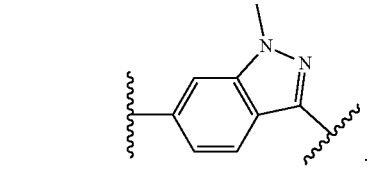
7. The compound of claim 1, wherein Q is
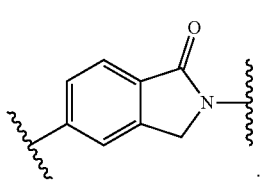 [SMILES: *c1ccc2c(c1)CN(*)C2=O]

8. The compound of claim 1, wherein R¹ is selected from
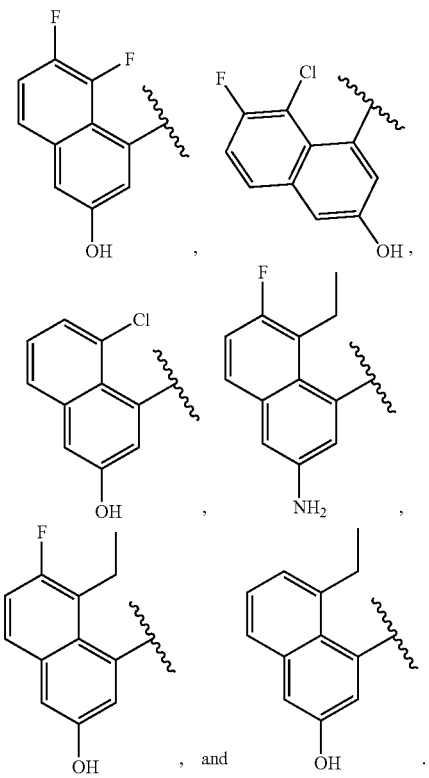
, and
9. The compound of claim 8, wherein R¹ is
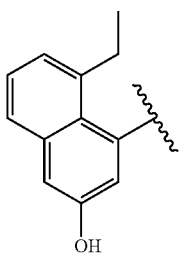
.
10. The compound of claim 8, wherein R¹ is
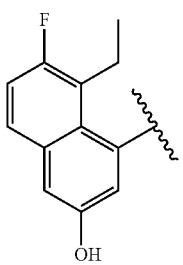
.
11. The compound of claim 1, wherein Y is O.
12. The compound of claim 1, wherein R³ is F.
13. The compound of claim 1, wherein the compound is selected from
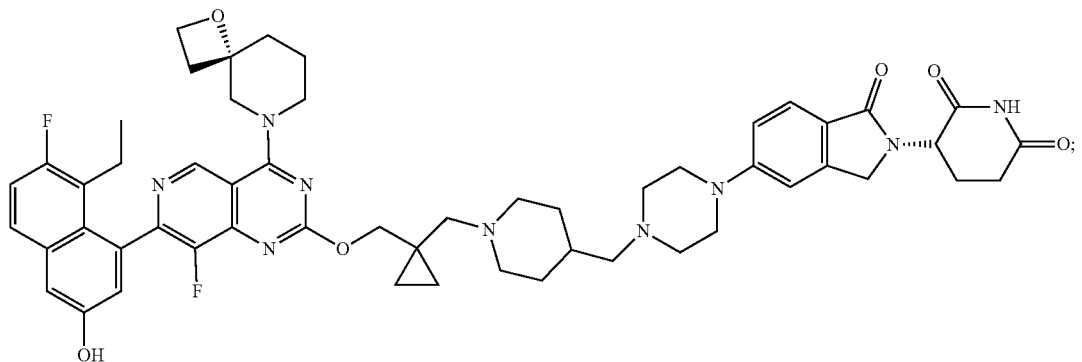
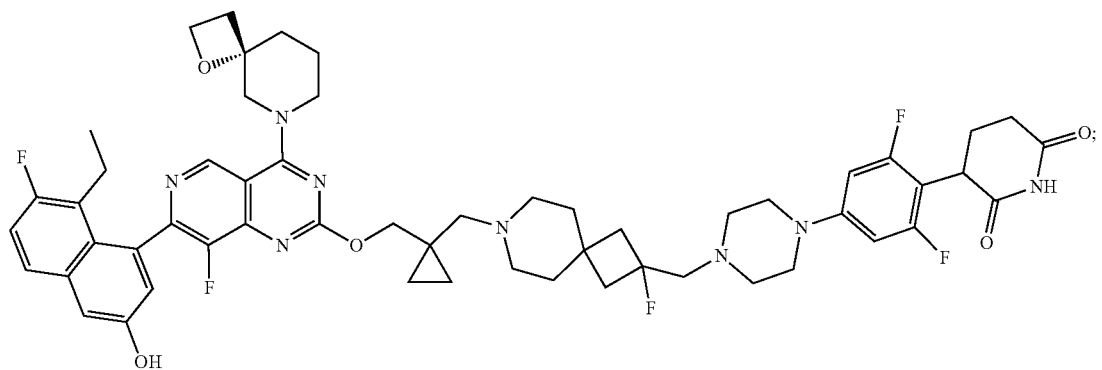

663
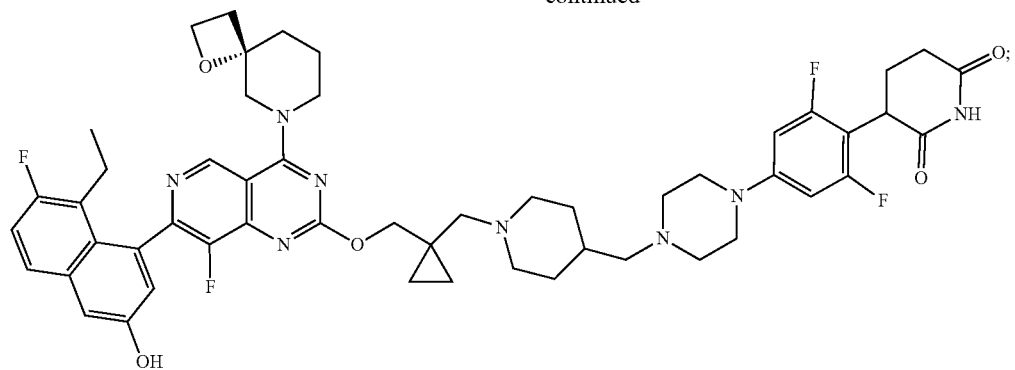
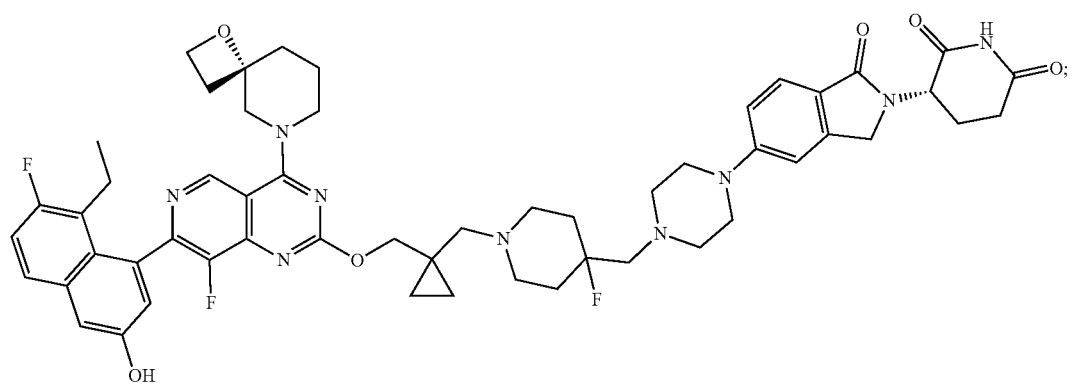
664
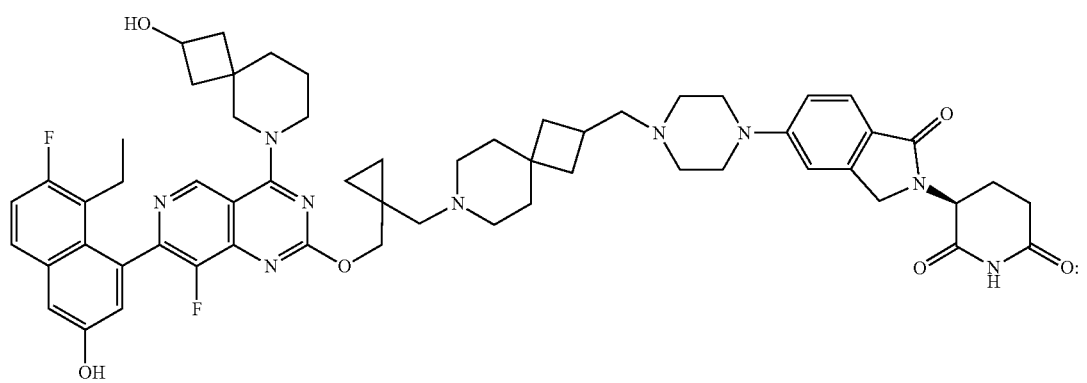
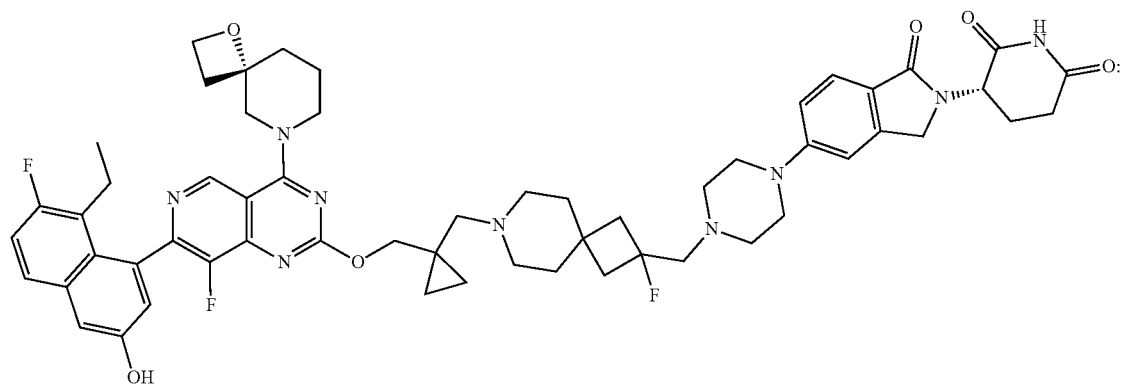

665 666
-continued
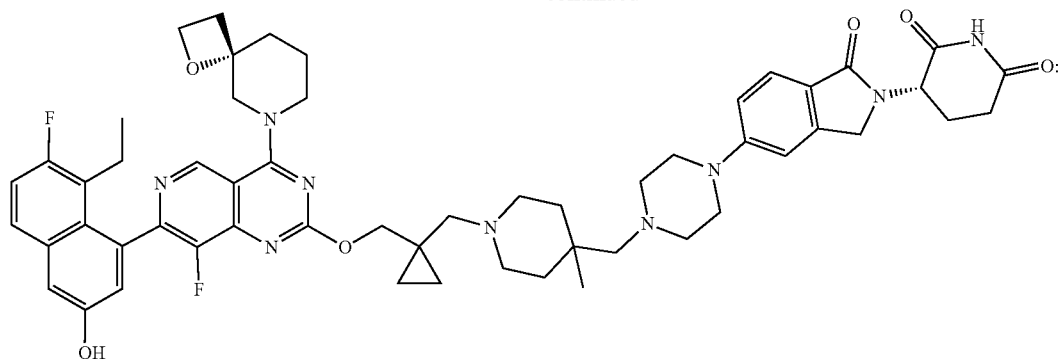
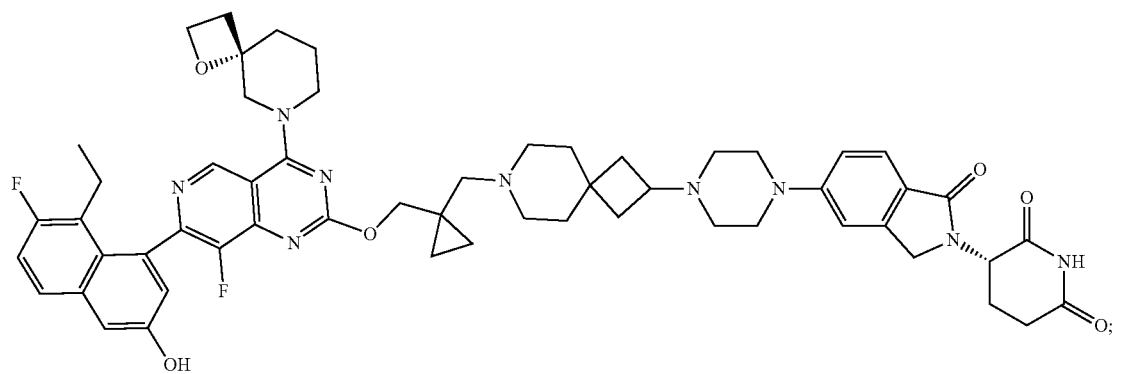
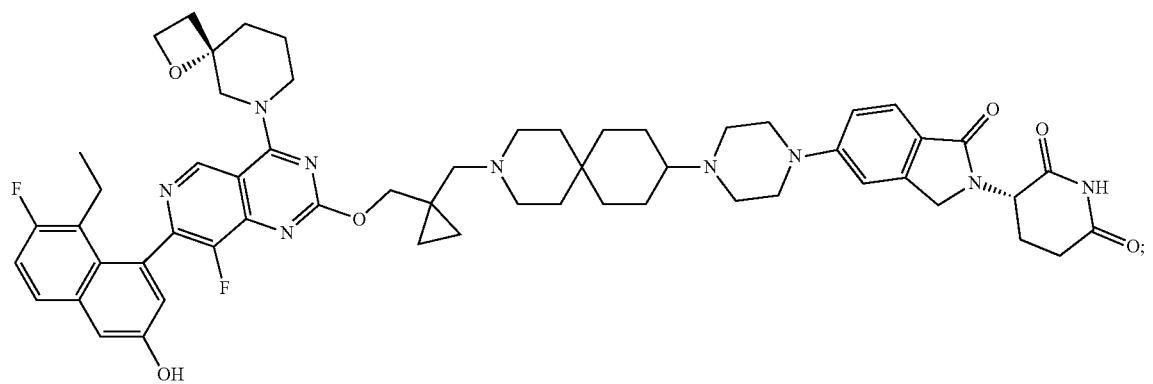
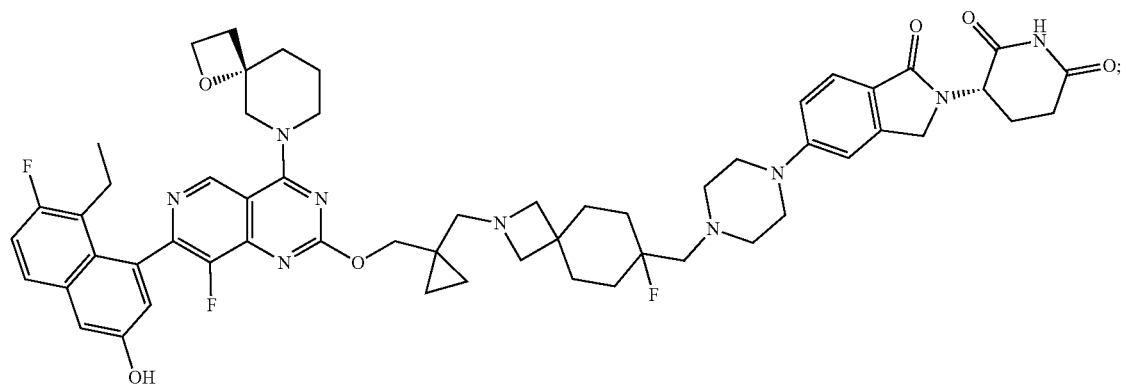

667
-continued
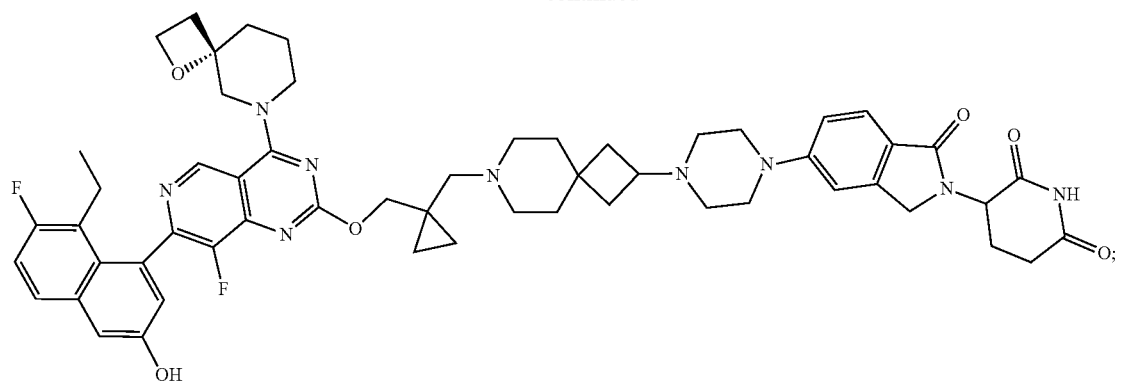
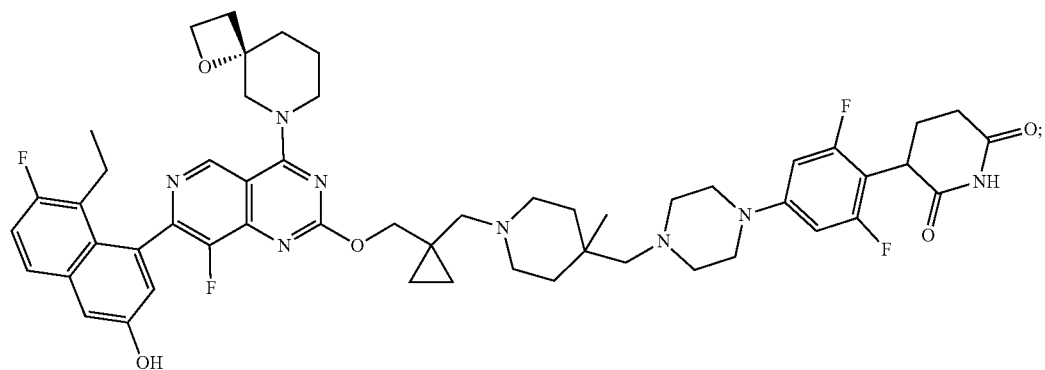
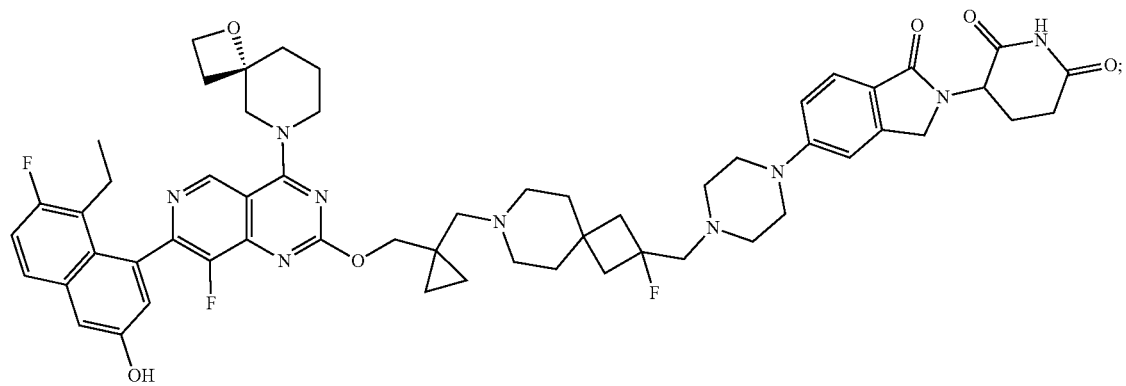
668
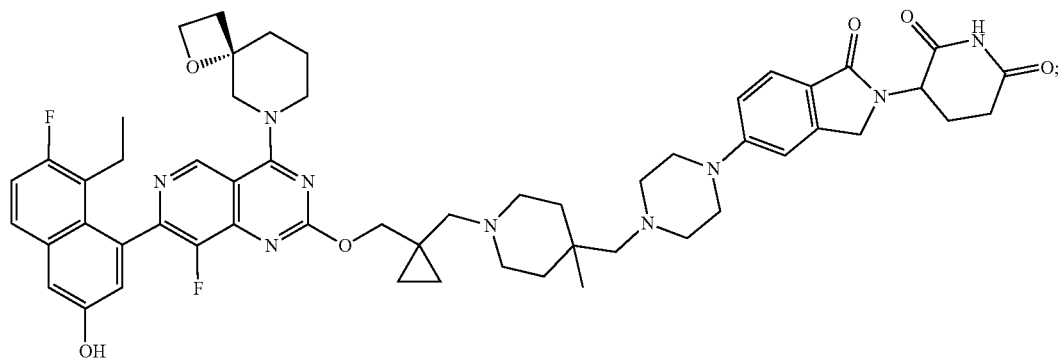

669                                                                 670
-continued
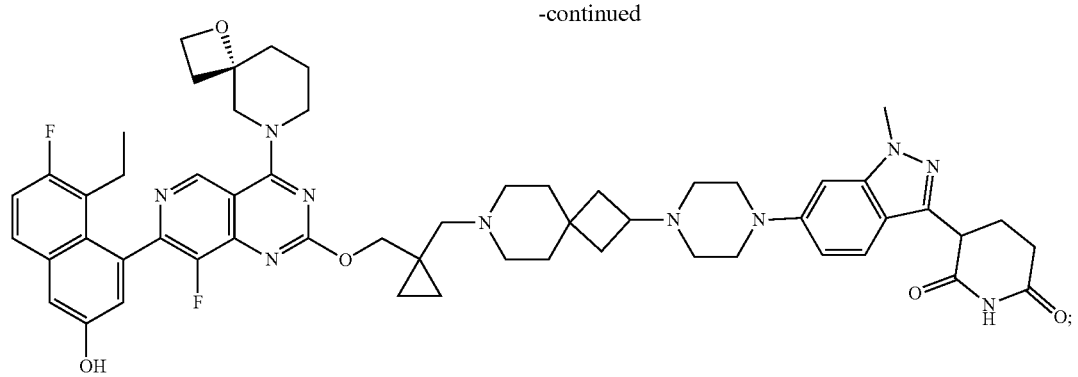
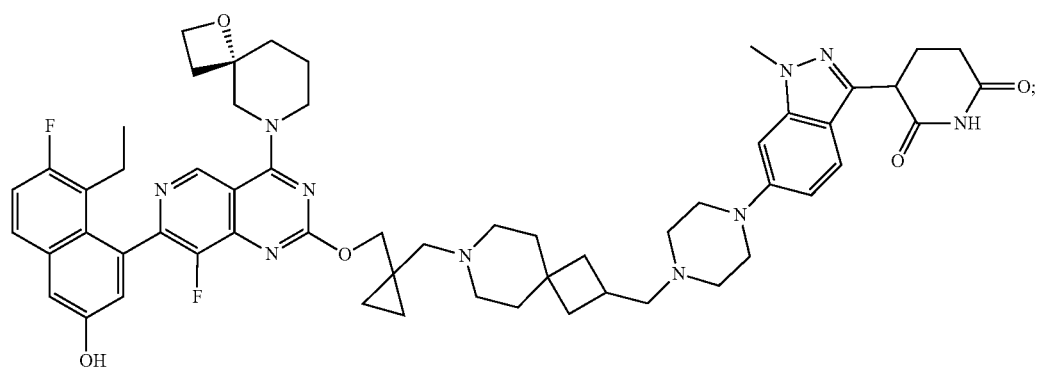
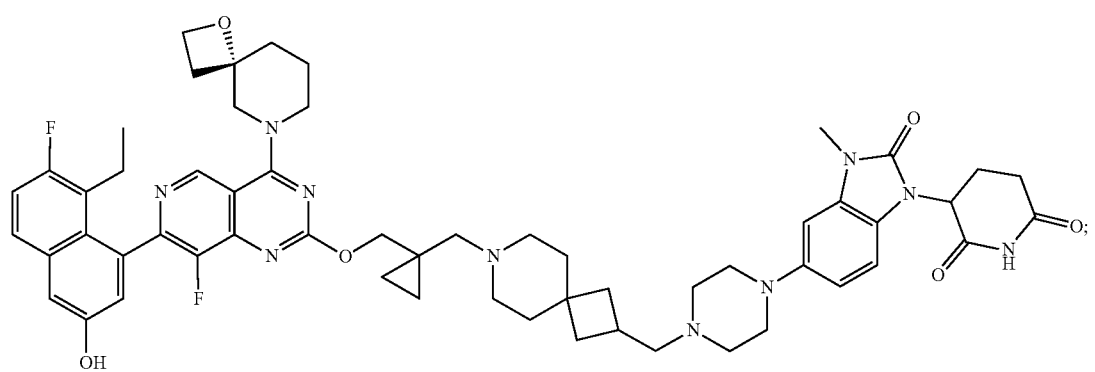
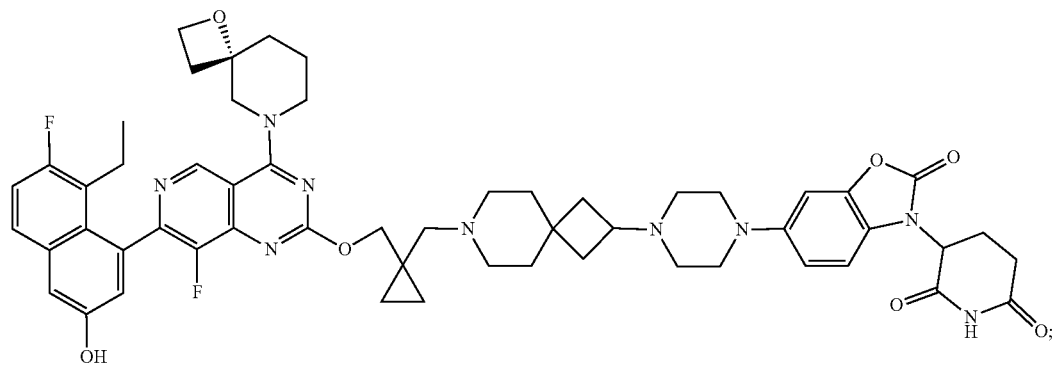

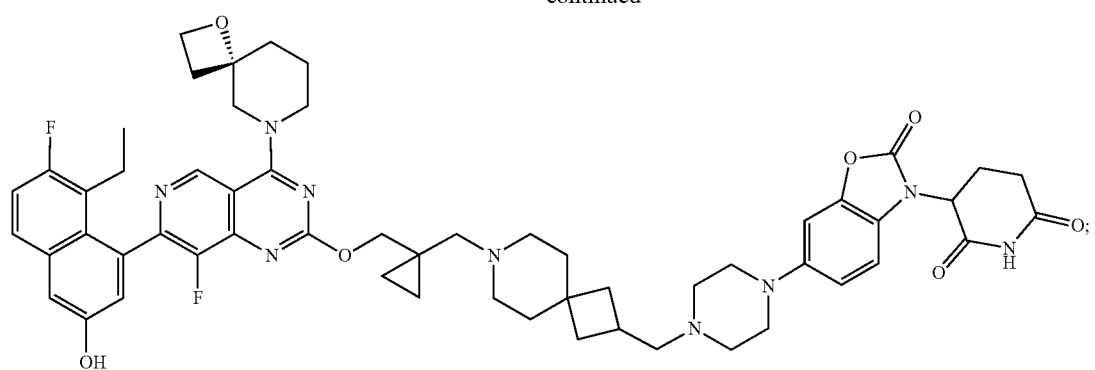
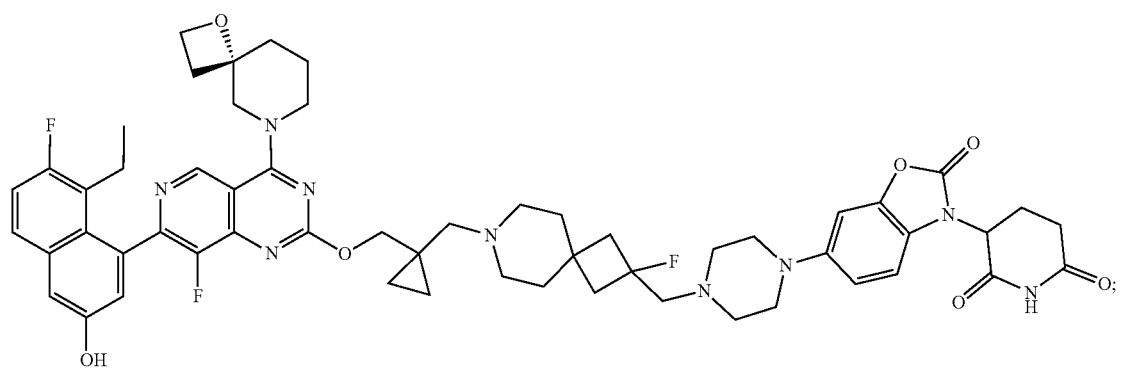
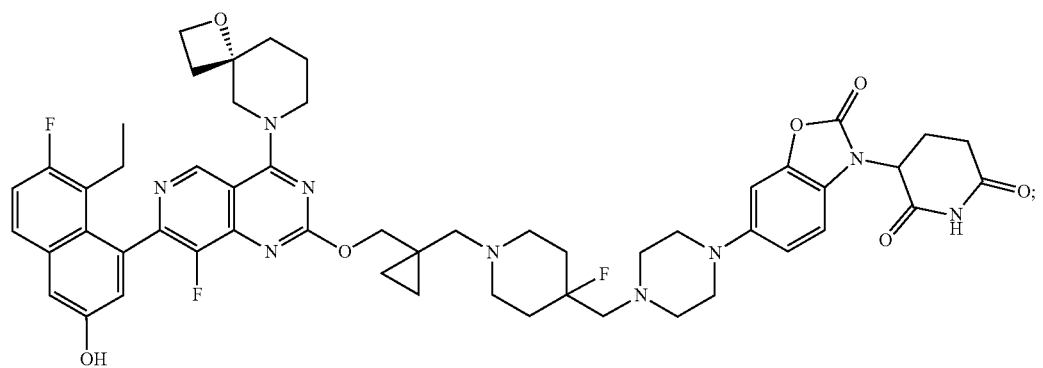
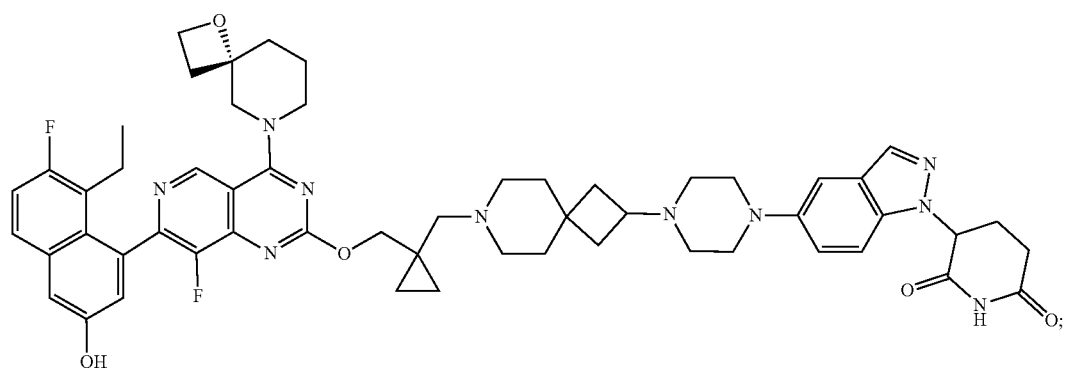

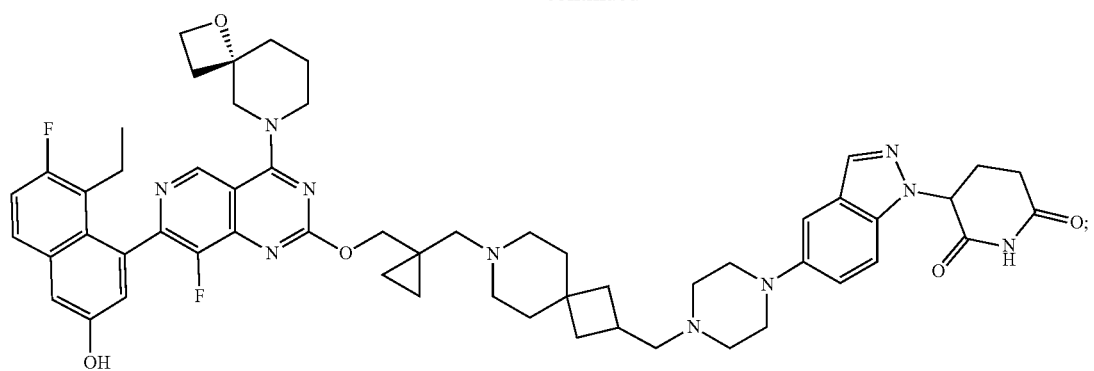
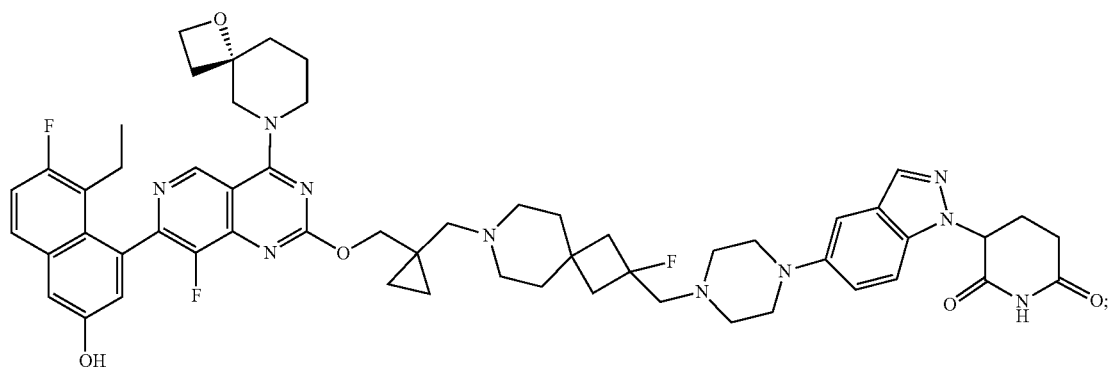
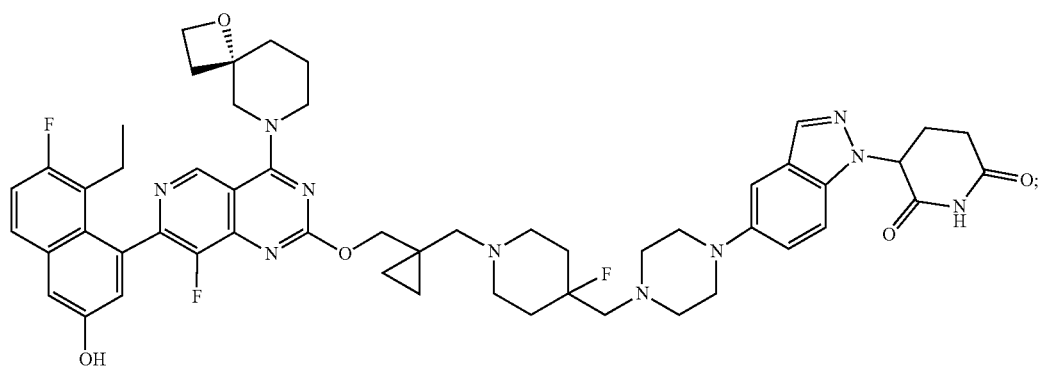
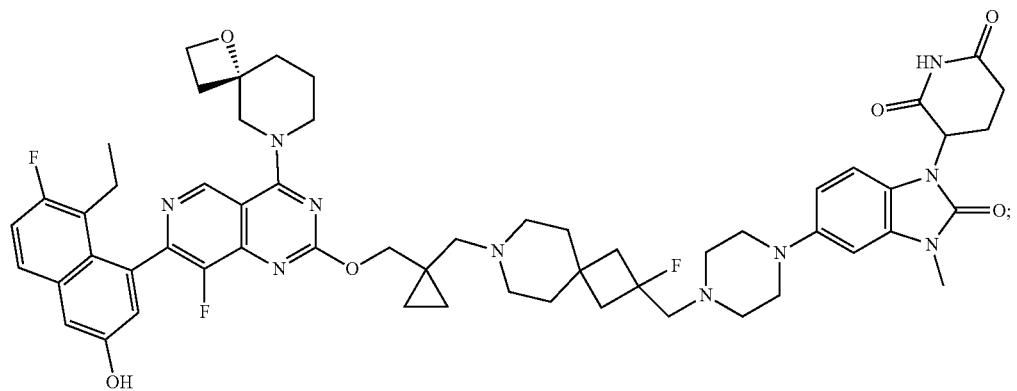

-continued

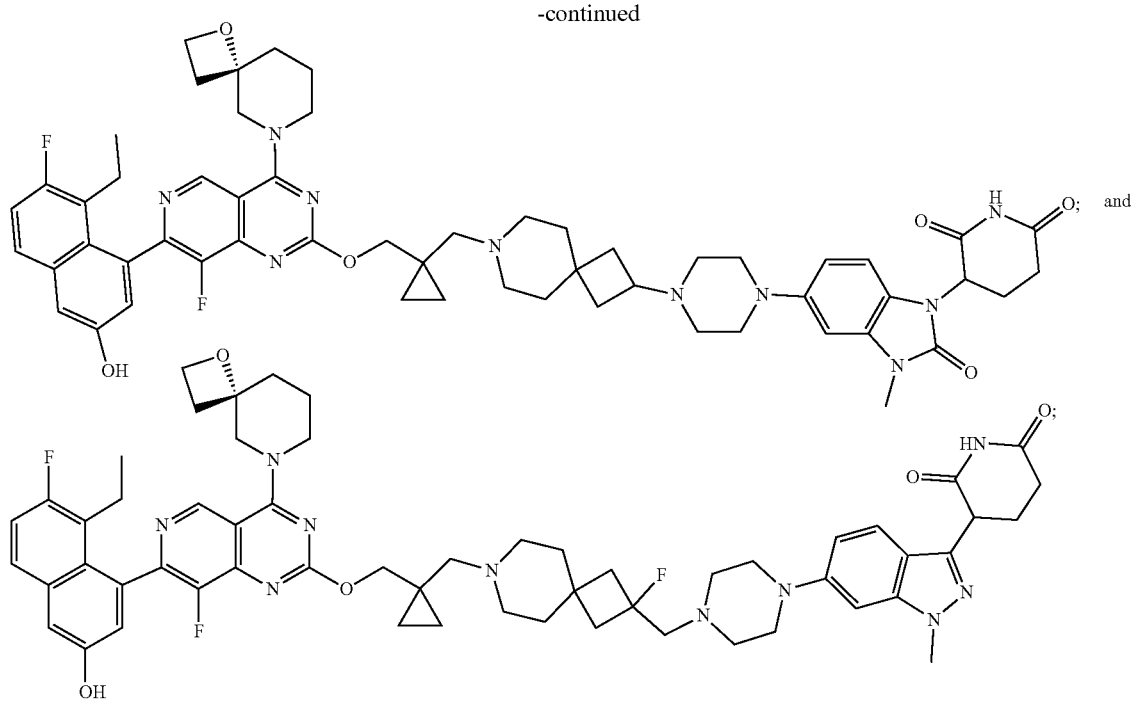

or a pharmaceutically acceptable salt thereof.

14. A pharmaceutical composition comprising a therapeutically effective amount of a compound according to claim 13 and one or more pharmaceutically acceptable carriers, pharmaceutically acceptable vehicles, pharmaceutically acceptable excipients, or combinations thereof.

15. A method for degrading mutant and/or wild-type KRAS in a cell, comprising contacting the cell with at least one compound according to claim 13.

16. A method of treating cancer in a subject in need thereof, comprising administering to the subject an effective amount of at least one compound according to claim 13, wherein the cancer is selected from lung cancer, pancreatic cancer, small bowel cancer, colorectal cancer, gall bladder cancer, thyroid cancer, liver cancer, bile duct cancer, cervical cancer, bladder cancer, prostate cancer, esophageal cancer, and blood cancer.

17. A method of treating cancer in a patient in need thereof, wherein the cancer is selected from lung cancer, pancreatic cancer, small bowel cancer, colorectal cancer, gall bladder cancer, thyroid cancer, liver cancer, bile duct cancer, cervical cancer, bladder cancer, prostate cancer, esophageal cancer, and blood cancer, the method comprising (a) determining that the cancer is associated with one or more KRAS mutations; and (b) administering to the patient a therapeutically effective amount of the compound according to claim 13.

18. A method of treating cancer associated with one or more KRAS mutations in a patient in need thereof, comprising administering to the patient a therapeutically effective amount of the compound according to claim 13, wherein the cancer is selected from lung cancer, pancreatic cancer, small bowel cancer, colorectal cancer, gall bladder cancer, thyroid cancer, liver cancer, bile duct cancer, cervical cancer, bladder cancer, prostate cancer, esophageal cancer, and blood cancer.

19. The compound of claim 1, wherein the compound is

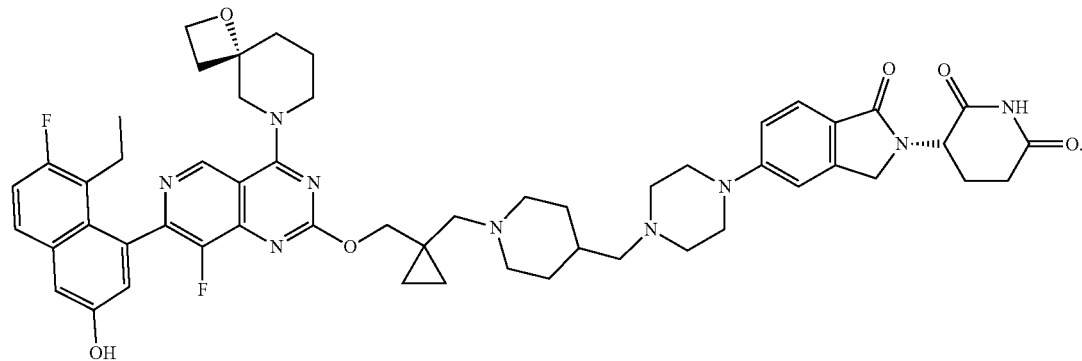

or a pharmaceutically acceptable salt thereof.

20. The compound of claim 1, wherein the compound is
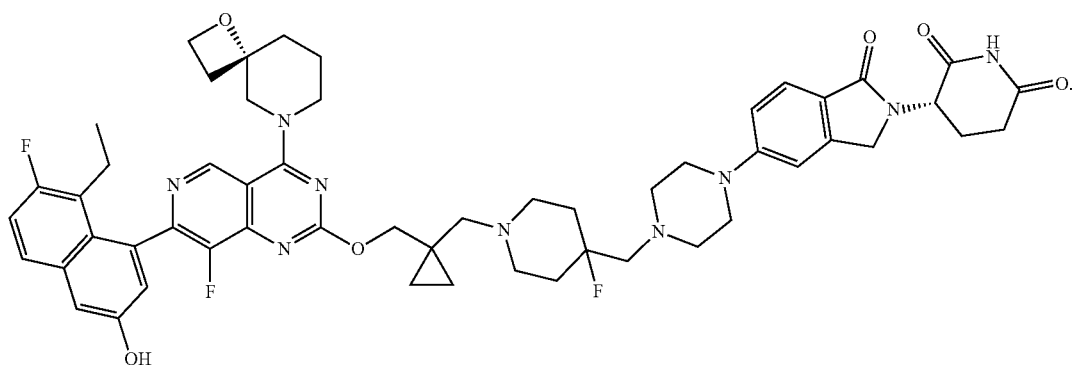 [SMILES: CCc1c(F)ccc2cc(O)cc(-c3ncc4c(N5CCC[C@]6(CCO6)C5)nc(OCC5(CN6CCC(F)(CN7CCN(c8ccc9c(c8)CN([C@H]8CCC(=O)NC8=O)C9=O)CC7)CC6)CC5)nc4c3F)c12]
or a pharmaceutically acceptable salt thereof.
21. The compound of claim 1, wherein the compound is
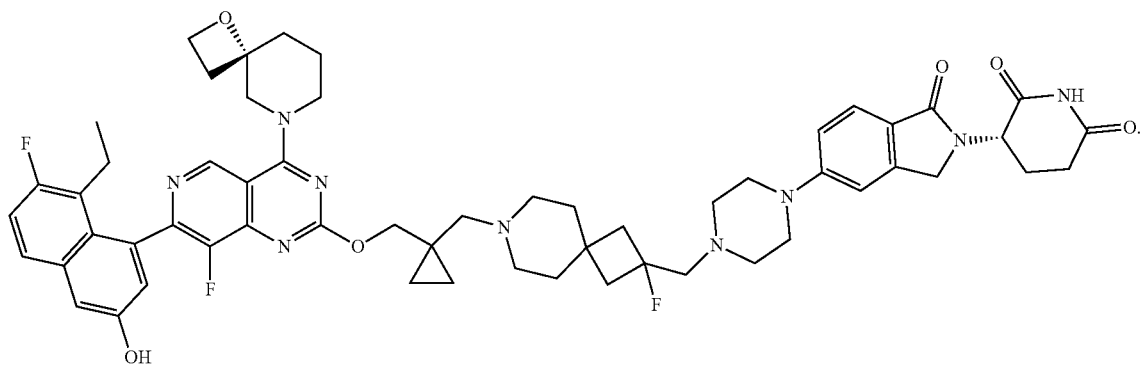 [SMILES: CCc1c(F)ccc2cc(O)cc(-c3ncc4c(N5CCC[C@]6(CCO6)C5)nc(OCC5(CN6CCC7(CC6)CC(F)(CN6CCN(c8ccc9c(c8)CN([C@H]8CCC(=O)NC8=O)C9=O)CC6)C7)CC5)nc4c3F)c12]
or a pharmaceutically acceptable salt thereof.
22. The compound of claim 1, wherein the compound is
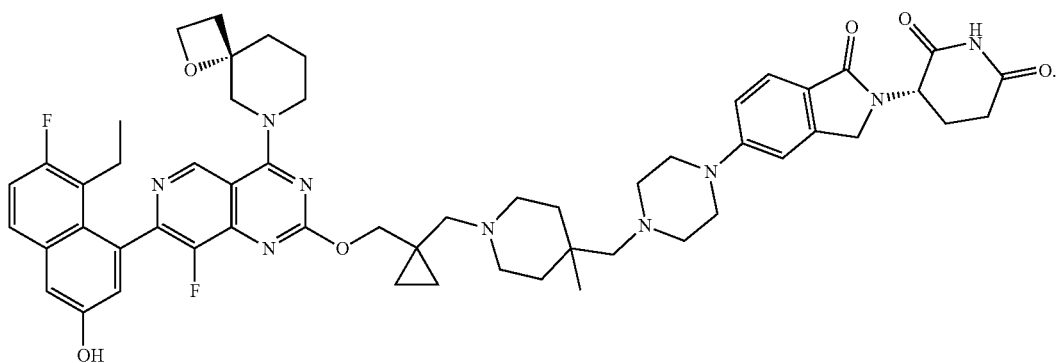 [SMILES: CCc1c(F)ccc2cc(O)cc(-c3ncc4c(N5CCC[C@]6(CCO6)C5)nc(OCC5(CN6CCC(C)(CN7CCN(c8ccc9c(c8)CN([C@H]8CCC(=O)NC8=O)C9=O)CC7)CC6)CC5)nc4c3F)c12]
or a pharmaceutically acceptable salt thereof.

23. The compound of claim 1, wherein the compound is
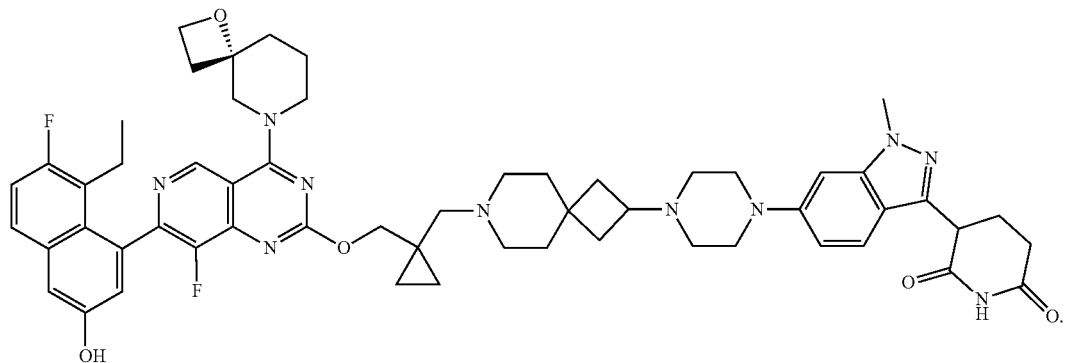 [SMILES: CCc1c(F)ccc2cc(O)cc(-c3ncc4c(N5CCC[C@]6(CCO6)C5)nc(OCC5(CN6CCC7(CC6)CC(N6CCN(c8ccc9c(C%10CCC(=O)NC%10=O)nn(C)c9c8)CC6)C7)CC5)nc4c3F)c12]
or a pharmaceutically acceptable salt thereof.
24. The compound of claim 1, wherein the compound is
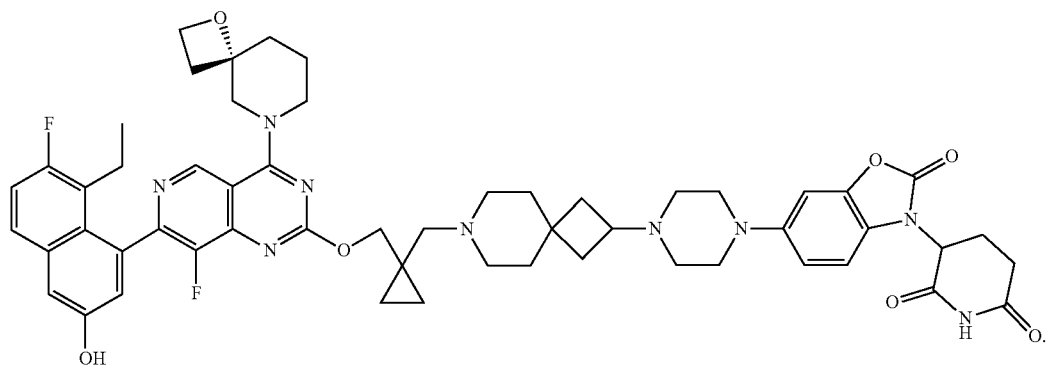 [SMILES: CCc1c(F)ccc2cc(O)cc(-c3ncc4c(N5CCC[C@]6(CCO6)C5)nc(OCC5(CN6CCC7(CC6)CC(N6CCN(c8ccc9c(c8)oc(=O)n9C8CCC(=O)NC8=O)CC6)C7)CC5)nc4c3F)c12]
or a pharmaceutically acceptable salt thereof.
25. The compound of claim 1, wherein the compound is
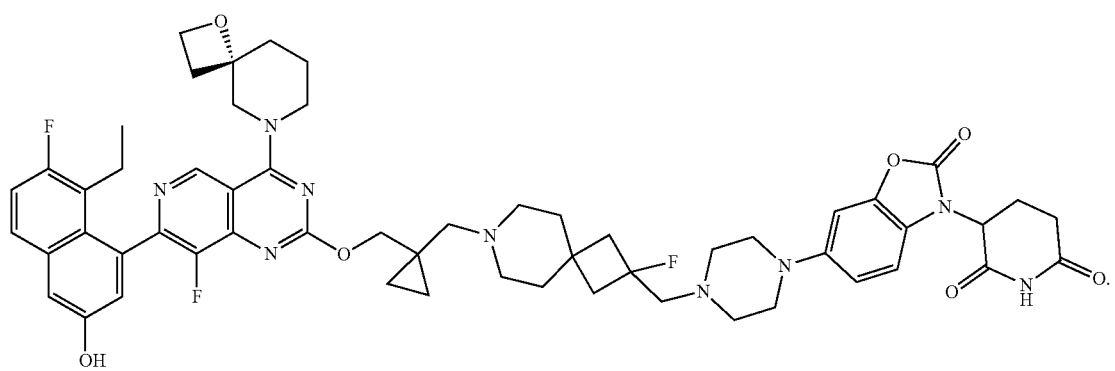 [SMILES: CCc1c(F)ccc2cc(O)cc(-c3ncc4c(N5CCC[C@]6(CCO6)C5)nc(OCC5(CN6CCC7(CC6)CC(F)(CN6CCN(c8ccc9c(c8)oc(=O)n9C8CCC(=O)NC8=O)CC6)C7)CC5)nc4c3F)c12]
or a pharmaceutically acceptable salt thereof.

26. The compound of claim 1, wherein the compound is
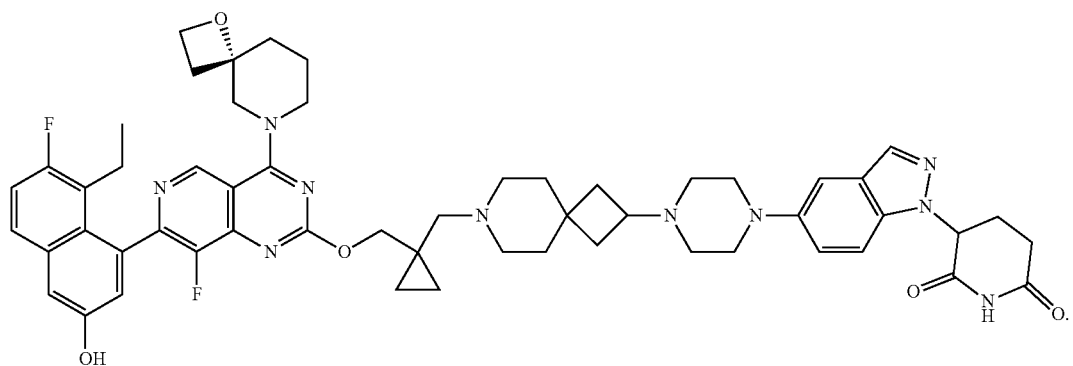 [SMILES: CCc1c(F)ccc2cc(O)cc(-c3ncc4c(N5CCC[C@]6(CCO6)C5)nc(OCC5(CN6CCC7(CC6)CC(N6CCN(c8ccc9c(cnn9C9CCC(=O)NC9=O)c8)CC6)C7)CC5)nc4c3F)c12]
or a pharmaceutically acceptable salt thereof.
27. The compound of claim 1, wherein the compound is
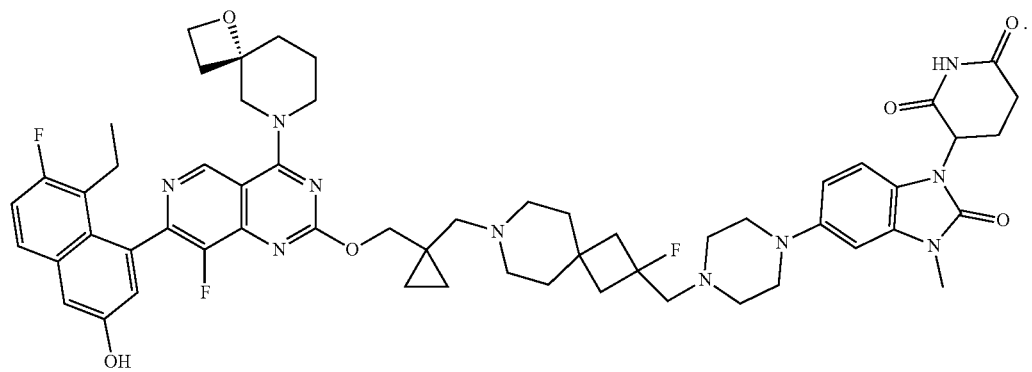 [SMILES: CCc1c(F)ccc2cc(O)cc(-c3ncc4c(N5CCC[C@]6(CCO6)C5)nc(OCC5(CN6CCC7(CC6)CC(F)(CN6CCN(c8ccc9c(c8)n(C)c(=O)n9C8CCC(=O)NC8=O)CC6)C7)CC5)nc4c3F)c12]
or a pharmaceutically acceptable salt thereof.
28. The compound of claim 1, wherein the compound is
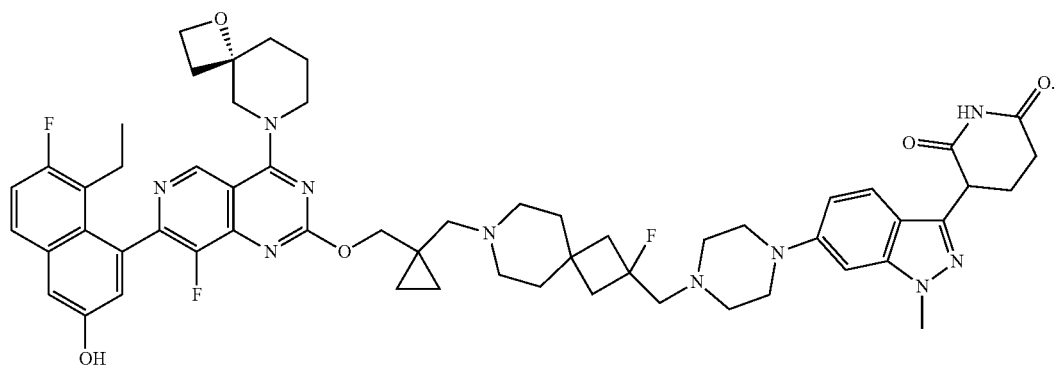 [SMILES: CCc1c(F)ccc2cc(O)cc(-c3ncc4c(N5CCC[C@]6(CCO6)C5)nc(OCC5(CN6CCC7(CC6)CC(F)(CN6CCN(c8ccc9c(C%10CCC(=O)NC%10=O)nn(C)c9c8)CC6)C7)CC5)nc4c3F)c12]
or a pharmaceutically acceptable salt thereof.

29. The compound of claim 1, wherein the compound is selected from
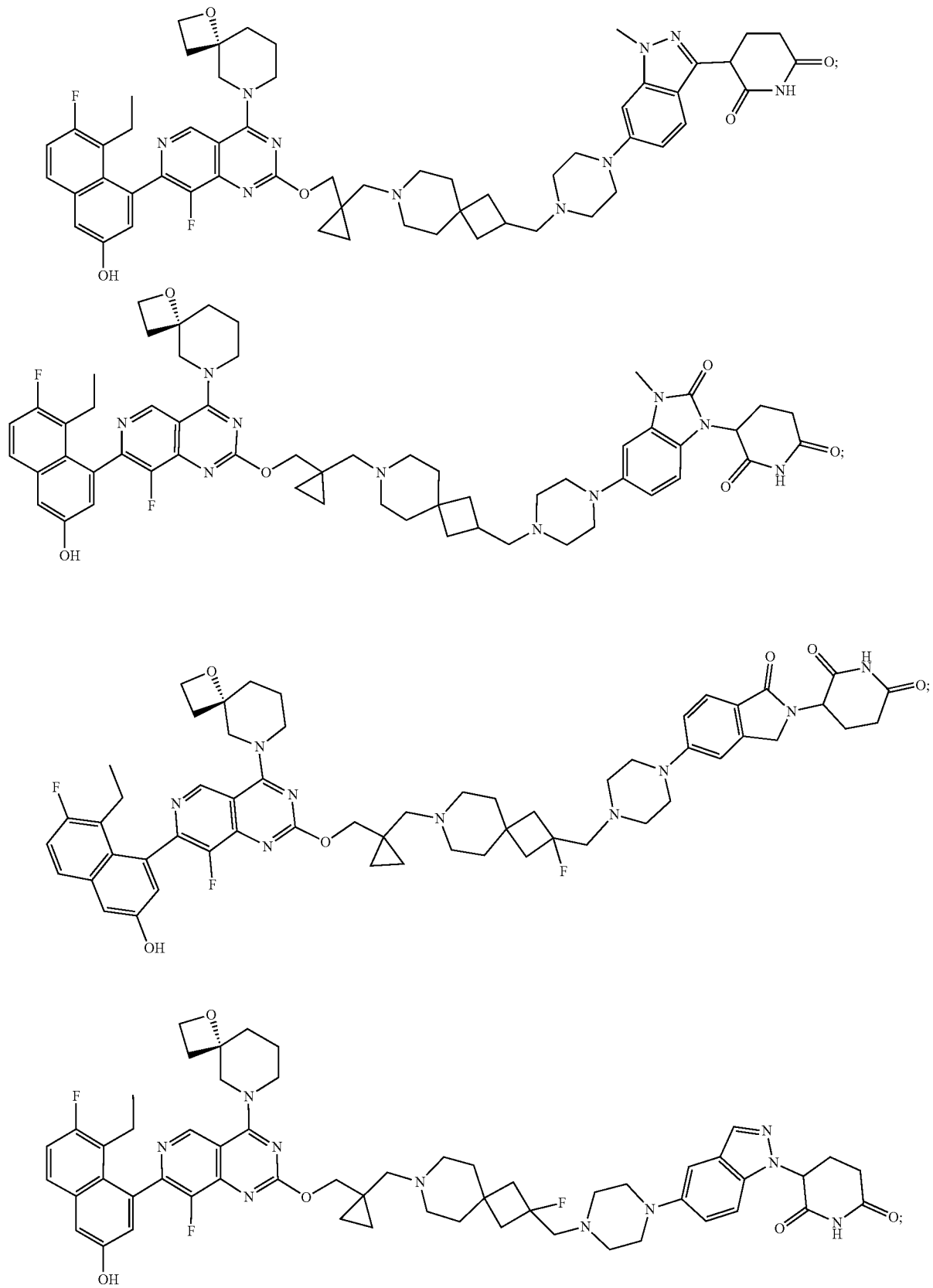

685
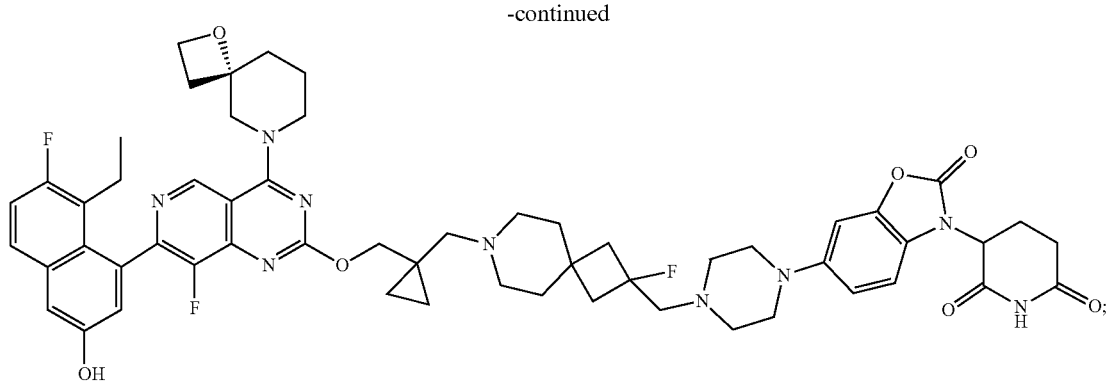
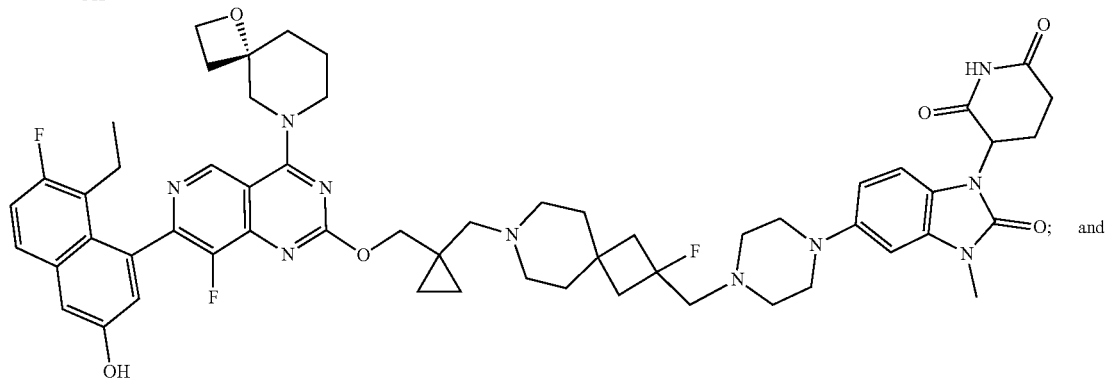
and
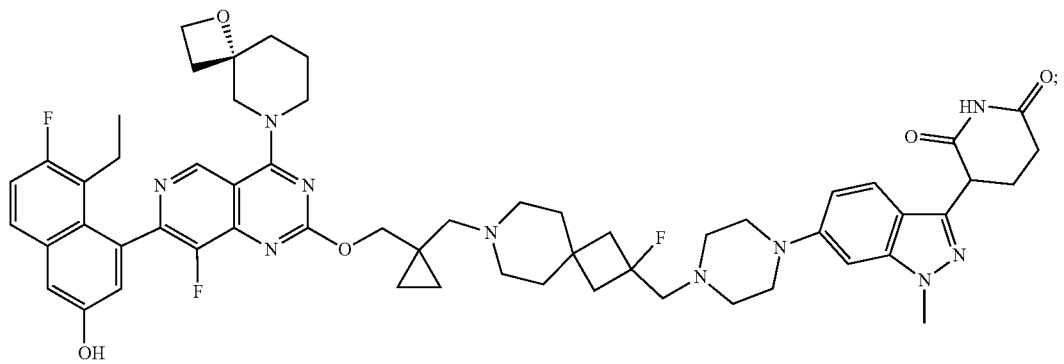
or a pharmaceutically acceptable salt thereof.
30. The compound of claim 1, wherein the compound is selected from
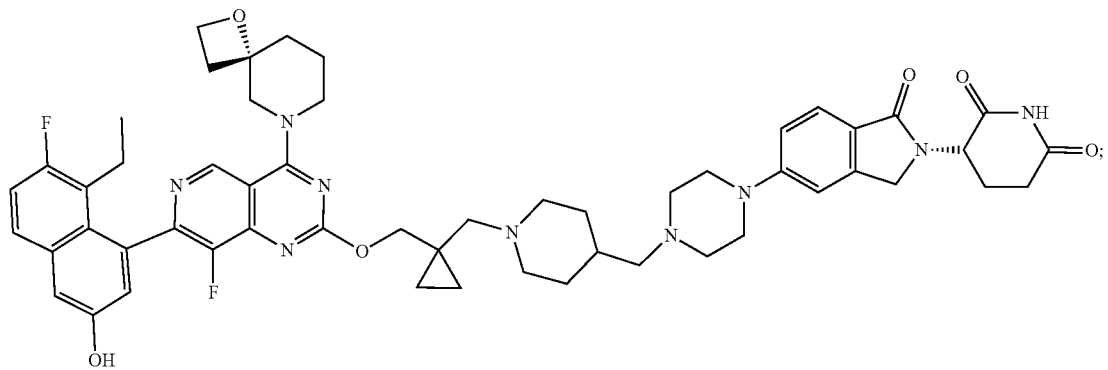

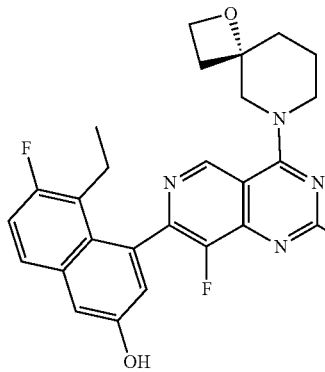
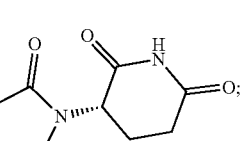
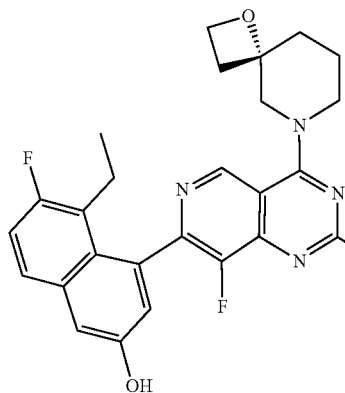
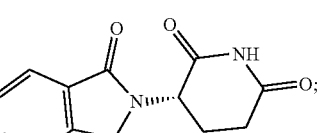
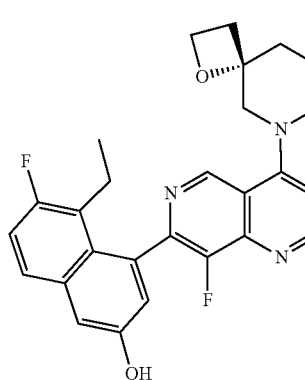
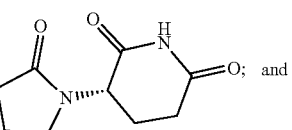
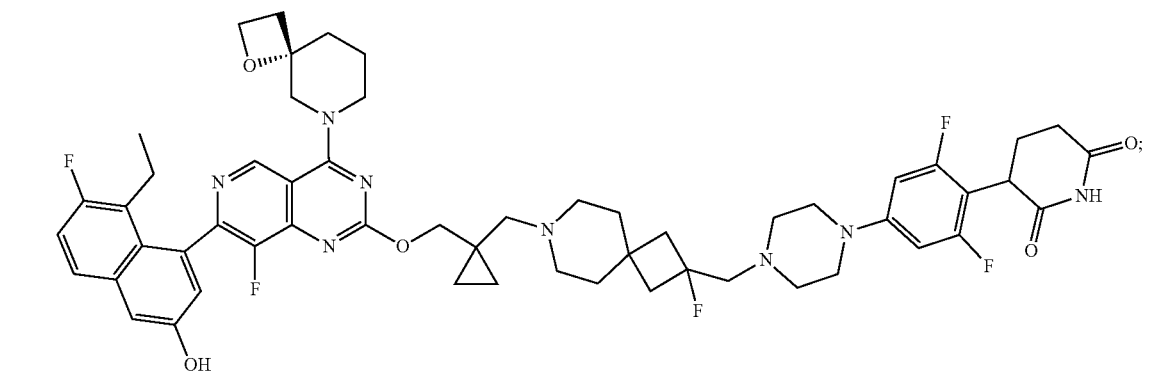 [SMILES: CCc1c(F)ccc2cc(O)cc(-c3ncc4c(N5CCC[C@]6(CCO6)C5)nc(OCC5(CN6CCC7(CC6)CC(F)(CN6CCN(c8cc(F)c(C9CCC(=O)NC9=O)c(F)c8)CC6)C7)CC5)nc4c3F)c12]
or a pharmaceutically acceptable salt thereof.

31. The compound of claim 1, wherein the compound is selected from

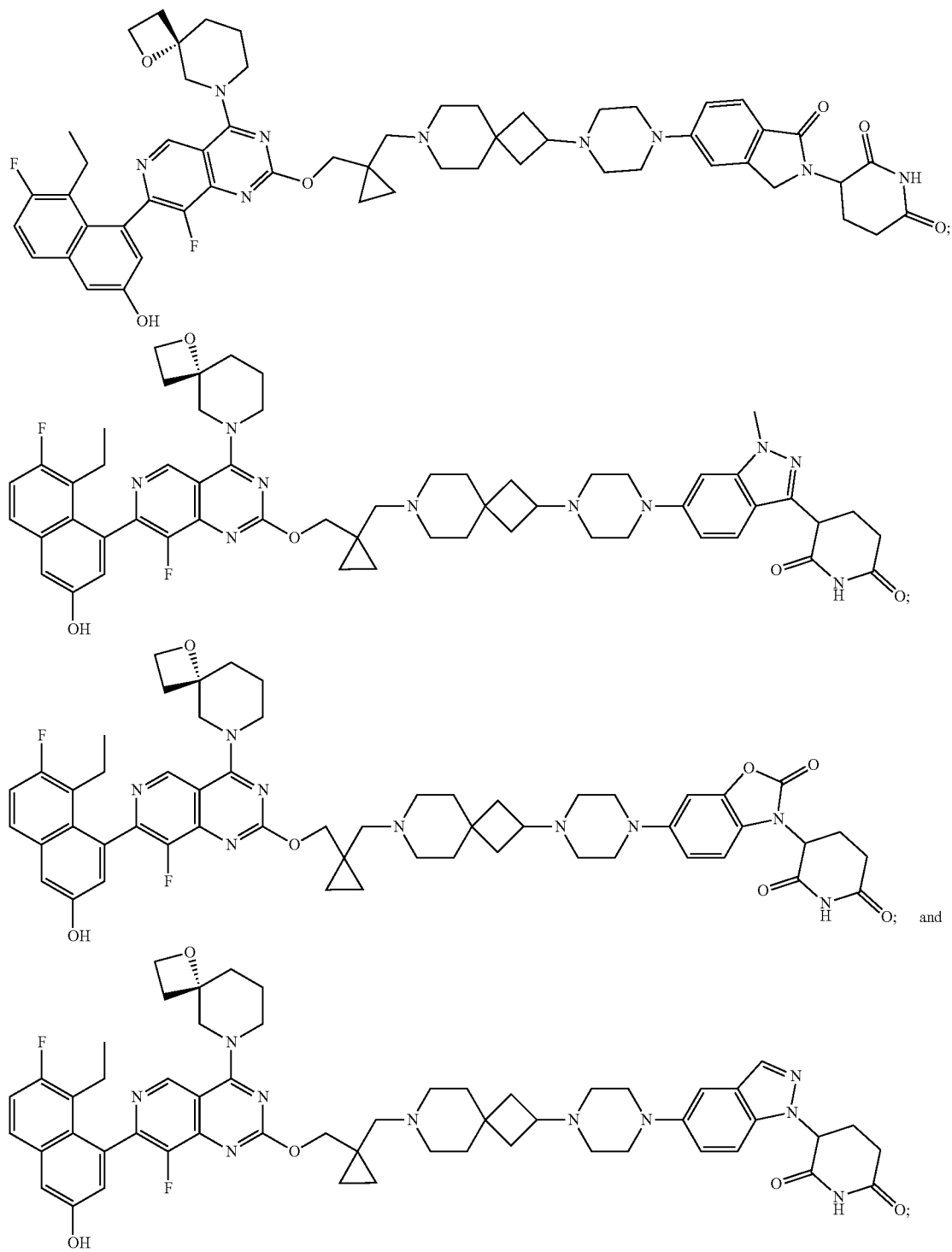

or a pharmaceutically acceptable salt thereof.

32. A pharmaceutical composition comprising a therapeutically effective amount of a compound according to claim 1 and one or more pharmaceutically acceptable carriers, pharmaceutically acceptable vehicles, pharmaceutically acceptable excipients, or combinations thereof.

33. A method for degrading mutant and/or wild-type KRAS in a cell, comprising contacting the cell with at least one compound according to claim 1.

34. A method of treating cancer associated with one or more KRAS mutations in a patient in need thereof, comprising administering to the patient a therapeutically effective amount of the compound according to claim 1, wherein the cancer is selected from lung cancer, pancreatic cancer, small bowel cancer, colorectal cancer, gall bladder cancer, thyroid cancer, liver cancer, bile duct cancer, cervical cancer, bladder cancer, prostate cancer, esophageal cancer, and blood cancer.

35. A pharmaceutical composition comprising a therapeutically effective amount of a compound according to claim 29 and one or more pharmaceutically acceptable carriers, pharmaceutically acceptable vehicles, pharmaceutically acceptable excipients, or combinations thereof.

36. A method for degrading mutant and/or wild-type KRAS in a cell, comprising contacting the cell with at least one compound according to claim 29.

37. A method of treating cancer associated with one or more KRAS mutations in a patient in need thereof, comprising administering to the patient a therapeutically effective amount of the compound according to claim 29, wherein the cancer is selected from lung cancer, pancreatic cancer, small bowel cancer, colorectal cancer, gall bladder cancer, thyroid cancer, liver cancer, bile duct cancer, cervical cancer, bladder cancer, prostate cancer, esophageal cancer, and blood cancer.

38. The method of claim 37, wherein the cancer is lung cancer, pancreatic cancer, or colorectal cancer.

39. A pharmaceutical composition comprising a therapeutically effective amount of a compound according to claim 30 and one or more pharmaceutically acceptable carriers, pharmaceutically acceptable vehicles, pharmaceutically acceptable excipients, or combinations thereof.

40. A method for degrading mutant and/or wild-type KRAS in a cell, comprising contacting the cell with at least one compound according to claim 30.

41. A method of treating cancer associated with one or more KRAS mutations in a patient in need thereof, comprising administering to the patient a therapeutically effective amount of the compound according to claim 30, wherein the cancer is selected from lung cancer, pancreatic cancer, small bowel cancer, colorectal cancer, gall bladder cancer, thyroid cancer, liver cancer, bile duct cancer, cervical cancer, bladder cancer, prostate cancer, esophageal cancer, and blood cancer.

42. The method of claim 41, wherein the cancer is lung cancer, pancreatic cancer, or colorectal cancer.

43. A pharmaceutical composition comprising a therapeutically effective amount of a compound according to claim 31 and one or more pharmaceutically acceptable carriers, pharmaceutically acceptable vehicles, pharmaceutically acceptable excipients, or combinations thereof.

44. A method for degrading mutant and/or wild-type KRAS in a cell, comprising contacting the cell with at least one compound according to claim 31.

45. A method of treating cancer associated with one or more KRAS mutations in a patient in need thereof, comprising administering to the patient a therapeutically effective amount of the compound according to claim 31, wherein the cancer is selected from lung cancer, pancreatic cancer, small bowel cancer, colorectal cancer, gall bladder cancer, thyroid cancer, liver cancer, bile duct cancer, cervical cancer, bladder cancer, prostate cancer, esophageal cancer, and blood cancer.

46. The method of claim 45, wherein the cancer is lung cancer, pancreatic cancer, or colorectal cancer.

\* \* \* \* \*